United States Patent
Oh et al.

(10) Patent No.: US 11,476,425 B2
(45) Date of Patent: Oct. 18, 2022

(54) HETEROCYCLIC COMPOUND AND ORGANIC LIGHT EMITTING ELEMENT COMPRISING SAME

(71) Applicant: LT MATERIALS CO., LTD., Yongin (KR)

(72) Inventors: Han-Kook Oh, Osan-si (KR); Yun-Ji Lee, Osan-si (KR); Hye-Su Ji, Osan-si (KR); Won-Jang Jeong, Hwaseong-si (KR); Jin-Seok Choi, Suwon-si (KR); Dae-Hyuk Choi, Yongin-si (KR)

(73) Assignee: LT MATERIALS CO., LTD., Yongin (KR)

( * ) Notice: Subject to any disclaimer, the term of this patent is extended or adjusted under 35 U.S.C. 154(b) by 343 days.

(21) Appl. No.: 16/649,528

(22) PCT Filed: Sep. 28, 2018

(86) PCT No.: PCT/KR2018/011605
§ 371 (c)(1),
(2) Date: Mar. 20, 2020

(87) PCT Pub. No.: WO2020/067593
PCT Pub. Date: Apr. 2, 2020

(65) Prior Publication Data
US 2021/0226133 A1    Jul. 22, 2021

(51) Int. Cl.
*H01L 51/00* (2006.01)
*C07D 495/04* (2006.01)
(Continued)

(52) U.S. Cl.
CPC ........ *H01L 51/0067* (2013.01); *C07D 495/04* (2013.01); *C07D 519/00* (2013.01);
(Continued)

(58) Field of Classification Search
CPC ................. H01L 51/00; H01L 51/0067; H01L 51/0071–0074; C07D 495/04; C07D 519/00
(Continued)

(56) References Cited

U.S. PATENT DOCUMENTS

| 4,356,429 A | 10/1982 | Tang |
| 2013/0292653 A1 | 11/2013 | Park et al. |

(Continued)

FOREIGN PATENT DOCUMENTS

| KR | 10-2013-0127567 A | 11/2013 |
| KR | 10-2016-0001702 A | 1/2016 |

(Continued)

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenylamino)triphenylamine (m-MTDATA), as Hole-Transport Materials," Advanced Materials. Vol. 6, No. 9, 1994, pp. 677-679.

*Primary Examiner* — Sheng-Bai Zhu
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

16 Claims, 3 Drawing Sheets

(51) Int. Cl.
*C07D 519/00* (2006.01)
*H01L 51/50* (2006.01)

(52) U.S. Cl.
CPC ...... *H01L 51/0071* (2013.01); *H01L 51/0072* (2013.01); *H01L 51/0073* (2013.01); *H01L 51/0074* (2013.01); *H01L 51/5016* (2013.01); *H01L 51/5072* (2013.01); *H01L 51/5092* (2013.01); *H01L 51/5096* (2013.01)

(58) Field of Classification Search
USPC .......................................................... 257/40
See application file for complete search history.

(56) References Cited

U.S. PATENT DOCUMENTS

| | | | |
|---|---|---|---|
| 2015/0207083 A1* | 7/2015 | Schaefer | H01L 51/00 252/500 |
| 2015/0263297 A1 | 11/2015 | Stoessel et al. | |
| 2016/0285010 A1* | 9/2016 | Yoon | C09K 11/06 |
| 2017/0033295 A1 | 2/2017 | Xia et al. | |
| 2017/0141325 A1 | 5/2017 | Lee et al. | |
| 2017/0213985 A1* | 7/2017 | Lee | C07D 209/86 |
| 2018/0047916 A1* | 2/2018 | Jang | C09K 11/06 |

FOREIGN PATENT DOCUMENTS

| | | |
|---|---|---|
| KR | 10-2016-0041822 A | 4/2016 |
| KR | 10-2016-0051212 A | 5/2016 |
| KR | 10-2017-0015216 A | 2/2017 |
| WO | WO 2007/117289 A2 | 10/2007 |
| WO | WO 2014/008982 A1 | 1/2014 |

\* cited by examiner

[FIG. 1]
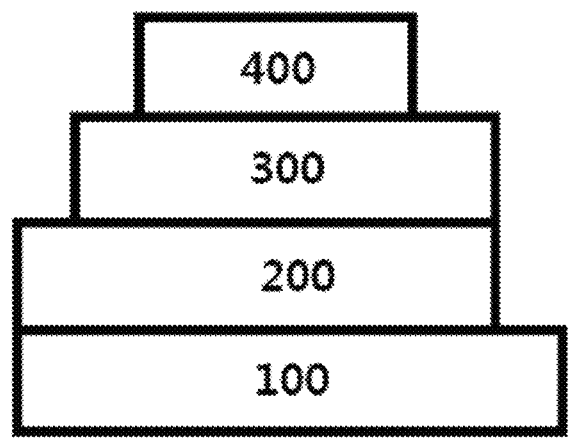
[FIG. 2]
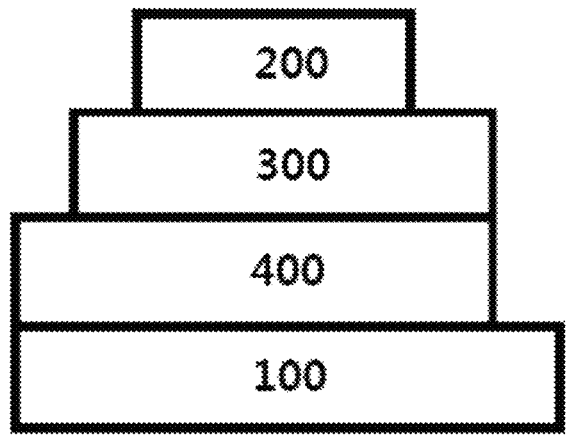

【FIG. 3】
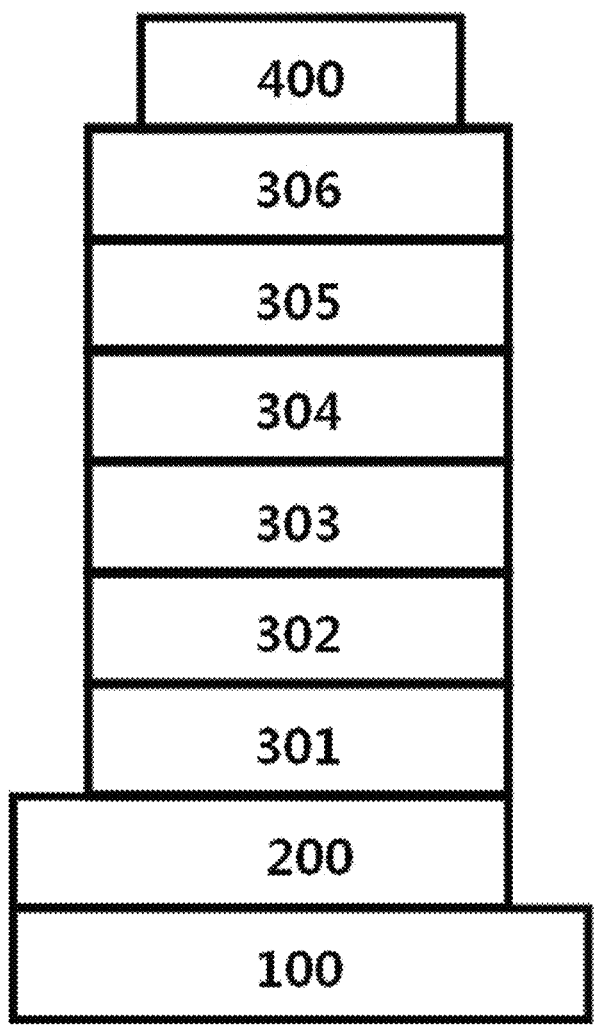

[FIG. 4]
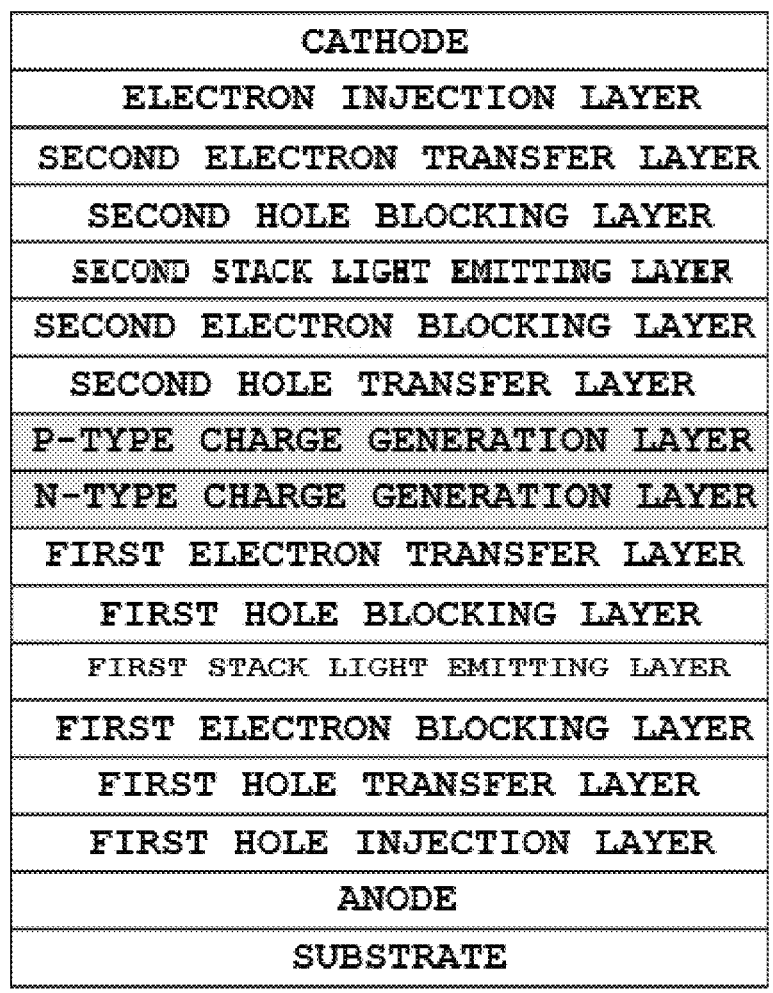

HETEROCYCLIC COMPOUND AND ORGANIC LIGHT EMITTING ELEMENT COMPRISING SAME

TECHNICAL FIELD

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

DISCLOSURE

Technical Problem

The present disclosure is directed to providing a heterocyclic compound and an organic light emitting device comprising the same.

Technical Solution

One embodiment of the present application provides a heterocyclic compound represented by the following Chemical Formula 1.

[Chemical Formula 1]

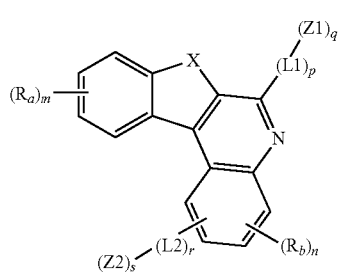

In Chemical Formula 1,

X is O or S,

L1 and L2 are the same as or different from each other, and each independently a substituted or unsubstituted arylene group; or a substituted or unsubstituted heteroarylene group, Z1 and Z2 are the same as or different from each other, and each independently hydrogen; a substituted or unsubstituted alkyl group; a substituted or unsubstituted aryl group; a substituted or unsubstituted heteroaryl group; —SiRR'R"; or —P(=O)RR', $R_a$ and $R_b$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring, R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, p and n are an integer of 1 to 3, m, q and s are an integer of 1 to 4, r is an integer of 0 to 4, and when r is an integer of 0 and Z2 is hydrogen, n is an integer of 2 or 3, and $R_b$ is a substituted or unsubstituted aryl group; or a substituted or unsubstituted heteroaryl group, or two or more groups adjacent to each other bond to each other to form a substituted or unsubstituted aliphatic or aromatic hydrocarbon ring.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

The compound described in the present specification can be used as an organic material layer material of an organic light emitting device. The compound is capable of performing a role of a hole injection material, a hole transfer material, a light emitting material, an electron transfer material, an electron injection material and the like in the organic light emitting device. Particularly, the heterocyclic compound represented by Chemical Formula 1 can be used as an electron transfer layer material, a hole blocking layer material or a charge generation layer material of the organic light emitting device. In addition, when using the compound represented by Chemical Formula 1 in the organic material layer, a driving voltage is lowered and light efficiency is enhanced in the device, and device lifetime properties can be enhanced by thermal stability of the compound.

Particularly, the heterocyclic compound represented by Chemical Formula 1 has both N-type and P-type substituents in one core structure, and by having a P-type substituent, hole properties can be strengthened in the molecule. The compound of Chemical Formula 1 is a bipolar type having both a P-type and an N-type, and is thereby capable of blocking hole leakage and effectively trapping excitons in a light emitting layer. In addition, hole properties are strengthened in a specific device structure changing electron mobility relatively slowly, which balances electrons and holes in the light emitting layer properly forming a recombination region of the excitons, and as a result, efficiency and lifetime increase.

DESCRIPTION OF DRAWINGS

FIG. 1 to FIG. 4 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

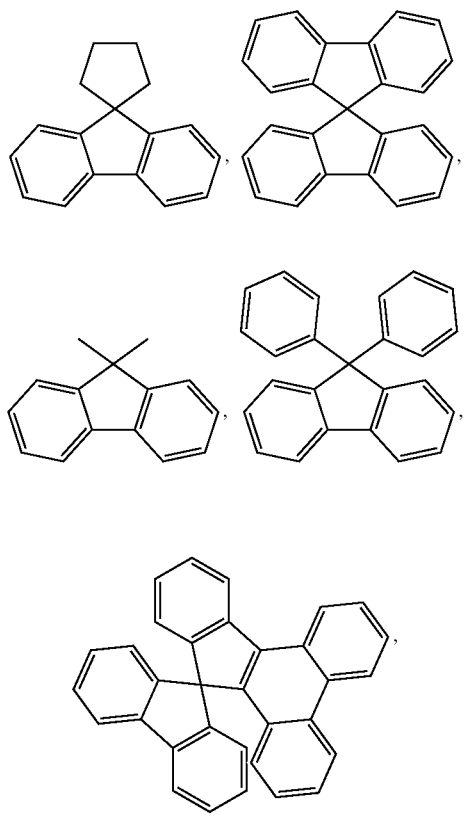

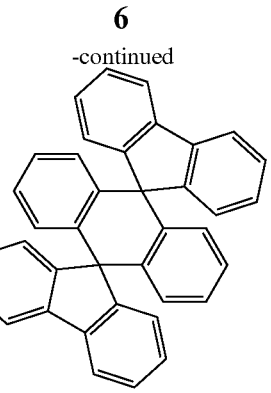

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a triazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a triazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, specific examples of the phosphine oxide group may comprise a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

In one embodiment of the present application, X of Chemical Formula 1 may be O or S.

In one embodiment of the present application, X of Chemical Formula 1 may be O.

In one embodiment of the present application, X of Chemical Formula 1 may be S.

In one embodiment of the present application, $R_a$ of Chemical Formula 1 may be selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aliphatic or aromatic hydrocarbon ring.

In another embodiment, $R_a$ of Chemical Formula 1 may be hydrogen; a substituted or unsubstituted aryl group; or a substituted or unsubstituted heteroaryl group.

In another embodiment, $R_a$ of Chemical Formula 1 may be hydrogen; a substituted or unsubstituted C6 to C60 aryl group; or a substituted or unsubstituted C2 to C60 heteroaryl group.

In another embodiment, $R_a$ of Chemical Formula 1 may be hydrogen; a C6 to C30 aryl group; or a C2 to C30 heteroaryl group.

In another embodiment, $R_a$ of Chemical Formula 1 may be hydrogen.

In one embodiment of the present application, L1 may be a substituted or unsubstituted arylene group; or a substituted or unsubstituted heteroarylene group.

In another embodiment, L1 may be a substituted or unsubstituted C6 to C60 arylene group; or a substituted or unsubstituted C2 to C60 heteroarylene group.

In another embodiment, L1 may be a substituted or unsubstituted C6 to C40 arylene group; or a substituted or unsubstituted C2 to C40 heteroarylene group.

In another embodiment, L1 may be a substituted or unsubstituted monocyclic or polycyclic C6 to C40 arylene group; or a substituted or unsubstituted C2 to C40 N-containing heteroarylene group.

In another embodiment, L1 may be a monocyclic or polycyclic C6 to C40 arylene group; or a C2 to C40 N-containing heteroarylene group.

In another embodiment, L1 may be a phenylene group; a biphenylene group; a triphenylenylene group; a naphthylene group; a phenanthrenylene group; a divalent pyridine group; a divalent pyrimidine group; a divalent phenanthroline group or a divalent triazine group.

In one embodiment of the present application, Z1 may be hydrogen; a substituted or unsubstituted alkyl group; a substituted or unsubstituted aryl group; a substituted or unsubstituted heteroaryl group; —SiRR'R"; or —P(=O)RR'.

In another embodiment, Z1 may be hydrogen; a substituted or unsubstituted C1 to C60 alkyl group; a substituted or unsubstituted C6 to C60 aryl group; a substituted or unsubstituted C2 to C60 heteroaryl group; —SiRR'R"; or —P(=O)RR'.

In another embodiment, Z1 may be hydrogen; a substituted or unsubstituted C1 to C40 alkyl group; a substituted or unsubstituted C6 to C40 aryl group; a substituted or unsubstituted C2 to C40 heteroaryl group; —SiRR'R"; or —P(=O)RR'.

In another embodiment, Z1 may be hydrogen; a substituted or unsubstituted C6 to C40 aryl group; a substituted or unsubstituted C2 to C40 heteroaryl group; or —P(=O)RR'.

In another embodiment, Z1 may be hydrogen; a C6 to C40 aryl group unsubstituted or substituted with one or more substituents selected from the group consisting of a C6 to C40 aryl group and a C2 to C40 heteroaryl group; a C2 to C40 heteroaryl group; or —P(=O)RR'.

In another embodiment, Z1 may be hydrogen; a phenyl group unsubstituted or substituted with a carbazole group, a dibenzofuran group or a dibenzothiophene group; a biphenyl group; a dibenzofuran group; a dibenzothiophene group; a pyridine group; a pyrimidine group; a triazine group; or —P(=O)RR'.

In one embodiment of the present application, $R_b$ of Chemical Formula 1 may be selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aliphatic or aromatic hydrocarbon ring.

In another embodiment, $R_b$ of Chemical Formula 1 may be selected from the group consisting of hydrogen; a substituted or unsubstituted C1 to C60 alkyl group; a substituted or unsubstituted C6 to C60 aryl group; a substituted or unsubstituted C2 to C60 heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other may bond to each other to form a substituted or unsubstituted aliphatic or aromatic hydrocarbon ring.

In another embodiment, $R_b$ of Chemical Formula 1 may be selected from the group consisting of hydrogen; a substituted or unsubstituted C6 to C60 aryl group; and a substituted or unsubstituted C2 to C60 heteroaryl group, or two or more groups adjacent to each other may bond to each other to form a substituted or unsubstituted aliphatic or aromatic hydrocarbon ring.

In another embodiment, $R_b$ of Chemical Formula 1 may be selected from the group consisting of hydrogen; a substituted or unsubstituted C6 to C40 aryl group; and a substituted or unsubstituted C2 to C40 heteroaryl group, or two or more groups adjacent to each other may bond to each other to form a substituted or unsubstituted aromatic hydrocarbon ring.

In another embodiment, $R_b$ of Chemical Formula 1 may be selected from the group consisting of hydrogen; a C6 to C40 aryl group unsubstituted or substituted with one or more substituents selected from the group consisting of a C6 to C40 aryl group and a C2 to C40 heteroaryl group; and a C2 to C40 heteroaryl group, or two or more groups adjacent to each other may bond to each other to form C6 to C40 aromatic hydrocarbon ring.

In another embodiment, $R_b$ of Chemical Formula 1 may be selected from the group consisting of hydrogen; a phenyl group unsubstituted or substituted with one or more substituents selected from the group consisting of a triphenylene group, a phenanthrene group, a dibenzothiophene group and a dibenzofuran group; a biphenyl group; a naphthyl group; a phenanthrene group; a triphenylene group; a dibenzofuran group; and a dibenzothiophene group, or two or more groups adjacent to each other may bond to each other to form a benzene ring.

In one embodiment of the present application, L2 may be a substituted or unsubstituted arylene group; or a substituted or unsubstituted heteroarylene group.

In another embodiment, L2 may be a substituted or unsubstituted C6 to C60 arylene group; or a substituted or unsubstituted C2 to C60 heteroarylene group.

In another embodiment, L2 may be a substituted or unsubstituted C6 to C40 arylene group; or a substituted or unsubstituted C2 to C40 heteroarylene group.

In another embodiment, L2 may be a C6 to C40 arylene group; or a C2 to C40 heteroarylene group.

In another embodiment, L2 may be a phenylene group; a biphenylene group; a triphenylenylene group; a phenanthrenylene group; a divalent pyridine group; a divalent pyrimidine group; a divalent quinoline group; a divalent phenanthroline group or a divalent triazine group.

In one embodiment of the present application, Z2 may be hydrogen; a substituted or unsubstituted aryl group; a substituted or unsubstituted heteroaryl group; or P(=O)RR'.

In another embodiment, Z2 may be hydrogen; a substituted or unsubstituted C6 to C60 aryl group; a substituted or unsubstituted C2 to C60 heteroaryl group; or P(=O)RR'.

In another embodiment, Z2 may be hydrogen; a substituted or unsubstituted C6 to C40 aryl group; a substituted or unsubstituted C2 to C40 heteroaryl group; or P(=O)RR'.

In another embodiment, Z2 may be hydrogen; a C6 to C40 aryl group unsubstituted or substituted with a C6 to C40 heteroaryl group; a C2 to C40 heteroaryl group; or P(=O)RR'.

In another embodiment, Z2 may be hydrogen; a phenyl group unsubstituted or substituted with a carbazole group, a dibenzofuran group or a dibenzothiophene group; a biphenyl group; a pyridine group; a pyrimidine group; a triazine group; or P(=O)RR'.

In one embodiment of the present application, R, R' and R" are the same as or different from each other, and may be each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group.

In another embodiment, R, R' and R" are the same as or different from each other, and may be each independently hydrogen; a substituted or unsubstituted aryl group; or a substituted or unsubstituted heteroaryl group.

In another embodiment, R, R' and R" are the same as or different from each other, and may be each independently hydrogen; a substituted or unsubstituted C6 to C60 aryl group; or a substituted or unsubstituted C2 to C60 heteroaryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a C6 to C60 aryl group.

In another embodiment, R, R' and R" are the same as or different from each other, and may be each independently a C6 to C40 aryl group.

In another embodiment, R, R' and R" are the same as or different from each other, and may be each independently a phenyl group.

In one embodiment of the present application, p of Chemical Formula 1 may be 1.

In one embodiment of the present application, p of Chemical Formula 1 may be 2.

In one embodiment of the present application, p of Chemical Formula 1 may be 3.

In one embodiment of the present application, q of Chemical Formula 1 may be 1.

In one embodiment of the present application, q of Chemical Formula 1 may be 2.

In one embodiment of the present application, q of Chemical Formula 1 may be 3.

In one embodiment of the present application, r of Chemical Formula 1 may be 0.

In one embodiment of the present application, r of Chemical Formula 1 may be 1.

In one embodiment of the present application, r of Chemical Formula 1 may be 2.

In one embodiment of the present application, r of Chemical Formula 1 may be 3.

In one embodiment of the present application, s of Chemical Formula 1 may be 1.

In one embodiment of the present application, s of Chemical Formula 1 may be 2.

In one embodiment of the present application, s of Chemical Formula 1 may be 3.

In one embodiment of the present application, s of Chemical Formula 1 may be 4.

In one embodiment of the present application, when r is an integer of 0 and Z2 is hydrogen in Chemical Formula 1, n is an integer of 2 or 3, and $R_b$ is a substituted or unsubstituted aryl group; or a substituted or unsubstituted heteroaryl group, or two or more groups adjacent to each other bond to each other to form a substituted or unsubstituted aliphatic or aromatic hydrocarbon ring.

In another embodiment, when r is an integer of 0 and Z2 is hydrogen in Chemical Formula 1, n is an integer of 2, and adjacent two $R_b$s may bond to each other to form a substituted or unsubstituted aliphatic or aromatic hydrocarbon ring.

In another embodiment, when r is an integer of 0 and Z2 is hydrogen in Chemical Formula 1, n is an integer of 2, and adjacent two $R_b$s may bond to each other to form a substituted or unsubstituted aromatic hydrocarbon ring.

In another embodiment, when r is an integer of 0 and Z2 is hydrogen in Chemical Formula 1, n is an integer of 2, and adjacent two $R_b$s may bond to each other to form a substituted or unsubstituted C3 to C60 aromatic hydrocarbon ring.

In another embodiment, when r is an integer of 0 and Z2 is hydrogen in Chemical Formula 1, n is an integer of 2, and adjacent two $R_b$s may bond to each other to form a substituted or unsubstituted C3 to C30 aromatic hydrocarbon ring.

In another embodiment, when r is an integer of 0 and Z2 is hydrogen in Chemical Formula 1, n is an integer of 2, and adjacent two $R_b$s may bond to each other to form a C3 to C30 aromatic hydrocarbon ring.

In another embodiment, when r is an integer of 0 and Z2 is hydrogen in Chemical Formula 1, n is an integer of 2, and adjacent two $R_b$s may bond to each other to form a benzene ring.

In the heterocyclic compound provided in one embodiment of the present application, Chemical Formula 1 is represented by any one of the following Chemical Formulae 2 to 5.

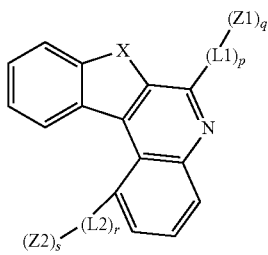

[Chemical Formula 2]

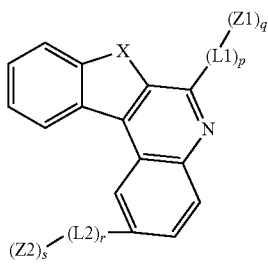

[Chemical Formula 3]

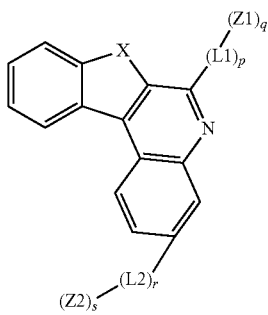

[Chemical Formula 4]

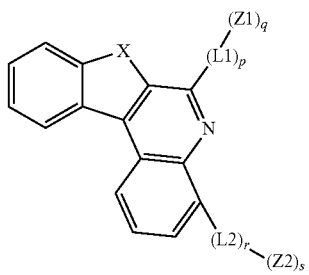

[Chemical Formula 5]

In Chemical Formulae 2 to 5,

L1, L2, Z1, Z2, X, p, q, r and s each have the same definition as in Chemical Formula 1.

In the heterocyclic compound provided in one embodiment of the present application, Chemical Formula 1 is represented by any one of the following Chemical Formulae 6 to 11.

[Chemical Formula 6]

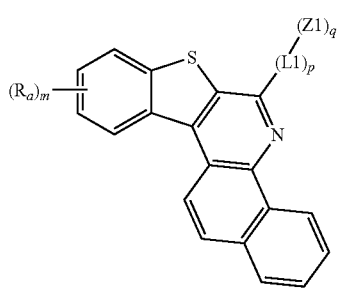

[Chemical Formula 7]

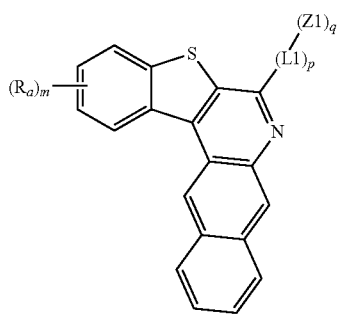

[Chemical Formula 8]

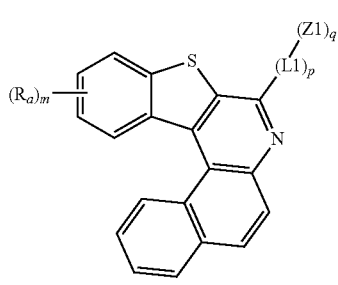

[Chemical Formula 9]

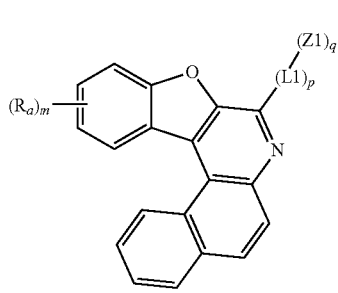

[Chemical Formula 10]

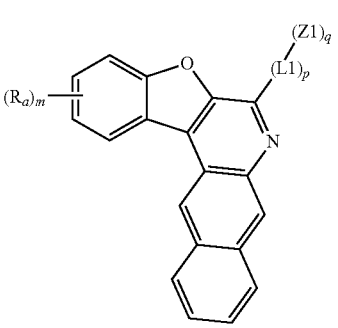

[Chemical Formula 11]

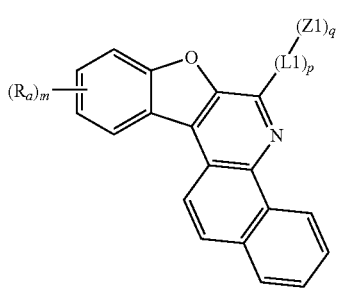

In Chemical Formulae 6 to 11, $R_a$, L1, Z1, p, q and m each have the same definition as in Chemical Formula 1.

The heterocyclic compound represented by Chemical Formula 1 has both N-type and P-type substituents in one core structure, and by having a P-type substituent, hole properties may be strengthened in the molecule. The compound of Chemical Formula 1 is a bipolar type having both a P-type and an N-type, and is thereby capable of blocking hole leakage and effectively trapping excitons in a light emitting layer. In addition, hole properties are strengthened in a specific device structure changing electron mobility relatively slowly, which balances electrons and holes in the light emitting layer properly forming a recombination region of the excitons, and as a result, efficiency and lifetime increase.

In the heterocyclic compound provided in one embodiment of the present application, Chemical Formula 1 is represented by any one of the following compounds.

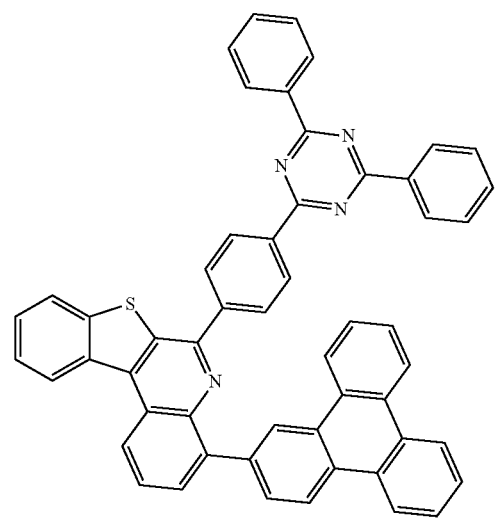

1

2
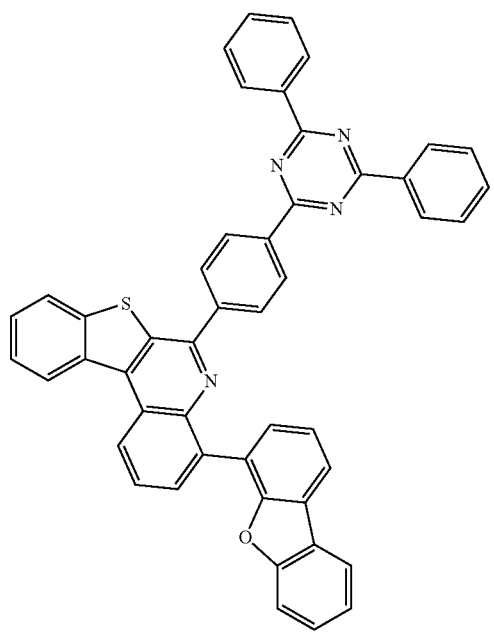
4
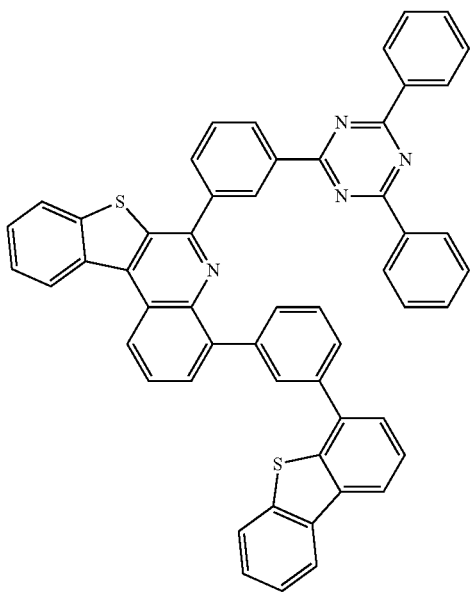
3
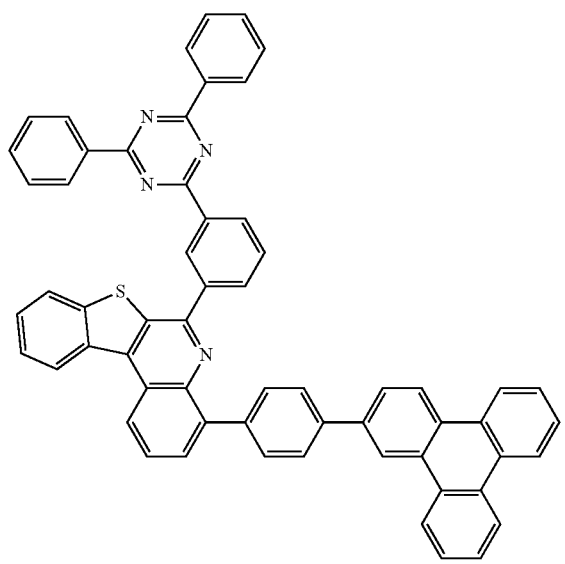
5

6
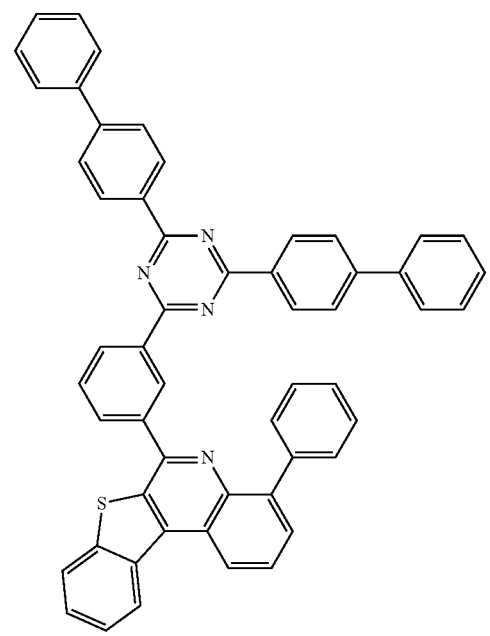
7
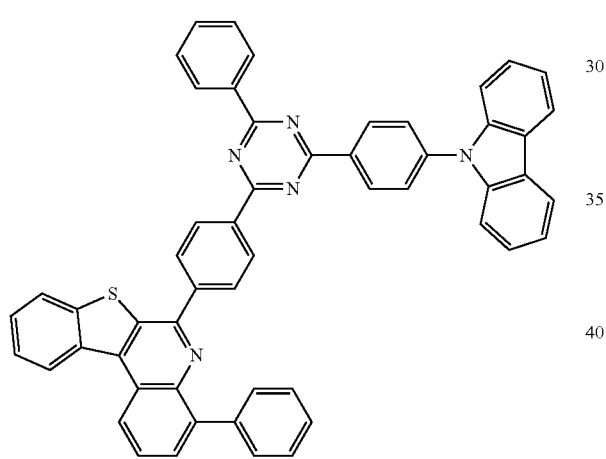
8
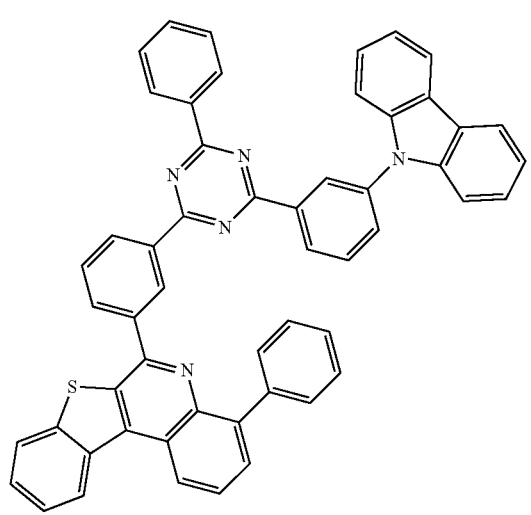
9
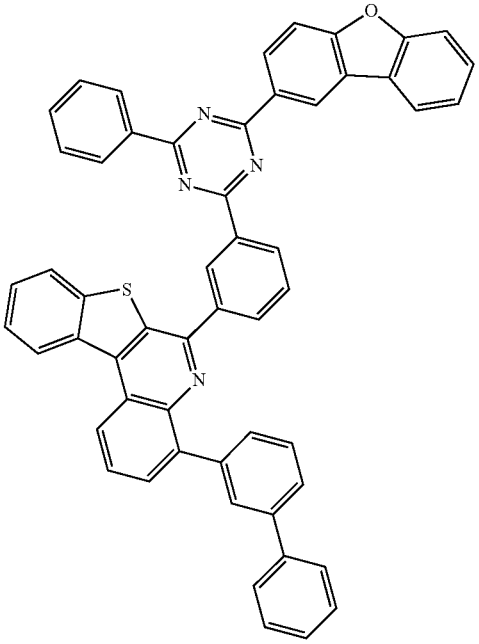
10
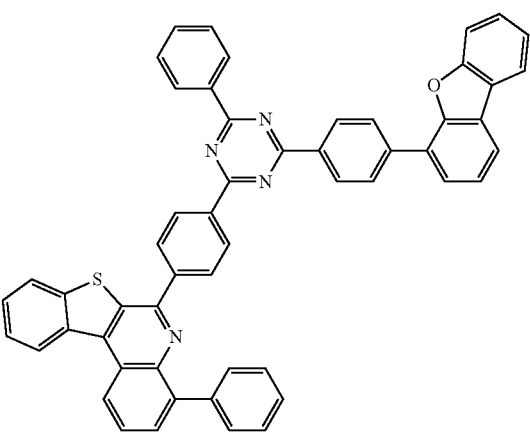

11
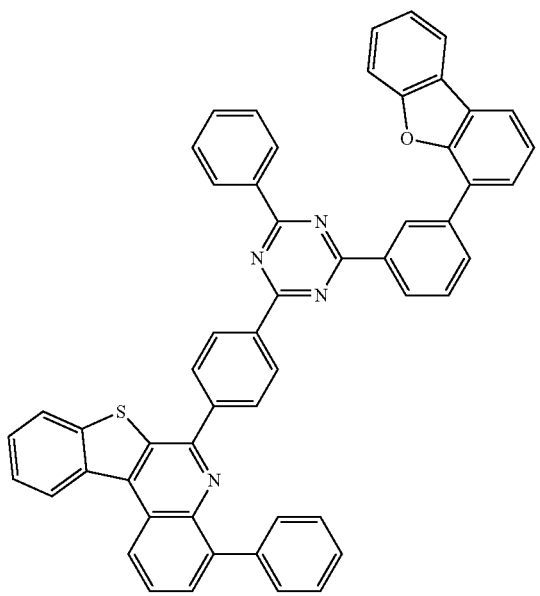
13
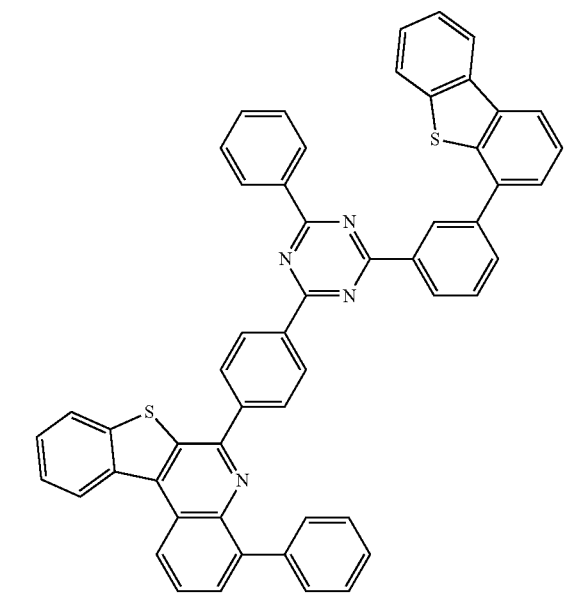
12
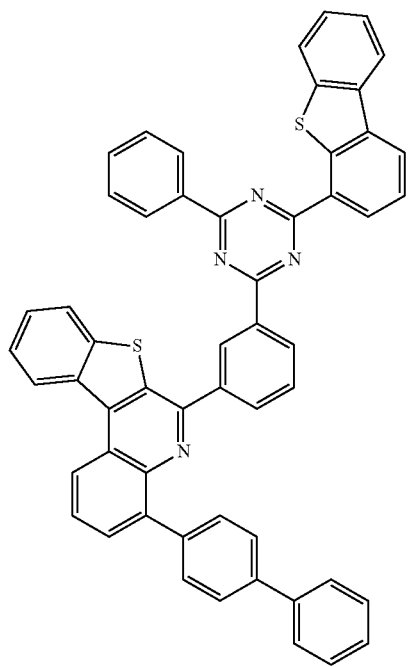
14
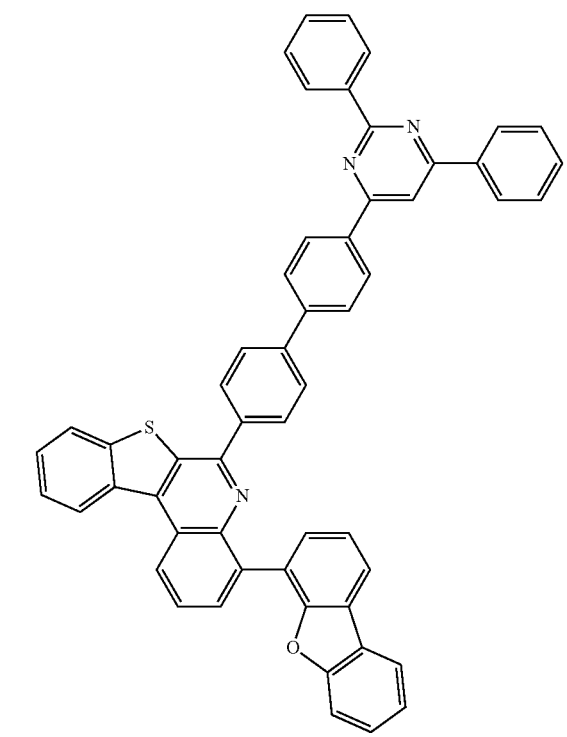

15
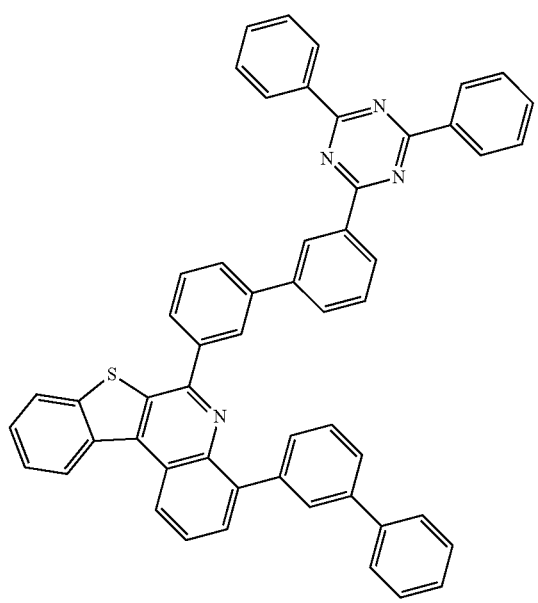
16
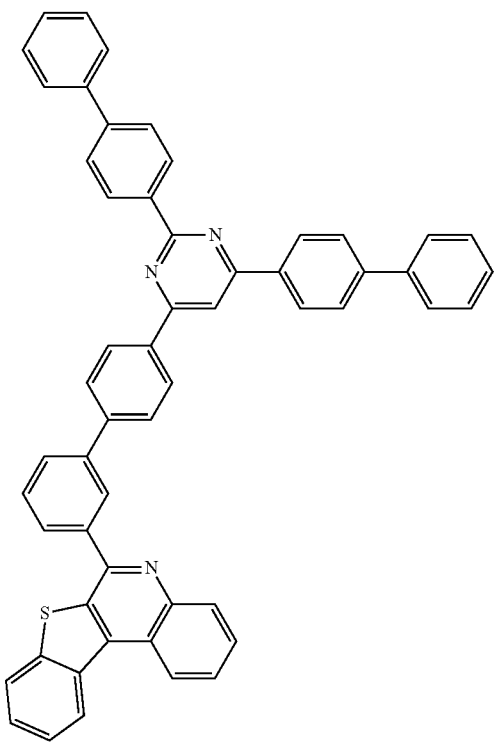
17
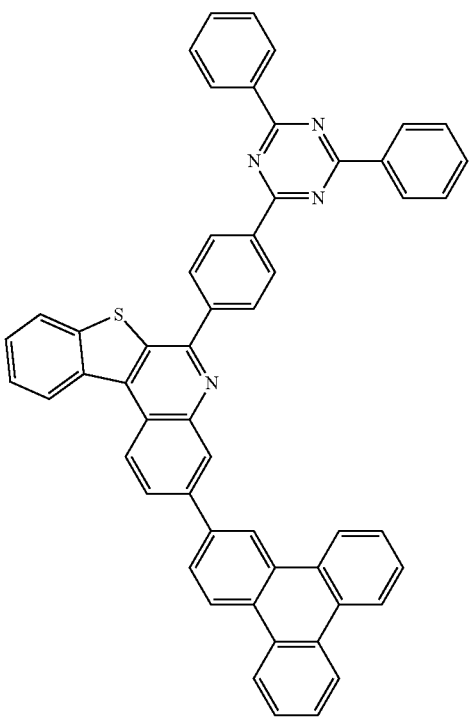
18
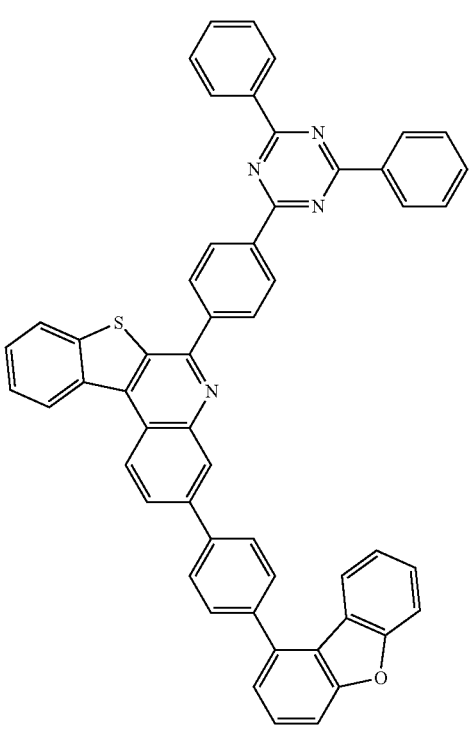

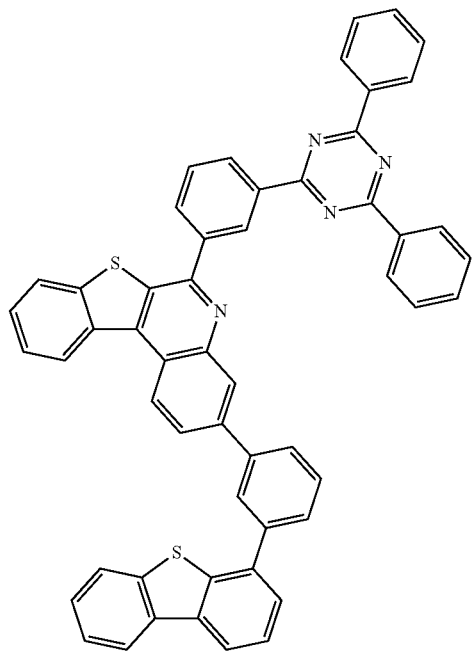
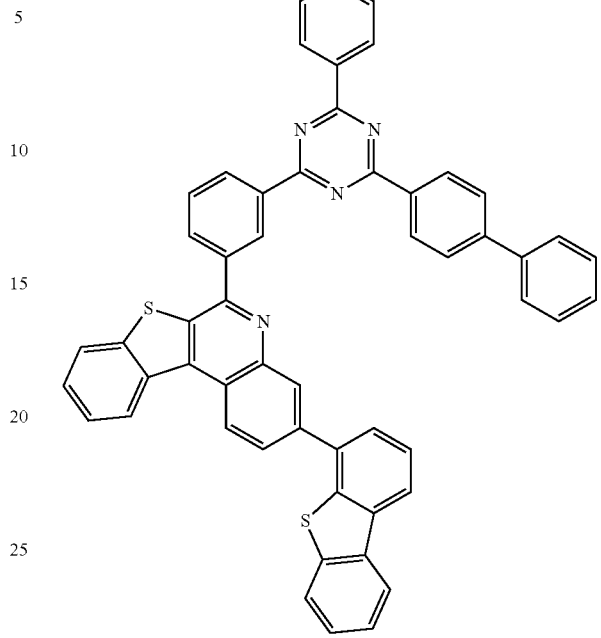
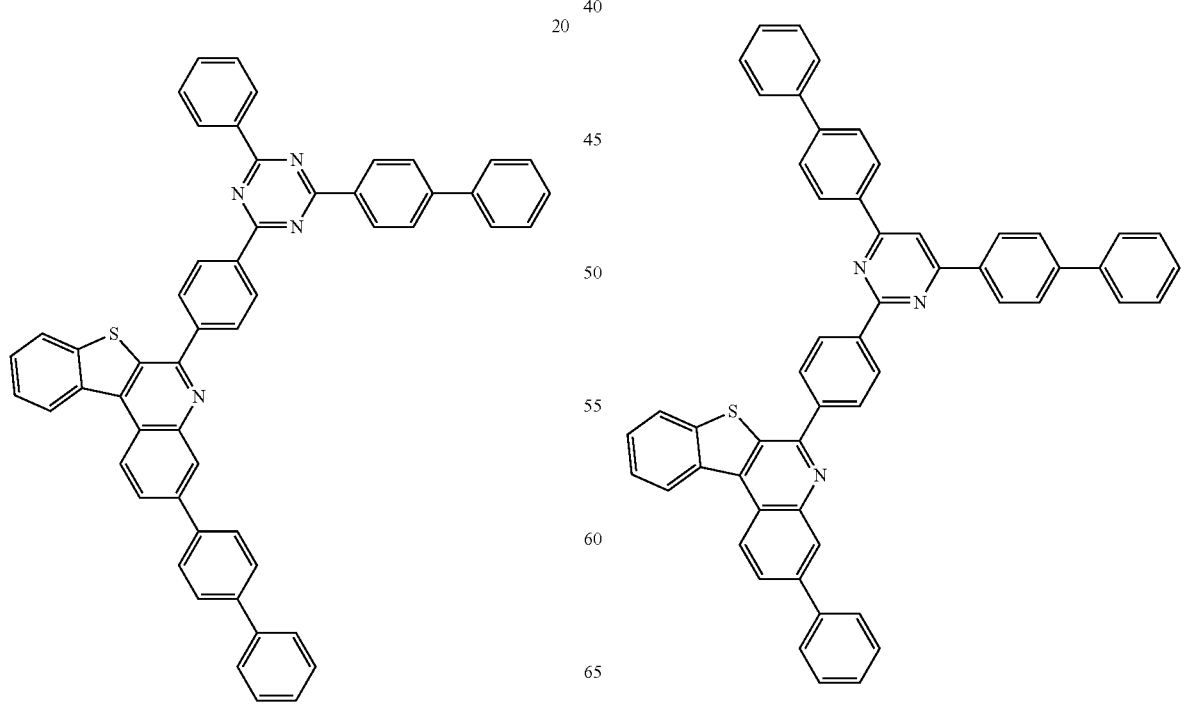

23
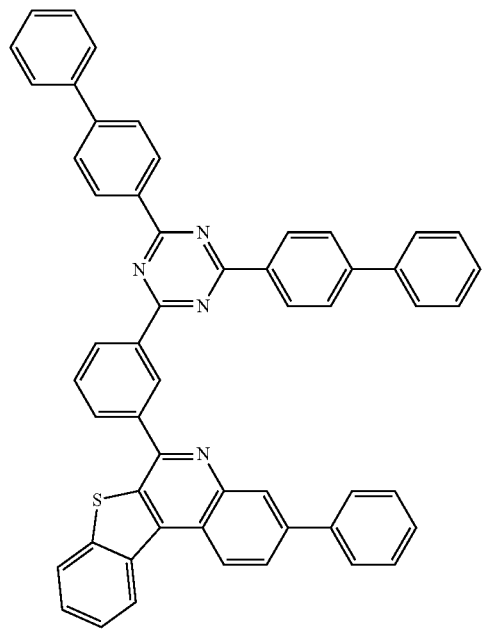
24
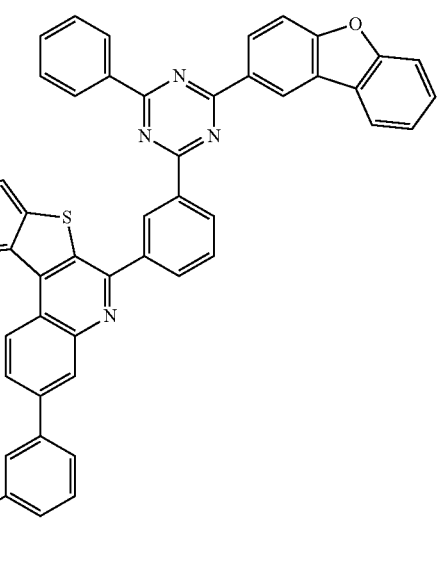
25
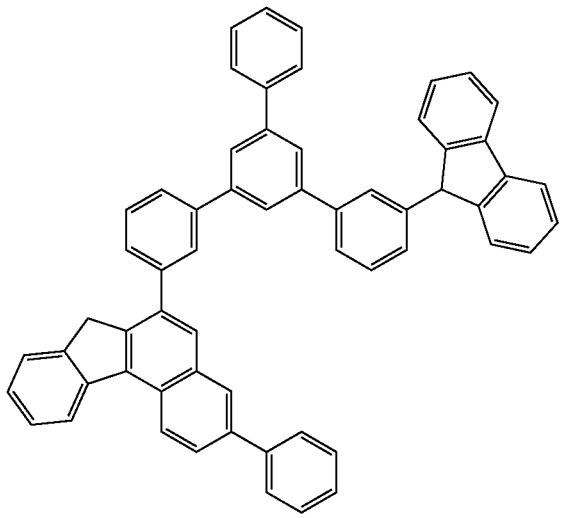
26

27
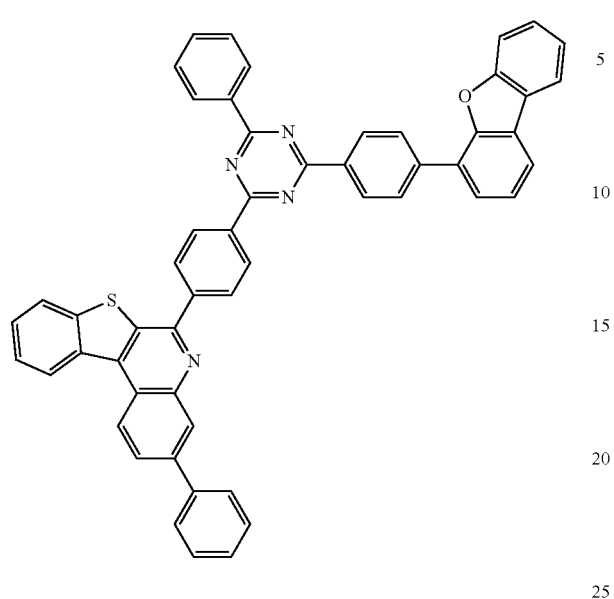
28
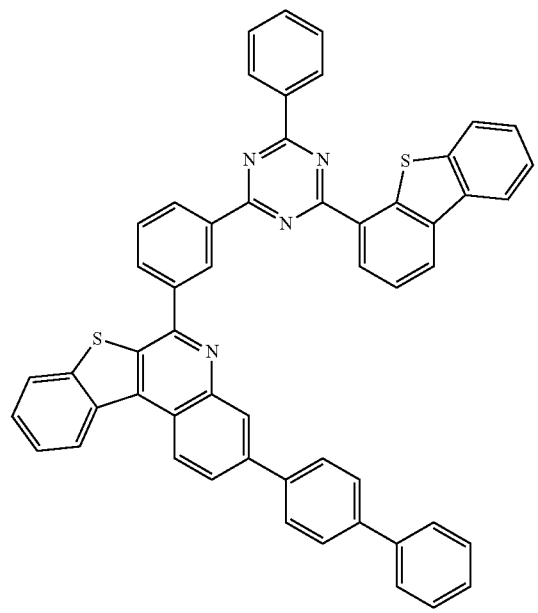
29
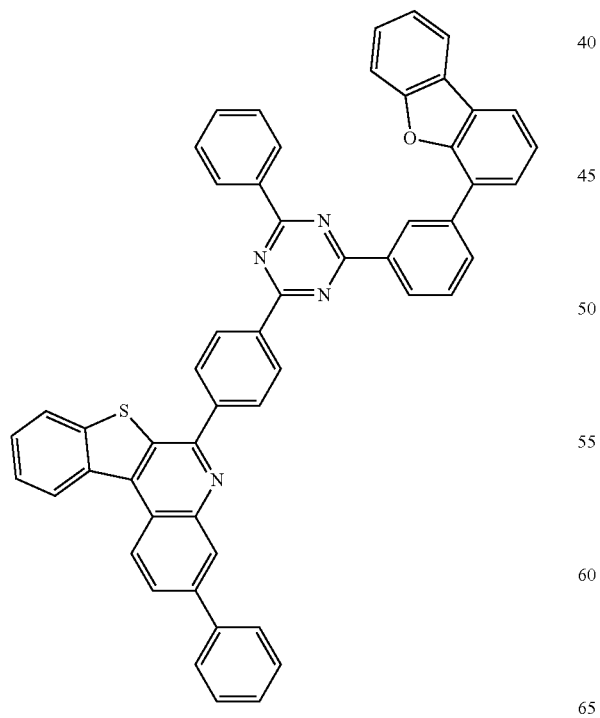
30

31
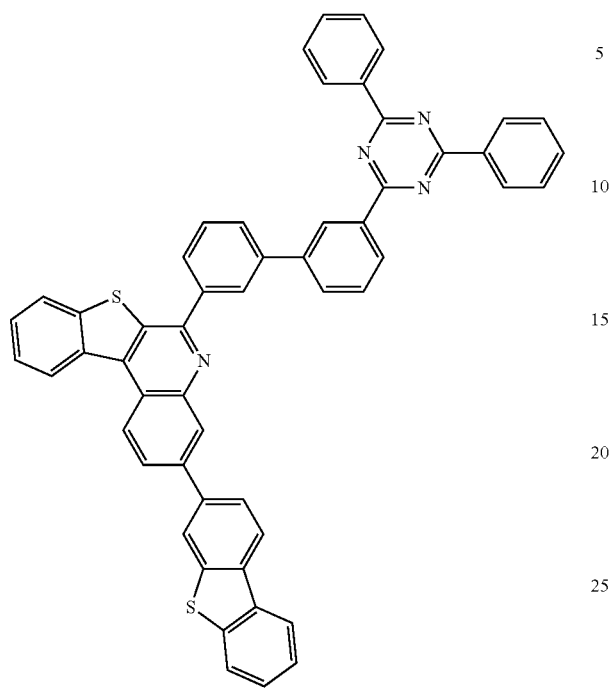
32
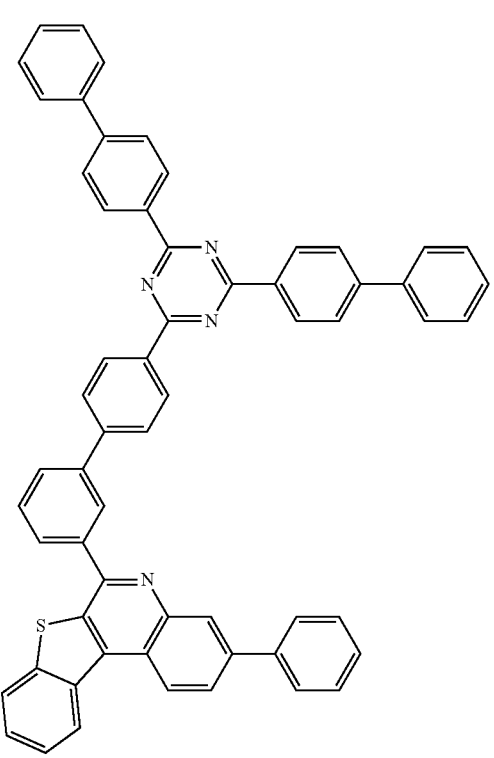
33
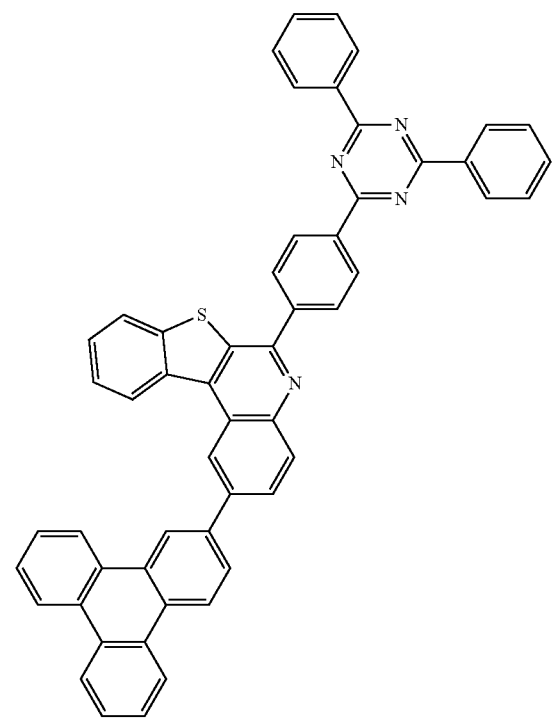
34
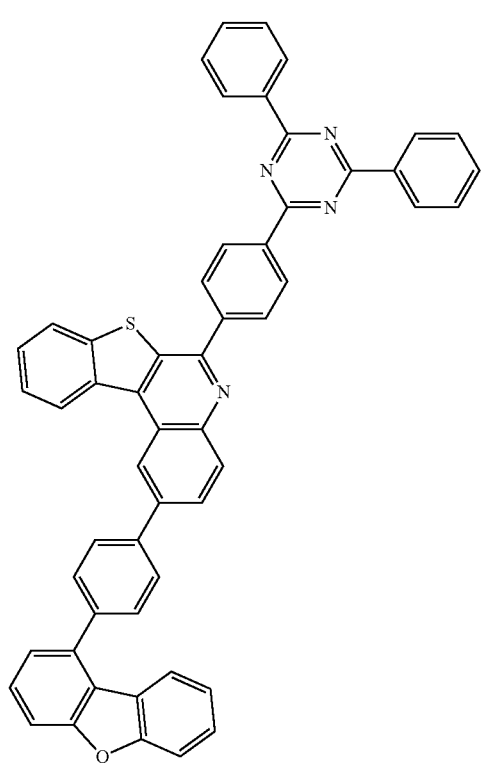

35
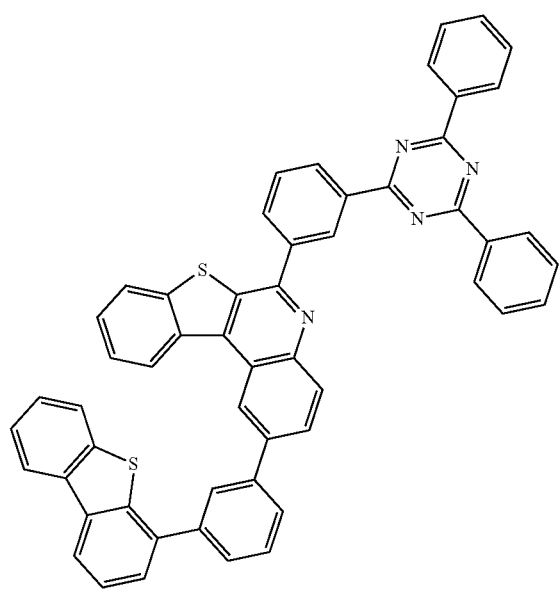
36
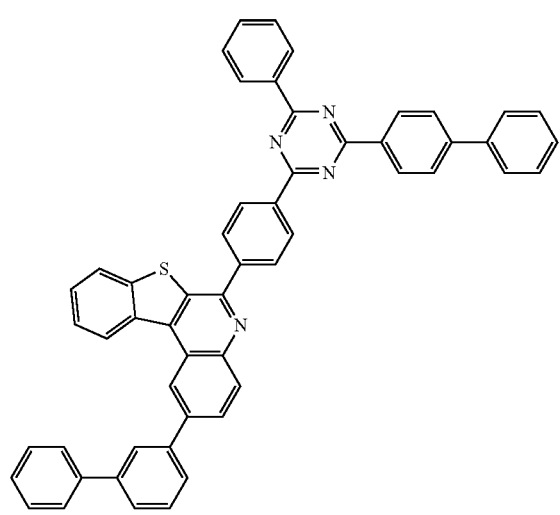
37
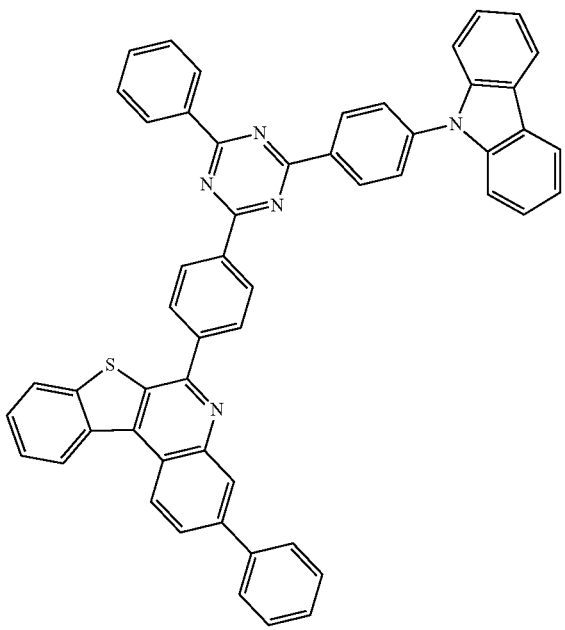
38
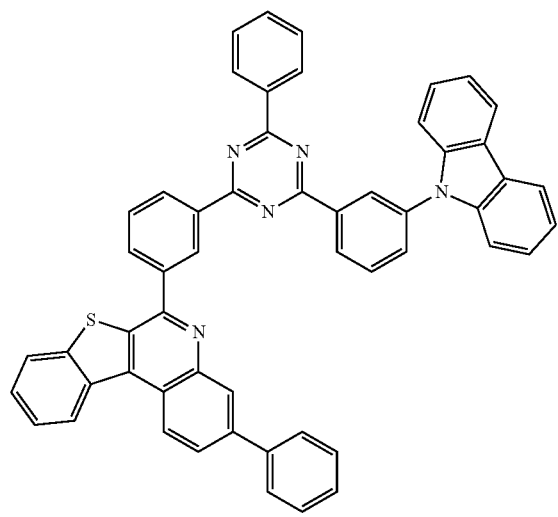

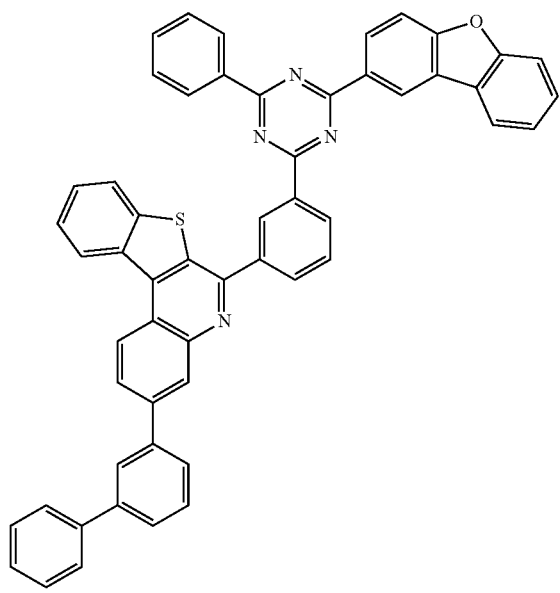
39
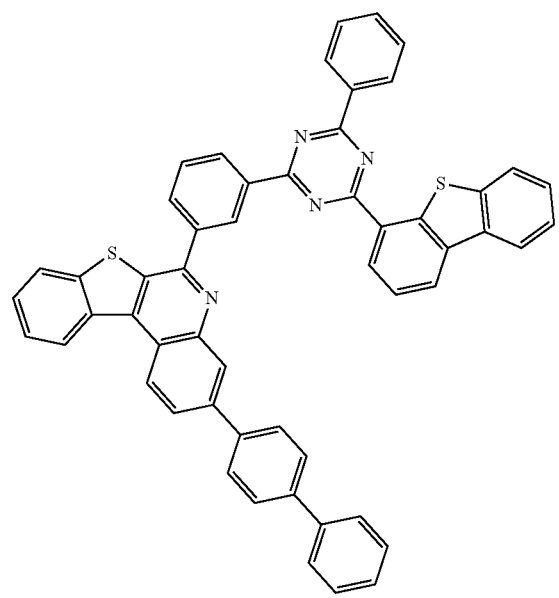
41
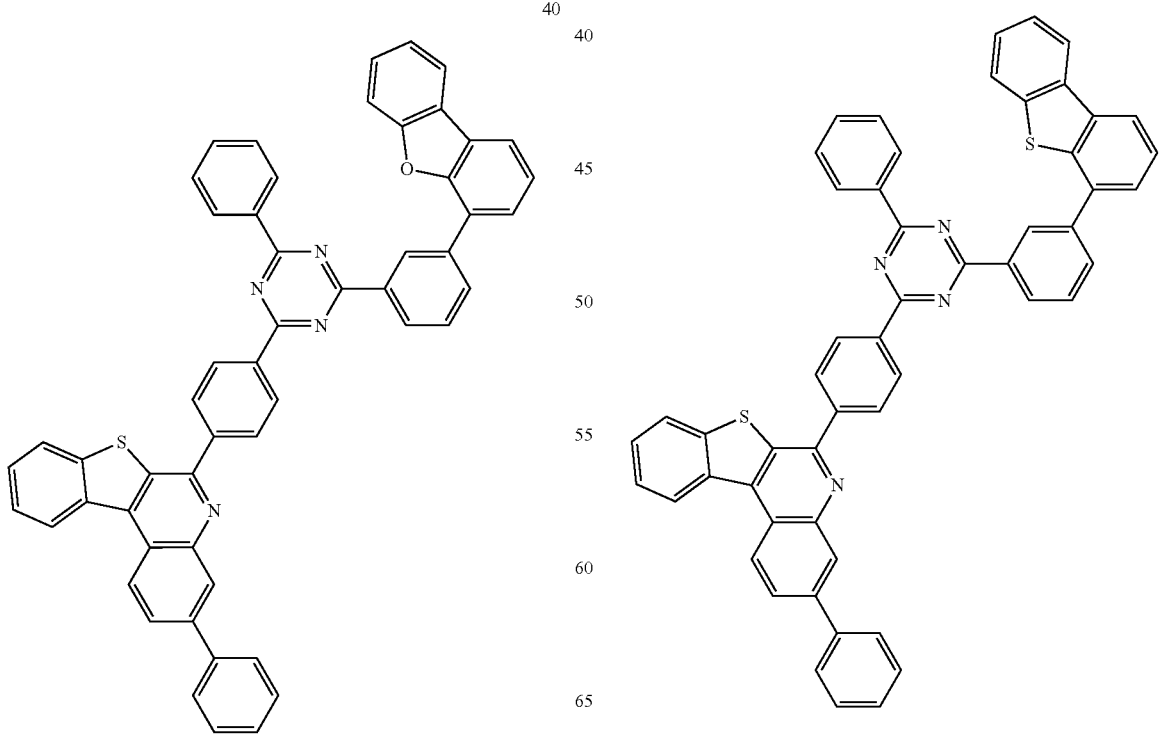

43
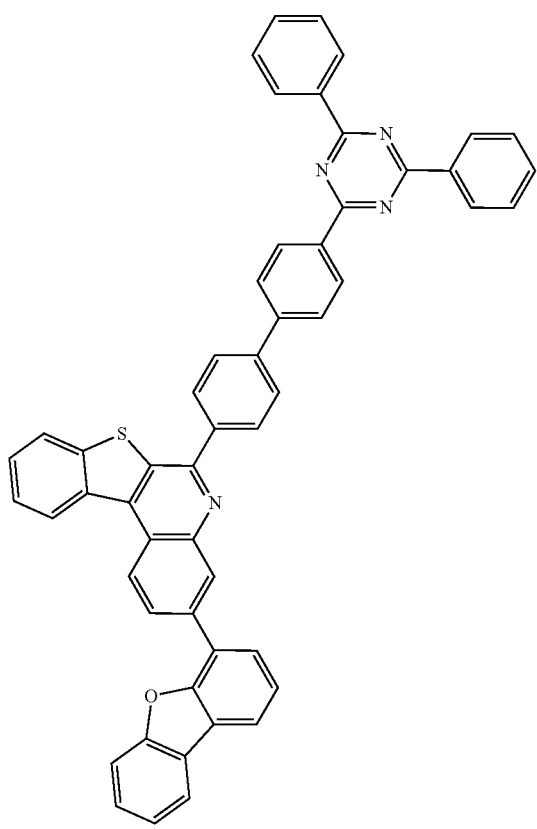
44
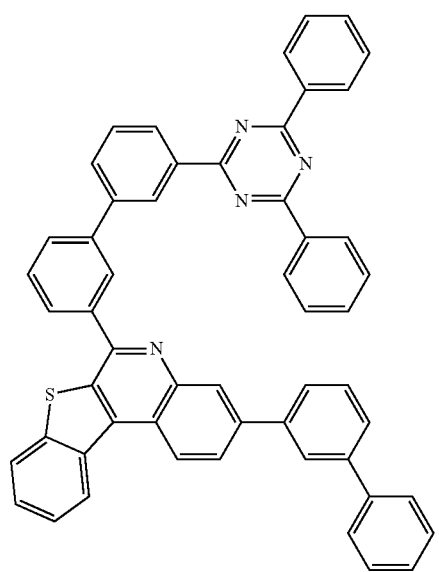
45
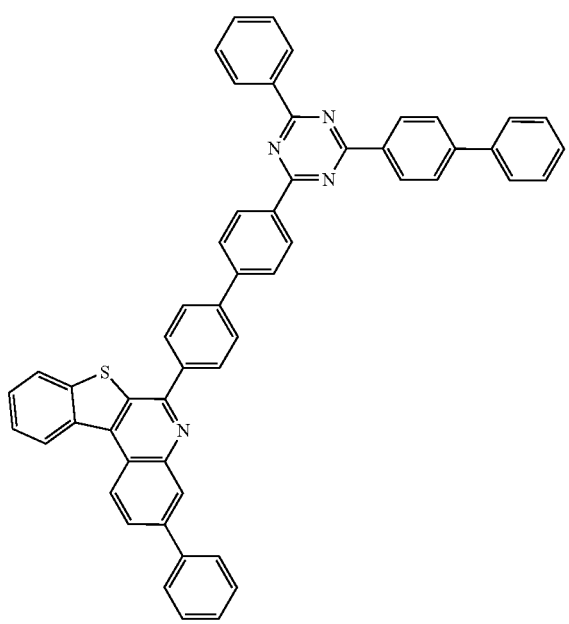
46
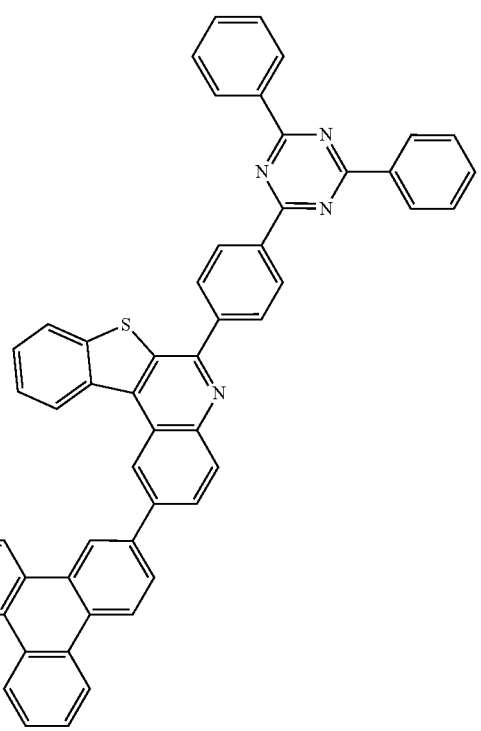

47
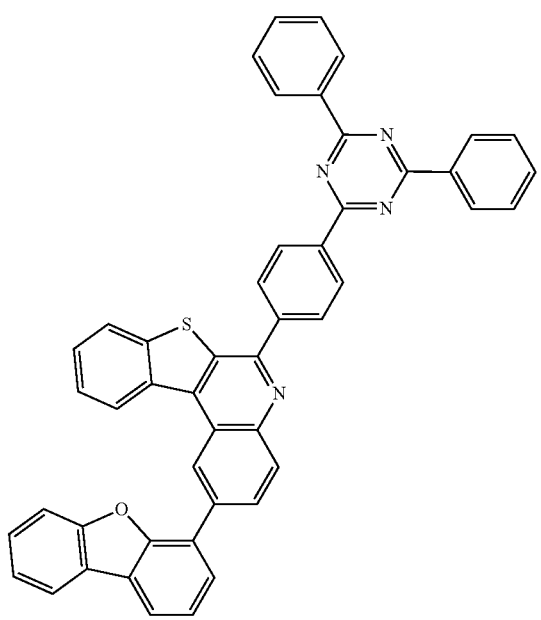
48
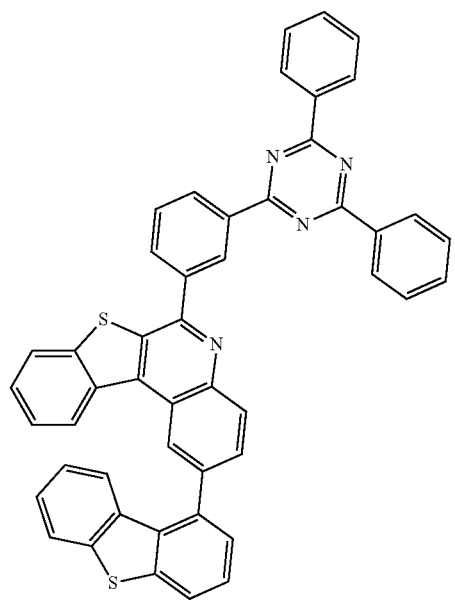
49
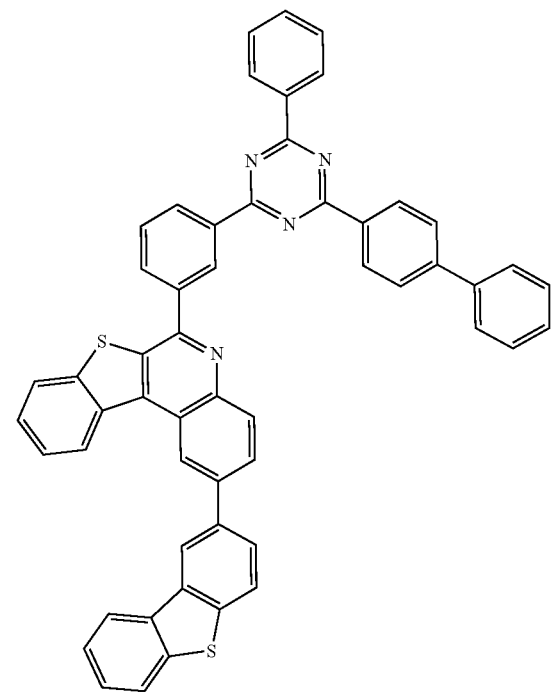
50
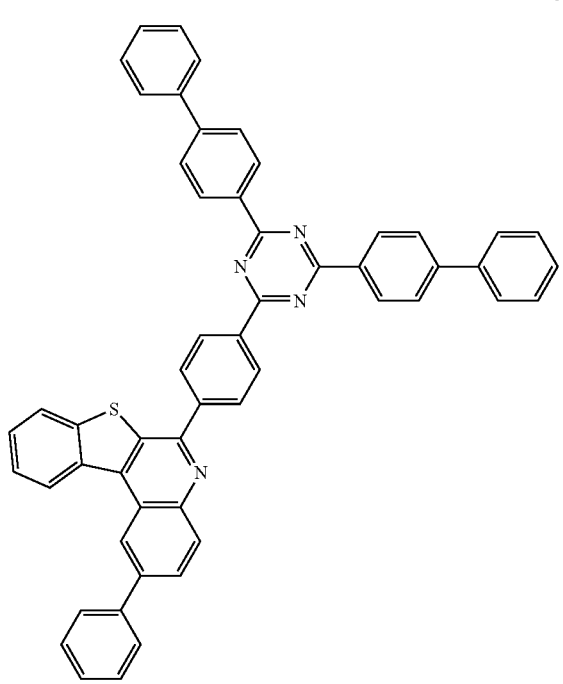

51
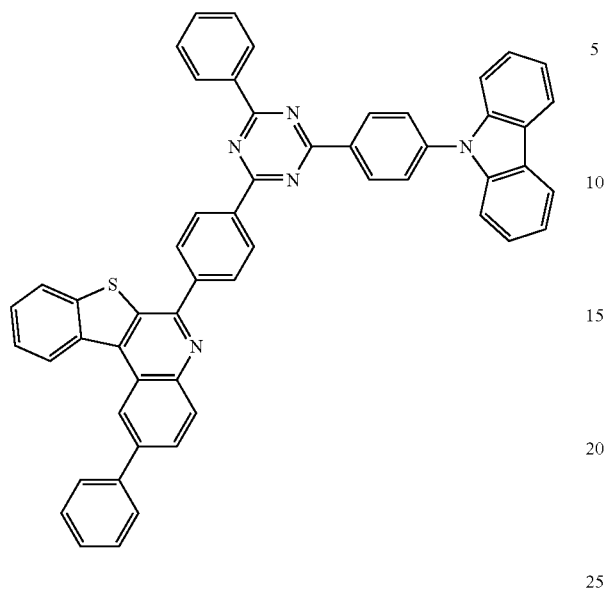
53
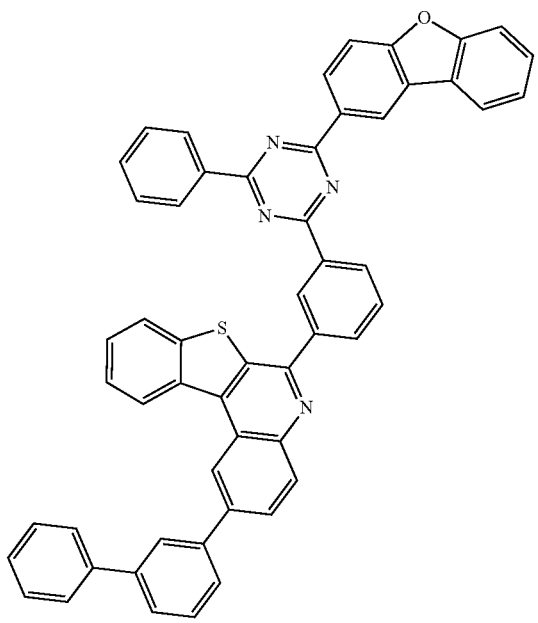
52
54
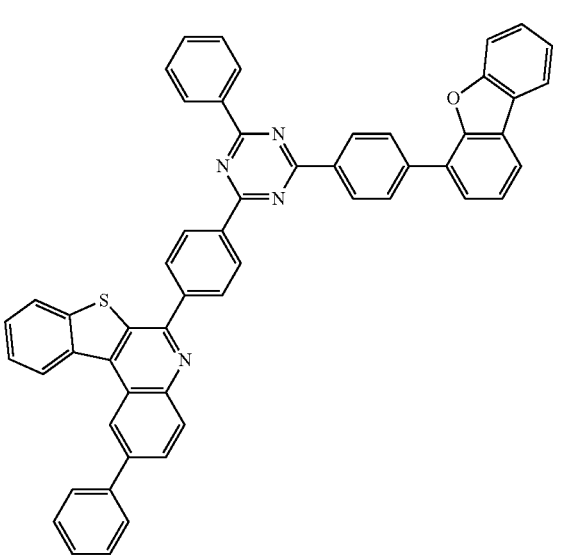

US 11,476,425 B2
41
-continued
55
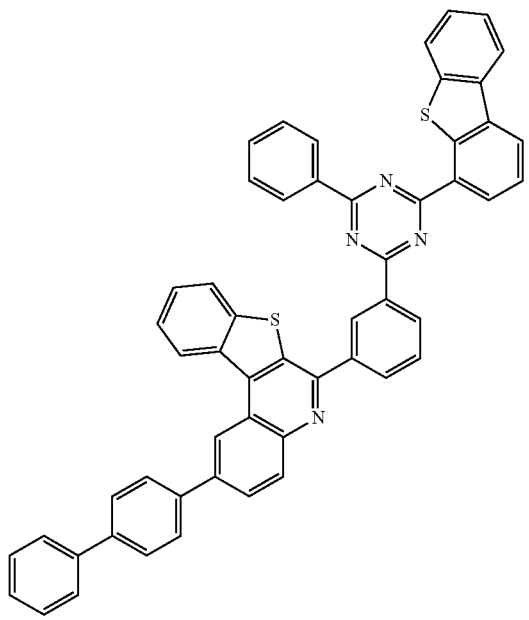
56
42
-continued
57
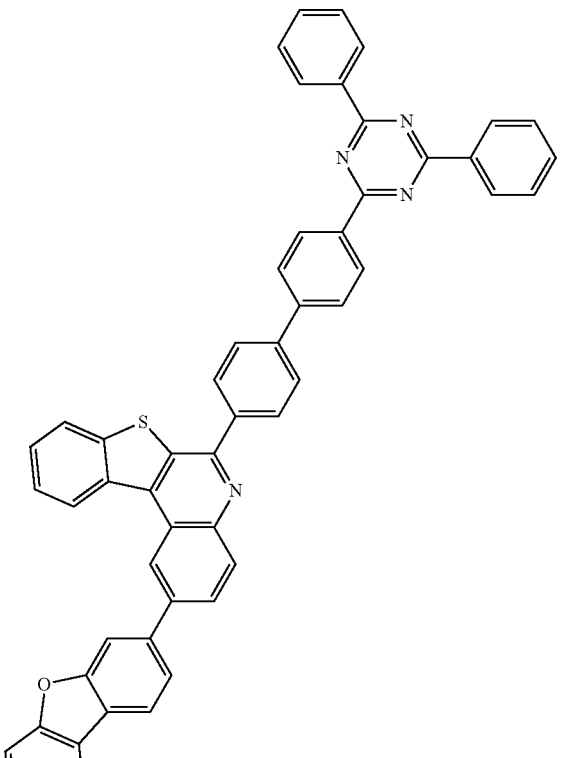
58

59
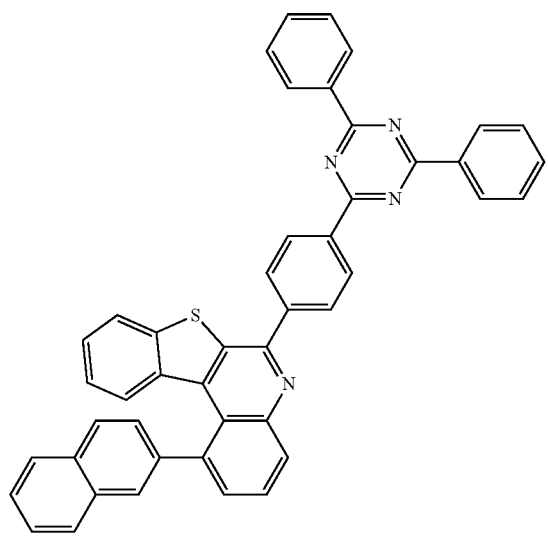
60
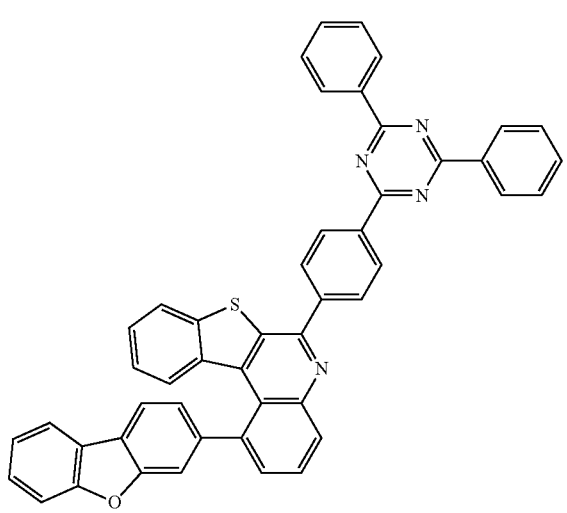
61
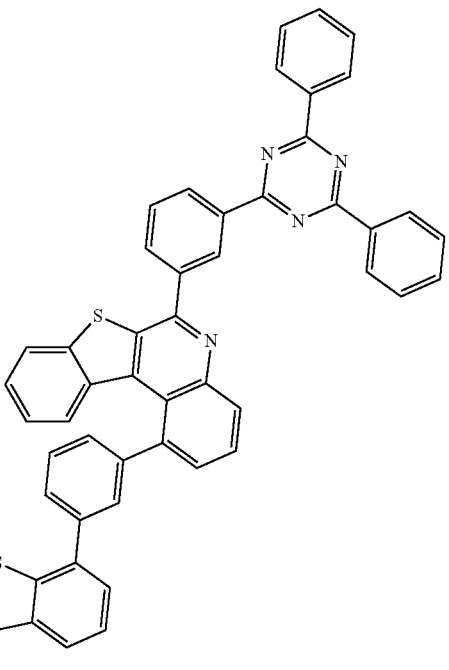
62
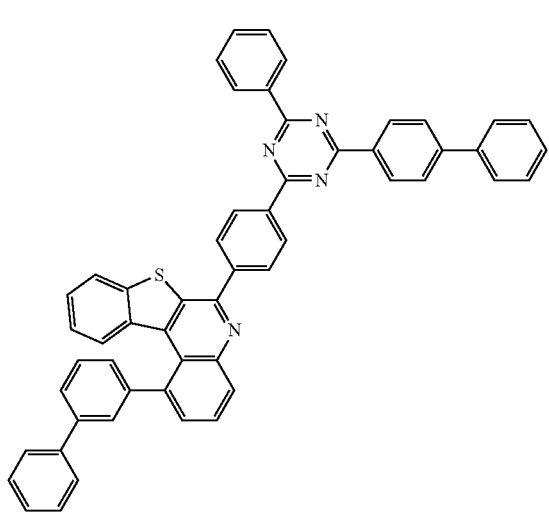

45
-continued
63
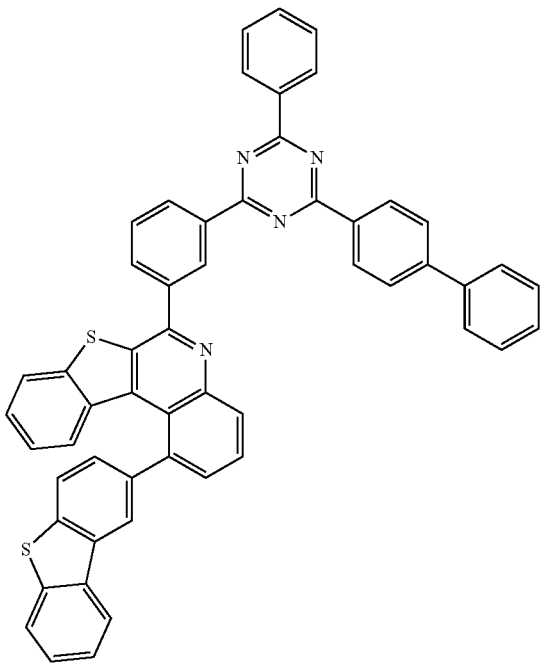
64
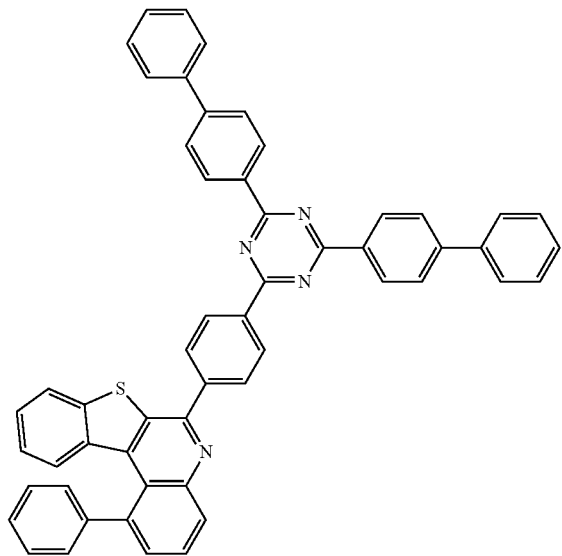
46
-continued
65
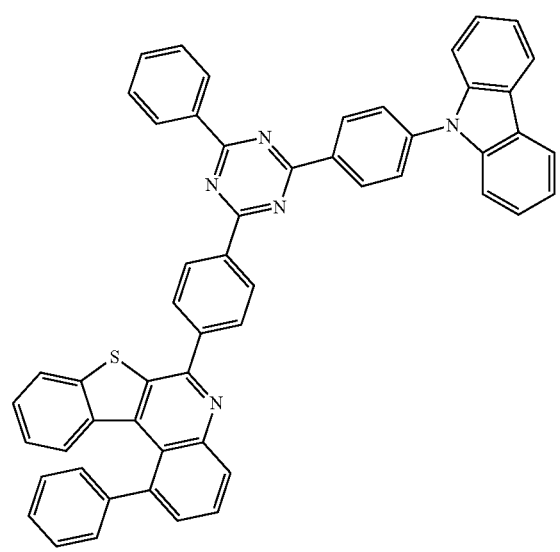
66

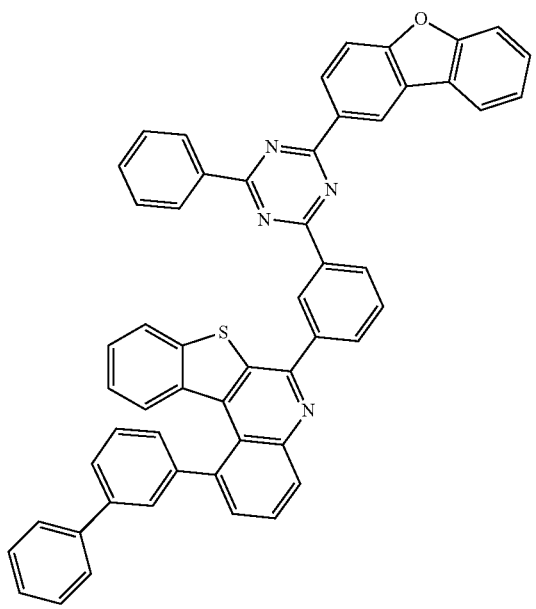
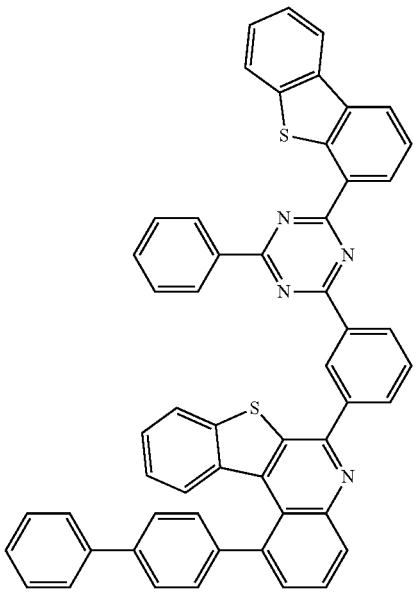
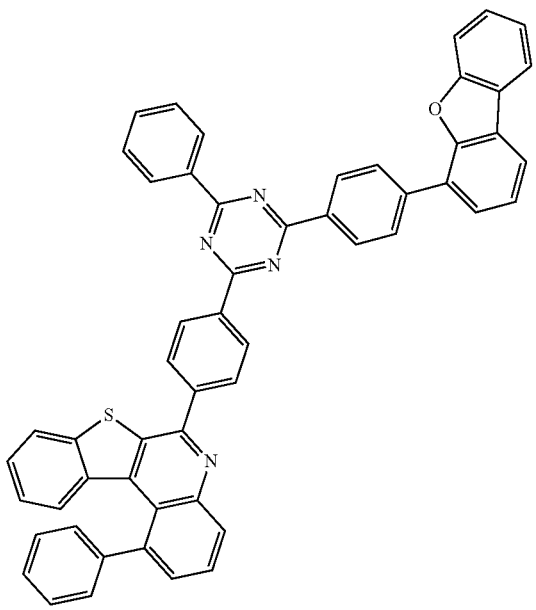
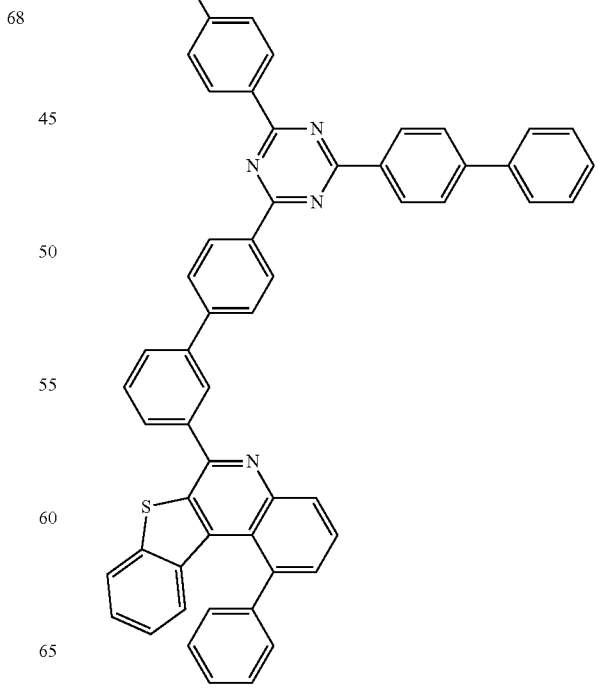

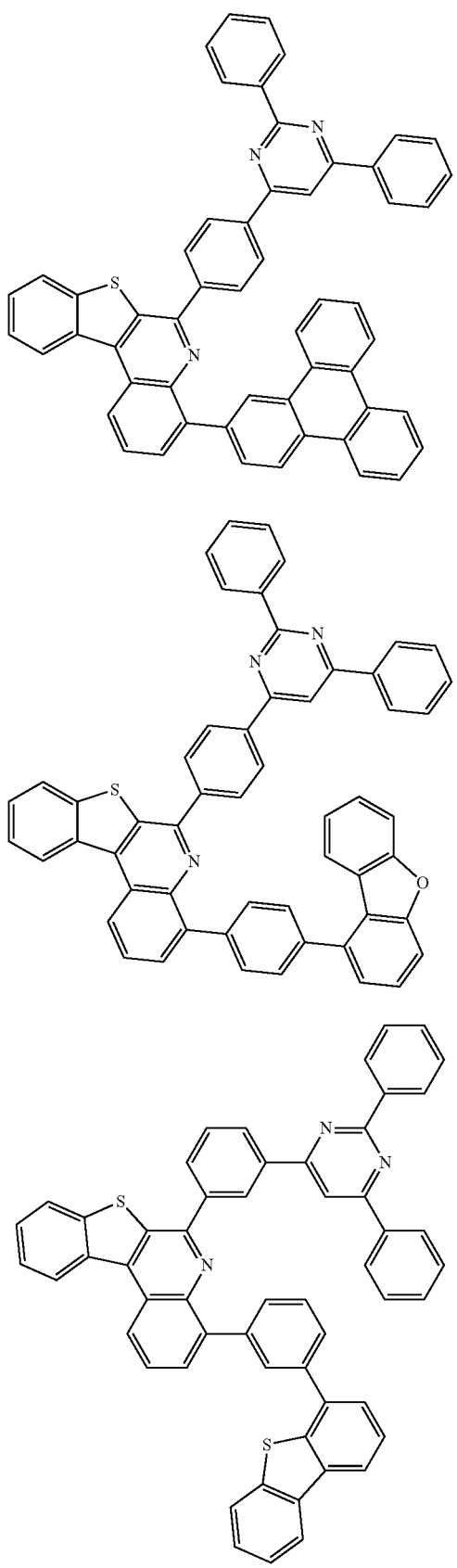
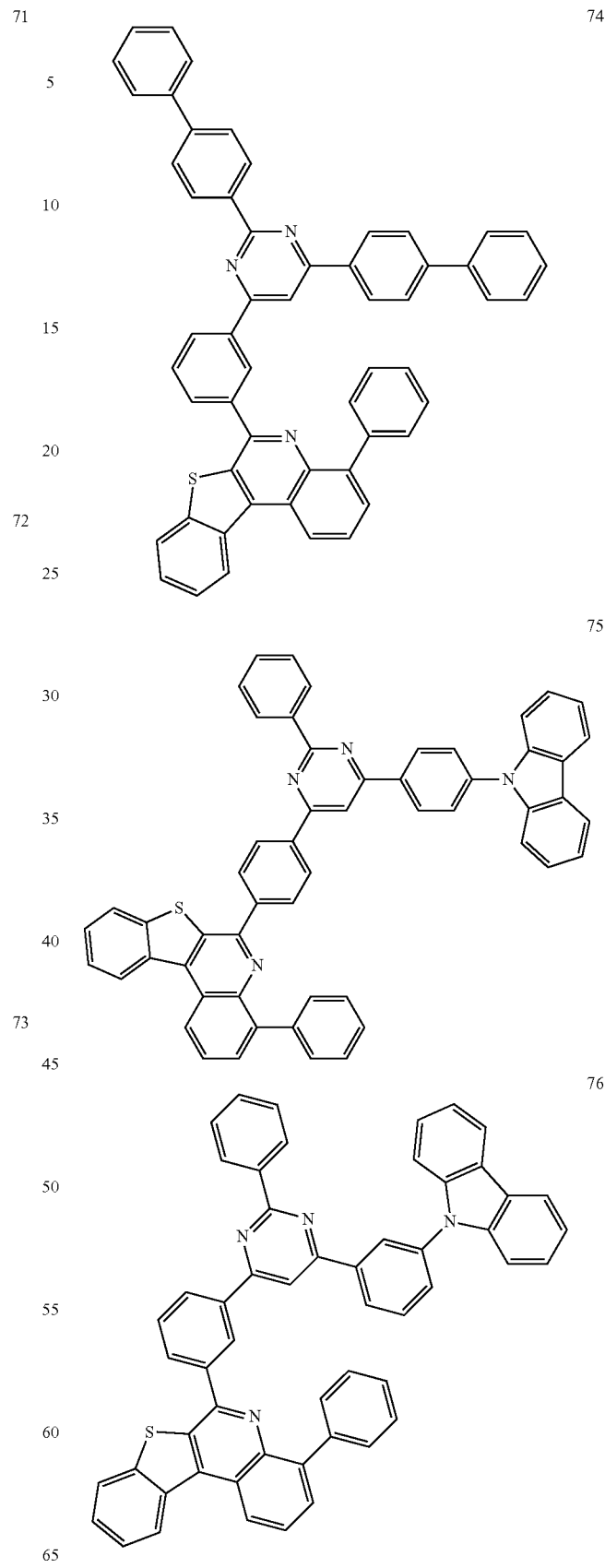

77
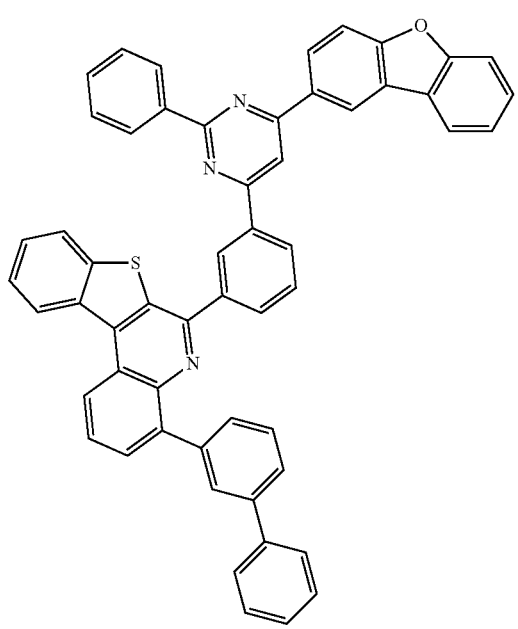
78
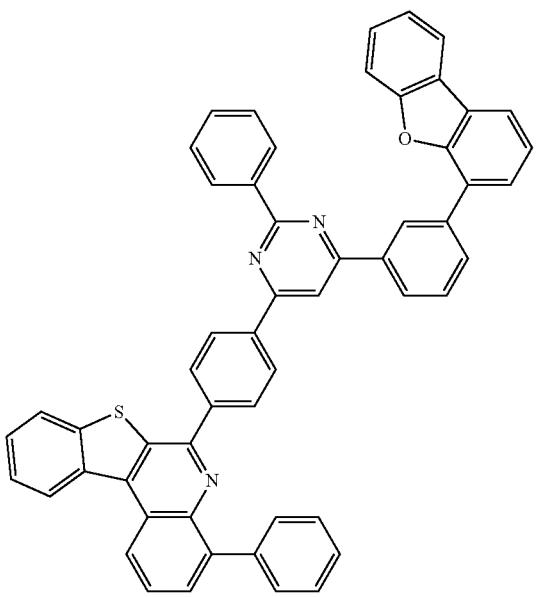
79
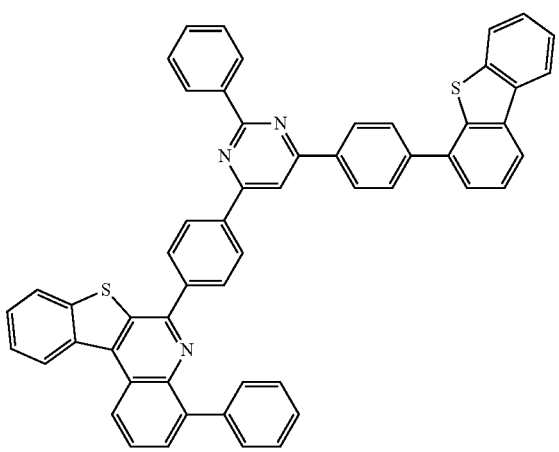
80
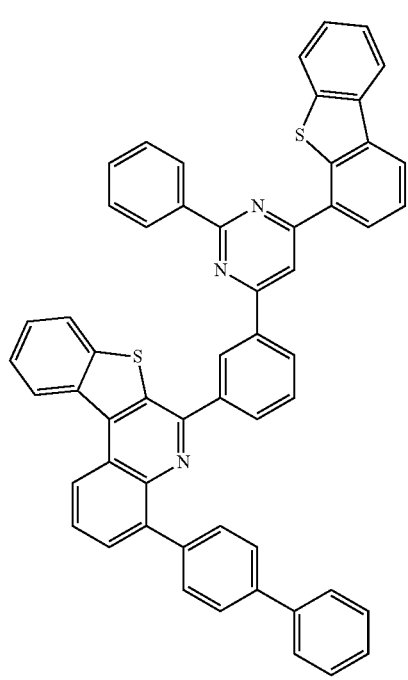

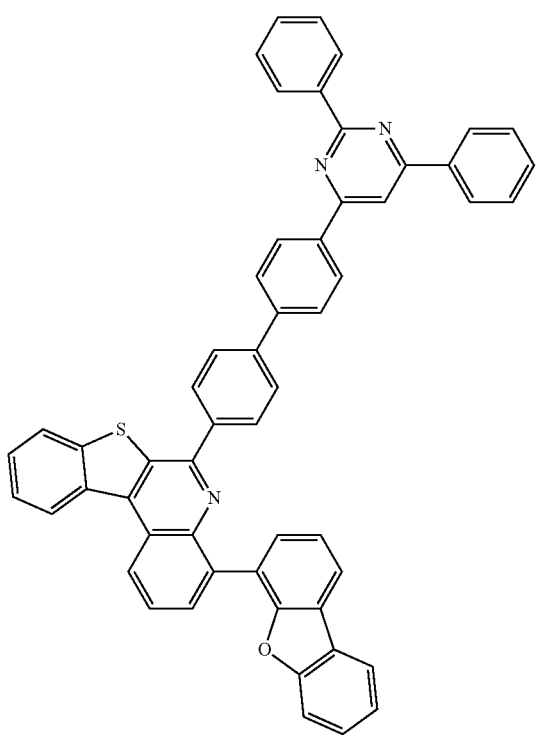
81
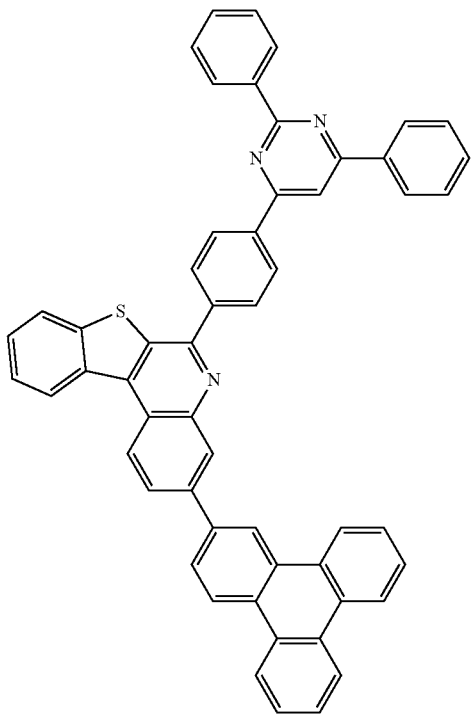
83
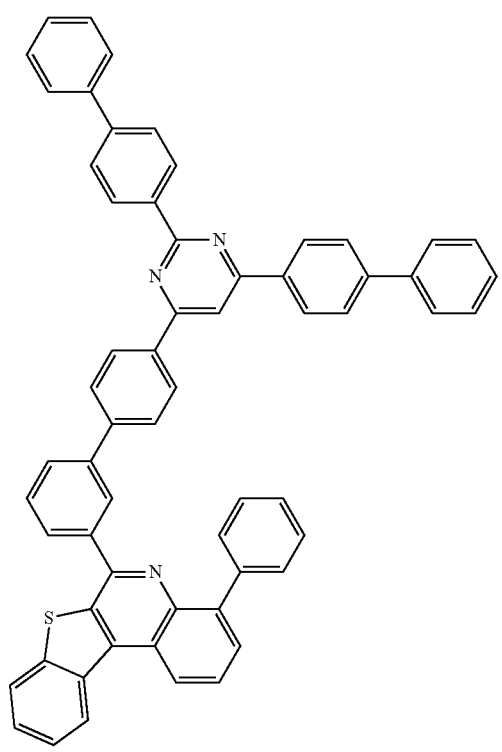
82
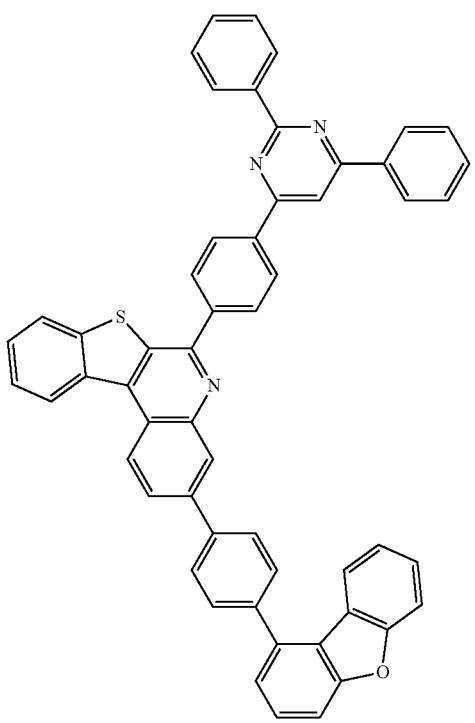
84

85
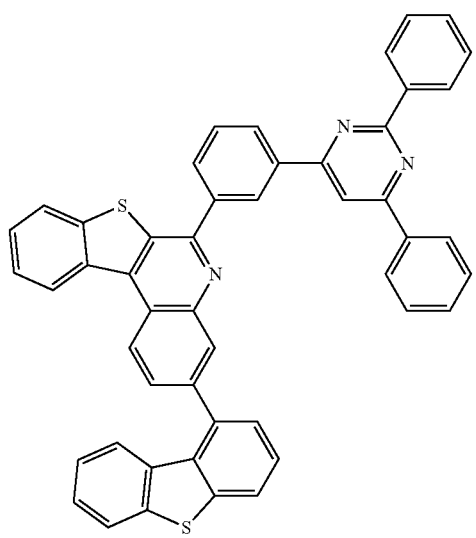
86
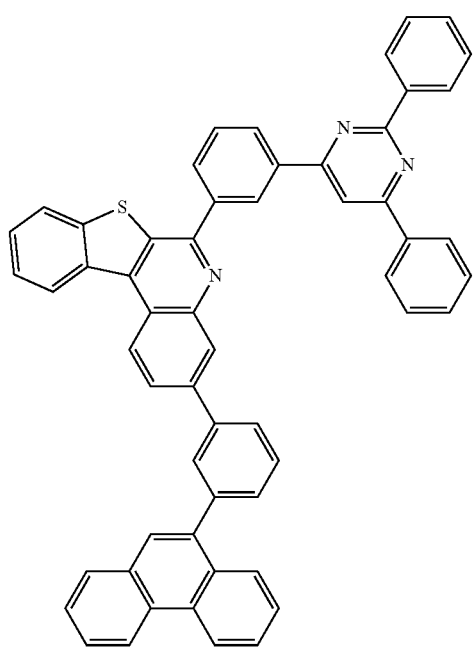
87
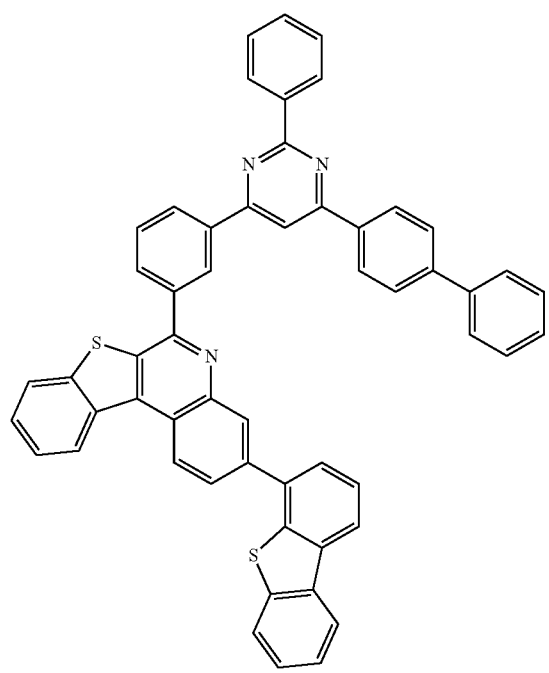
88
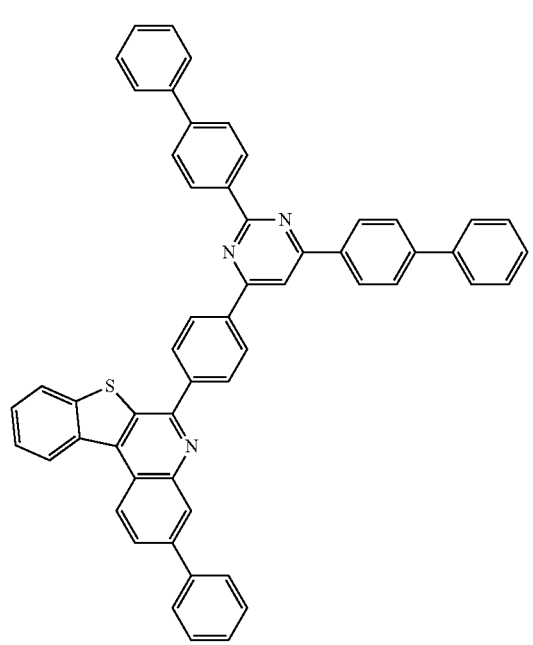

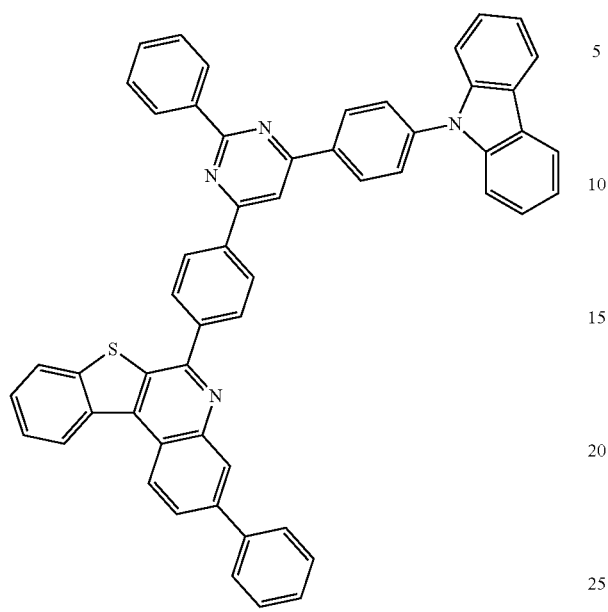
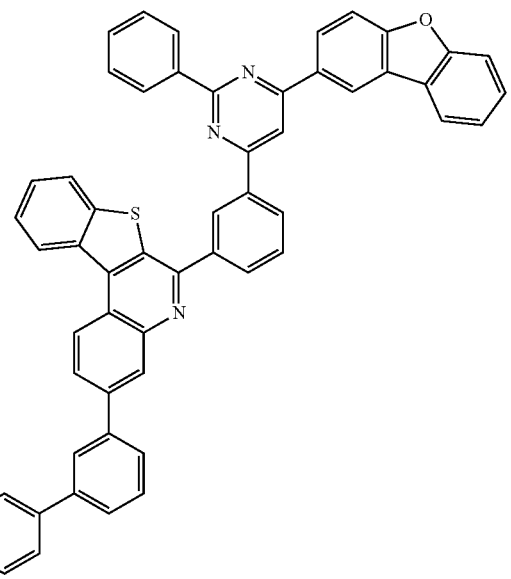
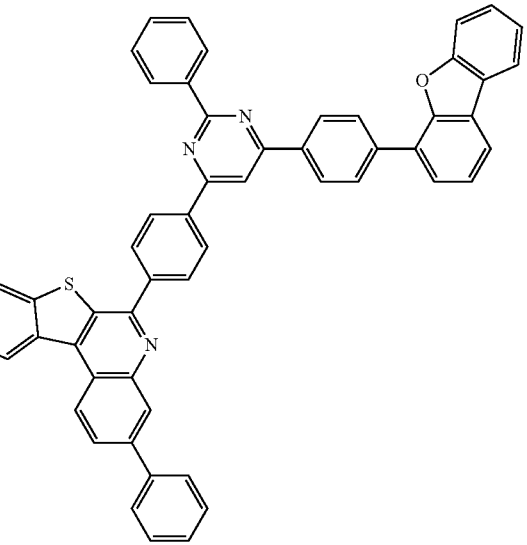

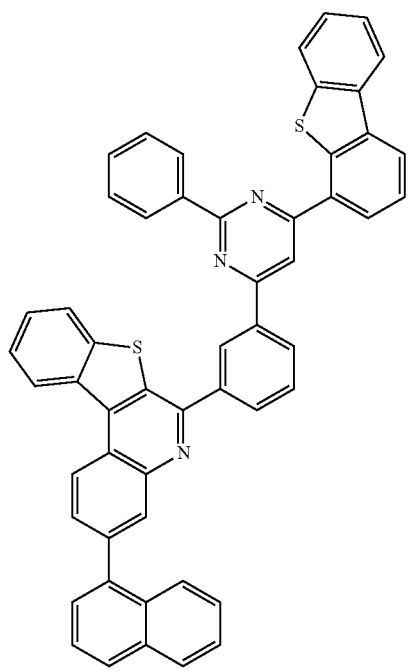
93
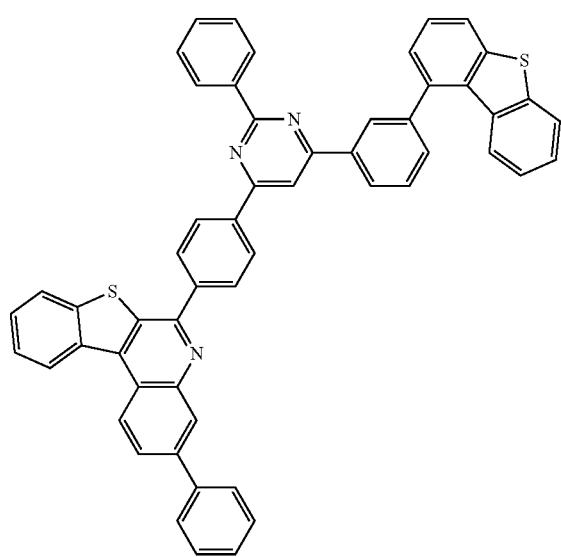
94
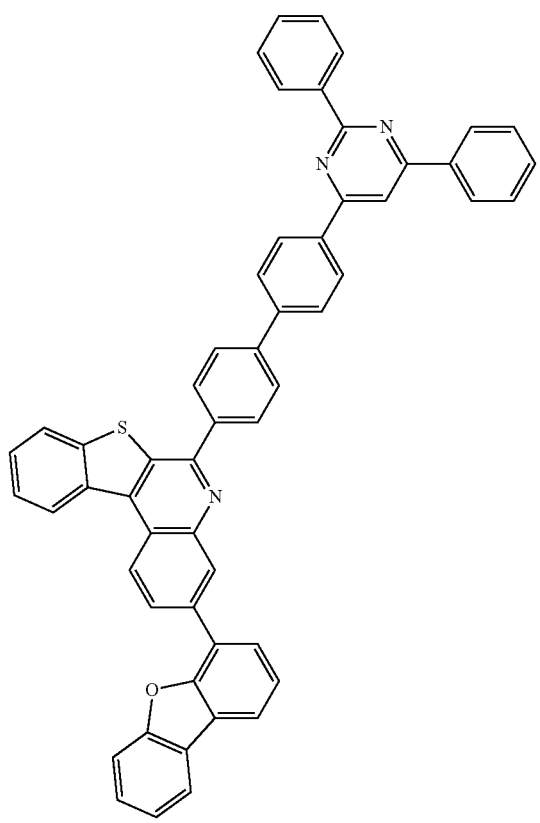
95
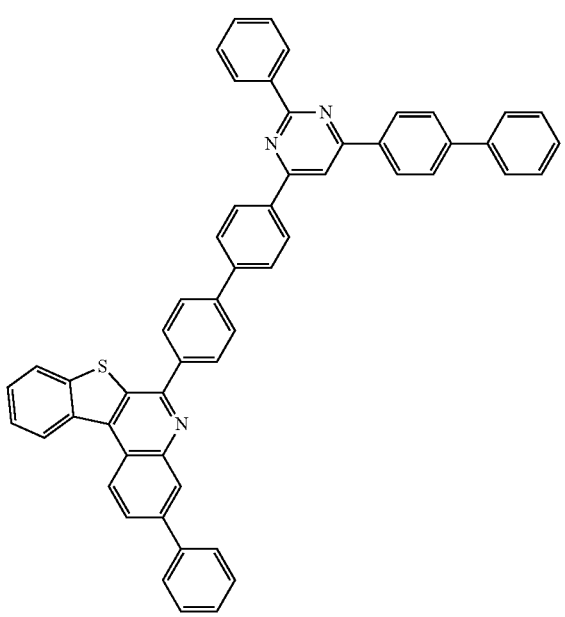
96

97
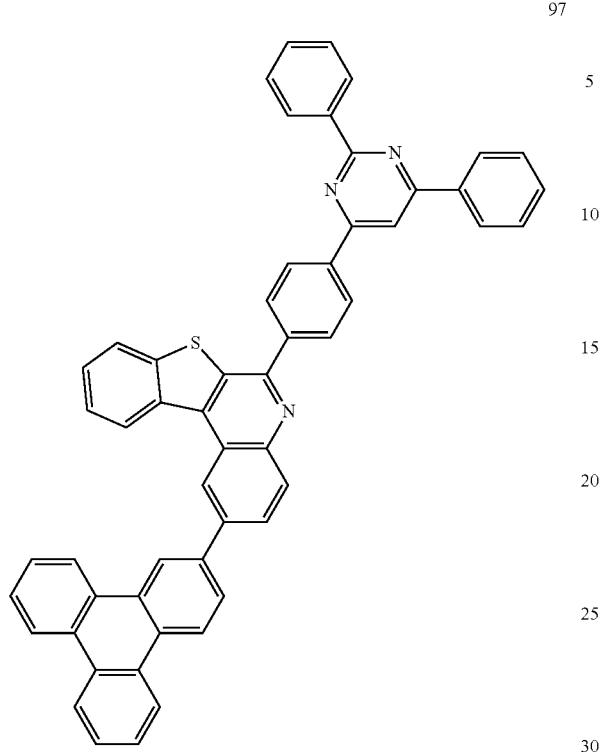
98
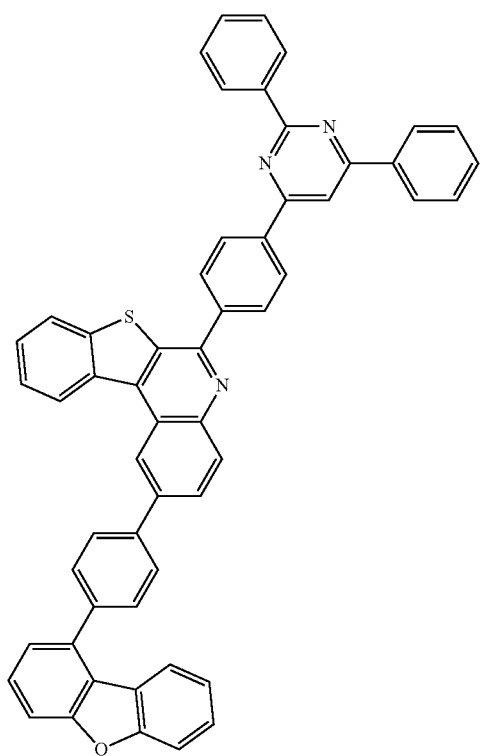
99
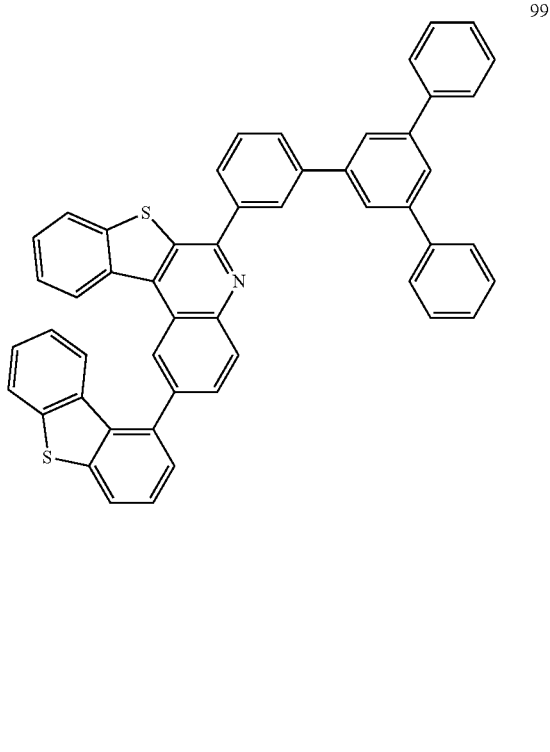
100
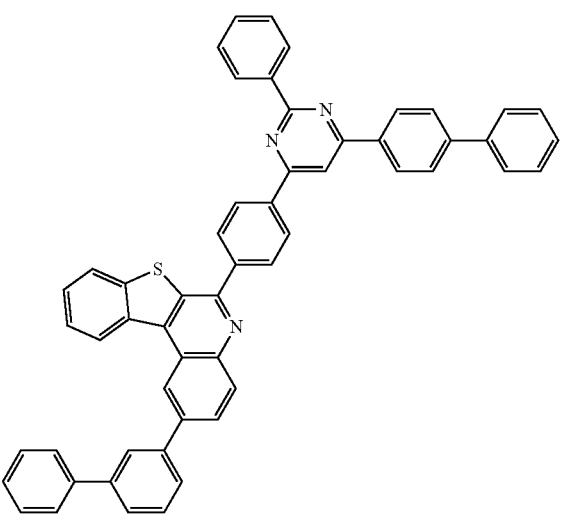

-continued
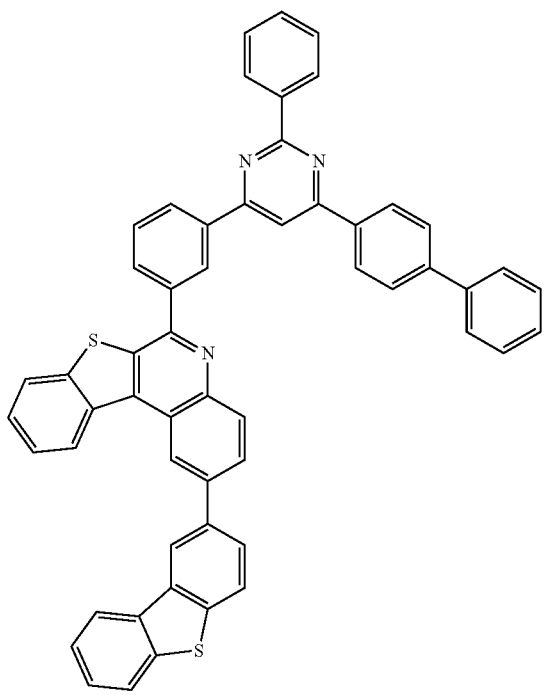
101
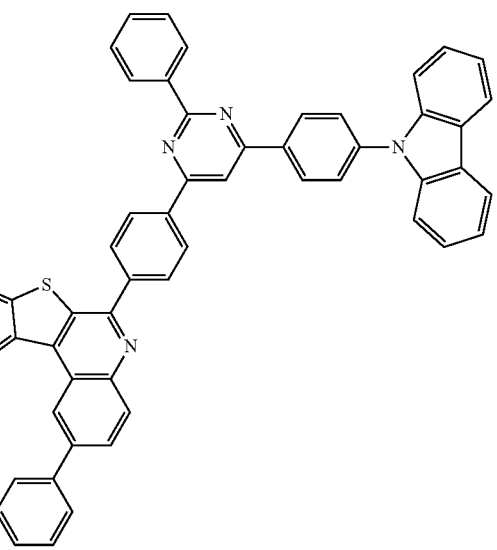
103
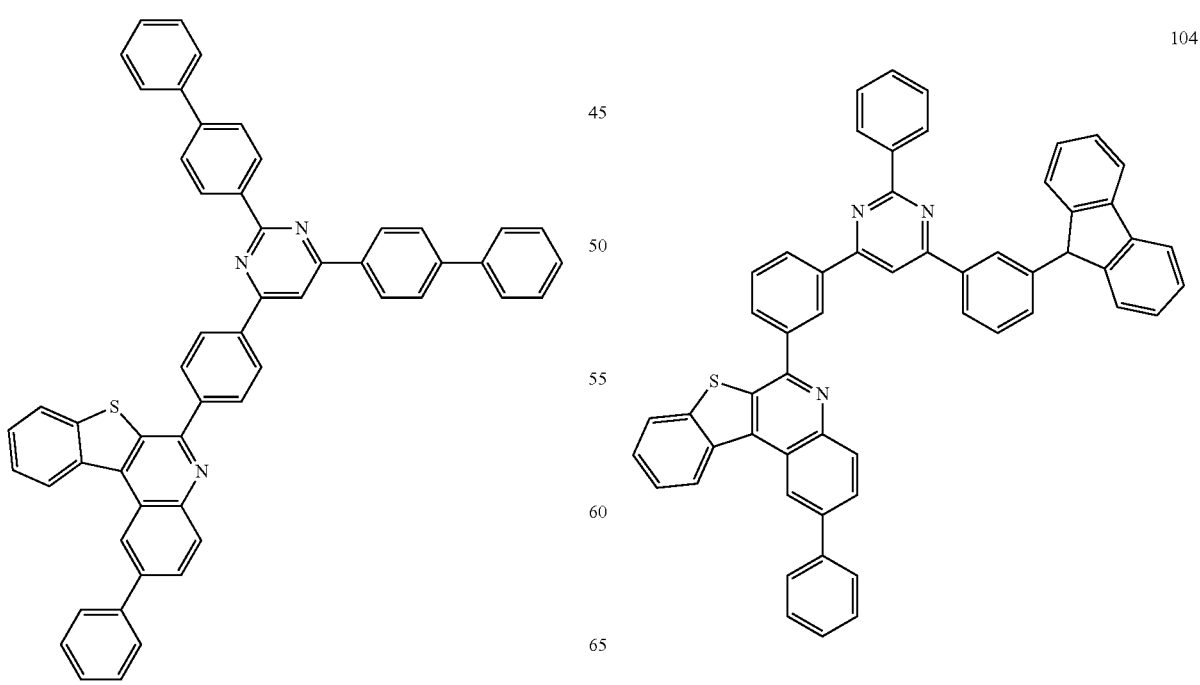
102
104

-continued
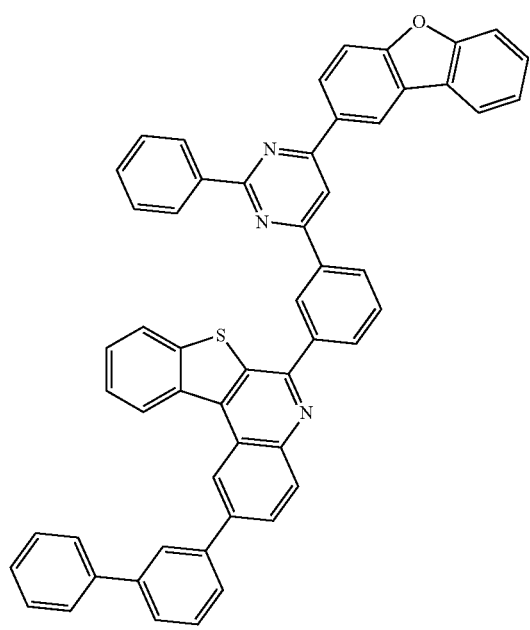
105
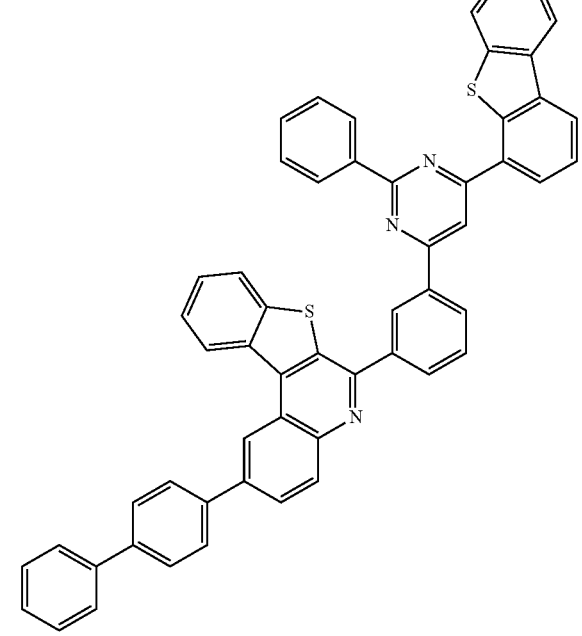
107
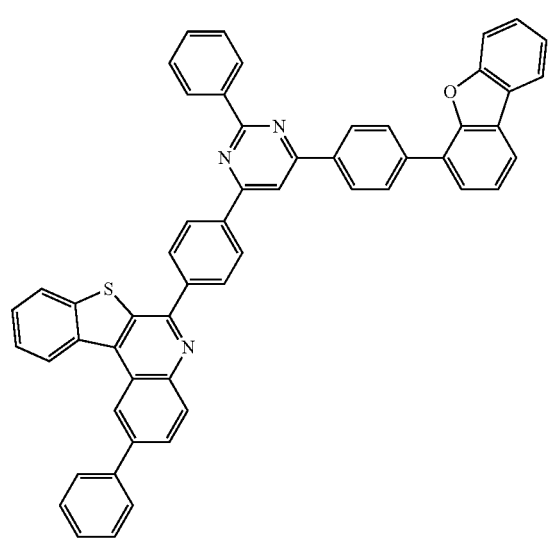
106
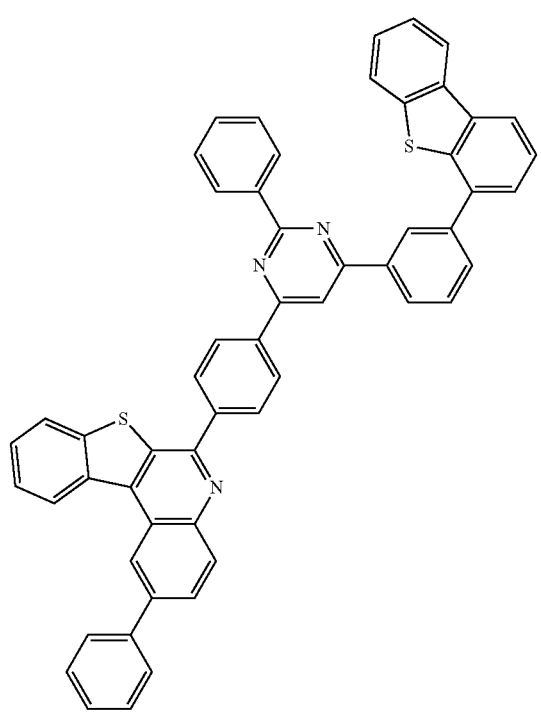
108

109
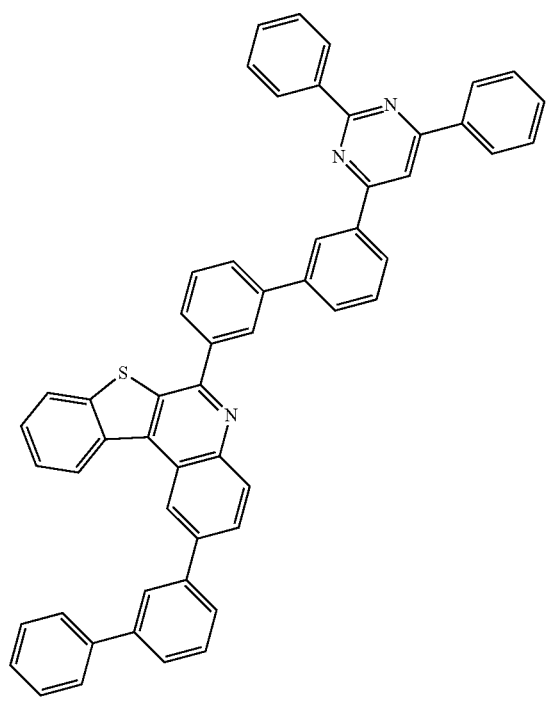
111
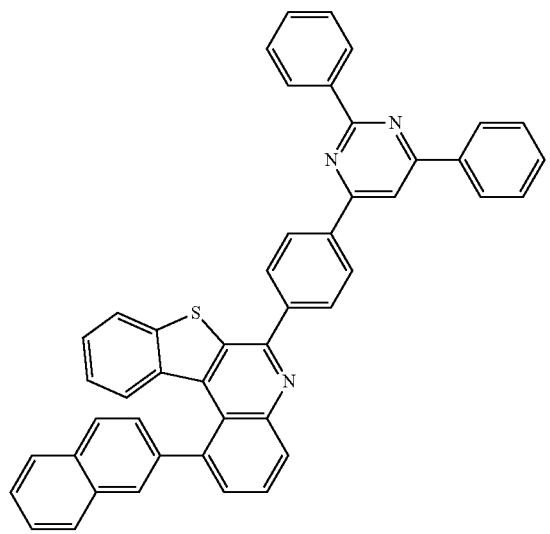
110
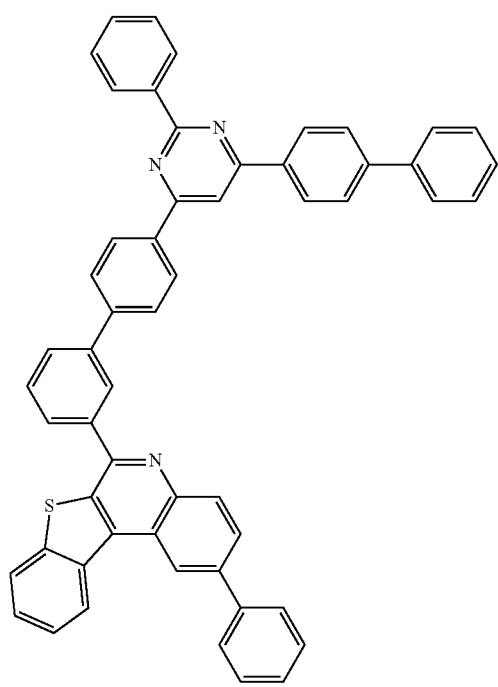
112
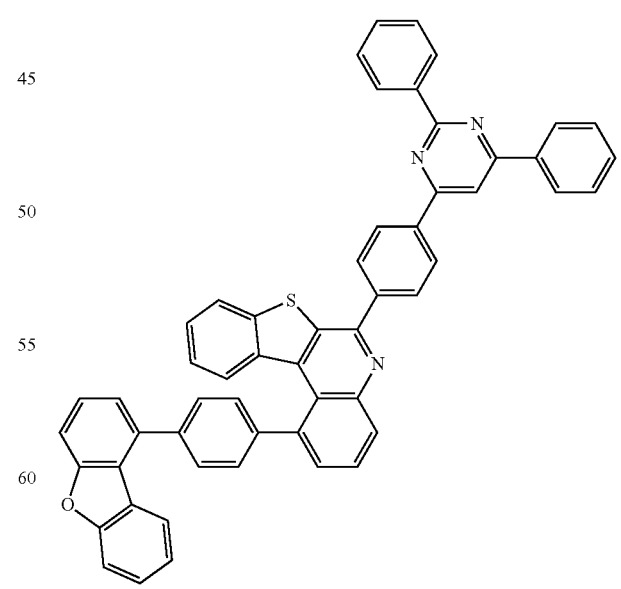

113
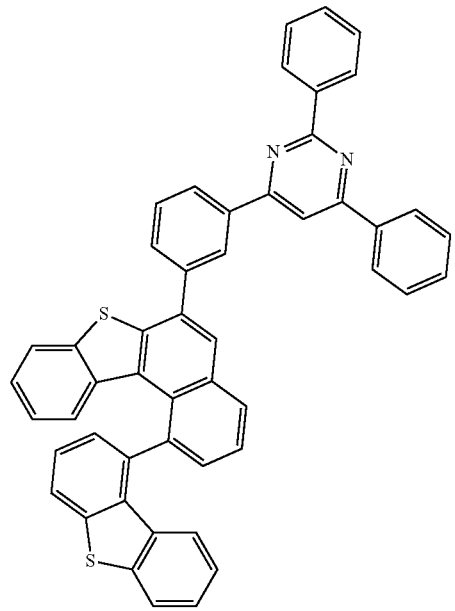
115
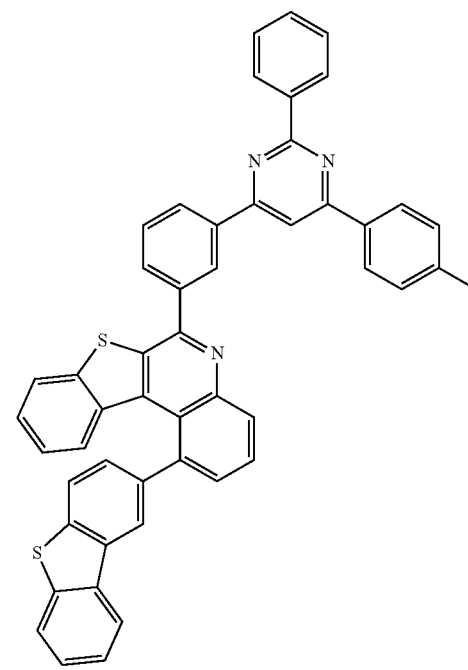
114
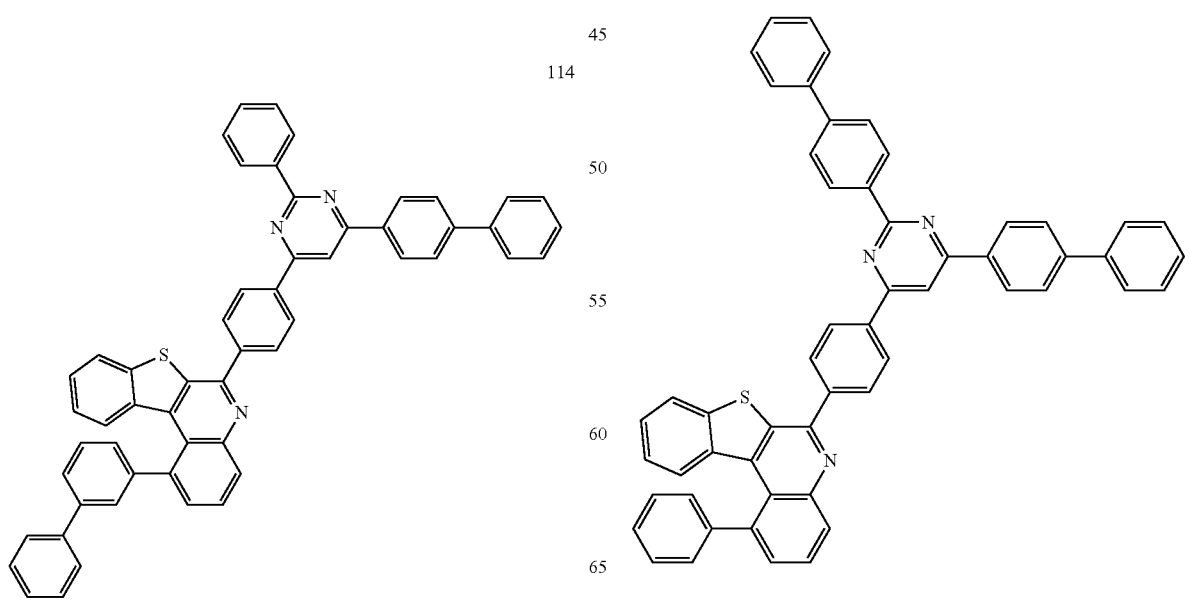
116

71
-continued
117
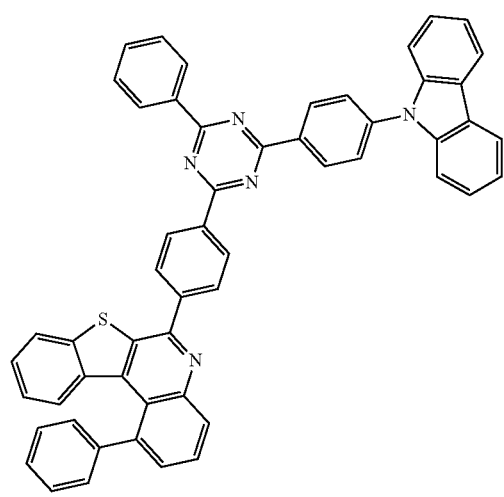
118
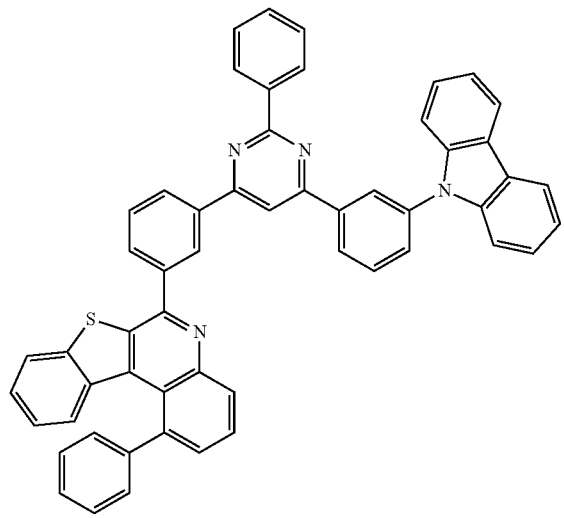
72
-continued
119
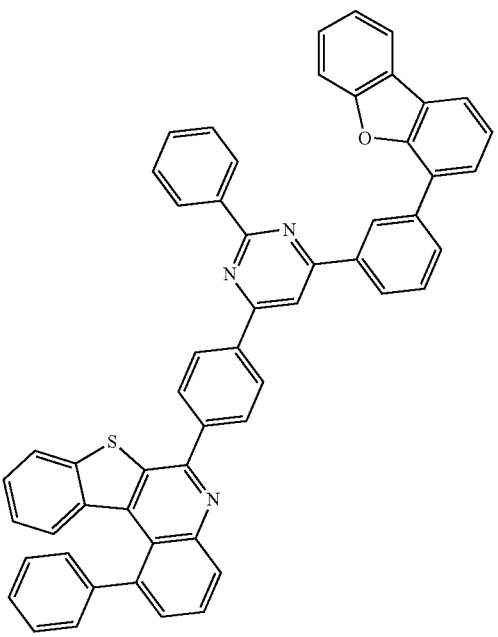
120
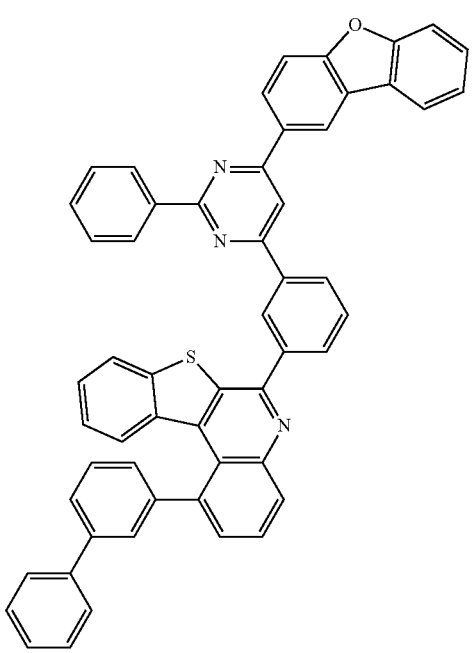

121
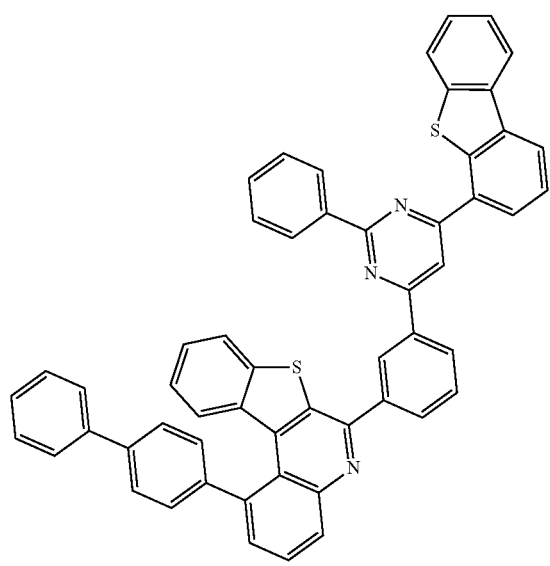
122
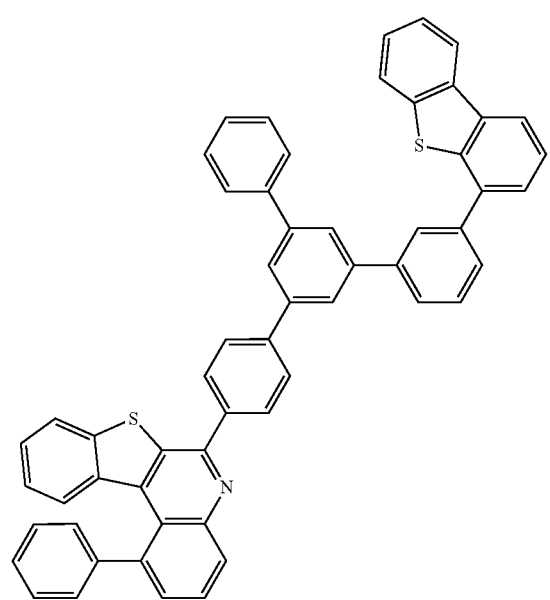
123
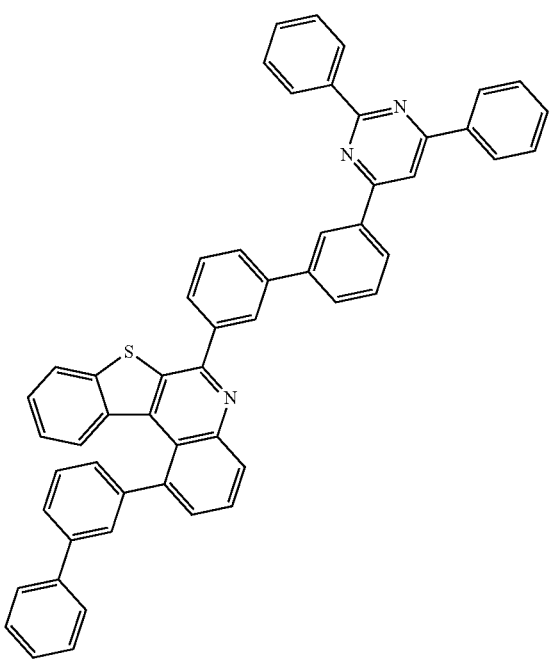
124
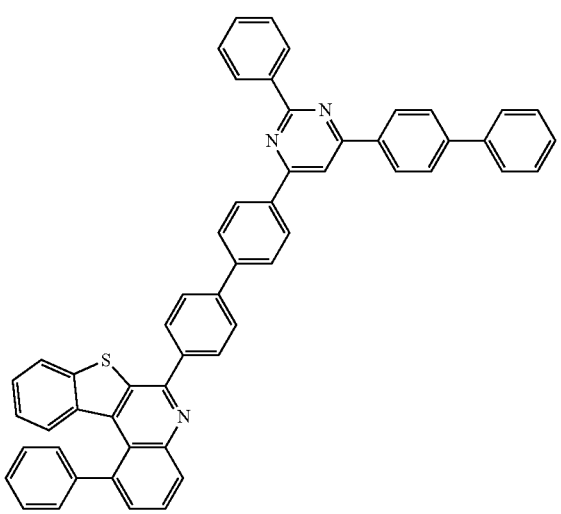

125
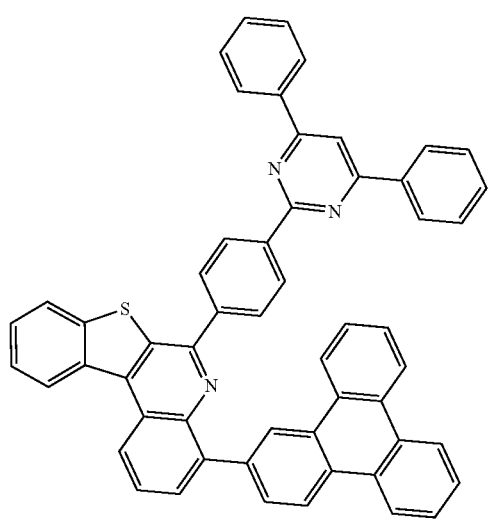
126
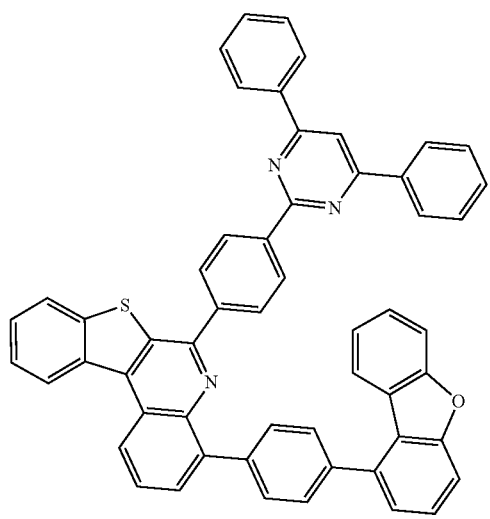
127
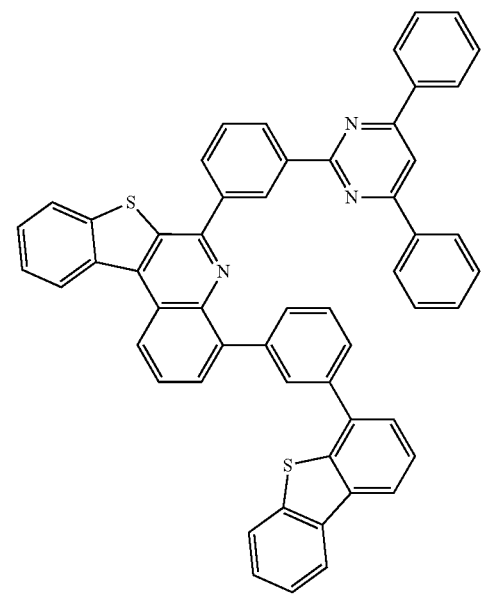
128
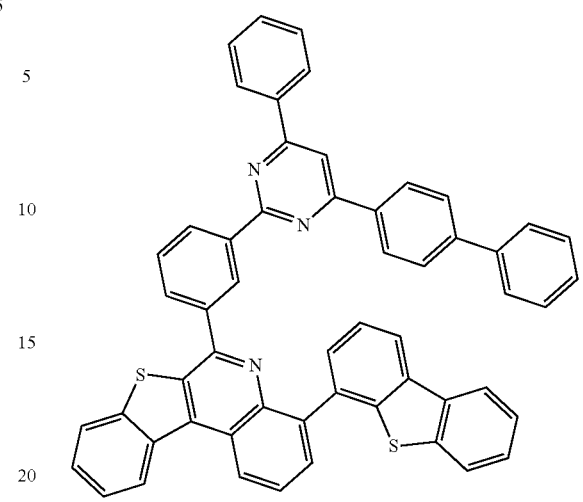
129
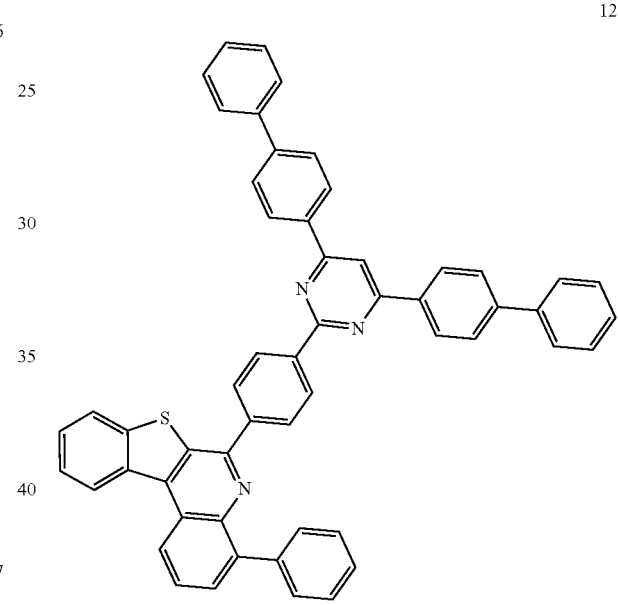
130

131
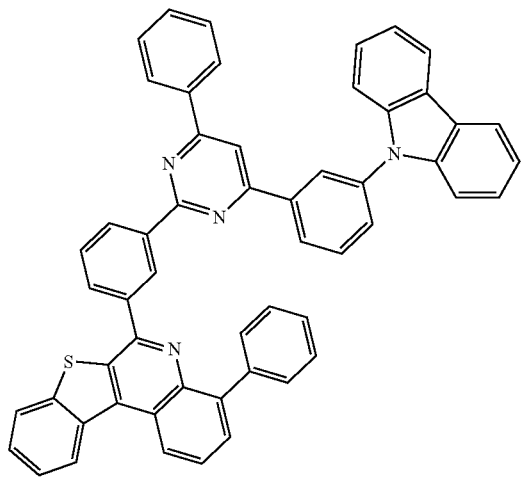
132
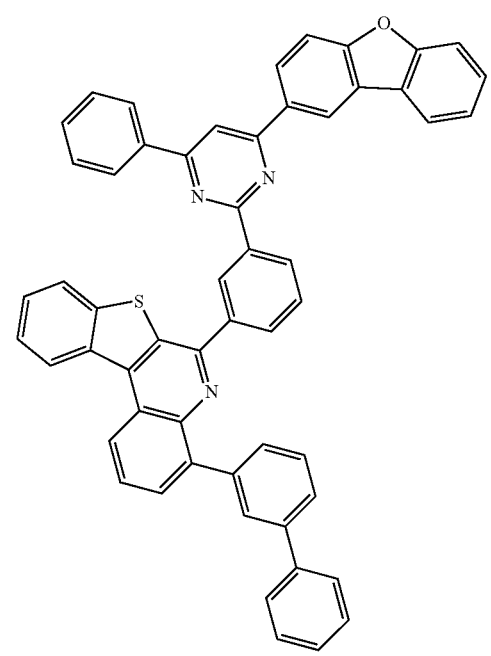
133
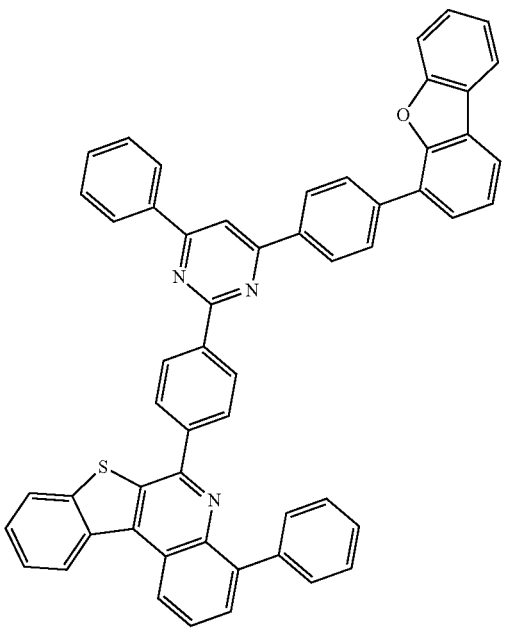
134
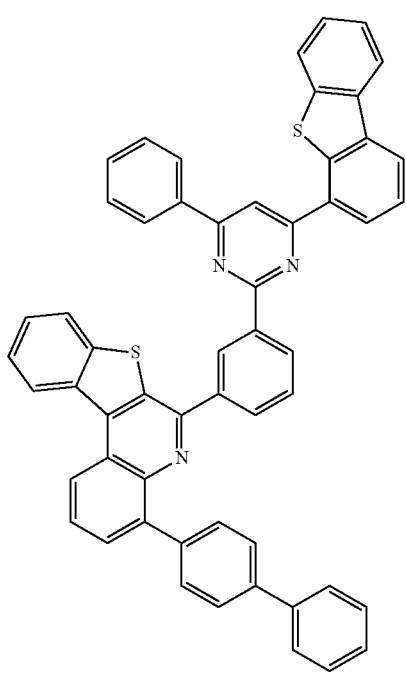

135
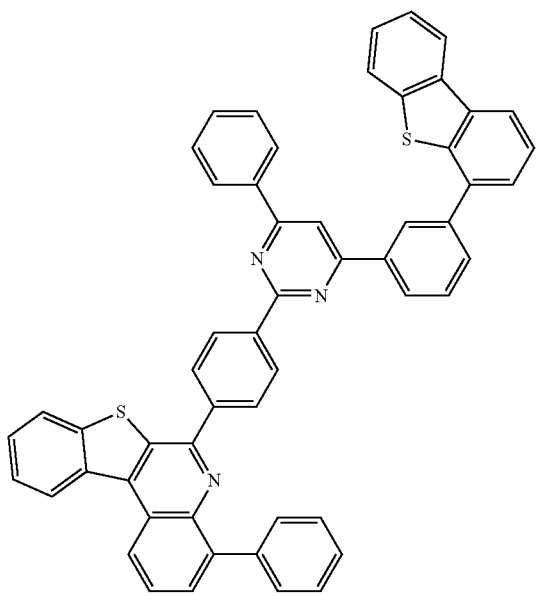
136
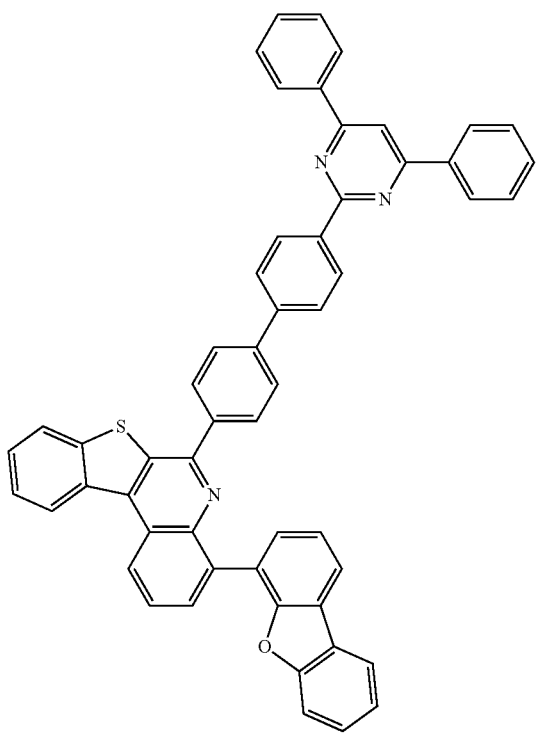
137
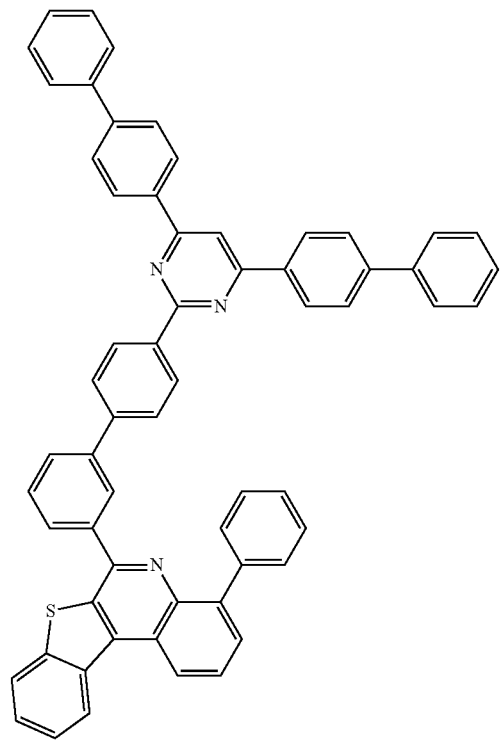
138
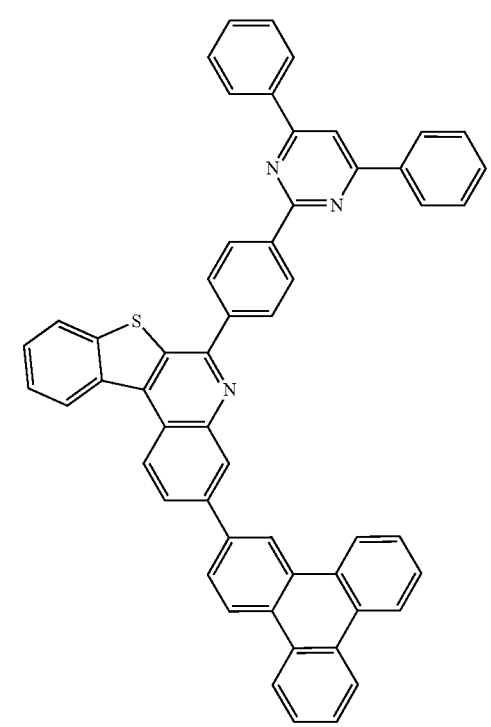

139
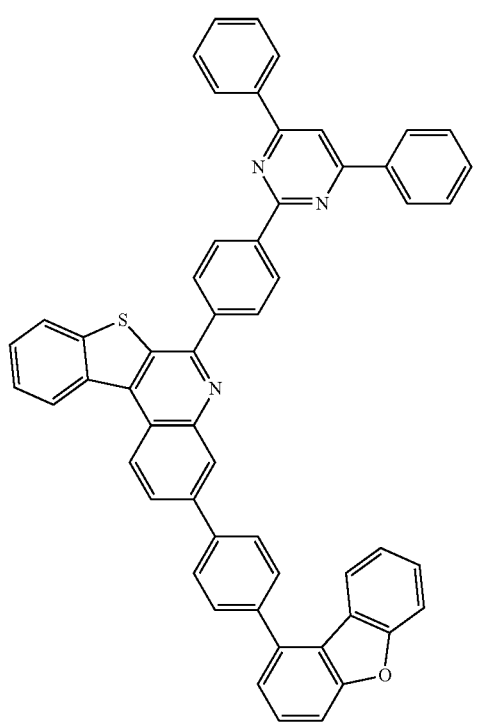
140
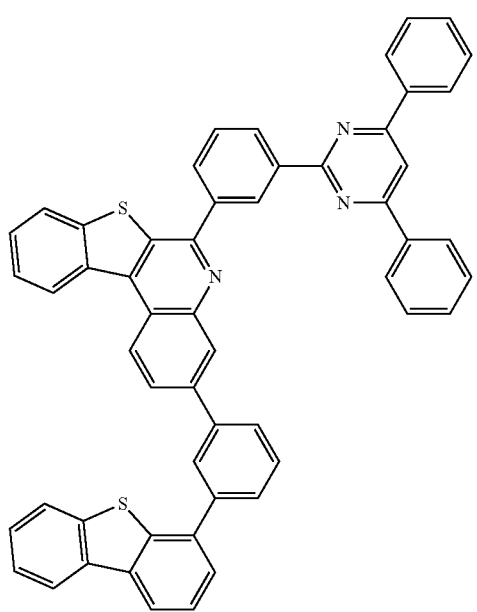
141
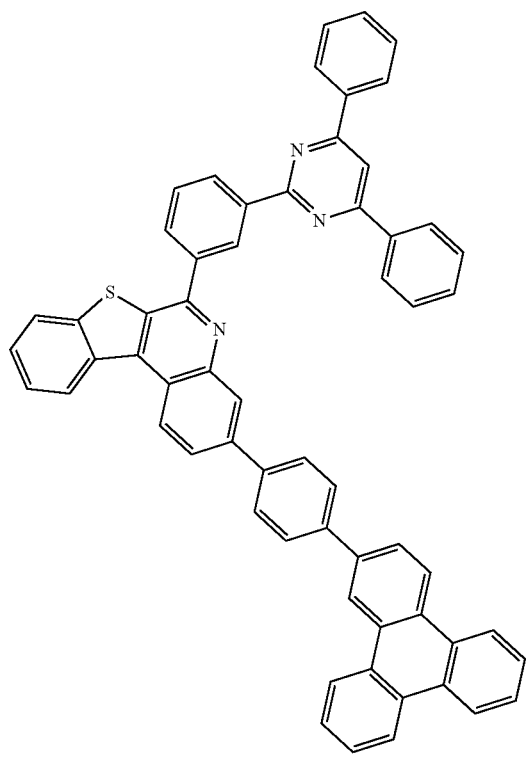
142
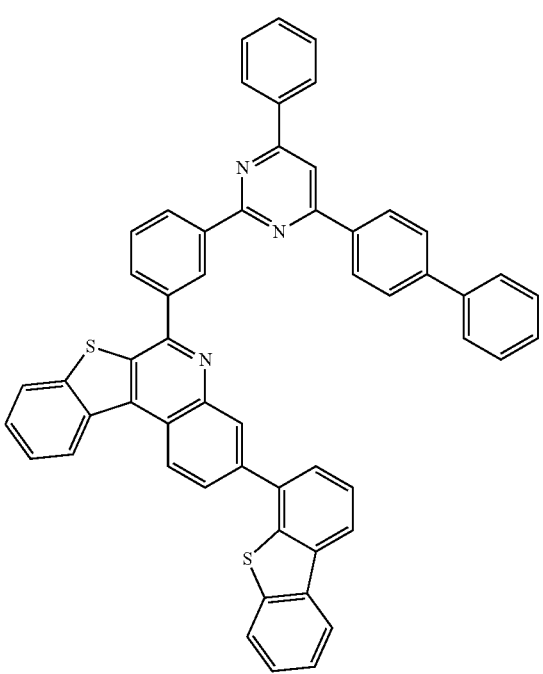

143
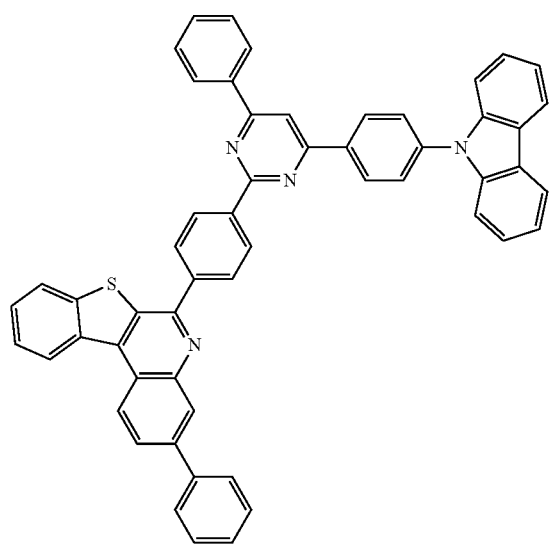
144
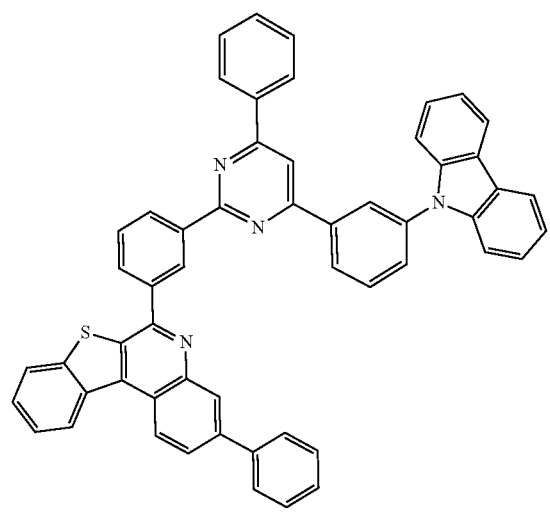
145
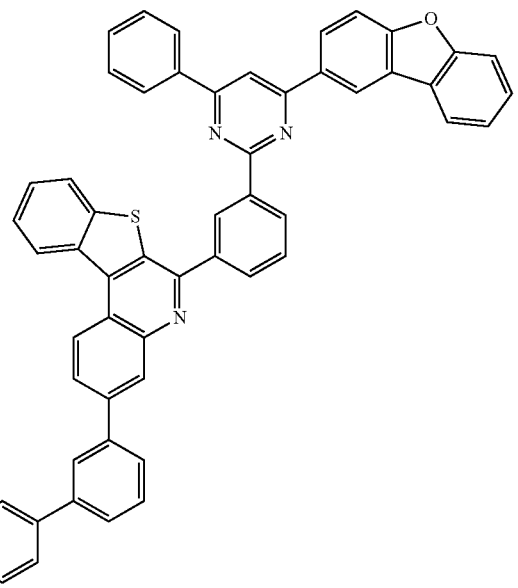
146
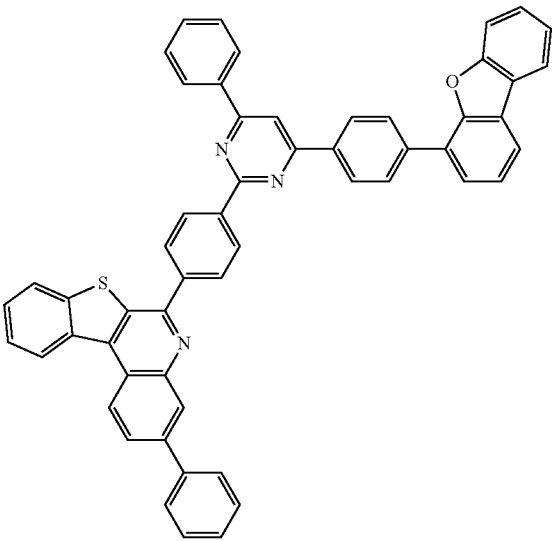

147
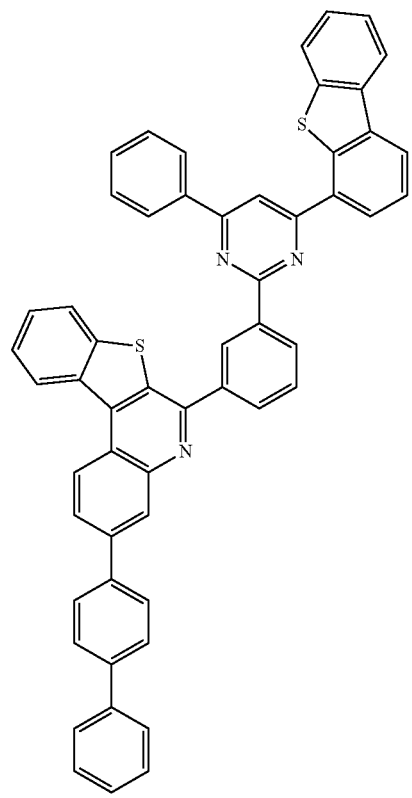
148
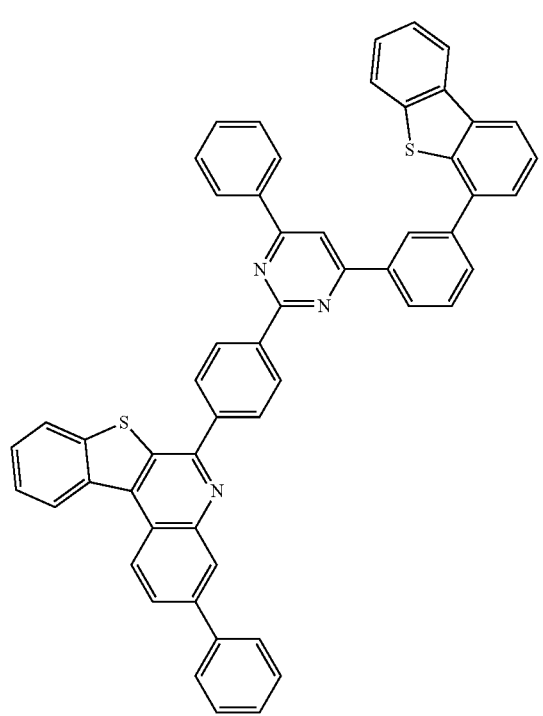
149
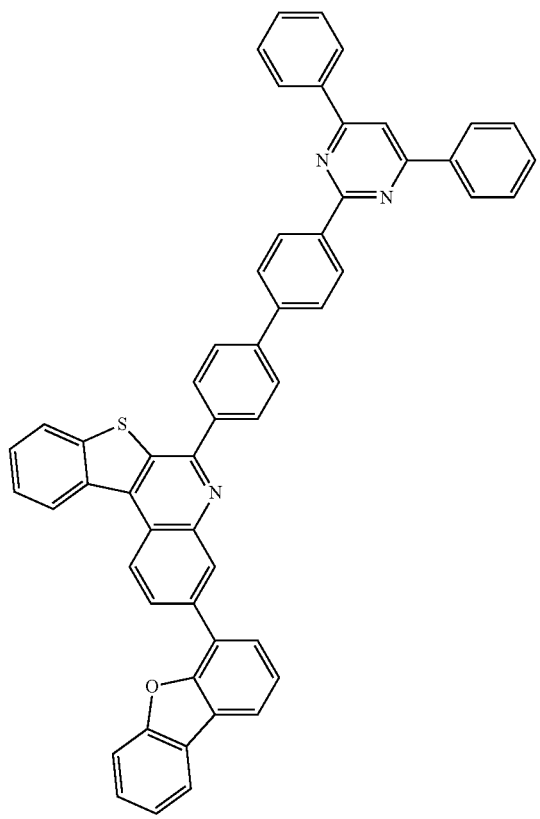
150
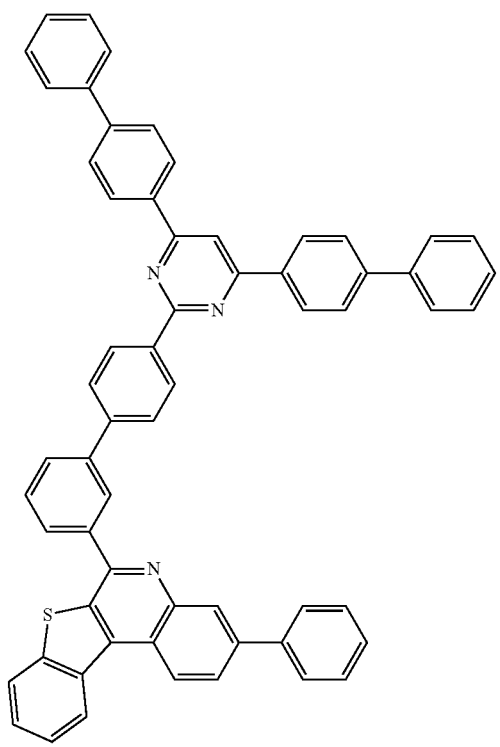

151
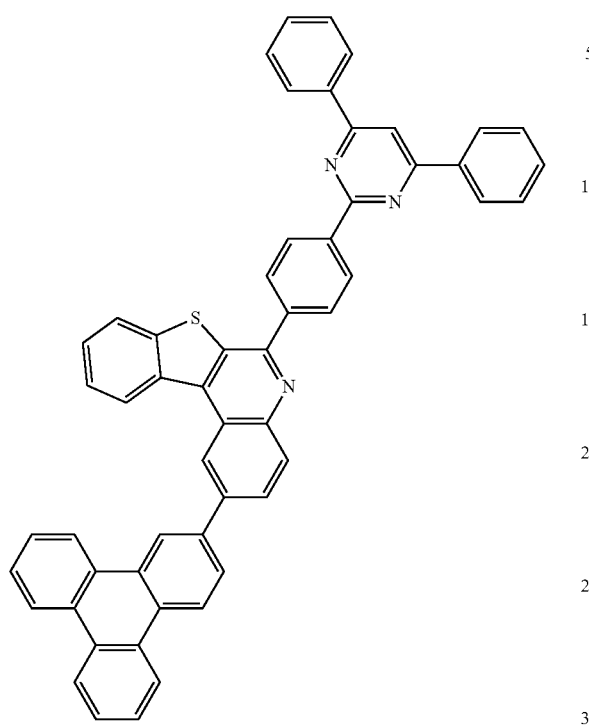
152
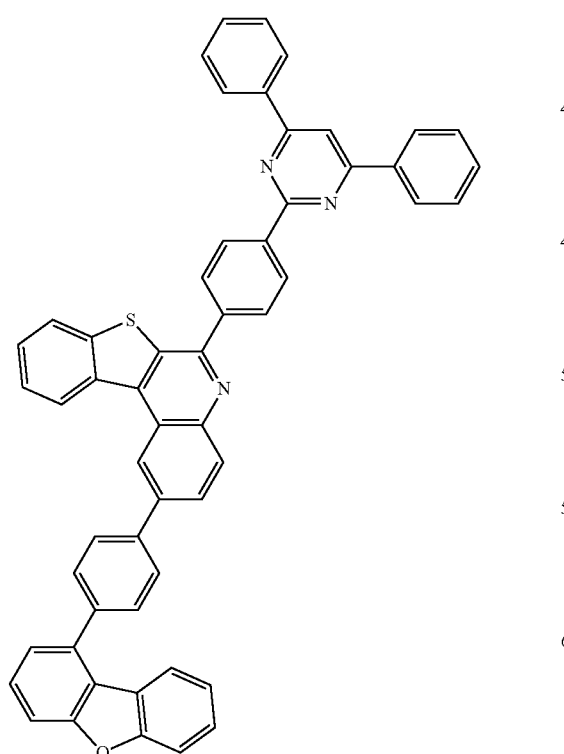
153
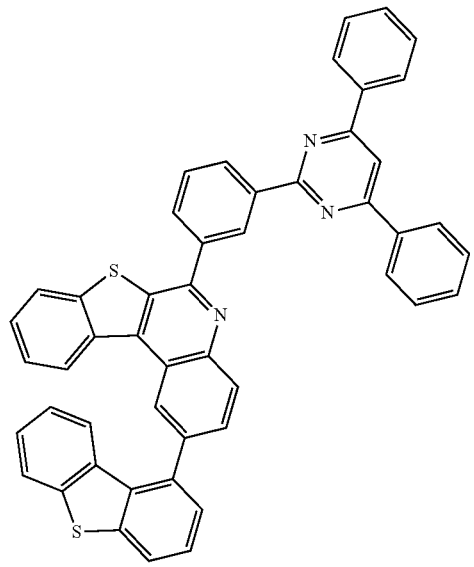
154
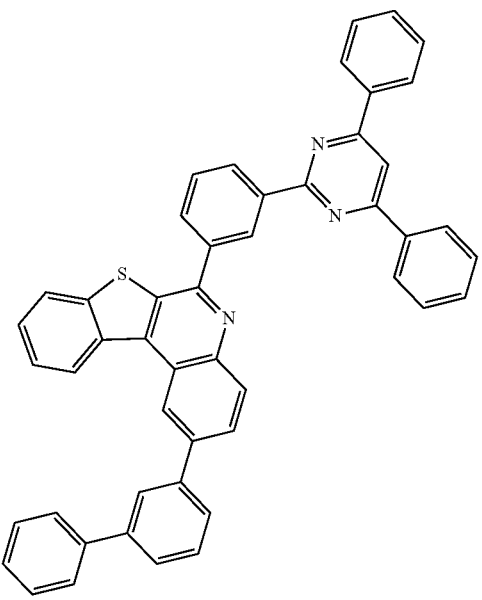

155
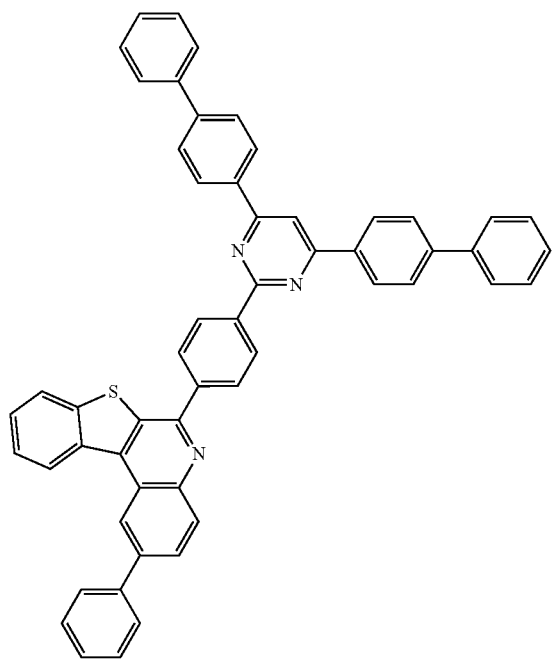
156
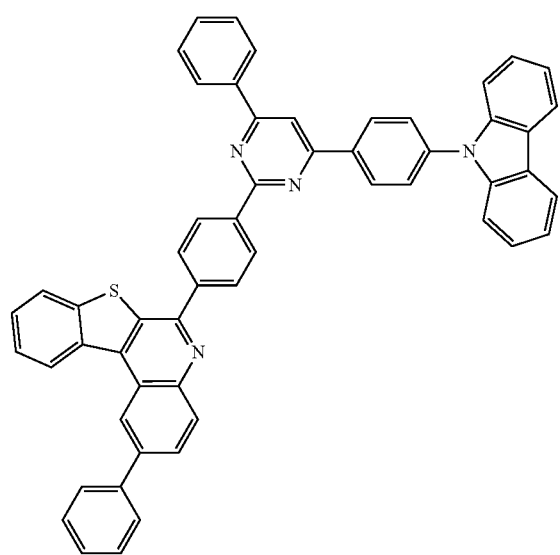
157
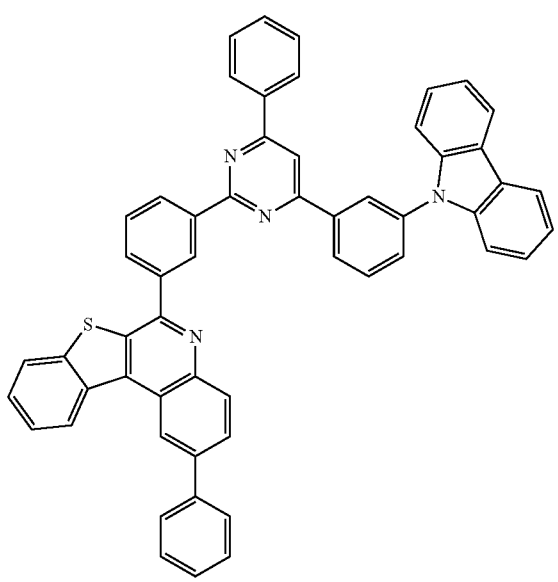
158
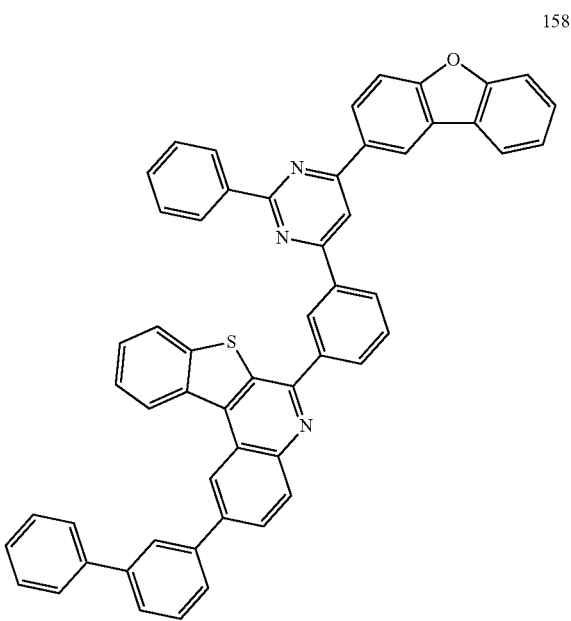

91
-continued
92
-continued
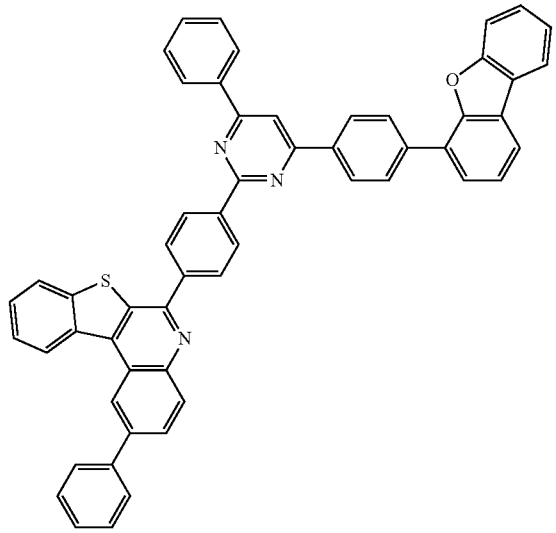
159
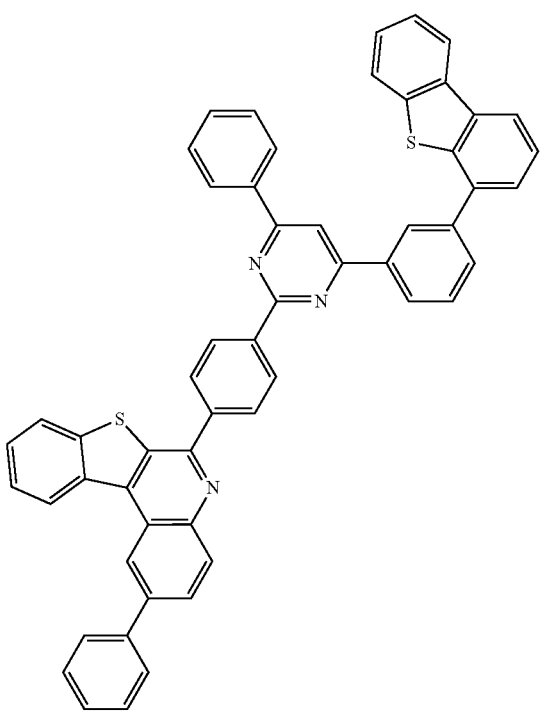
161
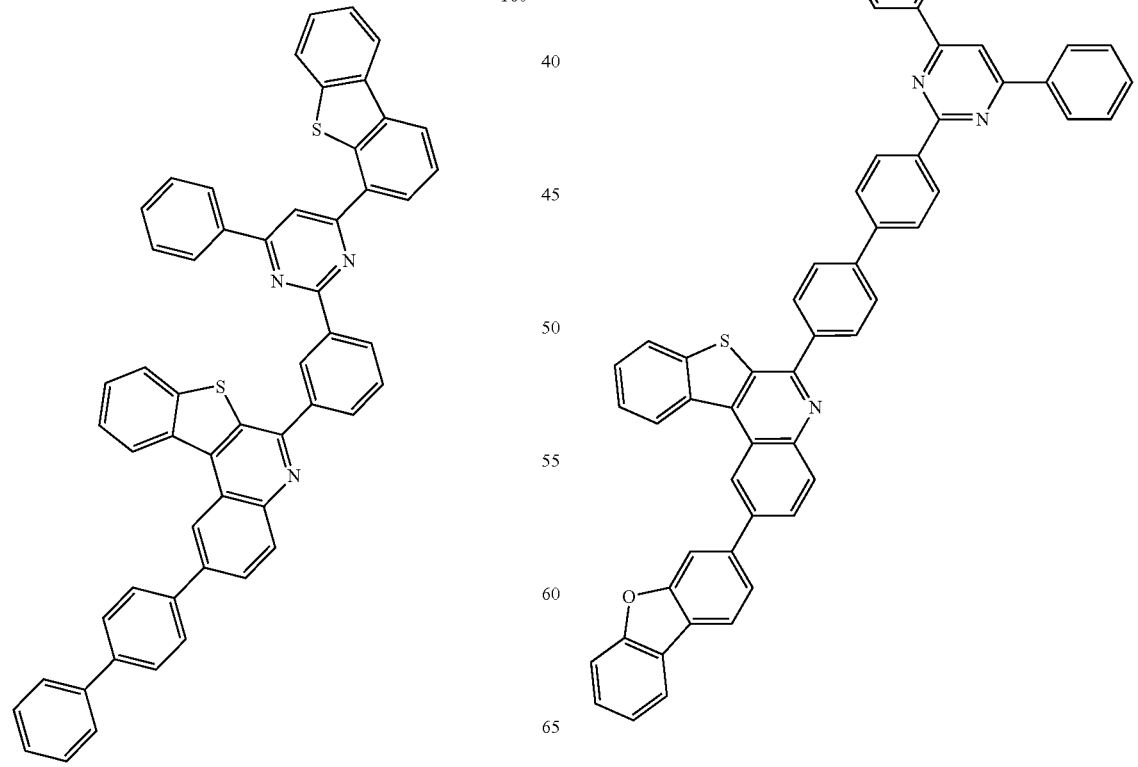

163
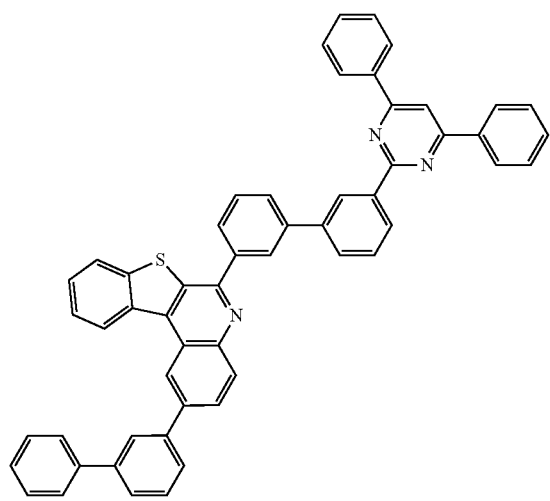
164
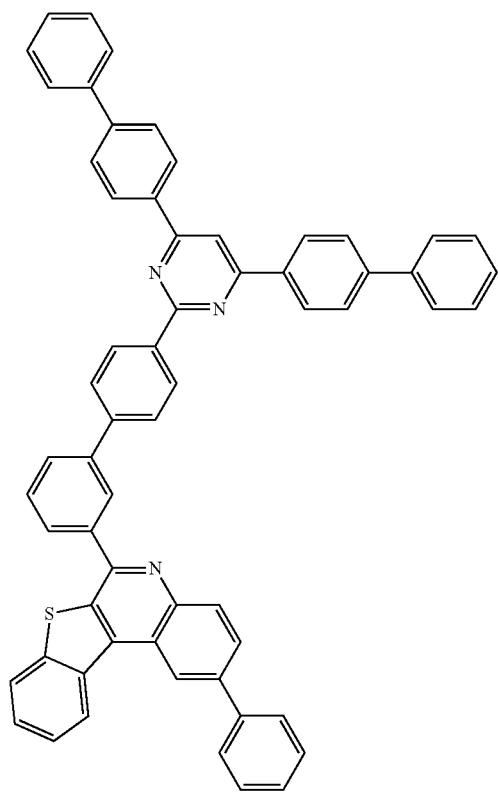
165
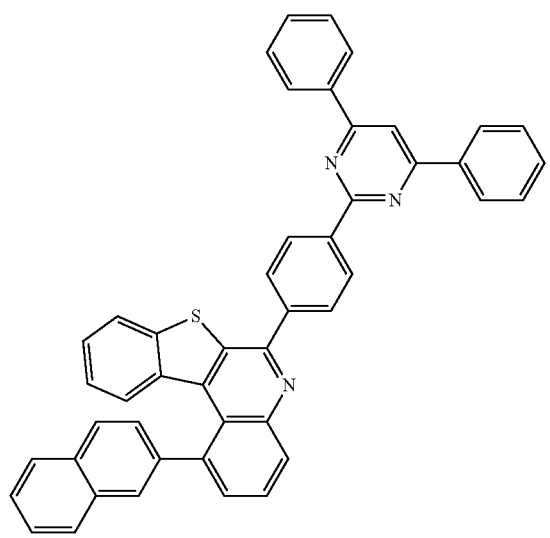
166
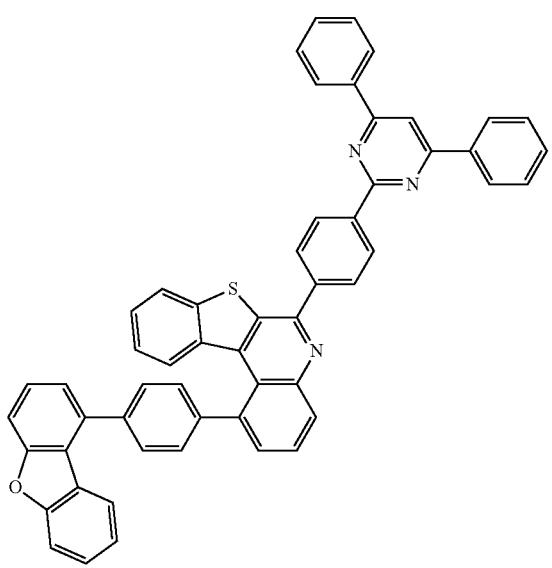

167
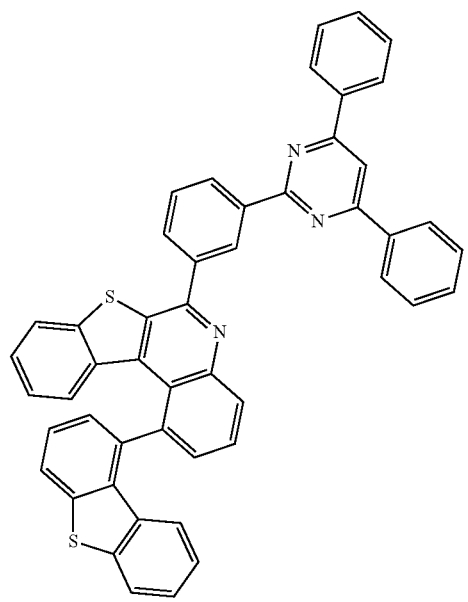
169
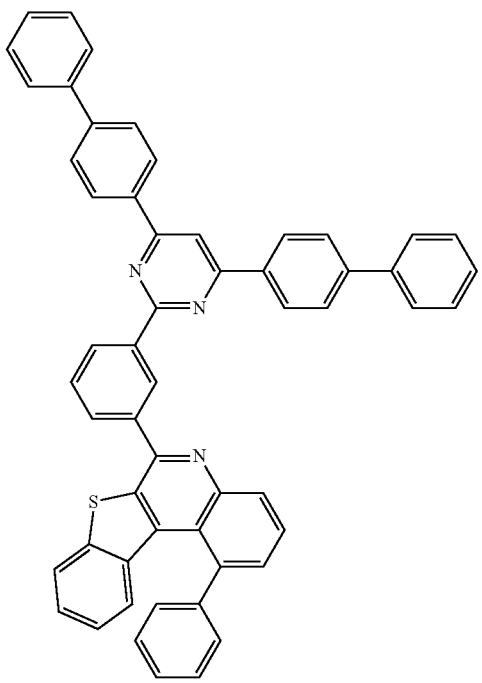
168
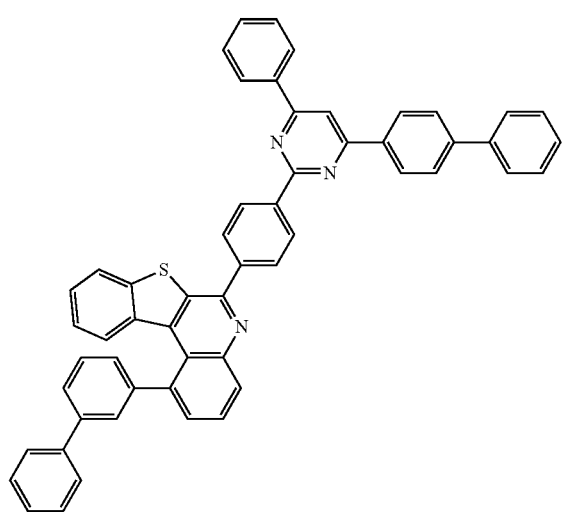
170
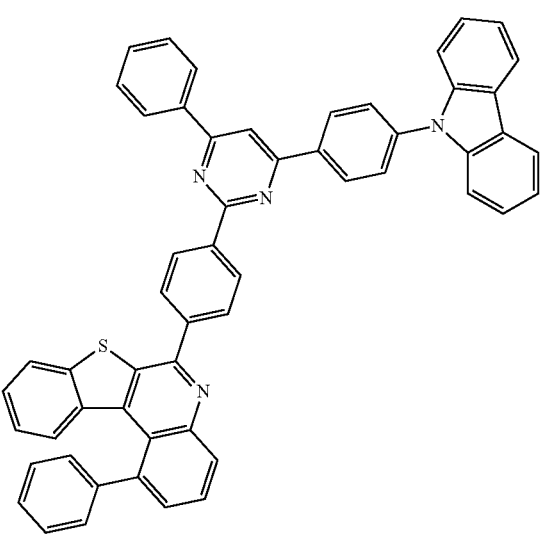

-continued
171
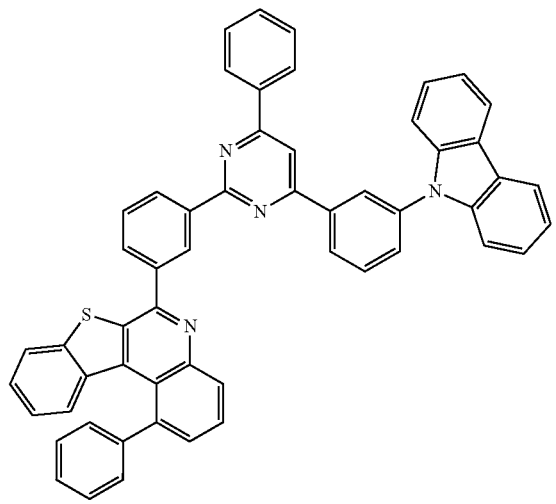
172
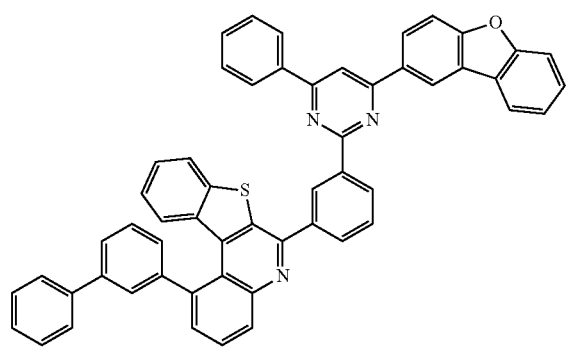
173
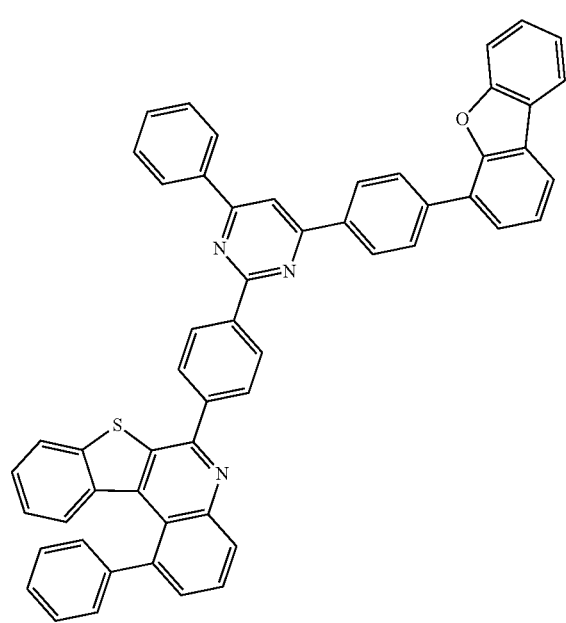
-continued
174
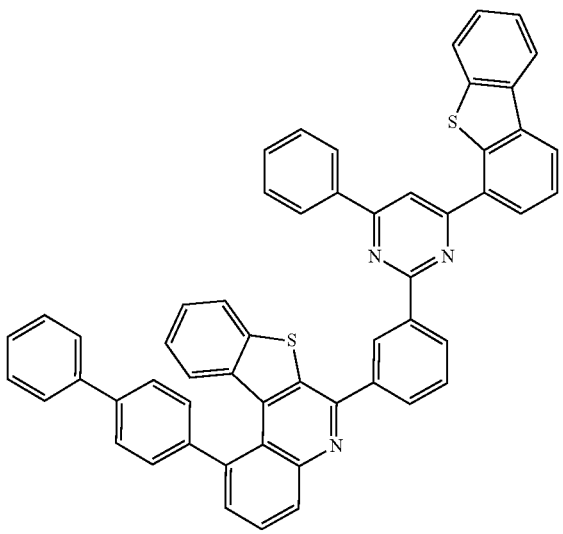
175
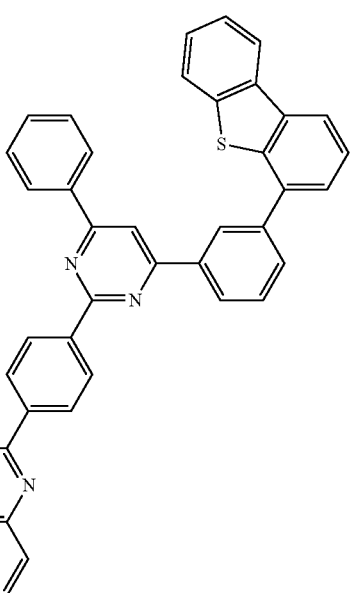

-continued
176
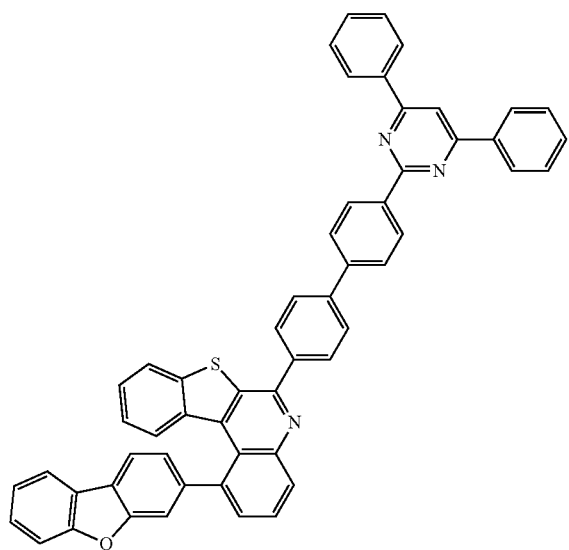
178
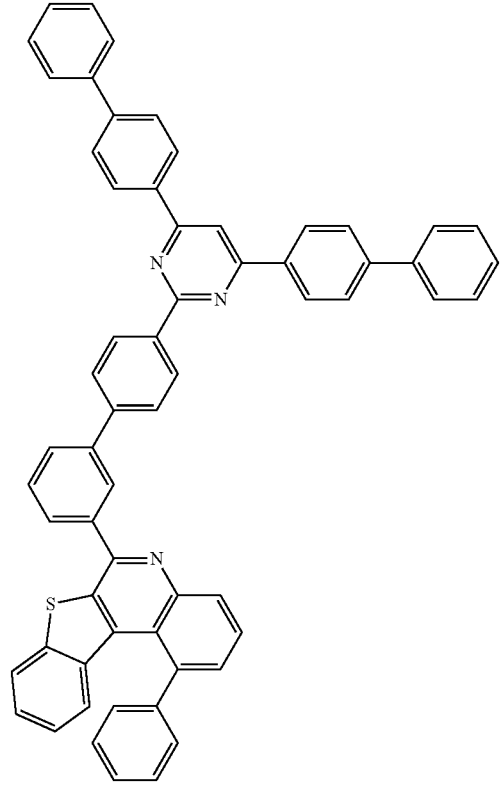
177
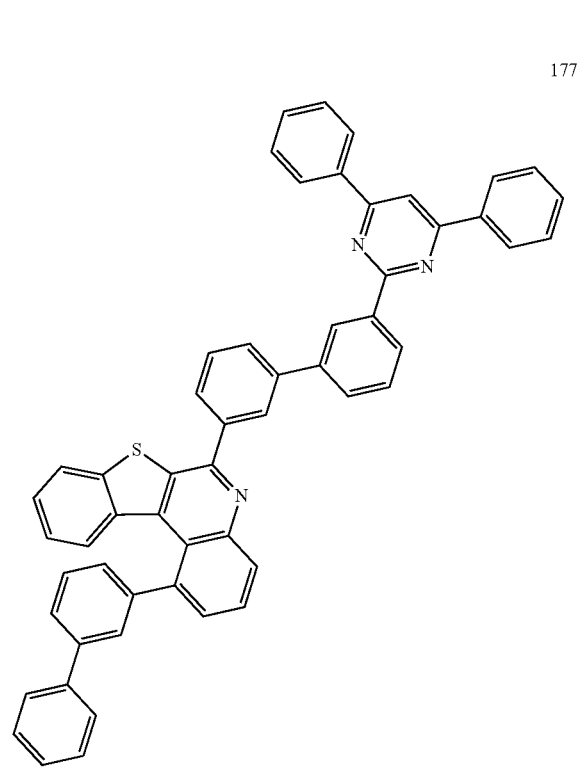
179
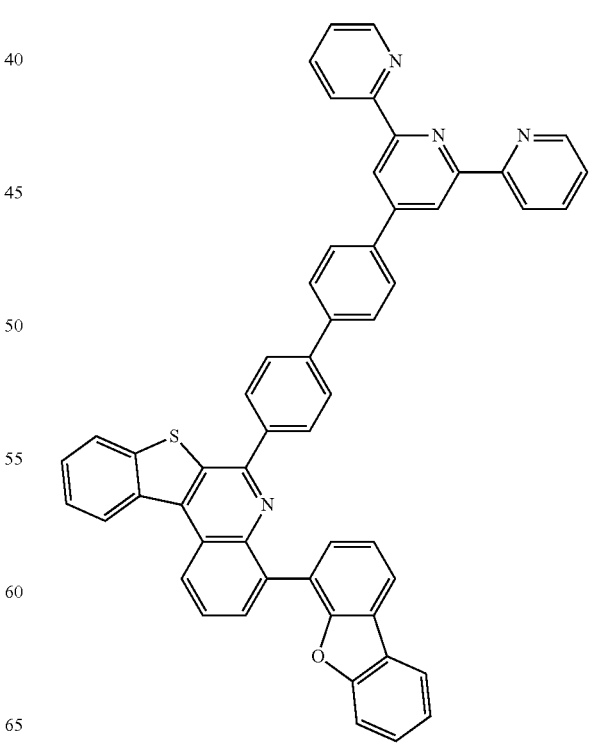

101
-continued
180
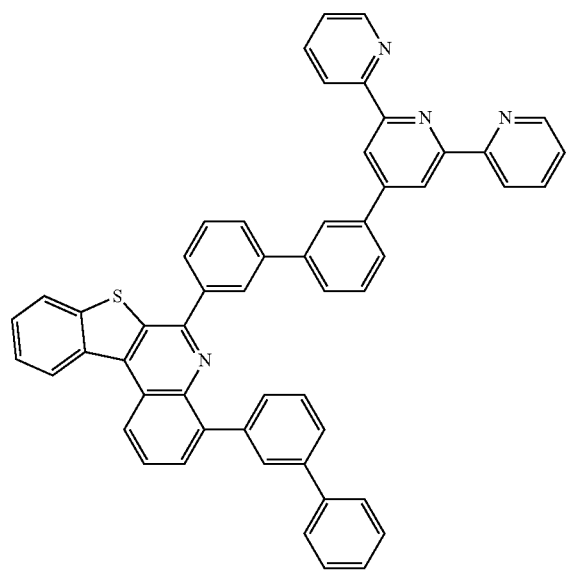
181
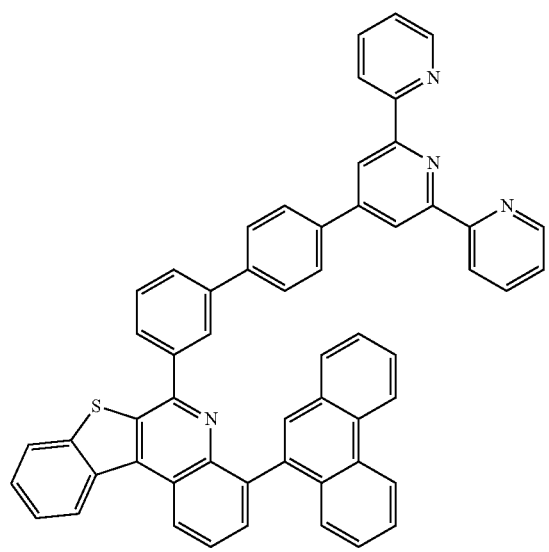
102
-continued
182
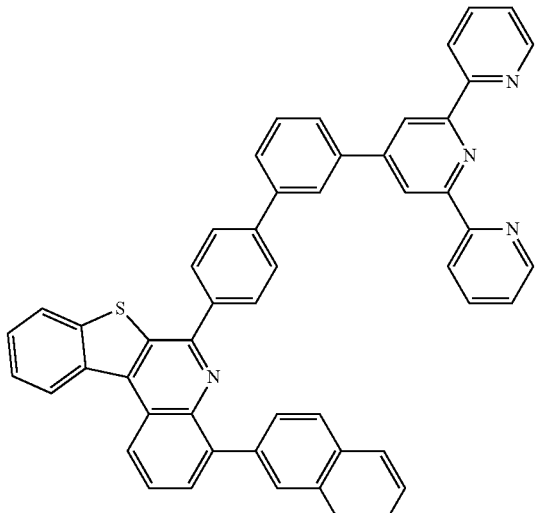
183
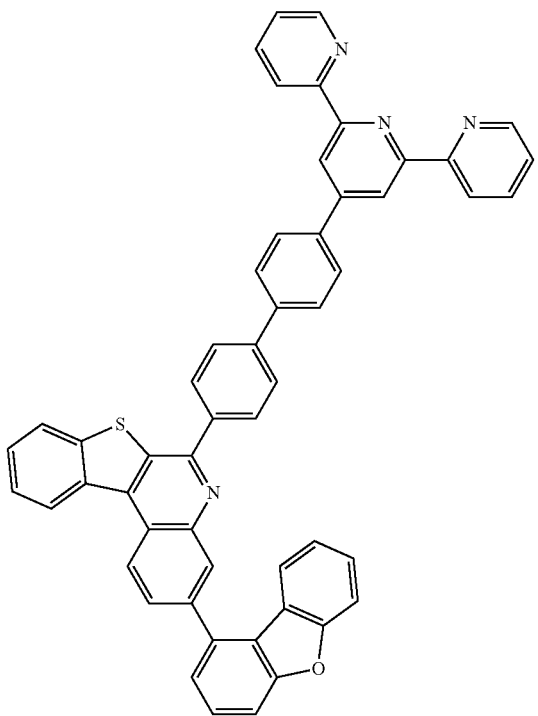

184
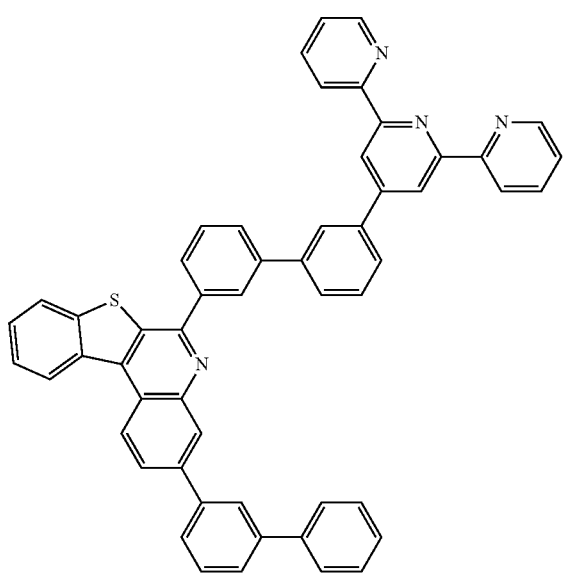
185
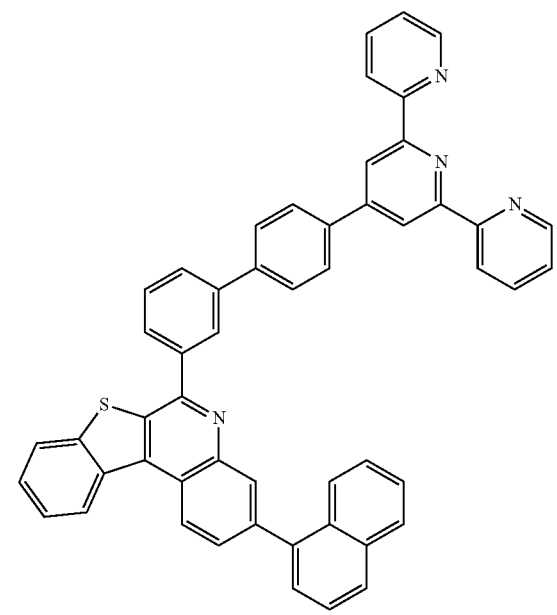
186
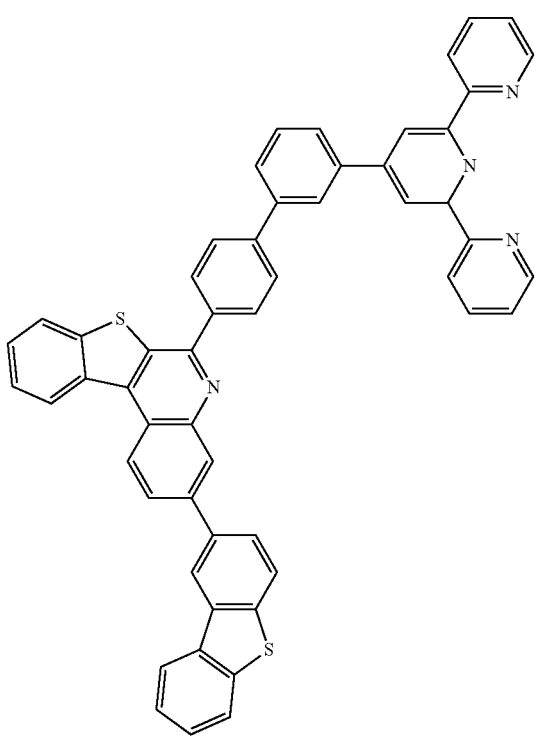
187
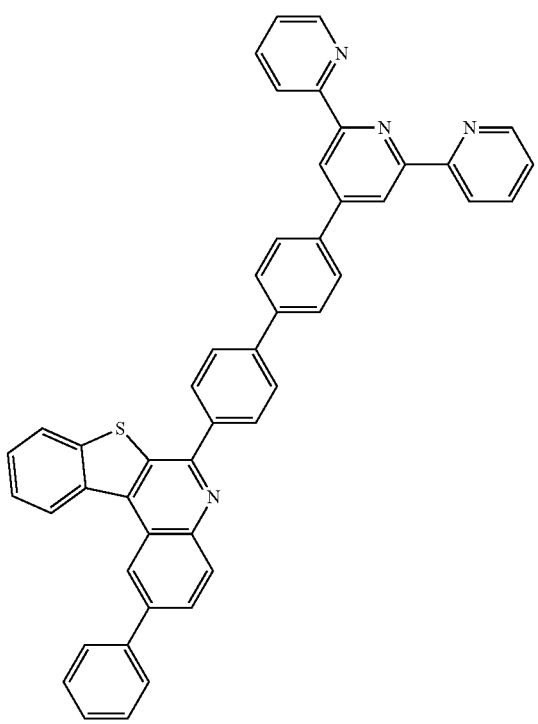

188
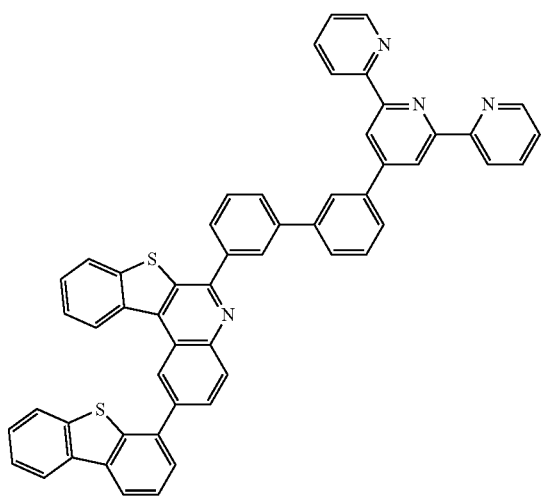
189
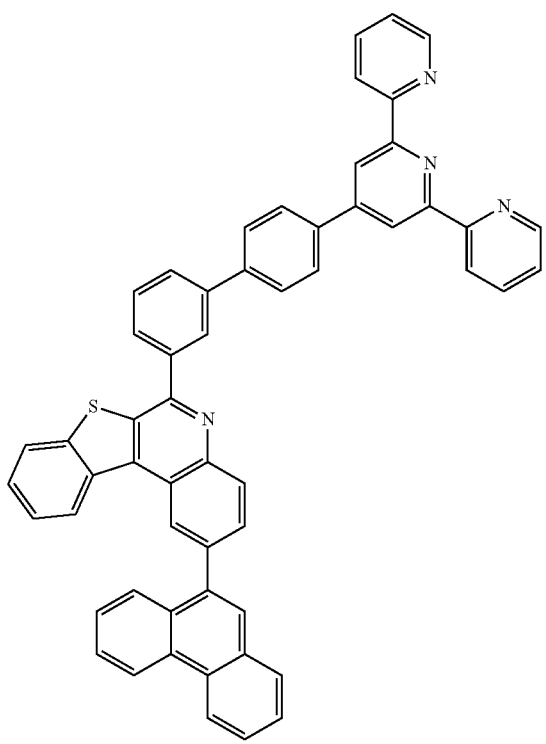
190
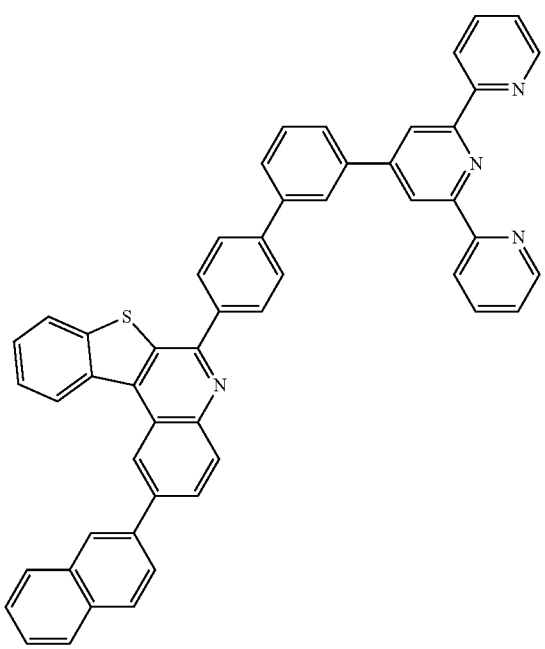
191
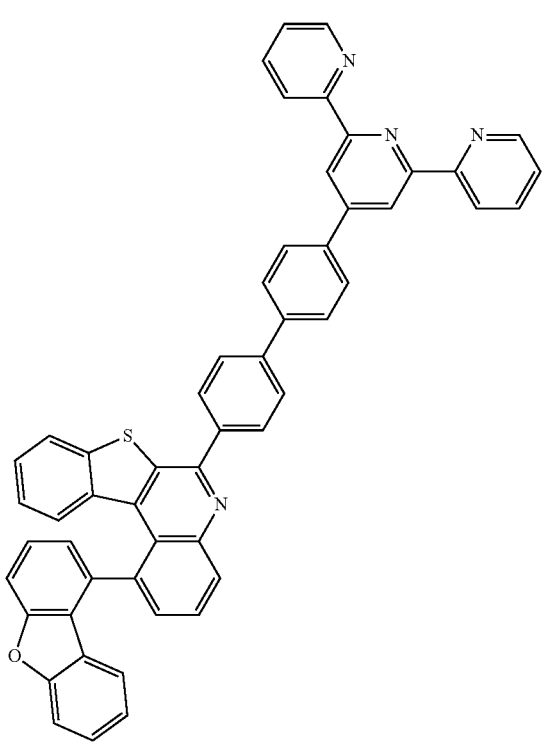

192
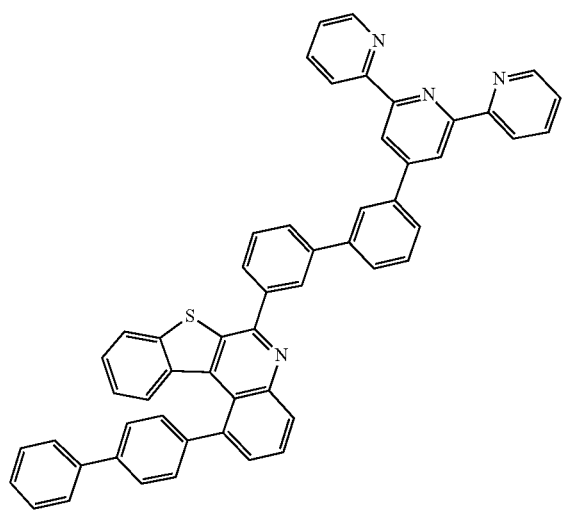
193
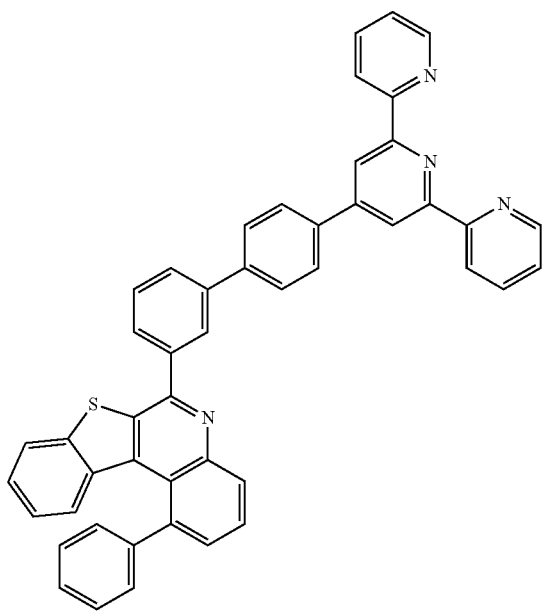
194
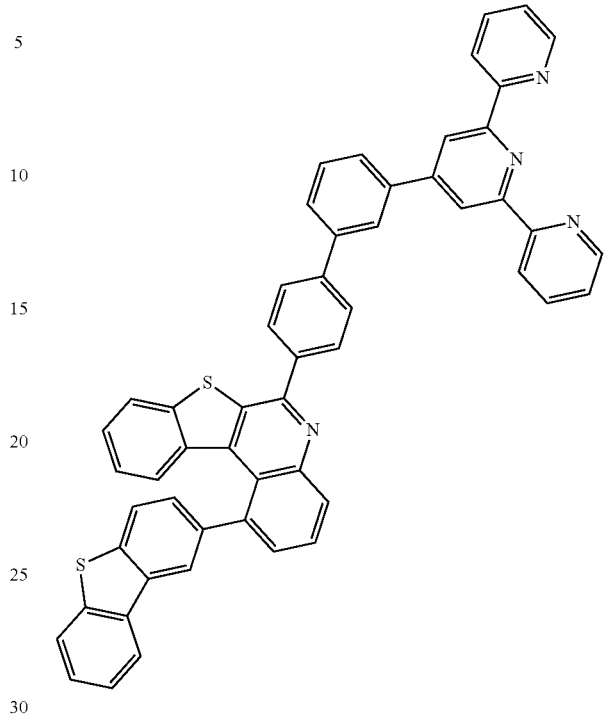
195
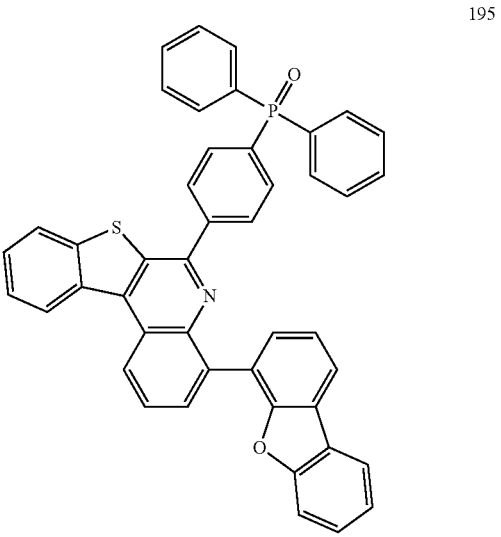

-continued
196
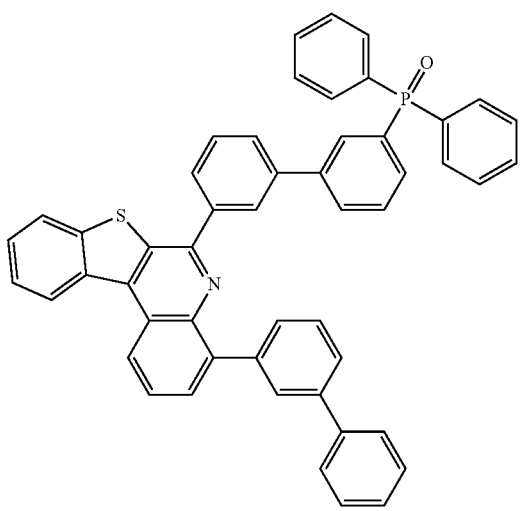
197
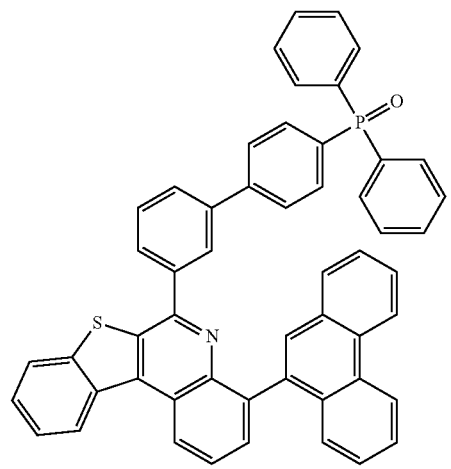
198
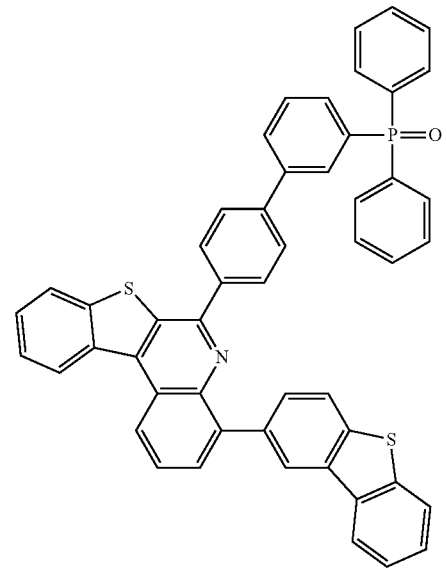
-continued
199
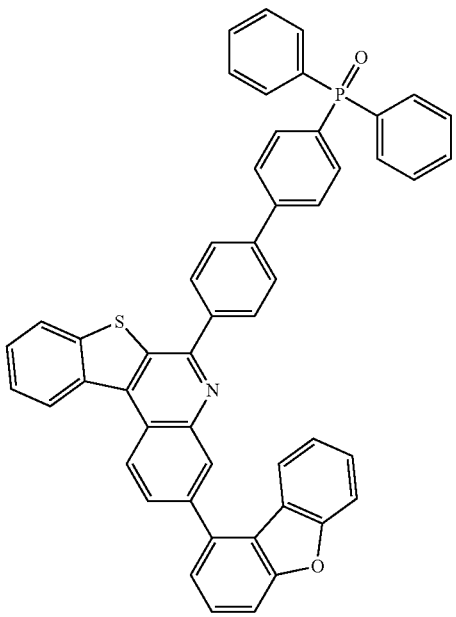
200
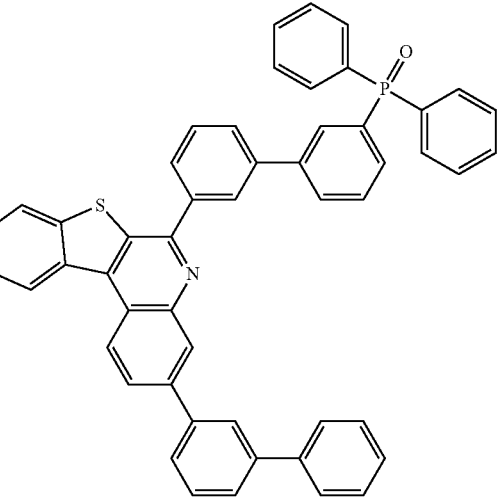
201
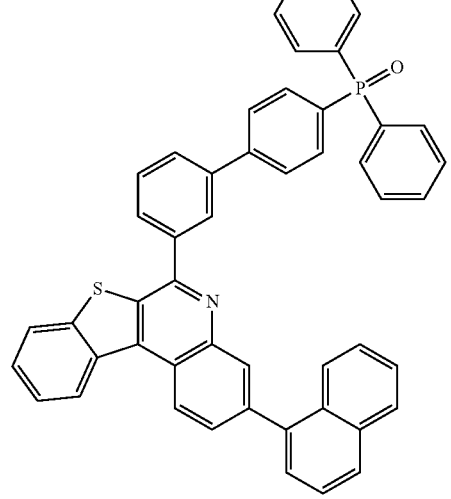

202
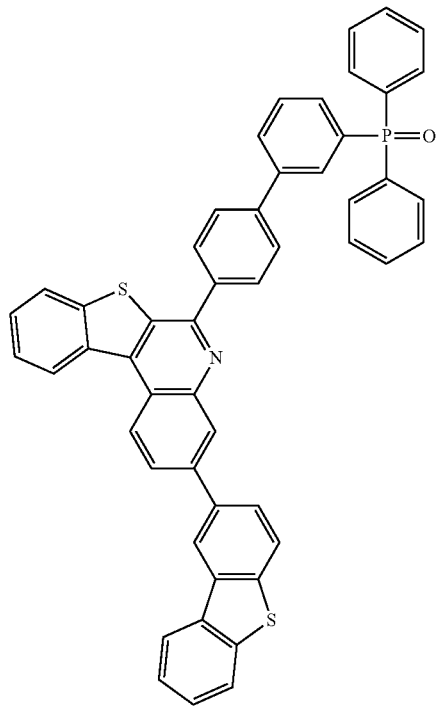
203
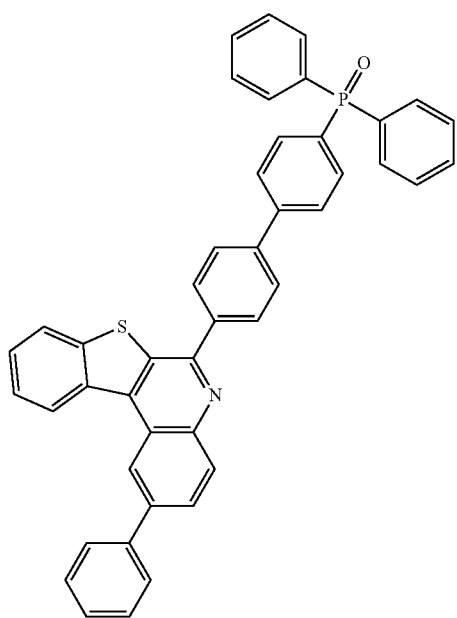
204
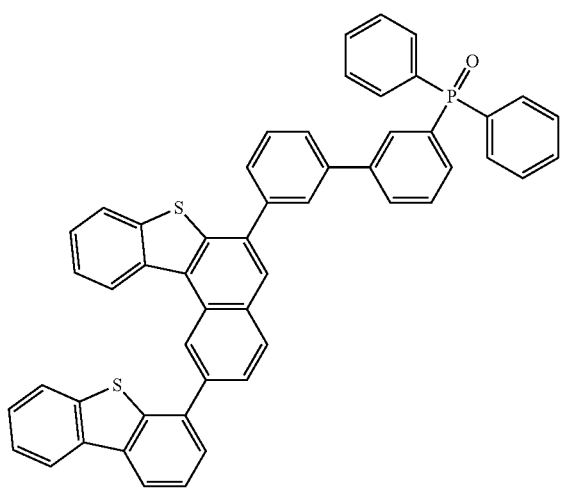
205
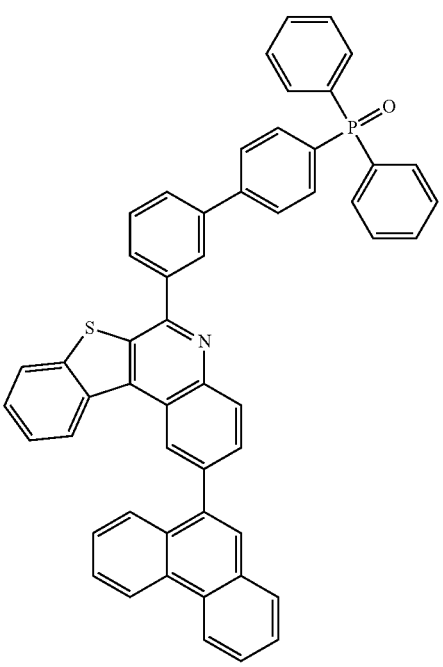

206
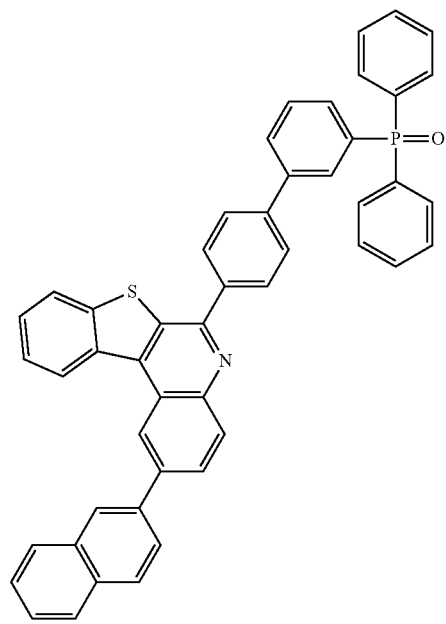
207
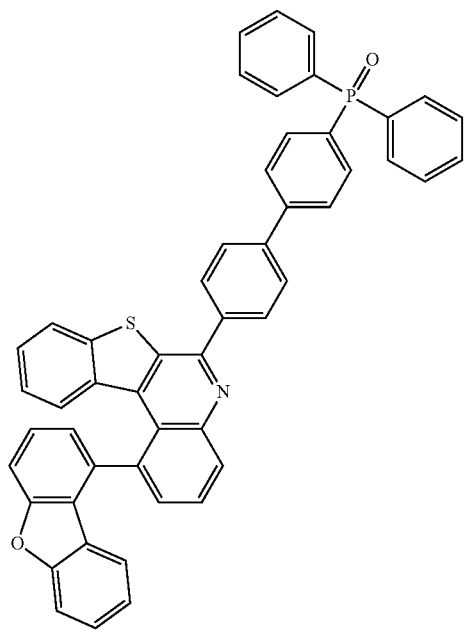
208
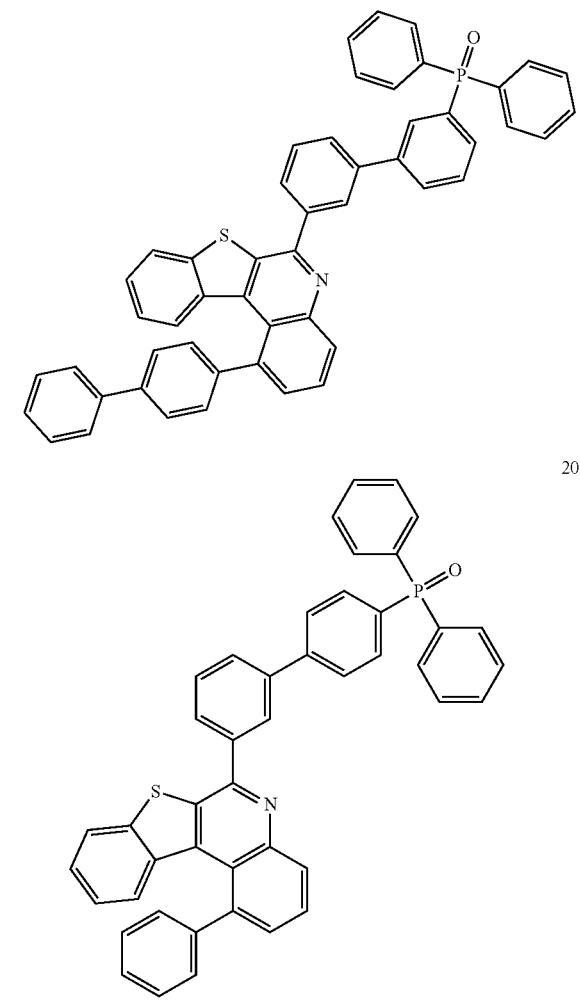
209
210
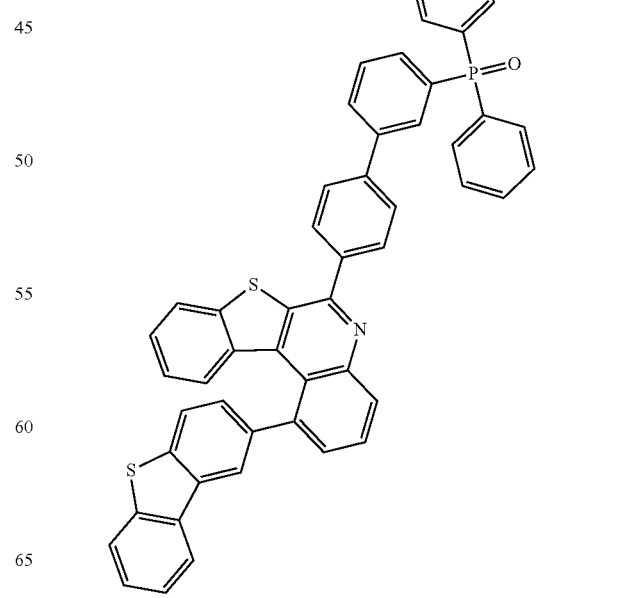

211
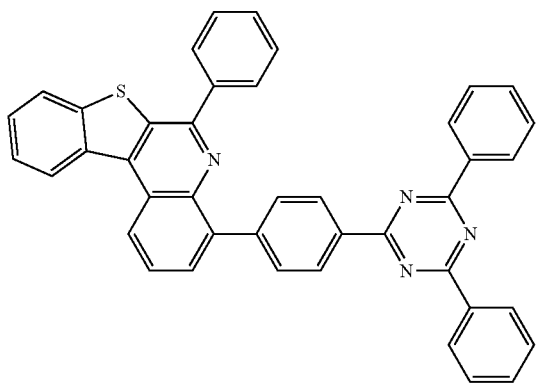
212
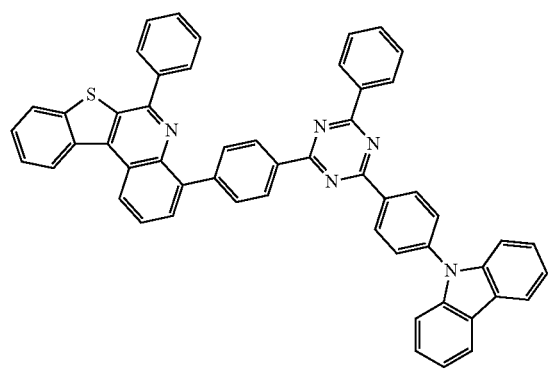
213
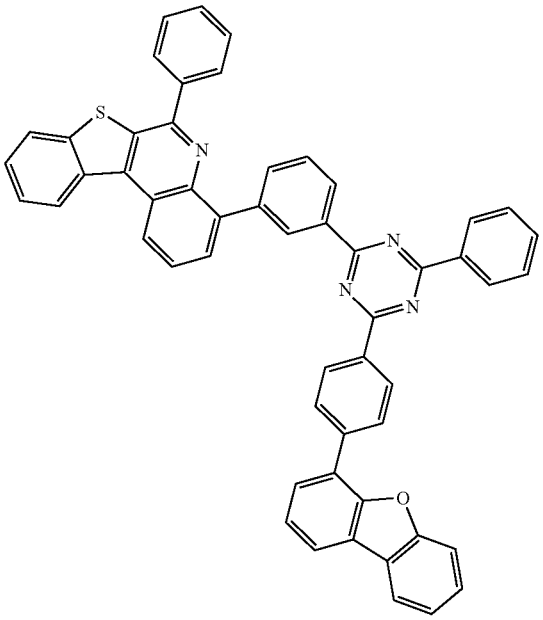
214
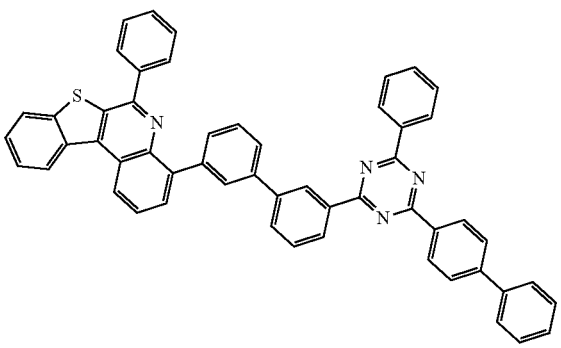
215
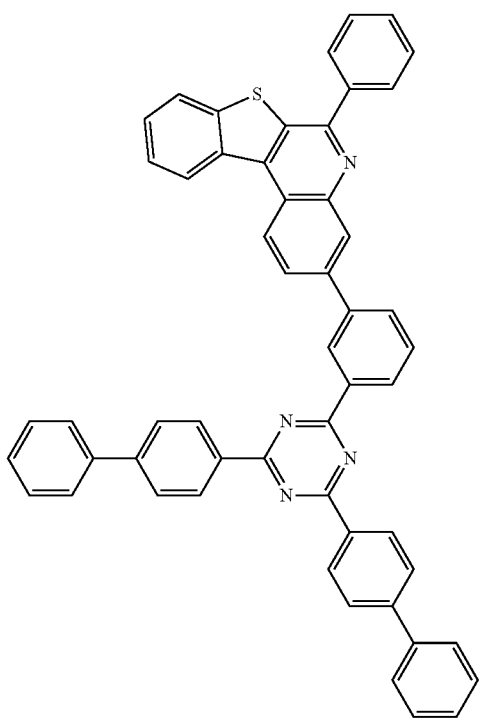

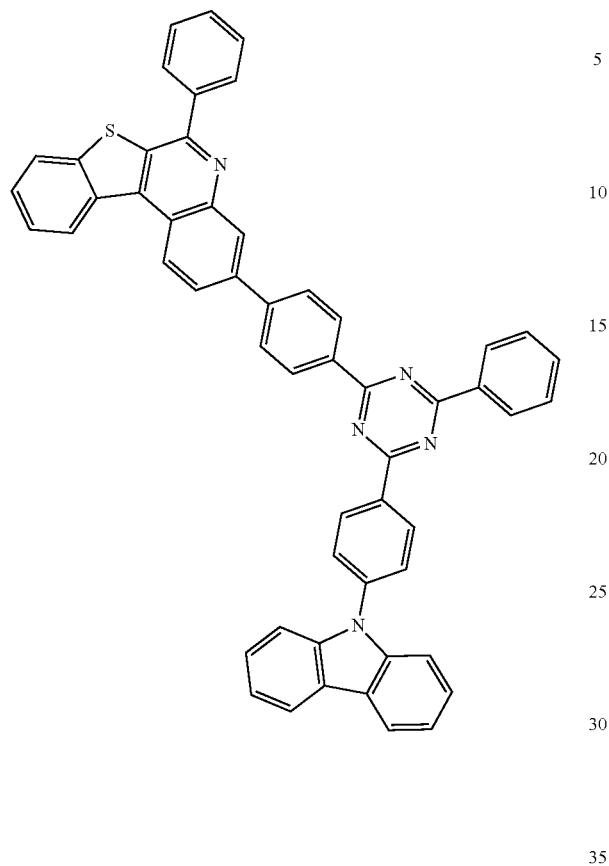
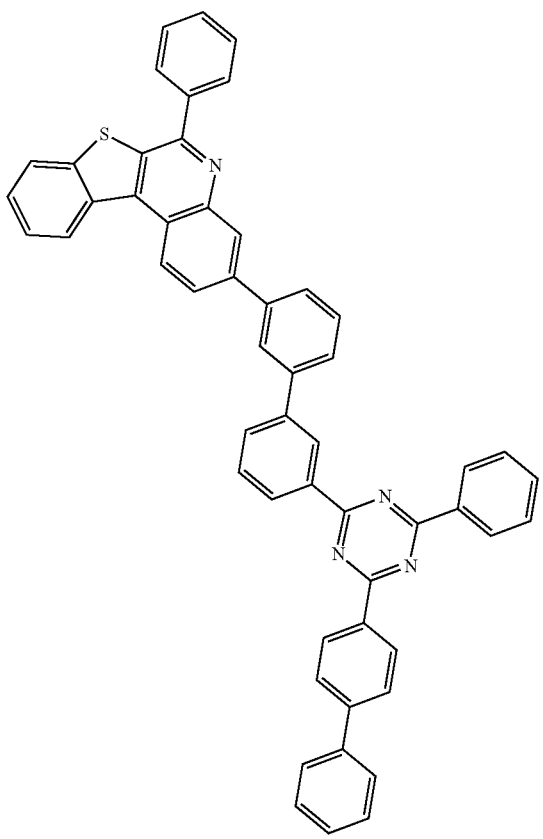

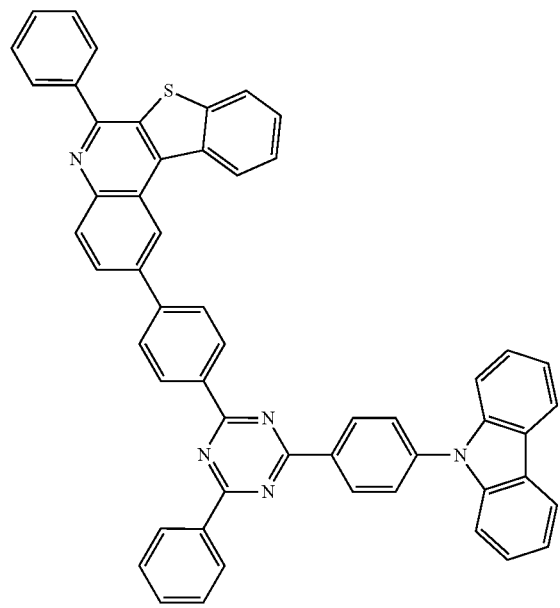
220
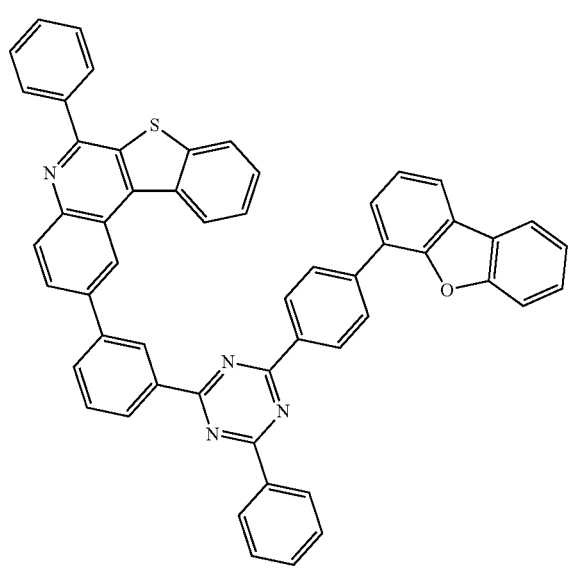
221
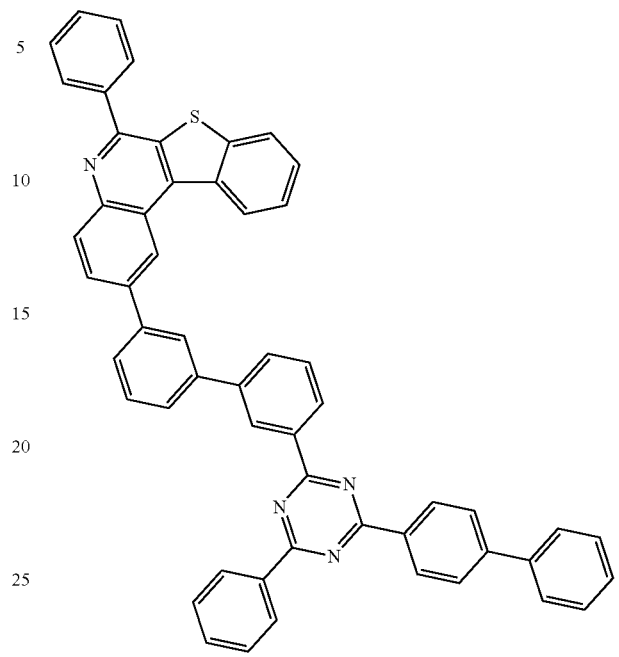
222
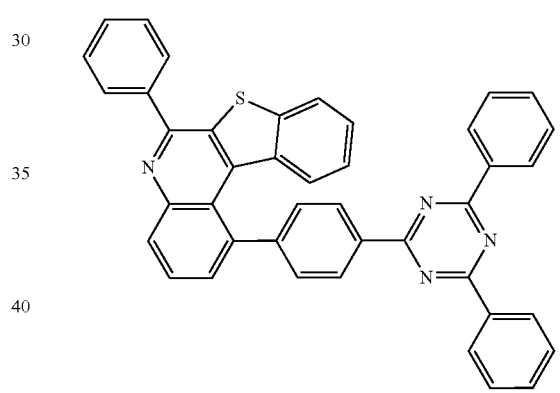
223
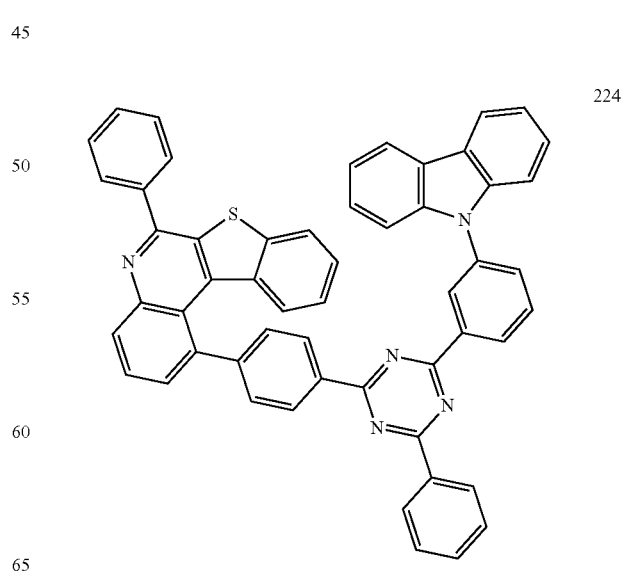
224

225
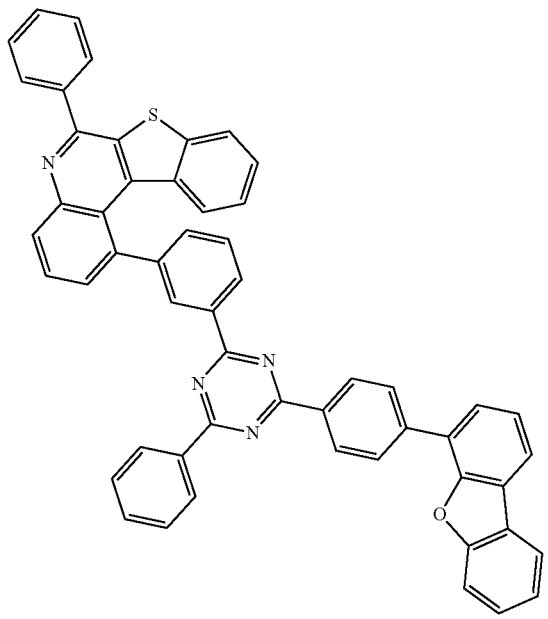
226
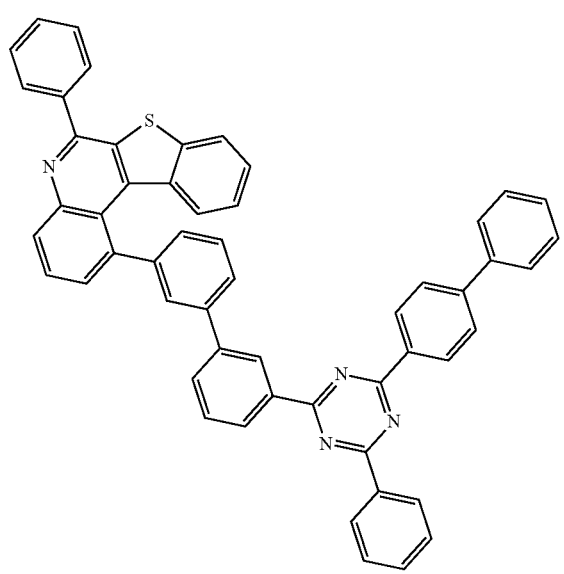
227
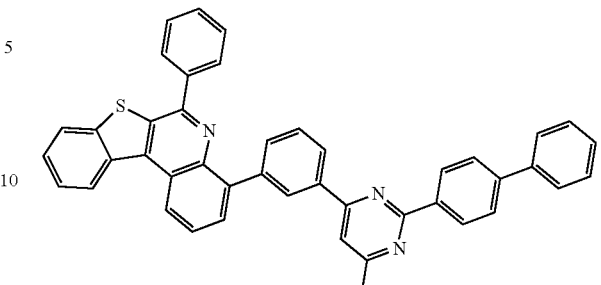
228
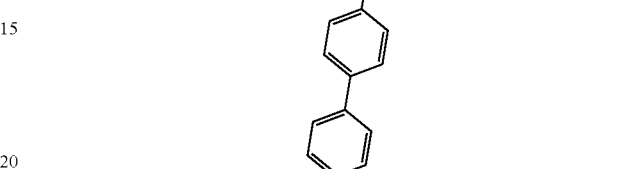
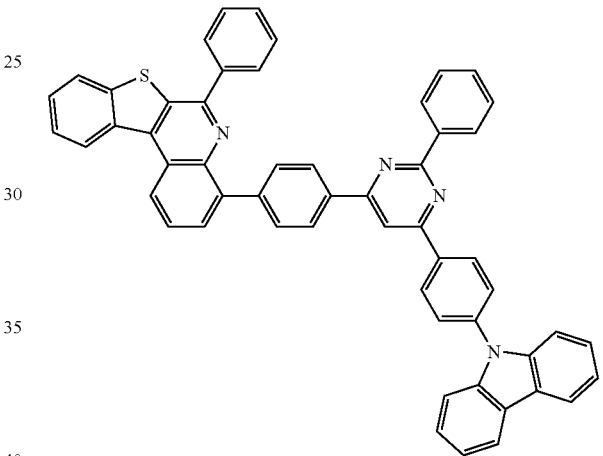
229
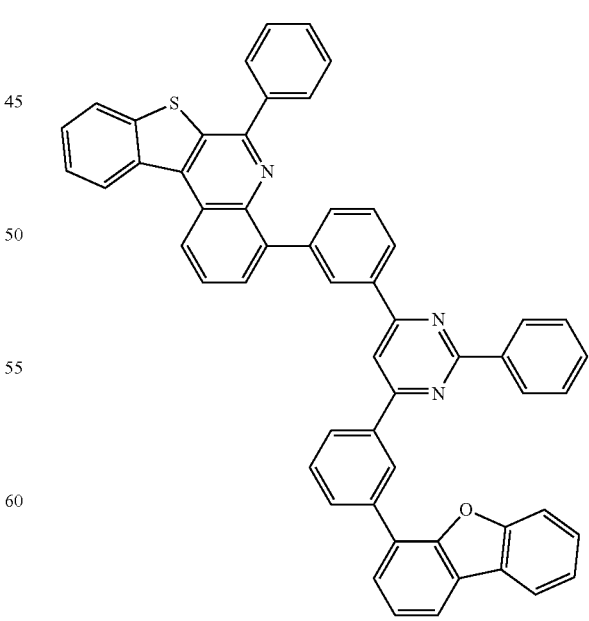

123 -continued
230
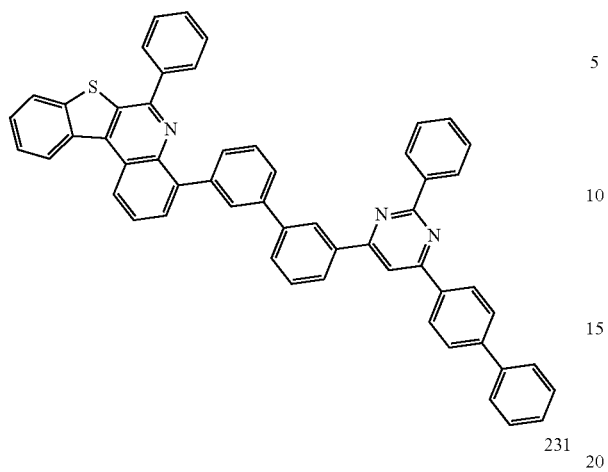
231
232
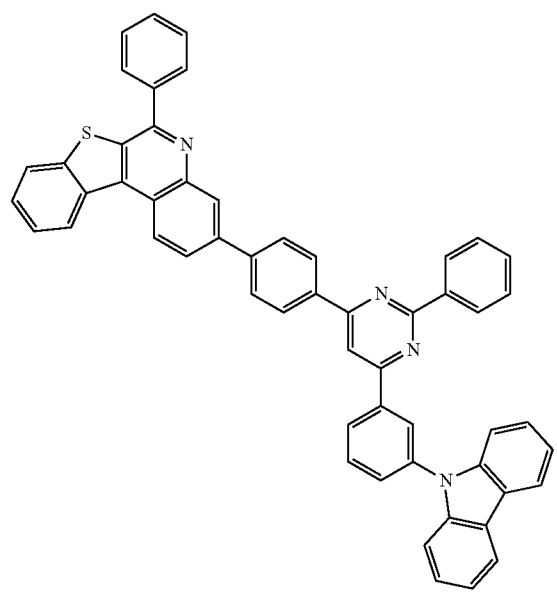
124 -continued
233
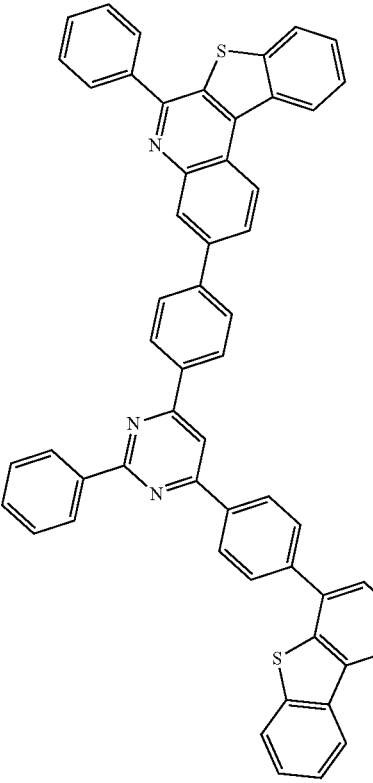
234

235
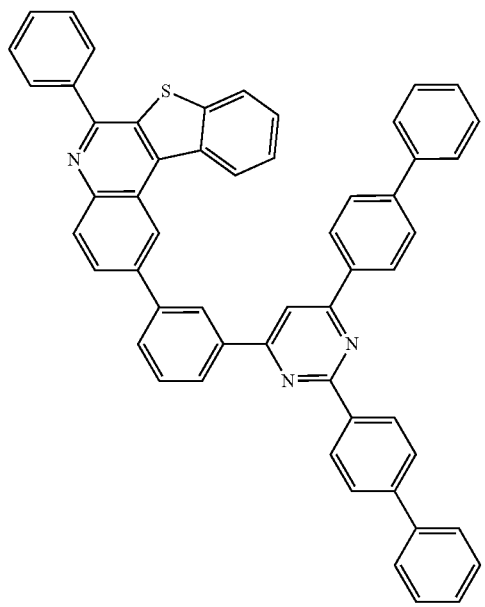
236
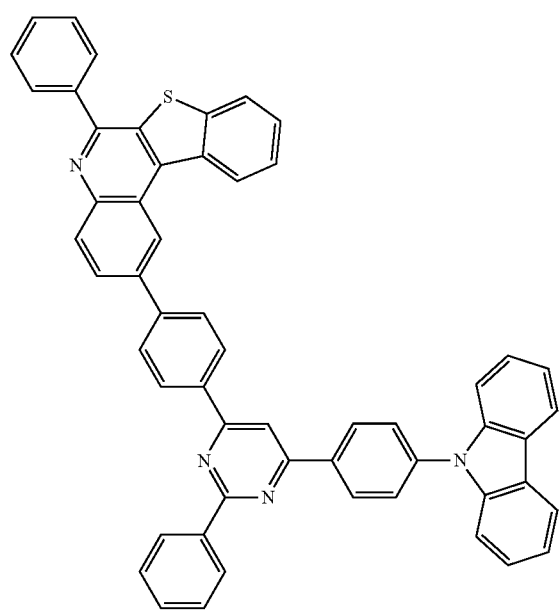
237
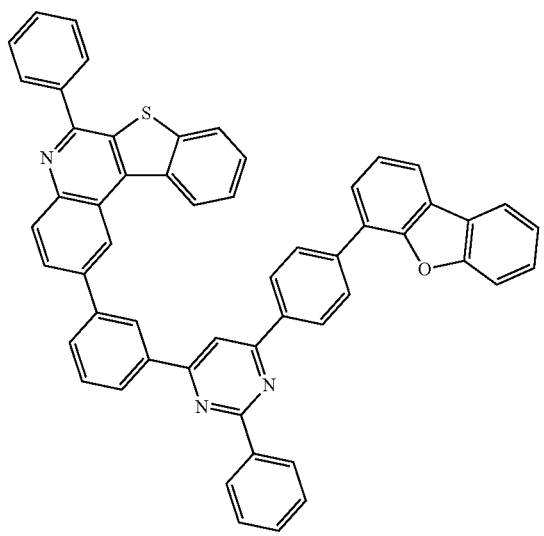
238
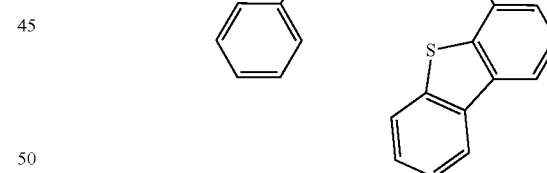
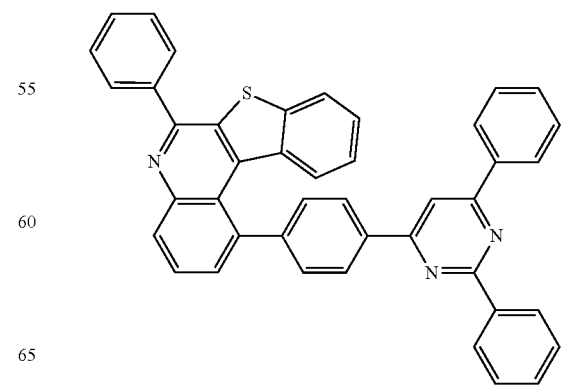
239

240
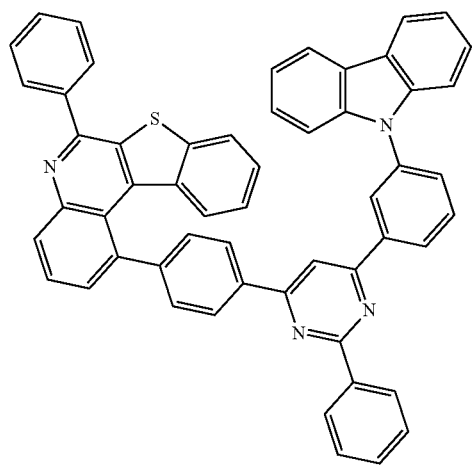
241
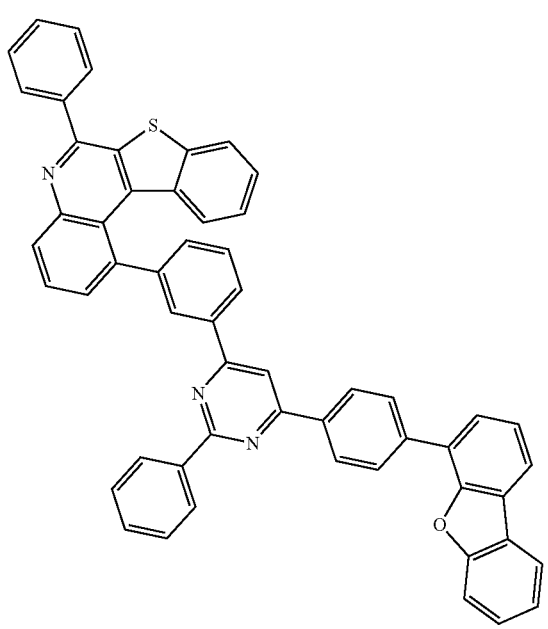
242
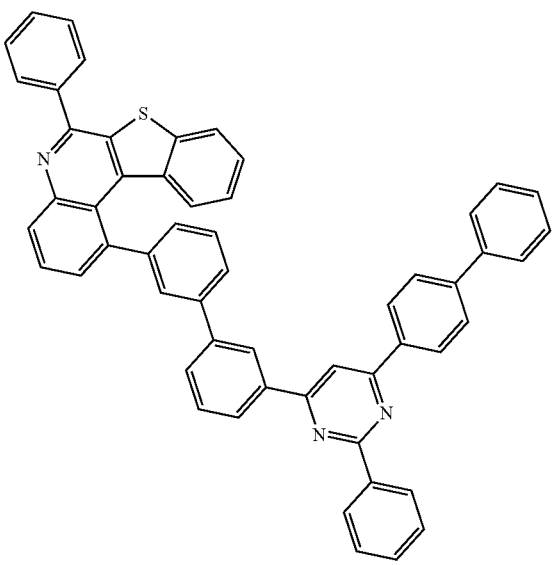
243
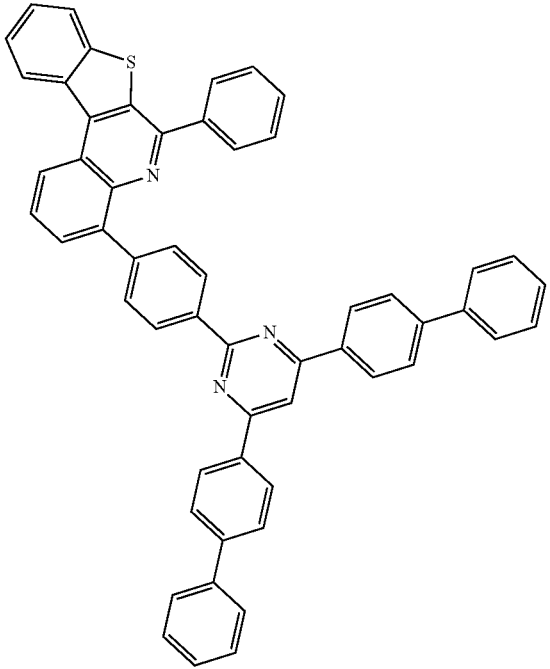

244
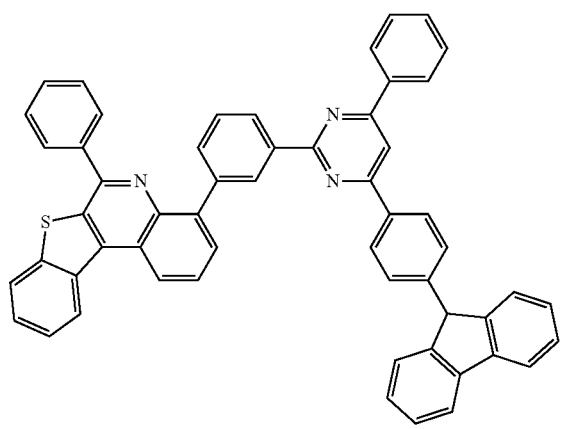
245
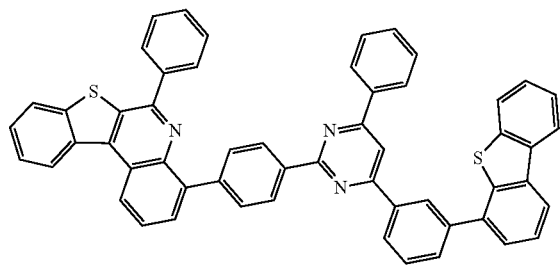
246
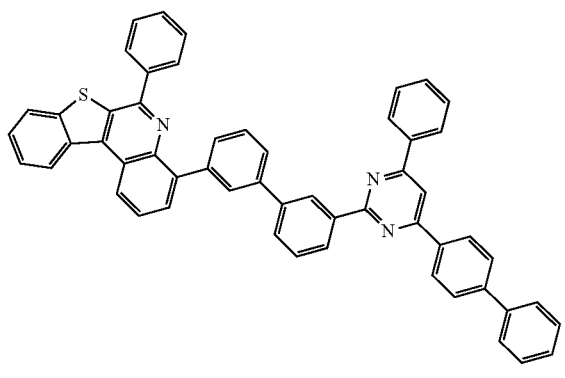
247
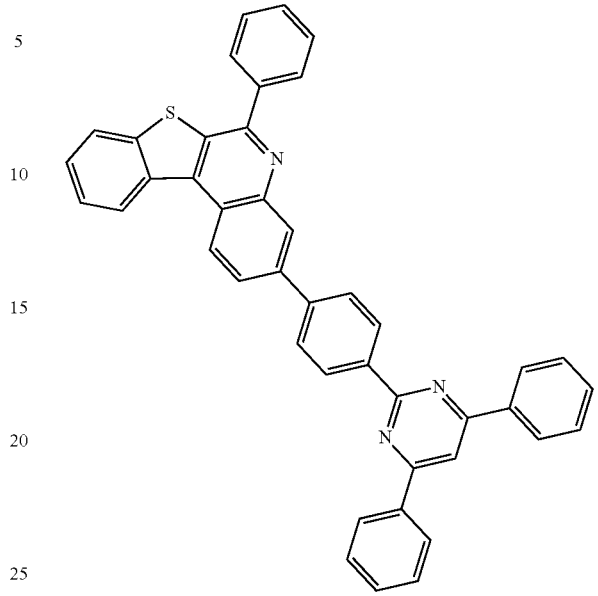
248
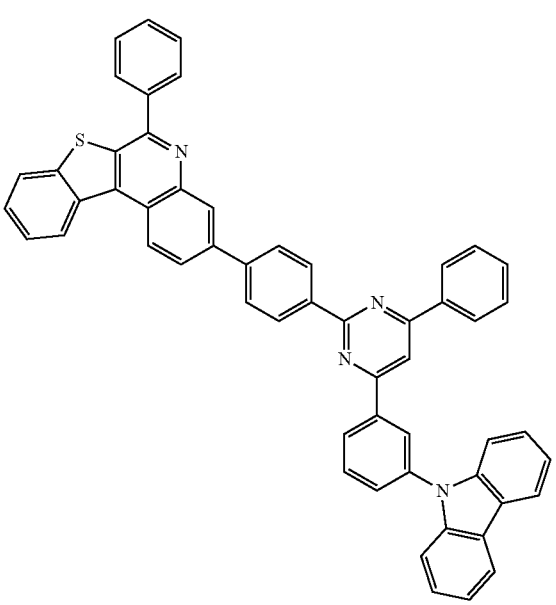

131
-continued
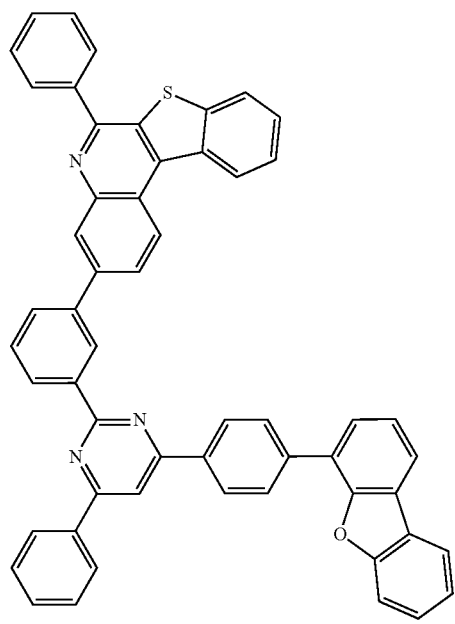
249
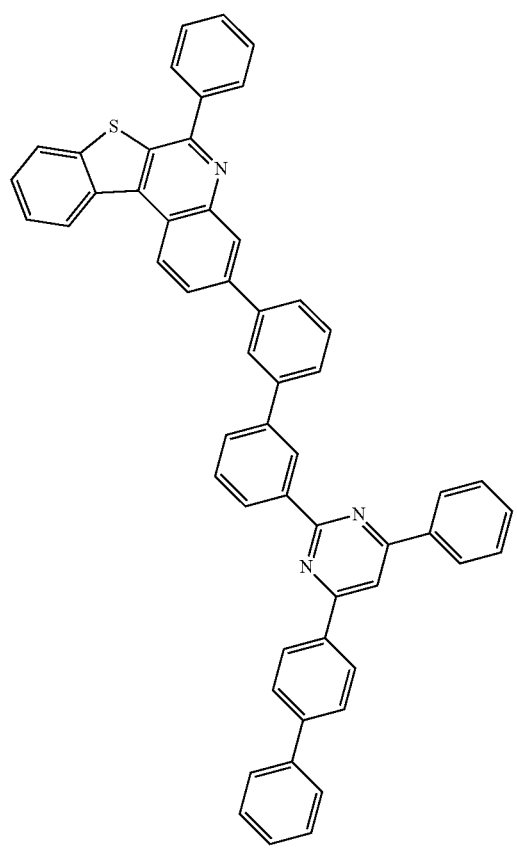
250
132
-continued
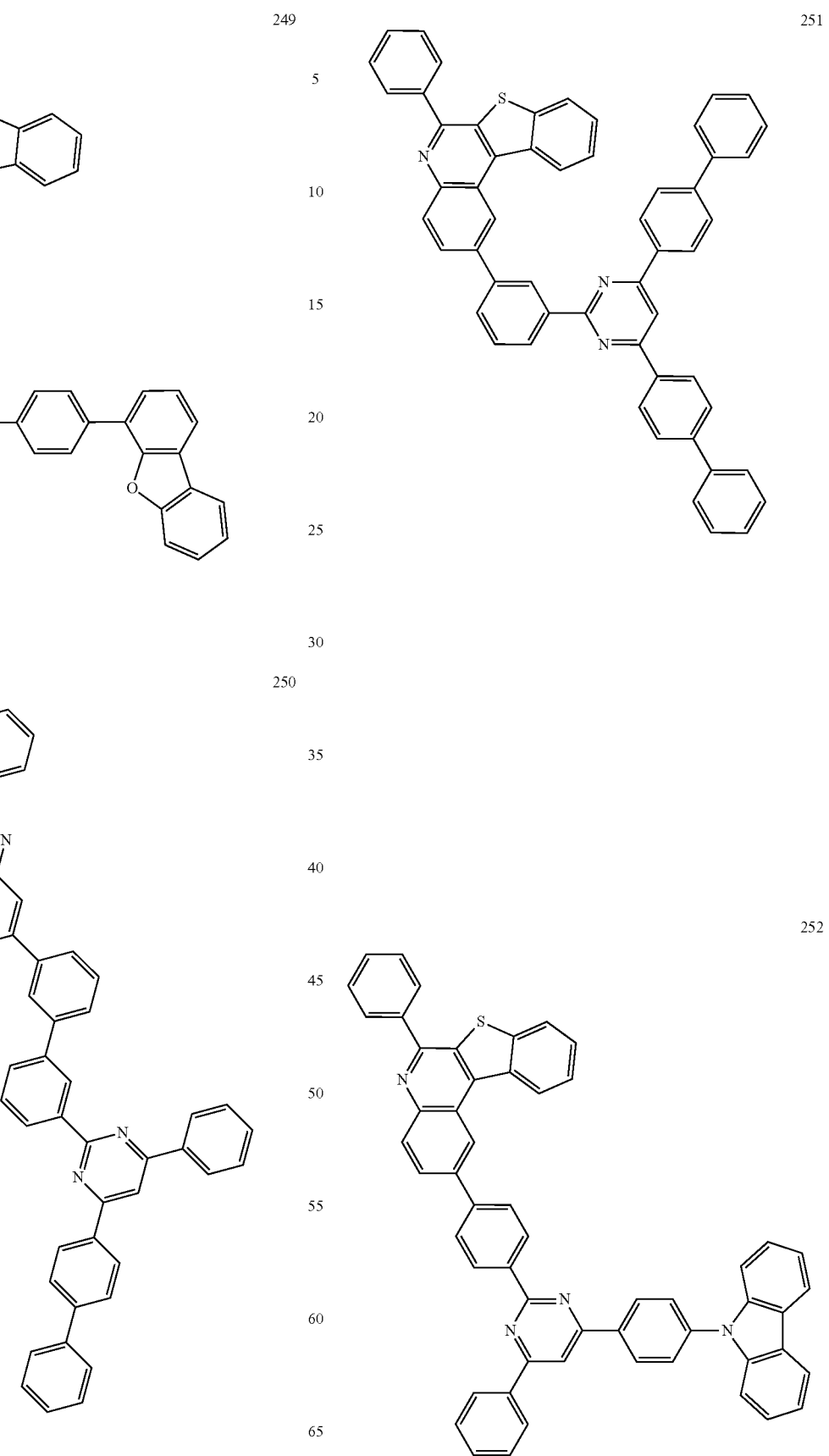
251
252

253
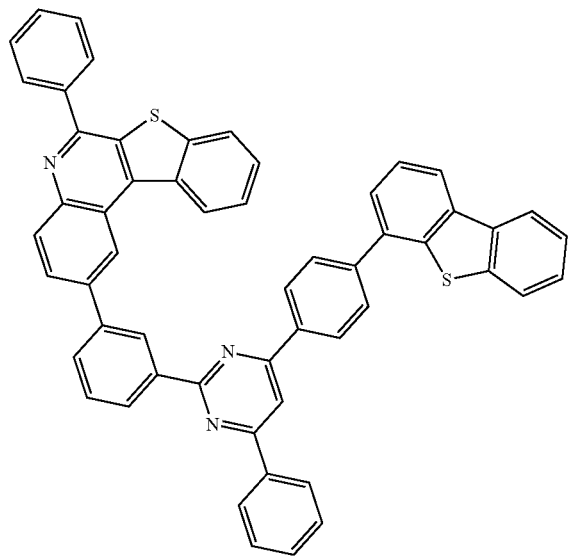
254
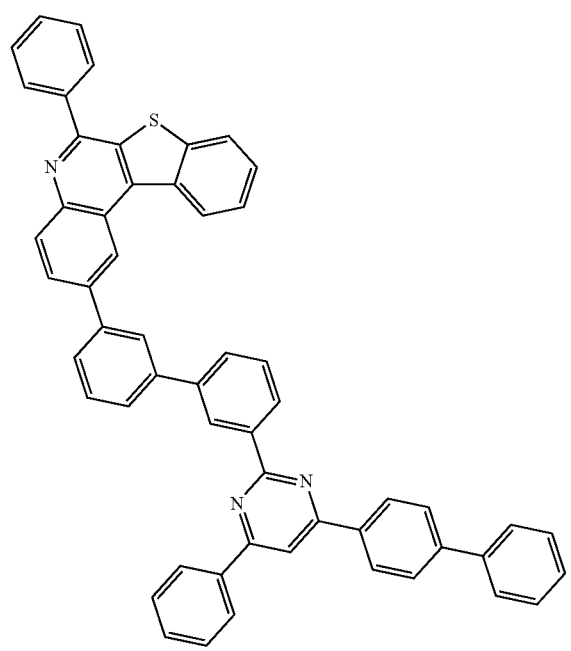
255
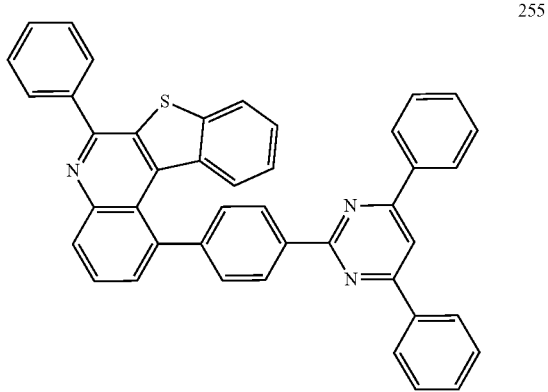
256
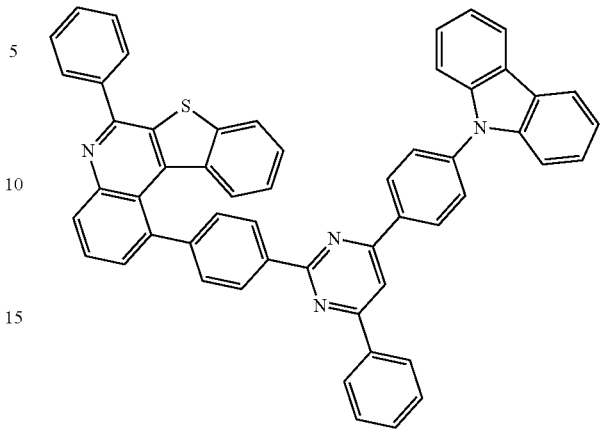
257
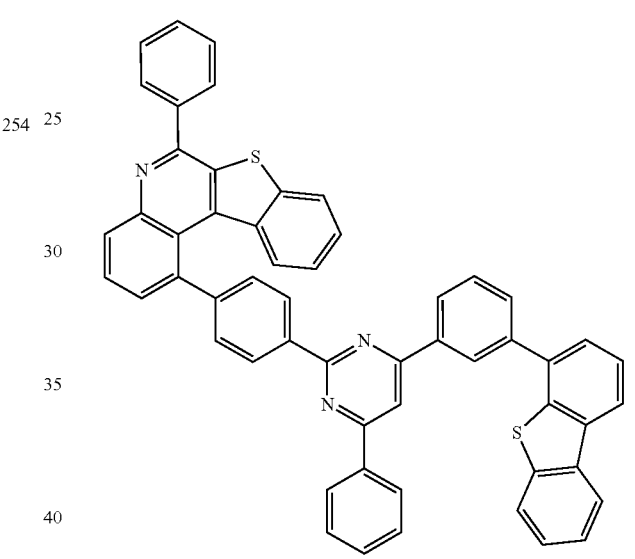
258
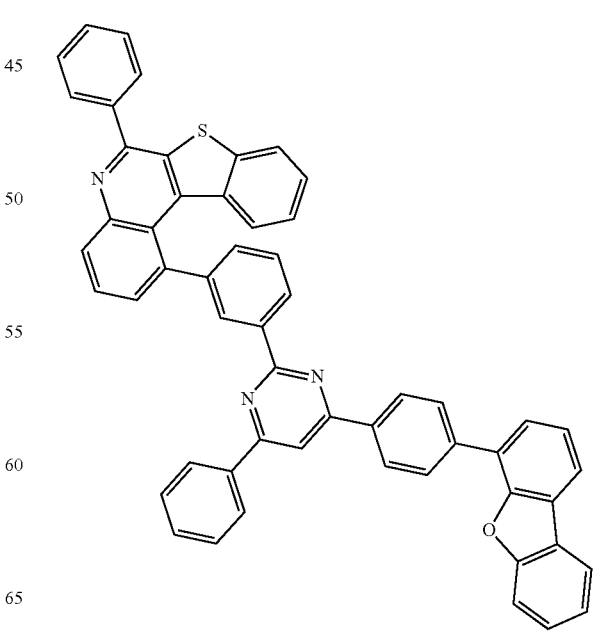

259
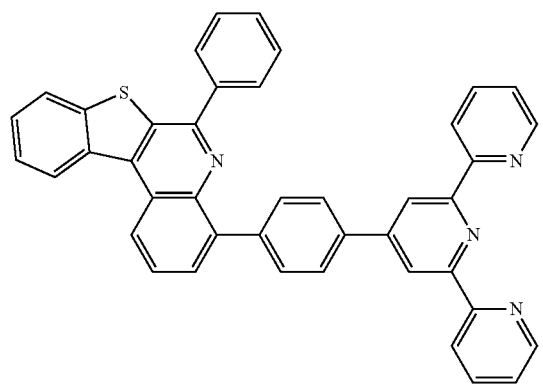
260
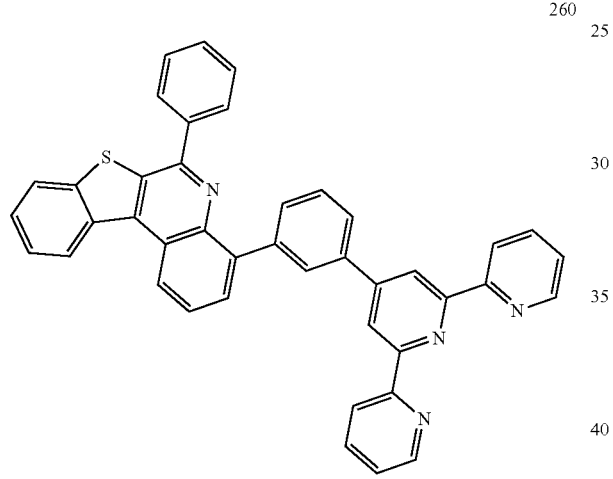
261
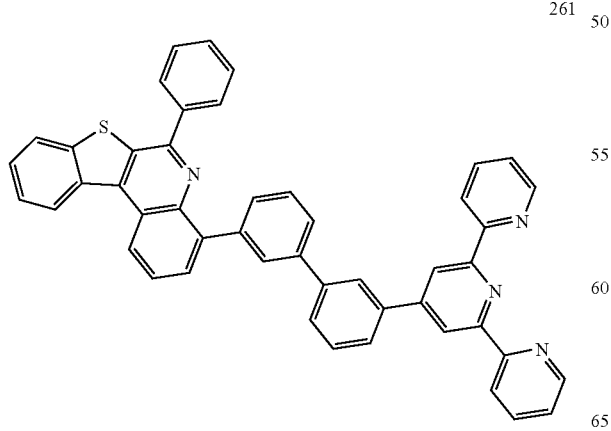
262
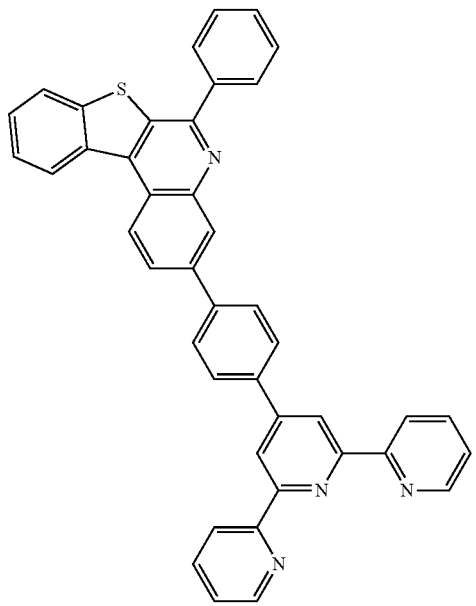
263
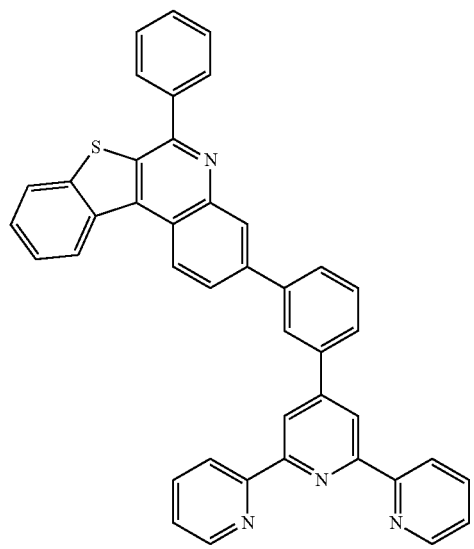

-continued
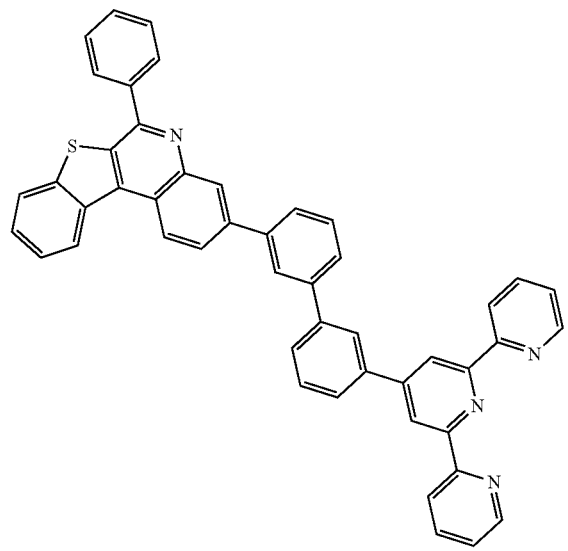
264
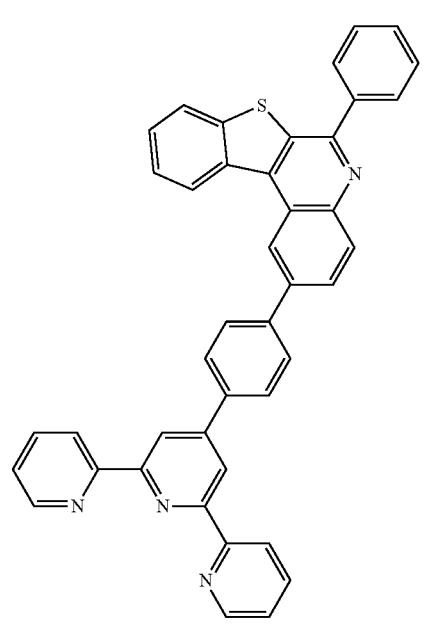
265
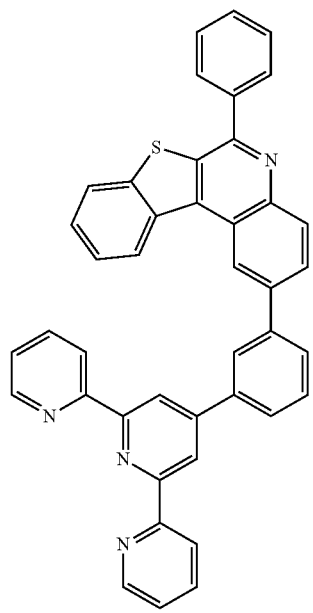
266
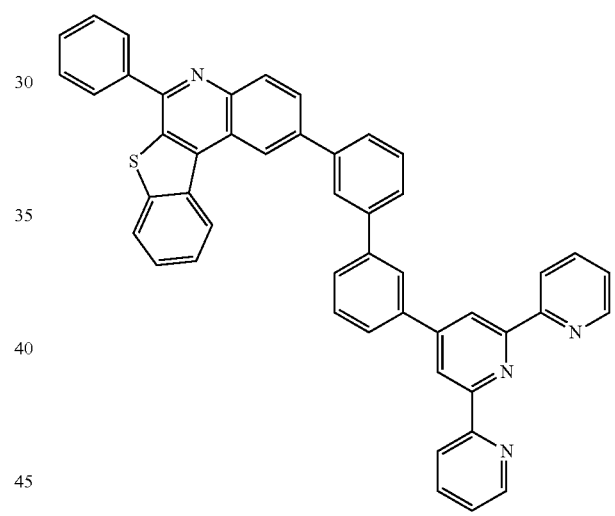
267
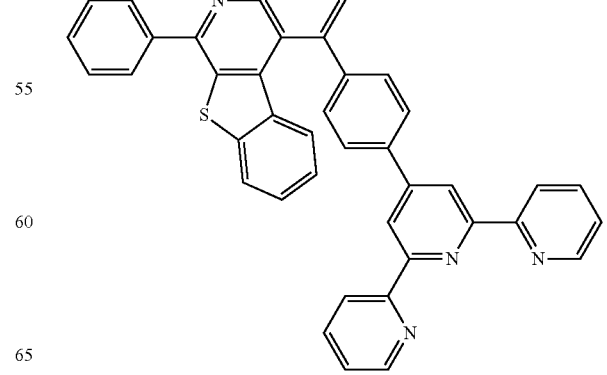
268

139
-continued
269
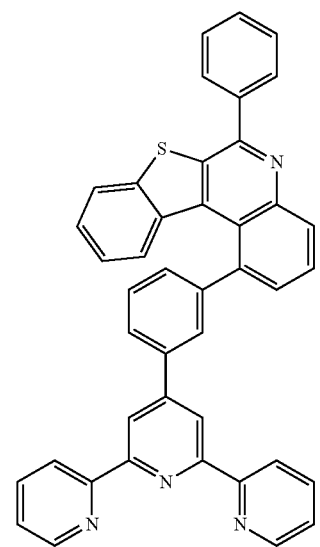
270
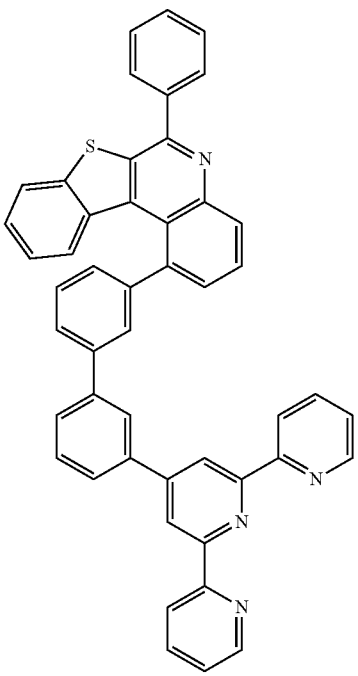
271
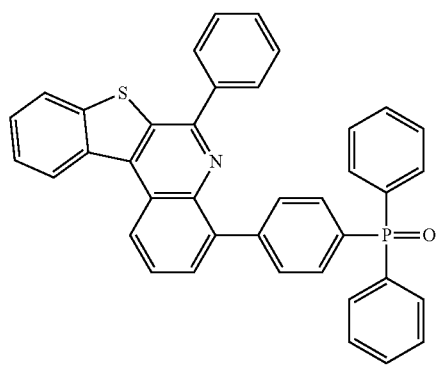
140
-continued
272
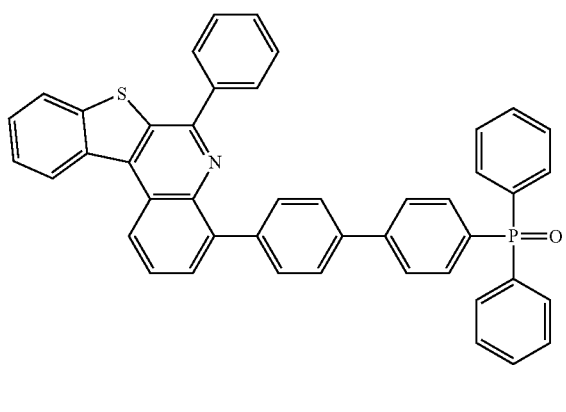
273
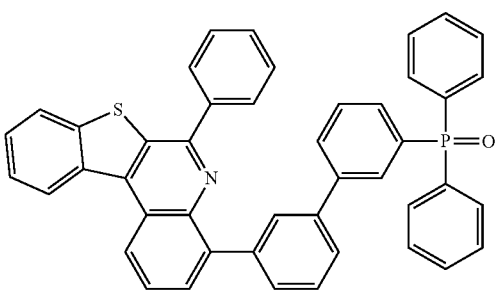
274
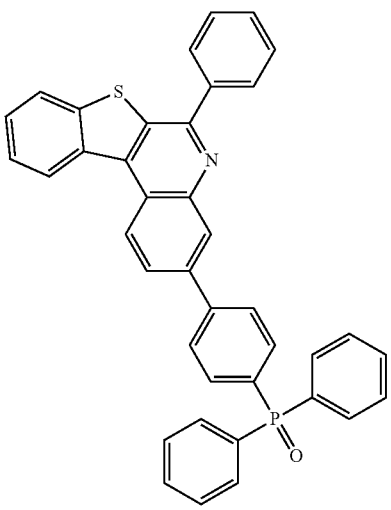

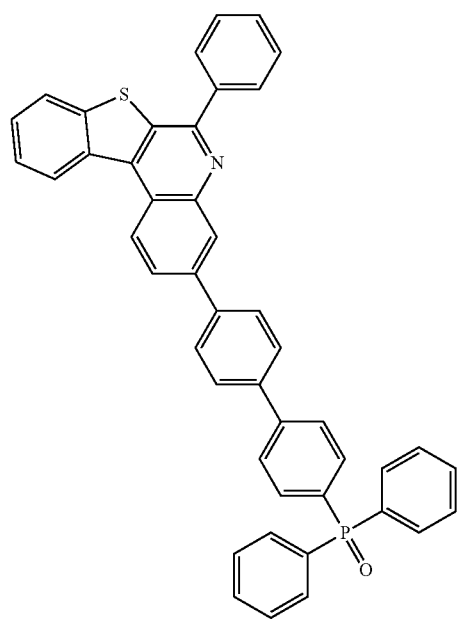
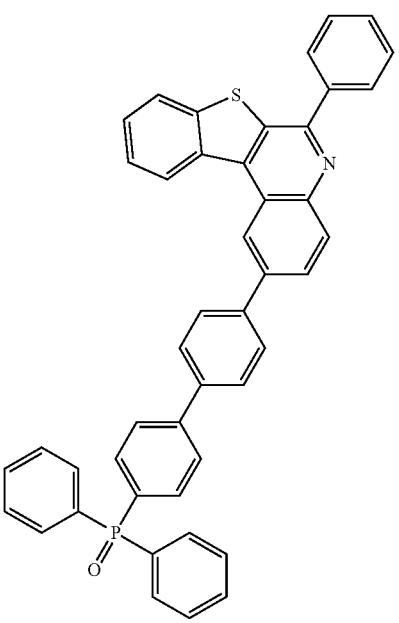

281
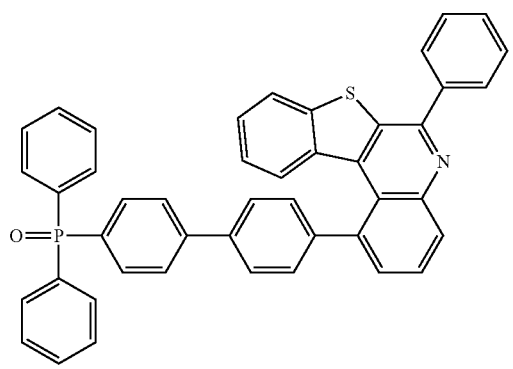
282
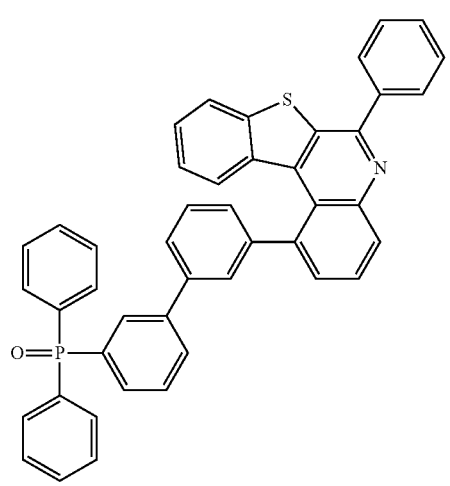
283
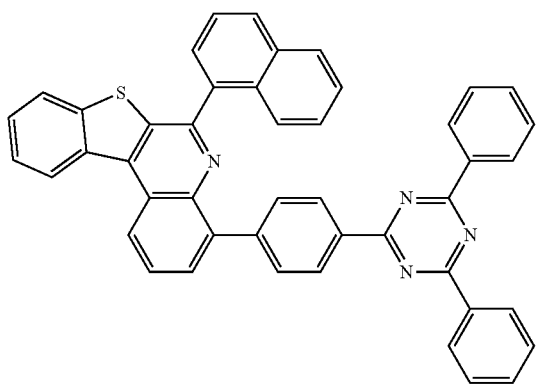
284
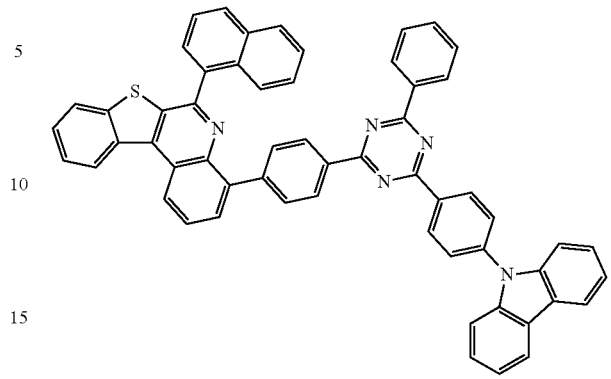
285
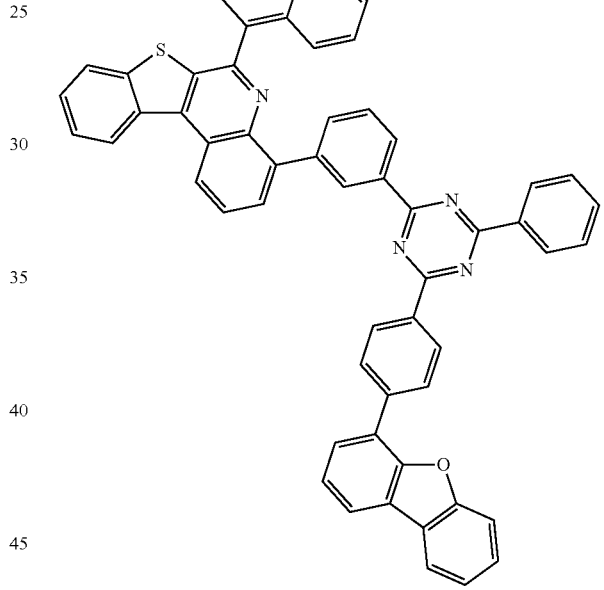
286
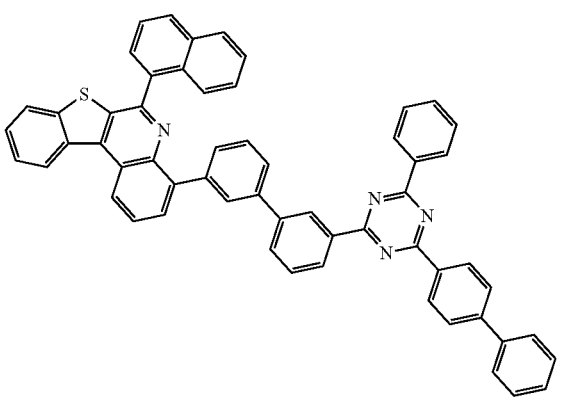

287
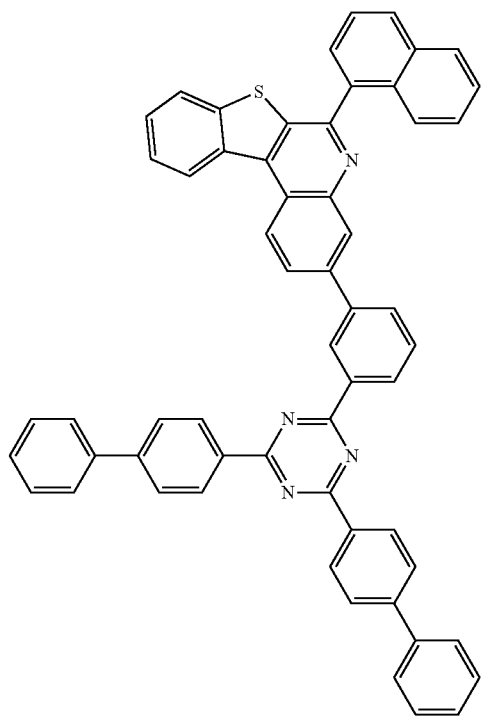
288
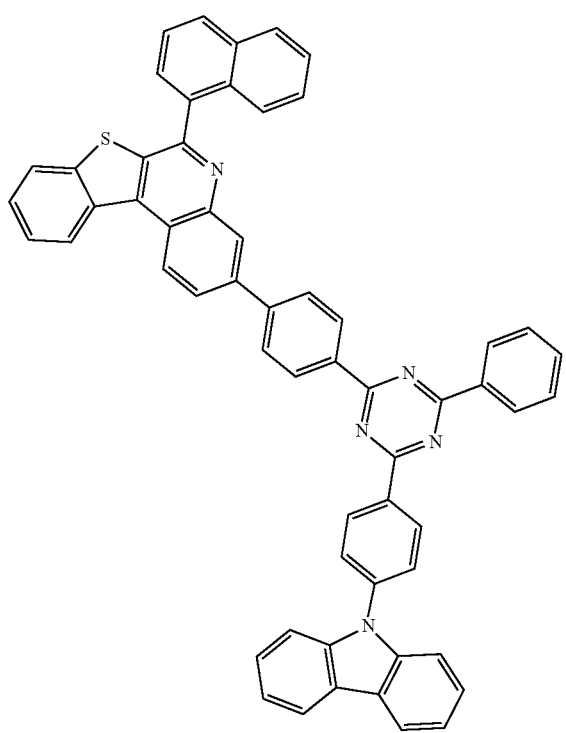
289
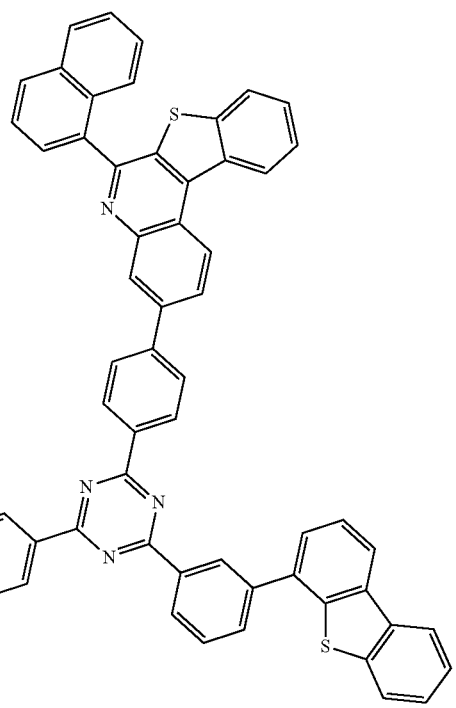
290
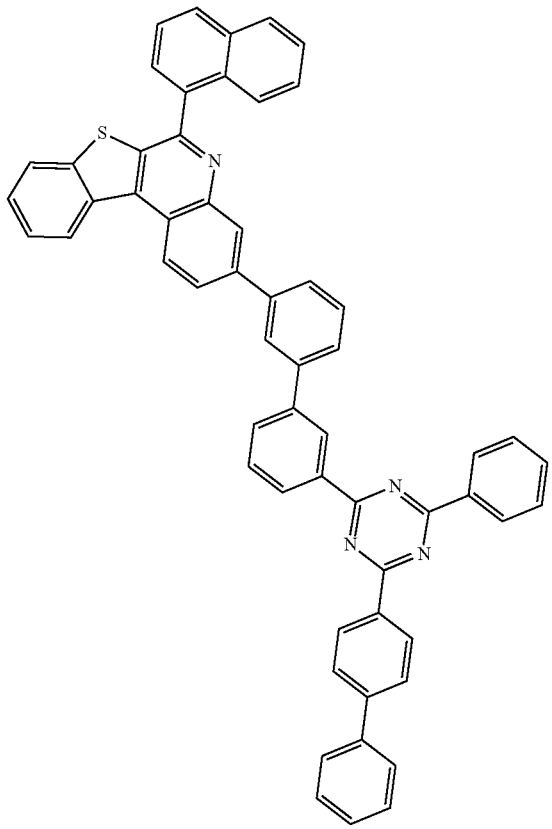

291
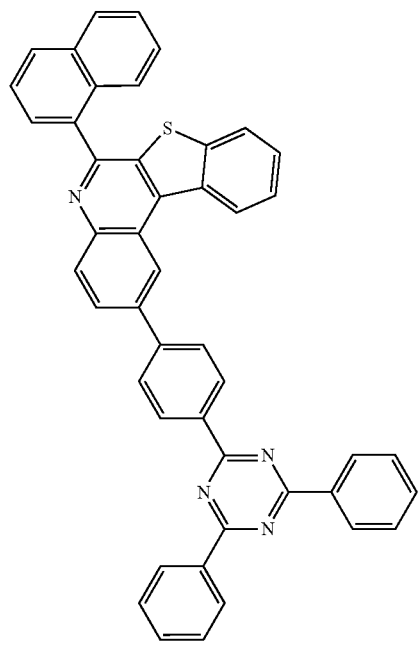
292
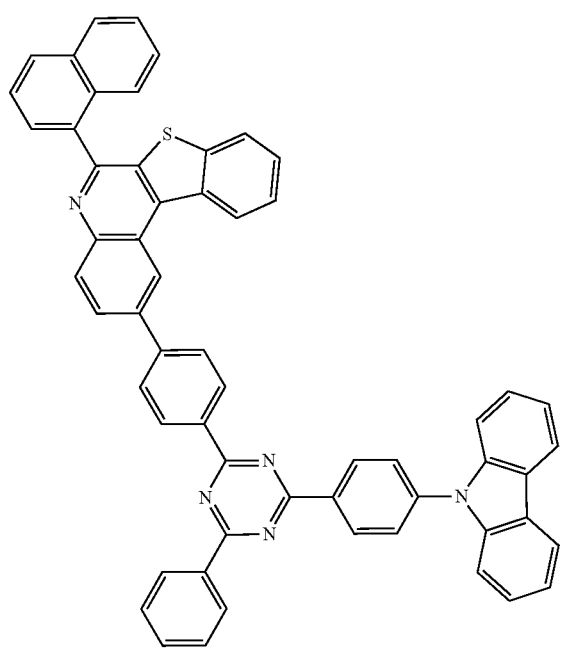
293
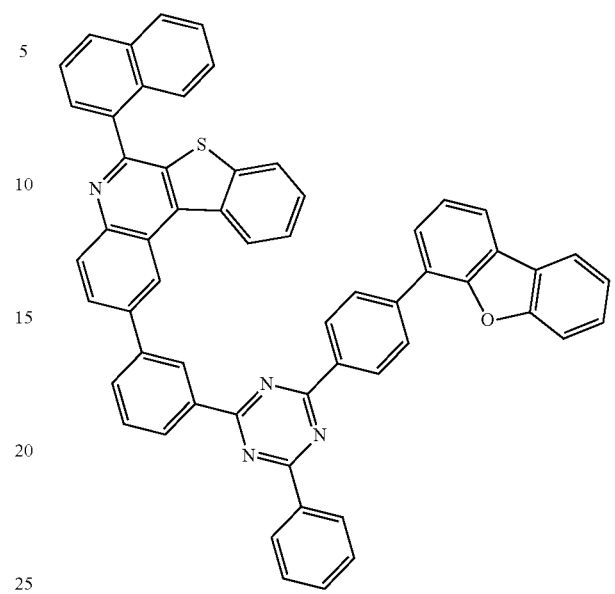
294
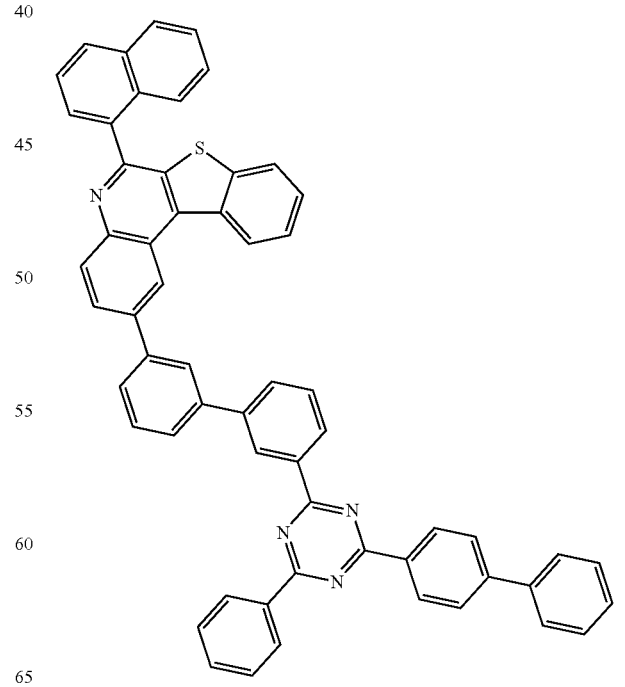

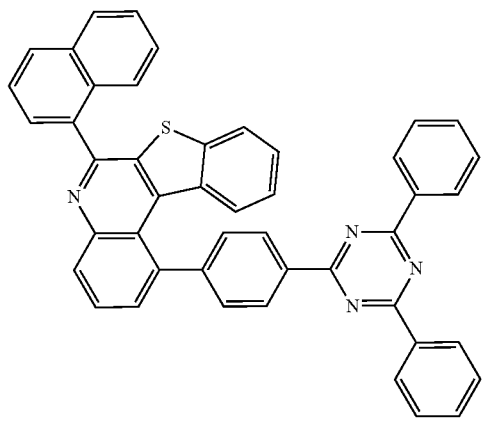
295
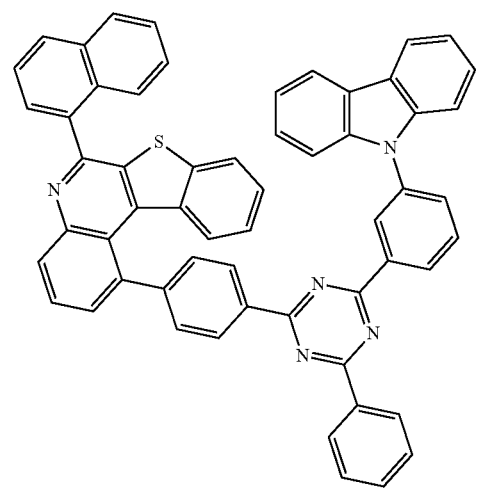
296
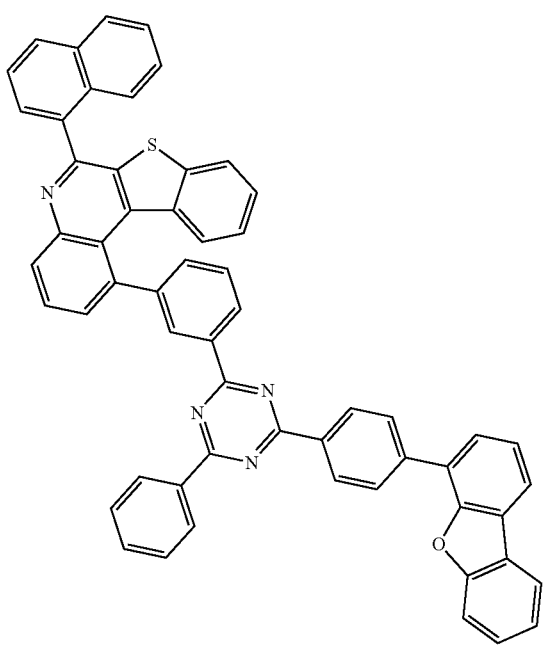
297
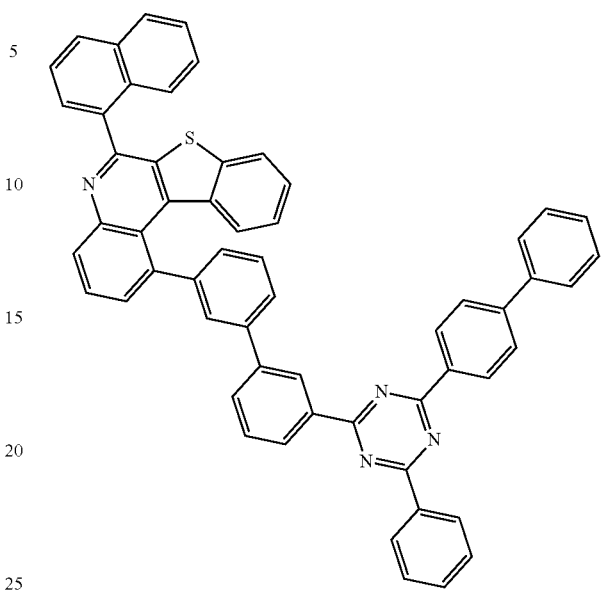
298
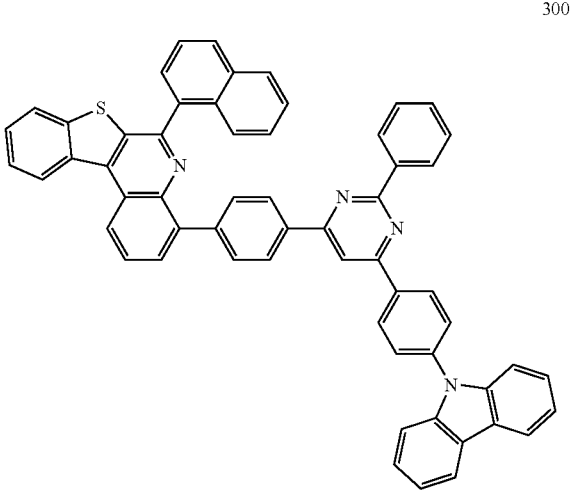
299
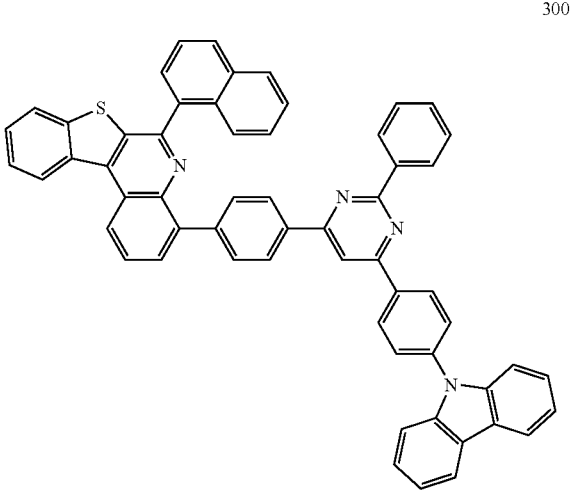
300

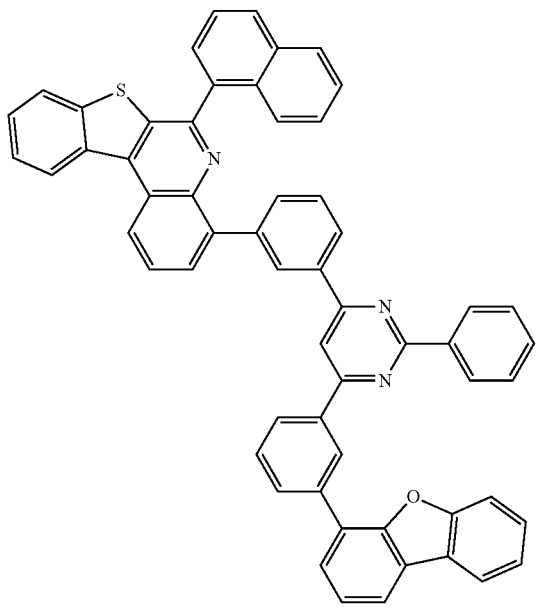
301
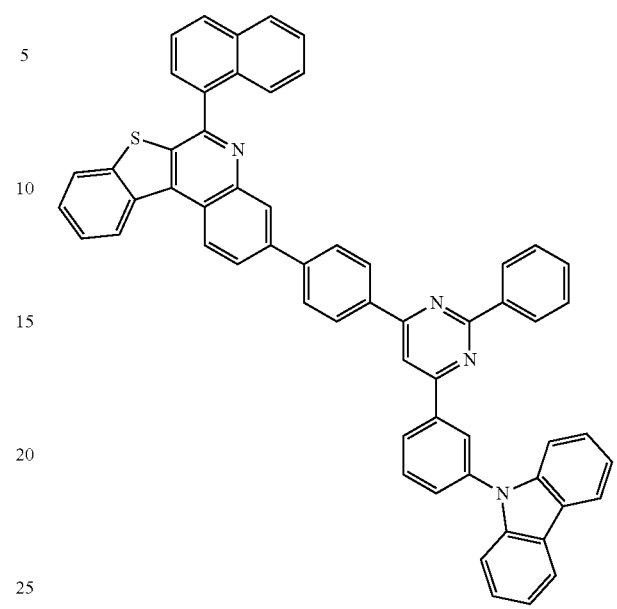
304
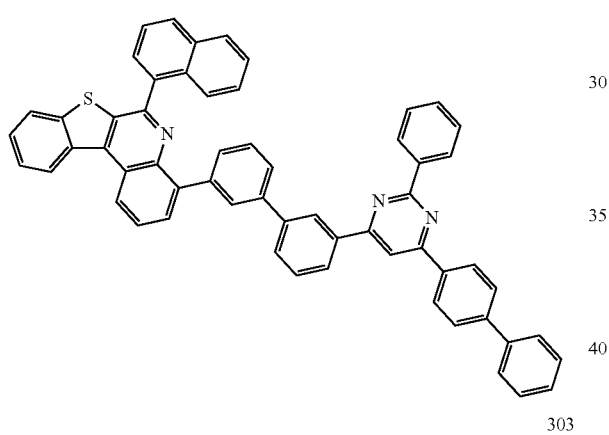
302
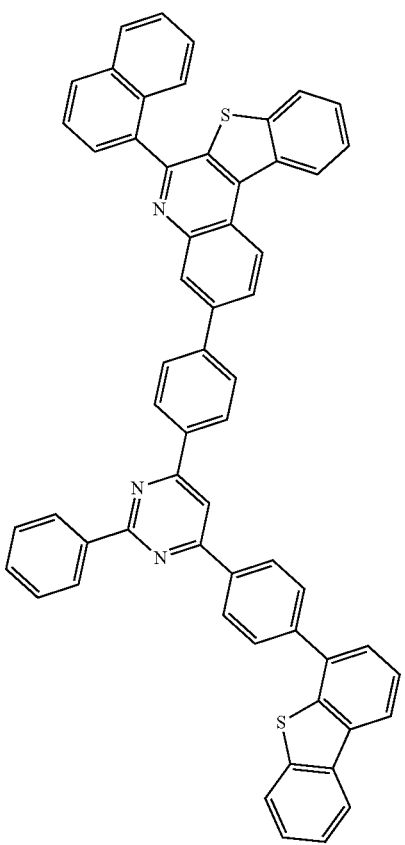
305
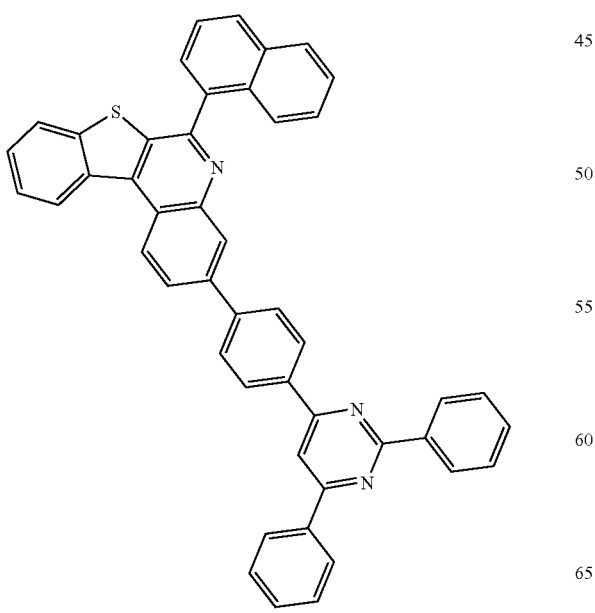
303

153
-continued
306
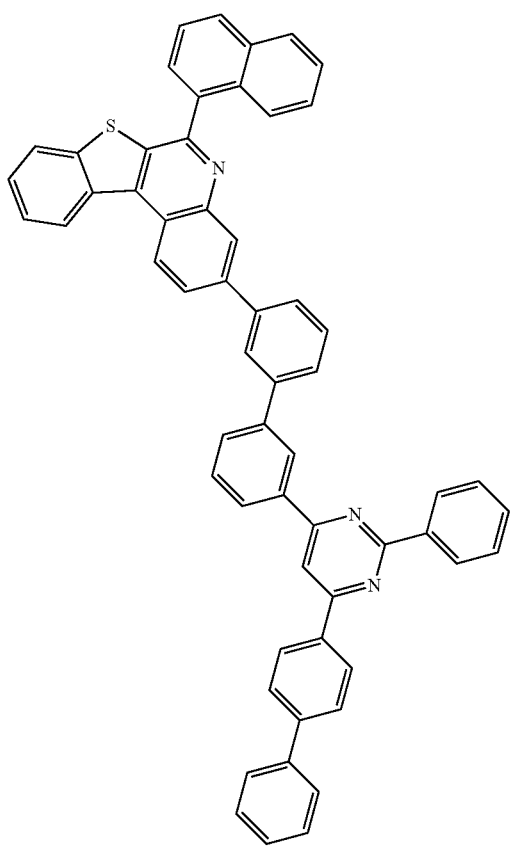
307
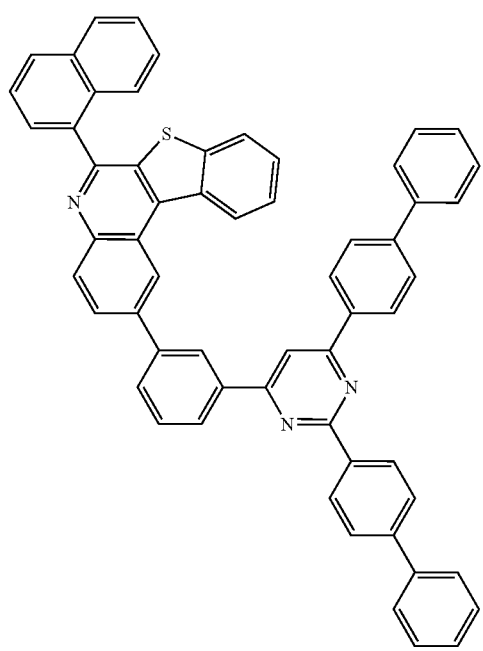
154
-continued
308
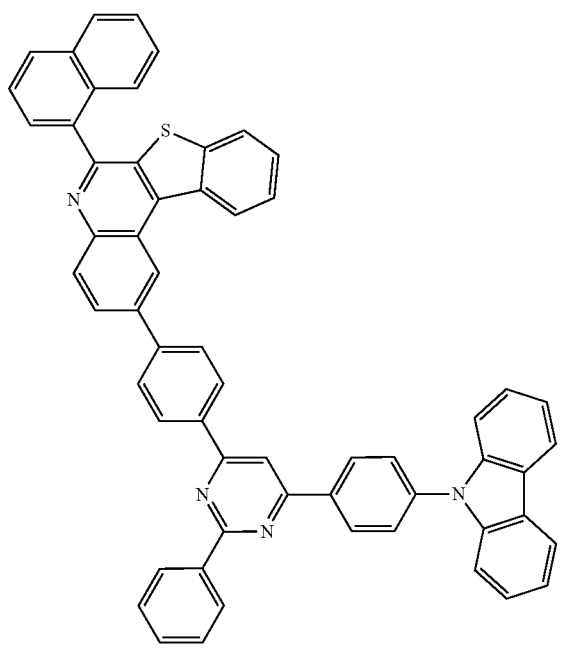
309
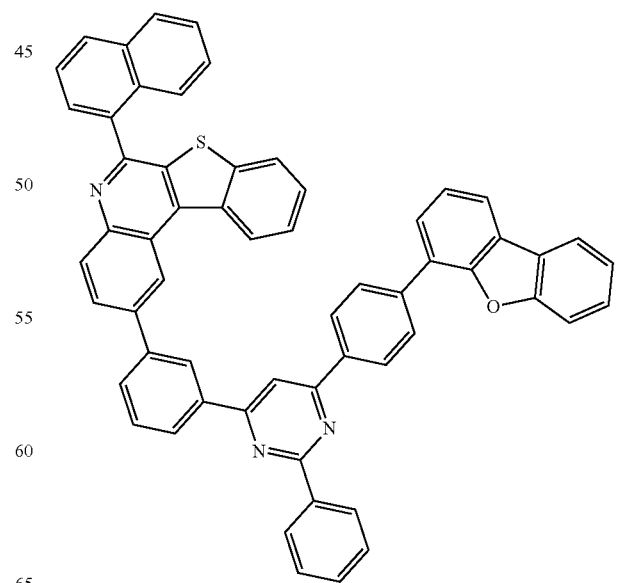

310
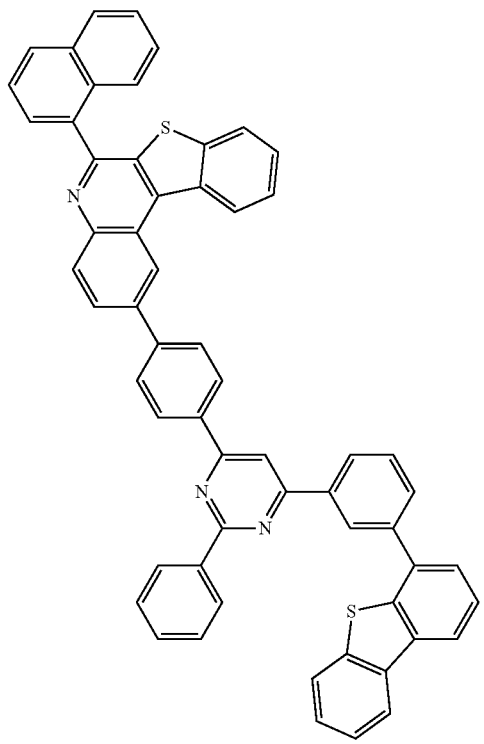
311
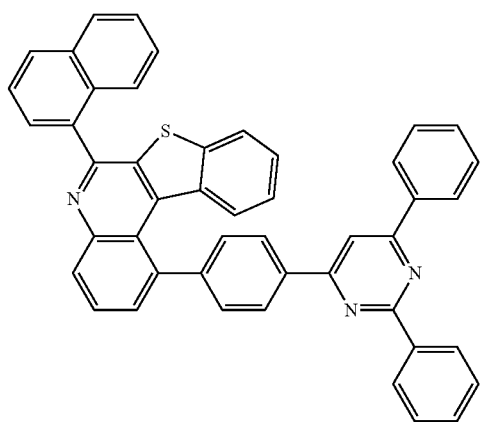
312
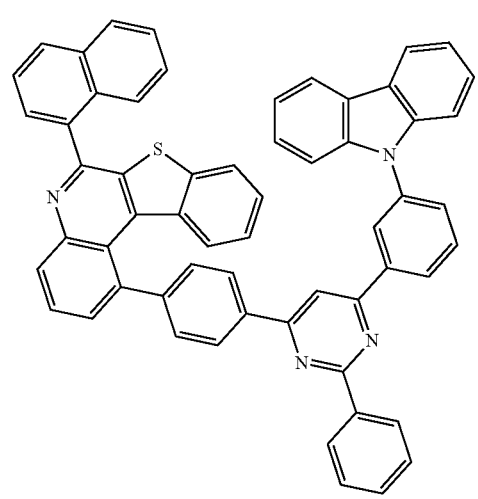
313
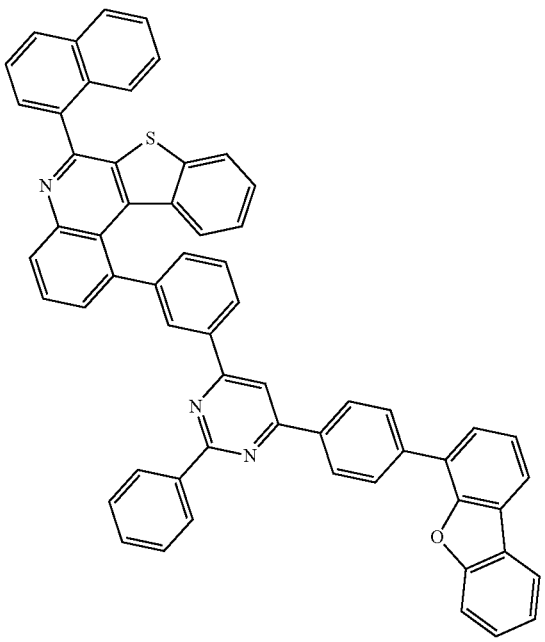
314
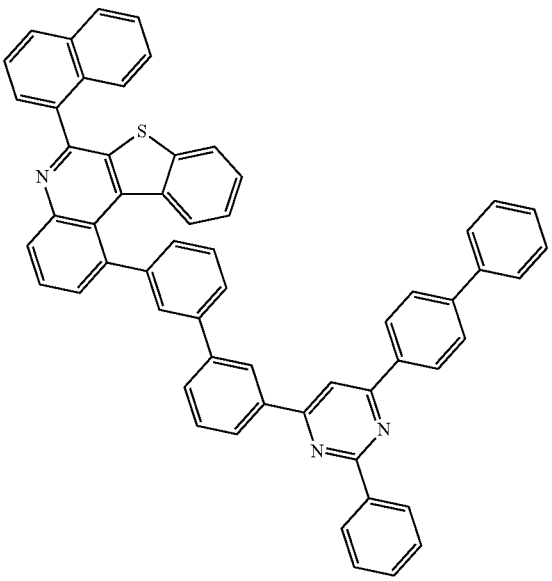

315
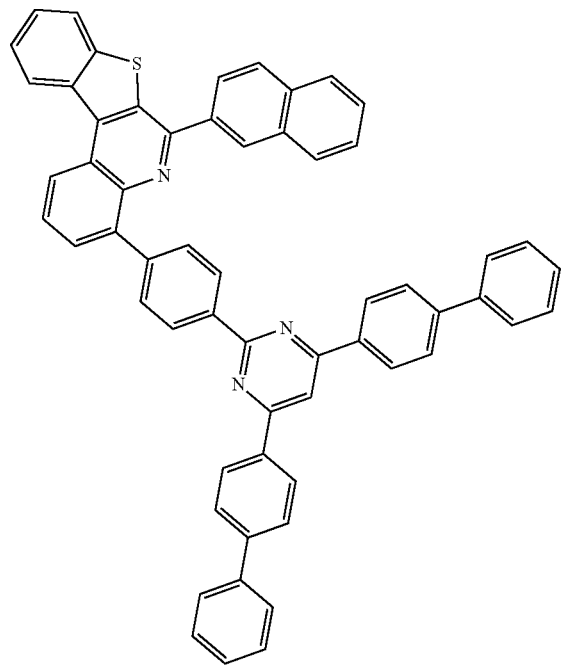
316
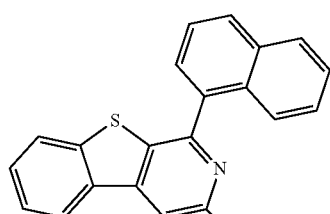
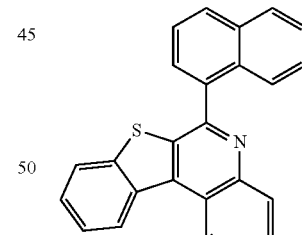
317
318
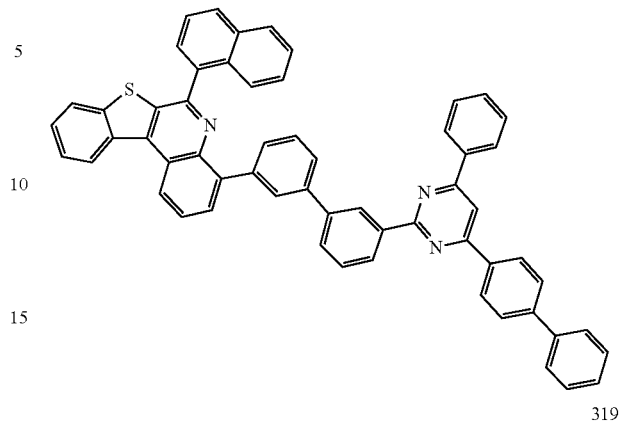
319
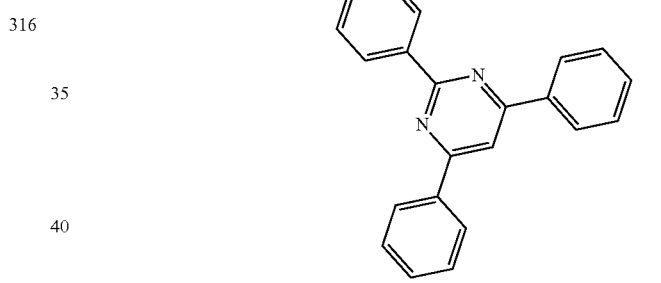
320
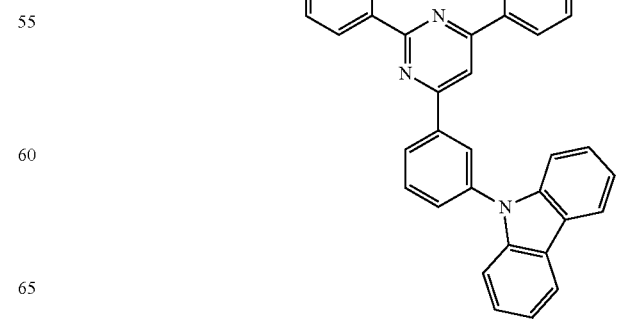

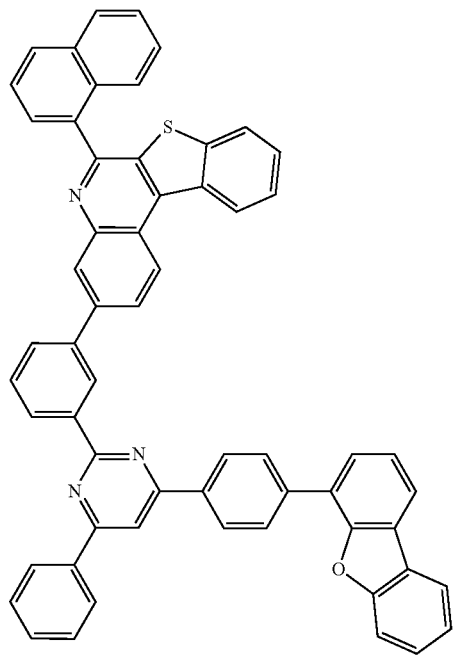
321
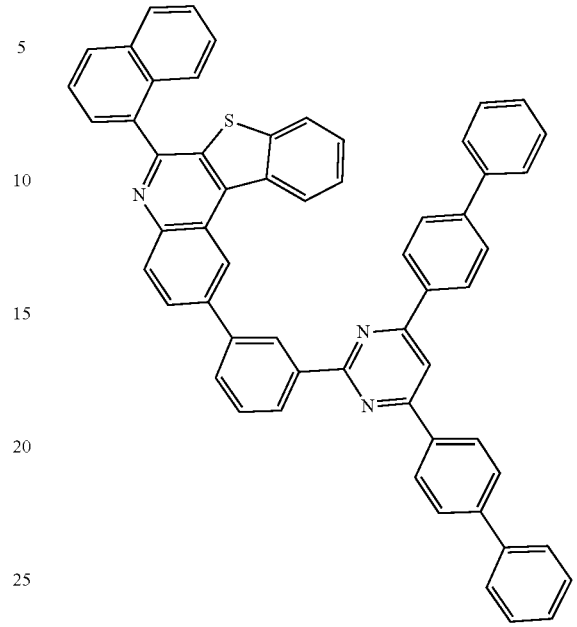
323
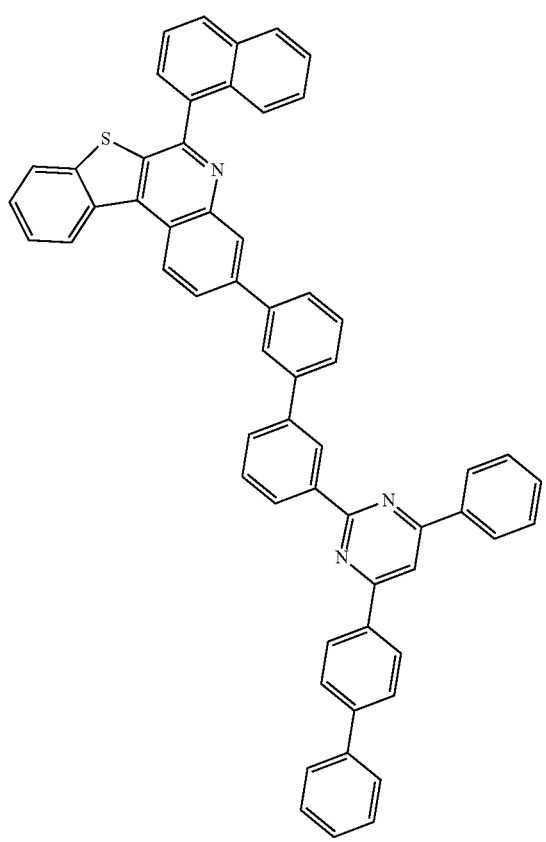
322
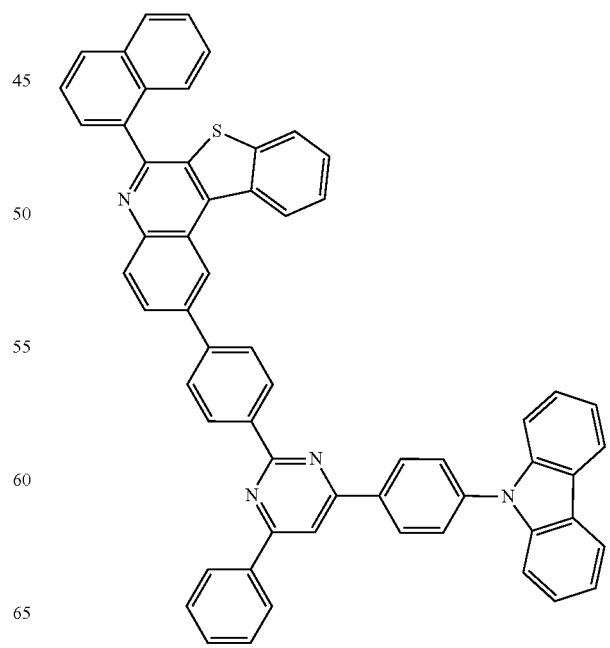
324

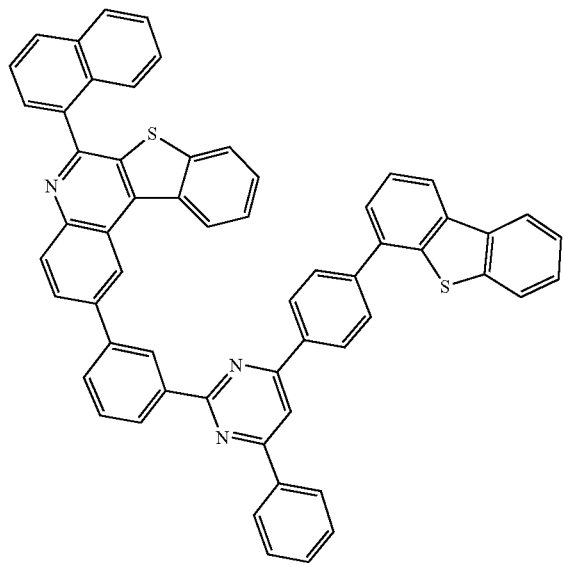
325
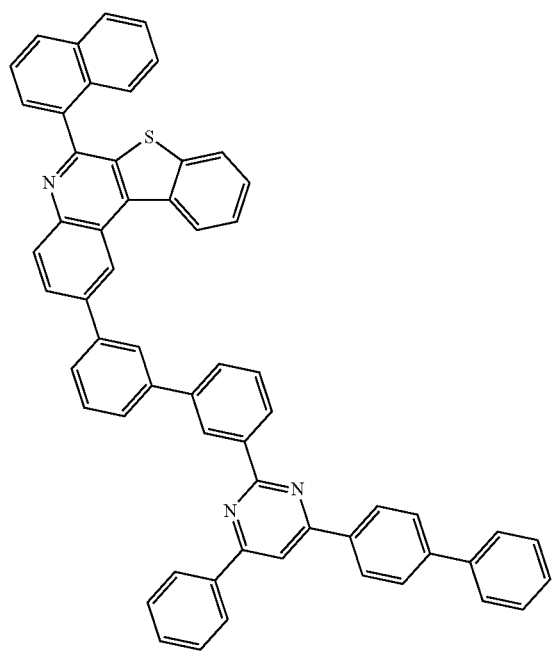
326
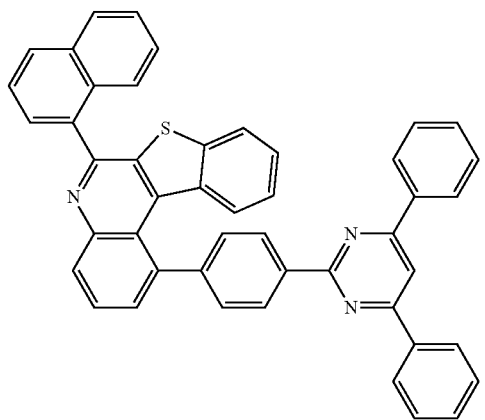
327
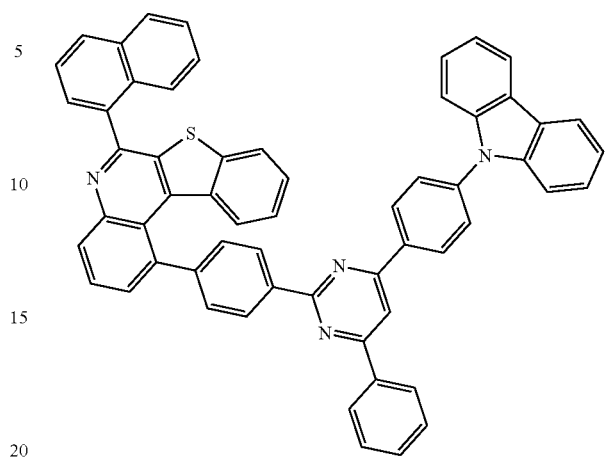
328
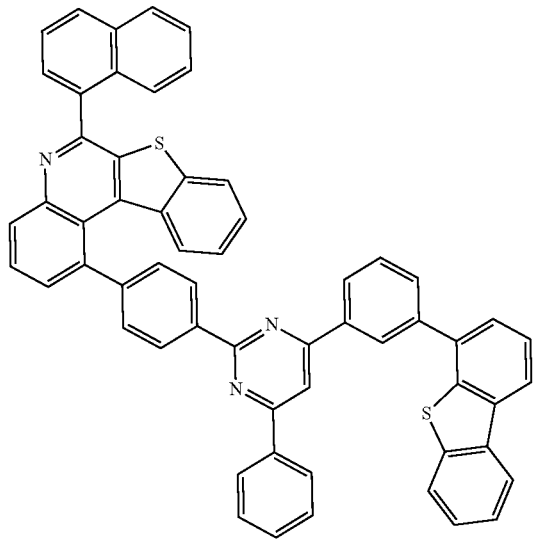
329

330
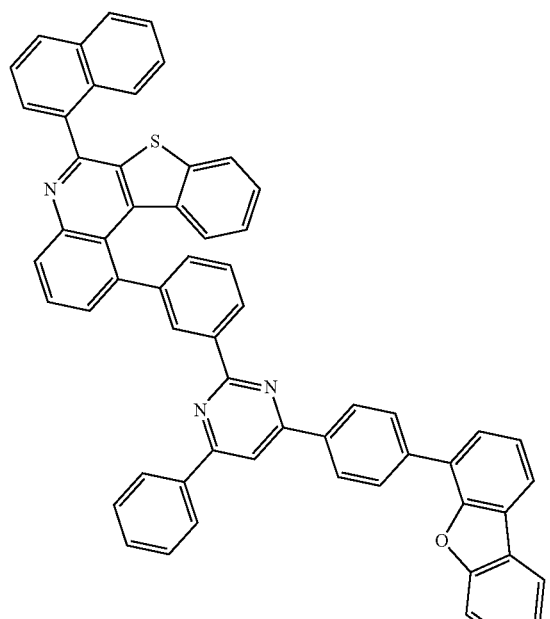
331
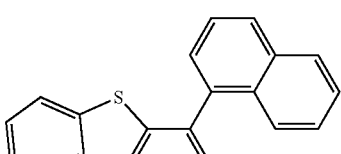
332
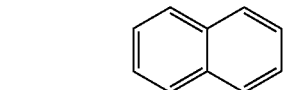
333
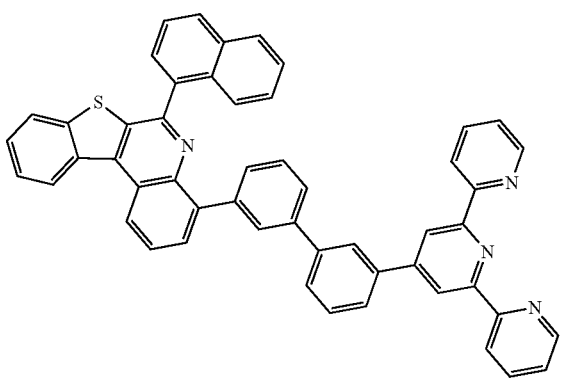
334
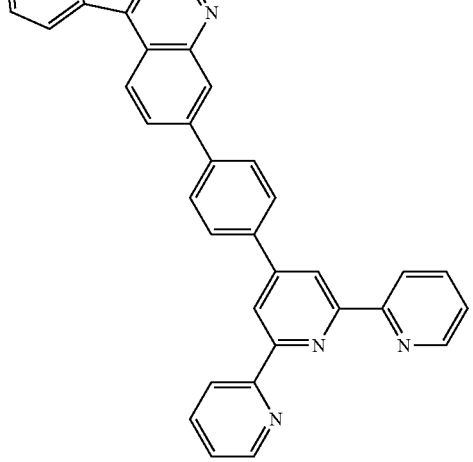
335
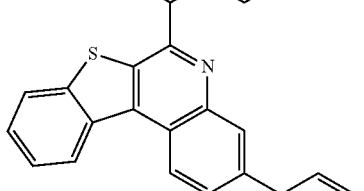
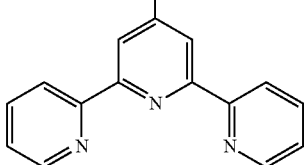

336
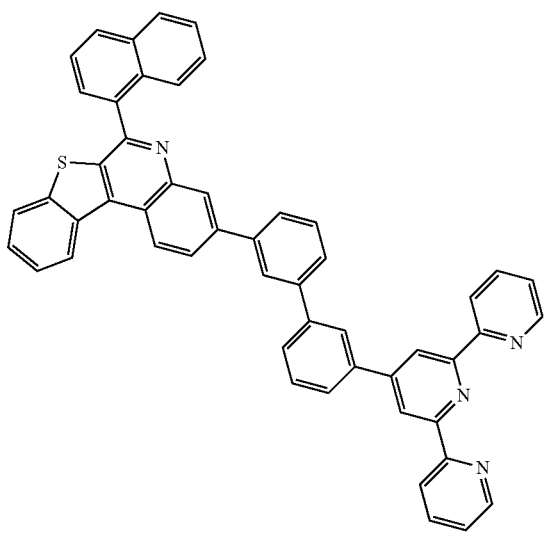
337
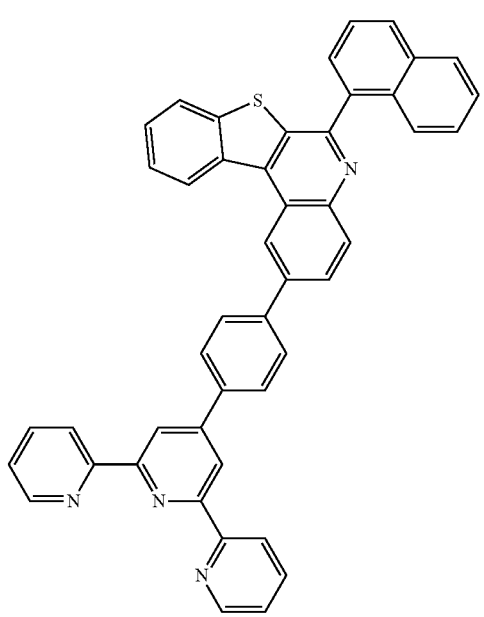
338
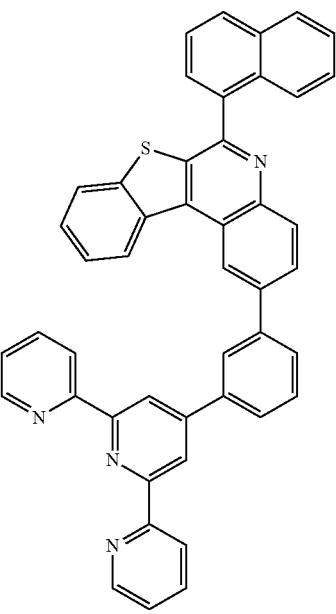
339
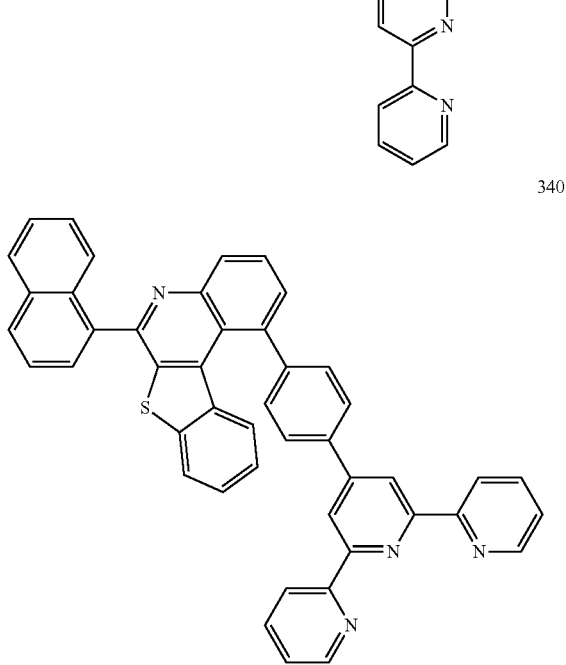
340

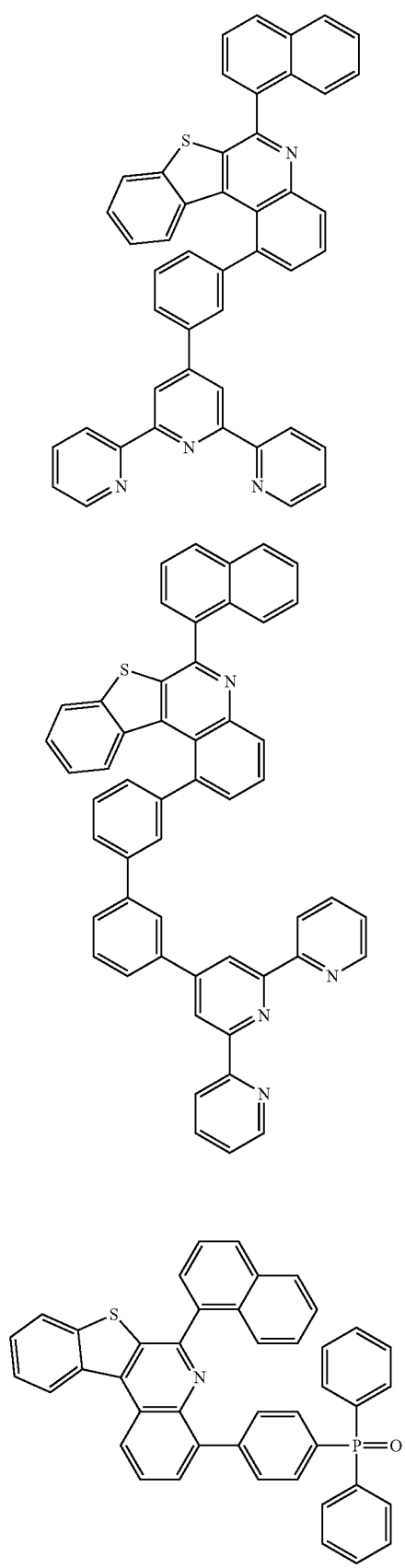
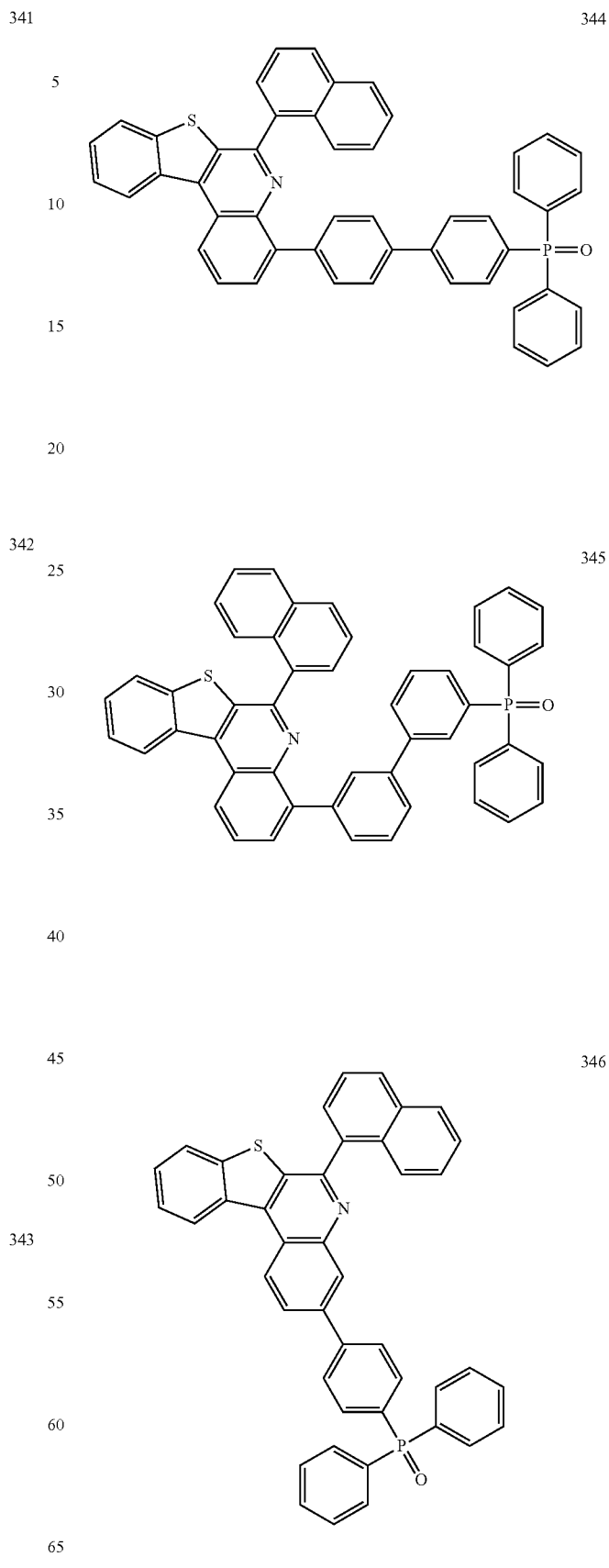

-continued
347
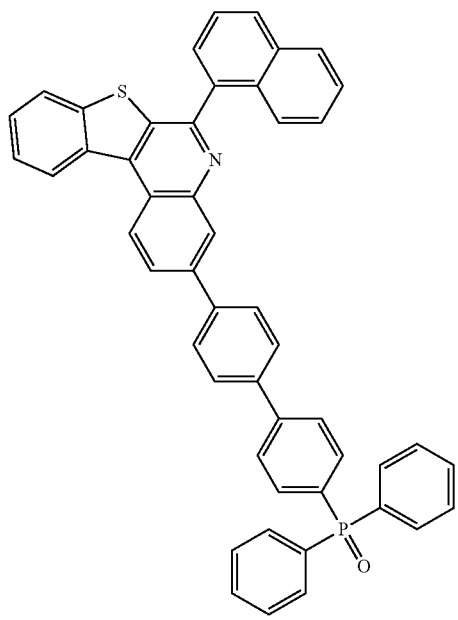
348
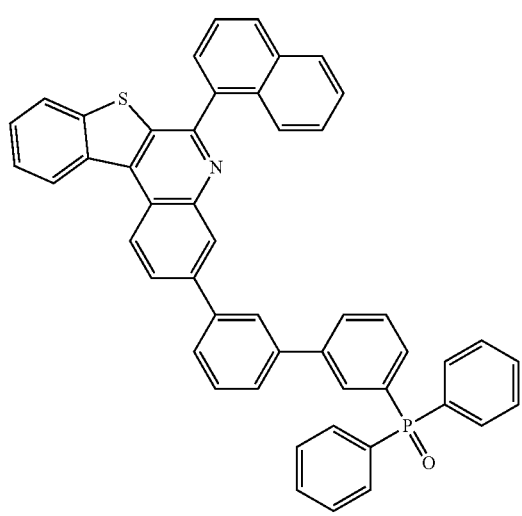
349
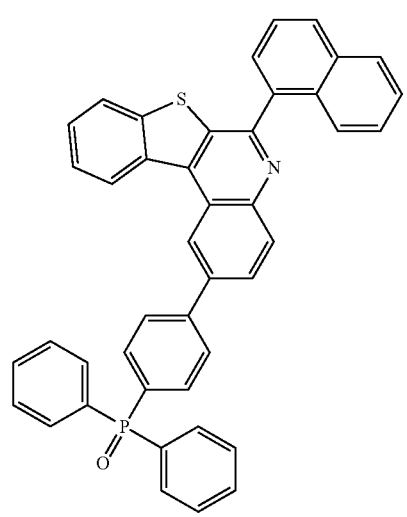
-continued
350
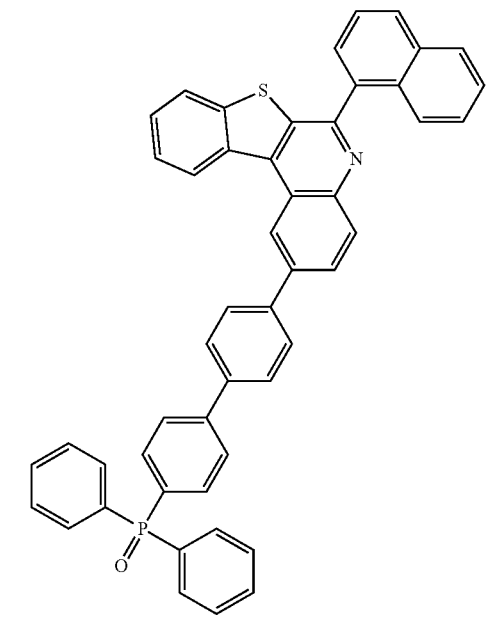
351
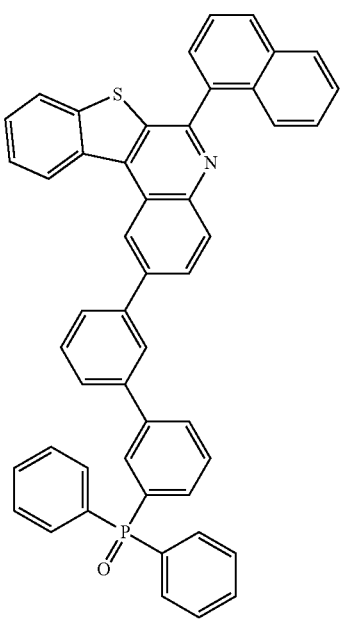
352
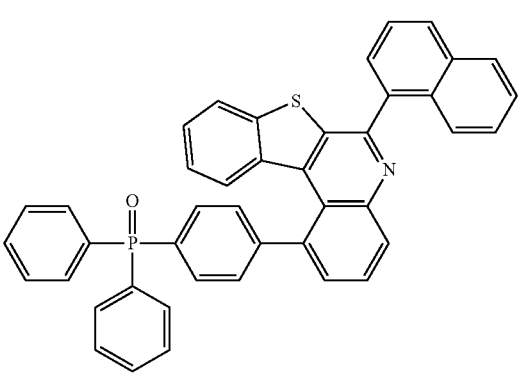

353
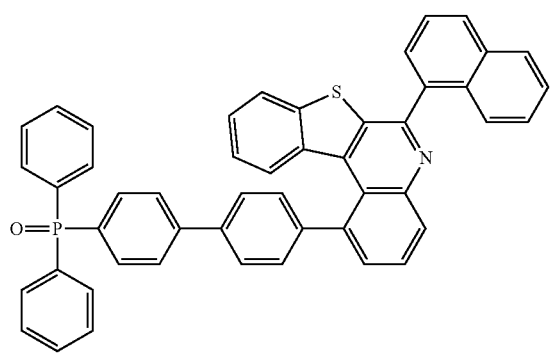
354
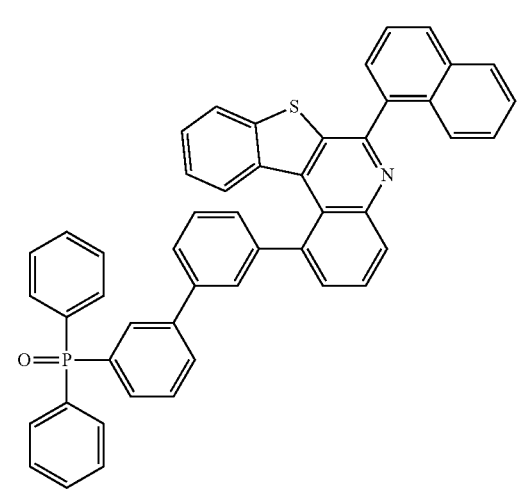
355
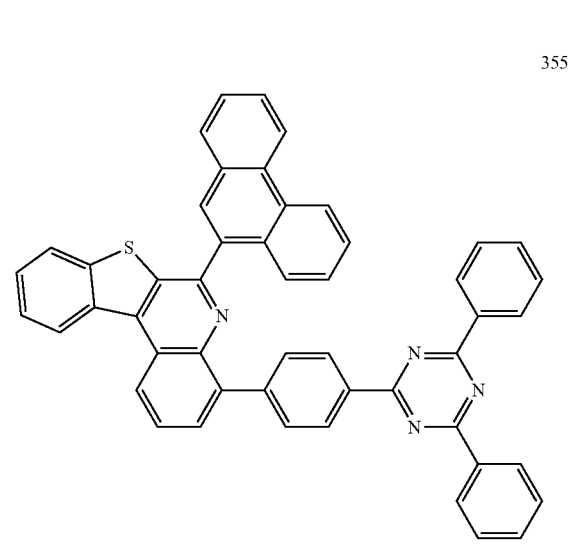
356
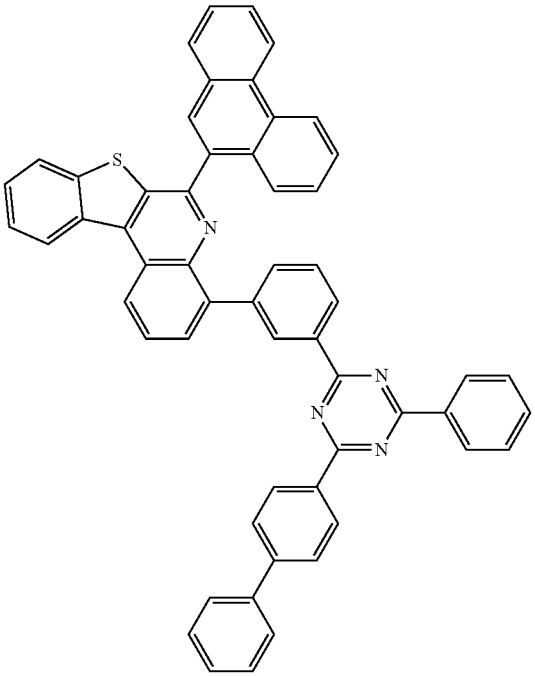
357
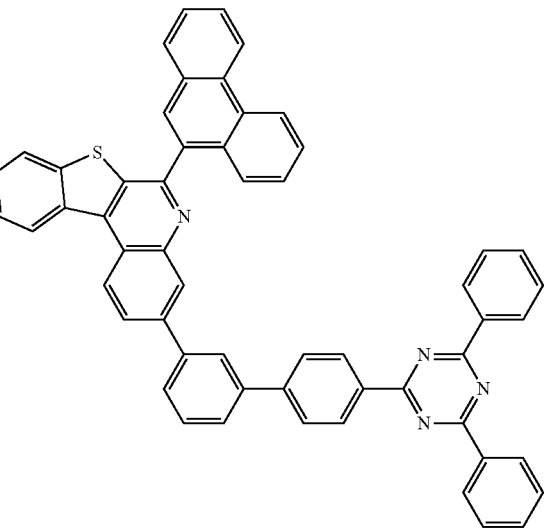

358
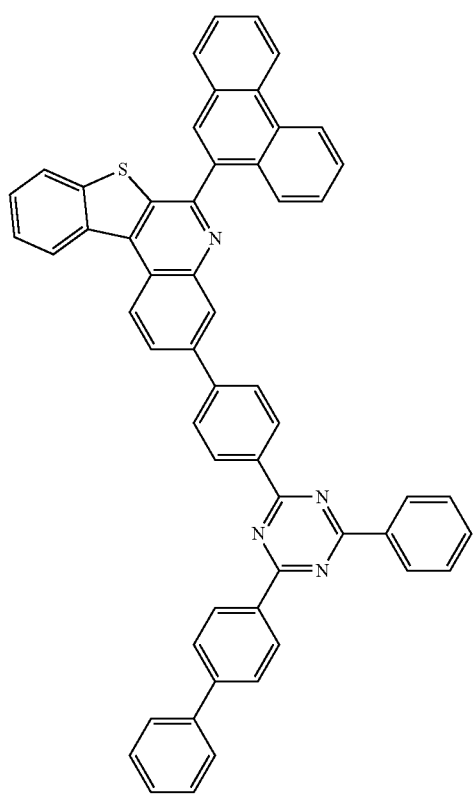
359
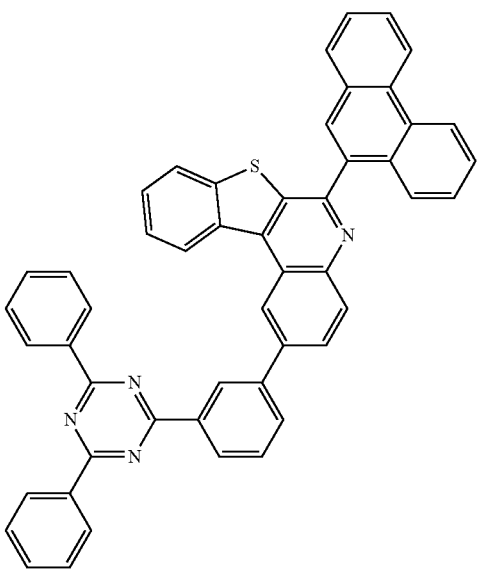
360
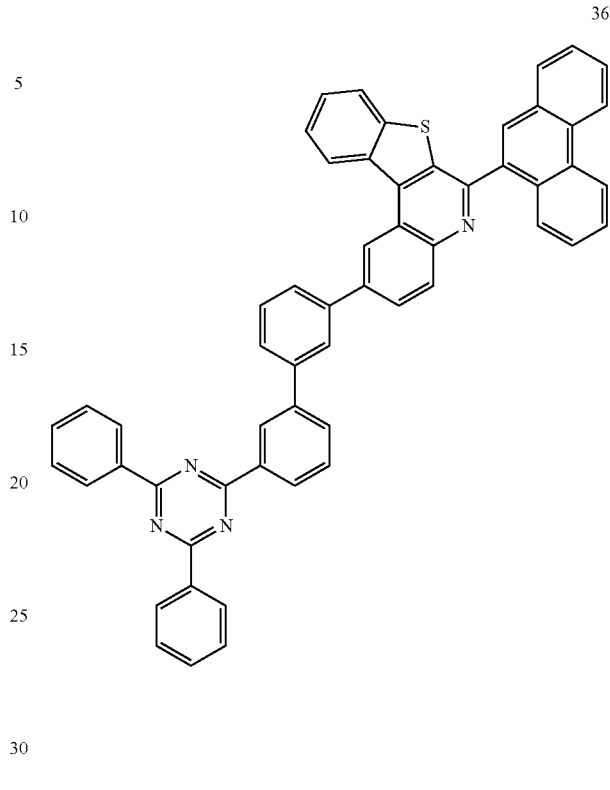
361
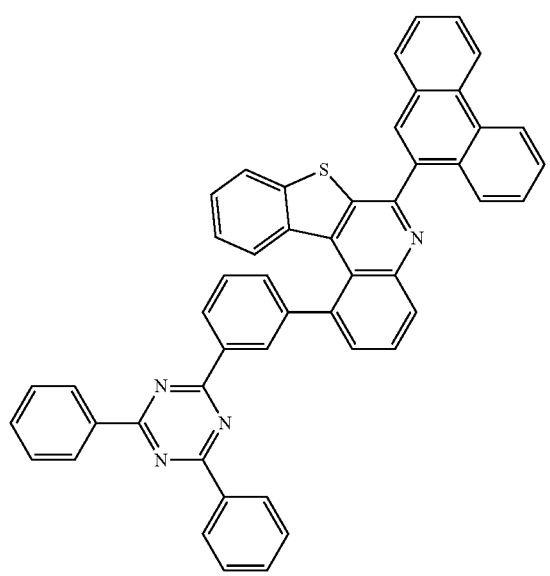

175
-continued
362
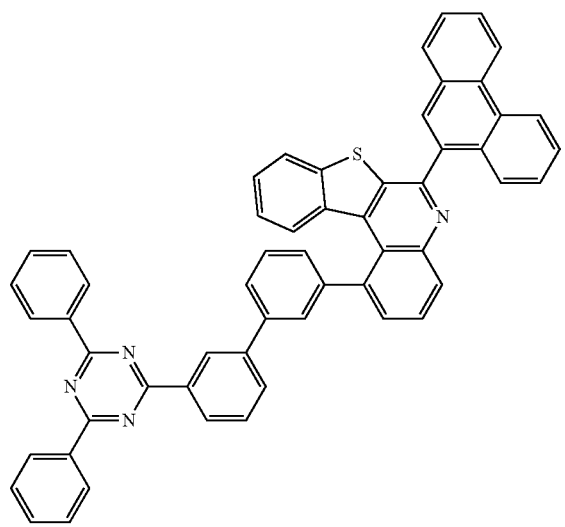
363
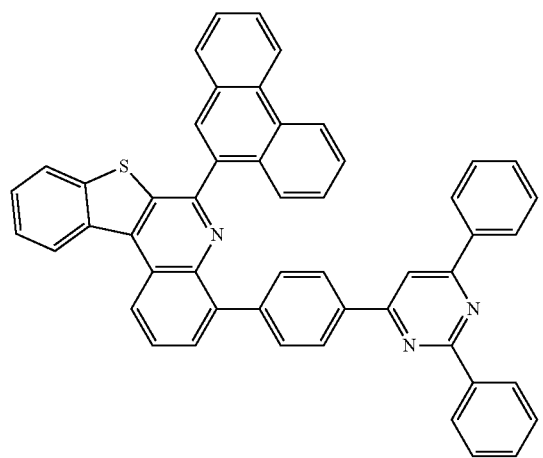
176
-continued
364
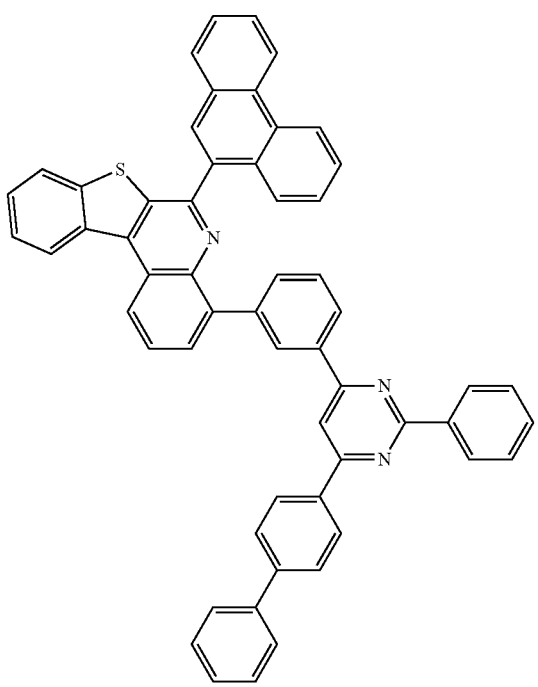
365
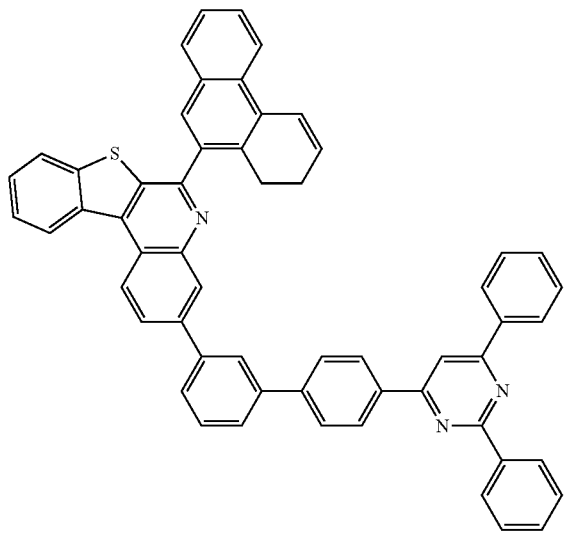

366
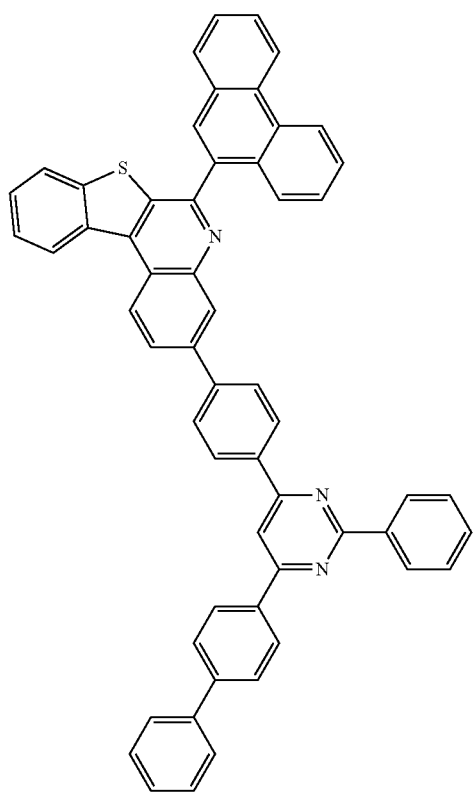
367
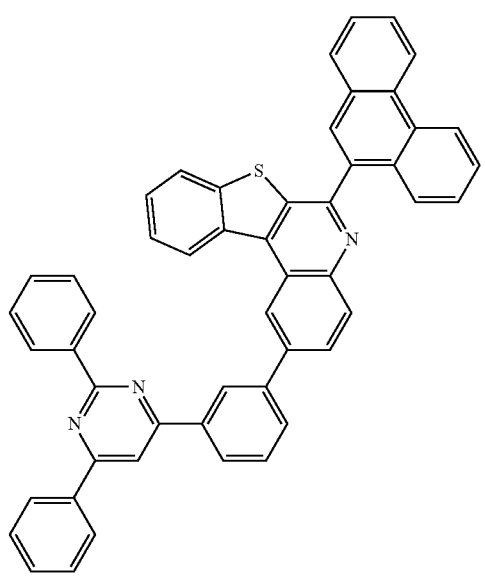
368
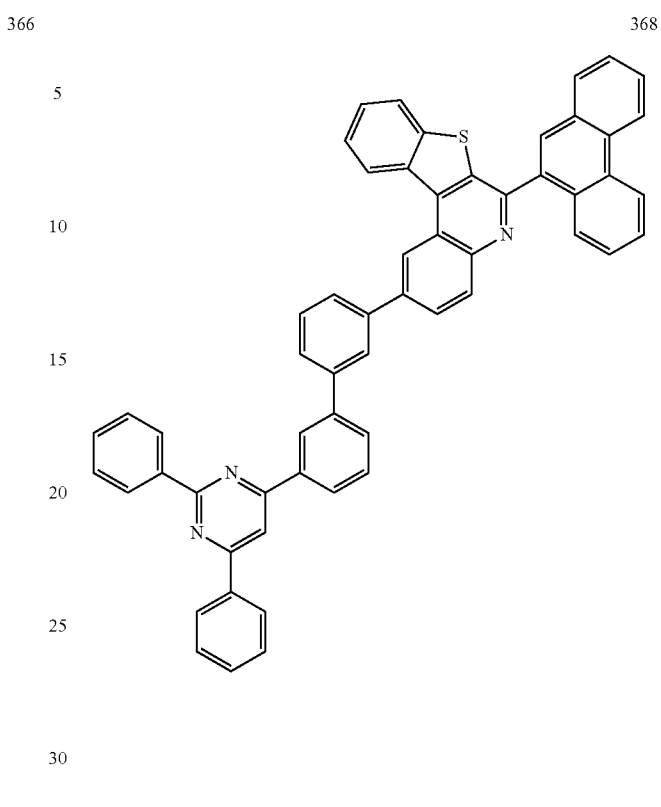
369
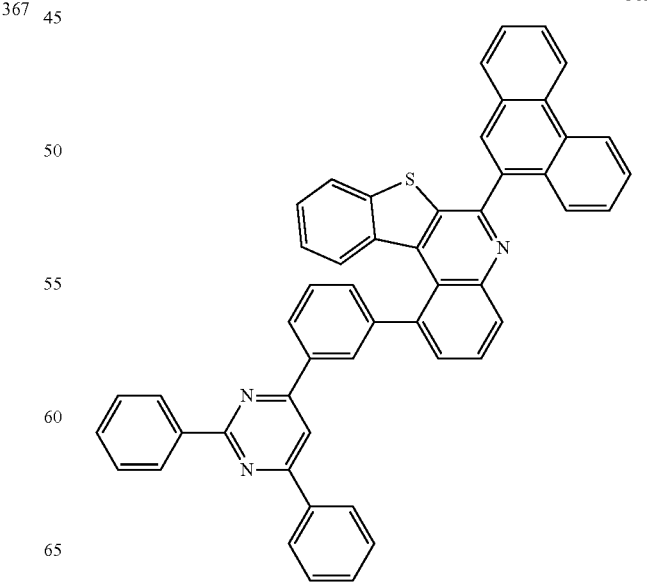

370
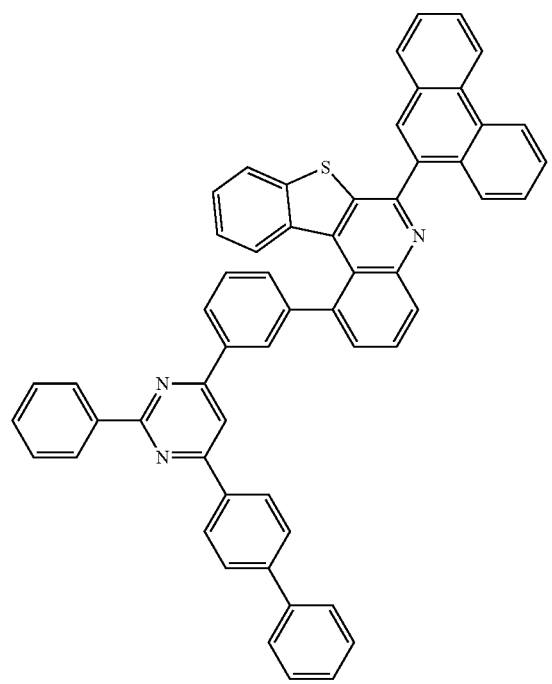
372
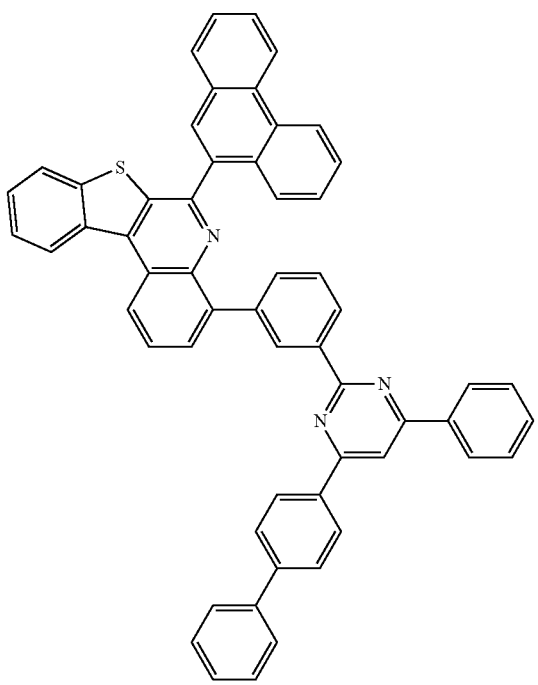
371
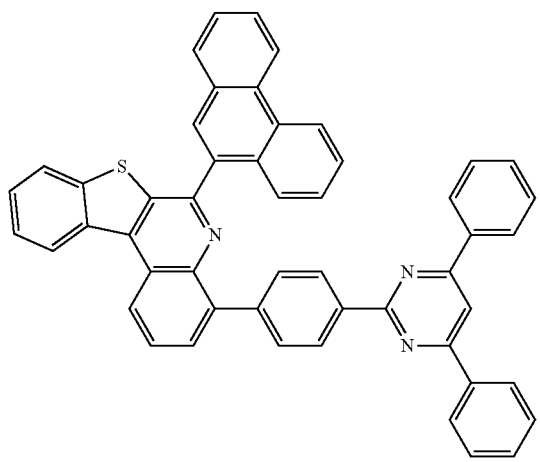
373
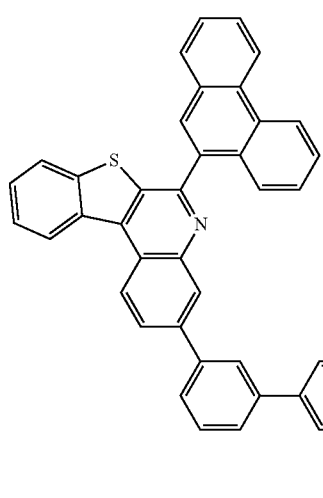

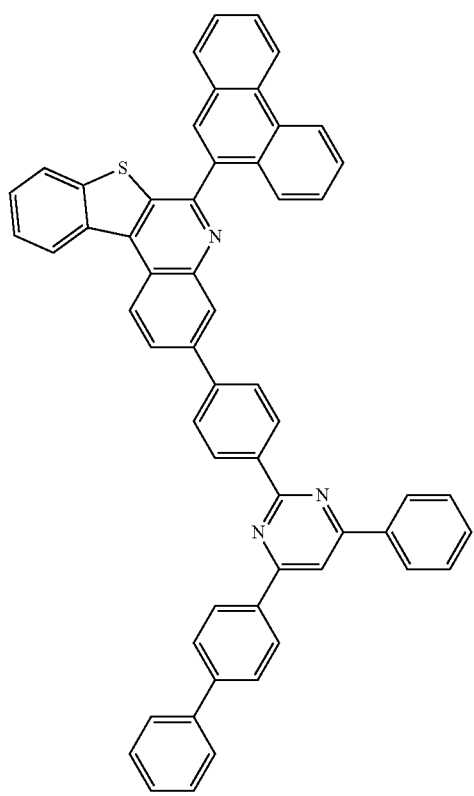
374
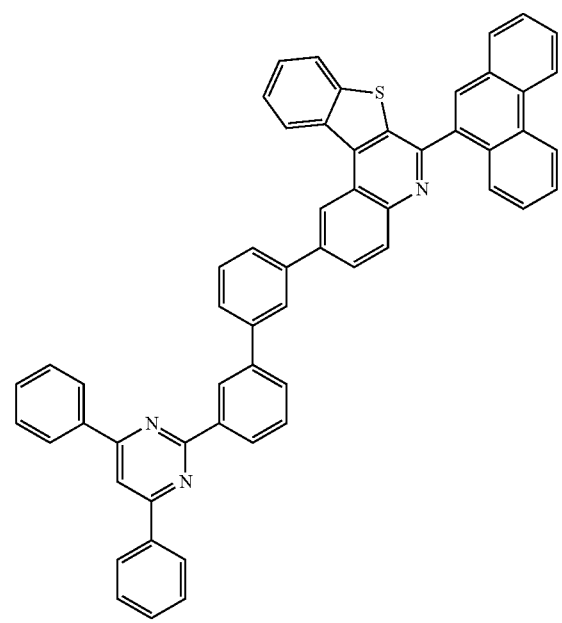
376
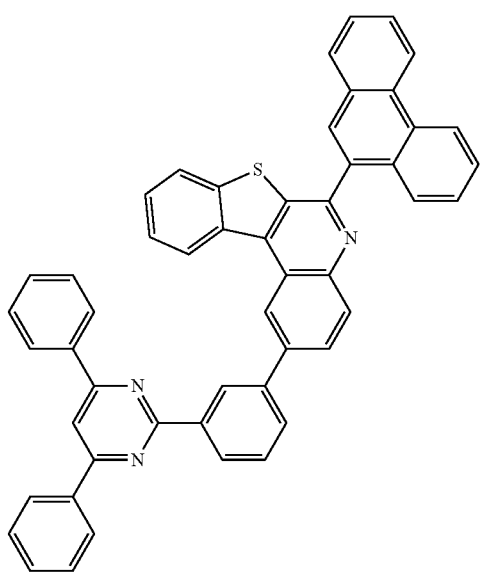
375
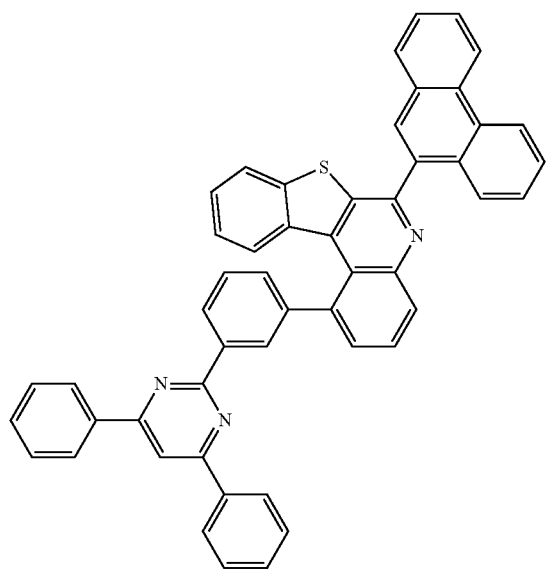
377

-continued
378
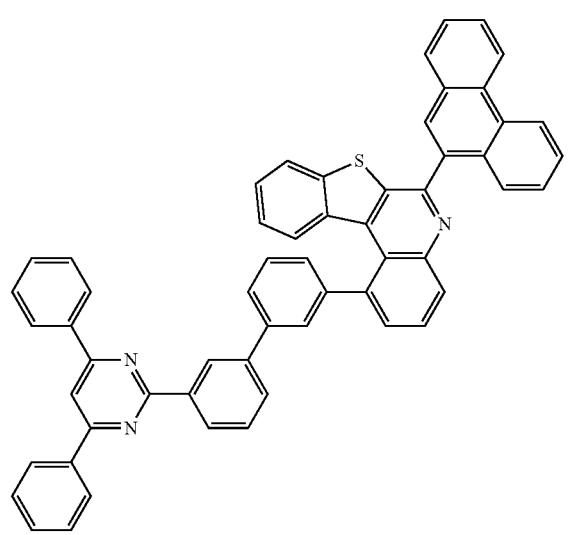
379
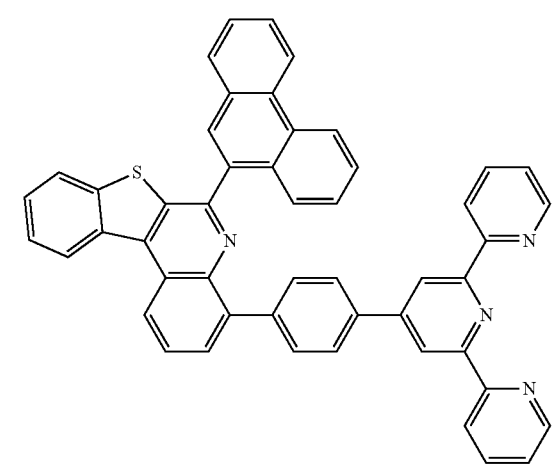
380
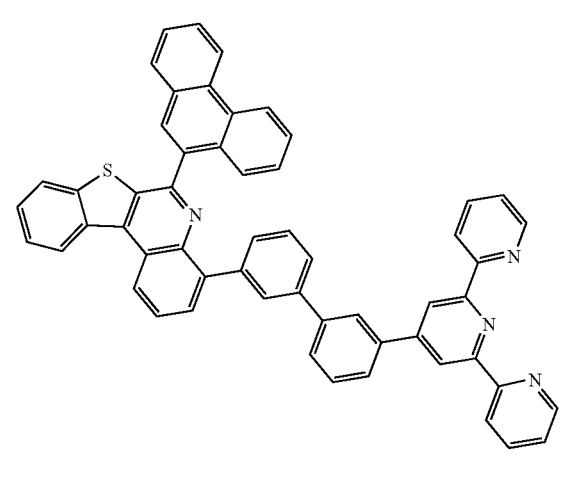
-continued
381
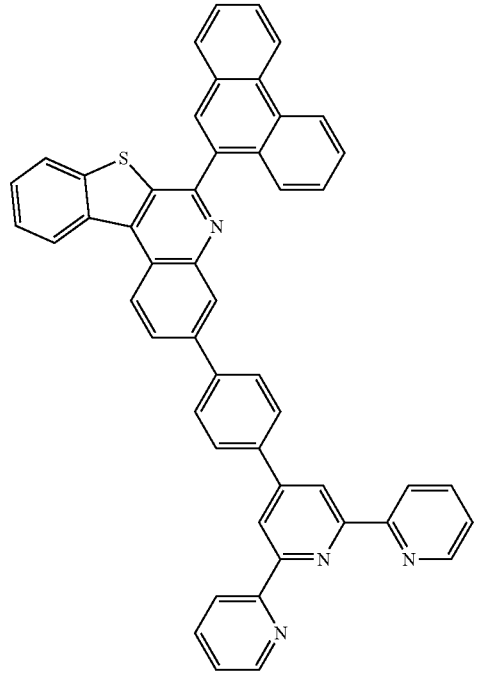
382
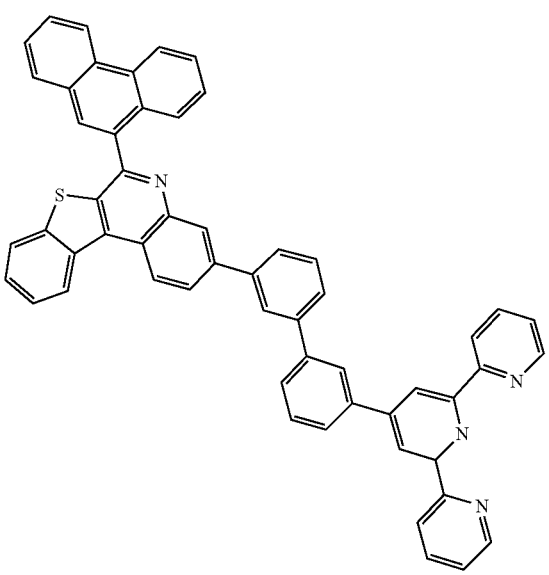

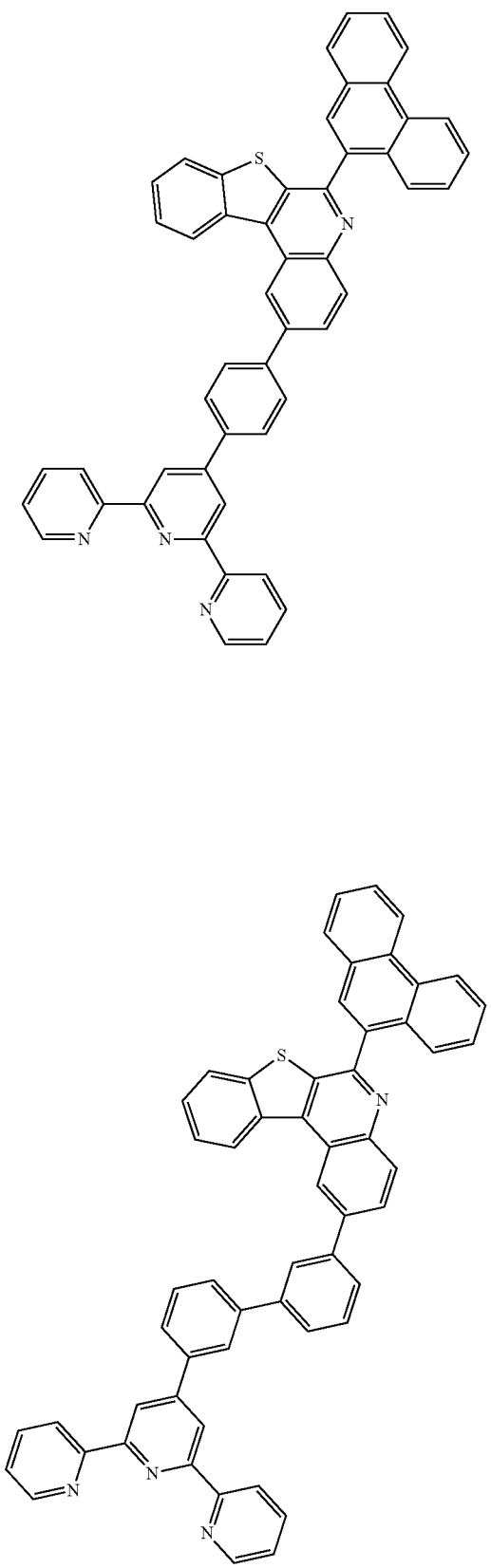
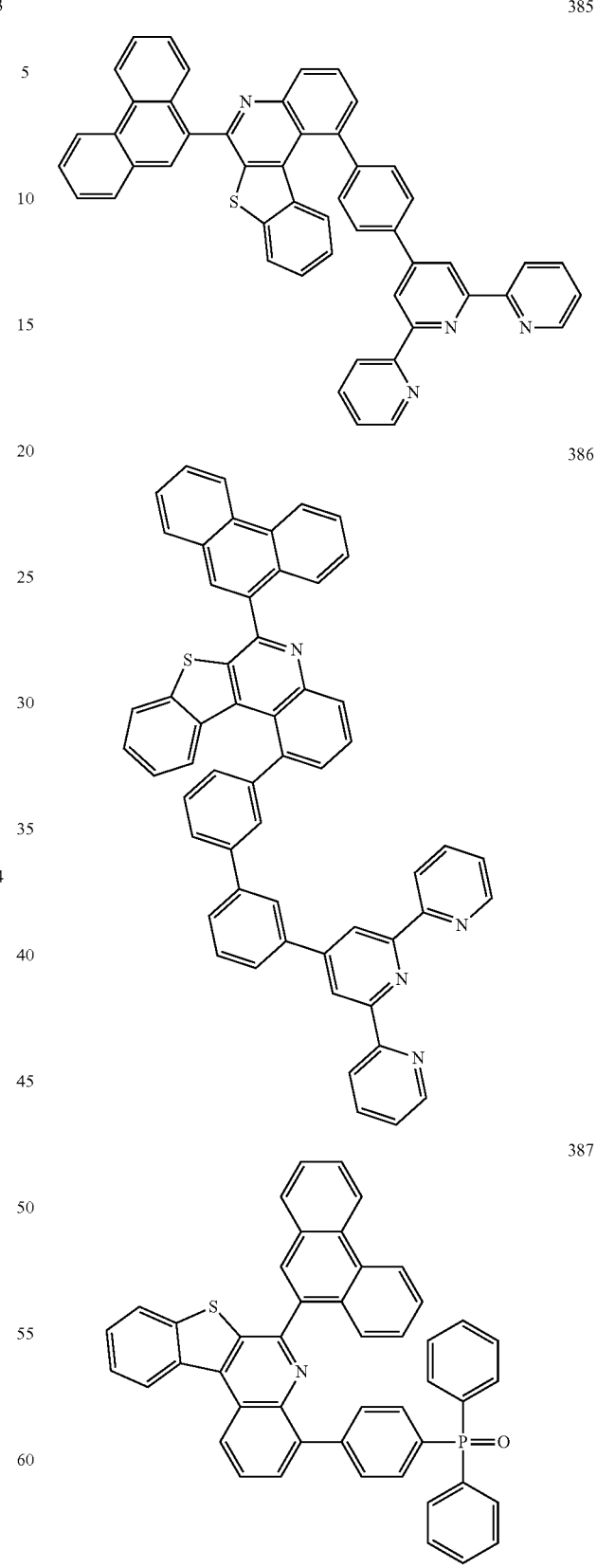

388
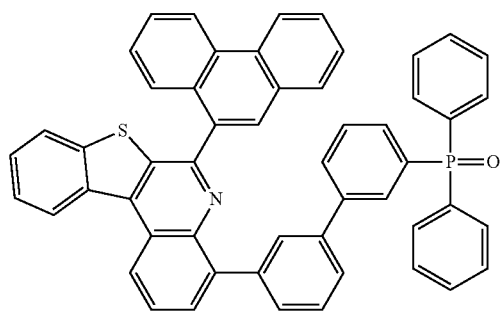
389
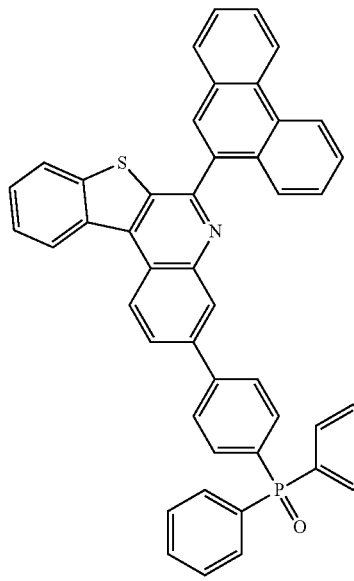
390
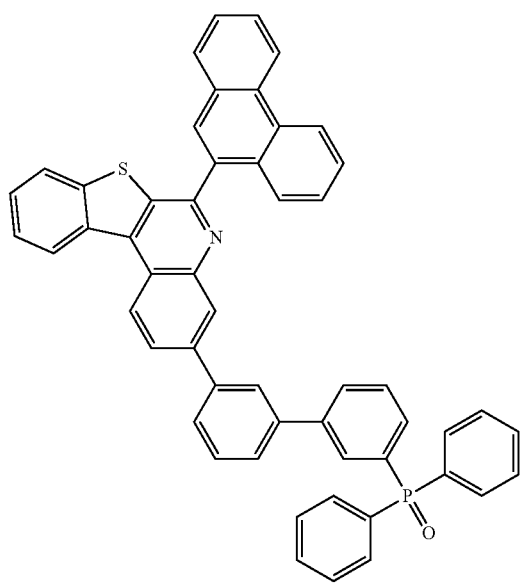
391
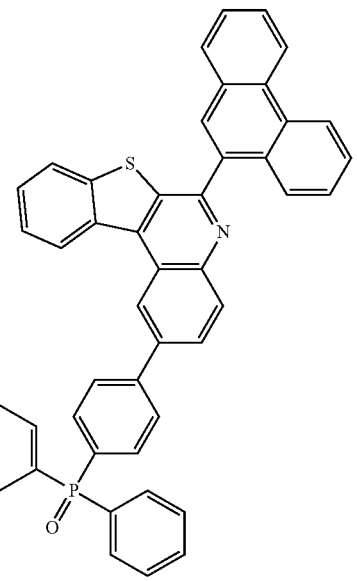
392
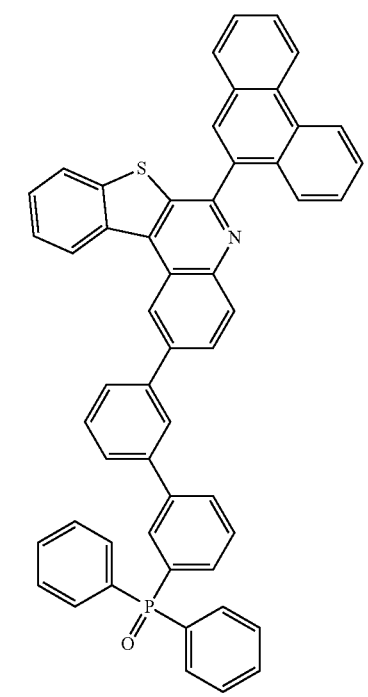

393
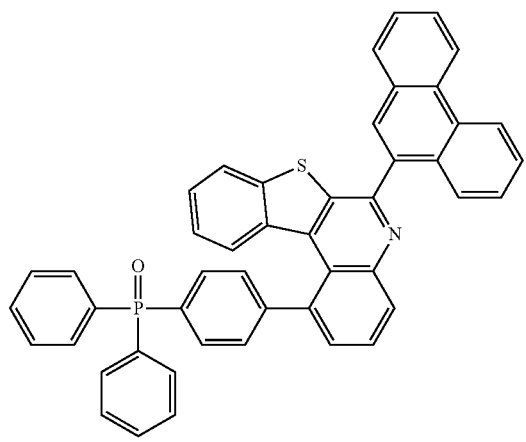
394
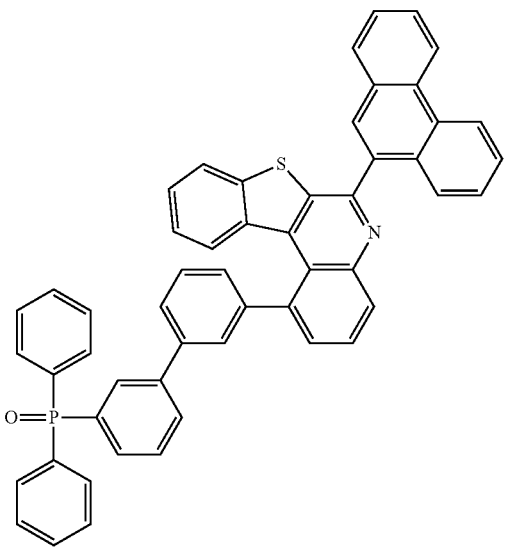
395
396
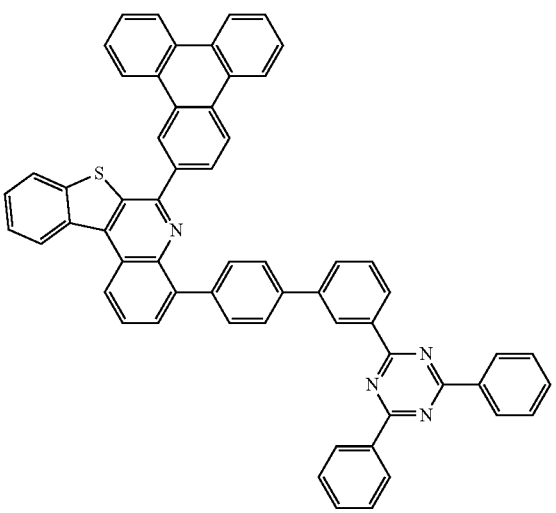
397
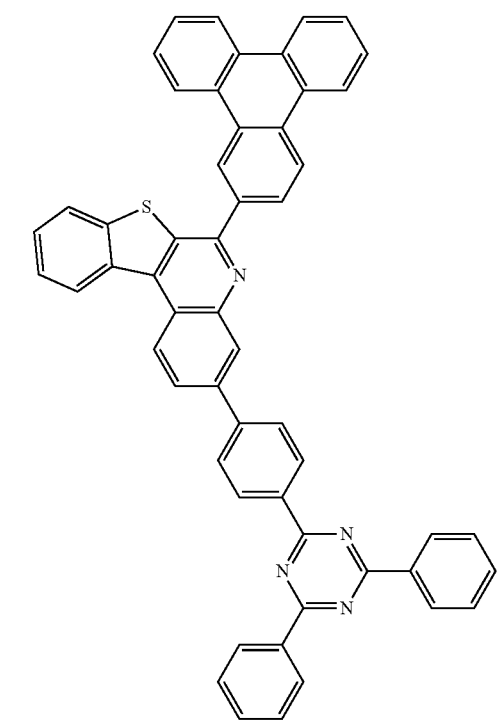

398
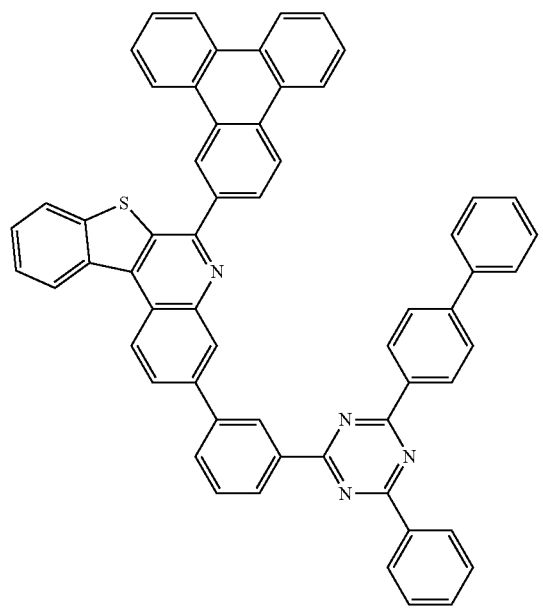
399
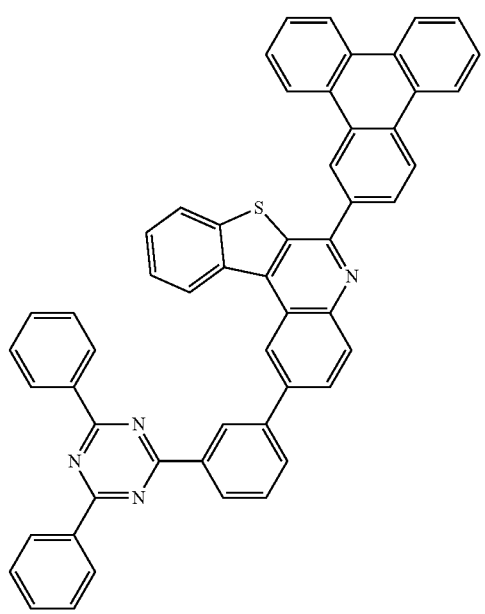
400
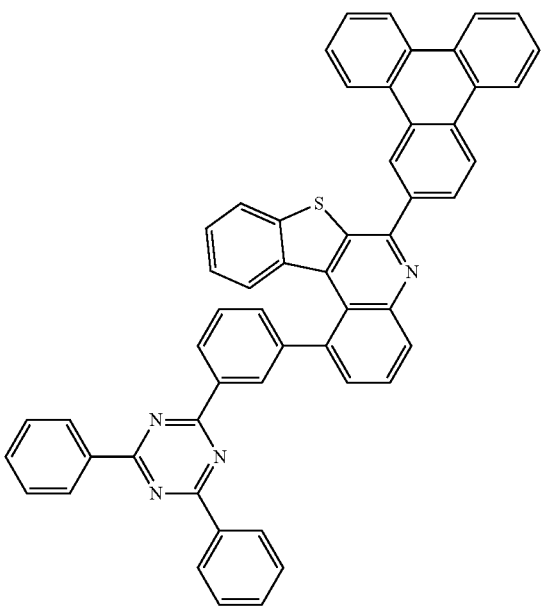
401
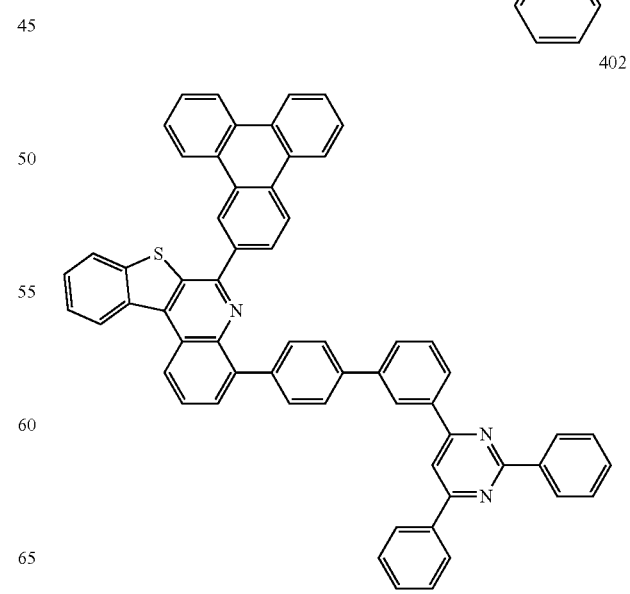
402

193
-continued
194
-continued
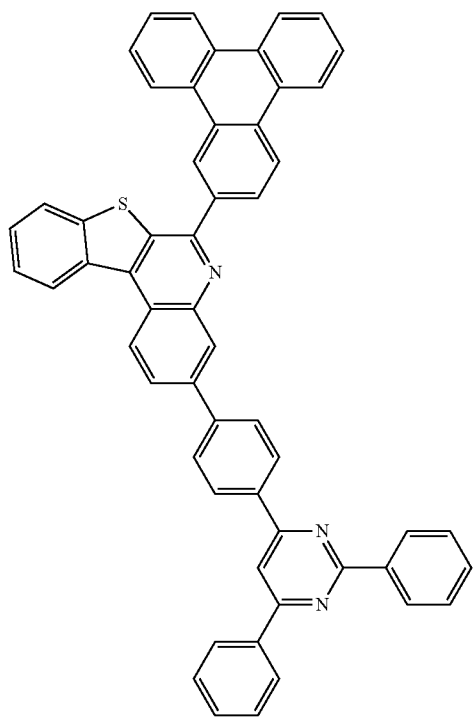
403
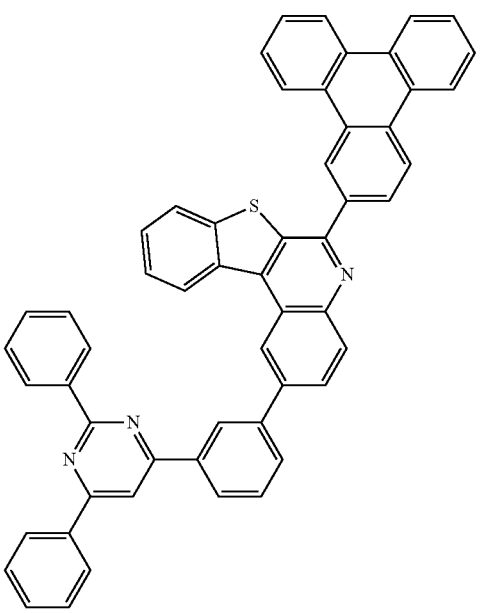
405
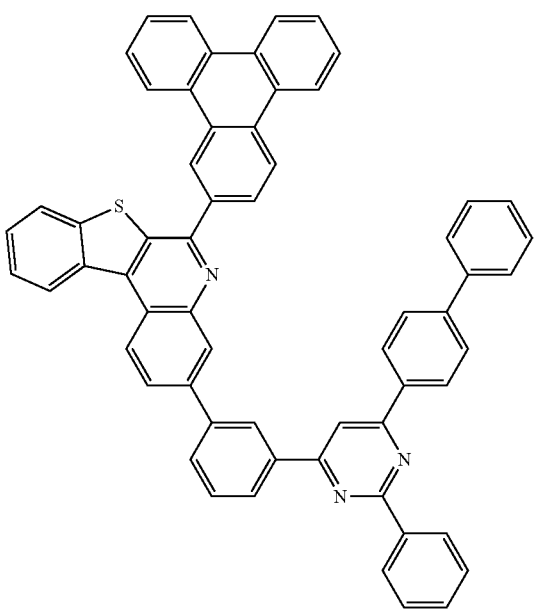
404
406

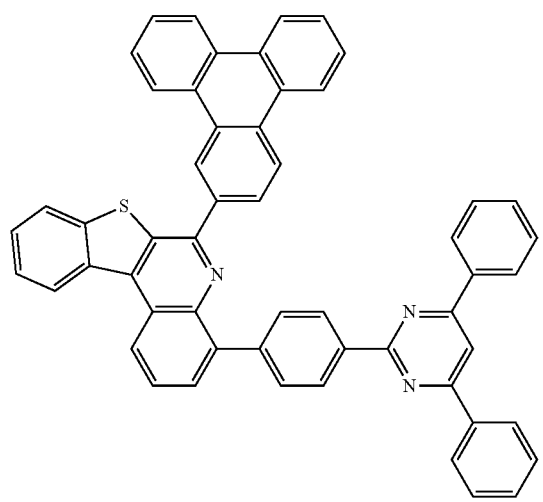
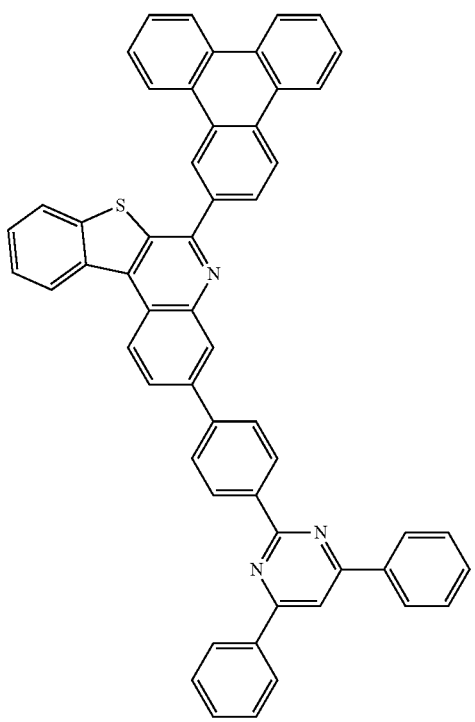
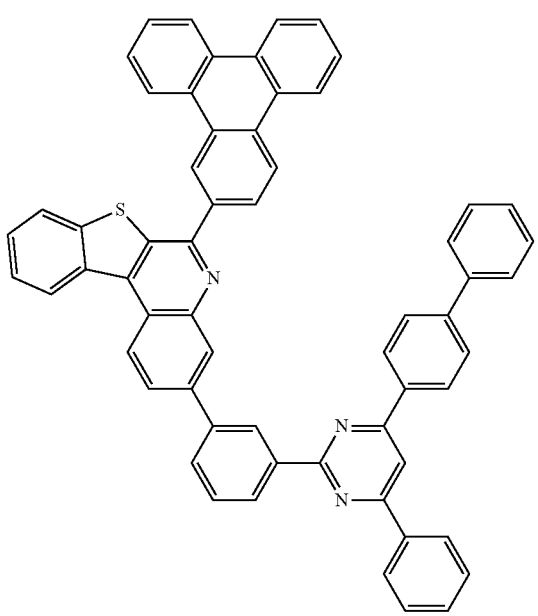

197
-continued
411
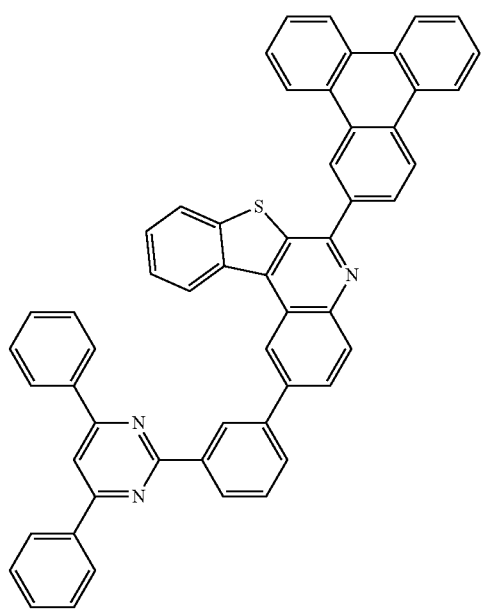
412
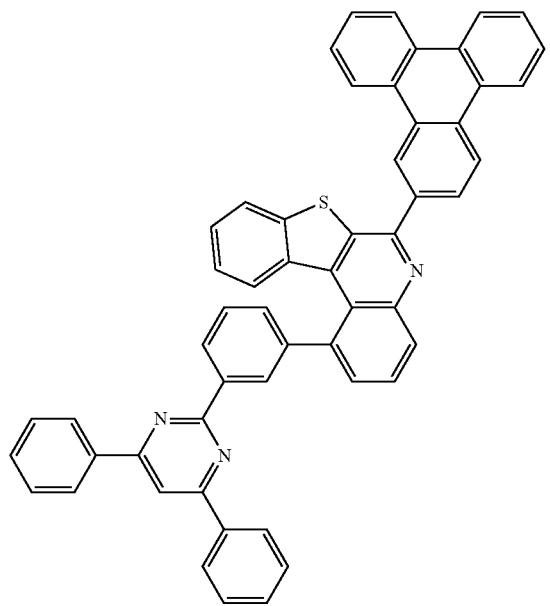
198
-continued
413
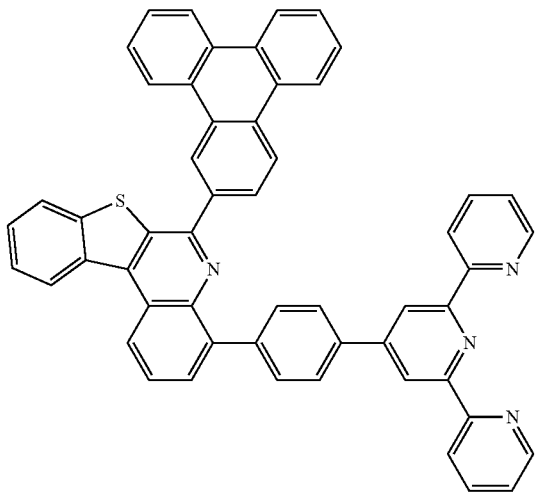
414
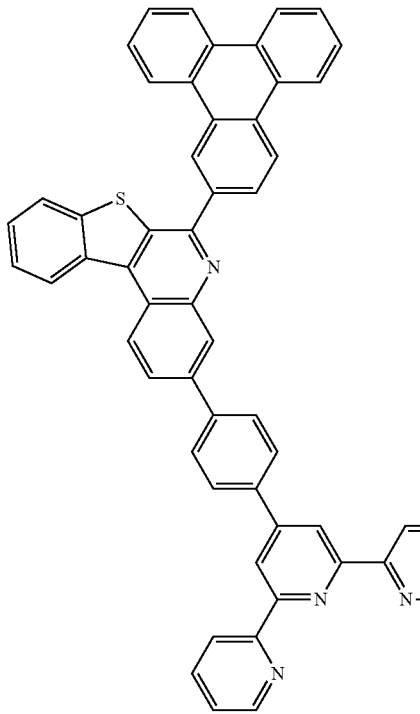

415
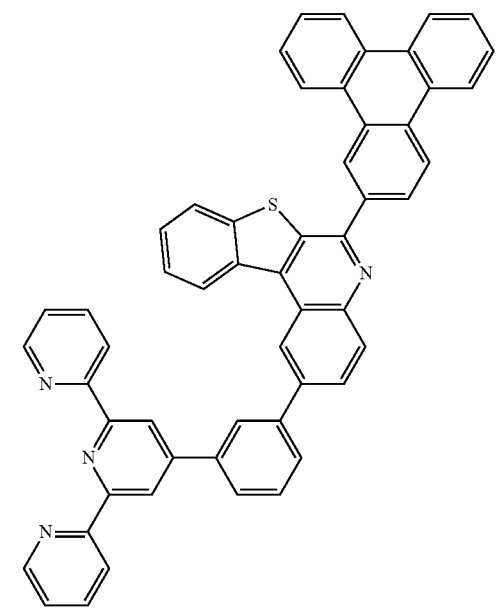
416
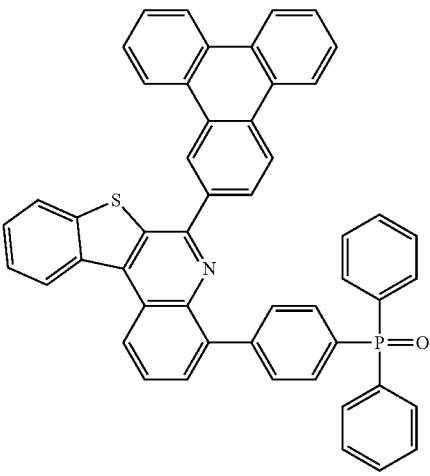
417
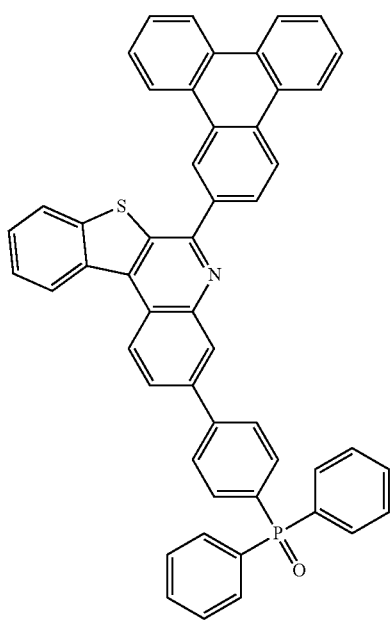
418
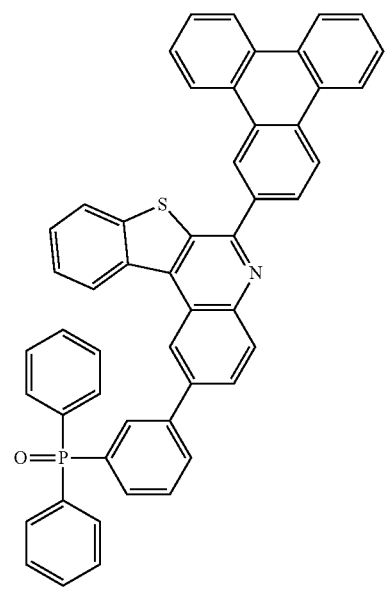
419

201
-continued
420
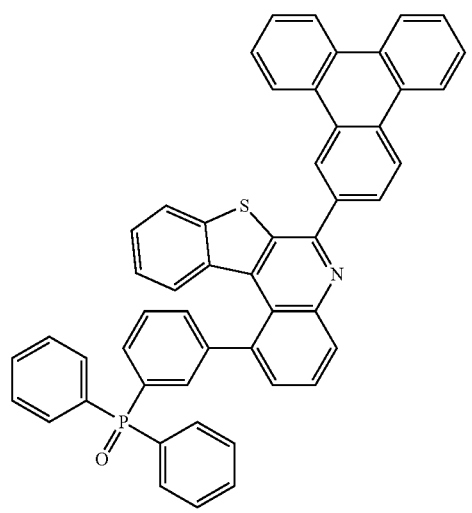
421
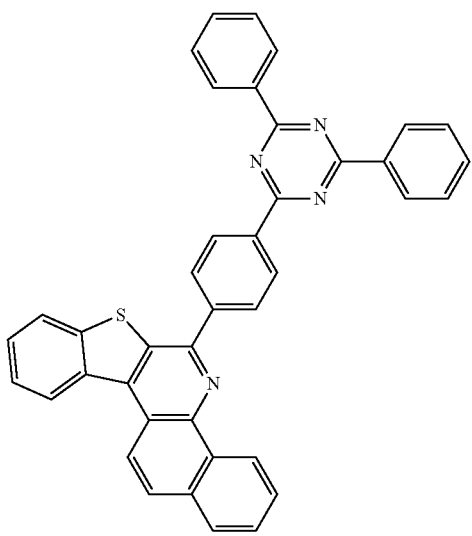
422
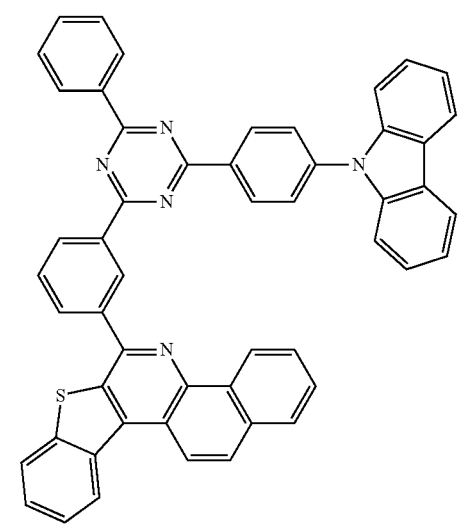
202
-continued
423
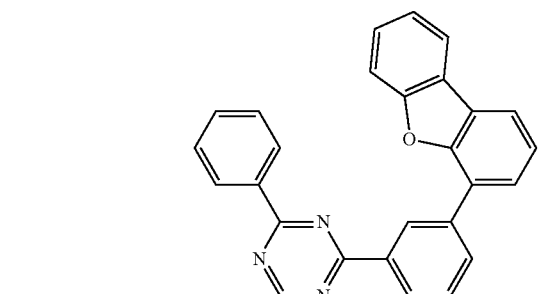
424
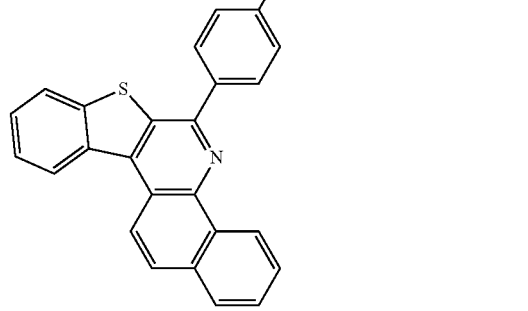
425
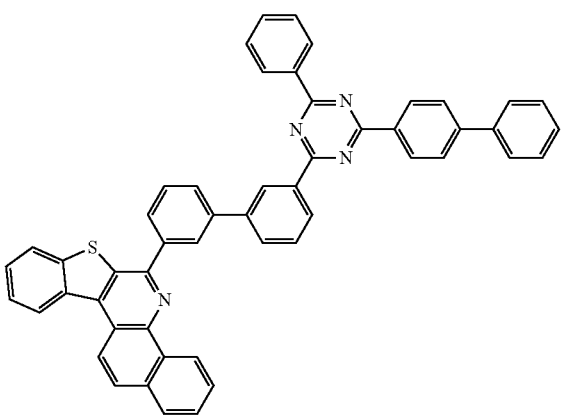

203
-continued
426
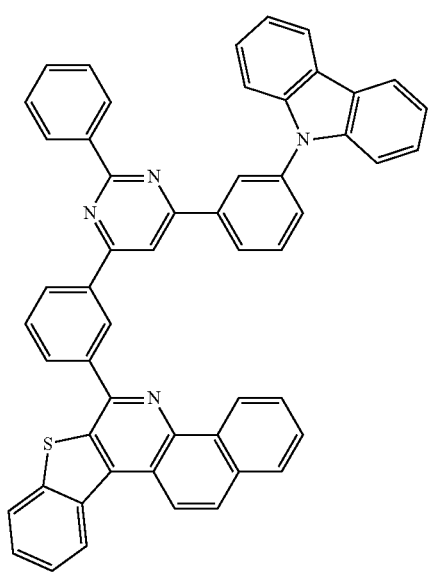
427
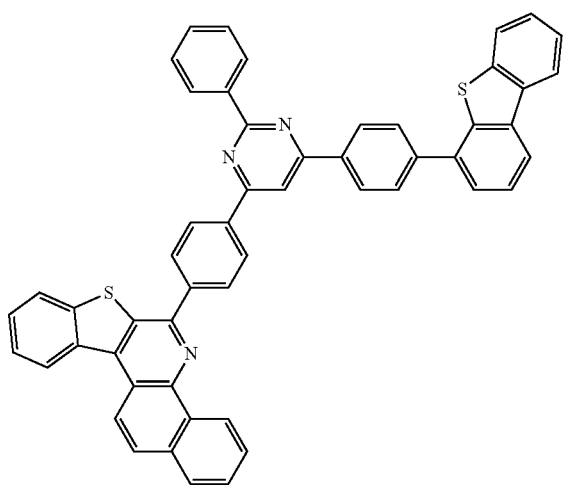
428
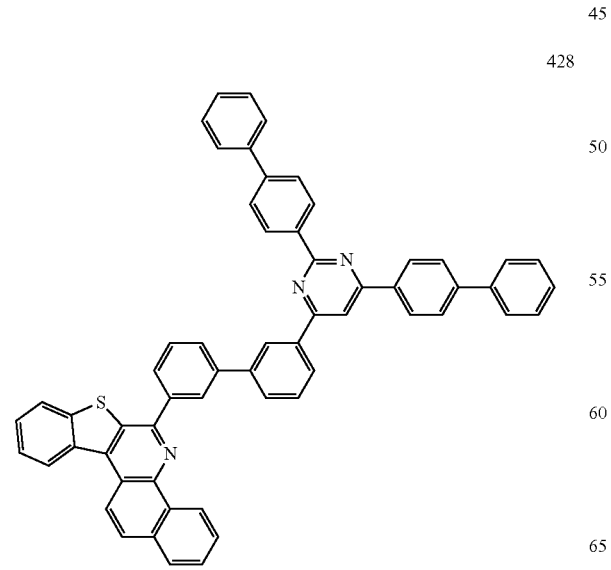
204
-continued
429
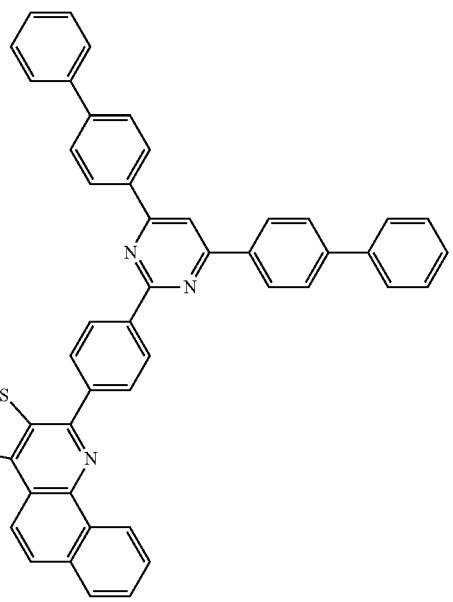
430
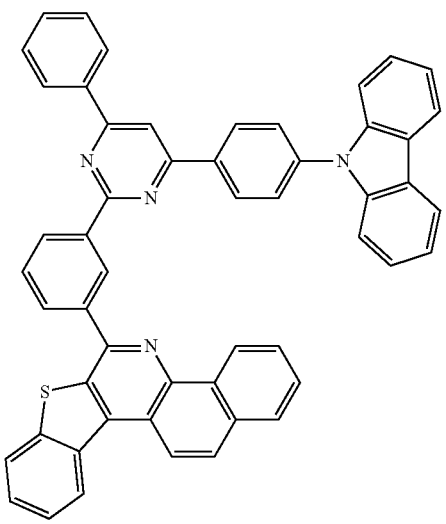

431
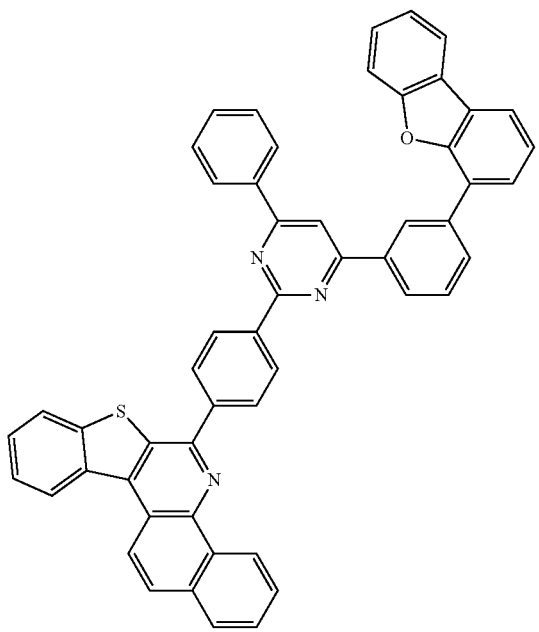
432
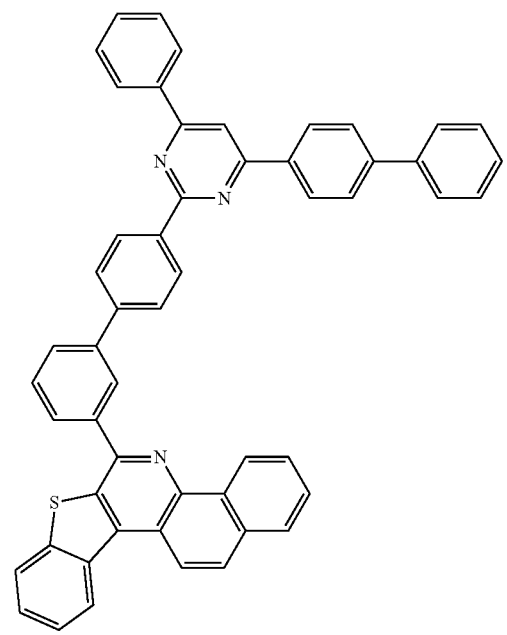
433
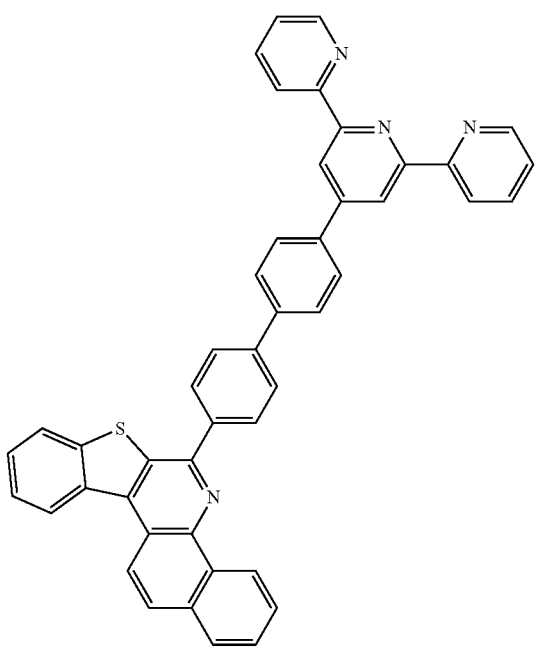
434
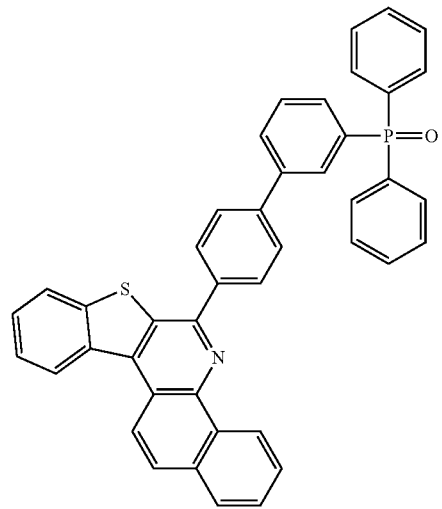

435
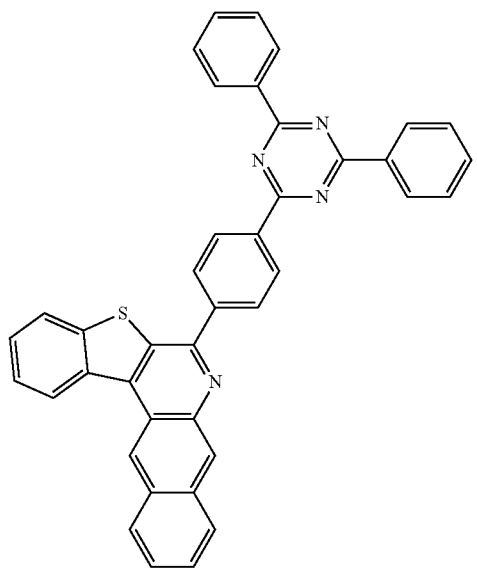
437
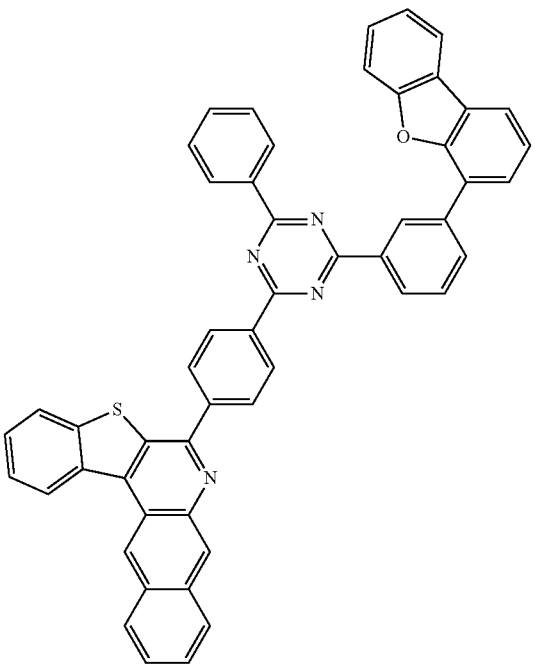
436
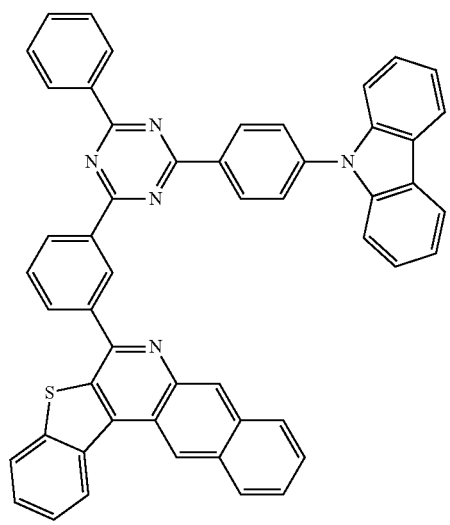
438
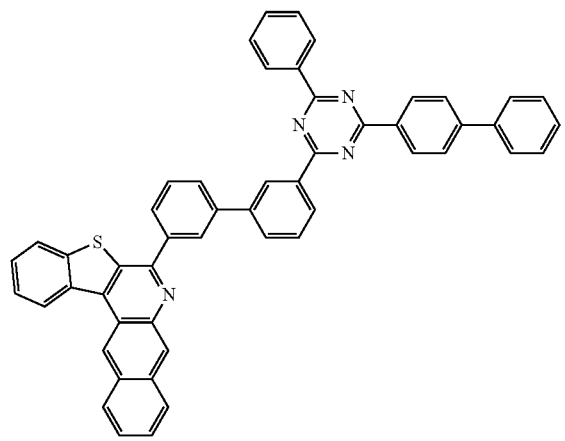

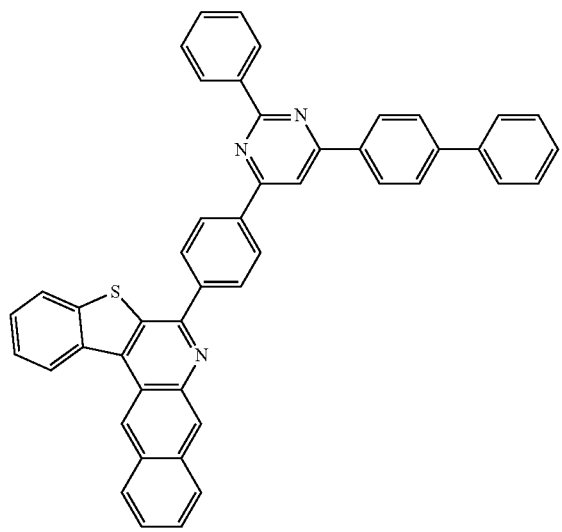
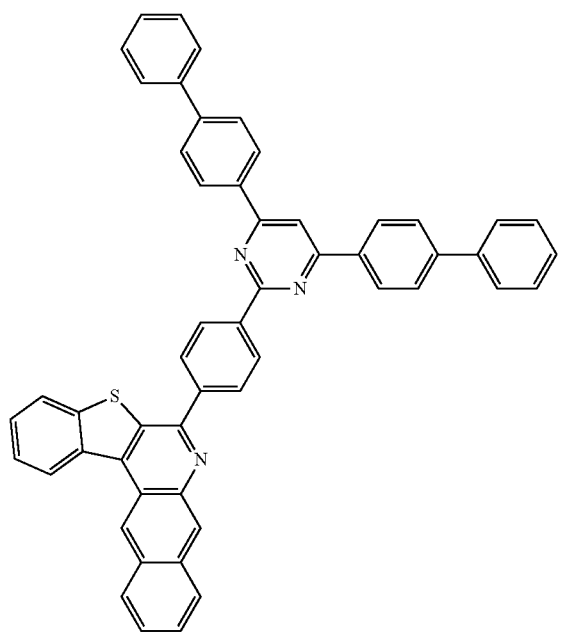
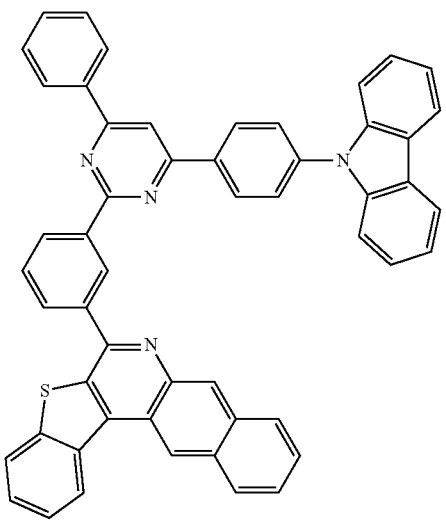

444
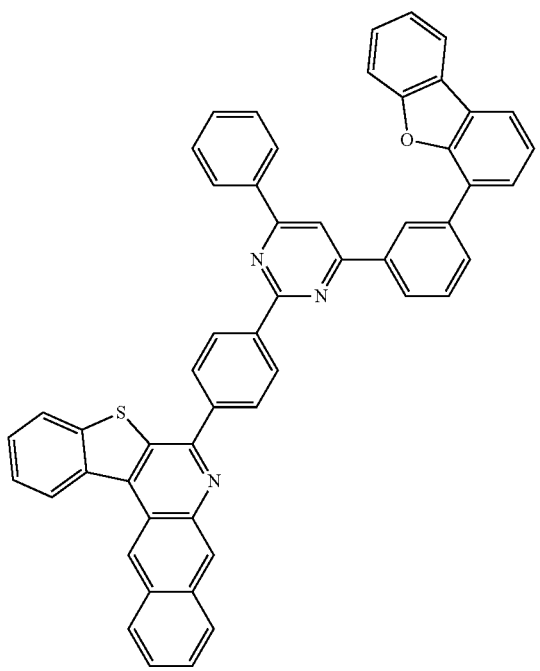
446
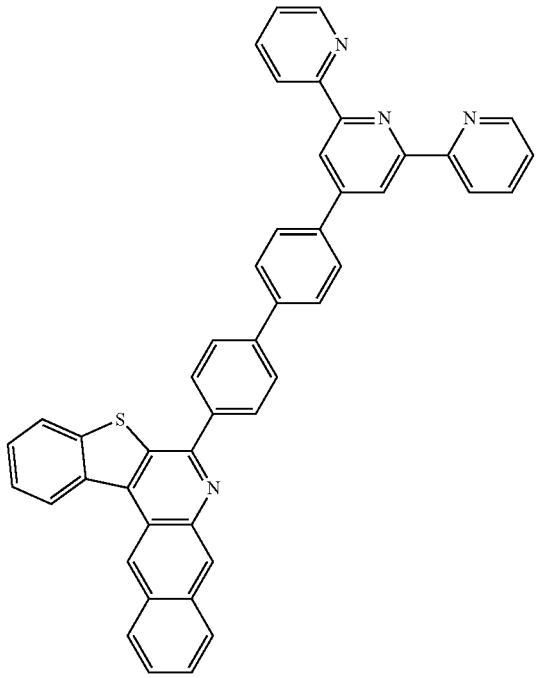
445
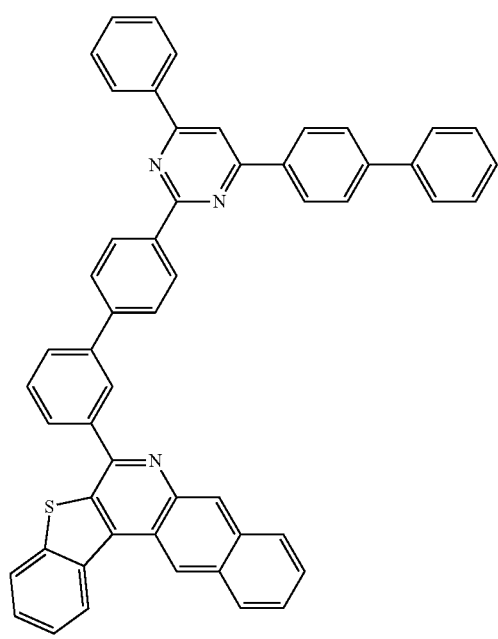
447
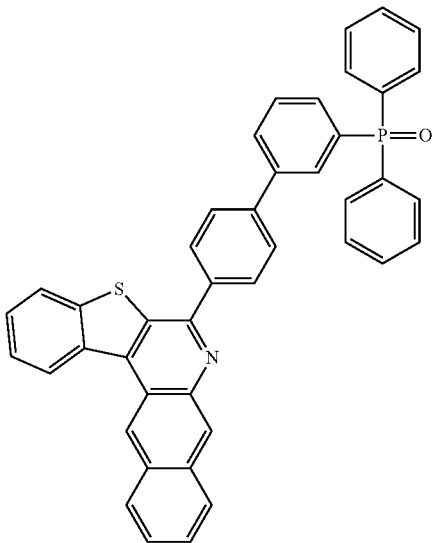

448
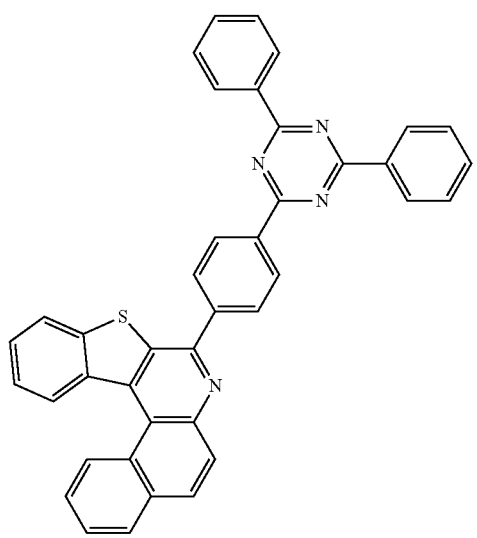
449
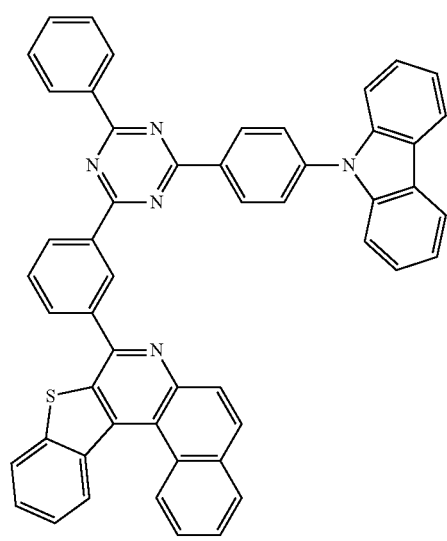
450
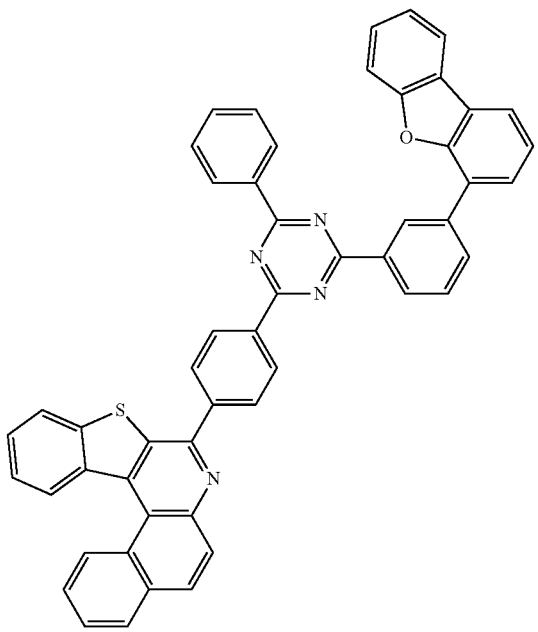
451
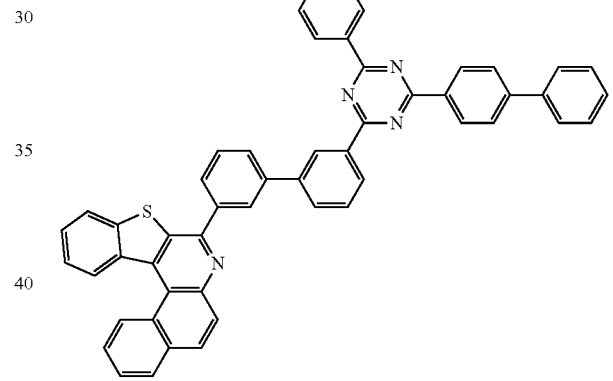
452
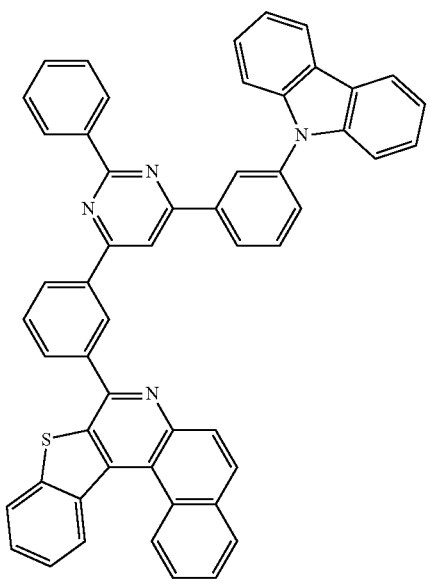

453
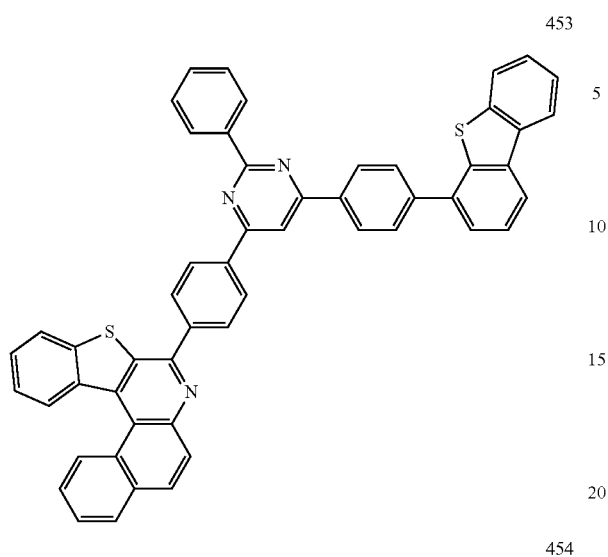
454
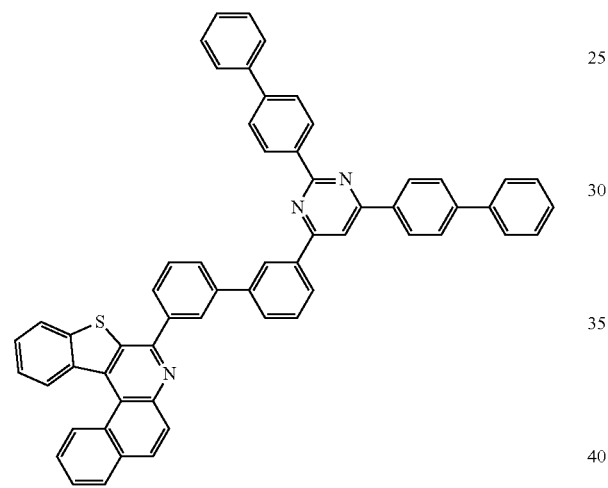
455
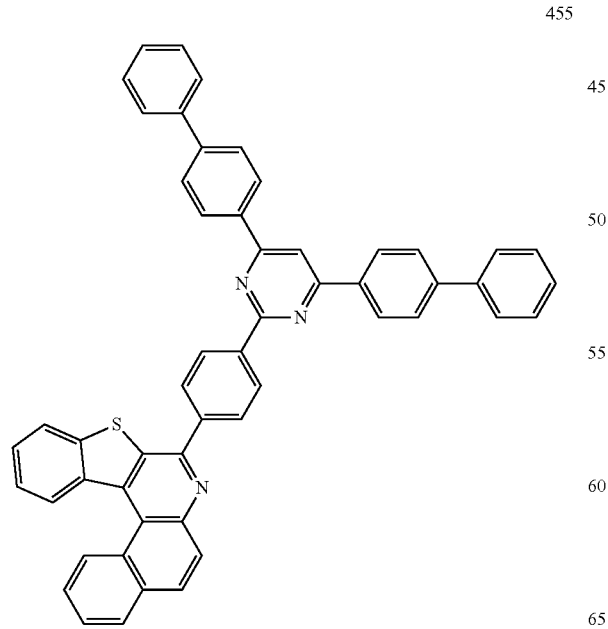
456
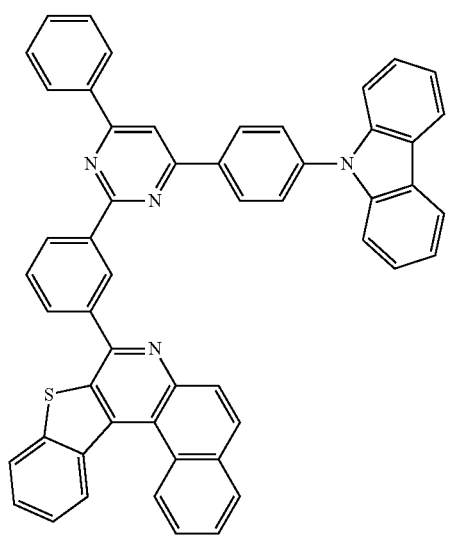
457
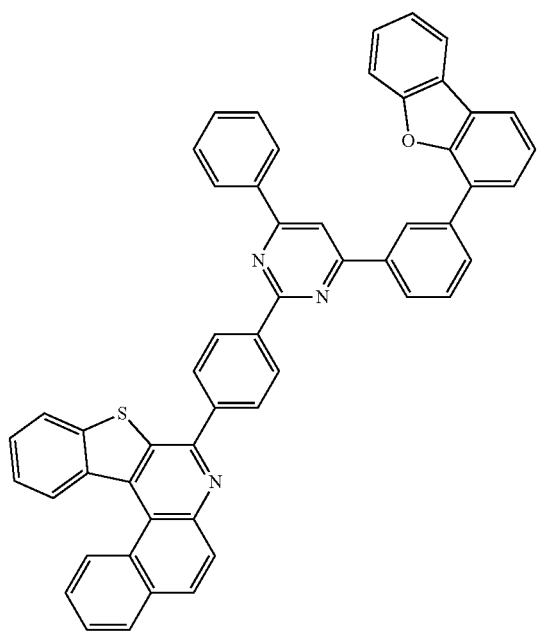

217
-continued
458
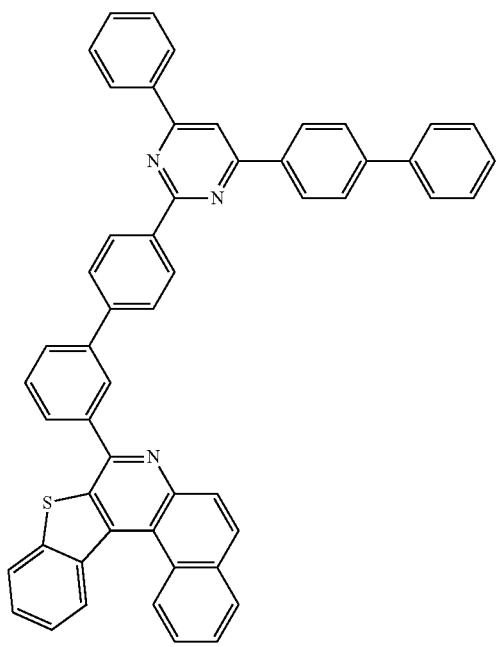
459
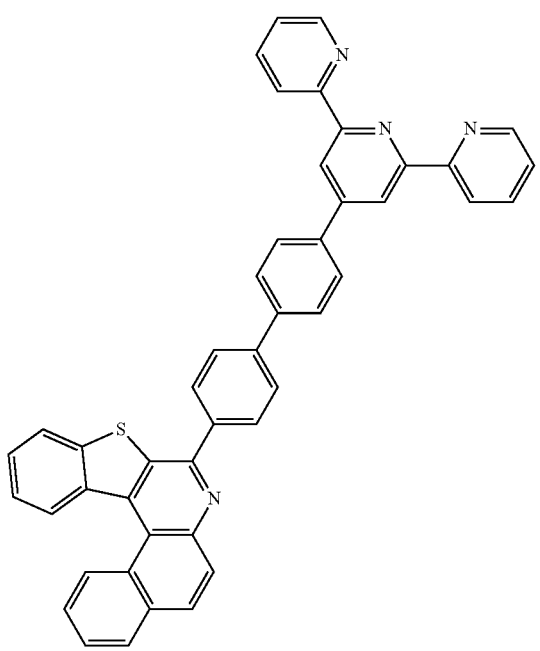
218
-continued
460
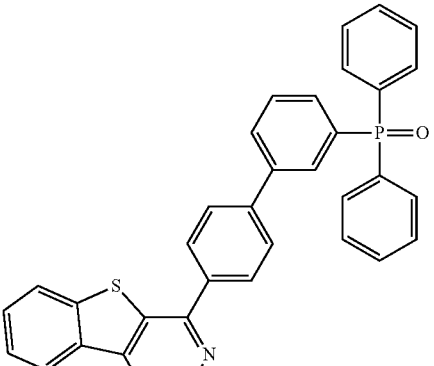
461
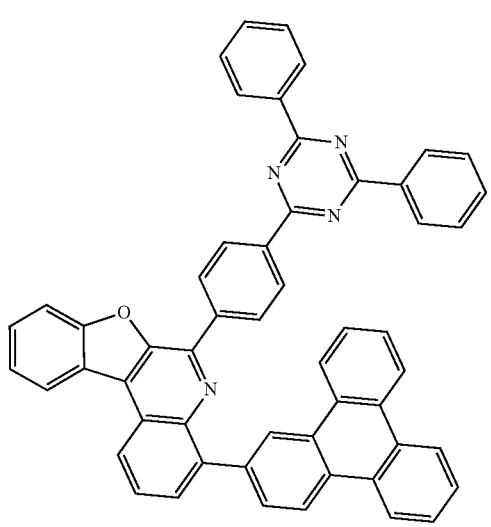
462
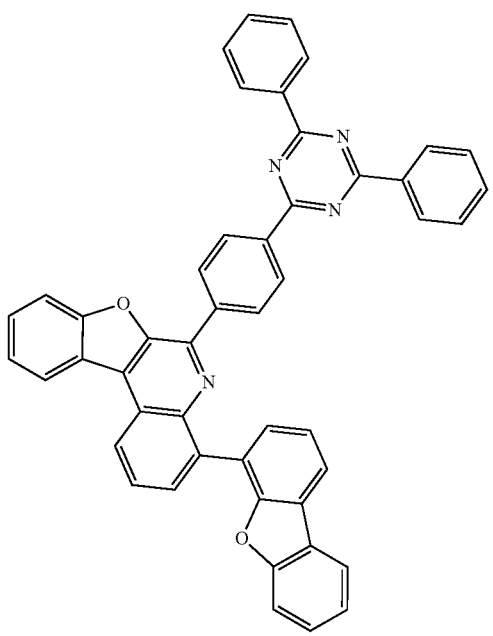

-continued
463
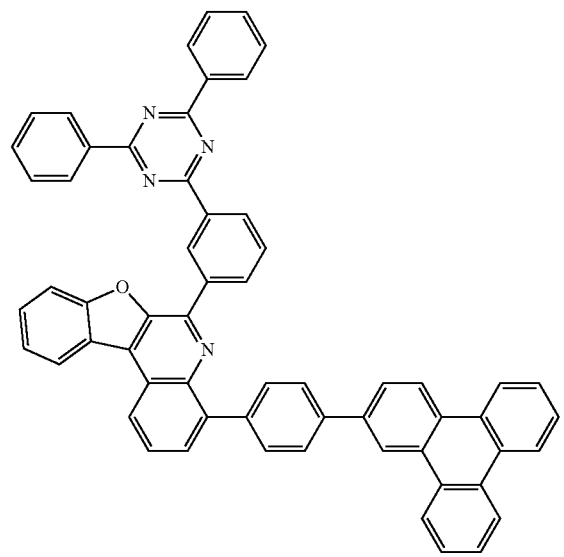
464
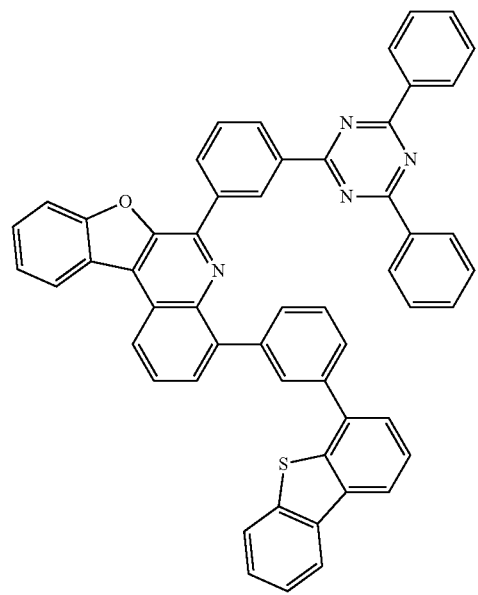
-continued
465
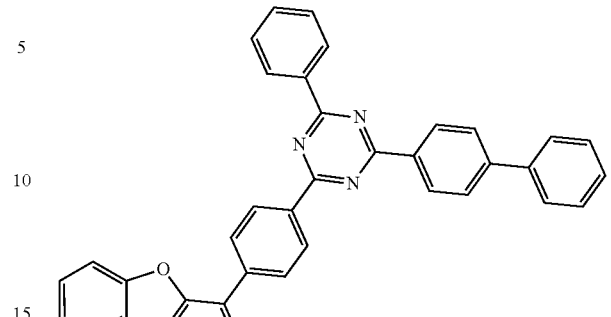
466
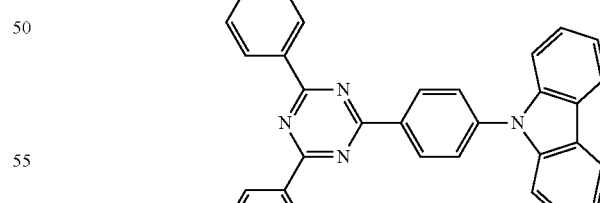
467
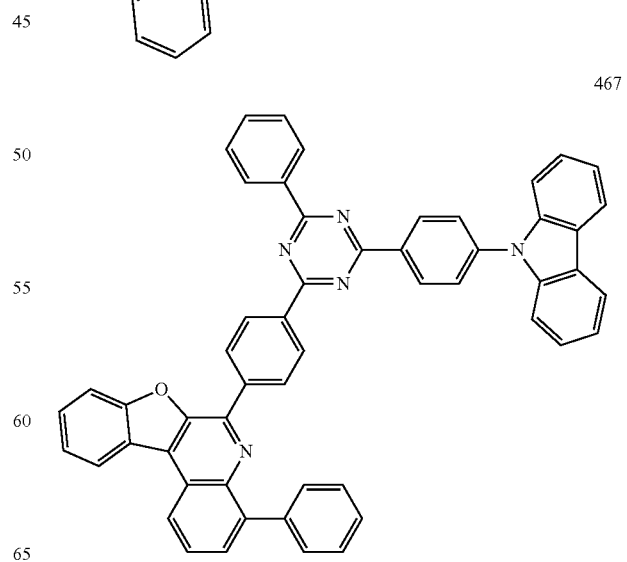

468
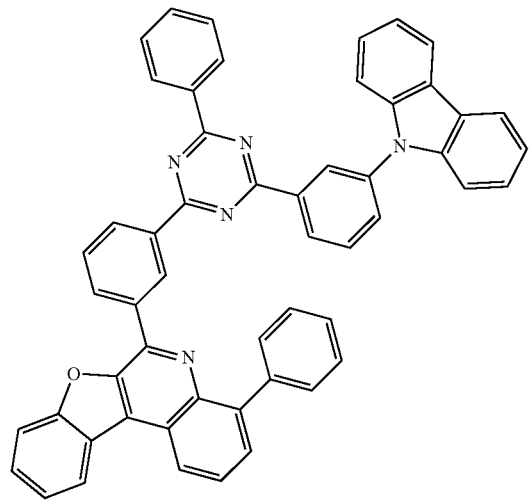
469
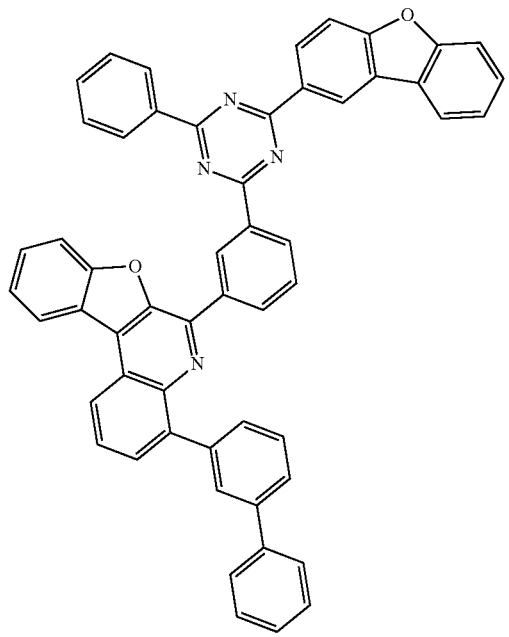
470
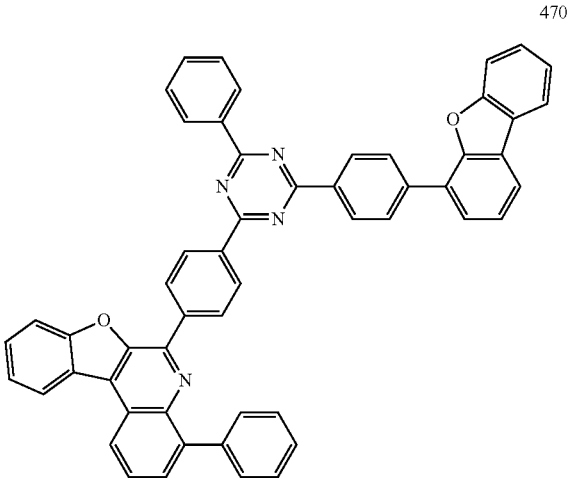
471
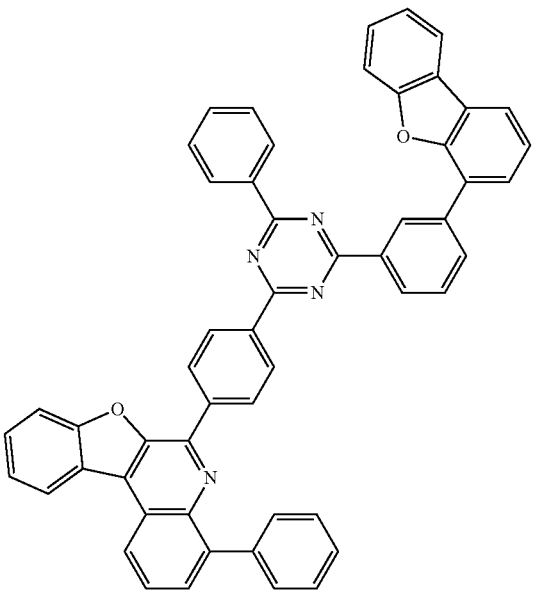
472
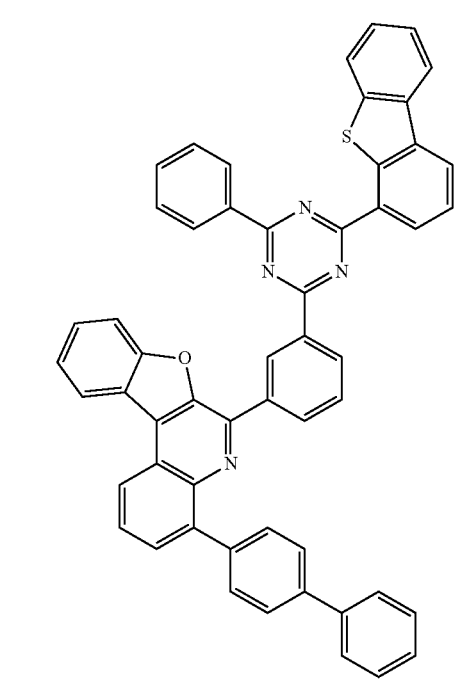

223
-continued
473
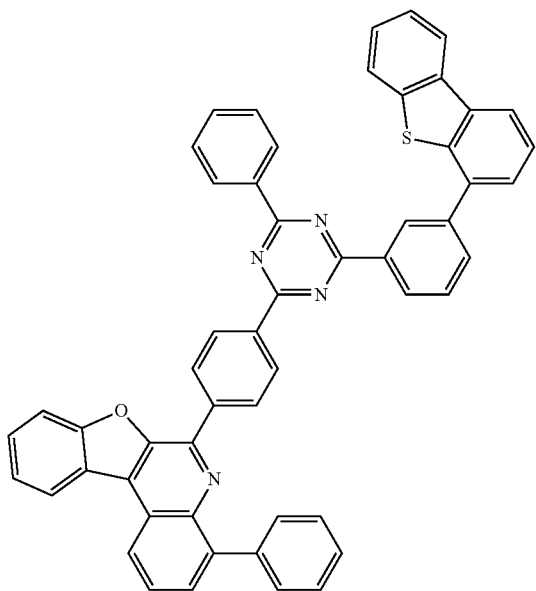
474
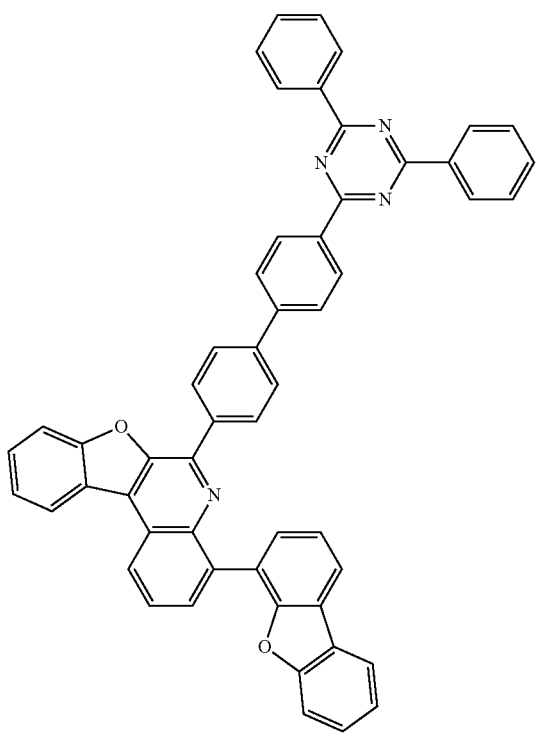
224
-continued
475
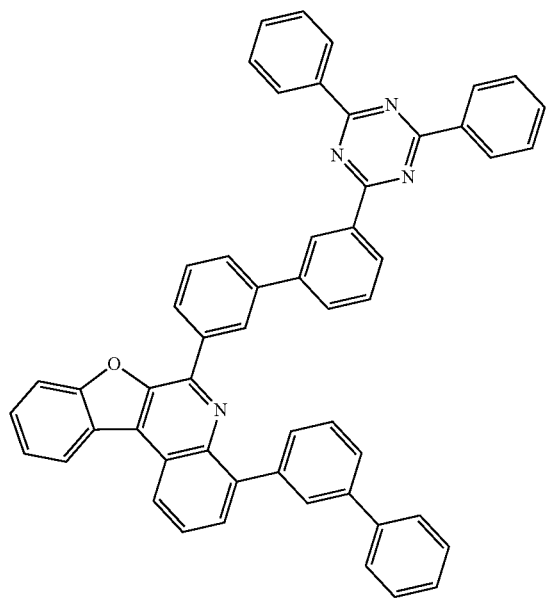
476
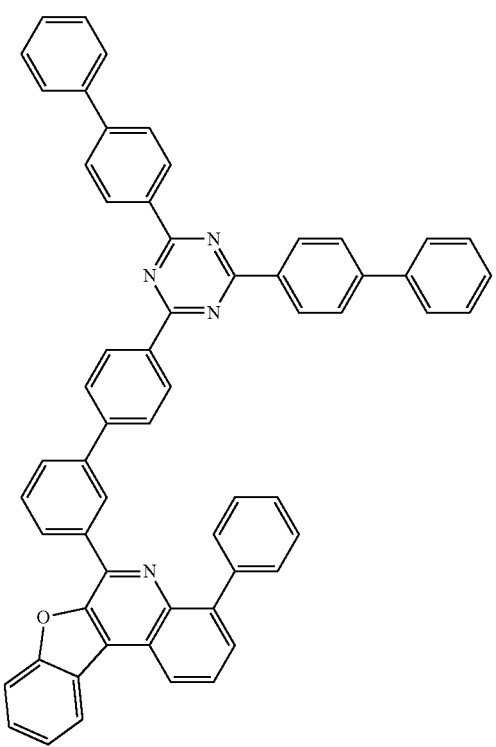

225
-continued
477
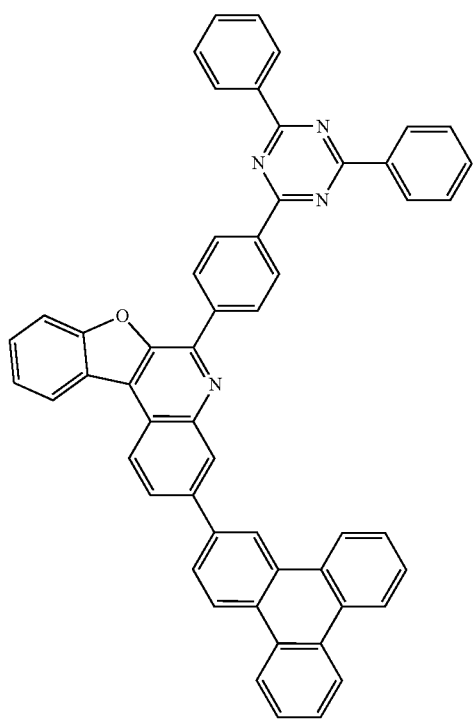
478
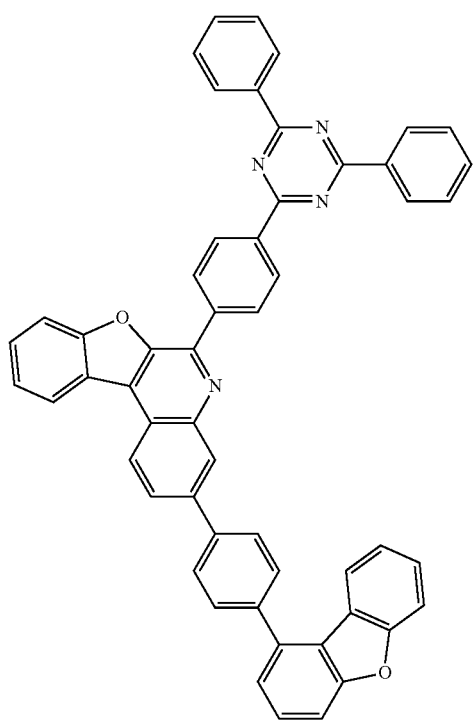
226
-continued
479
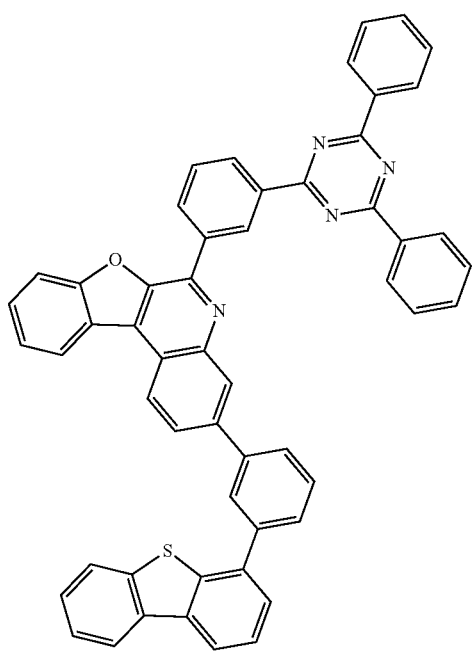
480
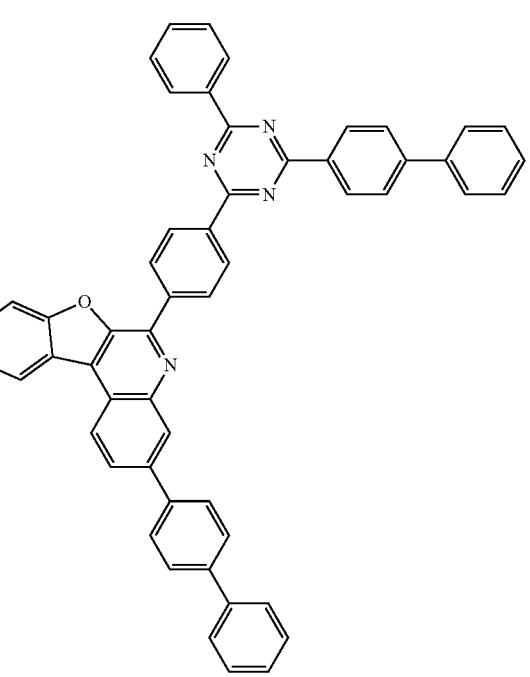

227
-continued
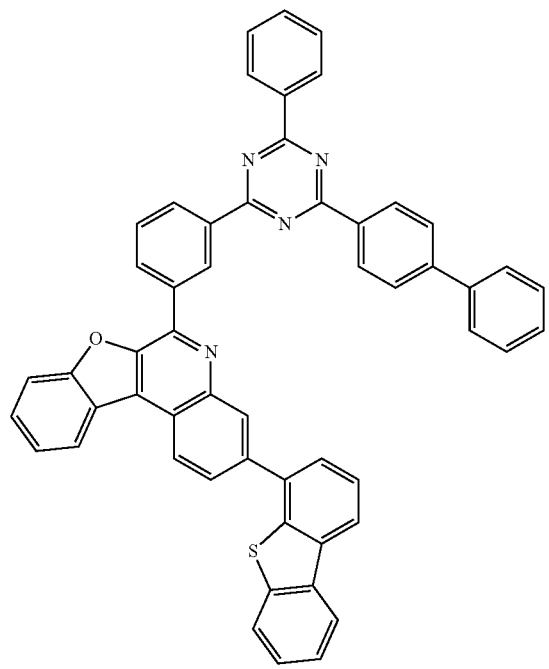
481
228
-continued
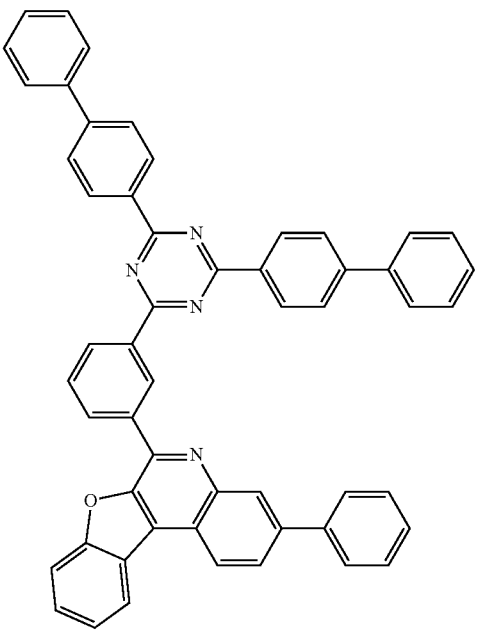
483
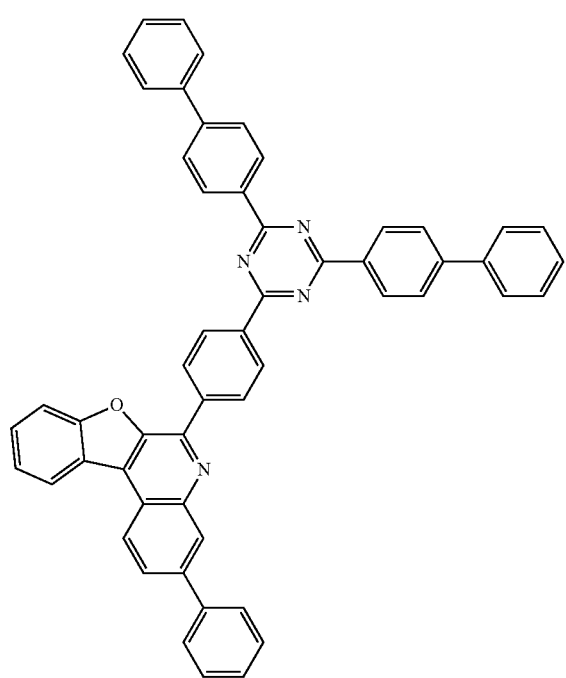
482
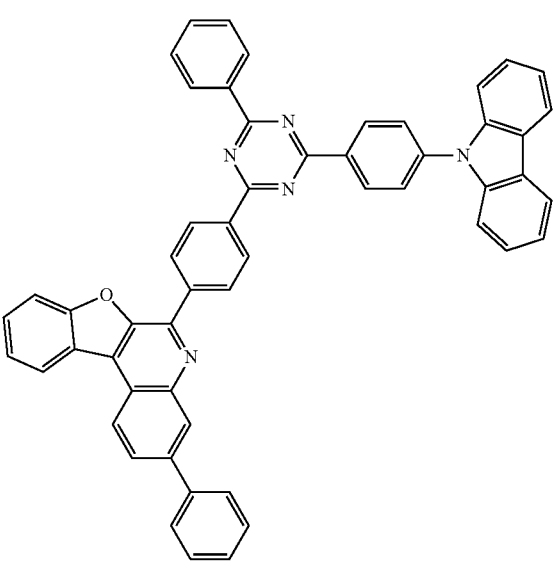
484

-continued
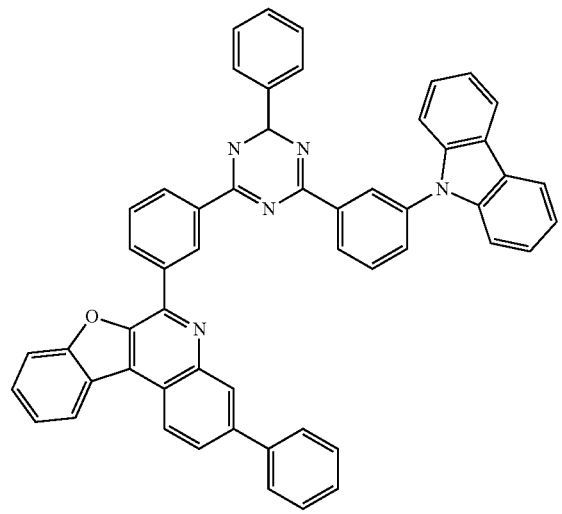
485
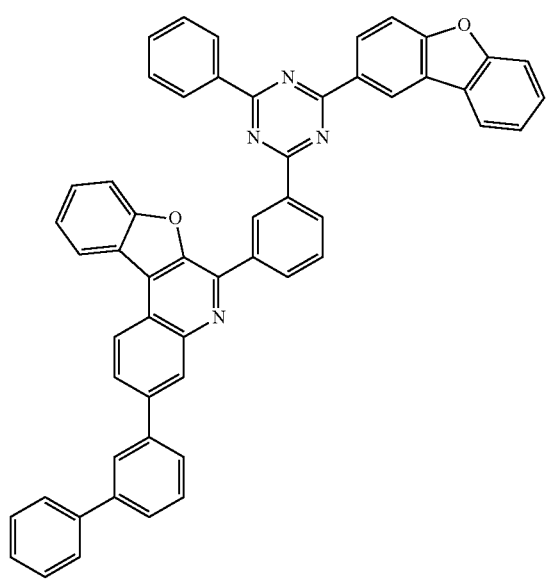
486
-continued
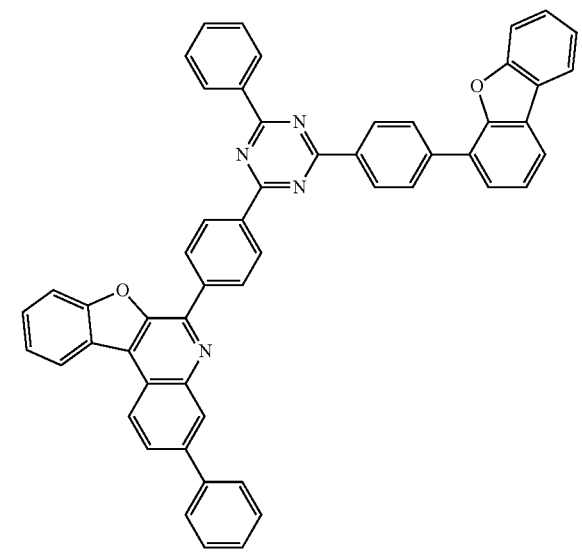
487
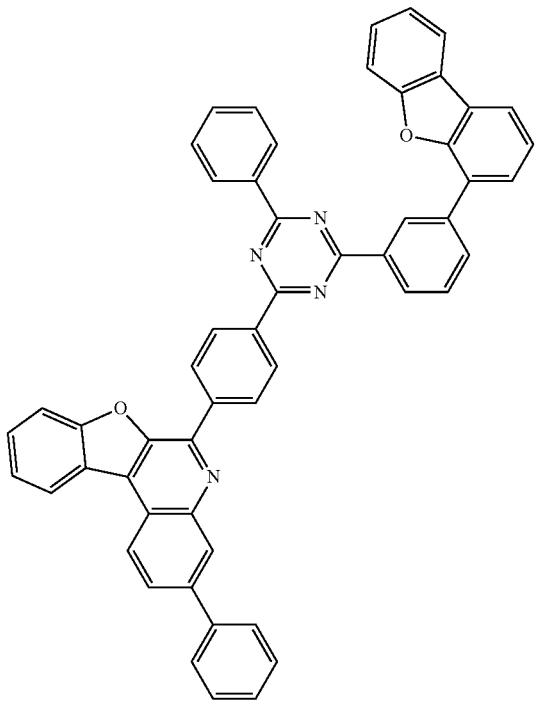
488

231
-continued
489
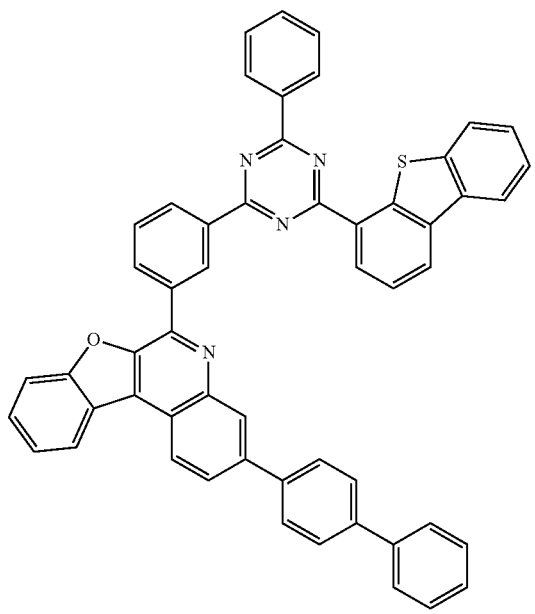
490
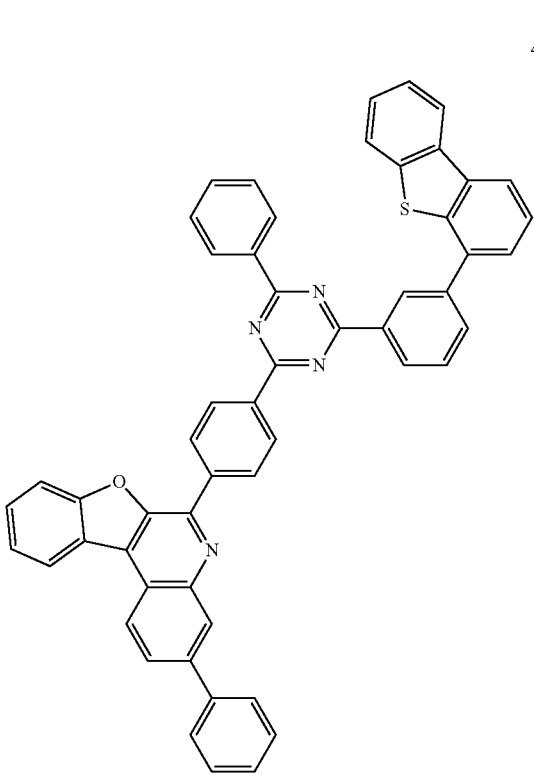
232
-continued
491
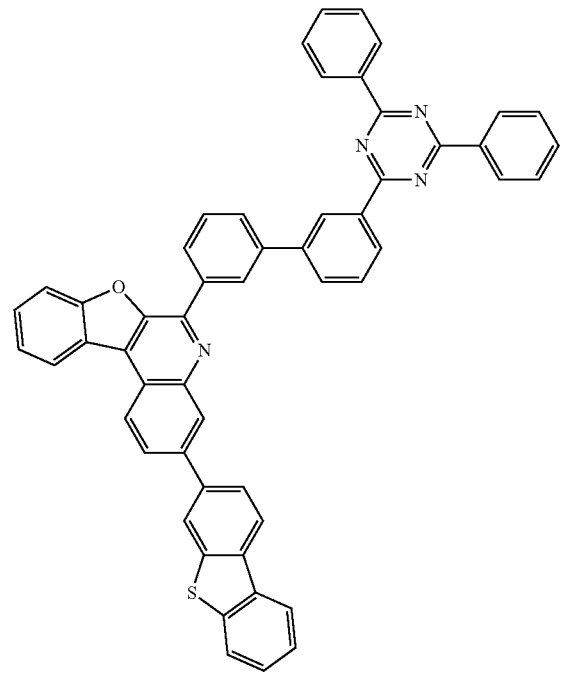
492
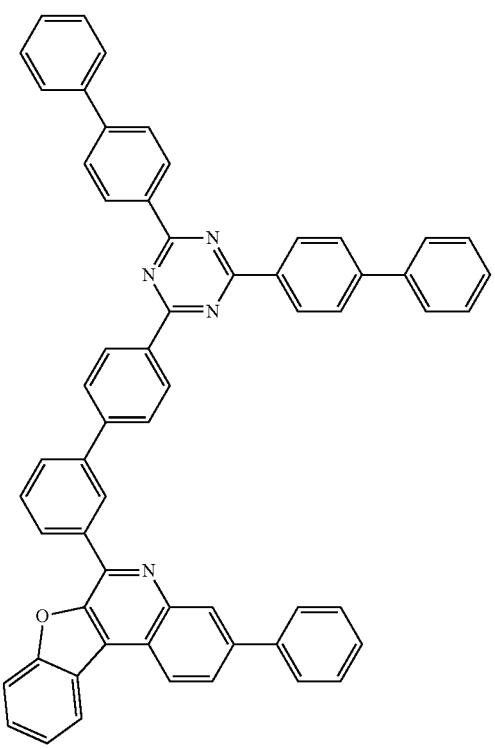

233
-continued
493
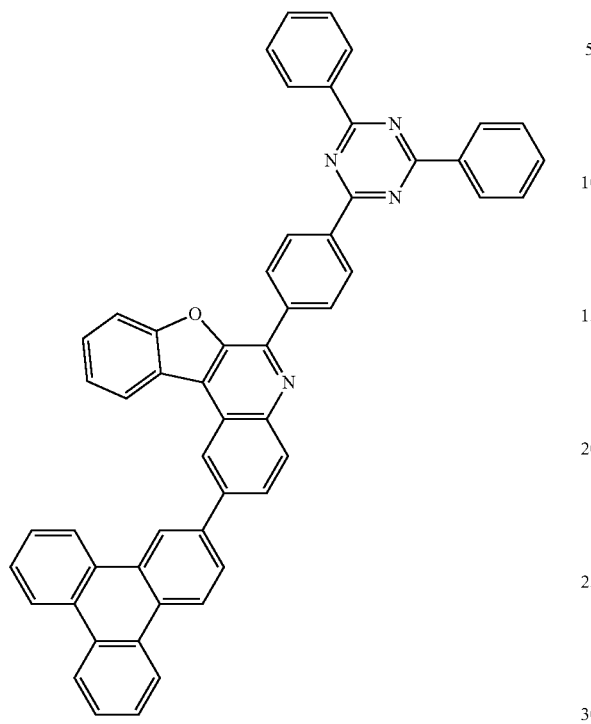
494
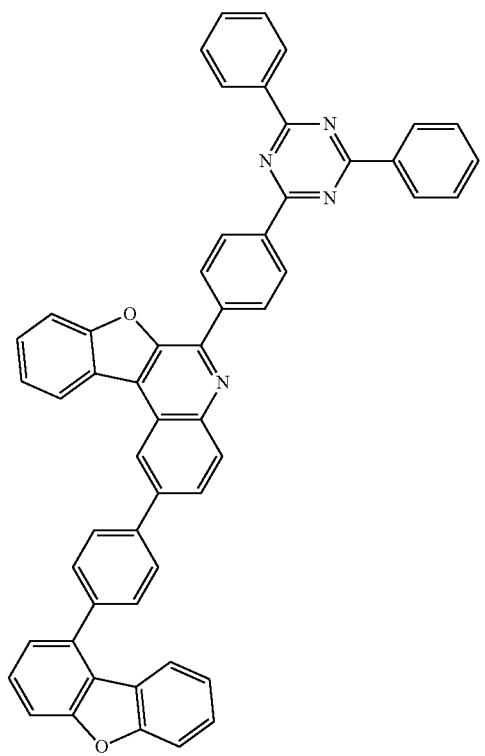
234
-continued
495
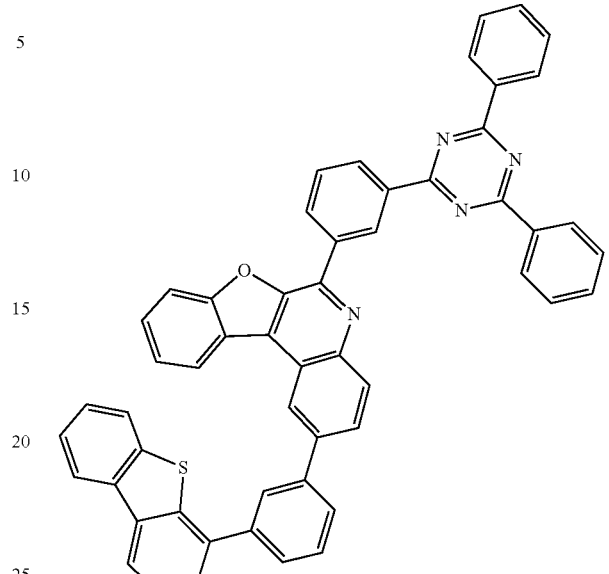
496
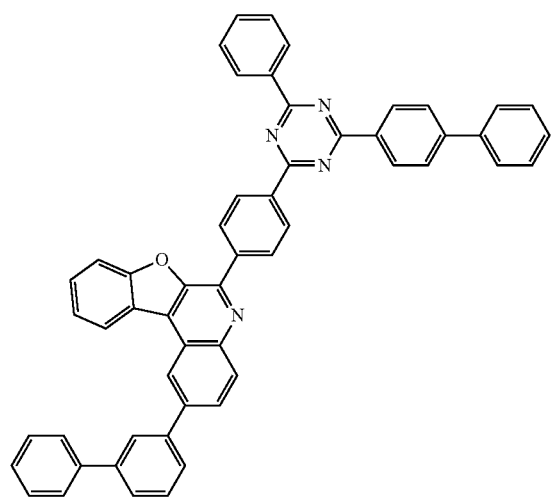

-continued

497

498

-continued

499

500

-continued
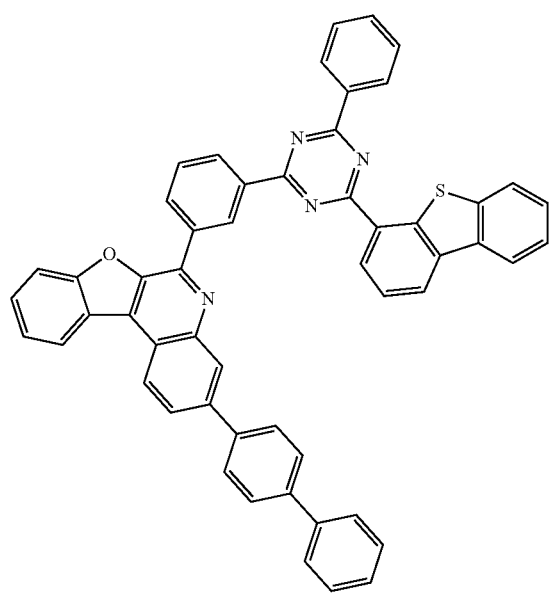
501
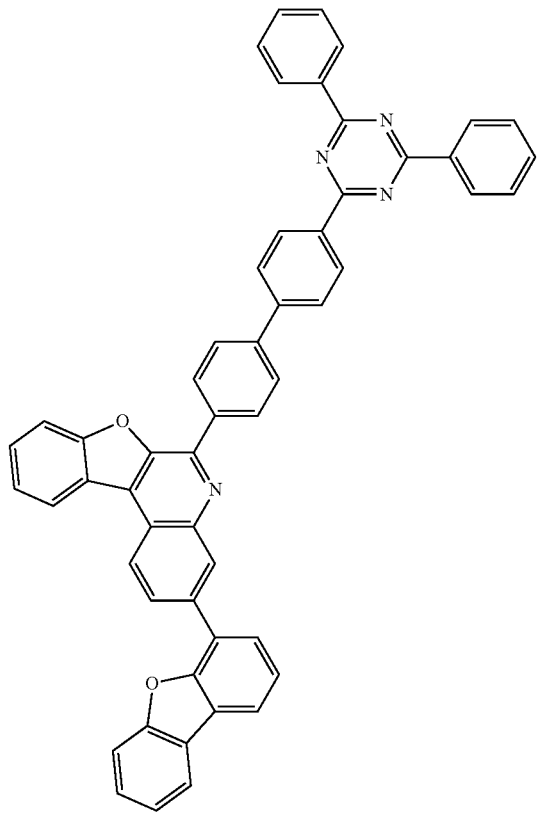
503
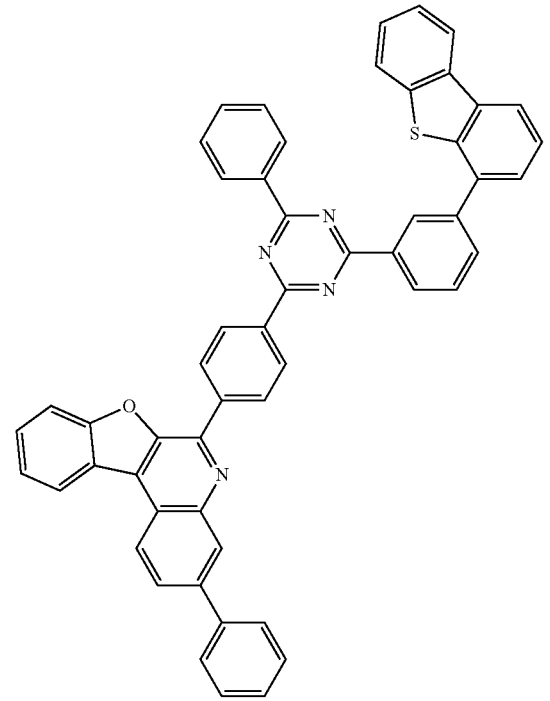
502
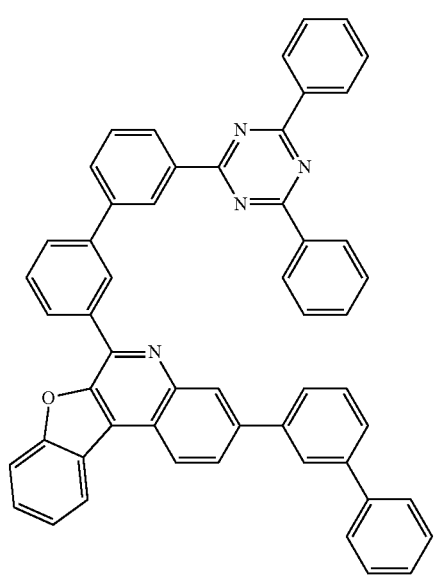
504

-continued
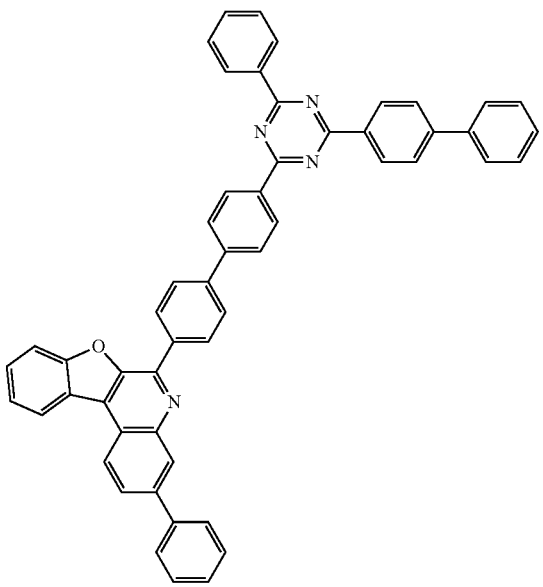
505
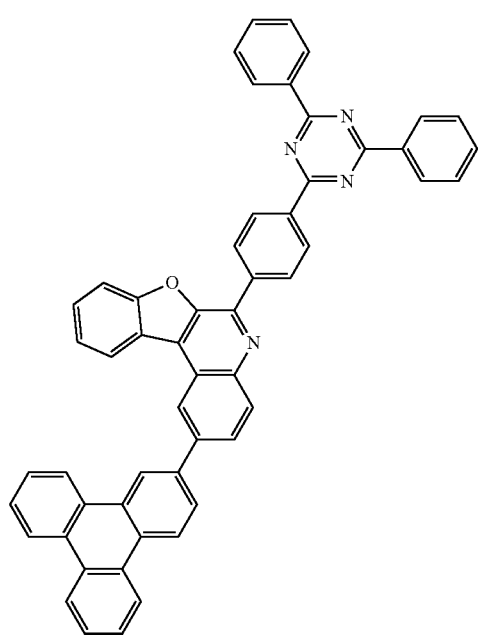
506
-continued
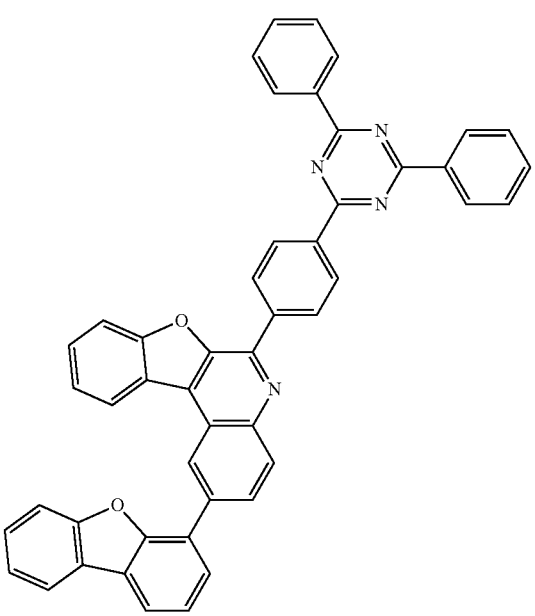
507
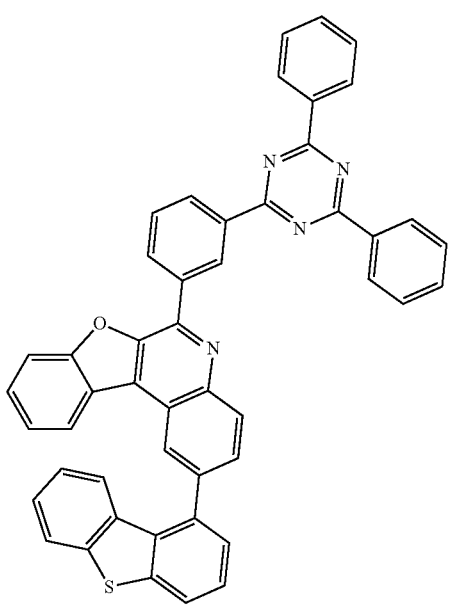
508

509
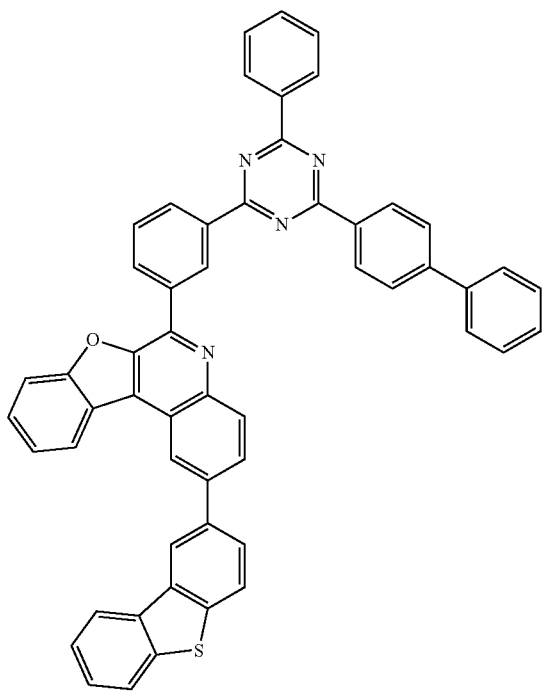
510
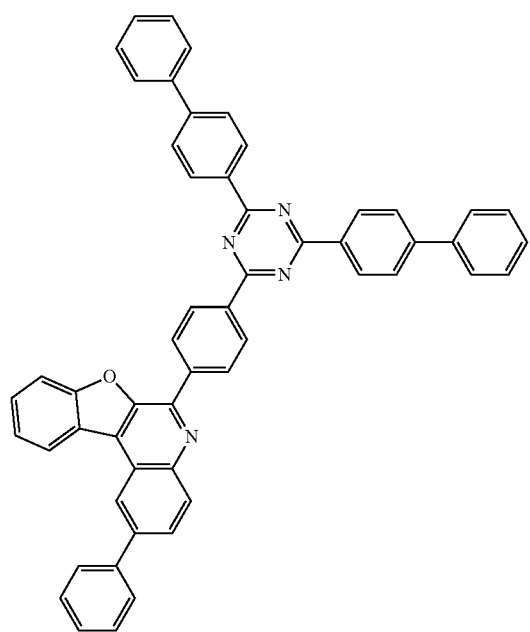
511
512
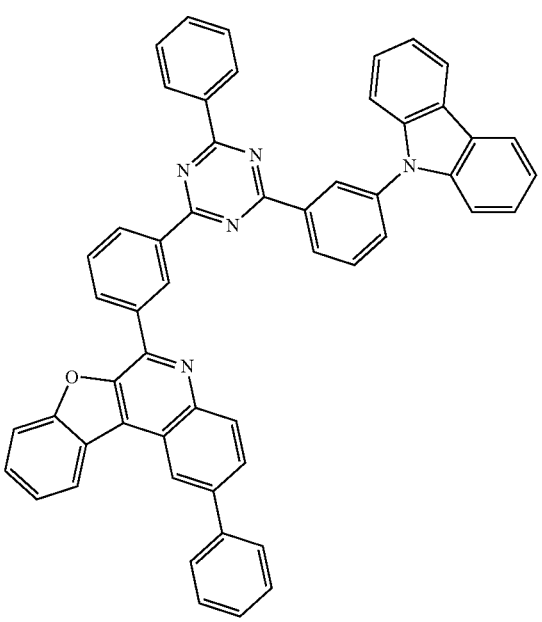

513
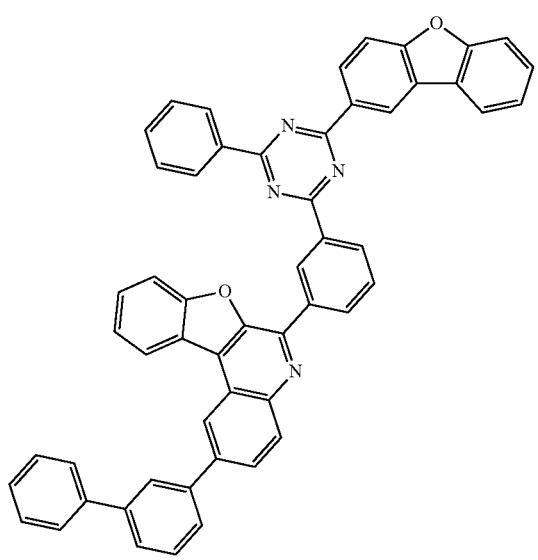
514
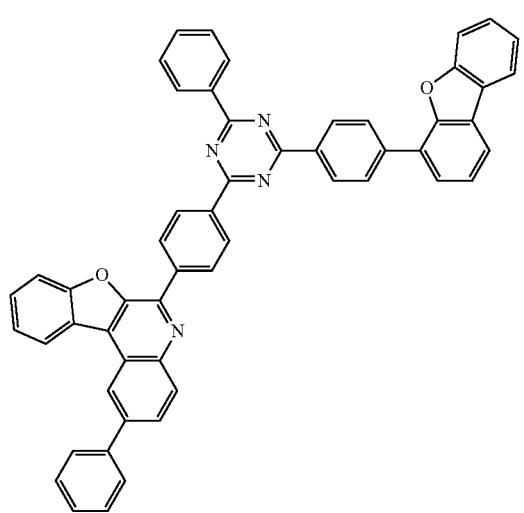
515
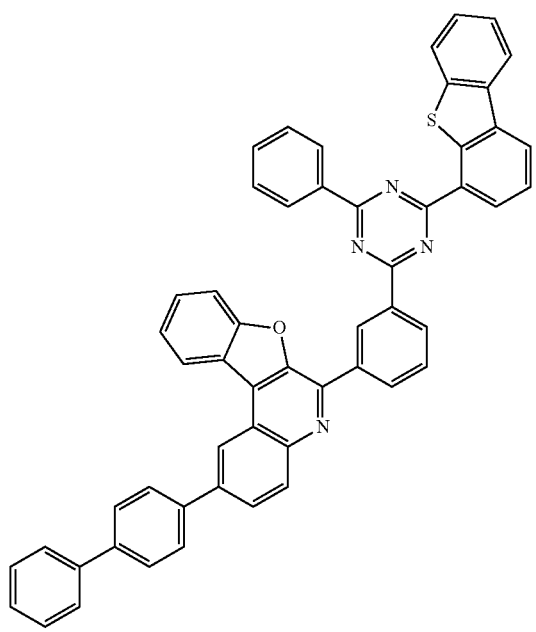
516
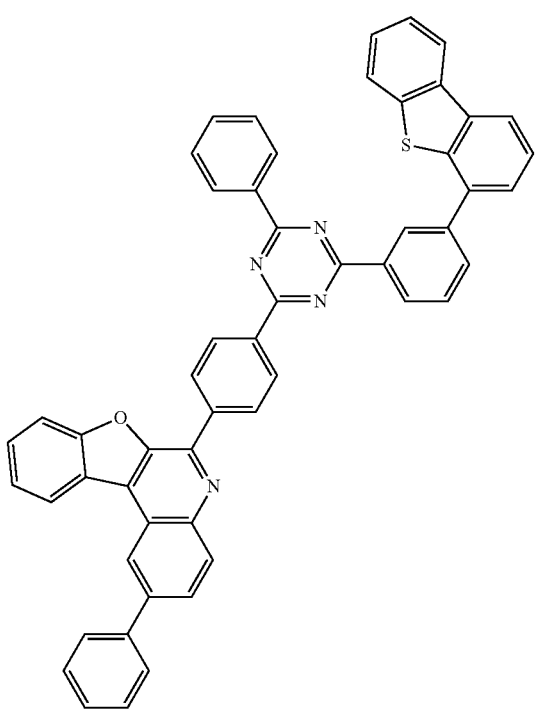

245
-continued
517
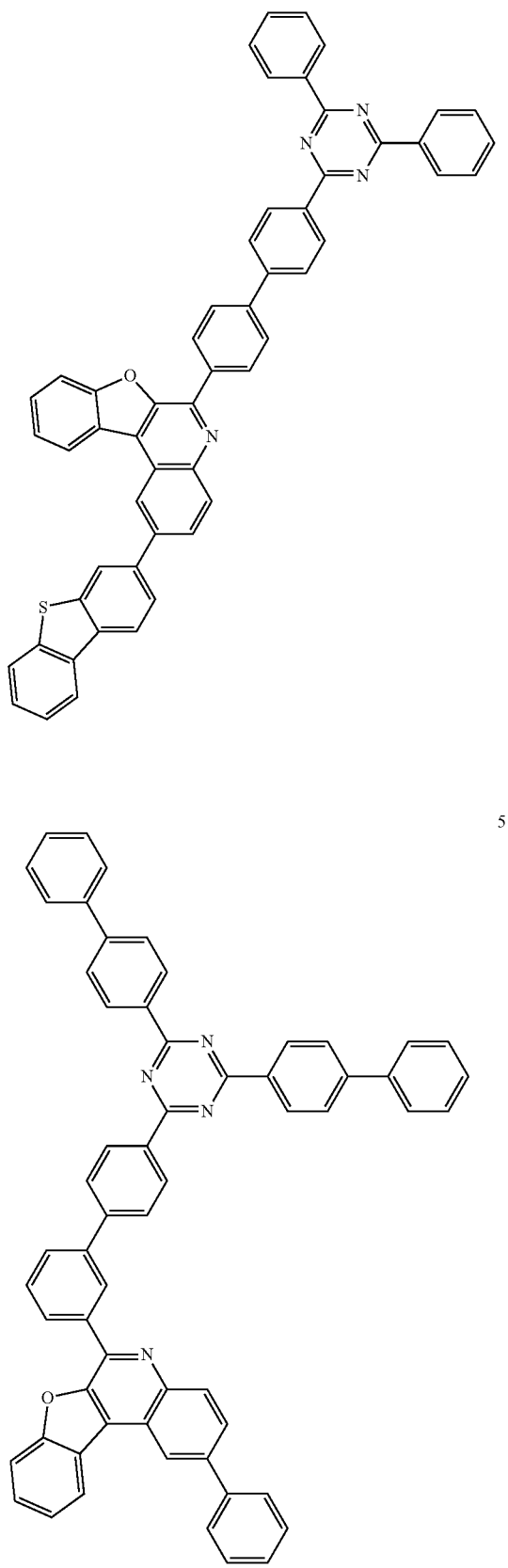
518
519
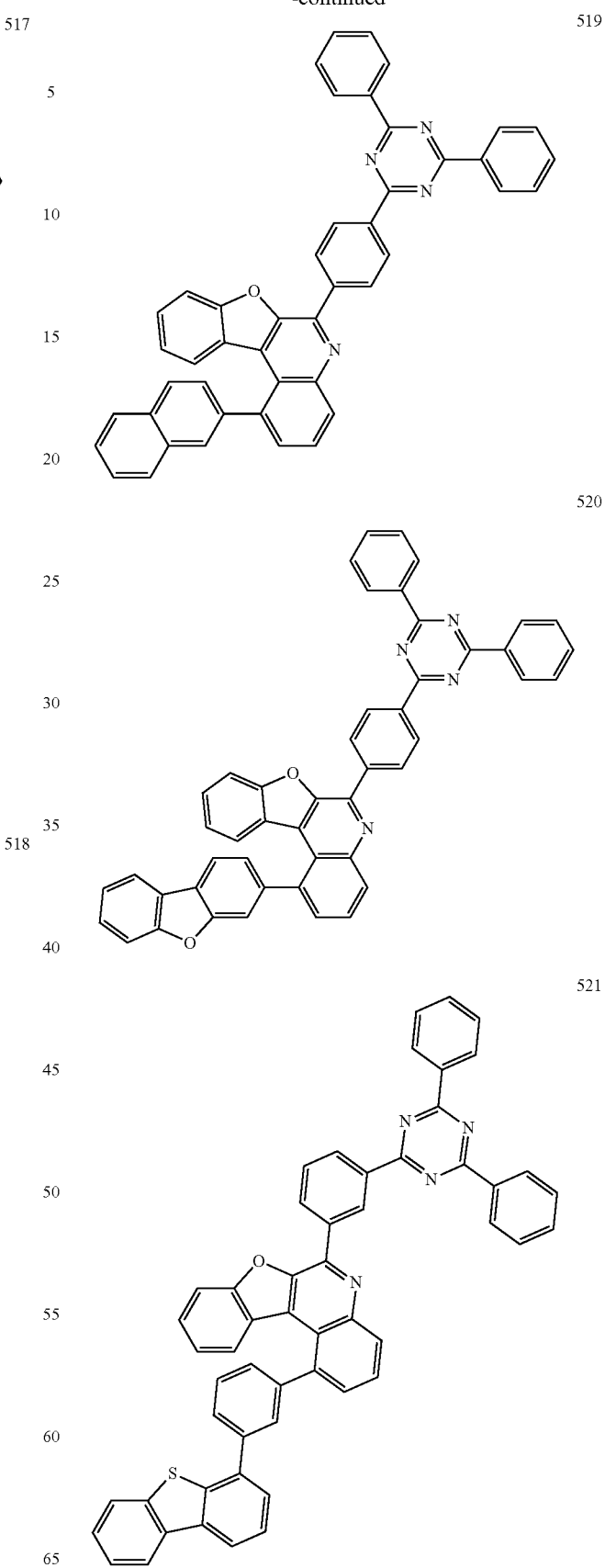
520
521

-continued
522
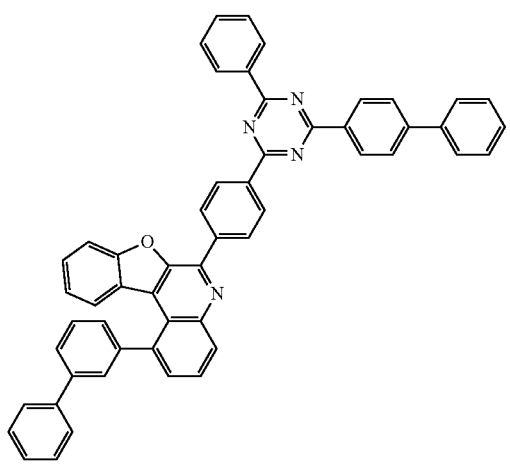
523
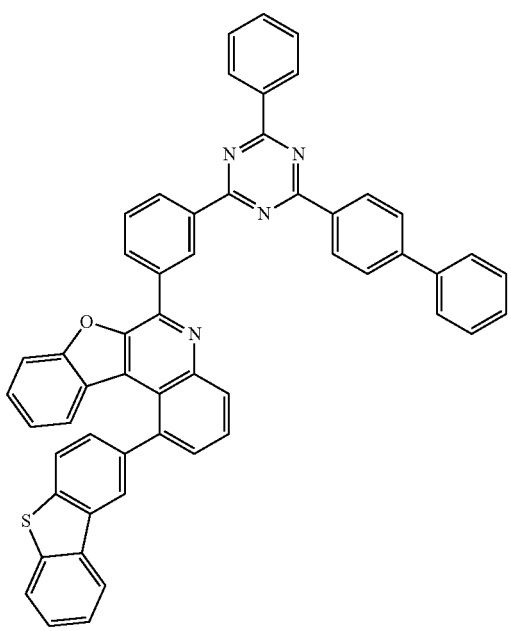
524
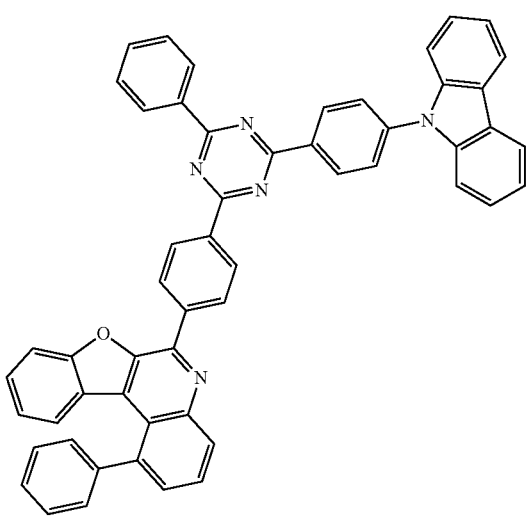
-continued
525
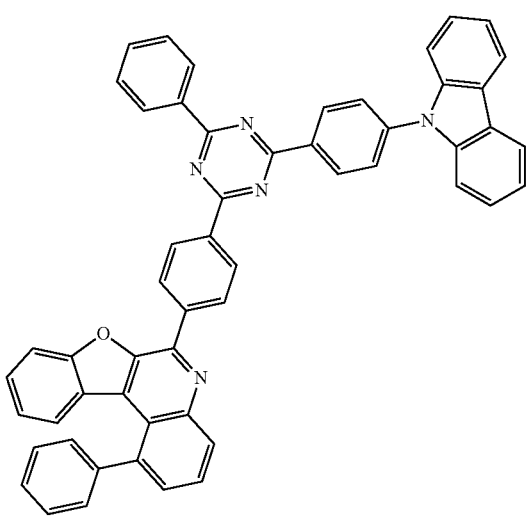
526
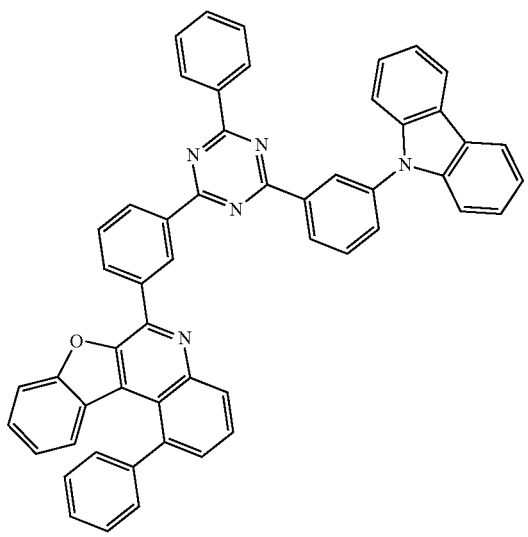

249
-continued
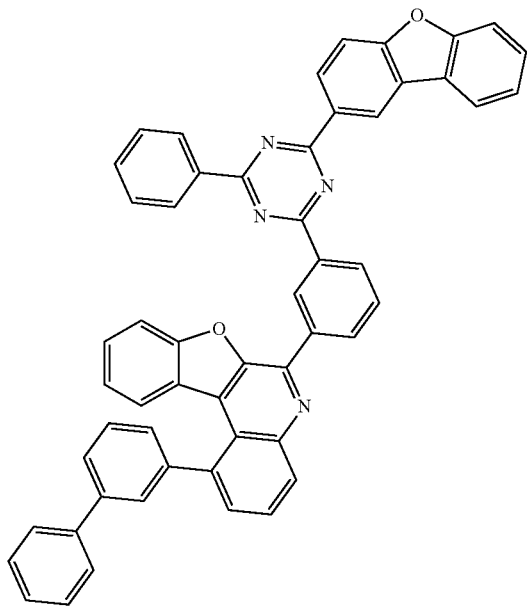
527
250
-continued
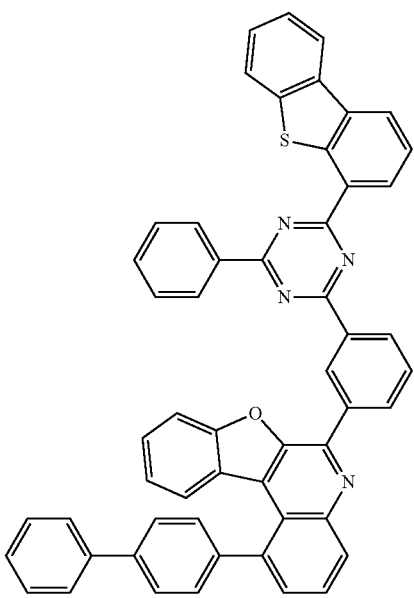
529
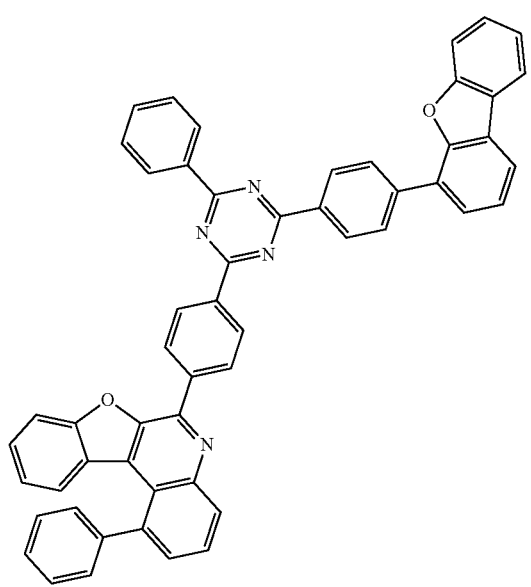
528
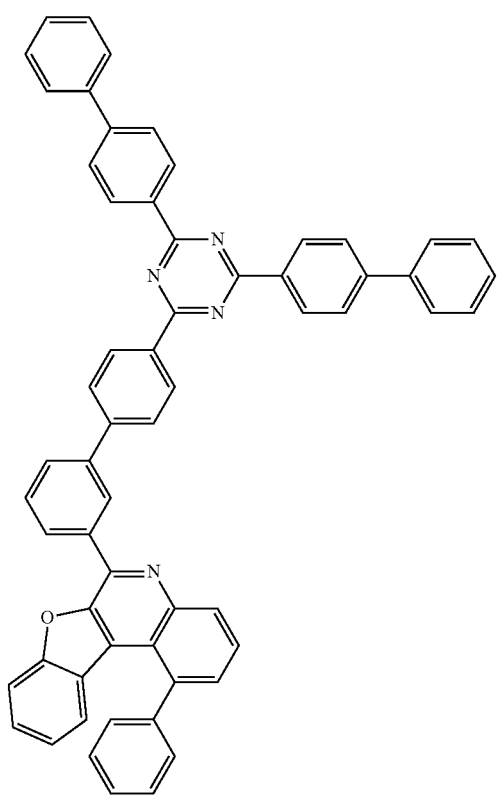
530

251
-continued
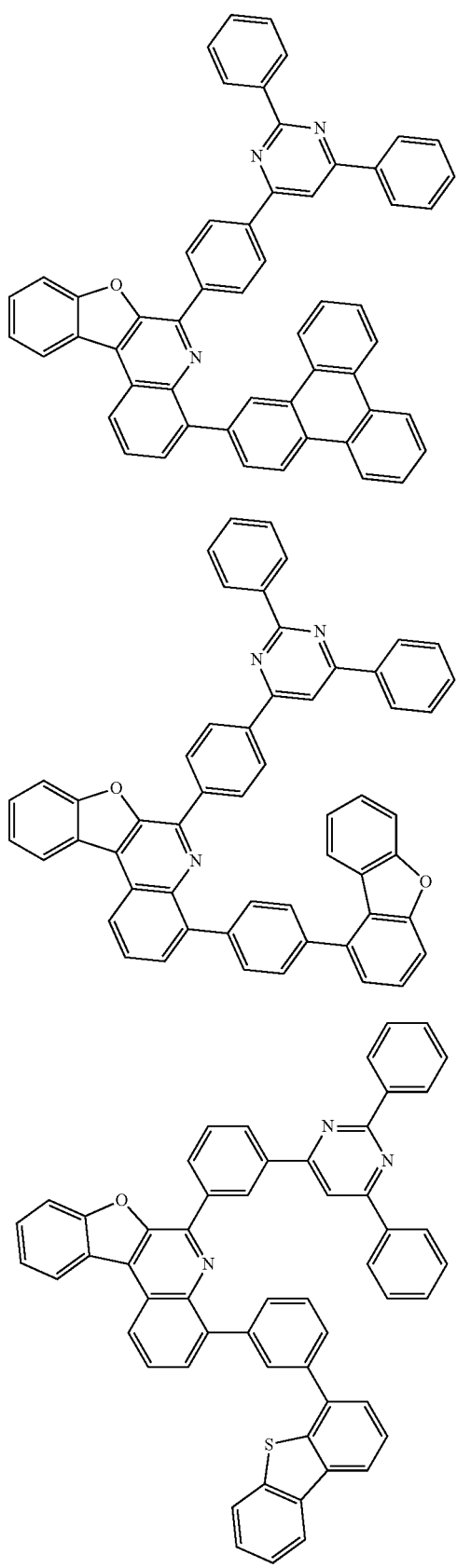
252
-continued
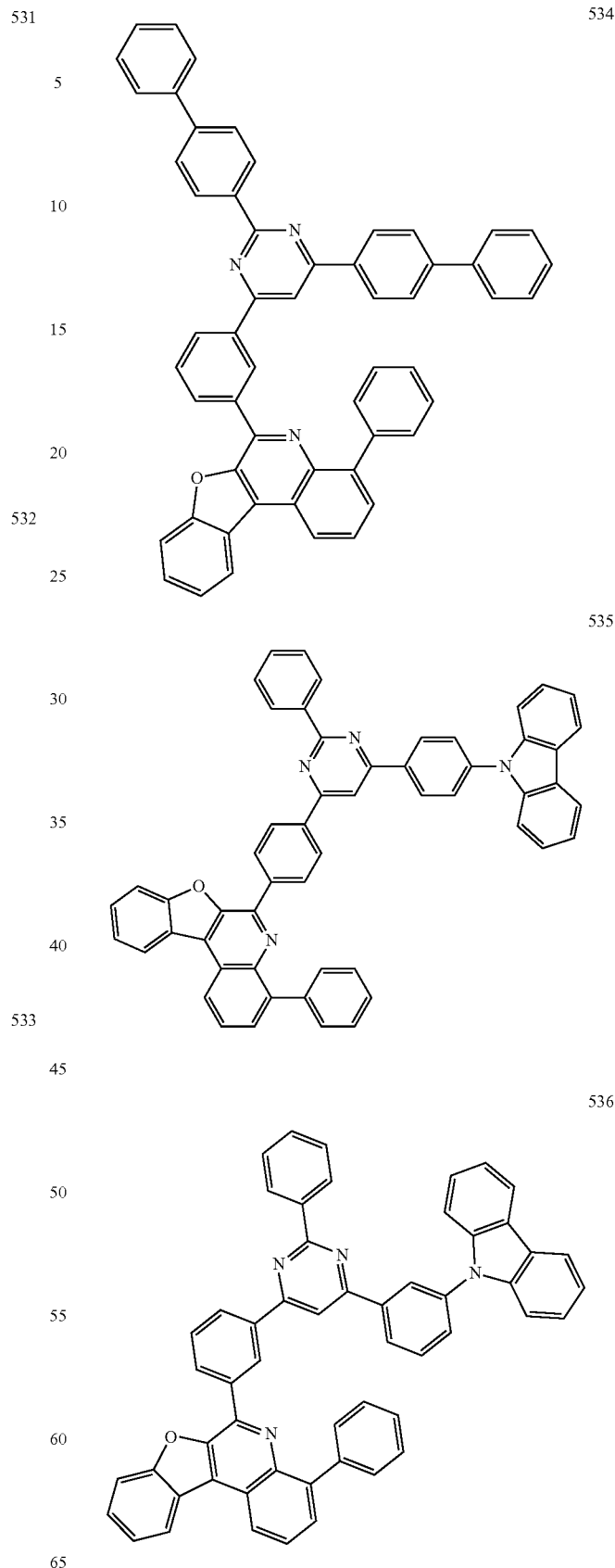

253
-continued
537
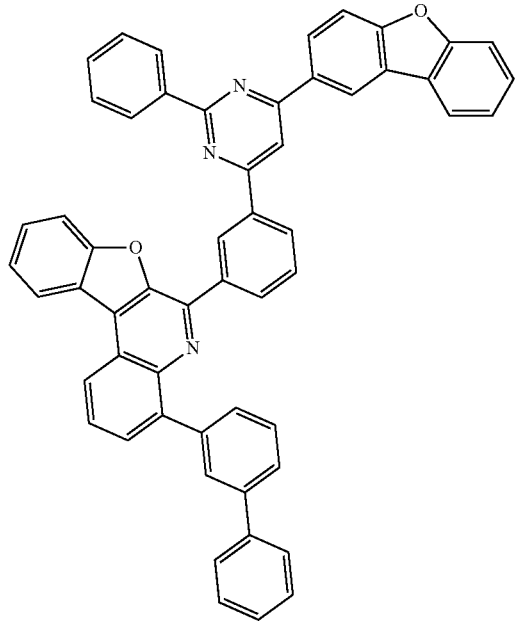
538
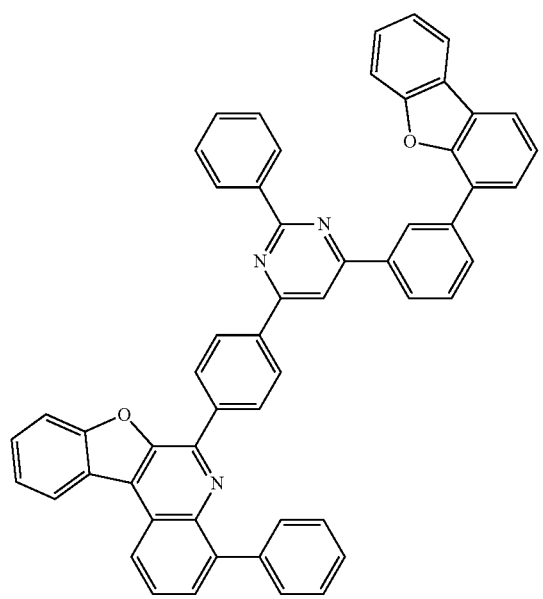
539
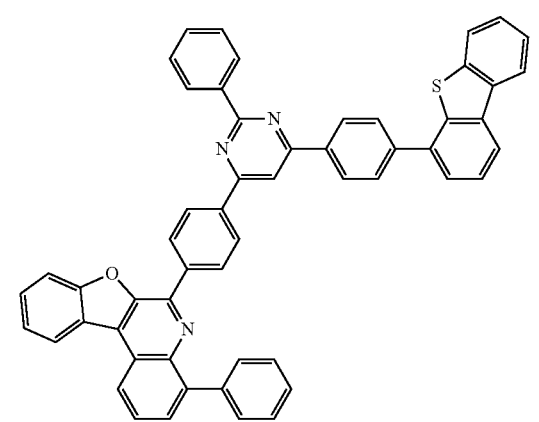
254
-continued
540
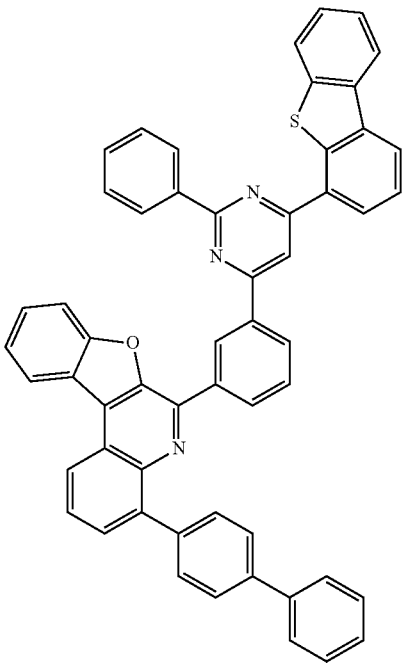
541
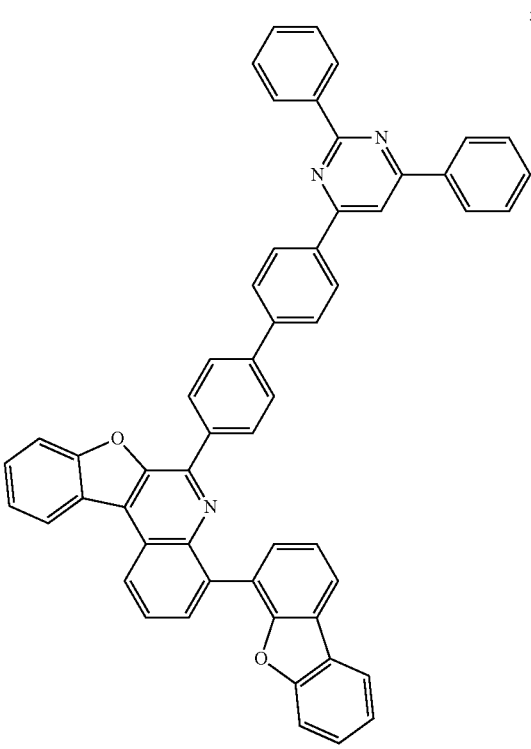

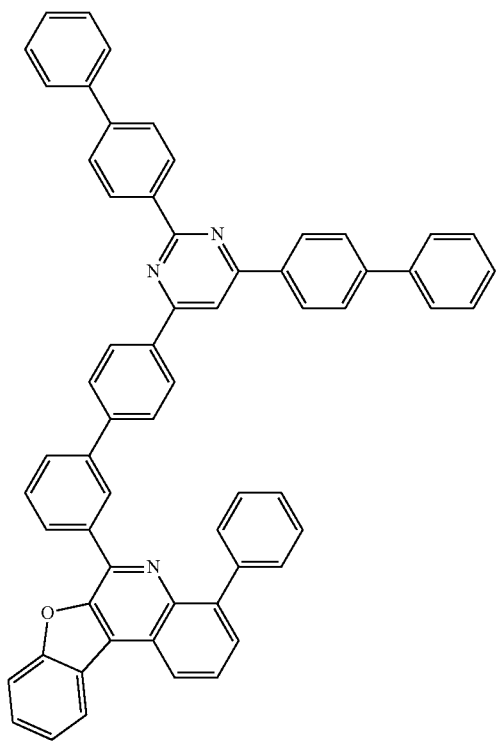
542
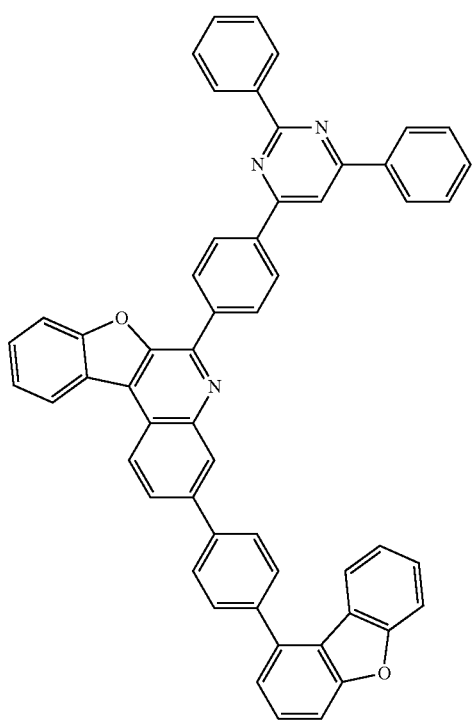
544
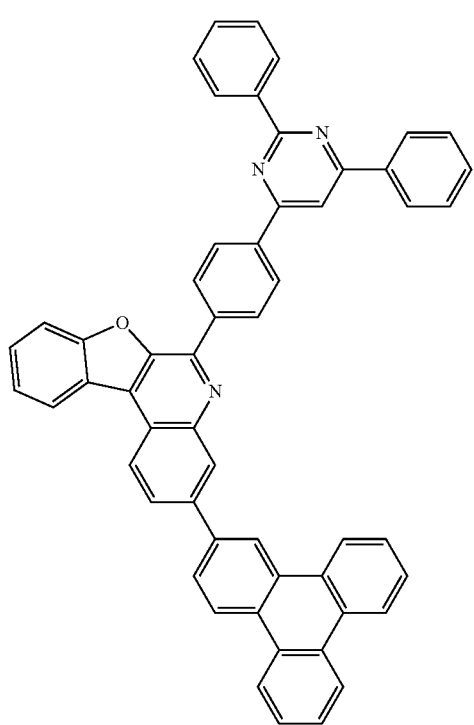
543
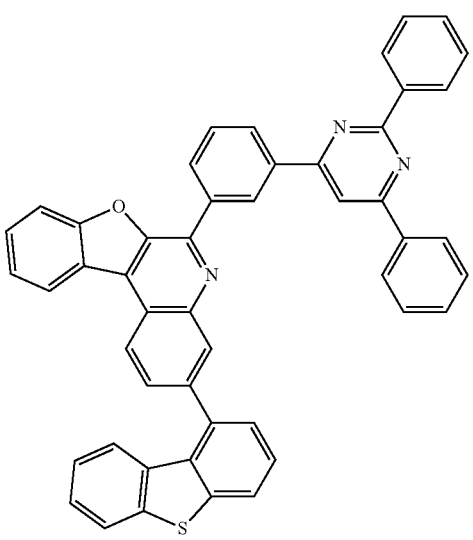
545

-continued
546
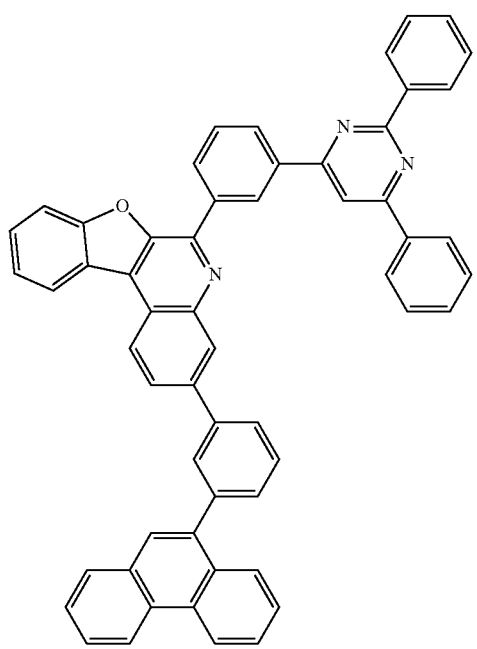
548
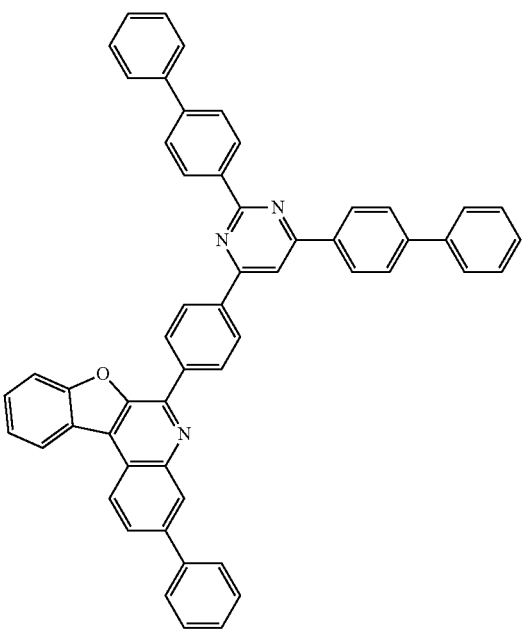
547
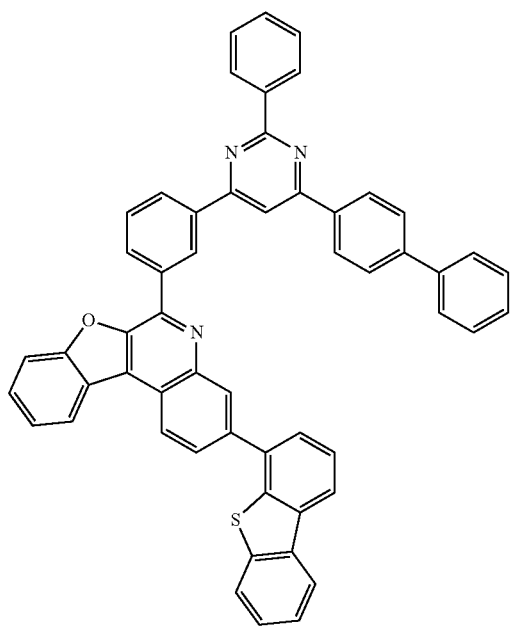
549
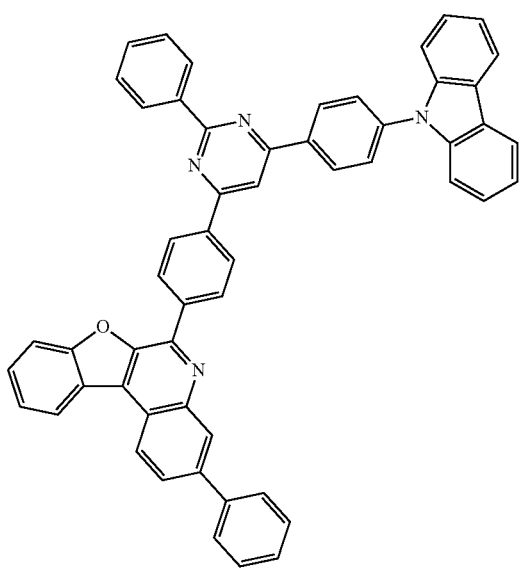

550
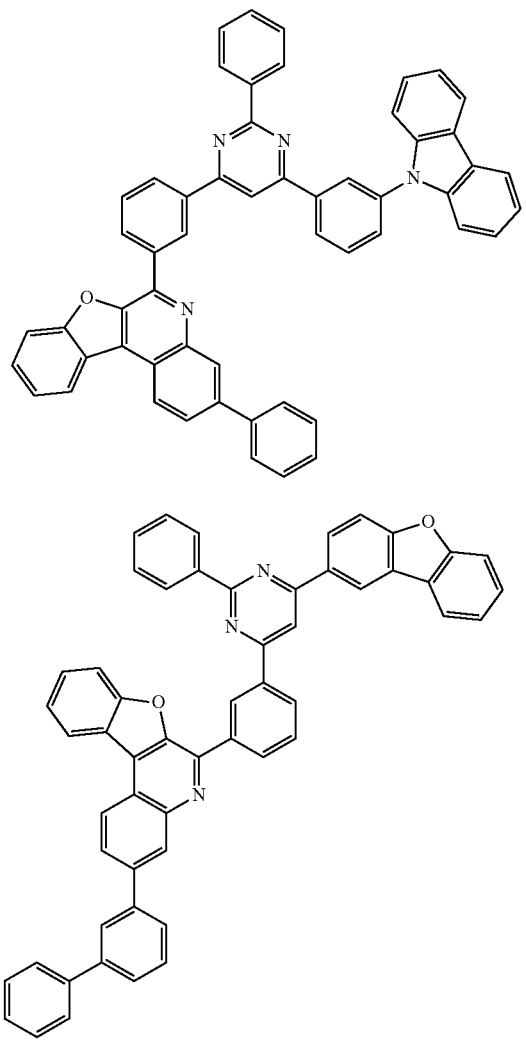
551
552
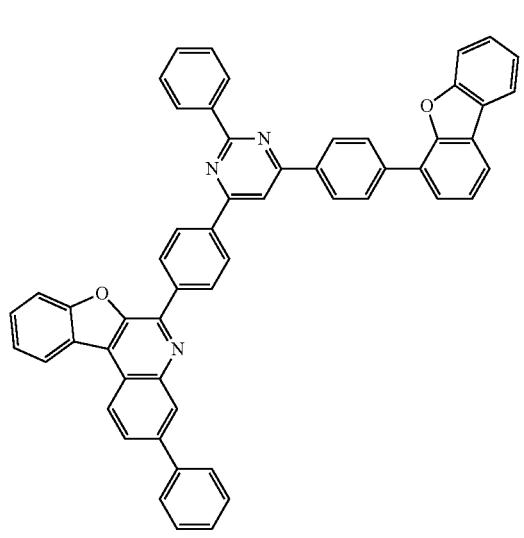
553
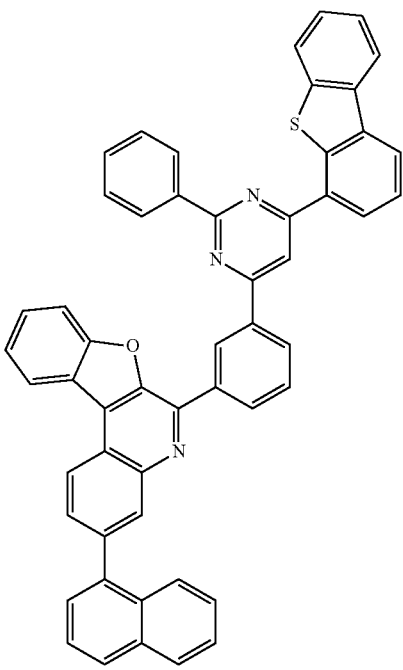
554
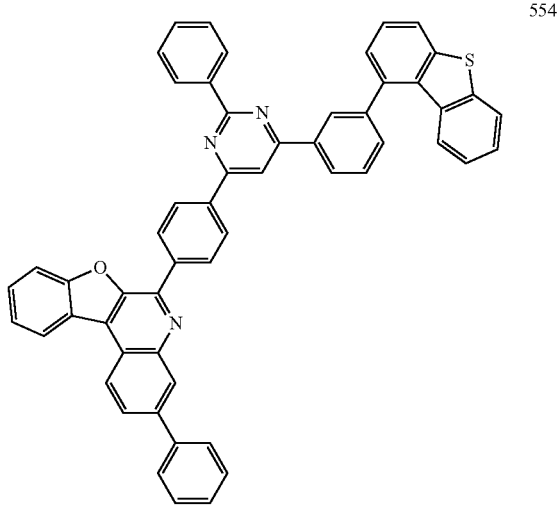

261
-continued
555
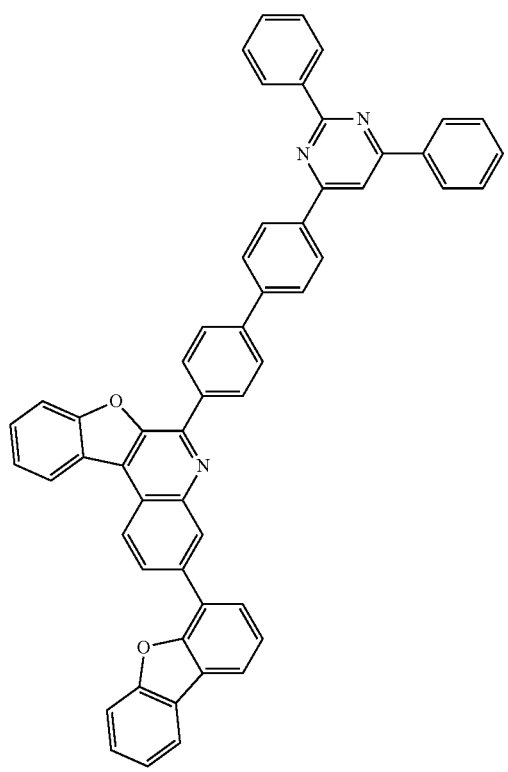
556
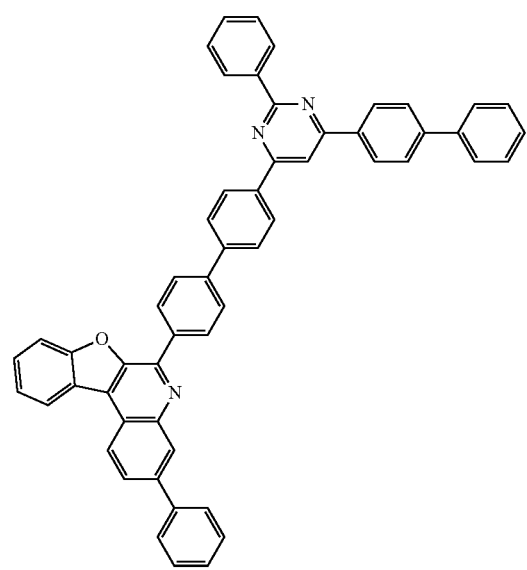
262
-continued
557
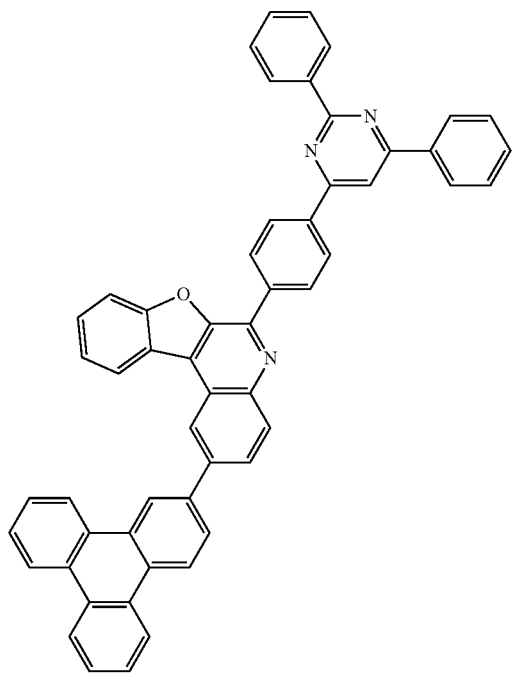
558
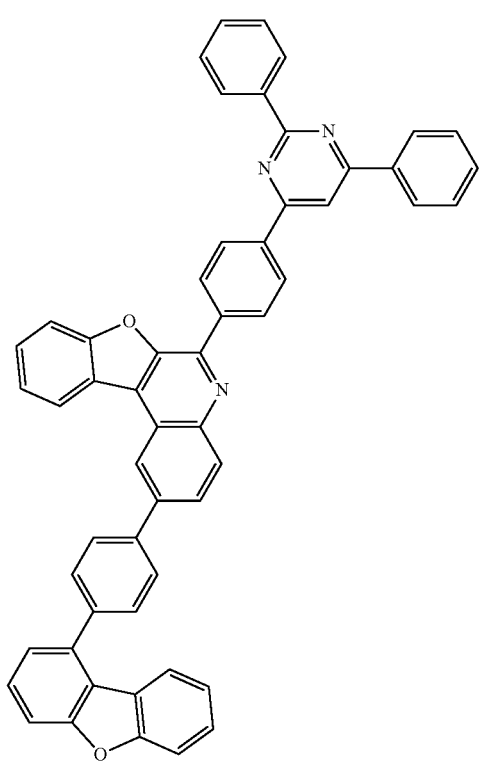

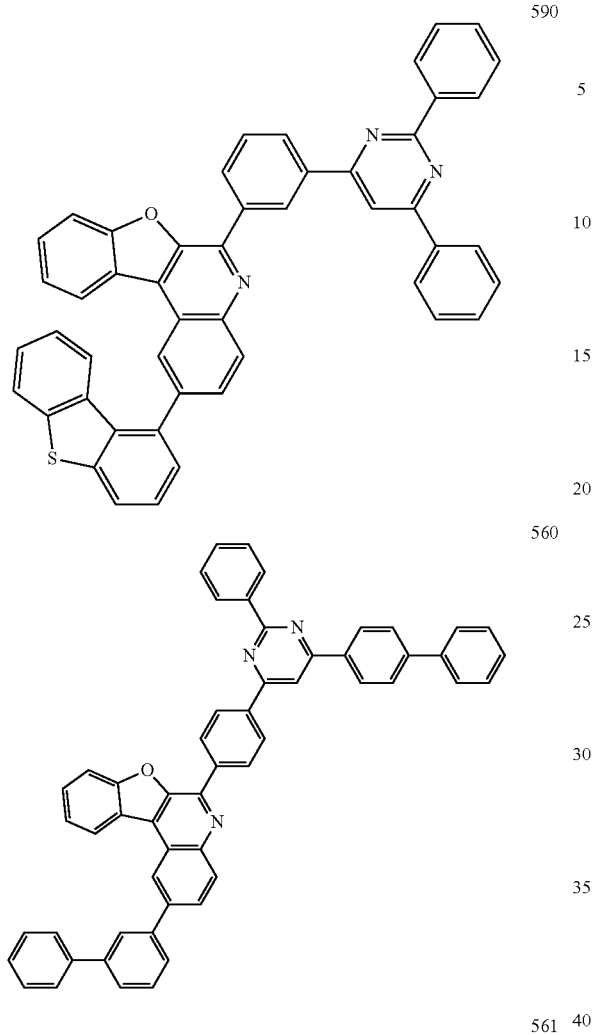
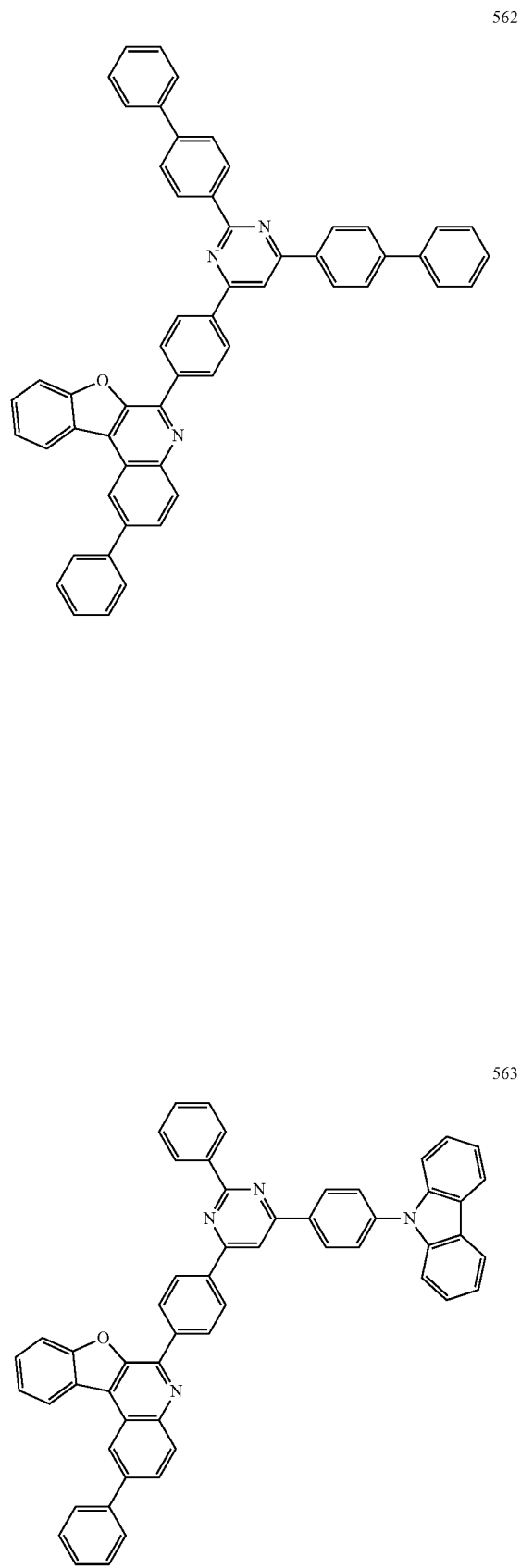

564
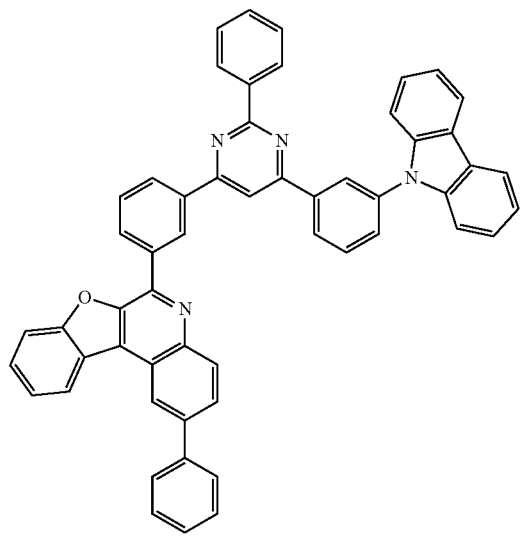
565
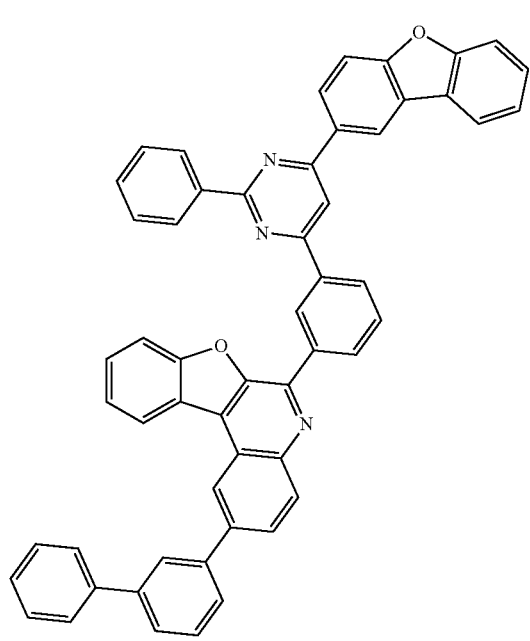
566
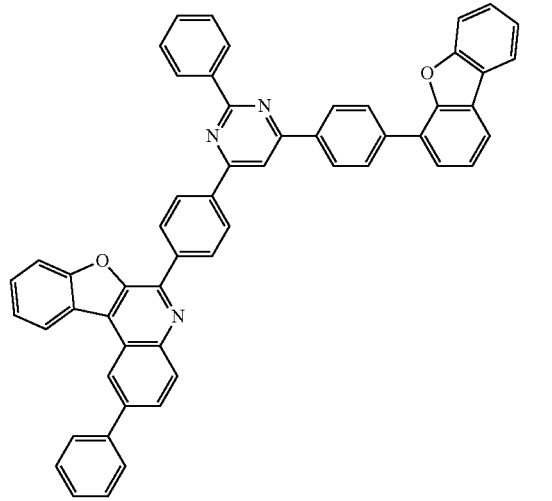
567
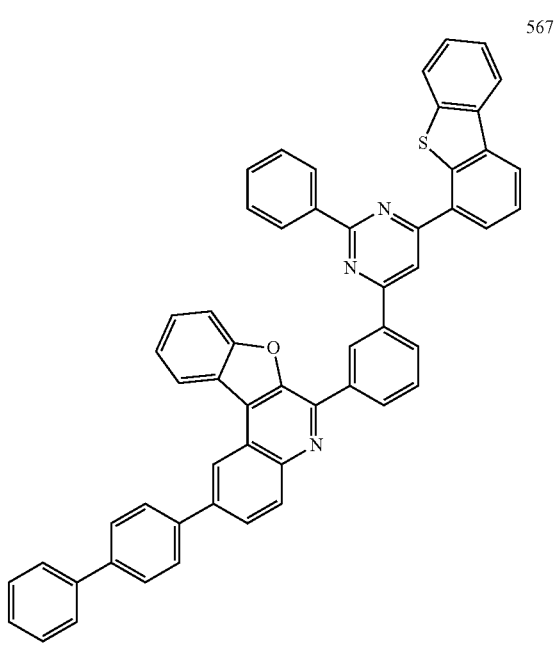

267
-continued
568
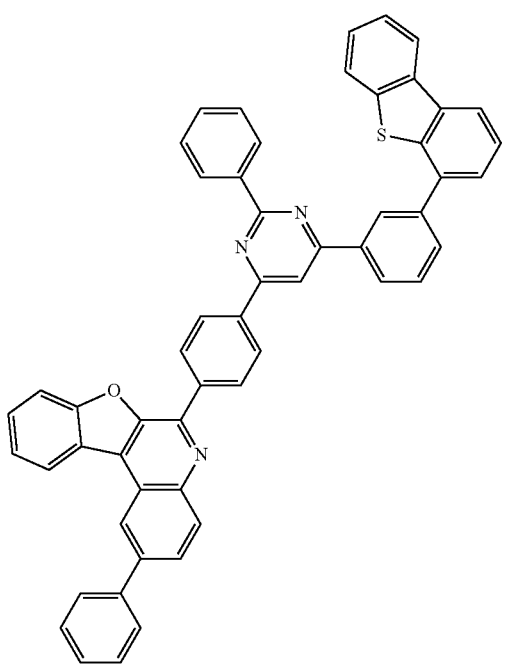
569
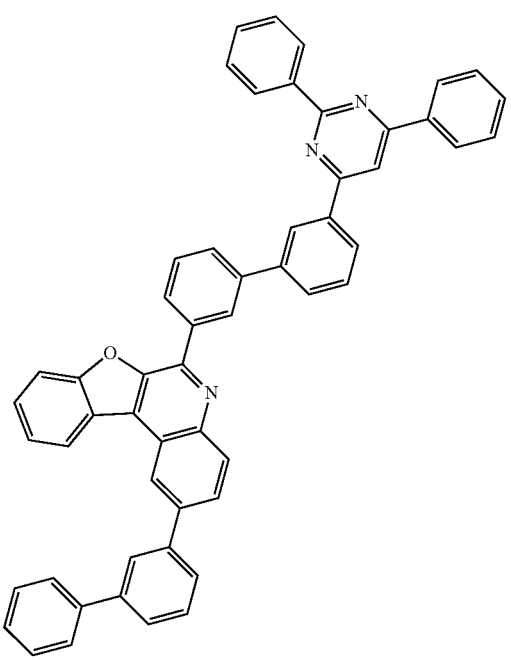
268
-continued
570
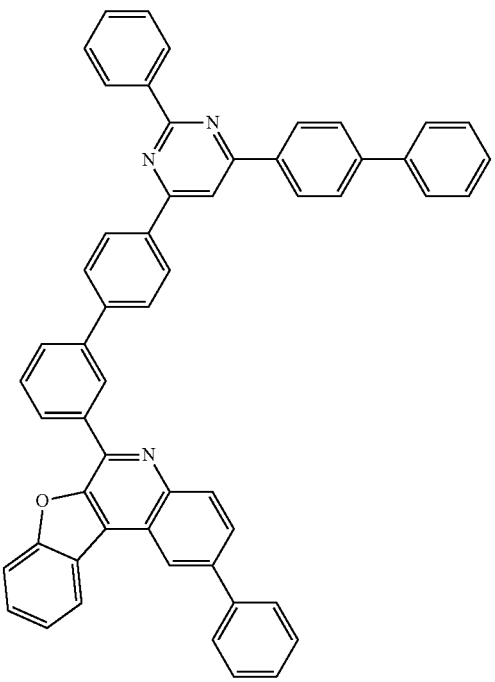
571
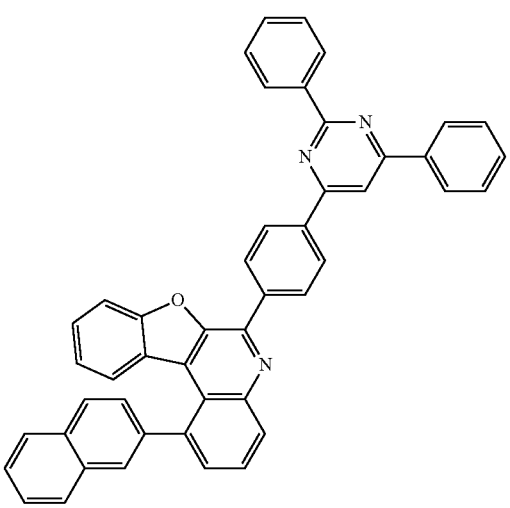

572
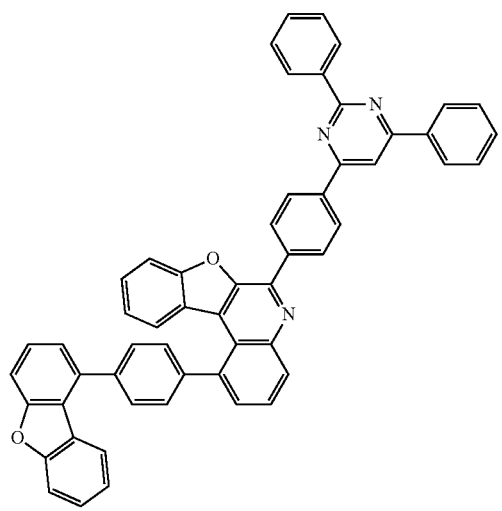
573
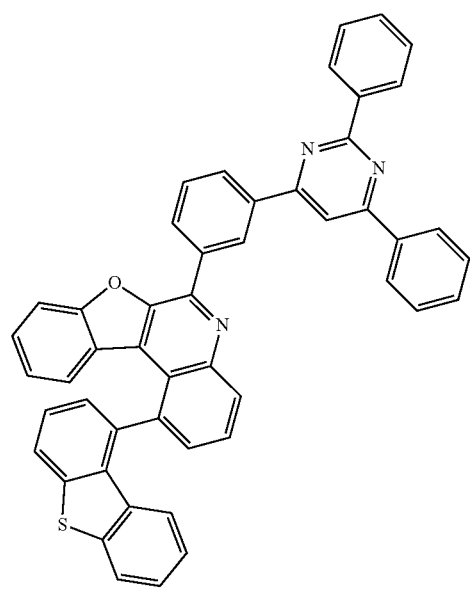
574
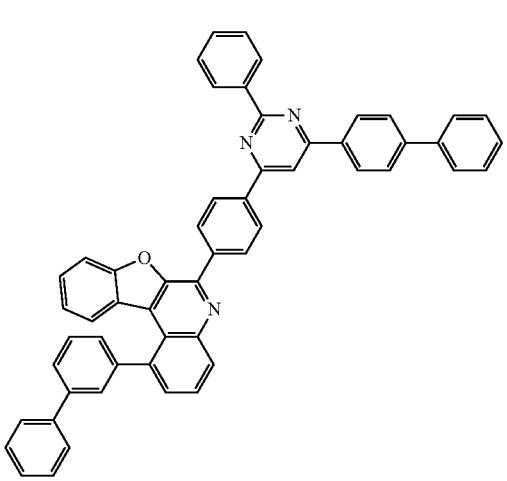
575
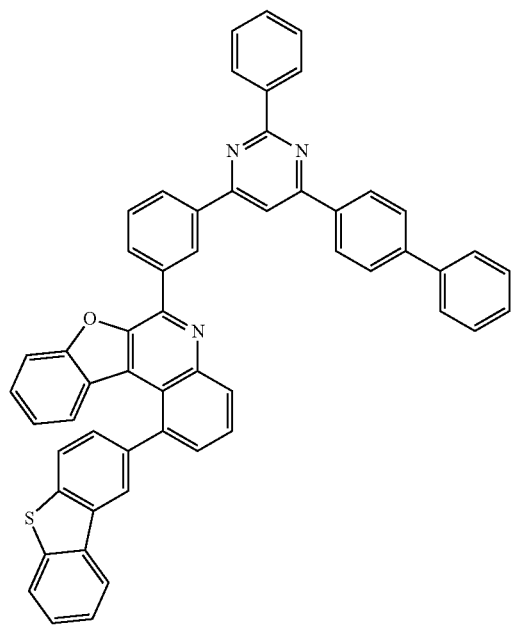
576
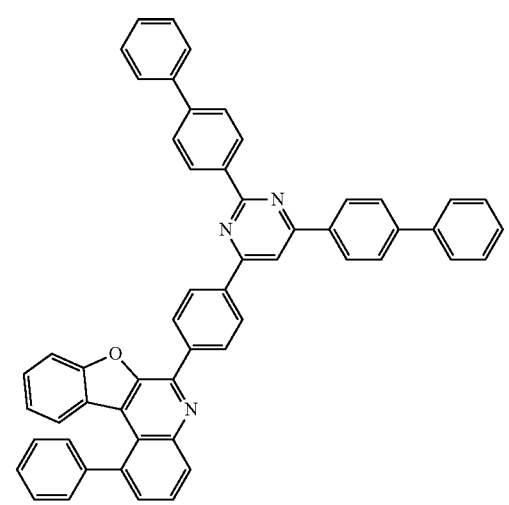
577
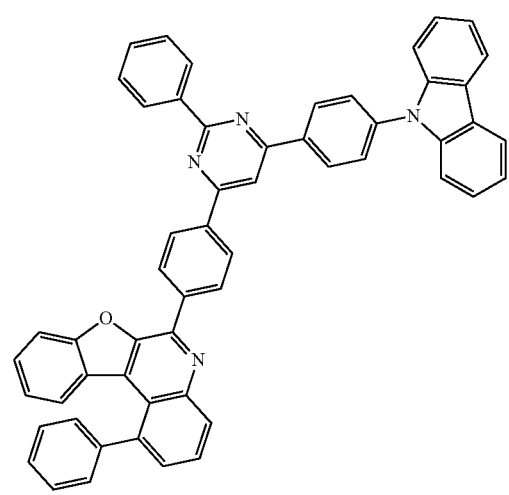

578
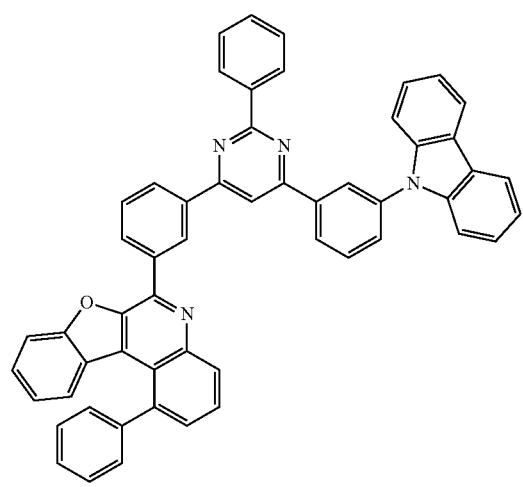
579
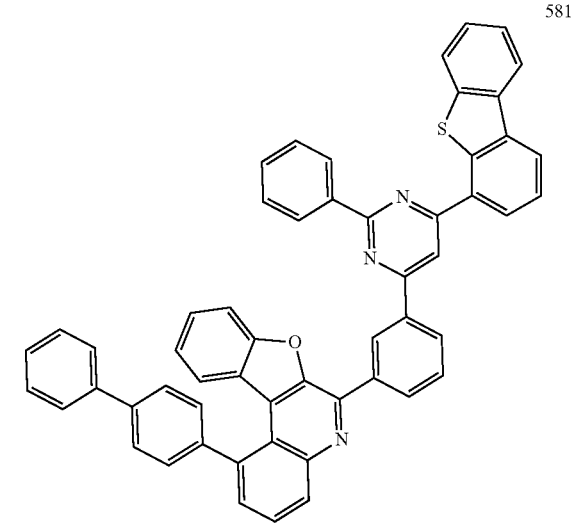
580
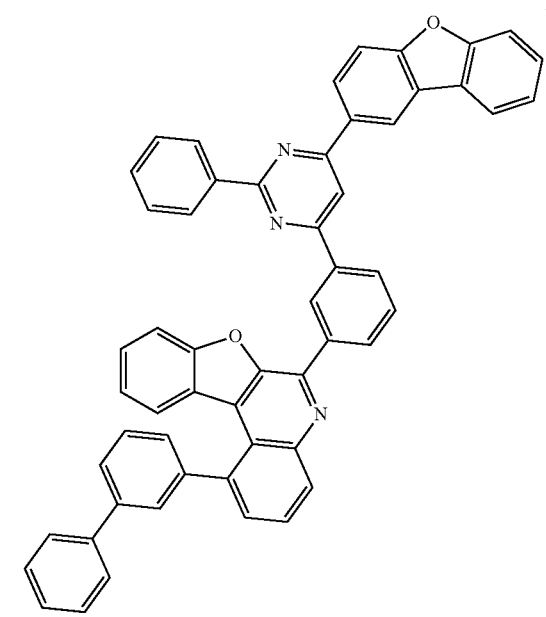
581
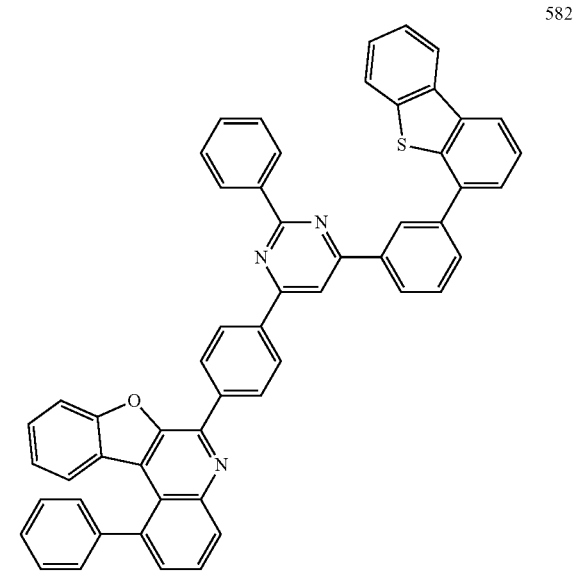
582

273
-continued
583
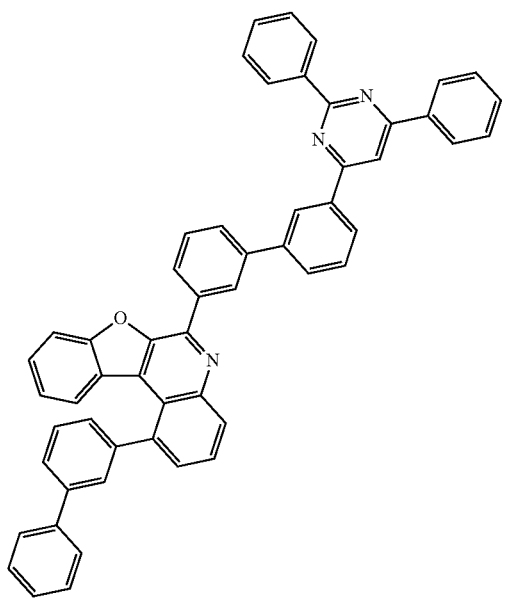
584
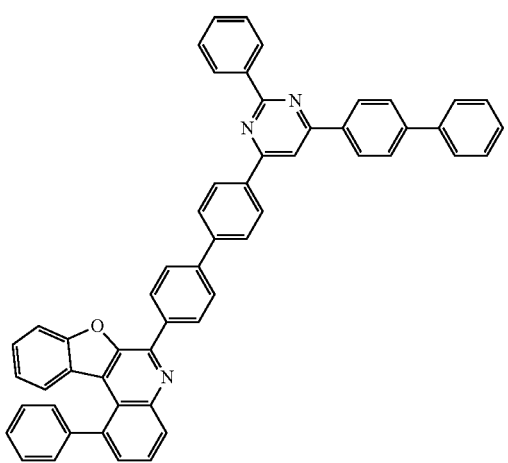
585
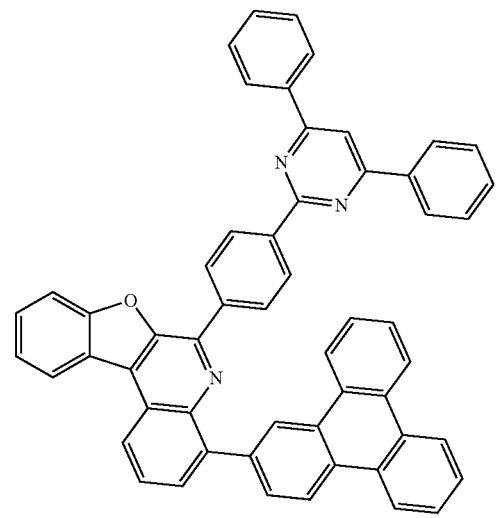
274
-continued
586
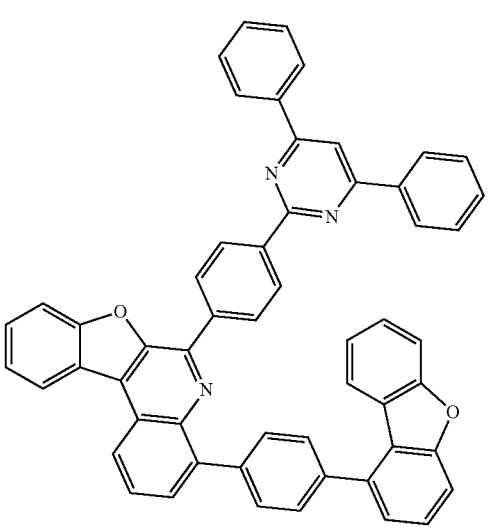
587
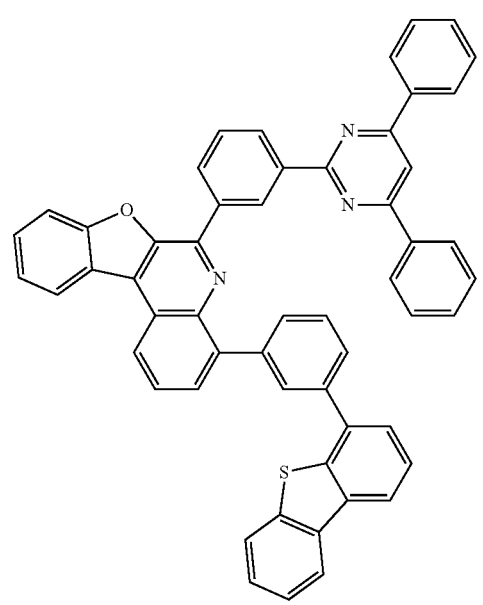
588
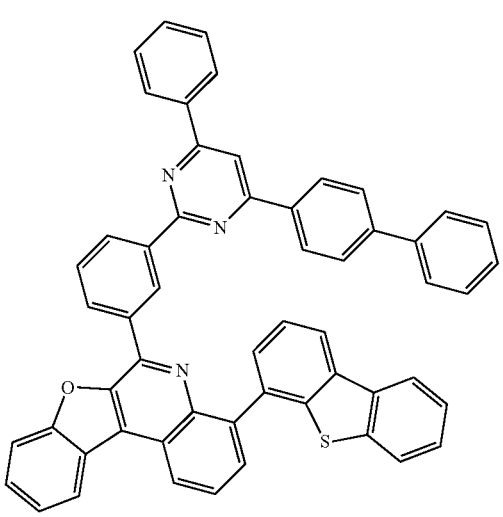

275
-continued
589
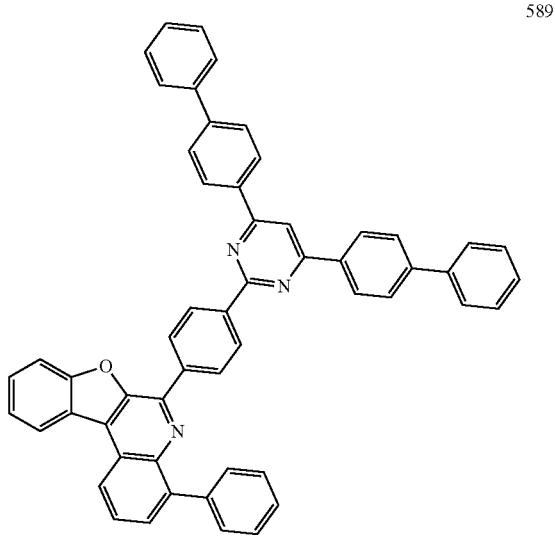
590
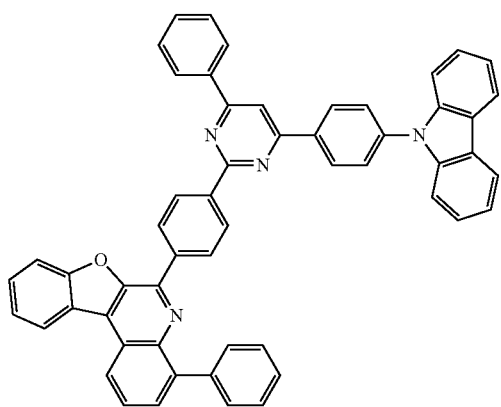
591
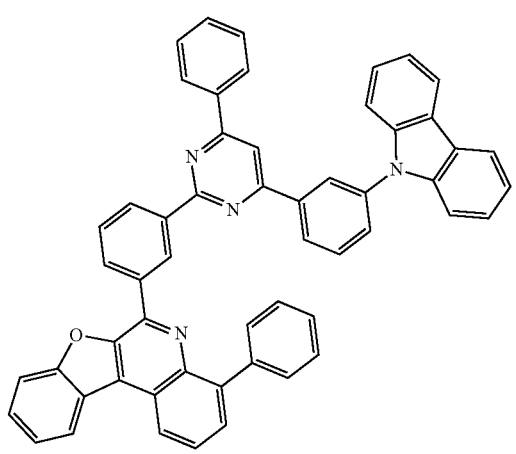
276
-continued
592
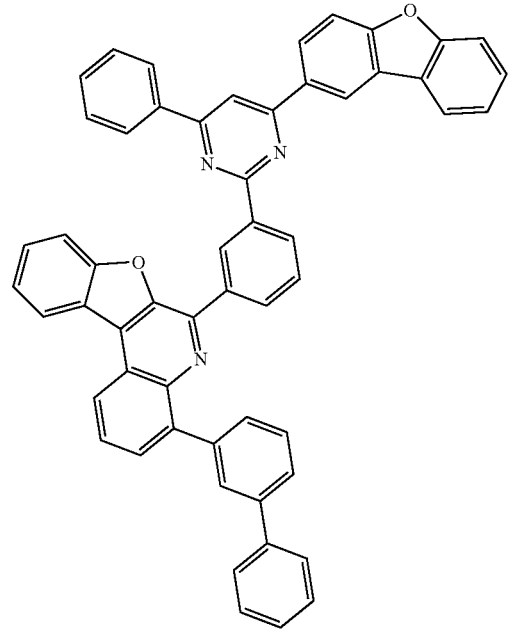
593
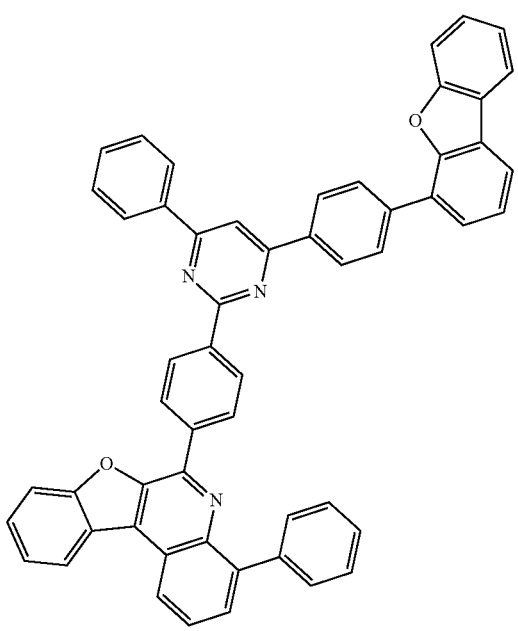

277
-continued
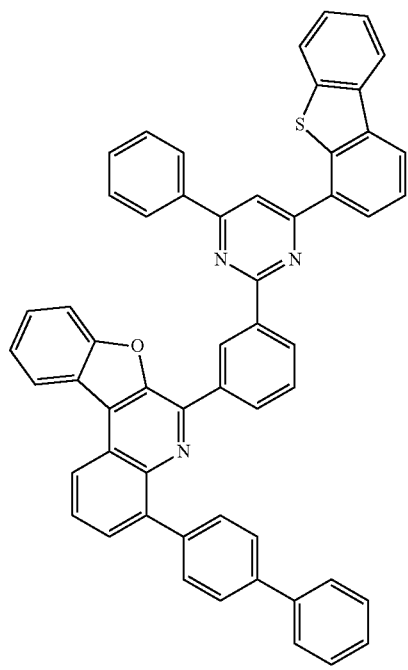
594
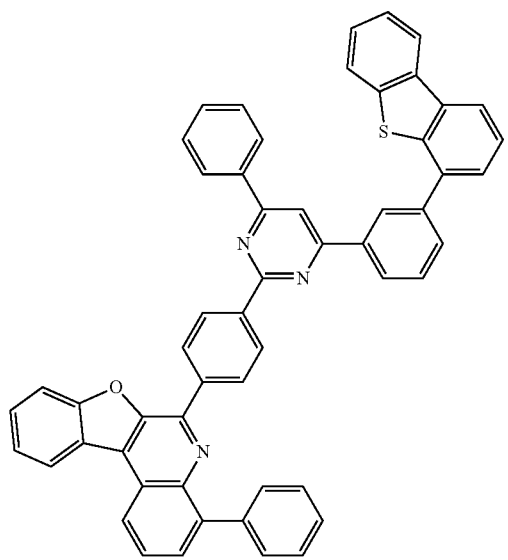
595
278
-continued
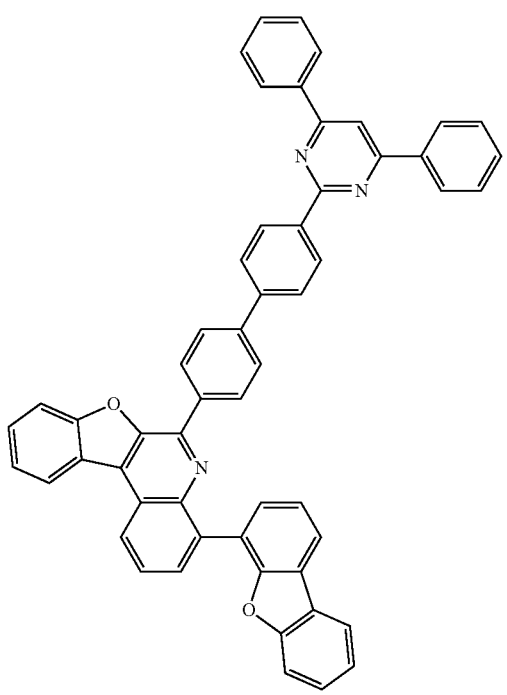
596
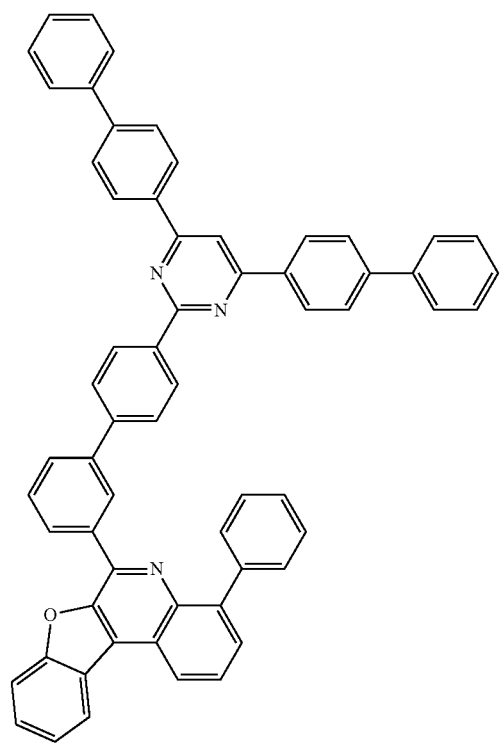
597

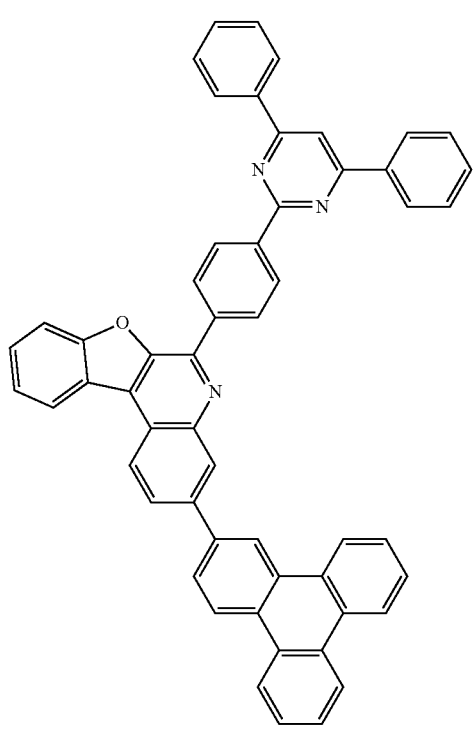
598
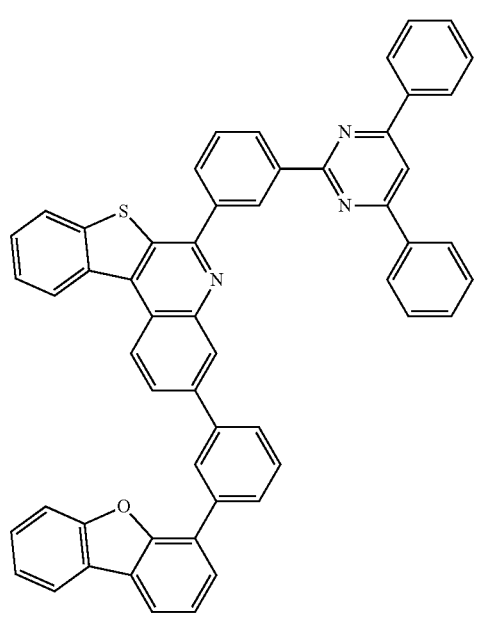
600
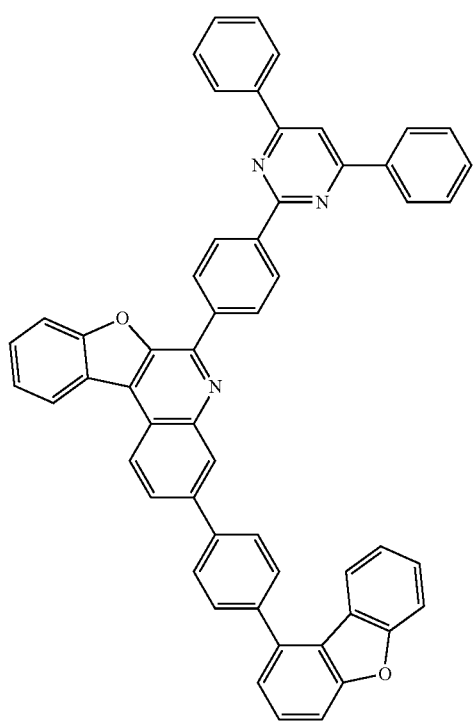
599

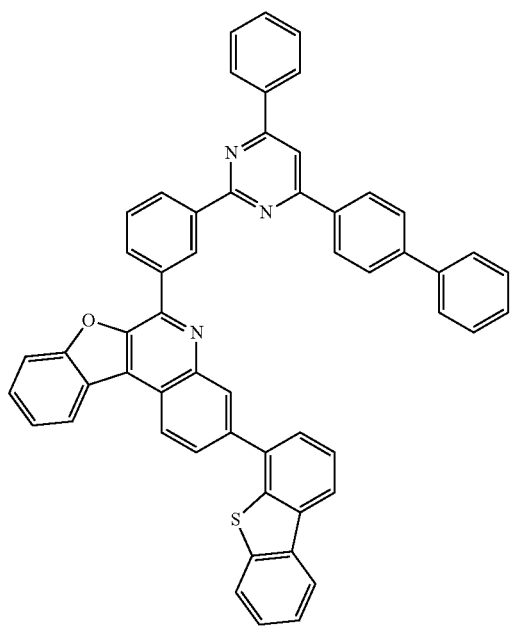
602
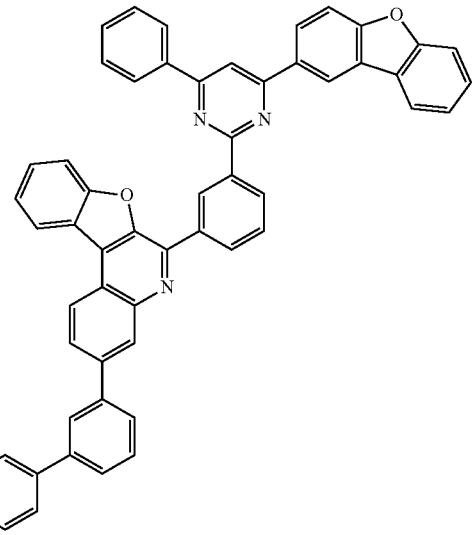
605
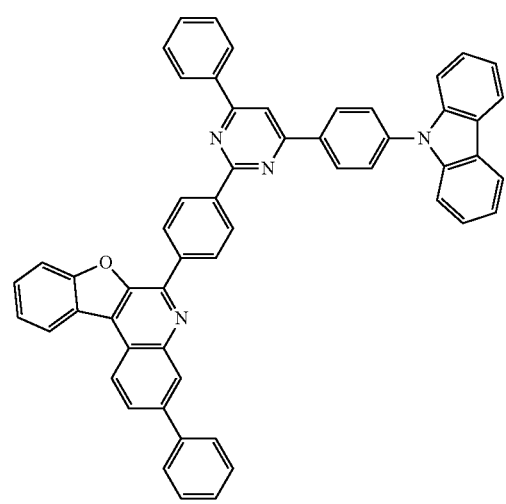
603
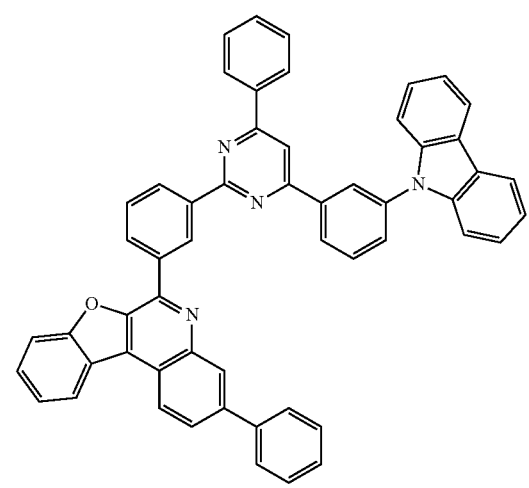
604
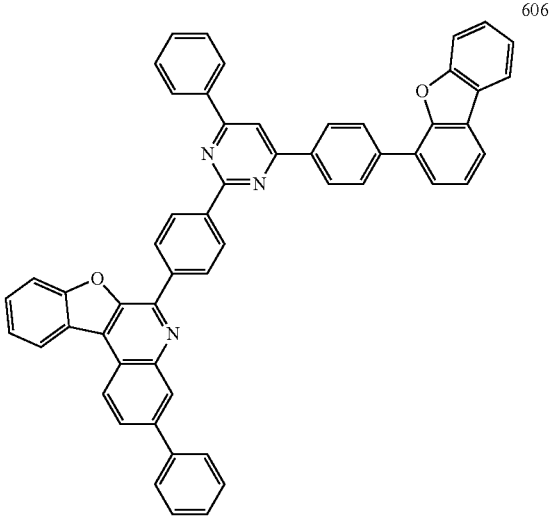
606

283
-continued
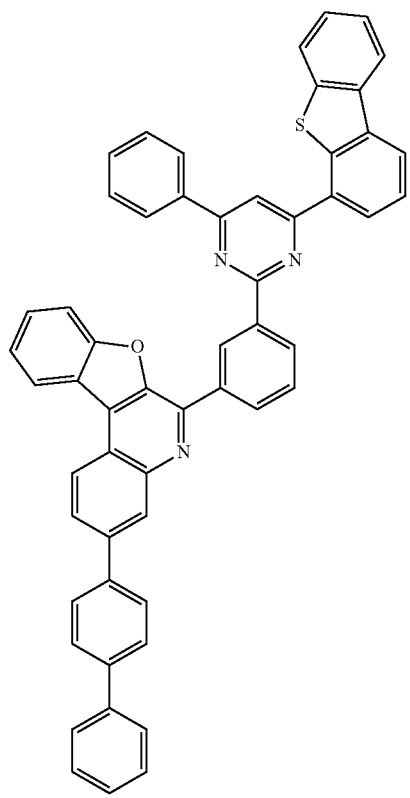
607
284
-continued
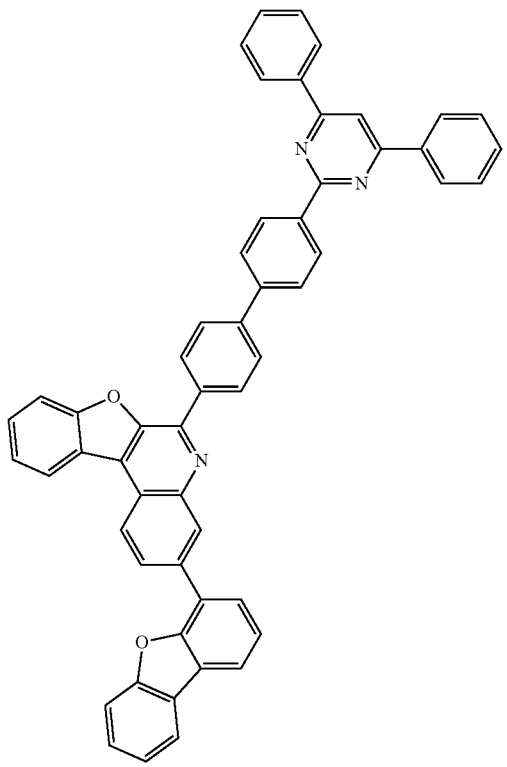
609
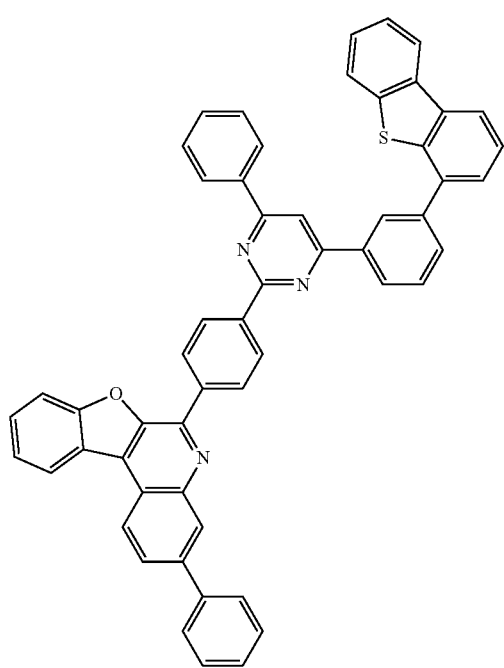
608
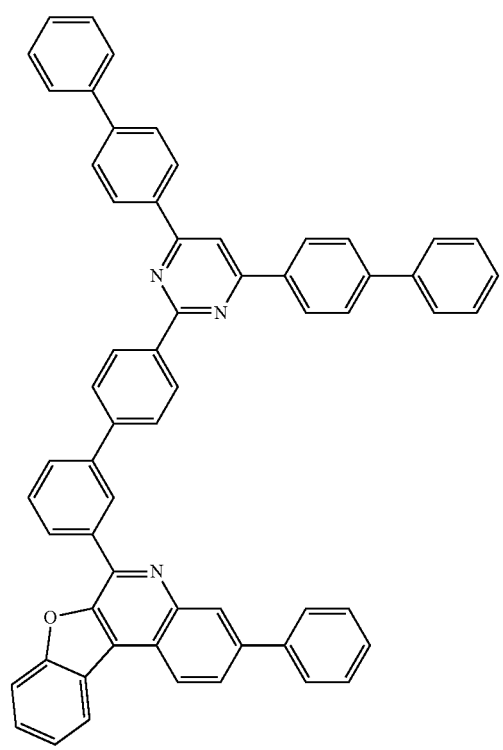
610

285
-continued
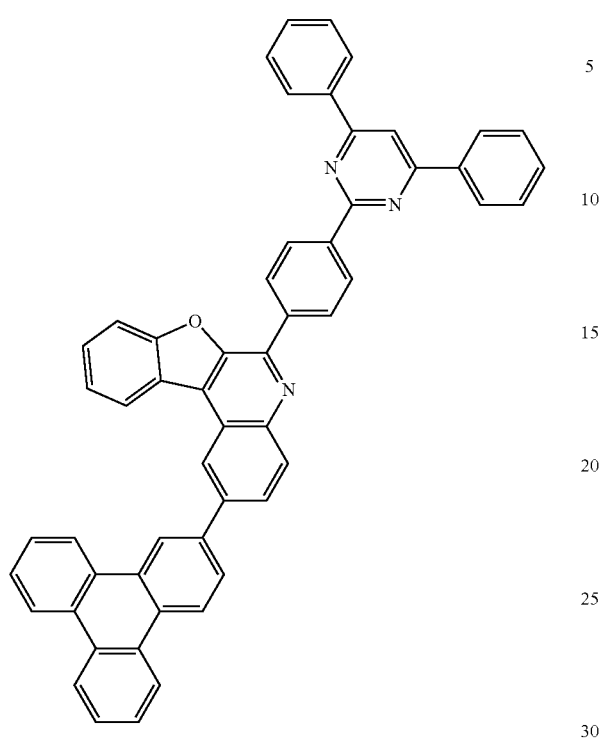
611
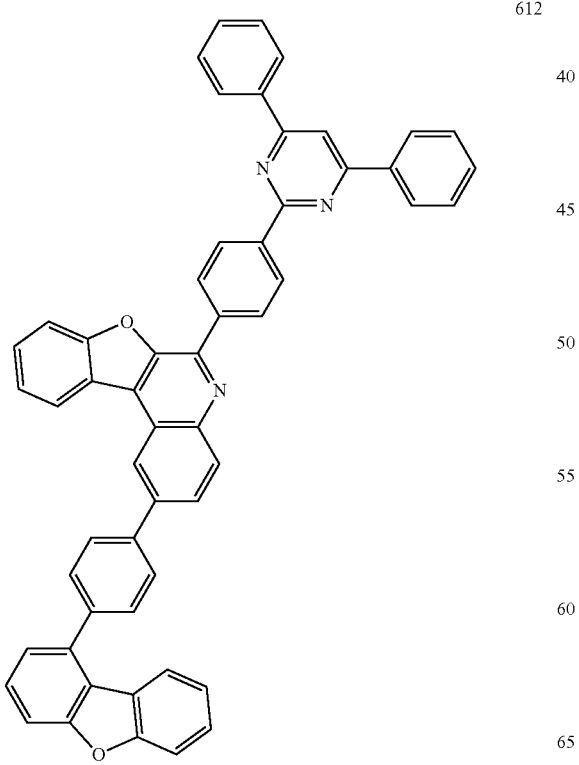
612
286
-continued
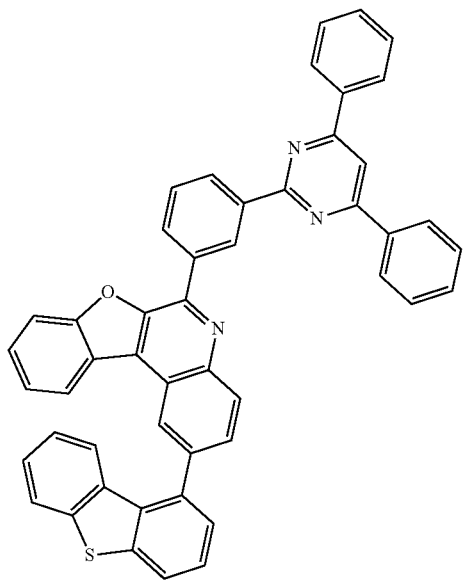
613
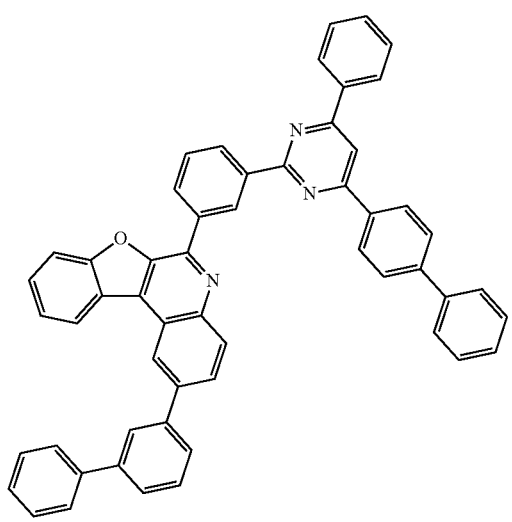
614

287
-continued
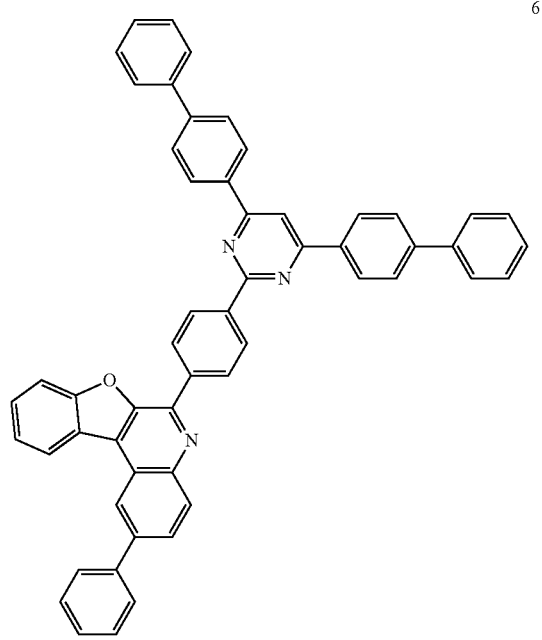
615
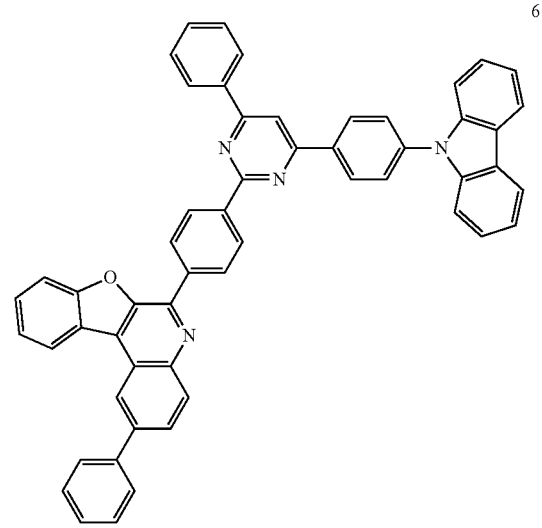
616
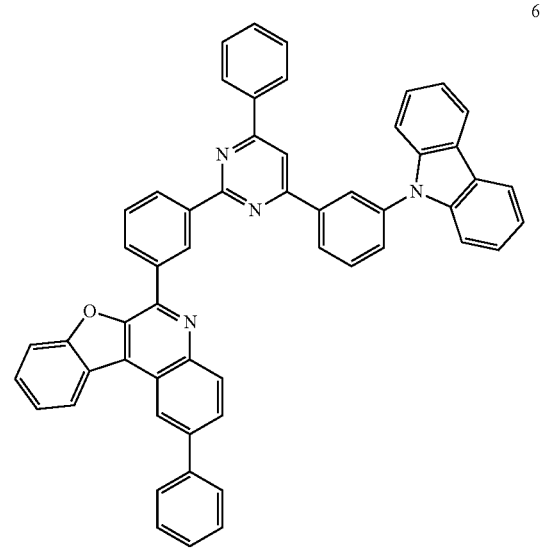
617
288
-continued
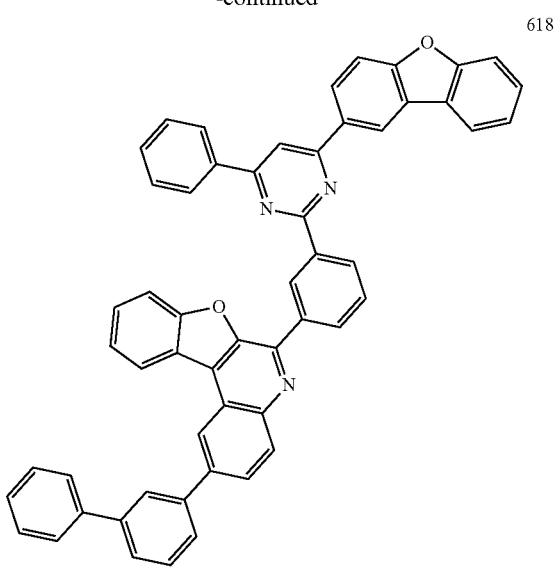
618
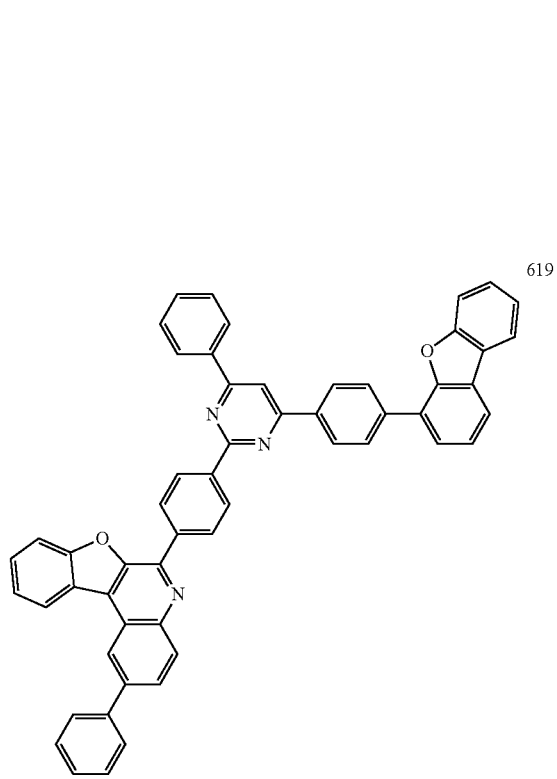
619

289
-continued
620
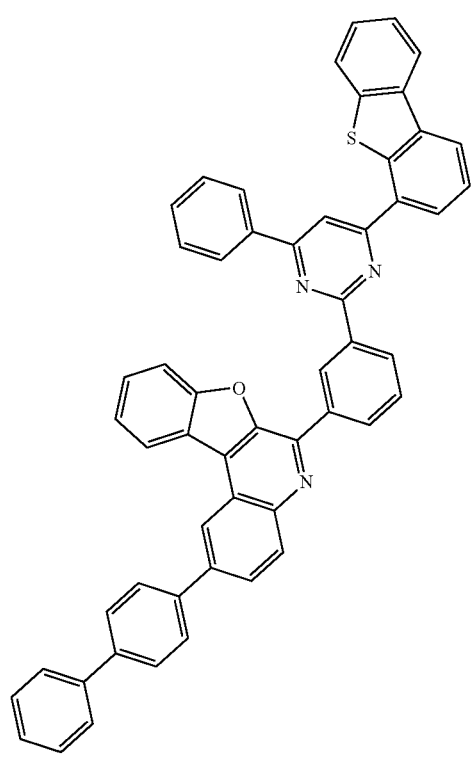
621
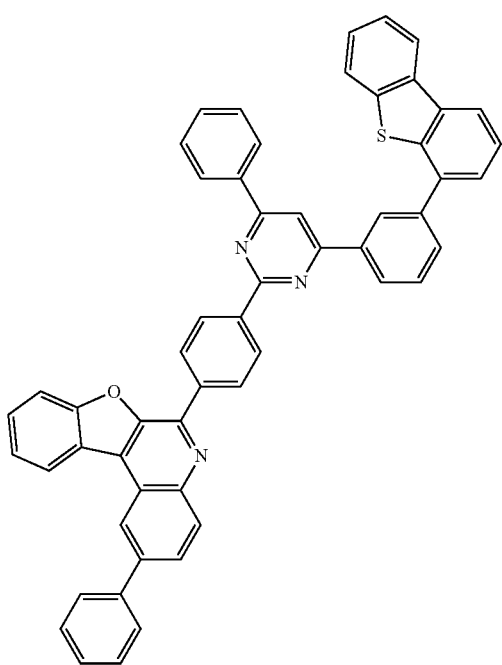
290
-continued
622
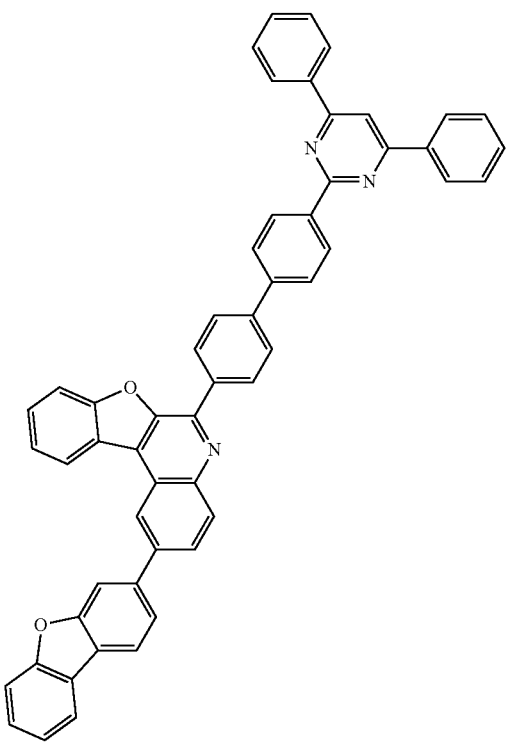
623
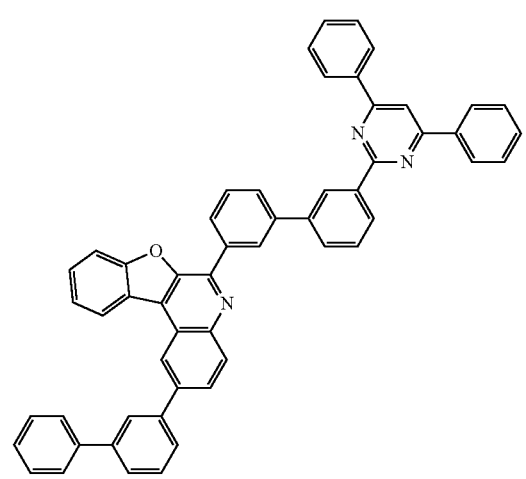

291
-continued
624
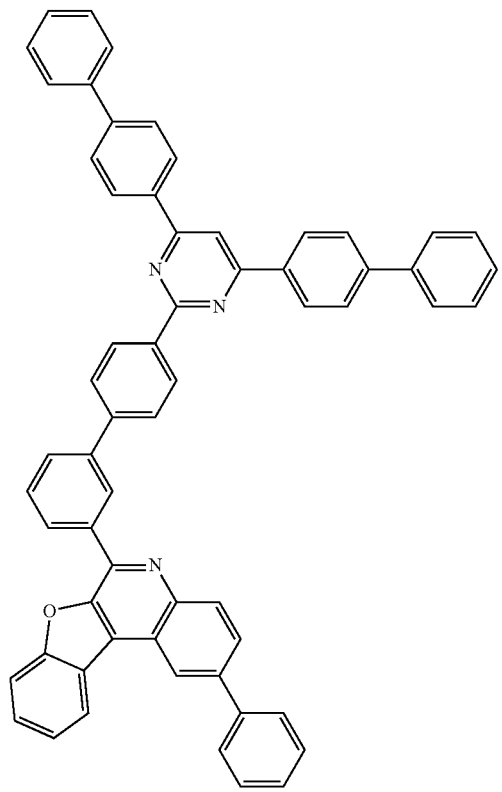
625
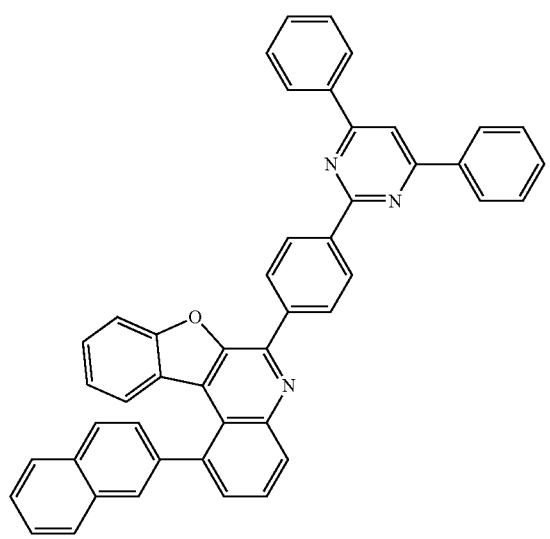
292
-continued
626
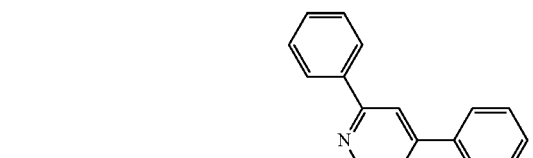
627
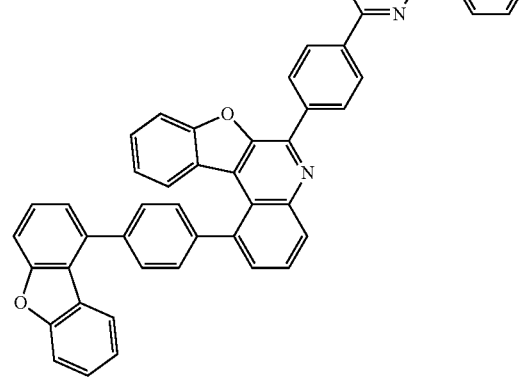
628
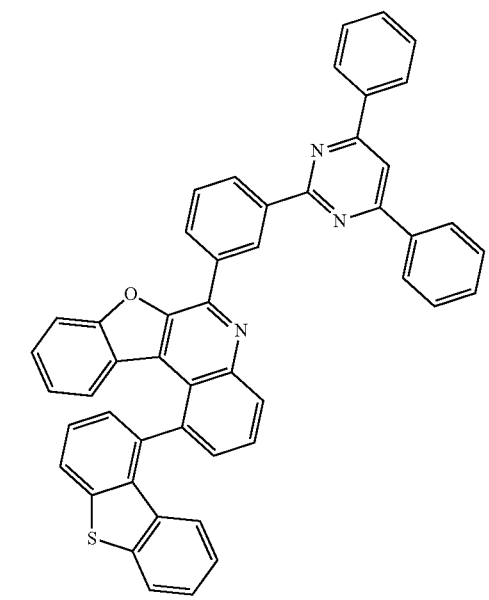

629
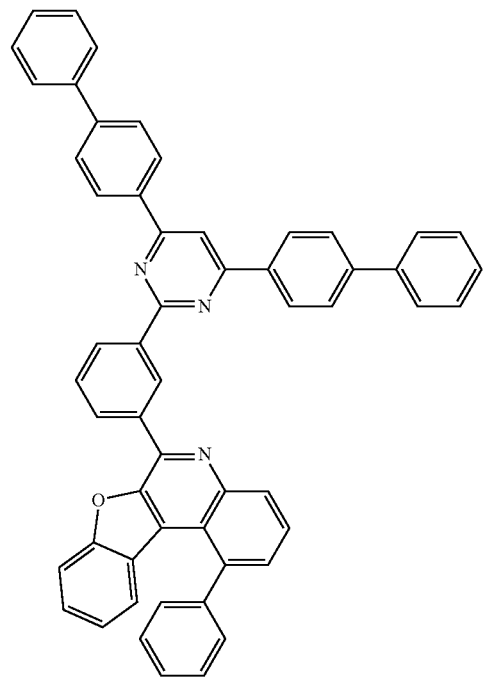
630
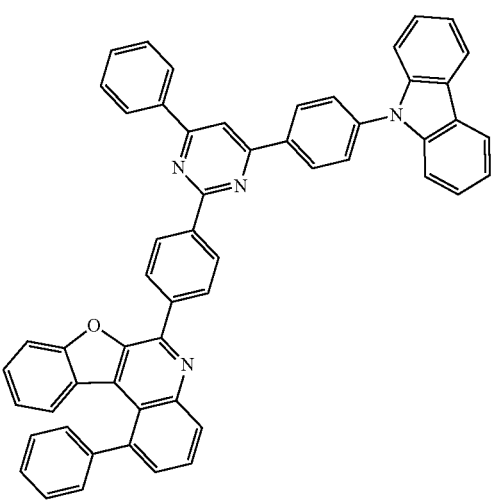
631
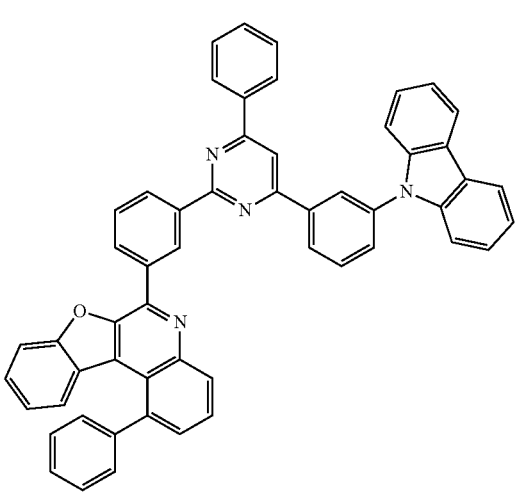
632
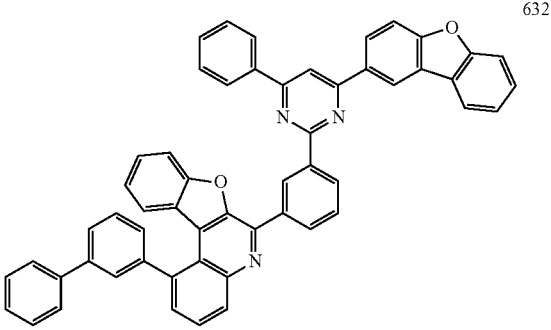
633
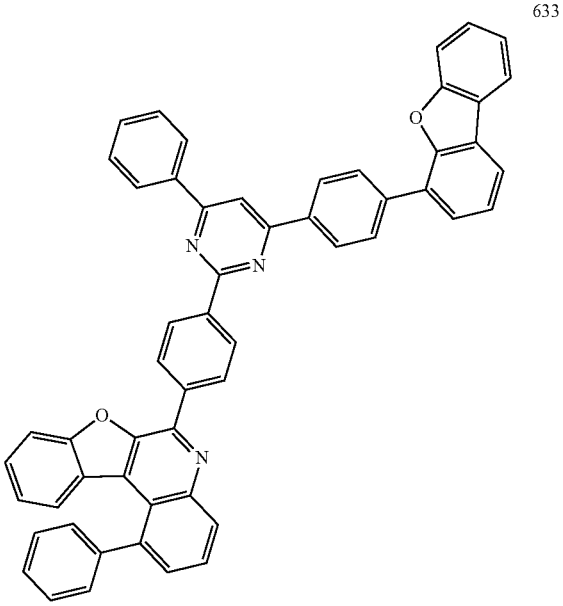
634
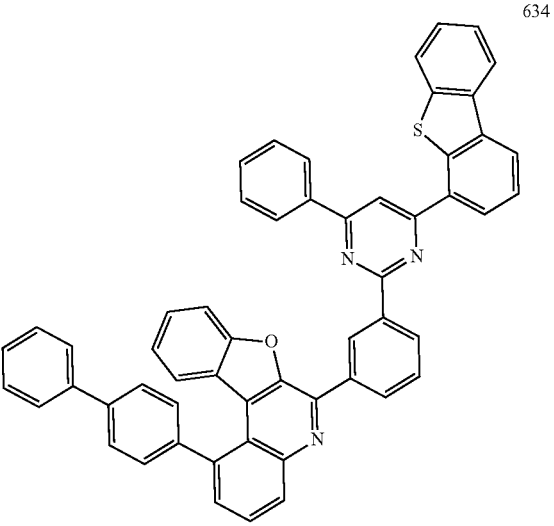

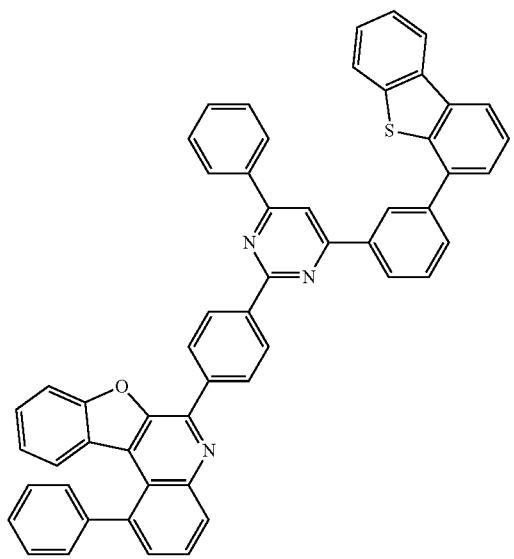
635
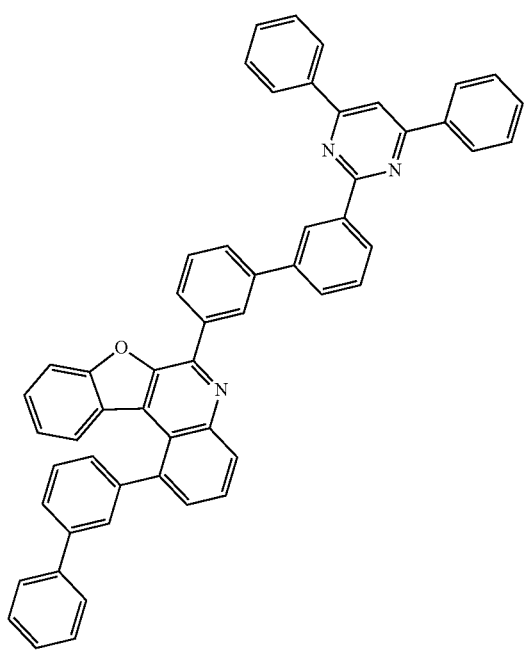
637
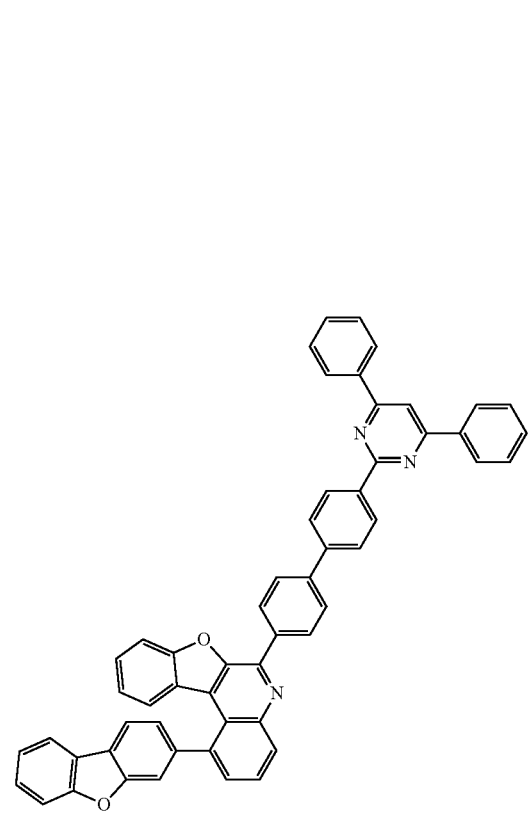
636
638

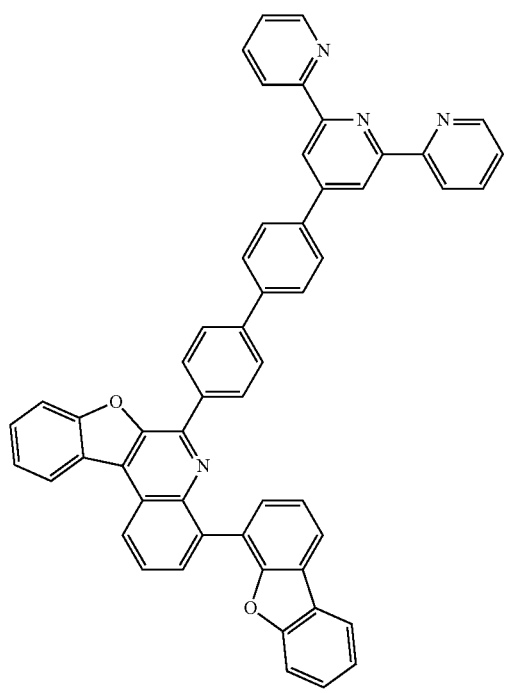
639
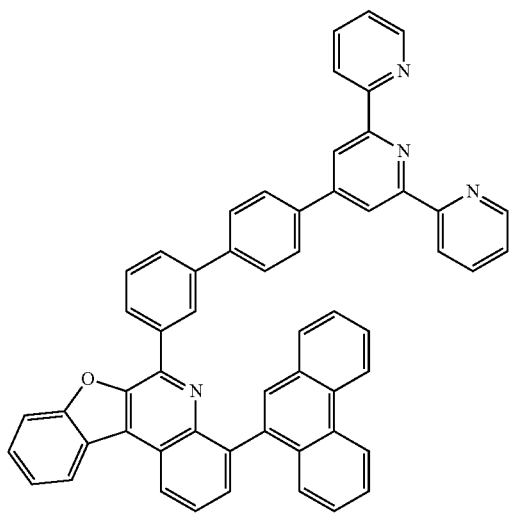
641
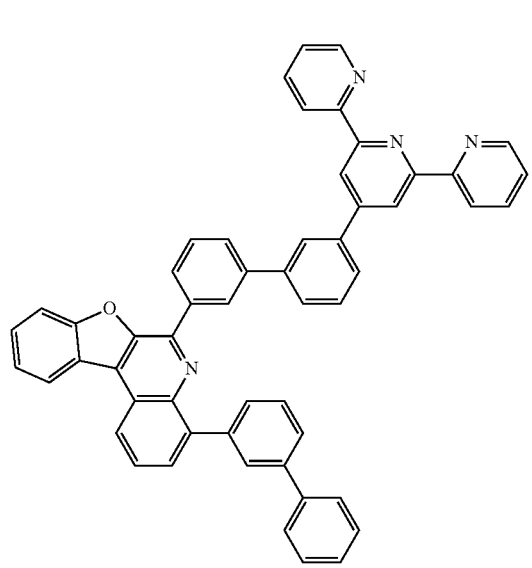
640
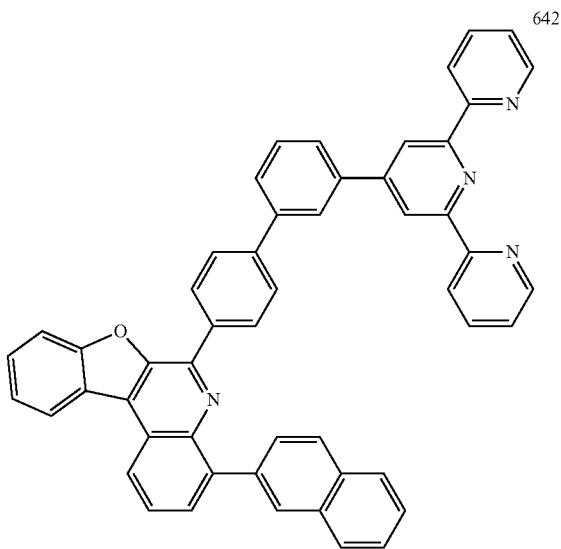
642

643
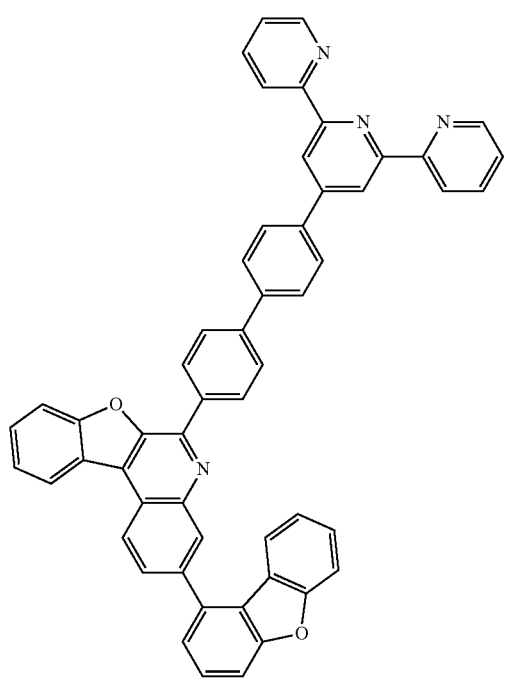
644
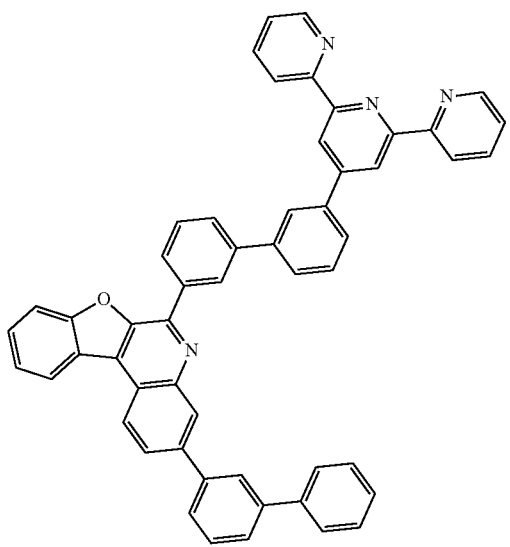
645
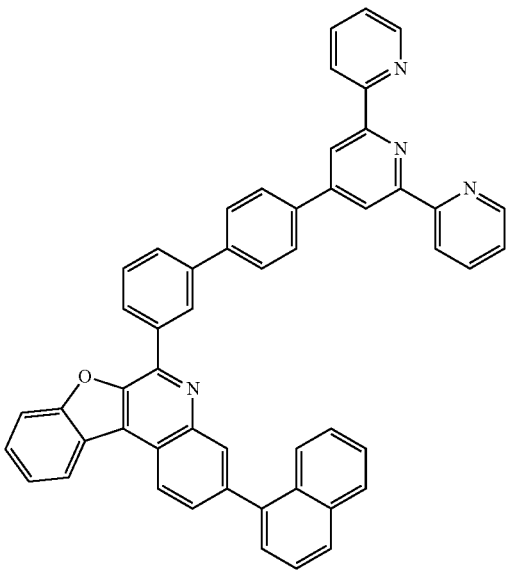
646
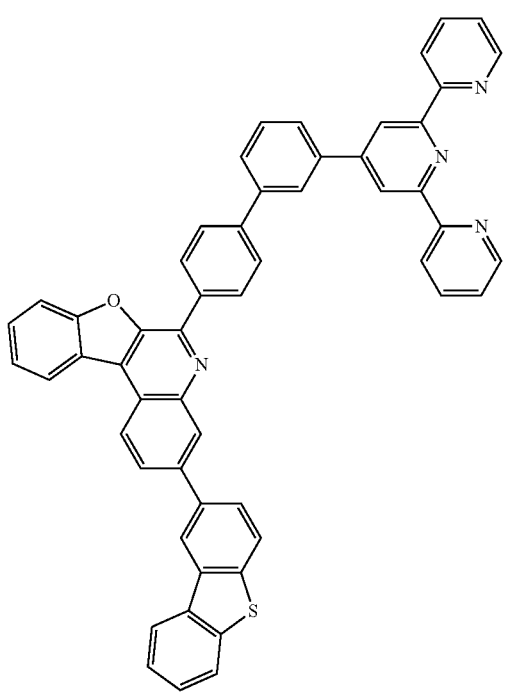

301
-continued
647
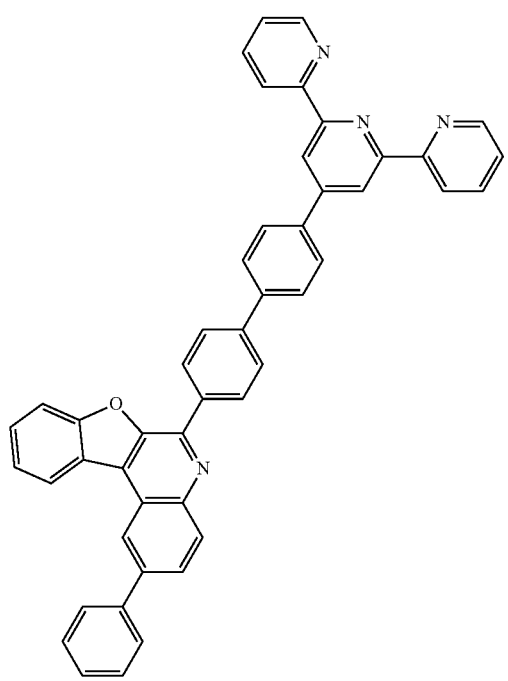
648
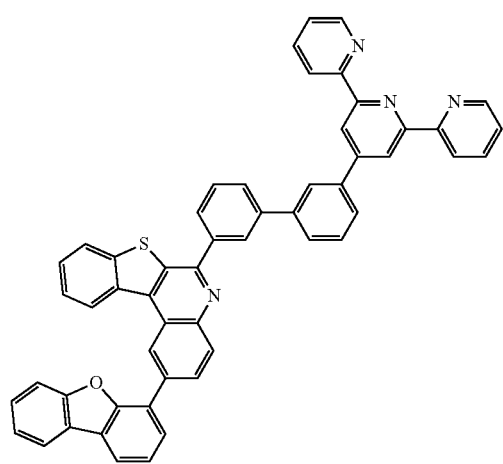
302
-continued
649
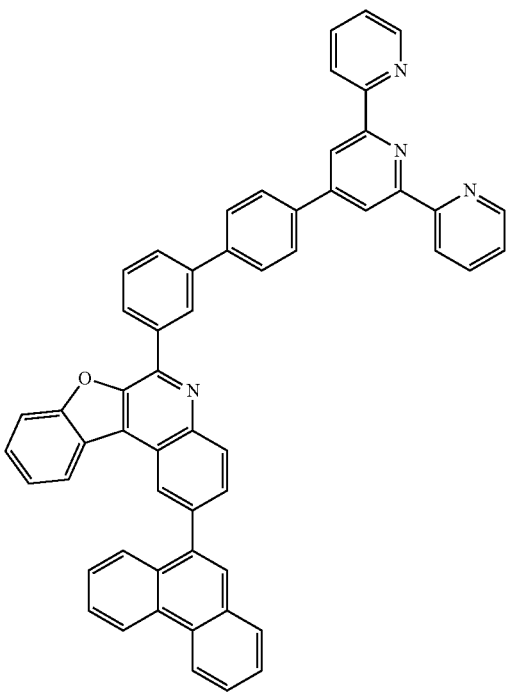
650
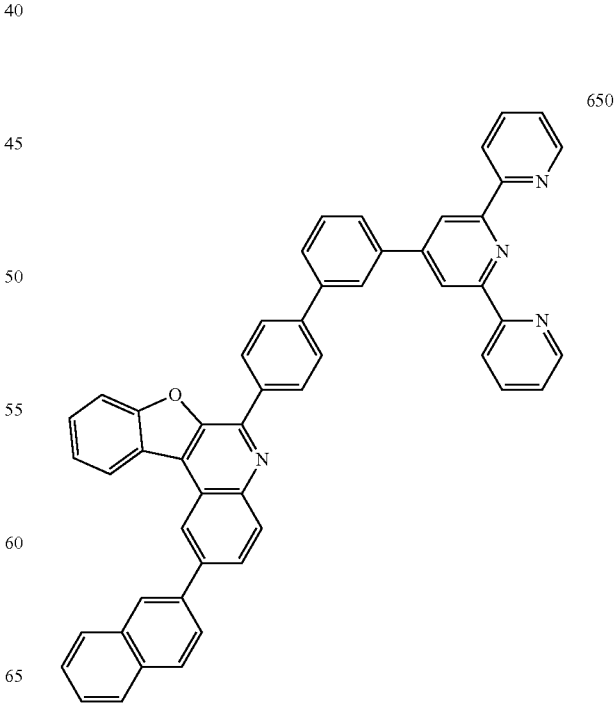

303
-continued
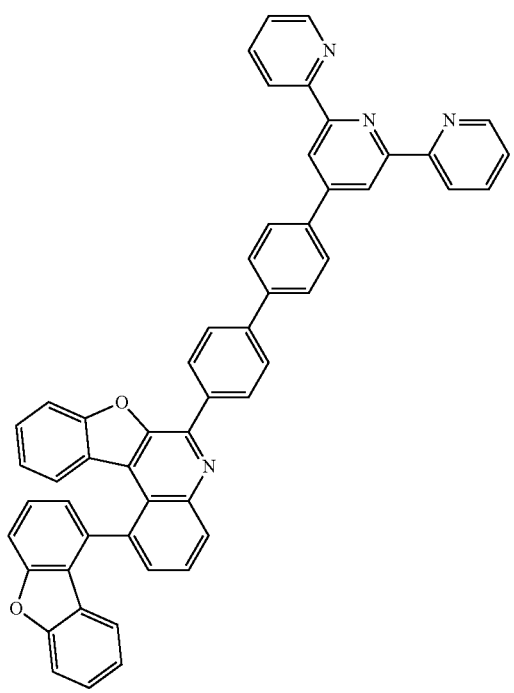
651
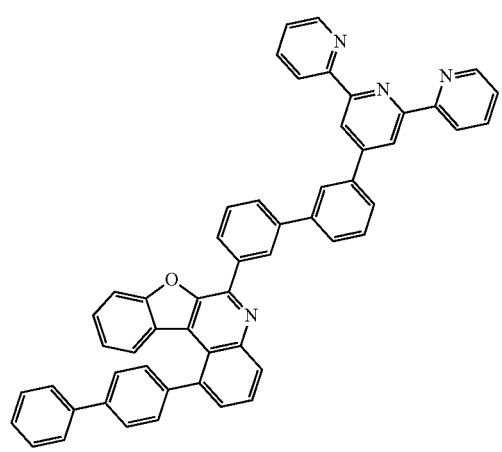
652
304
-continued
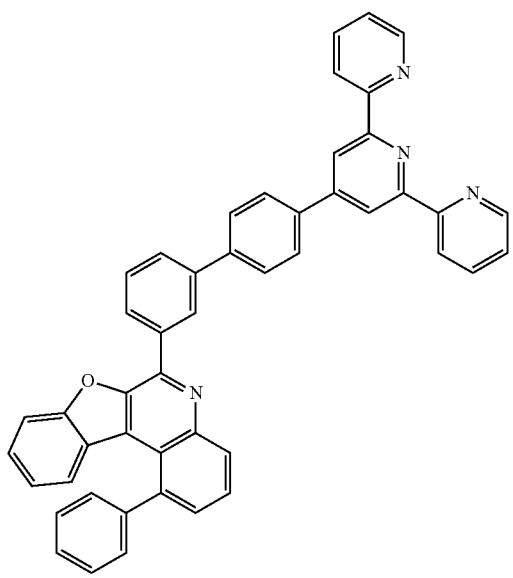
653
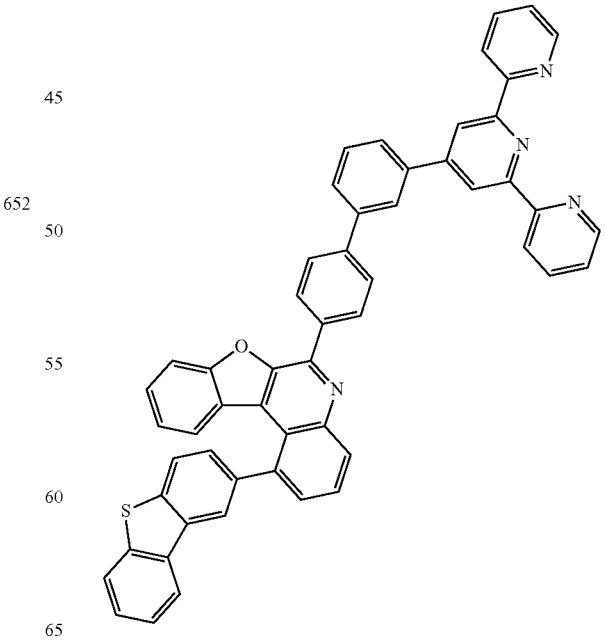
654

305
-continued
655
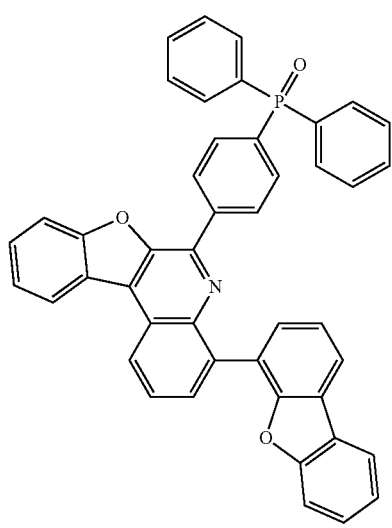
656
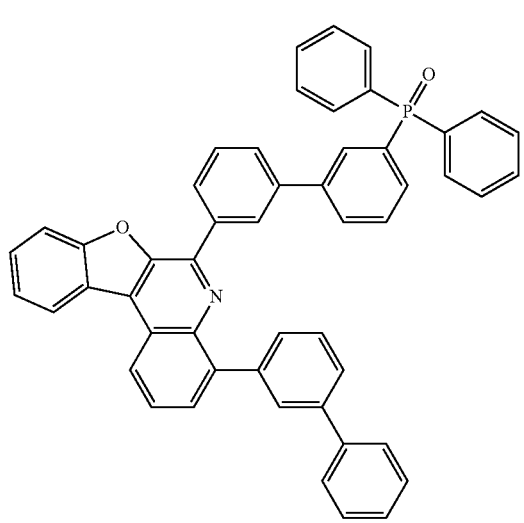
657
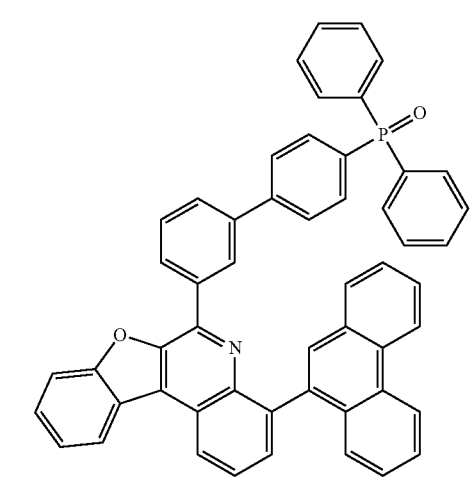
306
-continued
658
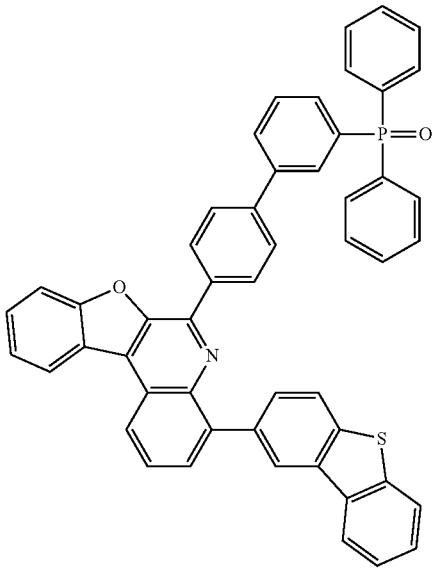
659
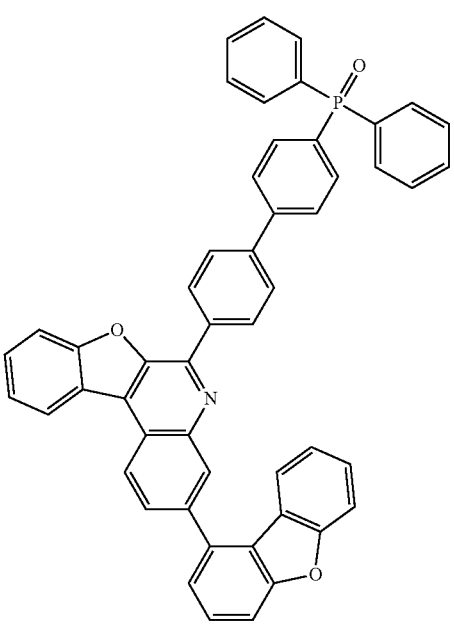

307
-continued
660
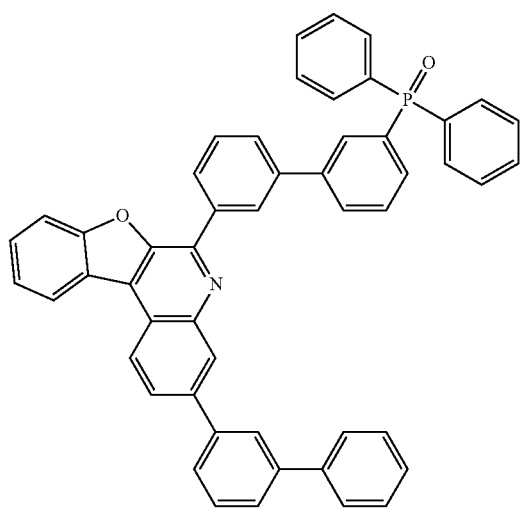
661
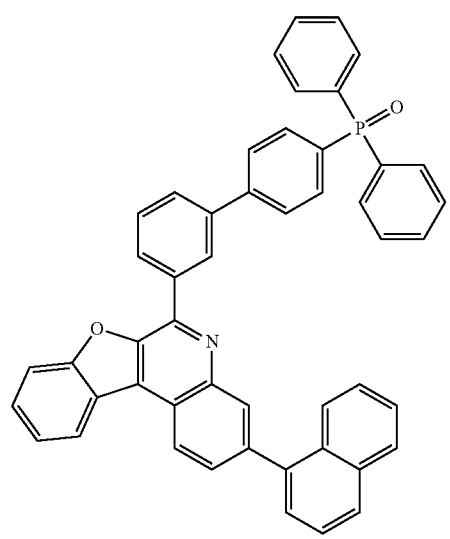
308
-continued
662
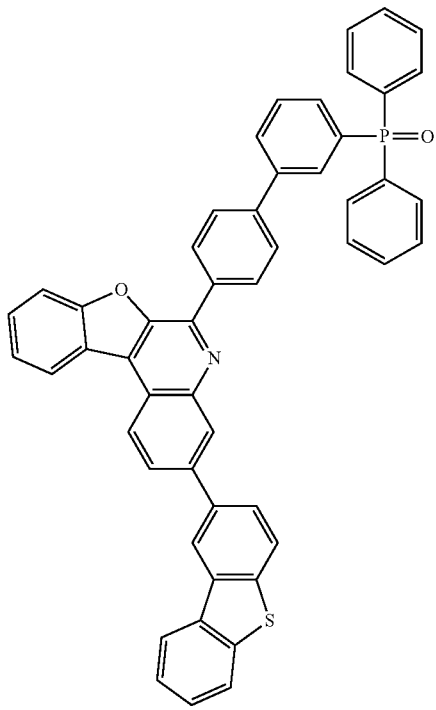
663
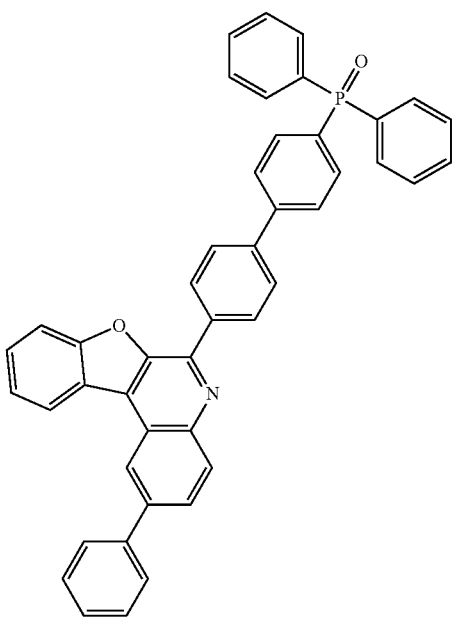

309
-continued
664
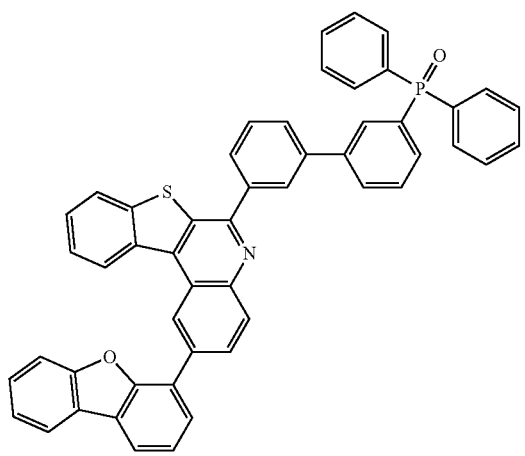
665
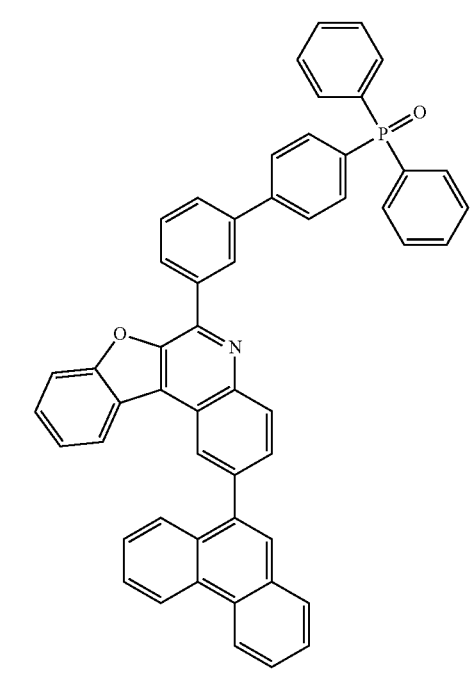
310
-continued
666
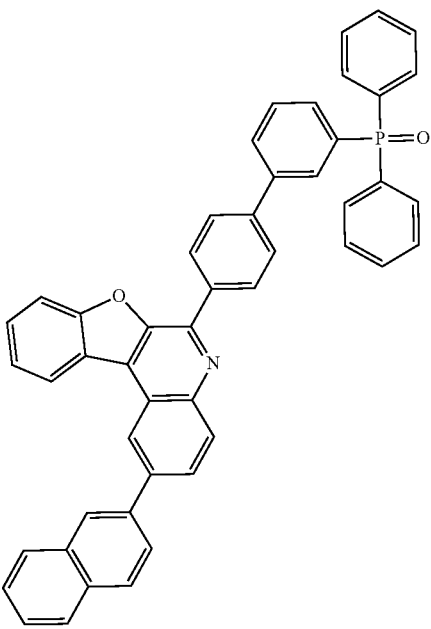
667
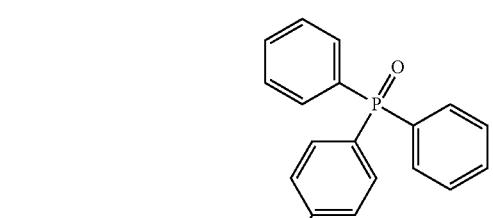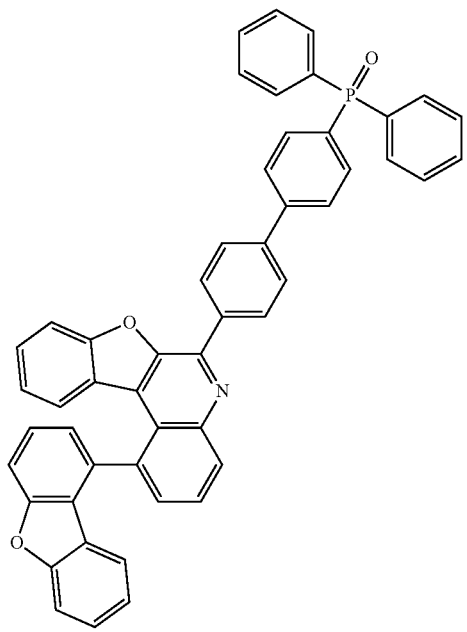
668
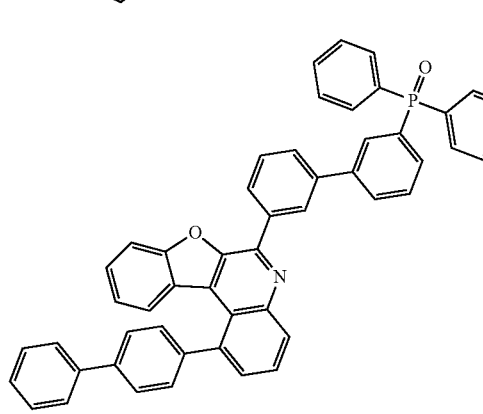

669
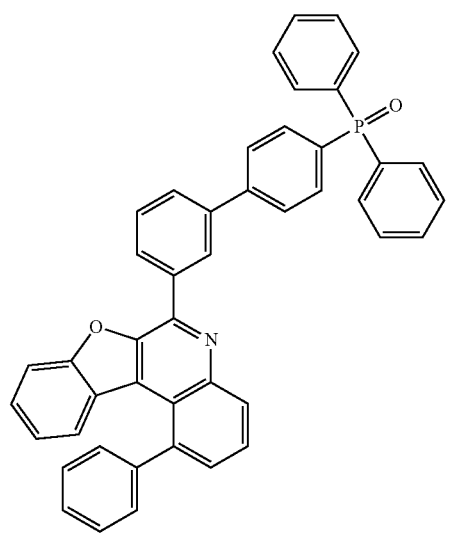
670
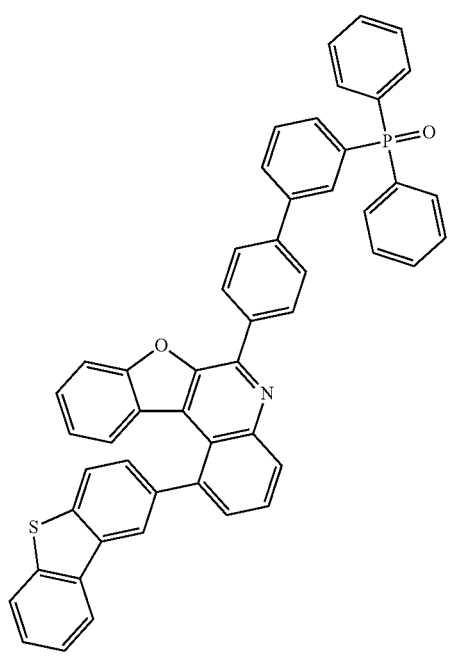
671
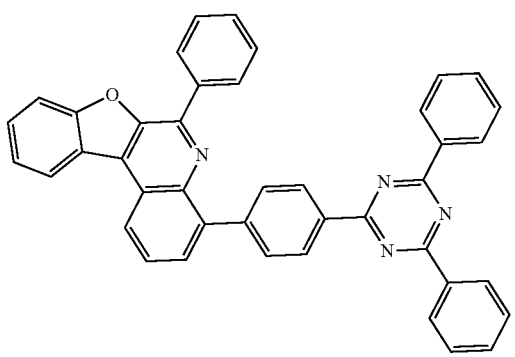
672
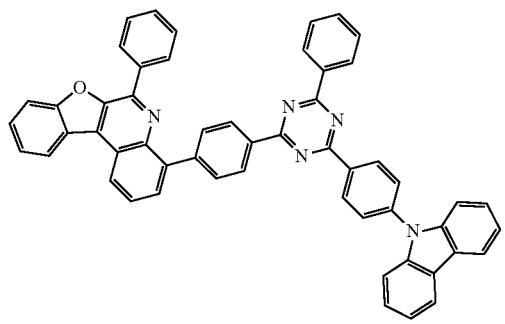
673
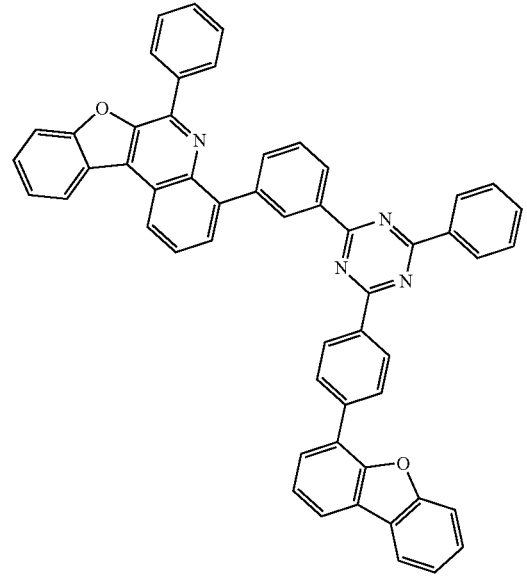
674
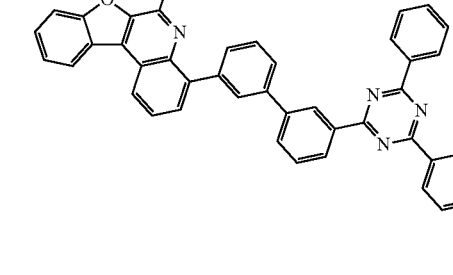

313
-continued
675
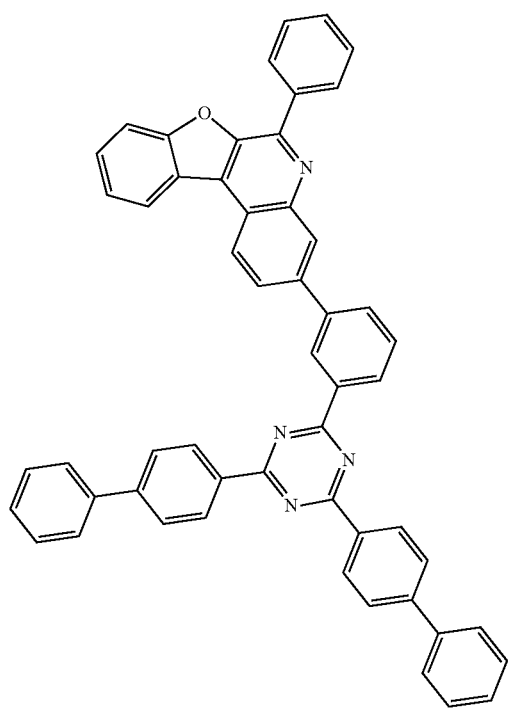
676
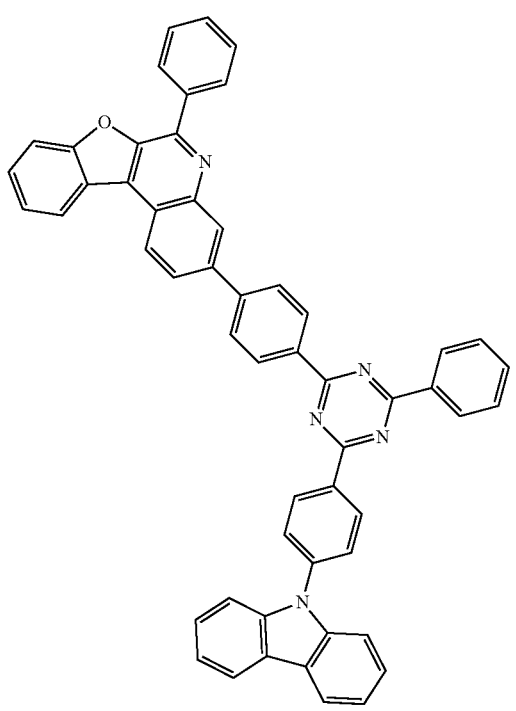
314
-continued
677
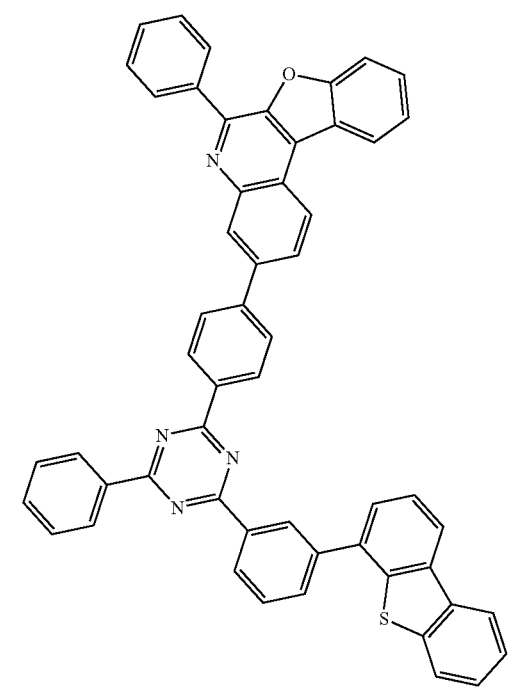
678
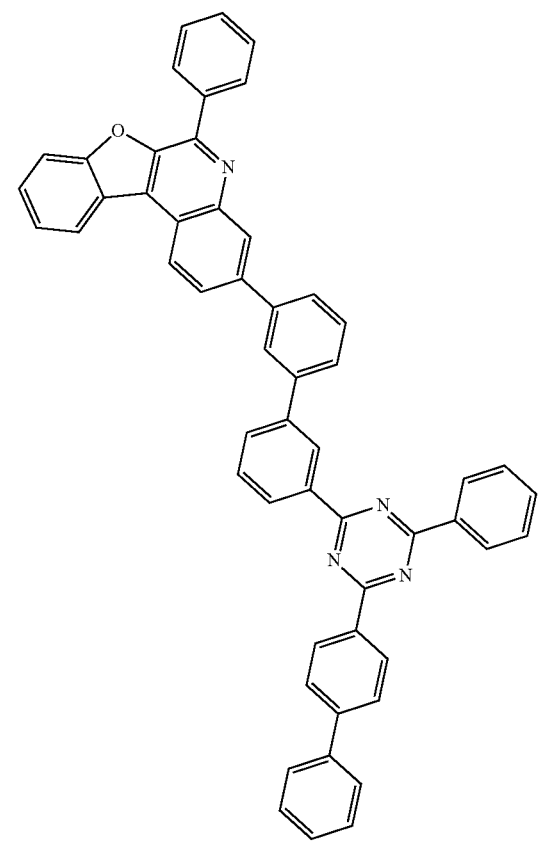

315
-continued
679
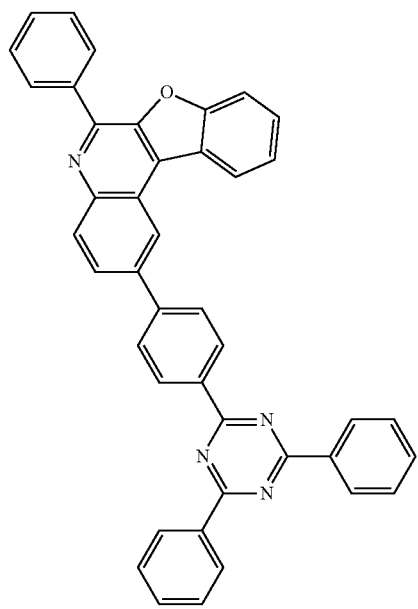
680
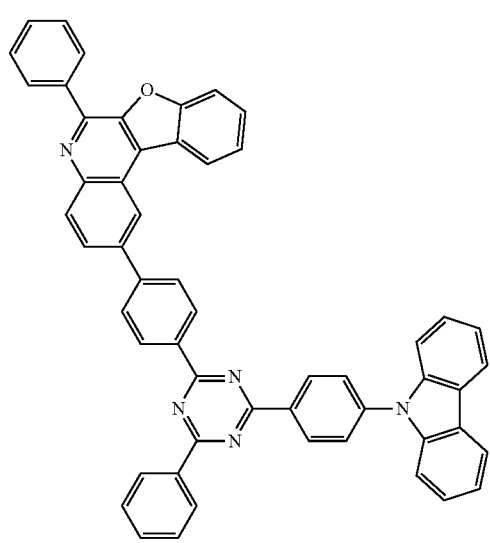
681
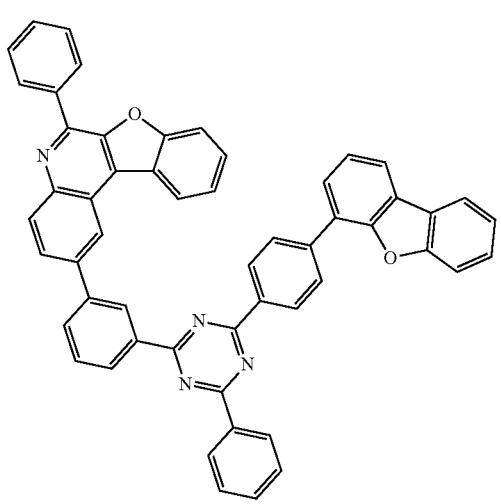
316
-continued
682
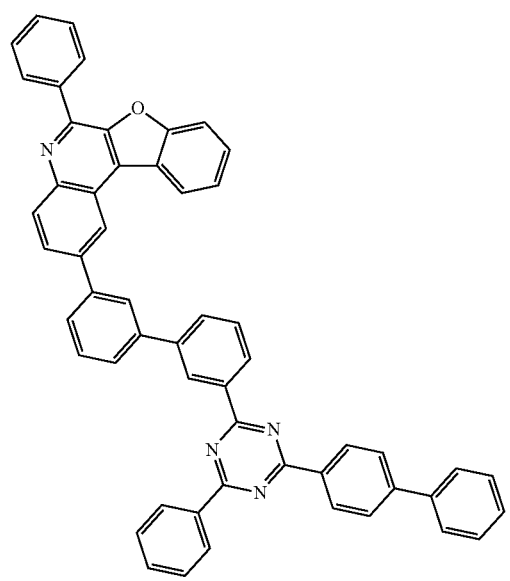
683
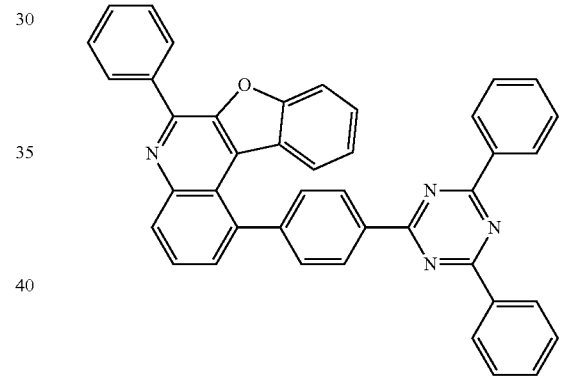
684
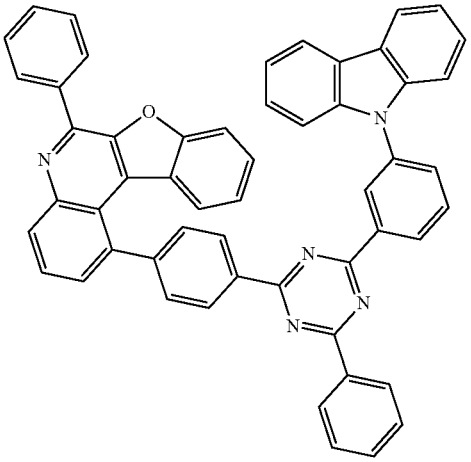

317
-continued
685
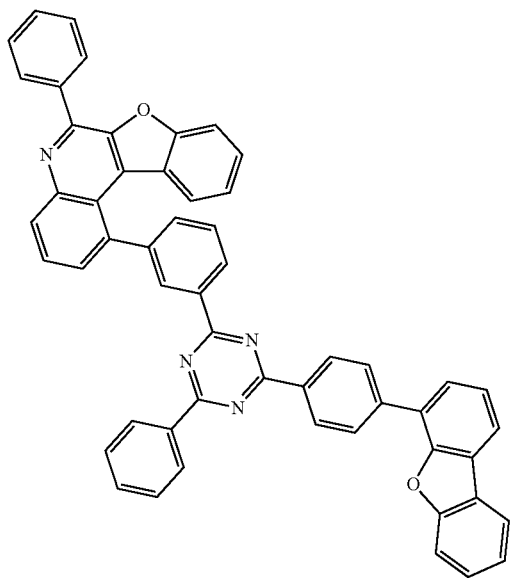
686
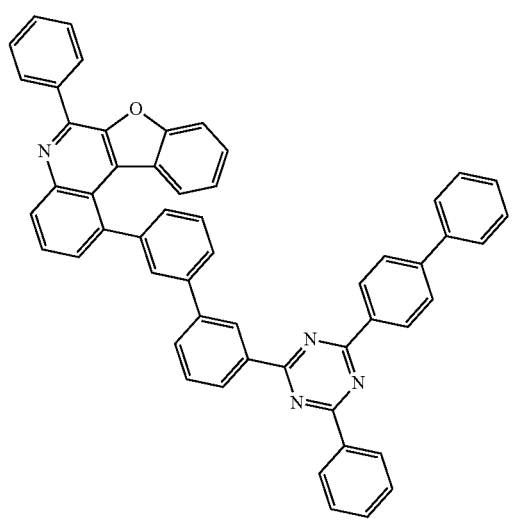
687
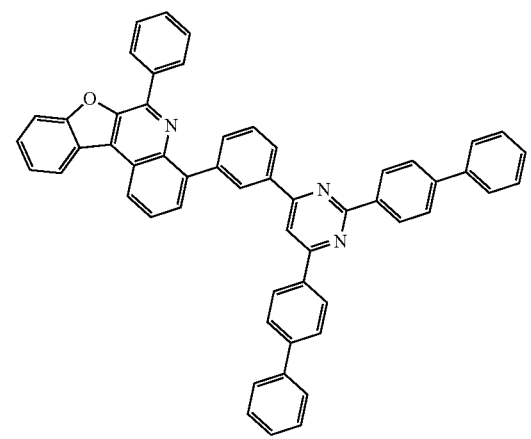
318
-continued
688
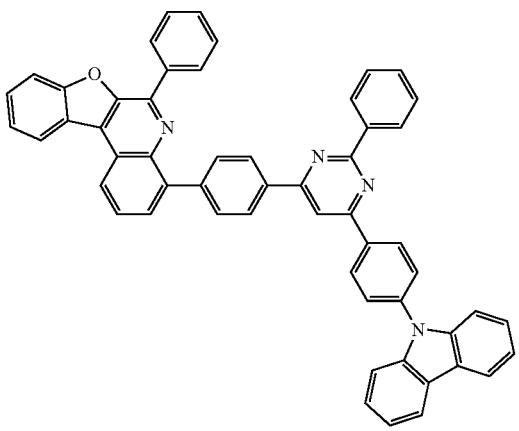
689
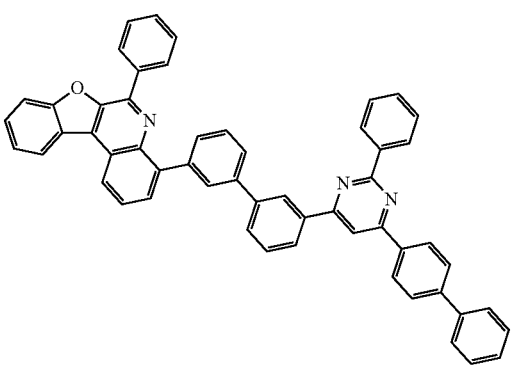
690

-continued
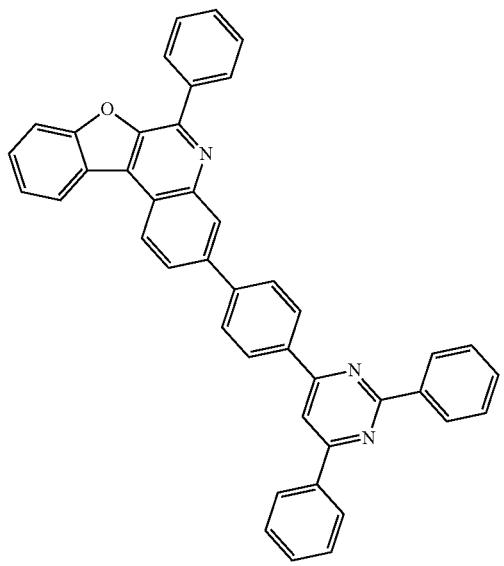
691
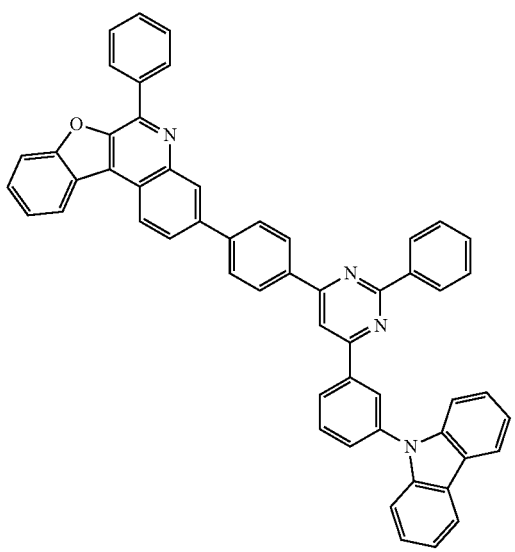
692
-continued
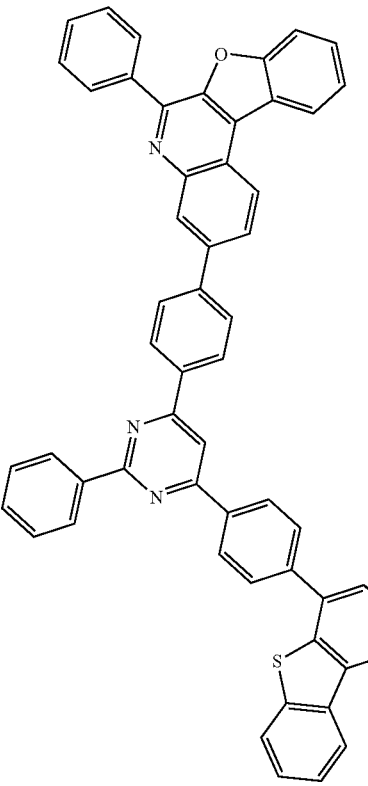
693
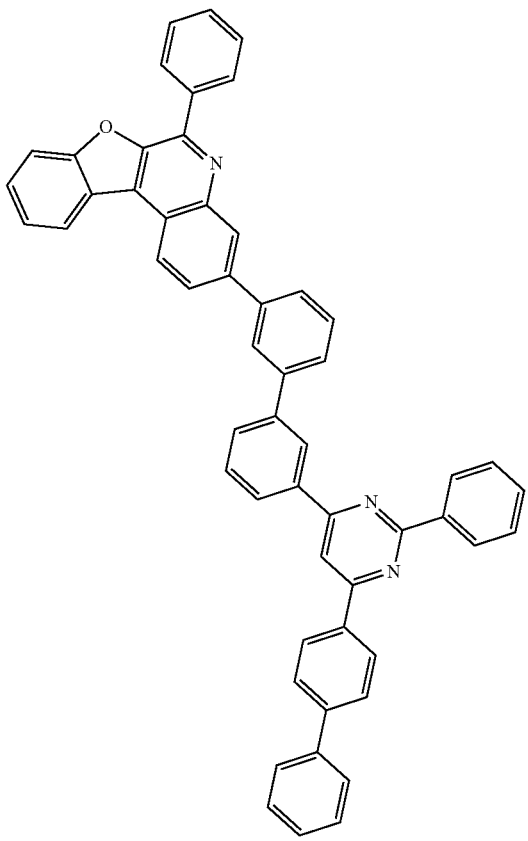
694

695
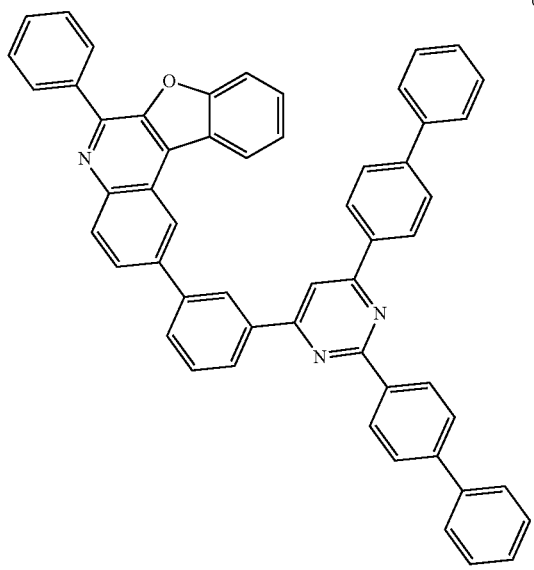
696
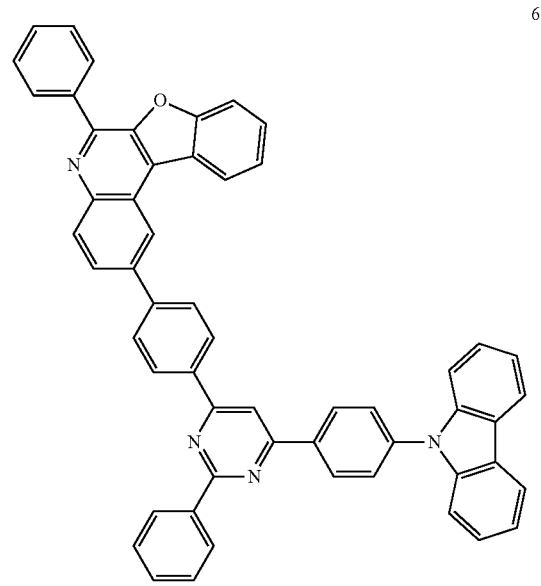
697
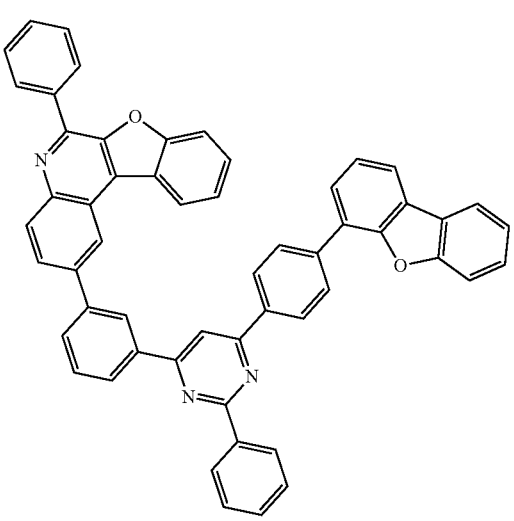
698
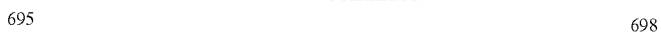
699
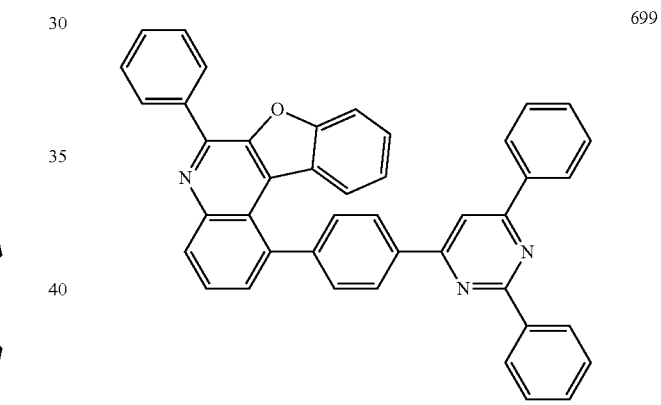
700
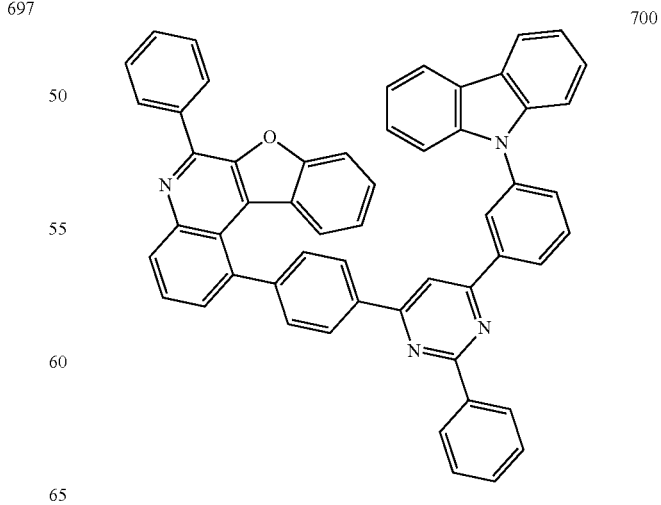

323
-continued
701
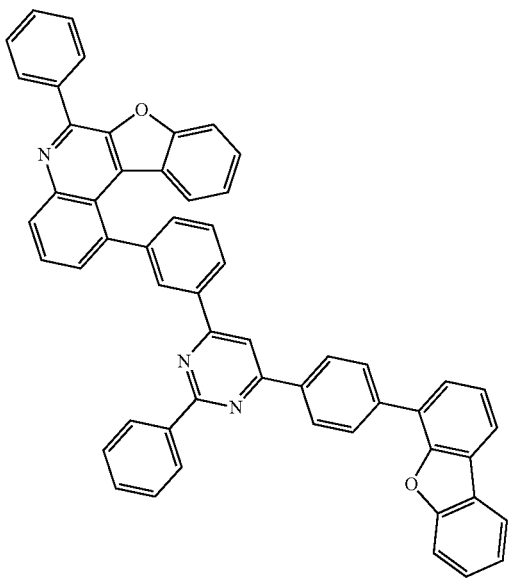
702
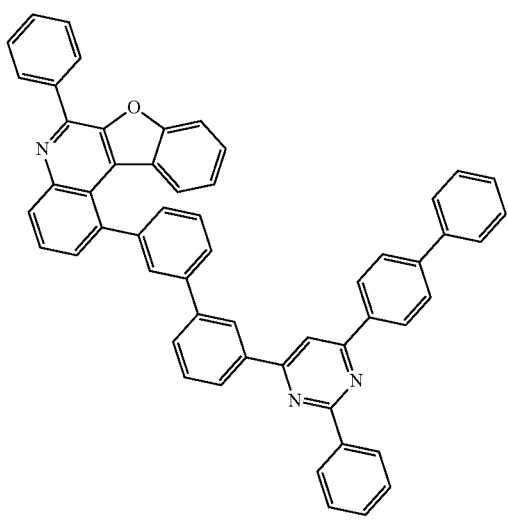
324
-continued
703
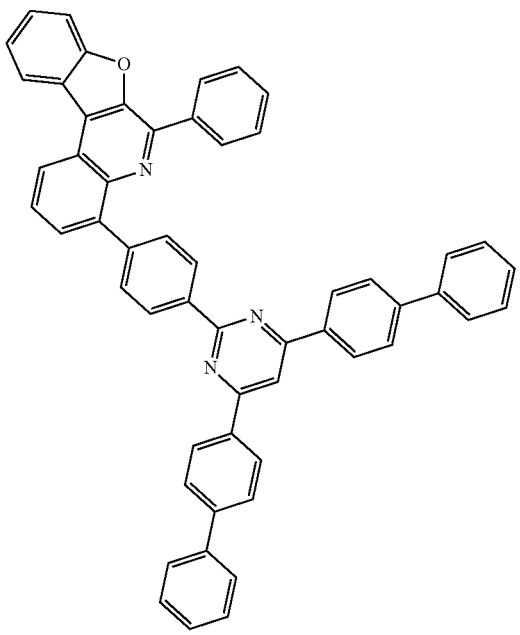
704
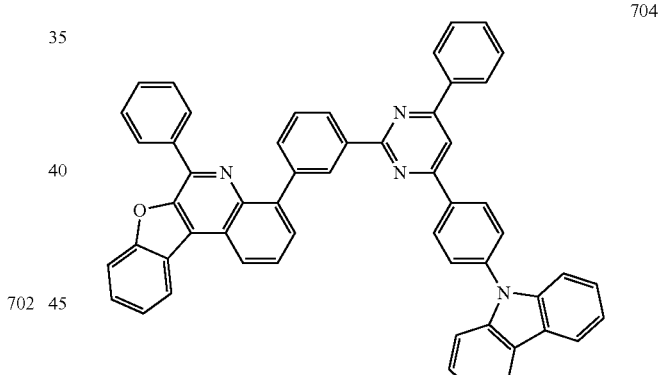
705
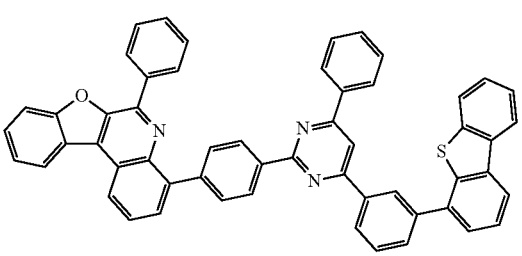

325
-continued
326
-continued
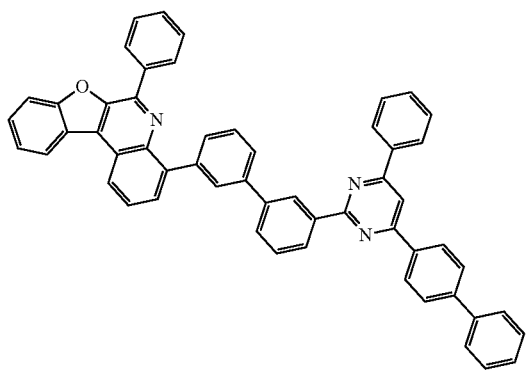
706
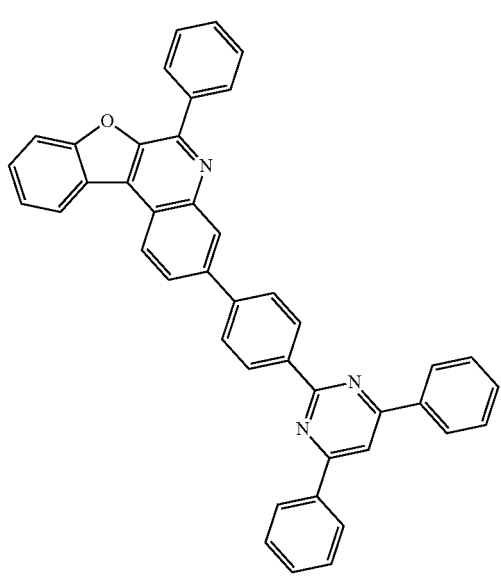
707
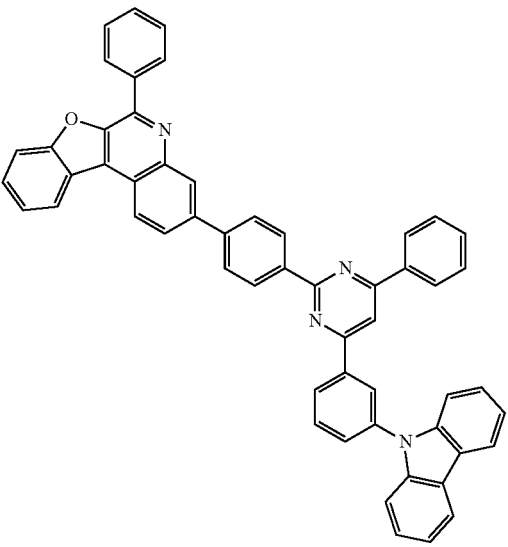
708
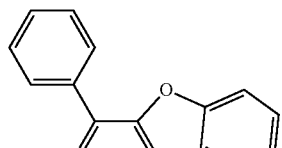
709
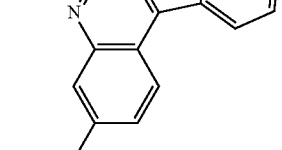
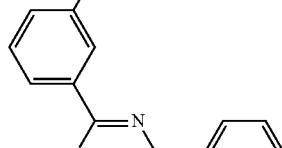
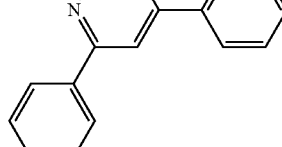

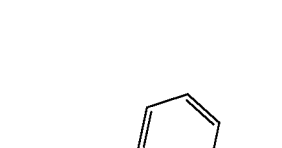
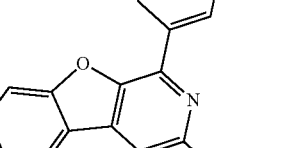
710
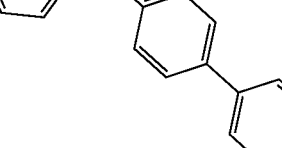
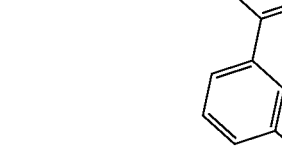
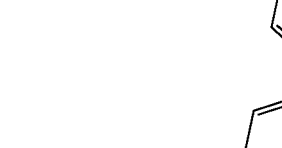

327
-continued
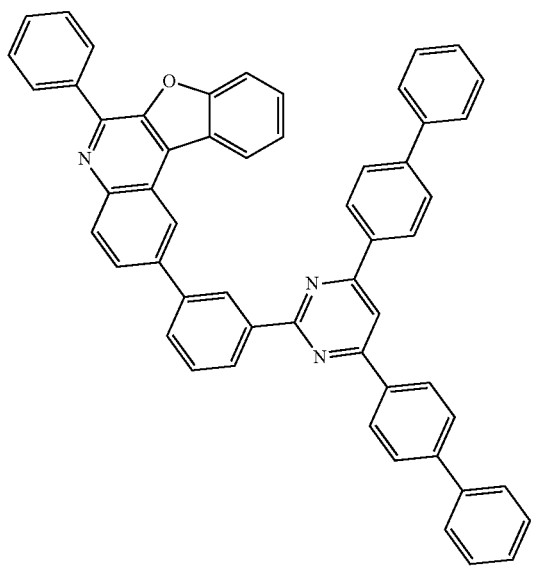
711
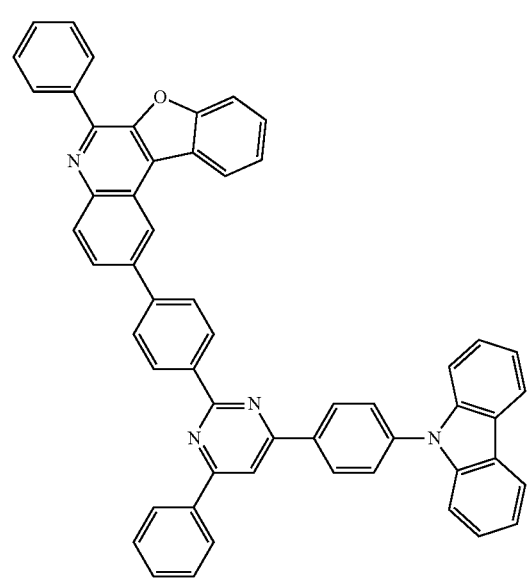
712
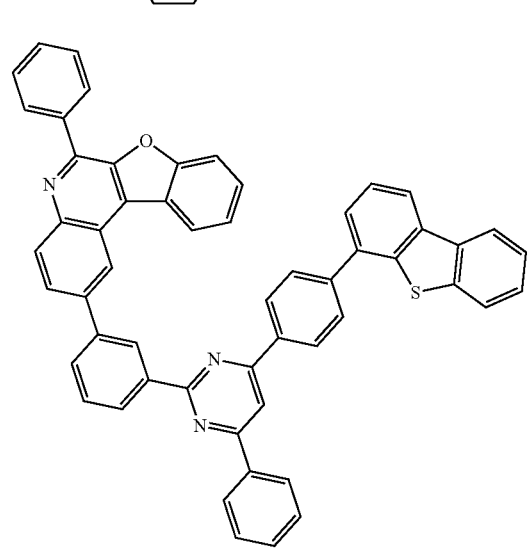
713
328
-continued
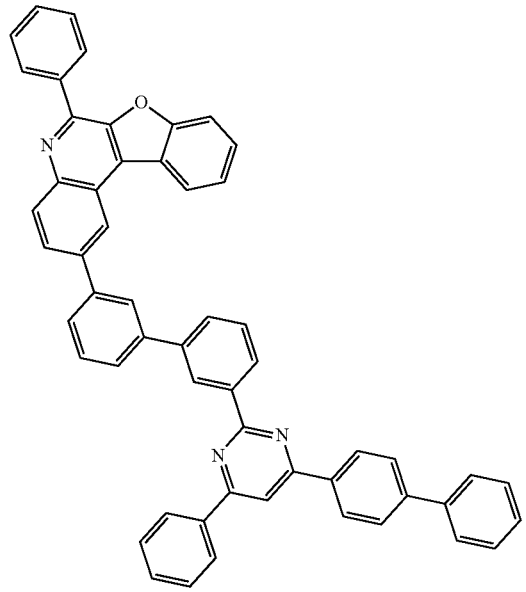
714
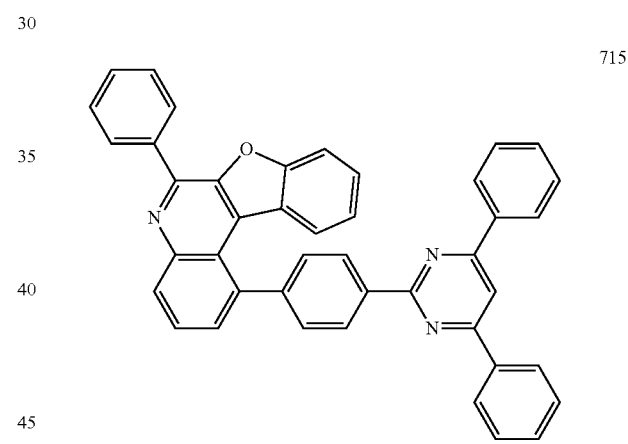
715
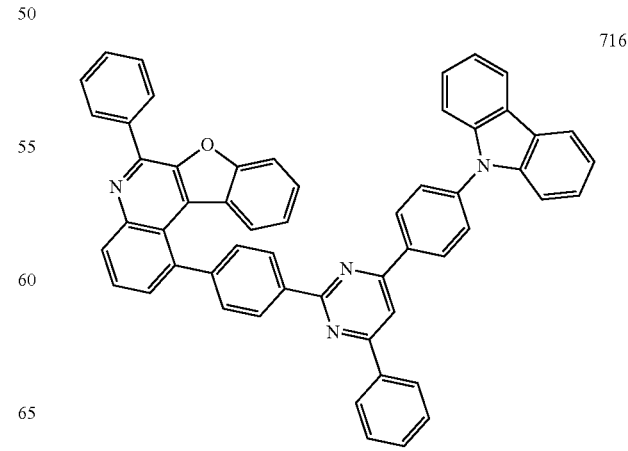
716

329
-continued
717
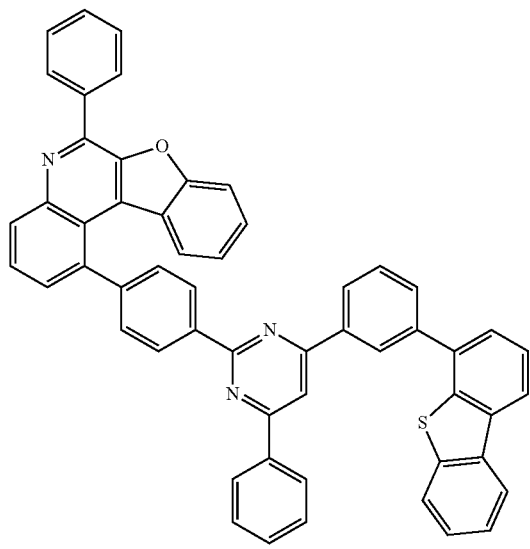
718
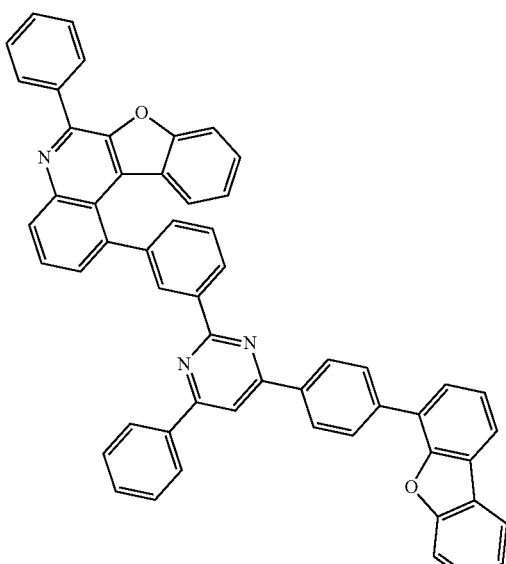
719
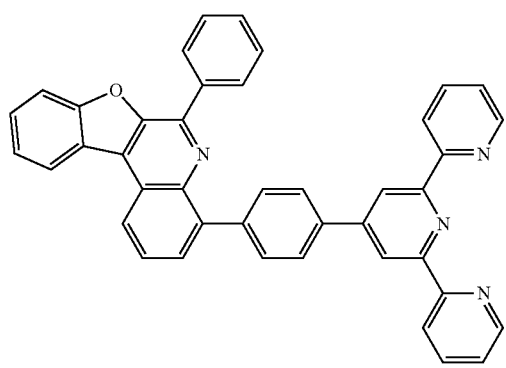
330
-continued
720
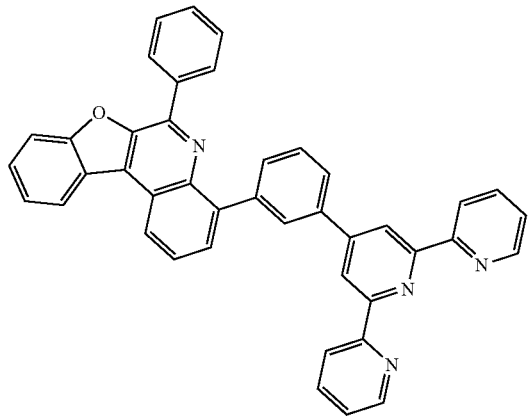
721
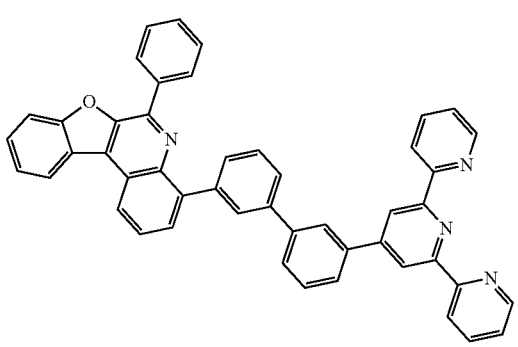
722
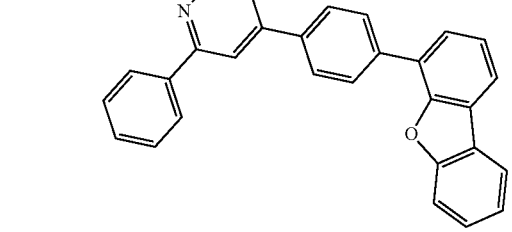

331
-continued
332
-continued
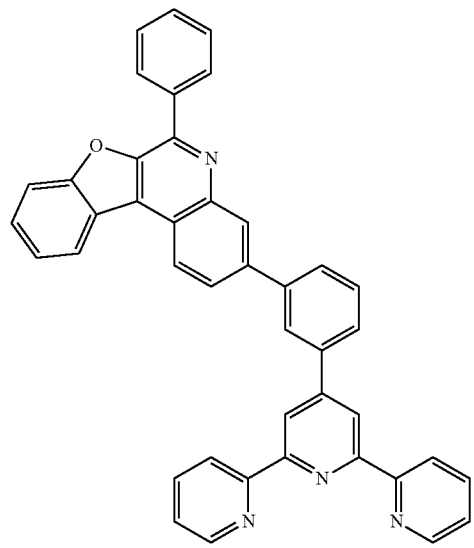
723
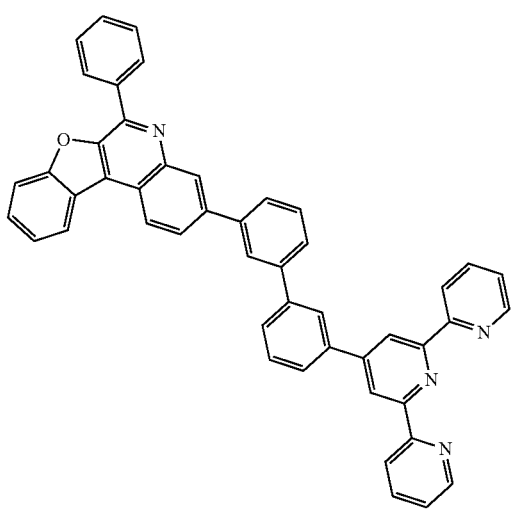
724
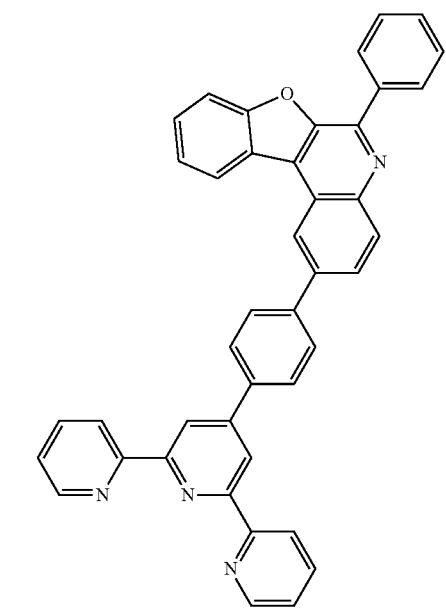
725
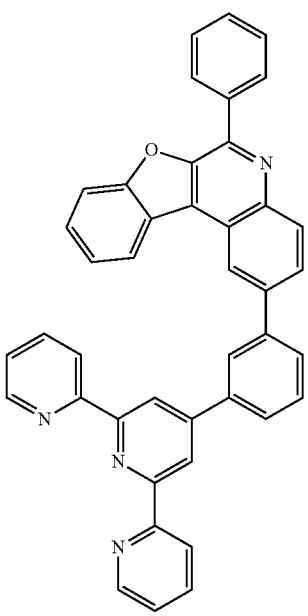
726
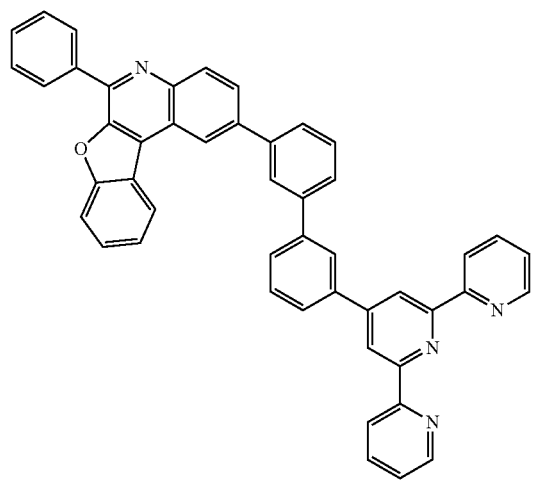
727
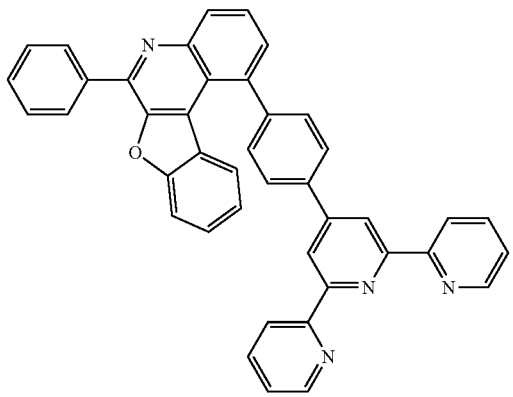
728

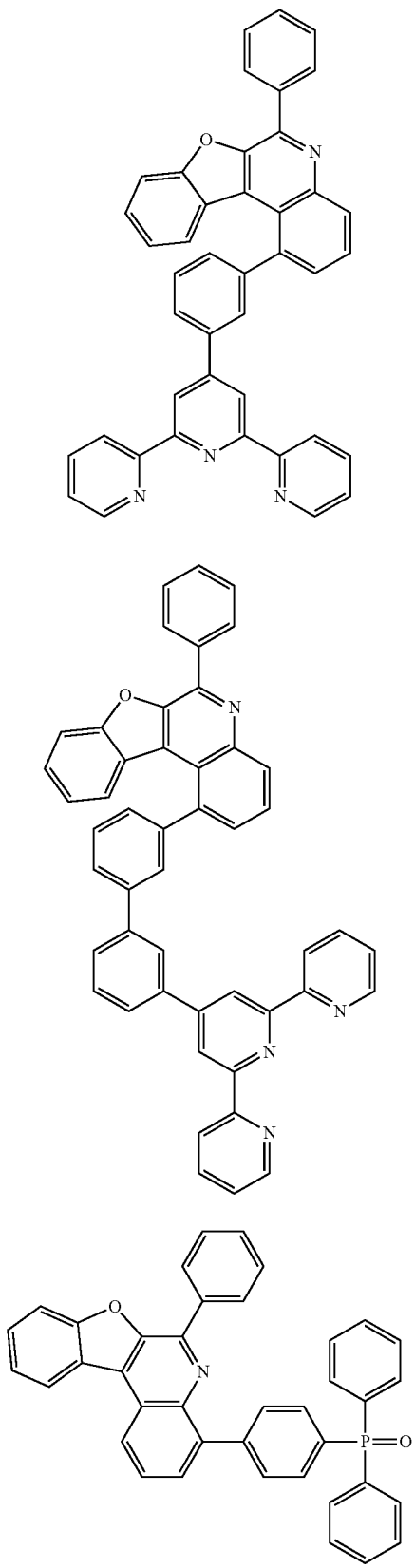
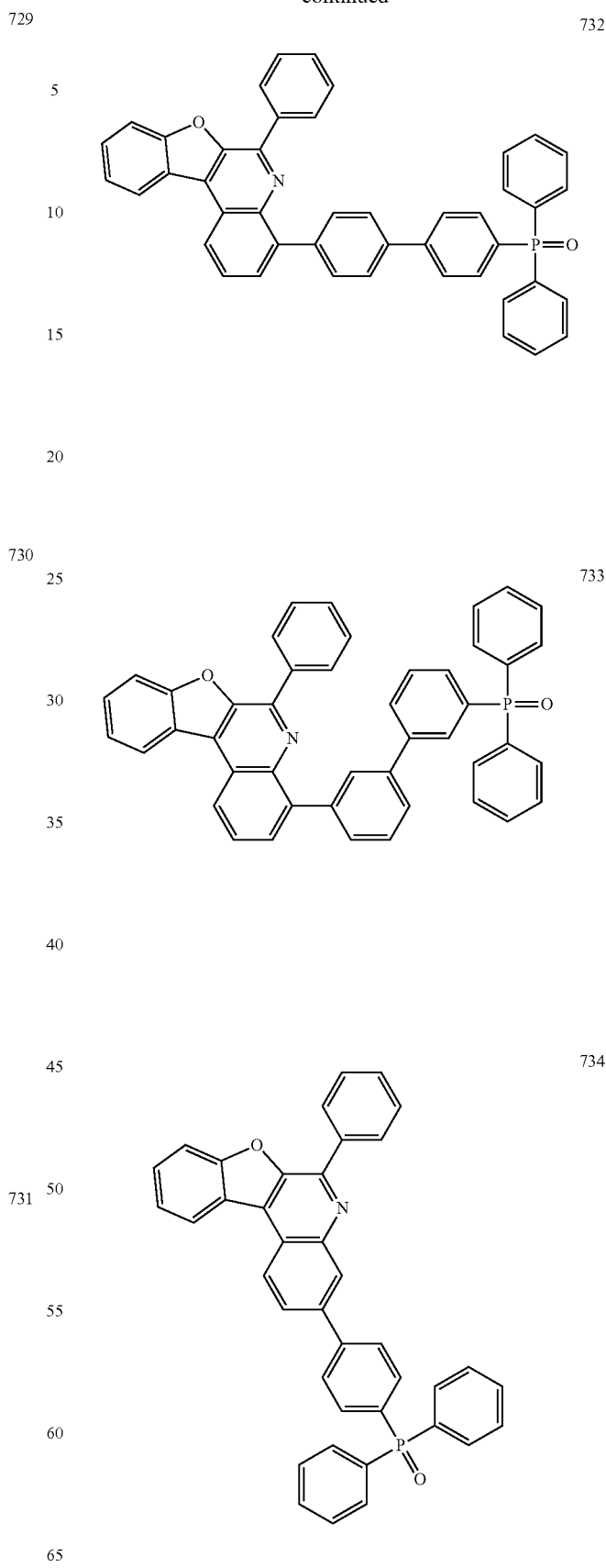

335
-continued
736
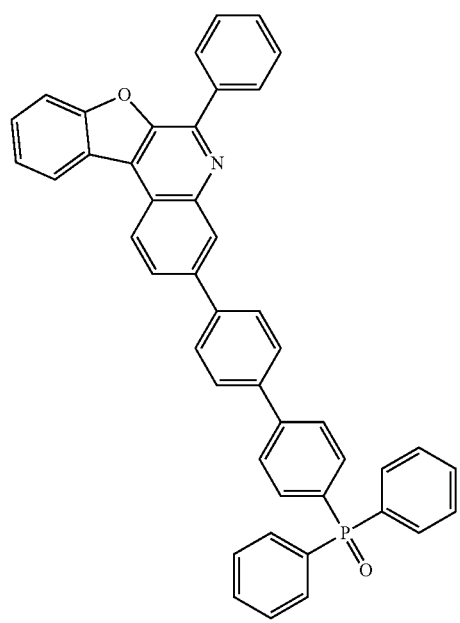
735
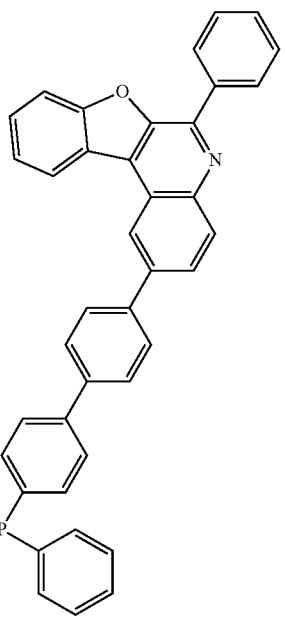
336
-continued
738
739
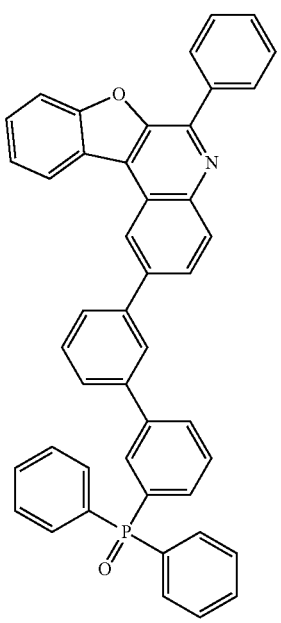
737
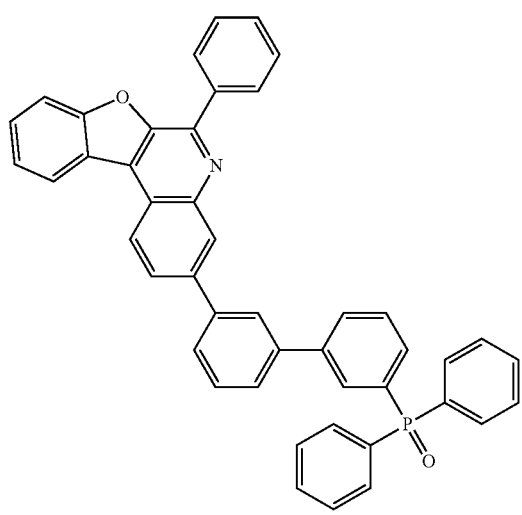
740
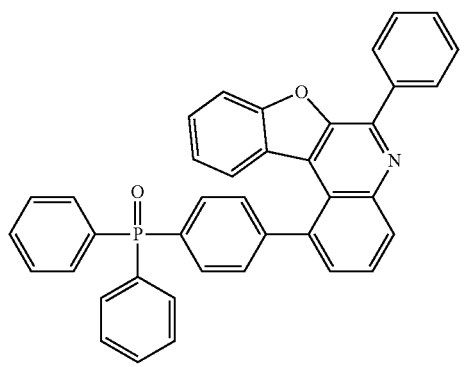

337
-continued
741
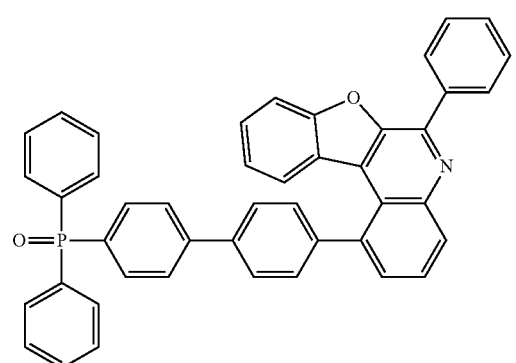
742
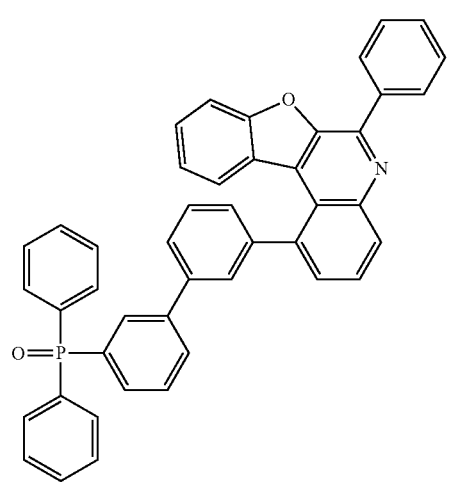
743
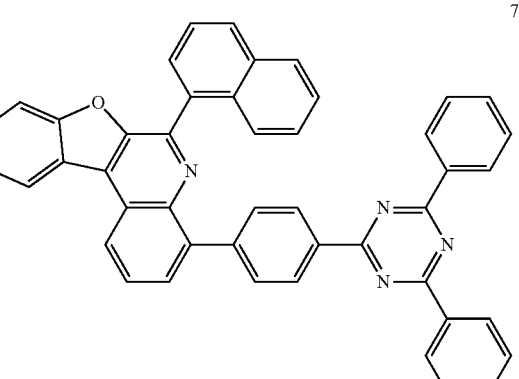
744
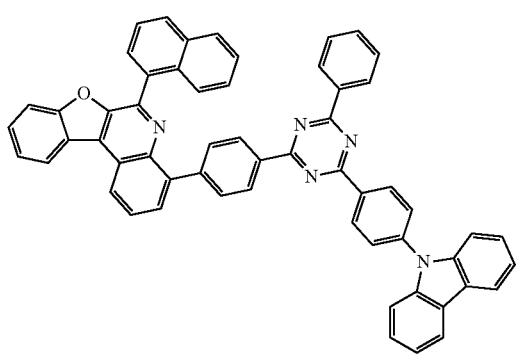
338
-continued
745
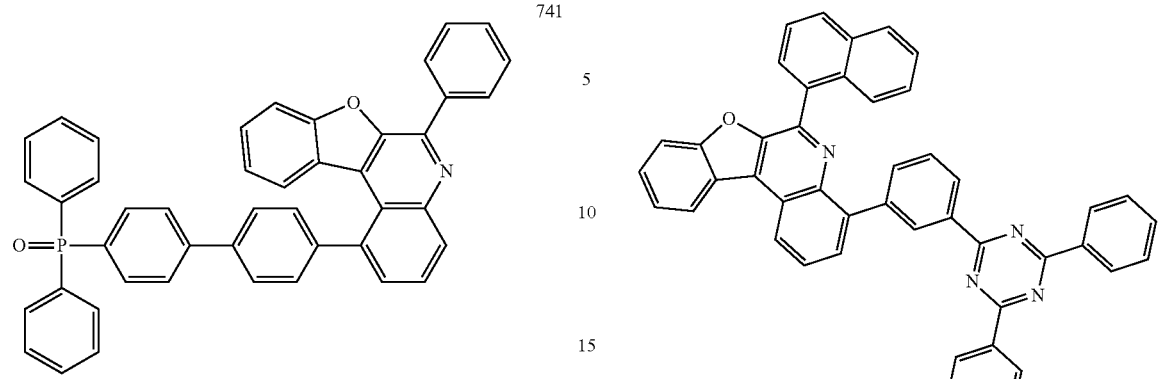
746
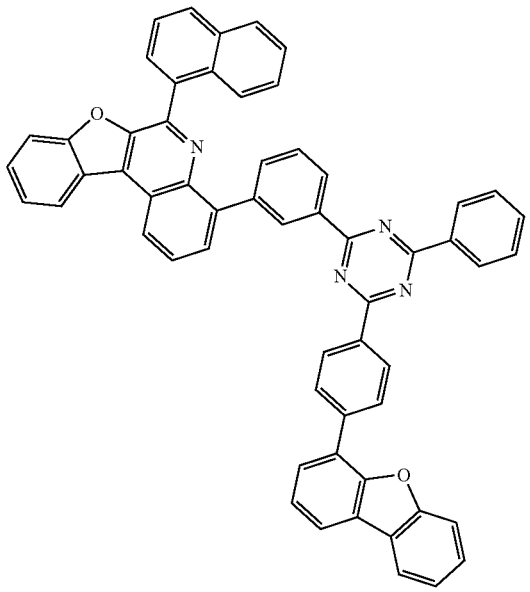
747
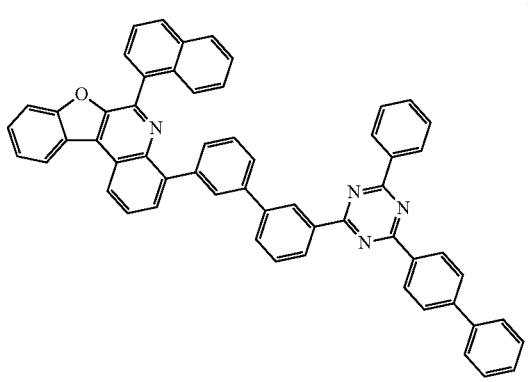
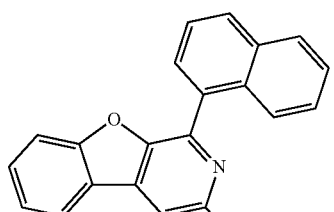
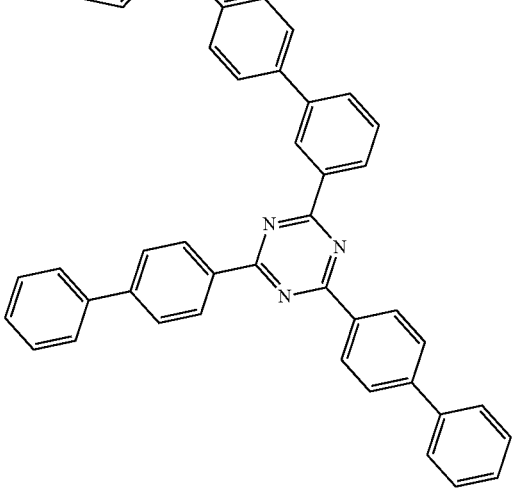

339
-continued
748
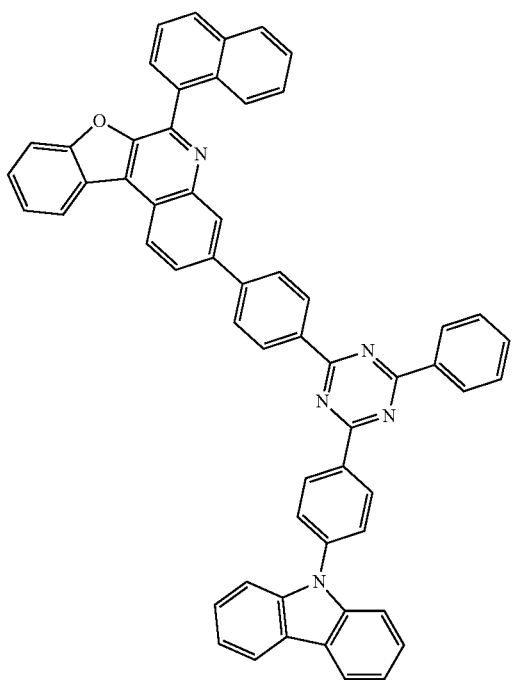
749
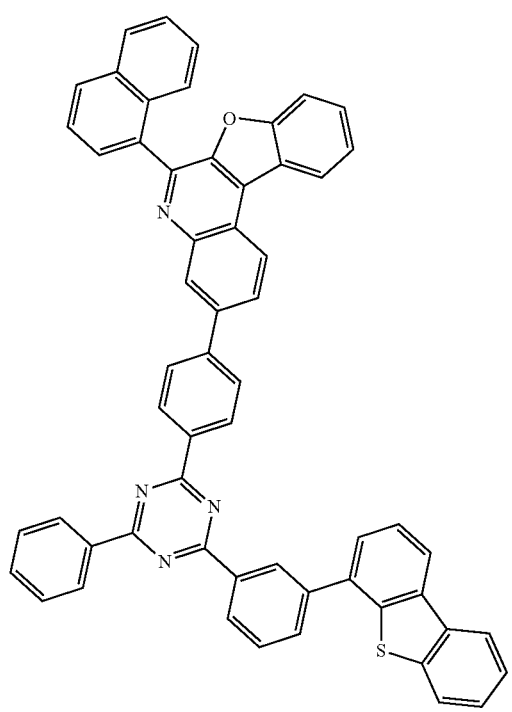
340
-continued
750
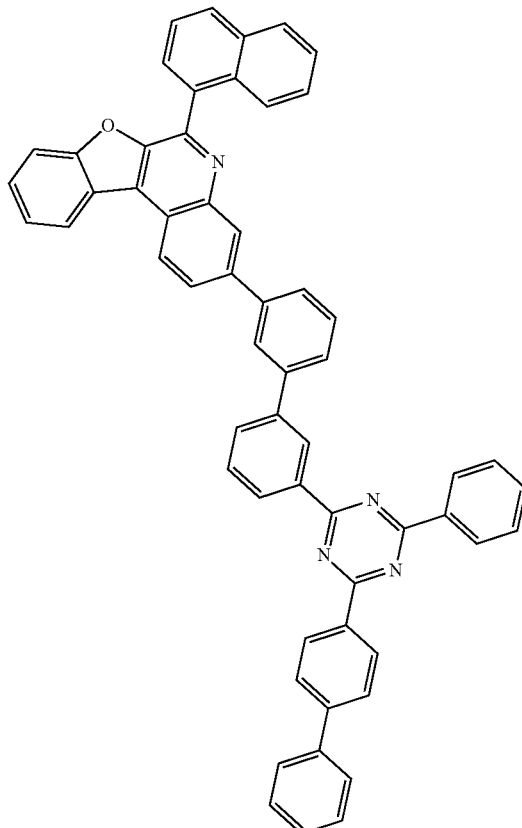
751
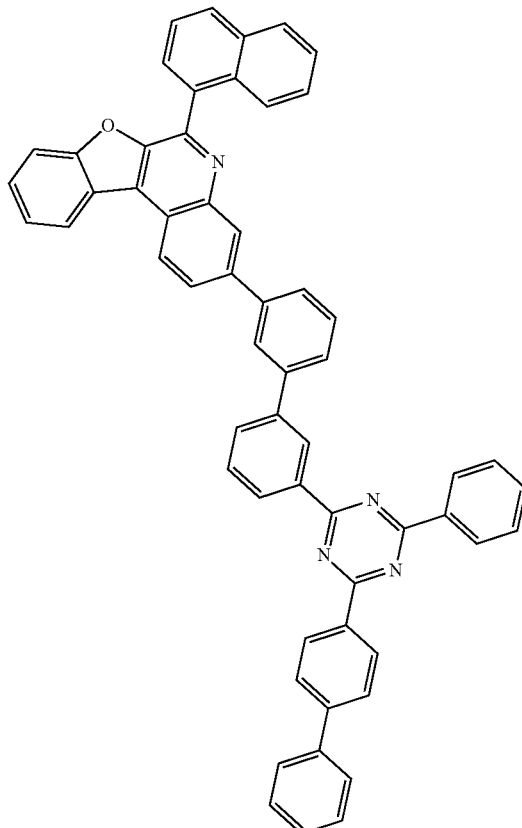

341
-continued
342
-continued
752
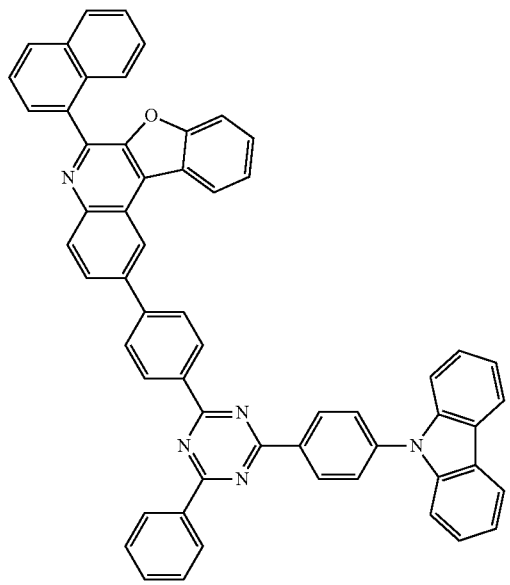
754
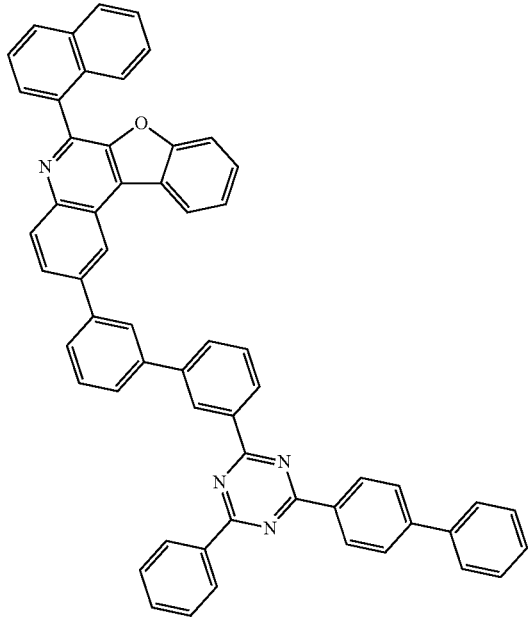
755
753
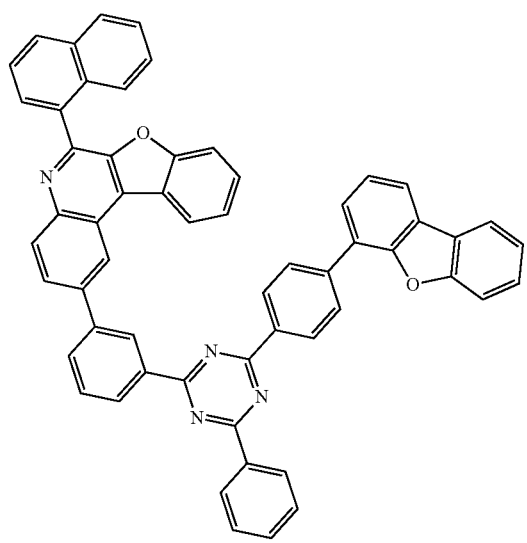
756
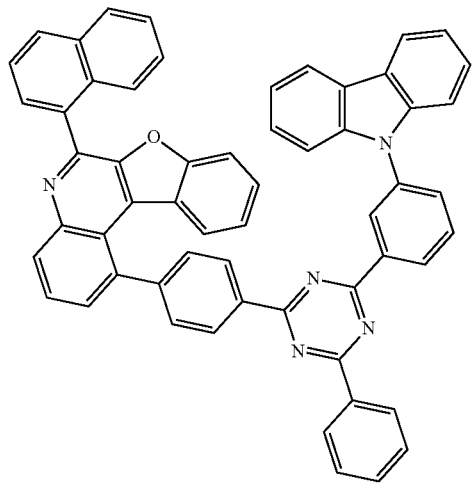

757
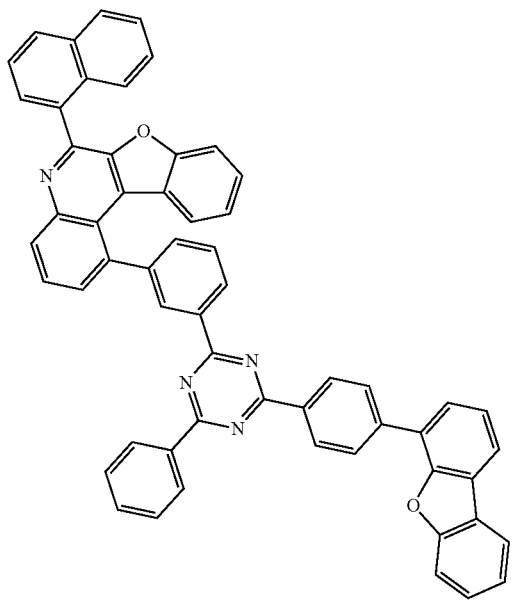
758
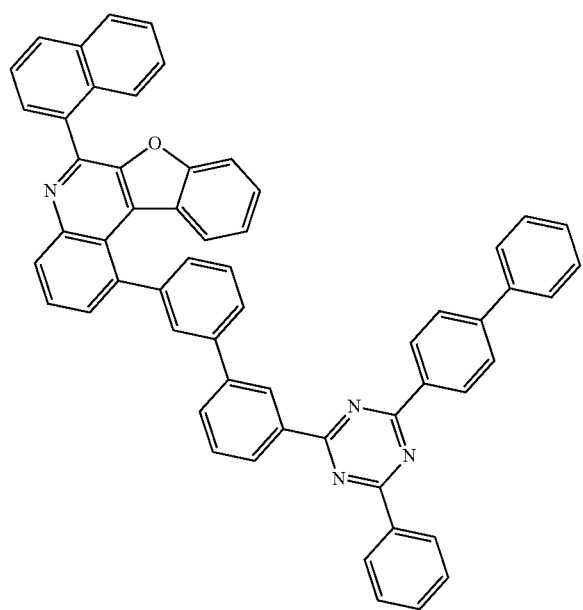
759
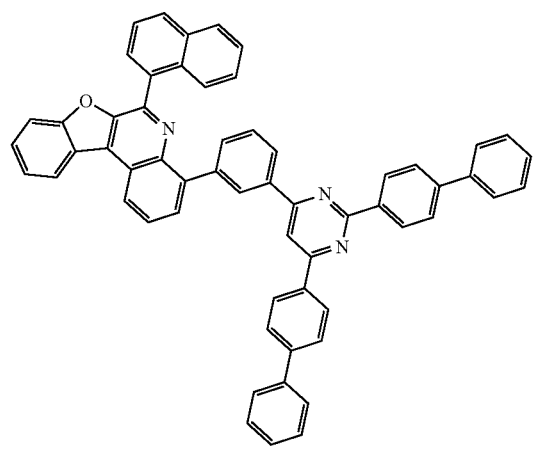
760
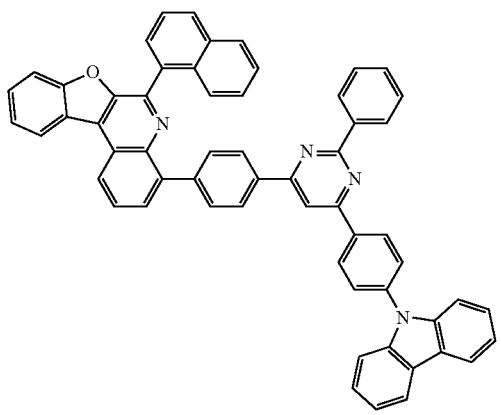
761
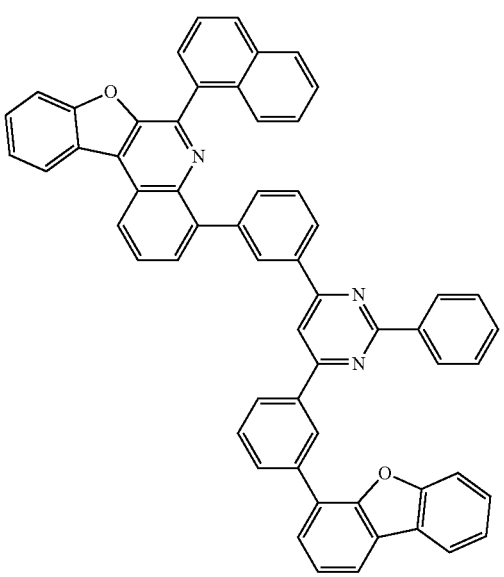
762
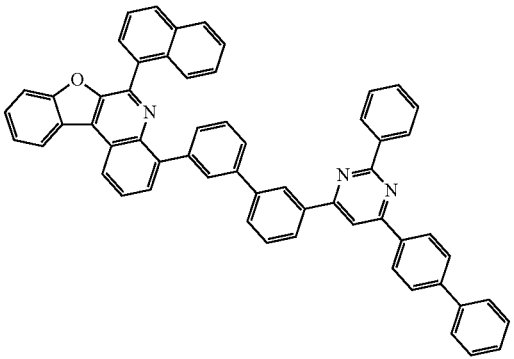

-continued
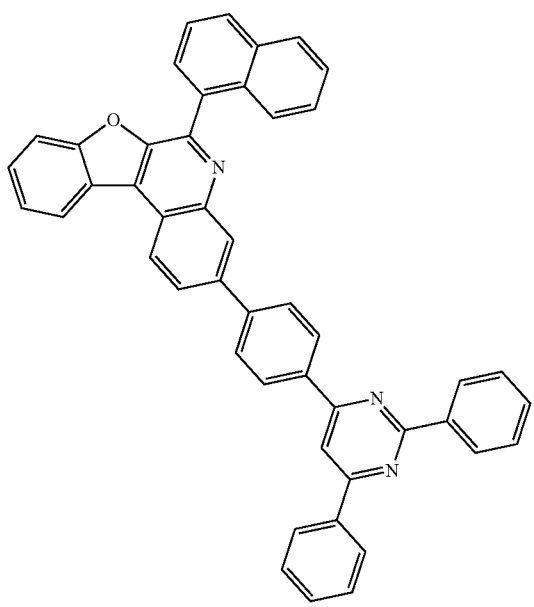
763
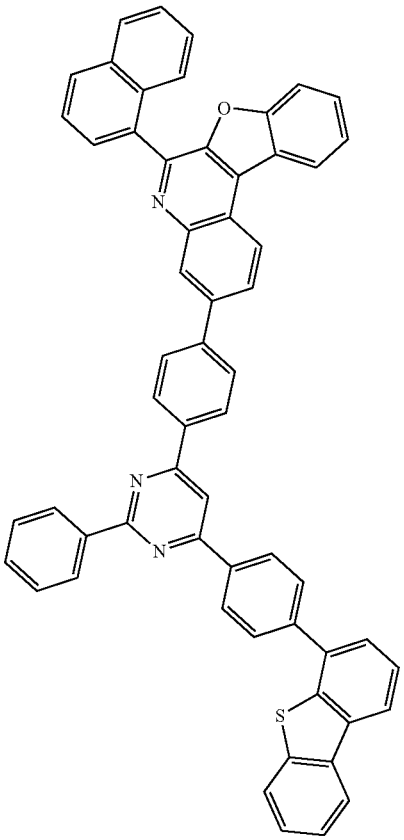
765
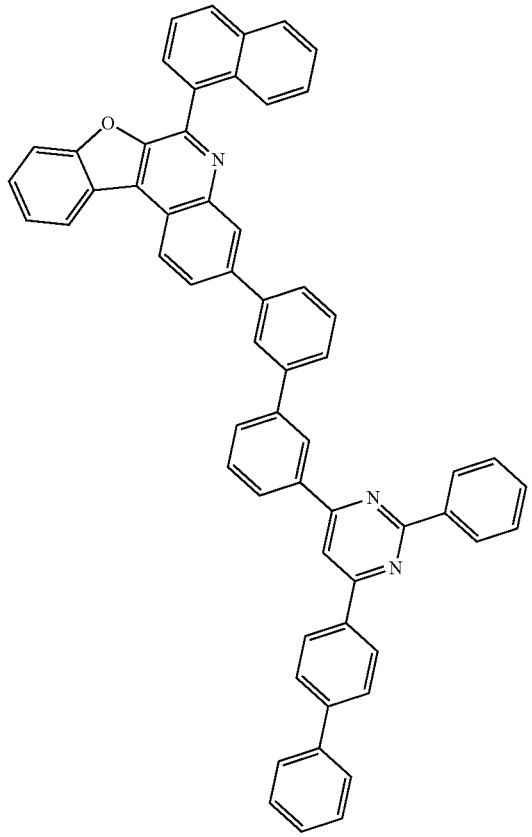
766

347
-continued
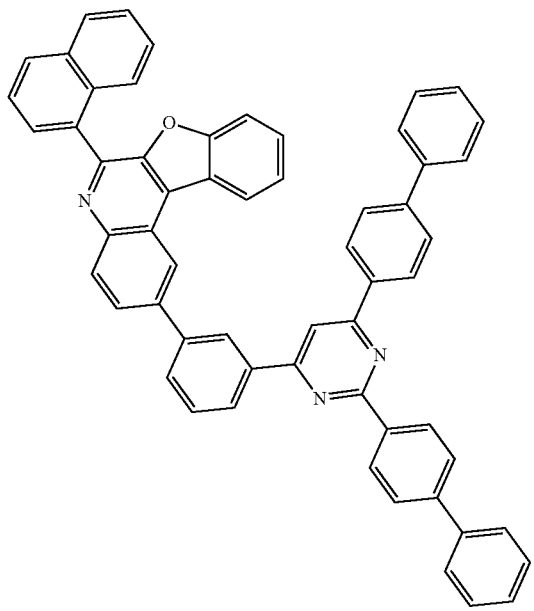
767
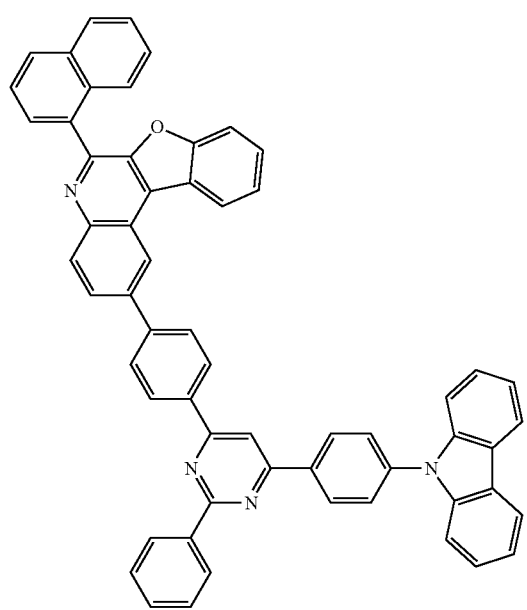
768
348
-continued
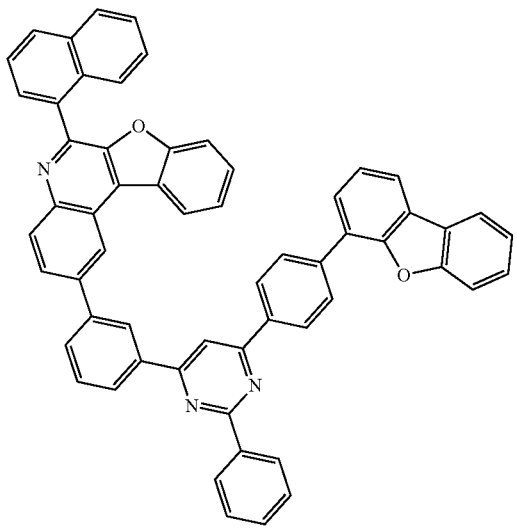
769
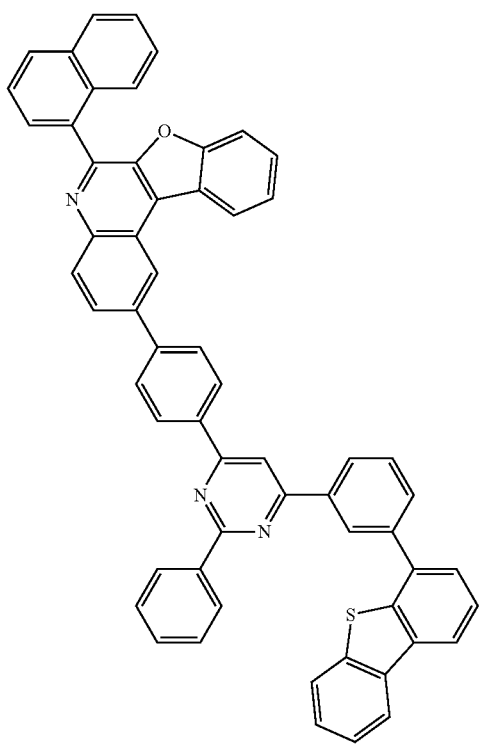
770

771 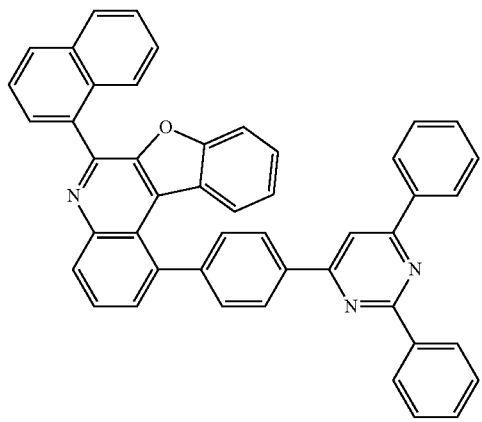
772 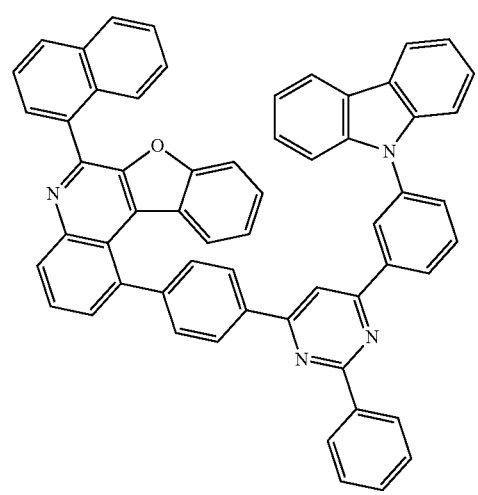
773 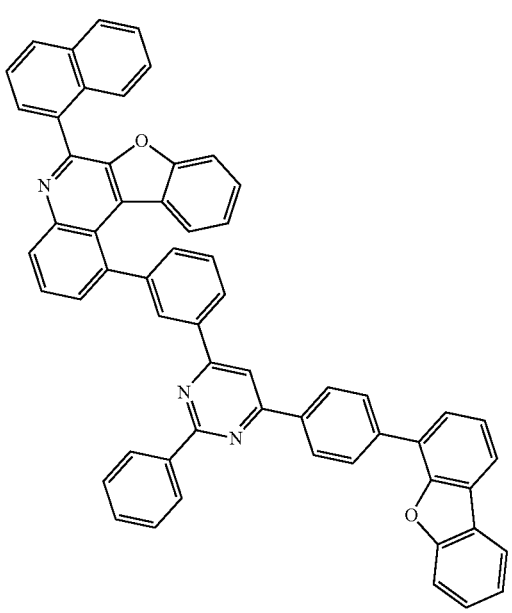
774 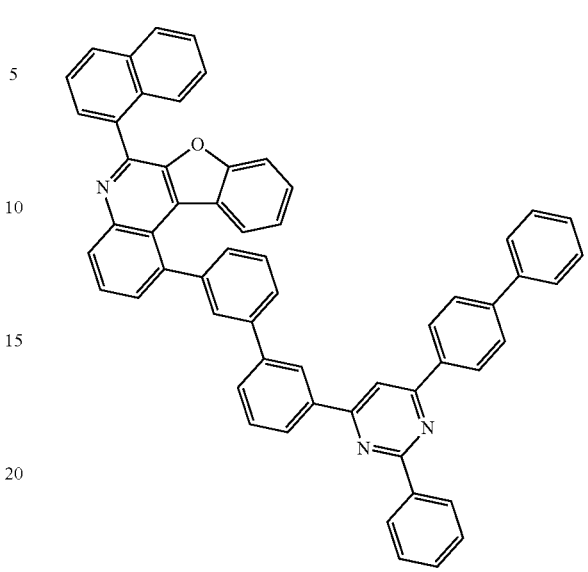
775 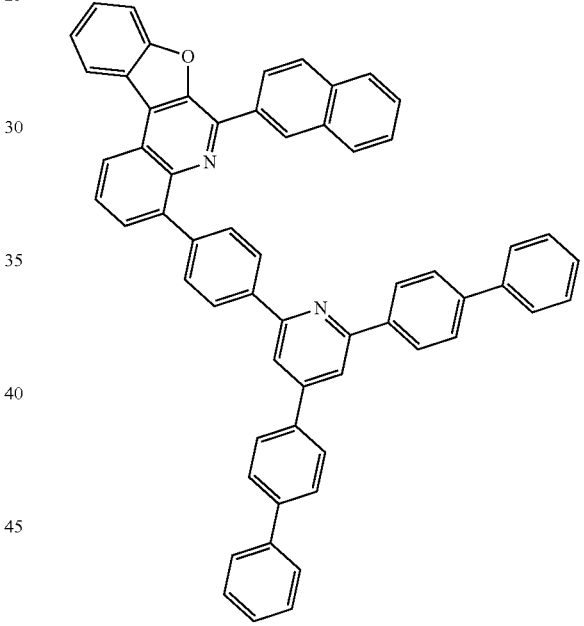
776 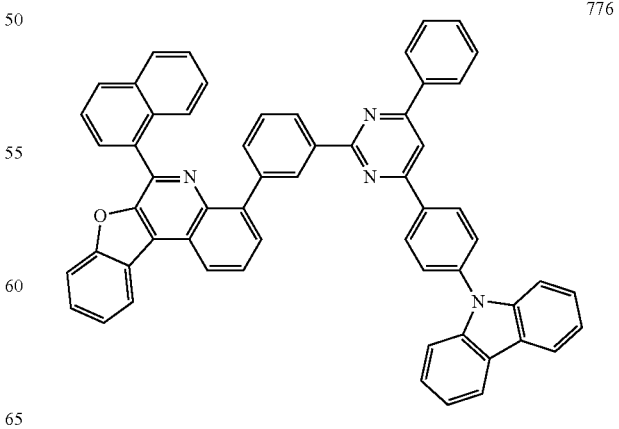

351
-continued
777
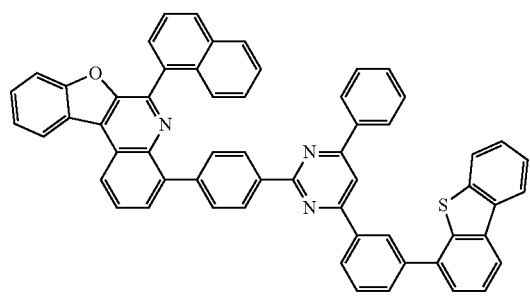
778
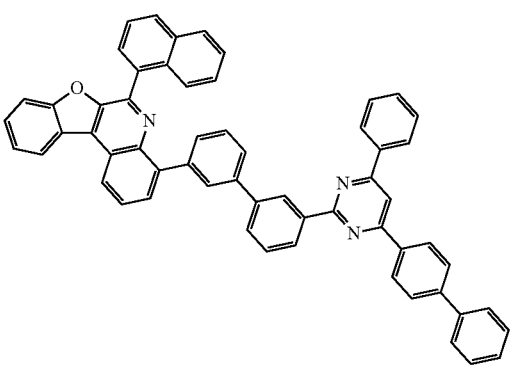
779
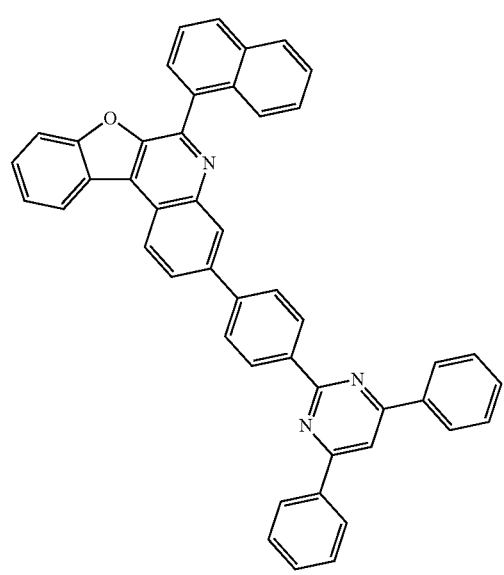
352
-continued
780
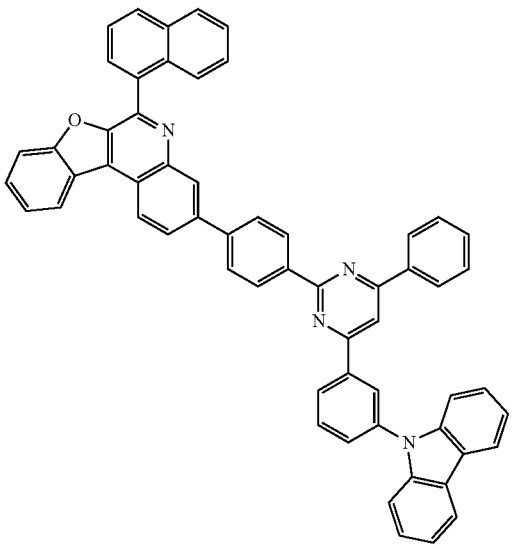
781
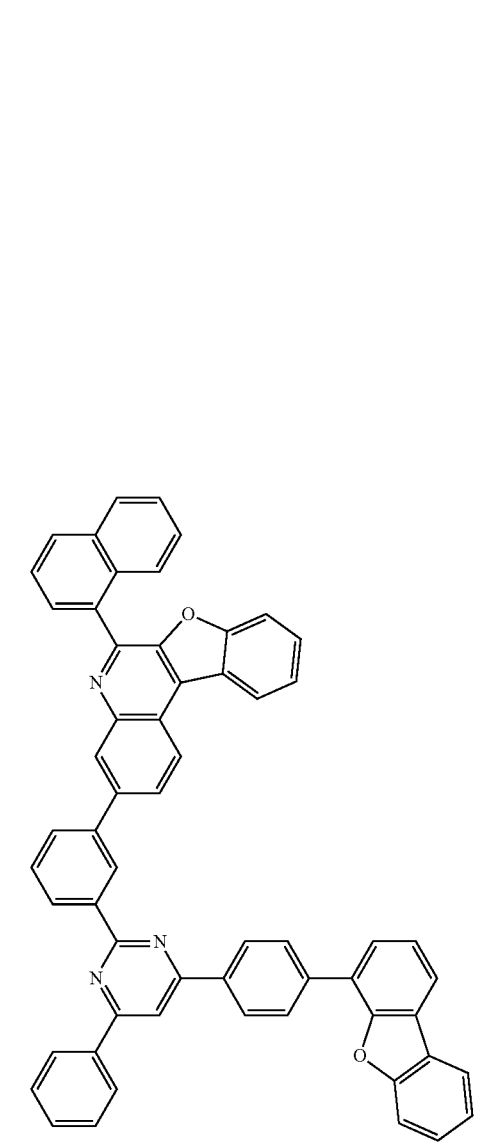

353
-continued
782
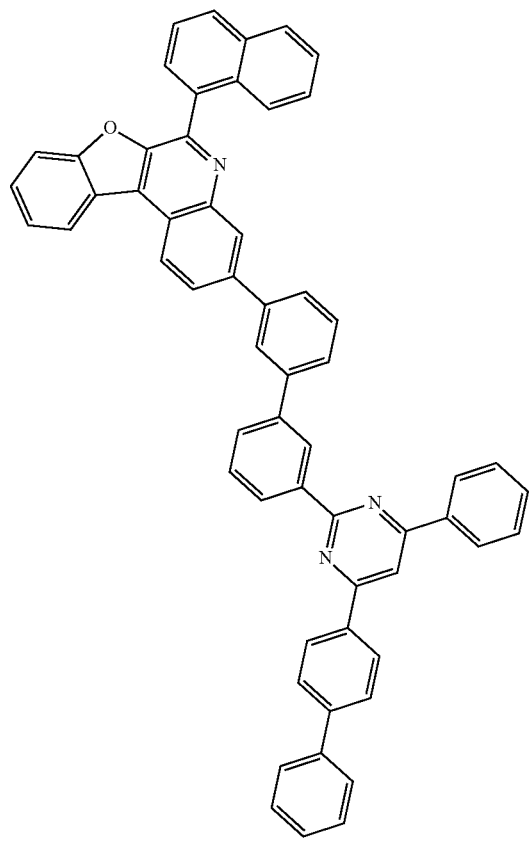
783
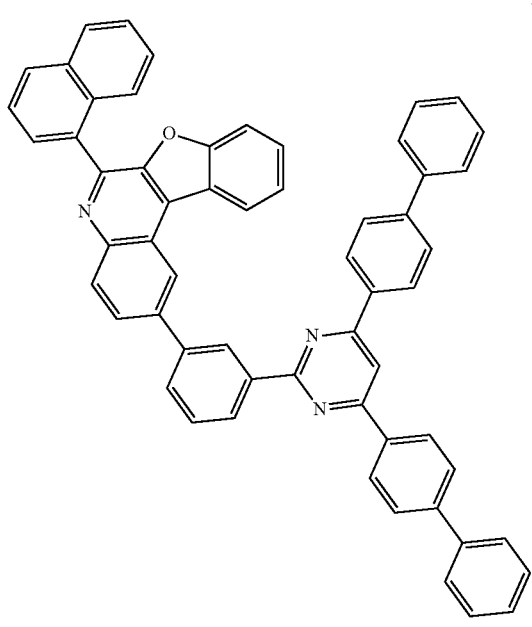
354
-continued
784
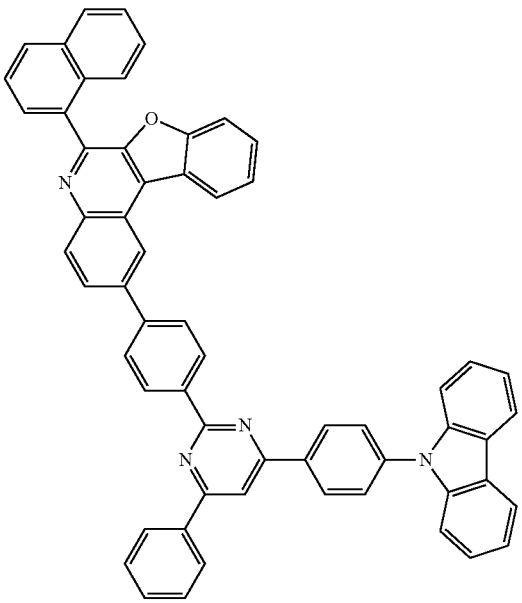
785
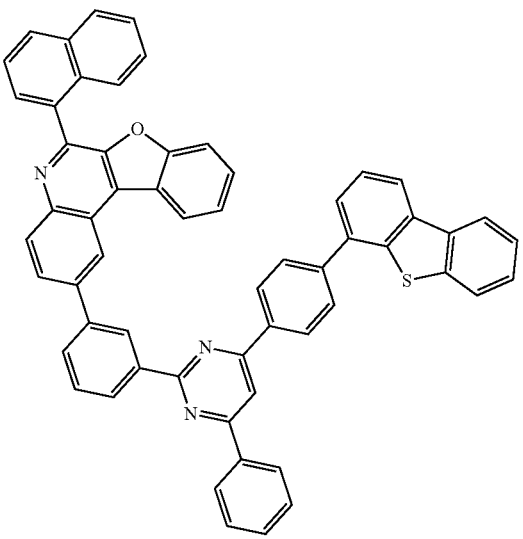

786
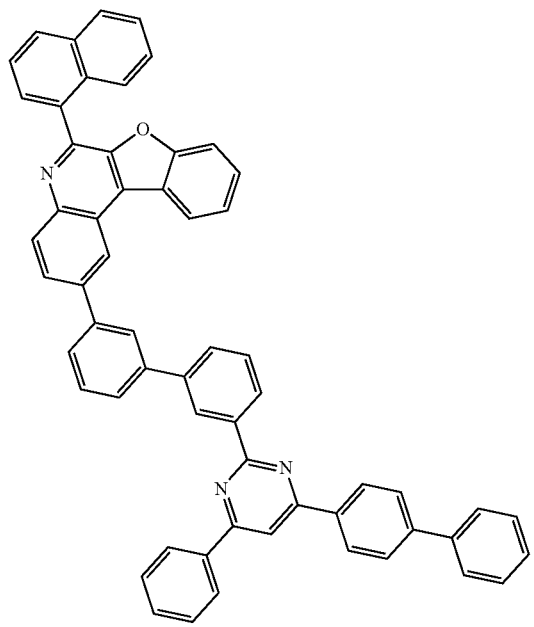
787
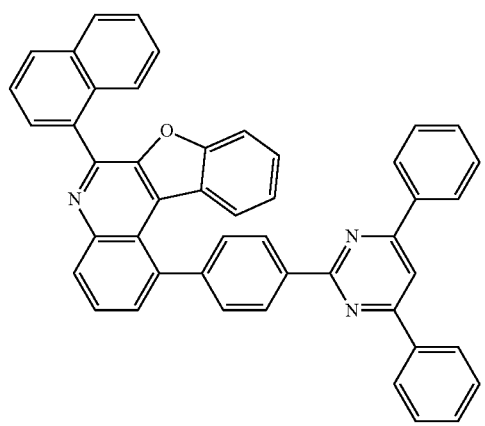
788
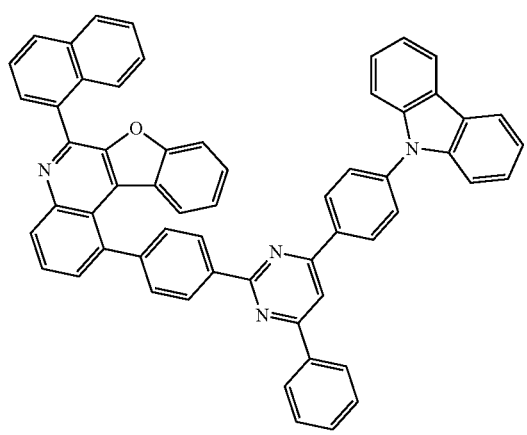
789
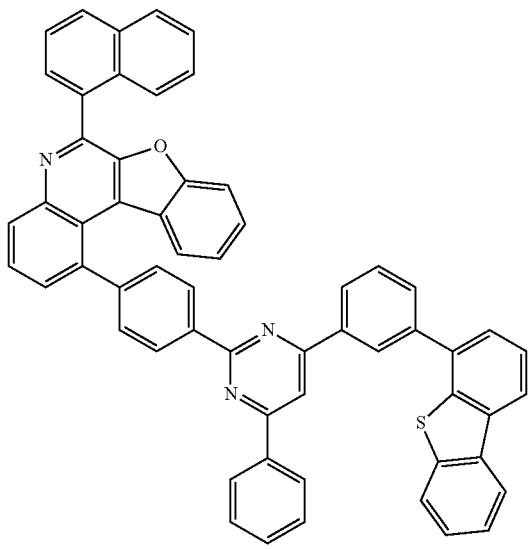
790
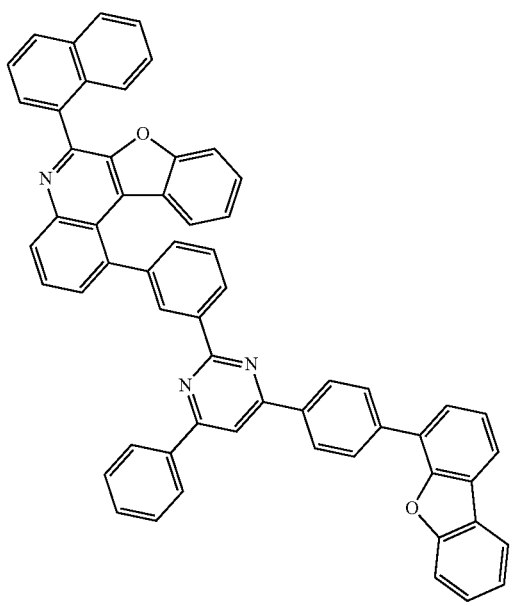
791
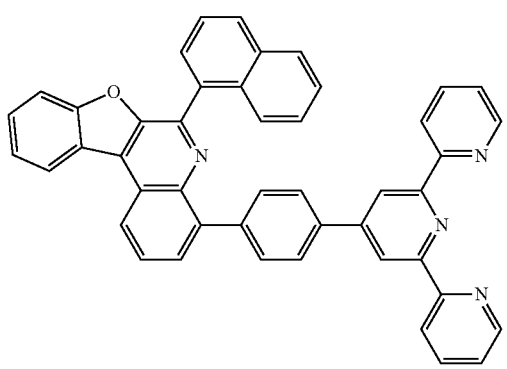

357
-continued
792
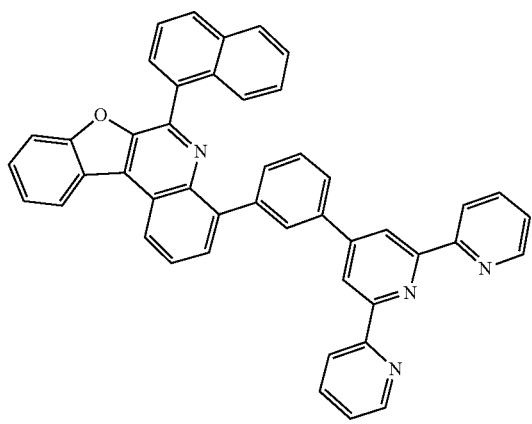
793
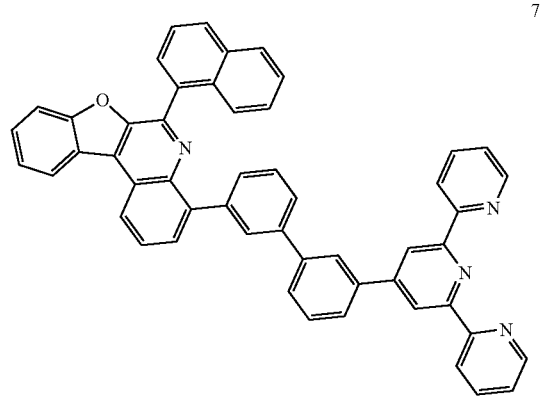
794
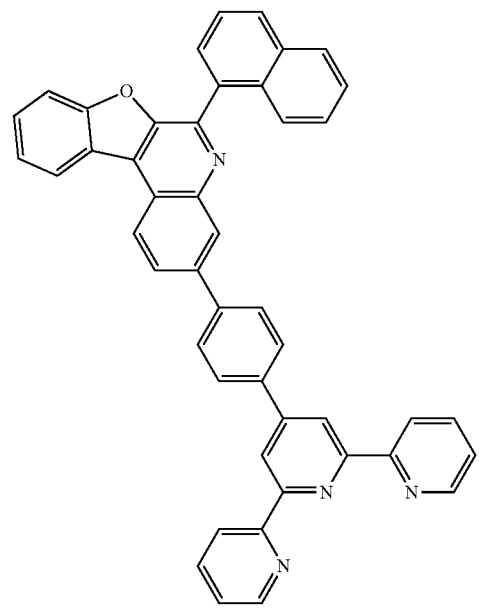
358
-continued
795
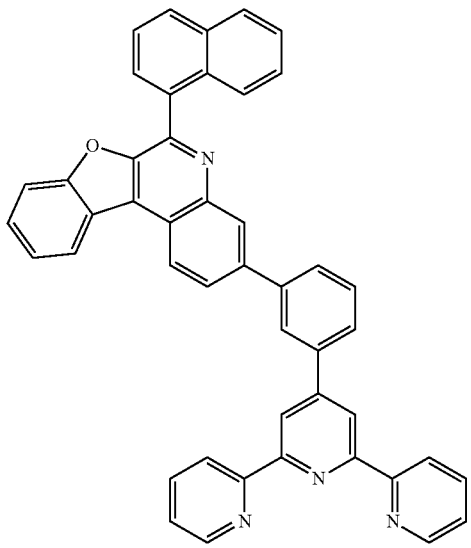
796
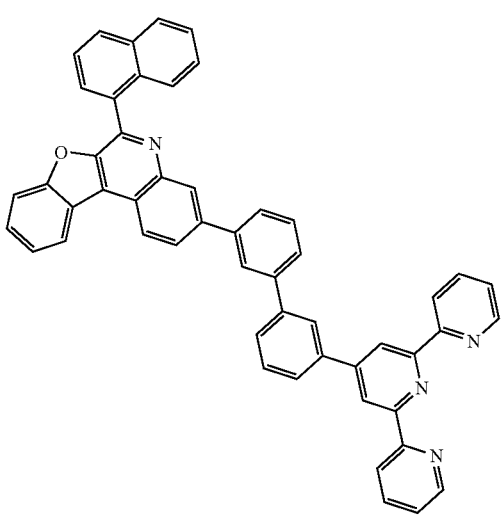
797
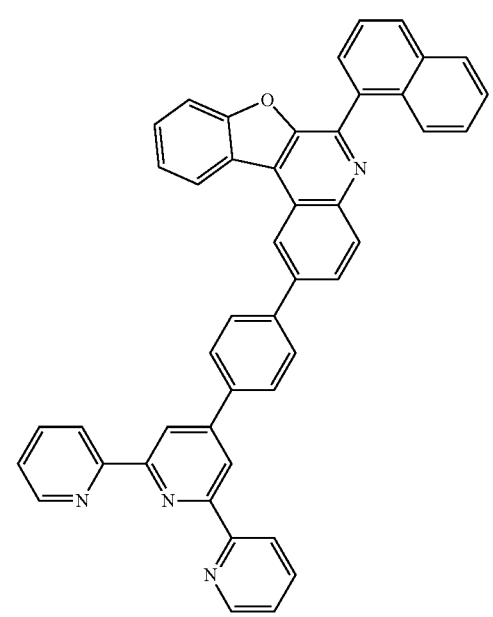

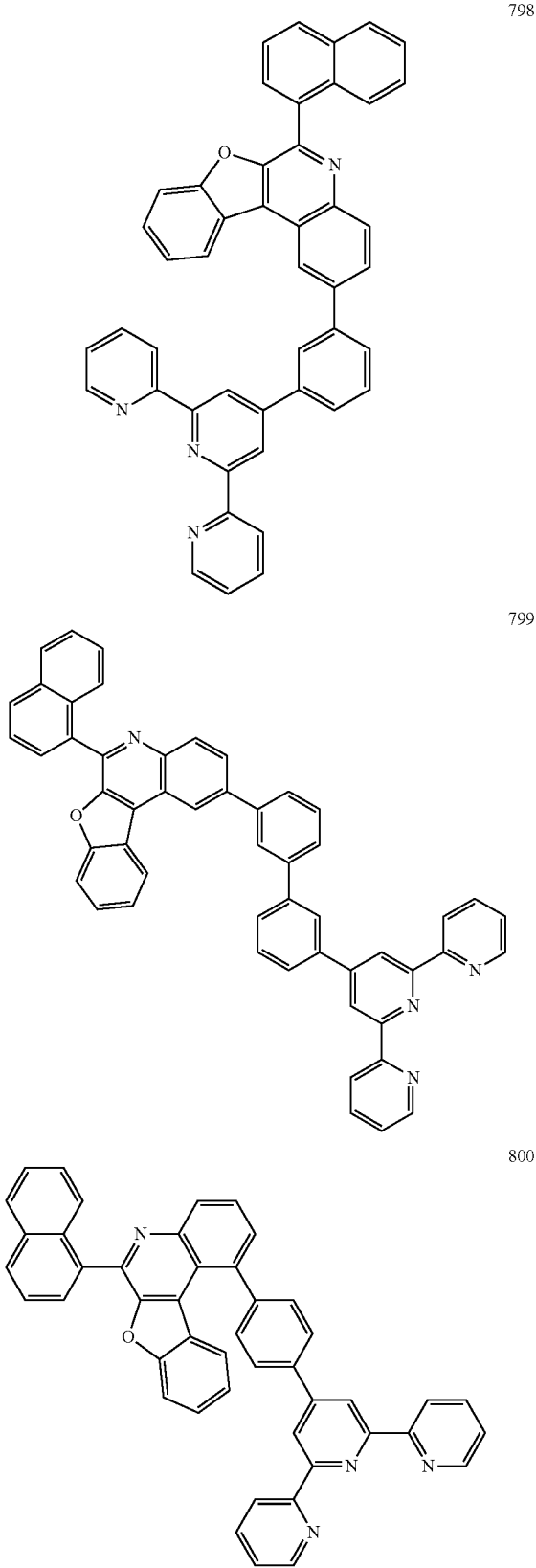
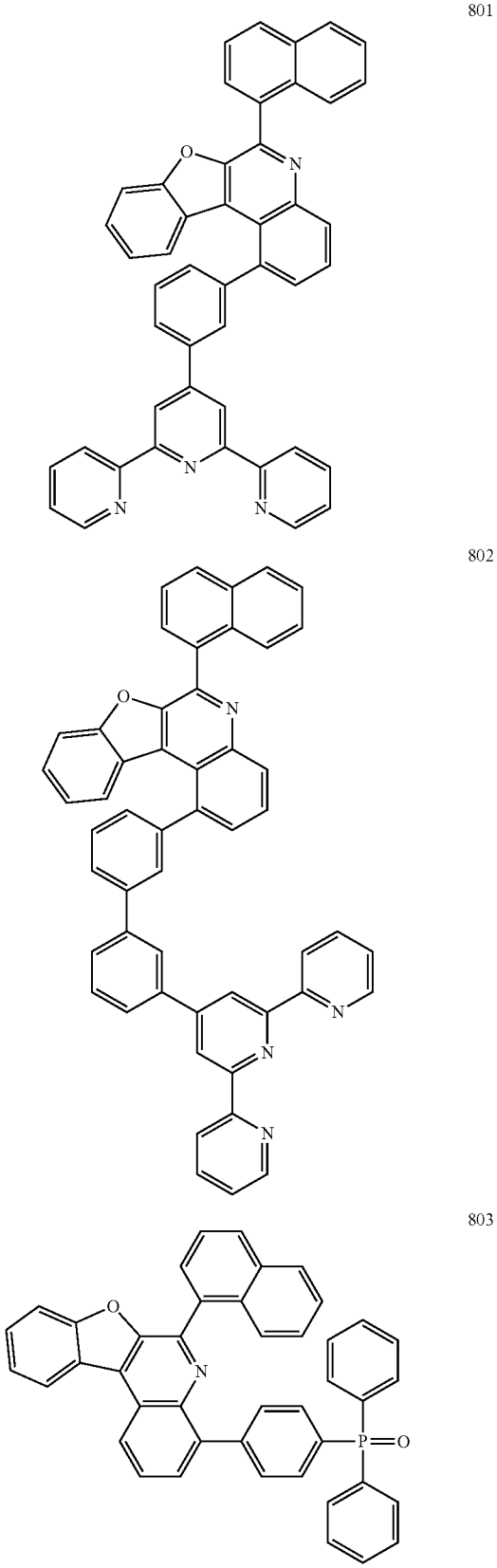

804
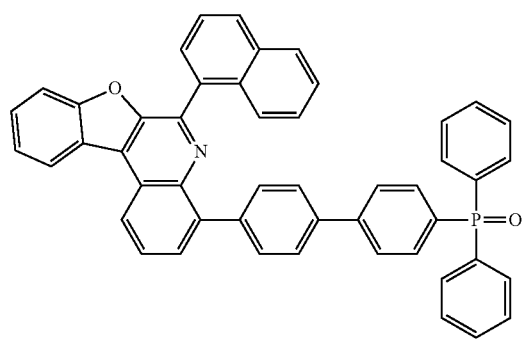
805
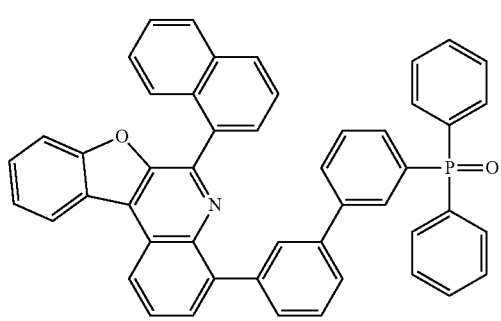
806
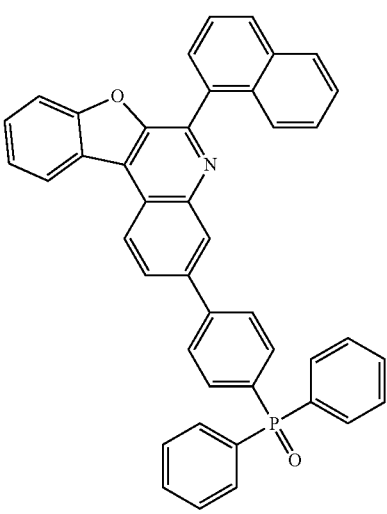
807
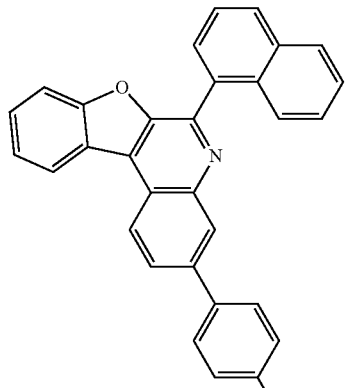
808
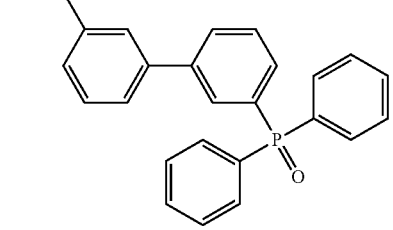
809
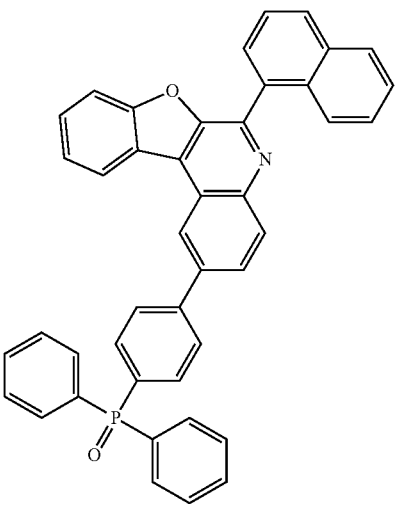

363
-continued
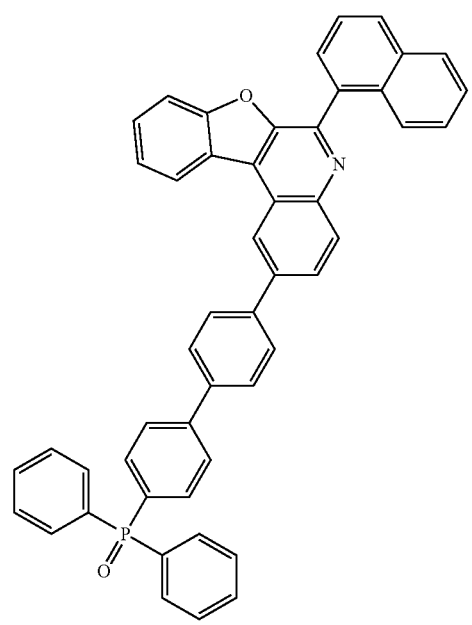
810
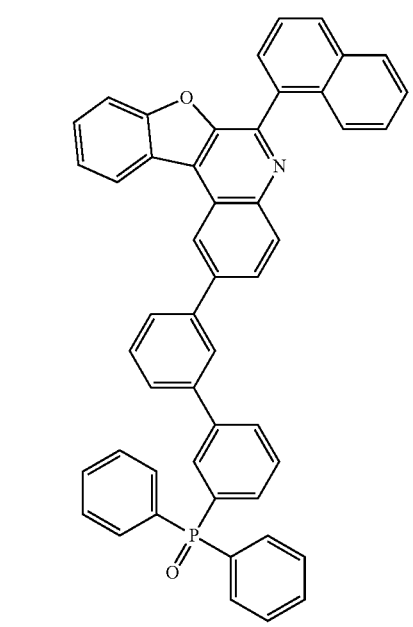
811
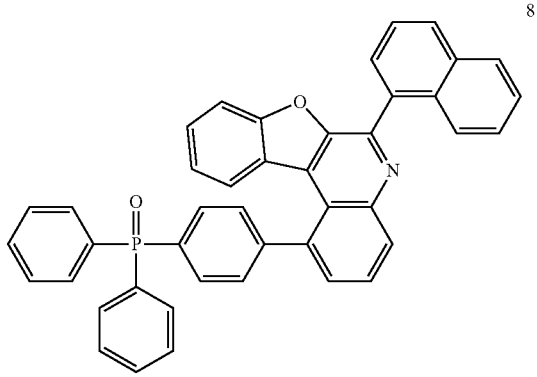
812
364
-continued
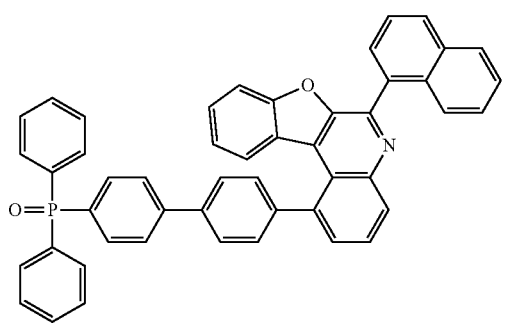
813
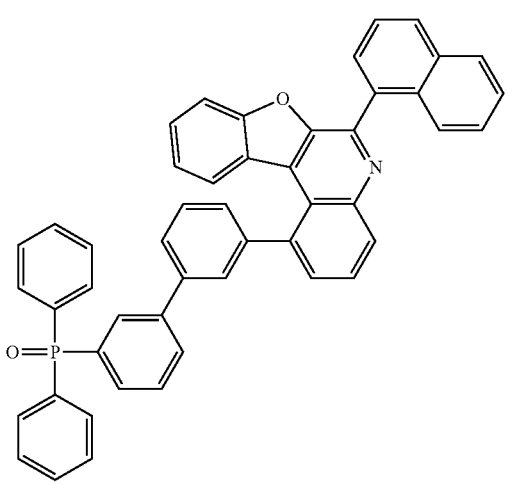
814
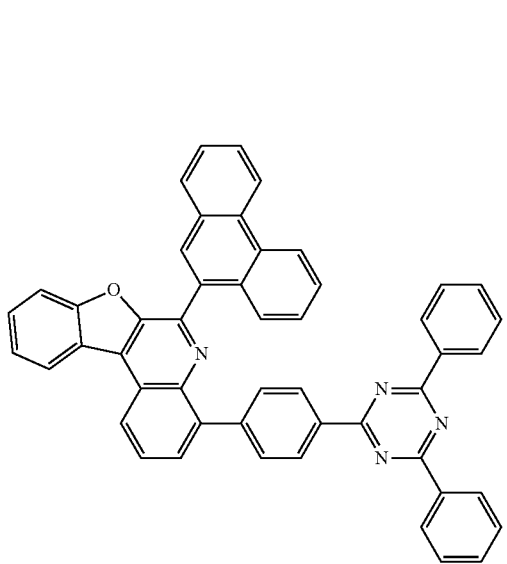
815

816
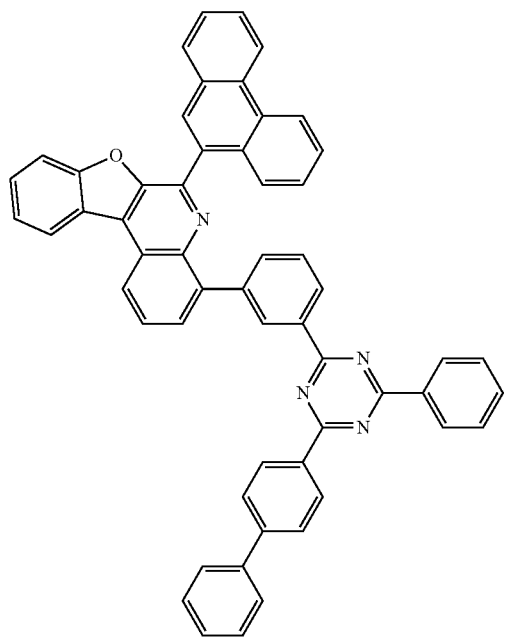
818
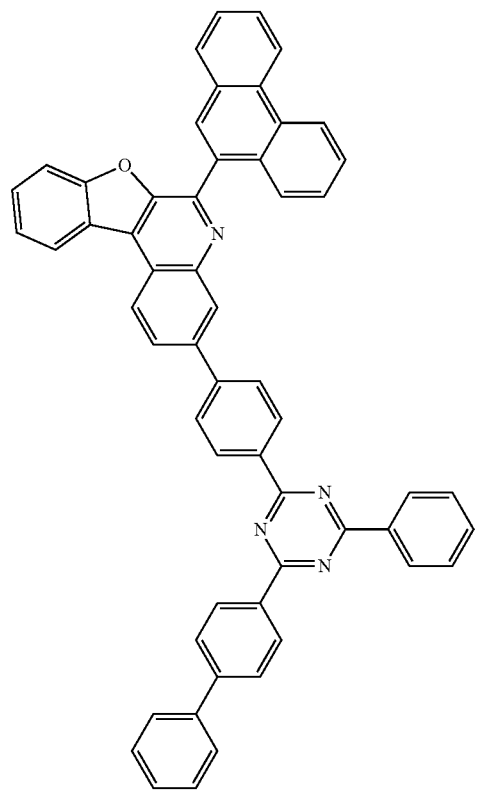
817
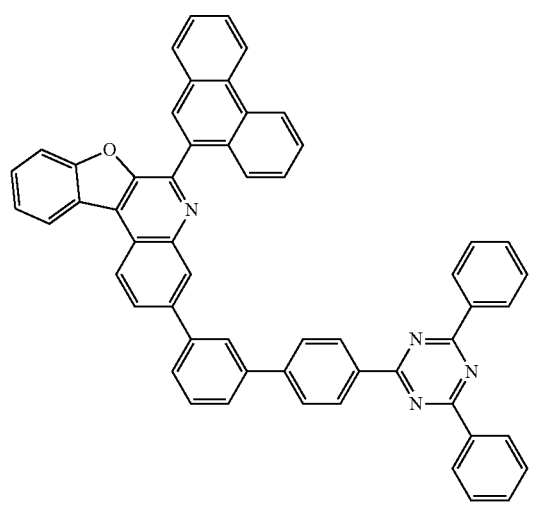
819
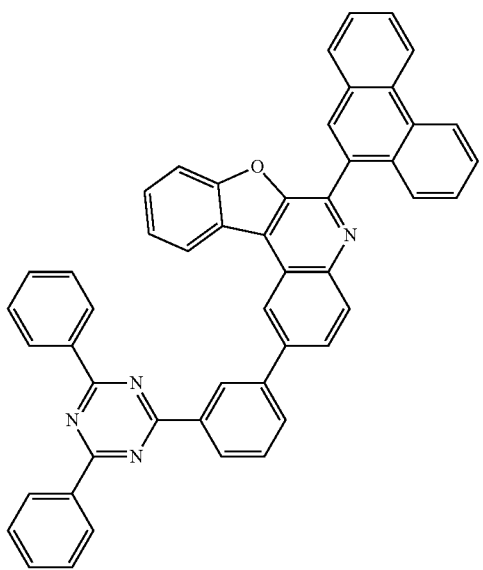

367
-continued
820
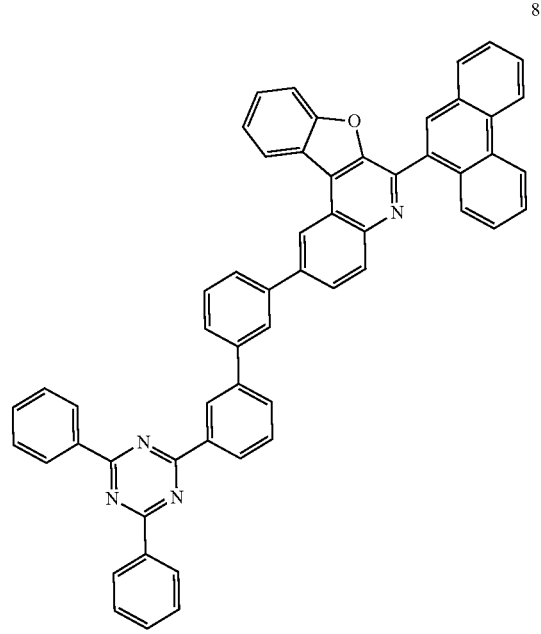
821
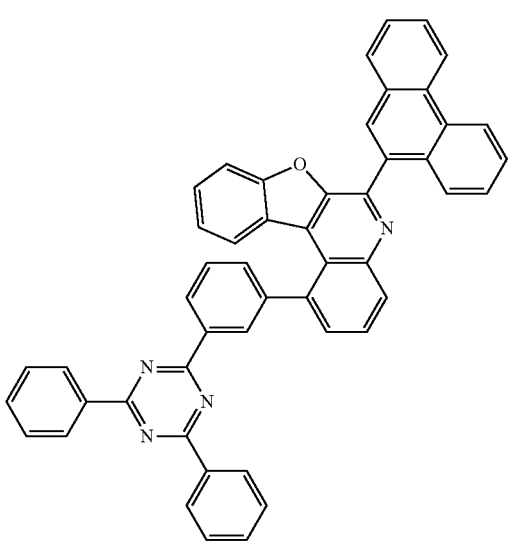
822
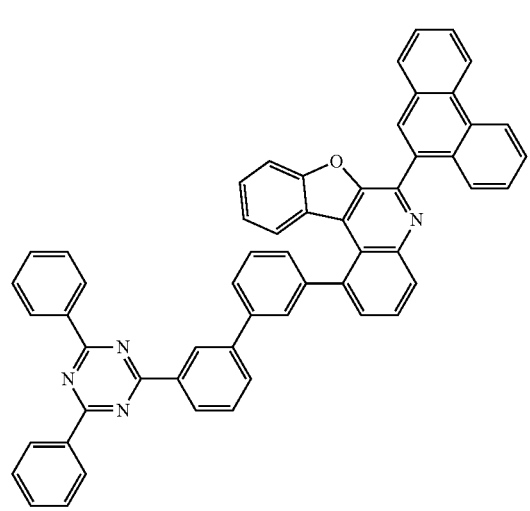
368
-continued
823
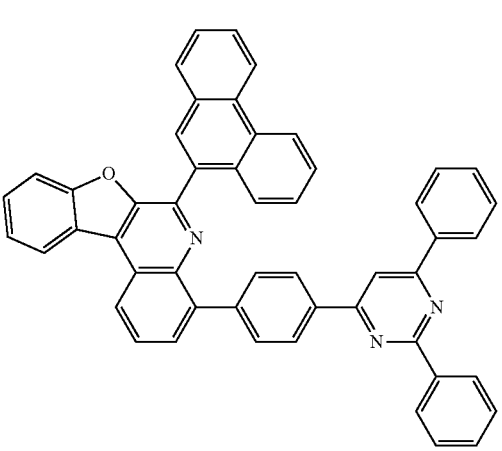
824
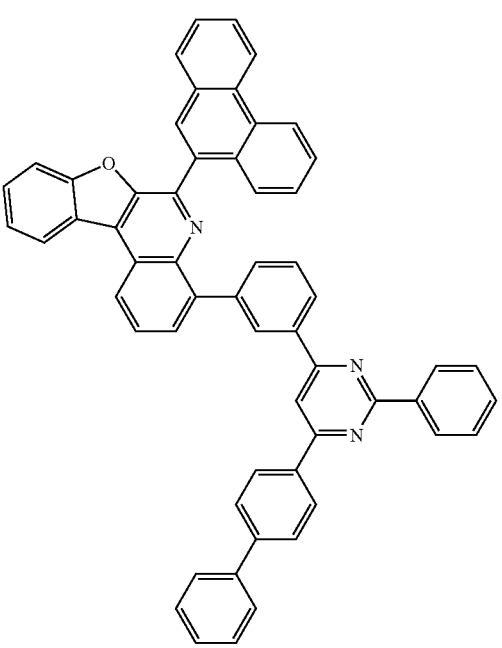
825
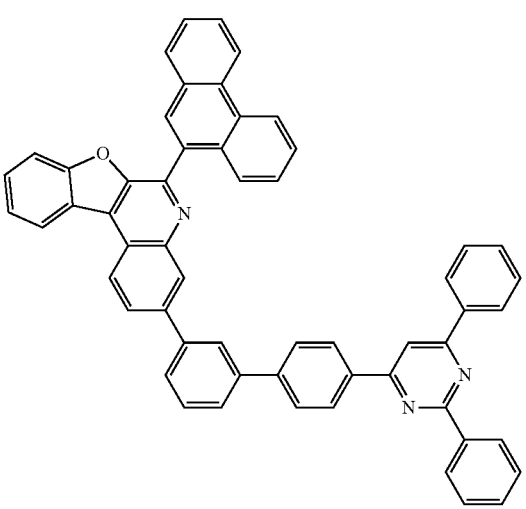

369
-continued
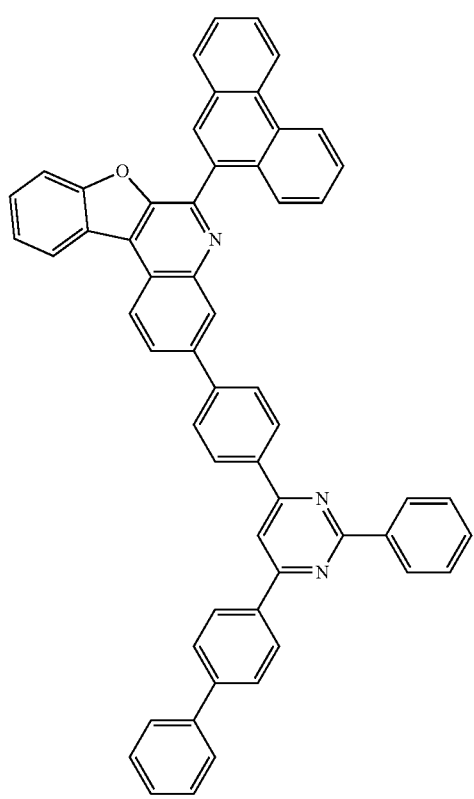
826
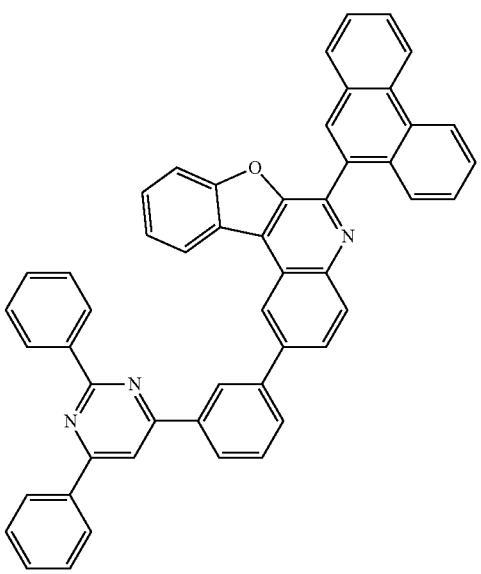
827
370
-continued
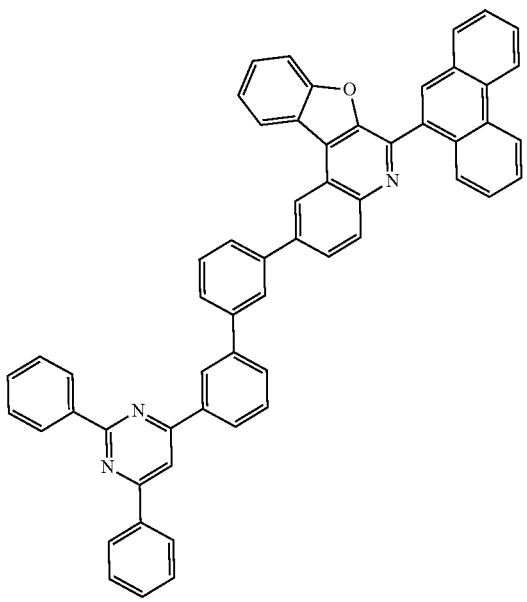
828
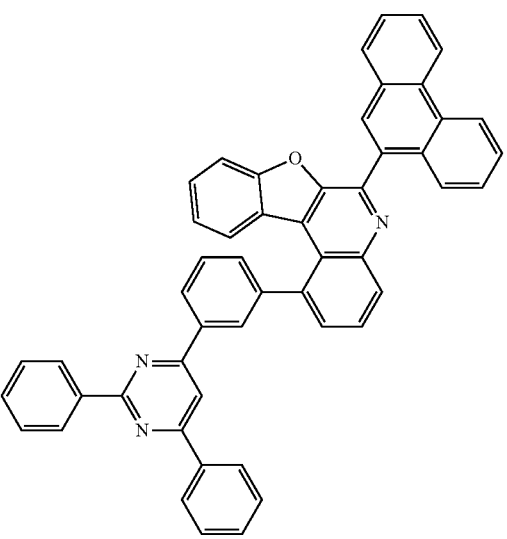
829

371
-continued
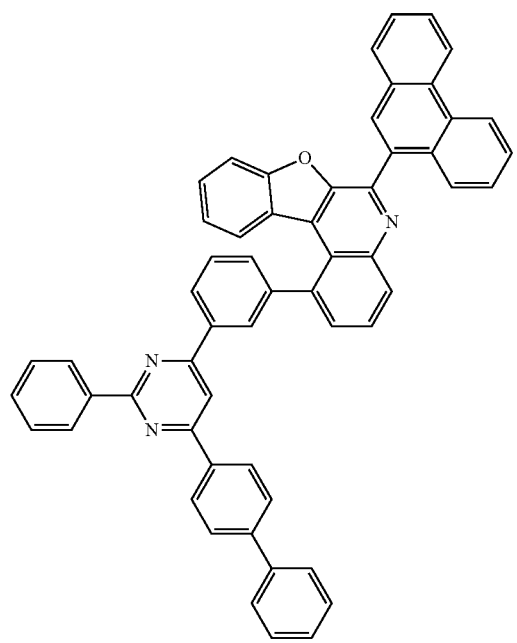
830
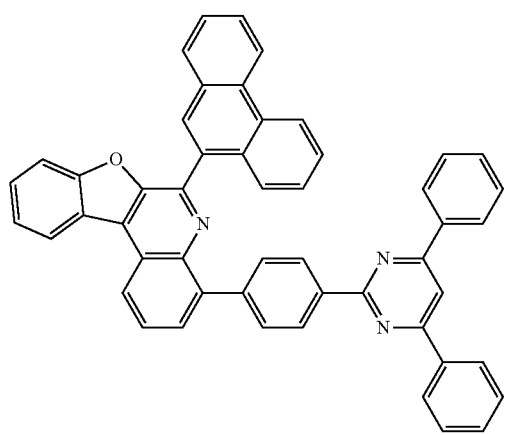
831
372
-continued
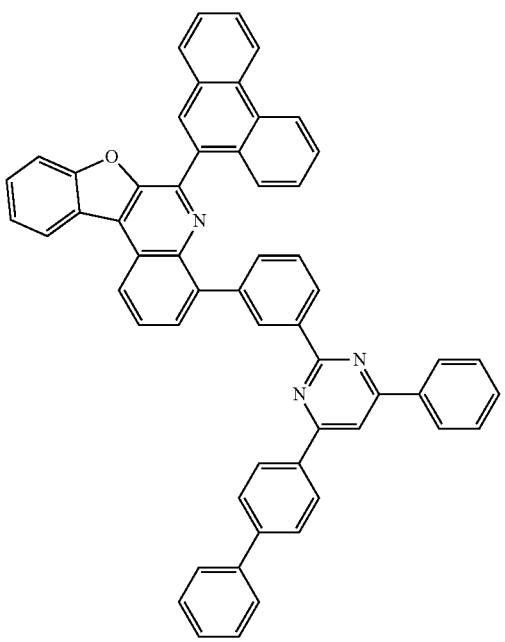
832
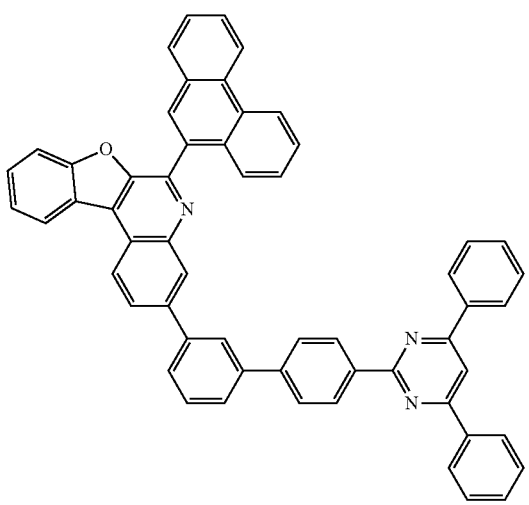
833

-continued
834
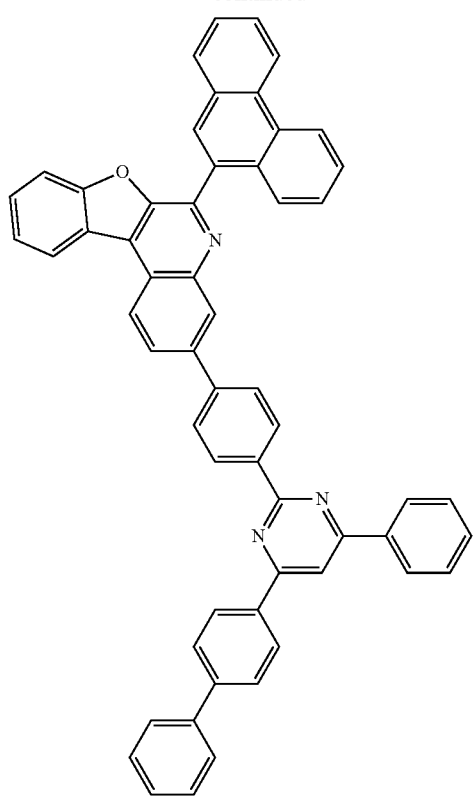
-continued
836
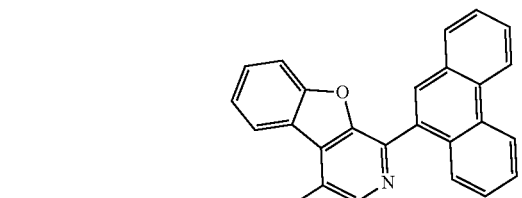
837
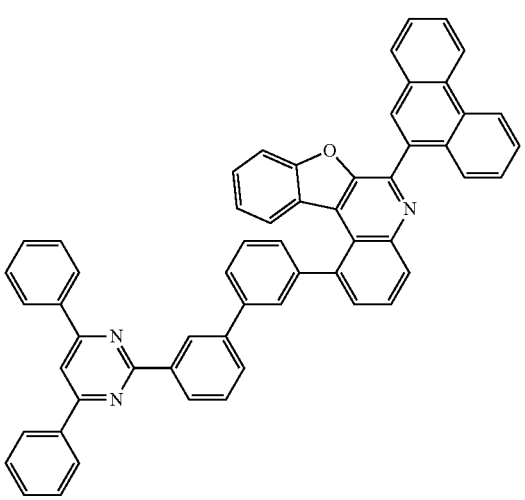
835
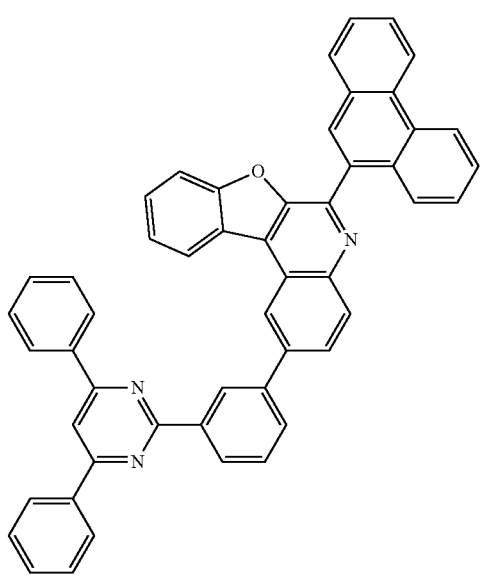
838

375
-continued
839
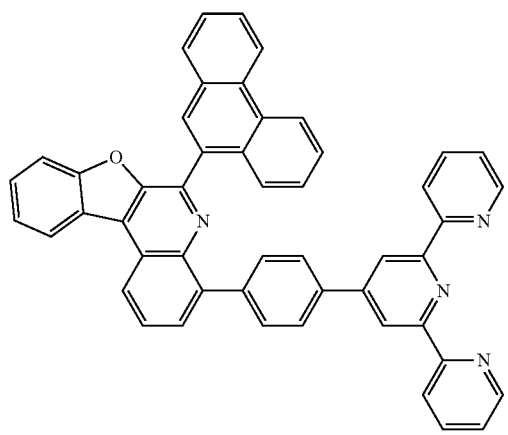
840
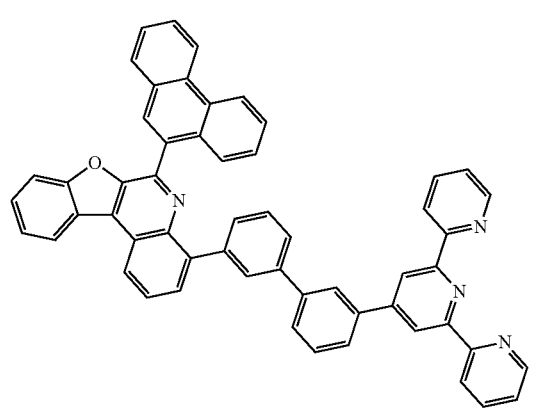
841
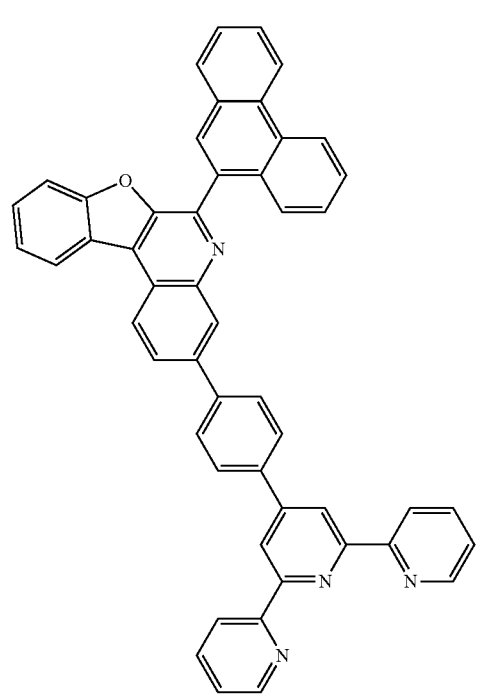
376
-continued
842
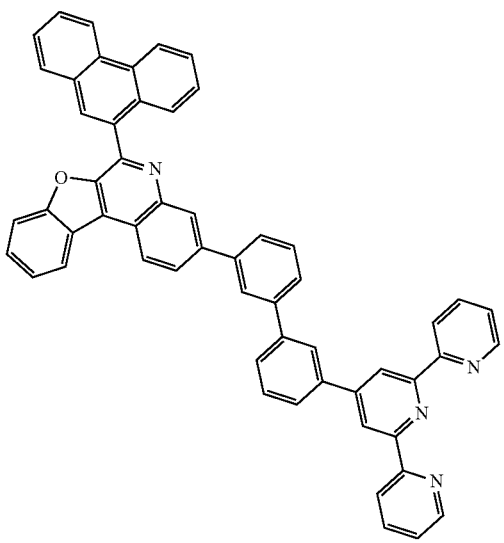
843
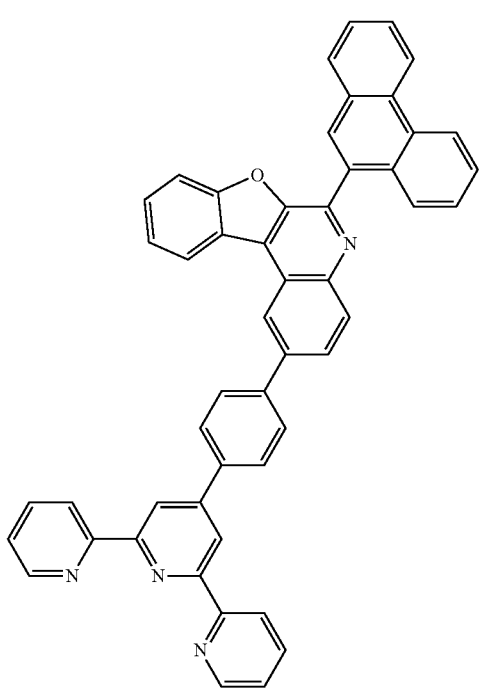

-continued
844
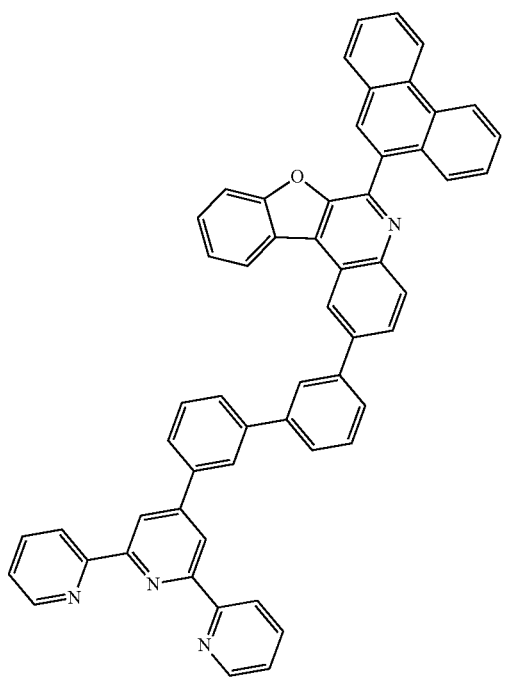
845
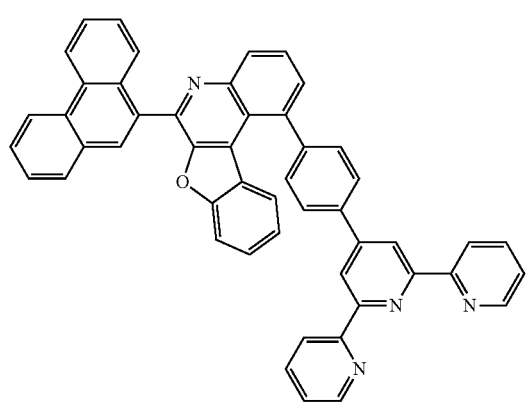
-continued
846
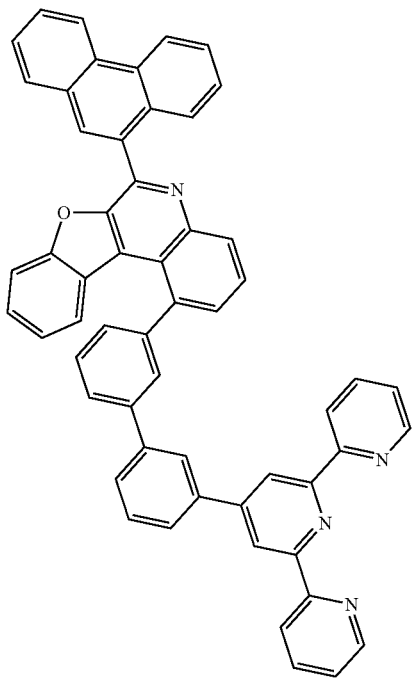
847
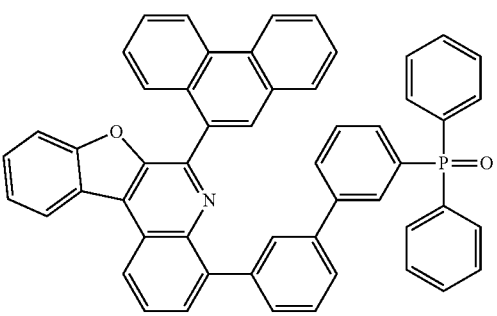
848

379
-continued
849
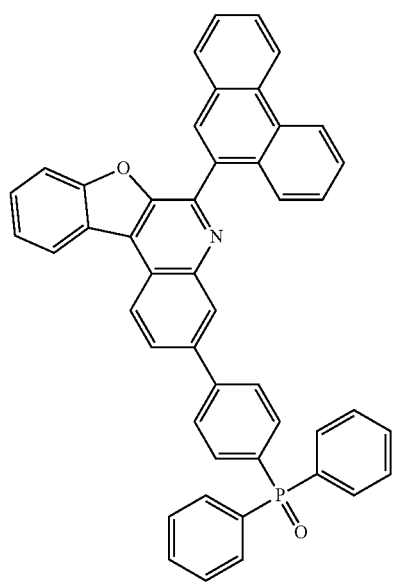
850
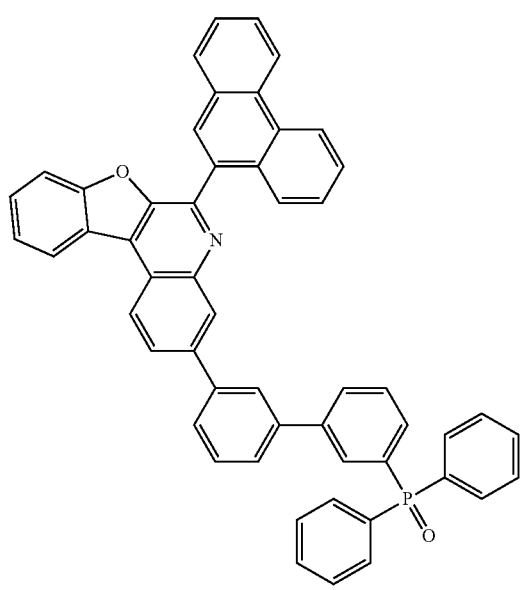
380
-continued
851
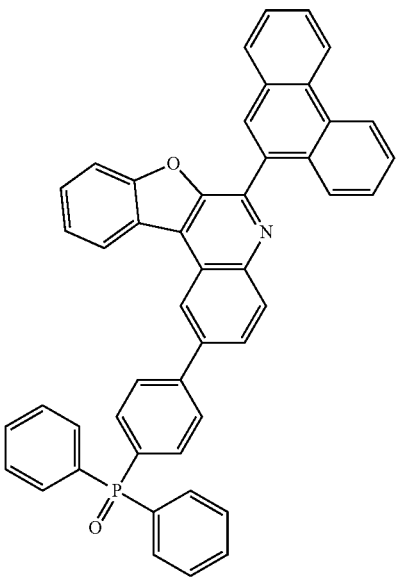
852
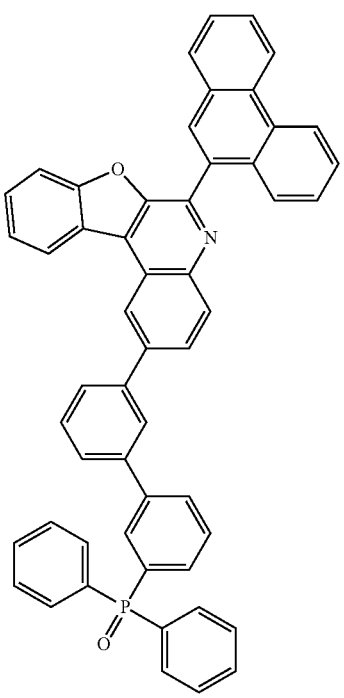

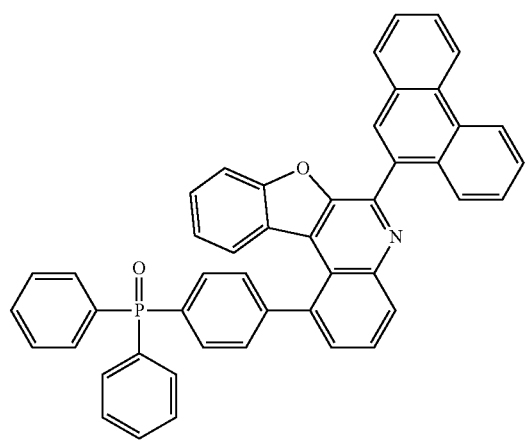
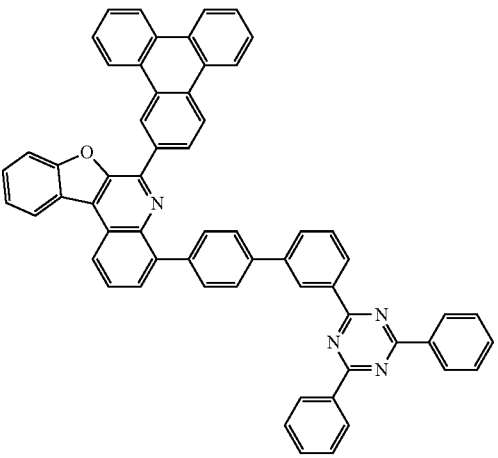
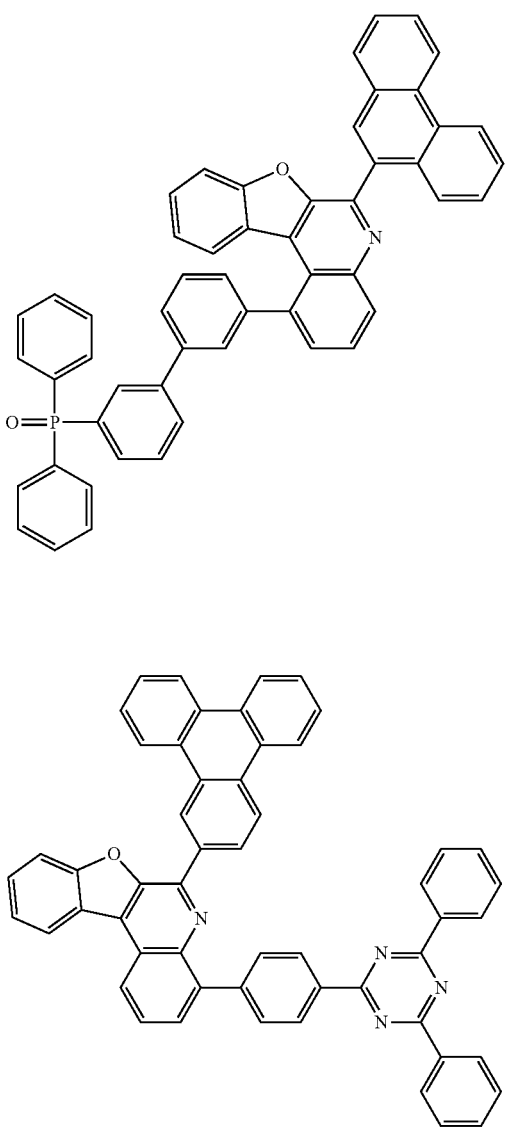
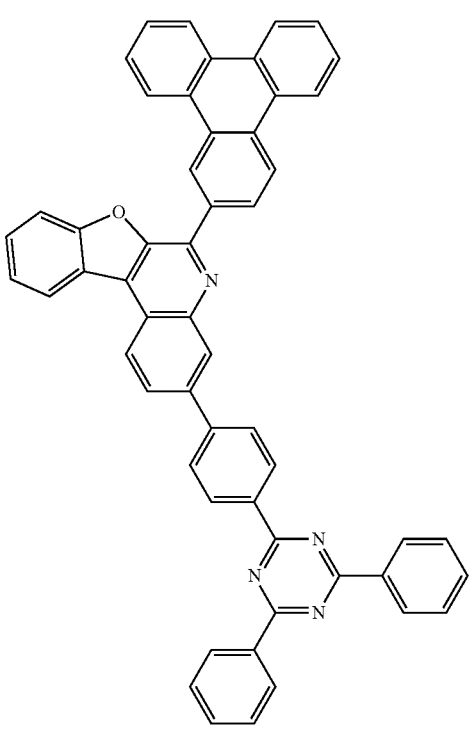

383
-continued
858
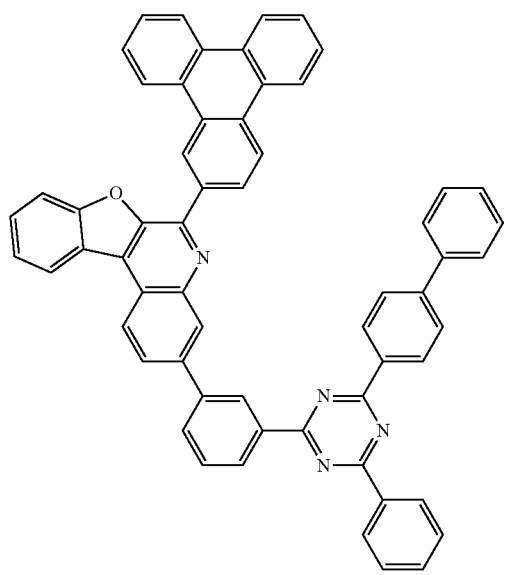
859
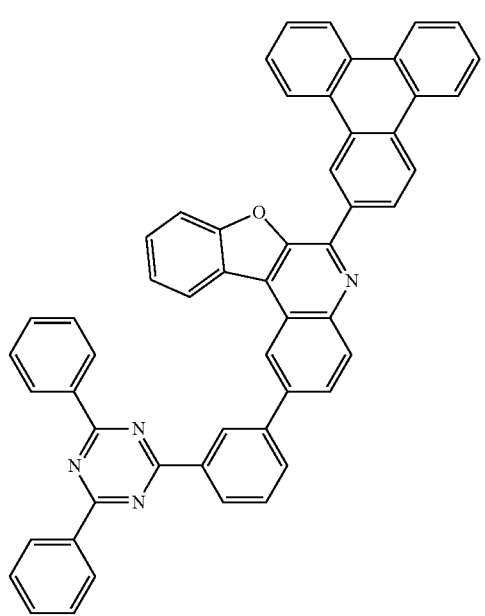
384
-continued
860
861
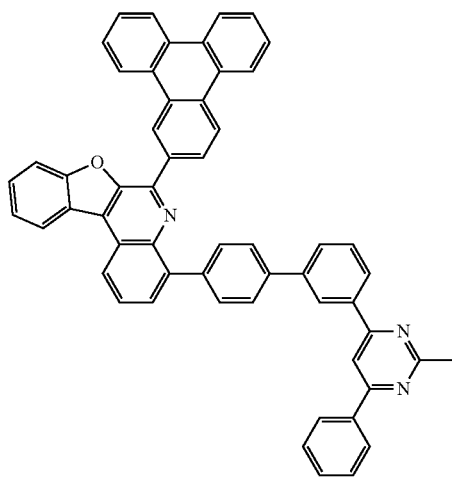
862

385
-continued
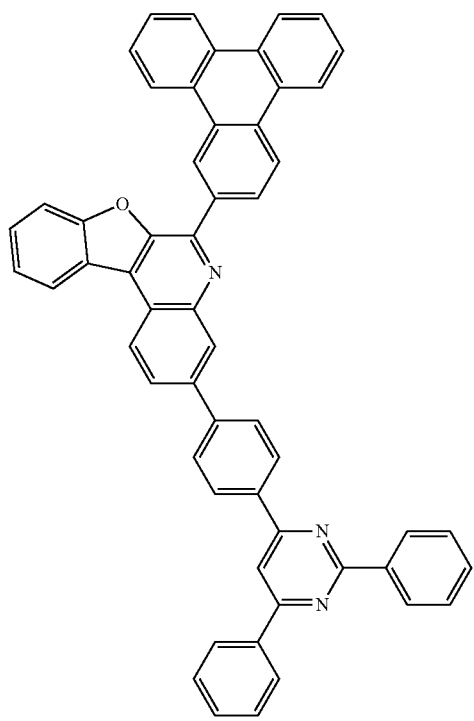
863
386
-continued
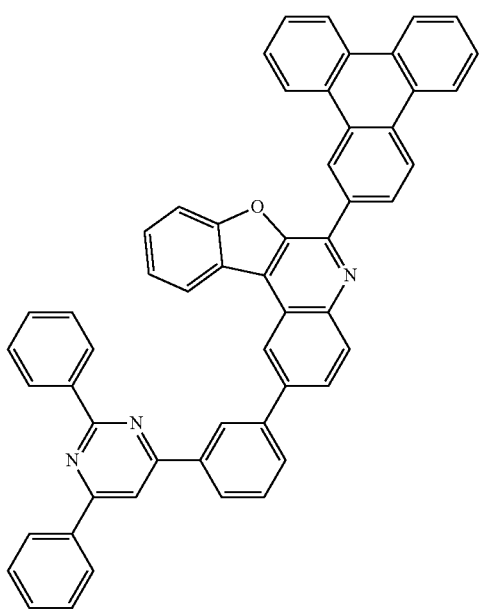
865
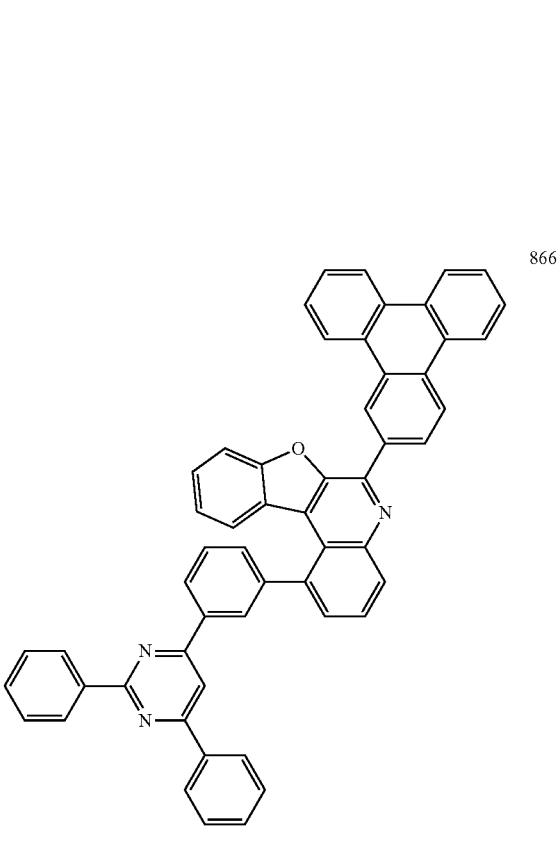
866
864

387
-continued
388
-continued
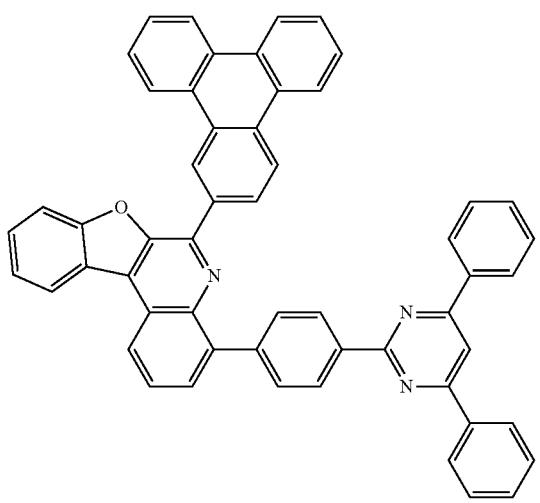
867
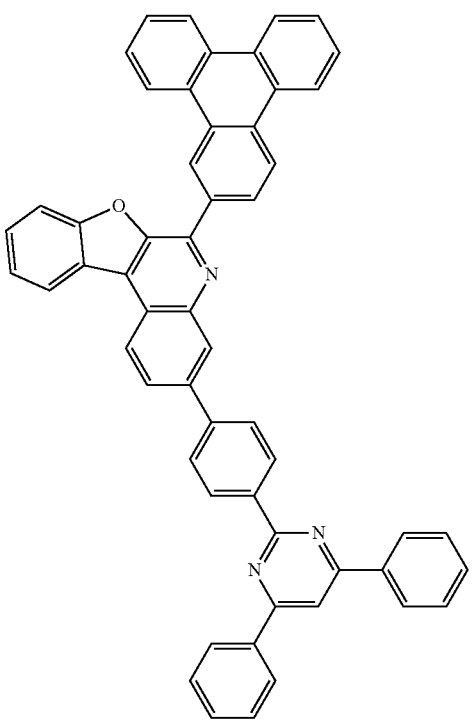
869
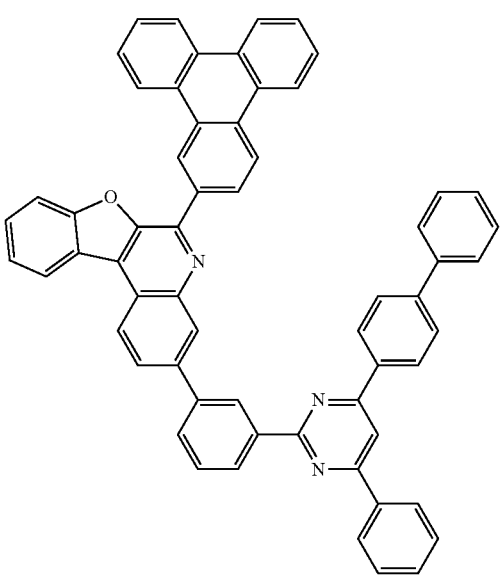
868
870

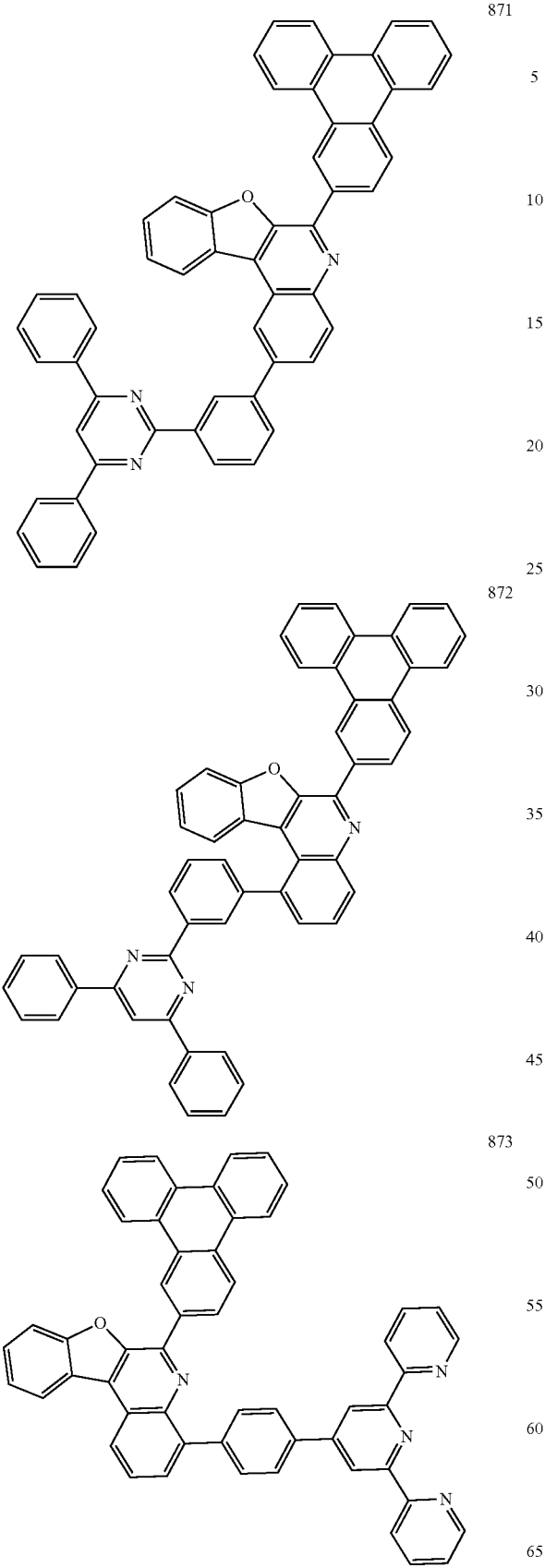
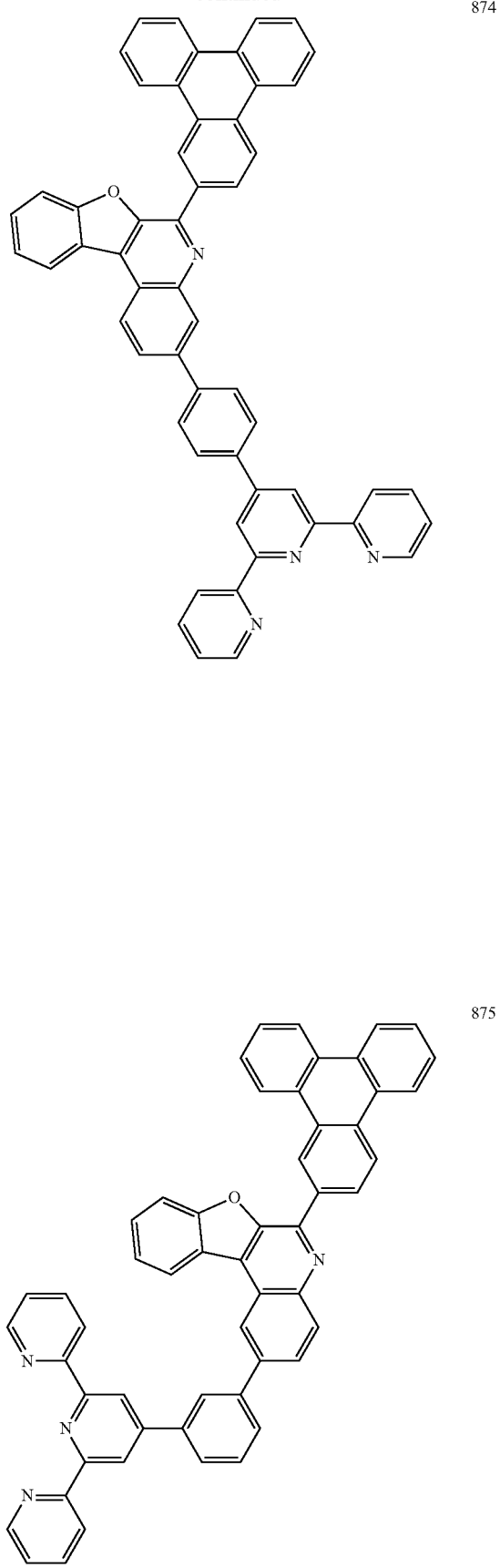

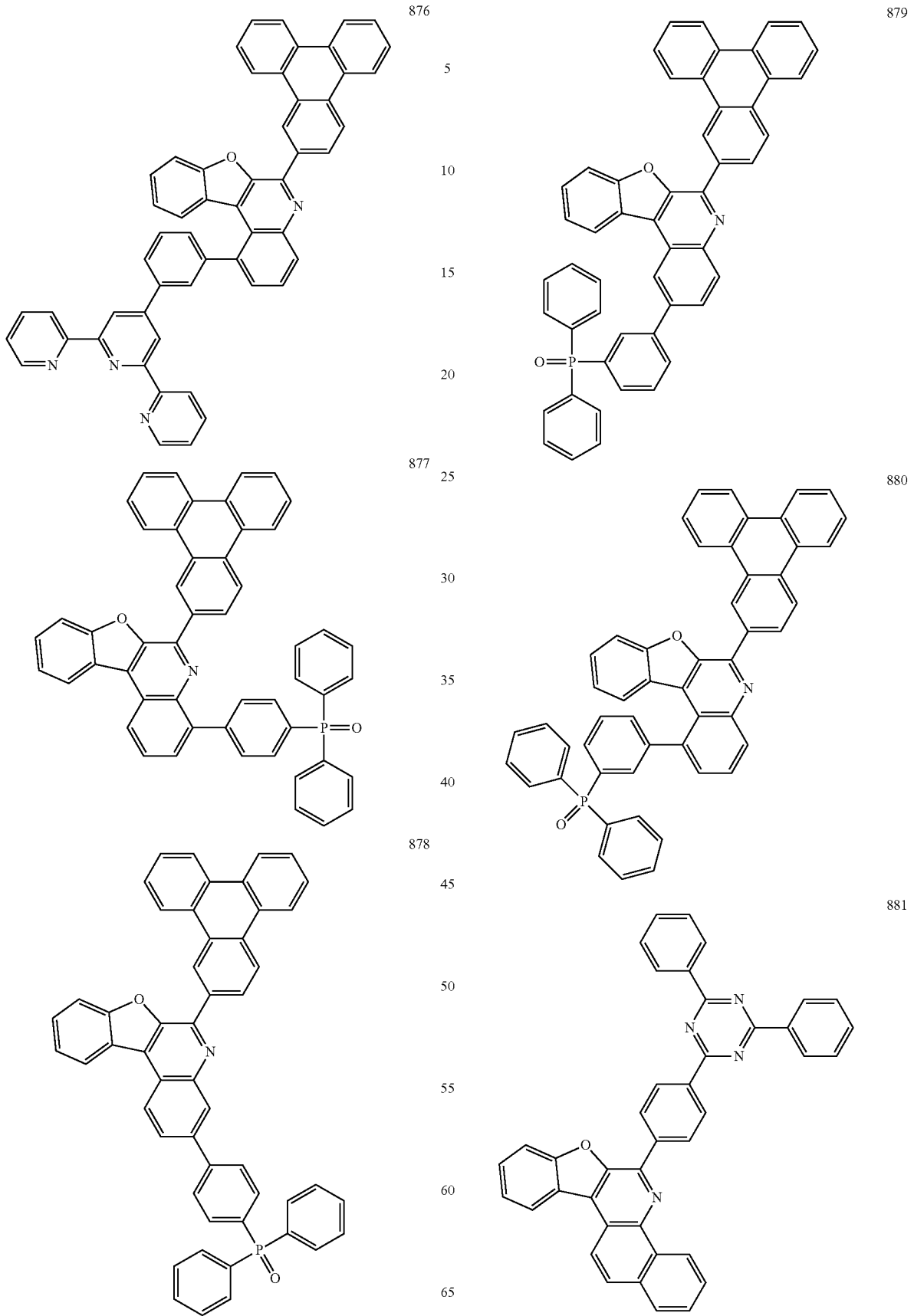

882
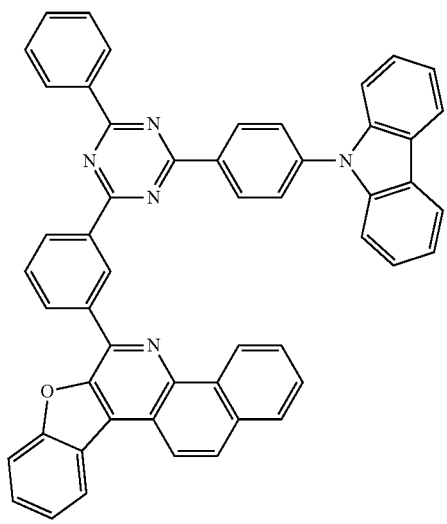
883
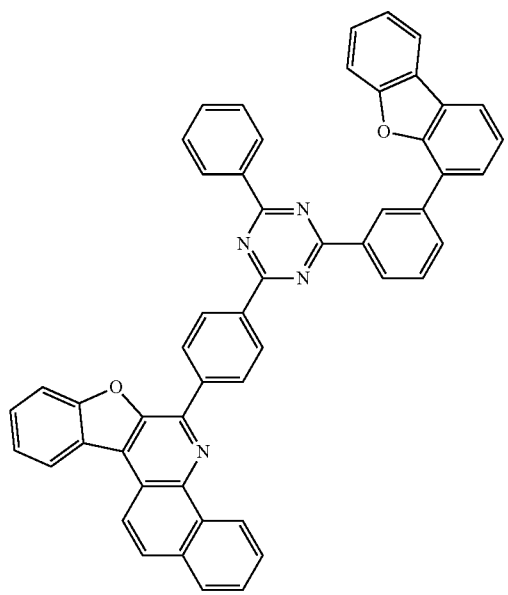
884
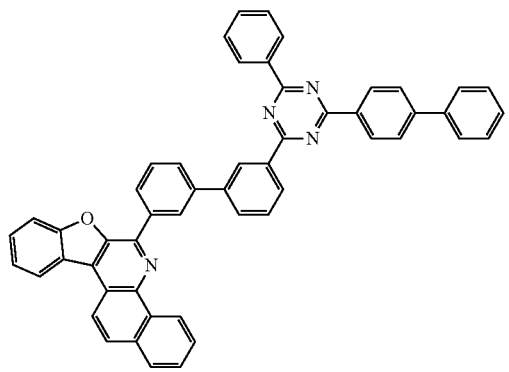
885
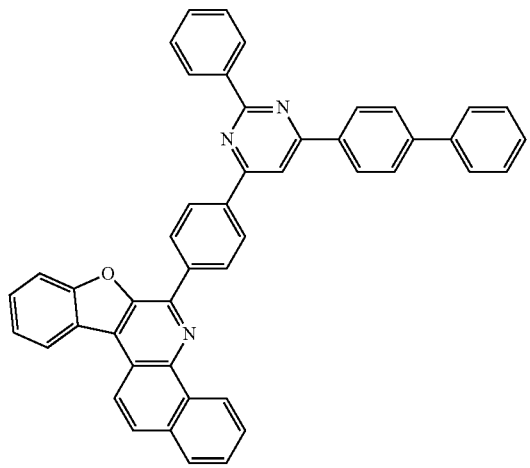
886
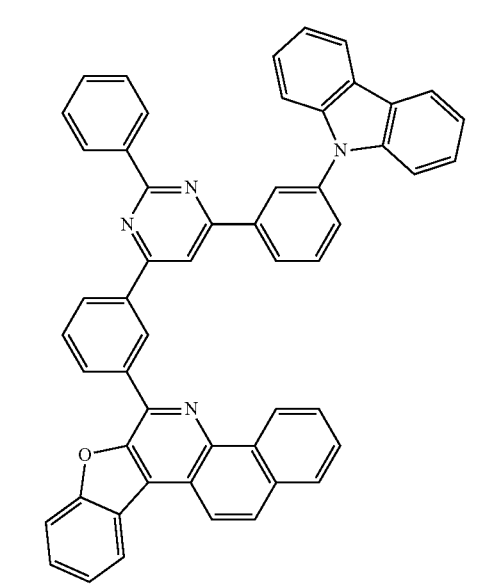
887
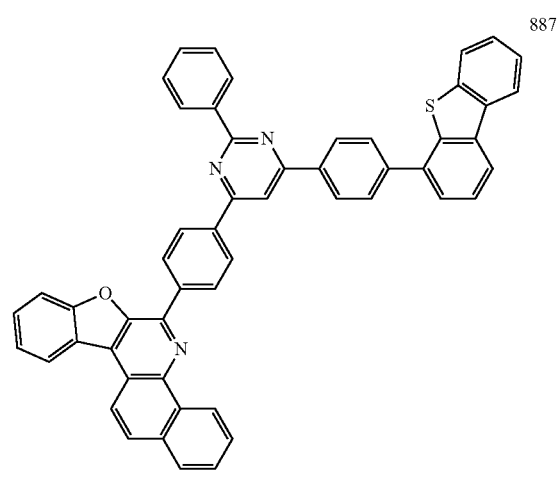

395
-continued
396
-continued
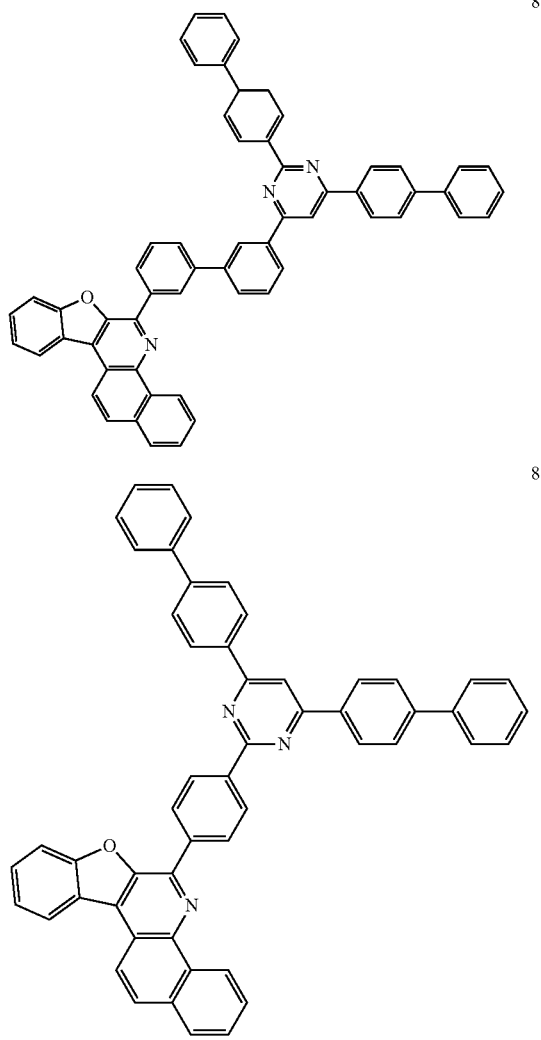
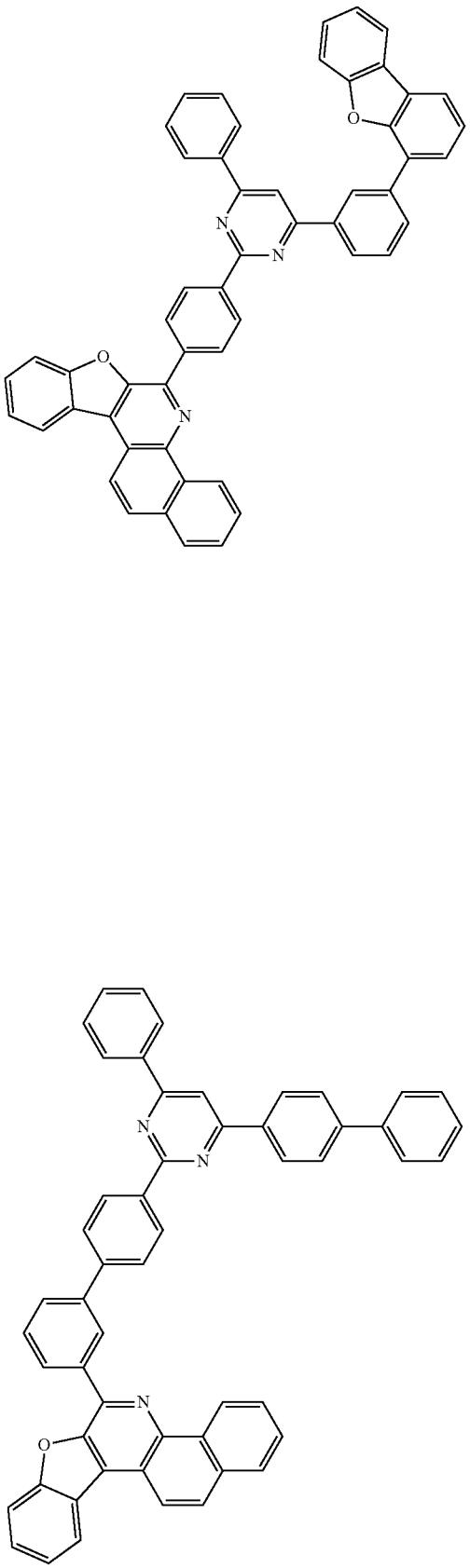
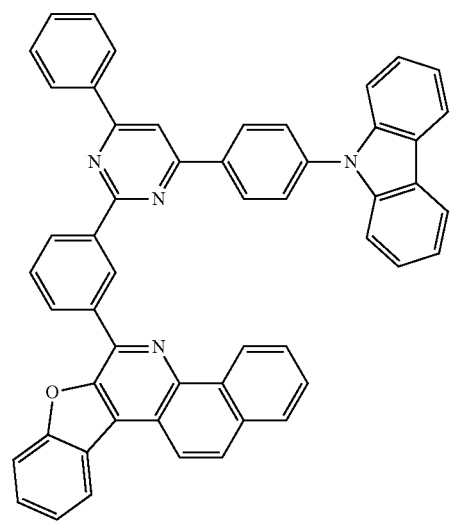

-continued
893
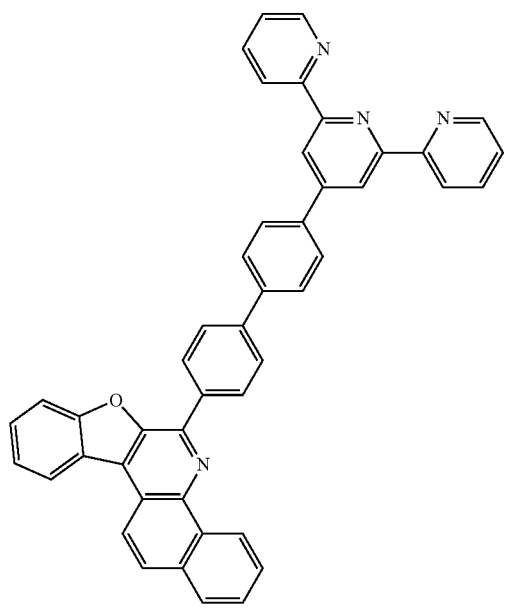
894
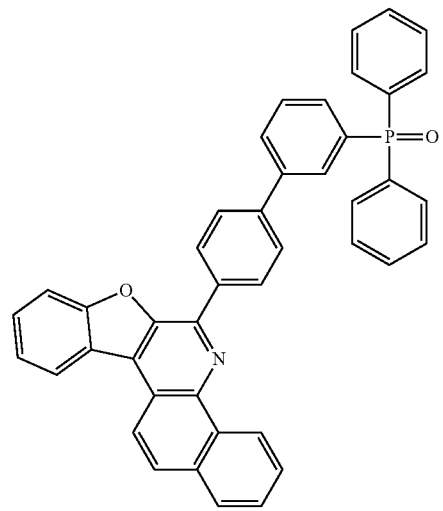
-continued
895
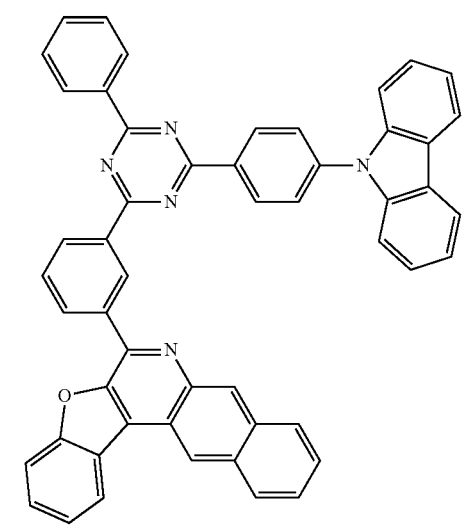
896

897
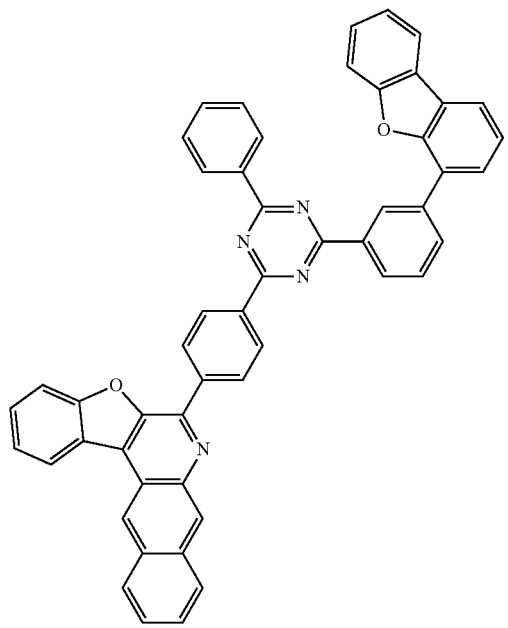
898
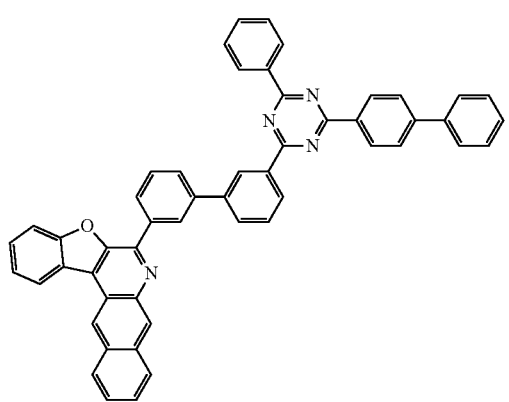
899
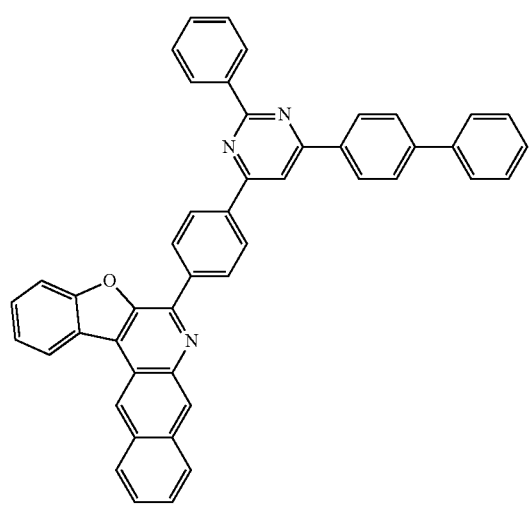
900
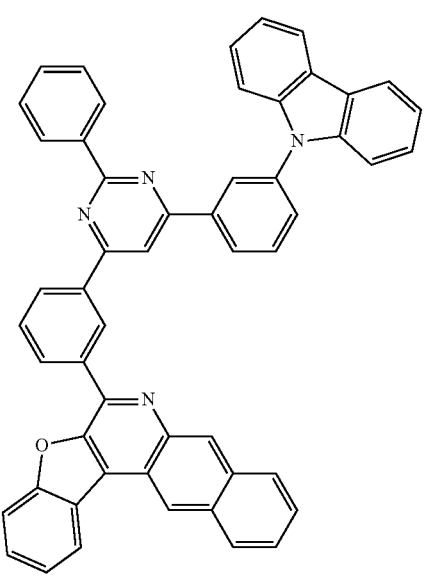
901
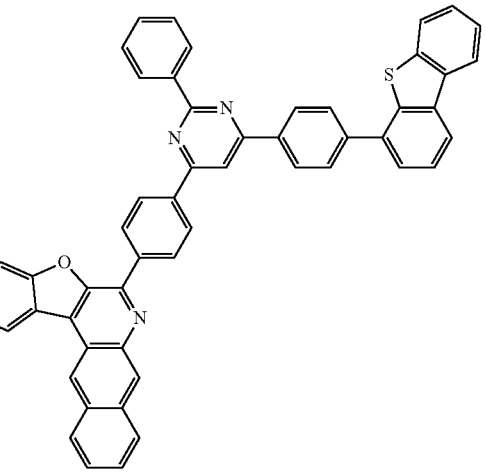
902
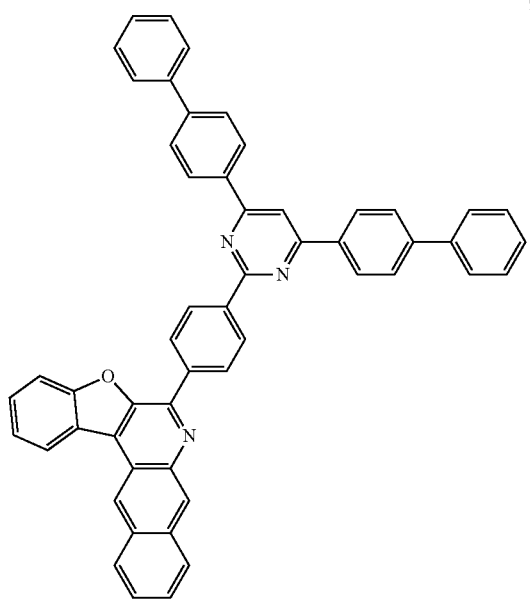

401
-continued
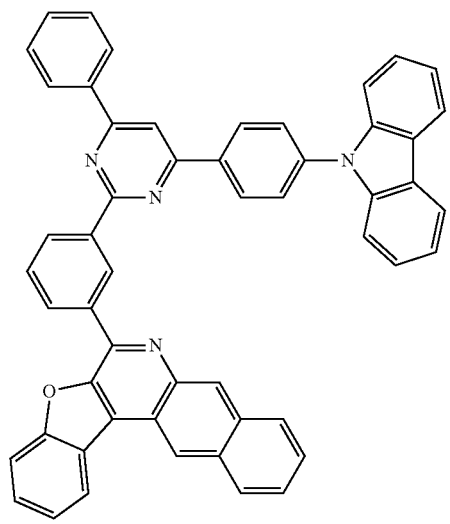
903
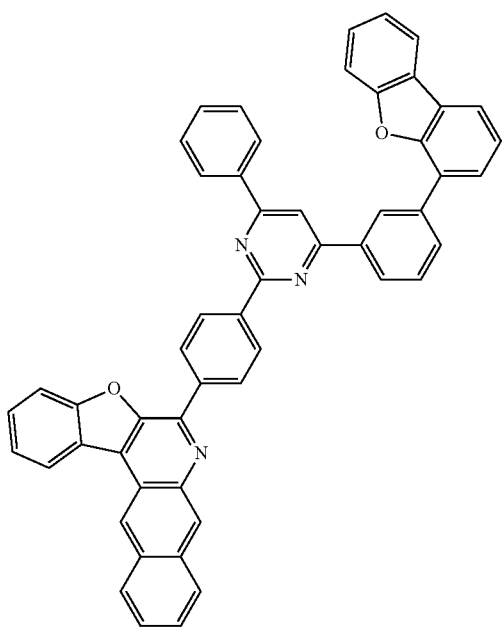
904
402
-continued
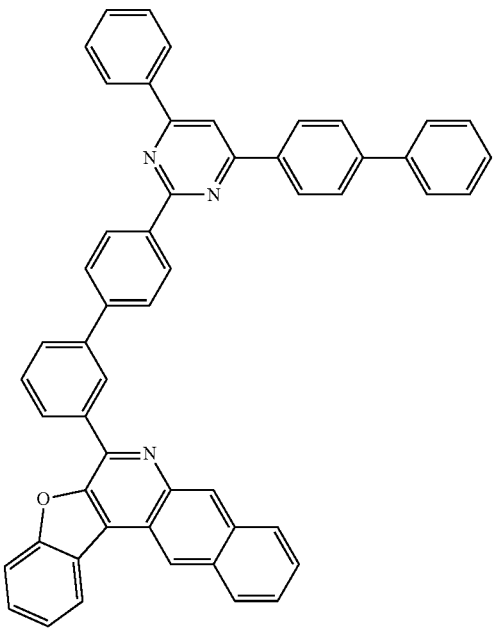
905
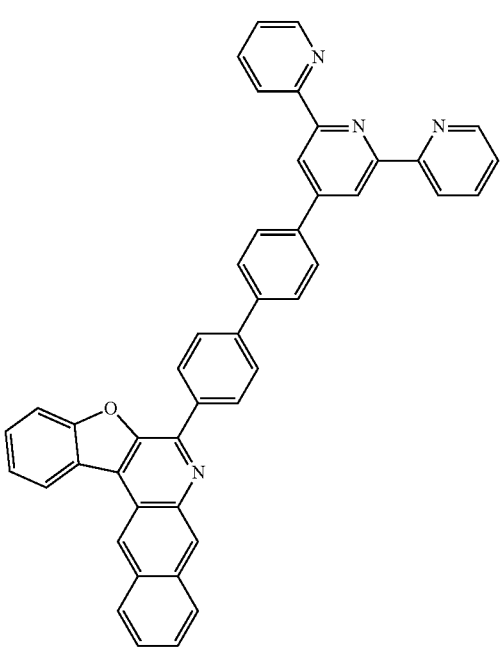
906

-continued
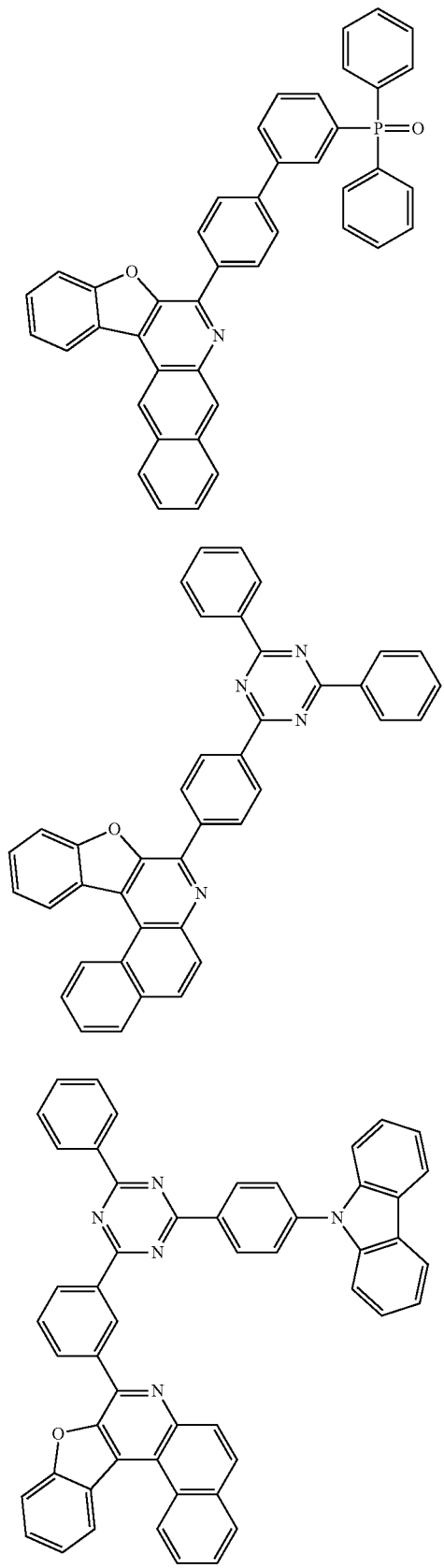
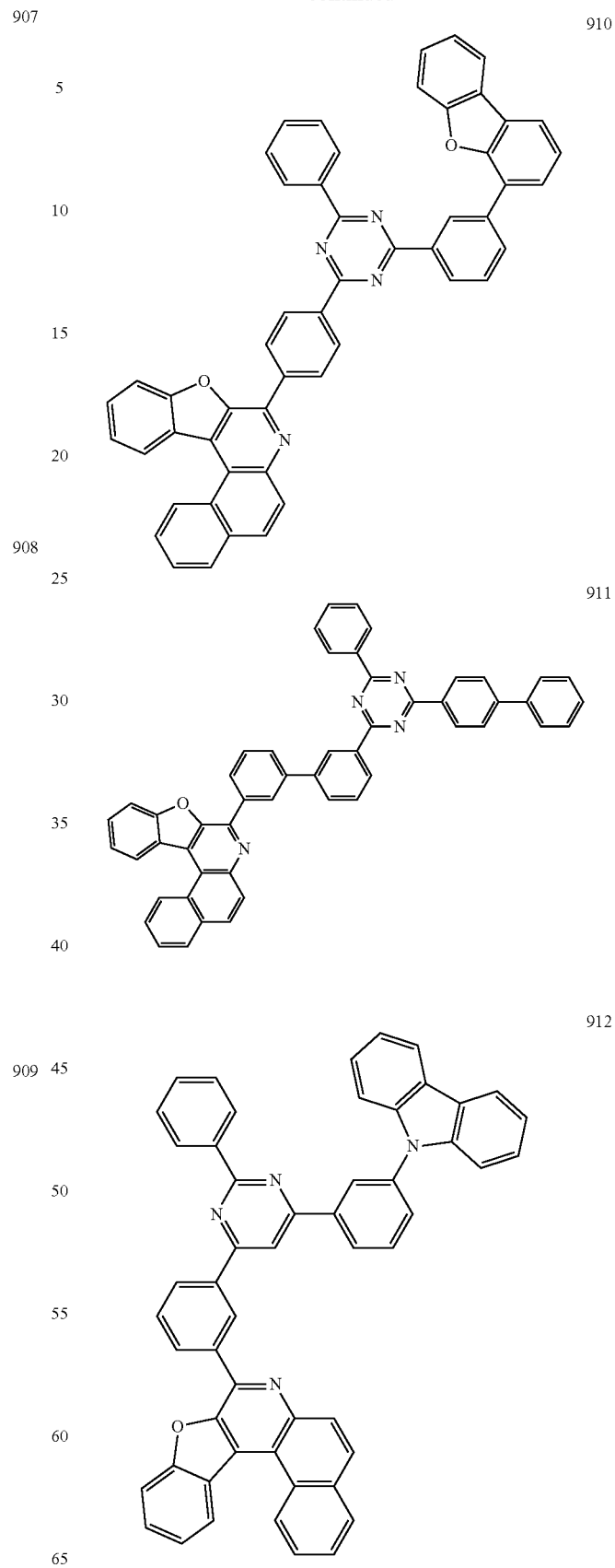

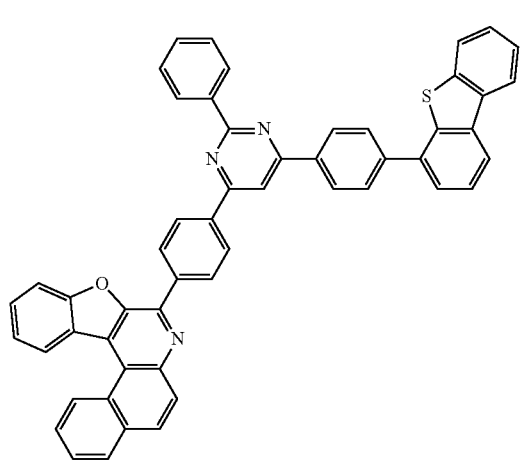
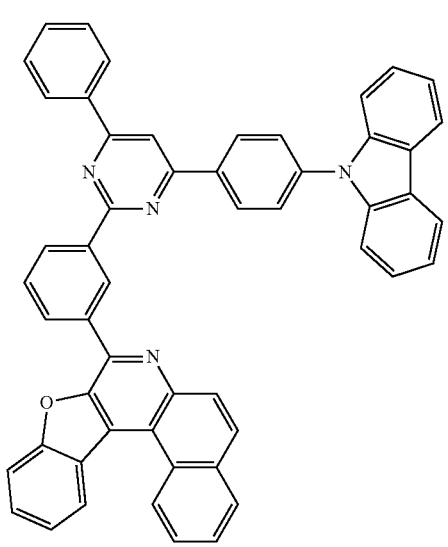

-continued
918
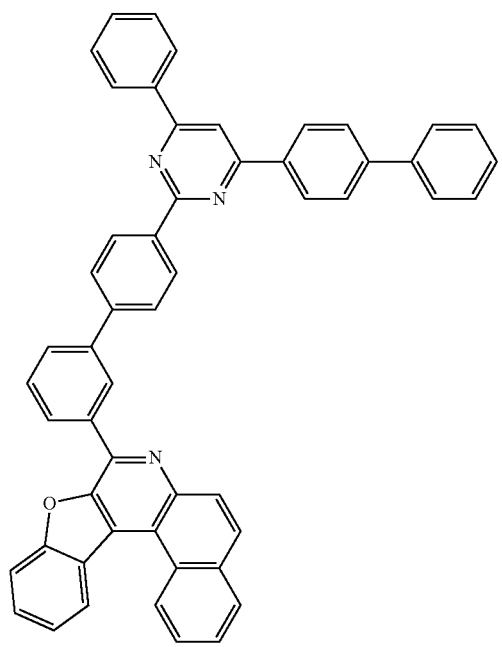
919
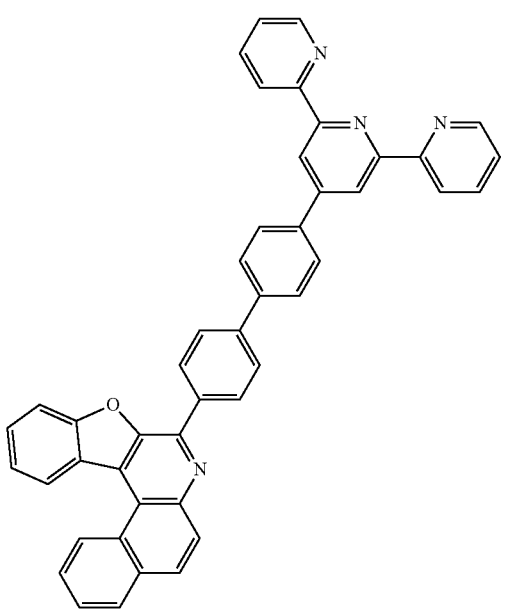
-continued
920
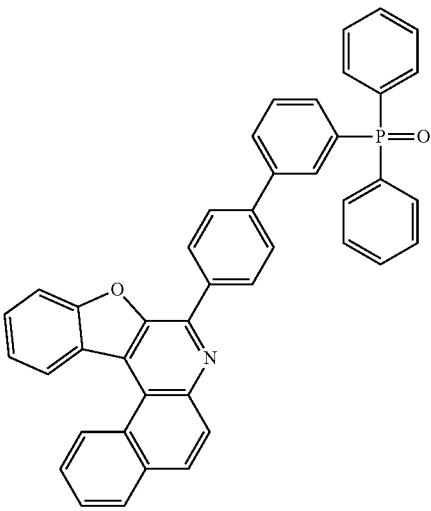
921
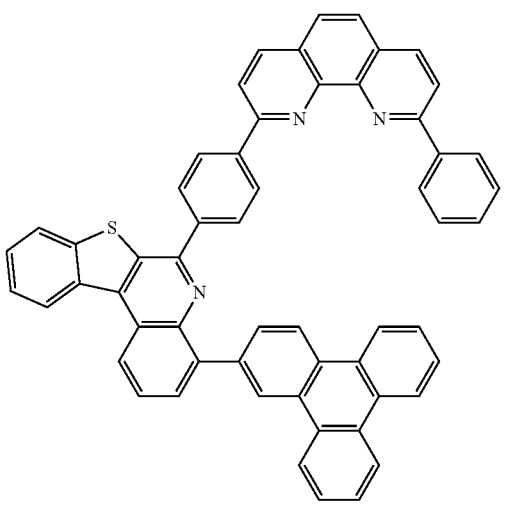
922
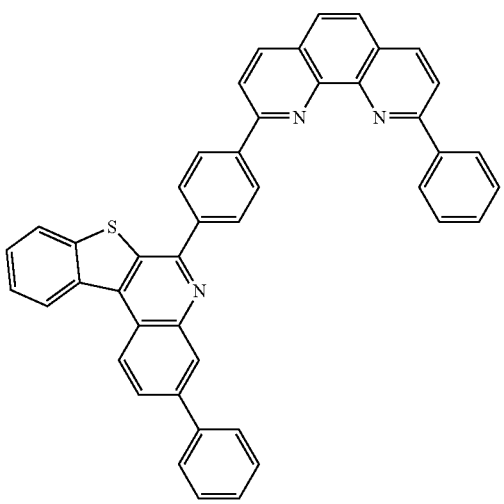

409
-continued
923
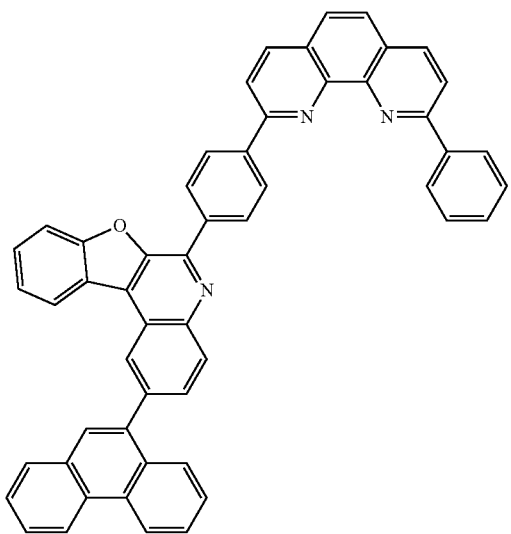
924
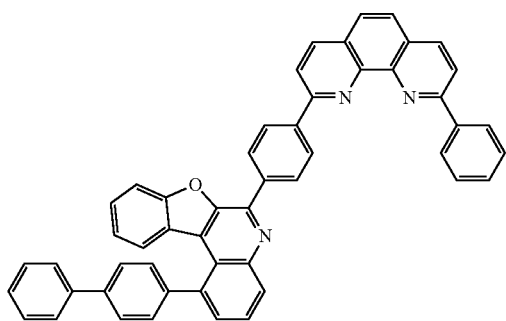
925
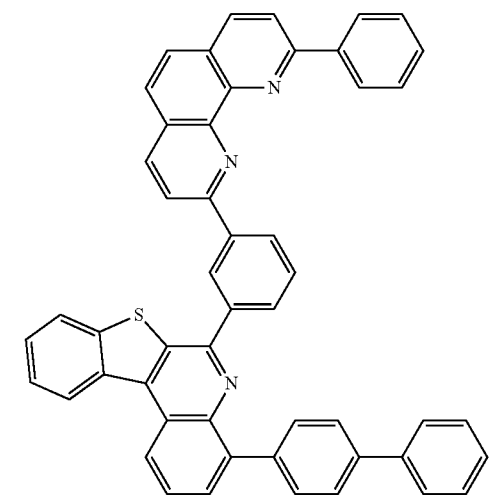
410
-continued
926
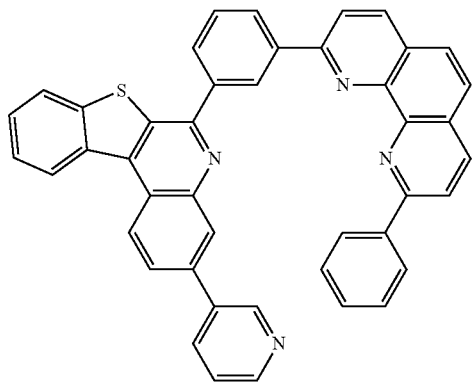
927
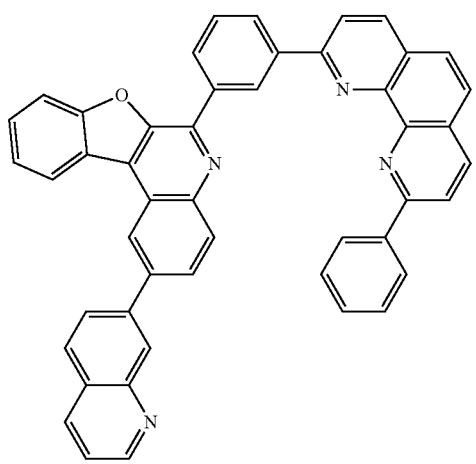
928
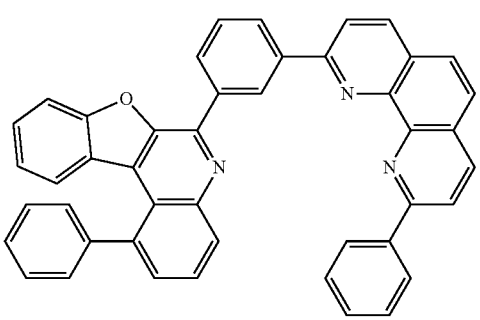
929
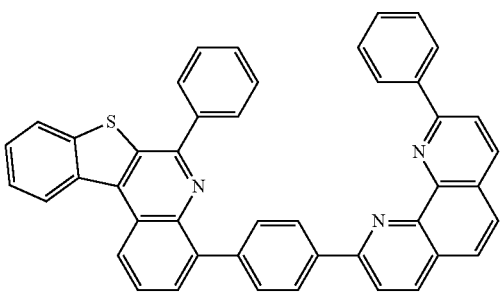

411
-continued
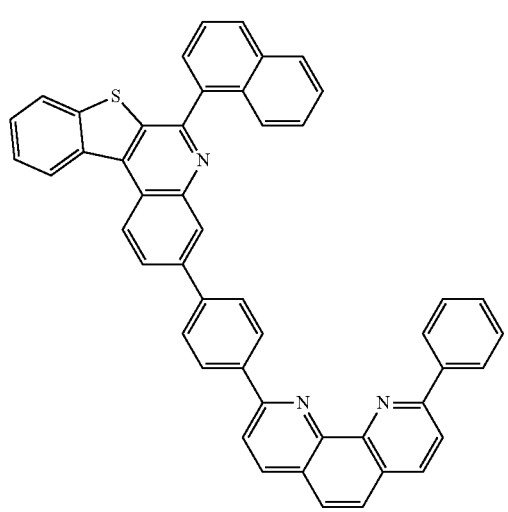
930
412
-continued
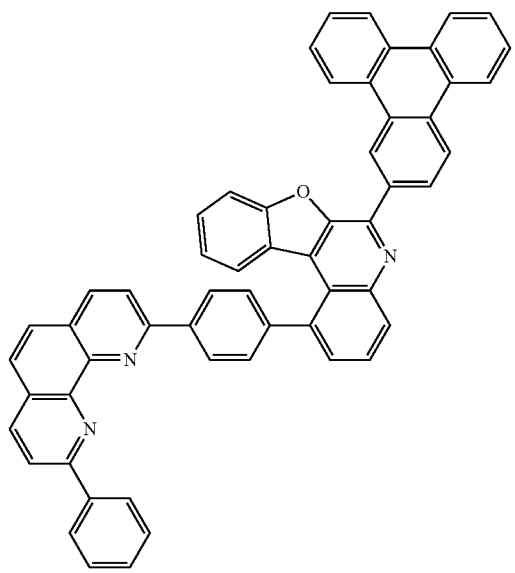
932
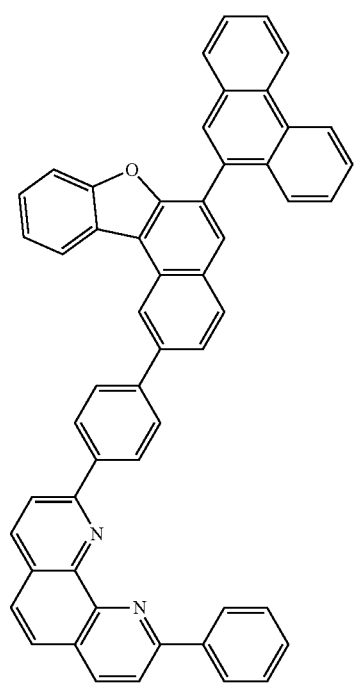
931
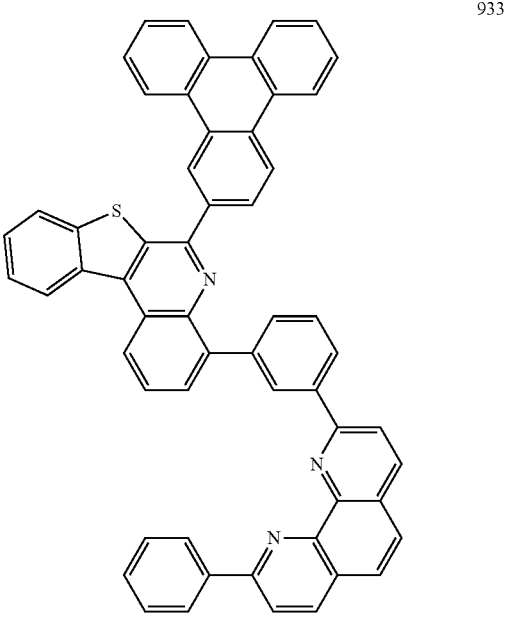
933

934
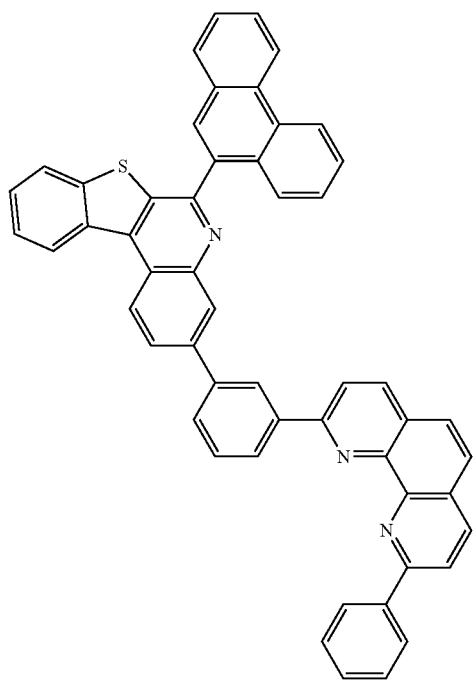
935
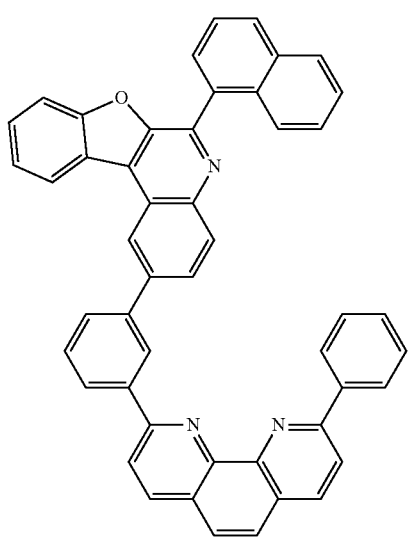
936
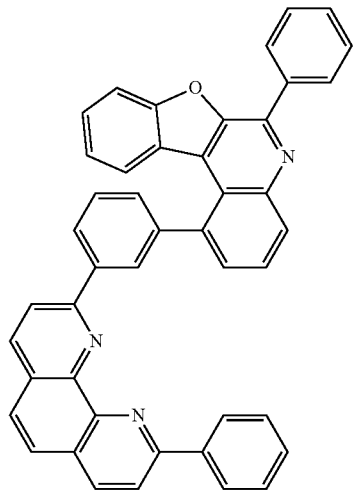
937
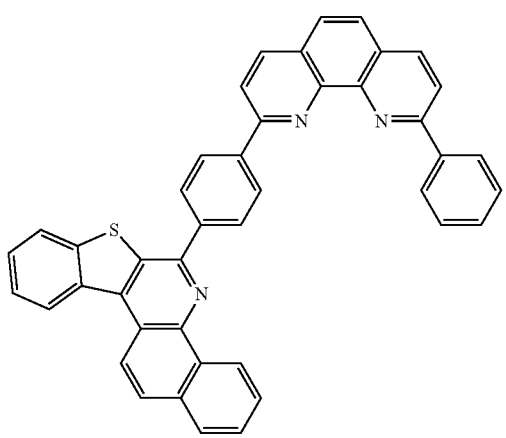
938
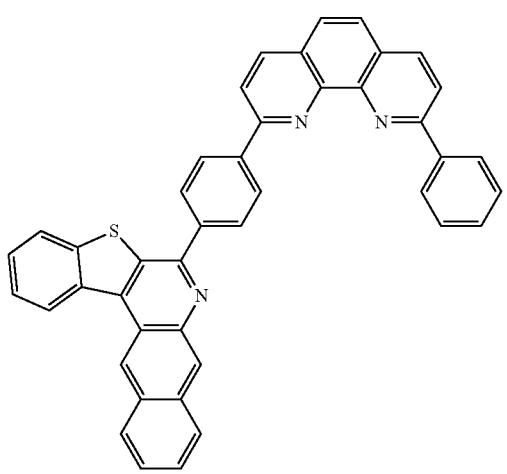

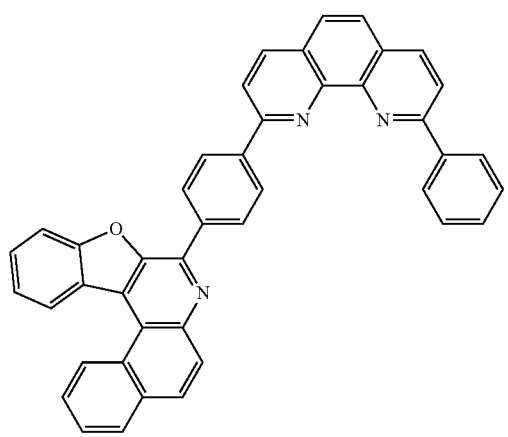
939
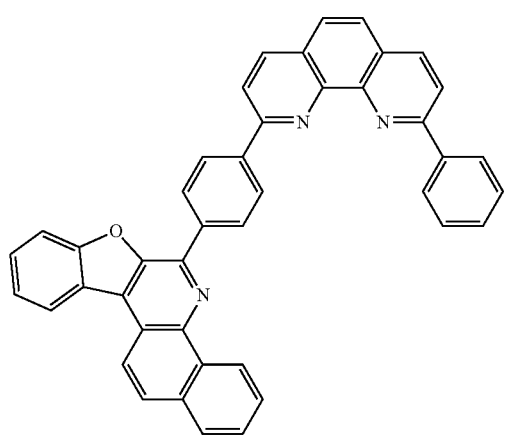
940
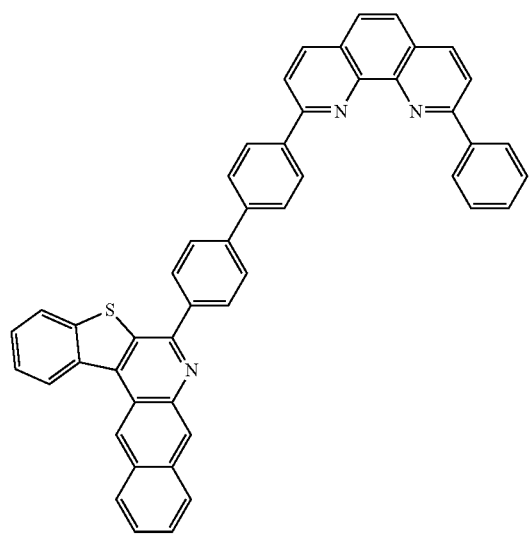
941
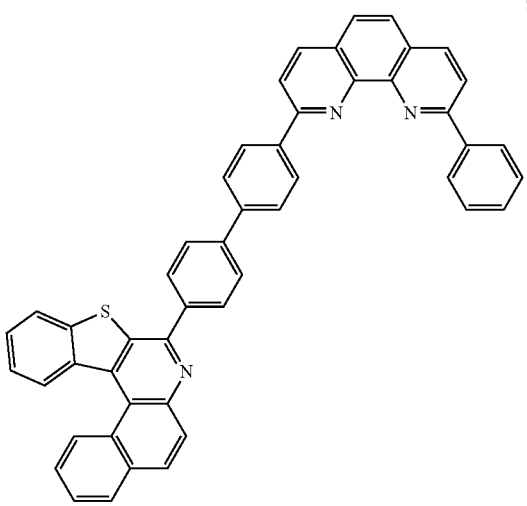
942
943
944

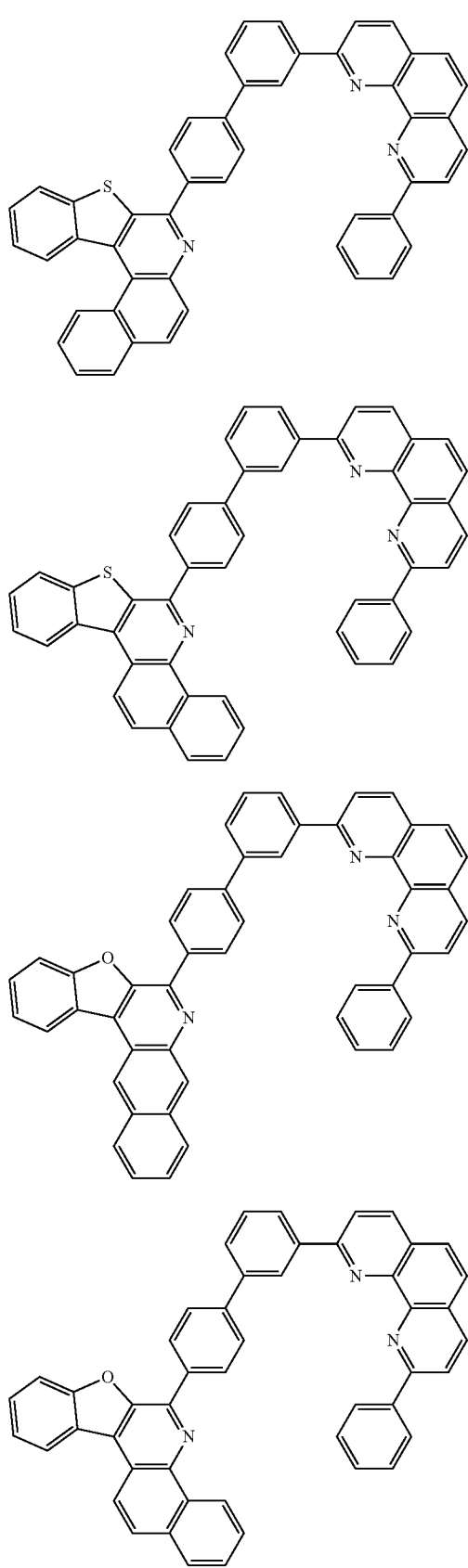
The compound according to one embodiment of the present application may be prepared according to the following General Formula 1.
[General Formula 1]
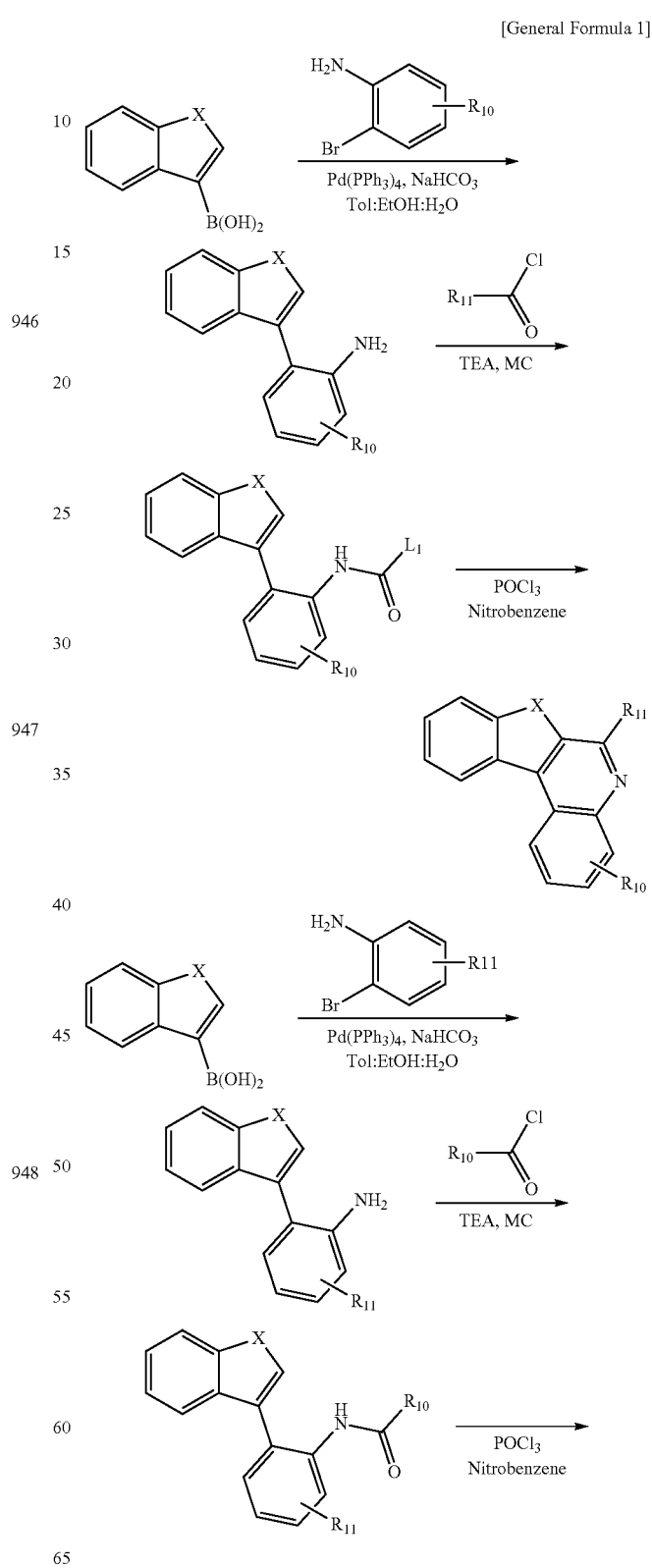

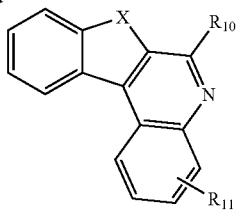

In General Formula 1, X has the same definition as X in Chemical Formula 1, and R10 or R11 has the same definition as

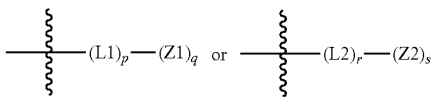

of Chemical Formula 1.

In addition, by introducing various substituents to the structures of Chemical Formulae 1 to 11, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structures of Chemical Formulae 1 to 11, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device of the present disclosure, the organic material layer may comprise a light emitting layer, and the light emitting layer may comprise the heterocyclic compound represented by Chemical Formula 1.

In another organic light emitting device, the organic material layer comprises a light emitting layer, the light emitting layer comprises a host material, and the host material may comprise the heterocyclic compound represented by Chemical Formula 1.

In another embodiment, the organic material layer comprising the heterocyclic compound comprises the heterocyclic compound represented by Chemical Formula 1 as a host, and may be used together with a phosphorescent dopant.

In another embodiment, the organic material layer comprising the heterocyclic compound comprises the heterocyclic compound represented by Chemical Formula 1 as a host, and may be used together with an iridium-based dopant.

As a material of the phosphorescent dopant, those known in the art may be used.

For example, phosphorescent dopant materials represented by LL'MX, LL'L"M, LMXX', L2MX and L3M may be used, however, the scope of the present disclosure is not limited to these examples.

Herein, L, L', L", X and X' are bidentate ligands different from each other, and M is a metal forming an octahedral complex.

M may comprise iridium, platinum, osmium or the like.

L is an anionic bidentate ligand coordinated to M as the iridium-based dopant by sp2 carbon and heteroatom, and X may perform a function of trapping electrons or holes. Nonlimiting examples of L may comprise 2-(1-naphthyl) benzoxazole, (2-phenylbenzoxazole), (2-phenylbenzothiazole), (2-phenylbenzthiazole), (7,8-benzoquinoline), (thiophene group pyrizine), phenylpyridine, benzothiophene group pyrizine, 3-methoxy-2-phenylpyridine, thiophene group pyrizine, tolylpyridine and the like. Nonlimiting examples of X may comprise acetylacetonate (acac), hexafluoroacetylacetonate, salicylidene, picolinate, 8-hydroxyquinolate and the like.

More specific examples thereof are presented below, however, the phosphorescent dopant is not limited to these examples.

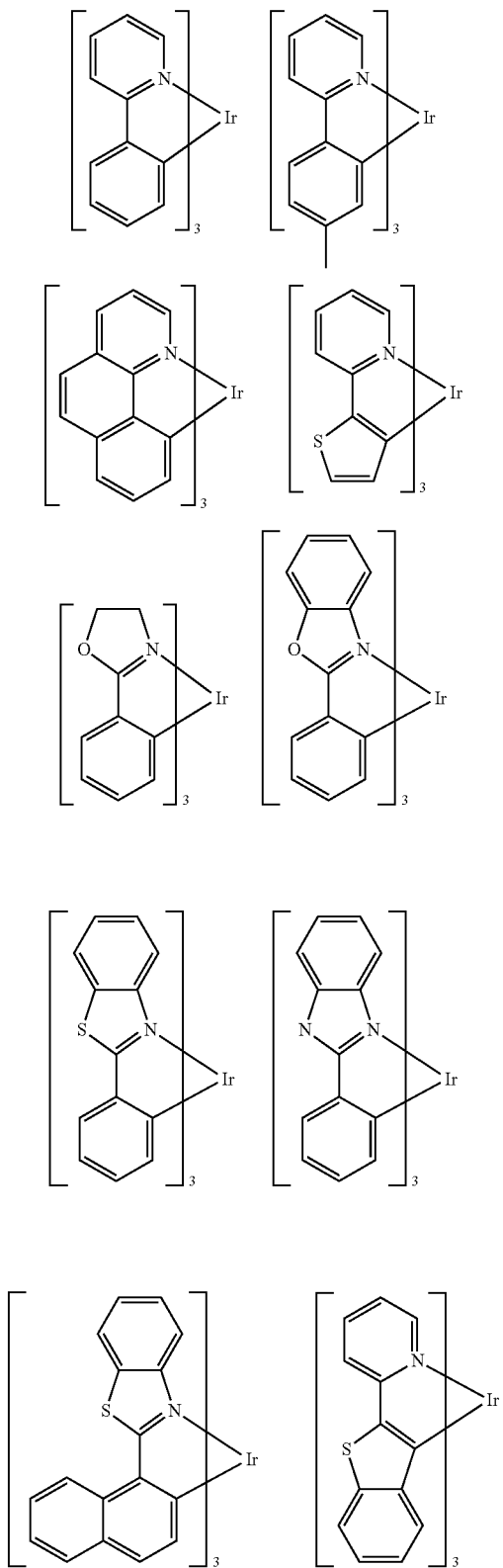

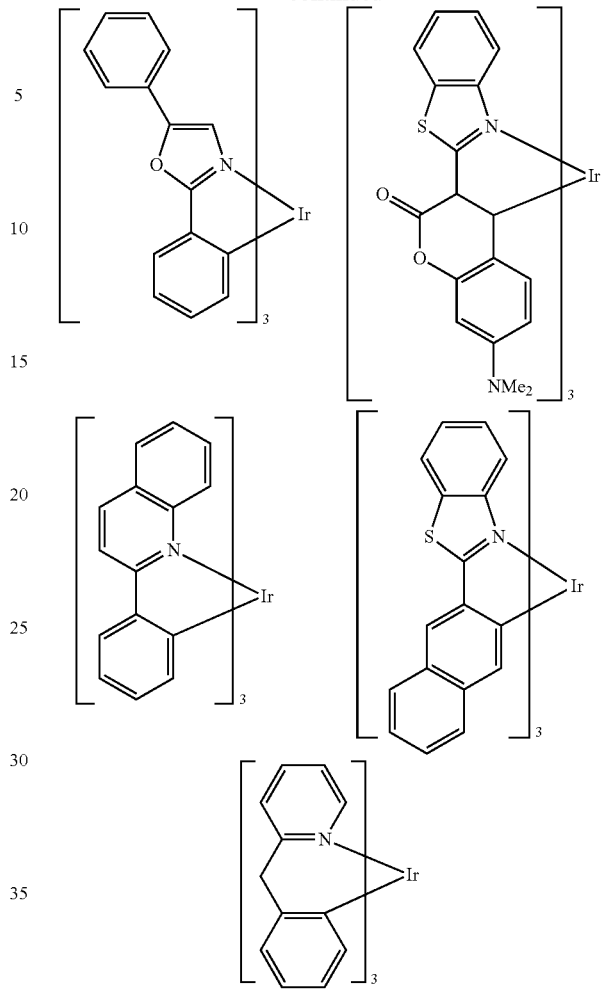

In one embodiment of the present application, as the iridium-based dopant, Ir(ppy)$_3$ may be used as a green phosphorescent dopant.

In one embodiment of the present application, the dopant content may be from 1% to 15%, preferably from 3% to 10% and more preferably from 5% to 10% based on the whole light emitting layer.

In the organic light emitting device of the present disclosure, the organic material layer comprises an electron injection layer or an electron transfer layer, and the electron injection layer or the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising Chemical Formula 1 may further comprise other materials as necessary.

In addition, the organic light emitting device according to one embodiment of the present application comprises a first electrode, a second electrode, and two or more stacks provided between the first electrode and the second electrode, wherein the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present application may comprise a first electrode, a first stack provided on the first electrode and comprising a first light emitting layer, a charge generation layer provided on the first stack, a second stack provided on the charge generation layer and comprising a second light emitting layer, and a second electrode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer described above and the like.

The charge generation layer may be an N-type charge generation layer, and the charge generation layer may further comprise a dopant known in the art in addition to the heterocyclic compound represented by Chemical Formula 1.

As the organic light emitting device according to one embodiment of the present application, an organic light emitting device having a 2-stack tandem structure is schematically illustrated in FIG. 4.

The organic material layer comprising Chemical Formula 1 may further comprise other materials as necessary.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or P-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

\<Preparation Example 1\>—Preparation of Compound 1

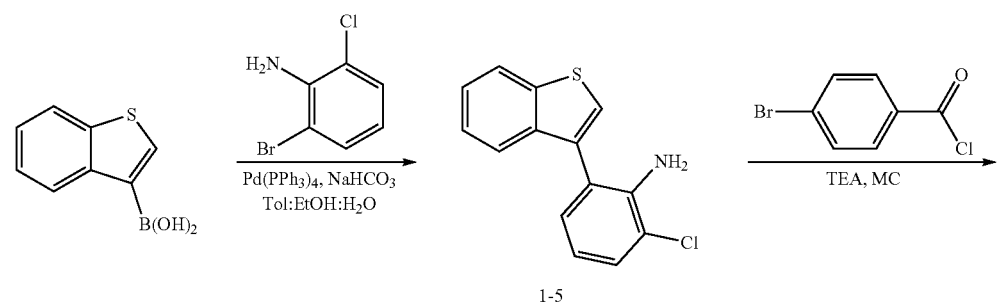

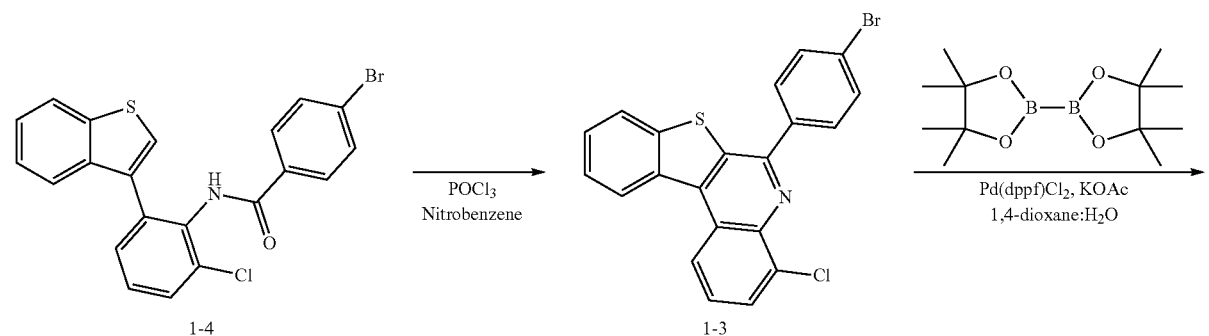

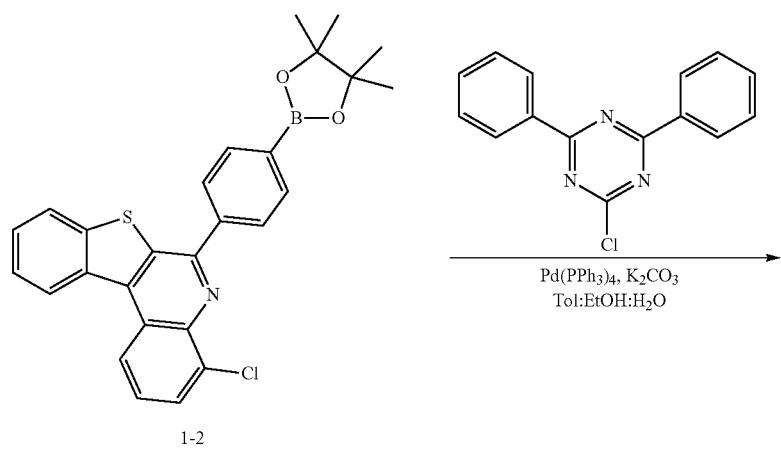

-continued

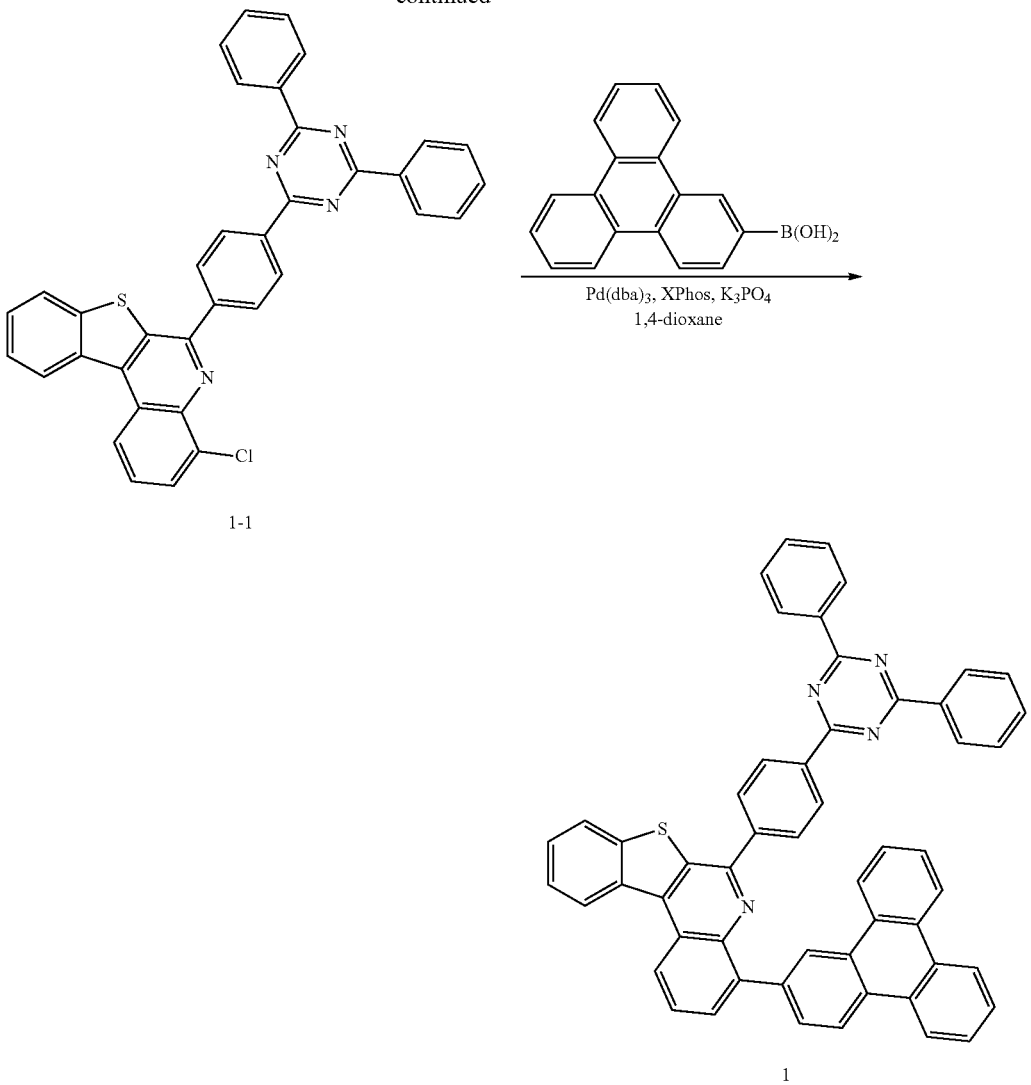

1) Preparation of Compound 1-5

After dissolving benzo[b]thiophen-3-ylboronic acid (162 g, 1000 mmol) and 2-bromo-6-chloroaniline (189 g, 1100 mmol) in toluene, EtOH and $H_2O$ (2000 mL:400 mL:400 mL), $Pd(PPh_3)_4$ (58 g, 50 mmol) and $NaHCO_3$ (252 g, 3000 mmol) were introduced thereto, and the result was refluxed for 4 hours. After the reaction was completed, the result was cooled to room temperature and extracted with MC. The result was dried with anhydrous MgSO4, and then the solvent was removed using a rotary evaporator. Target Compound 1-5 was obtained using column chromatography (MC:Hx=1:3). (190 g, 91%, brown oil)

2) Preparation of Compound 1-4

Compound 1-5 (95 g, 428 mmol) and triethylamine (190 mL, 1362 mmol) were introduced to MC (1500 mL) and dissolved therein. 4-Bromobenzoyl chloride (149 g, 681 mmol) dissolved in MC (300 mL) was slowly added dropwise to the mixture at 0° C. After the reaction was completed, MC and distilled water were introduced to the reaction solution for extraction. After that, the result was dried with anhydrous MgSO4, and, after removing the solvent using a rotary evaporator, recrystallized with EA/Hx to obtain Compound 1-4. (82 g, 91%, white solid)

3) Preparation of Compound 1-3

After dissolving Compound 1-4 (82 g, 210 mmol) in nitrobenzene (1000 mL), $POCl_3$ (24 mL, 210 mmol) was slowly added dropwise thereto. After that, the result was stirred for 12 hours at 150° C. After the reaction was completed, the reaction solution was neutralized with an aqueous $NaHCO_3$ solution. Solids produced from the neutralization were filtered. The solids were recrystallized with MC/MeOH to obtain target Compound 1-3. (69 g, 88%, white solid)

4) Preparation of Compound 1-2

After dissolving Compound 1-3 (61 g, 163 mmol), bis(pinacolato)diboron (62 g, 244 mmol), $Pd(dppf)Cl_2$ (6 g, 8.2 mmol) and KOAc (48 g, 489 mmol) in 1,4-dioxane (600 mL), the result was refluxed for 12 hours. After the reaction was completed, MC and distilled water were introduced to the reaction solution for extraction. After that, the result was dried with anhydrous MgSO4, and the solvent was removed using a rotary evaporator. After passing silica, the result went through MeOH slurry to obtain Compound 1-2. (69 g, 95%, pale pink solid)

5) Preparation of Compound 1-1

After dissolving Compound 1-2 (9cw g, 21.4 mmol) and 2-chloro-4,6-diphenyl-1,3,5-triazine (8.2 g, 21.4 mmol) in toluene, EtOH and H₂O (100 mL:20 mL:20 mL), Pd(PPh₃)₄ (1.3 g, 1.07 mmol) and K₂CO₃ (8.9 g, 64.2 mol) were introduced thereto, and the result was refluxed for 5 hours. After the reaction was completed, produced solids were filtered to obtain Compound 1-1. (11.4 g, 88%, white solid)

5) Preparation of Compound 1

After dissolving Compound 1-1 (10 g, 17.3 mmol), triphenylen-2-ylboronic acid (5.7 g, 20.8 mmol), Pd₂(dba)₃ (1.6 g, 1.7 mmol), XPhos (1.7 g, 3.4 mmol) and K₃PO₄ (11 g, 52 mmol) in 1,4-dioxane (100 mL), the result was refluxed for 12 hours. After the reaction was finished, produced solids were filtered. The solids were washed with distilled water and acetone to obtain target Compound 1. (9 g, 65%, white solid)

A target compound was synthesized in the same manner as in Preparation Example 1 except that Intermediate A of the following Table 1 was used instead of 2-chloro-4,6-diphenyl-1,3,5-triazine, and Intermediate B of the following Table 1 was used instead of triphenylen-2-ylboronic acid.

TABLE 1

| Compound Number | Intermediate A | Intermediate B | Target Compound | Yield |
|---|---|---|---|---|
| 7 | 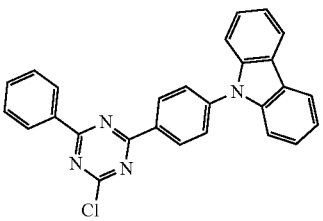 [SMILES: Clc1nc(-c2ccccc2)nc(-c2ccc(-n3c4ccccc4c4ccccc43)cc2)n1] | 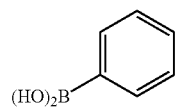 | 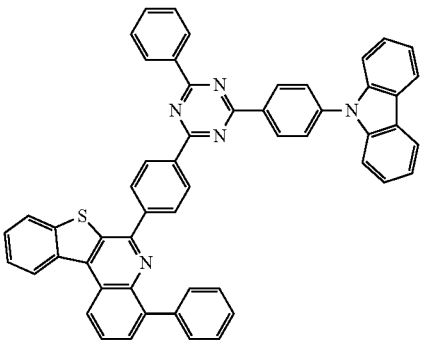 [SMILES: c1ccc(-c2nc(-c3ccc(-c4nc5c(-c6ccccc6)cccc5c5c4sc4ccccc45)cc3)nc(-c3ccc(-n4c5ccccc5c5ccccc54)cc3)n2)cc1] | 70% |
| 10 | 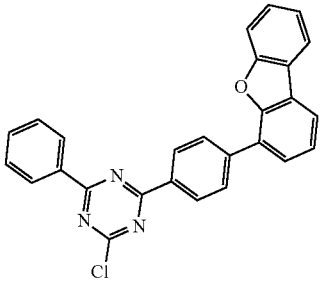 [SMILES: Clc1nc(-c2ccccc2)nc(-c2ccc(-c3cccc4c3oc3ccccc34)cc2)n1] | 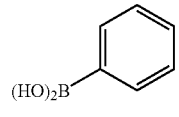 | 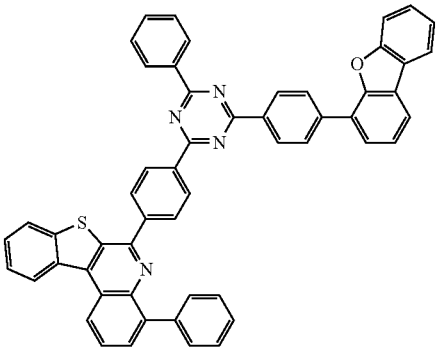 [SMILES: c1ccc(-c2nc(-c3ccc(-c4cccc5c4oc4ccccc45)cc3)nc(-c3ccc(-c4nc5c(-c6ccccc6)cccc5c5c4sc4ccccc45)cc3)n2)cc1] | 69% |
| 14 | 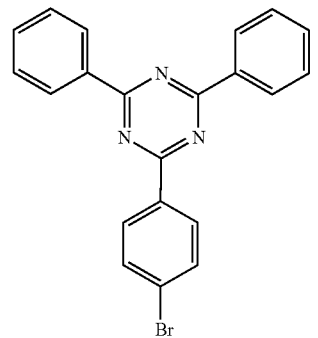 [SMILES: Brc1ccc(-c2nc(-c3ccccc3)nc(-c3ccccc3)n2)cc1] | 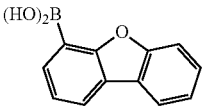 [SMILES: OB(O)c1cccc2c1oc1ccccc12] | 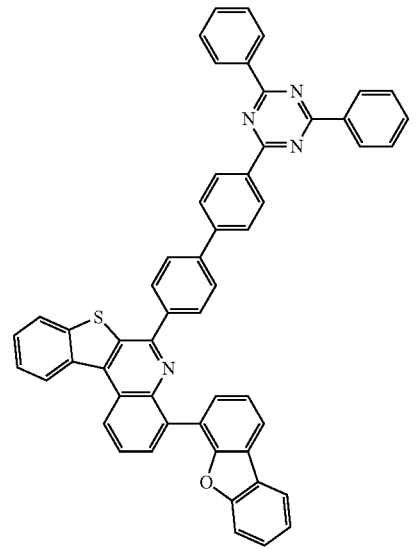 [SMILES: c1ccc(-c2nc(-c3ccccc3)nc(-c3ccc(-c4ccc(-c5nc6c(-c7cccc8c7oc7ccccc78)cccc6c6c5sc5ccccc56)cc4)cc3)n2)cc1] | 75% |

TABLE 1-continued
| Compound Number | Intermediate A | Intermediate B | Target Compound | Yield |
|---|---|---|---|---|
| 72 | 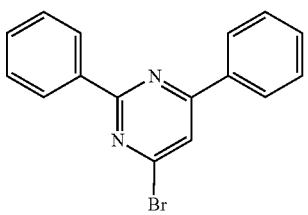 [SMILES: Brc1cc(-c2ccccc2)nc(-c2ccccc2)n1] | 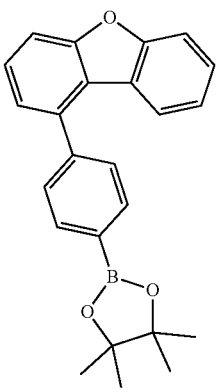 [SMILES: CC1(C)OB(c2ccc(-c3cccc4oc5ccccc5c34)cc2)OC1(C)C] | 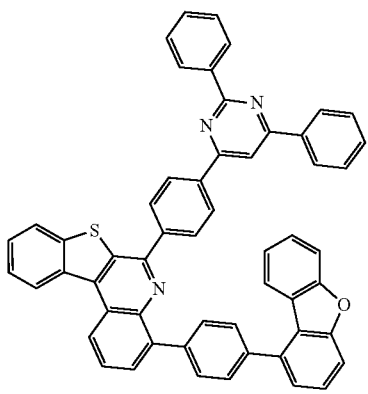 [SMILES: c1ccc(-c2cc(-c3ccc(-c4nc5c(-c6ccc(-c7cccc8oc9ccccc9c78)cc6)cccc5c5c4sc4ccccc45)cc3)nc(-c3ccccc3)n2)cc1] | 61% |
| 75 | 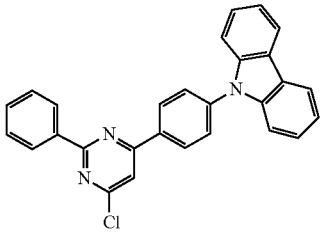 [SMILES: Clc1cc(-c2ccc(-n3c4ccccc4c4ccccc43)cc2)nc(-c2ccccc2)n1] | 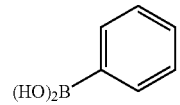 | 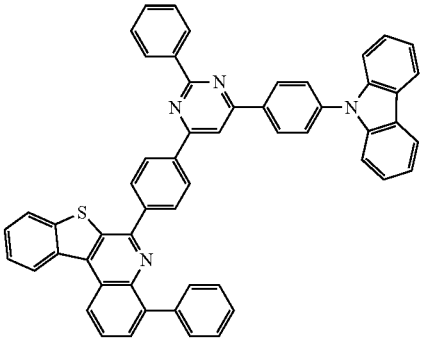 [SMILES: c1ccc(-c2nc(-c3ccc(-c4nc5c(-c6ccccc6)cccc5c5c4sc4ccccc45)cc3)cc(-c3ccc(-n4c5ccccc5c5ccccc54)cc3)n2)cc1] | 66% |
| 78 | 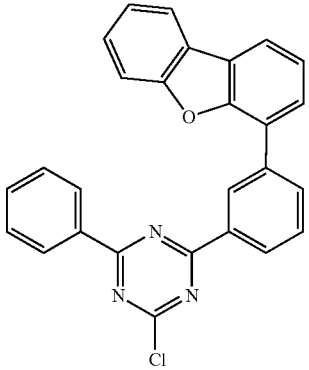 [SMILES: Clc1nc(-c2ccccc2)nc(-c2cccc(-c3cccc4c3oc3ccccc34)c2)n1] | 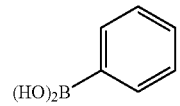 | 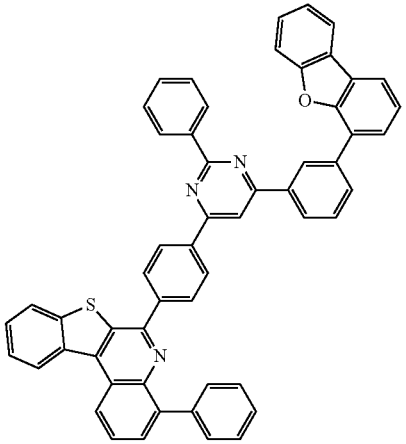 [SMILES: c1ccc(-c2nc(-c3ccc(-c4nc5c(-c6ccccc6)cccc5c5c4sc4ccccc45)cc3)cc(-c3cccc(-c4cccc5c4oc4ccccc45)c3)n2)cc1] | 70% |

TABLE 1-continued
| Compound Number | Intermediate A | Intermediate B | Target Compound | Yield |
|---|---|---|---|---|
| 125 | 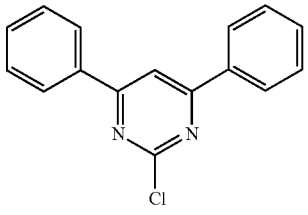 [SMILES: Clc1nc(-c2ccccc2)cc(-c2ccccc2)n1] | 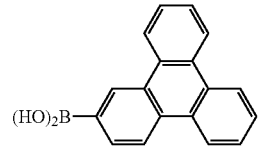 [SMILES: OB(O)c1ccc2c3ccccc3c3ccccc3c2c1] | 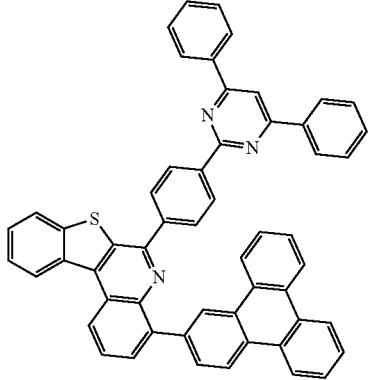 [SMILES: c1ccc(-c2cc(-c3ccccc3)nc(-c3ccc(-c4nc5c(-c6ccc7c8ccccc8c8ccccc8c7c6)cccc5c5c4sc4ccccc45)cc3)n2)cc1] | 75% |
| 130 | 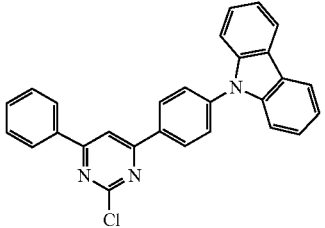 [SMILES: Clc1nc(-c2ccccc2)cc(-c2ccc(-n3c4ccccc4c4ccccc43)cc2)n1] | 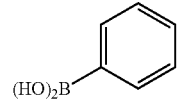 | 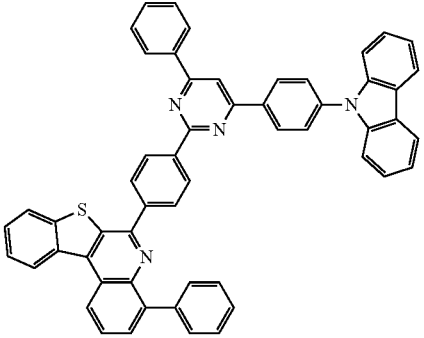 [SMILES: c1ccc(-c2cc(-c3ccc(-n4c5ccccc5c5ccccc54)cc3)nc(-c3ccc(-c4nc5c(-c6ccccc6)cccc5c5c4sc4ccccc45)cc3)n2)cc1] | 62% |

TABLE 1-continued
| Compound Number | Intermediate A | Intermediate B | Target Compound | Yield |
|---|---|---|---|---|
| 179 | 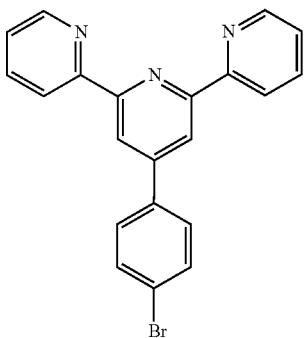 [SMILES: Brc1ccc(-c2cc(-c3ccccn3)nc(-c3ccccn3)c2)cc1] | 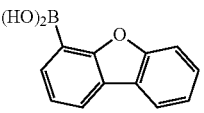 | 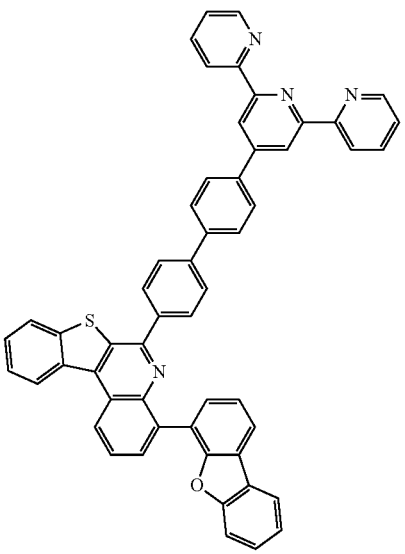 [SMILES: c1ccc(-c2cc(-c3ccc(-c4ccc(-c5nc6c(-c7cccc8c7oc7ccccc78)cccc6c6c5sc5ccccc56)cc4)cc3)cc(-c3ccccn3)n2)nc1] | 70% |
| 182 | 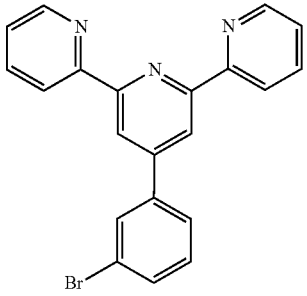 [SMILES: Brc1cccc(-c2cc(-c3ccccn3)nc(-c3ccccn3)c2)c1] | 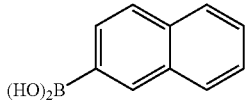 | 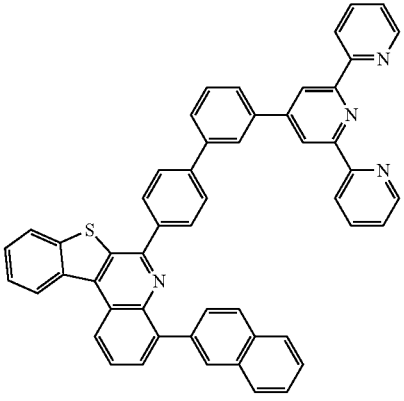 | 66% |
| 921 | 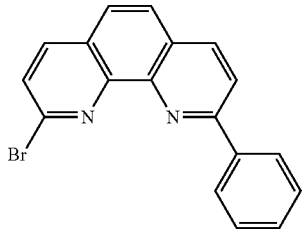 [SMILES: Brc1ccc2ccc3ccc(-c4ccccc4)nc3c2n1] | 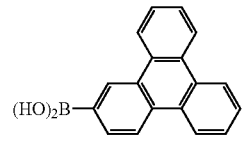 [SMILES: OB(O)c1ccc2c3ccccc3c3ccccc3c2c1] | 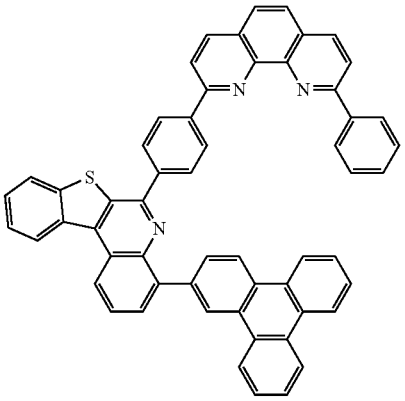 [SMILES: c1ccc(-c2ccc3ccc4ccc(-c5ccc(-c6nc7c(-c8ccc9c%10ccccc%10c%10ccccc%10c9c8)cccc7c7c6sc6ccccc67)cc5)nc4c3n2)cc1] | 68% |

A target compound was synthesized in the same manner as in Preparation Example 1 except that 3-bromobenzoyl chloride was used instead of 4-bromobenzoyl chloride, Intermediate C of the following Table 2 was used instead of 2-chloro-4,6-diphenyl-1,3,5-triazine, and Intermediate D of the following Table 2 was used instead of triphenylen-2-ylboronic acid.

TABLE 2

| Compound Number | Intermediate C | Intermediate D | Target Compound | Yield |
|---|---|---|---|---|
| 134 | 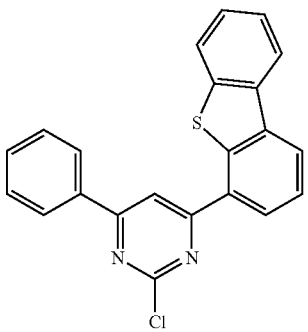 [SMILES: Clc1nc(-c2ccccc2)cc(-c2cccc3c2sc2ccccc23)n1] | 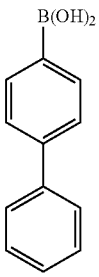 [SMILES: OB(O)c1ccc(-c2ccccc2)cc1] | 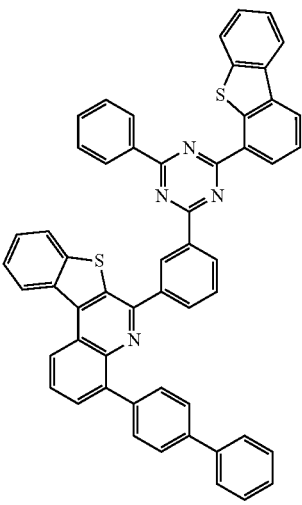 [SMILES: c1ccc(-c2ccc(-c3cccc4c3nc(-c3cccc(-c5nc(-c6ccccc6)nc(-c6cccc7c6sc6ccccc67)n5)c3)c3sc5ccccc5c34)cc2)cc1] | 70% |
| 197 | 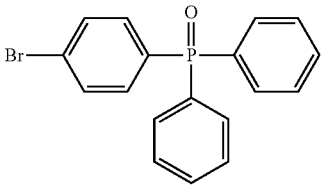 [SMILES: O=P(c1ccccc1)(c1ccccc1)c1ccc(Br)cc1] | 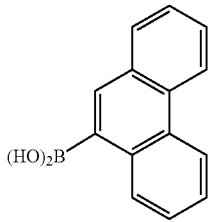 | 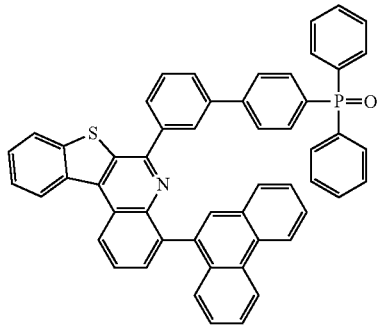 [SMILES: O=P(c1ccccc1)(c1ccccc1)c1ccc(-c2cccc(-c3nc4c(-c5cc6ccccc6c6ccccc56)cccc4c4c3sc3ccccc34)c2)cc1] | 69% |
| 925 | 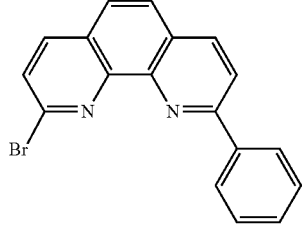 [SMILES: Brc1ccc2ccc3ccc(-c4ccccc4)nc3c2n1] | 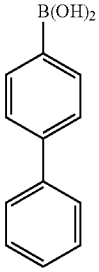 [SMILES: OB(O)c1ccc(-c2ccccc2)cc1] | 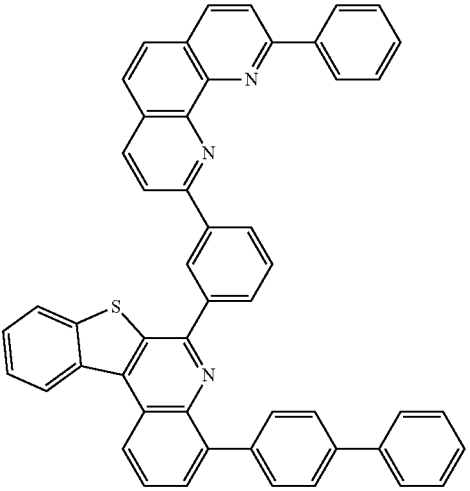 [SMILES: c1ccc(-c2ccc(-c3cccc4c3nc(-c3cccc(-c5ccc6ccc7ccc(-c8ccccc8)nc7c6n5)c3)c3sc5ccccc5c34)cc2)cc1] | 70% |

A target compound was synthesized in the same manner as in Preparation Example 1 except that 2-bromo-5-chloroaniline was used instead of 2-bromo-6-chloroaniline, Intermediate E of the following Table 3 was used instead of 2-chloro-4,6-diphenyl-1,3,5-triazine, and Intermediate F of the following Table 3 was used instead of triphenylen-2-ylboronic acid.

TABLE 3

| Compound Number | Intermediate E | Intermediate F | Target Compound | Yield |
|---|---|---|---|---|
| 17 | 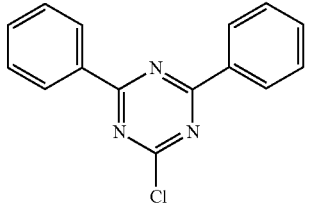 [SMILES: Clc1nc(-c2ccccc2)nc(-c2ccccc2)n1] | 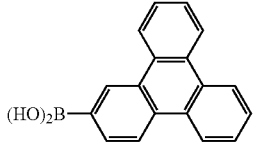 [SMILES: OB(O)c1ccc2c3ccccc3c3ccccc3c2c1] | 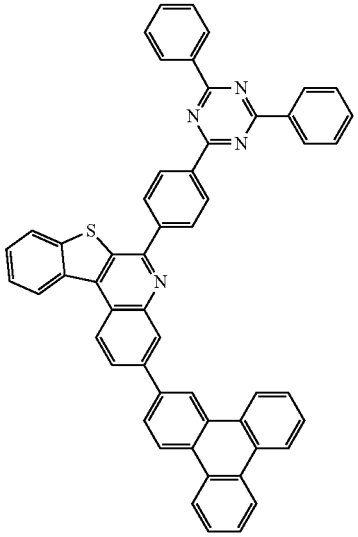 [SMILES: c1ccc(-c2nc(-c3ccccc3)nc(-c3ccc(-c4nc5cc(-c6ccc7c8ccccc8c8ccccc8c7c6)ccc5c5c4sc4ccccc45)cc3)n2)cc1] | 71% |
| 28 | 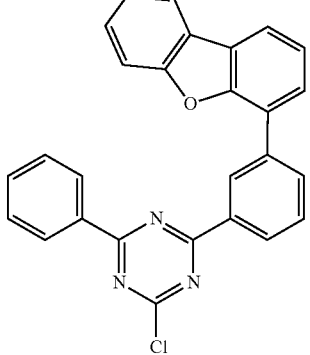 | 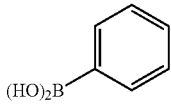 | 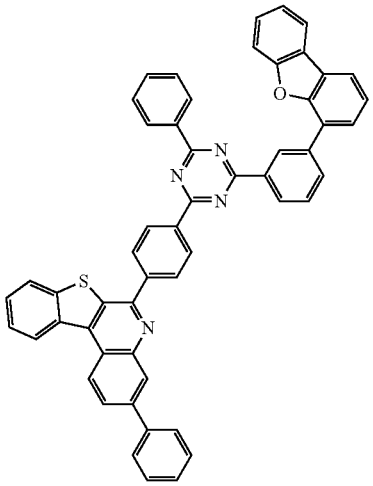 [SMILES: c1ccc(-c2ccc3c(c2)nc(-c2ccc(-c4nc(-c5ccccc5)nc(-c5cccc(-c6cccc7c6oc6ccccc67)c5)n4)cc2)c2sc4ccccc4c23)cc1] | 69% |

TABLE 3-continued

| Compound Number | Intermediate E | Intermediate F | Target Compound | Yield |
|---|---|---|---|---|
| 83 | | | | 75% |
| 89 | | | | 68% |
| 138 | | | | 60% |

TABLE 3-continued
| Compound Number | Intermediate E | Intermediate F | Target Compound | Yield |
|---|---|---|---|---|
| 143 | 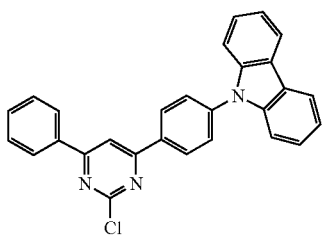 [SMILES: Clc1nc(-c2ccccc2)cc(-c2ccc(-n3c4ccccc4c4ccccc43)cc2)n1] | 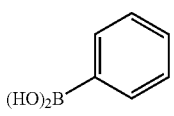 | 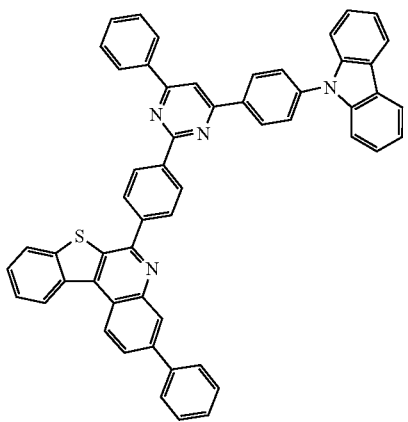 [SMILES: c1ccc(-c2ccc3c(c2)nc(-c2ccc(-c4nc(-c5ccccc5)cc(-c5ccc(-n6c7ccccc7c7ccccc76)cc5)n4)cc2)c2sc4ccccc4c23)cc1] | 65% |
| 149 | 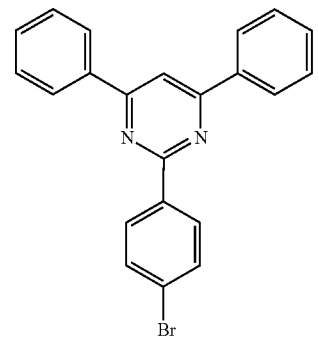 [SMILES: Brc1ccc(-c2nc(-c3ccccc3)cc(-c3ccccc3)n2)cc1] | 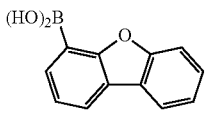 | 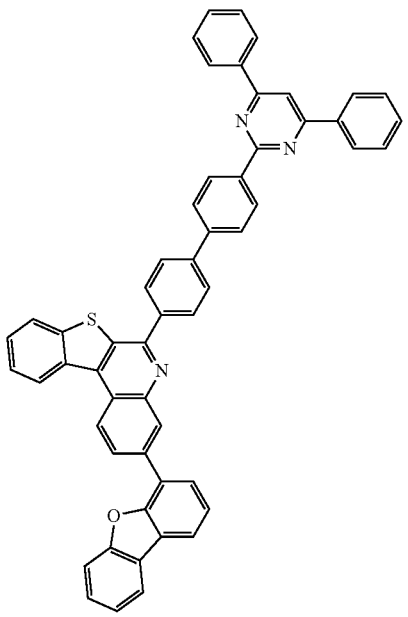 | 70% |

TABLE 3-continued

| Compound Number | Intermediate E | Intermediate F | Target Compound | Yield |
|---|---|---|---|---|
| 186 | 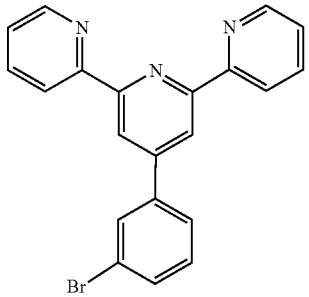 [SMILES: Brc1cccc(-c2cc(-c3ccccn3)nc(-c3ccccn3)c2)c1] | 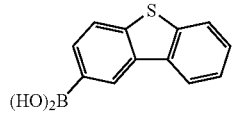 [SMILES: OB(O)c1ccc2sc3ccccc3c2c1] | 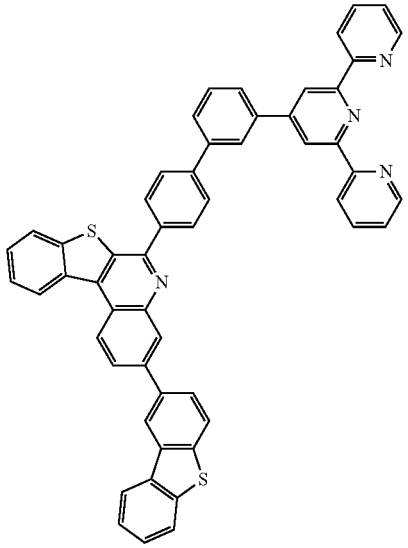 [SMILES: c1ccc(-c2cc(-c3cccc(-c4ccc(-c5nc6cc(-c7ccc8sc9ccccc9c8c7)ccc6c6c5sc5ccccc56)cc4)c3)cc(-c3ccccn3)n2)nc1] | 68% |
| 199 | 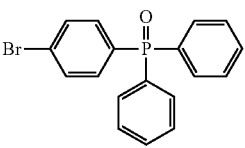 [SMILES: O=P(c1ccccc1)(c1ccccc1)c1ccc(Br)cc1] | 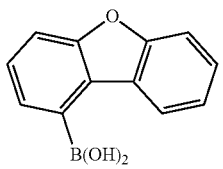 | 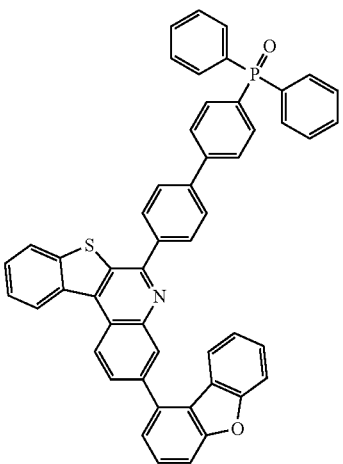 [SMILES: O=P(c1ccccc1)(c1ccccc1)c1ccc(-c2ccc(-c3nc4cc(-c5cccc6oc7ccccc7c56)ccc4c4c3sc3ccccc34)cc2)cc1] | 64% |

A target compound was synthesized in the same manner as in Preparation Example 1 except that 2-bromo-5-chloroaniline was used instead of 2-bromo-6-chloroaniline, 3-bromobenzoyl chloride was used instead of 4-bromobenzoyl chloride, Intermediate G of the following Table 4 was used instead of 2-chloro-4,6-diphenyl-1,3,5-triazine, and Intermediate H of the following Table 4 was used instead of triphenylen-2-ylboronic acid.

TABLE 4
| Compound Number | Intermediate G | Intermediate H | Target Compound | Yield |
|---|---|---|---|---|
| 25 | 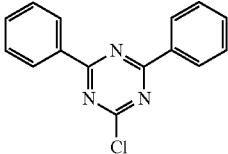 [SMILES: Clc1nc(-c2ccccc2)nc(-c2ccccc2)n1] | 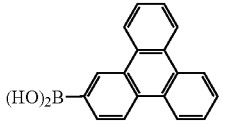 [SMILES: OB(O)c1ccc2c3ccccc3c3ccccc3c2c1] | 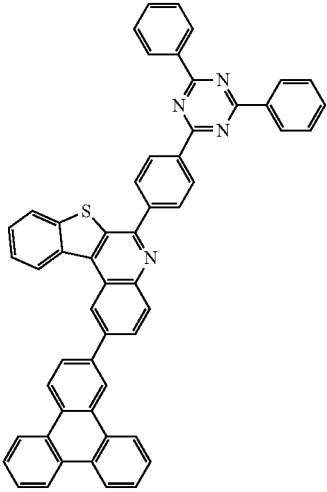 | 66% |
| 31 | 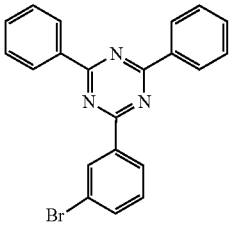 [SMILES: Brc1cccc(-c2nc(-c3ccccc3)nc(-c3ccccc3)n2)c1] | 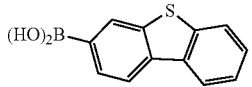 [SMILES: OB(O)c1ccc2c(c1)sc1ccccc12] | 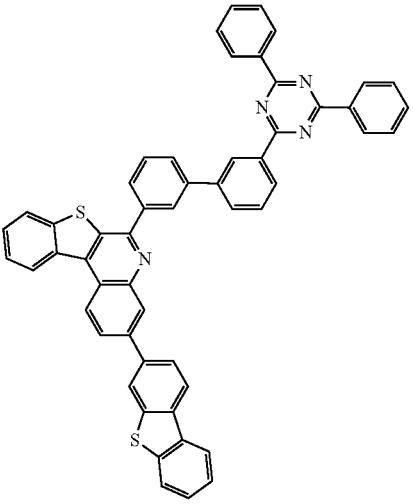 [SMILES: c1ccc(-c2nc(-c3ccccc3)nc(-c3cccc(-c4cccc(-c5nc6cc(-c7ccc8c(c7)sc7ccccc78)ccc6c6c5sc5ccccc56)c4)c3)n2)cc1] | 69% |
| 91 | 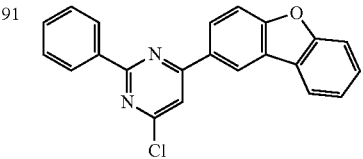 | 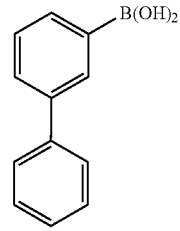 | 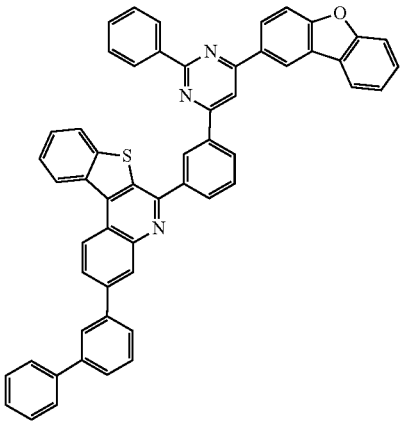 [SMILES: c1ccc(-c2cccc(-c3ccc4c(c3)nc(-c3cccc(-c5cc(-c6ccc7oc8ccccc8c7c6)nc(-c6ccccc6)n5)c3)c3sc5ccccc5c34)c2)cc1] | 75% |

TABLE 4-continued

| Compound Number | Intermediate G | Intermediate H | Target Compound | Yield |
|---|---|---|---|---|
| 926 | 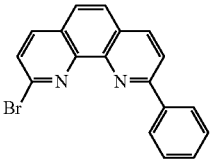 [SMILES: Brc1ccc2ccc3ccc(-c4ccccc4)nc3c2n1] | 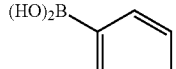 | 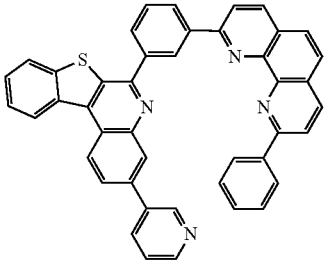 [SMILES: c1ccc(-c2ccc3ccc4ccc(-c5cccc(-c6nc7cc(-c8cccnc8)ccc7c7c6sc6ccccc67)c5)nc4c3n2)cc1] | 61% |

A target compound was synthesized in the same manner as in Preparation Example 1 except that 2-bromo-4-chloroaniline was used instead of 2-bromo-6-chloroaniline, Intermediate I of the following Table 5 was used instead of 2-chloro-4,6-diphenyl-1,3,5-triazine, and Intermediate J of the following Table 5 was used instead of triphenylen-2-ylboronic acid.

TABLE 5

| Compound Number | Intermediate I | Intermediate J | Target Compound | Yield |
|---|---|---|---|---|
| 33 | 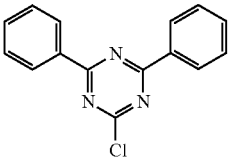 [SMILES: Clc1nc(-c2ccccc2)nc(-c2ccccc2)n1] | 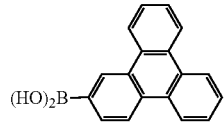 [SMILES: OB(O)c1ccc2c3ccccc3c3ccccc3c2c1] | 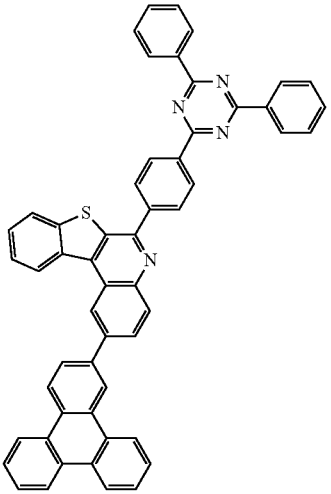 [SMILES: c1ccc(-c2nc(-c3ccccc3)nc(-c3ccc(-c4nc5ccc(-c6ccc7c8ccccc8c8ccccc8c7c6)cc5c5c4sc4ccccc45)cc3)n2)cc1] | 71% |
| 51 | 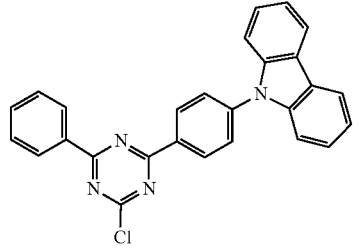 [SMILES: Clc1nc(-c2ccccc2)nc(-c2ccc(-n3c4ccccc4c4ccccc43)cc2)n1] | 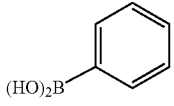 | 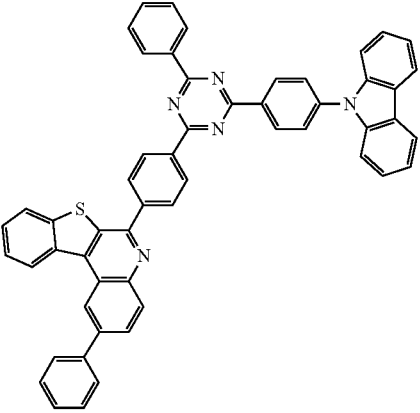 [SMILES: c1ccc(-c2ccc3nc(-c4ccc(-c5nc(-c6ccccc6)nc(-c6ccc(-n7c8ccccc8c8ccccc87)cc6)n5)cc4)c4sc5ccccc5c4c3c2)cc1] | 62% |

TABLE 5-continued

| Compound Number | Intermediate I | Intermediate J | Target Compound | Yield |
|---|---|---|---|---|
| 56 | | | | 75% |
| 57 | | | | 68% |

TABLE 5-continued
| Compound Number | Intermediate I | Intermediate J | Target Compound | Yield |
|---|---|---|---|---|
| 98 | 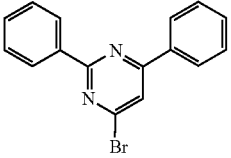 [SMILES: Brc1cc(-c2ccccc2)nc(-c2ccccc2)n1] | 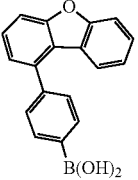 [SMILES: OB(O)c1ccc(-c2cccc3oc4ccccc4c23)cc1] | 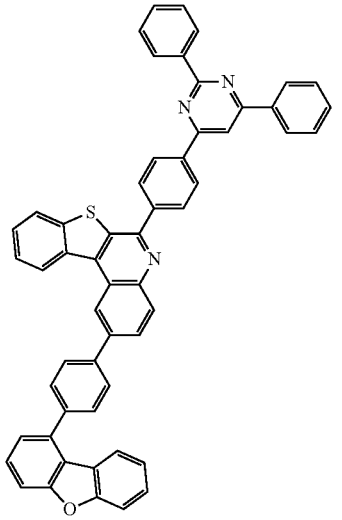 [SMILES: c1ccc(-c2cc(-c3ccc(-c4nc5ccc(-c6ccc(-c7cccc8oc9ccccc9c78)cc6)cc5c5c4sc4ccccc45)cc3)nc(-c3ccccc3)n2)cc1] | 64% |
| 100 | 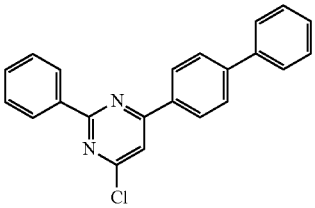 [SMILES: Clc1cc(-c2ccc(-c3ccccc3)cc2)nc(-c2ccccc2)n1] | 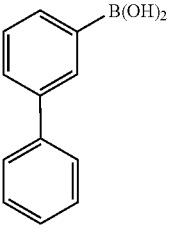 | 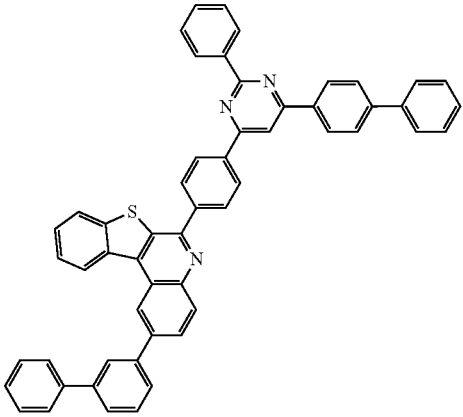 [SMILES: c1ccc(-c2ccc(-c3cc(-c4ccc(-c5nc6ccc(-c7cccc(-c8ccccc8)c7)cc6c6c5sc5ccccc56)cc4)nc(-c4ccccc4)n3)cc2)cc1] | 71% |
| 103 | 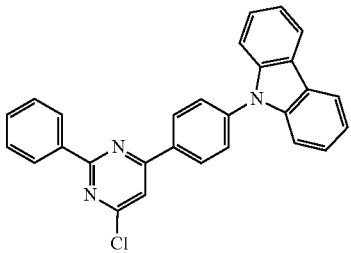 [SMILES: Clc1cc(-c2ccc(-n3c4ccccc4c4ccccc43)cc2)nc(-c2ccccc2)n1] | 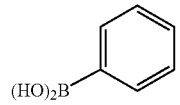 | 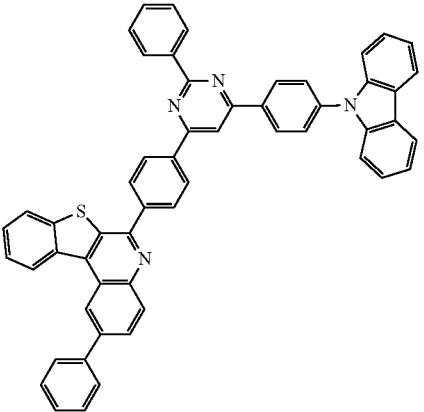 [SMILES: c1ccc(-c2ccc3nc(-c4ccc(-c5cc(-c6ccc(-n7c8ccccc8c8ccccc87)cc6)nc(-c6ccccc6)n5)cc4)c4sc5ccccc5c4c3c2)cc1] | 55% |

TABLE 5-continued
| Compound Number | Intermediate I | Intermediate J | Target Compound | Yield |
|---|---|---|---|---|
| 106 | 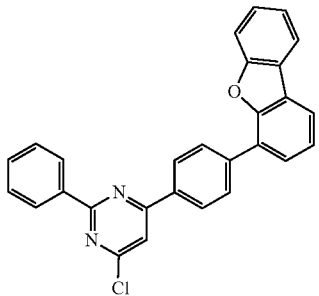 [SMILES: Clc1cc(-c2ccc(-c3cccc4c3oc3ccccc34)cc2)nc(-c2ccccc2)n1] | 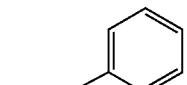 | 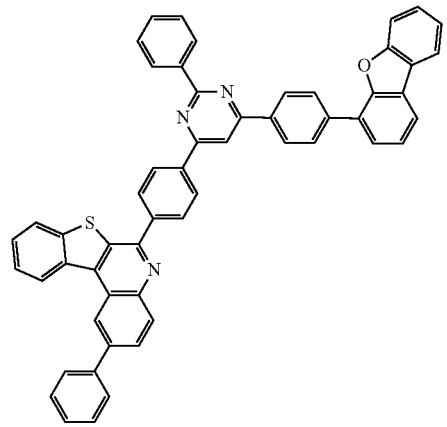 [SMILES: c1ccc(-c2ccc3nc(-c4ccc(-c5cc(-c6ccc(-c7cccc8c7oc7ccccc78)cc6)nc(-c6ccccc6)n5)cc4)c4sc5ccccc5c4c3c2)cc1] | 62% |
| 151 | 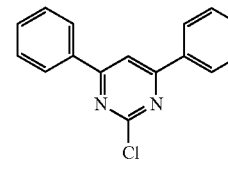 | 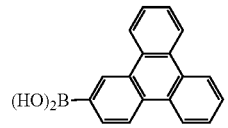 | 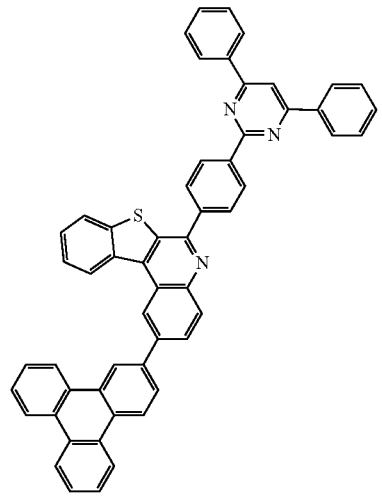 [SMILES: c1ccc(-c2cc(-c3ccccc3)nc(-c3ccc(-c4nc5ccc(-c6ccc7c8ccccc8c8ccccc8c7c6)cc5c5c4sc4ccccc45)cc3)n2)cc1] | 64% |
| 156 | 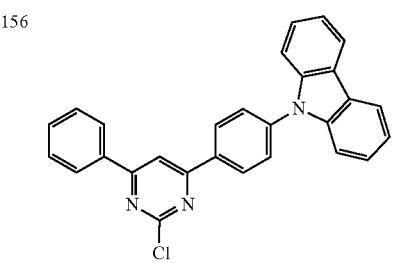 | 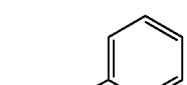 | 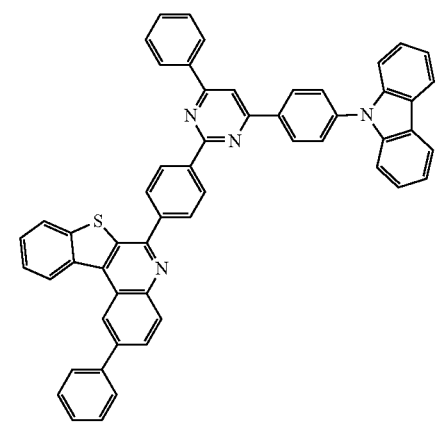 [SMILES: c1ccc(-c2ccc3nc(-c4ccc(-c5nc(-c6ccccc6)cc(-c6ccc(-n7c8ccccc8c8ccccc87)cc6)n5)cc4)c4sc5ccccc5c4c3c2)cc1] | 70% |

TABLE 5-continued
| Compound Number | Intermediate I | Intermediate J | Target Compound | Yield |
|---|---|---|---|---|
| 159 | 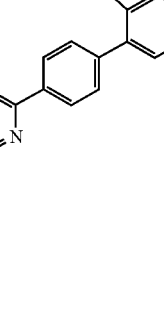 |  | 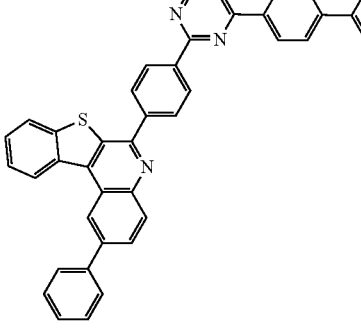 | 66% |
| 190 | 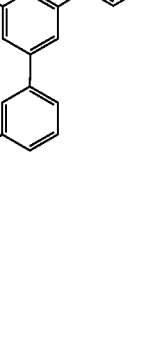 |  | 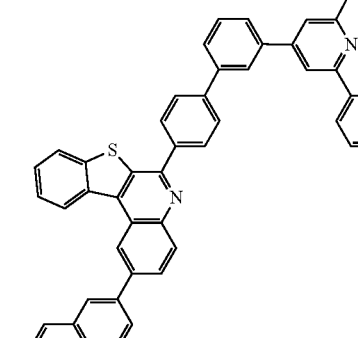 | 59% |
| 203 | 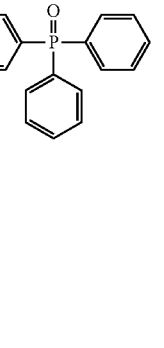 | 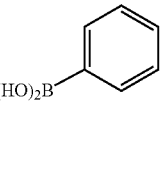 | 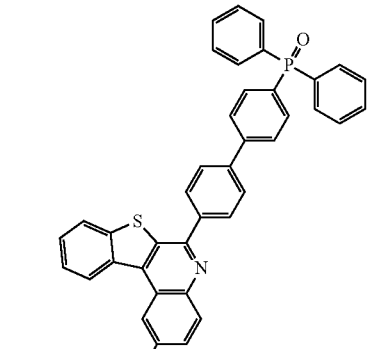 | 60% |

A target compound was synthesized in the same manner as in Preparation Example 1 except that 2-bromo-3-chloroaniline was used instead of 2-bromo-6-chloroaniline, Intermediate K of the following Table 6 was used instead of 2-chloro-4,6-diphenyl-1,3,5-triazine, and Intermediate L of the following Table 6 was used instead of triphenylen-2-ylboronic acid.

TABLE 6

| Compound Number | Intermediate K | Intermediate L | Target Compound | Yield |
|---|---|---|---|---|
| 59 | 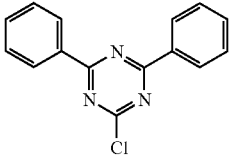 [SMILES: Clc1nc(-c2ccccc2)nc(-c2ccccc2)n1] | 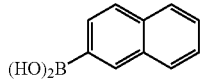 | 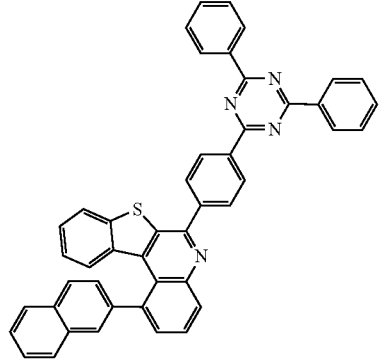 [SMILES: c1ccc(-c2nc(-c3ccccc3)nc(-c3ccc(-c4nc5cccc(-c6ccc7ccccc7c6)c5c5c4sc4ccccc45)cc3)n2)cc1] | 71% |
| 68 | 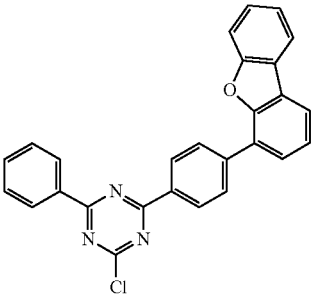 [SMILES: Clc1nc(-c2ccccc2)nc(-c2ccc(-c3cccc4c3oc3ccccc34)cc2)n1] | 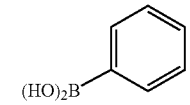 | 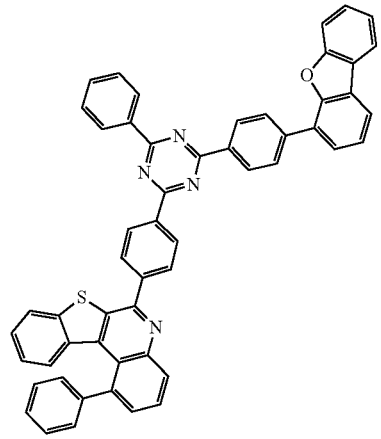 [SMILES: c1ccc(-c2nc(-c3ccc(-c4cccc5c4oc4ccccc45)cc3)nc(-c3ccc(-c4nc5cccc(-c6ccccc6)c5c5c4sc4ccccc45)cc3)n2)cc1] | 62% |
| 112 | 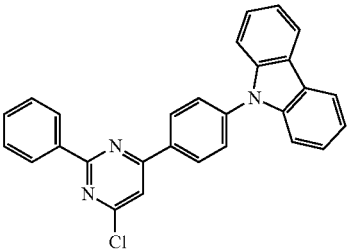 | 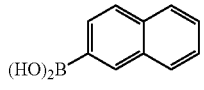 | 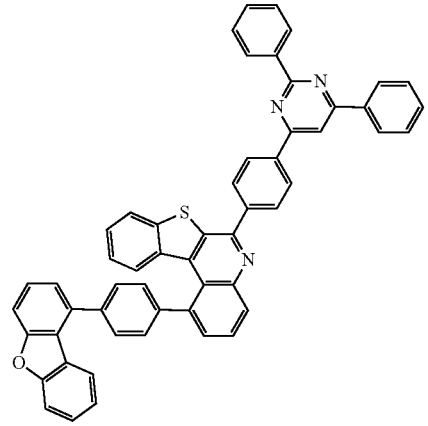 [SMILES: c1ccc(-c2cc(-c3ccc(-c4nc5cccc(-c6ccc(-c7cccc8oc9ccccc9c78)cc6)c5c5c4sc4ccccc45)cc3)nc(-c3ccccc3)n2)cc1] | 75% |

TABLE 6-continued

| Compound Number | Intermediate K | Intermediate L | Target Compound | Yield |
|---|---|---|---|---|
| 117 | | | | 63% |
| 119 | | | | 67% |
| 166 | | | | 71% |

TABLE 6-continued

| Compound Number | Intermediate K | Intermediate L | Target Compound | Yield |
|---|---|---|---|---|
| 207 | Br–C6H4–P(=O)(Ph)2 | dibenzofuran-B(OH)2 | (structure) | 70% |

A target compound was synthesized in the same manner as in Preparation Example 1 except that 2-bromo-3-chloroaniline was used instead of 2-bromo-6-chloroaniline, 3-bromobenzoyl chloride was used instead of 4-bromobenzoyl chloride, Intermediate M of the following Table 7 was used instead of 2-chloro-4,6-diphenyl-1,3,5-triazine, and Intermediate N of the following Table 7 was used instead of triphenylen-2-ylboronic acid.

TABLE 7

| Compound Number | Intermediate M | Intermediate N | Target Compound | Yield |
|---|---|---|---|---|
| 69 | (structure) | biphenyl-B(OH)2 | (structure) | 71% |
| 171 | (structure) | phenyl-B(OH)2 | (structure) | 62% |

TABLE 7-continued
| Compound Number | Intermediate M | Intermediate N | Target Compound | Yield |
|---|---|---|---|---|
| 174 | | | | 75% |
| 178 | | | | 67% |
<Preparation Example 2>—Preparation of Compound 212
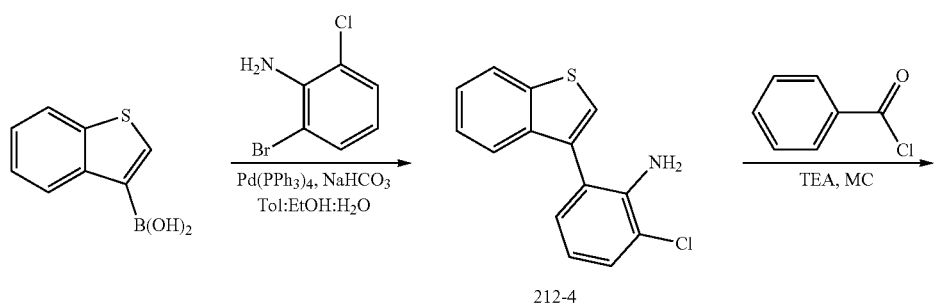

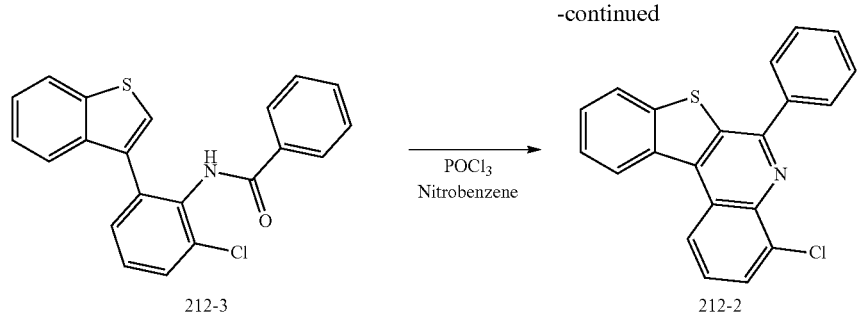
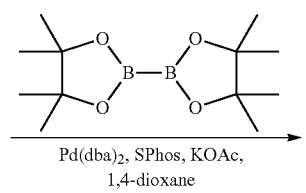
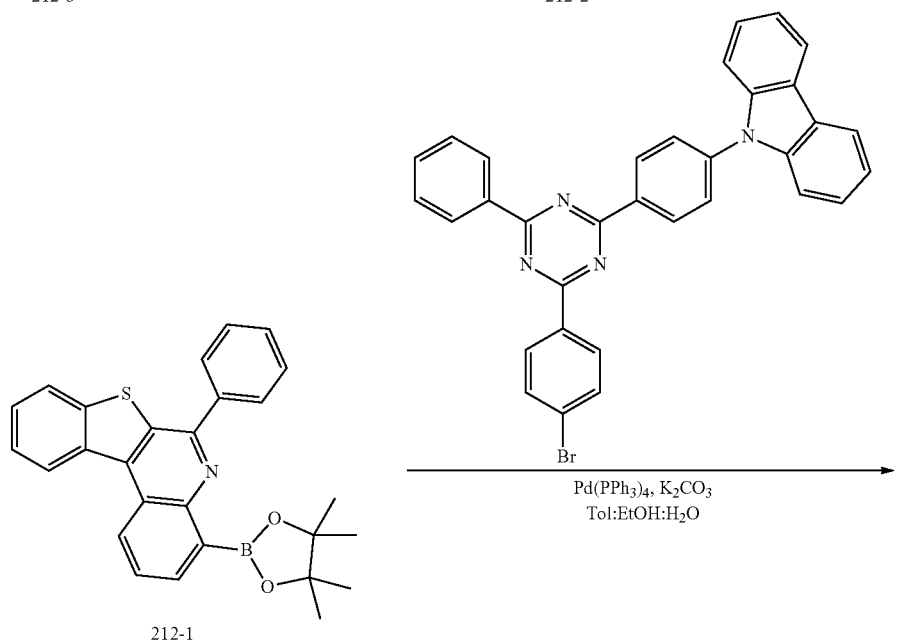
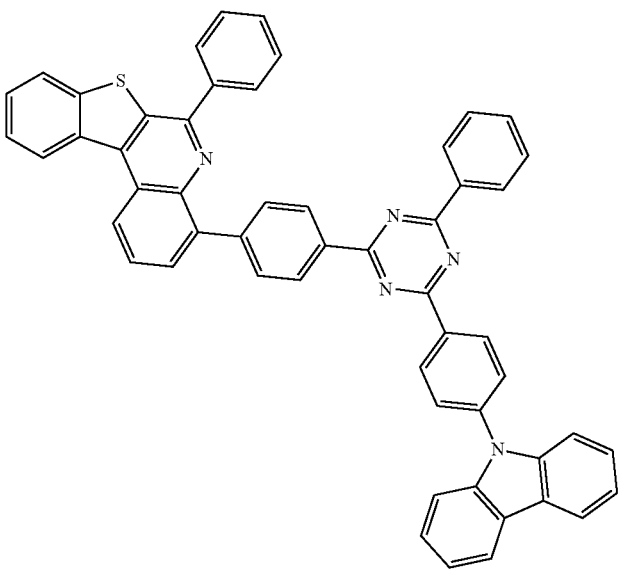

1) Preparation of Compound 212-4

After dissolving benzo[b]thiophen-3-ylboronic acid (80 g, 500 mmol) and 2-bromo-6-chloroaniline (95 g, 550 mmol) in toluene, EtOH and H$_2$O (1500 mL:300 mL:300 mL), Pd(PPh$_3$)$_4$ (29 g, 25 mmol) and NaHCO$_3$ (126 g, 1500 mmol) were introduced thereto, and the result was refluxed for 4 hours. After the reaction was completed, the result was cooled to room temperature and extracted with MC. The result was dried with anhydrous MgSO4, and then the solvent was removed using a rotary evaporator. Target Compound 212-4 was obtained using column chromatography (MC:Hx=1:3). (90 g, 91%, brown oil)

2) Preparation of Compound 212-3

Compound 212-4 (90 g, 219 mmol) and triethylamine (95 mL, 660 mmol) were introduced to MC (1500 mL) and dissolved therein. Benzoyl chloride (80 g, 250 mmol) dissolved in MC (300 mL) was slowly added dropwise to the mixture at 0° C. After the reaction was completed, MC and distilled water were introduced to the reaction solution for extraction. After that, the result was dried with anhydrous MgSO4, and, after removing the solvent using a rotary evaporator, recrystallized with EA/Hx to obtain Compound 212-3. (100 g, 91%, white solid)

3) Preparation of Compound 212-2

After dissolving Compound 212-3 (40 g, 110 mmol) in nitrobenzene (400 mL), POCl₃ (13 mL, 110 mmol) was slowly added dropwise thereto. After that, the result was stirred for 12 hours at 150° C. After the reaction was completed, the reaction solution was neutralized with an aqueous NaHCO₃ solution. Solids produced from the neutralization were filtered. The solids were recrystallized with MC/MeOH to obtain target Compound 212-2. (30 g, 88%, white solid)

4) Preparation of Compound 212-1

After dissolving Compound 212-2 (30 g, 70 mmol), bis(pinacolato)diboron (27 g, 105 mmol), Pd(dba)₂ (4 g, 7 mmol), XPhos (6.8 g, 14 mmol) and KOAc (48 g, 210 mmol) in 1,4-dioxane (300 mL), the result was refluxed for 12 hours. After the reaction was completed, MC and distilled water were introduced to the reaction solution for extraction. After that, the result was dried with anhydrous MgSO4, and the solvent was removed using a rotary evaporator. After passing silica, the result went through MeOH slurry to obtain Compound 212-1. (34 g, 85%, white solid)

5) Preparation of Compound 212

After dissolving Compound 212-1 (10 g, 22.9 mmol), 9-(4-(4-(4-bromophenyl)-6-phenyl-1,3,5-triazin-2-yl)phenyl)-9H-carbazole (13 g, 22.9 mmol), Pd(PPh₃)₄ (1.3 g, 1.2 mmol) and K₂CO₃ (10 g, 69 mmol) in toluene, EtOH and H₂O (100 mL:20 mL:20 mL), the result was refluxed for 12 hours. After the reaction was finished, produced solids were filtered. The solids were washed with distilled water and acetone to obtain target Compound 212. (9 g, 65%, white solid)

A target compound was synthesized in the same manner as in Preparation Example 2 except that Intermediate O of the following Table 8 was used instead of 9-(4-(4-(4-bromophenyl)-6-phenyl-1,3,5-triazin-2-yl)phenyl)-9H-carbazole.

TABLE 8

| Compound Number | Intermediate O | Target Compound | Yield |
| --- | --- | --- | --- |
| 228 | | | 60% |
| 243 | | | 70% |

TABLE 8-continued

| Compound Number | Intermediate O | Target Compound | Yield |
|---|---|---|---|
| 259 | | | 69% |
| 272 | | | 58% |
| 929 | | | 60% |

A target compound was synthesized in the same manner as in Preparation Example 2 except that 1-naphthoyl chloride was used instead of benzoyl chloride, and Intermediate P of the following Table 9 was used instead of 9-(4-(4-(4-bromophenyl)-6-phenyl-1,3,5-triazin-2-yl)phenyl)-9H-carbazole.

TABLE 9

| Compound Number | Intermediate P | Target Compound | Yield |
|---|---|---|---|
| 283 | | | 71% |

A target compound was synthesized in the same manner as in Preparation Example 2 except that phenanthrene-9-carbonyl chloride was used instead of benzoyl chloride, and Intermediate Q of the following Table 10 was used instead of 9-(4-(4-(4-bromophenyl)-6-phenyl-1,3,5-triazin-2-yl)phenyl)-9H-carbazole.

TABLE 10

| Compound Number | Intermediate Q | Target Compound | Yield |
|---|---|---|---|
| 379 | | | 66% |

A target compound was synthesized in the same manner as in Preparation Example 2 except that 2-bromo-5-chloroaniline was used instead of 2-bromo-6-chloroaniline, and Intermediate R of the following Table 11 was used instead of 9-(4-(4-(4-bromophenyl)-6-phenyl-1,3,5-triazin-2-yl)phenyl)-9H-carbazole.

TABLE 11

| Compound Number | Intermediate R | Target Compound | Yield |
|---|---|---|---|
| 217 | | | 67% |

TABLE 11-continued

| Compound Number | Intermediate R | Target Compound | Yield |
|---|---|---|---|
| 231 | | | 70% |
| 233 | | | 61% |
| 263 | | | 65% |

A target compound was synthesized in the same manner as in Preparation Example 2 except that 2-bromo-5-chloroaniline was used instead of 2-bromo-6-chloroaniline, 1-naphthoyl chloride was used instead of benzoyl chloride, and Intermediate S of the following Table 12 was used instead of 9-(4-(4-(4-bromophenyl)-6-phenyl-1,3,5-triazin-2-yl)phenyl)-9H-carbazole.

TABLE 12

| Compound Number | Intermediate S | Target Compound | Yield |
|---|---|---|---|
| 288 | | | 61% |
| 305 | | | 70% |

TABLE 12-continued

| Compound Number | Intermediate S | Target Compound | Yield |
|---|---|---|---|
| 319 | | | 58% |
| 334 | | | 63% |

TABLE 12-continued

| Compound Number | Intermediate S | Target Compound | Yield |
|---|---|---|---|
| 347 | | | 66% |

A target compound was synthesized in the same manner as in Preparation Example 2 except that 2-bromo-5-chloroaniline was used instead of 2-bromo-6-chloroaniline, phenanthrene-9-carbonyl chloride was used instead of benzoyl chloride, and Intermediate T of the following Table 13 was used instead of 9-(4-(4-(4-bromophenyl)-6-phenyl-1,3,5-triazin-2-yl)phenyl)-9H-carbazole.

TABLE 13

| Compound Number | Intermediate T | Target Compound | Yield |
|---|---|---|---|
| 358 | | | 65% |

TABLE 13-continued
| Compound Number | Intermediate T | Target Compound | Yield |
|---|---|---|---|
| 373 | 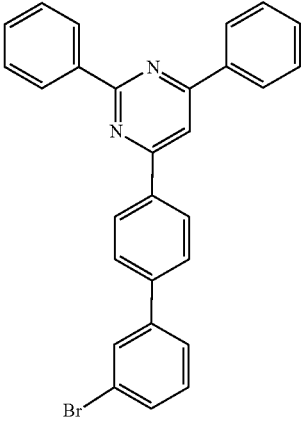 [SMILES: Brc1cccc(-c2ccc(-c3cc(-c4ccccc4)nc(-c4ccccc4)n3)cc2)c1] | 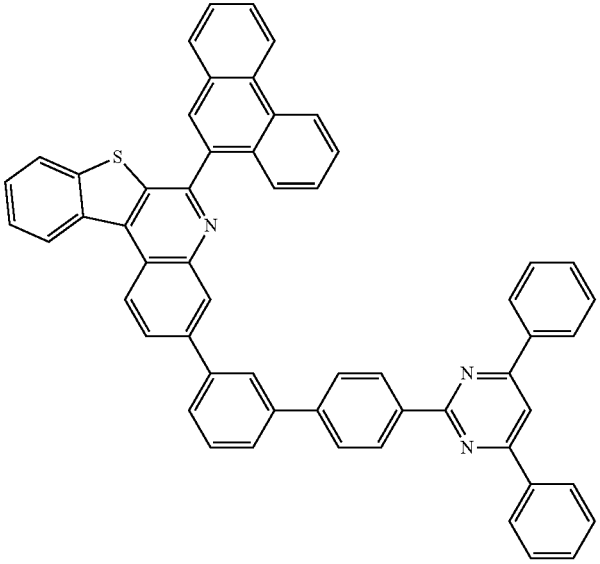<br>373 | 72% |
| 382 | 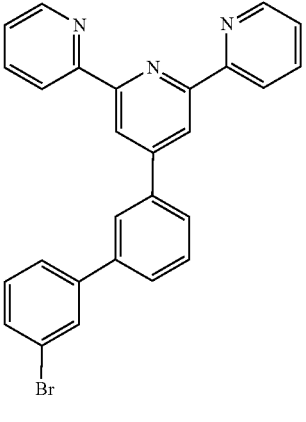 [SMILES: Brc1cccc(-c2cccc(-c3cc(-c4ccccn4)nc(-c4ccccn4)c3)c2)c1] | 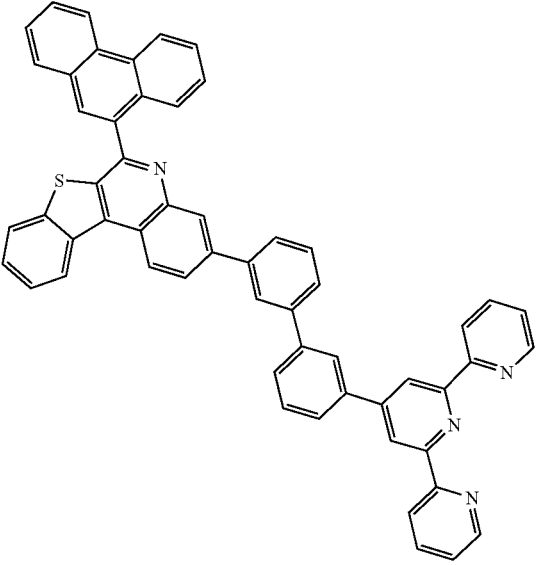 [SMILES: c1ccc(-c2cc(-c3cccc(-c4cccc(-c5ccc6c(c5)nc(-c5cc7ccccc7c7ccccc57)c5sc7ccccc7c56)c4)c3)cc(-c3ccccn3)n2)nc1] | 58% |

TABLE 13-continued

| Compound Number | Intermediate T | Target Compound | Yield |
|---|---|---|---|
| 389 | (structure) | (structure) | 61% |

A target compound was synthesized in the same manner as in Preparation Example 2 except that 2-bromo-5-chloroaniline was used instead of 2-bromo-6-chloroaniline, triphenylene-2-carbonyl chloride was used instead of benzoyl chloride, and Intermediate U of the following Table 14 was used instead of 9-(4-(4-(4-bromophenyl)-6-phenyl-1,3,5-triazin-2-yl)phenyl)-9H-carbazole.

TABLE 14

| Compound Number | Intermediate U | Target Compound | Yield |
|---|---|---|---|
| 397 | (structure) | (structure) | 73% |

A target compound was synthesized in the same manner as in Preparation Example 2 except that 2-bromo-4-chloroaniline was used instead of 2-bromo-6-chloroaniline, and Intermediate V of the following Table 15 was used instead of 9-(4-(4-(4-bromophenyl)-6-phenyl-1,3,5-triazin-2-yl)phenyl)-9H-carbazole.

TABLE 15

| Compound Number | Intermediate V | Target Compound | Yield |
|---|---|---|---|
| 219 | | | 77% |
| 236 | | | 73% |

TABLE 15-continued
| Compound Number | Intermediate V | Target Compound | Yield |
|---|---|---|---|
| 252 | 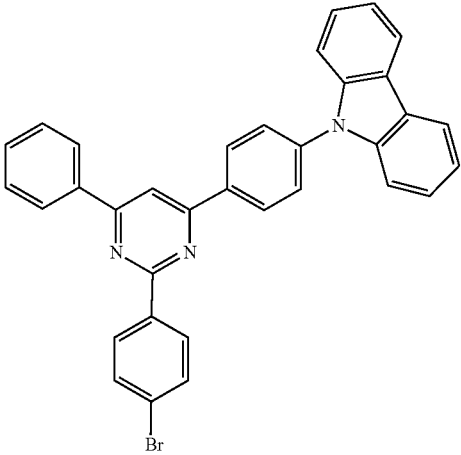 [SMILES: Brc1ccc(-c2nc(-c3ccccc3)cc(-c3ccc(-n4c5ccccc5c5ccccc54)cc3)n2)cc1] | 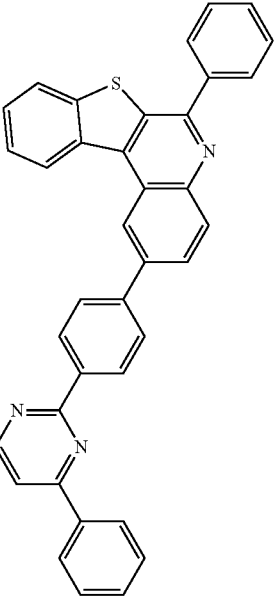 | 55% |
| 253 | 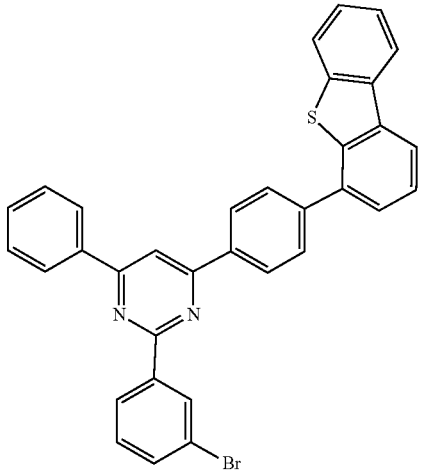 [SMILES: Brc1cccc(-c2nc(-c3ccccc3)cc(-c3ccc(-c4cccc5c4sc4ccccc45)cc3)n2)c1] | 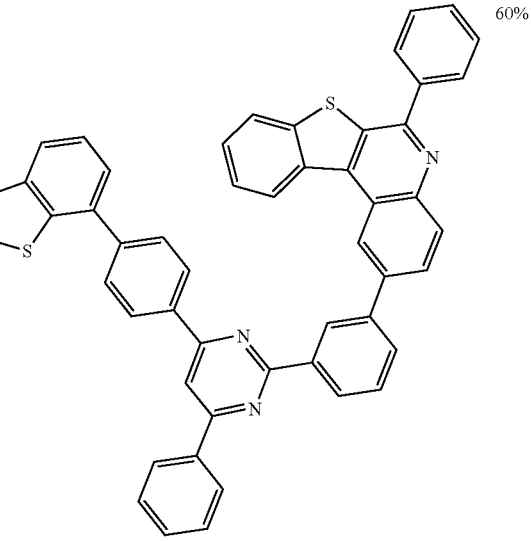 | 60% |

TABLE 15-continued
| Compound Number | Intermediate V | Target Compound | Yield |
|---|---|---|---|
| 265 | 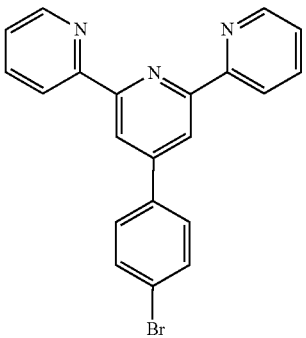 [SMILES: Brc1ccc(-c2cc(-c3ccccn3)nc(-c3ccccn3)c2)cc1] | 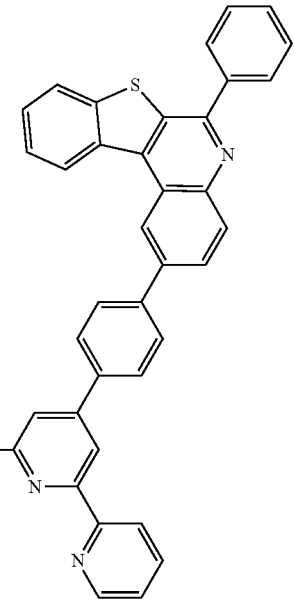 | 71% |
| 278 | 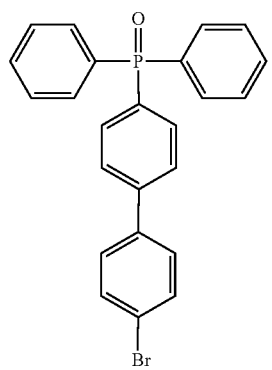 [SMILES: O=P(c1ccccc1)(c1ccccc1)c1ccc(-c2ccc(Br)cc2)cc1] | 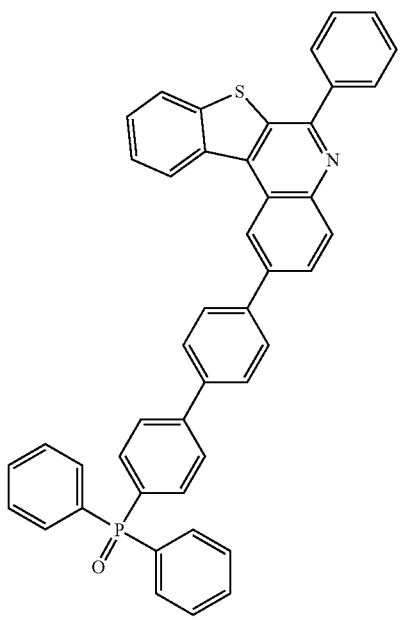 [SMILES: O=P(c1ccccc1)(c1ccccc1)c1ccc(-c2ccc(-c3ccc4nc(-c5ccccc5)c5sc6ccccc6c5c4c3)cc2)cc1] | 68% |

A target compound was synthesized in the same manner as in Preparation Example 2 except that 2-bromo-4-chloroaniline was used instead of 2-bromo-6-chloroaniline, 1-naphthoyl chloride was used instead of benzoyl chloride, and Intermediate W of the following Table 16 was used instead of 9-(4-(4-(4-bromophenyl)-6-phenyl-1,3,5-triazin-2-yl)phenyl)-9H-carbazole.

TABLE 16

| Compound Number | Intermediate W | Target Compound | Yield |
|---|---|---|---|
| 293 | | | 77% |
| 308 | | | 73% |

TABLE 16-continued

| Compound Number | Intermediate W | Target Compound | Yield |
|---|---|---|---|
| 324 | | | 71% |

A target compound was synthesized in the same manner as in Preparation Example 2 except that 2-bromo-4-chloroaniline was used instead of 2-bromo-6-chloroaniline, phenanthrene-9-carbonyl chloride was used instead of benzoyl chloride, and Intermediate X of the following Table 17 was used instead of 9-(4-(4-(4-bromophenyl)-6-phenyl-1,3,5-triazin-2-yl)phenyl)-9H-carbazole.

TABLE 17

| Compound Number | Intermediate X | Target Compound | Yield |
|---|---|---|---|
| 367 | | | 67% |

A target compound was synthesized in the same manner as in Preparation Example 2 except that 2-bromo-4-chloroaniline was used instead of 2-bromo-6-chloroaniline, triphenylene-2-carbonyl chloride was used instead of benzoyl chloride, and Intermediate Y of the following Table 18 was used instead of 9-(4-(4-(4-bromophenyl)-6-phenyl-1,3,5-triazin-2-yl)phenyl)-9H-carbazole.

TABLE 18

| Compound Number | Intermediate Y | Target Compound | Yield |
|---|---|---|---|
| 415 | | | 67% |
| 419 | | | 75% |

A target compound was synthesized in the same manner as in Preparation Example 2 except that 2-bromo-3-chloroaniline was used instead of 2-bromo-6-chloroaniline, and Intermediate Z of the following Table 19 was used instead of 9-(4-(4-(4-bromophenyl)-6-phenyl-1,3,5-triazin-2-yl)phenyl)-9H-carbazole.

TABLE 19

| Compound Number | Intermediate Z | Target Compound | Yield |
|---|---|---|---|
| 223 | | | 54% |
| 256 | | | 53% |

A target compound was synthesized in the same manner as in Preparation Example 2 except that 2-bromo-3-chloroaniline was used instead of 2-bromo-6-chloroaniline, 1-naphthoyl chloride was used instead of benzoyl chloride, and Intermediate AA of the following Table 20 was used instead of 9-(4-(4-(4-bromophenyl)-6-phenyl-1,3,5-triazin-2-yl)phenyl)-9H-carbazole.

TABLE 20

| Compound Number | Intermediate AA | Target Compound | Yield |
|---|---|---|---|
| 295 | | | 56% |
| 328 | | | 53% |
| 352 | | | 59% |

A target compound was synthesized in the same manner as in Preparation Example 2 except that 2-bromo-3-chloroaniline was used instead of 2-bromo-6-chloroaniline, phenanthrene-9-carbonyl chloride was used instead of benzoyl chloride, and Intermediate AB of the following Table 21 was used instead of 9-(4-(4-(4-bromophenyl)-6-phenyl-1,3,5-triazin-2-yl)phenyl)-9H-carbazole.

TABLE 21

| Compound Number | Intermediate AB | Target Compound | Yield |
|---|---|---|---|
| 393 | | | 51% |

A target compound was synthesized in the same manner as in Preparation Example 2 except that 2-bromo-3-chloroaniline was used instead of 2-bromo-6-chloroaniline, phenanthrene-9-carbonyl chloride was used instead of benzoyl chloride, and Intermediate AC of the following Table 22 was used instead of 9-(4-(4-(4-bromophenyl)-6-phenyl-1,3,5-triazin-2-yl)phenyl)-9H-carbazole.

TABLE 22

| Compound Number | Intermediate AC | Target Compound | Yield |
|---|---|---|---|
| 406 | | | 53% |

<Preparation Example 3>—Preparation of Compound 425

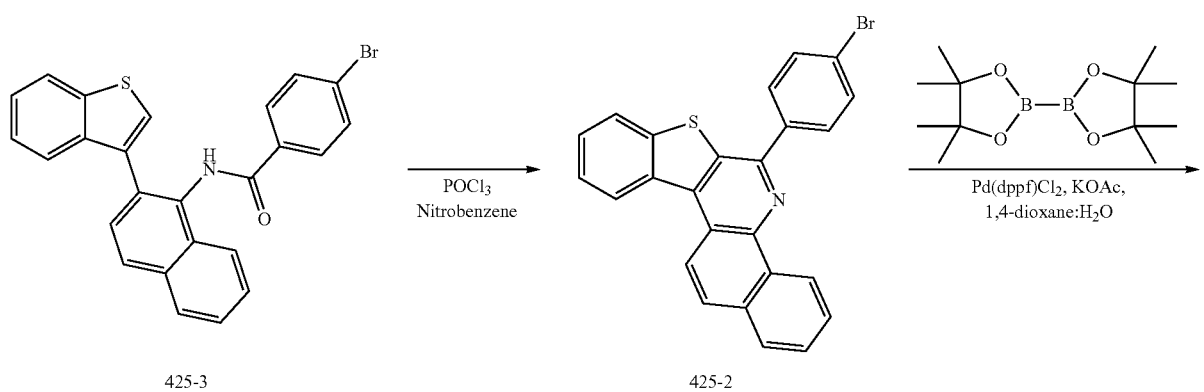
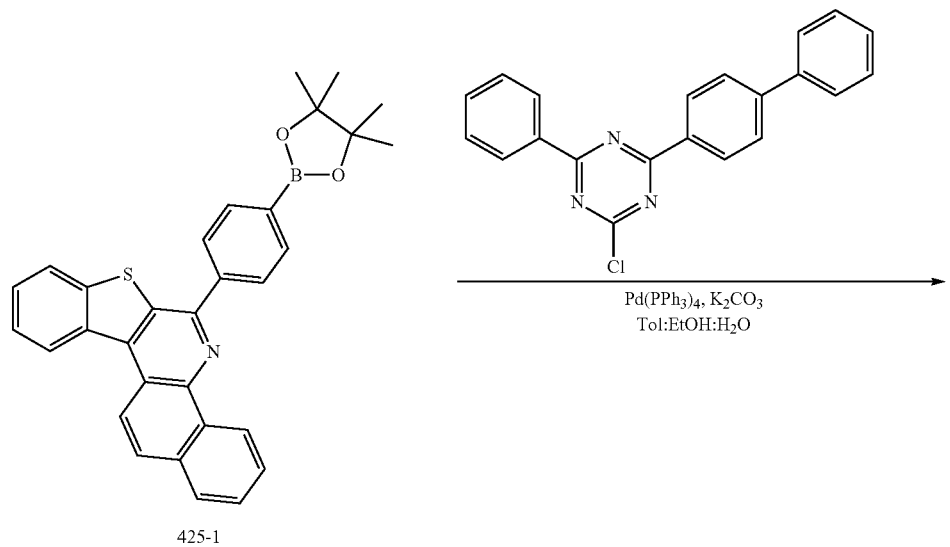

-continued

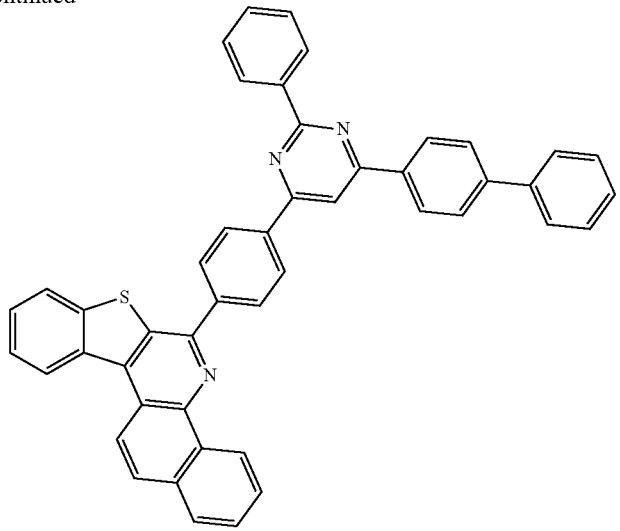

425

1) Preparation of Compound 425-4

After dissolving benzo[b]thiophen-3-ylboronic acid (40 g, 250 mmol) and 2-bromonaphthalen-1-amine (67 g, 300 mmol) in toluene, EtOH and H$_2$O (1000 mL:200 mL:200 mL), Pd(PPh$_3$)$_4$ (15 g, 13 mmol) and NaHCO$_3$ (63 g, 750 mmol) were introduced thereto, and the result was refluxed for 4 hours. After the reaction was completed, the result was cooled to room temperature and extracted with MC. The result was dried with anhydrous MgSO4, and then the solvent was removed using a rotary evaporator. Target Compound 425-4 was obtained using column chromatography (MC:Hx=1:3). (60 g, 88%, brown solid)

2) Preparation of Compound 425-3

Compound 425-4 (60 g, 218 mmol) and triethylamine (93 mL, 650 mmol) were introduced to MC (1500 mL) and dissolved therein. 4-Bromobenzoyl chloride (53 g, 240 mmol) dissolved in MC (300 mL) was slowly added dropwise to the mixture at 0° C. After the reaction was completed, MC and distilled water were introduced to the reaction solution for extraction. After that, the result was dried with anhydrous MgSO4, and, after removing the solvent using a rotary evaporator, recrystallized with EA/Hx to obtain Compound 425-3. (90 g, 90%, white solid)

3) Preparation of Compound 425-2

After dissolving Compound 425-3 (90 g, 200 mmol) in nitrobenzene (400 mL), POCl$_3$ (24 mL, 200 mmol) was slowly added dropwise thereto. After that, the result was stirred for 12 hours at 150° C. After the reaction was completed, the reaction solution was neutralized with an aqueous NaHCO$_3$ solution. Solids produced from the neutralization were filtered. The solids were recrystallized with MC/MeOH to obtain target Compound 425-2. (70 g, 80%, white solid)

4) Preparation of Compound 425-1

After dissolving Compound 425-2 (70 g, 159 mmol), bis(pinacolato)diboron (50 g, 191 mmol), Pd(dppf)Cl$_2$ (5.8 g, 8 mmol) and KOAc (48 g, 477 mmol) in 1,4-dioxane (300 mL), the result was refluxed for 12 hours. After the reaction was completed, MC and distilled water were introduced to the reaction solution for extraction. After that, the result was dried with anhydrous MgSO4, and the solvent was removed using a rotary evaporator. After passing silica, the result went through MeOH slurry to obtain Compound 425-1. (66 g, 85%, white solid)

5) Preparation of Compound 425

After dissolving Compound 425-1 (10 g, 20.5 mmol), 4-([1,1'-biphenyl]-4-yl)-6-chloro-2-phenylpyrimidine (7 g, 20.5 mmol), Pd(PPh$_3$)$_4$ (1.2 g, 1.1 mmol) and K$_2$CO$_3$ (8.5 g, 62 mmol) in toluene, EtOH and H$_2$O (100 mL:20 mL:20 mL), the result was refluxed for 12 hours. After the reaction was finished, produced solids were filtered. The solids were washed with distilled water and acetone to obtain target Compound 425. (11 g, 82%, white solid)

A target compound was synthesized in the same manner as in Preparation Example 3 except that Intermediate AD of the following Table 23 was used instead of 4-([1,1'-biphenyl]-4-yl)-6-chloro-2-phenylpyrimidine TABLE 23
| Compound Number | Intermediate AD | Target Compound | Yield |
|---|---|---|---|
| 423 | 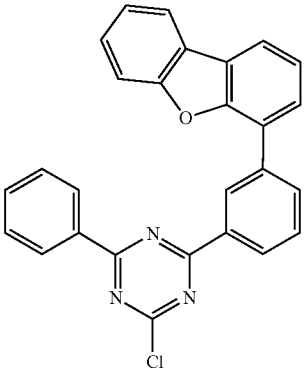 [SMILES: Clc1nc(-c2ccccc2)nc(-c2cccc(-c3cccc4c3oc3ccccc34)c2)n1] | 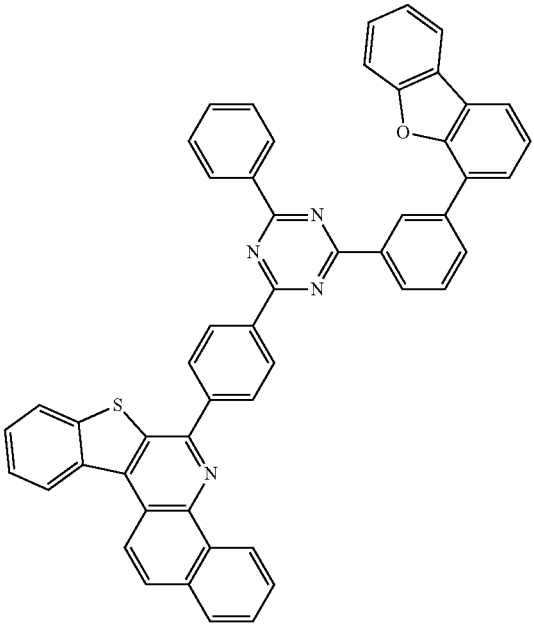 [SMILES: c1ccc(-c2nc(-c3ccc(-c4nc5c6ccccc6ccc5c5c4sc4ccccc45)cc3)nc(-c3cccc(-c4cccc5c4oc4ccccc45)c3)n2)cc1] | 85% |
| 433 | 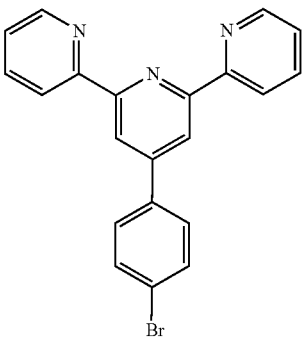 [SMILES: Brc1ccc(-c2cc(-c3ccccn3)nc(-c3ccccn3)c2)cc1] | 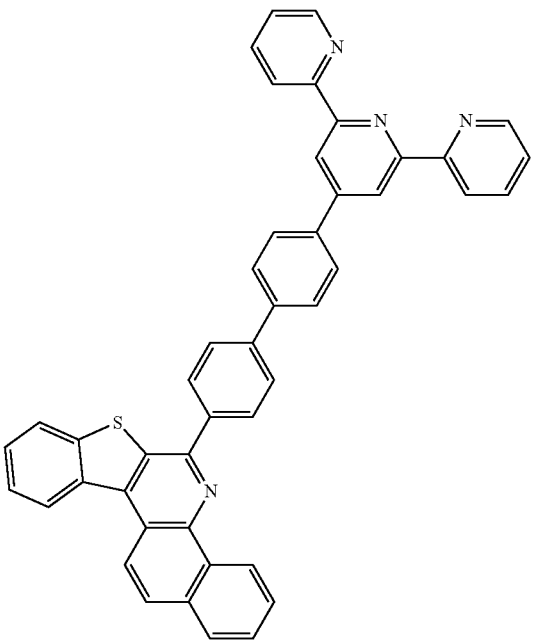 [SMILES: c1ccc(-c2cc(-c3ccc(-c4ccc(-c5nc6c7ccccc7ccc6c6c5sc5ccccc56)cc4)cc3)cc(-c3ccccn3)n2)nc1] | 90% |

TABLE 23-continued

| Compound Number | Intermediate AD | Target Compound | Yield |
|---|---|---|---|
| 937 | | | 91% |

A target compound was synthesized in the same manner as in Preparation Example 3 except that 3-bromonaphthalen-2-amine was used instead of 2-bromonaphthalen-1-amine, and Intermediate AE of the following Table 24 was used instead of 4-([1,1'-biphenyl]-4-yl)-6-chloro-2-phenylpyrimidine

TABLE 24

| Compound Number | Intermediate AE | Target Compound | Yield |
|---|---|---|---|
| 435 | | | 85% |

TABLE 24-continued

| Compound Number | Intermediate AE | Target Compound | Yield |
|---|---|---|---|
| 441 | | | 90% |
| 444 | | | 88% |
| 938 | | | 82% |

A target compound was synthesized in the same manner as in Preparation Example 3 except that 1-bromonaphthalen-2-amine was used instead of 2-bromonaphthalen-1-amine, and Intermediate AF of the following Table 25 was used instead of 4-([1,1'-biphenyl]-4-yl)-6-chloro-2-phenylpyrimidine.

TABLE 25

| Compound Number | Intermediate AF | Target Compound | Yield |
|---|---|---|---|
| 453 | | | 82% |
| 455 | | | 86% |
| 460 | | | 85% |

TABLE 25-continued
| Compound Number | Intermediate AF | Target Compound | Yield |
|---|---|---|---|
| 942 | | | 86% |
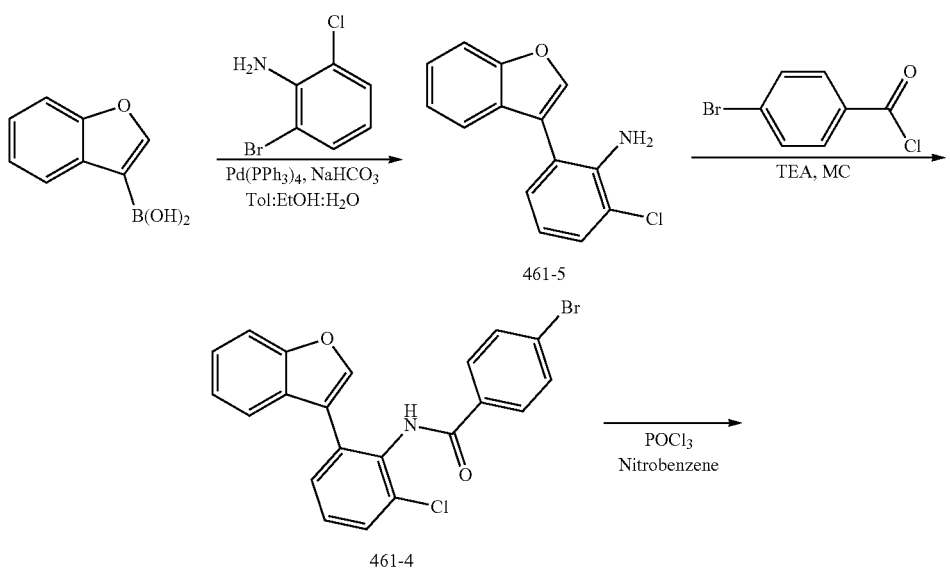
<Preparation Example 4>—Preparation of Compound 461
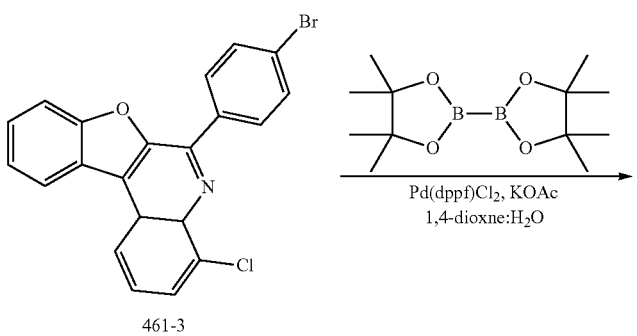

-continued
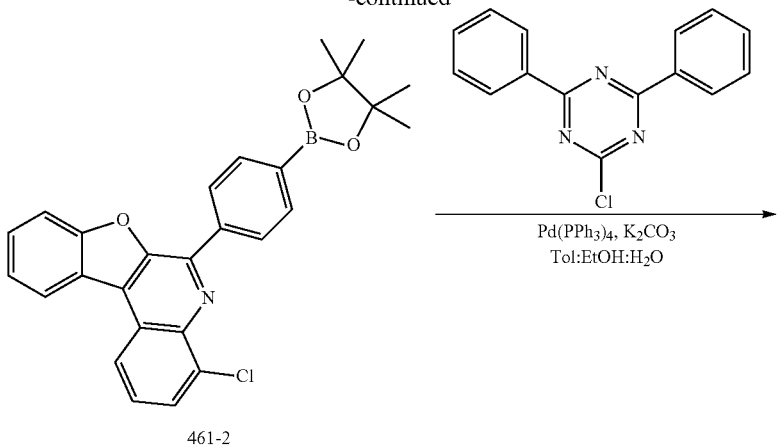
461-2
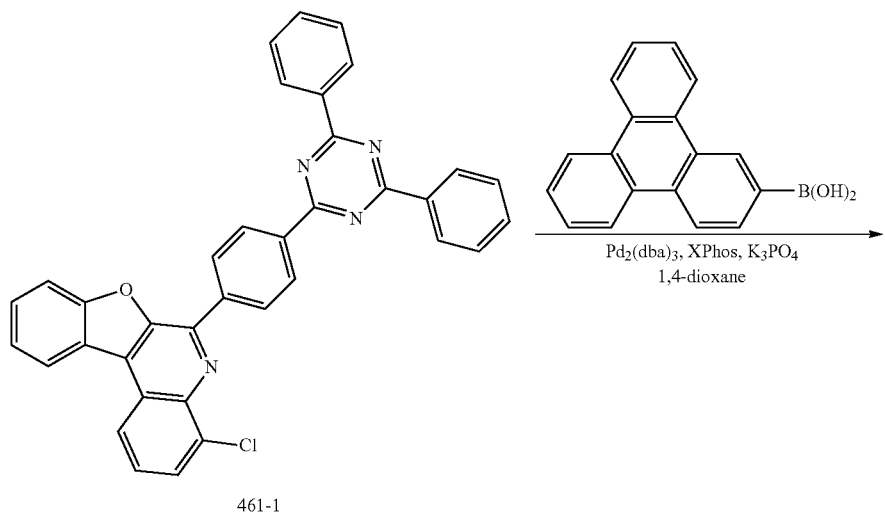
461-1
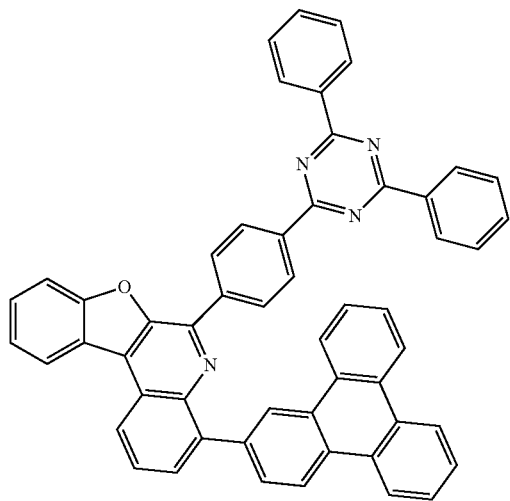
461

1) Preparation of Compound 461-5

After dissolving benzofuran-3-ylboronic acid (162 g, 1000 mmol) and 2-bromo-6-chloroaniline (189 g, 1100 mmol) in toluene, EtOH and H$_2$O (2000 mL:400 mL:400 mL), Pd(PPh$_3$)$_4$ (58 g, 50 mmol) and NaHCO$_3$ (252 g, 3000 mmol) were introduced thereto, and the result was refluxed for 4 hours. After the reaction was completed, the result was cooled to room temperature and extracted with MC. The result was dried with anhydrous MgSO4, and then the solvent was removed using a rotary evaporator. Target Compound 461-5 was obtained using column chromatography (MC:Hx=1:3). (190 g, 91%, brown oil)

2) Preparation of Compound 461-4

Compound 461-5 (95 g, 428 mmol) and triethylamine (190 mL, 1362 mmol) were introduced to MC (1500 mL) and dissolved therein. 4-Bromobenzoyl chloride (149 g, 681 mmol) dissolved in MC (300 mL) was slowly added dropwise to the mixture at 0° C. After the reaction was completed, MC and distilled water were introduced to the reaction solution for extraction. After that, the result was dried with anhydrous MgSO4, and, after removing the solvent using a rotary evaporator, recrystallized with MC/Hx to obtain Compound 461-4. (82 g, 91%, white solid)

3) Preparation of Compound 461-3

After dissolving Compound 461-4 (82 g, 210 mmol) in nitrobenzene (1000 mL), POCl$_3$ (24 mL, 210 mmol) was slowly added dropwise thereto. After that, the result was stirred for 12 hours at 150° C. After the reaction was completed, the reaction solution was neutralized with an aqueous NaHCO$_3$ solution. Solids produced from the neutralization were filtered. The solids were recrystallized with MC/MeOH to obtain target Compound 461-3. (69 g, 88%, white solid)

4) Preparation of Compound 461-2

After dissolving Compound 461-2 (61 g, 163 mmol), bis(pinacolato)diboron (62 g, 244 mmol), Pd(dppf)Cl$_2$ (6 g, 8.2 mmol) and KOAc (48 g, 489 mmol) in 1,4-dioxane (600 mL), the result was refluxed for 12 hours. After the reaction was completed, MC and distilled water were introduced to the reaction solution for extraction. After that, the result was dried with anhydrous MgSO4, and the solvent was removed using a rotary evaporator. After passing silica, the result went through MeOH slurry to obtain Compound 461-2. (69 g, 95%, pale pink solid)

5) Preparation of Compound 461-1

After dissolving Compound 461-2 (9cw g, 21.4 mmol) and 2-chloro-4,6-diphenyl-1,3,5-triazine (8.2 g, 21.4 mmol) in toluene, EtOH and H$_2$O (100 mL:20 mL:20 mL), Pd(PPh$_3$)$_4$ (1.3 g, 1.07 mmol) and K$_2$CO$_3$ (8.9 g, 64.2 mol) were introduced thereto, and the result was refluxed for 5 hours. After the reaction was completed, produced solids were filtered to obtain Compound 461-1. (10 g, 78%, white solid)

5) Preparation of Compound 461

After dissolving Compound 461-1 (10 g, 17.3 mmol), triphenylen-2-ylboronic acid (5.7 g, 20.8 mmol), Pd$_2$(dba)$_3$ (1.6 g, 1.7 mmol), XPhos (1.7 g, 3.4 mmol) and K$_3$PO$_4$ (11 g, 52 mmol) in 1,4-dioxane (100 mL), the result was refluxed for 12 hours. After the reaction was finished, produced solids were filtered. The solids were washed with distilled water and acetone to obtain target Compound 461. (9 g, 65%, white solid)

A target compound was synthesized in the same manner as in Preparation Example 4 except that Intermediate AG of the following Table 26 was used instead of 2-chloro-4,6-diphenyl-1,3,5-triazine, and Intermediate AH of the following Table 26 was used instead of triphenylen-2-ylboronic acid.

TABLE 26

| Compound Number | Intermediate AG | Intermediate AH |
| --- | --- | --- |
| 467 | ![structure] | (HO)$_2$B-phenyl |
| 470 | ![structure] | (HO)$_2$B-phenyl |

TABLE 26-continued
| | | |
|---|---|---|
| 474 | 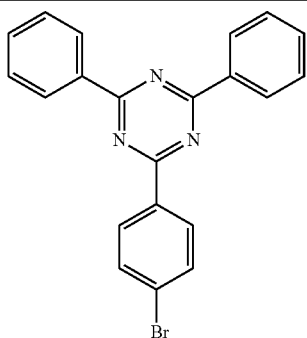 | 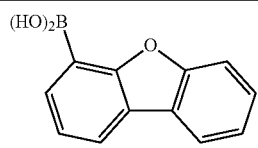 |
| 532 | 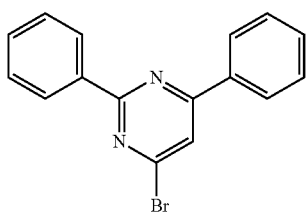 [SMILES: Brc1cc(-c2ccccc2)nc(-c2ccccc2)n1] | 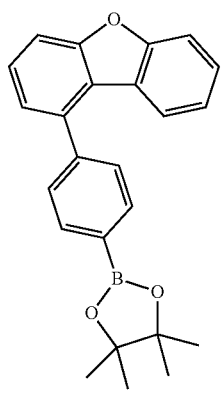 [SMILES: CC1(C)OB(c2ccc(-c3cccc4oc5ccccc5c34)cc2)OC1(C)C] |
| 535 | 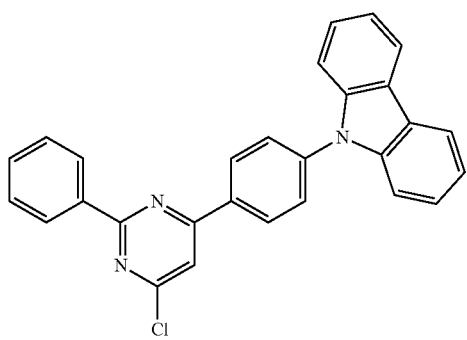 [SMILES: Clc1cc(-c2ccc(-n3c4ccccc4c4ccccc43)cc2)nc(-c2ccccc2)n1] | 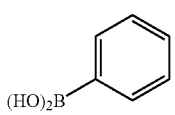 |
| 538 | 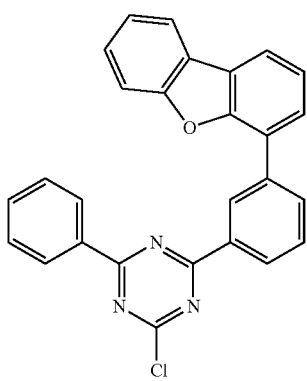 [SMILES: Clc1nc(-c2ccccc2)nc(-c2cccc(-c3cccc4c3oc3ccccc34)c2)n1] | 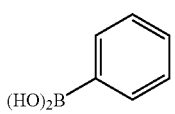 |
| 585 | 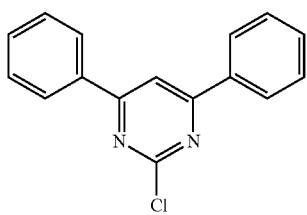 [SMILES: Clc1nc(-c2ccccc2)cc(-c2ccccc2)n1] | 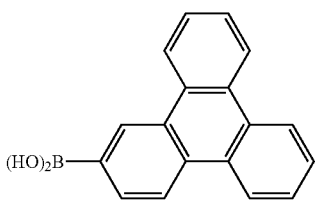 |

TABLE 26-continued
| | | |
|---|---|---|
| 590 | 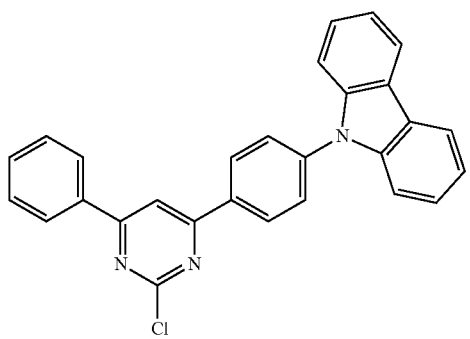 [SMILES: Clc1nc(-c2ccccc2)cc(-c2ccc(-n3c4ccccc4c4ccccc43)cc2)n1] | 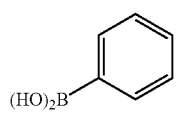 |
| 639 | 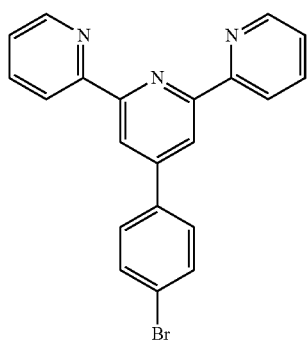 [SMILES: Brc1ccc(-c2cc(-c3ccccn3)nc(-c3ccccn3)c2)cc1] | 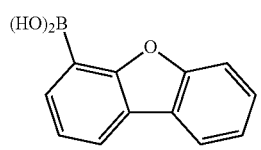 [SMILES: OB(O)c1cccc2c1oc1ccccc12] |
| 642 | 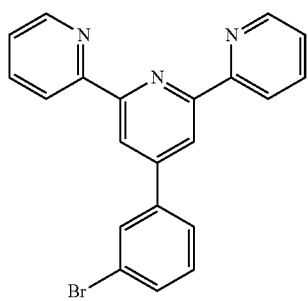 [SMILES: Brc1cccc(-c2cc(-c3ccccn3)nc(-c3ccccn3)c2)c1] | 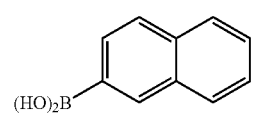 [SMILES: OB(O)c1ccc2ccccc2c1] |
| Compound Number | Target Compound | Yield |
|---|---|---|
| 467 | | 69% |

TABLE 26-continued
| 470 | 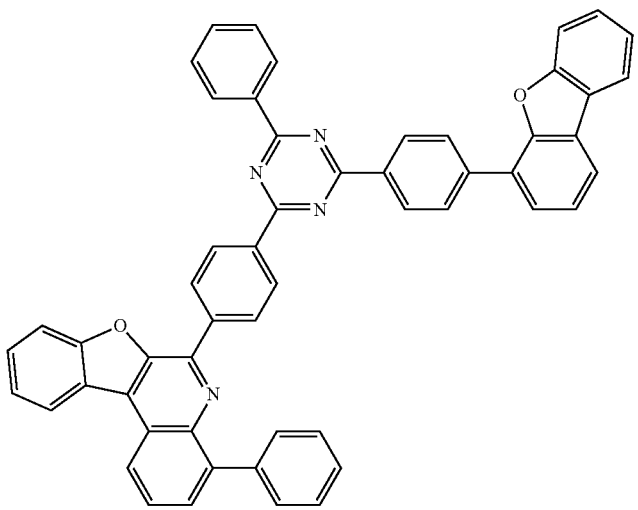 [SMILES: c1ccc(-c2nc(-c3ccc(-c4cccc5c4oc4ccccc45)cc3)nc(-c3ccc(-c4nc5c(-c6ccccc6)cccc5c5c4oc4ccccc45)cc3)n2)cc1] | 70% |
| 474 | 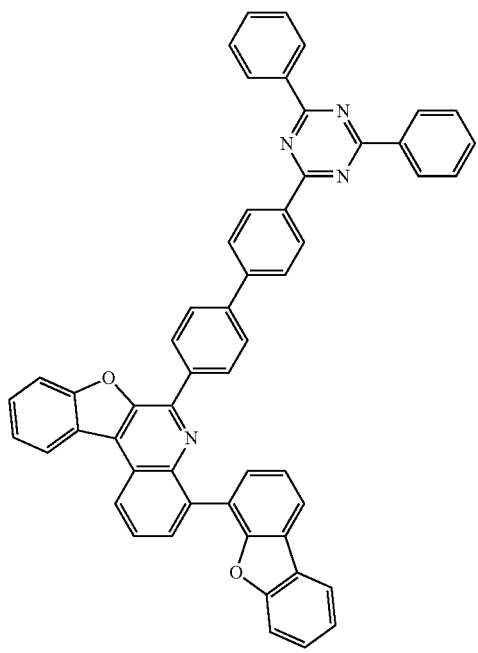 [SMILES: c1ccc(-c2nc(-c3ccccc3)nc(-c3ccc(-c4ccc(-c5nc6c(-c7cccc8c7oc7ccccc78)cccc6c6c5oc5ccccc56)cc4)cc3)n2)cc1] | 72% |
| 532 | 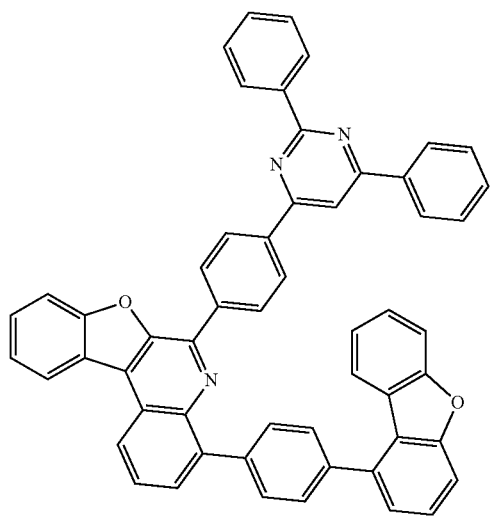 [SMILES: c1ccc(-c2cc(-c3ccc(-c4nc5c(-c6ccc(-c7cccc8oc9ccccc9c78)cc6)cccc5c5c4oc4ccccc45)cc3)nc(-c3ccccc3)n2)cc1] | 64% |

TABLE 26-continued
| 535 | 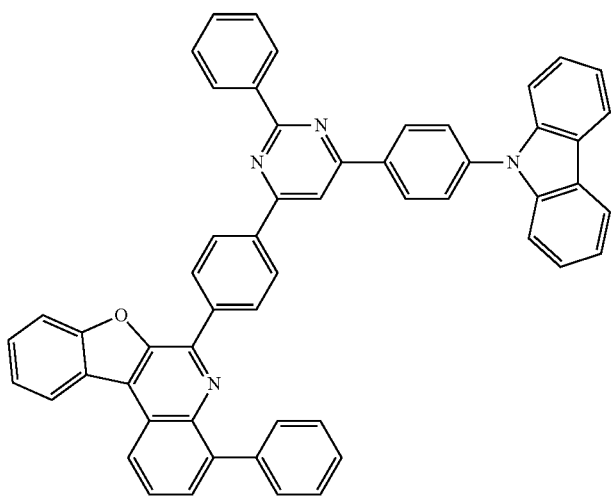 | 66% |
| 538 | 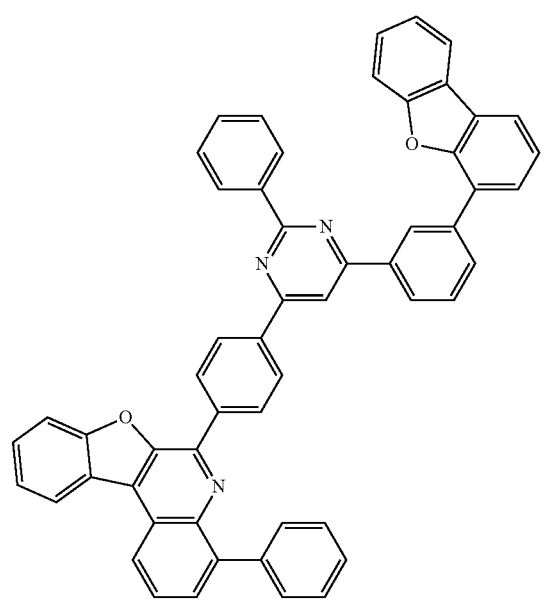 [SMILES: c1ccc(-c2nc(-c3ccc(-c4nc5c(-c6ccccc6)cccc5c5c4oc4ccccc45)cc3)cc(-c3cccc(-c4cccc5c4oc4ccccc45)c3)n2)cc1] | 71% |
| 585 | 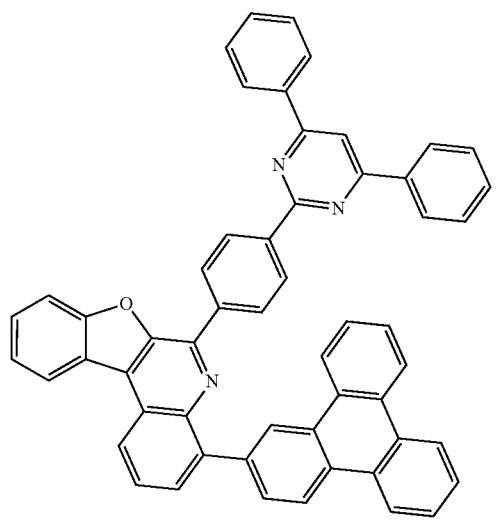 [SMILES: c1ccc(-c2cc(-c3ccccc3)nc(-c3ccc(-c4nc5c(-c6ccc7c8ccccc8c8ccccc8c7c6)cccc5c5c4oc4ccccc45)cc3)n2)cc1] | 71% |

TABLE 26-continued
| 590 | 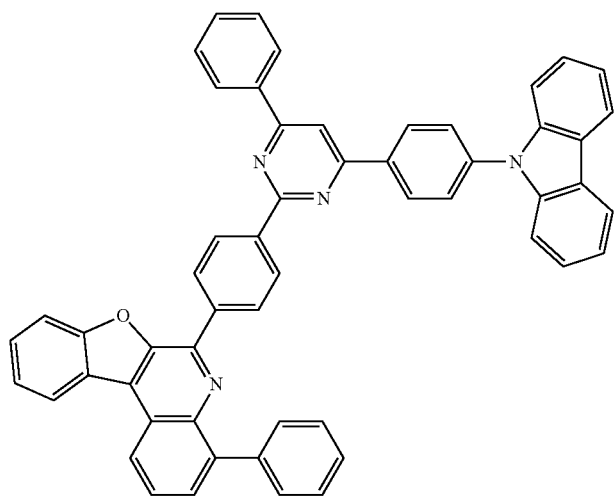 [SMILES: c1ccc(-c2cc(-c3ccc(-n4c5ccccc5c5ccccc54)cc3)nc(-c3ccc(-c4nc5c(-c6ccccc6)cccc5c5c4oc4ccccc45)cc3)n2)cc1] | 67% |
| 639 | 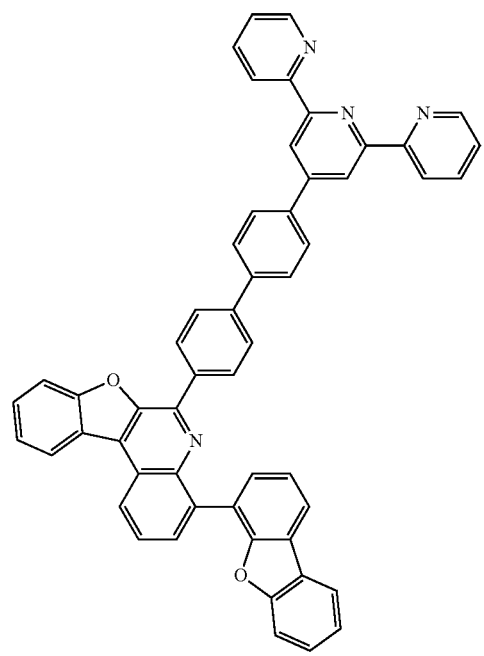 | 65% |

| 642 | 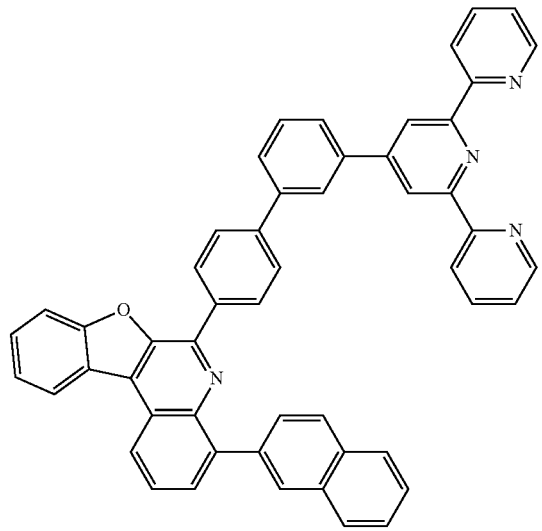 [SMILES: c1ccc(-c2cc(-c3cccc(-c4ccc(-c5nc6c(-c7ccc8ccccc8c7)cccc6c6c5oc5ccccc56)cc4)c3)cc(-c3ccccn3)n2)nc1] | 69% |

A target compound was synthesized in the same manner as in Preparation Example 4 except that 3-bromobenzoyl chloride was used instead of 4-bromobenzoyl chloride, Intermediate AI of the following Table 27 was used instead of 2-chloro-4,6-diphenyl-1,3,5-triazine, and Intermediate AJ of the following Table 27 was used instead of triphenylen-2-ylboronic acid.

TABLE 27

| Compound Number | Intermediate AI | Intermediate AJ | Target Compound | Yield |
|---|---|---|---|---|
| 594 | | | | 71% |

TABLE 27-continued

| Compound Number | Intermediate AI | Intermediate AJ | Target Compound | Yield |
|---|---|---|---|---|
| 657 | 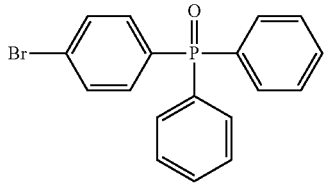 [SMILES: O=P(c1ccccc1)(c1ccccc1)c1ccc(Br)cc1] | 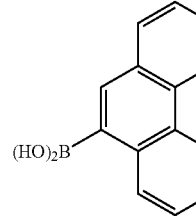 | 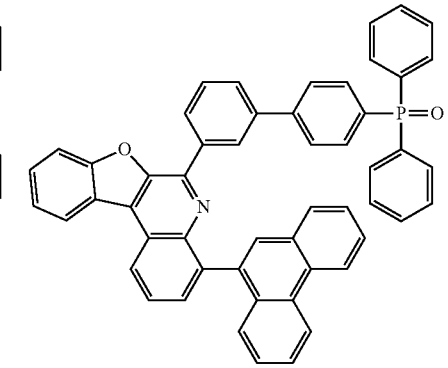 | 61% |

A target compound was synthesized in the same manner as in Preparation Example 4 except that 2-bromo-5-chloroaniline was used instead of 2-bromo-6-chloroaniline, Intermediate AK of the following Table 28 was used instead of 2-chloro-4,6-diphenyl-1,3,5-triazine, and Intermediate AL of the following Table 28 was used instead of triphenylen-2-ylboronic acid.

TABLE 28

| Compound Number | Intermediate AK | Intermediate AL |
|---|---|---|
| 477 | 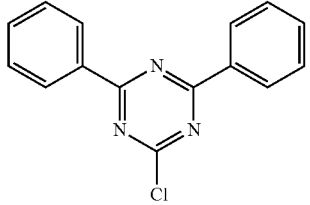 [SMILES: Clc1nc(-c2ccccc2)nc(-c2ccccc2)n1] | 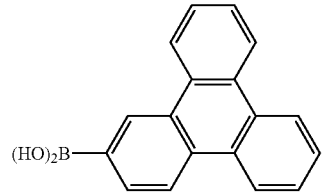 [SMILES: OB(O)c1ccc2c3ccccc3c3ccccc3c2c1] |
| 488 | 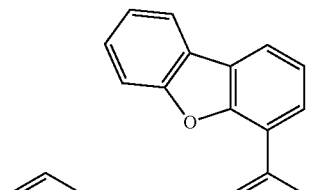 | 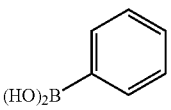 |
| 543 | 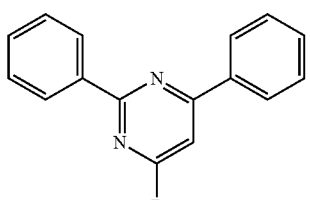 | 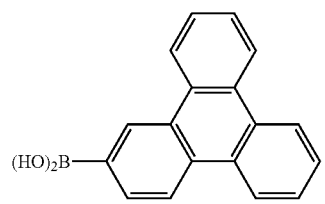 [SMILES: OB(O)c1ccc2c3ccccc3c3ccccc3c2c1] |

TABLE 28-continued
| 549 | 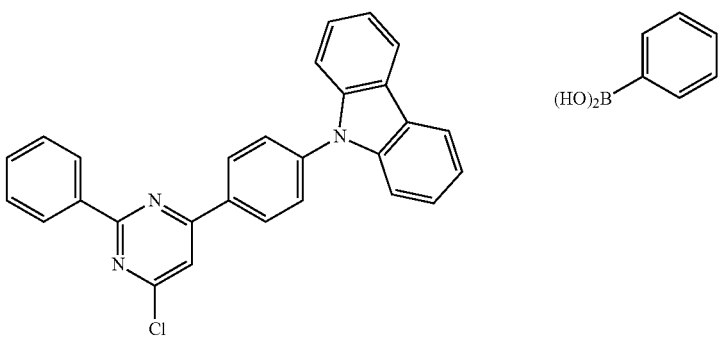 | 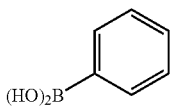 |
| 598 | 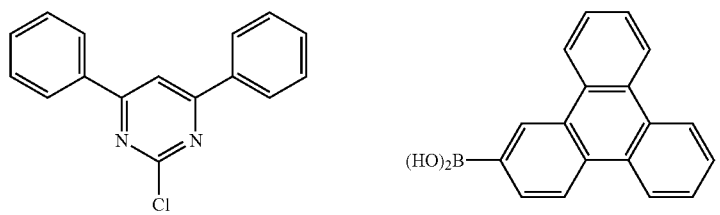 | 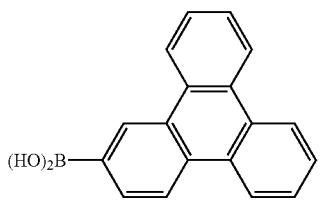 [SMILES: OB(O)c1ccc2c3ccccc3c3ccccc3c2c1] |
| 603 | 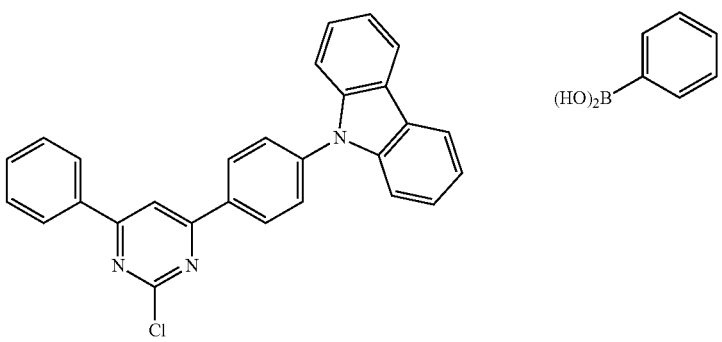 | 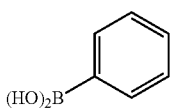 |
| 609 | 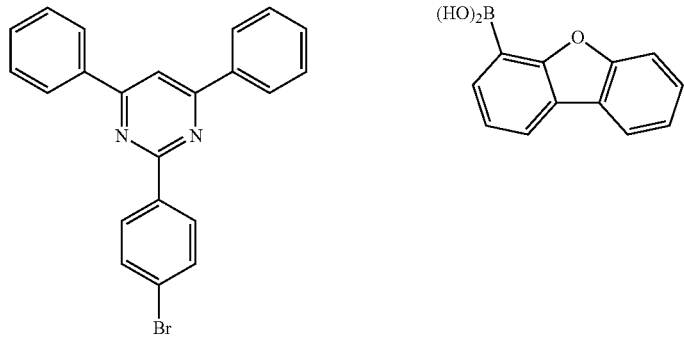 | 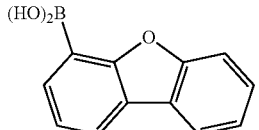 |
| 646 | 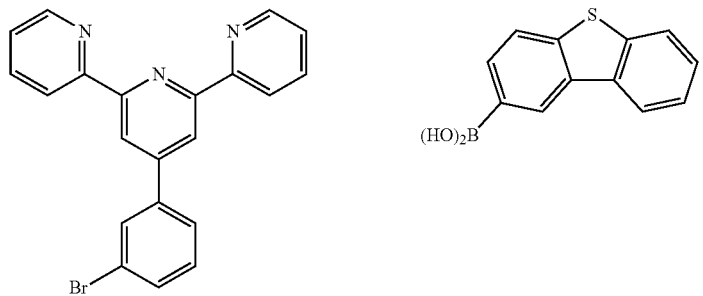 | 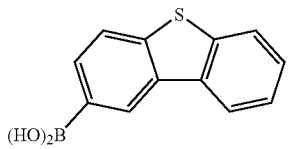 [SMILES: OB(O)c1ccc2sc3ccccc3c2c1] |

TABLE 28-continued
| 659 | 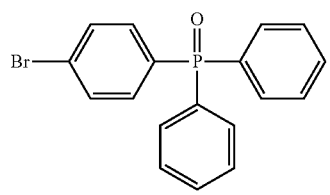 [SMILES: O=P(c1ccccc1)(c1ccccc1)c1ccc(Br)cc1] | 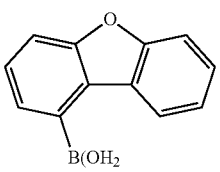 |
| Compound Number | Target Compound | Yield |
| --- | --- | --- |
| 477 | 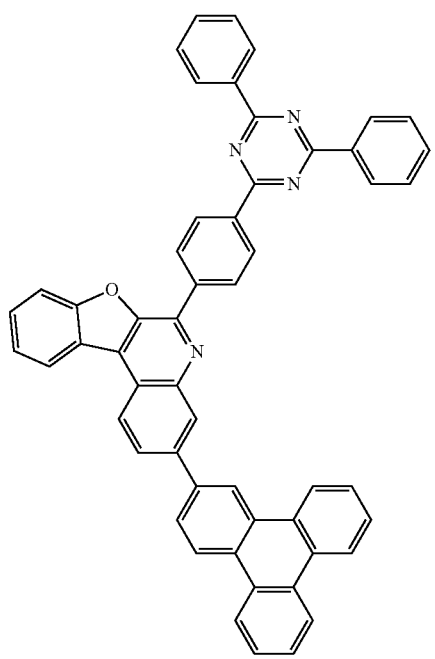 | 58% |
| 488 | 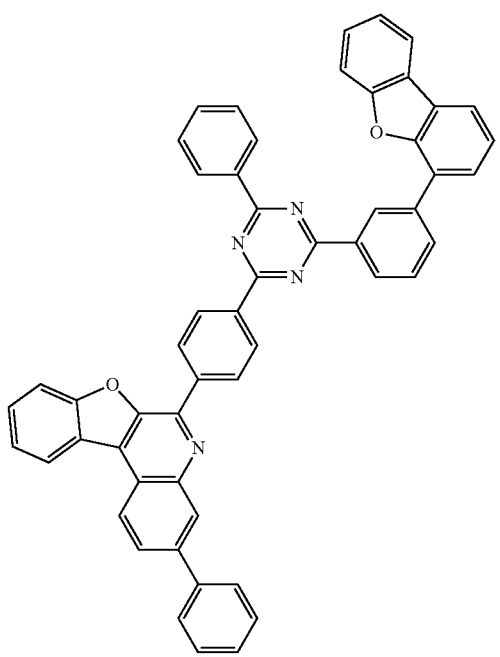 [SMILES: c1ccc(-c2ccc3c(c2)nc(-c2ccc(-c4nc(-c5ccccc5)nc(-c5cccc(-c6cccc7c6oc6ccccc67)c5)n4)cc2)c2oc4ccccc4c23)cc1] | 72% |

TABLE 28-continued
| 543 | 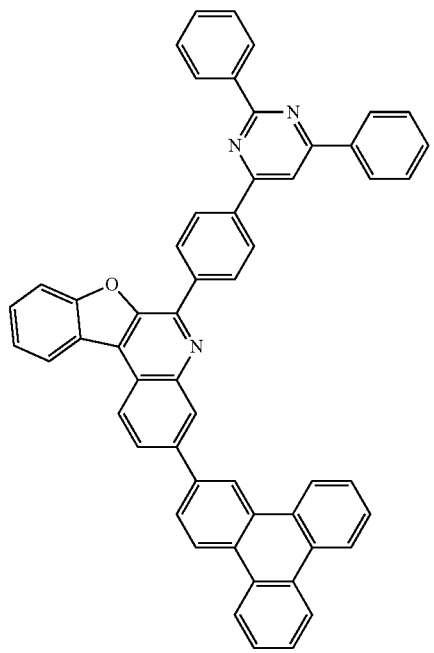 [SMILES: c1ccc(-c2cc(-c3ccc(-c4nc5cc(-c6ccc7c8ccccc8c8ccccc8c7c6)ccc5c5c4oc4ccccc45)cc3)nc(-c3ccccc3)n2)cc1] | 68% |
| 549 | 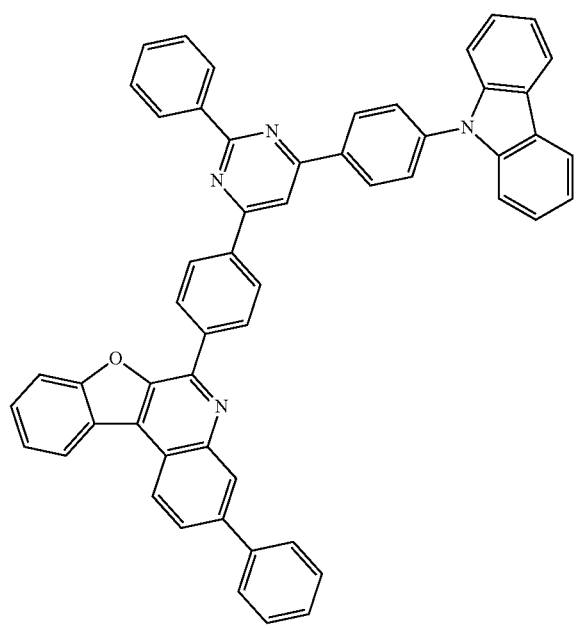 [SMILES: c1ccc(-c2ccc3c(c2)nc(-c2ccc(-c4cc(-c5ccc(-n6c7ccccc7c7ccccc76)cc5)nc(-c5ccccc5)n4)cc2)c2oc4ccccc4c23)cc1] | 71% |

TABLE 28-continued
| 598 | 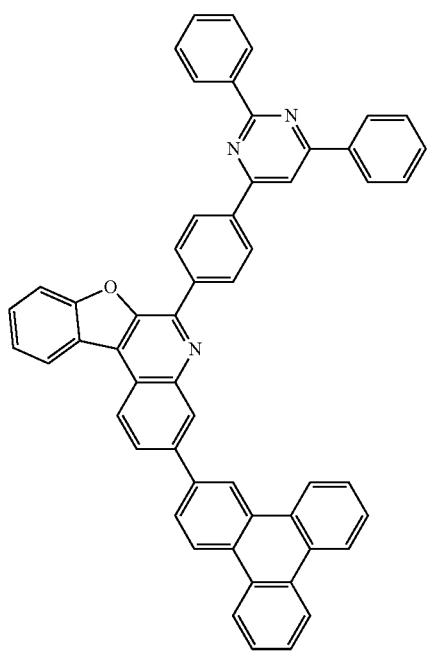 [SMILES: c1ccc(-c2cc(-c3ccc(-c4nc5cc(-c6ccc7c8ccccc8c8ccccc8c7c6)ccc5c5c4oc4ccccc45)cc3)nc(-c3ccccc3)n2)cc1] | 68% |
| 603 | 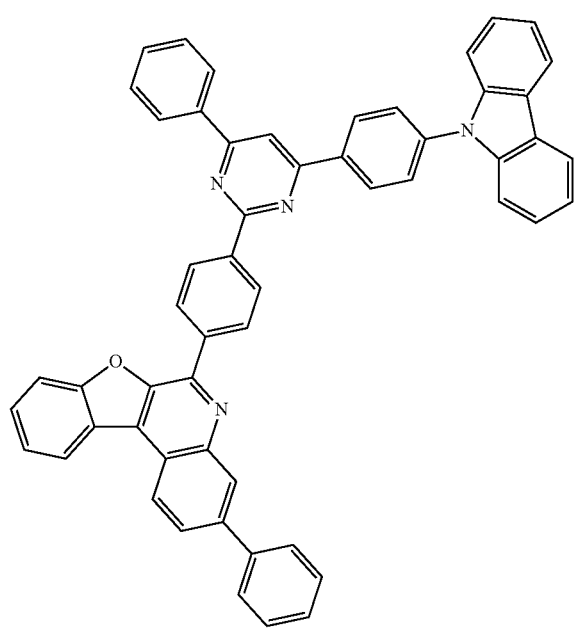 [SMILES: c1ccc(-c2ccc3c(c2)nc(-c2ccc(-c4nc(-c5ccccc5)cc(-c5ccc(-n6c7ccccc7c7ccccc76)cc5)n4)cc2)c2oc4ccccc4c23)cc1] | 61% |

| | | |
|---|---|---|
| 609 | 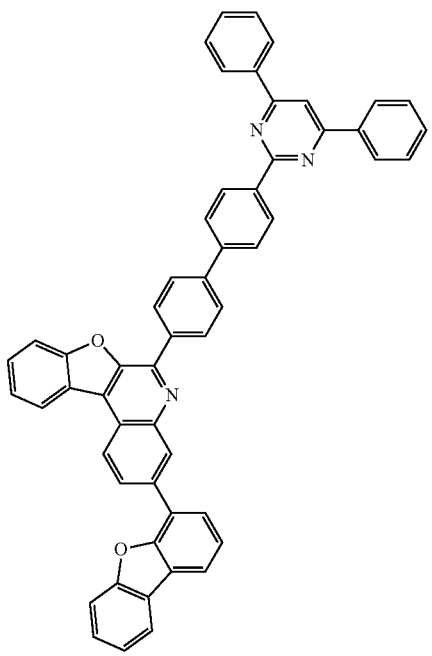 [SMILES: c1ccc(-c2cc(-c3ccccc3)nc(-c3ccc(-c4ccc(-c5nc6cc(-c7cccc8c7oc7ccccc78)ccc6c6c5oc5ccccc56)cc4)cc3)n2)cc1] | 58% |
| 646 | 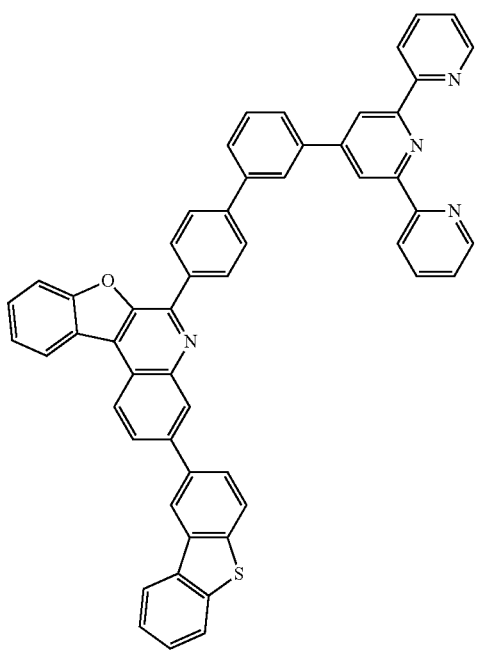 | 68% |

TABLE 28-continued

659 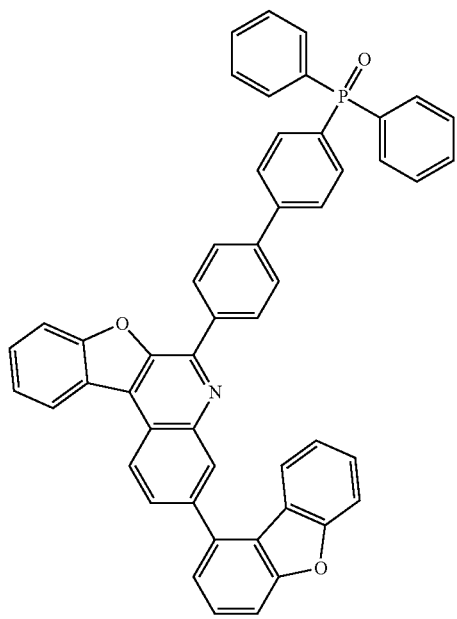 [SMILES: O=P(c1ccccc1)(c1ccccc1)c1ccc(-c2ccc(-c3nc4cc(-c5cccc6oc7ccccc7c56)ccc4c4c3oc3ccccc34)cc2)cc1] 67%

A target compound was synthesized in the same manner as in Preparation Example 4 except that 2-bromo-5-chloroaniline was used instead of 2-bromo-6-chloroaniline, 3-bromobenzoyl chloride was used instead of 4-bromobenzoyl chloride, Intermediate AM of the following Table 29 was used instead of 2-chloro-4,6-diphenyl-1,3,5-triazine, and Intermediate AN of the following Table 29 was used instead of triphenylen-2-ylboronic acid.

TABLE 29

| Compound Number | Intermediate AM | Intermediate AN |
|---|---|---|
| 485 | | |
| 491 | | |

TABLE 29-continued
| 551 | 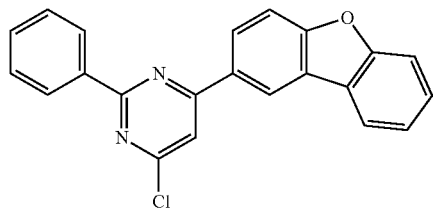 [SMILES: Clc1cc(-c2ccc3oc4ccccc4c3c2)nc(-c2ccccc2)n1] | 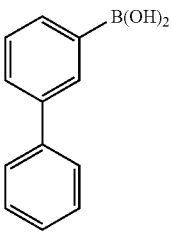 [SMILES: OB(O)c1cccc(-c2ccccc2)c1] |
| Compound Number | Target Compound | Yield |
| --- | --- | --- |
| 485 | | 69% |
| 491 | | 61% |

TABLE 29-continued

551 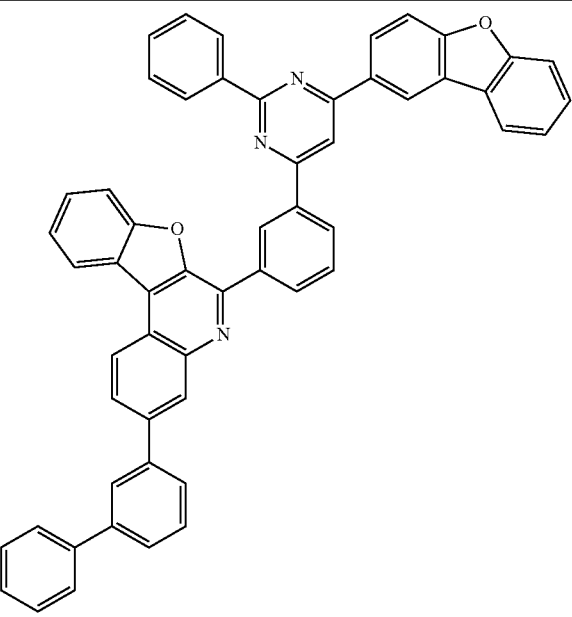 72%

A target compound was synthesized in the same manner as in Preparation Example 4 except that 2-bromo-4-chloroaniline was used instead of 2-bromo-6-chloroaniline, Intermediate AO of the following Table 30 was used instead of 2-chloro-4,6-diphenyl-1,3,5-triazine, and Intermediate AP of the following Table 30 was used instead of triphenylen-2-ylboronic acid.

TABLE 30

| Compound Number | Intermediate AO | Intermediate AP |
|---|---|---|
| 493 | | |
| 511 | | |

TABLE 30-continued
516 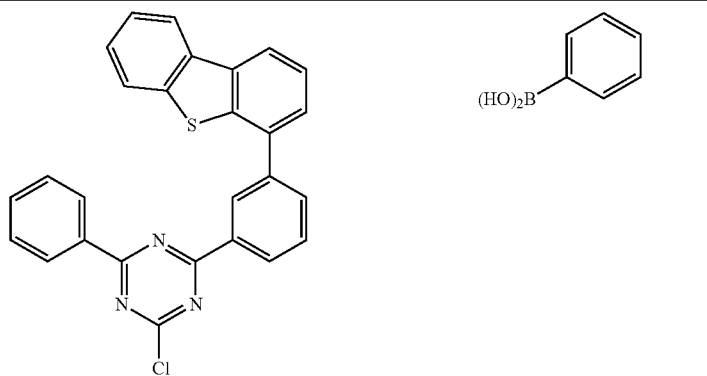
517 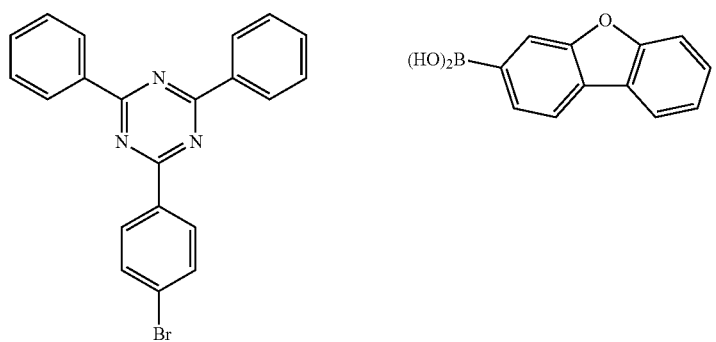
558 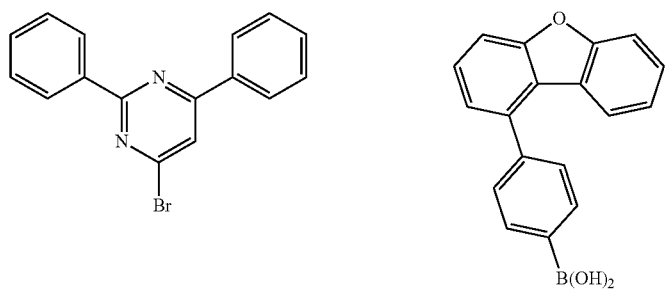
560 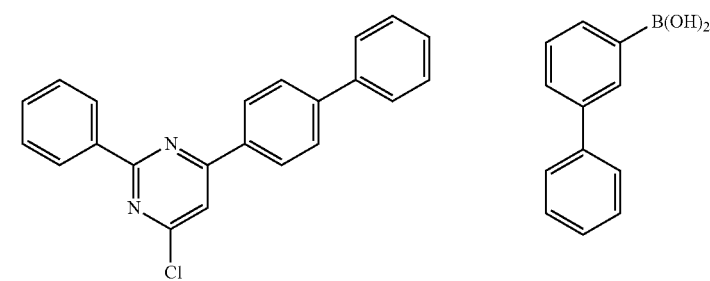
563 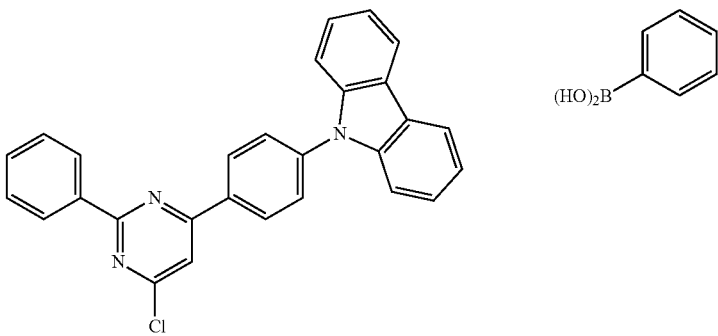

TABLE 30-continued
| | | |
|---|---|---|
| 566 | 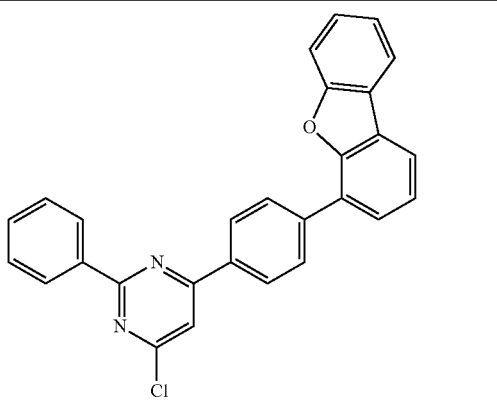 | 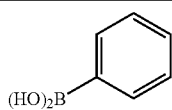 |
| 611 | 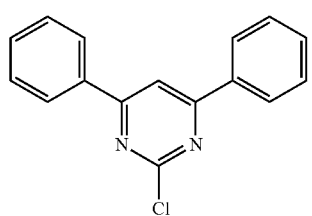 [SMILES: Clc1nc(-c2ccccc2)cc(-c2ccccc2)n1] | 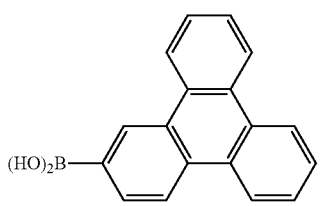 [SMILES: OB(O)c1ccc2c3ccccc3c3ccccc3c2c1] |
| 616 | 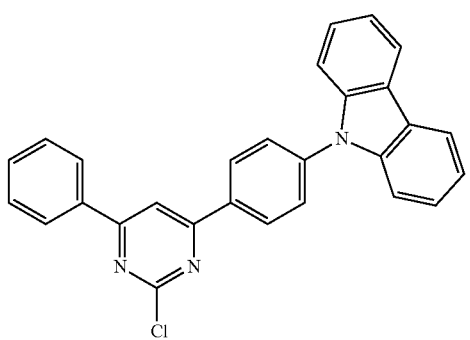 [SMILES: Clc1nc(-c2ccccc2)cc(-c2ccc(-n3c4ccccc4c4ccccc43)cc2)n1] | 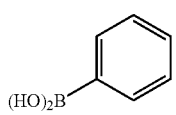 |
| 619 | 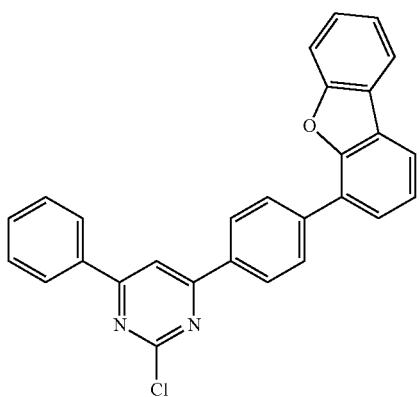 | 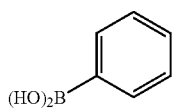 |
| 650 | 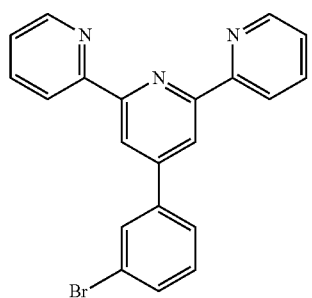 [SMILES: Brc1cccc(-c2cc(-c3ccccn3)nc(-c3ccccn3)c2)c1] | 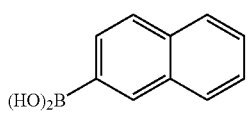 [SMILES: OB(O)c1ccc2ccccc2c1] |

TABLE 30-continued
| 663 | 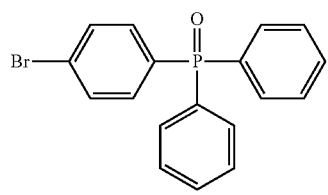 | 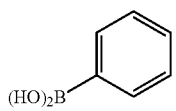 |
| Compound Number | Target Compound | Yield |
| --- | --- | --- |
| 493 | 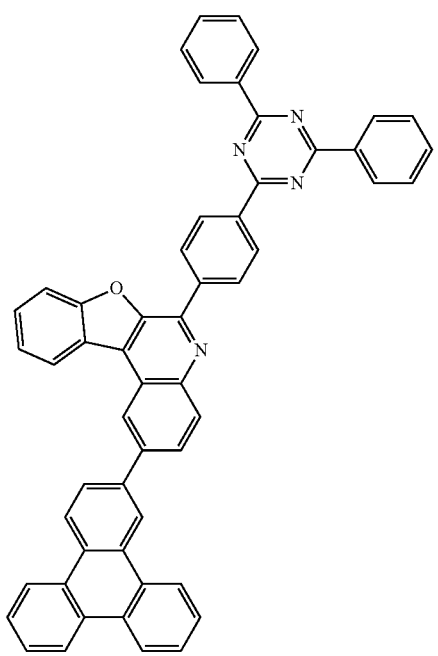 [SMILES: c1ccc(-c2nc(-c3ccccc3)nc(-c3ccc(-c4nc5ccc(-c6ccc7c8ccccc8c8ccccc8c7c6)cc5c5c4oc4ccccc45)cc3)n2)cc1] | 63% |
| 511 | 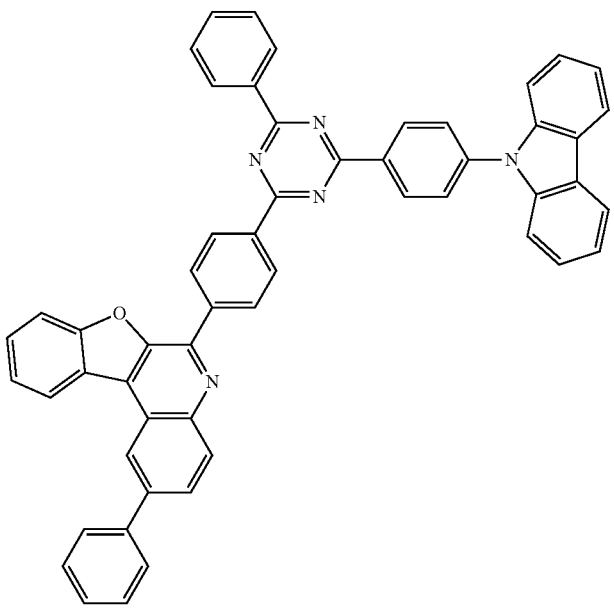 | 66% |

TABLE 30-continued
| | | |
|---|---|---|
| 516 | 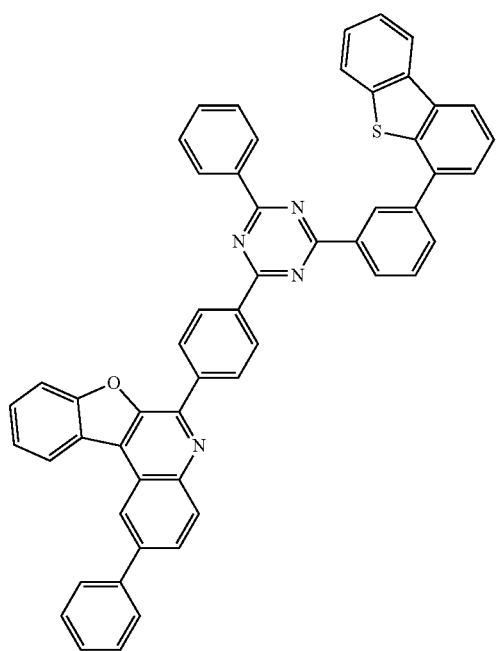 [SMILES: c1ccc(-c2ccc3nc(-c4ccc(-c5nc(-c6ccccc6)nc(-c6cccc(-c7cccc8c7sc7ccccc78)c6)n5)cc4)c4oc5ccccc5c4c3c2)cc1] | 70% |
| 517 | 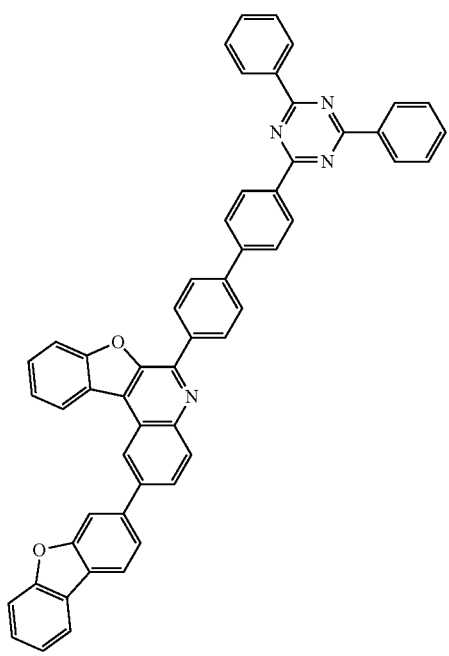 [SMILES: c1ccc(-c2nc(-c3ccccc3)nc(-c3ccc(-c4ccc(-c5nc6ccc(-c7ccc8c(c7)oc7ccccc78)cc6c6c5oc5ccccc56)cc4)cc3)n2)cc1] | 62% |

TABLE 30-continued
| 558 | 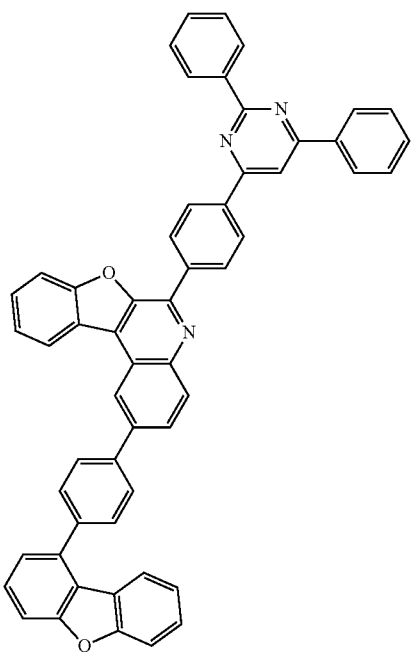 [SMILES: c1ccc(-c2cc(-c3ccc(-c4nc5ccc(-c6ccc(-c7cccc8oc9ccccc9c78)cc6)cc5c5c4oc4ccccc45)cc3)nc(-c3ccccc3)n2)cc1] | 67% |
| 560 | 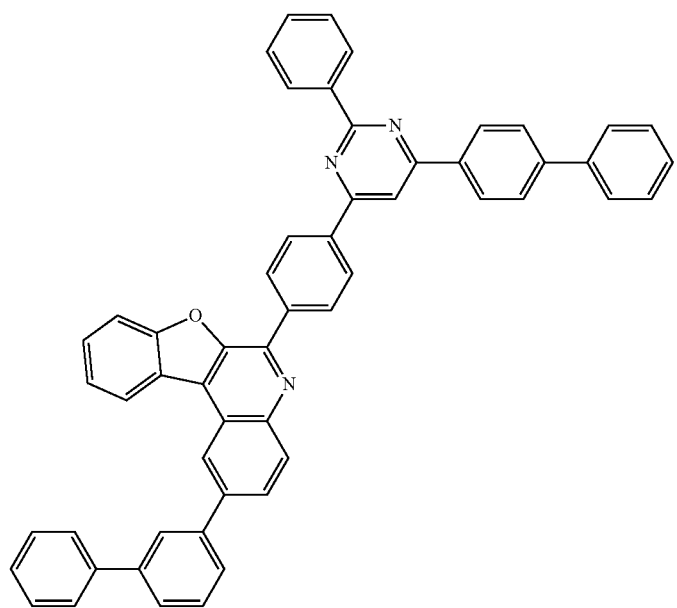 | 73% |

TABLE 30-continued
563 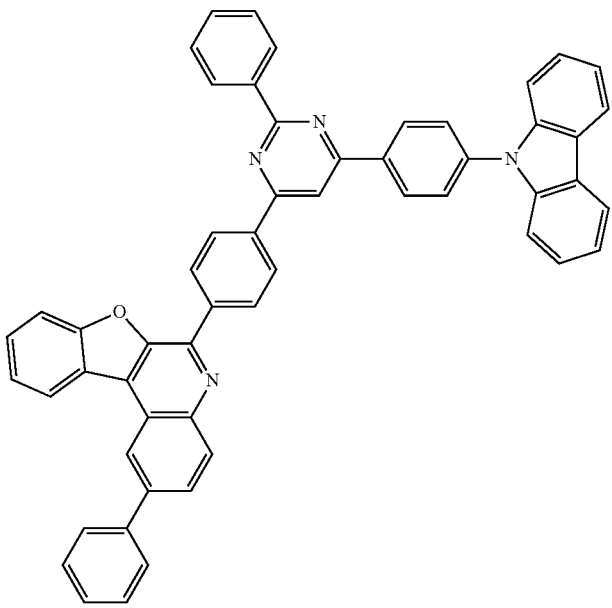 59%
566 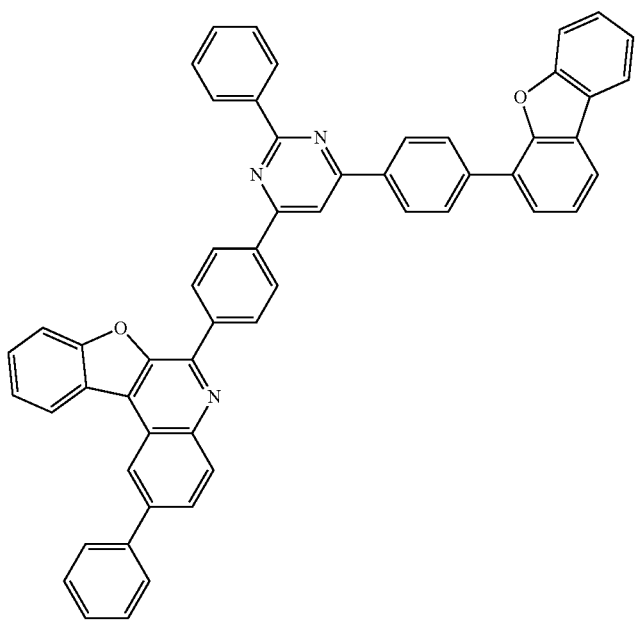 [SMILES: c1ccc(-c2ccc3nc(-c4ccc(-c5cc(-c6ccc(-c7cccc8c7oc7ccccc78)cc6)nc(-c6ccccc6)n5)cc4)c4oc5ccccc5c4c3c2)cc1] 69%

TABLE 30-continued
611 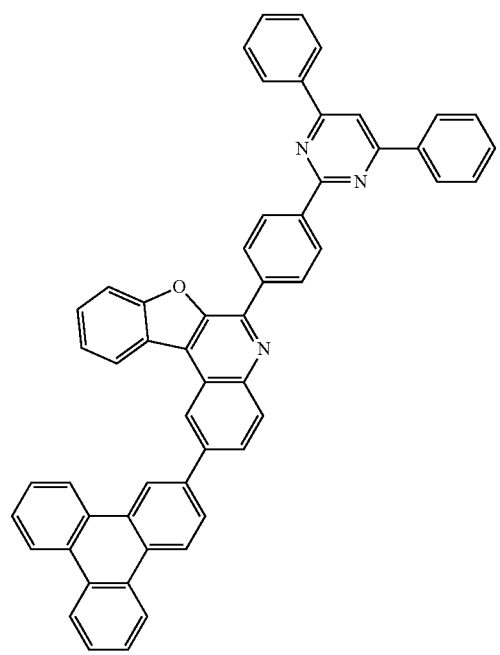 [SMILES: c1ccc(-c2cc(-c3ccccc3)nc(-c3ccc(-c4nc5ccc(-c6ccc7c8ccccc8c8ccccc8c7c6)cc5c5c4oc4ccccc45)cc3)n2)cc1] 64%
616 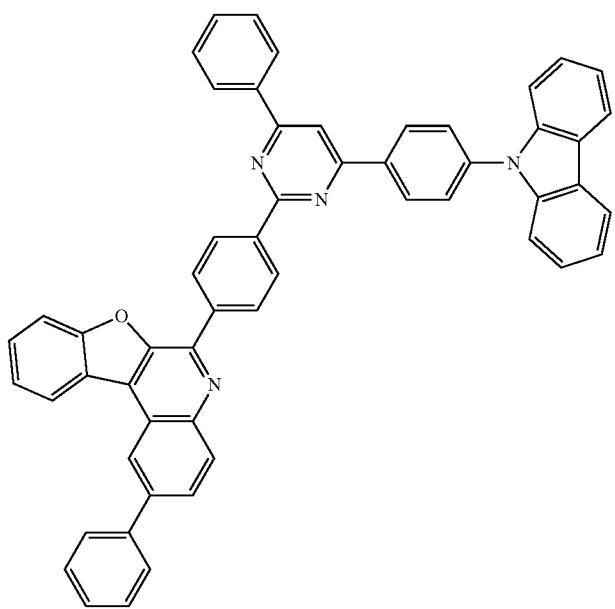 [SMILES: c1ccc(-c2ccc3nc(-c4ccc(-c5nc(-c6ccccc6)cc(-c6ccc(-n7c8ccccc8c8ccccc87)cc6)n5)cc4)c4oc5ccccc5c4c3c2)cc1] 58%

TABLE 30-continued
619 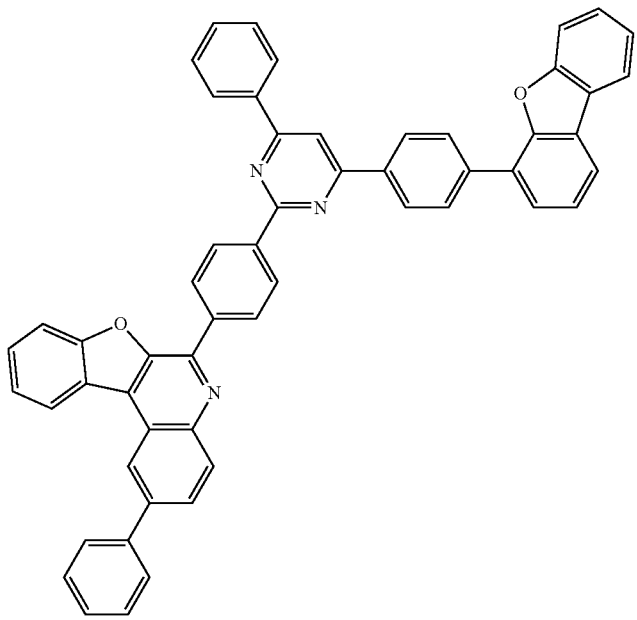 [SMILES: c1ccc(-c2ccc3nc(-c4ccc(-c5nc(-c6ccccc6)cc(-c6ccc(-c7cccc8c7oc7ccccc78)cc6)n5)cc4)c4oc5ccccc5c4c3c2)cc1] 61%
650 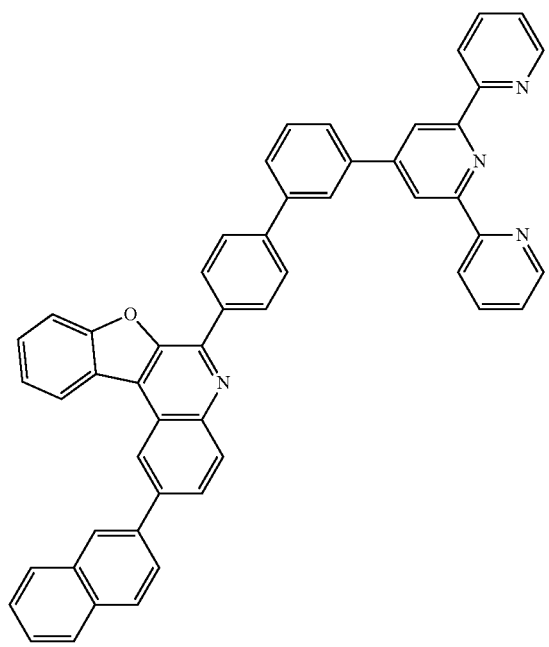 [SMILES: c1ccc(-c2cc(-c3cccc(-c4ccc(-c5nc6ccc(-c7ccc8ccccc8c7)cc6c6c5oc5ccccc56)cc4)c3)cc(-c3ccccn3)n2)nc1] 54%

| 663 | 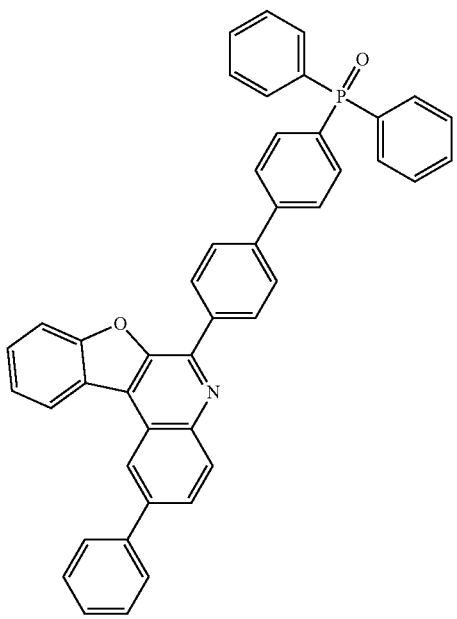 [SMILES: O=P(c1ccccc1)(c1ccccc1)c1ccc(-c2ccc(-c3nc4ccc(-c5ccccc5)cc4c4c3oc3ccccc34)cc2)cc1] | 65% |
A target compound was synthesized in the same manner as in Preparation Example 4 except that 2-bromo-3-chloroaniline was used instead of 2-bromo-6-chloroaniline, Intermediate AQ of the following Table 31 was used instead of 2-chloro-4,6-diphenyl-1,3,5-triazine, and Intermediate AR of the following Table 31 was used instead of triphenylen-2-ylboronic acid.

TABLE 31
| Compound Number | Intermediate AQ | Intermediate AR | Target Compound | Yield |
|---|---|---|---|---|
| 519 | 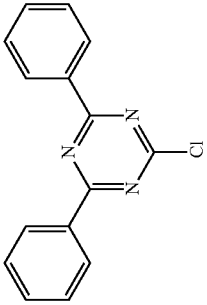 | 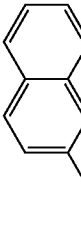 | 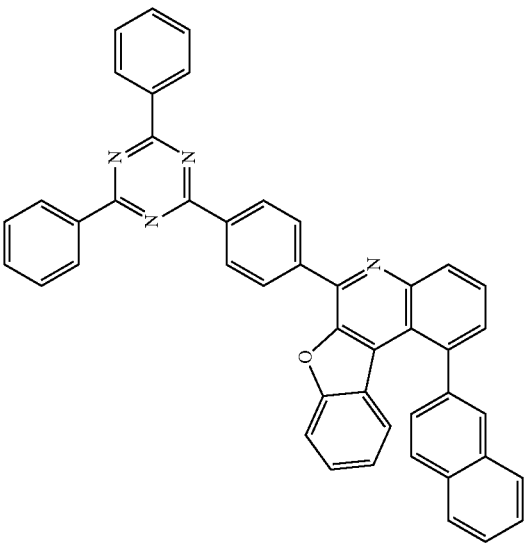 | 66% |

TABLE 31-continued

| Compound Number | Intermediate AQ | Intermediate AR | Target Compound | Yield |
|---|---|---|---|---|
| 528 | (structure) | (HO)₂B-Ph | (structure) | 67% |

TABLE 31-continued
| Compound Number | Intermediate AQ | Intermediate AR | Target Compound | Yield |
|---|---|---|---|---|
| 572 | 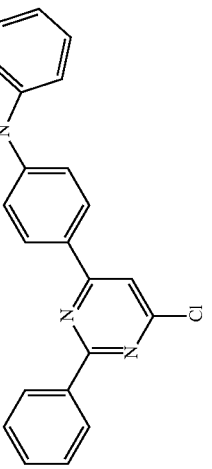 |  | 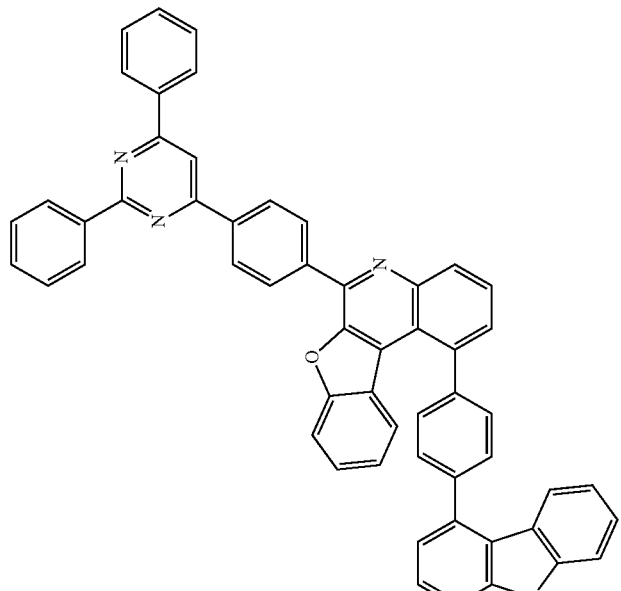 | 70% |

TABLE 31-continued

| Compound Number | Intermediate AQ | Intermediate AR | Target Compound | Yield |
|---|---|---|---|---|
| 577 | (structure) | (HO)₂B-Ph | (structure) | 66% |

TABLE 31-continued

| Compound Number | Intermediate AQ | Intermediate AR | Target Compound | Yield |
|---|---|---|---|---|
| 579 | (structure) | (structure) | (structure) | 61% |

TABLE 31-continued

| Compound Number | Intermediate AQ | Intermediate AR | Target Compound | Yield |
|---|---|---|---|---|
| 626 | (2-chloro-4,6-diphenylpyrimidine) | (4-(dibenzofuran-1-yl)phenyl)boronic acid | (structure) | 70% |

TABLE 31-continued

| Compound Number | Intermediate AQ | Intermediate AR | Target Compound | Yield |
|---|---|---|---|---|
| 667 | (4-bromophenyl)diphenylphosphine oxide | dibenzofuran-1-ylboronic acid | (structure) | 59% |

TABLE 31-continued
| Compound Number | Intermediate AQ | Intermediate AR | Target Compound | Yield |
|---|---|---|---|---|
| 924 | 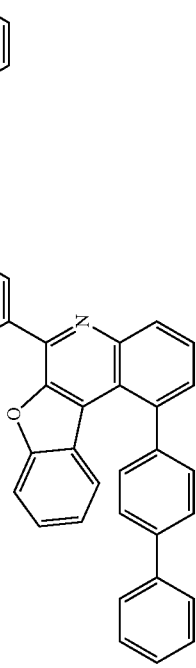 | 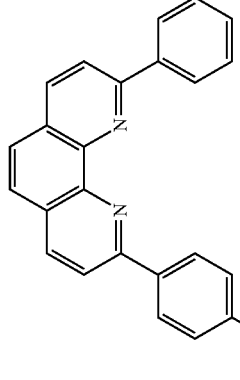 | 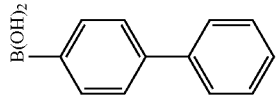 | 62% |

A target compound was synthesized in the same manner as in Preparation Example 4 except that 2-bromo-3-chloroaniline was used instead of 2-bromo-6-chloroaniline, 3-bromobenzoyl chloride was used instead of 4-bromobenzoyl chloride, Intermediate AS of the following Table 32 was used instead of 2-chloro-4,6-diphenyl-1,3,5-triazine, and Intermediate AT of the following Table 32 was used instead of triphenylen-2-ylboronic acid.

TABLE 32

| Compound Number | Intermediate AS | Intermediate AT | Target Compound | Yield |
|---|---|---|---|---|
| 529 | 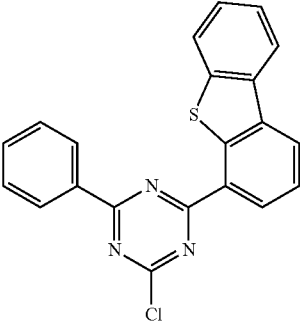 | 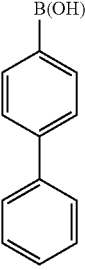 | 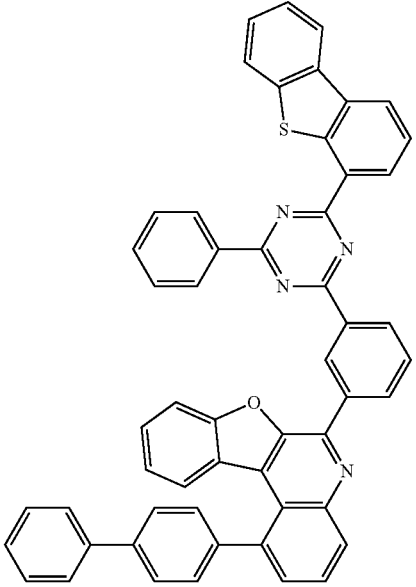 [SMILES: c1ccc(-c2ccc(-c3cccc4nc(-c5cccc(-c6nc(-c7ccccc7)nc(-c7cccc8c7sc7ccccc78)n6)c5)c5oc6ccccc6c5c34)cc2)cc1] | 65% |
| 631 | 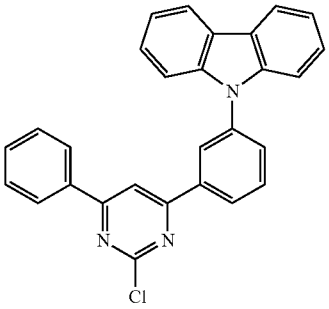 [SMILES: Clc1nc(-c2ccccc2)cc(-c2cccc(-n3c4ccccc4c4ccccc43)c2)n1] | 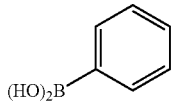 | 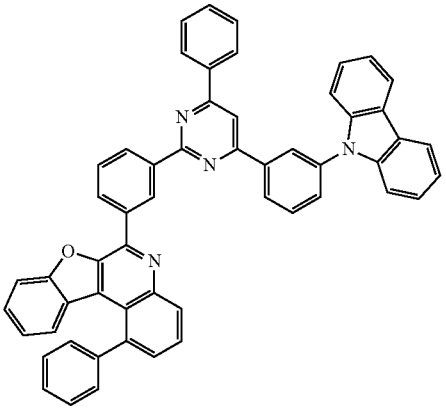 [SMILES: c1ccc(-c2cc(-c3cccc(-n4c5ccccc5c5ccccc54)c3)nc(-c3cccc(-c4nc5cccc(-c6ccccc6)c5c5c4oc4ccccc45)c3)n2)cc1] | 65% |
| 634 | 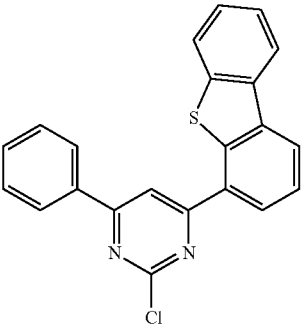 [SMILES: Clc1nc(-c2ccccc2)cc(-c2cccc3c2sc2ccccc23)n1] | 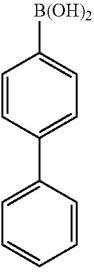 | 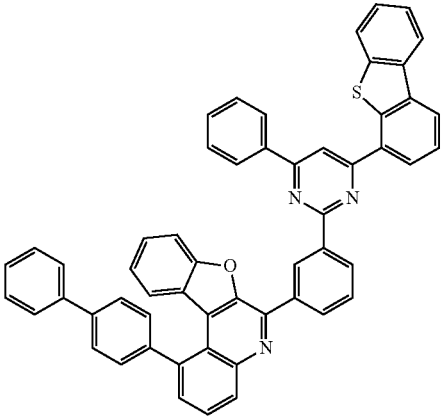 [SMILES: c1ccc(-c2ccc(-c3cccc4nc(-c5cccc(-c6nc(-c7ccccc7)cc(-c7cccc8c7sc7ccccc78)n6)c5)c5oc6ccccc6c5c34)cc2)cc1] | 63% |

TABLE 32-continued
| Compound Number | Intermediate AS | Intermediate AT | Target Compound | Yield |
|---|---|---|---|---|
| 638 | | | | 65% |
| 928 | | | | 61% |
<Preparation Example 5>—Preparation of Compound 672
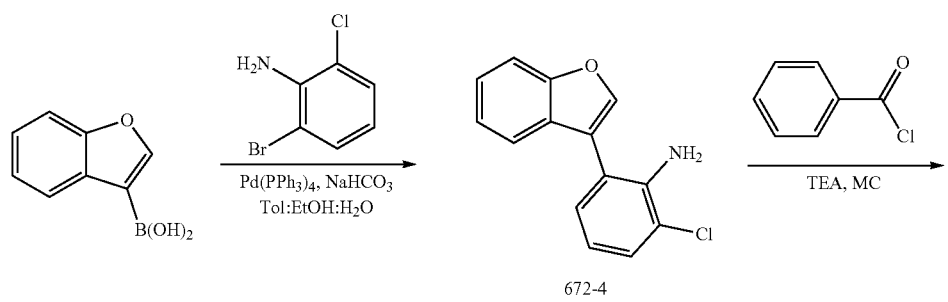

-continued
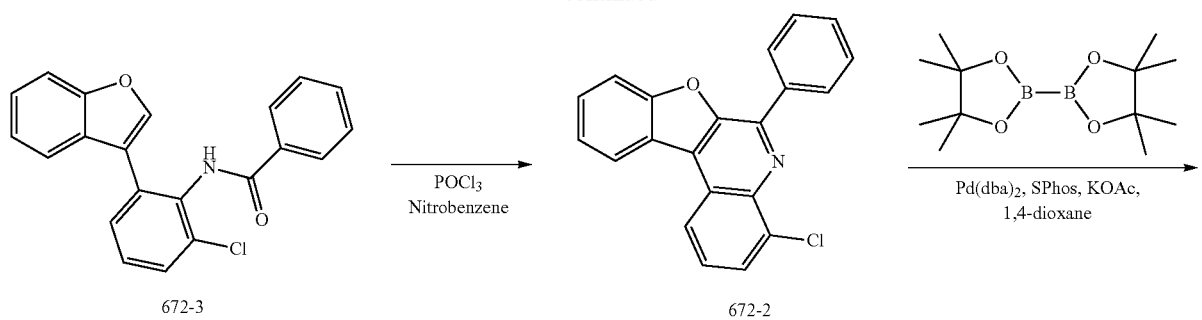
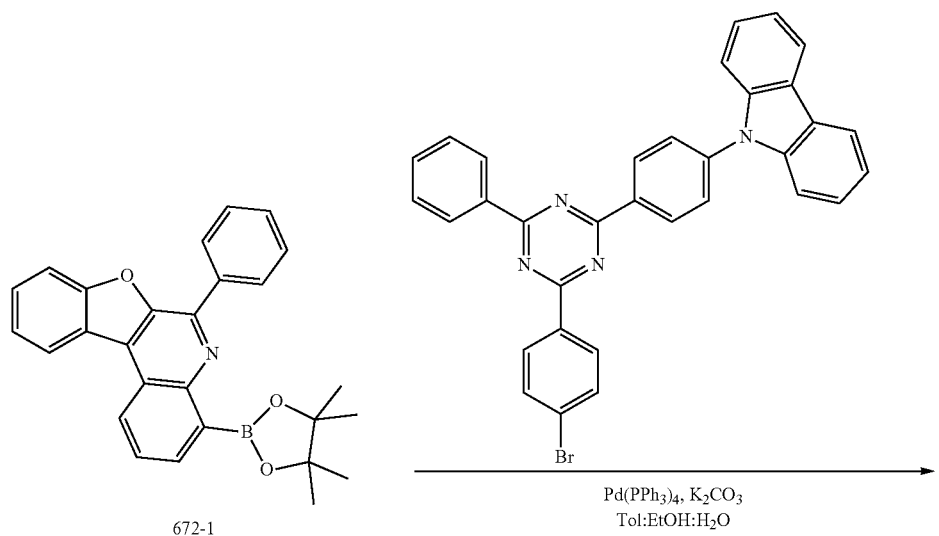
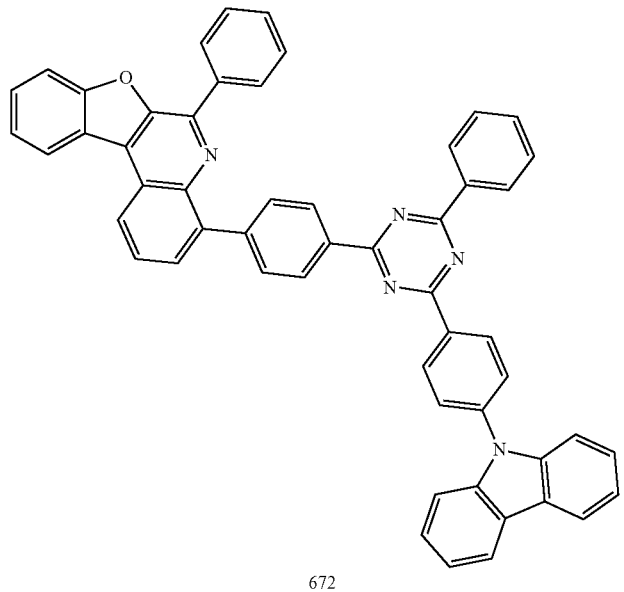

1) Preparation of Compound 672-4

After dissolving benzofuran-3-ylboronic acid (80 g, 500 mmol) and 2-bromo-6-chloroaniline (95 g, 550 mmol) in toluene, EtOH and H₂O (1500 mL:300 mL:300 mL), Pd(PPh₃)₄ (29 g, 25 mmol) and NaHCO₃ (126 g, 1500 mmol) were introduced thereto, and the result was refluxed for 4 hours. After the reaction was completed, the result was cooled to room temperature and extracted with MC. The result was dried with anhydrous MgSO4, and then the solvent was removed using a rotary evaporator. Target Compound 672-4 was obtained using column chromatography (MC:Hx=1:3). (80 g, 80%, brown oil)

2) Preparation of Compound 672-3

Compound 672-4 (90 g, 219 mmol) and triethylamine (95 mL, 660 mmol) were introduced to MC (1500 mL) and dissolved therein. Benzoyl chloride (80 g, 250 mmol) dissolved in MC (300 mL) was slowly added dropwise to the mixture at 0° C. After the reaction was completed, MC and distilled water were introduced to the reaction solution for extraction. After that, the result was dried with anhydrous MgSO4, and, after removing the solvent using a rotary evaporator, recrystallized with MC/Hx to obtain Compound 672-3. (100 g, 91%, white solid)

3) Preparation of Compound 672-2

After dissolving Compound 672-3 (40 g, 110 mmol) in nitrobenzene (400 mL), POCl₃ (13 mL, 110 mmol) was slowly added dropwise thereto. After that, the result was stirred for 12 hours at 150° C. After the reaction was completed, the reaction solution was neutralized with an aqueous NaHCO₃ solution. Solids produced from the neutralization were filtered. The solids were recrystallized with MC/MeOH to obtain target Compound 672-2. (30 g, 88%, white solid)

4) Preparation of Compound 672-1

After dissolving Compound 672-2 (30 g, 70 mmol), bis(pinacolato)diboron (27 g, 105 mmol), Pd(dba)₂ (4 g, 7 mmol), XPhos (6.8 g, 14 mmol) and KOAc (48 g, 210 mmol) in 1,4-dioxane (300 mL), the result was refluxed for 12 hours. After the reaction was completed, MC and distilled water were introduced to the reaction solution for extraction. After that, the result was dried with anhydrous MgSO4, and the solvent was removed using a rotary evaporator. After passing silica, the result went through MeOH slurry to obtain Compound 672-2. (34 g, 85%, white solid)

5) Preparation of Compound 672

After dissolving Compound 672-1 (10 g, 22.9 mmol), 9-(4-(4-(4-bromophenyl)-6-phenyl-1,3,5-triazin-2-yl)phenyl)-9H-carbazole (13 g, 22.9 mmol), Pd(PPh₃)₄ (1.3 g, 1.2 mmol) and K₂CO₃ (10 g, 69 mmol) in toluene, EtOH and H₂O (100 mL:20 mL:20 mL), the result was refluxed for 12 hours. After the reaction was finished, produced solids were filtered. The solids were washed with distilled water and acetone to obtain target Compound 672. (10 g, 70%, white solid)

A target compound was synthesized in the same manner as in Preparation Example 5 except that Intermediate AU of the following Table 33 was used instead of 9-(4-(4-(4-bromophenyl)-6-phenyl-1,3,5-triazin-2-yl)phenyl)-9H-carbazole.

TABLE 33

| Compound Number | Intermediate AU | Target Compound | Yield |
|---|---|---|---|
| 688 | | | 65% |

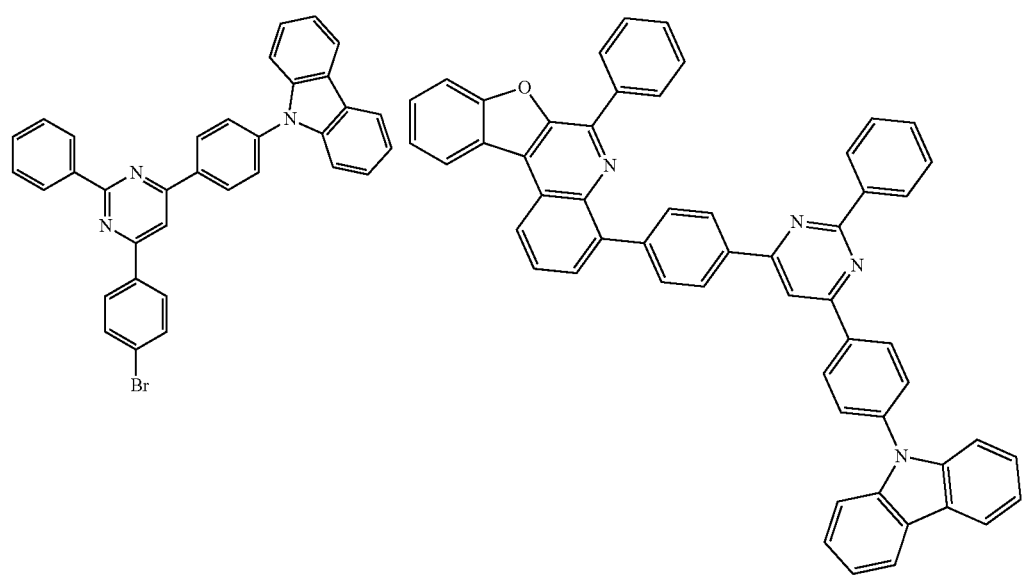

TABLE 33-continued

| Compound Number | Intermediate AU | Target Compound | Yield |
|---|---|---|---|
| 703 | | | 71% |
| 719 | | | 67% |
| 732 | | | 58% |

A target compound was synthesized in the same manner as in Preparation Example 5 except that 1-naphthoyl chloride was used instead of benzoyl chloride, and Intermediate AV of the following Table 34 was used instead of 9-(4-(4-(4-bromophenyl)-6-phenyl-1,3,5-triazin-2-yl)phenyl)-9H-carbazole.

TABLE 34

| Compound Number | Intermediate AV | Target Compound | Yield |
|---|---|---|---|
| 743 | | | 95% |

A target compound was synthesized in the same manner as in Preparation Example 5 except that phenanthrene-9-carbonyl chloride was used instead of benzoyl chloride, and Intermediate AW of the following Table 35 was used instead of 9-(4-(4-(4-bromophenyl)-6-phenyl-1,3,5-triazin-2-yl)phenyl)-9H-carbazole.

TABLE 35

| Compound Number | Intermediate AW | Target Compound | Yield |
|---|---|---|---|
| 839 | | | 66% |

A target compound was synthesized in the same manner as in Preparation Example 5 except that 2-bromo-5-chloroaniline was used instead of 2-bromo-6-chloroaniline, and Intermediate AX of the following Table 36 was used instead of 9-(4-(4-(4-bromophenyl)-6-phenyl-1,3,5-triazin-2-yl)phenyl)-9H-carbazole.

TABLE 36
| Compound Number | Intermediate AX | Target Compound | Yield |
|---|---|---|---|
| 677 | 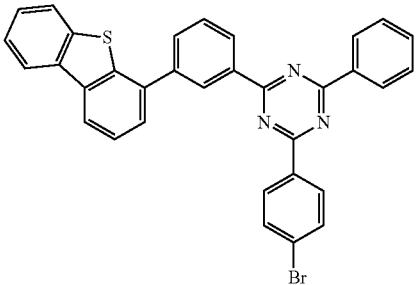 [SMILES: Brc1ccc(-c2nc(-c3ccccc3)nc(-c3cccc(-c4cccc5c4sc4ccccc45)c3)n2)cc1] | 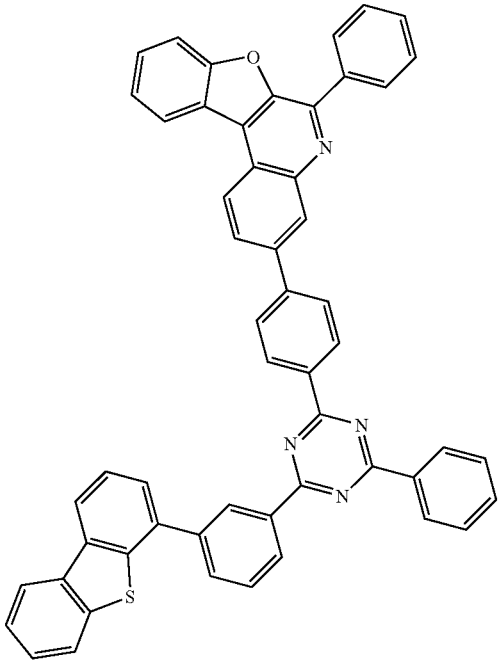 [SMILES: c1ccc(-c2nc(-c3ccc(-c4ccc5c(c4)nc(-c4ccccc4)c4oc6ccccc6c45)cc3)nc(-c3cccc(-c4cccc5c4sc4ccccc45)c3)n2)cc1] | 67% |
| 691 | 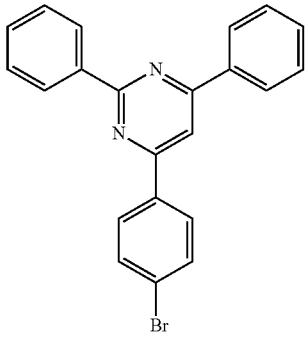 | 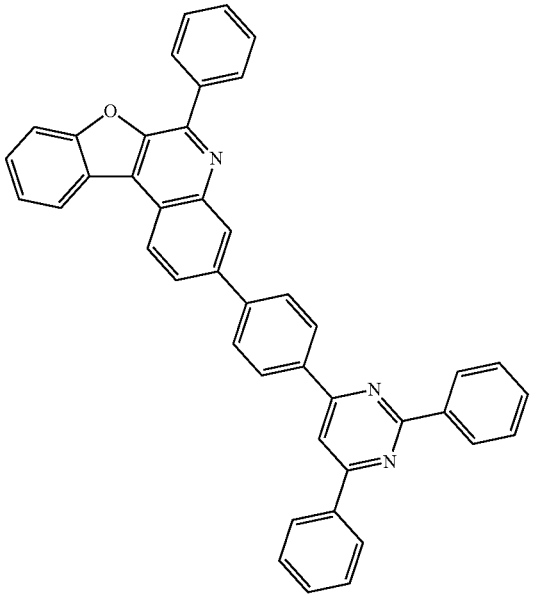 [SMILES: c1ccc(-c2cc(-c3ccc(-c4ccc5c(c4)nc(-c4ccccc4)c4oc6ccccc6c45)cc3)nc(-c3ccccc3)n2)cc1] | 71% |

TABLE 36-continued

| Compound Number | Intermediate AX | Target Compound | Yield |
|---|---|---|---|
| 693 | | | 67% |
| 723 | | | 65% |

A target compound was synthesized in the same manner as in Preparation Example 5 except that 2-bromo-5-chloroaniline was used instead of 2-bromo-6-chloroaniline, 1-naphthoyl chloride was used instead of benzoyl chloride, and Intermediate AY of the following Table 37 was used instead of 9-(4-(4-(4-bromophenyl)-6-phenyl-1,3,5-triazin-2-yl)phenyl)-9H-carbazole.

TABLE 37

| Compound Number | Intermediate AY | Target Compound | Yield |
|---|---|---|---|
| 748 | | | 61% |
| 765 | | | 78% |

TABLE 37-continued
| Compound Number | Intermediate AY | Target Compound | Yield |
|---|---|---|---|
| 779 | 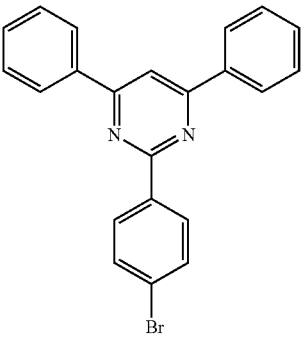 [SMILES: Brc1ccc(-c2nc(-c3ccccc3)cc(-c3ccccc3)n2)cc1] | 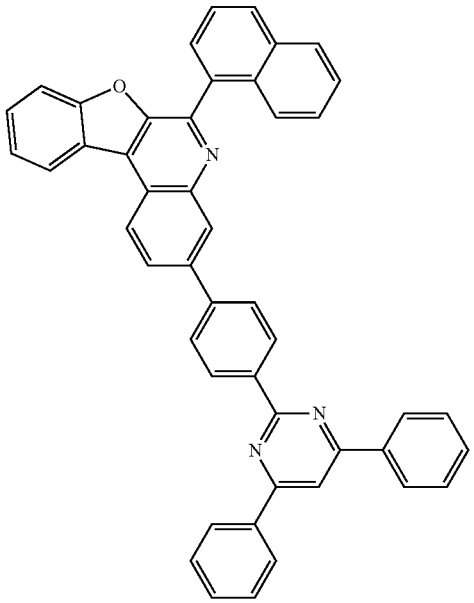 [SMILES: c1ccc(-c2cc(-c3ccccc3)nc(-c3ccc(-c4ccc5c(c4)nc(-c4cccc6ccccc46)c4oc6ccccc6c45)cc3)n2)cc1] | 58% |
| 794 | 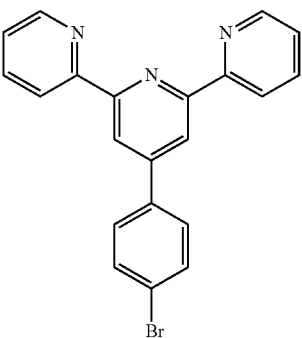 [SMILES: Brc1ccc(-c2cc(-c3ccccn3)nc(-c3ccccn3)c2)cc1] | 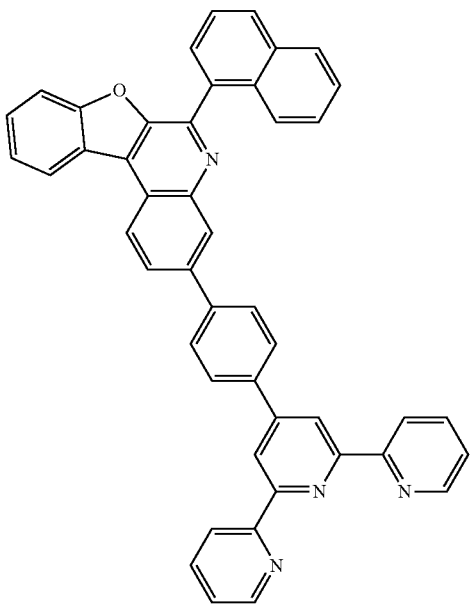 | 69% |

TABLE 37-continued

| Compound Number | Intermediate AY | Target Compound | Yield |
|---|---|---|---|
| 807 | 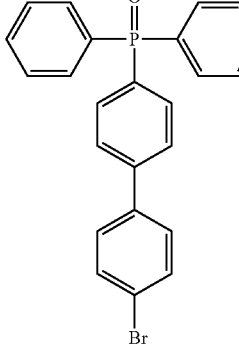 | 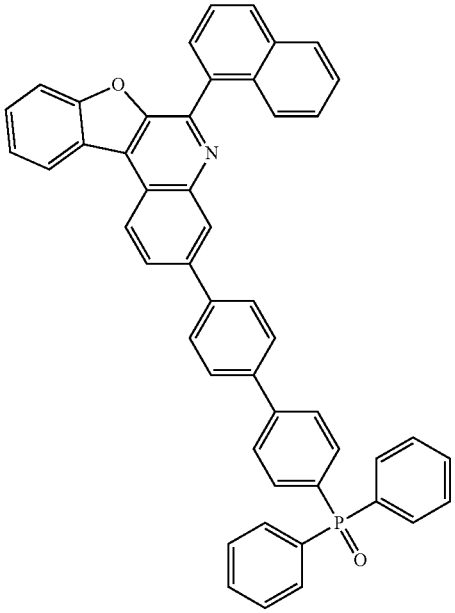 [SMILES: O=P(c1ccccc1)(c1ccccc1)c1ccc(-c2ccc(-c3ccc4c(c3)nc(-c3cccc5ccccc35)c3oc5ccccc5c34)cc2)cc1] | 66% |

A target compound was synthesized in the same manner as in Preparation Example 5 except that 2-bromo-5-chloroaniline was used instead of 2-bromo-6-chloroaniline, phenanthrene-9-carbonyl chloride was used instead of benzoyl chloride, and Intermediate AZ of the following Table 38 was used instead of 9-(4-(4-(4-bromophenyl)-6-phenyl-1,3,5-triazin-2-yl)phenyl)-9H-carbazole.

TABLE 38

| Compound Number | Intermediate AZ | Target Compound | Yield |
|---|---|---|---|
| 818 | 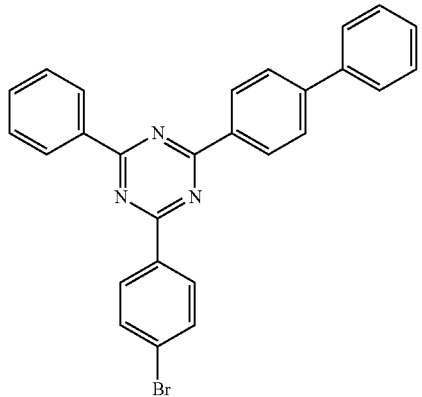 [SMILES: Brc1ccc(-c2nc(-c3ccccc3)nc(-c3ccc(-c4ccccc4)cc3)n2)cc1] | 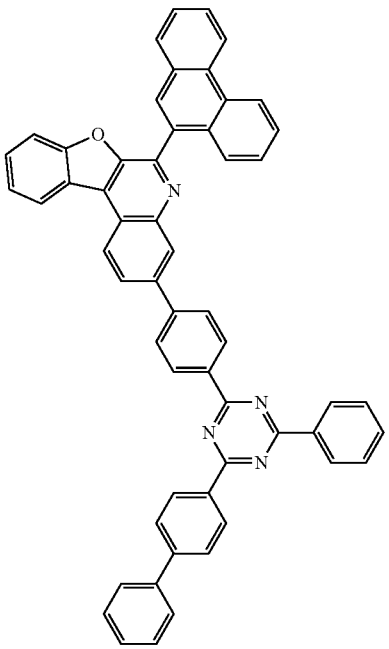 [SMILES: c1ccc(-c2ccc(-c3nc(-c4ccccc4)nc(-c4ccc(-c5ccc6c(c5)nc(-c5cc7ccccc7c7ccccc57)c5oc7ccccc7c56)cc4)n3)cc2)cc1] | 60% |

TABLE 38-continued
| Compound Number | Intermediate AZ | Target Compound | Yield |
|---|---|---|---|
| 833 | 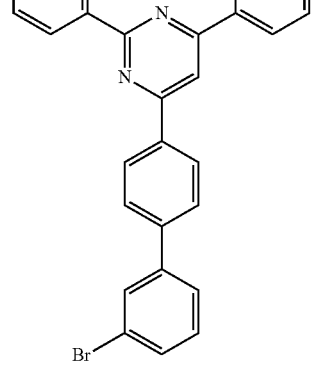 | 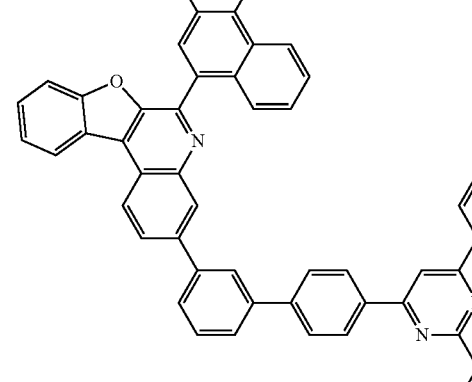 | 72% |
| 842 | 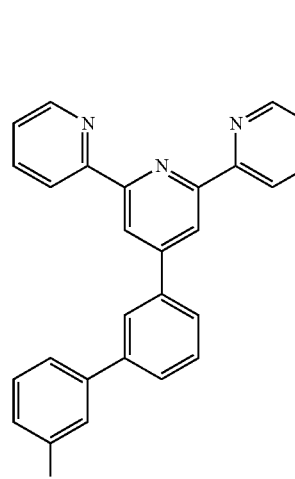 | 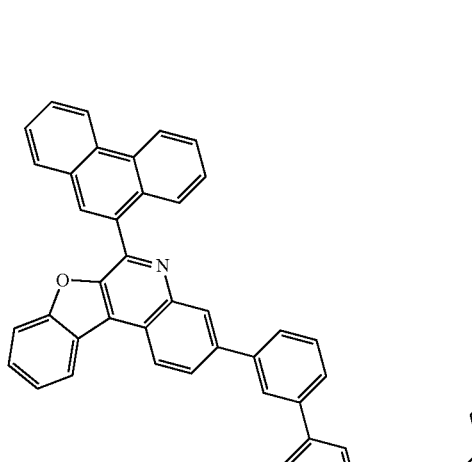 | 60% |

TABLE 38-continued

| Compound Number | Intermediate AZ | Target Compound | Yield |
|---|---|---|---|
| 849 | [structure] | [structure] | 61% |

A target compound was synthesized in the same manner as in Preparation Example 5 except that 2-bromo-5-chloroaniline was used instead of 2-bromo-6-chloroaniline, triphenylene-2-carbonyl chloride was used instead of benzoyl chloride, and Intermediate BA of the following Table 39 was used instead of 9-(4-(4-(4-bromophenyl)-6-phenyl-1,3,5-triazin-2-yl)phenyl)-9H-carbazole.

TABLE 39

| Compound Number | Intermediate BA | Target Compound | Yield |
|---|---|---|---|
| 857 | [structure] | [structure] | 68% |

A target compound was synthesized in the same manner as in Preparation Example 5 except that 2-bromo-4-chloroaniline was used instead of 2-bromo-6-chloroaniline, and Intermediate BB of the following Table 40 was used instead of 9-(4-(4-(4-bromophenyl)-6-phenyl-1,3,5-triazin-2-yl)phenyl)-9H-carbazole.

TABLE 40

| Compound Number | Intermediate BB | Target Compound | Yield |
|---|---|---|---|
| 679 | | | 71% |
| 696 | | | 67% |

TABLE 40-continued

| Compound Number | Intermediate BB | Target Compound | Yield |
|---|---|---|---|
| 712 | | | 60% |
| 713 | | | 60% |

TABLE 40-continued

| Compound Number | Intermediate BB | Target Compound | Yield |
| --- | --- | --- | --- |
| 725 | | | 71% |
| 738 | | | 68% |

A target compound was synthesized in the same manner as in Preparation Example 5 except that 2-bromo-4-chloroaniline was used instead of 2-bromo-6-chloroaniline, 1-naphthoyl chloride was used instead of benzoyl chloride, and Intermediate BC of the following Table 41 was used instead of 9-(4-(4-(4-bromophenyl)-6-phenyl-1,3,5-triazin-2-yl)phenyl)-9H-carbazole.

TABLE 41

| Compound Number | Intermediate BC | Target Compound | Yield |
|---|---|---|---|
| 753 | | | 77% |
| 768 | | | 73% |
| 784 | | | 71% |

TABLE 41-continued

| Compound Number | Intermediate BC | Target Compound | Yield |
|---|---|---|---|
| 935 | [structure] | [structure] | 80% |

A target compound was synthesized in the same manner as in Preparation Example 5 except that 2-bromo-4-chloroaniline was used instead of 2-bromo-6-chloroaniline, phenanthrene-9-carbonyl chloride was used instead of benzoyl chloride, and Intermediate BD of the following Table 42 was used instead of 9-(4-(4-(4-bromophenyl)-6-phenyl-1,3,5-triazin-2-yl)phenyl)-9H-carbazole.

TABLE 42

| Compound Number | Intermediate BD | Target Compound | Yield |
|---|---|---|---|
| 827 | [structure] | [structure] | 67% |

TABLE 42-continued

| Compound Number | Intermediate BD | Target Compound | Yield |
|---|---|---|---|
| 931 | | | 65% |

A target compound was synthesized in the same manner as in Preparation Example 5 except that 2-bromo-4-chloroaniline was used instead of 2-bromo-6-chloroaniline, triphenylene-2-carbonyl chloride was used instead of benzoyl chloride, and Intermediate BE of the following Table 43 was used instead of 9-(4-(4-(4-bromophenyl)-6-phenyl-1,3,5-triazin-2-yl)phenyl)-9H-carbazole.

TABLE 43

| Compound Number | Intermediate BE | Target Compound | Yield |
|---|---|---|---|
| 875 | | | 64% |

TABLE 43-continued

| Compound Number | Intermediate BE | Target Compound | Yield |
|---|---|---|---|
| 879 | | | 63% |

A target compound was synthesized in the same manner as in Preparation Example 5 except that 2-bromo-3-chloroaniline was used instead of 2-bromo-6-chloroaniline, and Intermediate BF of the following Table 44 was used instead of 9-(4-(4-(4-bromophenyl)-6-phenyl-1,3,5-triazin-2-yl)phenyl)-9H-carbazole.

TABLE 44

| Compound Number | Intermediate BF | Target Compound | Yield |
|---|---|---|---|
| 683 | | | 60% |

TABLE 44-continued

| Compound Number | Intermediate BF | Target Compound | Yield |
|---|---|---|---|
| 716 | [structure] | [structure] | 56% |

A target compound was synthesized in the same manner as in Preparation Example 5 except that 2-bromo-3-chloroaniline was used instead of 2-bromo-6-chloroaniline, 1-naphthoyl chloride was used instead of benzoyl chloride, and Intermediate BG of the following Table 45 was used instead of 9-(4-(4-(4-bromophenyl)-6-phenyl-1,3,5-triazin-2-yl)phenyl)-9H-carbazole.

TABLE 45

| Compound Number | Intermediate BG | Target Compound | Yield |
|---|---|---|---|
| 755 | [structure] | [structure] | 56% |

TABLE 45-continued

| Compound Number | Intermediate BG | Target Compound | Yield |
|---|---|---|---|
| 788 | | | 52% |
| 812 | | | 59% |

A target compound was synthesized in the same manner as in Preparation Example 5 except that 2-bromo-3-chloroaniline was used instead of 2-bromo-6-chloroaniline, phenanthrene-9-carbonyl chloride was used instead of benzoyl chloride, and Intermediate BH of the following Table 46 was used instead of 9-(4-(4-(4-bromophenyl)-6-phenyl-1,3,5-triazin-2-yl)phenyl)-9H-carbazole.

TABLE 46

| Compound Number | Intermediate BH | Target Compound | Yield |
|---|---|---|---|
| 853 | | | 51% |

A target compound was synthesized in the same manner as in Preparation Example 5 except that 2-bromo-3-chloroaniline was used instead of 2-bromo-6-chloroaniline, phenanthrene-9-carbonyl chloride was used instead of benzoyl chloride, and Intermediate BI of the following Table 47 was used instead of 9-(4-(4-(4-bromophenyl)-6-phenyl-1,3,5-triazin-2-yl)phenyl)-9H-carbazole.

TABLE 47

| Compound Number | Intermediate BI | Target Compound | Yield |
|---|---|---|---|
| 866 | | | 53% |

<Preparation Example 6>—Preparation of Compound 885

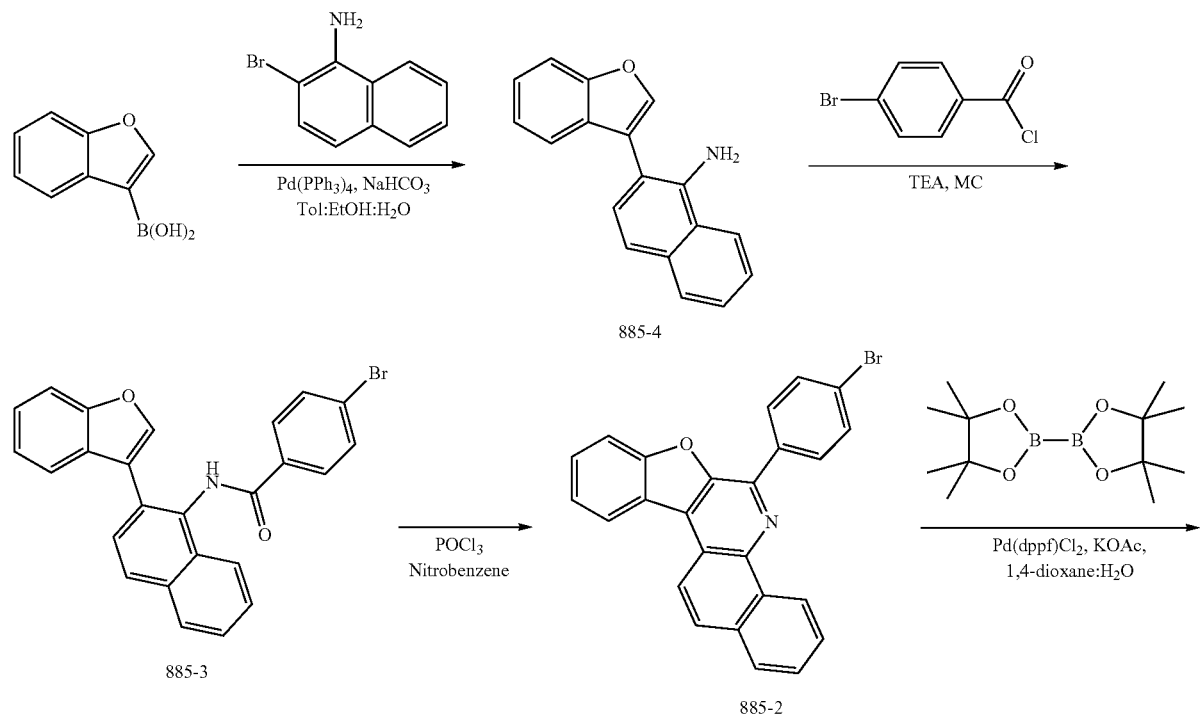

-continued

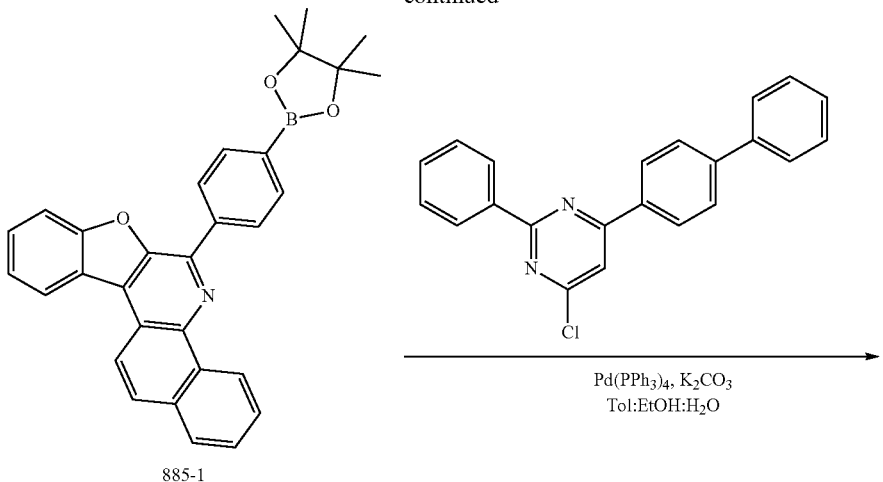
885-1

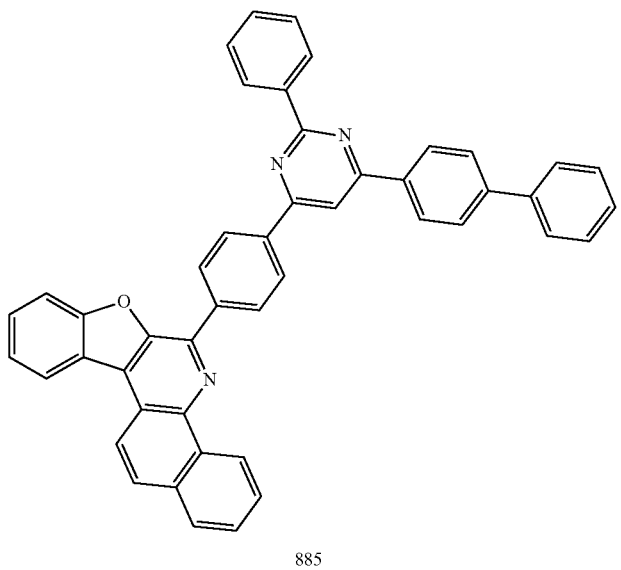

Pd(PPh₃)₄, K₂CO₃
Tol:EtOH:H₂O

885

1) Preparation of Compound 885-4

After dissolving benzofuran-3-ylboronic acid (40 g, 250 mmol) and 2-bromonaphthalen-1-amine (67 g, 300 mmol) in toluene, EtOH and H₂O (1000 mL:200 mL:200 mL), Pd(PPh₂)₄ (15 g, 13 mmol) and NaHCO₃ (63 g, 750 mmol) were introduced thereto, and the result was refluxed for 4 hours. After the reaction was completed, the result was cooled to room temperature and extracted with MC. The result was dried with anhydrous MgSO4, and then the solvent was removed using a rotary evaporator. Target Compound 885-4 was obtained using column chromatography (MC:Hx=1:3). (50 g, 78%, brown solid)

2) Preparation of Compound 885-3

Compound 885-4 (60 g, 218 mmol) and triethylamine (93 mL, 650 mmol) were introduced to MC (1500 mL) and dissolved therein. 4-Bromobenzoyl chloride (53 g, 240 mmol) dissolved in MC (300 mL) was slowly added dropwise to the mixture at 0° C. After the reaction was completed, MC and distilled water were introduced to the reaction solution for extraction. After that, the result was dried with anhydrous MgSO4, and, after removing the solvent using a rotary evaporator, recrystallized with EA/Hx to obtain Compound 885-3. (90 g, 90%, white solid)

3) Preparation of Compound 885-2

After dissolving Compound 885-3 (90 g, 200 mmol) in nitrobenzene (400 mL), POCl₃ (24 mL, 200 mmol) was slowly added dropwise thereto. After that, the result was stirred for 12 hours at 150° C. After the reaction was completed, the reaction solution was neutralized with an aqueous NaHCO₃ solution. Solids produced from the neutralization were filtered. The solids were recrystallized with MC/MeOH to obtain target Compound 885-2. (60 g, 70%, white solid)

4) Preparation of Compound 885-1

After dissolving Compound 885-2 (70 g, 159 mmol), bis(pinacolato)diboron (50 g, 191 mmol), Pd(dppf)Cl₂ (5.8 g, 8 mmol) and KOAc (48 g, 477 mmol) in 1,4-dioxane (300 mL), the result was refluxed for 12 hours. After the reaction was completed, MC and distilled water were introduced to the reaction solution for extraction. After that, the result was dried with anhydrous MgSO4, and the solvent was removed using a rotary evaporator. After passing silica, the result went through MeOH slurry to obtain Compound 885-1. (66 g, 85%, white solid)

5) Preparation of Compound 885

After dissolving Compound 885-1 (10 g, 20.5 mmol), 4-([1,1'-biphenyl]-4-yl)-6-chloro-2-phenylpyrimidine (7 g, 20.5 mmol), Pd(PPh₃)₄ (1.2 g, 1.1 mmol) and K₂CO₃ (8.5 g, 62 mmol) in toluene, EtOH and H₂O (100 mL:20 mL:20 mL), the result was refluxed for 12 hours. After the reaction was finished, produced solids were filtered. The solids were washed with distilled water and acetone to obtain target Compound 885. (9 g, 72%, white solid)

A target compound was synthesized in the same manner as in Preparation Example 6 except that Intermediate BJ of the following Table 48 was used instead of 4-([1,1'-biphenyl]-4-yl)-6-chloro-2-phenylpyrimidine.

TABLE 48

| Compound Number | Intermediate BJ | Target Compound | Yield |
|---|---|---|---|
| 883 | | | 75% |
| 893 | | | 80% |

TABLE 48-continued

| Compound Number | Intermediate BJ | Target Compound | Yield |
|---|---|---|---|
| 940 | | | 81% |

A target compound was synthesized in the same manner as in Preparation Example 6 except that 3-bromonaphthalen-2-amine was used instead of 2-bromonaphthalen-1-amine, and Intermediate BK of the following Table 49 was used instead of 4-([1,1'-biphenyl]-4-yl)-6-chloro-2-phenylpyrimidine.

TABLE 49

| Compound Number | Intermediate BK | Target Compound | Yield |
|---|---|---|---|
| 895 | | | 75% |

TABLE 49-continued

| Compound Number | Intermediate BK | Target Compound | Yield |
|---|---|---|---|
| 901 | | | 80% |
| 904 | | | 78% |

TABLE 49-continued

| Compound Number | Intermediate BK | Target Compound | Yield |
|---|---|---|---|
| 944 | | | 82% |

A target compound was synthesized in the same manner as in Preparation Example 6 except that 1-bromonaphthalen-2-amine was used instead of 2-bromonaphthalen-1-amine, and Intermediate BL of the following Table 50 was used instead of 4-([1,1'-biphenyl]-4-yl)-6-chloro-2-phenylpyrimidine.

TABLE 50

| Compound Number | Intermediate BL | Target Compound | Yield |
|---|---|---|---|
| 913 | | | 72% |

TABLE 50-continued

| Compound Number | Intermediate BL | Target Compound | Yield |
|---|---|---|---|
| 915 | | | 76% |
| 920 | | | 75% |
| 939 | | | 3% |

The following Table 51 and Table 52 present 1H NMR data and FD-MS data of the synthesized compounds, and through the following data, syntheses of target compounds are identified.

TABLE 51

| Compound Number | 1H NMR (CDCl3, 400 Mhz) |
|---|---|
| 1 | δ = 9.15(s, 1H), 8.93(d, 2H), 8.81(d, 2H), 8.45(d, 1H), 8.28-7.98(m, 11H), 8.05(d, 2H), 7.88-7.82(m, 6H), 7.66(t, 1H), 7.52-7.41(m, 8H) |
| 7 | δ = 8.81(d, 2H), 8.55(d, 1H), 8.45(d, 1H), 8.28(d, 2H), 8.21(d, 1H), 8.12(d, 1H), 8.02-7.94(m, 3H), 7.88(d, 2H), 7.79(d, 2H), 7.68-7.63(m, 4H), 7.52-7.41(m, 9H), 7.33-7.19(m, 5H) |
| 10 | δ = 8.81(d, 2H), 8.45(d, 1H), 8.28(dd, 2H), 8.21(d, 1H), 8.02-7.98(m, 2H), 7.89-7.81(m, 7H), 7.66(td, 2H), 7.52-7.50(m, 6H), 7.41-7.19(m, 9H) |
| 14 | δ = 8.81(d, 2H), 8.45(d, 1H), 8.28(dd, 4H), 8.21(d, 1H), 8.00(d, 2H), 7.89-7.85(m, 7H), 7.66(td, 2H), 7.52-7.50(m, 6H), 7.41-7.25(m, 7H) |
| 17 | δ = 9.15(s, 1H), 8.93(d, 2H), 8.81(d, 2H), 8.45(d, 1H), 8.28-8.27(m, 5H), 8.18-7.98(m, 7H), 7.88-7.82(m, 6H), 7.52-7.41(m, 8H) |
| 25 | δ = 8.55(d, 1H), 8.45(d, 1H), 8.30-8.21(m, 7H), 8.12-7.98(m, 6H), 7.63-7.50(m, 12H), 7.46-7.25(m, 6H) |
| 28 | δ = 8.81(d, 2H), 8.45(d, 1H), 8.28-8.24(m, 4H), 8.12(d, 1H), 8.03-7.98(m, 2H), 7.89-7.81(m, 5H), 7.66(d, 2H), 7.52-7.32(m, 15H) |
| 33 | δ = 9.15(s, 1H), 8.93(d, 2H), 8.81(d, 2H), 8.45(d, 1H), 8.28-8.12(m, 8H), 8.04-7.98(m, 3H), 7.90-7.82(m, 7H), 7.52-7.41(m, 8H) |
| 51 | δ = 8.81(d, 2H), 8.55(d, 1H), 8.45(d, 1H), 8.28(d, 2H), 8.21(d, 1H), 8.12(d, 1H), 8.04(d, 1H), 7.98-7.88(m, 5H), 7.79(d, 2H), 7.68-7.63(m, 3H), 7.52-7.25(m, 14H) |
| 56 | δ = 8.81(d, 2H), 8.45-8.41(m, 3H), 8.28-8.20(m, 5H), 8.04(d, 1H), 7.98(d 2H), 7.90(s, 1H), 7.88(d, 2H), 7.70(s, 1H), 7.58-7.41(m, 15H) |
| 57 | δ = 8.81(d, 2H), 8.45(d, 1H), 8.28-8.21(m, 5H), 8.04(d, 1H), 7.98-7.85(m, 8H), 7.75(d, 1H), 7.64(d, 2H), 7.52-7.32(m, 12H) |
| 59 | δ = 8.81(d, 2H), 8.45(d, 1H), 8.28(d, 4H), 8.03-7.88(m, 9H), 7.73(d, 1H), 7.59-7.41(m, 11H) |
| 68 | δ = 8.81(d, 2H), 8.45(d, 1H), 8.28(d, 2H), 8.03-7.81(m, 13H), 7.66(d, 1H), 7.52-7.25(m, 13H) |
| 69 | δ = 8.45-8.41(m, 3H), 8.30-8.21(m, 5H), 8.03-7.94(m, 5H), 7.80(d, 1H), 7.60-7.41(m, 14H), 7.25(dd, 4H) |
| 72 | δ = 8.81(d, 2H), 8.45(d, 1H), 8.33-8.21(m, 6H), 8.00(d, 2H), 7.89(d, 1H), 7.79-7.75(m, 3H), 7.66-7.62(m, 3H), 7.52-7.41(m, 11H), 7.25(d, 4H) |
| 75 | δ = 8.81(d, 2H), 8.55(d, 1H), 8.45(d, 1H), 8.33-8.21(m, 6H), 8.12(d, 1H), 8.02-7.94(m, 3H), 7.79(d, 2H), 7.68-7.63(m, 4H), 7.52-7.19(m, 14H) |
| 78 | δ = 8.45(d, 1H), 8.33-8.21(m, 6H), 8.00(d, 2H), 7.89-7.57(m, 7H), 7.52-7.38(m, 12H), 7.19(d, 2H) |
| 83 | δ = 9.15(s, 1H), 8.93(d, 2H), 8.81(d, 2H), 8.45(d, 1H), 8.28-8.12(m, 10H), 8.04-7.98(m, 3H), 7.88-7.79(m, 6H), 7.52-7.41(m, 8H) |
| 89 | δ = 8.81(d, 2H), 8.55(d, 1H), 8.45(d, 1H), 8.33-8.21(m, 6H), 8.12(d, 2H), 8.03-7.94(m, 3H), 7.79(d, 2H), 7.68-7.63(m, 3H), 7.52-7.25(m, 14H) |
| 91 | δ = 8.45(d, 1H), 8.28-8.23(m, 6H), 8.12(d, 1H), 8.00(dd, 2H), 7.89(d, 1H), 7.81(d, 2H), 7.72-7.32(m, 20H) |
| 98 | δ = 8.81(d, 2H), 8.45(d, 1H), 8.33-8.21(m, 6H), 8.01(d, 2H), 7.90(s, 1H), 7.79-7.75(m, 3H), 7.64(d, 2H), 7.52-7.32(m, 11H), 7.25(d, 4H) |
| 100 | δ = 8.81(d, 2H), 8.45(d, 1H), 8.33-8.21(m, 8H), 8.01(d, 2H), 7.90-7.85(m, 3H), 7.70(s, 1H), 7.52-7.41(m, 18H) |
| 103 | δ = 8.81(d, 2H), 8.55(d, 1H), 8.45(d, 1H), 8.33-8.21(m, 6H), 8.12(d, 2H), 8.03-7.90(m, 4H), 7.79(d, 2H), 7.68-7.63(m, 3H), 7.52-7.25(m, 14H) |
| 106 | δ = 8.81(d, 2H), 8.45(d, 1H), 8.33-8.21(m, 8H), 8.04(d, 1H), 7.98(d, 1H), 7.90-7.85(m, 4H), 7.66(d, 1H), 7.52-7.32 (m, 13H), 7.25(d, 2H) |
| 112 | δ = 8.81(d, 2H), 8.45(d, 1H), 8.33-8.23(m, 5H), 8.03-7.89(m, 5H), 7.79-7.75(m, 3H), 7.64(d, 2H), 7.52-7.25(m, 15H) |

TABLE 51-continued

| Compound Number | 1H NMR (CDCl3, 400 Mhz) |
|---|---|
| 117 | δ = 8.81(d, 2H), 8.55(d, 1H), 8.45(d, 1H), 8.33-8.23(m, 5H), 8.12(d, 1H), 8.03-7.94(m, 5H), 7.79(d, 2H), 7.68-7.63(m, 3H), 7.52-7.25(m, 12H) |
| 119 | δ = 8.81(d, 2H), 8.45(d, 1H), 8.33-8.23(m, 5H), 8.03-7.66(m, 12H), 7.52-7.32(m, 13H) |
| 124 | δ = 8.81(d, 2H), 8.45(d, 1H), 8.30-8.23(m, 7H), 8.03-7.79(m, 12H), 7.52-7.41(m, 13H) |
| 125 | δ = 9.15(s, 1H), 8.93(d, 2H), 8.81(d, 2H), 8.45(d, 1H), 8.23-8.12(m, 5H), 8.04-7.98(m, 2H), 7.88-7.79(m, 10H), 7.66(t, 1H), 7.52-7.41(m, 8H) |
| 130 | δ = 8.81(d, 2H), 8.55(d, 1H), 8.45(d, 1H), 8.23(s, 1H), 8.21(d, 1H), 8.12(d, 1H), 8.02-7.88(m, 5H), 7.79(d, 4H), 7.68-7.63(m, 3H), 7.52-7.19(m, 14H) |
| 134 | δ = 8.45-8.41(m, 3H), 8.30-8.21(m, 5H), 8.02-7.98(m, 3H), 7.80-7.79(m, 3H), 7.66-7.41(m, 15H), 7.52(d, 4H) |
| 138 | δ = 9.15(s, 1H), 8.93(d, 2H), 8.81(d, 2H), 8.45(d, 1H), 8.27-8.12(m, 6H), 8.04-7.98(m, 3H), 7.88-7.79(m, 10H), 7.52-7.41(m, 8H) |
| 143 | δ = 8.81(d, 2H), 8.55(d, 1H), 8.45(d, 1H), 8.27(s, 1H), 8.23(s, 1H), 8.21(d, 1H), 8.12(d, 2H), 8.03-7.88(m, 5H), 7.79(d, 4H), 7.68-7.63(m, 3H), 7.52-7.19(m, 14H) |
| 149 | δ = 8.81(d, 2H), 8.45(d, 1H), 8.27(s, 1H), 8.23(s, 1H), 8.01(d, 2H), 7.89-7.79(m, 11H), 7.66(d, 1H), 7.52-7.25(m, 13H) |
| 151 | δ = 9.15(s, 1H), 8.93(d, 2H), 8.81(d, 2H), 8.45(d, 1H), 8.23-8.12(m, 5H), 8.04-7.98(m, 3H), 7.88-7.79(m, 11H), 7.52-7.41(m, 8H) |
| 156 | δ = 8.81(d, 2H), 8.55(d, 1H), 8.45(d, 1H), 8.23(s, 1H), 8.21(d, 1H), 8.12(d, 1H), 8.04-7.88(m, 6H), 7.79(d, 4H), 7.68-7.63(m, 3H), 7.52-7.25(m, 14H) |
| 159 | δ = 8.81(d, 2H), 8.45(d, 1H), 8.30(d, 2H), 8.22(d, 2H), 8.01(d, 2H), 7.90-7.79(m, 8H), 7.66(d, 1H), 7.52-7.25(m, 15H) |
| 166 | δ = 8.81(d, 2H), 8.45(d, 1H), 8.23(s, 1H), 8.03-7.79(m, 12H), 7.64(d, 2H), 7.52-7.32 (m, 15H) |
| 171 | δ = 8.55(d, 1H), 8.45(d, 1H), 8.30-8.21(m, 4H), 8.12-7.94(m, 7H), 7.79(d, 5H), 7.52-7.25(m, 14H) |
| 174 | δ = 8.45-8.41(m, 3H), 8.30-8.21(m, 4H), 8.03-7.94(m, 5H), 7.80-7.79(m, 3H), 7.60-7.41(m, 13H), 7.52(d, 4H) |
| 178 | δ = 8.45(d, 1H), 8.30-8.21(m, 7H), 8.03-7.94(m, 4H), 7.85-7.79(m, 8H), 7.60-7.41(m, 17H), 7.52(d, 2H) |
| 179 | δ = 9.30(d, 2H), 9.15(s, 2H), 8.81(d, 2H), 8.53(d, 2H), 8.45(d, 1H), 8.21(d, 1H), 8.00(dd, 2H), 7.89-7.81(m, 5H), 7.70-7.66(m, 4H), 7.51(td, 2H), 7.38-7.25(m, 7H), 7.14(t, 2H) |
| 182 | δ = 9.30(d, 2H), 9.15(s, 2H), 8.81(d, 2H), 8.53(d, 2H), 8.45(d, 1H), 8.21(d, 1H), 8.02-7.88(m, 7H), 7.73-7.48(m, 13H), 7.14(t, 2H) |
| 186 | δ = 9.30(d, 2H), 9.15(s, 2H), 8.81(d, 2H), 8.53(d, 2H), 8.45(d, 1H), 8.27(d, 1H), 8.12(d, 1H), 8.03-7.98(m, 5H), 7.87(dd, 3H), 7.70(t, 3H), 7.57-7.48(m, 7H), 7.14(t, 2H) |
| 190 | δ = 9.30(d, 2H), 9.15(s, 2H), 8.81(d, 2H), 8.53(d, 2H), 8.45(d, 1H), 8.21(d, 1H), 8.04-7.88(m, 8H), 7.73-7.48(m, 12H), 7.14(t, 2H) |
| 197 | δ = 8.93(d, 2H), 8.45(d, 1H), 8.26-8.21(m, 3H), 8.12(d, 2H), 8.02-7.77(m, 15H), 7.66-7.45(m, 11H) |
| 199 | δ = 8.81(d, 2H), 8.45(d, 1H), 8.27(s, 1H), 8.12(d, 1H), 8.03-7.98(m, 2H), 7.89-7.75(m, 12H), 7.64(d, 2H), 7.52-7.32(m, 11H) |
| 203 | δ = 8.81(d, 2H), 8.45(d, 1H), 8.21(d, 1H), 8.04-7.98(m, 2H), 7.89-7.75(m, 12H), 7.64(d, 2H), 7.52-7.32 (m, 11H) |
| 207 | δ = 8.81(d, 2H), 8.45(d, 1H), 8.04-7.77(m, 16H), 7.64(d, 2H), 7.52-7.32 (m, 11H) |
| 212 | δ = 8.55(d, 1H), 8.45(d, 1H), 8.30-8.21(m, 5H), 8.12(d, 1H), 8.02-7.94(m, 3H), 7.85-7.79(dd, 4H), 7.68-7.65(m, 4H), 7.54-7.25(m, 14H) |
| 217 | δ = 8.45-8.41(m, 3H), 8.30-8.20(m, 7H), 8.12(d, 1H), 8.03-7.98(m, 3H), 7.85(d, 2H), 7.70(s, 1H), 7.58-7.48(m, 13H), 7.25(d, 2H) |
| 219 | δ = 8.45(d, 1H), 8.30-8.21(m, 7H), 8.01(d, 2H), 7.90-7.85(m, 3H), 7.54-7.41(m, 11H), 7.25(d, 2H) |
| 223 | δ = 8.45(d, 1H), 8.30-8.28(m, 6H), 8.03-7.94(m, 4H), 7.85(d, 2H), 7.54-7.41(m, 11H), 7.25(d, 2H) |
| 228 | δ = 8.55(d, 1H), 8.45(d, 1H), 8.30-8.21(m, 8H), 8.12(d, 1H), 8.02-7.94(m, 3H), 7.79(d, 2H), 7.68-7.63(m, 4H), 7.54-7.25(m, 14H) |

TABLE 51-continued

| Compound Number | ¹H NMR (CDCl₃, 400 Mhz) |
|---|---|
| 231 | δ = 8.45(d, 1H), 8.30-8.23(m, 8H), 8.12(d, 1H), 8.03-7.98(m, 2H), 7.85-7.799(m, 4H), 7.54-7.41(m, 11H) |
| 233 | δ = 8.45-8.41(m, 3H), 8.30-8.20(m, 11H), 8.12(d, 1H), 8.03-7.98(m, 3H), 7.85(d, 2H), 7.58-7.48(m, 11H), 7.25(d, 2H) |
| 236 | δ = 8.55(d, 1H), 8.45(d, 1H), 8.30-8.21(m, 8H), 8.12(d, 1H), 8.04(d, 1H), 7.98-7.79(m, 7H), 7.68-7.63(m, 3H), 7.54-7.25(m, 12H) |
| 243 | δ = 8.45(d, 1H), 8.30(d, 6H), 8.22(d, 2H), 8.02-7.98(d, 2H), 7.85(d, 6H), 7.66(d, 1H), 7.54-7.41(m, 15H), 7.25(d, 2H) |
| 252 | δ = 8.55(d, 1H), 8.45(d, 1H), 8.30(d, 2H), 8.22(d, 2H), 8.12(d, 1H), 8.04-7.79(m, 10H), 7.68-7.63(m, 4H), 7.54-7.25(m, 14H) |
| 253 | δ = 8.45-8.41(m, 3H), 8.30-8.20(m, 8H), 8.04-7.98(m, 3H), 7.90(s, 1H), 7.79(d, 2H), 7.70(s, 1H), 7.58-7.48(m, 13H), 7.25(d, 2H) |
| 256 | δ = 8.55(d, 1H), 8.45(d, 1H), 8.30(d, 2H), 8.23(s, 1H), 8.12(d, 1H), 8.03-7.94(m, 5H), 7.85-7.79(m, 6H), 7.68-7.63(m, 3H), 7.54-7.25(m, 14H) |
| 259 | δ = 9.30(d, 2H), 9.15(s, 2H), 8.81(d, 2H), 8.53(d, 2H), 8.45(d, 1H), 8.30(d, 2H), 8.21(d, 1H), 8.02-7.98(m, 2H), 7.70(t, 3H), 7.54-7.50(m, 5H), 7.25(d, 4H), 7.14(t, 2H) |
| 263 | δ = 9.30(d, 2H), 9.15(s, 2H), 8.53(d, 2H), 8.45(d, 1H), 8.30(d, 2H), 8.27(s, 1H), 8.12(d, 1H), 8.02-7.98(m, 2H), 7.70(t, 3H), 7.57-7.48(m, 8H), 7.14(t, 2H) |
| 265 | δ = 9.30(d, 2H), 9.15(s, 2H), 8.53(d, 2H), 8.45(d, 1H), 8.30(d, 2H), 8.21(d, 1H), 8.04-7.98(m, 2H), 7.90(s, 1H), 7.70(t, 2H), 7.57-7.50(m, 5H), 7.25(d, 4H), 7.14(t, 2H) |
| 272 | δ = 8.45(d, 1H), 8.30(d, 2H), 8.21(d, 1H), 8.02-7.98(m, 2H), 7.83-7.77(m, 8H), 7.66(t, 1H), 7.54-7.45(m, 11H), 7.25(d, 4H) |
| 278 | δ = 8.45(d, 1H), 8.30(d, 2H), 8.21(d, 1H), 8.04-7.98(m, 2H), 7.90(s, 1H), 7.83-7.77(m, 8H), 7.54-7.45(m, 11H), 7.25(d, 4H) |
| 283 | δ = 8.55(d, 1H), 8.45(d, 2H), 8.28(d, 4H), 8.21(d, 1H), 8.10-7.94(m, 4H), 7.85(d, 2H), 7.66-7.41(m, 12H), 7.25(d, 2H) |
| 288 | δ = 8.55(d, 1H), 8.45(d, 2H), 8.28(d, 3H), 8.12-7.94(m, 5H), 7.85-7.79(m, 4H), 7.68-7.63(m, 4H), 7.55-7.25(m, 13H) |
| 293 | δ = 8.55(d, 1H), 8.46(d, 2H), 8.28-8.21(m, 4H), 8.10-7.98(m, 5H), 7.90-7.81(m, 6H), 7.70-7.32(m, 15H), 7.25(m, 2H) |
| 295 | δ = 8.55(d, 1H), 8.46(d, 2H), 8.28(d, 4H), 8.10-7.94(m, 6H), 7.64(t, 1H), 7.55-7.41(m, 10H), 7.25(d, 2H) |
| 305 | δ = 8.55(d, 1H), 8.46(d, 2H), 8.30-8.20(m, 9H), 8.12-7.98(m, 5H), 7.85(d, 2H), 7.64-7.41(m, 11H), 7.25(d, 2H) |
| 308 | δ = 8.55(d, 2H), 8.46(d, 2H), 8.30-8.21(m, 6H), 8.12-7.90(m, 7H), 7.85-7.79(m, 4H), 7.64-7.25(m, 15H) |
| 319 | δ = 8.55(d, 1H), 8.46(d, 2H), 8.27(s, 1H), 8.23(s, 1H), 8.12-7.98(m, 5H), 7.85-7.79(m, 4H), 7.64-7.41(m, 11H), 7.25(d, 2H) |
| 324 | δ = 8.55(d, 2H), 8.46(d, 2H), 8.23(s, 1H), 8.21(s, 1H), 8.12-7.79(m, 13H), 7.68(d, 2H), 7.64-7.25(m, 17H) |
| 328 | δ = 8.55(d, 2H), 8.46(d, 2H), 8.23(s, 1H), 8.12-7.94(m, 9H), 7.85-7.79(m, 6H), 7.68(d, 2H), 7.64-7.25(m, 15H) |
| 334 | δ = 9.30(d, 2H), 9.15(s, 2H), 8.55-8.45(m, 5H), 8.27(s, 1H), 8.12-7.98(m, 5H), 7.70-7.50(m, 7H), 7.25(d, 4H), 7.14(t, 2H) |
| 347 | δ = 8.55(d, 1H), 8.46(d, 2H), 8.27(s, 1H), 8.12-7.98(m, 5H), 7.83-7.79(m, 8H), 7.64(t, 1H), 7.55-7.45(m, 10H), 7.25(d, 4H) |
| 352 | δ = 8.55(d, 1H), 8.46(d, 2H), 8.12-7.94(m, 6H), 7.79-7.77(m, 8H), 7.64(t, 3H), 7.57-7.45(m, 10H) |
| 358 | δ = 8.93(d, 2H), 8.44(d, 2H), 8.28(d, 3H), 8.12(d, 3H), 8.03-7.98(m, 2H), 7.88-7.82(m, 8H), 7.52-7.41(m, 10H), 7.25(d, 4H) |
| 367 | δ = 8.93(d, 2H), 8.45(d, 2H), 8.28-8.21(m, 4H), 8.12(d, 2H), 8.04-7.98(m, 2H), 7.90-7.70(m, 9H), 7.52-7.41(m, 10H) |
| 373 | δ = 8.93(d, 2H), 8.45(d, 2H), 8.27(s, 1H), 8.23(s, 1H), 8.12(d, 3H), 8.03-7.98(m, 2H), 7.88-7.79(m, 10H), 7.70(s, 1H), 7.57-7.41(m, 11H), 7.25(d, 2H) |
| 379 | δ = 9.30(d, 2H), 9.15(s, 2H), 8.93(d, 2H), 8.53-8.44(m, 4H), 8.21(d, 1H), 8.12(d, 2H), 8.02-7.98(m, 2H), 7.88-7.82(m, 4H), 7.70-7.66(m, 3H), 7.51(dd, 2H), 7.25(d, 4H), 7.14(t, 2H) |
| 382 | δ = 9.30(d, 2H), 9.15(s, 2H), 8.93(d, 2H), 8.53-8.44(m, 4H), 8.27(s, 1H), 8.12(d, 3H), 8.02-7.98(m, 2H), 7.88-7.82(m, 4H), 7.70(t, 4H), 7.57-7.48(m, 8H), 7.14(t, 2H) |
| 389 | δ = 8.93(d, 2H), 8.44(d, 2H), 8.27(s, 1H), 8.12(d, 3H), 8.03-7.98(m, 2H), 7.88-7.77(m, 12H), 7.52-7.45(m, 8H) |
| 393 | δ = 8.93(d, 2H), 8.44(d, 2H), 8.12(d, 2H), 8.03-7.77(m, 16H), 7.52-7.45(m, 8H) |
| 397 | δ = 9.66(s, 1H), 8.93(d, 2H), 8.55(d, 1H), 8.45(d, 1H), 8.28-8.21(m, 4H), 8.12(d, 3H), 8.03-7.98(m, 2H), 7.88-7.82(m, 6H), 7.52-7.41(m, 8H), 7.25(d, 2H) |
| 406 | δ = 9.66(s, 1H), 8.93(d, 2H), 8.55(d, 1H), 8.45(d, 1H), 8.28-8.21(m, 4H), 8.12(d, 2H), 8.03-7.70(m, 12H), 7.52-7.41(m, 10H) |
| 415 | δ = 9.66(s, 1H), 9.30(d, 2H), 9.15(s, 2H), 8.93(d, 2H), 8.54(d, 3H), 8.45(d, 1H), 8.21-7.82(m, 11H), 7.70(t, 3H), 7.57-7.48(m, 5H), 7.14(t, 2H) |
| 419 | δ = 9.66(s, 1H), 8.93(d, 2H), 8.55(d, 1H), 8.45(d, 1H), 8.21(d, 2H), 8.12(d, 2H), 8.04-7.98(m, 2H), 7.88-7.77(m, 11H), 7.52-7.45(m, 10H) |
| 423 | δ = 8.81(d, 2H), 8.48(dd, 2H), 8.28-8.16(m, 4H), 8.06-7.81(m, 8H), 7.70-7.32(m, 14H) |
| 425 | δ = 8.81(d, 2H), 8.48(dd, 2H), 8.33-8.23(m, 7H), 8.16(d, 1H), 8.06(d, 1H), 7.98(d, 1H), 7.85-7.81(m, 3H), 7.67(t, 2H), 7.52-7.41(m, 10H) |
| 433 | δ = 9.30(d, 2H), 9.15(s, 2H), 8.81(d, 2H), 8.53-8.45(m, 4H), 8.16(d, 1H), 8.06(d, 1H), 7.98(d, 1H), 7.88-7.81(m, 3H), 7.70-7.67(m, 4H), 7.52-7.50(m, 2H), 7.25(d, 4H), 7.14(t, 2H) |
| 435 | δ = 8.81(d, 2H), 8.45(d, 1H), 8.28(d, 4H), 8.16(d, 2H), 8.05(s, 1H), 7.98(d, 1H), 7.88(d, 2H), 7.68-7.67(t, 2H), 7.52-7.41(m, 8H) |
| 441 | δ = 8.81(d, 2H), 8.45-8.41(m, 3H), 8.33-8.16(m, 10H), 7.98(d, 1H), 7.67(t, 3H), 7.58-7.41(m, 8H), 7.25(d, 2H) |
| 444 | δ = 8.81(d, 2H), 8.45(d, 1H), 8.23(s, 1H), 8.16(d, 2H), 8.05(s, 1H), 7.98(d, 1H), 7.89-7.67(m, 13H), 7.57-7.32(m, 10H) |
| 453 | δ = 8.81(d, 2H), 8.54(d, 1H), 8.45(d, 2H), 8.41-8.16(m, 10H), 7.98(d, 4H), 7.67(t, 2H), 7.58-7.41(m, 8H), 7.25(d, 2H) |
| 455 | δ = 8.81(d, 2H), 8.54(d, 1H), 8.45(d, 2H), 8.30(d, 4H), 8.23(s, 1H), 8.16(d, 1H), 7.98(d, 3H), 7.88-7.85(m, 6H), 7.67(t, 2H), 7.52-7.41(m, 12H) |
| 460 | δ = 8.81(d, 2H), 8.54(d, 1H), 8.45(d, 1H), 8.16(d, 1H), 7.98(d, 3H), 7.88(d, 2H), 7.77-7.67(m, 8H), 7.52-7.45(m, 10H) |
| 461 | δ = 9.15(s, 1H), 8.93(d, 2H), 8.81(d, 2H), 8.28-8.18(m, 6H), 8.12-8.02(m, 4H), 7.88-7.82(m, 7H), 7.66(t, 2H), 7.51-7.32(m, 8H) |
| 467 | δ = 8.81(d, 2H), 8.55(d, 1H), 8.28(d, 2H), 8.21(d, 1H), 8.12(d, 1H), 8.02(d, 1H), 7.94-7.79(m, 6H), 7.68-7.63(m, 5H), 7.50-7.19(m, 14H) |
| 470 | δ = 8.81(d, 2H), 8.28(d, 2H), 8.21(d, 1H), 8.02(d, 1H), 7.89-7.85(m, 8H), 7.66(td, 3H), 7.51-7.19(m, 15H) |
| 474 | δ = 8.81(d, 2H), 8.28(d, 4H), 8.21(d, 1H), 8.02(d, 1H), 7.89-7.85(m, 8H), 7.66(t, 3H), 7.51-7.25(m, 13H) |
| 477 | δ = 9.15(s, 1H), 8.93(d, 2H), 8.81(d, 2H), 8.28(d, 5H), 8.18-8.03(m, 6H), 7.89-7.82(m, 7H), 7.66(d, 1H), 7.51-7.32(m, 8H) |
| 485 | δ = 8.55(d, 1H), 8.30-8.21(m, 7H), 8.12-8.03(m, 4H), 7.91(d, 2H), 7.66-7.60(m, 3H), 7.52-7.25(m, 16H) |
| 488 | δ = 8.81(d, 2H), 8.28-8.24(m, 4H), 8.12(d, 1H), 8.03(d, 1H), 7.89-7.85(m, 6H), 7.57-7.32(m, 15H) |
| 493 | δ = 9.15(s, 1H), 8.93(d, 2H), 8.81(d, 2H), 8.28-8.04(m, 10H), 7.90-7.82(m, 8H), 7.66(d, 1H), 7.51-7.32(m, 8H) |
| 511 | δ = 8.81(d, 2H), 8.55(d, 1H), 8.28(d, 2H), 8.21(d, 1H), 8.12(d, 1H), 8.04(d, 1H), 7.94-7.88(m, 5H), 7.79(d, 2H), 7.68-7.63(m, 4H), 7.51-7.25(m, 14H) |
| 516 | δ = 8.81(d, 2H), 8.43(d, 2H), 8.28-8.20(m, 5H), 8.01(d, 2H), 7.90-7.88(m, 4H), 7.70-7.32(m, 17H) |
| 517 | δ = 8.81(5, 2H), 8.28-8.21(m, 5H), 8.04(d, 1H), 7.95-7.85(m, 8H), 7.75(d, 1H), 7.64(d, 3H), 7.51-7.25(m, 12H) |

TABLE 51-continued

| Compound Number | ¹H NMR (CDCl₃, 400 Mhz) |
|---|---|
| 519 | δ = 8.81(d, 2H), 8.28(d, 4H), 8.03-7.88(m, 9H), 7.73-7.32(m, 13H) |
| 528 | δ = 8.81(d, 2H), 8.28(d, 2H), 8.03-7.79(m, 13H), 7.66(d, 1H), 7.52-7.25(m, 13H) |
| 529 | δ = 8.45-8.41(m, 2H), 8.30-8.21(m, 5H), 8.03-7.89(m, 5H), 7.80(d, 1H), 7.66-7.50(m, 11H), 7.41-7.25(m, 6H) |
| 532 | δ = 8.81(d, 2H), 8.33-8.21(m, 6H), 8.02(d, 1H), 7.89(d, 2H), 7.79-7.75(m, 3H), 7.66-7.62(m, 4H), 7.51-7.25(d, 14H) |
| 535 | δ = 8.81(d, 1H), 8.33-8.21(m, 6H), 8.12(d, 1H), 8.02(d, 1H), 7.94-7.89(m, 2H), 7.79(d, 2H), 7.68-7.63(m, 5H), 7.51-7.19(m, 14H) |
| 538 | δ = 8.81(d, 2H), 8.33-8.21(m, 6H), 8.02(d, 1H), 7.89-7.57(m, 18H), 7.51-7.32(m, 12H), 7.19(d, 2H) |
| 543 | δ = 9.15(s, 1H), 8.93(d, 2H), 8.81(d, 2H), 8.33-8.12(m, 10H), 8.04(d, 2H), 7.89-7.79(m, 7H), 7.66(d, 1H), 7.51-7.32(m, 8H) |
| 549 | δ = 8.81(d, 2H), 8.55(d, 1H), 8.33-8.21(m, 6H), 8.12(d, 2H), 8.03(d, 1H), 7.94-7.89(m, 2H), 7.79(d, 2H), 7.68-7.63(m, 4H), 7.52-7.25(m, 14H) |
| 551 | δ = 8.28-8.23(m, 6H), 8.12(d, 1H), 8.03(d, 1H), 7.89(d, 2H), 7.81(d, 2H), 7.72-7.32(m, 21H) |
| 558 | δ = 8.81(d, 2H), 8.33-8.21(m, 6H), 8.04(d, 1H), 7.90(s, 1H), 7.89(d, 2H), 7.79-7.75(m, 3H), 7.64(d, 3H), 7.51-7.32(m, 11H), 7.25(d, 4H) |
| 560 | δ = 8.81(d, 2H), 8.33-8.21(m, 8H), 8.04(d, 1H), 7.90-7.85(m, 4H), 7.70(s, 1H), 7.66(d, 1H), 7.52-7.32(m, 18H) |
| 563 | δ = 8.81(d, 2H), 8.55(d, 1H), 8.33-8.21(m, 6H), 8.12(d, 2H), 8.04-7.90(m, 4H), 7.79(d, 2H), 7.68-7.63(m, 3H), 7.52-7.25(m, 14H) |
| 566 | δ = 8.81(d, 2H), 8.33-8.21(m, 8H), 8.04(d, 1H), 7.90-7.81(m, 5H), 7.66(d, 1H), 7.52-7.32 (m, 15H) |
| 572 | δ = 8.81(d, 2H), 8.33-8.23(m, 5H), 8.03-7.89(m, 5H), 7.79-7.75(m, 3H), 7.64(d, 2H), 7.52-7.25(m, 15H) |
| 577 | δ = 8.81(d, 2H), 8.55(d, 1H), 8.33-8.23(m, 5H), 8.12(d, 1H), 8.03-7.94(m, 5H), 7.79(d, 2H), 7.68-7.63(m, 4H), 7.52-7.25(m, 12H) |
| 579 | δ = 8.81(d, 2H), 8.33-8.23(m, 5H), 8.03-7.66(m, 12H), 7.52-7.32(m, 13H) |
| 584 | δ = 8.81(d, 2H), 8.30-8.23(m, 7H), 8.03-7.79(m, 12H), 7.66(d, 1H), 7.52-7.32(m, 13H) |
| 585 | δ = 9.15(s, 1H), 8.93(d, 2H), 8.81(d, 2H), 8.23-8.02(m, 7H), 7.88-7.79(m, 11H), 7.66(t, 2H), 7.51-7.32(m, 8H) |
| 590 | δ = 8.81(d, 2H), 8.55(d, 1H), 8.23(s, 1H), 8.21(d, 1H), 8.12(d, 1H), 8.02(d, 1H), 7.89-7.79(m, 8H), 7.68-7.63(m, 5H), 7.51-7.19(m, 14H) |
| 594 | δ = 8.45-8.41(m, 2H), 8.30-8.21(m, 5H), 8.00(d, 2H), 7.89(d, 1H), 7.80(d, 3H), 7.66-7.32(m, 16H), 7.25(d, 4H) |
| 598 | δ = 9.15(s, 1H), 8.93(d, 2H), 8.81(d, 2H), 8.27-8.03(m, 8H), 7.88-7.79(m, 11H), 7.66(d, 1H), 7.51-7.32(m, 8H) |
| 603 | δ = 8.81(d, 2H), 8.55(d, 1H), 8.27(s, 1H), 8.23(s, 1H), 8.12(d, 2H), 8.03(d, 1H), 7.94-7.88(m, 4H), 7.79(d, 4H), 7.68-7.63(m, 4H), 7.52-7.29(m, 14H) |
| 609 | δ = 8.81(d, 2H), 8.27(s, 1H), 8.23(s, 1H), 8.12(d, 1H), 8.03(d, 1H), 7.89-7.79(m, 12H), 7.66(d, 1H), 7.51-7.25(m, 13H) |
| 611 | δ = 9.15(s, 1H), 8.93(d, 2H), 8.81(d, 2H), 8.23-8.04(m, 7H), 7.90-7.79(m, 12H), 7.66(d, 1H), 7.51-7.32(m, 8H) |
| 616 | δ = 8.81(d, 2H), 8.55(d, 1H), 8.23(s, 1H), 8.21(d, 1H), 8.12(d, 1H), 8.04(d, 1H), 7.94-7.88(m, 5H), 7.79(d, 4H), 7.68-7.63(m, 4H), 7.52-7.25(m, 14H) |
| 619 | δ = 8.81(d, 2H), 8.30(d, 2H), 8.23(s, 1H), 8.21(d, 1H), 8.04(d, 1H), 7.90-7.79(m, 9H), 7.66(d, 2H), 7.52-7.25 (m, 15H) |
| 626 | δ = 8.81(d, 2H), 8.23(s, 1H), 8.03-7.79(m, 12H), 7.64(d, 3H), 7.52-7.32(m, 11H), 7.25(d, 4H) |
| 631 | δ = 8.55(d, 1H), 8.30-8.21(m, 4H), 8.12-7.89(m, 7H), 7.79(d, 5H), 7.66-7.25(m, 17H) |
| 634 | δ = 8.45-8.41(m, 3H), 8.30-8.23(m, 4H), 8.03-7.89(m, 5H), 7.80-7.79(m, 3H), 7.66-7.32(m, 15H), 7.25(d, 4H) |
| 638 | δ = 8.30-8.21(m, 7H), 8.03(d, 1H), 7.95-7.79(m, 11H), 7.60-7.32(m, 20H), 7.52(d, 2H) |
| 639 | δ = 9.30(d, 2H), 9.15(s, 2H), 8.81(d, 2H), 8.53(d, 2H), 8.21(d, 1H), 8.02(d, 1H), 7.89-7.81(m, 6H), 7.70-7.66(m, 4H), 7.38-7.25(m, 9H), 7.14(t, 2H) |
| 642 | δ = 9.30(d, 2H), 9.15(s, 2H), 8.81(d, 2H), 8.53(d, 2H), 8.21(d, 1H), 8.02-7.88(m, 7H), 7.73-7.48(m, 12H), 7.38-7.32(m, 5H), 7.14(t, 2H) |
| 646 | δ = 9.30(d, 2H), 9.15(s, 2H), 8.81(d, 2H), 8.53(d, 2H), 8.45(d, 1H), 8.27(s, 1H), 8.12(d, 1H), 8.03-7.98(m, 8H), 7.70-7.48(m, 9H), 7.38(t, 1H), 7.32(t, 1H), 7.14(t, 2H) |
| 650 | δ = 9.30(d, 2H), 9.15(s, 2H), 8.81(d, 2H), 8.53(d, 2H), 8.21(d, 1H), 8.04-7.88(m, 8H), 7.73-7.48(m, 11H), 7.38(t, 1H), 7.32(t, 1H), 7.14(t, 2H) |
| 657 | δ = 8.93(d, 2H), 8.45(d, 1H), 8.26-8.21(m, 3H), 8.12(d, 2H), 8.02(d, 1H), 7.93-7.77(m, 14H), 7.66-7.32(m, 12H) |
| 659 | δ = 8.81(d, 2H), 8.27(s, 1H), 8.12(d, 1H), 8.03(d, 1H), 7.89-7.75(m, 13H), 7.64(d, 3H), 7.45-7.32 (m, 11H) |
| 663 | δ = 8.81(d, 2H), 8.21(d, 1H), 8.04(d, 1H), 7.90-7.77(m, 12H), 7.66(d, 1H), 7.52-7.32(m, 13H) |
| 667 | δ = 8.81(d, 2H), 8.03-7.77(m, 16H), 7.64(d, 3H), 7.45-7.32 (m, 11H) |
| 672 | δ = 8.55(d, 1H), 8.30-8.21(m, 5H), 8.12(d, 1H), 8.02(d, 1H), 7.94-7.79(m, 6H), 7.68-7.63(m, 5H), 7.54-7.25(m, 14H) |
| 677 | δ = 8.45-8.41(m, 2H), 8.30-8.20(m, 7H), 8.12(d, 1H), 8.01(d, 2H), 7.89-7.85(m, 3H), 7.70-7.32(m, 15H), 7.25(d, 2H) |
| 679 | δ = 8.30-8.21(m, 7H), 8.04(d, 1H), 7.90-7.85(m, 4H), 7.66(d, 1H), 7.54-7.32(m, 11H), 7.25(d, 2H) |
| 683 | δ = 8.30-8.28(m, 6H), 8.03-7.85(m, 6H), 7.66(d, 1H), 7.54-7.32(m, 11H), 7.25(d, 2H) |
| 688 | δ = 8.55(d, 1H), 8.30-8.21(m, 8H), 8.12(d, 1H), 8.02(d, 1H), 7.91(d, 2H), 7.79(d, 2H), 7.68-7.63(m, 5H), 7.54-7.25(m, 14H) |
| 691 | δ = 8.30-8.23(m, 8H), 8.12(d, 1H), 8.03(d, 1H), 7.89-7.79(m, 5H), 7.66(d, 1H), 7.54-7.32(m, 11H) |
| 693 | δ = 8.45-8.41(m, 2H), 8.30-8.20(m, 11H), 8.12(d, 1H), 8.01(d, 2H), 7.89-7.85(m, 3H), 7.58-7.48(m, 12H), 7.25(d, 2H) |
| 696 | δ = 8.55(d, 1H), 8.30-8.21(m, 8H), 8.12(d, 1H), 8.04(d, 1H), 7.94-7.79(m, 7H), 7.68-7.63(m, 4H), 7.54-7.25(m, 12H) |
| 703 | δ = 8.30(d, 6H), 8.22(d, 2H), 8.02(d, 1H), 7.89-7.85(m, 7H), 7.66(t, 2H), 7.54-7.32(m, 15H), 7.25(d, 2H) |
| 712 | δ = 8.55(d, 1H), 8.30-8.21(m, 4H), 8.12(d, 1H), 8.04(d, 1H), 7.94-7.79(m, 9H), 7.68-7.63(m, 4H), 7.54-7.25(m, 14H) |
| 713 | δ = 8.45-8.41(m, 2H), 8.30-8.20(m, 8H), 8.04-7.98(m, 2H), 7.90(s, 1H), 7.89(d, 1H), 7.79(d, 2H), 7.70(s, 1H), 7.66-7.32(m, 14H), 7.25(d, 2H) |
| 716 | δ = 8.55(d, 1H), 8.30(d, 2H), 8.23(s, 1H), 8.12(d, 1H), 8.03-7.79(m, 11H), 7.68-7.63(m, 4H), 7.54-7.25(m, 14H) |
| 719 | δ = 9.30(d, 2H), 9.15(s, 2H), 8.53(d, 2H), 8.30(d, 2H), 8.21(d, 1H), 8.02(d, 1H), 7.98(d, 1H), 7.68(td, 4H), 7.54-7.32(m, 5H), 7.25(d, 4H), 7.14(t, 2H) |
| 723 | δ = 9.30(d, 2H), 9.15(s, 2H), 8.53(d, 2H), 8.30(d, 2H), 8.27(s, 1H), 8.12(d, 1H), 8.03(d, 1H), 7.98(d, 1H), 7.70(t, 3H), 7.57-7.32(m, 9H), 7.14(t, 2H) |
| 725 | δ = 9.30(d, 2H), 9.15(s, 2H), 8.53(d, 2H), 8.30(d, 2H), 8.21(d, 1H), 8.04(d, 1H), 7.90(d, 2H), 7.70(t, 2H), 7.66(d, 1H), 7.54-7.32(m, 5H), 7.25(d, 4H), 7.14(t, 2H) |
| 732 | δ = 8.30(d, 2H), 8.21(d, 1H), 8.02(d, 1H), 7.89-7.77(m, 9H), 7.66(t, 2H), 7.54-7.32(m, 11H), 7.25(d, 4H) |
| 738 | δ = 8.30(d, 2H), 8.21(d, 1H), 8.04(d, 1H), 7.89-7.77(m, 10H), 7.66(d, 1H), 7.54-7.32(m, 11H), 7.25(d, 4H) |
| 743 | δ = 8.55(d, 1H), 8.46(d, 1H), 8.28-8.21(m, 5H), 8.10-8.02(m, 3H), 7.89-7.85(m, 3H), 7.65(t, 3H), 7.55-7.32(m, 10), 7.25(d, 2H) |
| 748 | δ = 8.55(d, 1H), 8.46(d, 1H), 8.28(d, 3H), 8.12-8.03(m, 5H), 7.94-7.79(m, 6H), 7.68-7.63(m, 5H), 7.55-7.25(m, 11H) |
| 753 | δ = 8.55(d, 1H), 8.46(d, 1H), 8.28-8.21(m, 4H), 8.10-8.04(m, 3H), 7.90-7.85(m, 7H), 7.70-7.32(m, 16H), 7.25(m, 2H) |

TABLE 51-continued

| Compound Number | $^1$H NMR (CDCl$_3$, 400 Mhz) |
|---|---|
| 755 | δ = 8.55(d, 1H), 8.46(d, 11H), 8.28(d, 4H), 8.10-7.85(m, 8H), 7.66(d, 1H), 7.64(t, 1H), 7.55-7.41(m, 10H), 7.25(d, 2H) |
| 765 | δ = 8.55(d, 1H), 8.46-8.41(m, 3H), 8.30-8.20(m, 9H), 8.12-7.98(m, 5H), 7.89(d, 1H), 7.85(d, 2H), 7.66-7.32(m, 12H), 7.25(d, 2H) |
| 768 | δ = 8.55(d, 2H), 8.46(d, 1H), 8.30-8.21(m, 6H), 8.12-8.04(m, 4H), 7.94-7.79(m, 7H), 7.64-7.25(m, 16H) |
| 779 | δ = 8.55(d, 1H), 8.46(d, 1H), 8.27(s, 1H), 8.23(s, 1H), 8.12-8.03(m, 4H), 7.89-7.79(m, 7H), 7.66-7.32(m, 12H), 7.25(d, 2H) |
| 784 | δ = 8.55(d, 2H), 8.46(d, 1H), 8.23(s, 1H), 8.21(s, 1H), 8.12-8.04(m, 4H), 7.94-7.79(m, 9H), 7.68-7.64(m, 5H), 7.55-7.25(m, 13H) |
| 788 | δ = 8.55(d, 2H), 8.46(d, 1H), 8.23(s, 1H), 8.12-7.94(m, 8H), 7.85-7.79(m, 6H), 7.68(d, 2H), 7.64-7.25(m, 16H) |
| 794 | δ = 9.30(d, 2H), 9.15(s, 2H), 8.55-8.46(m, 4H), 8.27(s, 1H), 8.12-8.03(m, 4H), 7.89(d, 1H), 7.70-7.55(m, 6H), 7.35(t, 2H), 7.25(d, 4H), 7.14(t, 2H) |
| 807 | δ = 8.55(d, 1H), 8.46(d, 1H), 8.27(s, 1H), 8.12-8.03(m, 4H), 7.89-7.77(m, 9H), 7.64-7.55(m, 4H), 7.45-7.32(m, 8H), 7.25(d, 4H) |
| 812 | δ = 8.55(d, 1H), 8.46(d, 1H), 8.10-7.77(m, 14H), 7.64-7.55(m, 4H), 7.45-7.32(m, 8H) |
| 818 | δ = 8.93(d, 2H), 8.44(d, 1H), 8.28(d, 3H), 8.12(d, 3H), 8.03(d, 1H), 7.89-7.82(m, 9H), 7.66(d, 1H), 7.52-7.32(m, 10H), 7.25(d, 4H) |
| 827 | δ = 8.93(d, 2H), 8.44(d, 1H), 8.28-8.21(m, 4H), 8.12-8.04(m, 3h), 7.90-7.66(m, 11H), 7.57-7.32(m, 10H) |
| 833 | δ = 8.93(d, 2H), 8.44(d, 1H), 8.27(s, 1H), 8.23(s, 1H), 8.12(d, 3H), 8.03(d, 1H), 7.89-7.79(m, 11H), 7.70(s, 1H), 7.66(d, 1H), 7.57-7.32(m, 11H), 7.25(d, 2H) |
| 839 | δ = 9.30(d, 2H), 9.15(s, 2H), 8.93(d, 2H), 8.53(d, 2H), 8.44(s, 1H), 8.21(d, 1H), 8.12(d, 2H), 8.02(d, 1H), 7.89-7.82(m, 5H), 7.70-7.66(m, 4H), 7.38(t, 1H), 7.32(t, 1H), 7.25(d, 4H), 7.14(t, 2H) |
| 842 | δ = 9.30(d, 2H), 9.15(s, 2H), 8.93(d, 2H), 8.53(d, 2H), 8.44(s, 1H), 8.27(s, 1H), 8.12(d, 3H), 8.03(d, 1H), 7.89-7.82(m, 5H), 7.70(t, 4H), 7.57-7.32(m, 8H9), 7.14(t, 2H) |
| 849 | δ = 8.93(d, 2H), 8.44(s, 1H), 8.27(s, 1H), 8.12(d, 3H), 8.03(d, 1H), 7.89-7.77(m, 13H), 7.66(d, 1H), 7.45-7.32(m, 8H) |
| 853 | δ = 8.93(d, 2H), 8.44(s, 1H), 8.12(d, 2H), 8.03-7.77(m, 15H), 7.66(d, 1H), 7.45-7.32(m, 8H) |
| 857 | δ = 9.66(s, 1H), 8.93(d, 2H), 8.55(d, 1H), 8.28-8.21(m, 6H), 8.12(d, 3H), 8.03(m, 1H), 7.89-7.82(m, 7H), 7.66(d, 1H), 7.51-7.25(m, 10H) |
| 866 | δ = 9.66(s, 1H), 8.93(d, 2H), 8.55(d, 1H), 8.28-8.21(m, 4H), 8.12(d, 2H), 8.03-7.70(m, 12H), 7.52-7.41(m, 10H) |
| 875 | δ = 9.66(s, 1H), 9.30(d, 2H), 9.15(s, 2H), 8.93(d, 2H), 8.54(d, 3H), 8.21-8.04(m, 5H), 7.90-7.82(m, 6H), 7.70(t, 3H), 7.66-7.32(m, 6H), 7.14(t, 2H) |
| 879 | δ = 9.66(s, 1H), 8.93(d, 2H), 8.55(d, 1H), 8.45(d, 1H), 8.21(d, 2H), 8.12(d, 2H), 8.04(d, 1H), 7.89-7.77(m, 13H), 7.52-7.32(m, 10H) |
| 883 | δ = 8.81(d, 2H), 8.51(d, 1H), 8.28-8.16(m, 4H), 8.06(d, 1H), 7.89-7.81(m, 7H), 7.70-7.32(m, 15H) |
| 885 | δ = 8.81(d, 2H), 8.51(d, 1H), 8.33-8.23(m, 7H), 8.16(d, 1H), 8.06(d, 1H), 7.89-7.81(m, 4H), 7.67(t, 3H), 7.52-7.32(m, 10H) |
| 893 | δ = 9.30(d, 2H), 9.15(s, 2H), 8.81(d, 2H), 8.52(d, 3H), 8.16(d, 1H), 8.06(d, 1H), 7.89-7.81(m, 4H), 7.70-7.66(m, 5H), 7.38(t, 1H), 7.32(t, 1H), 7.25(d, 4H), 7.14(t, 2H) |
| 895 | δ = 8.81(d, 2H), 8.28(d, 4H), 8.16(d, 2H), 8.05(s, 1H), 7.88(d, 3H), 7.68-7.66(m, 4H), 7.51-7.32(m, 8H) |
| 901 | δ = 8.81(d, 2H), 8.45-8.16(m, 12H), 8.05(s, 1H), 7.98(d, 1H), 7.89(d, 1H), 7.68-7.32(m, 12H), 7.25(d, 2H) |
| 904 | δ = 8.81(d, 2H), 8.23(s, 1H), 8.16(d, 2H), 8.05(s, 1H), 7.98-7.67(m, 15H), 7.57-7.32(m, 11H) |
| 913 | δ = 8.81(d, 2H), 8.54(d, 1H), 8.45-8.16(m, 11H), 7.98(d, 3H), 7.89(d, 1H), 7.58-7.41(m, 9H), 7.38-7.25(m, 4H) |
| 915 | δ = 8.81(d, 2H), 8.54(d, 1H), 8.30(d, 4H), 8.23(s, 1H), 8.16(d, 1H), 7.98(d, 2H), 7.89-7.85(m, 7H), 7.67(t, 3H), 7.51-7.32(m, 12H) |
| 920 | δ = 8.81(d, 2H), 8.54(d, 1H), 8.16(d, 1H), 7.98(d, 2H), 7.88(d, 3H), 7.77-7.66(m, 9H), 7.52-7.32(m, 10H) |
| 921 | δ = 9.15(s, 1H), 8.93(d, 2H), 8.84(d, 4H), 8.45(d, 1H), 8.30(d, 2H), 8.21-7.98(m, 10H), 7.88-7.80(m, 5H), 7.66(t, 1H), 7.54-7.47(m, 5H), 7.35(d, 2H) |
| 924 | δ = 8.84(d, 4H), 8.30(d, 2H), 8.10-7.89(m, 7H), 7.81(d, 1H), 7.66(d, 1H), 7.54-7.32(m, 12H), 7.25(d, 4H) |
| 925 | δ = 8.72(s, 1H), 8.45(d, 1H), 8.31(d, 4H), 8.21(d, 1H), 8.10-7.98(m, 5H), 7.81(d, 1H), 7.64(t, 2H), 7.54-7.41(m, 10H), 7.35(d, 2H), 7.25(d, 4H) |
| 926 | δ = 8.78(s, 1H), 8.72(s, 1H), 8.54-8.45(m, 3H), 8.31(d, 4H), 8.15-7.98(m, 5H), 7.81(d, 1H), 7.63-7.50(m, 7H), 7.35(d, 2H), 7.26(d, 1H), 7.00(t, 1H) |
| 928 | δ = 8.72(s, 1H), 8.31(d, 4H), 8.10-8.03(m, 4H), 7.95-7.89(m, 3H), 7.80(d, 3H), 7.64(t, 2H), 7.54-7.32(m, 10H) |
| 929 | δ = 8.81(d, 2H), 8.45(d, 1H), 8.30(d, 4H), 8.21(d, 1H), 8.10-7.98(m, 5H), 7.81(d, 1H), 7.66(t, 1H), 7.54-7.47(m, 8H), 7.35-7.28(m, 4H) |
| 931 | δ = 8.93(d, 2H), 8.81(d, 2H), 8.32(d, 3H), 8.12-8.06(m, 5H), 7.93-7.66(m, 12H), 7.54-7.32(m, 8H) |
| 935 | δ = 8.55(d, 1H), 8.46(d, 1H), 8.30-8.21(m, 5H), 8.10-8.04(m, 6H), 7.90(d, 2H), 7.81(d, 1H), 7.66-7.47(m, 9H), 7.38-7.32(m, 4H) |
| 937 | δ = 8.84(d, 4H), 8.48(d, 1H), 8.30(d, 2H), 8.16-7.98(m, 6H), 7.81(d, 2H), 7.67(d, 2H), 7.54-7.47(m, 5H), 7.35(d, 2H) |
| 938 | δ = 8.84(d, 4H), 8.45(d, 1H), 8.30(d, 2H), 8.16-7.98(m, 7H), 7.81(d, 1H), 7.67(d, 3H), 7.54-7.47(m, 5H), 7.35(d, 2H) |
| 939 | δ = 8.84(d, 4H), 8.54(d, 1H), 8.30(d, 2H), 8.16-8.06(m, 4H), 7.99(d, 2H), 7.89(d, 1H), 7.81(d, 2H), 7.67(td, 3H), 7.54-7.47(m, 3H), 7.38-7.32(m, 4H) |
| 940 | δ = 8.84(d, 4H), 8.51(d, 1H), 8.30(d, 2H), 8.16-8.06(m, 5H), 7.89(d, 1H), 7.81(d, 2H), 7.67(td, 3H), 7.54-7.47(m, 3H), 7.38-7.32(m, 4H) |
| 942 | δ = 8.81(d, 4H), 8.54(d, 1H), 8.45(d, 1H), 8.30(d, 2H), 8.16-8.06(m, 4H), 7.99(d, 3H), 7.88-7.81(m, 5H), 7.67(t, 2H), 7.54-7.47(m, 5H), 7.35(d, 2H) |
| 944 | δ = 8.81(d, 4H), 8.30(d, 2H), 8.16-8.05(m, 6H), 7.89-7.81(m, 6H), 7.67(t, 4H), 7.54-7.47(m, 3H), 7.35(m, 4H) |

TABLE 52

| Compound | FD-Mass | Compound | FD-Mass |
|---|---|---|---|
| 1 | m/z = 762.92 (C54H32N4S = 768.23) | 2 | m/z = 708.83 (C48H28N4OS = 708.20) |
| 3 | m/z = 845.02 (C60H36N4S = 844.27) | 4 | m/z = 800.99 (C54H32N4S2 = 800.21) |
| 5 | m/z = 784.92 (C54H32N4OS = 784.23) | 6 | m/z = 770.94 (C54H34N4S = 770.25) |
| 7 | m/z = 783.94 (C54H33N5S = 783.25) | 8 | m/z = 783.94 (C54H33N5S = 783.25) |

TABLE 52-continued

| Compound | FD-Mass | Compound | FD-Mass |
|---|---|---|---|
| 9 | m/z = 784.92 (C54H32N4OS = 784.23) | 10 | m/z = 784.92 (C54H32N4OS = 784.23) |
| 11 | m/z = 784.92 (C54H32N4OS = 784.23) | 12 | m/z = 800.99 (C54H32N4S2 = 800.21) |
| 13 | m/z = 800.99 (C54H32N4S2 = 800.21) | 14 | m/z = 784.92 (C54H32N4OS = 784.23) |
| 15 | m/z = 770.94 (C54H34N4S = 770.25) | 16 | m/z = 847.04 (C60H38N4S = 846.28) |
| 17 | m/z = 768.92 (C54H32N4S = 768.23) | 18 | m/z = 784.92 (C54H32N4OS = 784.23) |
| 19 | m/z = 800.99 (C54H32N4S2 = 800.21) | 20 | m/z = 770.94 (C54H34N4S = 770.25) |
| 21 | m/z = 800.99 (C54H32N4S2 = 800.21) | 22 | m/z = 770.94 (C54H34N4S = 770.25) |
| 23 | m/z = 770.94 (C54H34N4S = 770.25) | 24 | m/z = 783.94 (C54H33N5S = 783.25) |
| 25 | m/z = 783.94 (C54H33N5S = 783.25) | 26 | m/z = 784.92 (C54H32N4OS = 784.23) |
| 27 | m/z = 784.92 (C54H32N4OS = 784.23) | 28 | m/z = 784.92 (C54H32N4OS = 784.23) |
| 29 | m/z = 800.99 (C54H32N4S2 = 800.21) | 30 | m/z = 800.99 (C54H32N4S2 = 800.21) |
| 31 | m/z = 800.99 (C54H32N4S2 = 800.21) | 32 | m/z = 847.04 (C60H38N4S = 846.28) |
| 33 | m/z = 768.92 (C54H32N4S = 768.23) | 34 | m/z = 784.92 (C54H32N4OS = 784.23) |
| 35 | m/z = 800.99 (C54H32N4S2 = 800.21) | 36 | m/z = 770.94 (C54H34N4S = 770.25) |
| 37 | m/z = 783.94 (C54H33N5S = 783.25) | 38 | m/z = 783.94 (C54H33N5S = 783.25) |
| 39 | m/z = 784.92 (C54H32N4OS = 784.23) | 40 | m/z = 784.92 (C54H32N4OS = 784.23) |
| 41 | m/z = 800.99 (C54H32N4S2 = 800.21) | 42 | m/z = 800.99 (C54H32N4S2 = 800.21) |
| 43 | m/z = 784.92 (C54H32N4OS = 784.23) | 44 | m/z = 770.94 (C54H34N4S = 770.25) |
| 45 | m/z = 770.94 (C54H34N4S = 770.25) | 46 | m/z = 768.92 (C54H32N4S = 768.23) |
| 47 | m/z = 708.83 (C48H28N4OS = 708.20) | 48 | m/z = 724.89 (C48H28N4S2 = 724.18) |
| 49 | m/z = 800.99 (C54H32N4S2 = 800.21) | 50 | m/z = 770.94 (C54H34N4S = 770.25) |
| 51 | m/z = 783.94 (C54H33N5S = 783.25) | 52 | m/z = 783.94 (C54H33N5S = 783.25) |
| 53 | m/z = 784.92 (C54H32N4OS = 784.23) | 54 | m/z = 784.92 (C54H32N4OS = 784.23) |
| 55 | m/z = 800.99 (C54H32N4S2 = 800.21) | 56 | m/z = 800.99 (C54H32N4S2 = 800.21) |
| 57 | m/z = 784.92 (C54H32N4OS = 784.23) | 58 | m/z = 847.04 (C60H38N4S = 846.28) |
| 59 | m/z = 668.81 (C46H28N4S = 668.20) | 60 | m/z = 708.83 (C48H28N4OS = 708.20) |
| 61 | m/z = 800.99 (C54H32N4S2 = 800.21) | 62 | m/z = 770.94 (C54H34N4S = 770.25) |
| 63 | m/z = 800.99 (C54H32N4S2 = 800.21) | 64 | m/z = 770.94 (C54H34N4S = 770.25) |
| 65 | m/z = 783.94 (C54H33N5S = 783.25) | 66 | m/z = 783.94 (C54H33N5S = 783.25) |
| 67 | m/z = 784.92 (C54H32N4OS = 784.23) | 68 | m/z = 784.92 (C54H32N4OS = 784.23) |
| 69 | m/z = 800.99 (C54H32N4S2 = 800.21) | 70 | m/z = 847.04 (C60H38N4S = 846.28) |
| 71 | m/z = 767.94 (C55H33N3S = 767.24) | 72 | m/z = 783.94 (C55H33N3OS = 783.23) |
| 73 | m/z = 800.00 (C55H33N3S2 = 799.21) | 74 | m/z = 769.95 (C55H35N3S = 769.26) |
| 75 | m/z = 782.95 (C55H34N4S = 782.25) | 76 | m/z = 782.95 (C55H34N4S = 782.25) |
| 77 | m/z = 783.94 (C55H33N3OS = 783.23) | 78 | m/z = 783.94 (C55H33N3OS = 783.23) |
| 79 | m/z = 800.00 (C55H33N3S2 = 799.21) | 80 | m/z = 800.00 (C55H33N3S2 = 799.21) |
| 81 | m/z = 783.94 (C55H33N3OS = 783.23) | 82 | m/z = 846.05 (C61H39N3S = 845.29) |
| 83 | m/z = 767.94 (C55H33N3S = 767.24) | 84 | m/z = 783.94 (C55H33N3OS = 783.23) |
| 85 | m/z = 723.90 (C49H29N3S2 = 723.18) | 86 | m/z = 793.97 (C57H35N3S = 793.26) |

TABLE 52-continued

| Compound | FD-Mass | Compound | FD-Mass |
|---|---|---|---|
| 87 | m/z = 800.00 (C55H33N3S2 = 799.21) | 88 | m/z = 769.95 (C55H35N3S = 769.26) |
| 89 | m/z = 782.95 (C55H34N4S = 782.25) | 90 | m/z = 782.95 (C55H34N4S = 782.25) |
| 91 | m/z = 783.94 (C55H33N3OS = 783.23) | 92 | m/z = 783.94 (C55H33N3OS = 783.23) |
| 93 | m/z = 773.96 (C53H31N3S2 = 773.20) | 94 | m/z = 800.00 (C55H33N3S2 = 799.21) |
| 95 | m/z = 783.94 (C55H33N3OS = 783.23) | 96 | m/z = 769.95 (C55H35N3S = 769.26) |
| 97 | m/z = 767.94 (C55H33N3S = 767.24) | 98 | m/z = 783.94 (C55H33N3OS = 783.23) |
| 99 | m/z = 723.90 (C49H29N3S2 = 723.18) | 100 | m/z = 769.95 (C55H35N3S = 769.26) |
| 101 | m/z = 800.00 (C55H33N3S2 = 799.21) | 102 | m/z = 769.95 (C55H35N3S = 769.26) |
| 103 | m/z = 782.95 (C55H34N4S = 782.25) | 104 | m/z = 782.95 (C55H34N4S = 782.25) |
| 105 | m/z = 783.94 (C55H33N3OS = 783.23) | 106 | m/z = 783.94 (C55H33N3OS = 783.23) |
| 107 | m/z = 800.00 (C55H33N3S2 = 799.21) | 108 | m/z = 800.00 (C55H33N3S2 = 799.21) |
| 109 | m/z = 769.95 (C55H35N3S = 769.26) | 110 | m/z = 769.95 (C55H35N3S = 769.26) |
| 111 | m/z = 667.82 (C47H29N3S = 667.21) | 112 | m/z = 783.94 (C55H33N3OS = 783.23) |
| 113 | m/z = 723.90 (C49H29N3S2 = 723.18) | 114 | m/z = 769.95 (C55H35N3S = 769.26) |
| 115 | m/z = 800.00 (C55H33N3S2 = 799.21) | 116 | m/z = 769.95 (C55H35N3S = 769.26) |
| 117 | m/z = 782.95 (C55H34N4S = 782.25) | 118 | m/z = 782.95 (C55H34N4S = 782.25) |
| 119 | m/z = 783.94 (C55H33N3OS = 783.23) | 120 | m/z = 783.94 (C55H33N3OS = 783.23) |
| 121 | m/z = 800.00 (C55H33N3S2 = 799.21) | 122 | m/z = 800.00 (C55H33N3S2 = 799.21) |
| 123 | m/z = 769.95 (C55H35N3S = 769.26) | 124 | m/z = 769.95 (C55H35N3S = 769.26) |
| 125 | m/z = 767.94 (C55H33N3S = 767.24) | 126 | m/z = 783.94 (C55H33N3OS = 783.23) |
| 127 | m/z = 800.00 (C55H33N3S2 = 799.21) | 128 | m/z = 800.00 (C55H33N3S2 = 799.21) |
| 129 | m/z = 769.95 (C55H35N3S = 769.26) | 130 | m/z = 782.95 (C55H34N4S = 782.25) |
| 131 | m/z = 782.95 (C55H34N4S = 782.25) | 132 | m/z = 783.94 (C55H33N3OS = 783.23) |
| 133 | m/z = 783.94 (C55H33N3OS = 783.23) | 134 | m/z = 800.00 (C55H33N3S2 = 799.21) |
| 135 | m/z = 800.00 (C55H33N3S2 = 799.21) | 136 | m/z = 783.94 (C55H33N3OS = 783.23) |
| 137 | m/z = 846.05 (C61H39N3S = 845.29) | 138 | m/z = 767.94 (C55H33N3S = 767.24) |
| 139 | m/z = 783.94 (C55H33N3OS = 783.23) | 140 | m/z = 800.00 (C55H33N3S2 = 799.21) |
| 141 | m/z = 844.03 (C61H37N3S = 843.27) | 142 | m/z = 800.00 (C55H33N3S2 = 799.21) |
| 143 | m/z = 782.95 (C55H34N4S = 782.25) | 144 | m/z = 782.95 (C55H34N4S = 782.25) |
| 145 | m/z = 783.94 (C55H33N3OS = 783.23) | 146 | m/z = 783.94 (C55H33N3OS = 783.23) |
| 147 | m/z = 800.00 (C55H33N3S2 = 799.21) | 148 | m/z = 800.00 (C55H33N3S2 = 799.21) |
| 149 | m/z = 783.94 (C55H33N3OS = 783.23) | 150 | m/z = 846.05 (C61H39N3S = 845.29) |
| 151 | m/z = 767.94 (C55H33N3S = 767.24) | 152 | m/z = 783.94 (C55H33N3OS = 783.23) |
| 153 | m/z = 723.90 (C49H29N3S2 = 723.18) | 154 | m/z = 769.95 (C55H35N3S = 769.26) |
| 155 | m/z = 769.95 (C55H35N3S = 769.26) | 156 | m/z = 769.95 (C55H35N3S = 769.26) |
| 157 | m/z = 782.95 (C55H34N4S = 782.25) | 158 | m/z = 783.94 (C55H33N3OS = 783.23) |
| 159 | m/z = 783.94 (C55H33N3OS = 783.23) | 160 | m/z = 800.00 (C55H33N3S2 = 799.21) |
| 161 | m/z = 800.00 (C55H33N3S2 = 799.21) | 162 | m/z = 783.94 (C55H33N3OS = 783.23) |
| 163 | m/z = 769.95 (C55H35N3S = 769.26) | 164 | m/z = 846.05 (C61H39N3S = 845.29) |

TABLE 52-continued

| Compound | FD-Mass | Compound | FD-Mass |
|---|---|---|---|
| 165 | m/z = 667.82 (C47H29N3S = 667.21) | 166 | m/z = 783.94 (C55H33N3S = 783.23) |
| 167 | m/z = 723.90 (C49H29N3S2 = 723.18) | 168 | m/z = 769.95 (C55H35N3S = 769.26) |
| 169 | m/z = 769.95 (C55H35N3S = 769.26) | 170 | m/z = 782.95 (C55H34N4S = 782.25) |
| 171 | m/z = 783.94 (C55H33N3OS = 783.23) | 172 | m/z = 783.94 (C55H33N3OS = 783.23) |
| 173 | m/z = 783.94 (C55H33N3OS = 783.23) | 174 | m/z = 800.00 (C55H33N3S2 = 799.21) |
| 175 | m/z = 800.00 (C55H33N3S2 = 799.21) | 176 | m/z = 783.94 (C55H33N3OS = 783.23) |
| 177 | m/z = 769.95 (C55H35N3S = 769.26) | 178 | m/z = 846.05 (C61H39N3S = 845.29) |
| 179 | m/z = 784.92 (C54H32N4OS = 784.23) | 180 | m/z = 770.94 (C54H34N4S = 770.25) |
| 181 | m/z = 794.96 (C56H34N4S = 794.25) | 182 | m/z = 744.90 (C52H32N4S = 744.23) |
| 183 | m/z = 784.92 (C54H32N4OS = 784.23) | 184 | m/z = 770.94 (C54H34N4S = 770.25) |
| 185 | m/z = 744.90 (C52H32N4S = 744.23) | 186 | m/z = 800.99 (C54H32N4S2 = 800.21) |
| 187 | m/z = 694.84 (C48H30N4S = 694.22) | 188 | m/z = 800.99 (C54H32N4S2 = 800.21) |
| 189 | m/z = 794.96 (C56H34N4S = 794.25) | 190 | m/z = 744.90 (C52H32N4S = 744.23) |
| 191 | m/z = 784.92 (C54H32N4OS = 784.23) | 192 | m/z = 770.94 (C54H34N4S = 770.25) |
| 193 | m/z = 694.84 (C48H30N4S = 694.22) | 194 | m/z = 800.99 (C54H32N4S2 = 800.21) |
| 195 | m/z = 677.75 (C45H28NO2PS = 677.16) | 196 | m/z = 739.86 (C51H34NOPS = 739.21) |
| 197 | m/z = 763.88 (C53H34NOPS = 763.21) | 198 | m/z = 769.91 (C51H32NOPS2 = 769.17) |
| 199 | m/z = 753.84 (C51H32NO2PS = 753.19) | 200 | m/z = 739.86 (C51H34NOPS = 739.21) |
| 201 | m/z = 713.82 (C49H32NOPS = 713.19) | 202 | m/z = 769.91 (C51H32NOPS2 = 769.17) |
| 203 | m/z = 663.76 (C45H30NOPS = 663.18) | 204 | m/z = 769.91 (C51H32NOPS2 = 769.17) |
| 205 | m/z = 763.88 (C53H34NOPS = 763.21) | 206 | m/z = 713.82 (C49H32NOPS = 713.19) |
| 207 | m/z = 753.84 (C51H32NO2PS = 753.19) | 208 | m/z = 739.86 (C51H34NOPS = 739.21) |
| 209 | m/z = 663.76 (C45H30NOPS = 663.18) | 210 | m/z = 769.91 (C51H32NOPS2 = 769.17) |
| 211 | m/z = 618.75 (C42H26N4S = 618.19) | 212 | m/z = 783.94 (C54H33N5S = 783.25) |
| 213 | m/z = 784.92 (C54H32N4OS = 784.23) | 214 | m/z = 770.94 (C54H34N4S = 770.25) |
| 215 | m/z = 770.94 (C54H34N4S = 770.25) | 216 | m/z = 783.94 (C54H33N5S = 783.25) |
| 217 | m/z = 800.99 (C54H32N4S2 = 800.21) | 218 | m/z = 770.94 (C54H34N4S = 770.25) |
| 219 | m/z = 618.75 (C42H26N4S = 618.19) | 220 | m/z = 783.94 (C55H33N3OS = 783.23) |
| 221 | m/z = 784.92 (C54H32N4OS = 784.23) | 222 | m/z = 770.94 (C54H34N4S = 770.25) |
| 223 | m/z = 618.75 (C42H26N4S = 618.19) | 224 | m/z = 783.94 (C54H33N5S = 783.25) |
| 225 | m/z = 784.92 (C54H32N4OS = 784.23) | 226 | m/z = 770.94 (C54H34N4S = 770.25) |
| 227 | m/z = 769.95 (C55H35N3S = 769.26) | 228 | m/z = 782.95 (C55H34N4S = 782.25) |
| 229 | m/z = 783.94 (C55H33N3OS = 783.23) | 230 | m/z = 769.95 (C55H35N3S = 769.26) |
| 231 | m/z = 617.76 (C43H27N3S = 617.19) | 232 | m/z = 782.95 (C55H34N4S = 782.25) |
| 233 | m/z = 800.00 (C55H33N3S2 = 799.21) | 234 | m/z = 769.95 (C55H35N3S = 769.26) |
| 235 | m/z = 769.95 (C55H35N3S = 769.26) | 236 | m/z = 782.95 (C55H34N4S = 782.25) |
| 237 | m/z = 783.94 (C55H33N3OS = 783.23) | 238 | m/z = 800.00 (C55H33N3S2 = 799.21) |
| 239 | m/z = 617.76 (C43H27N3S = 617.19) | 240 | m/z = 782.95 (C55H34N4S = 782.25) |
| 241 | m/z = 783.94 (C55H33N3OS = 783.23) | 242 | m/z = 769.95 (C55H35N3S = 769.26) |

TABLE 52-continued

| Compound | FD-Mass | Compound | FD-Mass |
|---|---|---|---|
| 243 | m/z = 769.95 (C55H35N3S = 769.26) | 244 | m/z = 782.95 (C55H34N4S = 782.25) |
| 245 | m/z = 800.00 (C55H33N3S2 = 799.21) | 246 | m/z = 769.95 (C55H35N3S = 769.26) |
| 247 | m/z = 617.76 (C43H27N3S = 617.19) | 248 | m/z = 782.95 (C55H34N4S = 782.25) |
| 249 | m/z = 783.94 (C55H33N3OS = 783.23) | 250 | m/z = 769.95 (C55H35N3S = 769.26) |
| 251 | m/z = 769.95 (C55H35N3S = 769.26) | 252 | m/z = 782.95 (C55H34N4S = 782.25) |
| 253 | m/z = 800.00 (C55H33N3S2 = 799.21) | 254 | m/z = 769.95 (C55H35N3S = 769.26) |
| 255 | m/z = 617.76 (C43H27N3S = 617.19) | 256 | m/z = 782.95 (C55H34N4S = 782.25) |
| 257 | m/z = 800.00 (C55H33N3S2 = 799.21) | 258 | m/z = 783.94 (C55H33N3OS = 783.23) |
| 259 | m/z = 618.75 (C42H26N4S = 618.19) | 260 | m/z = 618.75 (C42H26N4S = 618.19) |
| 261 | m/z = 694.84 (C48H30N4S = 694.22) | 262 | m/z = 618.75 (C42H26N4S = 618.19) |
| 263 | m/z = 618.75 (C42H26N4S = 618.19) | 264 | m/z = 694.84 (C48H30N4S = 694.22) |
| 265 | m/z = 618.75 (C42H26N4S = 618.19) | 266 | m/z = 618.75 (C42H26N4S = 618.19) |
| 267 | m/z = 694.84 (C48H30N4S = 694.22) | 268 | m/z = 618.75 (C42H26N4S = 618.19) |
| 269 | m/z = 618.75 (C42H26N4S = 618.19) | 270 | m/z = 694.84 (C48H30N4S = 694.22) |
| 271 | m/z = 587.67 (C39H26NOPS = 587.15) | 272 | m/z = 663.76 (C45H30NOPS = 663.18) |
| 273 | m/z = 663.76 (C45H30NOPS = 663.18) | 274 | m/z = 587.67 (C39H26NOPS = 587.15) |
| 275 | m/z = 663.76 (C45H30NOPS = 663.18) | 276 | m/z = 663.76 (C45H30NOPS = 663.18) |
| 277 | m/z = 587.67 (C39H26NOPS = 587.15) | 278 | m/z = 663.76 (C45H30NOPS = 663.18) |
| 279 | m/z = 663.76 (C45H30NOPS = 663.18) | 280 | m/z = 587.67 (C39H26NOPS = 587.15) |
| 281 | m/z = 663.76 (C45H30NOPS = 663.18) | 282 | m/z = 663.76 (C45H30NOPS = 663.18) |
| 283 | m/z = 668.81 (C46H28N4S = 668.20) | 284 | m/z = 834.00 (C58H35N5S = 833.26) |
| 285 | m/z = 834.98 (C58H34N4OS = 834.25) | 286 | m/z = 821.00 (C58H36N4S = 820.27) |
| 287 | m/z = 821.00 (C58H36N4S = 820.27) | 288 | m/z = 834.00 (C58H35N5S = 833.26) |
| 289 | m/z = 851.05 (C58H34N4S2 = 850.22) | 290 | m/z = 821.00 (C58H36N4S = 820.27) |
| 291 | m/z = 668.81 (C46H28N4S = 668.20) | 292 | m/z = 834.00 (C58H35N5S = 833.26) |
| 293 | m/z = 834.98 (C58H34N4OS = 834.25) | 294 | m/z = 821.00 (C58H36N4S = 820.27) |
| 295 | m/z = 668.81 (C46H28N4S = 668.20) | 296 | m/z = 834.00 (C58H35N5S = 833.26) |
| 297 | m/z = 834.98 (C58H34N4OS = 834.25) | 298 | m/z = 821.00 (C58H36N4S = 820.27) |
| 299 | m/z = 820.01 (C59H37N3S = 819.27) | 300 | m/z = 833.01 (C59H36N4S = 832.27) |
| 301 | m/z = 833.99 (C59H35N3OS = 833.25) | 302 | m/z = 820.01 (C59H37N3S = 819.27) |
| 303 | m/z = 833.01 (C59H36N4S = 832.27) | 304 | m/z = 833.01 (C59H36N4S = 832.27) |
| 305 | m/z = 850.06 (C59H35N3S2 = 849.23) | 306 | m/z = 820.01 (C59H37N3S = 819.27) |
| 307 | m/z = 820.01 (C59H37N3S = 819.27) | 308 | m/z = 833.01 (C59H36N4S = 832.27) |
| 309 | m/z = 833.99 (C59H35N3OS = 833.25) | 310 | m/z = 850.06 (C59H35N3S2 = 849.23) |
| 311 | m/z = 667.82 (C47H29N3S = 667.21) | 312 | m/z = 833.01 (C59H36N4S = 832.27) |
| 313 | m/z = 833.99 (C59H35N3OS = 833.25) | 314 | m/z = 820.01 (C59H37N3S = 819.27) |
| 315 | m/z = 820.01 (C59H37N3S = 819.27) | 316 | m/z = 833.01 (C59H36N4S = 832.27) |
| 317 | m/z = 850.06 (C59H35N3S2 = 849.23) | 318 | m/z = 820.01 (C59H37N3S = 819.27) |
| 319 | m/z = 667.82 (C47H29N3S = 667.21) | 320 | m/z = 833.01 (C59H36N4S = 832.27) |

TABLE 52-continued

| Compound | FD-Mass | Compound | FD-Mass |
|---|---|---|---|
| 321 | m/z = 833.99 (C59H35N3OS = 833.25) | 322 | m/z = 820.01 (C59H37N3S = 819.27) |
| 323 | m/z = 820.01 (C59H37N3S = 819.27) | 324 | m/z = 833.01 (C59H36N4S = 832.27) |
| 325 | m/z = 850.06 (C59H35N3S2 = 849.23) | 326 | m/z = 820.01 (C59H37N3S = 819.27) |
| 327 | m/z = 667.82 (C47H29N3S = 667.21) | 328 | m/z = 833.01 (C59H36N4S = 832.27) |
| 329 | m/z = 850.06 (C59H35N3S2 = 849.23) | 330 | m/z = 833.99 (C59H35N3OS = 833.25) |
| 331 | m/z = 668.81 (C46H28N4S = 668.20) | 332 | m/z = 668.81 (C46H28N4S = 668.20) |
| 333 | m/z = 668.81 (C46H28N4S = 668.20) | 334 | m/z = 668.81 (C46H28N4S = 668.20) |
| 335 | m/z = 668.81 (C46H28N4S = 668.20) | 336 | m/z = 744.90 (C52H32N4S = 744.23) |
| 337 | m/z = 668.81 (C46H28N4S = 668.20) | 338 | m/z = 668.81 (C46H28N4S = 668.20) |
| 339 | m/z = 744.90 (C52H32N4S = 744.23) | 340 | m/z = 668.81 (C46H28N4S = 668.20) |
| 341 | m/z = 668.81 (C46H28N4S = 668.20) | 342 | m/z = 744.90 (C52H32N4S = 744.23) |
| 343 | m/z = 637.73 (C43H28NOPS = 637.16) | 344 | m/z = 713.82 (C49H32NOPS = 713.19) |
| 345 | m/z = 713.82 (C49H32NOPS = 713.19) | 346 | m/z = 637.73 (C43H28NOPS = 637.16) |
| 347 | m/z = 713.82 (C49H32NOPS = 713.19) | 348 | m/z = 713.82 (C49H32NOPS = 713.19) |
| 349 | m/z = 637.73 (C43H28NOPS = 637.16) | 350 | m/z = 713.82 (C49H32NOPS = 713.19) |
| 351 | m/z = 713.82 (C49H32NOPS = 713.19) | 352 | m/z = 637.73 (C43H28NOPS = 637.16) |
| 353 | m/z = 713.82 (C49H32NOPS = 713.19) | 354 | m/z = 713.82 (C49H32NOPS = 713.19) |
| 355 | m/z = 718.87 (C50H30N4S = 718.22) | 356 | m/z = 794.96 (C56H34N4S = 794.25) |
| 357 | m/z = 794.96 (C56H34N4S = 794.25) | 358 | m/z = 794.96 (C56H34N4S = 794.25) |
| 359 | m/z = 718.87 (C50H30N4S = 718.22) | 360 | m/z = 794.96 (C56H34N4S = 794.25) |
| 361 | m/z = 718.87 (C50H30N4S = 718.22) | 362 | m/z = 794.96 (C56H34N4S = 794.25) |
| 363 | m/z = 717.88 (C51H31N3S = 717.22) | 364 | m/z = 793.97 (C57H35N3S = 793.26) |
| 365 | m/z = 793.97 (C57H35N3S = 793.26) | 366 | m/z = 793.97 (C57H35N3S = 793.26) |
| 367 | m/z = 717.88 (C51H31N3S = 717.22) | 368 | m/z = 793.97 (C57H35N3S = 793.26) |
| 369 | m/z = 717.88 (C51H31N3S = 717.22) | 370 | m/z = 793.97 (C57H35N3S = 793.26) |
| 371 | m/z = 717.88 (C51H31N3S = 717.22) | 372 | m/z = 793.97 (C57H35N3S = 793.26) |
| 373 | m/z = 793.97 (C57H35N3S = 793.26) | 374 | m/z = 793.97 (C57H35N3S = 793.26) |
| 375 | m/z = 717.88 (C51H31N3OS = 717.22) | 376 | m/z = 793.97 (C57H35N3S = 793.26) |
| 377 | m/z = 717.88 (C51H31N3S = 717.22) | 378 | m/z = 793.97 (C57H35N3S = 793.26) |
| 379 | m/z = 718.87 (C50H30N4S = 718.22) | 380 | m/z = 794.96 (C56H34N4S = 794.25) |
| 381 | m/z = 718.87 (C50H30N4S = 718.22) | 382 | m/z = 794.96 (C56H34N4S = 794.25) |
| 383 | m/z = 718.87 (C50H30N4S = 718.22) | 384 | m/z = 794.96 (C56H34N4S = 794.25) |
| 385 | m/z = 718.87 (C50H30N4S = 718.22) | 386 | m/z = 794.96 (C56H34N4S = 794.25) |
| 387 | m/z = 687.79 (C47H30NOPS = 687.18) | 388 | m/z = 763.88 (C53H34NOPS = 763.21) |
| 389 | m/z = 687.79 (C47H30NOPS = 687.18) | 390 | m/z = 763.88 (C53H34NOPS = 763.21) |
| 391 | m/z = 687.79 (C47H30NOPS = 687.18) | 392 | m/z = 763.88 (C53H34NOPS = 763.21) |
| 393 | m/z = 687.79 (C47H30NOPS = 687.18) | 394 | m/z = 763.88 (C53H34NOPS = 763.21) |
| 395 | m/z = 768.92 (C54H32N4S = 768.23) | 396 | m/z = 845.02 (C60H36N4S = 844.27) |
| 397 | m/z = 768.92 (C54H32N4S = 768.23) | 398 | m/z = 845.02 (C60H36N4S = 844.27) |

TABLE 52-continued

| Compound | FD-Mass | Compound | FD-Mass |
|---|---|---|---|
| 399 | m/z = 768.92 (C54H32N4S = 768.23) | 400 | m/z = 768.92 (C54H32N4S = 768.23) |
| 401 | m/z = 767.94 (C55H33N3S = 767.24) | 402 | m/z = 844.03 (C61H37N3S = 843.27) |
| 403 | m/z = 767.94 (C55H33N3S = 767.24) | 404 | m/z = 844.03 (C61H37N3S = 843.27) |
| 405 | m/z = 767.94 (C55H33N3S = 767.24) | 406 | m/z = 844.03 (C61H37N3S = 843.27) |
| 407 | m/z = 767.94 (C55H33N3S = 767.24) | 408 | m/z = 844.03 (C61H37N3S = 843.27) |
| 409 | m/z = 767.94 (C55H33N3S = 767.24) | 410 | m/z = 844.03 (C61H37N3S = 843.27) |
| 411 | m/z = 767.94 (C55H33N3S = 767.24) | 412 | m/z = 767.94 (C55H33N3S = 767.24) |
| 413 | m/z = 768.92 (C54H32N4S = 768.23) | 414 | m/z = 768.92 (C54H32N4S = 768.23) |
| 415 | m/z = 768.92 (C54H32N4S = 768.23) | 416 | m/z = 768.92 (C54H32N4S = 768.23) |
| 417 | m/z = 737.84 (C51H32NOPS = 737.19) | 418 | m/z = 737.84 (C51H32NOPS = 737.19) |
| 419 | m/z = 737.84 (C51H32NOPS = 737.19) | 420 | m/z = 737.84 (C51H32NOPS = 737.19) |
| 421 | m/z = 592.71 (C40H24N4S = 592.17) | 422 | m/z = 757.90 (C52H31N5S = 757.23) |
| 423 | m/z = 758.89 (C52H30N4OS = 758.21) | 424 | m/z = 744.90 (C52H32N4S = 744.23) |
| 425 | m/z = 667.82 (C47H29N3S = 667.21) | 426 | m/z = 756.91 (C53H32N4S = 756.23) |
| 427 | m/z = 773.96 (C53H31N3S2 = 773.20) | 428 | m/z = 820.01 (C59H37N3S = 819.27) |
| 429 | m/z = 743.91 (C53H33N3S = 743.24) | 430 | m/z = 756.91 (C53H32N4S = 756.23) |
| 431 | m/z = 757.90 (C53H31N3OS = 757.22) | 432 | m/z = 743.91 (C53H33N3S = 743.24) |
| 433 | m/z = 668.81 (C46H28N4S = 668.20) | 434 | m/z = 637.73 (C43H28NOPS = 637.16) |
| 435 | m/z = 592.71 (C40H24N4S = 592.17) | 436 | m/z = 757.90 (C52H31N5S = 757.23) |
| 437 | m/z = 758.89 (C52H30N4OS = 758.21) | 438 | m/z = 744.90 (C52H32N4S = 744.23) |
| 439 | m/z = 667.82 (C47H29N3S = 667.21) | 440 | m/z = 756.91 (C53H32N4S = 756.23) |
| 441 | m/z = 773.96 (C53H31N3S2 = 773.20) | 442 | m/z = 743.91 (C53H33N3S = 743.24) |
| 443 | m/z = 756.91 (C53H32N4S = 756.23) | 444 | m/z = 757.90 (C53H31N3OS = 757.22) |
| 445 | m/z = 743.91 (C53H33N3S = 743.24) | 446 | m/z = 668.81 (C46H28N4S = 668.20) |
| 447 | m/z = 637.73 (C43H28NOPS = 637.16) | 448 | m/z = 592.71 (C40H24N4S = 592.17) |
| 449 | m/z = 757.90 (C53H31N3OS = 757.22) | 450 | m/z = 758.89 (C52H30N4OS = 758.21) |
| 451 | m/z = 744.90 (C52H32N4S = 744.23) | 452 | m/z = 756.91 (C53H32N4S = 756.23) |
| 453 | m/z = 773.96 (C53H31N3S2 = 773.20) | 454 | m/z = 820.01 (C59H37N3S = 819.27) |
| 455 | m/z = 743.91 (C53H33N3S = 743.24) | 456 | m/z = 756.91 (C53H32N4S = 756.23) |
| 457 | m/z = 757.90 (C53H31N3OS = 757.22) | 458 | m/z = 743.91 (C53H33N3S = 743.24) |
| 459 | m/z = 668.81 (C46H28N4S = 668.20) | 460 | m/z = 637.73 (C43H28NOPS = 637.16) |
| 461 | m/z = 752.86 (C54H32N4O = 752.26) | 462 | m/z = 692.76 (C48H28N4O2 = 692.22) |
| 463 | m/z = 828.95 (C60H36N4O = 828.29) | 464 | m/z = 784.92 (C54H32N4OS = 784.23) |
| 465 | m/z = 768.86 (C54H32N4O2 = 768.25) | 466 | m/z = 754.87 (C54H34N4O = 754.27) |
| 467 | m/z = 767.87 (C54H33N5O = 767.27) | 468 | m/z = 767.87 (C54H33N5O = 767.27) |
| 469 | m/z = 768.86 (C54H32N4O2 = 768.25) | 470 | m/z = 768.86 (C54H32N4O2 = 768.25) |
| 471 | m/z = 768.86 (C54H32N4O2 = 768.25) | 472 | m/z = 784.92 (C54H32N4OS = 784.23) |
| 473 | m/z = 784.92 (C54H32N4OS = 784.23) | 474 | m/z = 754.87 (C54H34N4O = 754.27) |
| 475 | m/z = 754.87 (C54H34N4O = 754.27) | 476 | m/z = 830.97 (C60H38N4O = 830.30) |

TABLE 52-continued

| Compound | FD-Mass | Compound | FD-Mass |
|---|---|---|---|
| 477 | m/z = 752.86 (C54H32N4O = 752.26) | 478 | m/z = 768.86 (C54H32N4O2 = 768.25) |
| 479 | m/z = 784.92 (C54H32N4OS = 784.23) | 480 | m/z = 754.87 (C54H34N4O = 754.27) |
| 481 | m/z = 784.92 (C54H32N4OS = 784.23) | 482 | m/z = 754.87 (C54H34N4O = 754.27) |
| 483 | m/z = 754.87 (C54H34N4O = 754.27) | 484 | m/z = 767.87 (C54H33N5O = 767.27) |
| 485 | m/z = 767.87 (C54H33N5O = 767.27) | 486 | m/z = 768.86 (C54H32N4O2 = 768.25) |
| 487 | m/z = 768.86 (C54H32N4O2 = 768.25) | 488 | m/z = 768.86 (C54H32N4O2 = 768.25) |
| 489 | m/z = 784.92 (C54H32N4OS = 784.23) | 490 | m/z = 784.92 (C54H32N4OS = 784.23) |
| 491 | m/z = 784.92 (C54H32N4OS = 784.23) | 492 | m/z = 830.97 (C60H38N4O = 830.30) |
| 493 | m/z = 752.86 (C54H32N4O = 752.26) | 494 | m/z = 768.86 (C54H32N4O2 = 768.25) |
| 495 | m/z = 784.92 (C54H32N4OS = 784.23) | 496 | m/z = 754.87 (C54H34N4O = 754.27) |
| 497 | m/z = 767.87 (C54H33N5O = 767.27) | 498 | m/z = 767.87 (C54H33N5O = 767.27) |
| 499 | m/z = 768.86 (C54H32N4O2 = 768.25) | 500 | m/z = 768.86 (C54H32N4O2 = 768.25) |
| 501 | m/z = 784.92 (C54H32N4OS = 784.23) | 502 | m/z = 784.92 (C54H32N4OS = 784.23) |
| 503 | m/z = 768.86 (C54H32N4O2 = 768.25) | 504 | m/z = 754.87 (C54H34N4O = 754.27) |
| 505 | m/z = 754.87 (C54H34N4O = 754.27) | 506 | m/z = 752.86 (C54H32N4O = 752.26) |
| 507 | m/z = 692.76 (C48H28N4O2 = 692.22) | 508 | m/z = 708.83 (C48H28N4OS = 708.20) |
| 509 | m/z = 784.92 (C54H32N4OS = 784.23) | 510 | m/z = 754.87 (C54H34N4O = 754.27) |
| 511 | m/z = 767.87 (C54H33N5O = 767.27) | 512 | m/z = 767.87 (C54H33N5O = 767.27) |
| 513 | m/z = 768.86 (C54H32N4O2 = 768.25) | 514 | m/z = 768.86 (C54H32N4O2 = 768.25) |
| 515 | m/z = 784.92 (C54H32N4OS = 784.23) | 516 | m/z = 784.92 (C54H32N4OS = 784.23) |
| 517 | m/z = 768.86 (C54H32N4O2 = 768.25) | 518 | m/z = 830.97 (C60H38N4O = 830.30) |
| 519 | m/z = 652.74 (C46H28N4O = 652.23) | 520 | m/z = 692.76 (C48H28N4O2 = 692.22) |
| 521 | m/z = 784.92 (C54H32N4OS = 784.23) | 522 | m/z = 754.87 (C54H34N4O = 754.27) |
| 523 | m/z = 784.92 (C54H32N4OS = 784.23) | 524 | m/z = 754.87 (C54H34N4O = 754.27) |
| 525 | m/z = 767.87 (C54H33N5O = 767.27) | 526 | m/z = 767.87 (C54H33N5O = 767.27) |
| 527 | m/z = 768.86 (C54H32N4O2 = 768.25) | 528 | m/z = 768.86 (C54H32N4O2 = 768.25) |
| 529 | m/z = 784.92 (C54H32N4OS = 784.23) | 530 | m/z = 830.97 (C60H38N4O = 830.30) |
| 531 | m/z = 751.87 (C55H33N3O = 751.26) | 532 | m/z = 767.87 (C55H33N3O2 = 767.26) |
| 533 | m/z = 783.94 (C55H33N3OS = 783.23) | 534 | m/z = 753.89 (C55H35N3O = 753.28) |
| 535 | m/z = 766.88 (C55H34N4O = 766.27) | 536 | m/z = 766.88 (C55H34N4O = 766.27) |
| 537 | m/z = 767.87 (C55H33N3O2 = 767.26) | 538 | m/z = 767.87 (C55H33N3O2 = 767.26) |
| 539 | m/z = 783.94 (C55H33N3OS = 783.23) | 540 | m/z = 783.94 (C55H33N3OS = 783.23) |
| 541 | m/z = 767.87 (C55H33N3O2 = 767.26) | 542 | m/z = 829.98 (C61H39N3O = 829.31) |
| 543 | m/z = 751.87 (C55H33N3O = 751.26) | 544 | m/z = 767.87 (C55H33N3O2 = 767.26) |
| 545 | m/z = 707.84 (C49H29N3OS = 707.20) | 546 | m/z = 777.91 (C57H35N3O = 777.28) |
| 547 | m/z = 783.94 (C55H33N3OS = 783.23) | 548 | m/z = 753.89 (C55H35N3O = 753.28) |
| 549 | m/z = 766.88 (C55H34N4O = 766.27) | 550 | m/z = 766.88 (C55H34N4O = 766.27) |
| 551 | m/z = 767.87 (C55H33N3O2 = 767.26) | 552 | m/z = 767.87 (C55H33N3O2 = 767.26) |
| 553 | m/z = 757.90 (C53H31N3OS = 757.22) | 554 | m/z = 783.94 (C55H33N3OS = 783.23) |

TABLE 52-continued

| Compound | FD-Mass | Compound | FD-Mass |
|---|---|---|---|
| 555 | m/z = 767.87 (C55H33N3O2 = 767.26) | 556 | m/z = 753.89 (C55H35N3O = 753.28) |
| 557 | m/z = 751.87 (C55H33N3O = 751.26) | 558 | m/z = 767.87 (C55H33N3O2 = 767.26) |
| 559 | m/z = 707.84 (C49H29N3OS = 707.20) | 560 | m/z = 753.89 (C55H35N3O = 753.28) |
| 561 | m/z = 783.94 (C55H33N3OS = 783.23) | 562 | m/z = 753.89 (C55H35N3O = 753.28) |
| 563 | m/z = 766.88 (C55H34N4O = 766.27) | 564 | m/z = 766.88 (C55H34N4O = 766.27) |
| 565 | m/z = 767.87 (C55H33N3O2 = 767.26) | 566 | m/z = 767.87 (C55H33N3O2 = 767.26) |
| 567 | m/z = 783.94 (C55H33N3OS = 783.23) | 568 | m/z = 783.94 (C55H33N3OS = 783.23) |
| 569 | m/z = 753.89 (C55H35N3O = 753.28) | 570 | m/z = 753.89 (C55H35N3O = 753.28) |
| 571 | m/z = 651.75 (C47H29N3O = 651.23) | 572 | m/z = 767.87 (C55H33N3O2 = 767.26) |
| 573 | m/z = 707.84 (C49H29N3OS = 707.20) | 574 | m/z = 753.89 (C55H35N3O = 753.28) |
| 575 | m/z = 783.94 (C55H33N3OS = 783.23) | 576 | m/z = 753.89 (C55H35N3O = 753.28) |
| 577 | m/z = 766.88 (C55H34N4O = 766.27) | 578 | m/z = 766.88 (C55H34N4O = 766.27) |
| 579 | m/z = 767.87 (C55H33N3O2 = 767.26) | 580 | m/z = 767.87 (C55H33N3O2 = 767.26) |
| 581 | m/z = 783.94 (C55H33N3OS = 783.23) | 582 | m/z = 783.94 (C55H33N3OS = 783.23) |
| 583 | m/z = 753.89 (C55H35N3O = 753.28) | 584 | m/z = 753.89 (C55H35N3O = 753.28) |
| 585 | m/z = 751.87 (C55H33N3O = 751.26) | 586 | m/z = 767.87 (C55H33N3O2 = 767.26) |
| 587 | m/z = 783.94 (C55H33N3OS = 783.23) | 588 | m/z = 783.94 (C55H33N3OS = 783.23) |
| 589 | m/z = 753.89 (C55H35N3O = 753.28) | 590 | m/z = 766.88 (C55H34N4O = 766.27) |
| 591 | m/z = 766.88 (C55H34N4O = 766.27) | 592 | m/z = 767.87 (C55H33N3O2 = 767.26) |
| 593 | m/z = 767.87 (C55H33N3O2 = 767.26) | 594 | m/z = 783.94 (C55H33N3OS = 783.23) |
| 595 | m/z = 783.94 (C55H33N3OS = 783.23) | 596 | m/z = 767.87 (C55H33N3O2 = 767.26) |
| 597 | m/z = 829.98 (C61H39N3O = 829.31) | 598 | m/z = 751.87 (C55H33N3O = 751.26) |
| 599 | m/z = 767.87 (C55H33N3O2 = 767.26) | 600 | m/z = 783.94 (C55H33N3OS = 783.23) |
| 601 | m/z = 827.97 (C61H37N3O = 827.29) | 602 | m/z = 783.94 (C55H33N3OS = 783.23) |
| 603 | m/z = 766.88 (C55H34N4O = 766.27) | 604 | m/z = 766.88 (C55H34N4O = 766.27) |
| 605 | m/z = 767.87 (C55H33N3O2 = 767.26) | 606 | m/z = 767.87 (C55H33N3O2 = 767.26) |
| 607 | m/z = 783.94 (C55H33N3OS = 783.23) | 608 | m/z = 783.94 (C55H33N3OS = 783.23) |
| 609 | m/z = 767.87 (C55H33N3O2 = 767.26) | 610 | m/z = 829.98 (C61H39N3O = 829.31) |
| 611 | m/z = 751.87 (C55H33N3O = 751.26) | 612 | m/z = 767.87 (C55H33N3O2 = 767.26) |
| 613 | m/z = 707.84 (C49H29N3OS = 707.20) | 614 | m/z = 753.89 (C55H35N3O = 753.28) |
| 615 | m/z = 753.89 (C55H35N3O = 753.28) | 616 | m/z = 766.88 (C55H34N4O = 766.27) |
| 617 | m/z = 766.88 (C55H34N4O = 766.27) | 618 | m/z = 767.87 (C55H33N3O2 = 767.26) |
| 619 | m/z = 767.87 (C55H33N3O2 = 767.26) | 620 | m/z = 783.94 (C55H33N3OS = 783.23) |
| 621 | m/z = 783.94 (C55H33N3OS = 783.23) | 622 | m/z = 767.87 (C55H33N3O2 = 767.26) |
| 623 | m/z = 753.89 (C55H35N3O = 753.28) | 624 | m/z = 829.98 (C61H39N3O = 829.31) |
| 625 | m/z = 651.75 (C47H29N3O = 651.23) | 626 | m/z = 767.87 (C55H33N3O2 = 767.26) |
| 627 | m/z = 707.84 (C49H29N3OS = 707.20) | 628 | m/z = 753.89 (C55H35N3O = 753.28) |
| 629 | m/z = 753.89 (C55H35N3O = 753.28) | 630 | m/z = 766.88 (C55H34N4O = 766.27) |
| 631 | m/z = 766.88 (C55H34N4O = 766.27) | 632 | m/z = 767.87 (C55H33N3O2 = 767.26) |

TABLE 52-continued

| Compound | FD-Mass | Compound | FD-Mass |
|---|---|---|---|
| 633 | m/z = 767.87 (C55H33N3O2 = 767.26) | 634 | m/z = 783.94 (C55H33N3OS = 783.23) |
| 635 | m/z = 783.94 (C55H33N3OS = 783.23) | 636 | m/z = 767.87 (C55H33N3O2 = 767.26) |
| 637 | m/z = 753.89 (C55H35N3O = 753.28) | 638 | m/z = 829.98 (C61H39N3O = 829.31) |
| 639 | m/z = 768.86 (C54H32N4O2 = 768.25) | 640 | m/z = 754.87 (C54H34N4O = 754.27) |
| 641 | m/z = 778.90 (C56H34N4O = 778.27) | 642 | m/z = 728.84 (C52H32N4O = 728.26) |
| 643 | m/z = 768.86 (C54H32N4O2 = 768.25) | 644 | m/z = 754.87 (C54H34N4O = 754.27) |
| 645 | m/z = 728.84 (C52H32N4O = 728.26) | 646 | m/z = 784.92 (C54H32N4OS = 784.23) |
| 647 | m/z = 678.78 (C48H30N4O = 678.24) | 648 | m/z = 784.92 (C54H32N4OS = 784.23) |
| 649 | m/z = 778.90 (C56H34N4O = 778.27) | 650 | m/z = 728.84 (C52H32N4O = 728.26) |
| 651 | m/z = 768.86 (C54H32N4O2 = 768.25) | 652 | m/z = 754.87 (C54H34N4O = 754.27) |
| 653 | m/z = 678.78 (C48H30N4O = 678.24) | 654 | m/z = 784.92 (C54H32N4OS = 784.23) |
| 655 | m/z = 661.68 (C45H28NO3P = 661.18) | 656 | m/z = 723.79 (C51H34NO2P = 723.23) |
| 657 | m/z = 747.82 (C53H34NO2P = 747.23) | 658 | m/z = 753.84 (C51H32NO2PS = 753.19) |
| 659 | m/z = 737.78 (C51H32NO3P = 737.21) | 660 | m/z = 723.79 (C51H34NO2P = 723.23) |
| 661 | m/z = 697.76 (C49H32NO2P = 697.22) | 662 | m/z = 753.84 (C51H32NO2PS = 753.19) |
| 663 | m/z = 647.70 (C45H30NO2P = 647.20) | 664 | m/z = 753.84 (C51H32NO2PS = 753.19) |
| 665 | m/z = 747.82 (C53H34NO2P = 747.23) | 666 | m/z = 697.76 (C49H32NO2P = 697.22) |
| 667 | m/z = 737.78 (C51H32NO3P = 737.21) | 668 | m/z = 723.79 (C51H34NO2P = 723.23) |
| 669 | m/z = 647.70 (C45H30NO2P = 647.20 | 670 | m/z = 753.84 (C51H32NO2PS = 753.19) |
| 671 | m/z = 602.68 (C42H26N4O = 602.21) | 672 | m/z = 767.87 (C54H33N5O = 767.27) |
| 673 | m/z = 768.86 (C54H32N4O2 = 768.25) | 674 | m/z = 754.87 (C54H34N4O = 754.27) |
| 675 | m/z = 754.87 (C54H34N4O = 754.27) | 676 | m/z = 767.87 (C54H33N5O = 767.27) |
| 677 | m/z = 784.92 (C54H32N4OS = 784.23) | 678 | m/z = 754.87 (C54H34N4O = 754.27) |
| 679 | m/z = 602.68 (C42H26N4O = 602.21) | 680 | m/z = 767.87 (C54H33N5O = 767.27) |
| 681 | m/z = 768.86 (C54H32N4O2 = 768.25) | 682 | m/z = 754.87 (C54H34N4O = 754.27) |
| 683 | m/z = 602.68 (C42H26N4O = 602.21) | 684 | m/z = 767.87 (C54H33N5O = 767.27) |
| 685 | m/z = 768.86 (C54H32N4O2 = 768.25) | 686 | m/z = 754.87 (C54H34N4O = 754.27) |
| 687 | m/z = 753.89 (C55H35N3O = 753.28) | 688 | m/z = 766.88 (C55H34N4O = 766.27) |
| 689 | m/z = 767.87 (C55H33N3O2 = 767.26) | 690 | m/z = 753.89 (C55H35N3O = 753.28) |
| 691 | m/z = 601.69 (C43H27N3O = 601.22) | 692 | m/z = 766.88 (C55H34N4O = 766.27) |
| 693 | m/z = 783.94 (C55H33N3OS = 783.23) | 694 | m/z = 753.89 (C55H35N3O = 753.28) |
| 695 | m/z = 753.89 (C55H35N3O = 753.28) | 696 | m/z = 766.88 (C55H34N4O = 766.27) |
| 697 | m/z = 767.87 (C55H33N3O2 = 767.26) | 698 | m/z = 783.94 (C55H33N3OS = 783.23) |
| 699 | m/z = 601.69 (C43H27N3O = 601.22) | 700 | m/z = 766.88 (C55H34N4O = 766.27) |
| 701 | m/z = 767.87 (C55H33N3O2 = 767.26) | 702 | m/z = 753.89 (C55H35N3O = 753.28) |
| 703 | m/z = 753.89 (C55H35N3O = 753.28) | 704 | m/z = 766.88 (C55H34N4O = 766.27) |
| 705 | m/z = 783.94 (C55H33N3OS = 783.23) | 706 | m/z = 753.89 (C55H35N3O = 753.28) |
| 707 | m/z = 601.69 (C43H27N3O = 601.22) | 708 | m/z = 766.88 (C55H34N4O = 766.27) |
| 709 | m/z = 767.87 (C55H33N3O2 = 767.26) | 710 | m/z = 753.89 (C55H35N3O = 753.28) |

TABLE 52-continued

| Compound | FD-Mass | Compound | FD-Mass |
| --- | --- | --- | --- |
| 711 | m/z = 753.89 (C55H35N3O = 753.28) | 712 | m/z = 766.88 (C55H34N4O = 766.27) |
| 713 | m/z = 783.94 (C55H33N3OS = 783.23) | 714 | m/z = 753.89 (C55H35N3O = 753.28) |
| 715 | m/z = 601.69 (C43H27N3O = 601.22) | 716 | m/z = 766.88 (C55H34N4O = 766.27) |
| 717 | m/z = 783.94 (C55H33N3OS = 783.23) | 718 | m/z = 767.87 (C55H33N3O2 = 767.26) |
| 719 | m/z = 602.68 (C42H26N4O = 602.21) | 720 | m/z = 602.68 (C42H26N4O = 602.21) |
| 721 | m/z = 678.78 (C48H30N4O = 678.24) | 722 | m/z = 602.68 (C42H26N4O = 602.21) |
| 723 | m/z = 602.68 (C42H26N4O = 602.21) | 724 | m/z = 678.78 (C48H30N4O = 678.24) |
| 725 | m/z = 602.68 (C42H26N4O = 602.21) | 726 | m/z = 602.68 (C42H26N4O = 602.21) |
| 727 | m/z = 678.78 (C48H30N4O = 678.24) | 728 | m/z = 602.68 (C42H26N4O = 602.21) |
| 729 | m/z = 602.68 (C42H26N4O = 602.21) | 730 | m/z = 678.78 (C48H30N4O = 678.24) |
| 731 | m/z = 571.60 (C39H26NO2P = 571.17) | 732 | m/z = 647.70 (C45H30NO2P = 647.20) |
| 733 | m/z = 647.70 (C45H30NO2P = 647.20) | 734 | m/z = 571.60 (C39H26NO2P = 571.17) |
| 735 | m/z = 647.70 (C45H30NO2P = 647.20) | 736 | m/z = 647.70 (C45H30NO2P = 647.20) |
| 737 | m/z = 571.60 (C39H26NO2P = 571.17) | 738 | m/z = 647.70 (C45H30NO2P = 647.20) |
| 739 | m/z = 647.70 (C45H30NO2P = 647.20) | 740 | m/z = 571.60 (C39H26NO2P = 571.17) |
| 741 | m/z = 647.70 (C45H30NO2P = 647.20) | 742 | m/z = 647.70 (C45H30NO2P = 647.20) |
| 743 | m/z = 652.74 (C46H28N4O = 652.23) | 744 | m/z = 817.93 (C58H35N5O = 817.28) |
| 745 | m/z = 818.92 (C58H34N4O2 = 818.27) | 746 | m/z = 804.93 (C58H36N4O = 804.29) |
| 747 | m/z = 804.93 (C58H36N4O = 804.29) | 748 | m/z = 817.93 (C58H35N5O = 817.28) |
| 749 | m/z = 834.98 (C58H34N4OS = 834.25) | 750 | m/z = 804.93 (C58H36N4O = 804.29) |
| 751 | m/z = 652.74 (C46H28N4O = 652.23) | 752 | m/z = 817.93 (C58H35N5O = 817.28) |
| 753 | m/z = 818.92 (C58H35N5O = 818.27) | 754 | m/z = 804.93 (C58H36N4O = 804.29) |
| 755 | m/z = 652.74 (C46H28N4O = 652.23) | 756 | m/z = 817.93 (C58H35N5O = 817.28) |
| 757 | m/z = 818.92 (C58H35N5O = 818.27) | 758 | m/z = 804.93 (C58H36N4O = 804.29) |
| 759 | m/z = 803.94 (C59H37N3O = 803.29) | 760 | m/z = 816.94 (C59H36N4O = 816.29) |
| 761 | m/z = 817.93 (C58H35N5O = 817.28) | 762 | m/z = 803.94 (C59H37N3O = 803.29) |
| 763 | m/z = 651.75 (C47H29N3O = 651.23) | 764 | m/z = 816.94 (C59H36N4O = 816.29) |
| 765 | m/z = 833.99 (C59H35N3OS = 833.25) | 766 | m/z = 803.94 (C59H37N3O = 803.29) |
| 767 | m/z = 803.94 (C59H37N3O = 803.29) | 768 | m/z = 816.94 (C59H36N4O = 816.29) |
| 769 | m/z = 817.93 (C58H35N5O = 817.28) | 770 | m/z = 833.99 (C59H35N3OS = 833.25) |
| 771 | m/z = 651.75 (C47H29N3O = 651.23) | 772 | m/z = 816.94 (C59H36N4O = 816.29) |
| 773 | m/z = 817.93 (C58H35N5O = 817.28) | 774 | m/z = 803.94 (C59H37N3O = 803.29) |
| 775 | m/z = 803.94 (C59H37N3O = 803.29) | 776 | m/z = 816.94 (C59H36N4O = 816.29) |
| 777 | m/z = 833.99 (C59H35N3OS = 833.25) | 778 | m/z = 803.94 (C59H37N3O = 803.29) |
| 779 | m/z = 651.75 (C47H29N3O = 651.23) | 780 | m/z = 816.94 (C59H36N4O = 816.29) |
| 781 | m/z = 817.93 (C58H35N5O = 817.28) | 782 | m/z = 803.94 (C59H37N3O = 803.29) |
| 783 | m/z = 803.94 (C59H37N3O = 803.29) | 784 | m/z = 816.94 (C59H36N4O = 816.29) |
| 785 | m/z = 833.99 (C59H35N3OS = 833.25) | 786 | m/z = 803.94 (C59H37N3O = 803.29) |
| 787 | m/z = 651.75 (C47H29N3O = 651.23) | 788 | m/z = 816.94 (C59H36N4O = 816.29) |

TABLE 52-continued

| Compound | FD-Mass | Compound | FD-Mass |
|---|---|---|---|
| 789 | m/z = 833.99 (C59H35N3OS = 833.25) | 790 | m/z = 817.93 (C58H35N5O = 817.28) |
| 791 | m/z = 652.74 (C46H28N4O = 652.23) | 792 | m/z = 652.74 (C46H28N4O = 652.23) |
| 793 | m/z = 728.84 (C52H32N4O = 728.26) | 794 | m/z = 652.74 (C46H28N4O = 652.23) |
| 795 | m/z = 652.74 (C46H28N4O = 652.23) | 796 | m/z = 728.84 (C52H32N4O = 728.26) |
| 797 | m/z = 652.74 (C46H28N4O = 652.23) | 798 | m/z = 652.74 (C46H28N4O = 652.23) |
| 799 | m/z = 728.84 (C52H32N4O = 728.26) | 800 | m/z = 652.74 (C46H28N4O = 652.23) |
| 801 | m/z = 652.74 (C46H28N4O = 652.23) | 802 | m/z = 728.84 (C52H32N4O = 728.26) |
| 803 | m/z = 621.66 (C43H28NO2P = 621.19) | 804 | m/z = 697.76 (C49H32NO2P = 697.22) |
| 805 | m/z = 697.76 (C49H32NO2P = 697.22) | 806 | m/z = 621.66 (C43H28NO2P = 621.19) |
| 807 | m/z = 697.76 (C49H32NO2P = 697.22) | 808 | m/z = 697.76 (C49H32NO2P = 697.22) |
| 809 | m/z = 621.66 (C43H28NO2P = 621.19) | 810 | m/z = 697.76 (C49H32NO2P = 697.22) |
| 811 | m/z = 697.76 (C49H32NO2P = 697.22) | 812 | m/z = 621.66 (C43H28NO2P = 621.19) |
| 813 | m/z = 697.76 (C49H32NO2P = 697.22) | 814 | m/z = 697.76 (C49H32NO2P = 697.22) |
| 815 | m/z = 702.80 (C50H30N4O = 702.24) | 816 | m/z = 778.90 (C56H34N4O = 778.27) |
| 817 | m/z = 778.90 (C56H34N4O = 778.27) | 818 | m/z = 778.90 (C56H34N4O = 778.27) |
| 819 | m/z = 702.80 (C50H30N4O = 702.24) | 820 | m/z = 778.90 (C56H34N4O = 778.27) |
| 821 | m/z = 702.80 (C50H30N4O = 702.24) | 822 | m/z = 778.90 (C56H34N4O = 778.27) |
| 823 | m/z = 701.81 (C51H31N3O = 701.25) | 824 | m/z = 777.91 (C57H35N3O = 777.28) |
| 825 | m/z = 777.91 (C57H35N3O = 777.28) | 826 | m/z = 777.91 (C57H35N3O = 777.28) |
| 827 | m/z = 701.81 (C51H31N3O = 701.25) | 828 | m/z = 777.91 (C57H35N3O = 777.28) |
| 829 | m/z = 701.81 (C51H31N3O = 701.25) | 830 | m/z = 777.91 (C57H35N3O = 777.28) |
| 831 | m/z = 701.81 (C51H31N3O = 701.25) | 832 | m/z = 777.91 (C57H35N3O = 777.28) |
| 833 | m/z = 777.91 (C57H35N3O = 777.28) | 834 | m/z = 777.91 (C57H35N3O = 777.28) |
| 835 | m/z = 701.81 (C51H31N3O = 701.25) | 836 | m/z = 777.91 (C57H35N3O = 777.28) |
| 837 | m/z = 701.81 (C51H31N3O = 701.25) | 838 | m/z = 777.91 (C57H35N3O = 777.28) |
| 839 | m/z = 702.80 (C50H30N4O = 702.24) | 840 | m/z = 778.90 (C56H34N4O = 778.27) |
| 841 | m/z = 702.80 (C50H30N4O = 702.24) | 842 | m/z = 778.90 (C56H34N4O = 778.27) |
| 843 | m/z = 702.80 (C50H30N4O = 702.24) | 844 | m/z = 778.90 (C56H34N4O = 778.27) |
| 845 | m/z = 702.80 (C50H30N4O = 702.24) | 846 | m/z = 778.90 (C56H34N4O = 778.27) |
| 847 | m/z = 671.72 (C47H30NO2P = 671.20) | 848 | m/z = 747.82 (C53H34NO2P = 747.23) |
| 849 | m/z = 671.72 (C47H30NO2P = 671.20) | 850 | m/z = 747.82 (C53H34NO2P = 747.23) |
| 851 | m/z = 671.72 (C47H30NO2P = 671.20) | 852 | m/z = 747.82 (C53H34NO2P = 747.23) |
| 853 | m/z = 671.72 (C47H30NO2P = 671.20) | 854 | m/z = 747.82 (C53H34NO2P = 747.23) |
| 855 | m/z = 752.86 (C54H32N4O = 752.26) | 856 | m/z = 828.95 (C60H36N4O = 828.29) |
| 857 | m/z = 752.86 (C54H32N4O = 752.26) | 858 | m/z = 828.95 (C60H36N4O = 828.29) |
| 859 | m/z = 752.86 (C54H32N4O = 752.26) | 860 | m/z = 752.86 (C54H32N4O = 752.26) |
| 861 | m/z = 751.87 (C55H33N3O = 751.26) | 862 | m/z = 827.97 (C61H37N3O = 827.29) |
| 863 | m/z = 751.87 (C55H33N3O = 751.26) | 864 | m/z = 827.97 (C61H37N3O = 827.29) |
| 865 | m/z = 751.87 (C55H33N3O = 751.26) | 866 | m/z = 751.87 (C55H33N3O = 751.26) |

TABLE 52-continued

| Compound | FD-Mass | Compound | FD-Mass |
|---|---|---|---|
| 867 | m/z = 751.87 (C55H33N3O = 751.26) | 868 | m/z = 827.97 (C61H37N3O = 827.29) |
| 869 | m/z = 751.87 (C55H33N3O = 751.26) | 870 | m/z = 827.97 (C61H37N3O = 827.29) |
| 871 | m/z = 751.87 (C55H33N3O = 751.26) | 872 | m/z = 751.87 (C55H33N3O = 751.26) |
| 873 | m/z = 752.86 (C54H32N4O = 752.26) | 874 | m/z = 752.86 (C54H32N4O = 752.26) |
| 875 | m/z = 752.86 (C54H32N4O = 752.26) | 876 | m/z = 752.86 (C54H32N4O = 752.26) |
| 877 | m/z = 721.78 (C51H32NO2P = 721.22) | 878 | m/z = 721.78 (C51H32NO2P = 721.22) |
| 879 | m/z = 721.78 (C51H32NO2P = 721.22) | 880 | m/z = 721.78 (C51H32NO2P = 721.22) |
| 881 | m/z = 576.64 (C40H24N4O = 576.20) | 882 | m/z = 741.84 (C52H31N5O = 741.25) |
| 883 | m/z = 742.82 (C52H30N4O2 = 742.24) | 884 | m/z = 728.84 (C52H32N4O = 728.26) |
| 885 | m/z = 651.75 (C47H29N3O = 651.23) | 886 | m/z = 740.85 (C53H32N4O = 740.26) |
| 887 | m/z = 757.90 (C53H31N3OS = 757.22) | 888 | m/z = 803.94 (C59H37N3O = 803.29) |
| 889 | m/z = 727.85 (C53H33N3O = 727.26) | 890 | m/z = 740.85 (C53H32N4O = 740.26) |
| 891 | m/z = 741.83 (C53H31N3O2 = 741.24) | 892 | m/z = 727.85 (C53H33N3O = 727.26) |
| 893 | m/z = 652.74 (C46H28N4O = 652.23) | 894 | m/z = 621.66 (C43H28NO2P = 621.19) |
| 895 | m/z = 576.64 (C40H24N4O = 576.20) | 896 | m/z = 741.84 (C52H31N5O = 741.25) |
| 897 | m/z = 742.82 (C52H30N4O2 = 742.24) | 898 | m/z = 728.84 (C52H32N4O = 728.26) |
| 899 | m/z = 651.75 (C47H29N3O = 651.23) | 900 | m/z = 740.85 (C53H32N4O = 740.26) |
| 901 | m/z = 757.90 (C53H31N3OS = 757.22) | 902 | m/z = 727.85 (C53H33N3O = 727.26) |
| 903 | m/z = 740.85 (C53H32N4O = 740.26) | 904 | m/z = 741.84 (C52H31N5O = 741.25) |
| 905 | m/z = 727.85 (C53H33N3O = 727.26) | 906 | m/z = 652.74 (C46H28N4O = 652.23) |
| 907 | m/z = 621.66 (C43H28NO2P = 621.19) | 908 | m/z = 576.64 (C40H24N4O = 576.20) |
| 909 | m/z = 741.84 (C52H31N5O = 741.25) | 910 | m/z = 742.82 (C52H30N4O2 = 742.24) |
| 911 | m/z = 728.84 (C52H32N4O = 728.26) | 912 | m/z = 740.85 (C53H32N4O = 740.26) |
| 913 | m/z = 757.90 (C53H31N3OS = 757.22) | 914 | m/z = 803.94 (C59H37N3O = 803.29) |
| 915 | m/z = 727.85 (C53H33N3O = 727.26) | 916 | m/z = 740.85 (C53H32N4O = 740.26) |
| 917 | m/z = 741.83 (C53H31N3O2 = 741.24) | 918 | m/z = 727.85 (C53H33N3O = 727.26) |
| 919 | m/z = 652.74 (C46H28N4O = 652.23) | 920 | m/z = 621.66 (C43H28NO2P = 621.19) |
| 921 | m/z = 791.96 (C57H33N3S = 791.24) | 922 | m/z = 641.78 (C45H27N3S = 641.19) |
| 923 | m/z = 725.83 (C53H31N3O = 725.25) | 924 | m/z = 701.81 (C51H31N3O = 701.25) |
| 925 | m/z = 717.88 (C51H31N3S = 717.22) | 926 | m/z = 642.77 (C44H26N4S = 642.19) |
| 927 | m/z = 676.76 (C48H28N4O = 676.23) | 928 | m/z = 625.72 (C45H27N3O = 625.22) |
| 929 | m/z = 641.78 (C45H2d7N3S = 641.19) | 930 | m/z = 691.84 (C49H29N3S = 691.21) |
| 931 | m/z = 676.76 (C48H28N4O = 676.23) | 932 | m/z = 775.89 (C57H33N3O = 775.26) |
| 933 | m/z = 791.96 (C57H33N3S = 791.24) | 934 | m/z = 741.90 (C53H31N3S = 741.22) |
| 935 | m/z = 675.77 (C49H29N3O = 675.23) | 936 | m/z = 625.72 (C45H27N3O = 625.22) |
| 937 | m/z = 615.74 (C43H25N3S = 615.18) | 938 | m/z = 615.74 (C43H25N3S = 615.18) |
| 939 | m/z = 599.68 (C43H25N3O = 599.20) | 940 | m/z = 599.68 (C43H25N3O = 599.20) |
| 941 | m/z = 691.84 (C49H29N3S = 691.21) | 942 | m/z = 691.84 (C49H29N3S = 691.21) |
| 943 | m/z = 675.77 (C49H29N3O = 675.23) | 944 | m/z = 675.77 (C49H29N3O = 675.23) |

TABLE 52-continued

| Compound | FD-Mass | Compound | FD-Mass |
| --- | --- | --- | --- |
| 945 | m/z = 691.84 (C49H29N3S = 691.21) | 946 | m/z = 691.84 (C49H29N3S = 691.21) |
| 947 | m/z = 675.77 (C49H29N3O = 675.23) | 948 | m/z = 675.77 (C49H29N3O = 675.23) |

<Experimental Example 1>—Manufacture of Organic Light Emitting Device

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

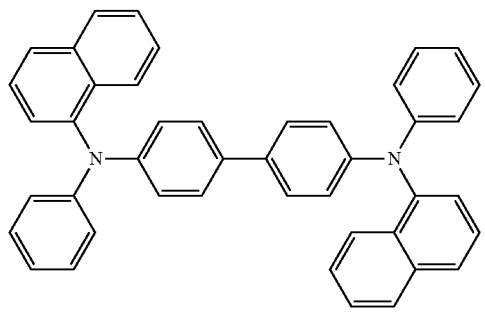

NPB

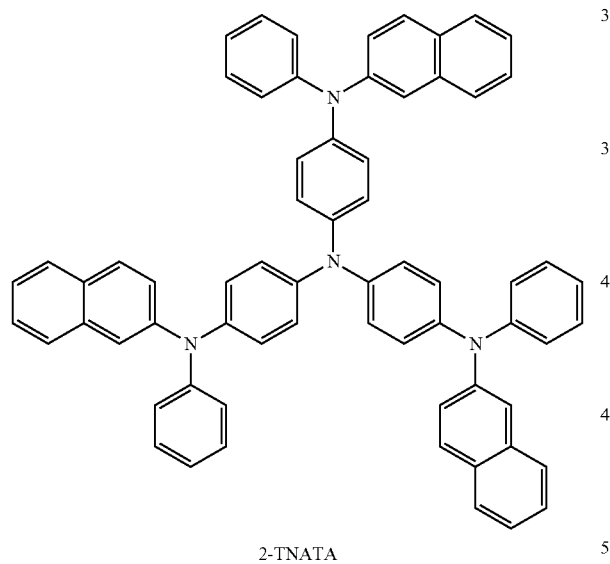

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum depositor, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon by 5% with respect to the host material.

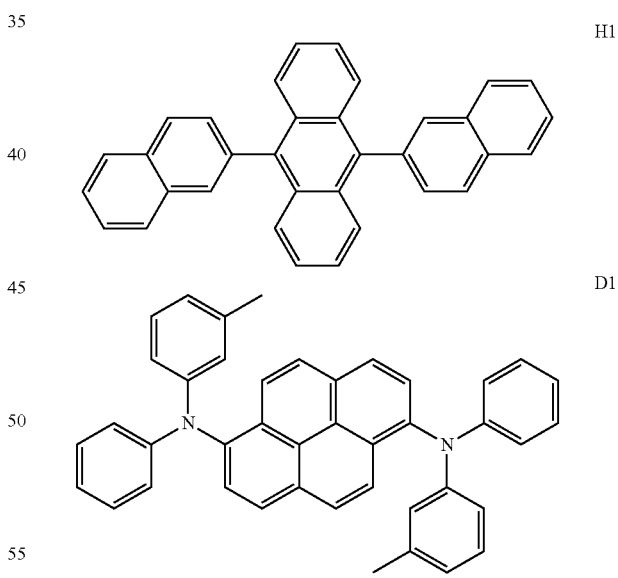

Subsequently, one of compounds described in the following Table 53 was deposited to a thickness of 300 Å as an electron transfer layer.

As an electron injection layer, lithium fluoride (LiF) was deposited to a thickness of 10 Å, and an Al cathode was employed to have a thickness of 1,000 Å to manufacture an OLED. Meanwhile, all the organic compounds required to manufacture the OLED were vacuum sublimation purified under $10^{-6}$ torr to $10^{-8}$ torr by each material to be used in the OLED manufacture.

For the organic electroluminescent device manufactured as above, electroluminescent light emission (EL) properties were measured using M7000 manufactured by McScience Inc., and with the measurement results, $T_{95}$ when standard luminance was 700 cd/m² was measured using a lifetime measurement system (M6000) manufactured by McScience Inc. Results of measuring a driving voltage, light emission efficiency, external quantum efficiency and a color coordinate (CIE) of the blue organic electroluminescent device manufactured according to the present disclosure are as shown in the following Table 53.

TABLE 53

| Compound | Driving Voltage (V) | Light Emission Efficiency (cd/A) | CIE (x, y) | Lifetime (T95) |
|---|---|---|---|---|
| Example 1 | 1 | 4.42 | 6.93 | (0.134, 0.099) | 40 |
| Example 2 | 7 | 4.48 | 6.86 | (0.134, 0.099) | 41 |
| Example 3 | 10 | 4.47 | 6.87 | (0.134, 0.100) | 40 |
| Example 4 | 14 | 4.51 | 7.05 | (0.134, 0.099) | 42 |
| Example 5 | 17 | 4.67 | 6.64 | (0.129, 0.100) | 38 |
| Example 6 | 25 | 4.82 | 6.55 | (0.130, 0.099) | 36 |
| Example 7 | 28 | 4.77 | 6.68 | (0.132, 0.098) | 36 |
| Example 8 | 33 | 4.44 | 6.97 | (0.134, 0.101) | 40 |
| Example 9 | 51 | 4.61 | 6.89 | (0.134, 0.103) | 40 |
| Example 10 | 56 | 4.88 | 6.72 | (0.128, 0.099) | 36 |
| Example 11 | 57 | 4.70 | 6.75 | (0.127, 0.100) | 37 |
| Example 12 | 59 | 5.35 | 6.30 | (0.134, 0.102) | 33 |
| Example 13 | 68 | 5.28 | 6.28 | (0.134, 0.102) | 32 |
| Example 14 | 69 | 5.61 | 6.19 | (0.130, 0.099) | 28 |
| Example 15 | 72 | 5.60 | 6.07 | (0.129, 0.100) | 29 |
| Example 16 | 75 | 5.55 | 6.10 | (0.130, 0.101) | 30 |
| Example 17 | 78 | 5.71 | 6.15 | (0.129, 0.098) | 28 |
| Example 18 | 83 | 4.57 | 6.74 | (0.128, 0.099) | 36 |
| Example 19 | 89 | 4.60 | 6.69 | (0.129, 0.102) | 36 |
| Example 20 | 91 | 4.49 | 6.96 | (0.134, 0.100) | 40 |
| Example 21 | 98 | 4.62 | 6.72 | (0.133, 0.100) | 37 |
| Example 22 | 100 | 4.55 | 6.85 | (0.134, 0.101) | 39 |
| Example 23 | 103 | 4.80 | 6.69 | (0.130, 0.100) | 38 |
| Example 24 | 106 | 5.42 | 6.13 | (0.134, 0.101) | 29 |
| Example 25 | 112 | 5.67 | 6.02 | (0.132, 0.103) | 25 |
| Example 26 | 117 | 5.58 | 6.15 | (0.130, 0.099) | 25 |
| Example 27 | 119 | 5.70 | 6.07 | (0.129, 0.100) | 28 |
| Example 28 | 124 | 4.54 | 6.92 | (0.134, 0.101) | 41 |
| Example 29 | 125 | 4.30 | 6.81 | (0.134, 0.101) | 41 |
| Example 30 | 130 | 4.50 | 6.98 | (0.134, 0.100) | 40 |
| Example 31 | 134 | 4.44 | 7.09 | (0.134, 0.100) | 39 |
| Example 32 | 138 | 4.61 | 7.01 | (0.134, 0.099) | 38 |
| Example 33 | 143 | 4.60 | 6.87 | (0.131, 0.100) | 37 |
| Example 34 | 149 | 4.64 | 7.08 | (0.134, 0.099) | 40 |
| Example 35 | 151 | 4.53 | 6.91 | (0.134, 0.101) | 41 |
| Example 36 | 156 | 4.97 | 6.59 | (0.134, 0.100) | 34 |
| Example 37 | 159 | 4.54 | 6.95 | (0.134, 0.103) | 42 |
| Example 38 | 166 | 5.33 | 6.17 | (0.134, 0.102) | 29 |
| Example 39 | 171 | 5.63 | 6.11 | (0.131, 0.098) | 28 |
| Example 40 | 174 | 5.58 | 6.23 | (0.129, 0.101) | 30 |
| Example 41 | 178 | 5.61 | 6.20 | (0.134, 0.102) | 31 |
| Example 42 | 179 | 5.66 | 6.04 | (0.131, 0.102) | 30 |
| Example 43 | 182 | 5.65 | 6.08 | (0.134, 0.101) | 28 |
| Example 44 | 186 | 5.35 | 6.32 | (0.134, 0.102) | 30 |
| Example 45 | 190 | 5.43 | 6.25 | (0.134, 0.101) | 29 |
| Example 46 | 197 | 5.40 | 6.49 | (0.134, 0.101) | 31 |
| Example 47 | 199 | 5.59 | 6.14 | (0.131, 0.101) | 28 |
| Example 48 | 203 | 5.60 | 6.22 | (0.129, 0.100) | 29 |
| Example 49 | 207 | 5.48 | 6.18 | (0.129, 0.099) | 28 |
| Example 50 | 212 | 5.59 | 6.07 | (0.128, 0.102) | 30 |
| Example 51 | 217 | 4.74 | 5.89 | (0.134, 0.100) | 37 |
| Example 52 | 219 | 4.70 | 6.01 | (0.134, 0.101) | 36 |
| Example 53 | 223 | 5.40 | 6.31 | (0.134, 0.102) | 31 |
| Example 54 | 228 | 5.71 | 6.19 | (0.131, 0.100) | 27 |
| Example 55 | 231 | 5.63 | 6.06 | (0.128, 0.102) | 27 |
| Example 56 | 233 | 5.49 | 6.14 | (0.130, 0.101) | 29 |
| Example 57 | 236 | 4.73 | 6.78 | (0.130, 0.100) | 35 |
| Example 58 | 243 | 4.67 | 6.65 | (0.129, 0.098) | 36 |
| Example 59 | 252 | 4.69 | 6.92 | (0.130, 0.101) | 35 |
| Example 60 | 253 | 4.52 | 6.75 | (0.129, 0.097) | 37 |
| Example 61 | 256 | 5.32 | 6.22 | (0.134, 0.102) | 32 |
| Example 62 | 259 | 5.36 | 6.30 | (0.134, 0.100) | 34 |
| Example 63 | 263 | 4.72 | 6.98 | (0.134, 0.100) | 51 |
| Example 64 | 265 | 4.80 | 6.89 | (0.134, 0.102) | 58 |
| Example 65 | 272 | 4.76 | 6.95 | (0.134, 0.102) | 50 |
| Example 66 | 278 | 4.68 | 6.93 | (0.134, 0.100) | 50 |
| Example 67 | 283 | 4.88 | 6.84 | (0.134, 0.102) | 57 |
| Example 68 | 288 | 4.77 | 6.90 | (0.134, 0.102) | 51 |
| Example 69 | 293 | 4.98 | 6.05 | (0.134, 0.101) | 34 |
| Example 70 | 295 | 5.11 | 6.12 | (0.134, 0.102) | 48 |
| Example 71 | 305 | 4.96 | 6.10 | (0.134, 0.100) | 36 |
| Example 72 | 308 | 5.30 | 6.20 | (0.134, 0.101) | 40 |
| Example 73 | 319 | 5.22 | 6.03 | (0.134, 0.101) | 43 |
| Example 74 | 324 | 4.82 | 6.84 | (0.134, 0.101) | 52 |
| Example 75 | 328 | 4.84 | 6.97 | (0.134, 0.102) | 51 |
| Example 76 | 334 | 4.90 | 6.81 | (0.134, 0.101) | 56 |
| Example 77 | 347 | 4.88 | 6.82 | (0.134, 0.102) | 57 |
| Example 78 | 352 | 4.74 | 6.75 | (0.134, 0.101) | 51 |
| Example 79 | 358 | 4.81 | 6.82 | (0.134, 0.102) | 53 |
| Example 80 | 367 | 5.26 | 6.44 | (0.134, 0.102) | 32 |
| Example 81 | 373 | 5.21 | 6.38 | (0.134, 0.101) | 41 |
| Example 82 | 379 | 5.16 | 6.20 | (0.134, 0.101) | 38 |
| Example 83 | 382 | 5.15 | 6.42 | (0.134, 0.102) | 39 |
| Example 84 | 389 | 5.31 | 6.30 | (0.134, 0.103) | 37 |
| Example 85 | 393 | 5.33 | 6.22 | (0.134, 0.102) | 40 |
| Example 86 | 397 | 5.32 | 5.95 | (0.134, 0.101) | 41 |
| Example 87 | 406 | 4.82 | 6.35 | (0.134, 0.100) | 50 |
| Example 88 | 415 | 4.84 | 6.60 | (0.134, 0.100) | 49 |
| Example 89 | 419 | 4.94 | 6.68 | (0.134, 0.101) | 52 |
| Example 90 | 423 | 4.96 | 6.70 | (0.134, 0.101) | 47 |
| Example 91 | 425 | 4.91 | 6.69 | (0.134, 0.102) | 51 |
| Example 92 | 433 | 4.90 | 6.71 | (0.134, 0.102) | 50 |
| Example 93 | 435 | 5.32 | 6.22 | (0.134, 0.102) | 32 |
| Example 94 | 441 | 5.36 | 6.30 | (0.134, 0.100) | 34 |
| Example 95 | 444 | 4.72 | 6.98 | (0.134, 0.100) | 51 |
| Example 96 | 453 | 4.80 | 6.89 | (0.134, 0.102) | 58 |
| Example 97 | 455 | 4.76 | 6.95 | (0.134, 0.102) | 50 |
| Example 98 | 460 | 4.68 | 6.93 | (0.134, 0.100) | 50 |
| Example 99 | 461 | 4.88 | 6.84 | (0.134, 0.102) | 57 |
| Example 100 | 467 | 4.77 | 6.90 | (0.134, 0.102) | 51 |
| Example 101 | 470 | 4.98 | 6.05 | (0.134, 0.101) | 34 |
| Example 102 | 474 | 5.11 | 6.12 | (0.134, 0.102) | 48 |
| Example 103 | 477 | 4.96 | 6.10 | (0.134, 0.100) | 36 |
| Example 104 | 485 | 5.30 | 6.20 | (0.134, 0.101) | 40 |
| Example 105 | 488 | 5.22 | 6.03 | (0.134, 0.101) | 43 |
| Example 106 | 493 | 4.82 | 6.84 | (0.134, 0.101) | 52 |
| Example 107 | 511 | 4.84 | 6.97 | (0.134, 0.102) | 51 |
| Example 108 | 516 | 4.90 | 6.81 | (0.134, 0.101) | 56 |
| Example 109 | 517 | 4.88 | 6.82 | (0.134, 0.102) | 57 |
| Example 110 | 519 | 4.74 | 6.75 | (0.134, 0.101) | 51 |
| Example 111 | 528 | 4.81 | 6.82 | (0.134, 0.102) | 53 |
| Example 112 | 529 | 5.26 | 6.44 | (0.134, 0.102) | 32 |
| Example 113 | 532 | 5.21 | 6.38 | (0.134, 0.101) | 41 |
| Example 114 | 535 | 5.44 | 6.47 | (0.134, 0.102) | 36 |
| Example 115 | 538 | 5.41 | 6.44 | (0.134, 0.101) | 43 |
| Example 116 | 543 | 5.34 | 6.38 | (0.134, 0.101) | 39 |
| Example 117 | 549 | 5.38 | 6.20 | (0.134, 0.103) | 40 |
| Example 118 | 551 | 5.60 | 6.12 | (0.134, 0.101) | 43 |
| Example 119 | 558 | 5.45 | 6.21 | (0.134, 0.101) | 37 |
| Example 120 | 560 | 5.44 | 6.22 | (0.134, 0.102) | 34 |
| Example 121 | 563 | 5.62 | 5.95 | (0.134, 0.103) | 42 |
| Example 122 | 566 | 5.40 | 6.12 | (0.134, 0.101) | 39 |
| Example 123 | 572 | 5.50 | 5.89 | (0.134, 0.100) | 41 |
| Example 124 | 577 | 5.44 | 6.01 | (0.134, 0.101) | 36 |
| Example 125 | 579 | 5.34 | 6.58 | (0.134, 0.100) | 45 |
| Example 126 | 584 | 5.38 | 6.93 | (0.134, 0.100) | 43 |
| Example 127 | 585 | 4.91 | 6.32 | (0.134, 0.100) | 41 |
| Example 128 | 590 | 4.98 | 6.44 | (0.134, 0.100) | 40 |
| Example 129 | 594 | 5.62 | 6.38 | (0.134, 0.100) | 35 |
| Example 130 | 598 | 4.72 | 6.20 | (0.134, 0.100) | 48 |
| Example 131 | 603 | 5.45 | 6.44 | (0.134, 0.103) | 33 |
| Example 132 | 609 | 5.44 | 6.34 | (0.134, 0.102) | 36 |
| Example 133 | 611 | 5.62 | 6.20 | (0.134, 0.101) | 39 |
| Example 134 | 616 | 5.40 | 6.12 | (0.134, 0.103) | 44 |
| Example 135 | 619 | 5.60 | 6.21 | (0.134, 0.102) | 43 |

TABLE 53-continued

| | Compound | Driving Voltage (V) | Light Emission Efficiency (cd/A) | CIE (x, y) | Lifetime (T95) |
|---|---|---|---|---|---|
| Example 136 | 626 | 5.45 | 6.22 | (0.134, 0.101) | 37 |
| Example 137 | 631 | 5.39 | 5.95 | (0.134, 0.102) | 33 |
| Example 138 | 634 | 4.96 | 5.95 | (0.134, 0.101) | 42 |
| Example 139 | 638 | 4.91 | 6.13 | (0.134, 0.101) | 39 |
| Example 140 | 639 | 4.91 | 5.85 | (0.134, 0.100) | 41 |
| Example 141 | 642 | 4.98 | 6.38 | (0.134, 0.101) | 42 |
| Example 142 | 646 | 5.62 | 6.20 | (0.134, 0.100) | 45 |
| Example 143 | 650 | 4.72 | 6.12 | (0.134, 0.100) | 43 |
| Example 144 | 657 | 4.91 | 6.21 | (0.134, 0.101) | 41 |
| Example 145 | 659 | 4.98 | 6.22 | (0.134, 0.100) | 40 |
| Example 146 | 663 | 5.62 | 5.95 | (0.134, 0.100) | 33 |
| Example 147 | 667 | 5.44 | 6.13 | (0.134, 0.102) | 36 |
| Example 148 | 672 | 5.44 | 5.89 | (0.134, 0.102) | 36 |
| Example 149 | 677 | 5.44 | 6.41 | (0.134, 0.102) | 47 |
| Example 150 | 679 | 5.34 | 6.44 | (0.134, 0.102) | 36 |
| Example 151 | 683 | 5.38 | 6.38 | (0.134, 0.101) | 39 |
| Example 152 | 688 | 5.38 | 6.20 | (0.134, 0.103) | 40 |
| Example 153 | 691 | 5.39 | 6.62 | (0.134, 0.102) | 43 |
| Example 154 | 693 | 4.96 | 6.21 | (0.134, 0.101) | 37 |
| Example 155 | 696 | 4.91 | 6.22 | (0.134, 0.102) | 33 |
| Example 156 | 703 | 4.91 | 6.12 | (0.134, 0.101) | 42 |
| Example 157 | 712 | 4.98 | 6.51 | (0.134, 0.101) | 39 |
| Example 158 | 713 | 5.62 | 6.21 | (0.134, 0.100) | 41 |
| Example 159 | 716 | 5.39 | 5.95 | (0.134, 0.101) | 34 |
| Example 160 | 719 | 4.96 | 6.88 | (0.134, 0.100) | 45 |
| Example 161 | 723 | 4.91 | 6.93 | (0.134, 0.102) | 43 |
| Example 162 | 725 | 4.91 | 6.95 | (0.134, 0.100) | 41 |
| Example 163 | 732 | 4.98 | 6.22 | (0.134, 0.100) | 40 |
| Example 164 | 738 | 5.62 | 5.68 | (0.134, 0.101) | 33 |
| Example 165 | 743 | 4.96 | 6.88 | (0.134, 0.100) | 35 |
| Example 166 | 748 | 4.91 | 6.93 | (0.134, 0.100) | 43 |
| Example 167 | 753 | 4.77 | 6.95 | (0.134, 0.100) | 41 |
| Example 168 | 755 | 4.98 | 6.22 | (0.134, 0.100) | 40 |
| Example 169 | 765 | 5.62 | 5.98 | (0.134, 0.100) | 33 |
| Example 170 | 768 | 4.71 | 6.51 | (0.134, 0.102) | 48 |
| Example 171 | 779 | 4.72 | 6.53 | (0.134, 0.102) | 38 |
| Example 172 | 784 | 4.91 | 6.78 | (0.134, 0.100) | 43 |
| Example 173 | 788 | 4.90 | 6.95 | (0.134, 0.100) | 41 |
| Example 174 | 794 | 4.98 | 6.22 | (0.134, 0.100) | 40 |
| Example 175 | 807 | 5.62 | 5.98 | (0.134, 0.100) | 33 |
| Example 176 | 812 | 4.72 | 6.53 | (0.134, 0.102) | 48 |
| Example 177 | 818 | 4.74 | 6.59 | (0.134, 0.102) | 45 |
| Example 178 | 827 | 5.42 | 6.13 | (0.134, 0.101) | 39 |
| Example 179 | 833 | 5.44 | 5.89 | (0.134, 0.100) | 41 |
| Example 180 | 839 | 5.36 | 6.01 | (0.134, 0.101) | 32 |
| Example 181 | 842 | 4.96 | 6.82 | (0.134, 0.100) | 45 |
| Example 182 | 849 | 4.91 | 6.93 | (0.134, 0.100) | 43 |
| Example 183 | 853 | 4.95 | 6.95 | (0.134, 0.100) | 41 |
| Example 184 | 857 | 4.98 | 6.22 | (0.134, 0.100) | 40 |
| Example 185 | 866 | 5.62 | 5.98 | (0.134, 0.100) | 33 |
| Example 186 | 875 | 4.75 | 6.53 | (0.134, 0.102) | 40 |
| Example 187 | 879 | 4.72 | 6.35 | (0.134, 0.102) | 48 |
| Example 188 | 883 | 4.91 | 6.93 | (0.134, 0.100) | 43 |
| Example 189 | 885 | 4.93 | 6.95 | (0.134, 0.100) | 40 |
| Example 190 | 893 | 4.98 | 6.21 | (0.134, 0.100) | 40 |
| Example 191 | 895 | 5.62 | 5.98 | (0.134, 0.100) | 34 |
| Example 192 | 901 | 4.72 | 6.53 | (0.134, 0.102) | 35 |
| Example 193 | 904 | 4.79 | 6.55 | (0.134, 0.102) | 48 |
| Example 194 | 913 | 5.40 | 6.13 | (0.134, 0.101) | 39 |
| Example 195 | 915 | 5.44 | 5.89 | (0.134, 0.100) | 41 |
| Example 196 | 920 | 5.39 | 6.01 | (0.134, 0.101) | 34 |
| Comparative Example 1-1 | E1 | 6.00 | 5.12 | (0.134, 0.100) | 25 |
| Comparative Example 1-2 | E2 | 6.23 | 4.23 | (0.134, 0.111) | 16 |
| Comparative Example 1-3 | E3 | 6.34 | 4.33 | (0.134, 0.109) | 14 |
| Comparative Example 1-4 | E4 | 6.11 | 4.55 | (0.134, 0.099) | 17 |
| Comparative Example 1-5 | E5 | 6.08 | 4.64 | (0.134, 0.098) | 20 |

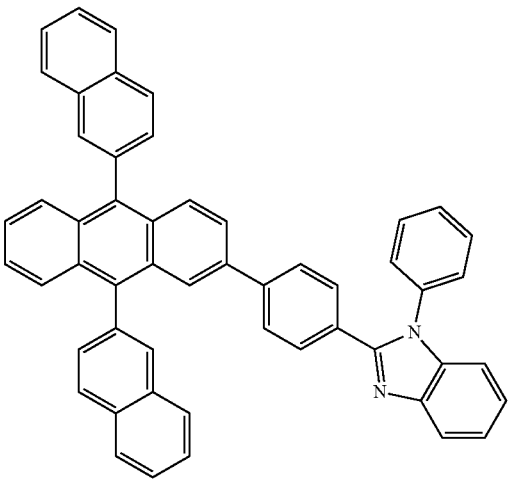

E1

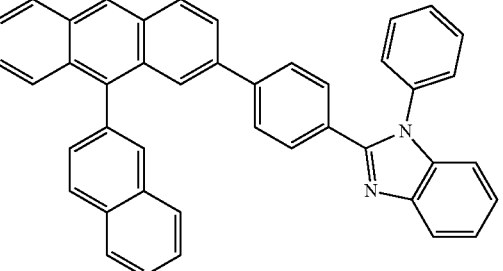

E2

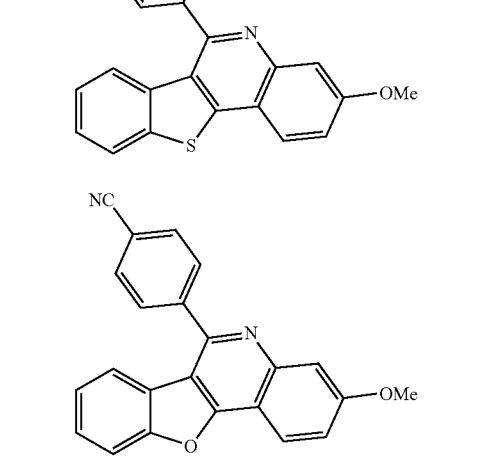

E3

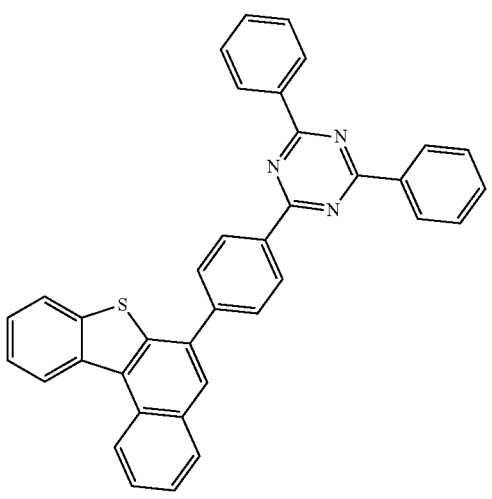

E4

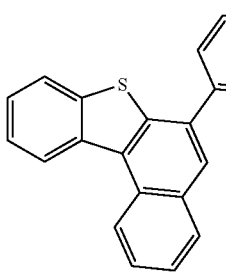

E5

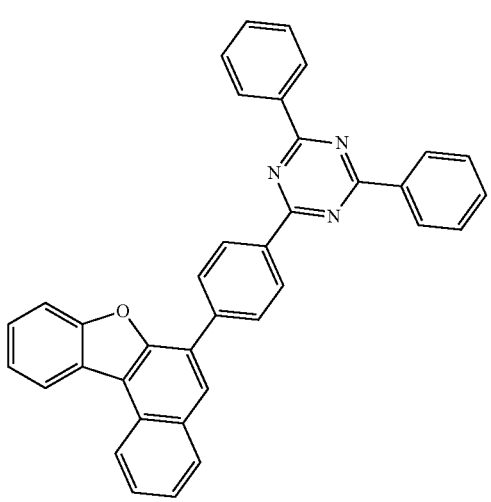

As seen from the results of Table 53, the organic electroluminescent device using the electron transfer layer material of the blue organic electroluminescent device of the present disclosure had a lower driving voltage, and significantly improved light emission efficiency and lifetime compared to Comparative Examples 1-1, 1-2, 1-3, 1-4 and 1-5.

Such a result is considered to be due to the fact that, when using the disclosed compound having proper length, strength and flat properties as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transfer electrons without the compound being decomposed or destroyed. For reference, those that are stable when excited are considered to be aryl or acene compounds, or polycyclic hetero-compounds. Accordingly, it is considered that excellent results in all aspects of driving, efficiency and lifetime are obtained by the compound of the present disclosure enhancing enhanced electron-transfer properties or improved stability.

Experimental Example 2

1) Manufacture of Organic Light Emitting Device

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum depositor, and the following 4,4',4"-tris(N,N-(2-naphthyl)-phenylamino)triphenylamine (2-TNATA) was introduced to a cell in the vacuum depositor.

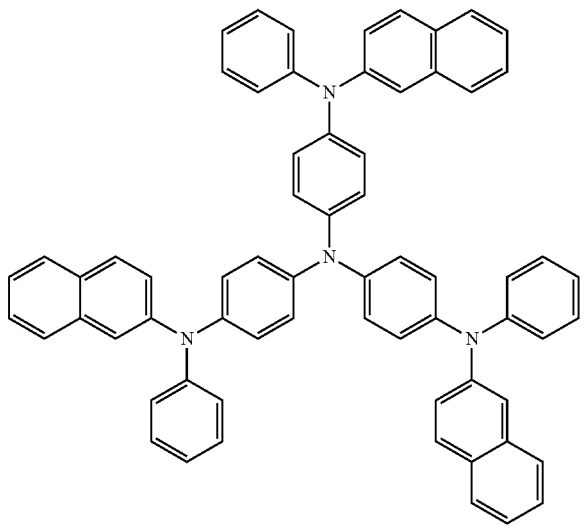

2-TNATA

After forming the hole injection layer and the hole transfer layer as above, a blue light emitting material having a structure as below was deposited thereon as a light emitting layer. Specifically, in one side cell in the vacuum depositor, H1, a blue light emitting host material, was vacuum deposited to a thickness of 200 Å, and D1, a blue light emitting dopant material, was vacuum deposited thereon by 5% with respect to the host material.

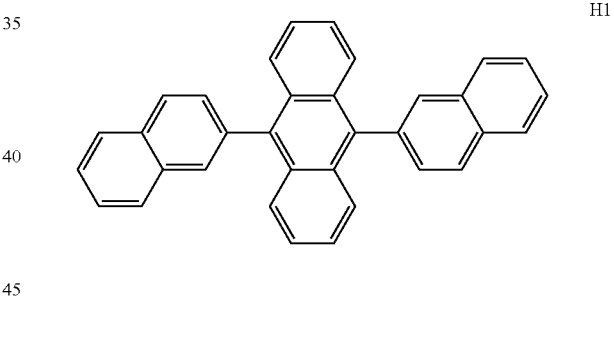

H1

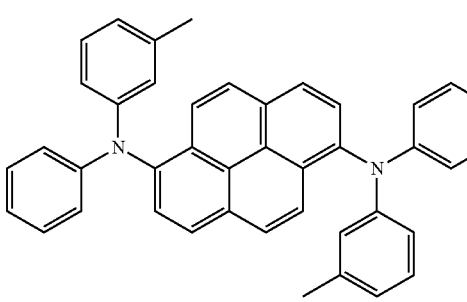

D1

Subsequently, a compound of the following structural formula E1 was deposited to a thickness of 300 Å as an electron transfer layer.

E1

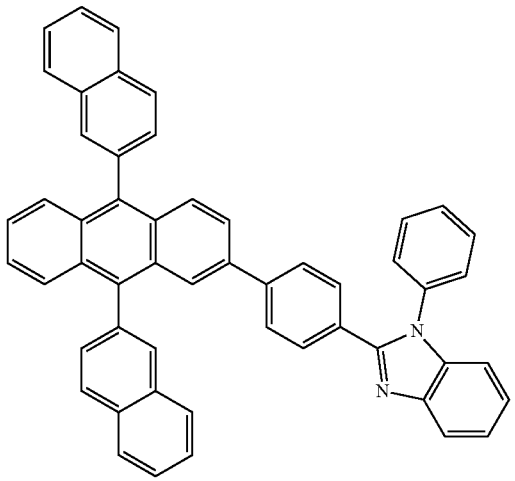

As an electron injection layer, lithium fluoride (LiF) was deposited to a thickness of 10 Å, and an Al cathode was employed to have a thickness of 1,000 Å to manufacture an OLED. Meanwhile, all the organic compounds required to manufacture the OLED were vacuum sublimation purified under $10^{-6}$ torr to $10^{-8}$ torr by each material to be used in the OLED manufacture.

An organic electroluminescent device was manufactured in the same manner as in Experimental Example 2 except that, after forming the electron transfer layer E1 to a thickness of 250 Å, a hole blocking layer was formed on the electron transfer layer to a thickness of 50 Å using a compound presented in the following Table 54.

For the organic electroluminescent device manufactured as above, electroluminescent light emission (EL) properties were measured using M7000 manufactured by McScience Inc., and with the measurement results, $T_{95}$ when standard luminance was 700 cd/m² was measured using a lifetime measurement system (M6000) manufactured by McScience Inc. Results of measuring a driving voltage, light emission efficiency, external quantum efficiency and a color coordinate (CIE) of the blue organic electroluminescent device manufactured according to the present disclosure are as shown in Table 54.

TABLE 54

|  | Compound | Driving Voltage (V) | Light Emission Efficiency (cd/A) | CIE (x, y) | Lifetime (T95) |
| --- | --- | --- | --- | --- | --- |
| Example 197 | 1 | 4.42 | 6.93 | (0.134, 0.099) | 40 |
| Example 198 | 7 | 4.48 | 6.86 | (0.134, 0.099) | 41 |
| Example 199 | 10 | 4.47 | 6.87 | (0.134, 0.100) | 40 |
| Example 200 | 17 | 4.67 | 6.64 | (0.129, 0.100) | 38 |
| Example 201 | 25 | 4.82 | 6.55 | (0.130, 0.099) | 36 |
| Example 202 | 33 | 4.44 | 6.97 | (0.134, 0.101) | 40 |
| Example 203 | 51 | 4.61 | 6.89 | (0.134, 0.103) | 40 |
| Example 204 | 59 | 5.35 | 6.30 | (0.134, 0.102) | 33 |
| Example 205 | 68 | 5.28 | 6.28 | (0.134, 0.102) | 32 |
| Example 206 | 83 | 4.57 | 6.74 | (0.128, 0.099) | 36 |
| Example 207 | 98 | 4.62 | 6.72 | (0.133, 0.100) | 37 |
| Example 208 | 100 | 4.55 | 6.85 | (0.134, 0.101) | 39 |
| Example 209 | 124 | 4.54 | 6.92 | (0.134, 0.101) | 41 |
| Example 210 | 125 | 4.30 | 6.81 | (0.134, 0.101) | 41 |
| Example 211 | 130 | 4.50 | 6.98 | (0.134, 0.100) | 40 |
| Example 212 | 134 | 4.44 | 7.09 | (0.134, 0.100) | 39 |

TABLE 54-continued

|  | Compound | Driving Voltage (V) | Light Emission Efficiency (cd/A) | CIE (x, y) | Lifetime (T95) |
| --- | --- | --- | --- | --- | --- |
| Example 213 | 149 | 4.64 | 7.08 | (0.134, 0.099) | 40 |
| Example 214 | 151 | 4.53 | 6.91 | (0.134, 0.101) | 41 |
| Example 215 | 156 | 4.97 | 6.59 | (0.134, 0.100) | 34 |
| Example 216 | 171 | 5.63 | 6.11 | (0.131, 0.098) | 28 |
| Example 217 | 179 | 5.66 | 6.04 | (0.131, 0.102) | 30 |
| Example 218 | 197 | 5.40 | 6.49 | (0.134, 0.101) | 31 |
| Example 219 | 203 | 5.60 | 6.22 | (0.129, 0.100) | 29 |
| Example 220 | 219 | 4.70 | 6.01 | (0.134, 0.100) | 36 |
| Example 221 | 223 | 5.40 | 6.31 | (0.134, 0.102) | 31 |
| Example 222 | 236 | 4.73 | 6.78 | (0.130, 0.100) | 35 |
| Example 223 | 243 | 4.67 | 6.65 | (0.129, 0.098) | 36 |
| Example 224 | 252 | 4.69 | 6.92 | (0.130, 0.101) | 35 |
| Example 225 | 253 | 4.52 | 6.75 | (0.129, 0.097) | 37 |
| Example 226 | 265 | 4.80 | 6.89 | (0.134, 0.102) | 58 |
| Example 227 | 272 | 4.76 | 6.95 | (0.134, 0.102) | 50 |
| Example 228 | 288 | 4.77 | 6.90 | (0.134, 0.102) | 51 |
| Example 229 | 295 | 5.11 | 6.12 | (0.134, 0.102) | 48 |
| Example 230 | 305 | 4.96 | 6.10 | (0.134, 0.100) | 36 |
| Example 231 | 308 | 5.30 | 6.20 | (0.134, 0.101) | 40 |
| Example 232 | 319 | 5.22 | 6.03 | (0.134, 0.101) | 43 |
| Example 233 | 334 | 4.90 | 6.81 | (0.134, 0.101) | 56 |
| Example 234 | 347 | 4.88 | 6.82 | (0.134, 0.102) | 57 |
| Example 235 | 352 | 4.74 | 6.75 | (0.134, 0.101) | 51 |
| Example 236 | 358 | 4.81 | 6.82 | (0.134, 0.102) | 53 |
| Example 237 | 379 | 5.16 | 6.20 | (0.134, 0.101) | 38 |
| Example 238 | 382 | 5.15 | 6.42 | (0.134, 0.102) | 39 |
| Example 239 | 389 | 5.31 | 6.30 | (0.134, 0.103) | 37 |
| Example 240 | 406 | 4.82 | 6.35 | (0.134, 0.100) | 50 |
| Example 241 | 415 | 4.84 | 6.60 | (0.134, 0.100) | 49 |
| Example 242 | 425 | 4.91 | 6.69 | (0.134, 0.102) | 51 |
| Example 243 | 433 | 4.90 | 6.71 | (0.134, 0.102) | 50 |
| Example 244 | 444 | 4.72 | 6.98 | (0.134, 0.100) | 51 |
| Example 245 | 453 | 4.80 | 6.89 | (0.134, 0.102) | 58 |
| Example 246 | 455 | 4.76 | 6.95 | (0.134, 0.102) | 50 |
| Example 247 | 467 | 4.77 | 6.90 | (0.134, 0.102) | 51 |
| Example 248 | 470 | 4.98 | 6.05 | (0.134, 0.101) | 34 |
| Example 249 | 488 | 5.22 | 6.03 | (0.134, 0.101) | 43 |
| Example 250 | 493 | 4.82 | 6.84 | (0.134, 0.101) | 52 |
| Example 251 | 511 | 4.84 | 6.97 | (0.134, 0.102) | 51 |
| Example 252 | 519 | 4.74 | 6.75 | (0.134, 0.101) | 51 |
| Example 253 | 528 | 4.81 | 6.82 | (0.134, 0.102) | 53 |
| Example 254 | 529 | 5.26 | 6.44 | (0.134, 0.102) | 32 |
| Example 255 | 532 | 5.21 | 6.38 | (0.134, 0.101) | 41 |
| Example 256 | 535 | 5.44 | 6.47 | (0.134, 0.102) | 36 |
| Example 257 | 549 | 5.38 | 6.20 | (0.134, 0.103) | 40 |
| Example 258 | 551 | 5.60 | 6.12 | (0.134, 0.102) | 43 |
| Example 259 | 558 | 5.45 | 6.21 | (0.134, 0.101) | 37 |
| Example 260 | 560 | 5.44 | 6.22 | (0.134, 0.102) | 34 |
| Example 261 | 572 | 5.50 | 5.89 | (0.134, 0.100) | 41 |
| Example 262 | 577 | 5.44 | 6.01 | (0.134, 0.101) | 36 |
| Example 263 | 585 | 4.91 | 6.32 | (0.134, 0.100) | 41 |
| Example 264 | 590 | 4.98 | 6.44 | (0.134, 0.100) | 40 |
| Example 265 | 594 | 5.62 | 6.38 | (0.134, 0.100) | 35 |
| Example 266 | 609 | 5.44 | 6.34 | (0.134, 0.102) | 36 |
| Example 267 | 611 | 5.62 | 6.20 | (0.134, 0.101) | 39 |
| Example 268 | 619 | 5.60 | 6.21 | (0.134, 0.102) | 43 |
| Example 269 | 626 | 5.45 | 6.22 | (0.134, 0.101) | 37 |
| Example 270 | 634 | 4.96 | 5.95 | (0.134, 0.101) | 42 |
| Example 271 | 646 | 5.62 | 6.20 | (0.134, 0.100) | 45 |
| Example 272 | 650 | 4.72 | 6.12 | (0.134, 0.100) | 43 |
| Example 273 | 677 | 5.44 | 6.41 | (0.134, 0.102) | 47 |
| Example 274 | 688 | 5.38 | 6.20 | (0.134, 0.103) | 40 |
| Example 275 | 691 | 5.39 | 6.62 | (0.134, 0.102) | 43 |
| Example 276 | 703 | 4.91 | 6.12 | (0.134, 0.101) | 42 |
| Example 277 | 712 | 4.98 | 6.51 | (0.134, 0.101) | 39 |
| Example 278 | 719 | 4.96 | 6.88 | (0.134, 0.100) | 45 |
| Example 279 | 723 | 4.91 | 6.93 | (0.134, 0.102) | 43 |
| Example 280 | 755 | 4.98 | 6.22 | (0.134, 0.100) | 40 |
| Example 281 | 765 | 5.62 | 5.98 | (0.134, 0.100) | 33 |
| Example 282 | 779 | 4.72 | 6.53 | (0.134, 0.102) | 38 |
| Example 283 | 784 | 4.91 | 6.78 | (0.134, 0.100) | 43 |
| Example 284 | 794 | 4.98 | 6.22 | (0.134, 0.100) | 40 |
| Example 285 | 807 | 5.62 | 5.98 | (0.134, 0.100) | 33 |
| Example 286 | 812 | 4.72 | 6.53 | (0.134, 0.102) | 48 |
| Example 287 | 827 | 5.42 | 6.13 | (0.134, 0.101) | 39 |

TABLE 54-continued

| | Compound | Driving Voltage (V) | Light Emission Efficiency (cd/A) | CIE (x, y) | Lifetime (T95) |
|---|---|---|---|---|---|
| Example 288 | 833 | 5.44 | 5.89 | (0.134, 0.100) | 41 |
| Example 289 | 842 | 4.96 | 6.82 | (0.134, 0.100) | 45 |
| Example 290 | 857 | 4.98 | 6.22 | (0.134, 0.100) | 40 |
| Example 291 | 866 | 5.62 | 5.98 | (0.134, 0.100) | 33 |
| Example 292 | 879 | 4.72 | 6.35 | (0.134, 0.102) | 48 |
| Example 293 | 883 | 4.91 | 6.93 | (0.134, 0.100) | 43 |
| Example 294 | 895 | 5.62 | 5.98 | (0.134, 0.100) | 34 |
| Example 295 | 901 | 4.72 | 6.53 | (0.134, 0.102) | 35 |
| Example 296 | 904 | 4.79 | 6.55 | (0.134, 0.102) | 48 |
| Example 297 | 920 | 5.39 | 6.01 | (0.134, 0.101) | 34 |
| Comparative Example 2-1 | E1 | 6.02 | 5.01 | (0.134, 0.100) | 21 |
| Comparative Example 2-2 | E2 | 6.55 | 4.44 | (0.134, 0.102) | 11 |
| Comparative Example 2-3 | E3 | 6.54 | 4.46 | (0.134, 0.099) | 10 |
| Comparative Example 2-4 | E4 | 6.23 | 4.65 | (0.134, 0.101) | 19 |
| Comparative Example 2-5 | E5 | 6.29 | 4.67 | (0.134, 0.101) | 18 |

As seen from the results of Table 54, the organic light emitting device using the hole blocking layer material of the blue organic light emitting device of the present disclosure had a lower driving voltage, and significantly improved light emission efficiency and lifetime compared to Comparative Examples 2-1, 2-2, 2-3, 2-4 and 2-5.

Such a reason is due to the fact that the heterocyclic compound of Chemical Formula 1 of the present application is a bipolar type having both a P-type and an N-type, and is capable of blocking hole leakage and effectively trapping excitons in the light emitting layer.

Experimental Example 3

1) Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), an organic material was formed in a 2 stack white organic light emitting device (WOLED) structure. As for the first stack, TAPC was thermal vacuum deposited to a thickness of 300 Å first to form a hole transfer layer. After forming the hole transfer layer, a light emitting layer was thermal vacuum deposited thereon as follows. The light emitting layer was deposited to 300 Å by doping Flrpic to TCz1, a host, by 8% as a blue phosphorescent dopant. After forming an electron transfer layer to 400 Å using TmPyPB, a charge generation layer was formed to 100 Å by doping $Cs_2CO_3$ to the compound described in the following Table 55 by 20%.

As for the second stack, $MoO_3$ was thermal vacuum deposited to a thickness of 50 Å first to form a hole injection layer. A hole transfer layer, a common layer, was formed by doping $MoO_3$ to TAPC by 20% to 100 Å and depositing TAPC to 300 Å. A light emitting layer was deposited thereon to 300 Å by doping $Ir(ppy)_3$, a green phosphorescent dopant, to TCz1, a host, by 8%, and an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic electroluminescent device.

Meanwhile, all the organic compounds required to manufacture the OLED were vacuum sublimation purified under $10^{-6}$ torr to $10^{-8}$ torr by each material to be used in the OLED manufacture.

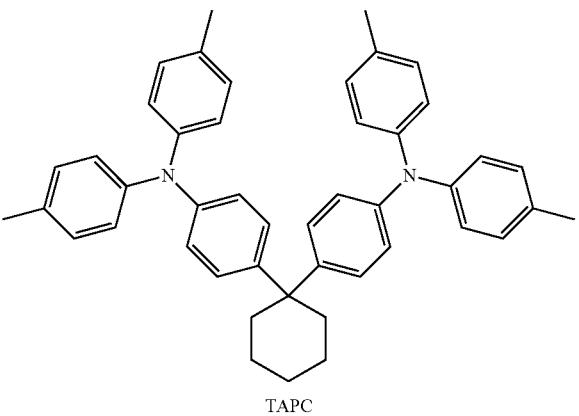

TAPC

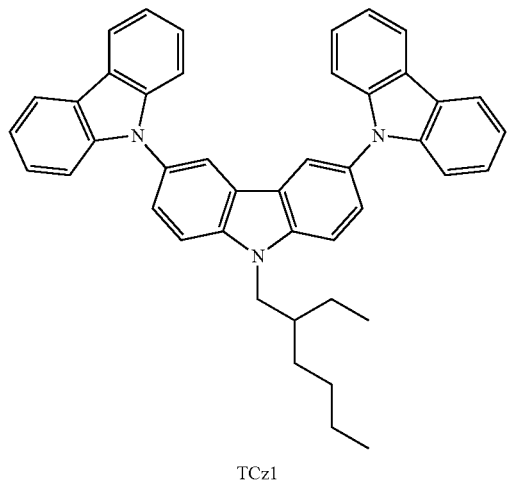

TCz1

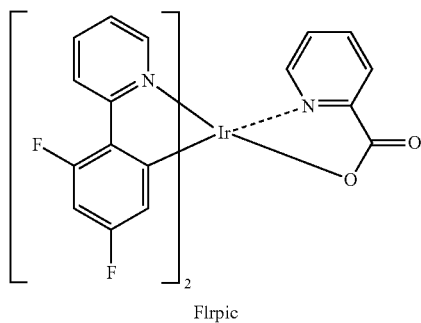

Flrpic

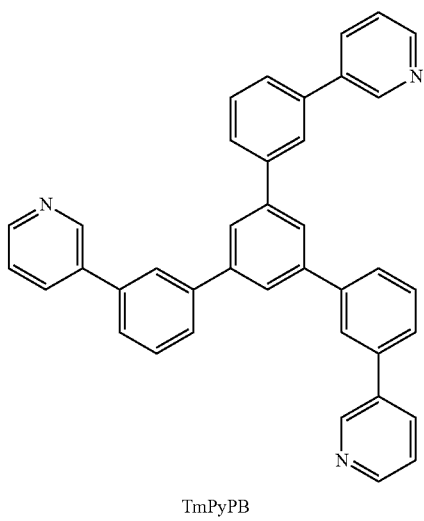

TmPyPB

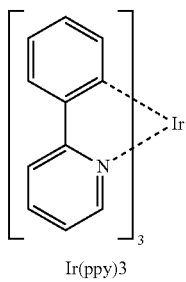

Ir(ppy)3

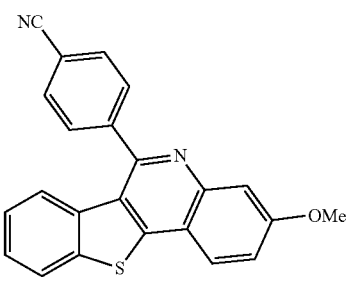

E2

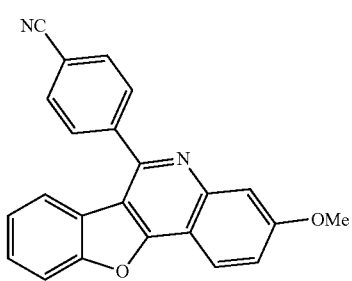

E3

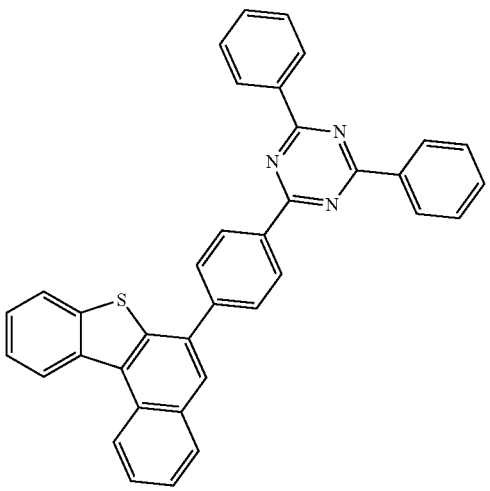

E4

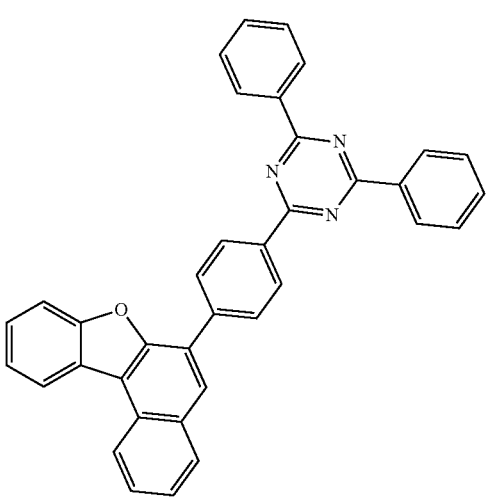

E5

For the organic electroluminescent devices manufactured as above, electroluminescent light emission (EL) properties were measured using M7000 manufactured by McScience Inc., and with the measurement results, 195 when standard luminance was 3,500 cd/m$^2$ was measured using a lifetime measurement system (M6000) manufactured by McScience Inc. Results of measuring a driving voltage, light emission efficiency, external quantum efficiency and a color coordinate (CIE) of the white organic electroluminescent device manufactured according to the present disclosure are as shown in Table 55.

TABLE 55

| | Compound | Driving Voltage (V) | Light Emission Efficiency (cd/A) | CIE (x, y) | Lifetime (T95) |
|---|---|---|---|---|---|
| Example 298 | 921 | 7.29 | 65.55 | (0.220, 0.432) | 53 |
| Example 299 | 924 | 7.31 | 66.32 | (0.221, 0.433) | 51 |
| Example 300 | 925 | 7.05 | 67.93 | (0.221, 0.428) | 50 |
| Example 301 | 926 | 7.06 | 69.82 | (0.221, 0.440) | 42 |
| Example 302 | 928 | 7.08 | 69.45 | (0.220, 0.430) | 40 |
| Example 303 | 929 | 7.12 | 68.55 | (0.215, 0.422) | 44 |
| Example 304 | 931 | 7.08 | 68.21 | (0.214, 0.422) | 45 |
| Example 305 | 935 | 7.02 | 67.44 | (0.212, 0.417) | 40 |
| Example 306 | 937 | 7.09 | 68.01 | (0.211, 0.422) | 42 |

TABLE 55-continued

| Compound | Driving Voltage (V) | Light Emission Efficiency (cd/A) | CIE (x, y) | Lifetime (T95) |
|---|---|---|---|---|
| Example 307 | 938 | 7.11 | 69.44 | (0.223, 0.428) | 41 |
| Example 308 | 939 | 7.02 | 68.08 | (0.222, 0.430) | 42 |
| Example 309 | 940 | 7.04 | 69.11 | (0.231, 0.434) | 40 |
| Example 310 | 942 | 7.08 | 69.45 | (0.220, 0.430) | 40 |
| Example 311 | 944 | 7.12 | 68.55 | (0.216, 0.426) | 35 |
| Comparative Example 3-1 | E2 | 8.57 | 33.11 | (0.201, 0.398) | 9 |
| Comparative Example 3-2 | E3 | 8.43 | 32.12 | (0.189, 0.388) | 6 |
| Comparative Example 3-3 | E4 | 8.46 | 33.01 | (0.188, 0.388) | 6 |
| Comparative Example 3-4 | E5 | 8.52 | 32.56 | (0.199, 0.398) | 8 |

As seen from the results of Table 55, the organic electroluminescent device using the charge generation layer material of the 2-stack white organic electroluminescent device of the present disclosure had a lower driving voltage and improved light emission efficiency compared to Comparative Examples 3-1, 3-2, 3-3 and 3-4.

Such a result is considered to be due to the fact that the compound of the present disclosure used as the N-type charge generation layer formed with the disclosed skeleton having proper length, strength and flat properties and a proper hetero-compound capable of binding with a metal forms a gap state in the N-type charge generation layer by doping an alkali metal or an alkaline earth metal, and electrons produced from the P-type charge generation layer are readily injected to the electron transfer layer through the gap state produced in the N-type charge generation layer. Accordingly, it is considered that the P-type charge generation layer favorably injects and transfers electrons to the N-type charge generation layer, and as a result, a driving voltage was lowered, and efficiency and lifetime were improved in the organic light emitting device.

The invention claimed is:

1. A heterocyclic compound represented by the following Chemical Formula 1:

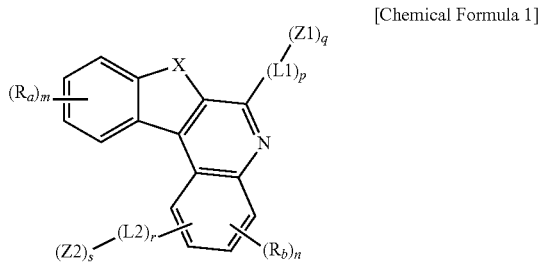

[Chemical Formula 1]

wherein, in Chemical Formula 1,

X is O or S;

L1 and L2 are the same as or different from each other, and each independently a substituted or unsubstituted arylene group; or a substituted or unsubstituted heteroarylene group;

Z1 and Z2 are the same as or different from each other, and each independently hydrogen; a substituted or unsubstituted alkyl group; a substituted or unsubstituted aryl group; a substituted or unsubstituted heteroaryl group; —SiRR'R''; or —P(=O)RR';

$R_a$ and $R_b$ are the same as or different from each other, and each independently hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R''; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring;

R, R' and R'' are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;

p and n are an integer of 1 to 3;

m, q and s are an integer of 1 to 4;

r is an integer of 0 to 4; and when r is an integer of 0 and Z2 is hydrogen, n is an integer of 2 or 3, and $R_b$ is a substituted or unsubstituted aryl group; or a substituted or unsubstituted heteroaryl group, or two or more groups adjacent to each other bond to each other to form a substituted or unsubstituted aliphatic or aromatic hydrocarbon ring.

2. The heterocyclic compound of claim 1, wherein the "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R''; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted; and R, R' and R'' have the same definitions as in Chemical Formula 1.

3. The heterocyclic compound of claim 1, wherein Chemical Formula 1 is represented by any one of the following Chemical Formulae 2 to 5:

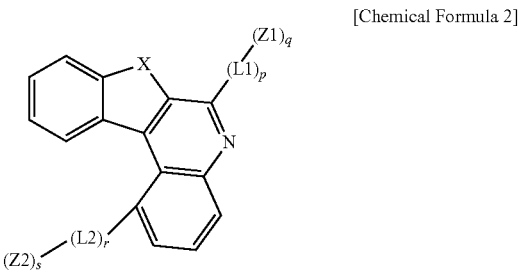

[Chemical Formula 2]

in Chemical Formulae 2 to 5,
L1, L2, Z1, Z2, X, p, q, r and s each have the same definition as in Chemical Formula 1.

4. The heterocyclic compound of claim 1, wherein $R_a$ is hydrogen.

5. The heterocyclic compound of claim 1, wherein L1 is a substituted or unsubstituted monocyclic or polycyclic C6 to C40 arylene group; or a substituted or unsubstituted C2 to C40 N-containing heteroarylene group;
Z1 is hydrogen; a C6 to C40 aryl group unsubstituted or substituted with one or more substituents selected from the group consisting of a C6 to C40 aryl group and a C2 to C40 heteroaryl group; a C2 to C40 heteroaryl group; or —P(=O)RR'; and
R and R' have the same definitions as in Chemical Formula 1.

6. The heterocyclic compound of claim 1, wherein L2 is a C6 to C40 arylene group; or a C2 to C40 heteroarylene group;
Z2 is hydrogen; a C6 to C40 aryl group unsubstituted or substituted with a C6 to C40 heteroaryl group; a C2 to C40 heteroaryl group; or P(=O)RR'; and
R and R' are the same as or different from each other, and each independently hydrogen; a substituted or unsubstituted aryl group; or a substituted or unsubstituted heteroaryl group.

7. The heterocyclic compound of claim 1, wherein Chemical Formula 1 is represented by any one of the following Chemical Formulae 6 to 11:

[Chemical Formula 11]
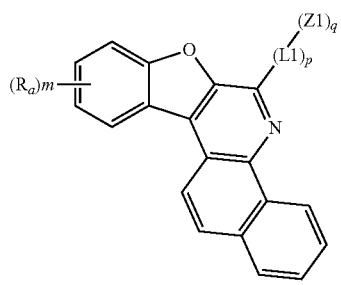
in Chemical Formulae 6 to 11,
$R_a$, L1, Z1, p, q and m each have the same definition as in Chemical Formula 1.
8. The heterocyclic compound of claim 1, wherein Chemical Formula 1 is represented by any one of the following compounds:
1
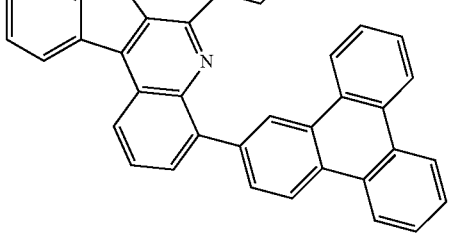
2
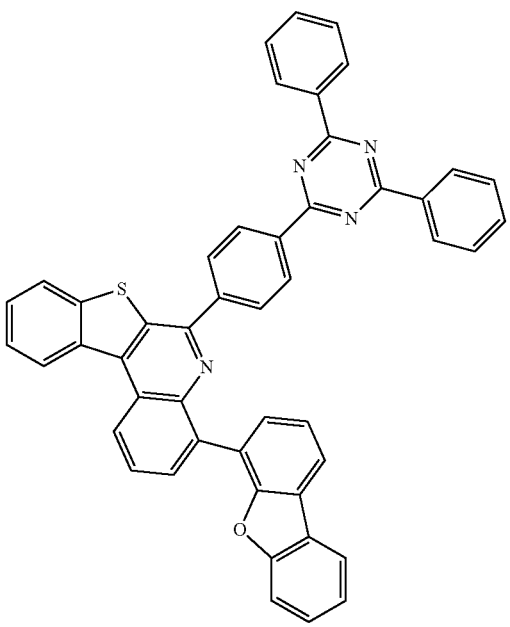
3
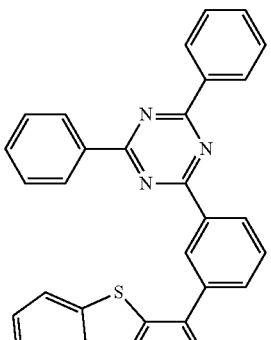
4
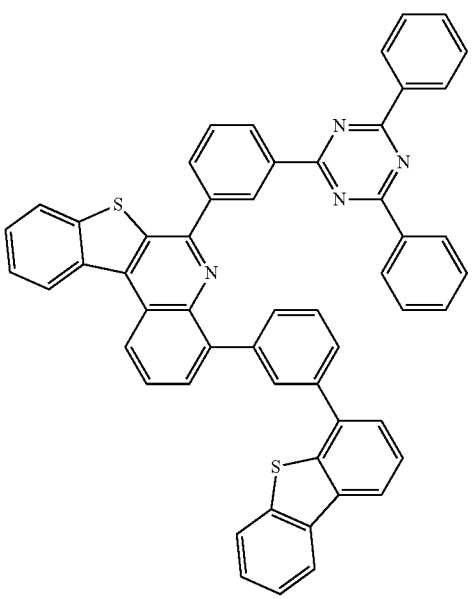

697
-continued
5
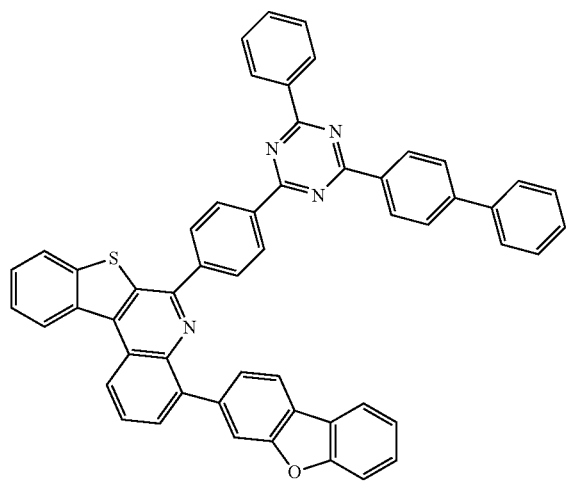
6
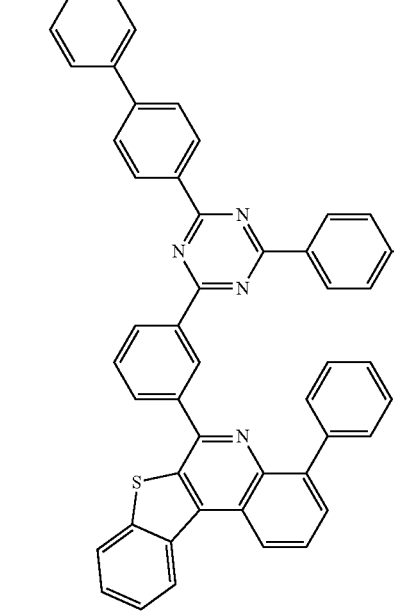
7
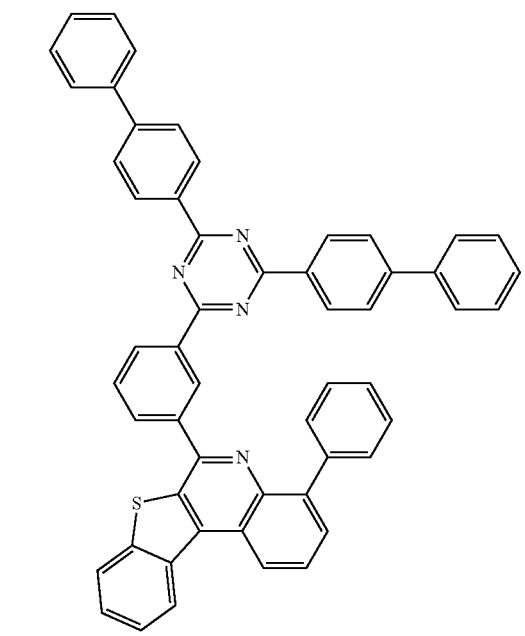
698
-continued
8
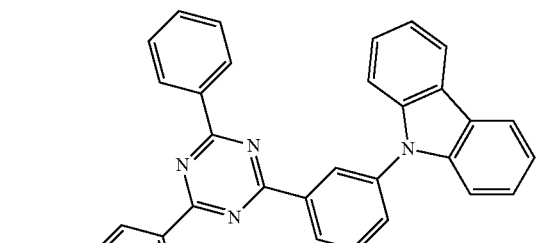
9
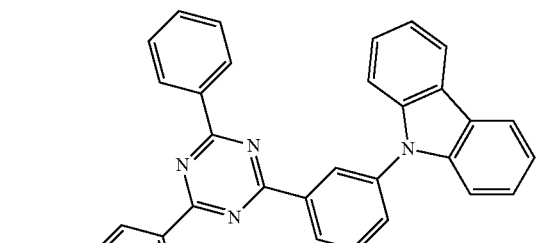
10
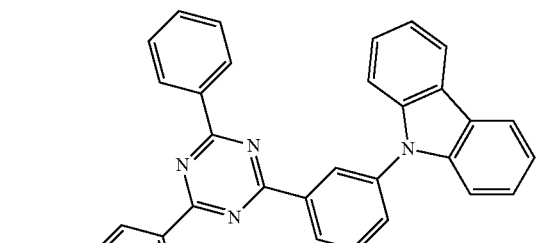

699
-continued
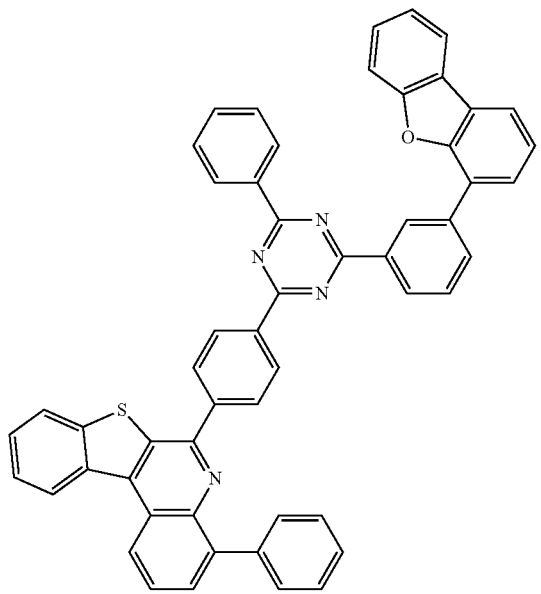
11
700
-continued
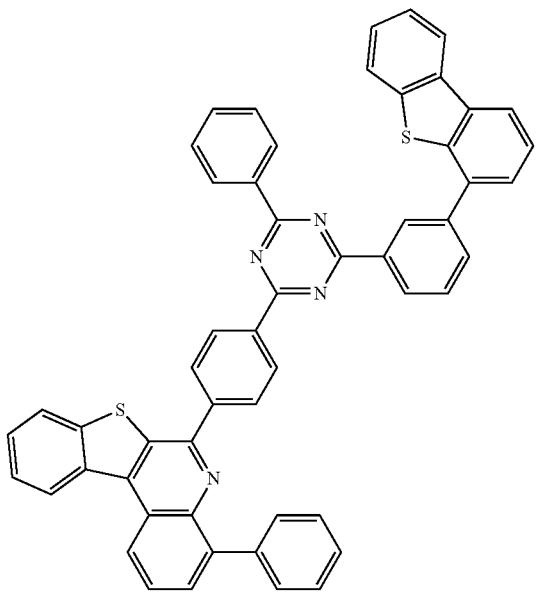
13
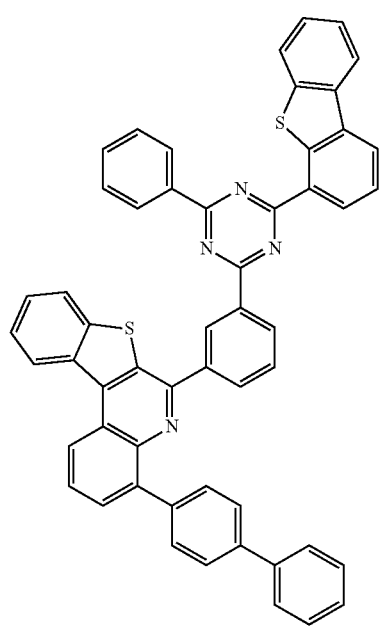
12
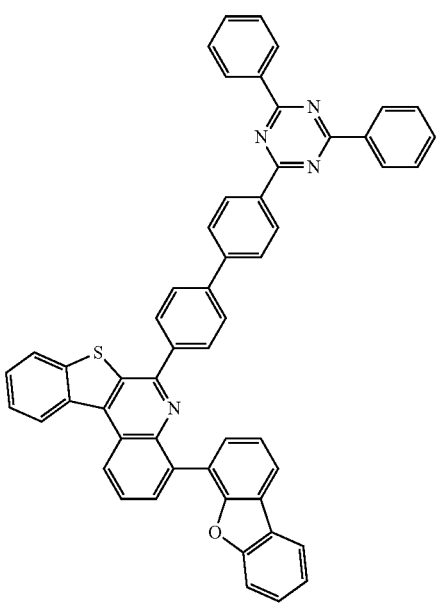
14

701
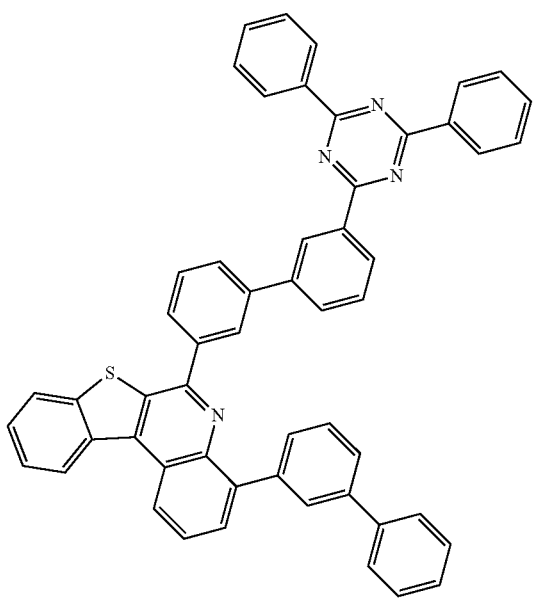
702
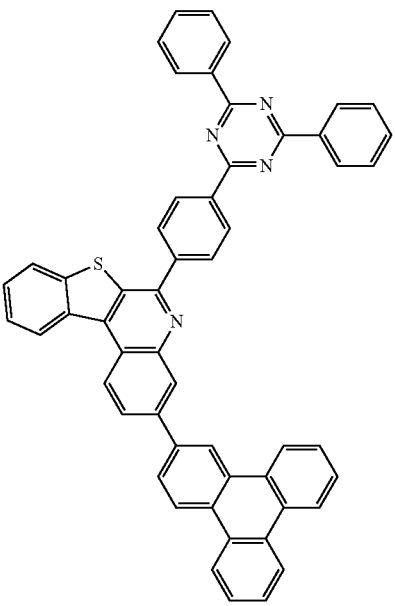
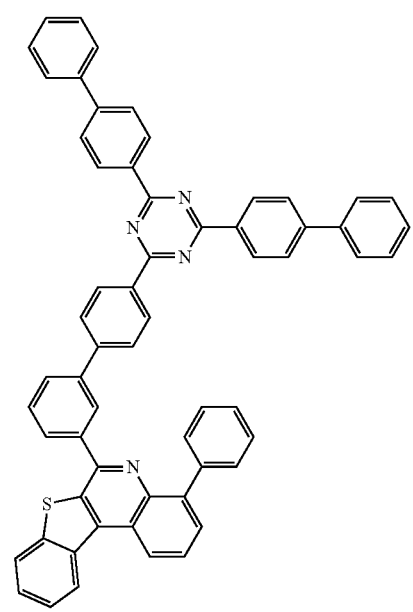
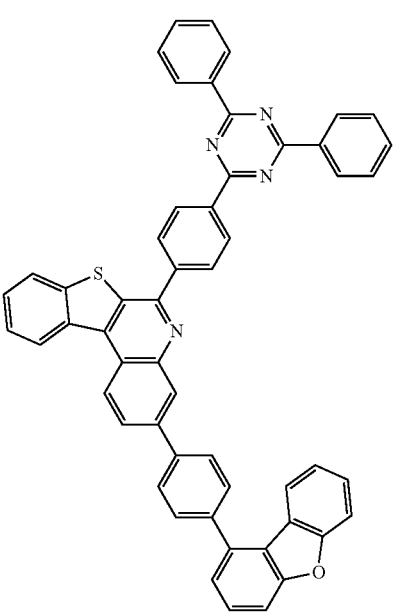

703 704
-continued -continued
19 21
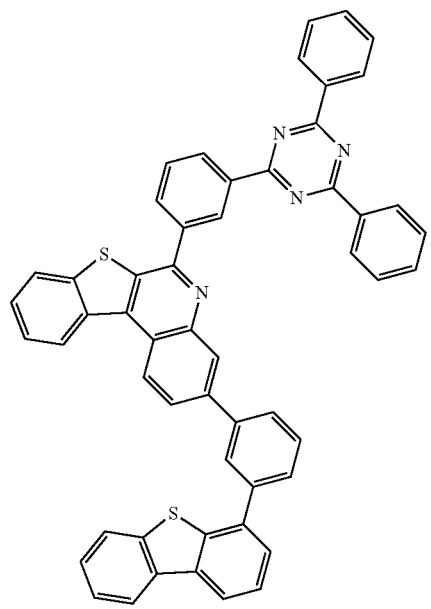
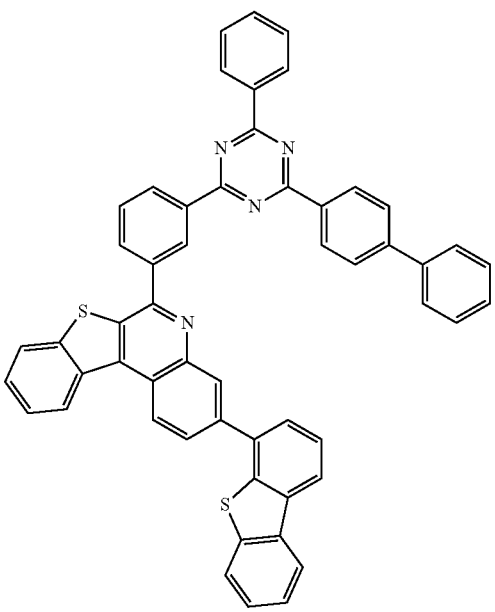
20 22

23
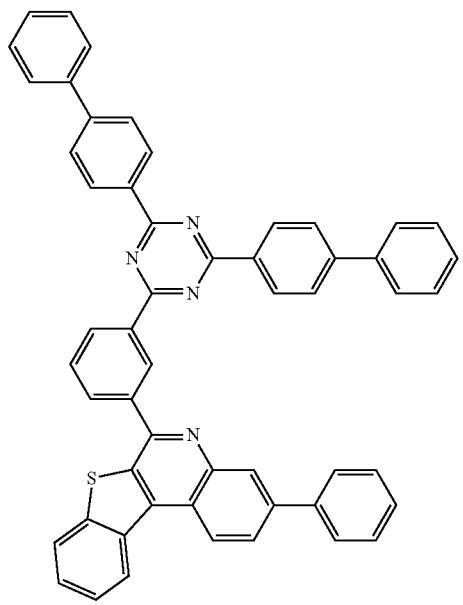
24
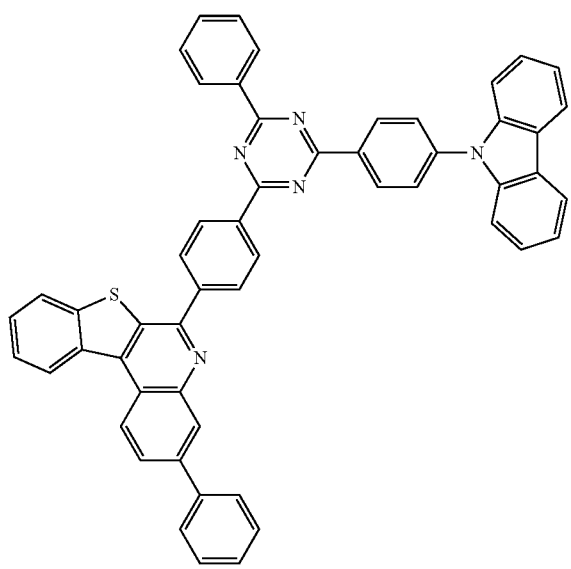
25
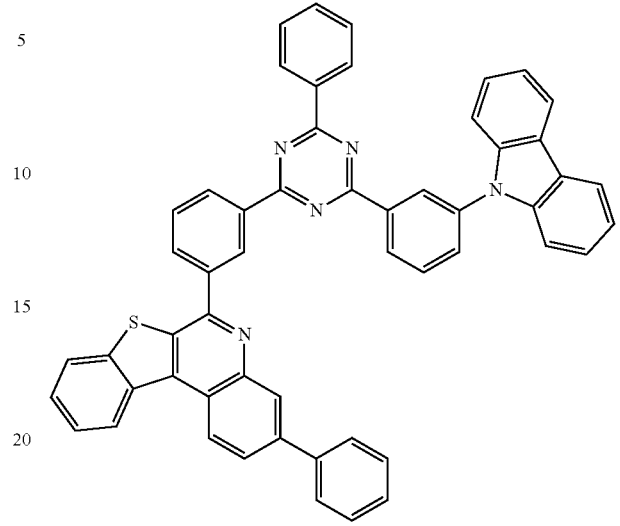
26
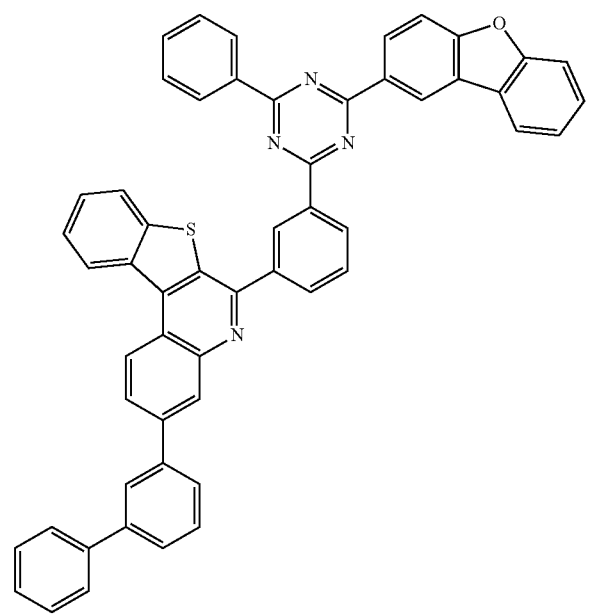

707
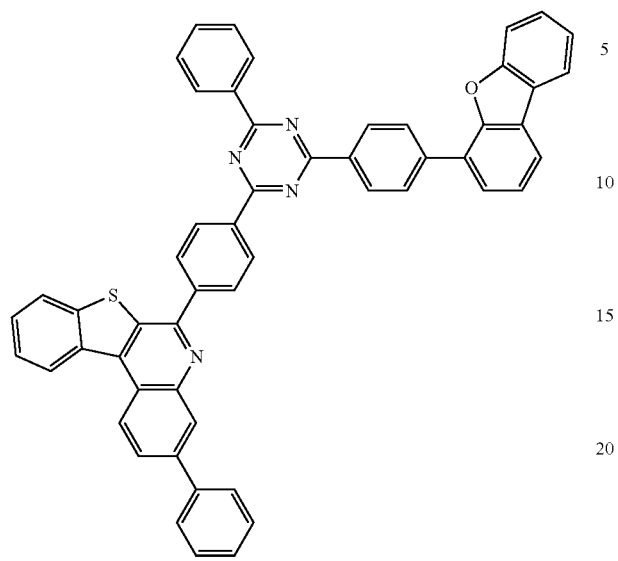
708
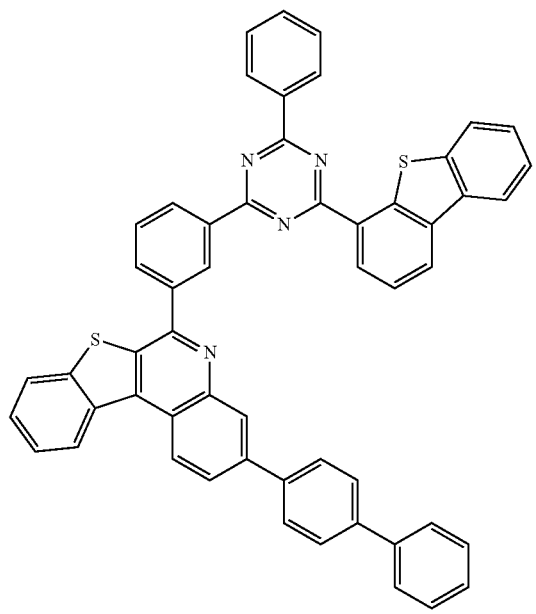
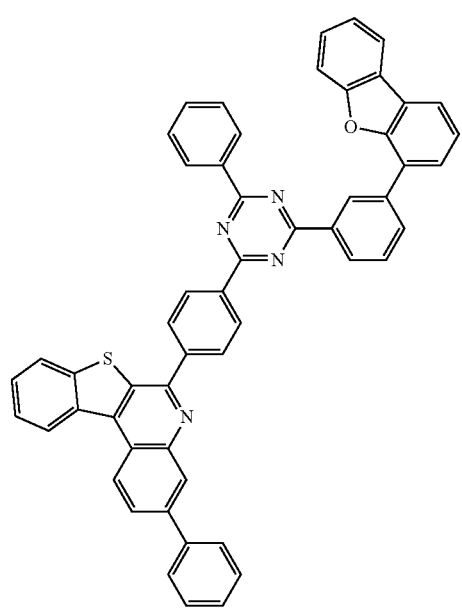
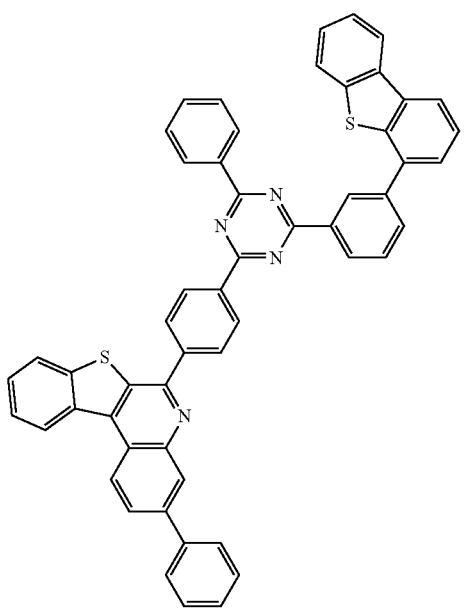

709
-continued
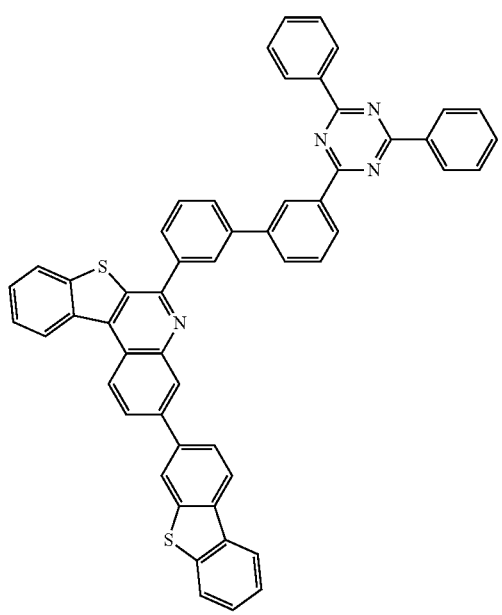
710
-continued
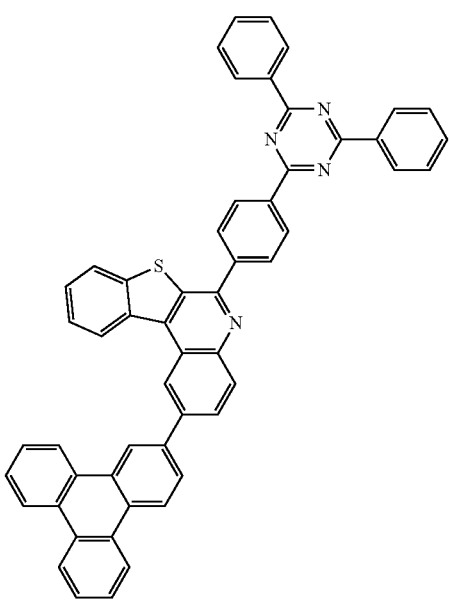
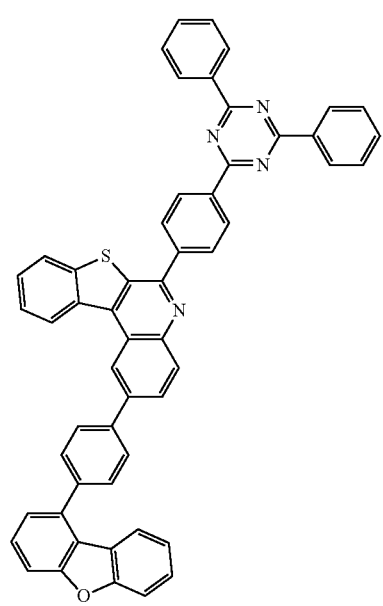

711
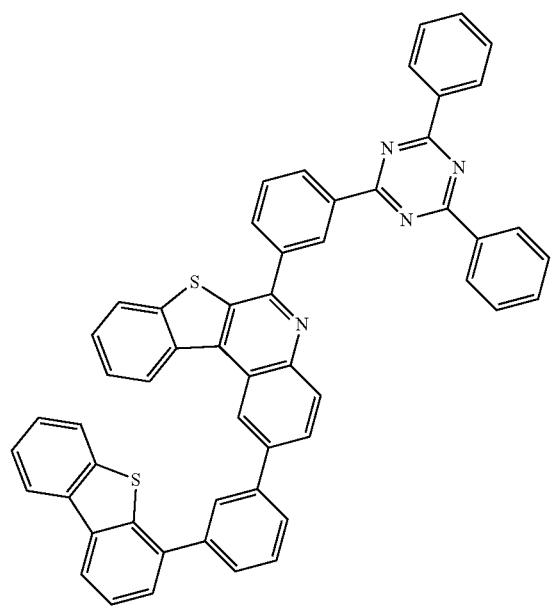
712
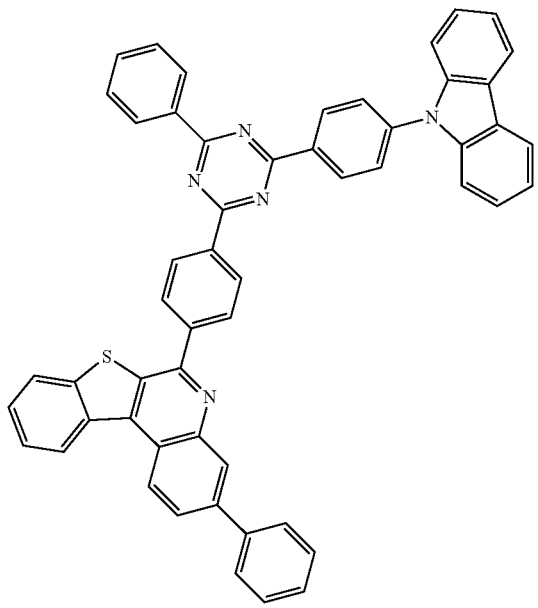
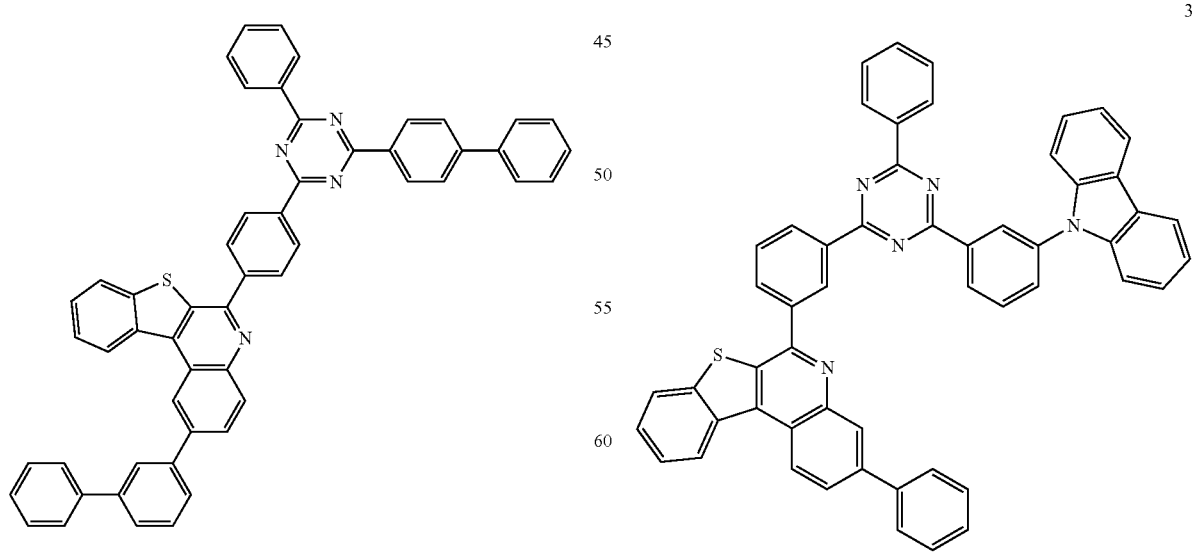

713
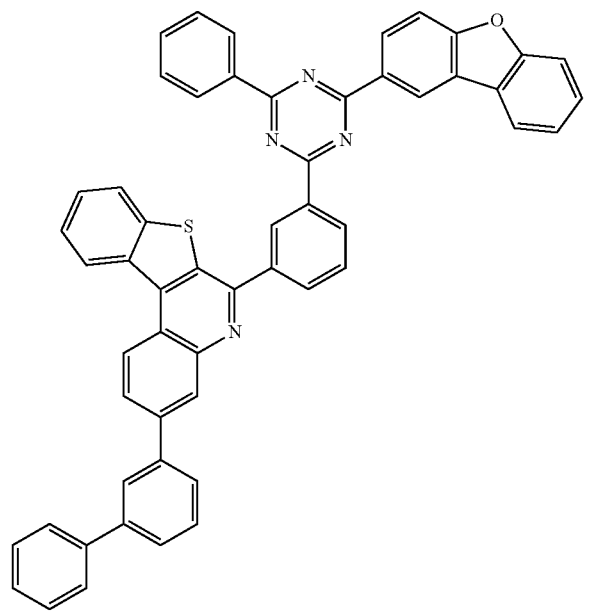
714
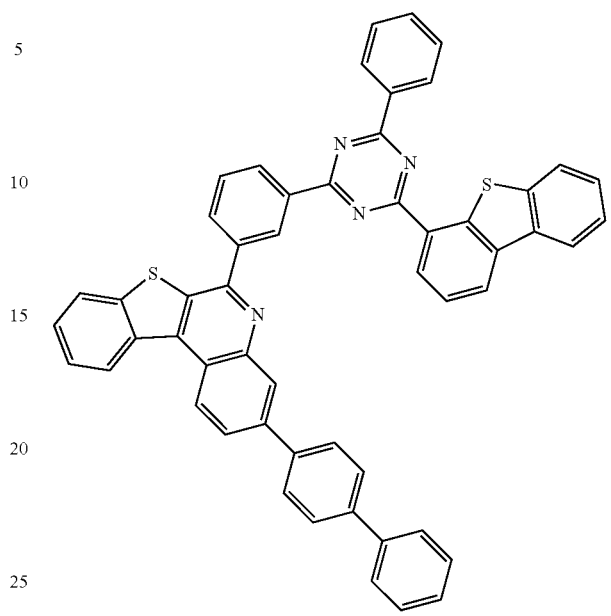
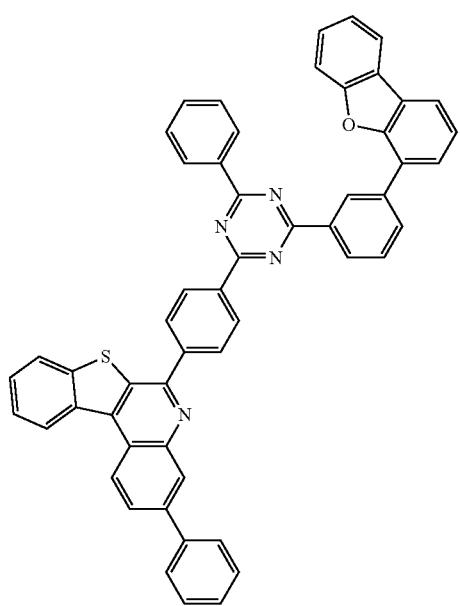
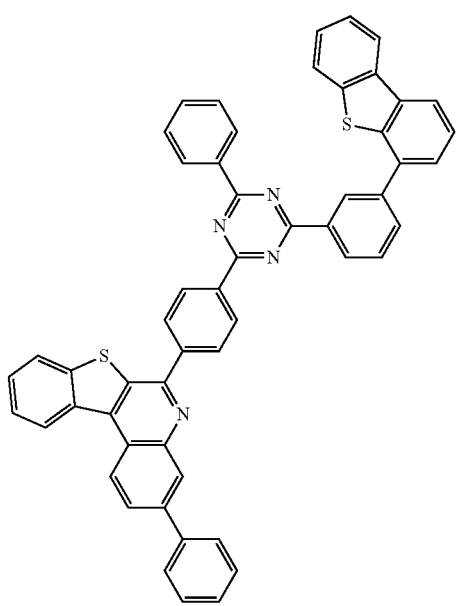

715
-continued
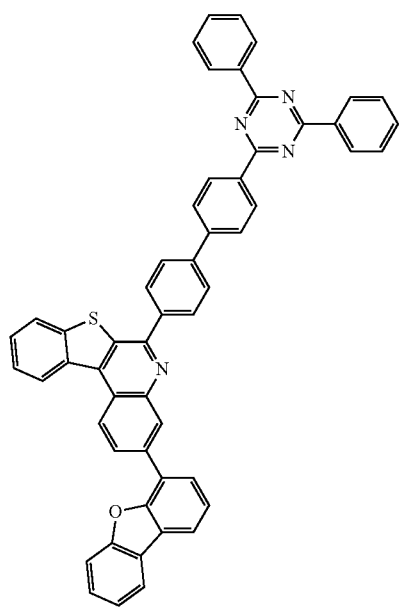
716
-continued
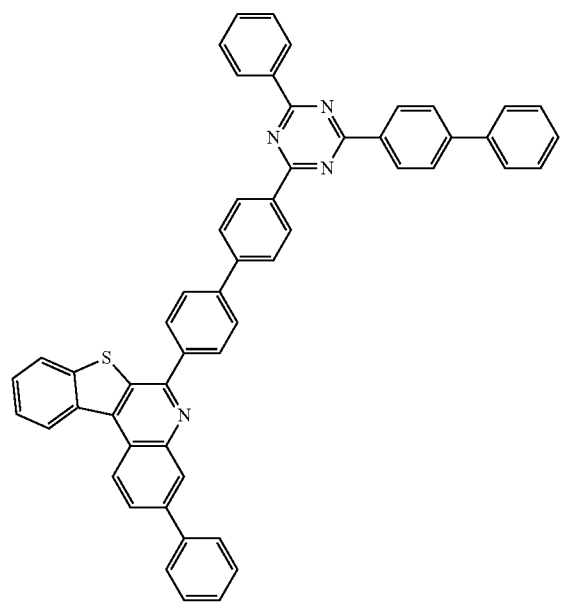
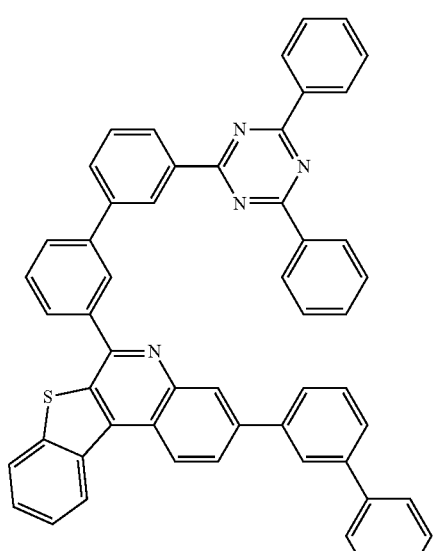
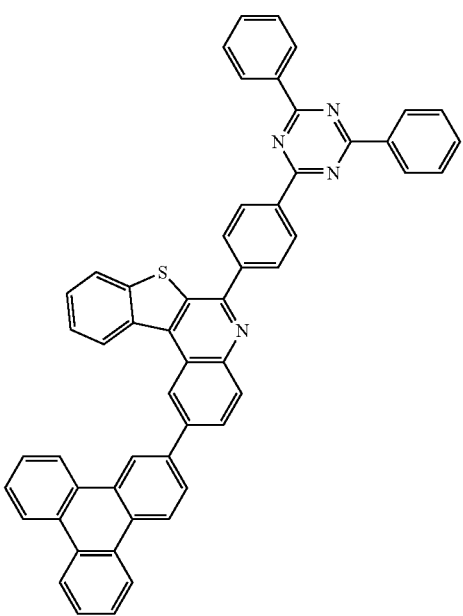

717
-continued
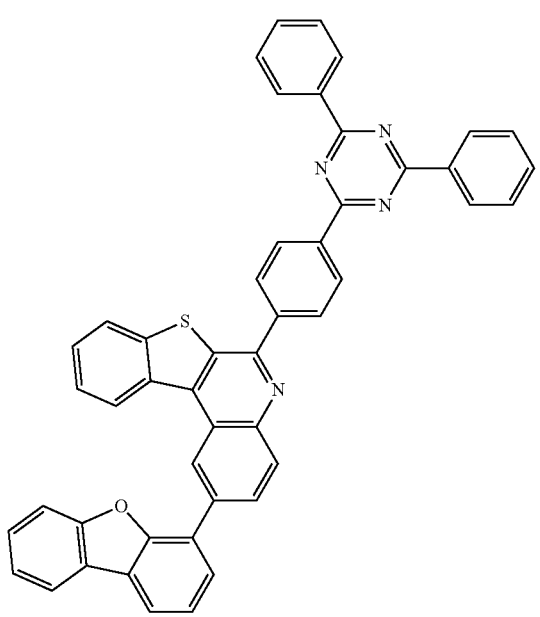
47
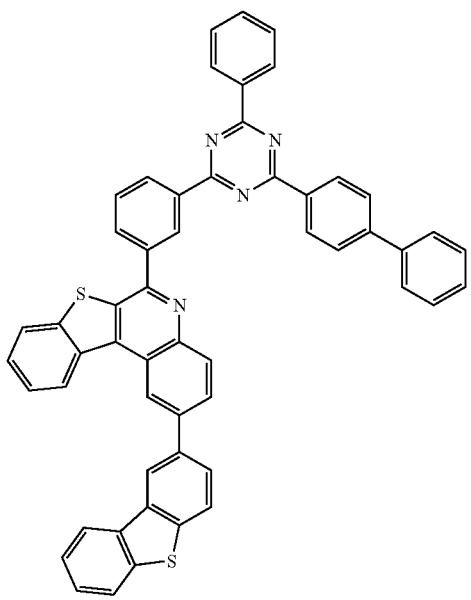
49
718
-continued
48
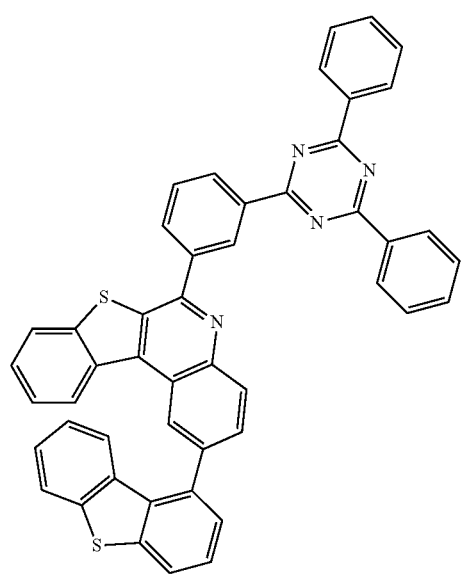
50
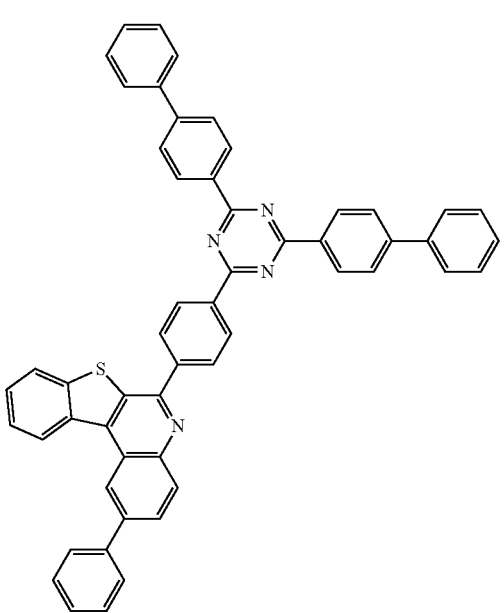

719
-continued
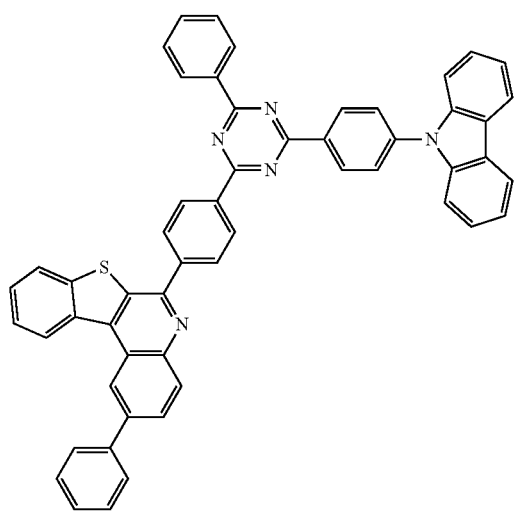
51
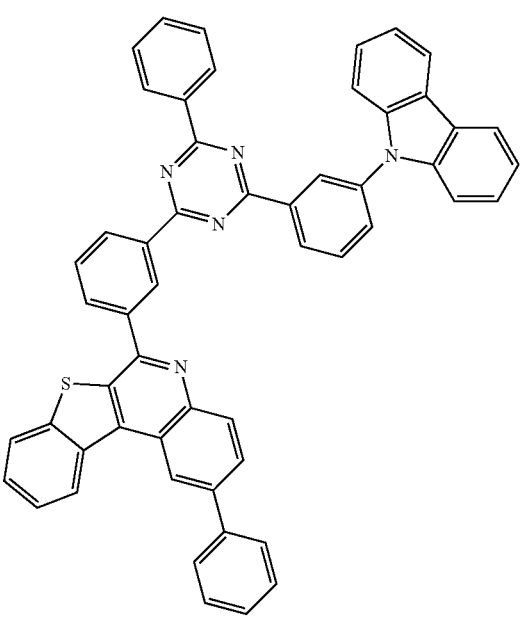
52
720
-continued
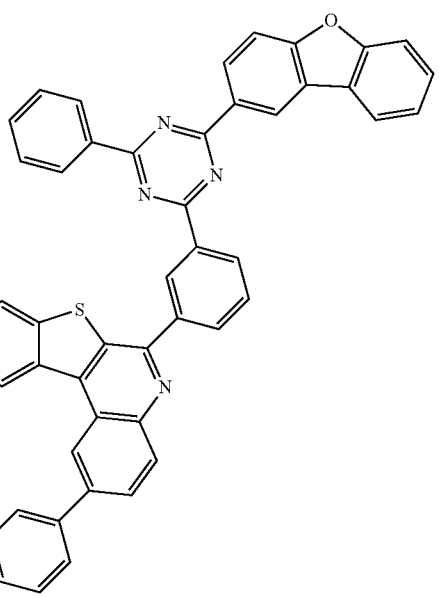
53
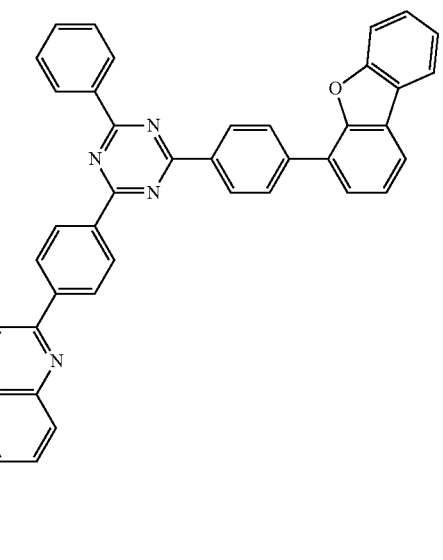
54

721
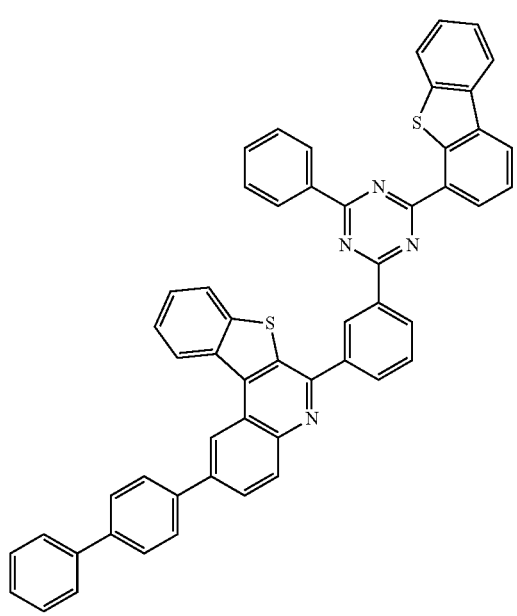
722
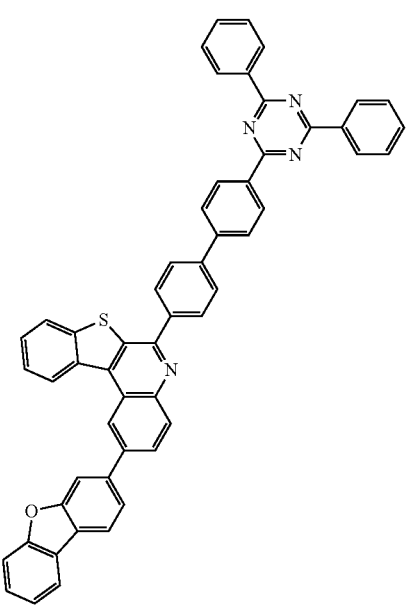
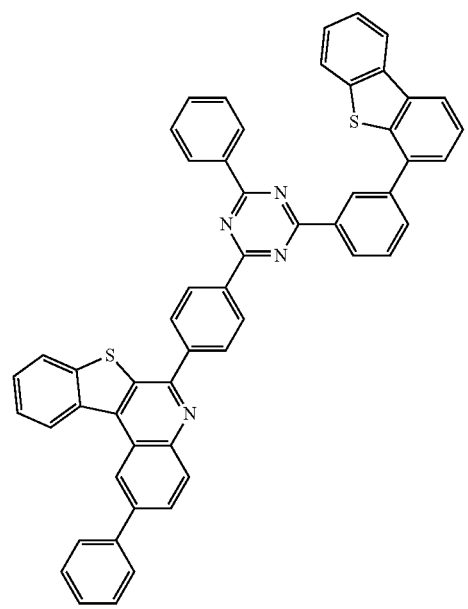
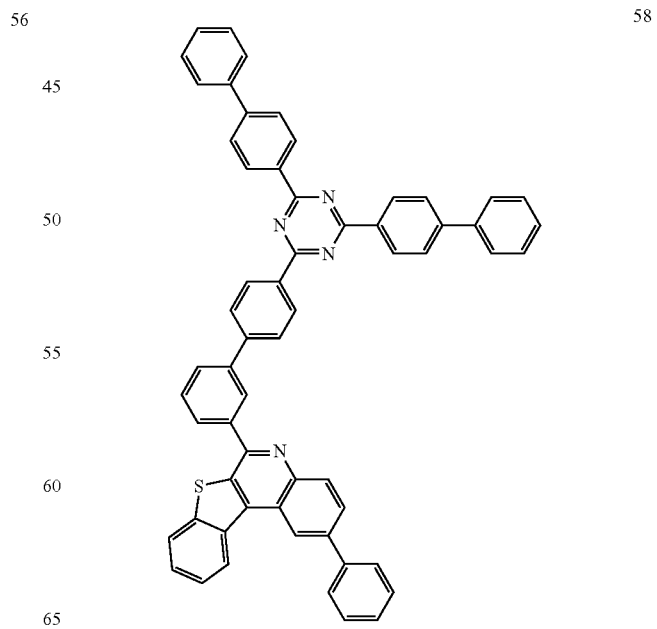

723
-continued
59
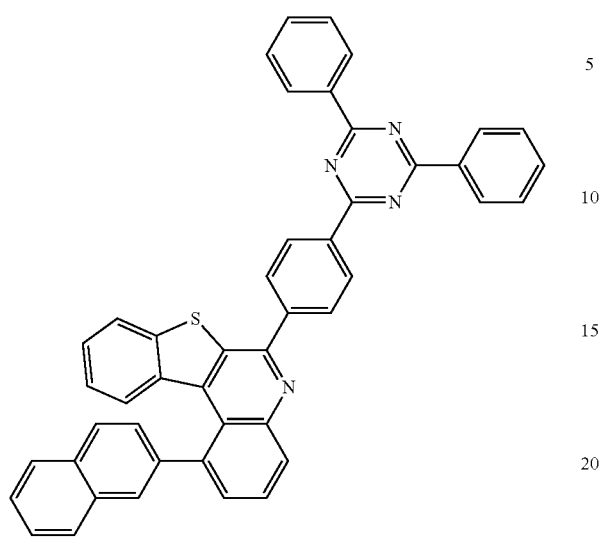
60
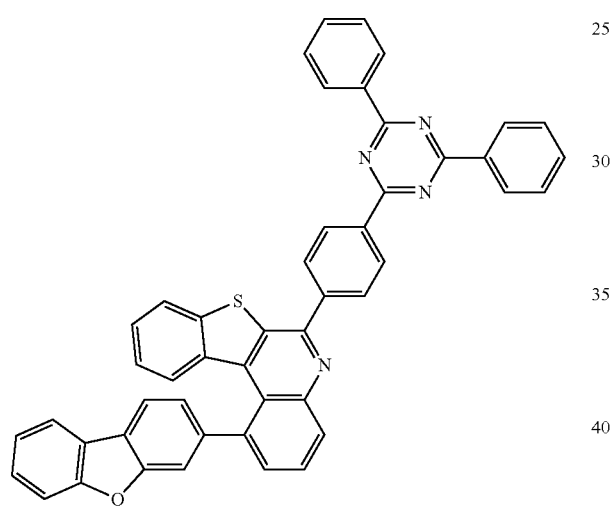
61
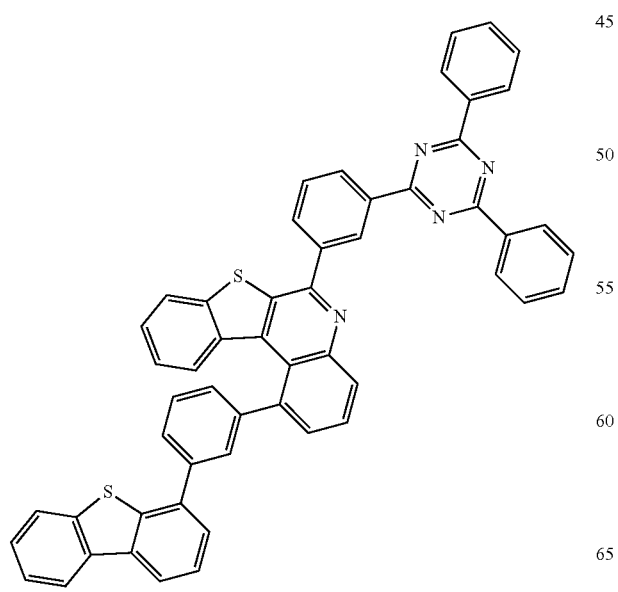
724
-continued
62
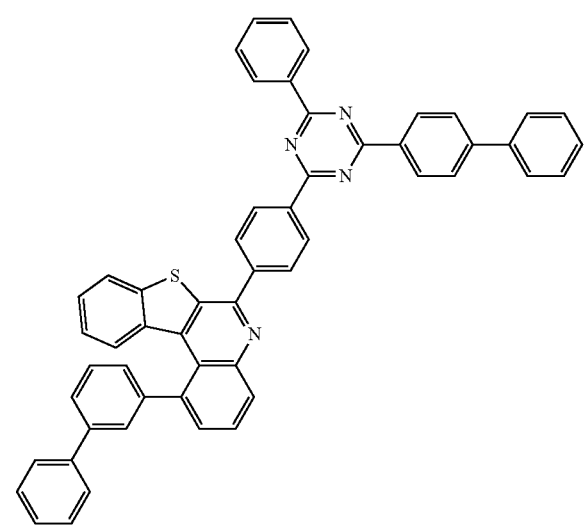
63
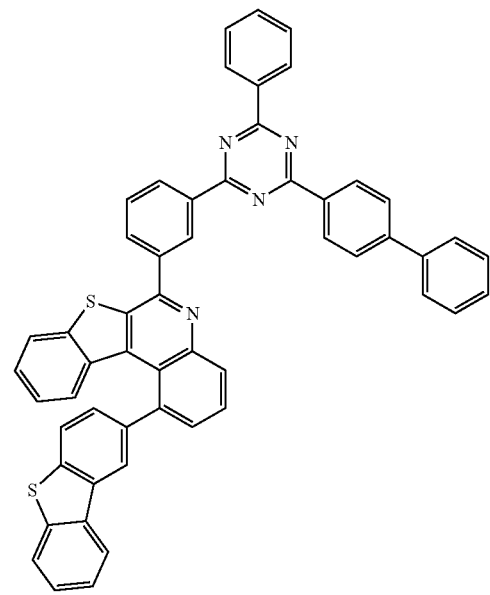

725
-continued
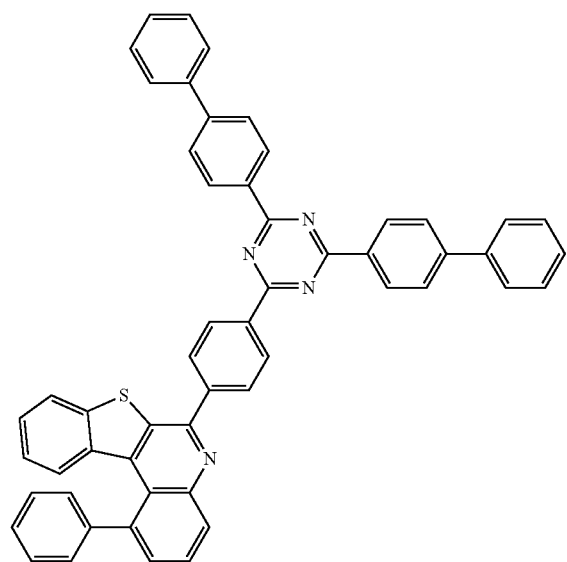
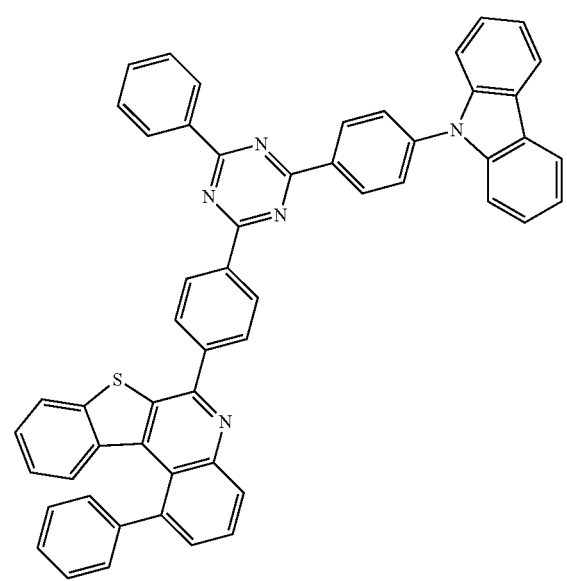
726
-continued
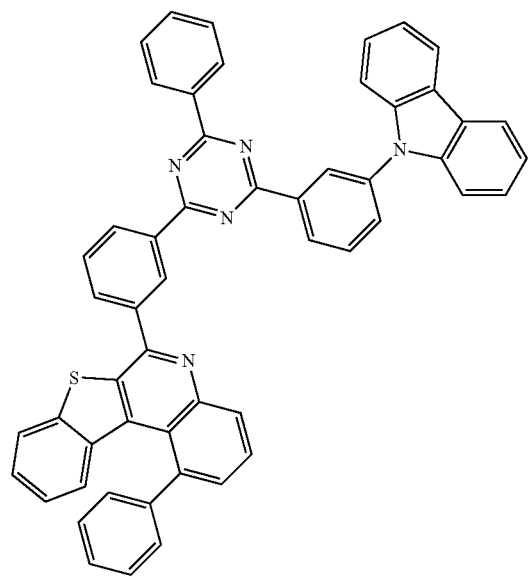
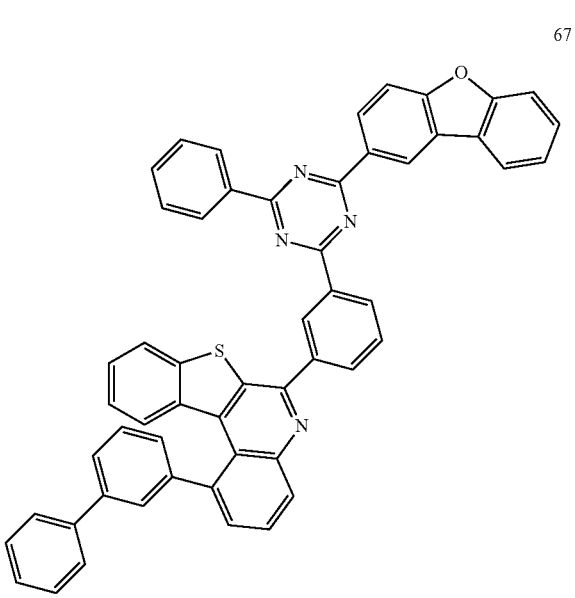

727
-continued
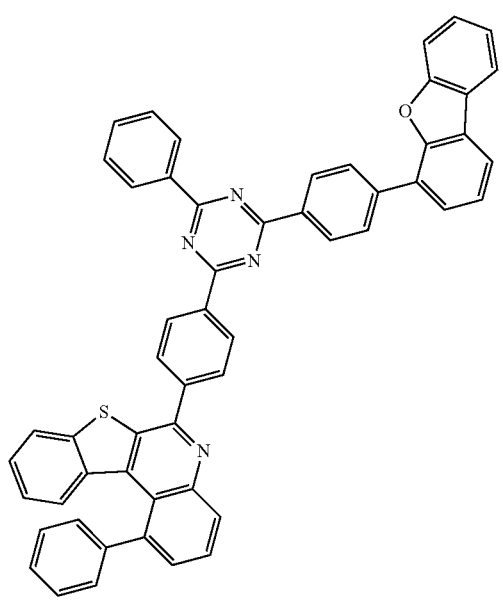
68
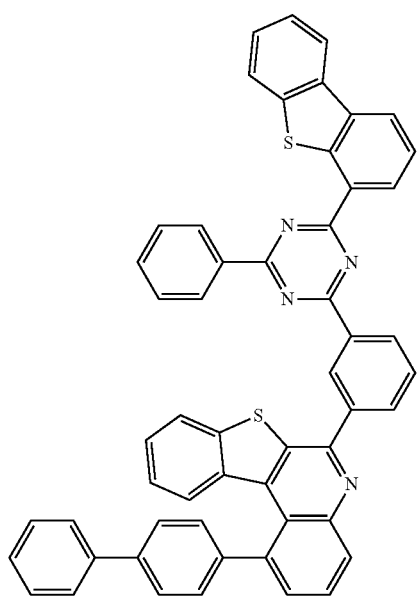
69
728
-continued
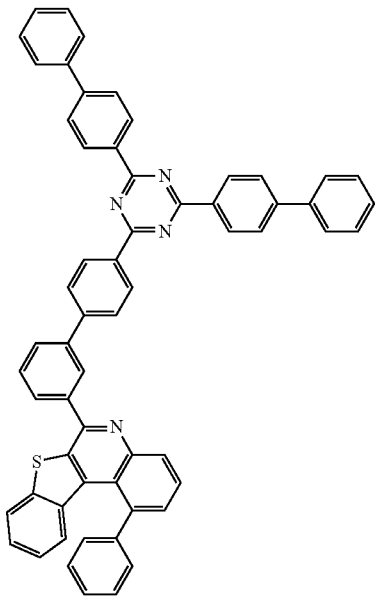
70
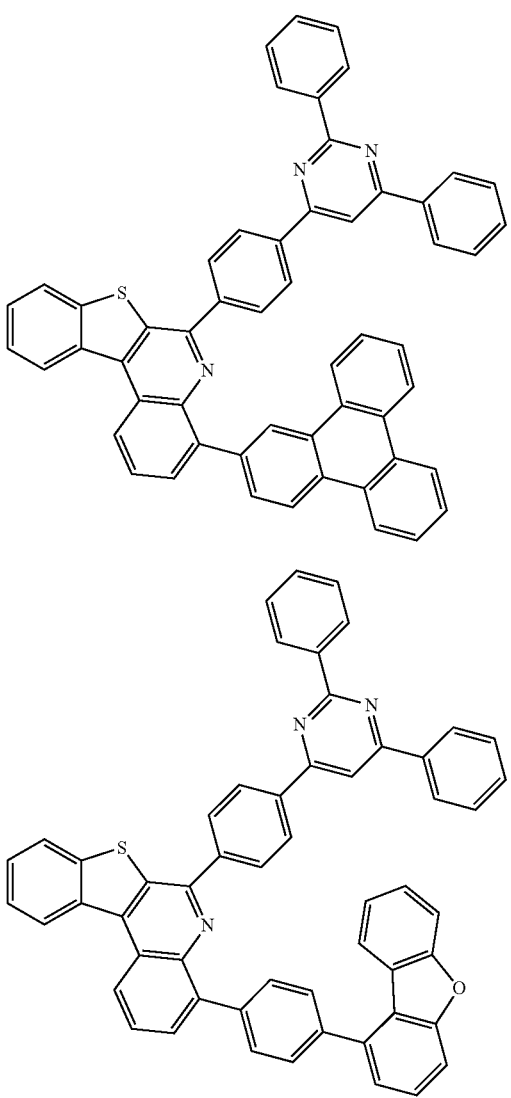

73
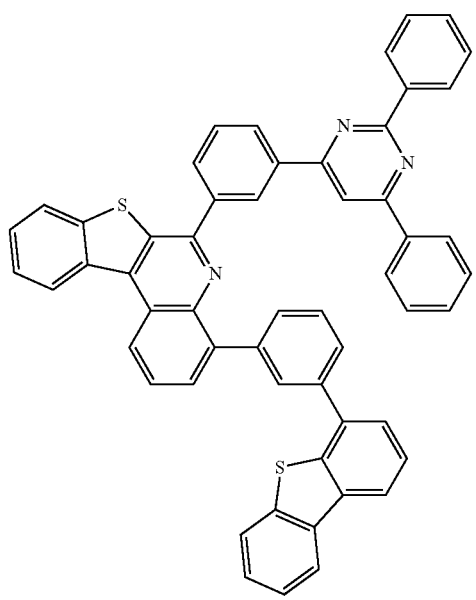
74
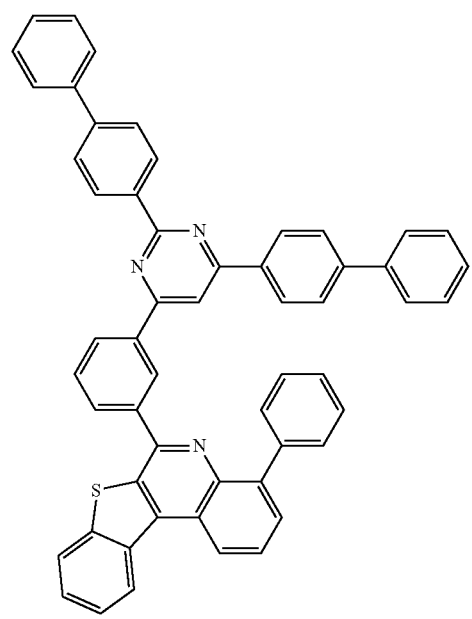
75
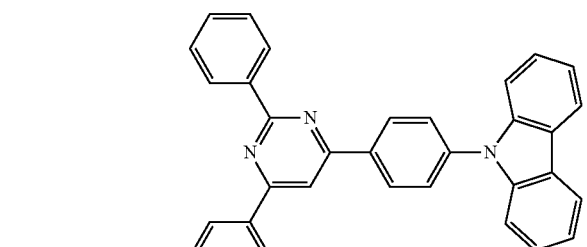
76
77
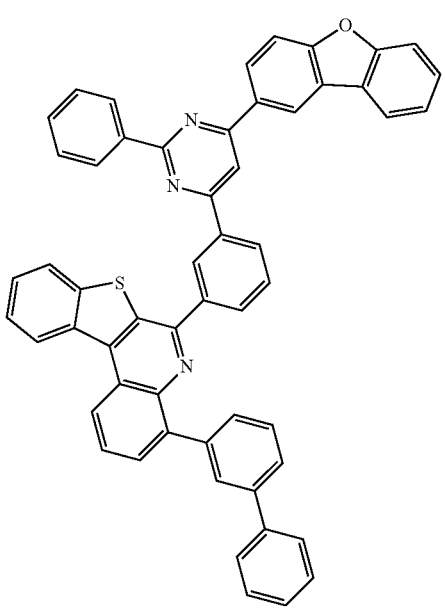

731
-continued
78
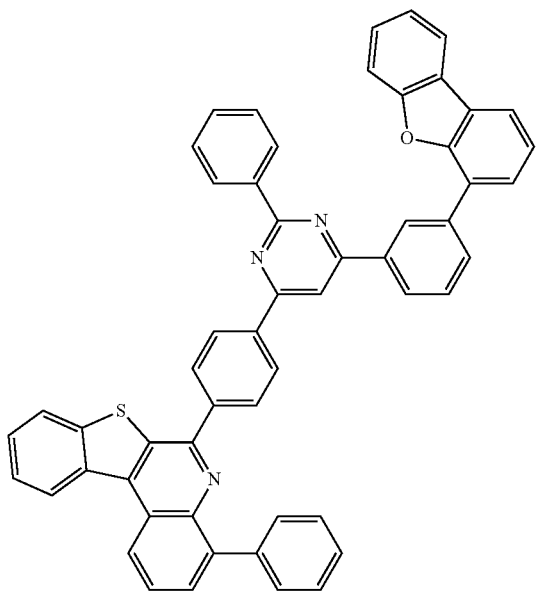
79
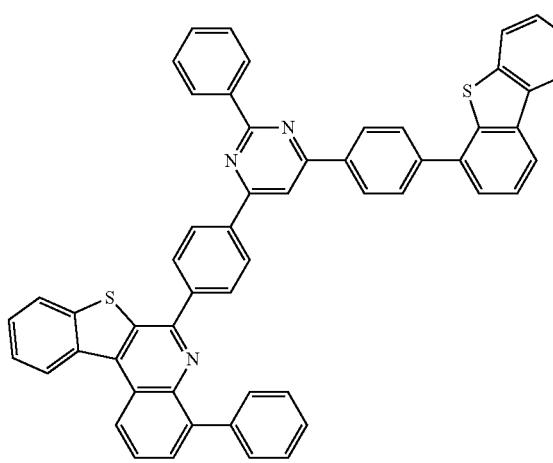
80
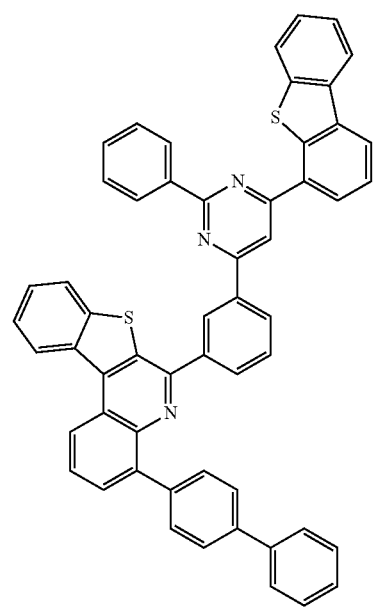
732
-continued
81
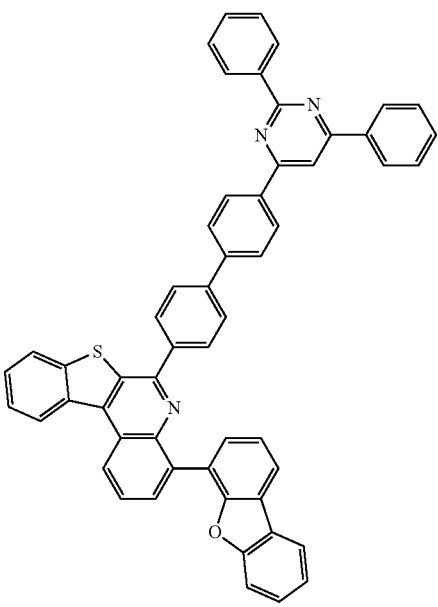
82
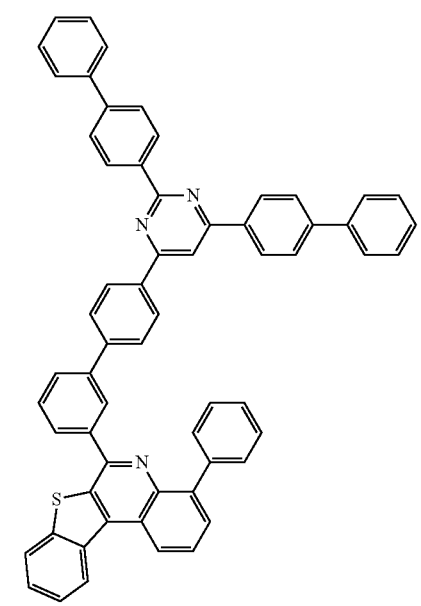

733
-continued
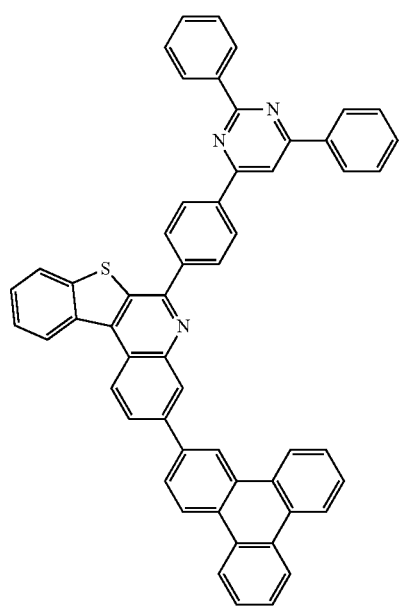
734
-continued
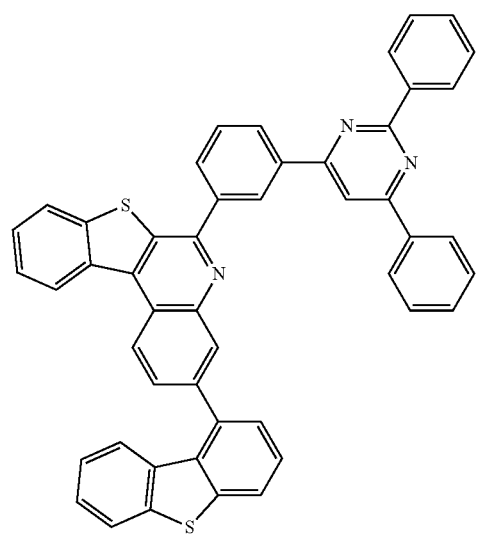
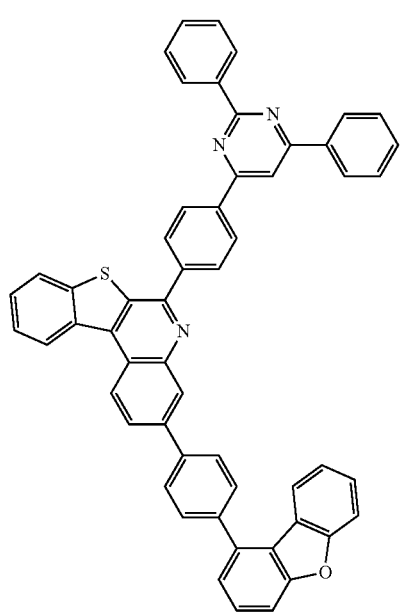
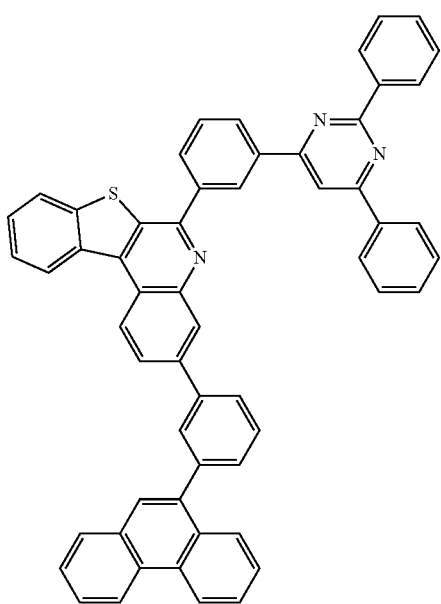

735 -continued
87
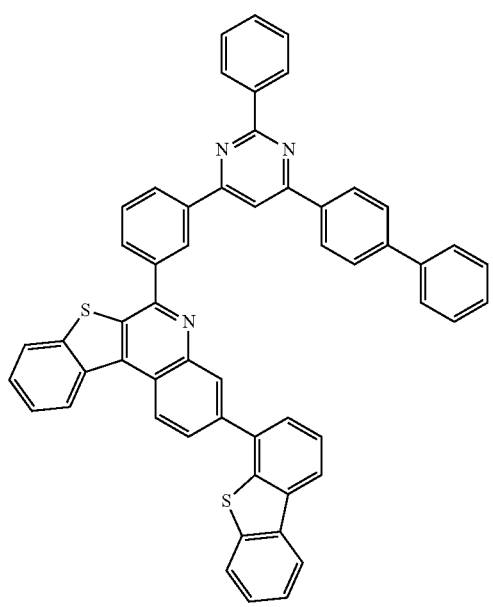
88
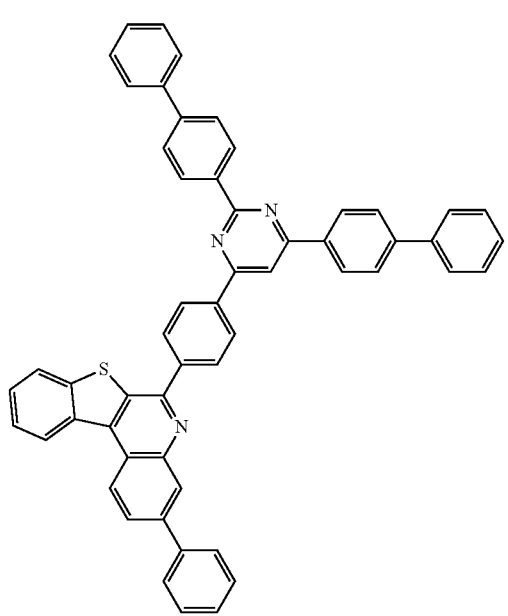
736 -continued
89
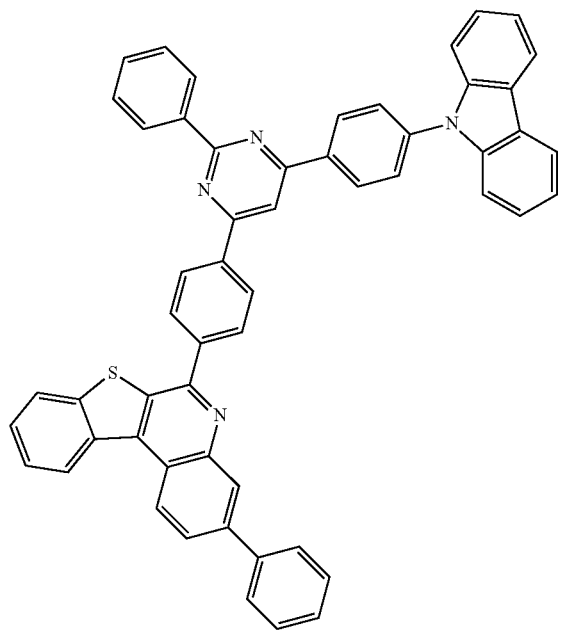
90
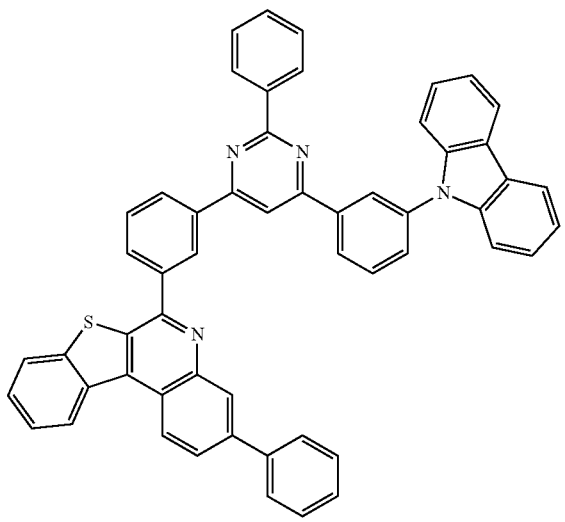

737
-continued
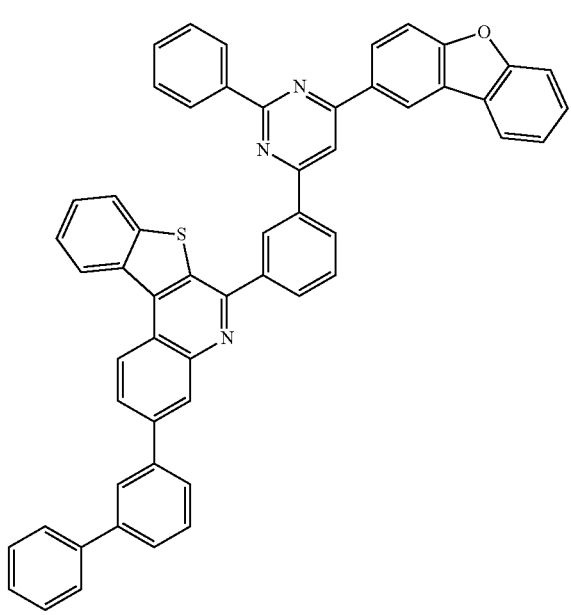
91
738
-continued
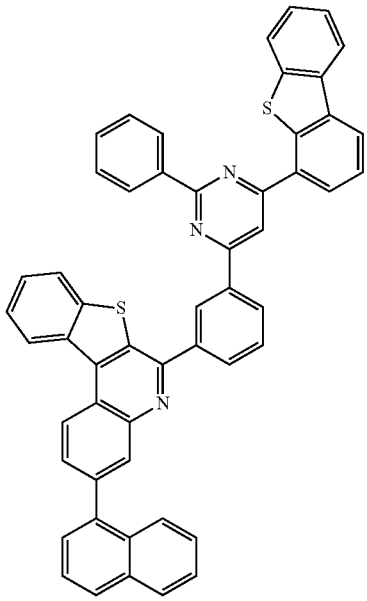
93
92
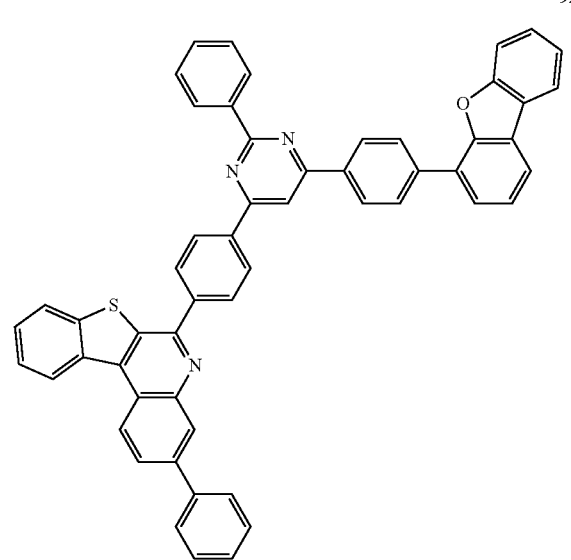
94
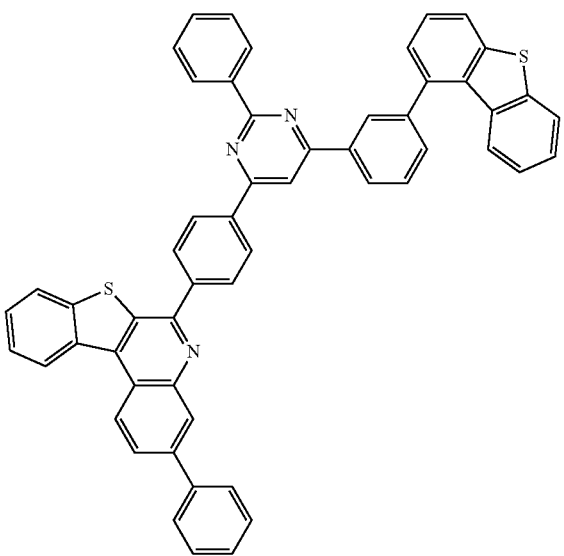

95
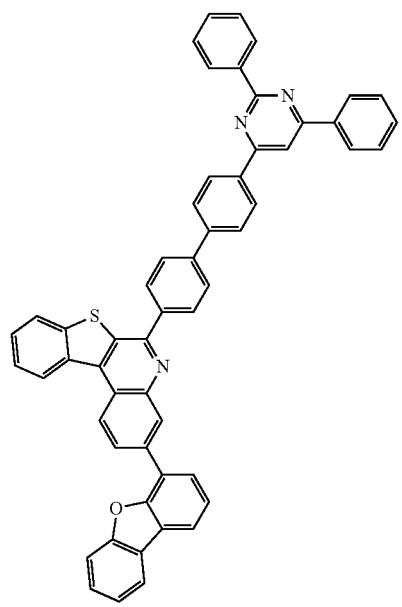
97
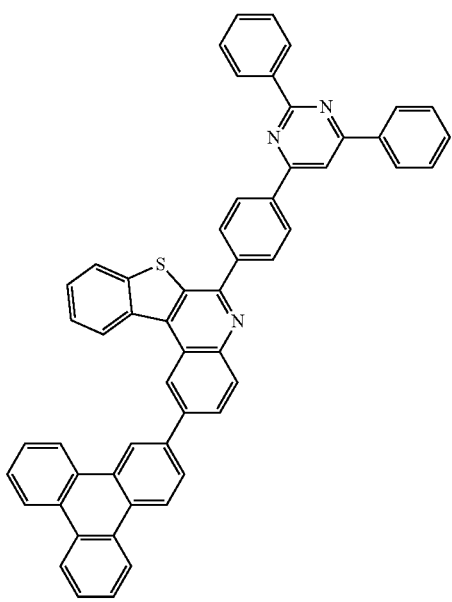
96
98
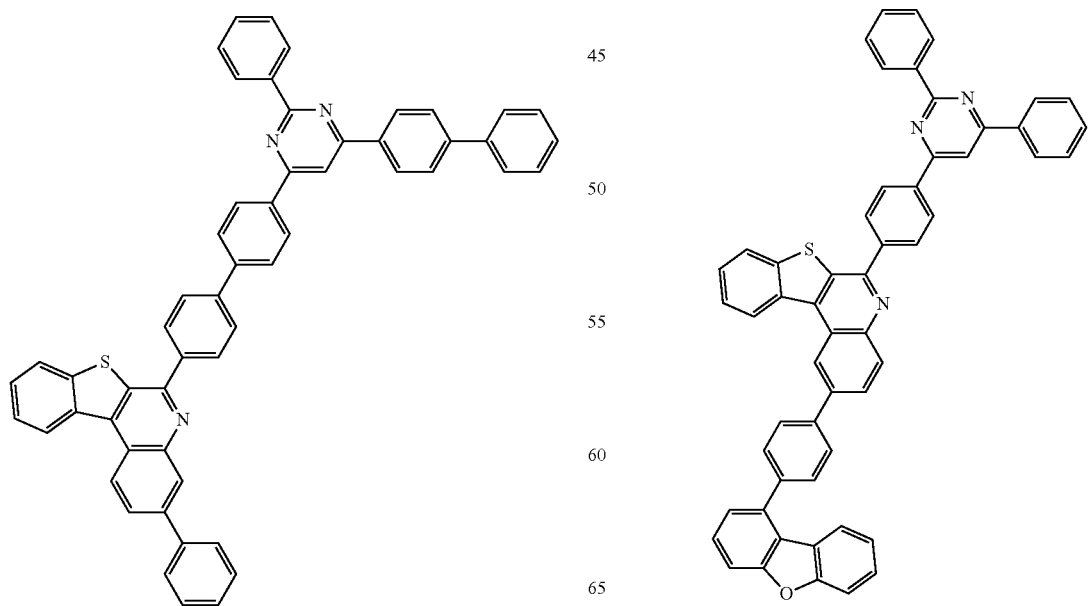

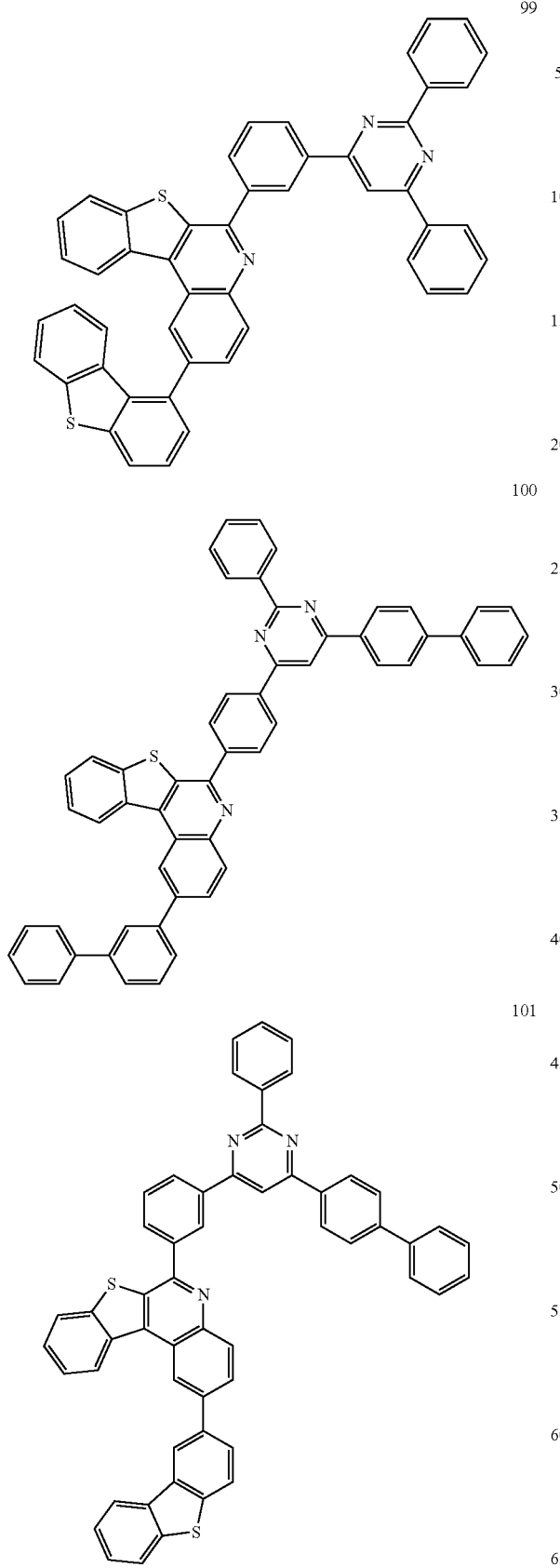
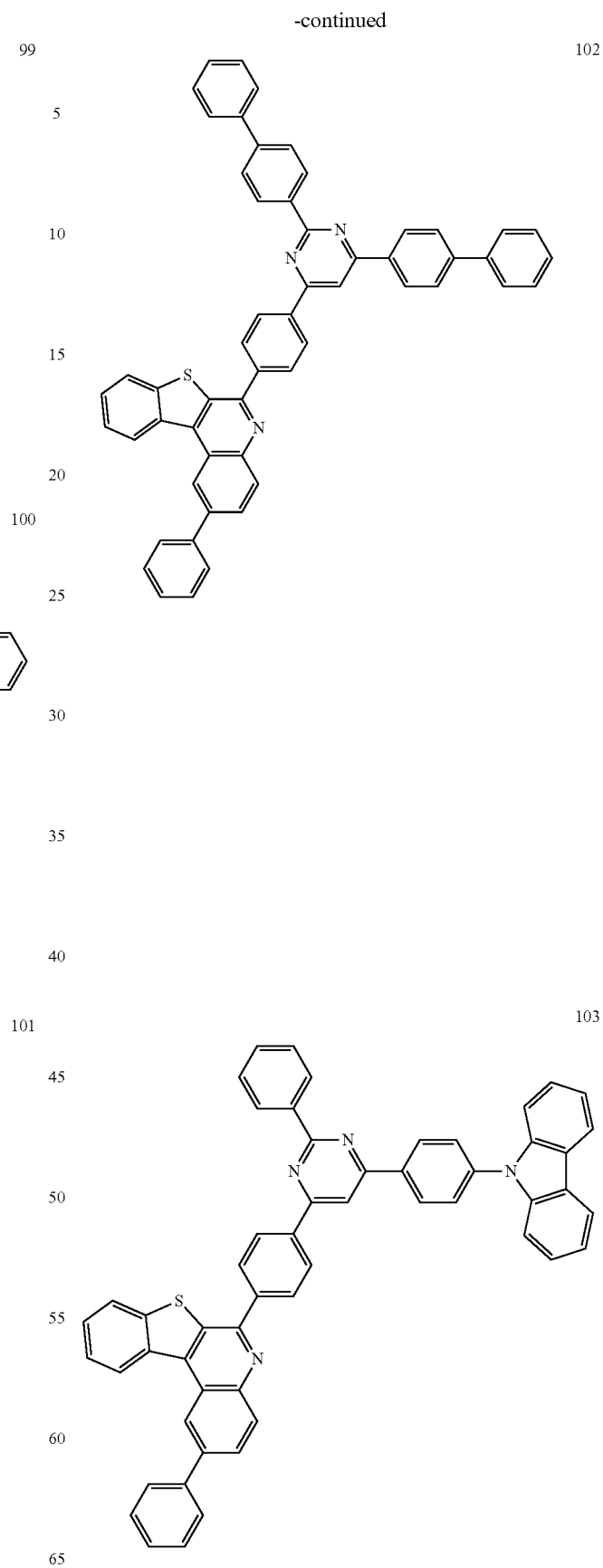

743
-continued
744
-continued
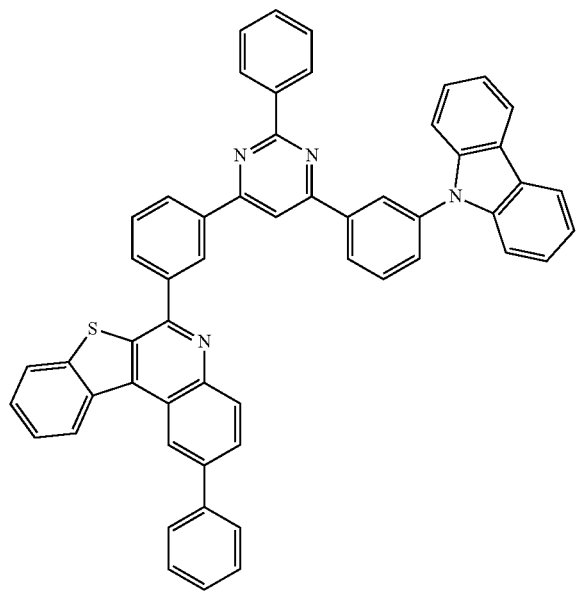
104
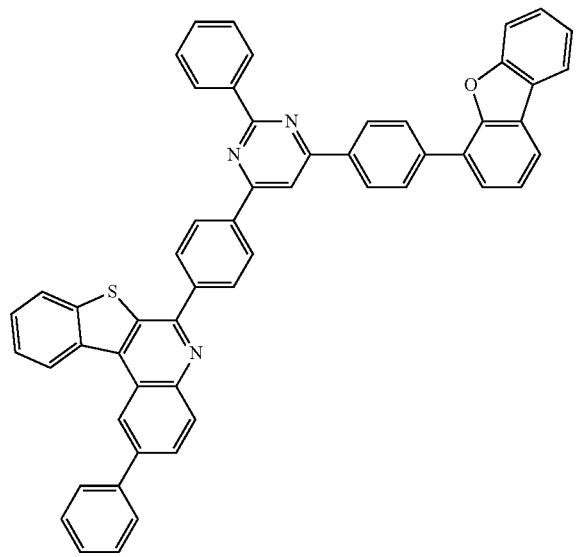
106
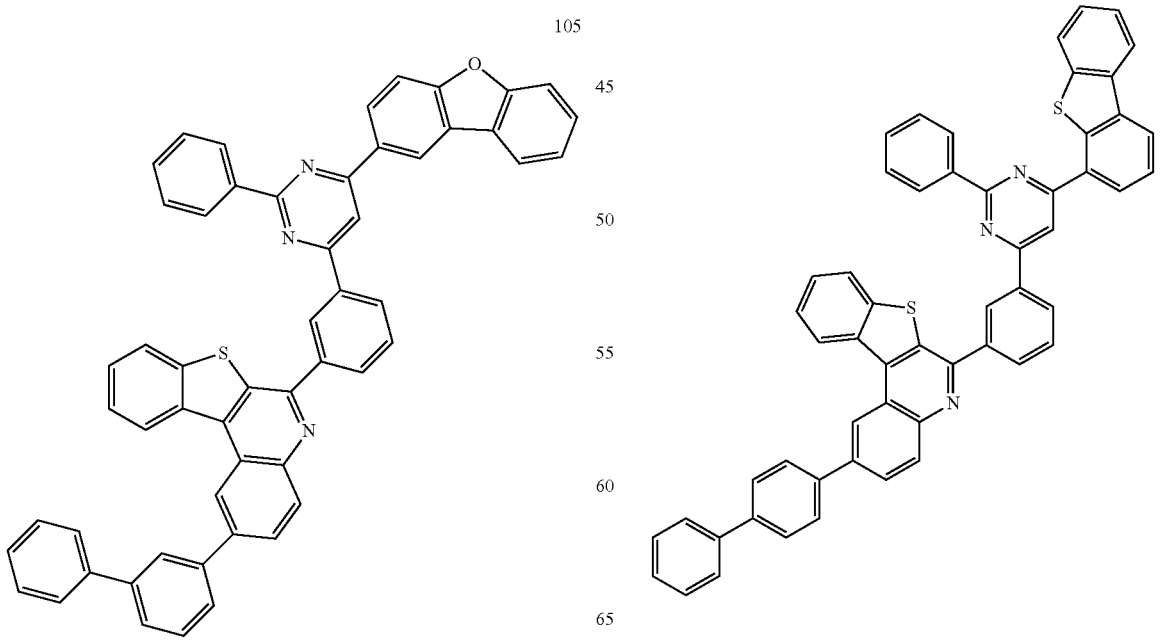

108
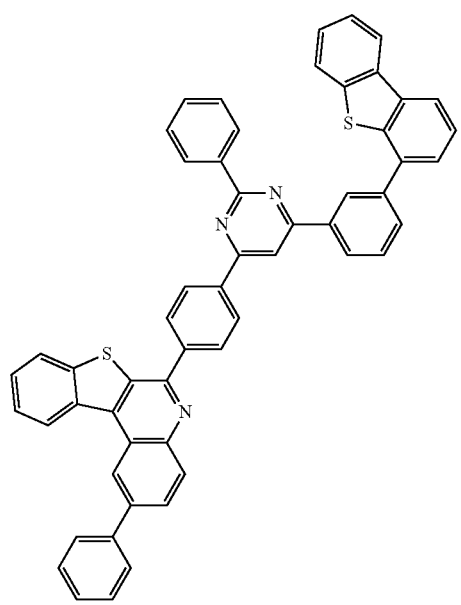
110
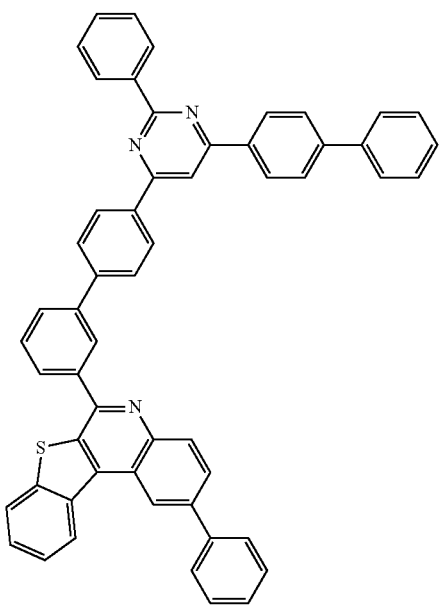
109
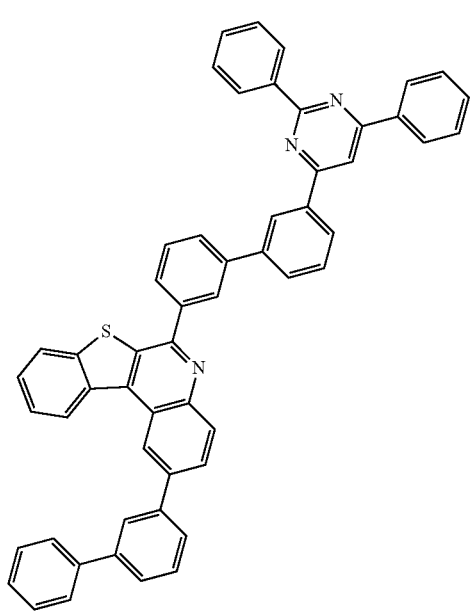
111
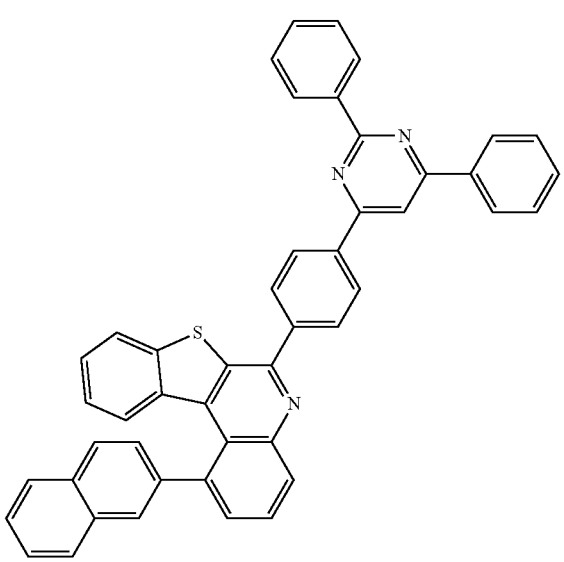

112
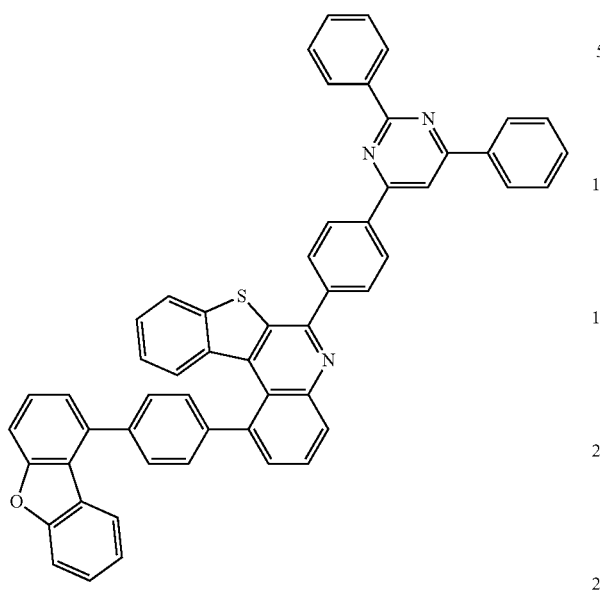
113
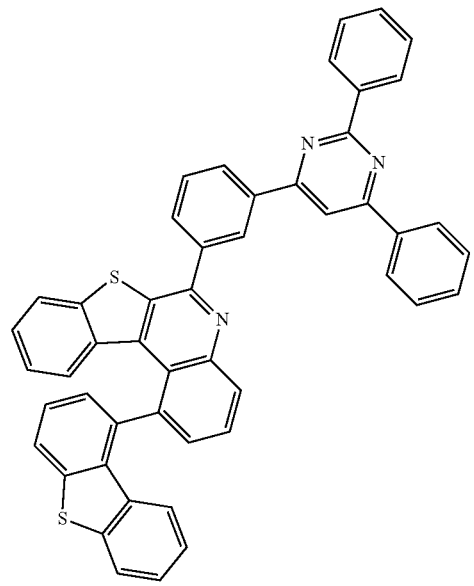
114
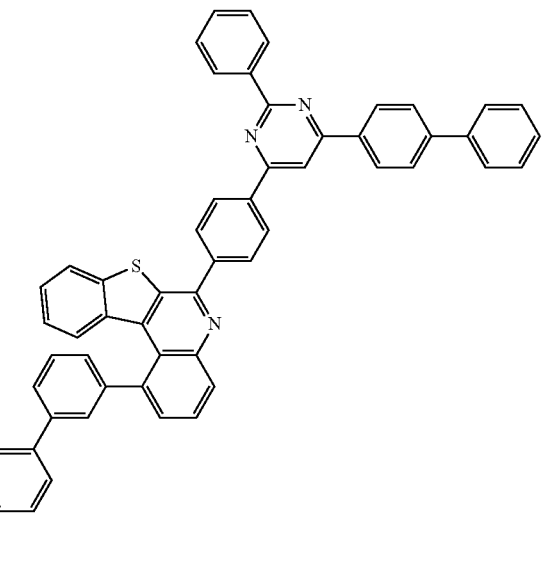
115
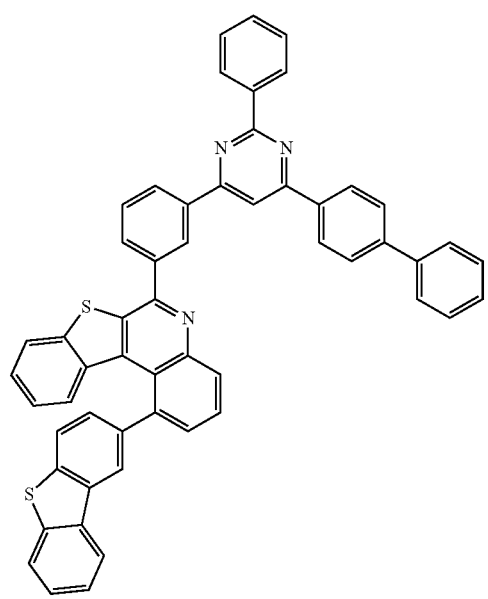

116
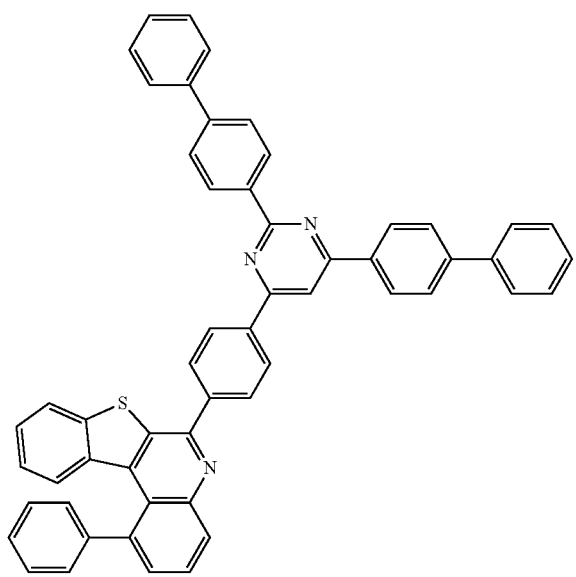
117
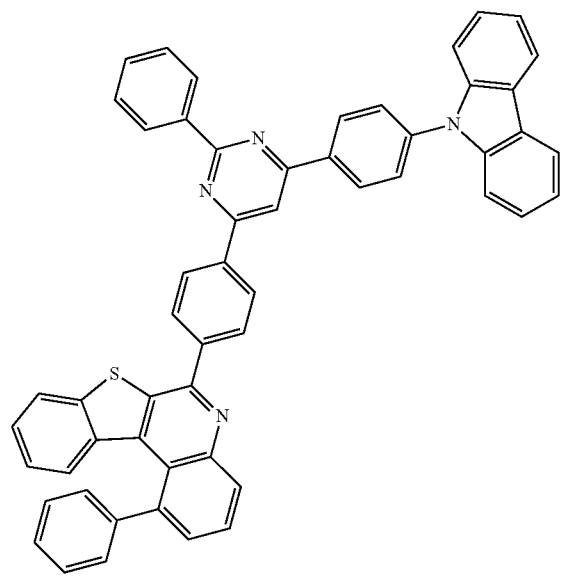
118
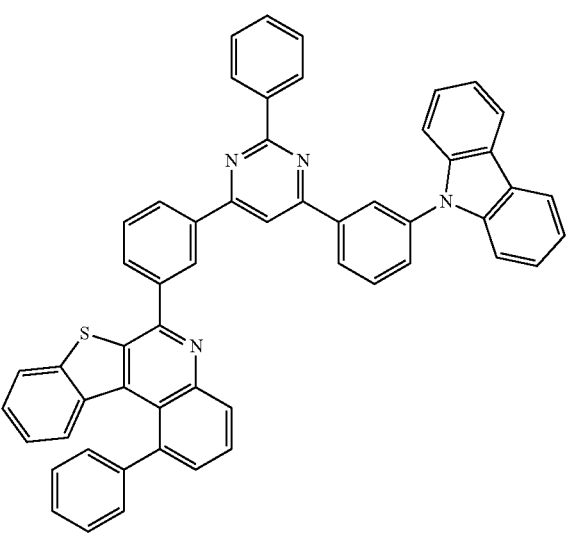
119
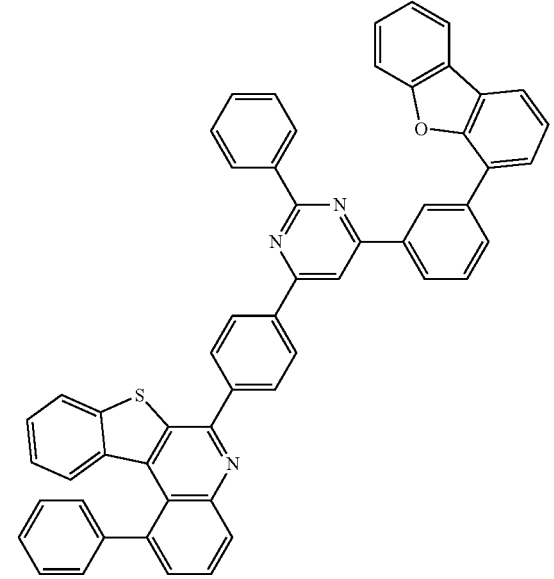

751
-continued
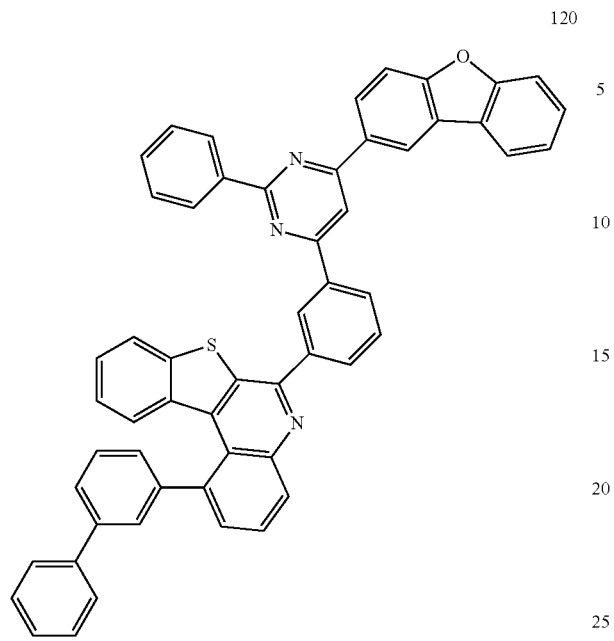
120
121
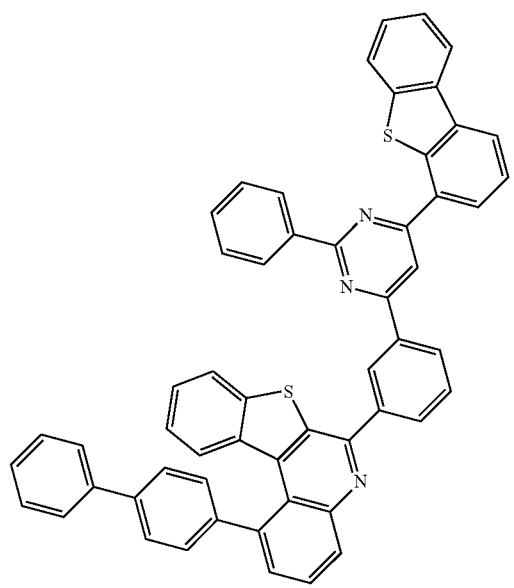
752
-continued
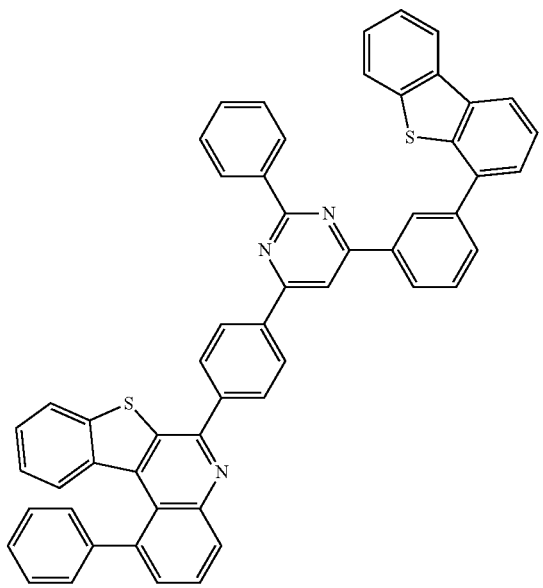
122
123

753
-continued
124
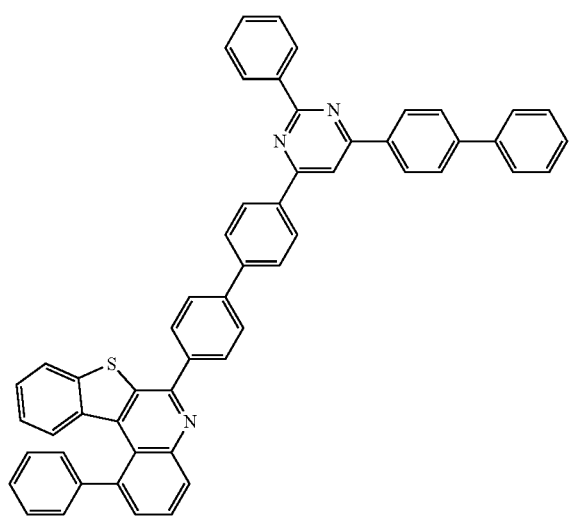
125
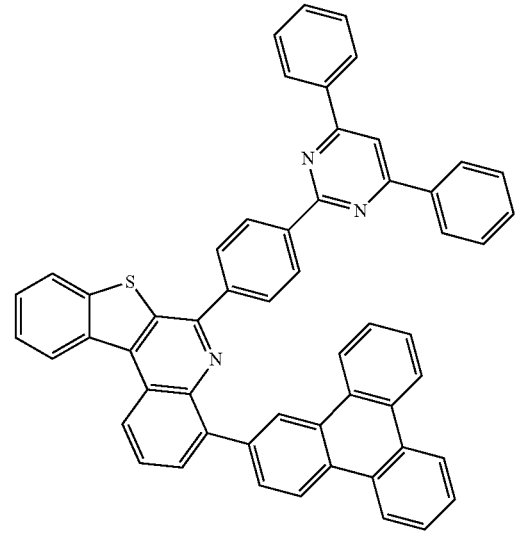
126
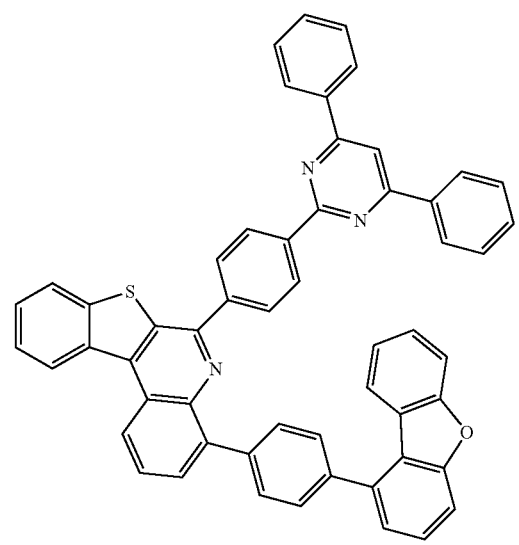
754
-continued
127
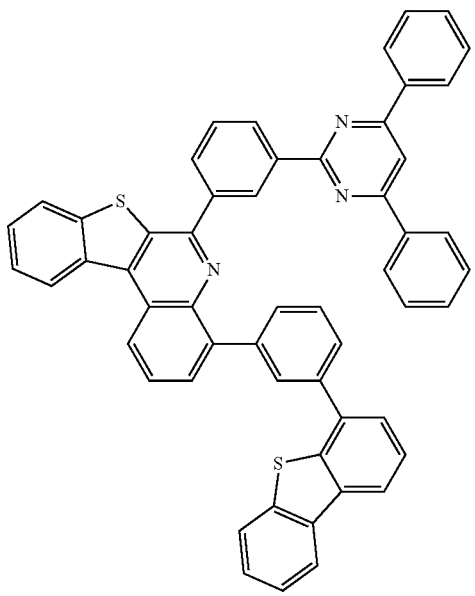
128
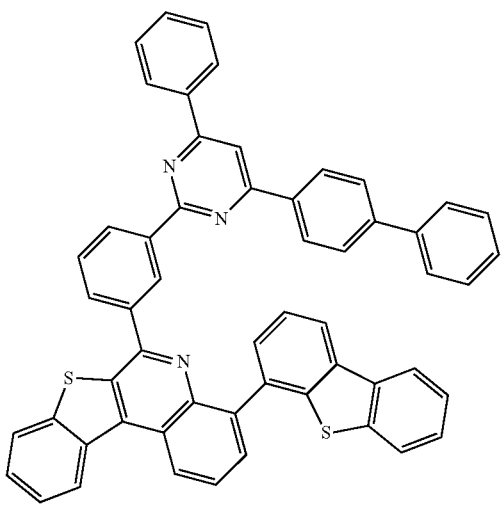

129
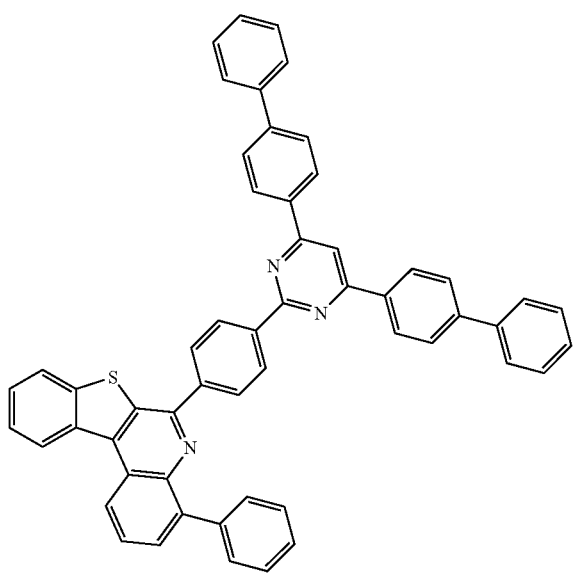
130
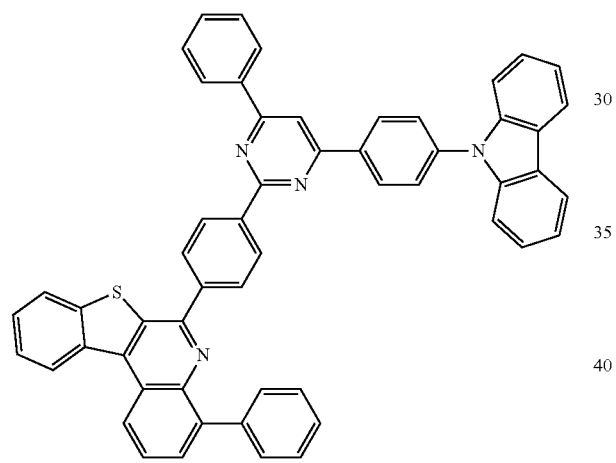
131
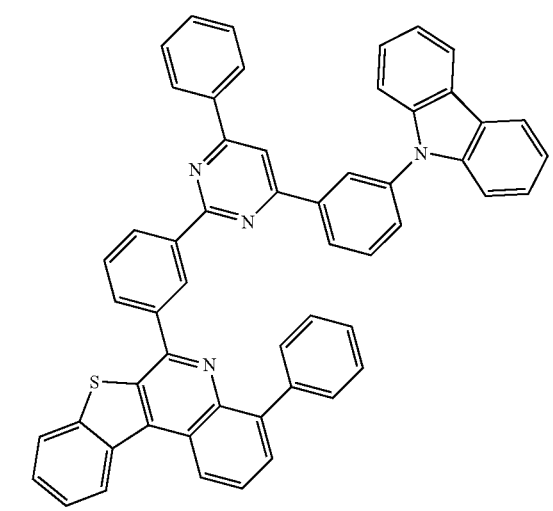
132
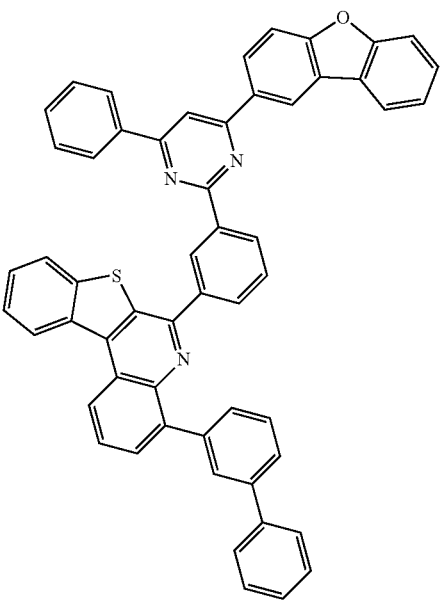
133
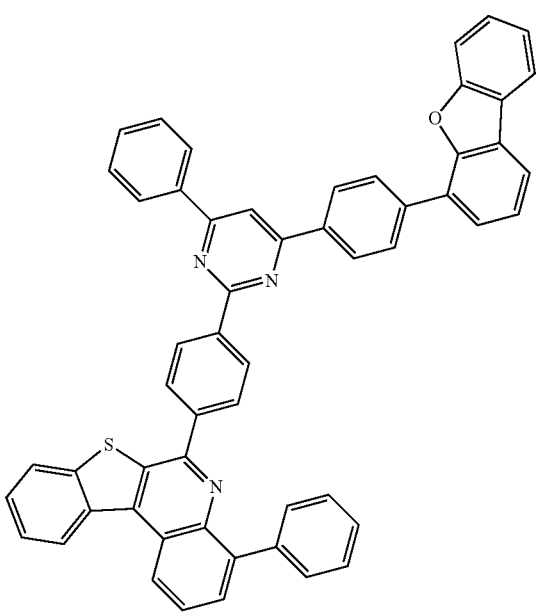

757
-continued
134
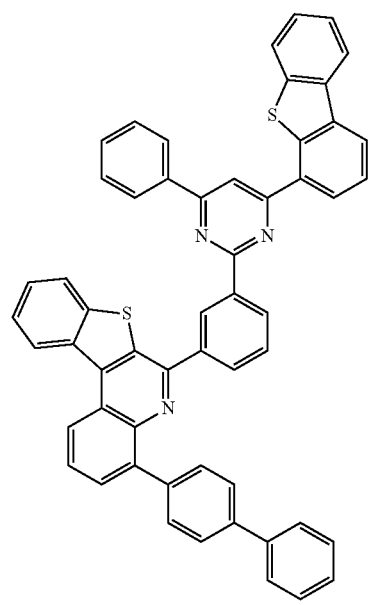
135
758
-continued
136
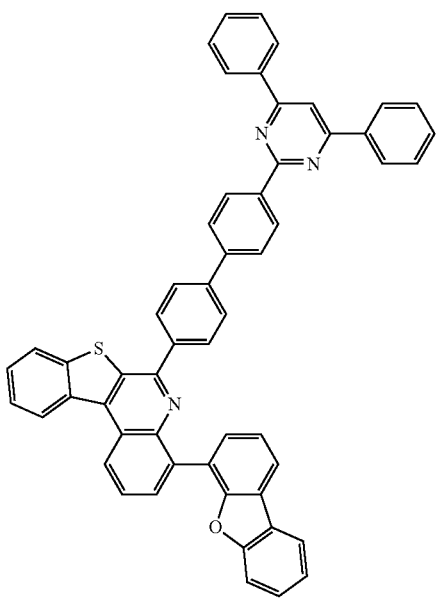
137

138
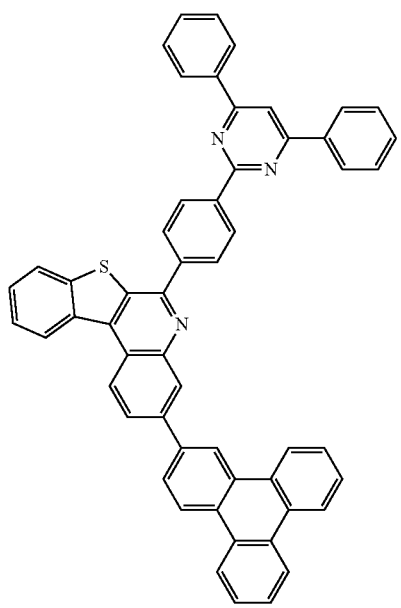
139
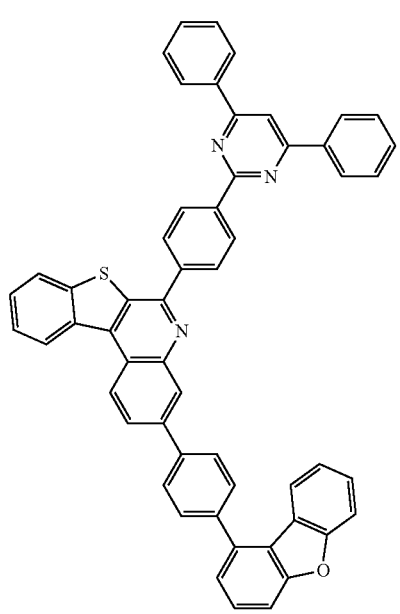
140
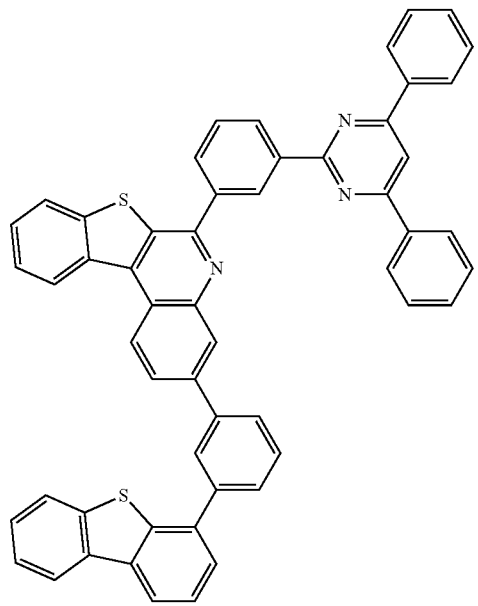
141
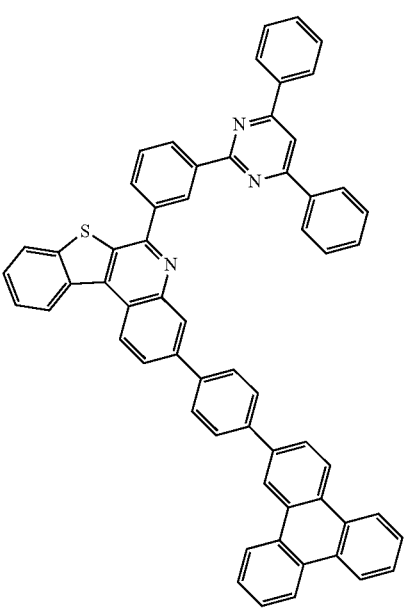

142
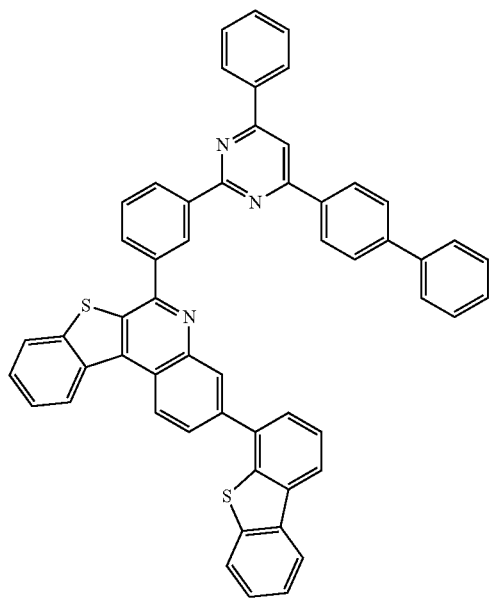
143
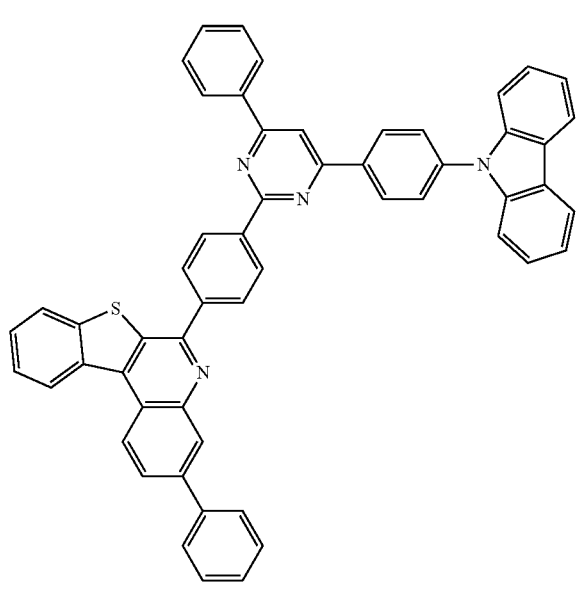
144
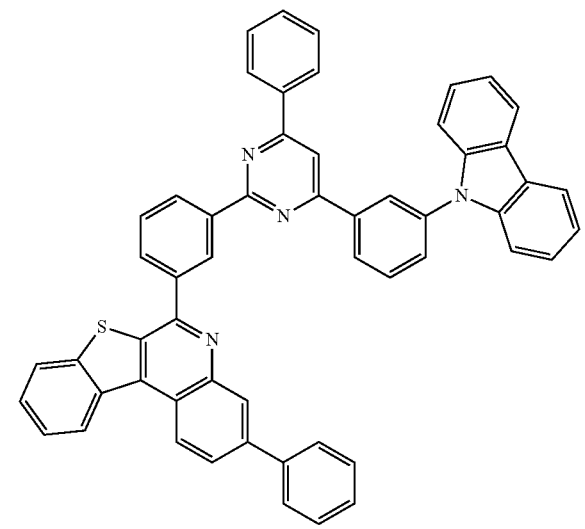
145
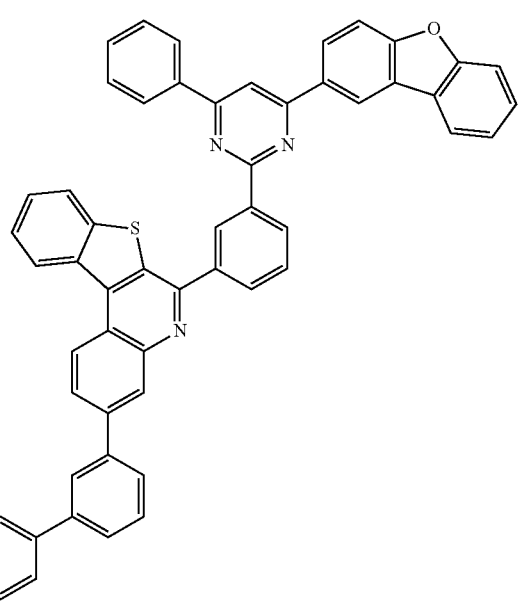

763
-continued
146
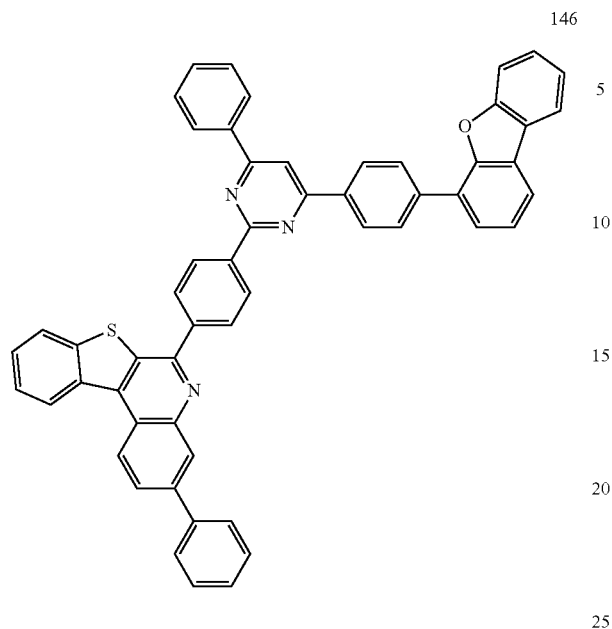
147
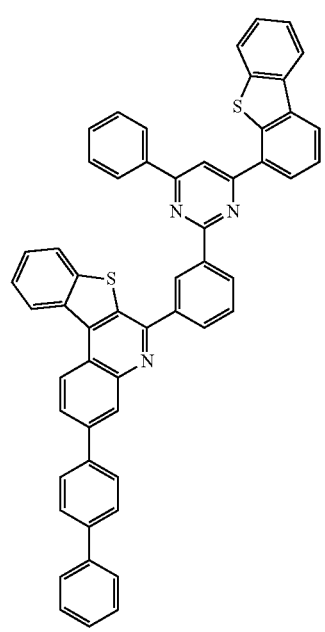
764
-continued
148
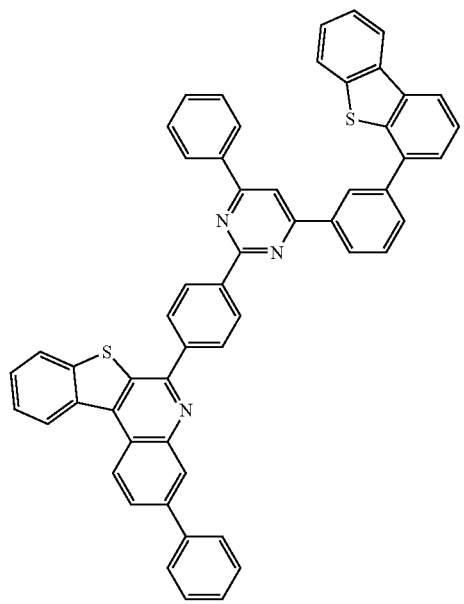
149
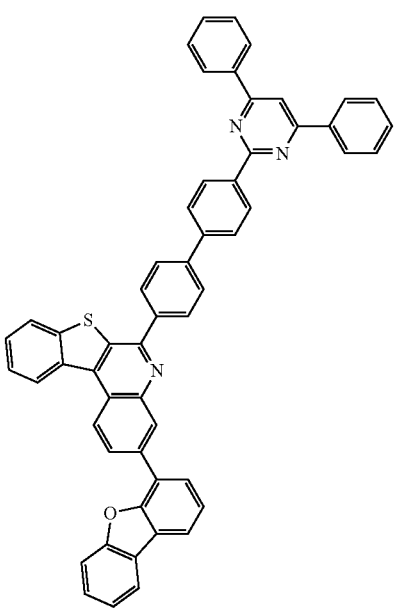

150

151

152

153

154
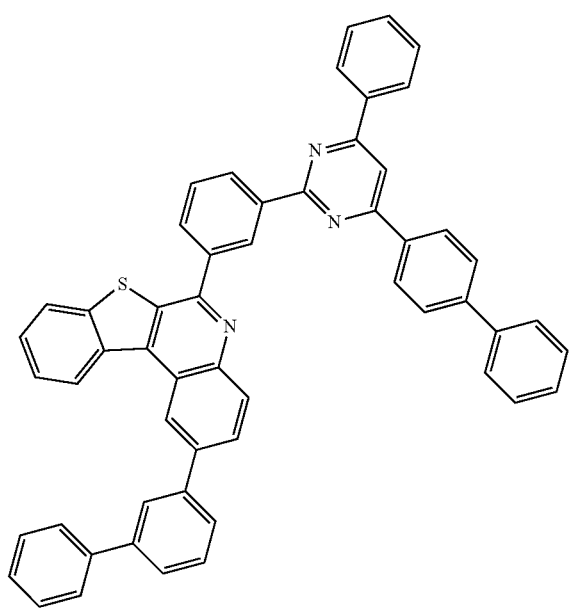
156
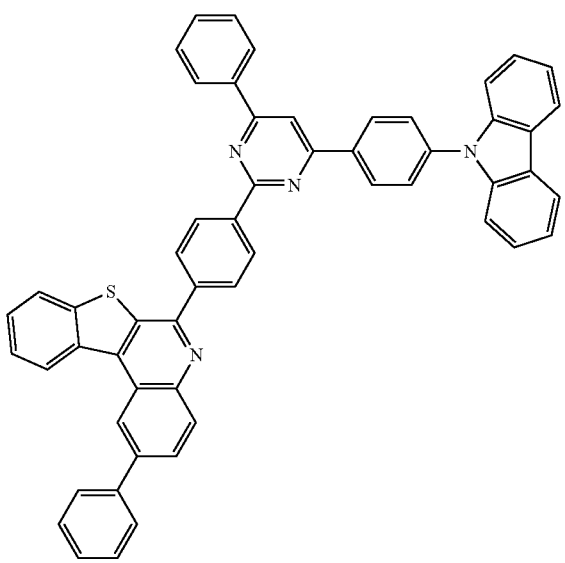
155
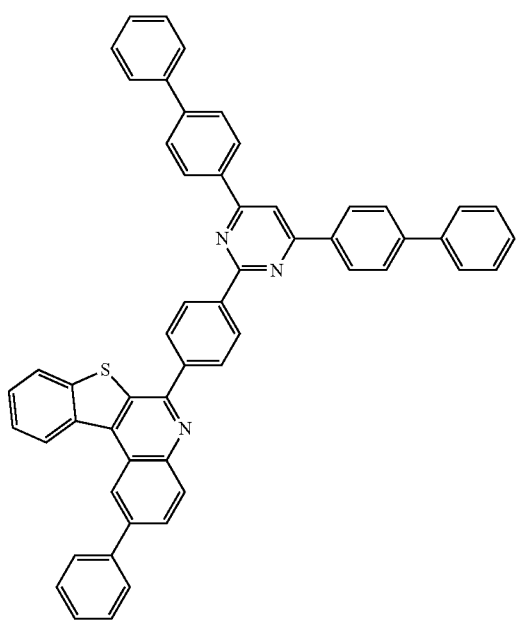
157
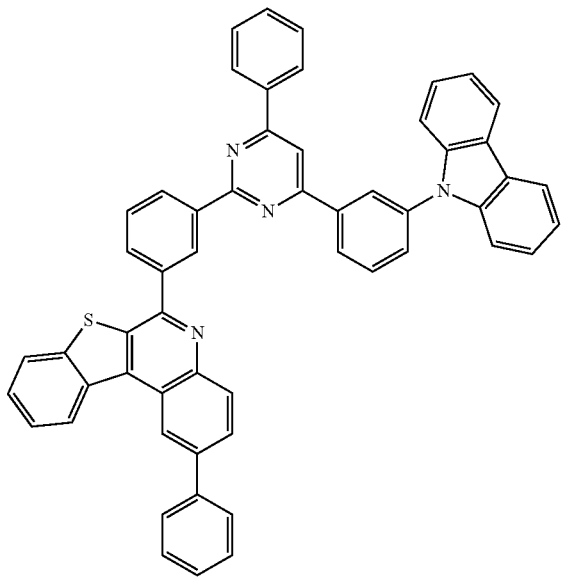

769
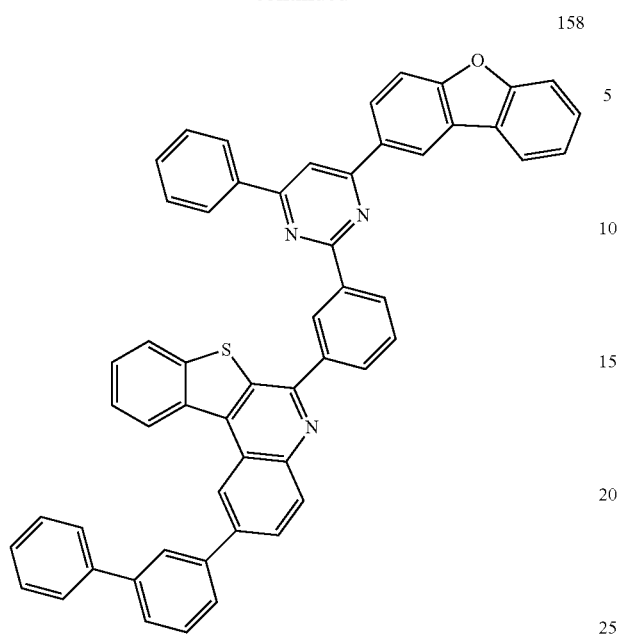
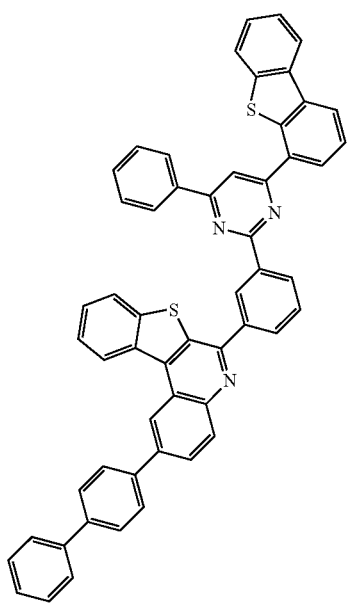
770
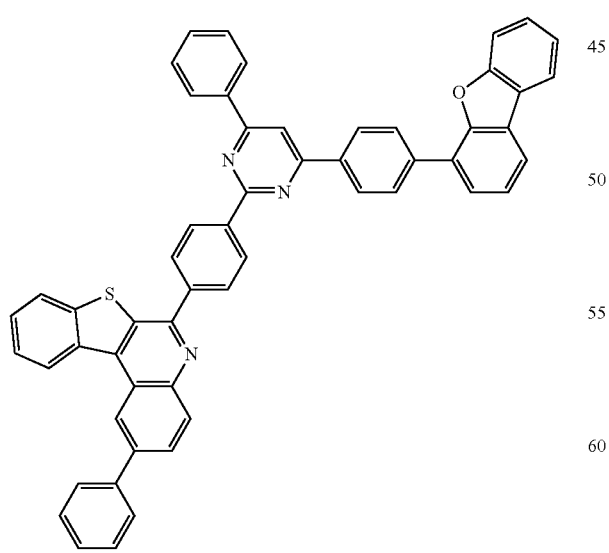
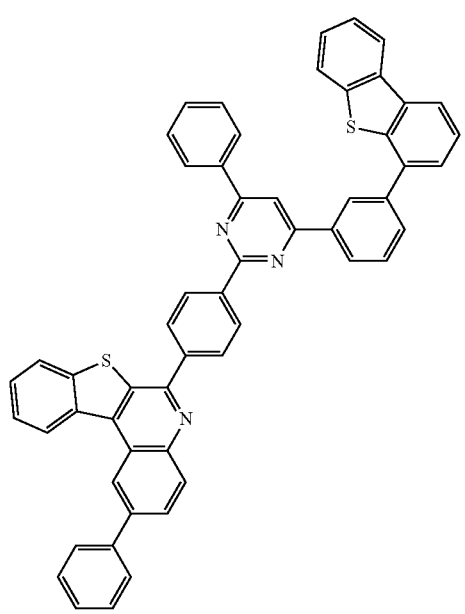

771
-continued
162
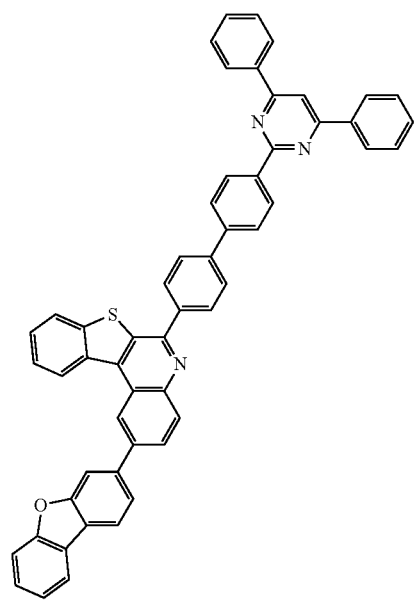
163
772
-continued
164
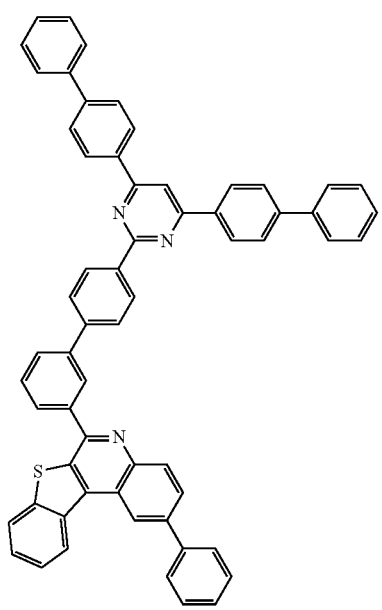
165
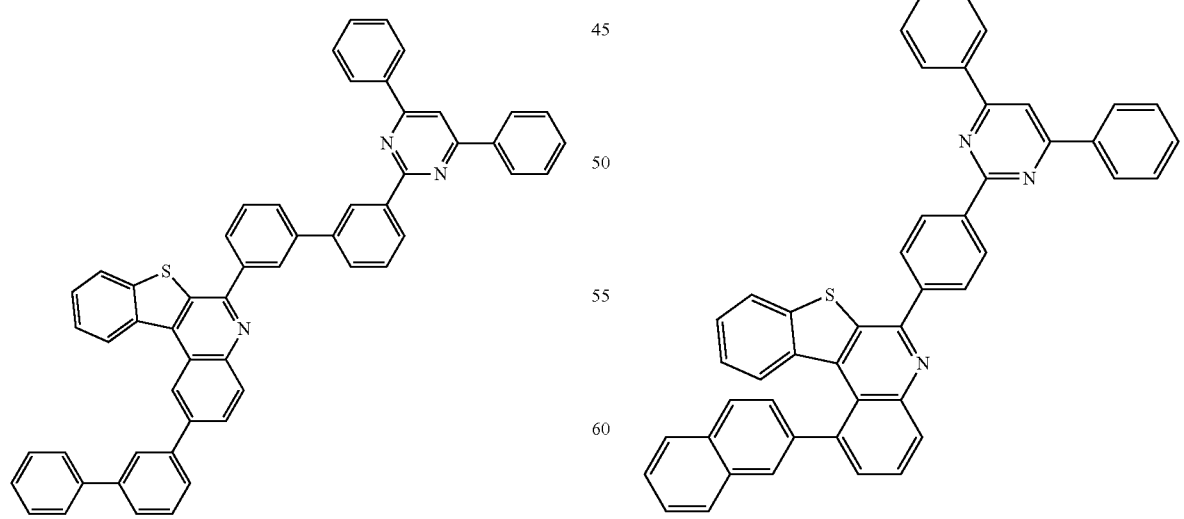

773
-continued
166
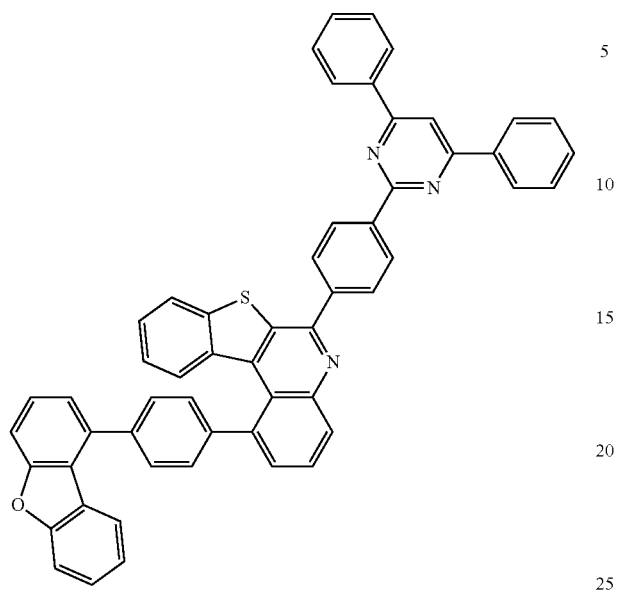
167
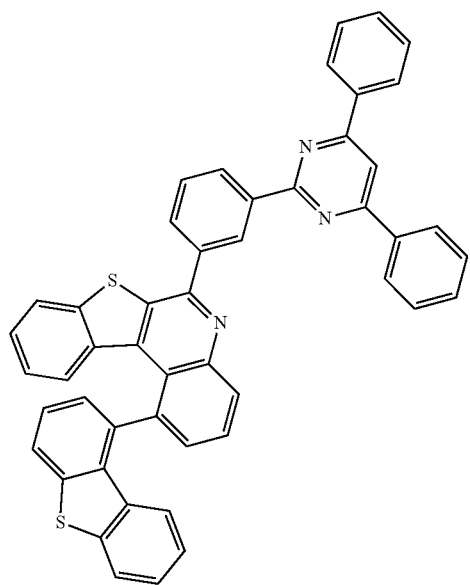
774
-continued
168
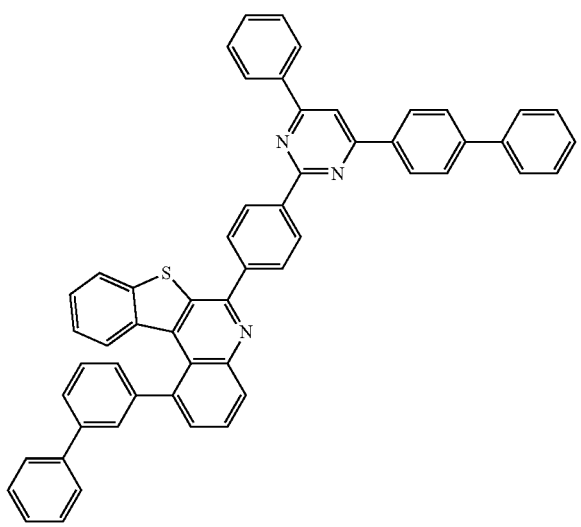
169
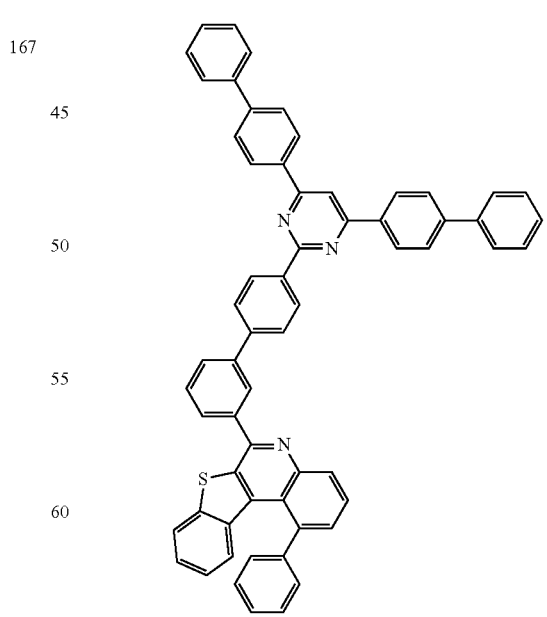

170
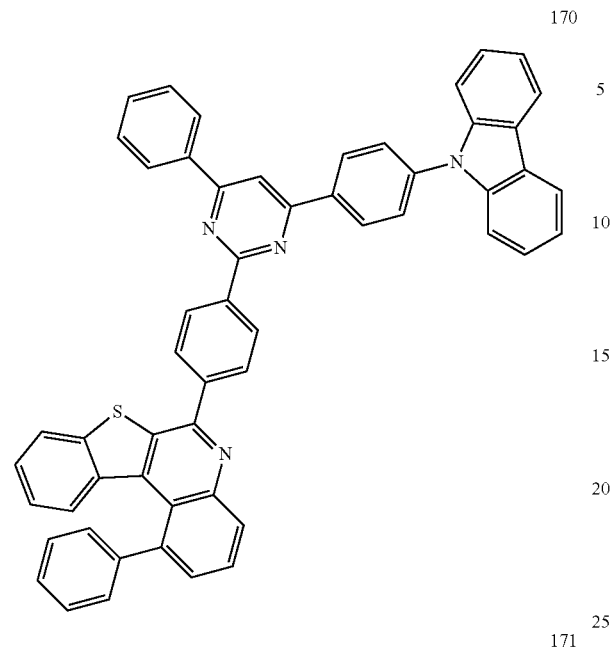
171
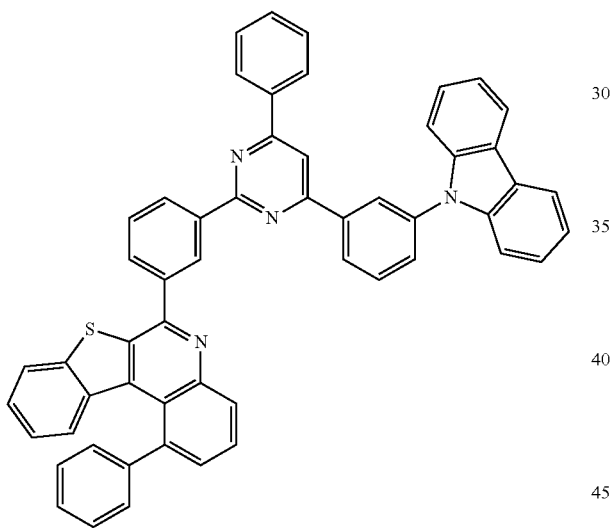
172
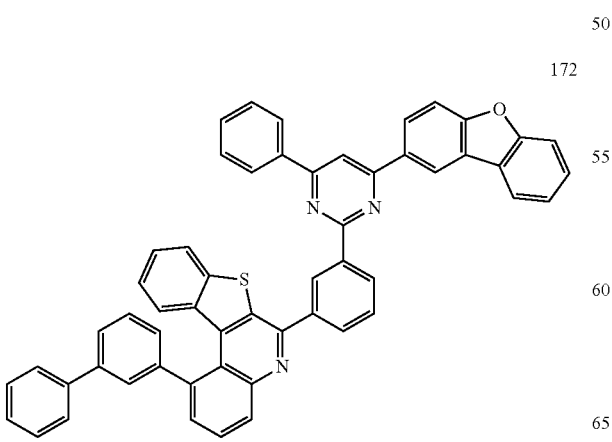
173
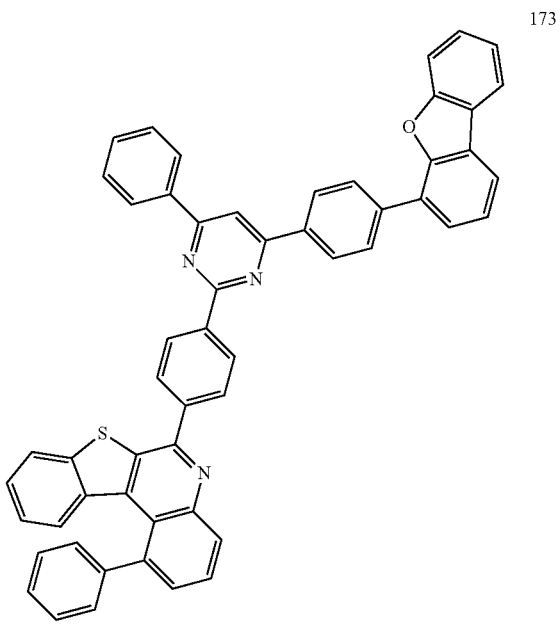
174
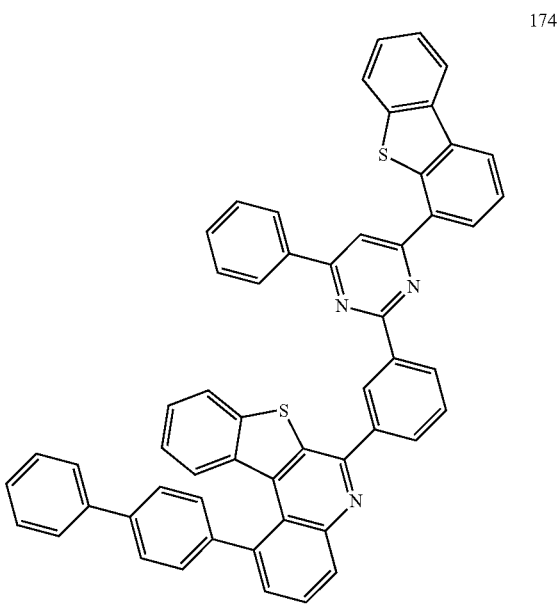

777
-continued
778
-continued
175
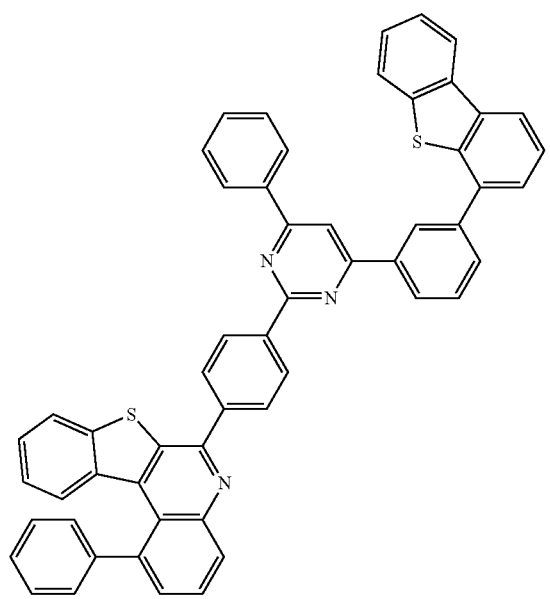
177
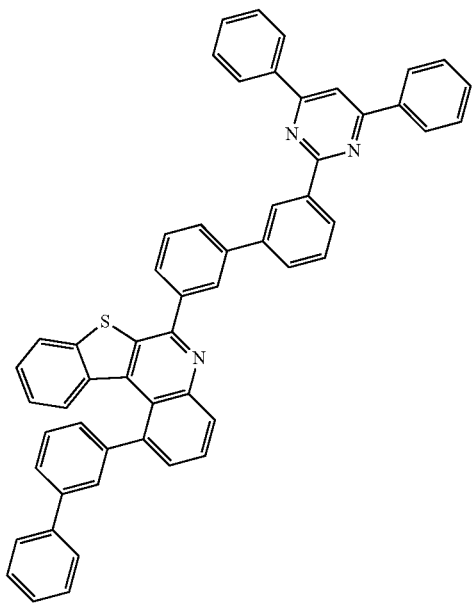
176
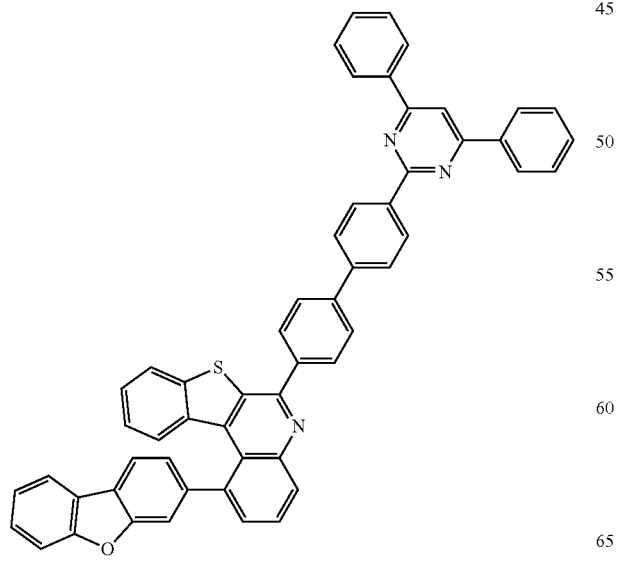
178
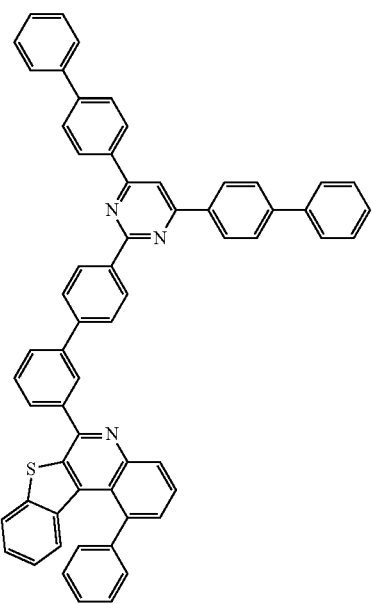

779
-continued
179
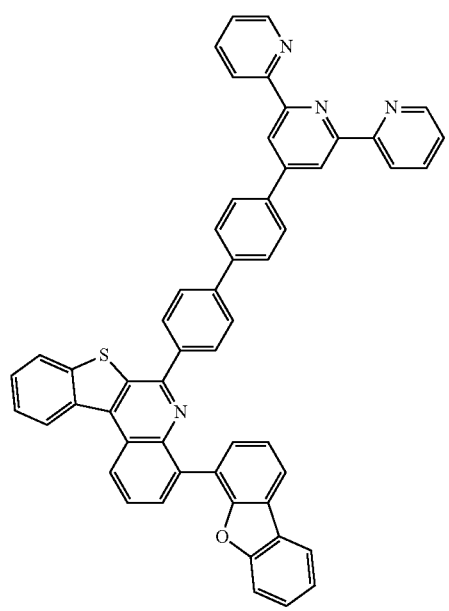
180
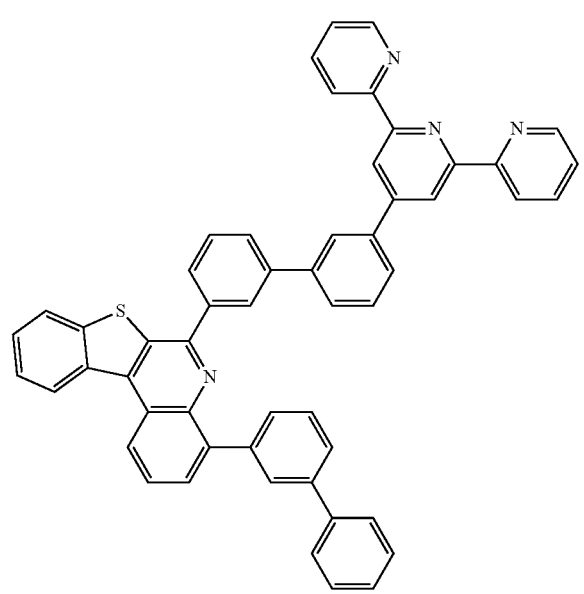
780
-continued
181
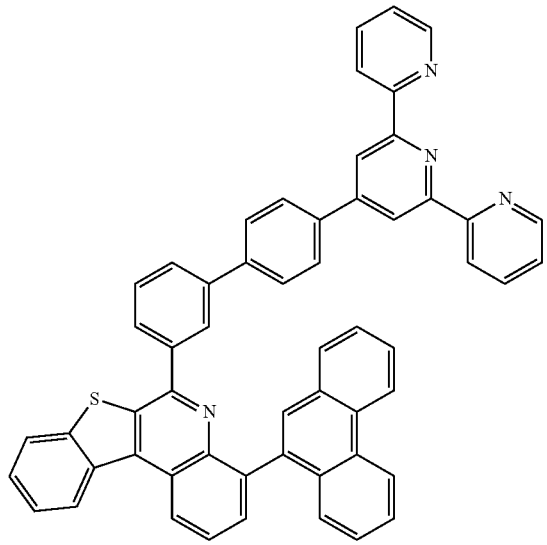
182

183
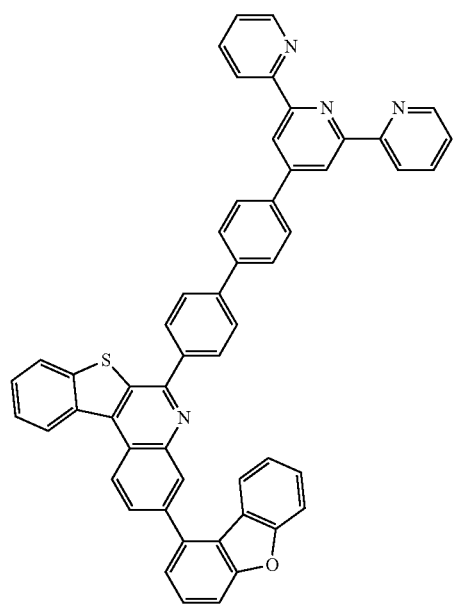
184
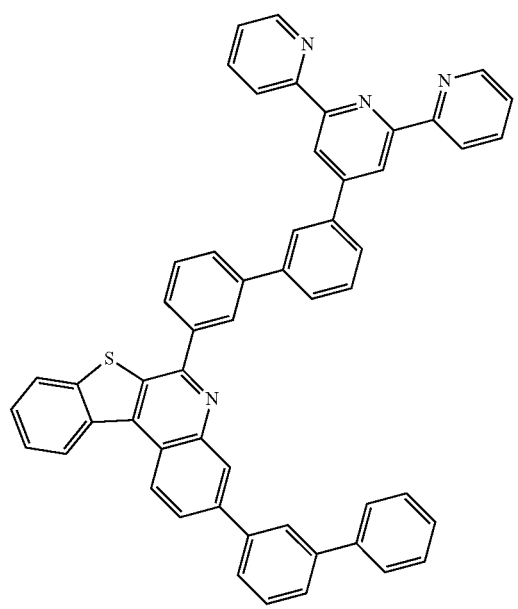
185
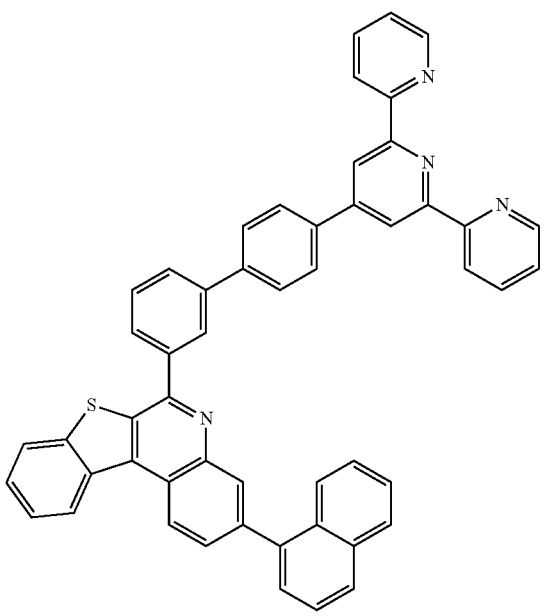
186
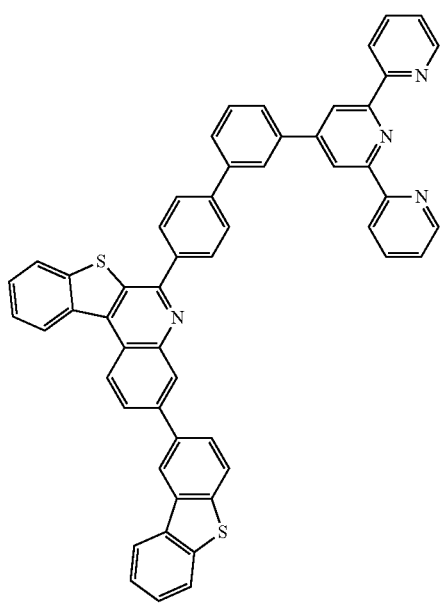

187
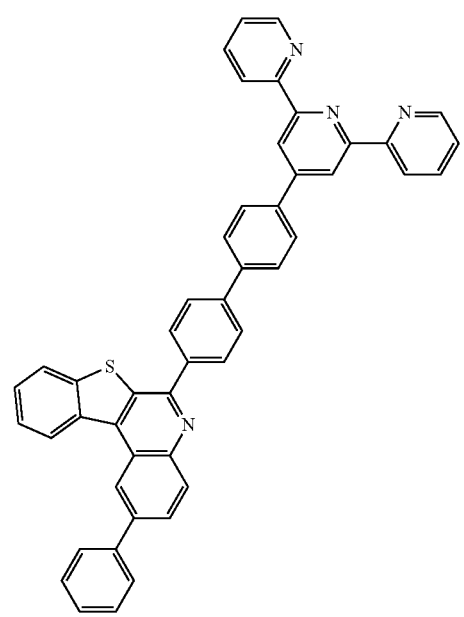
188
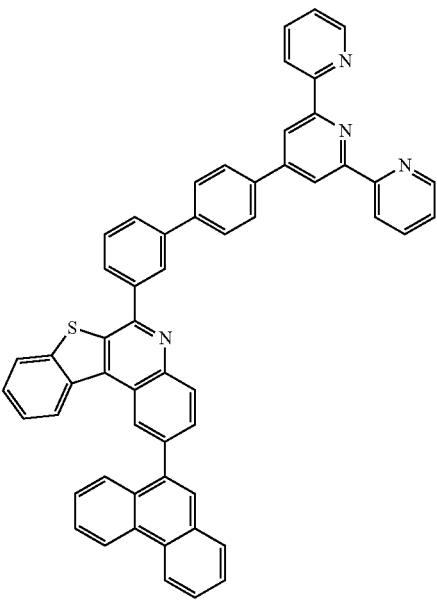
189
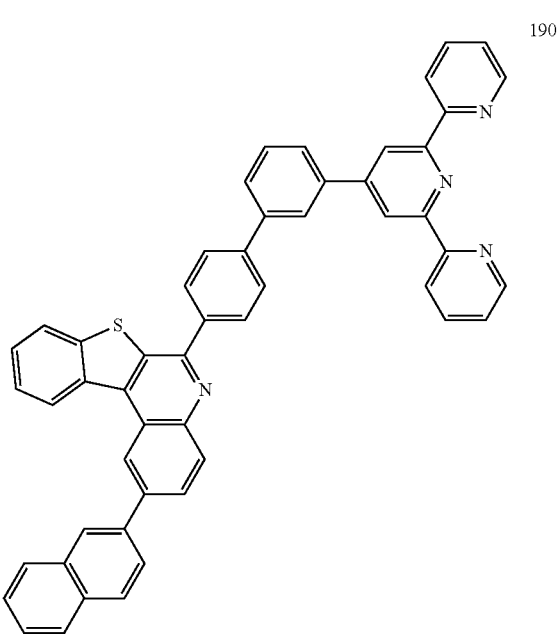
190

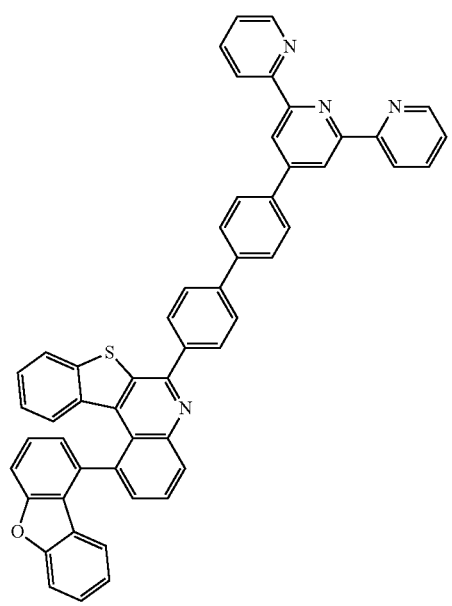
191
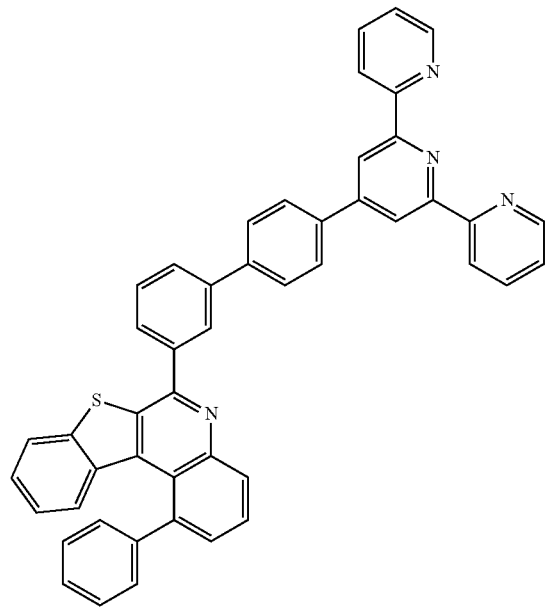
193
192
194

787
-continued
195
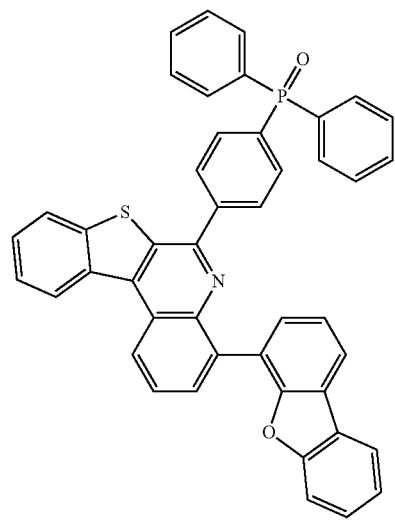
196
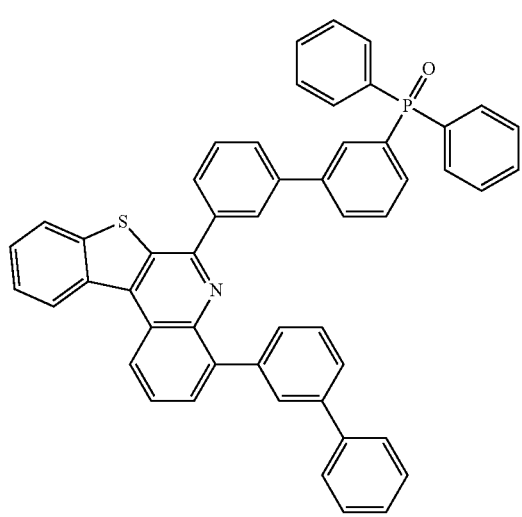
197
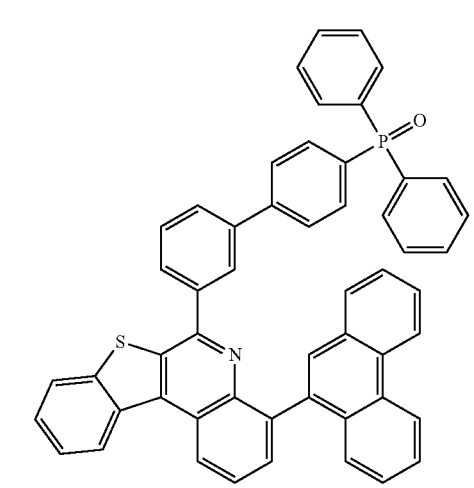
788
-continued
198
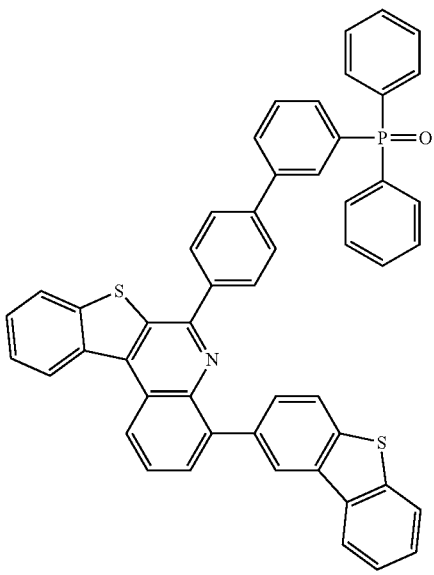
199
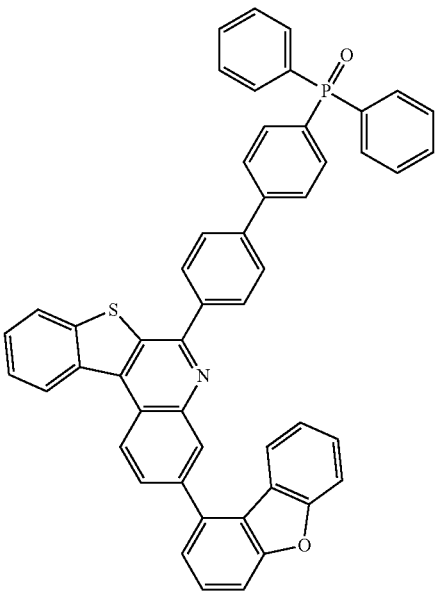
200
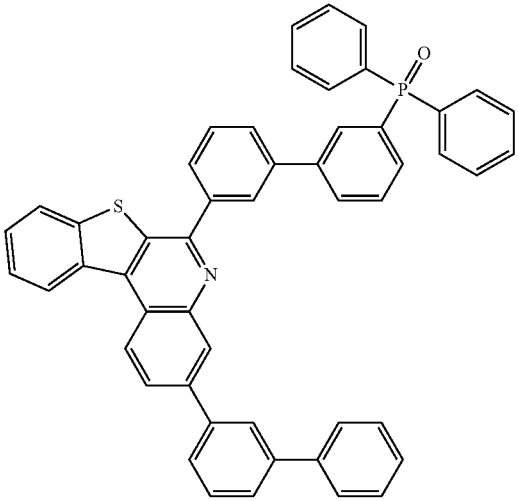

789
-continued
790
-continued
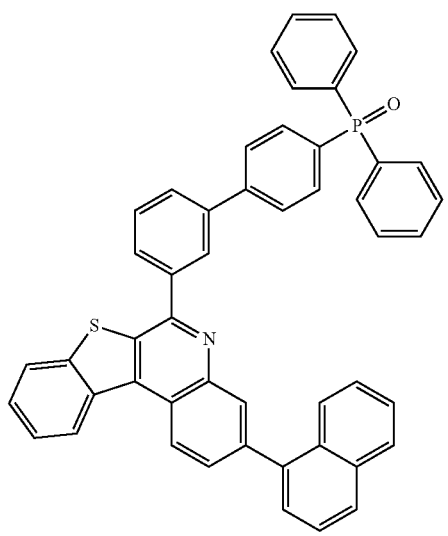
201
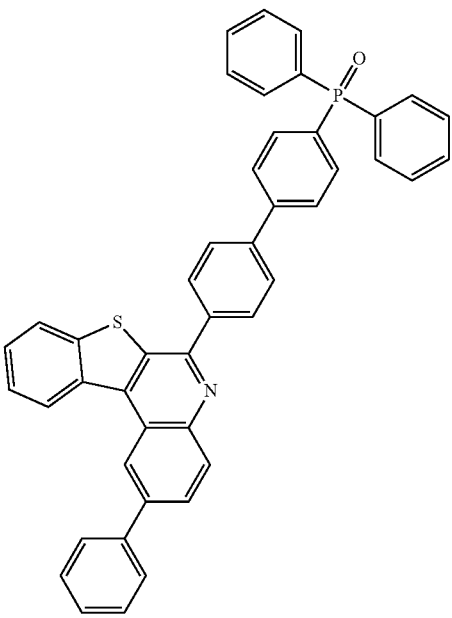
203
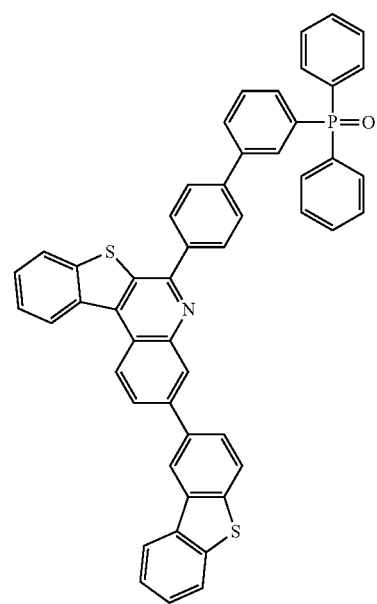
202
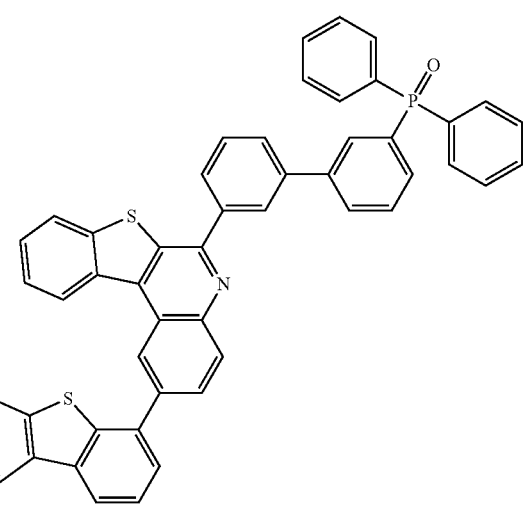
204

205
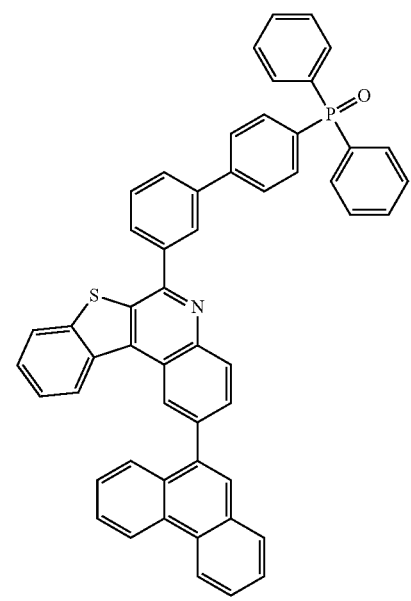
206
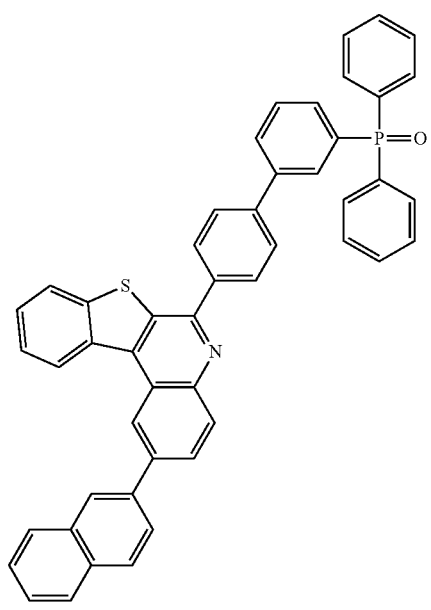
207
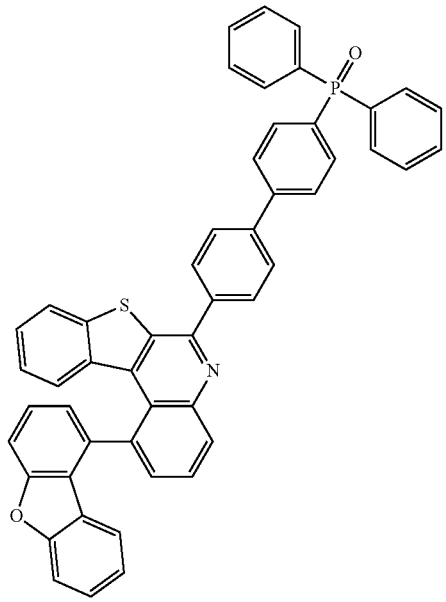
208
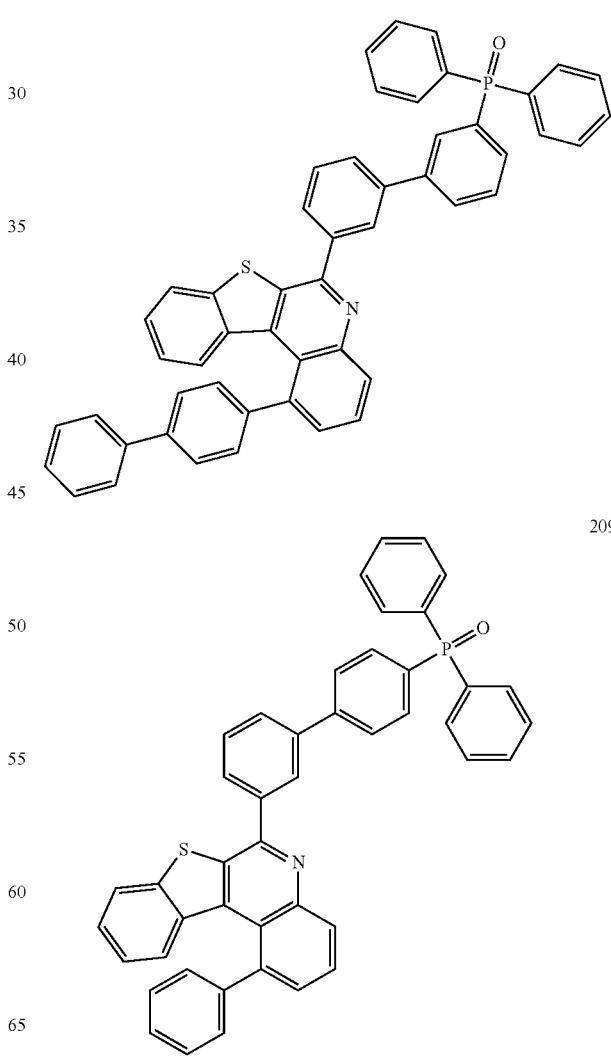
209
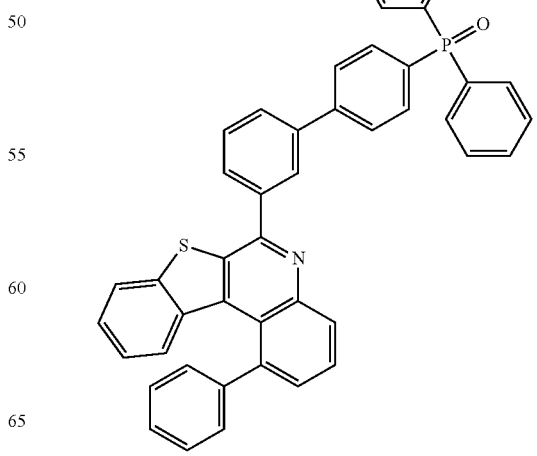

793
-continued
794
-continued
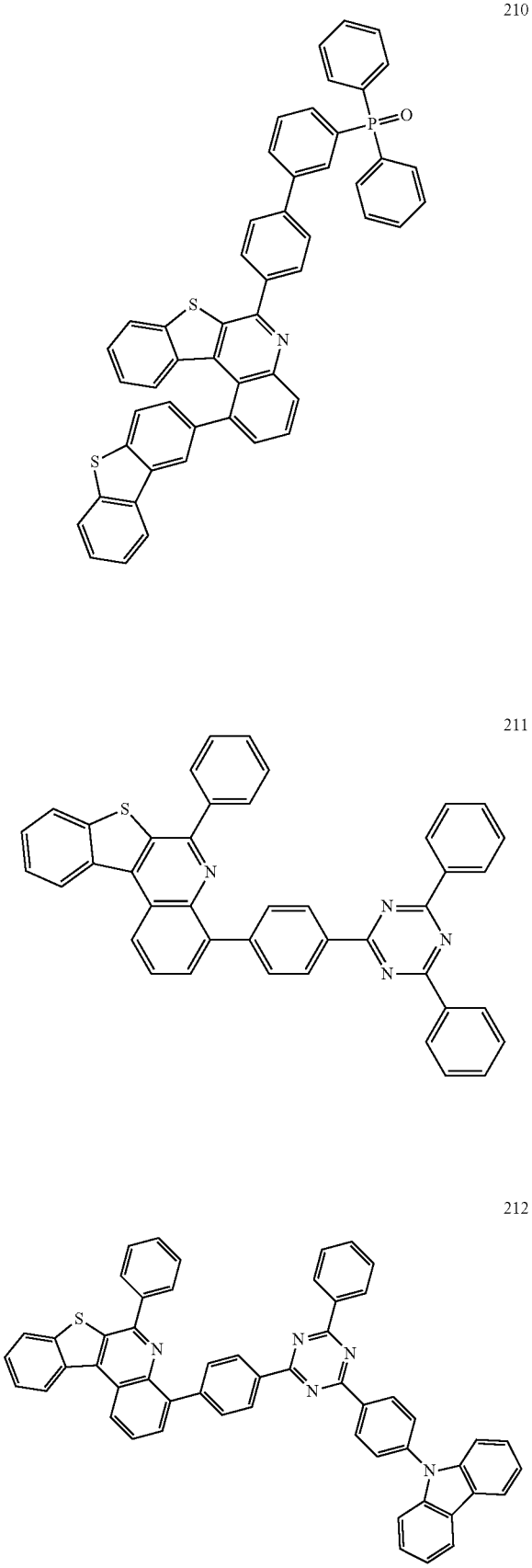
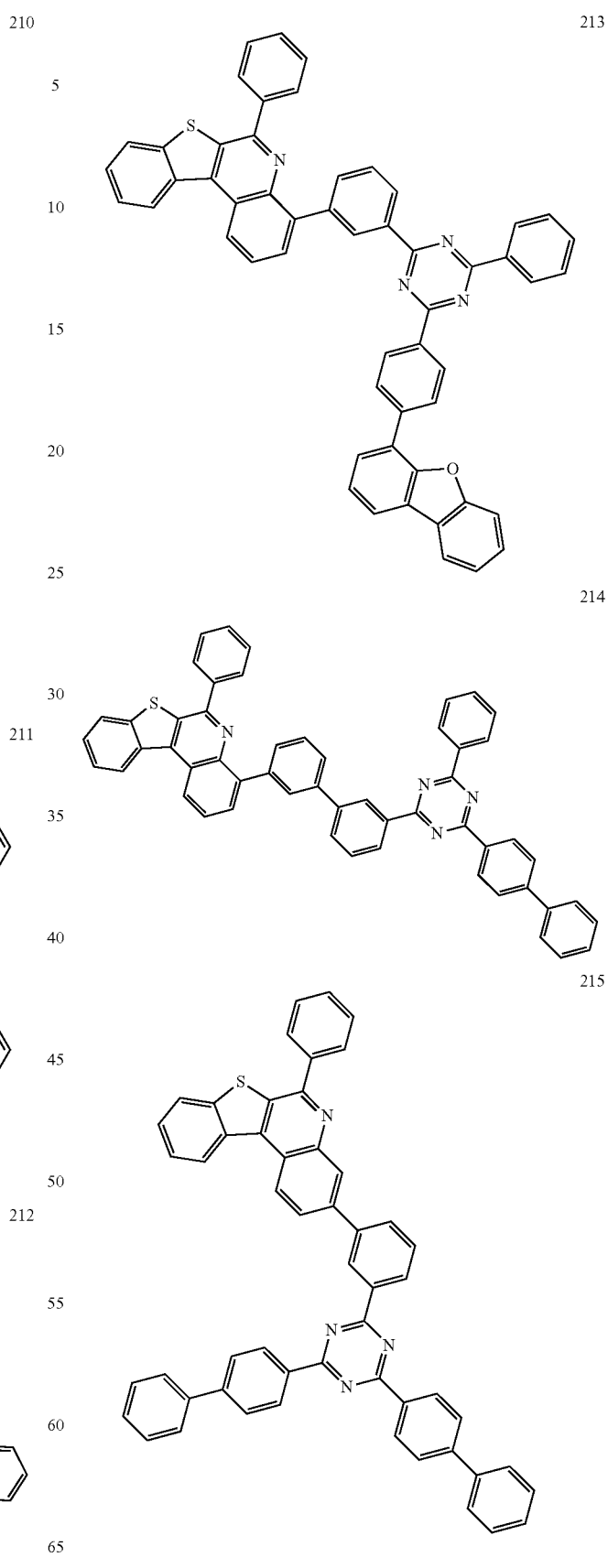

216

795
-continued

217

218

796
-continued

219

220
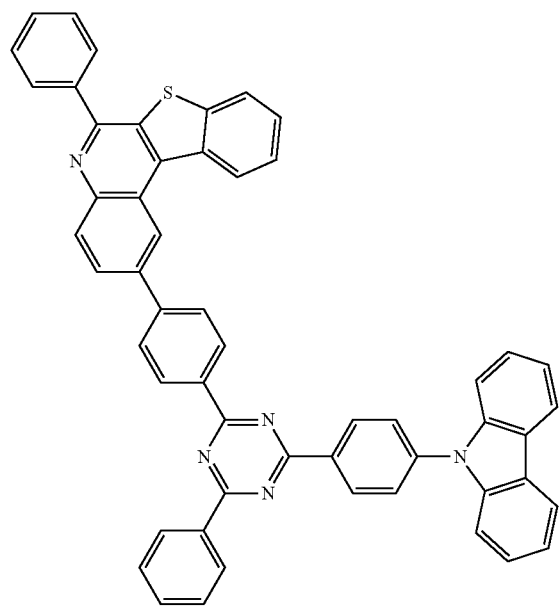
221
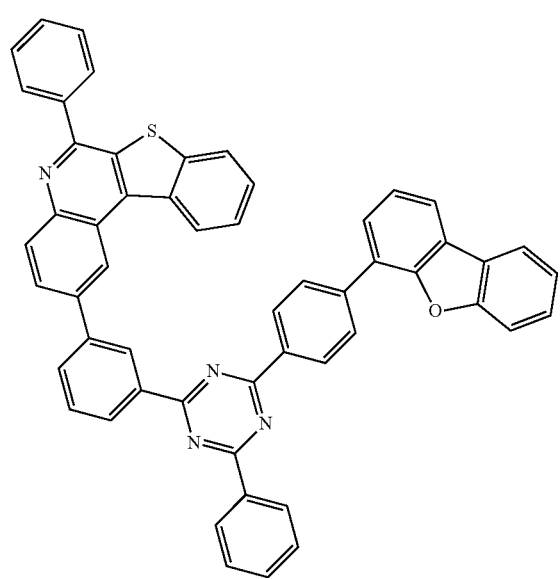
222
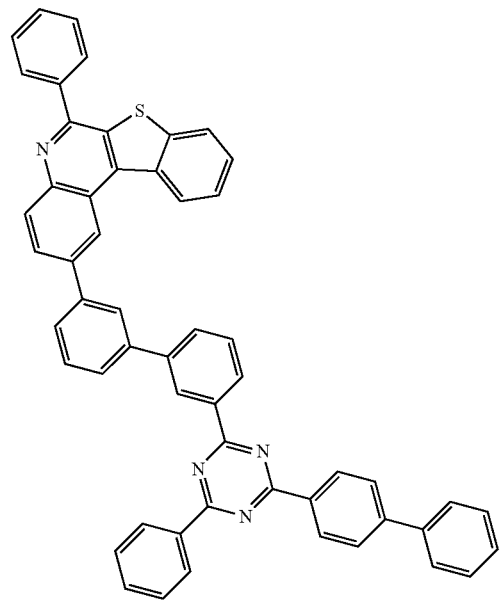
223
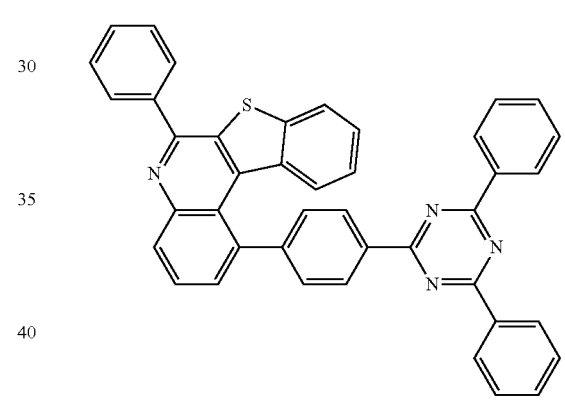
224
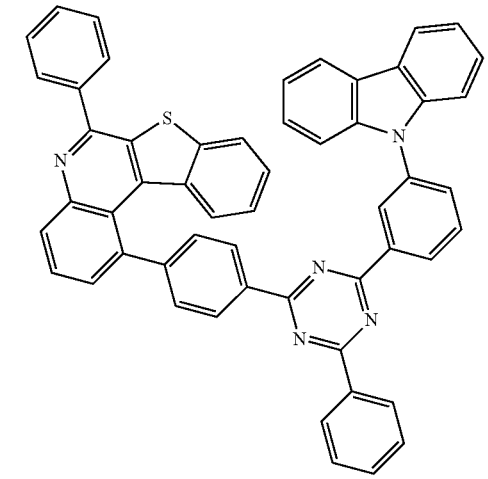

799
-continued
225
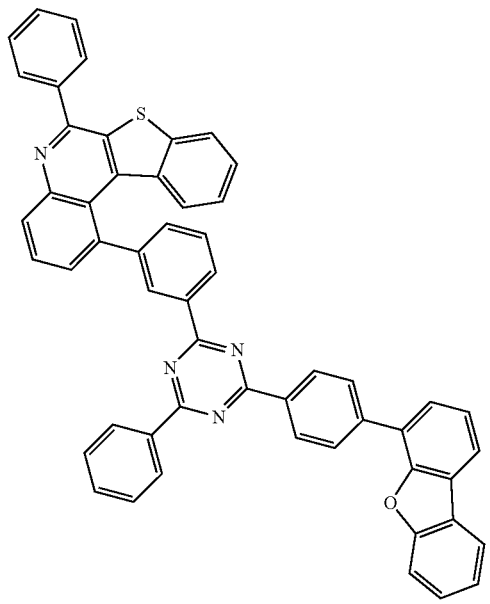
226
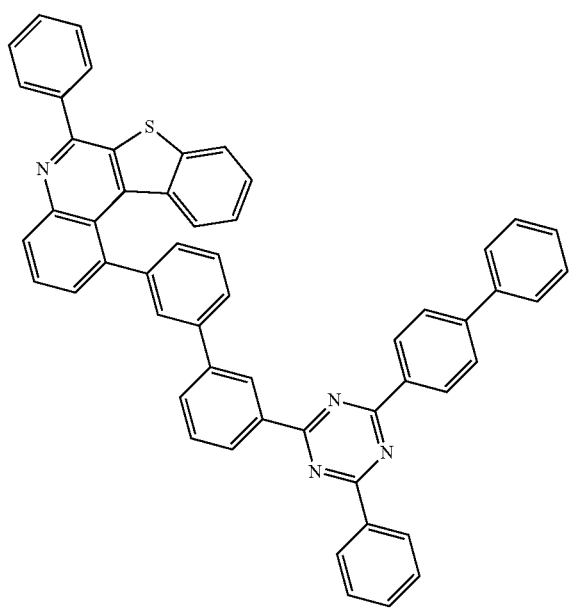
800
-continued
227
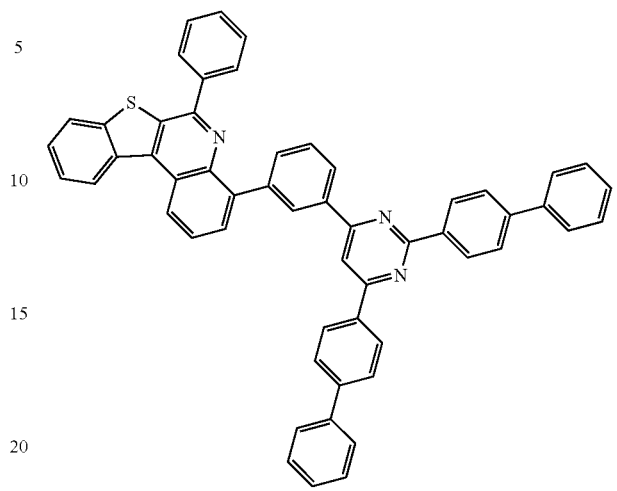
228
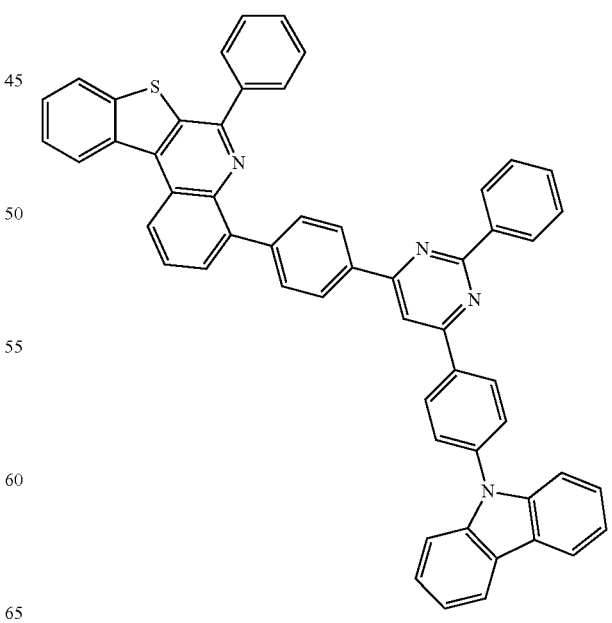

801
-continued
229
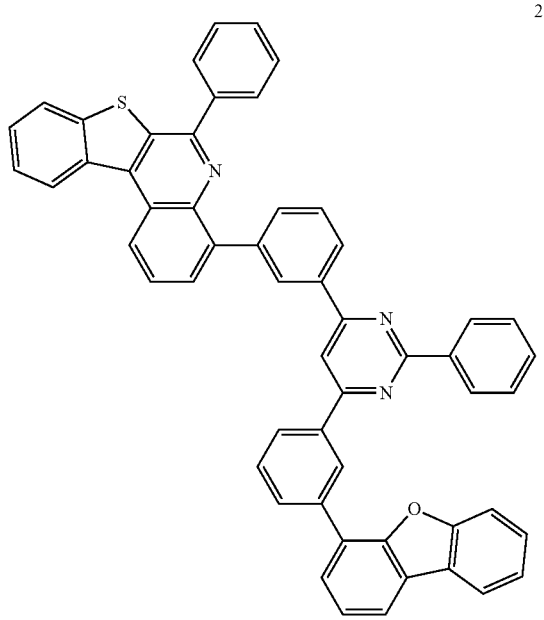
230
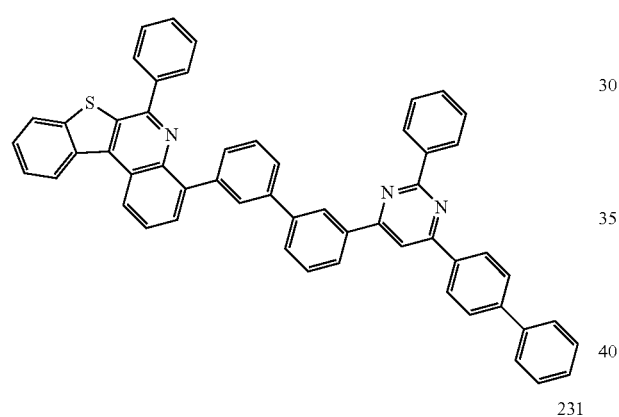
231
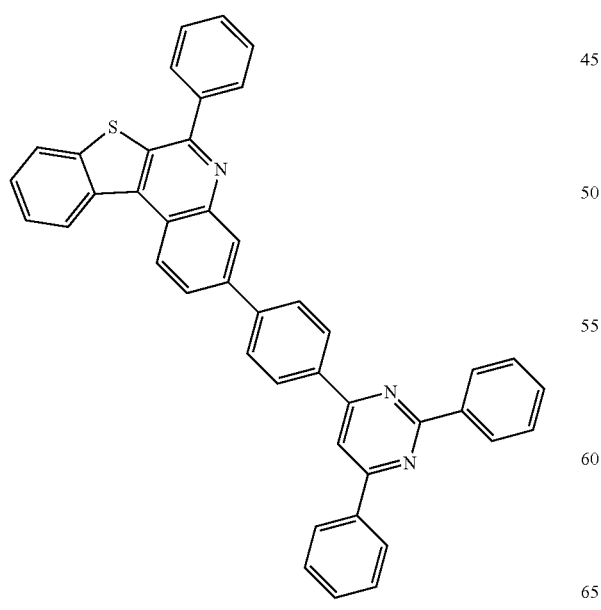
802
-continued
232
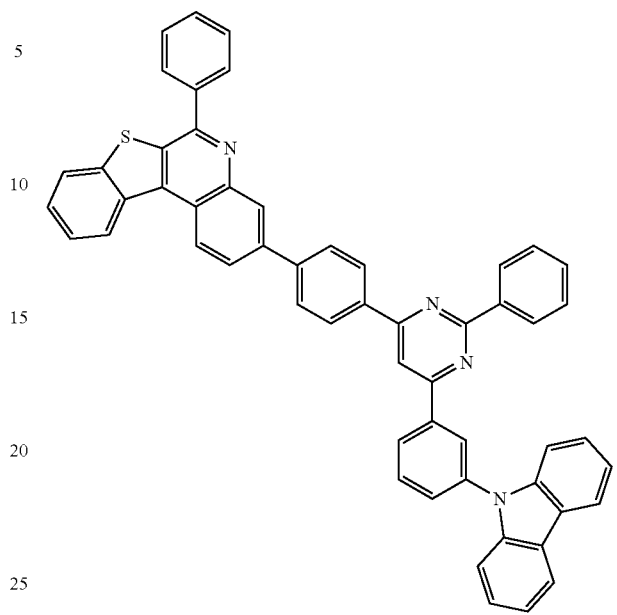
233
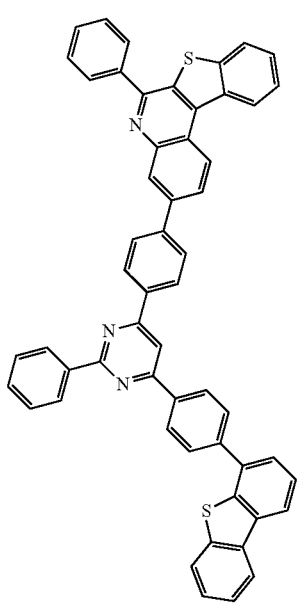

803
-continued
234
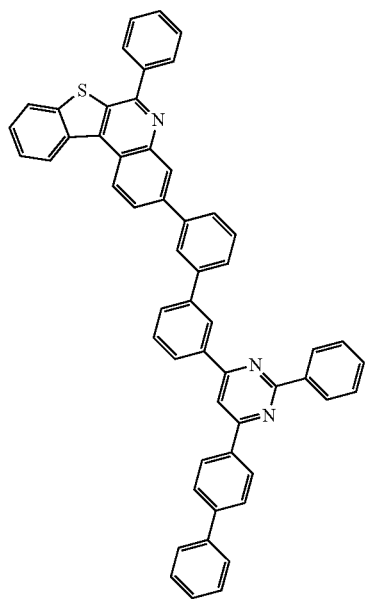
236
235
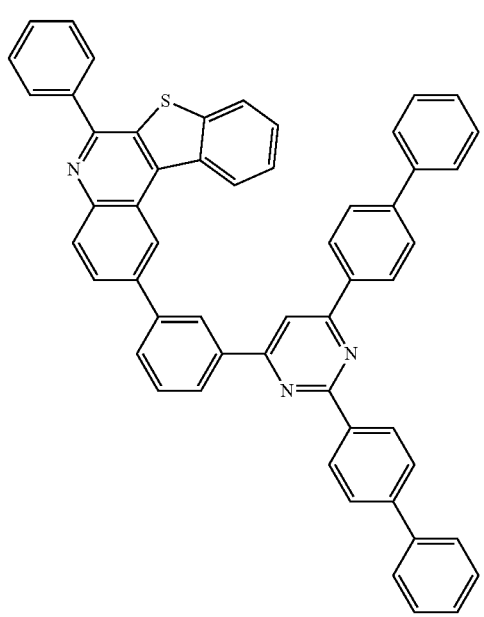
804
-continued
237
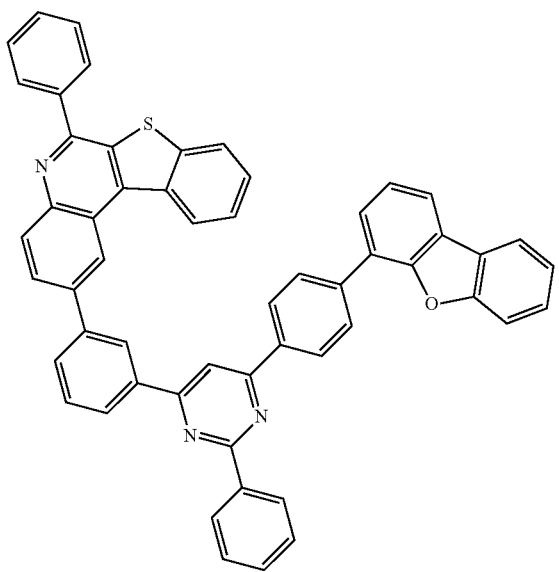

805
-continued
806
-continued
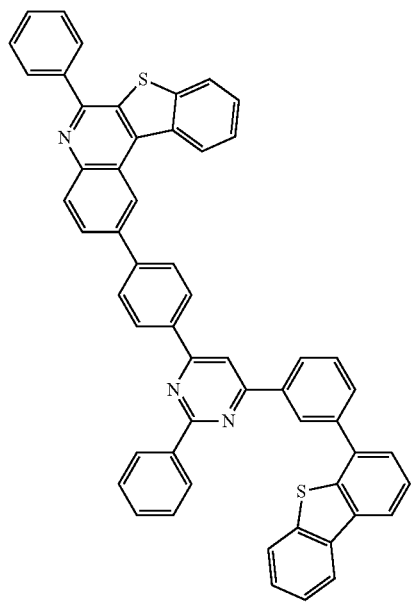
238
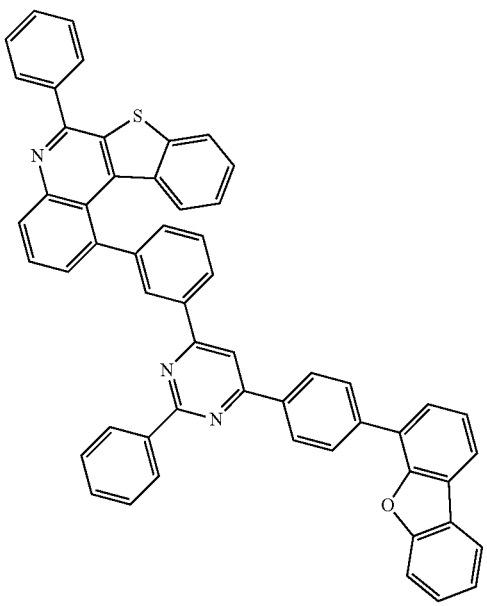
241
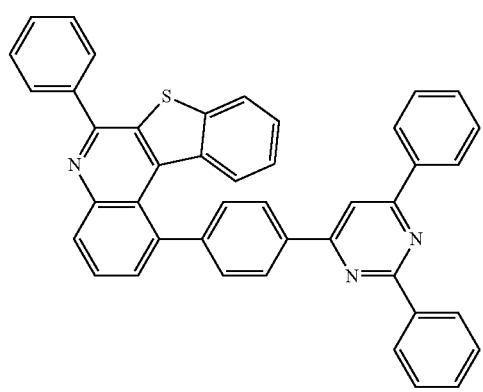
239
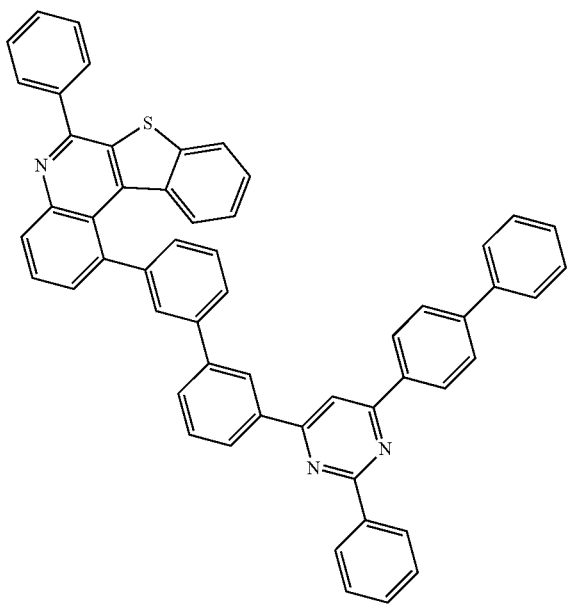
242

243
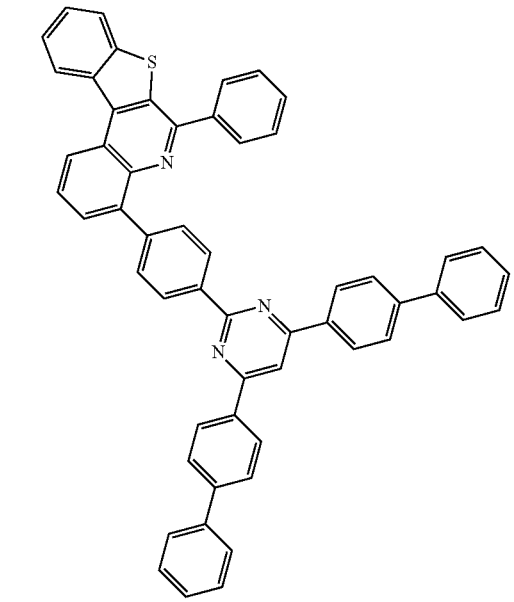
244
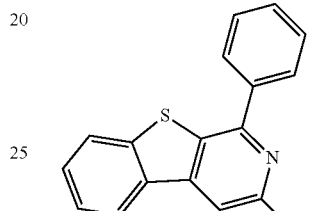
245
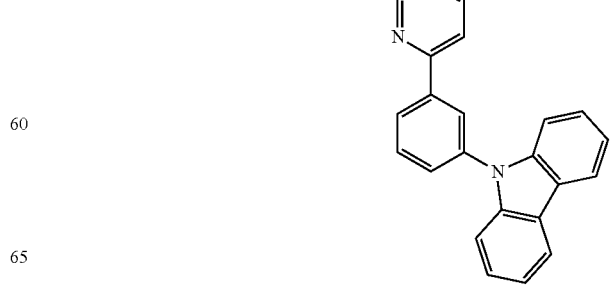
246
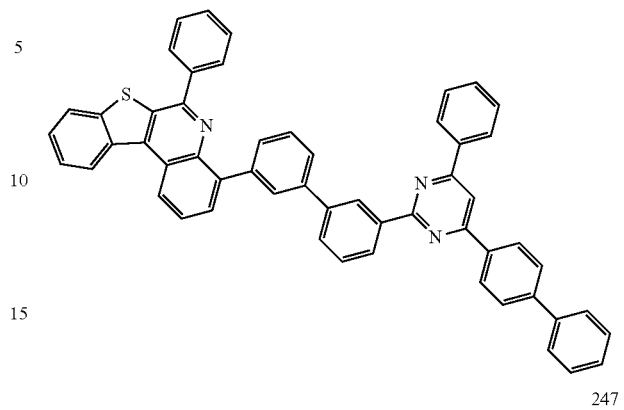
247
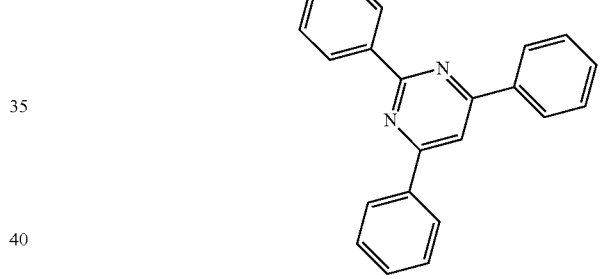
248
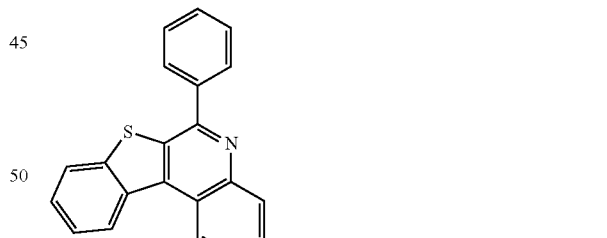

809 -continued
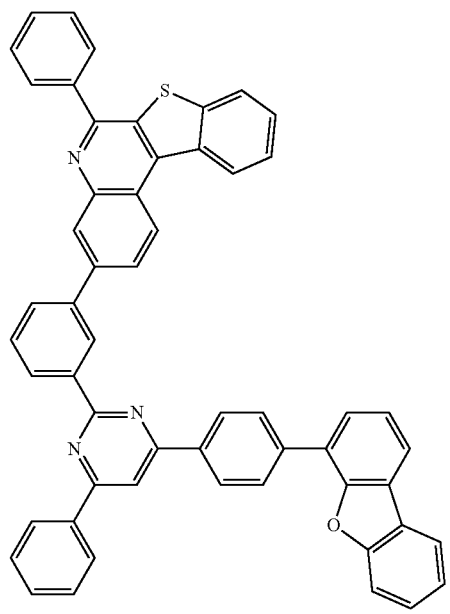
249
810 -continued
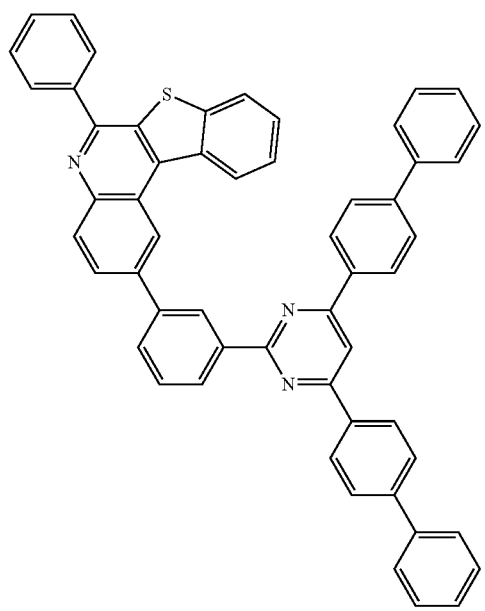
251
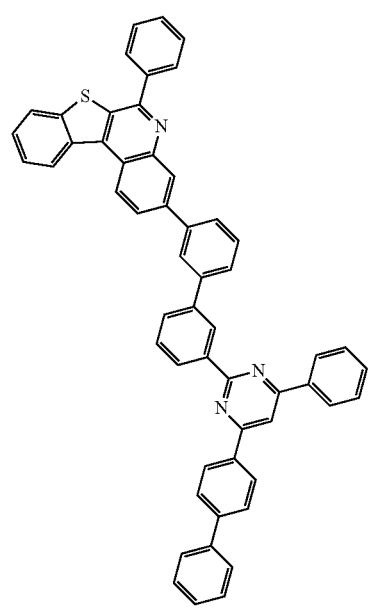
250
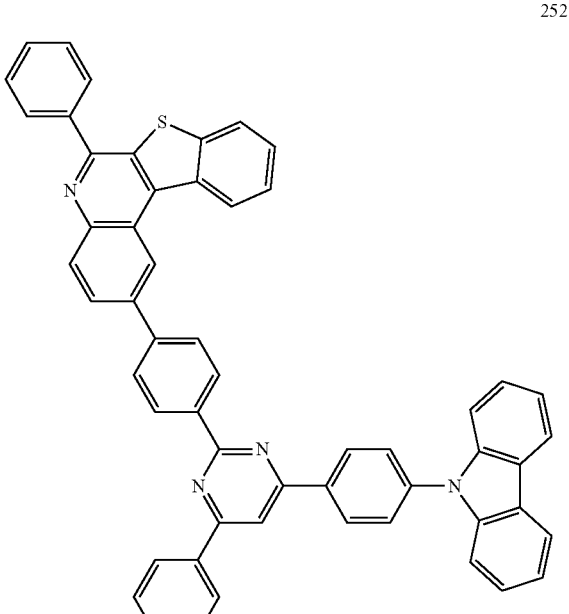
252

811
-continued
812
-continued
253
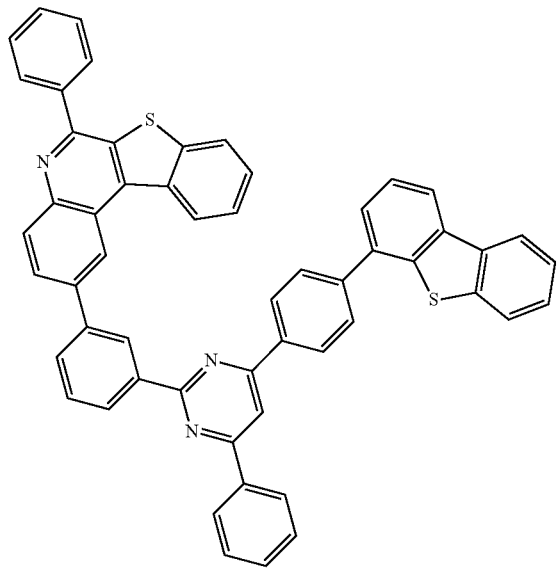
254
256
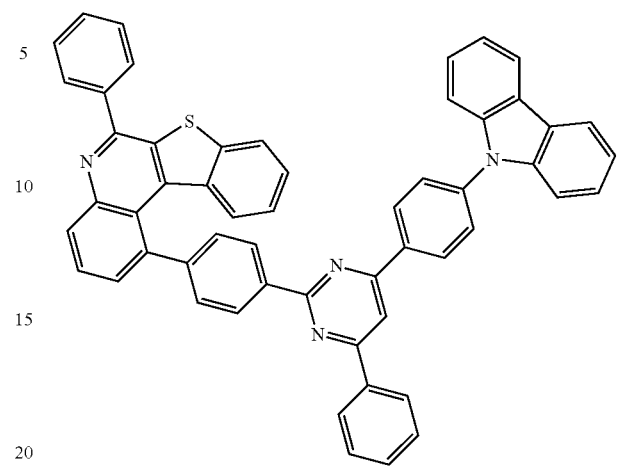
257
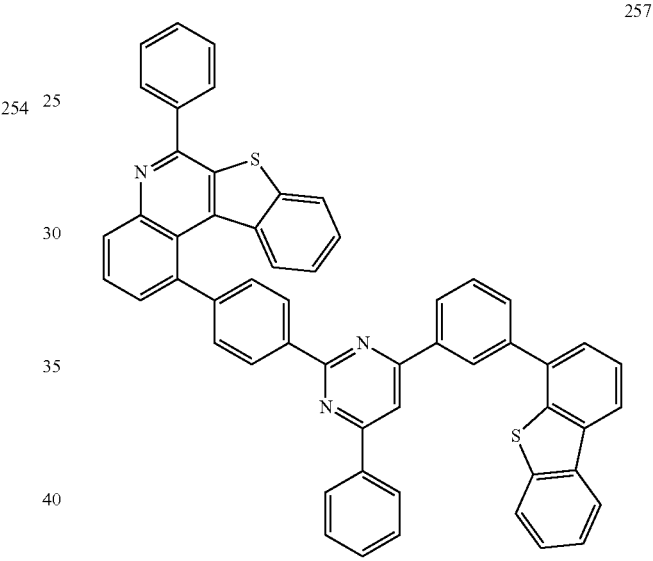
255
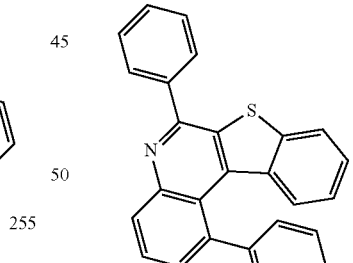
258
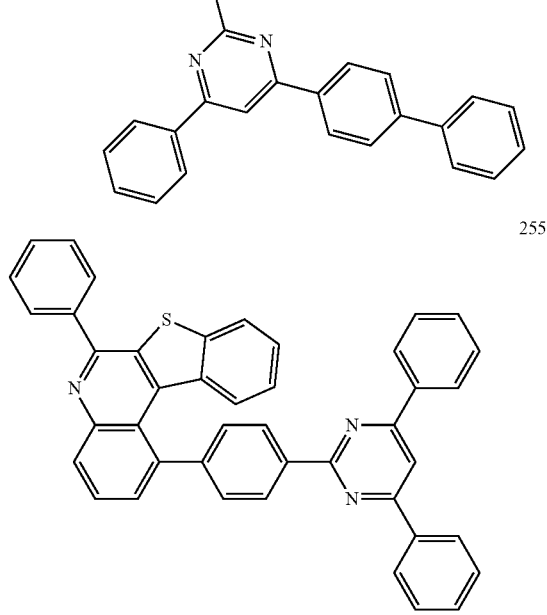

813
-continued
259
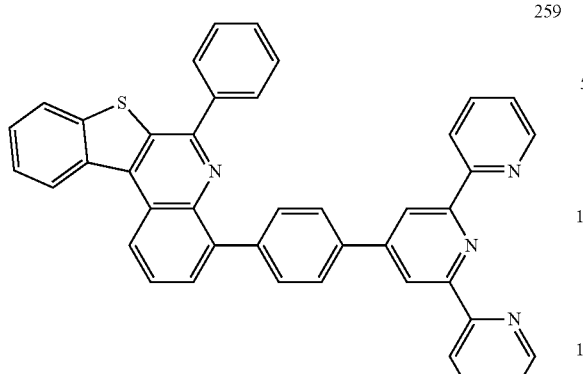
260
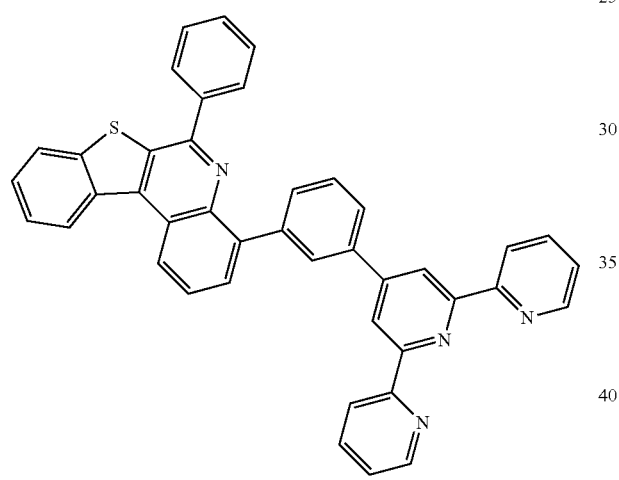
261
814
-continued
262
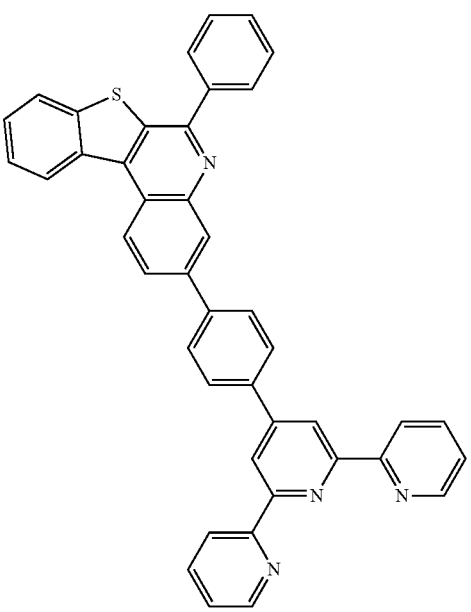
263
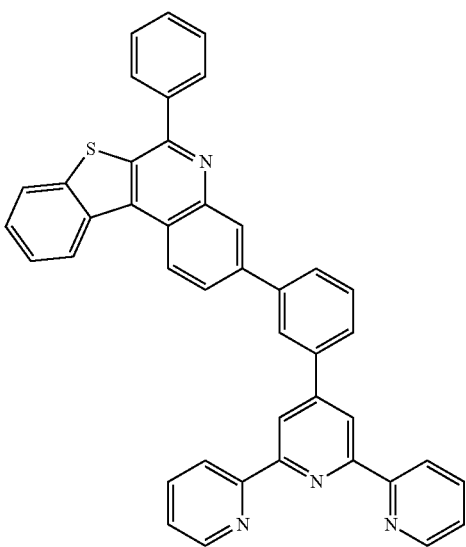

815
-continued
264
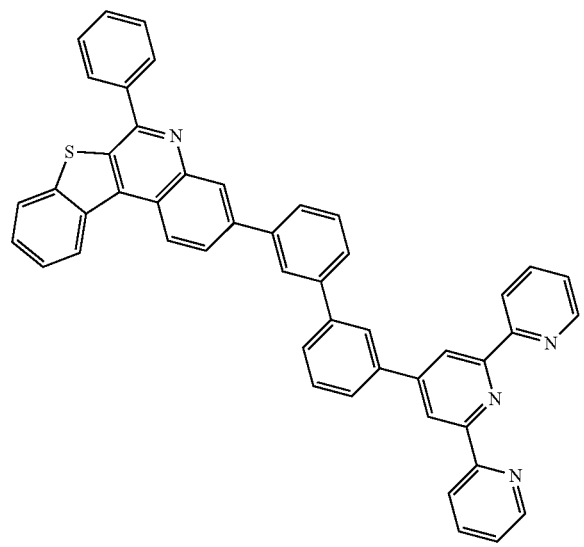
265
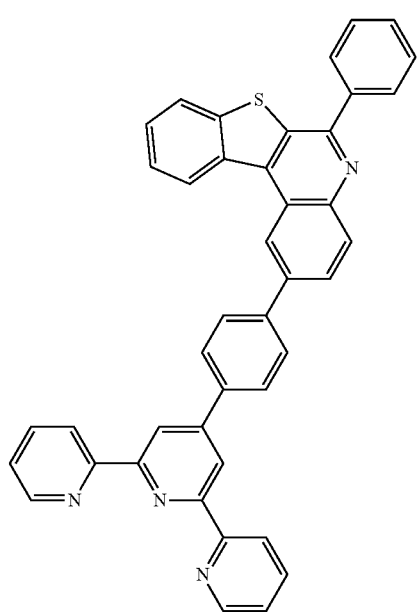
816
-continued
266
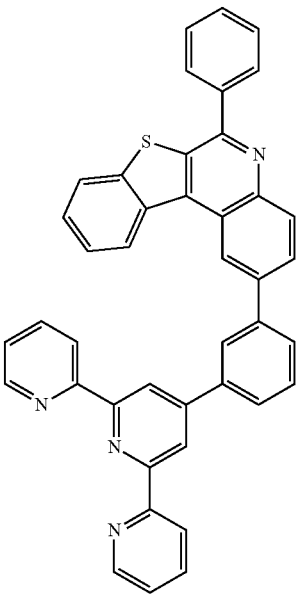
267
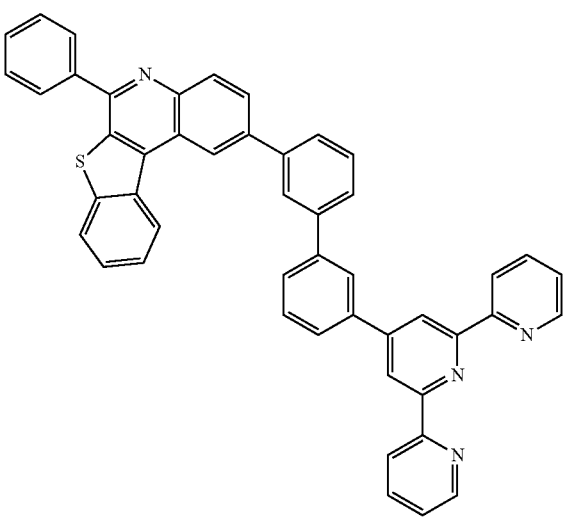
268
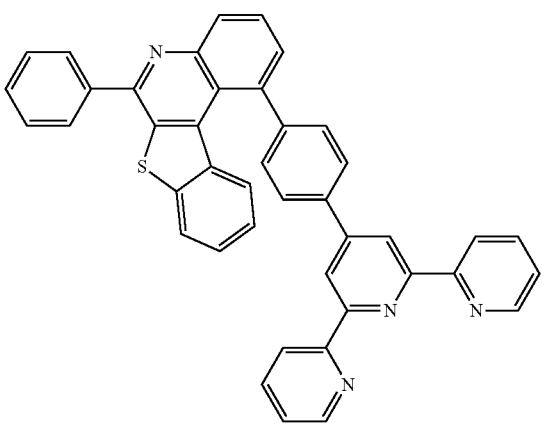

269
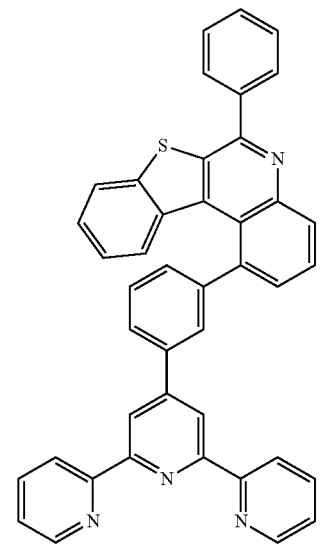
270
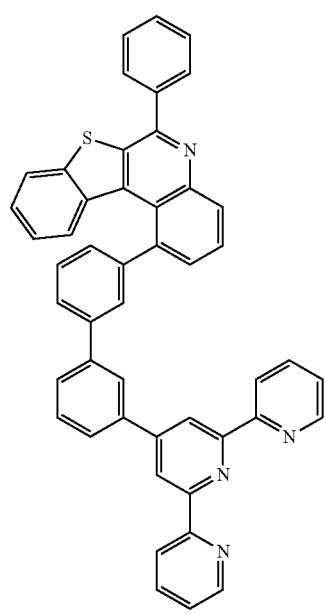
271
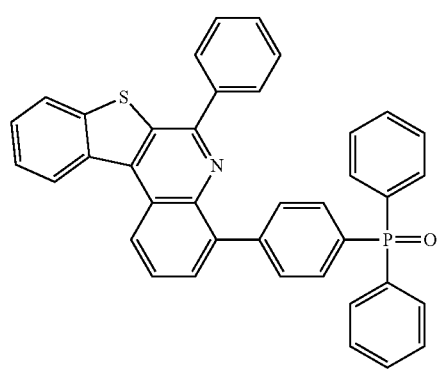
272
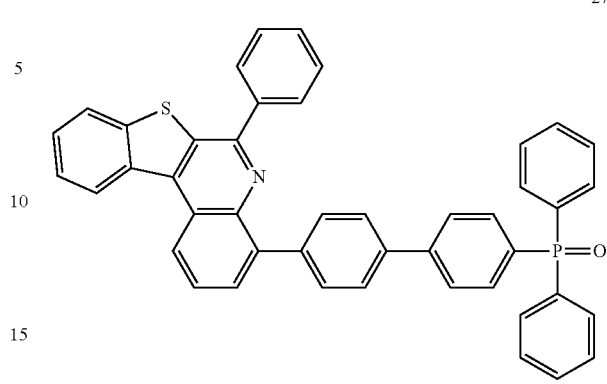
273
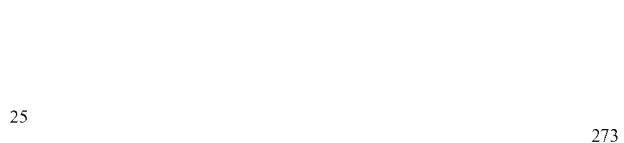
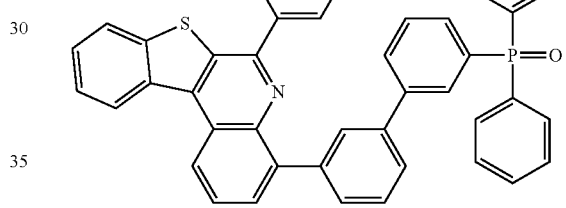
274
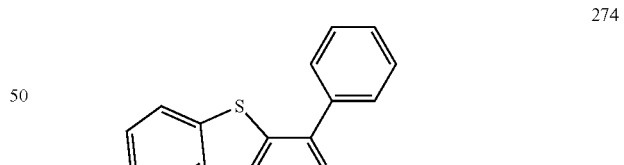
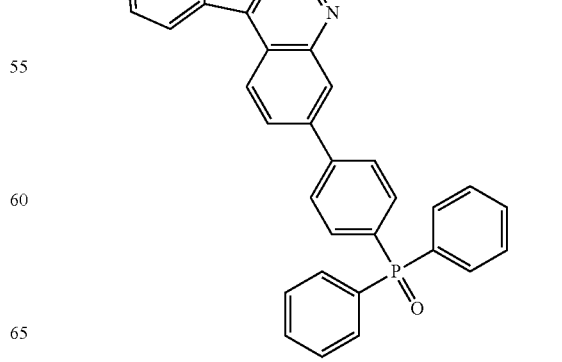

819
-continued
820
-continued
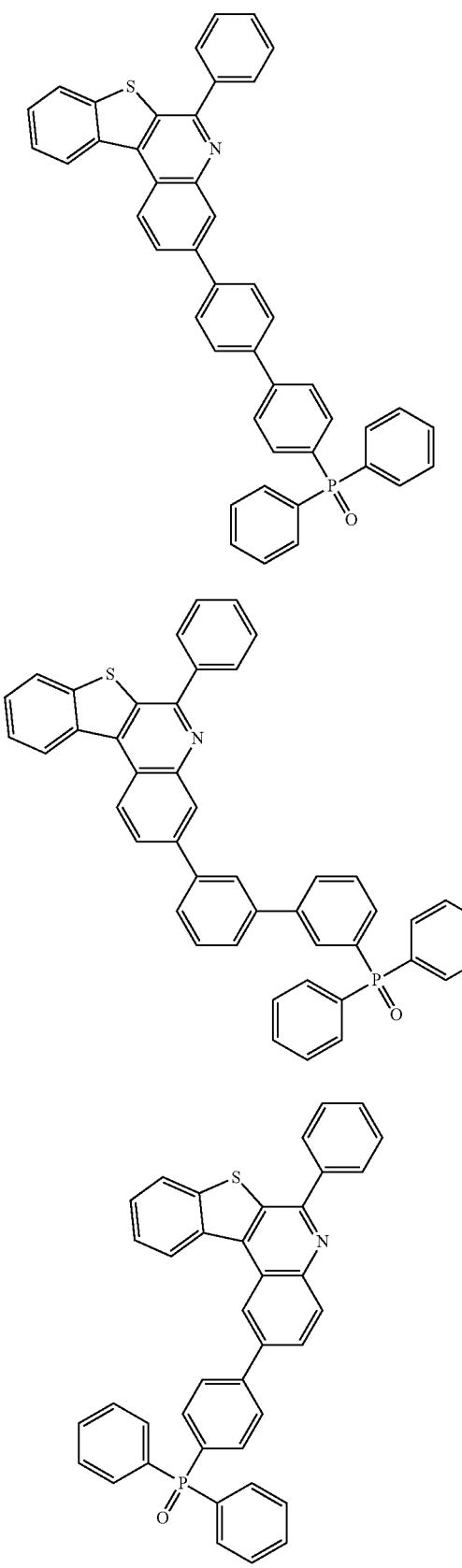
275
276
277
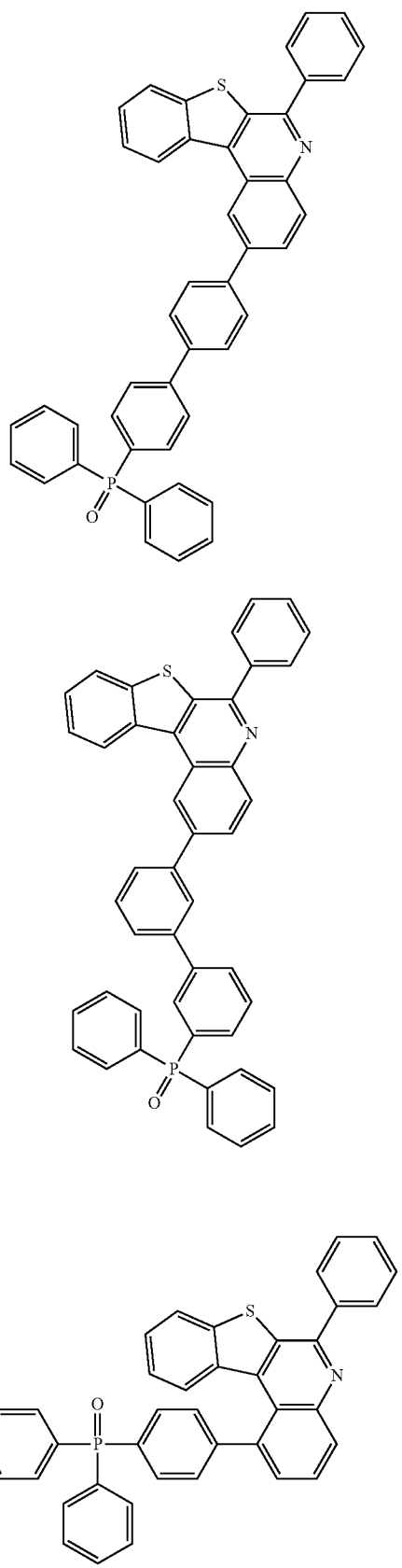
278
279
280

281
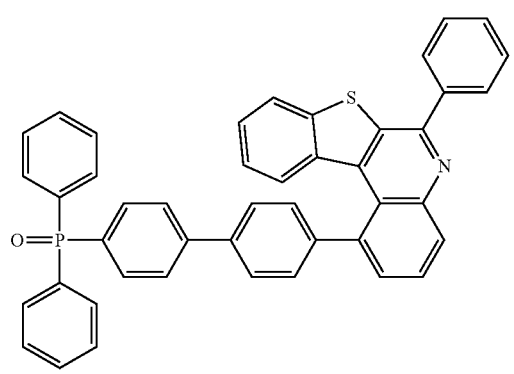
282
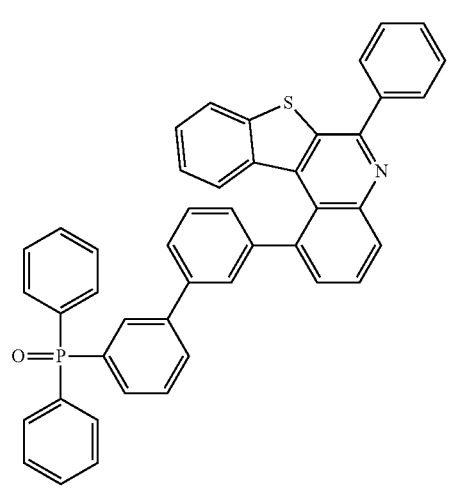
283
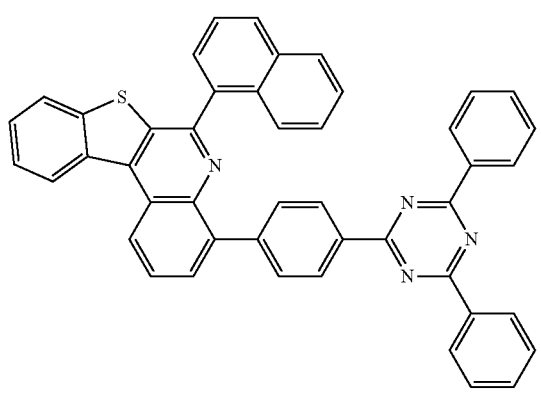
284
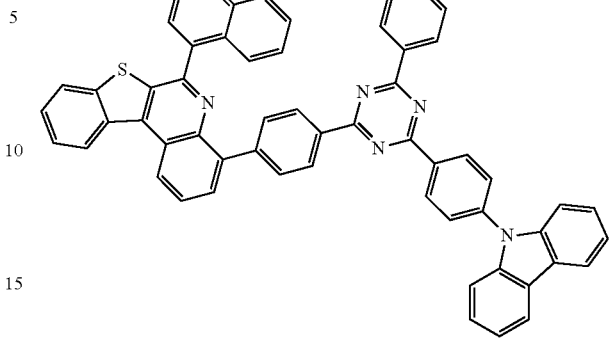
285
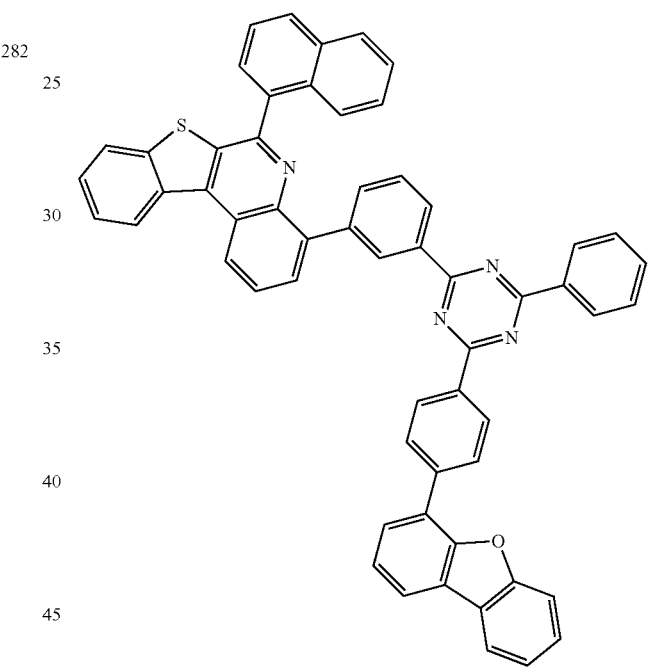
286
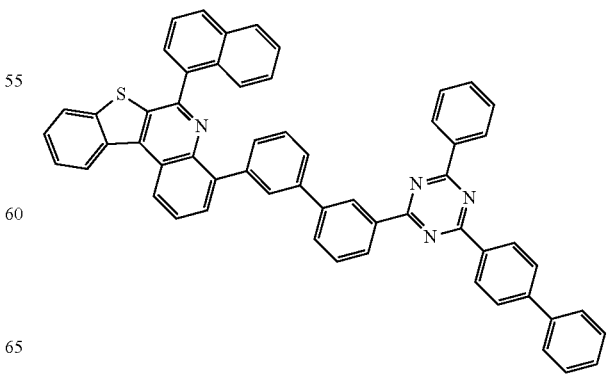

287
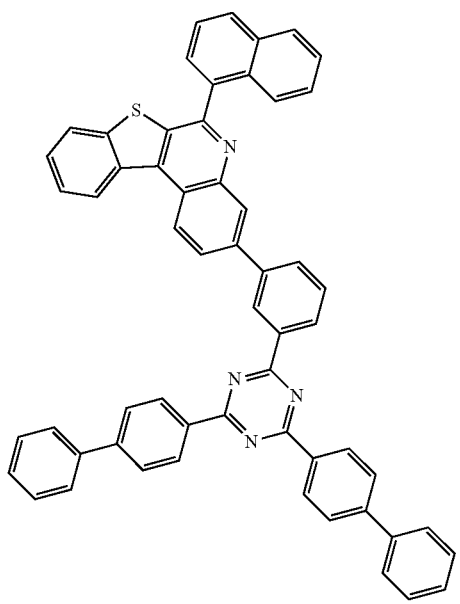
288
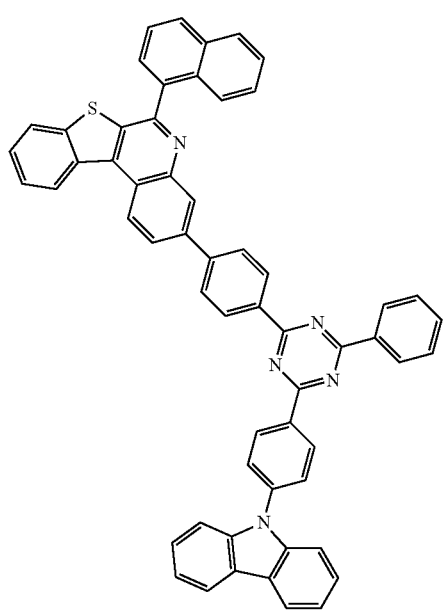
289
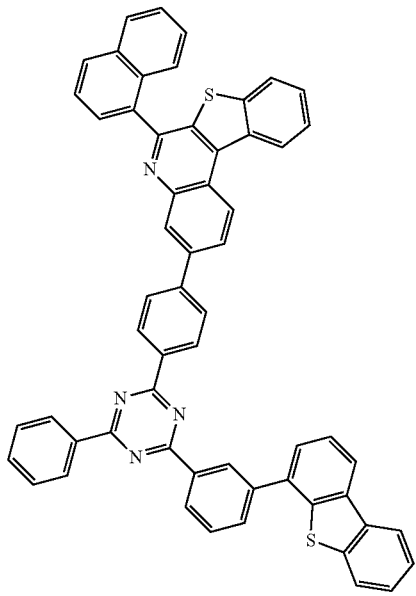
290
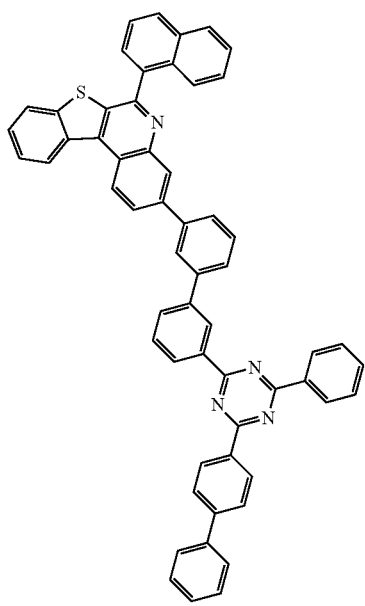

291
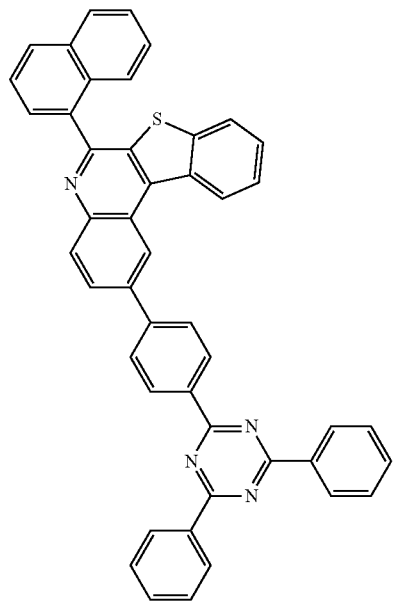
292
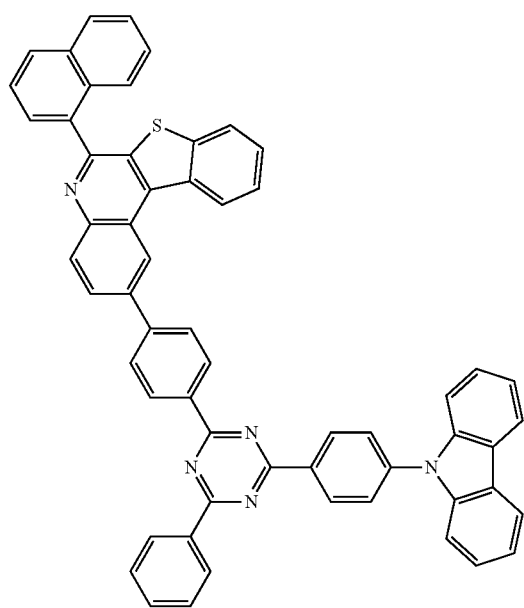
293
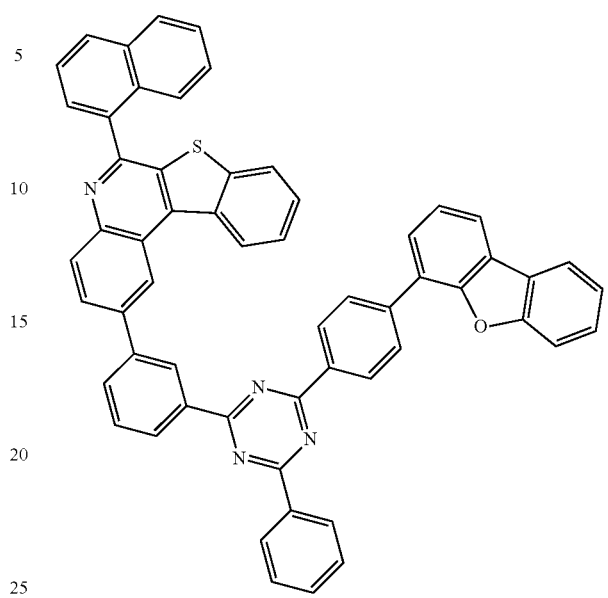
294
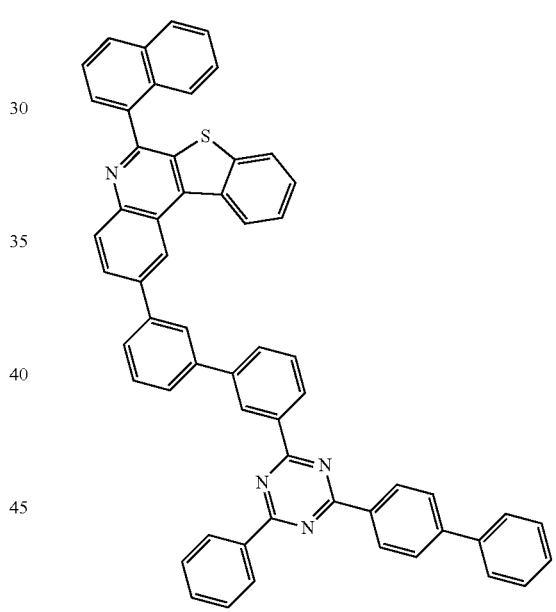
295
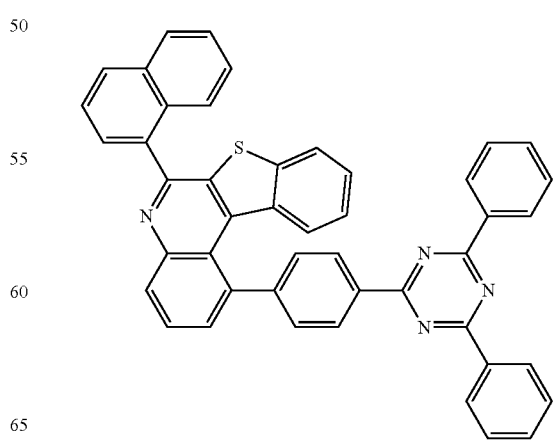

296
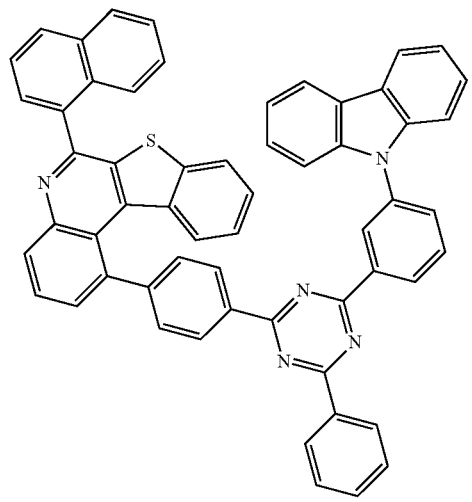
297
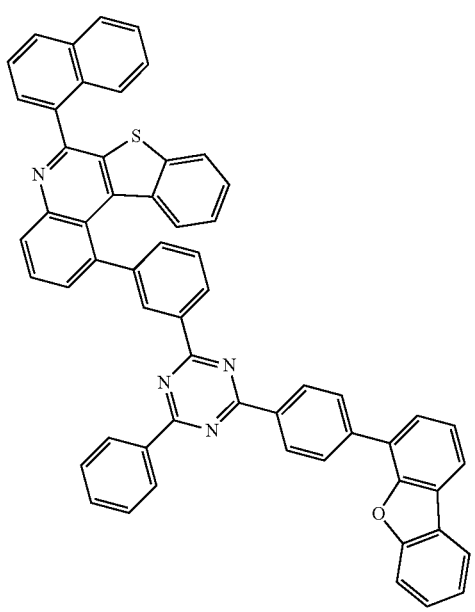
298
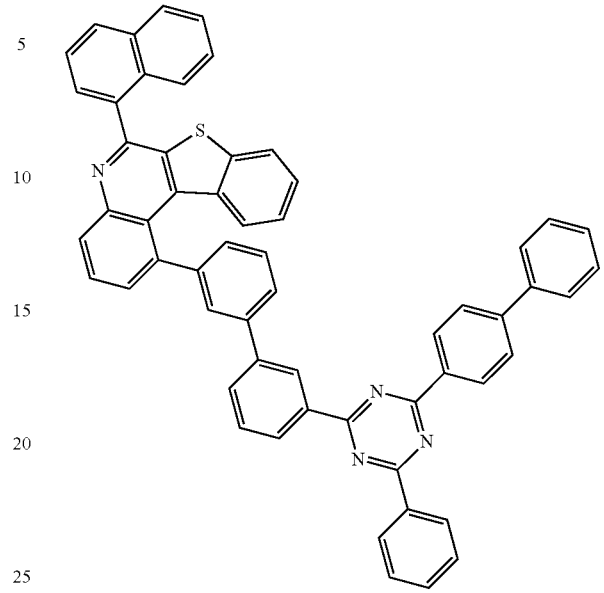
299
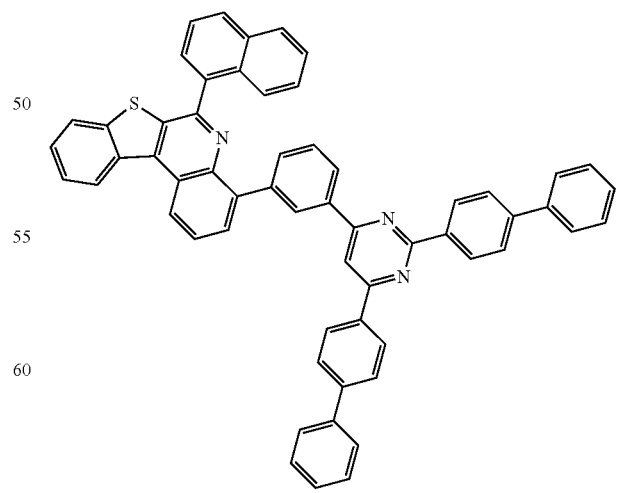

829
-continued
300
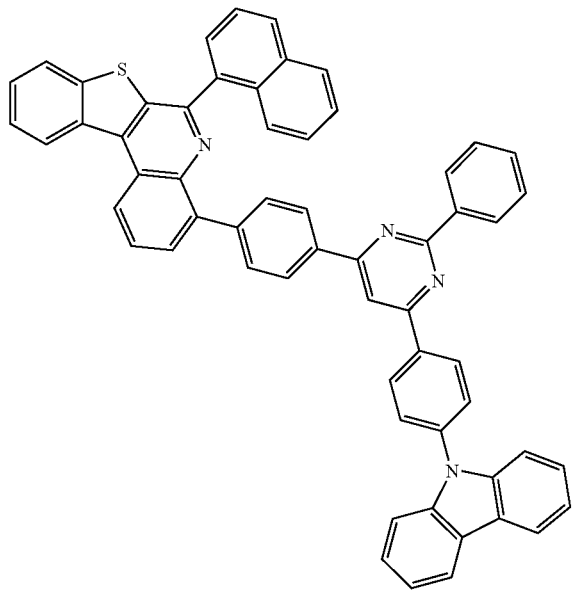
301
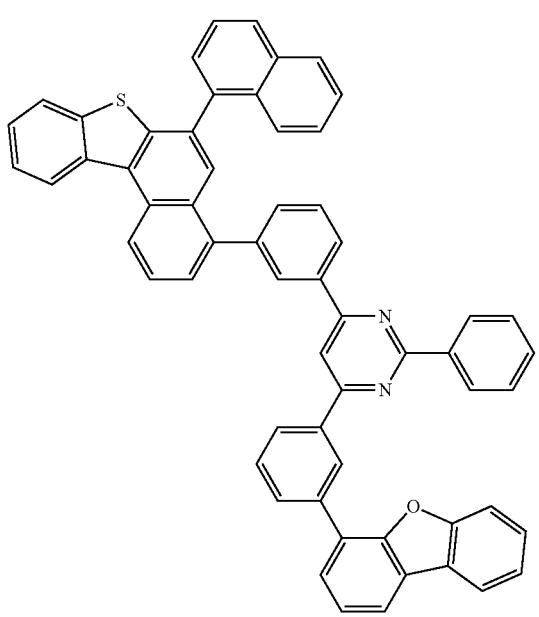
830
-continued
302
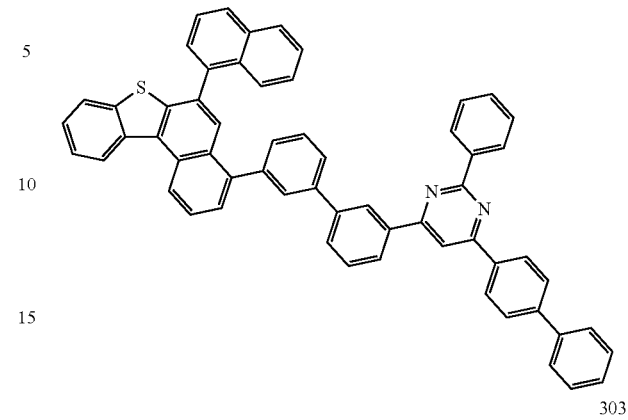
303
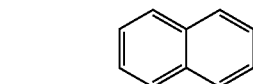
304
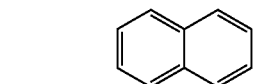

831
-continued
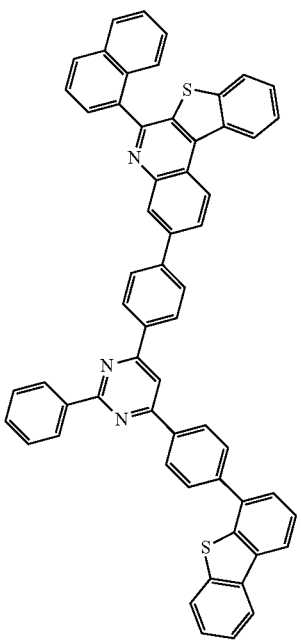
832
-continued
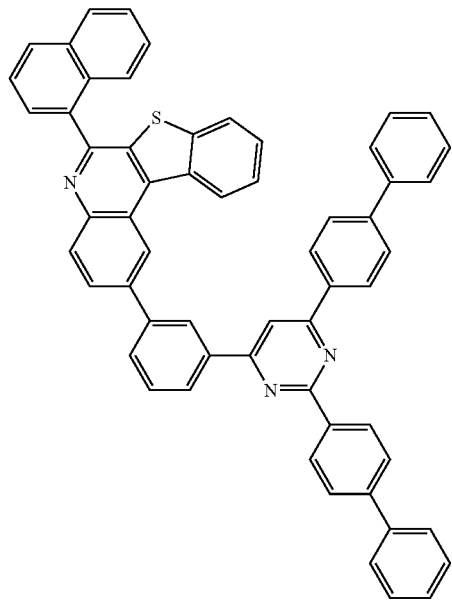
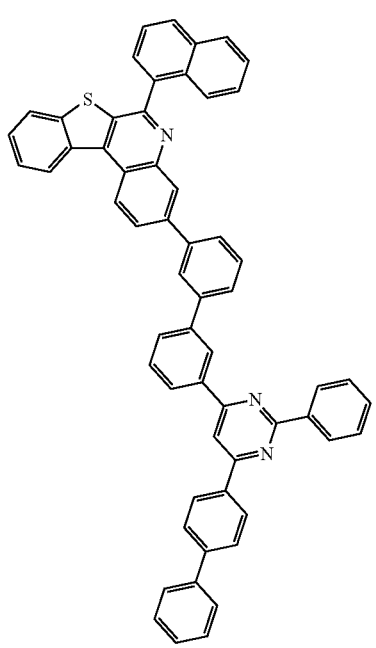
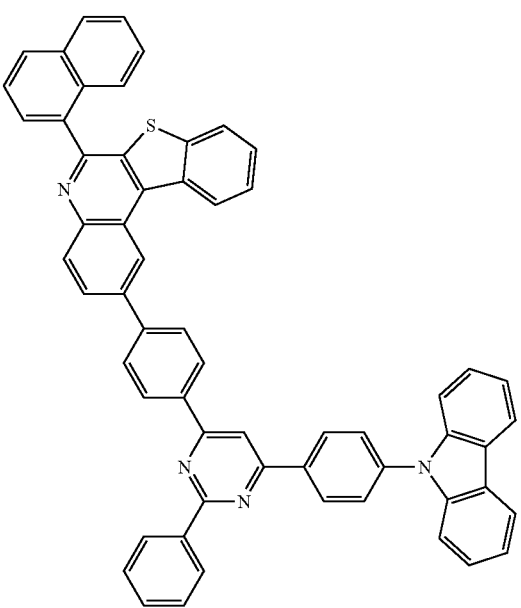

833
-continued
309
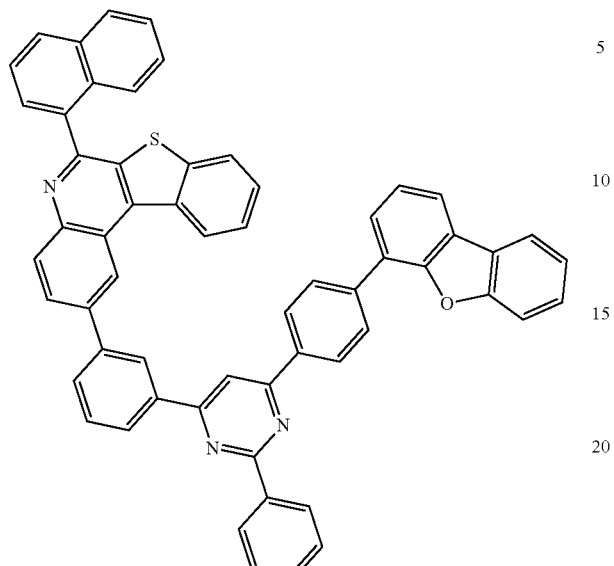
310
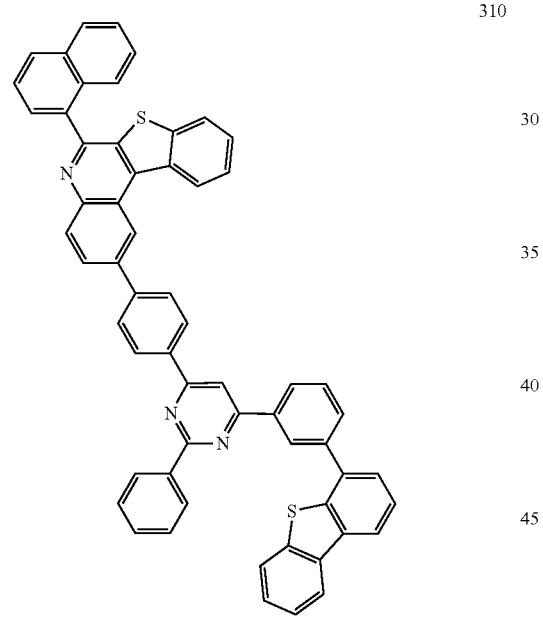
311
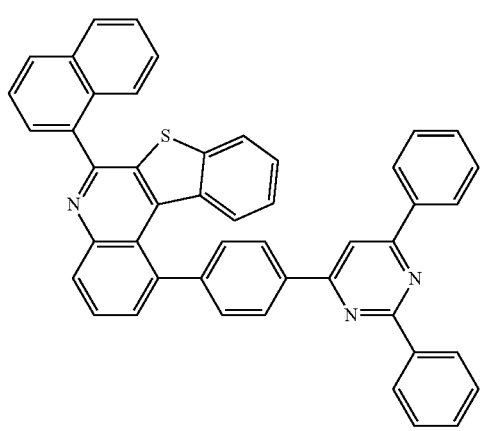
834
-continued
312
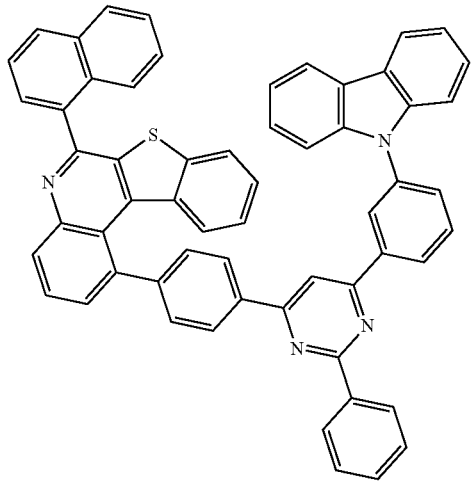
313

835
-continued
314
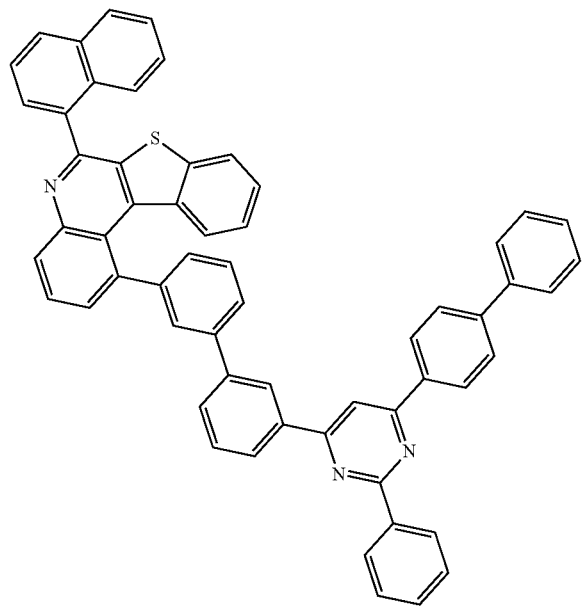
315
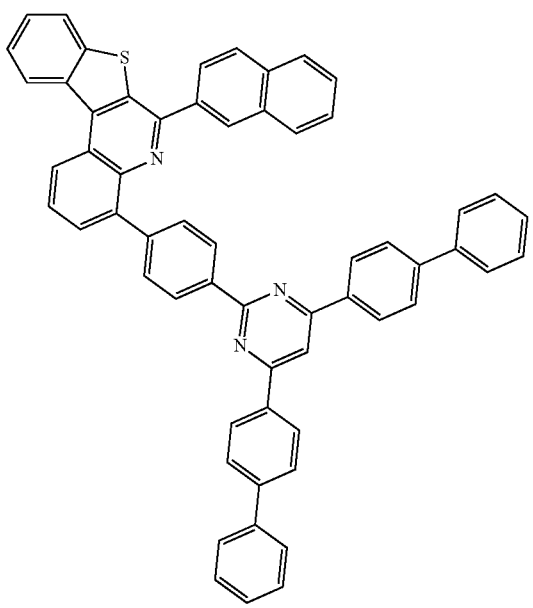
836
-continued
316
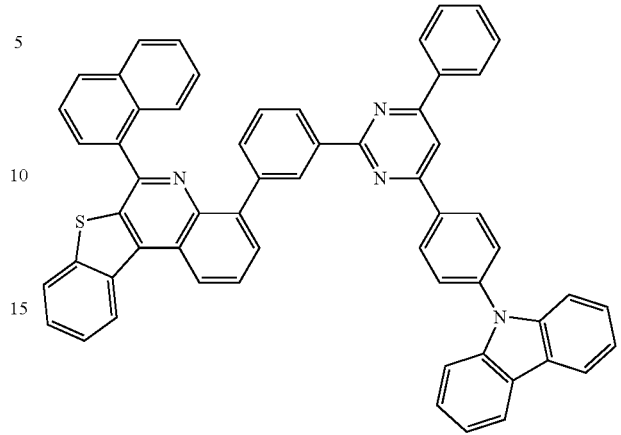
317
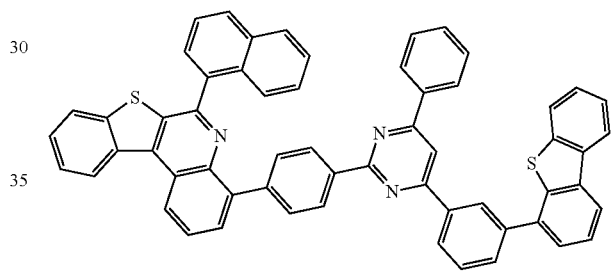
318
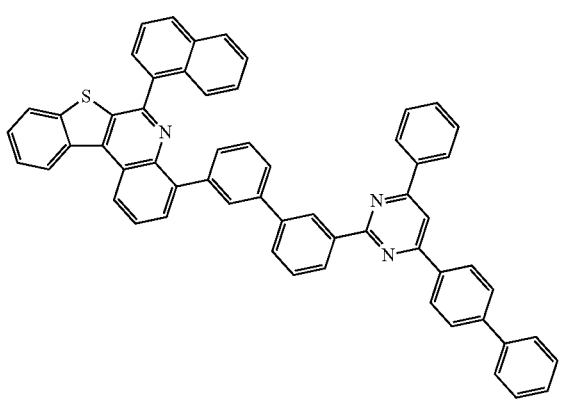

319
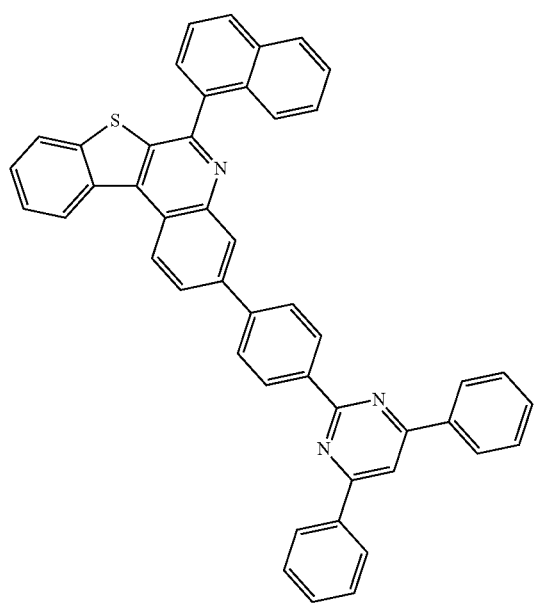
321
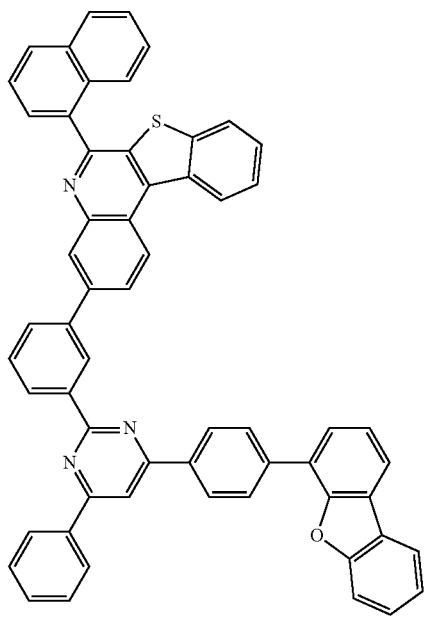
320
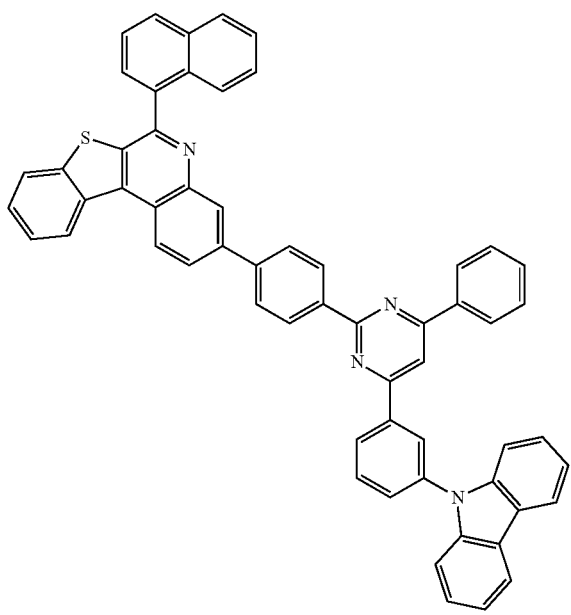
322
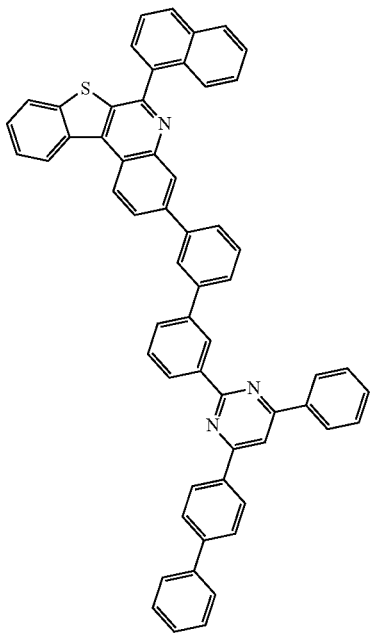

323
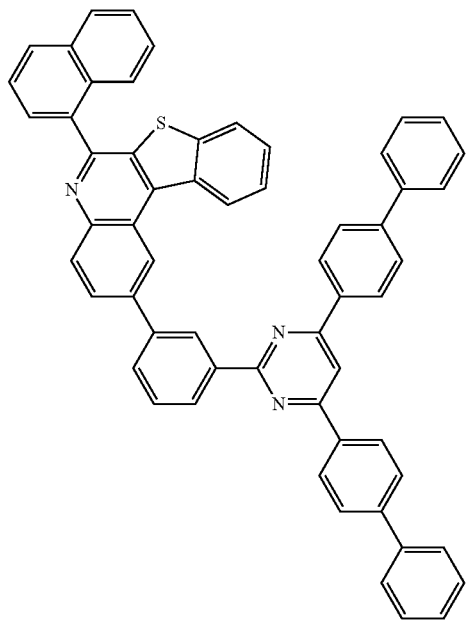
324
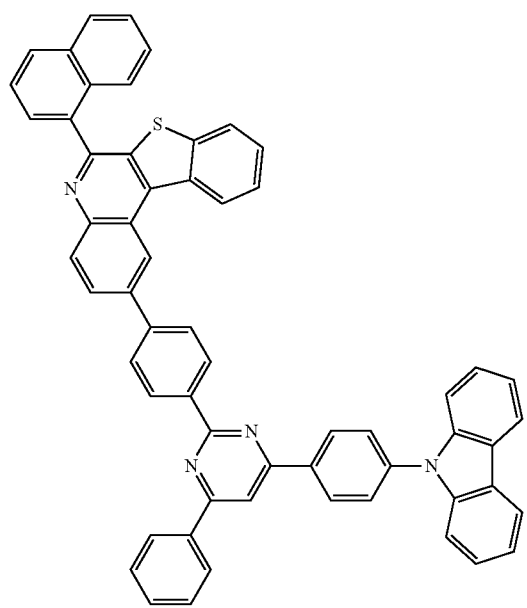
325
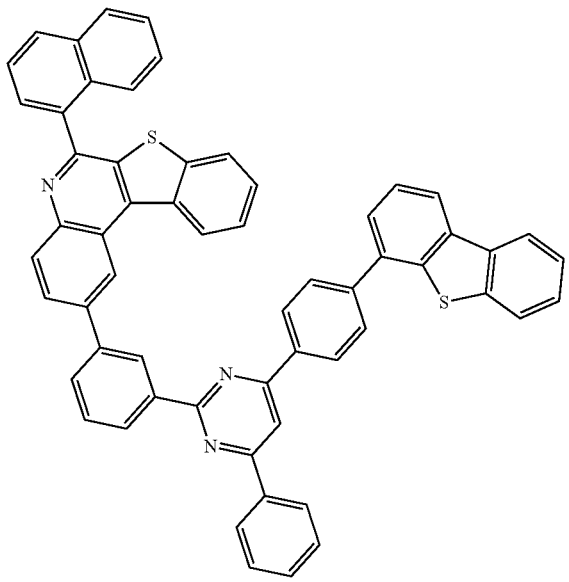
326
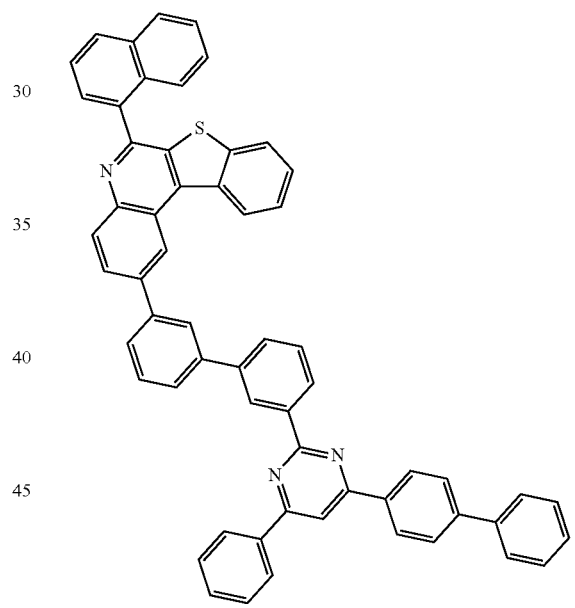
327
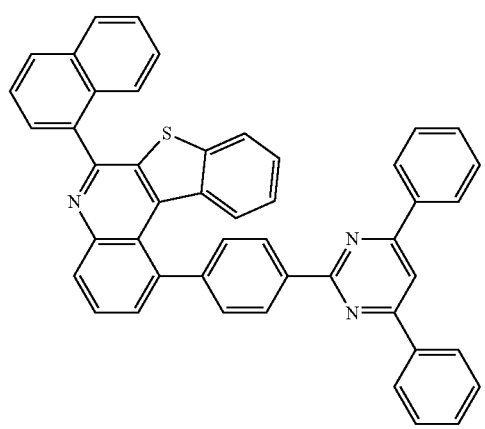

328
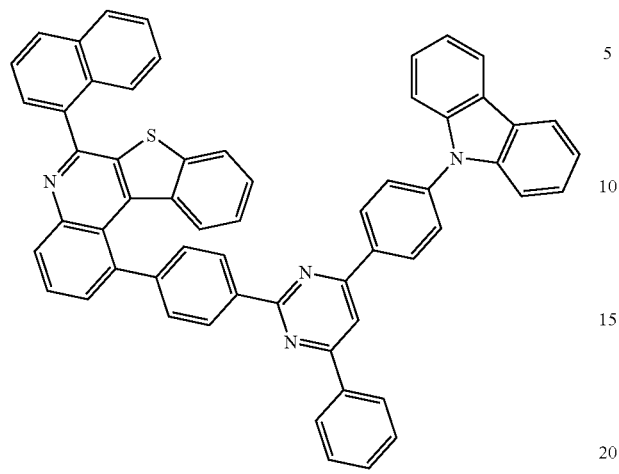
329
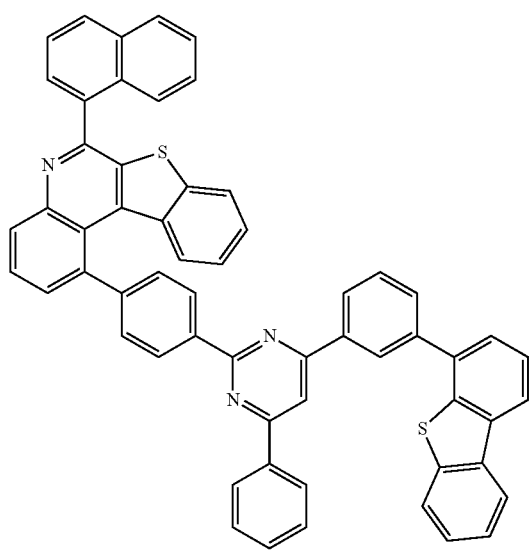
330
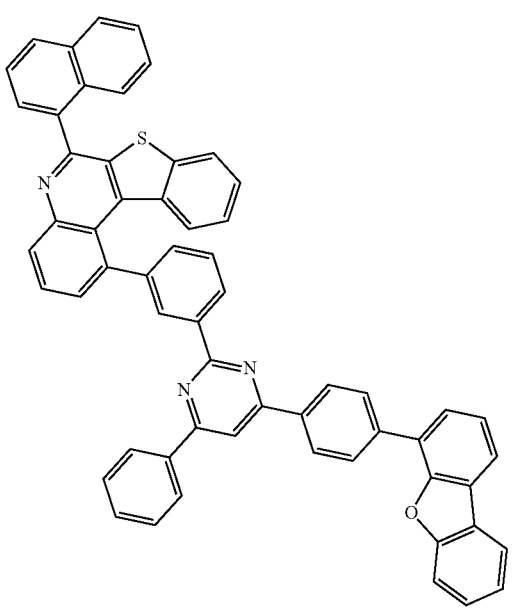
331
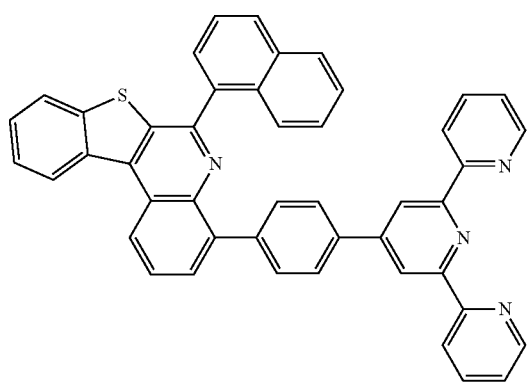
332
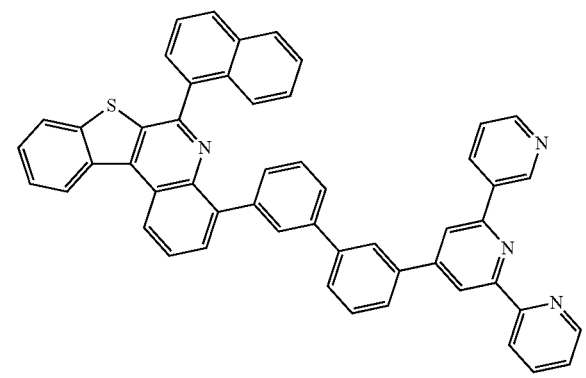
333

-continued
334
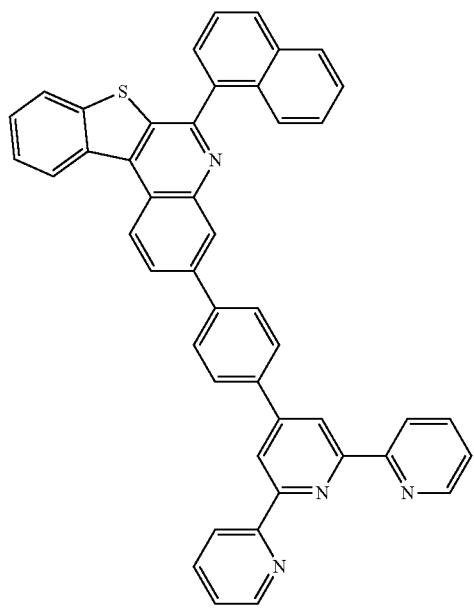
335
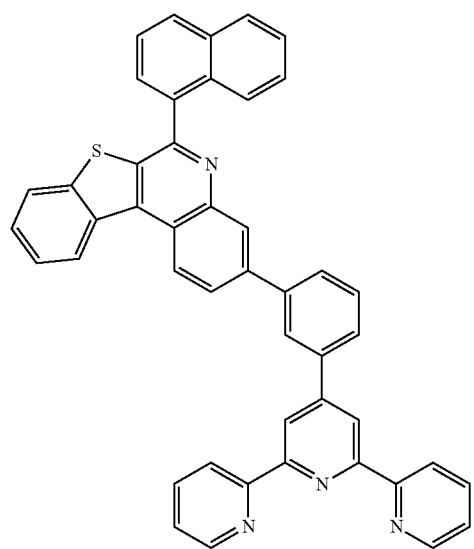
-continued
336
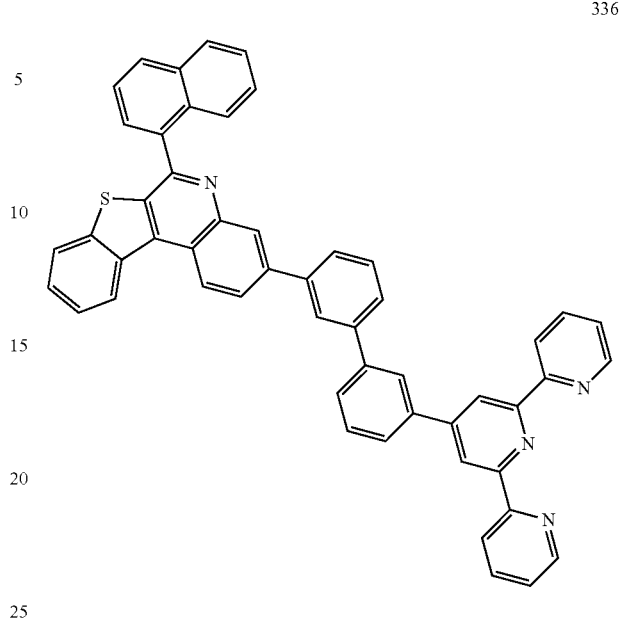
337
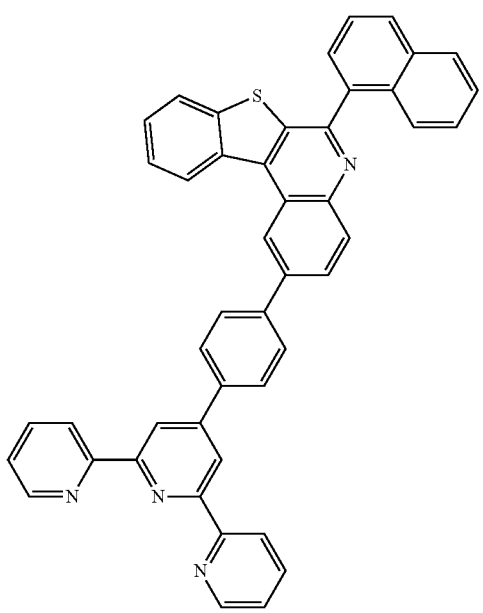

338
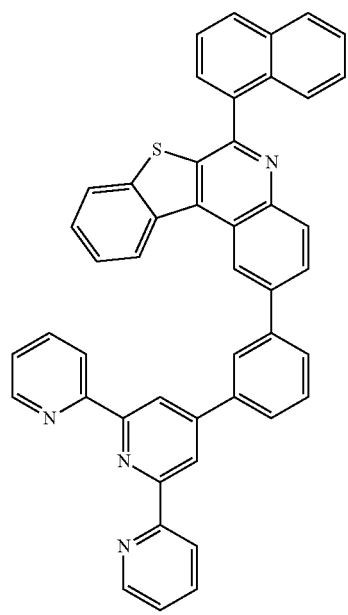
339
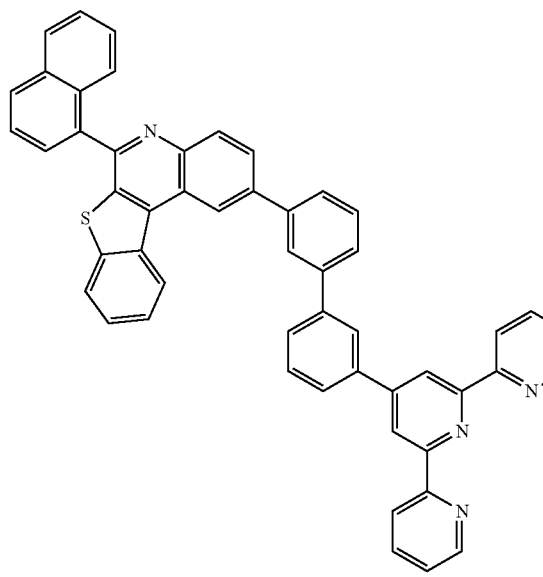
340
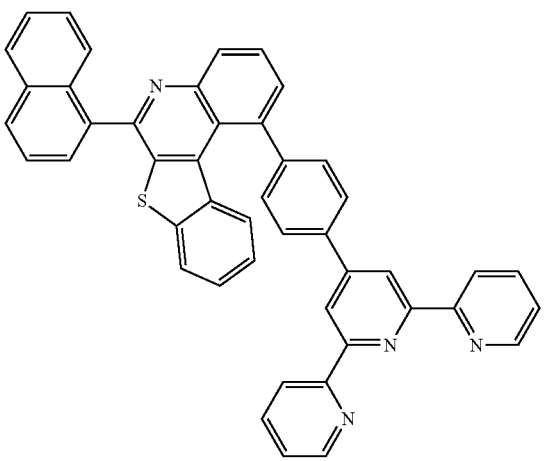
341
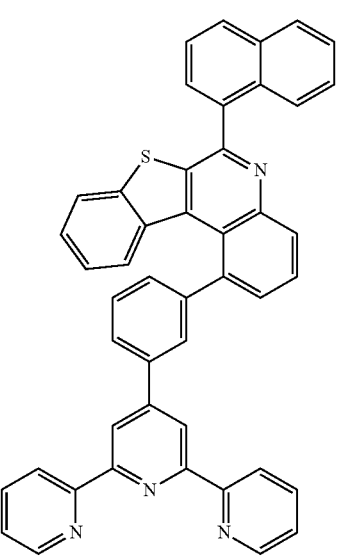
342
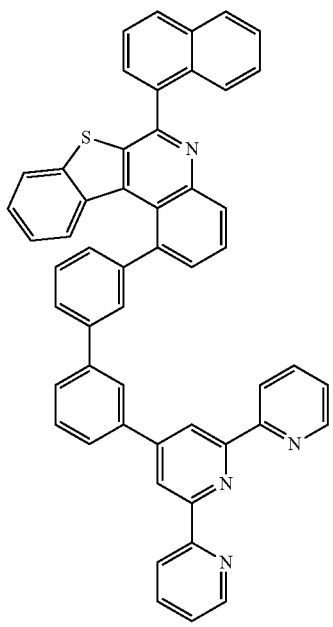

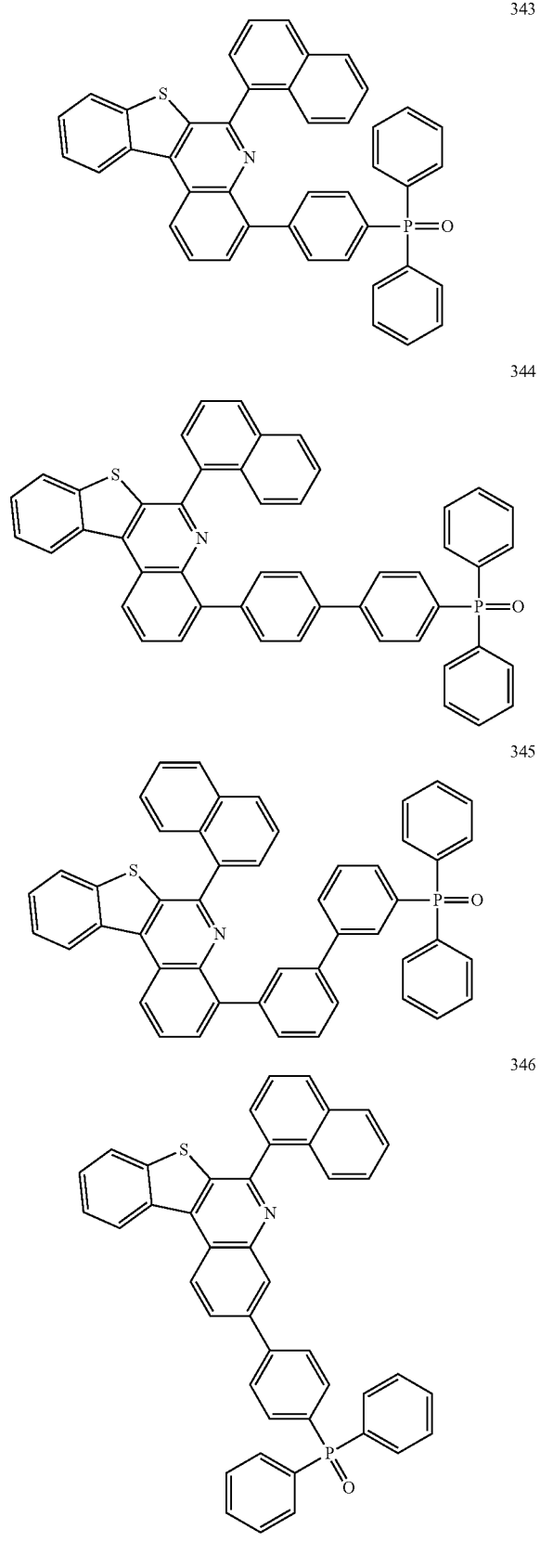
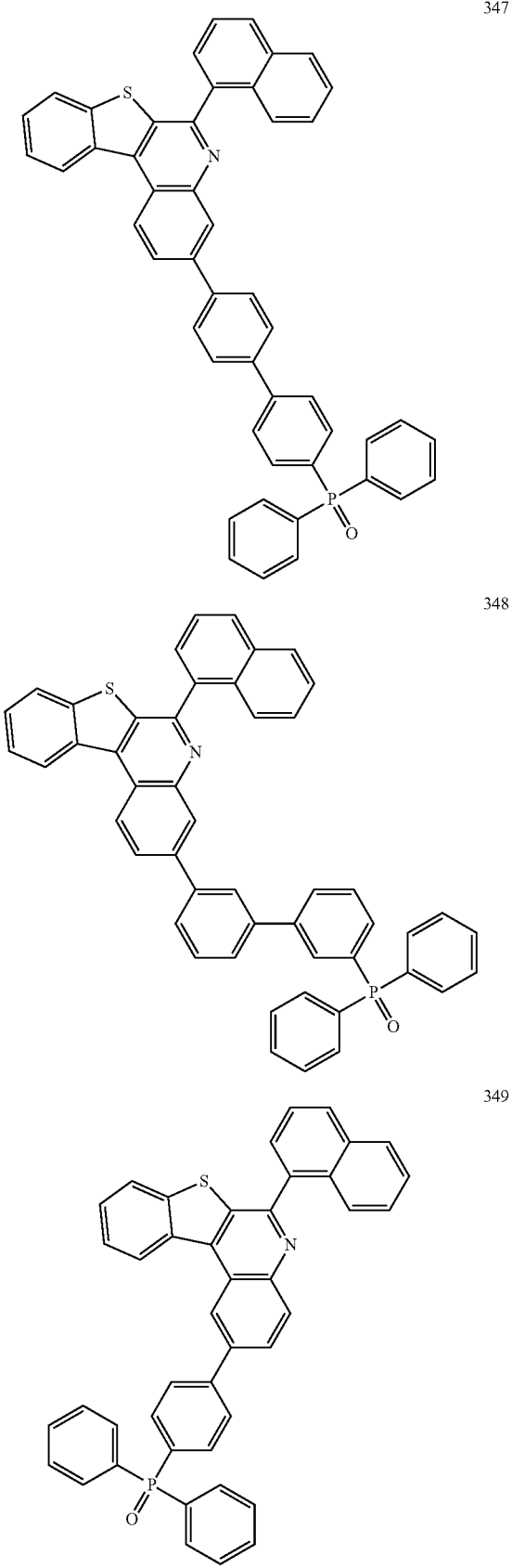

849
-continued
350
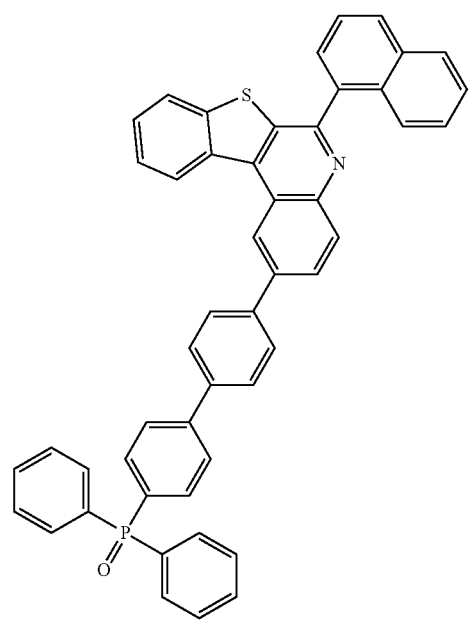
351
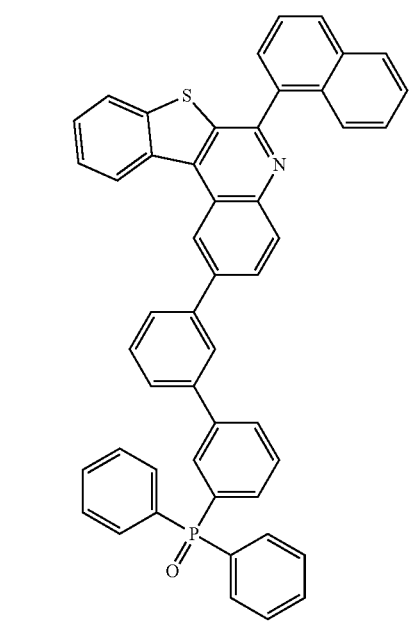
352
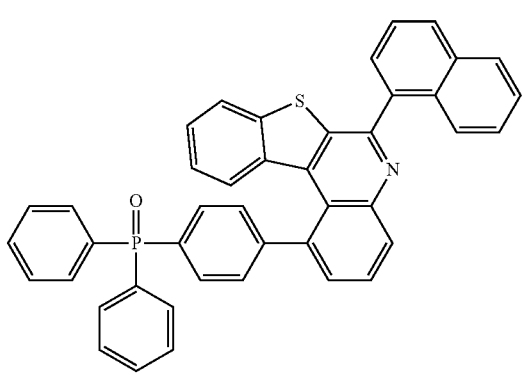
850
-continued
353
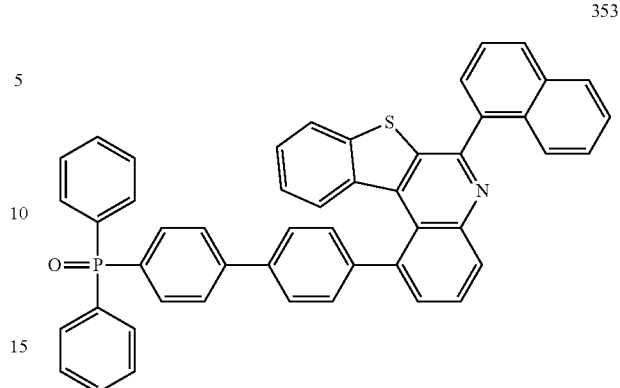
354
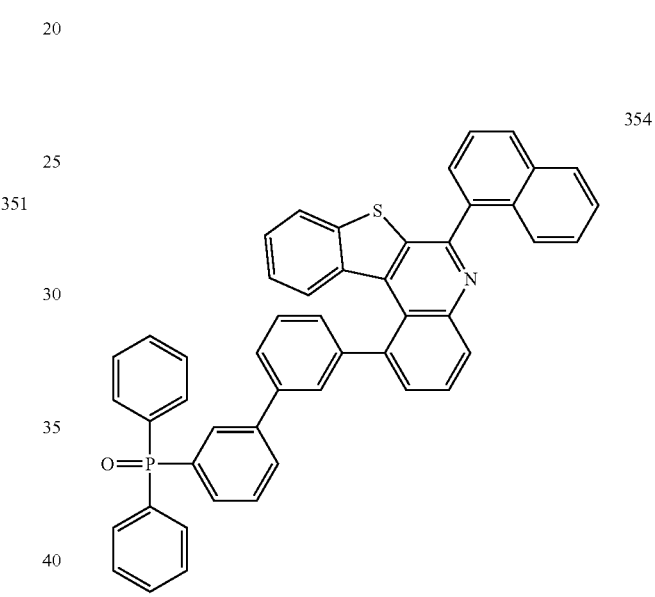
355
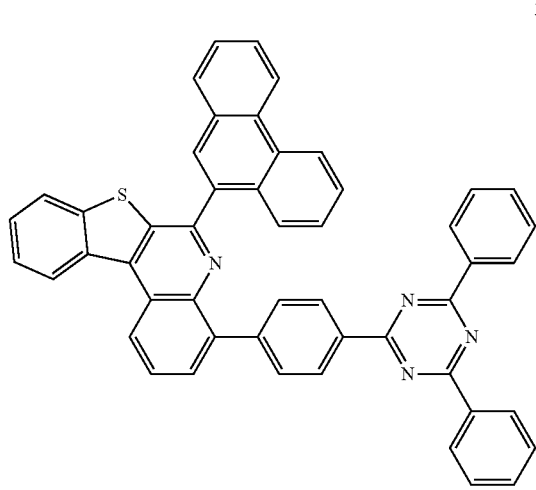

851
-continued
356
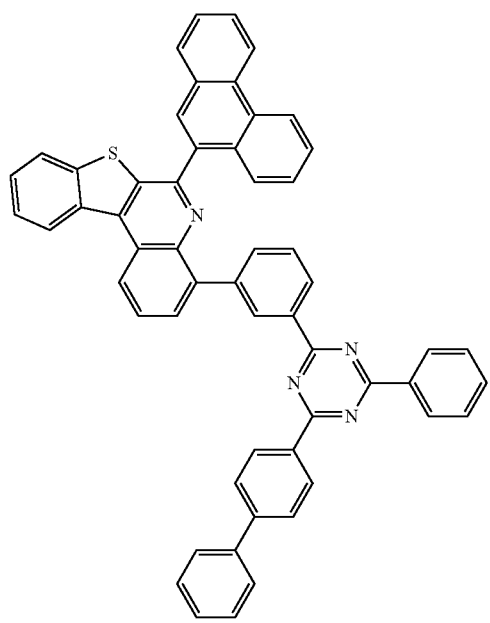
357
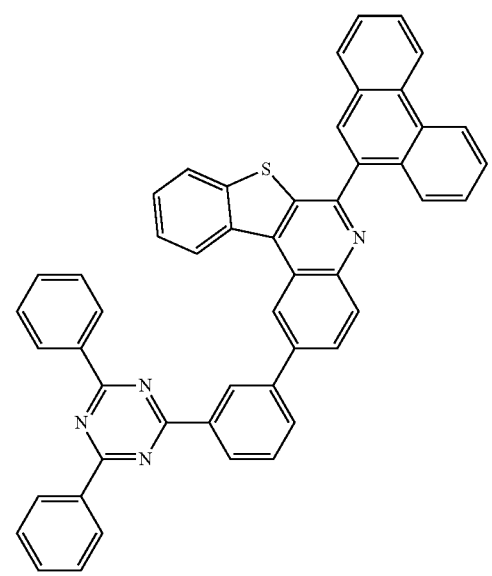
852
-continued
358
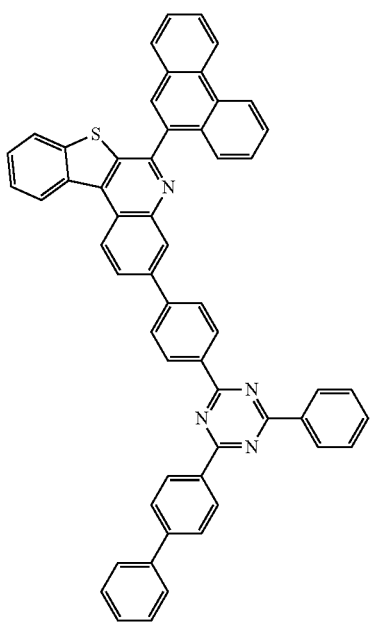
359

853
-continued
360
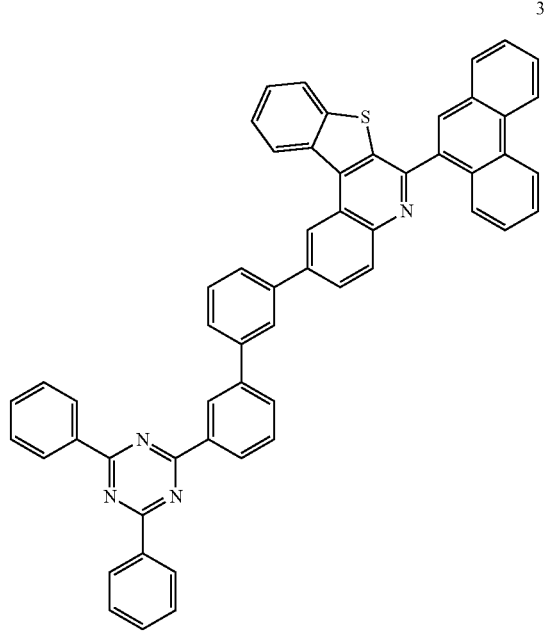
361
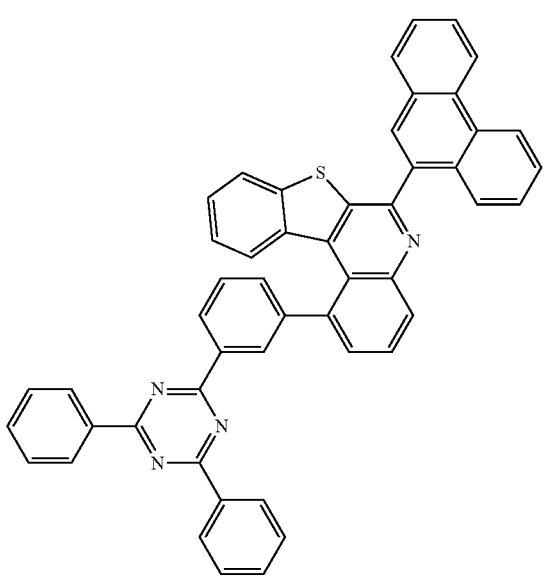
854
-continued
362
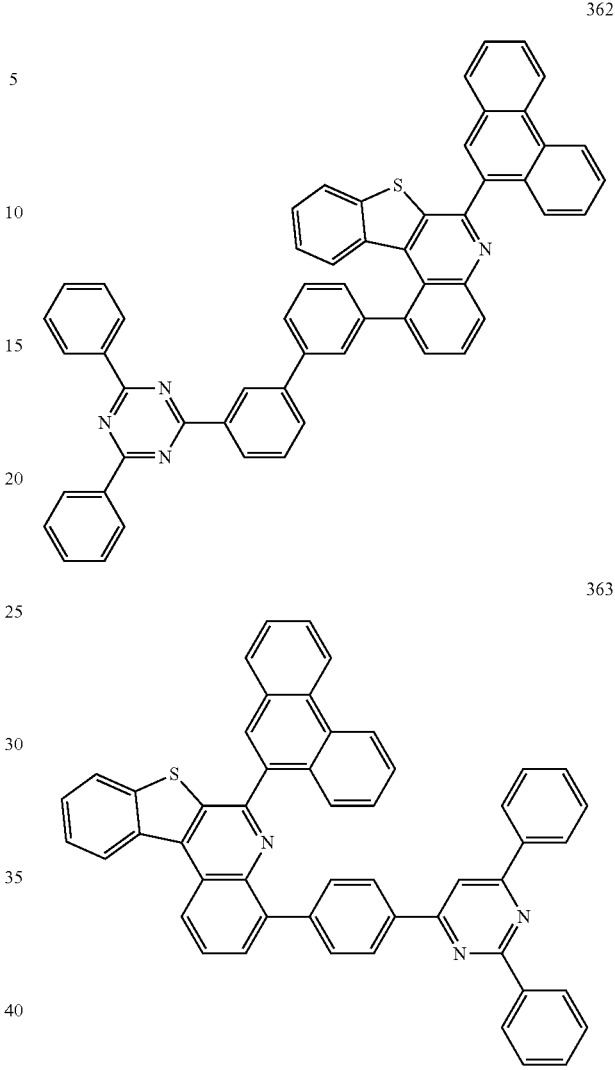
363
364
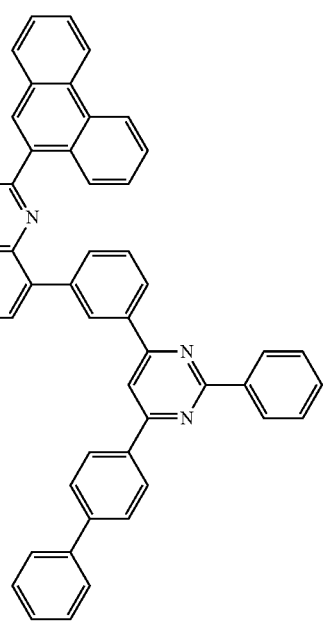

855
-continued
365
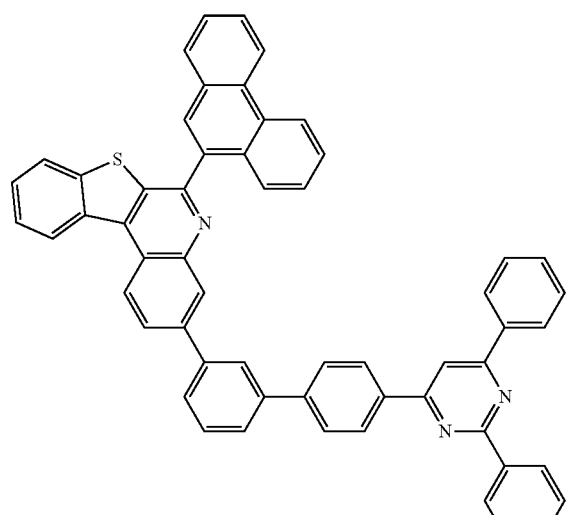
366
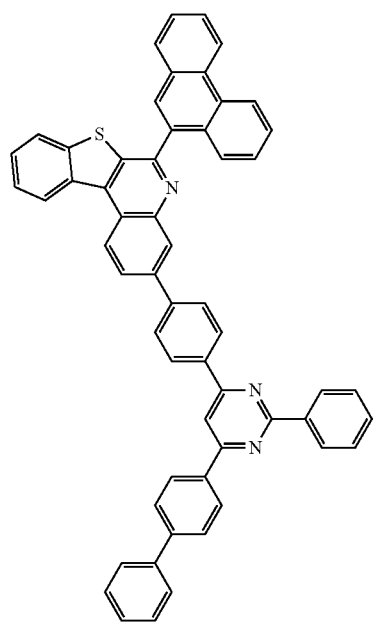
856
-continued
367
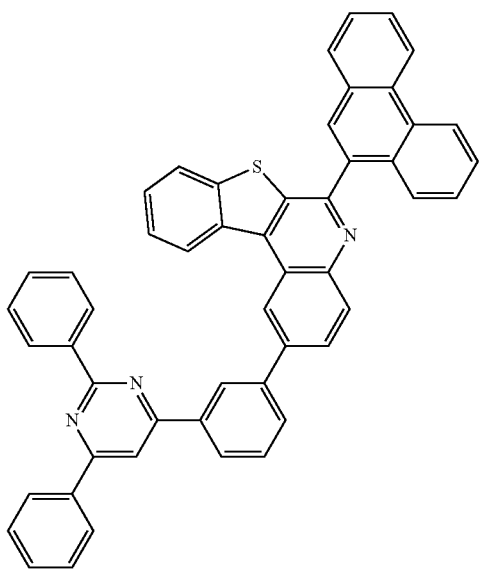
368
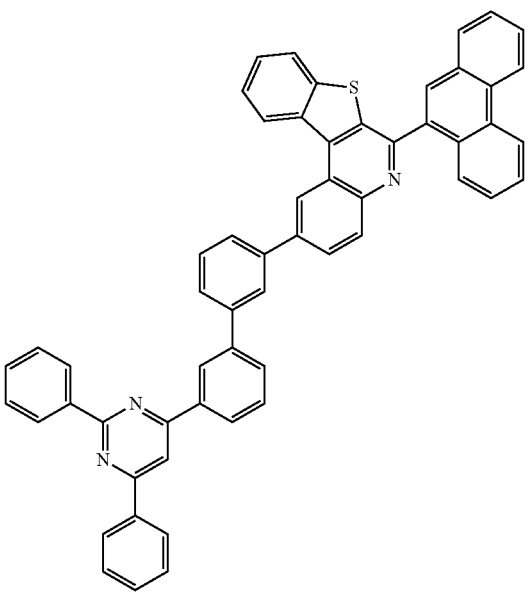

369
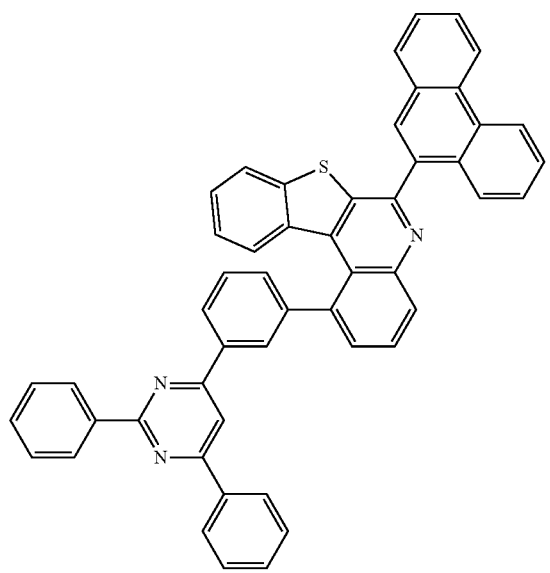
370
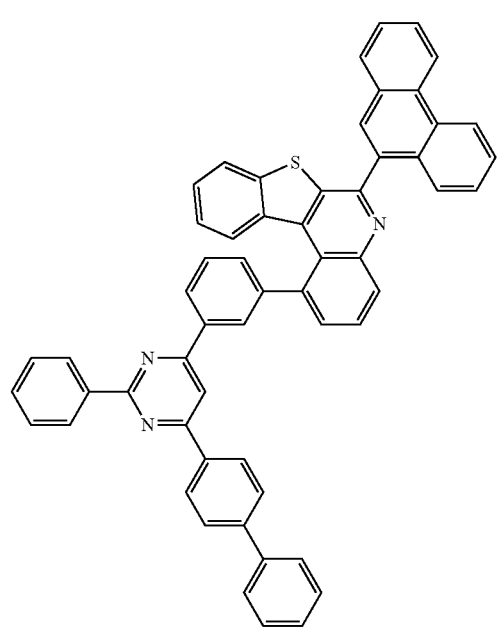
371
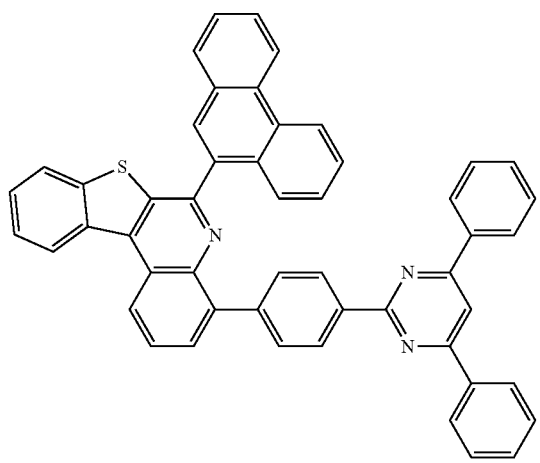
372
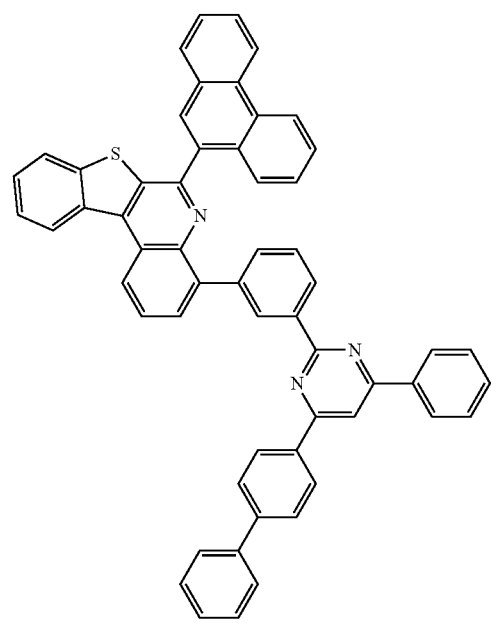
373

| 374 | 376 |
|---|---|
| 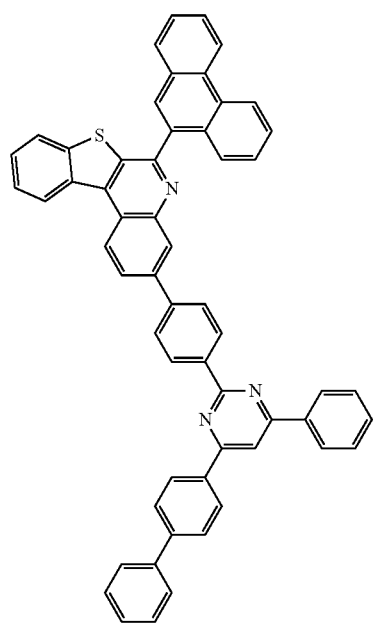 | 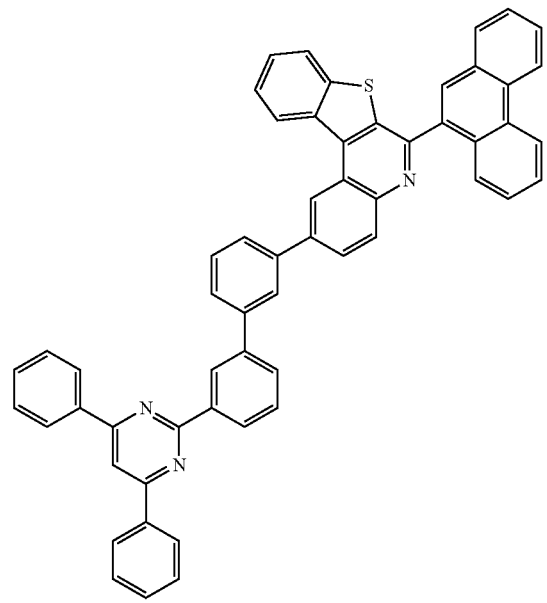 |
| 375 | 377 |
| 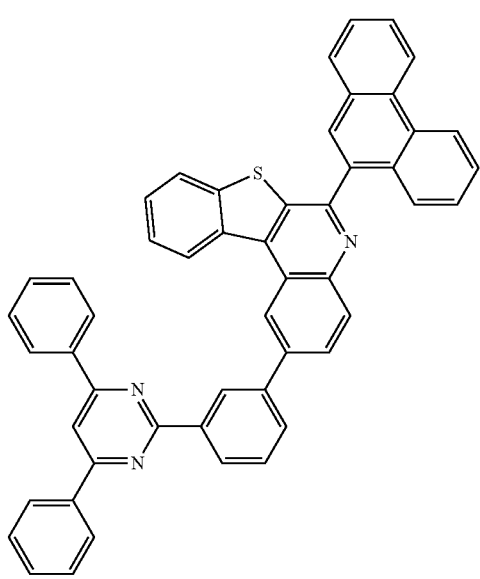 | 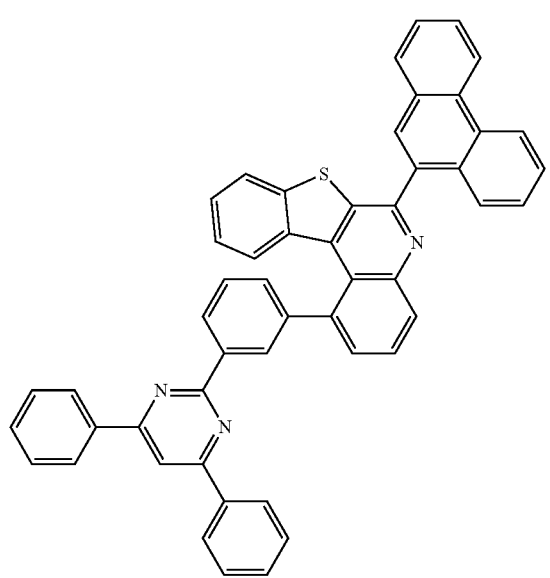 |

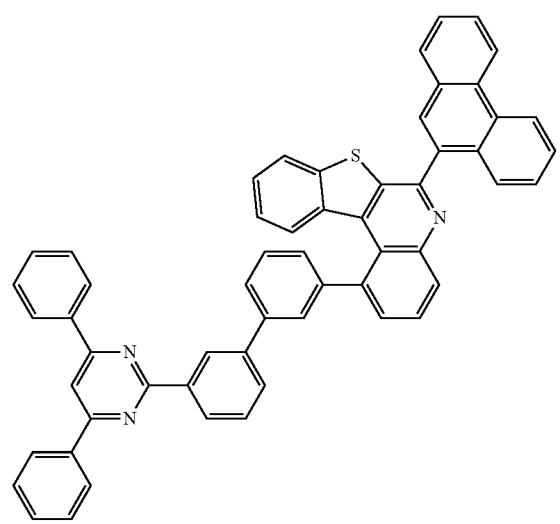
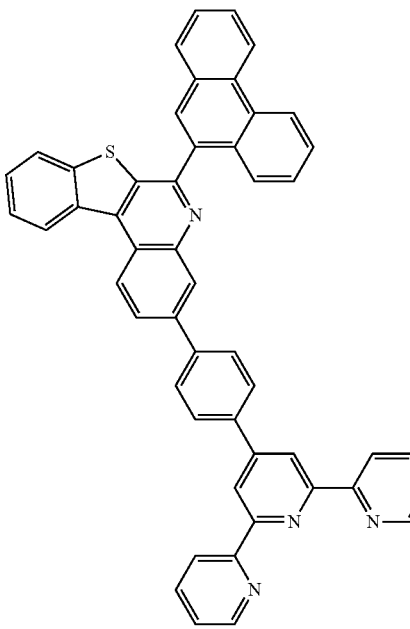
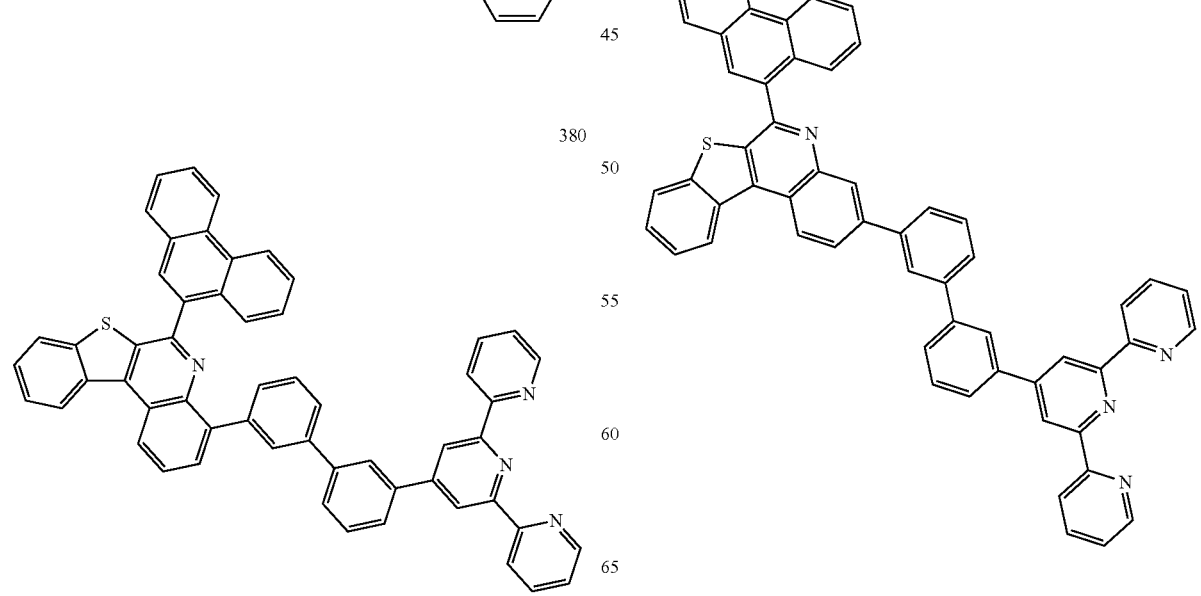

-continued
383
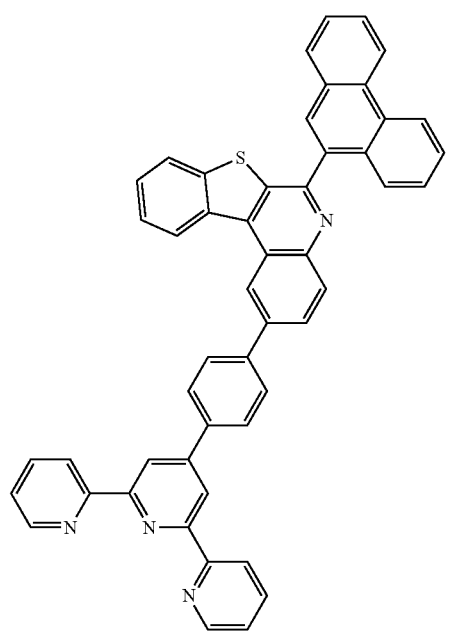
385
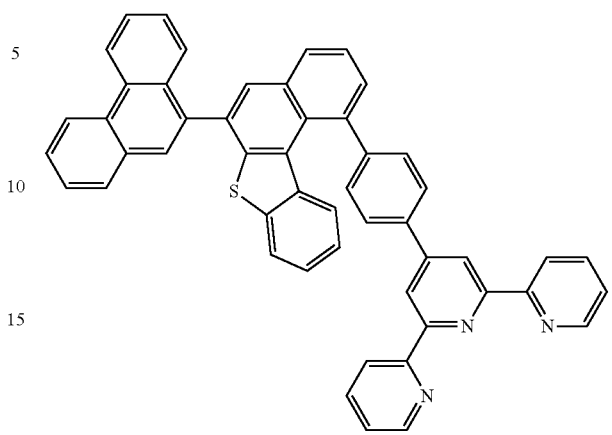
386
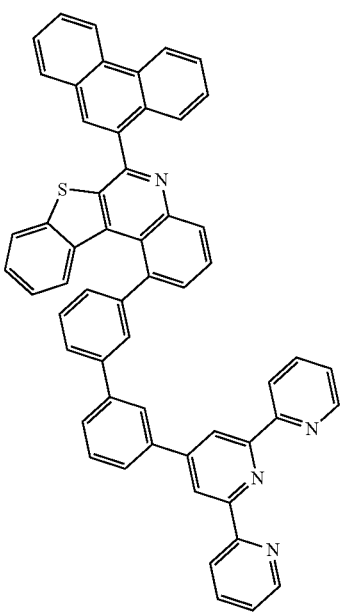
384
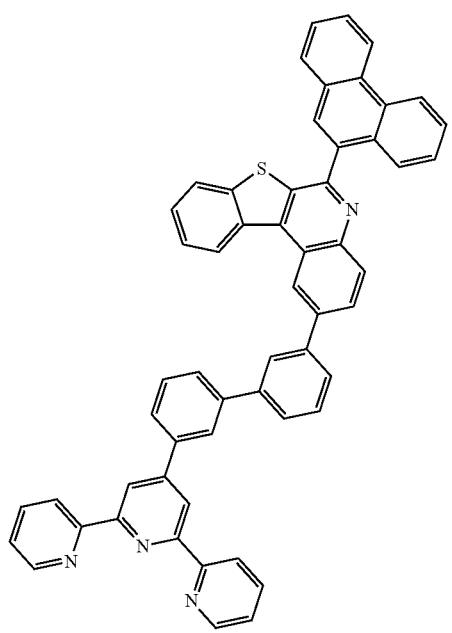
387
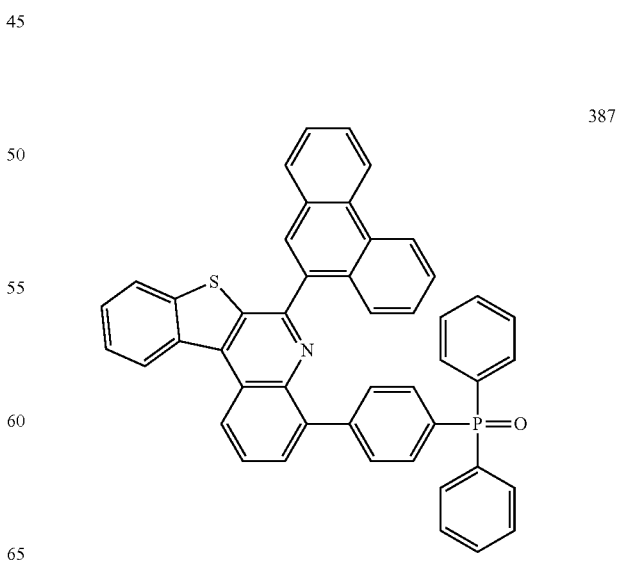

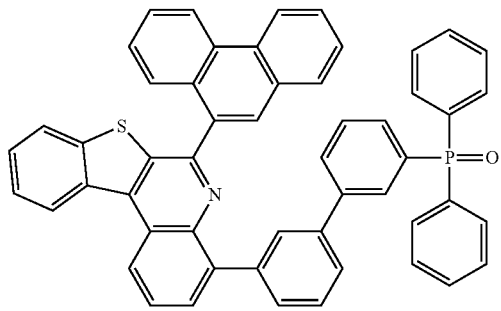
388
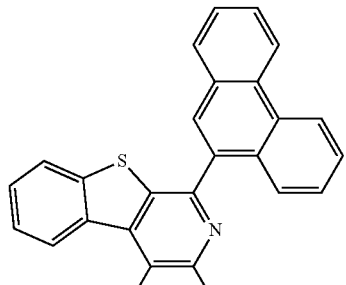
389
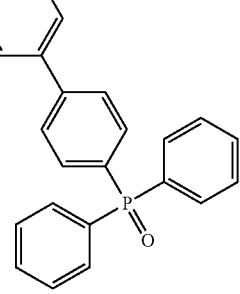
390
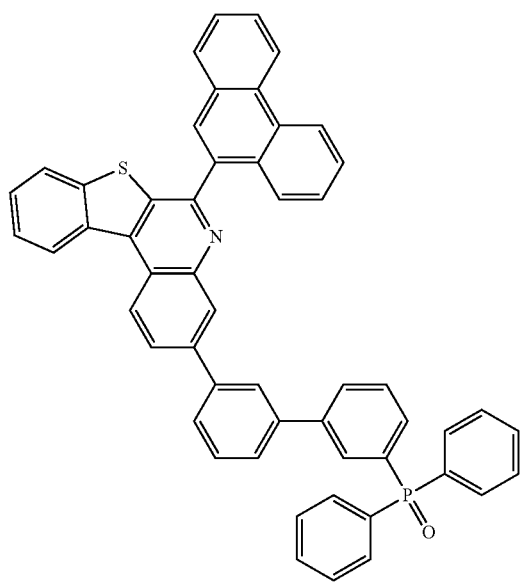
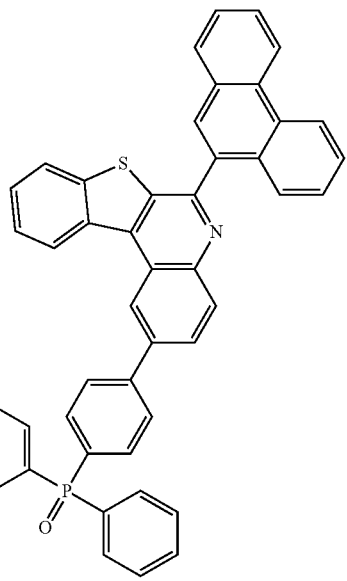
391
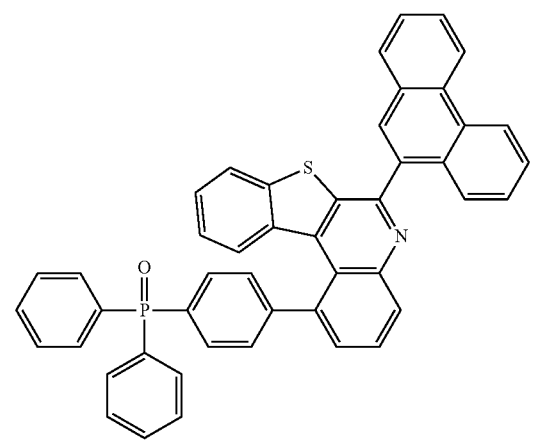
393
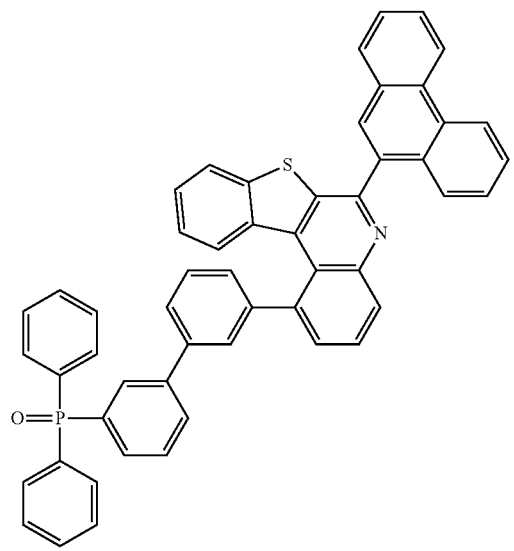
394

867
-continued
395
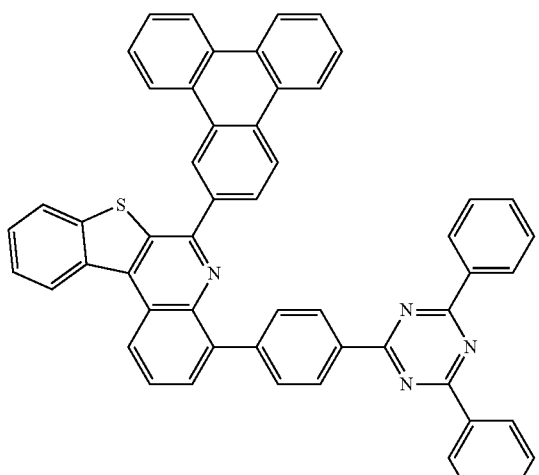
396
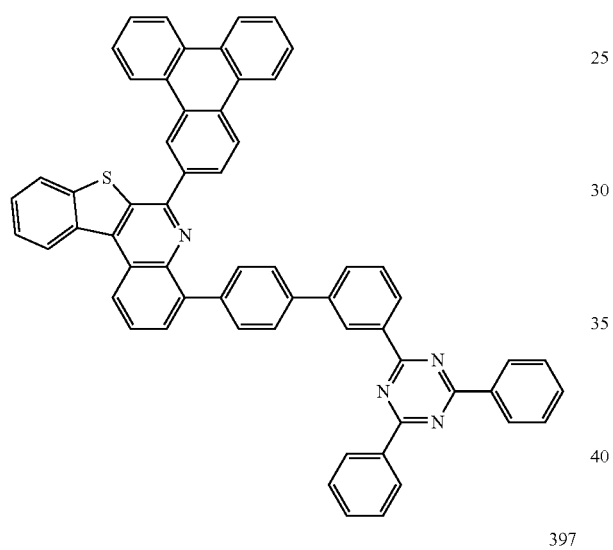
397
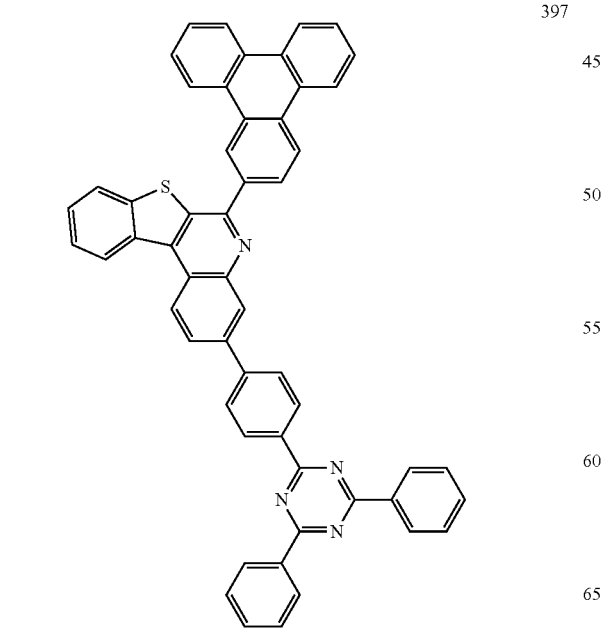
868
-continued
398
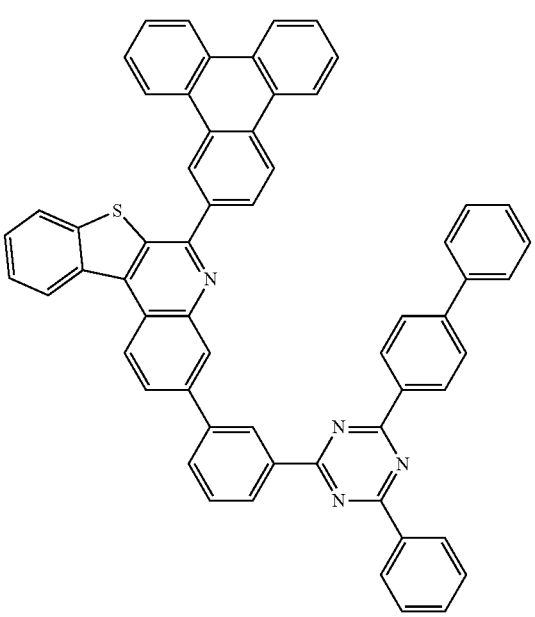
399
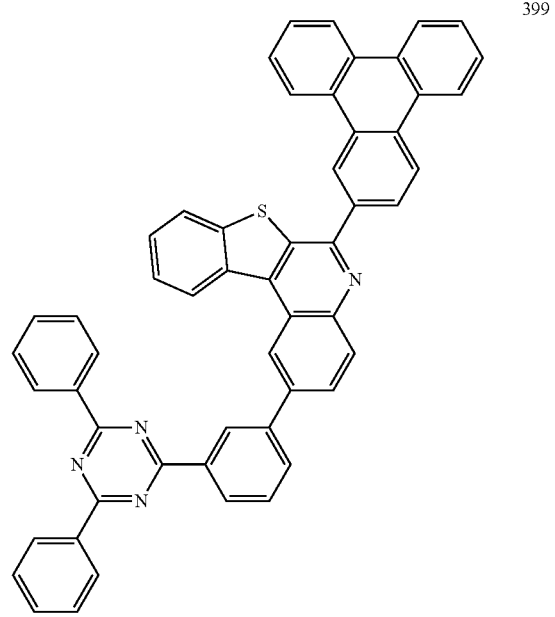

869
-continued
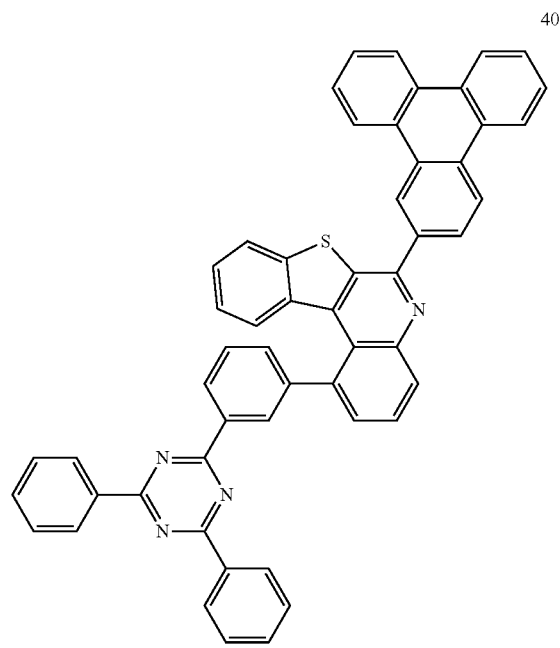
400
870
-continued
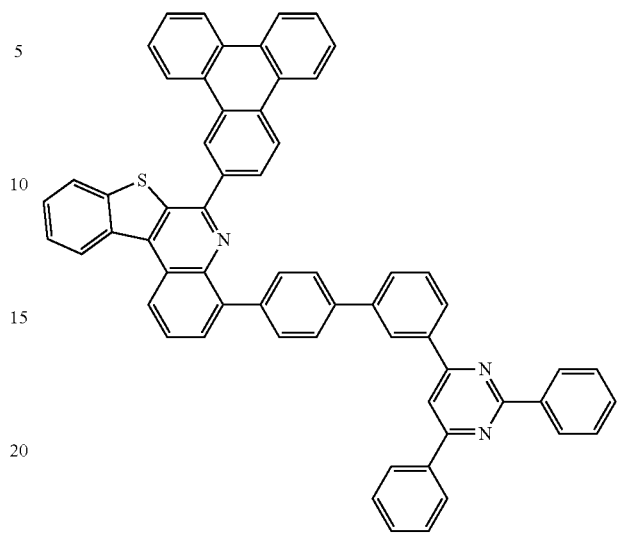
402
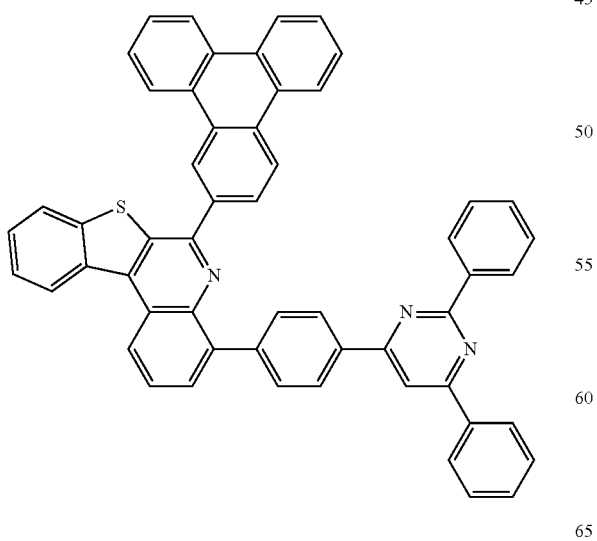
401
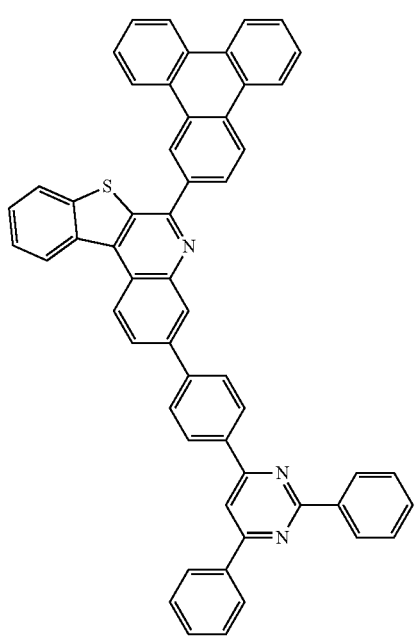
403

871
-continued
404
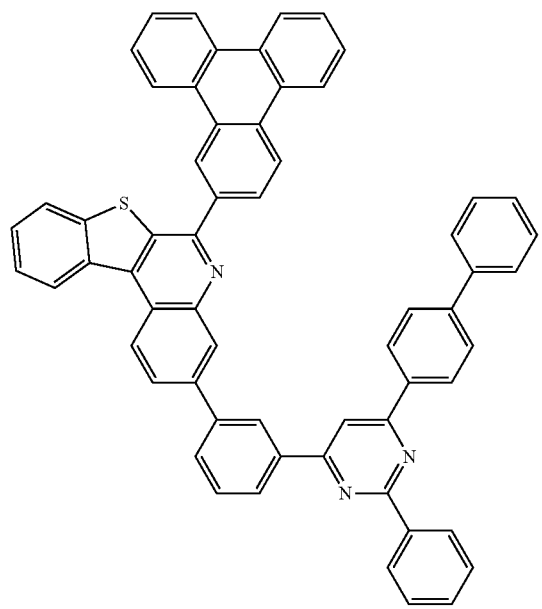
405
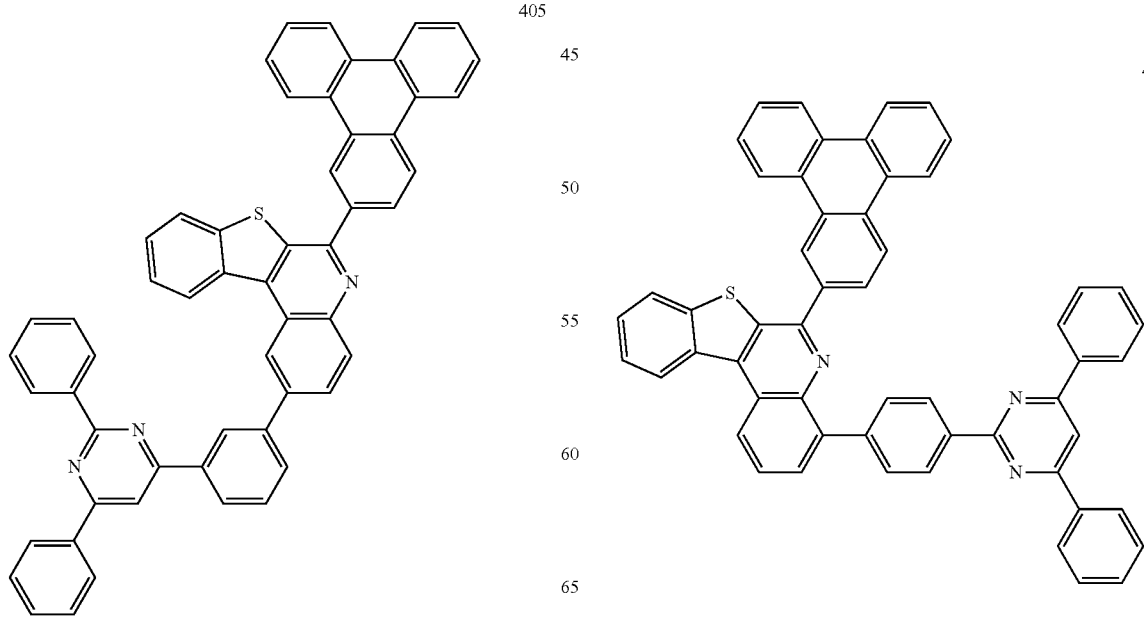
872
-continued
406
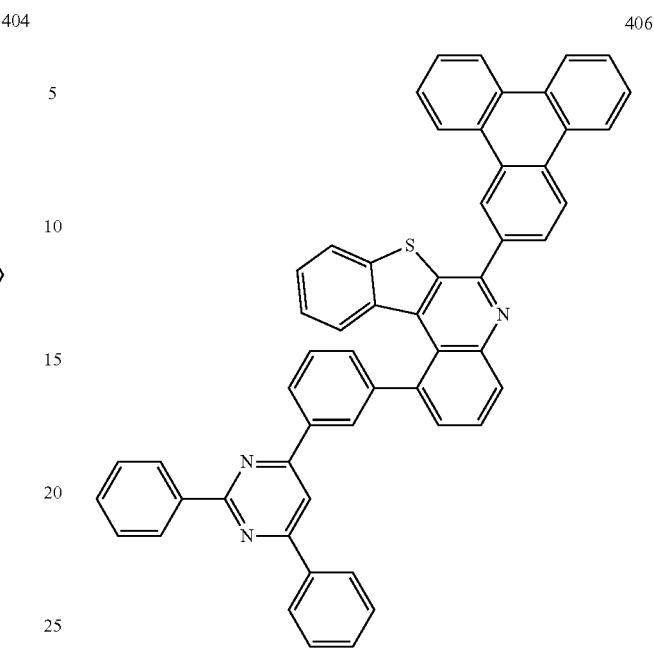
407

873
-continued
408
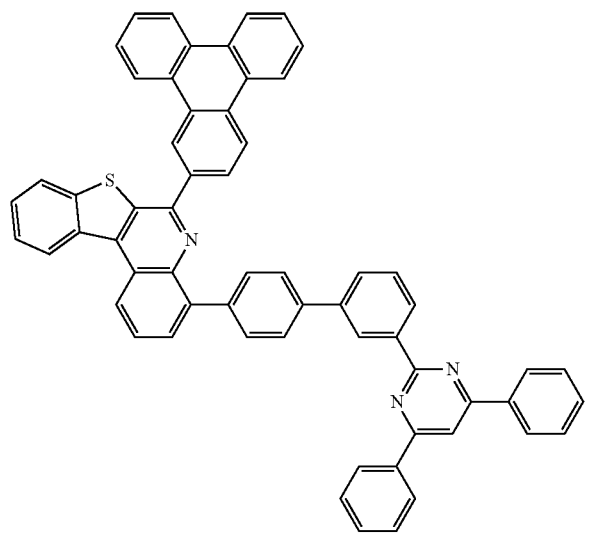
409
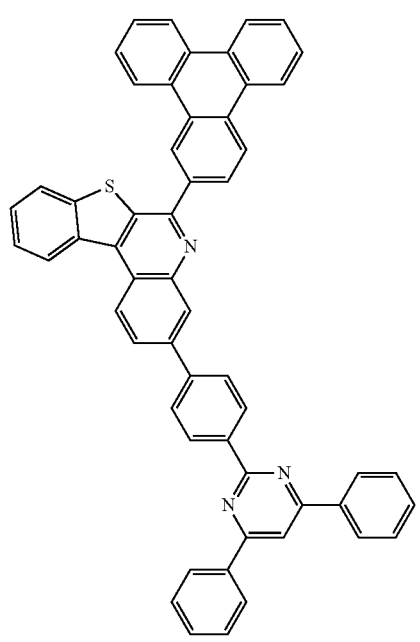 [SMILES: c1ccc(-c2nc(-c3ccccc3)nc(-c3ccc(-c4ccc5c(c4)nc(-c4ccc6c7ccccc7c7ccccc7c6c4)c4oc6ccccc6c45)cc3)n2)cc1]
874
-continued
410
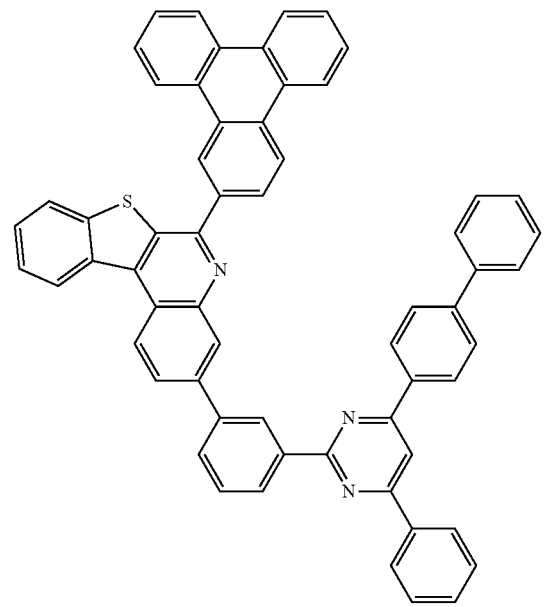
411
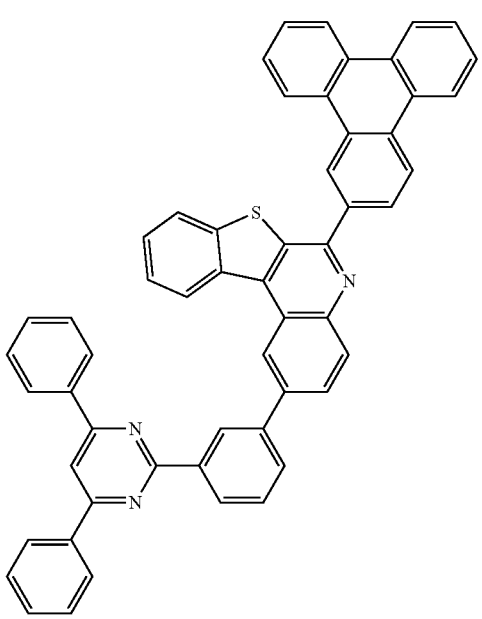

875
-continued
876
-continued
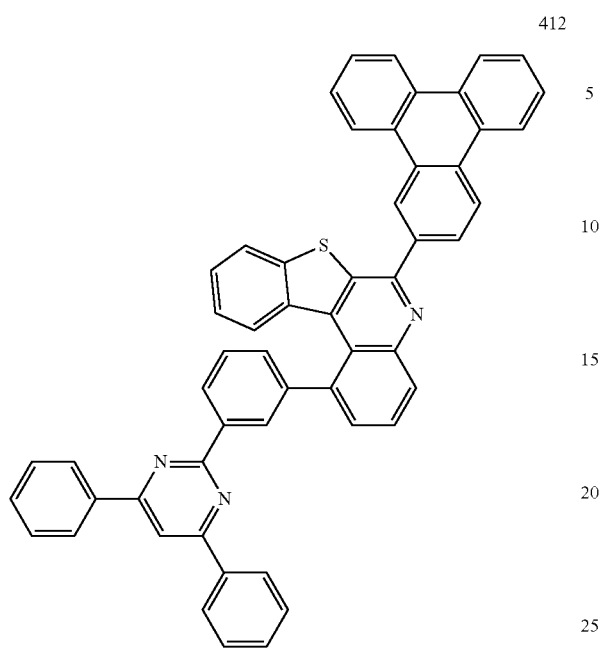
412
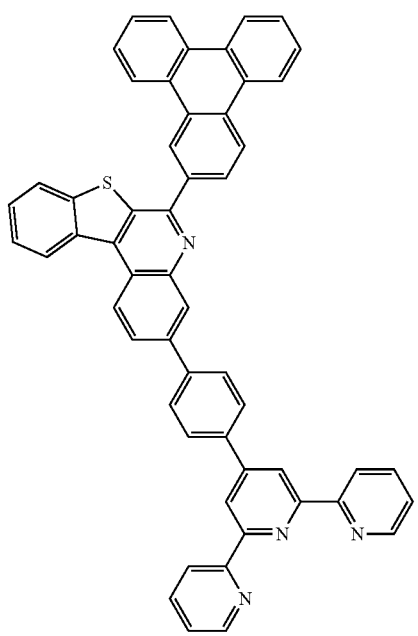
414
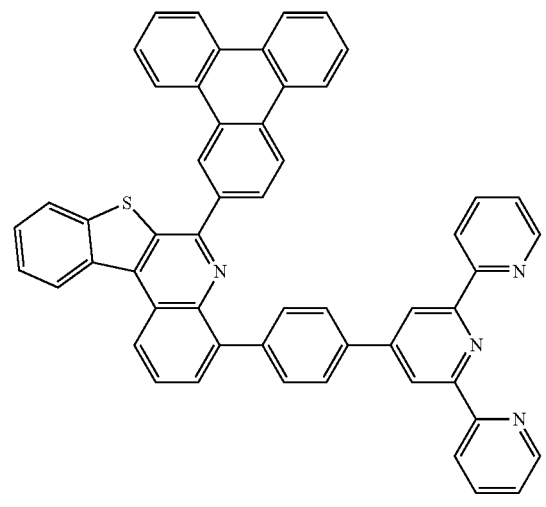
413
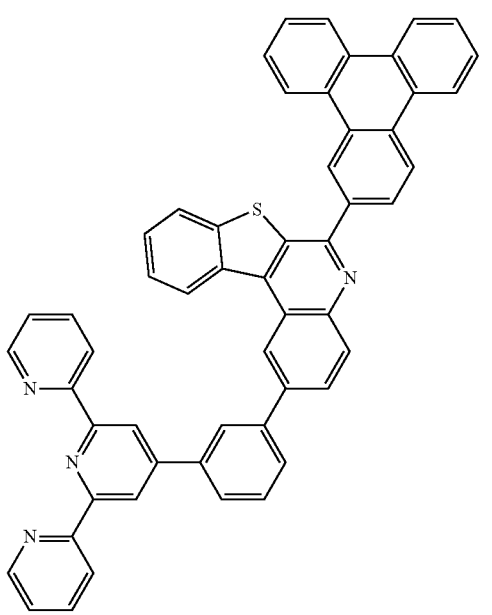
415

877
-continued
416
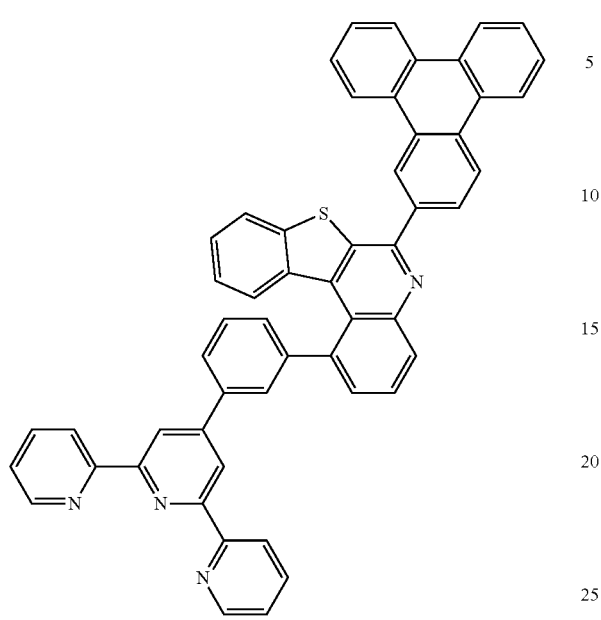
878
-continued
418
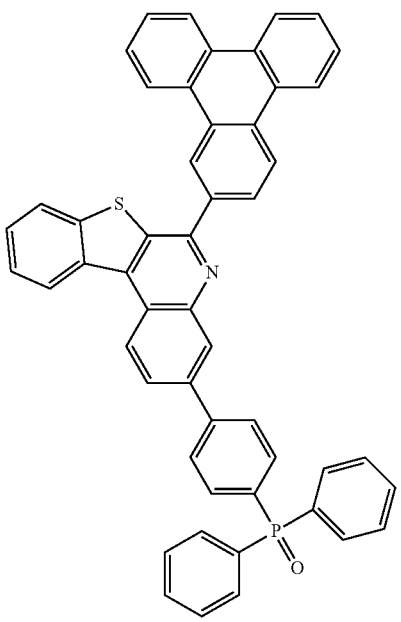
417

419
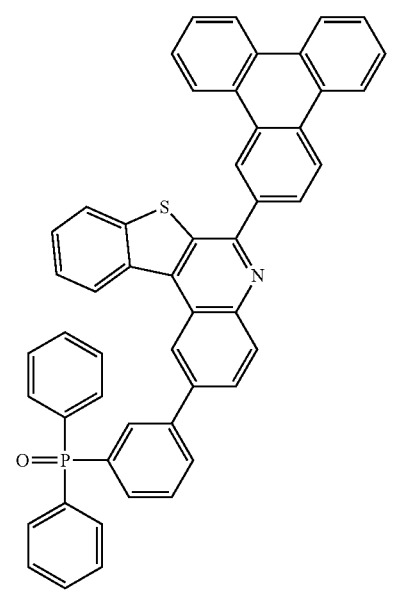

879
-continued
880
-continued
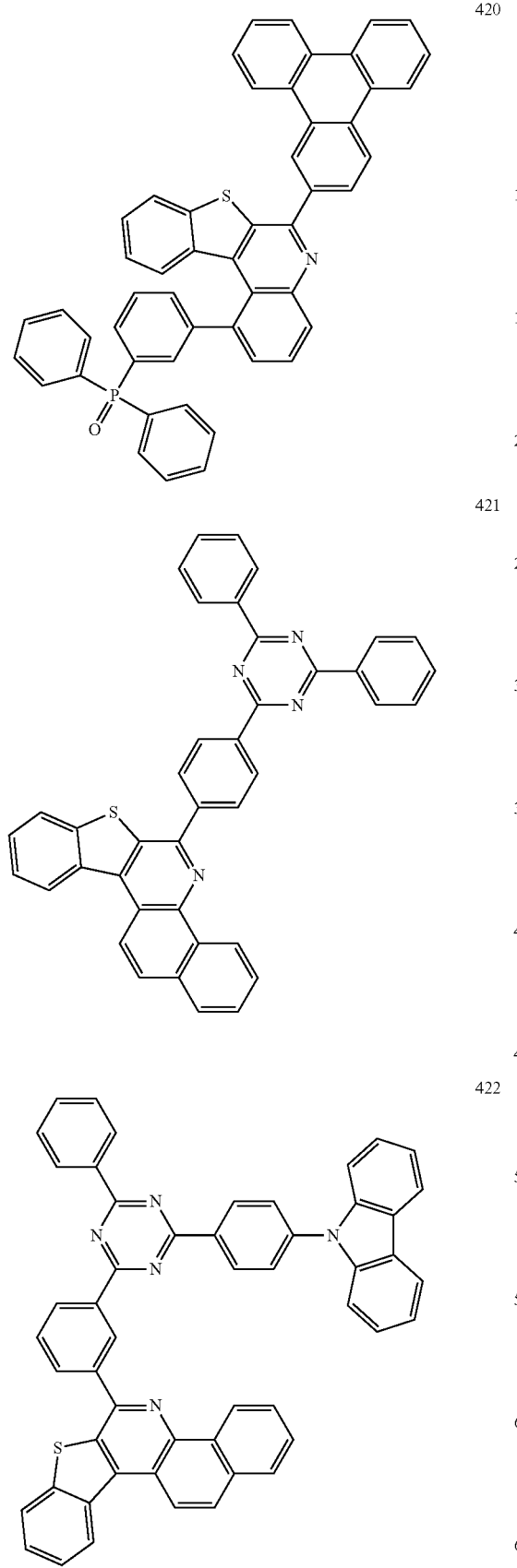
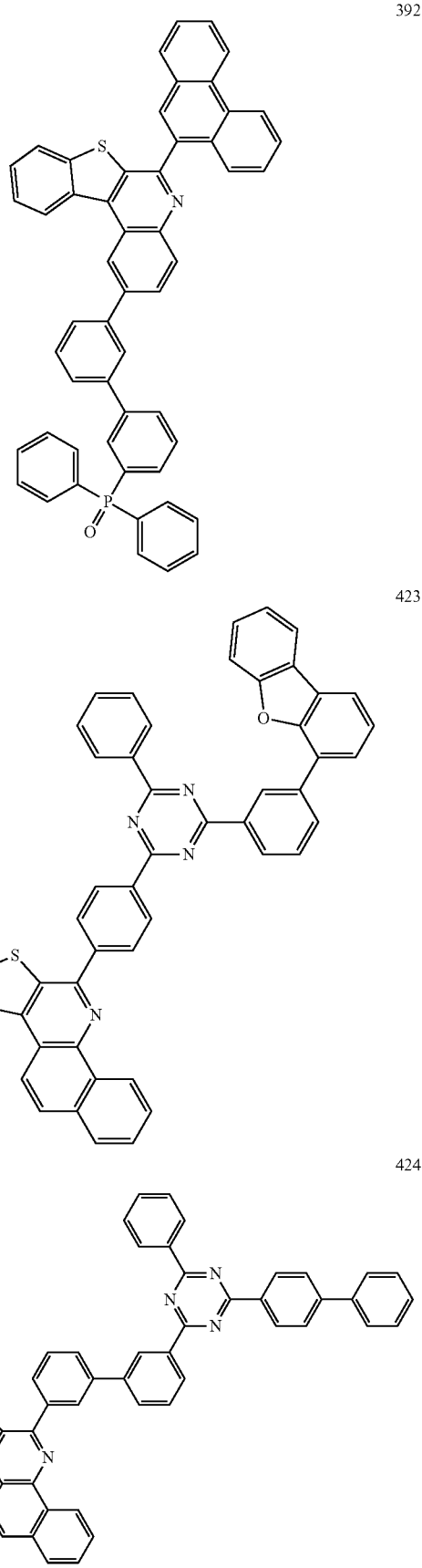

881
-continued
425
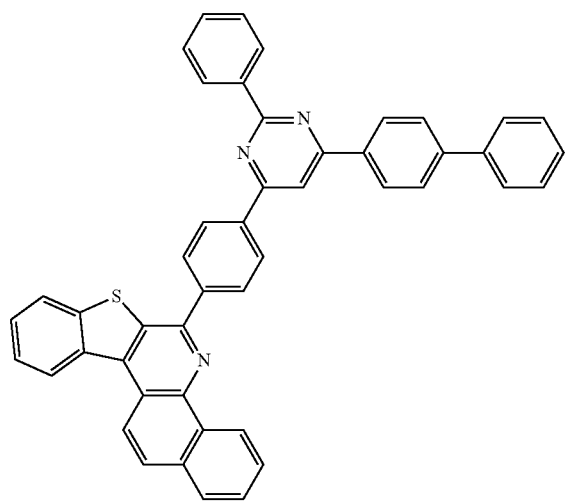
426
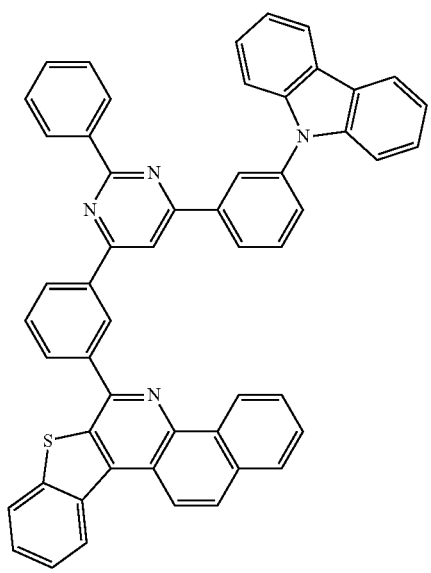
427
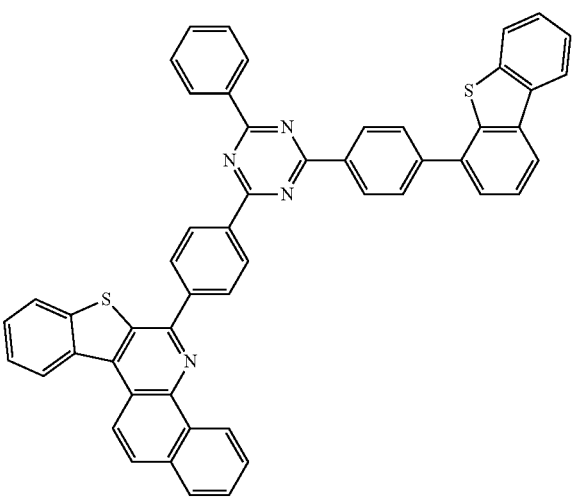
882
-continued
428
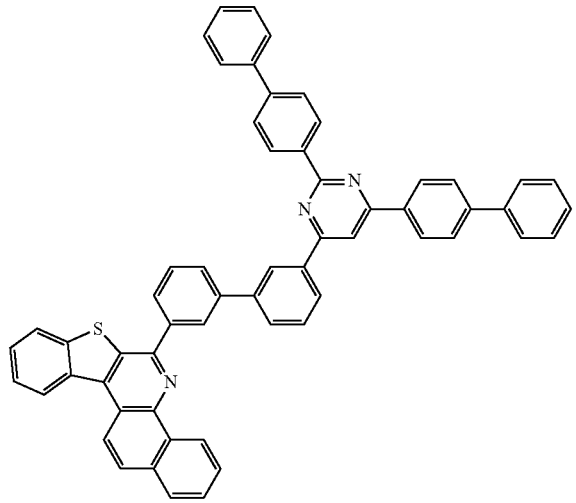
429
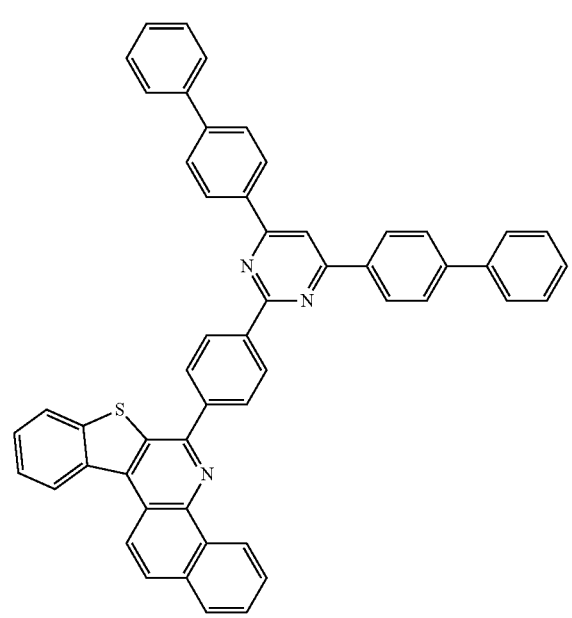
430
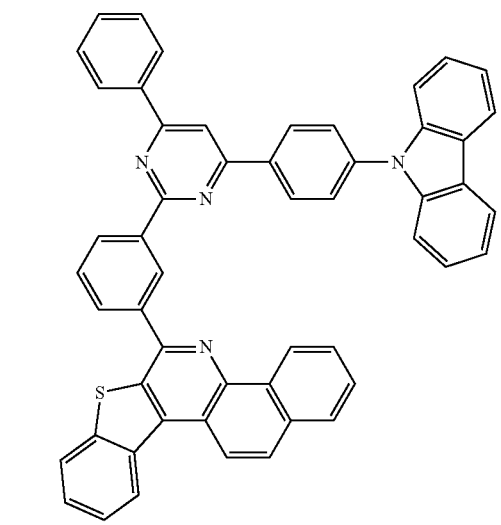

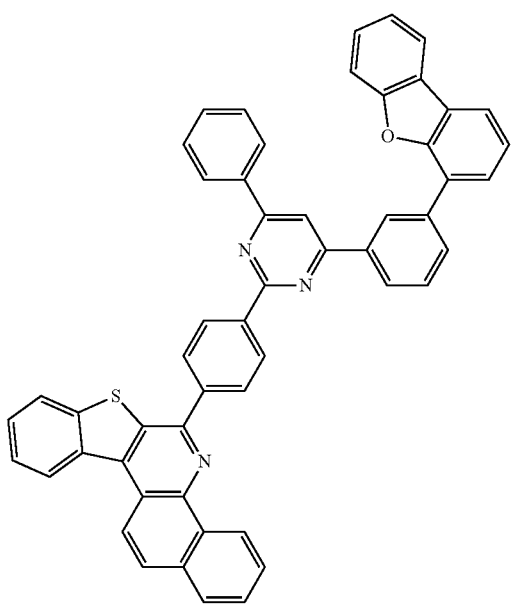
431
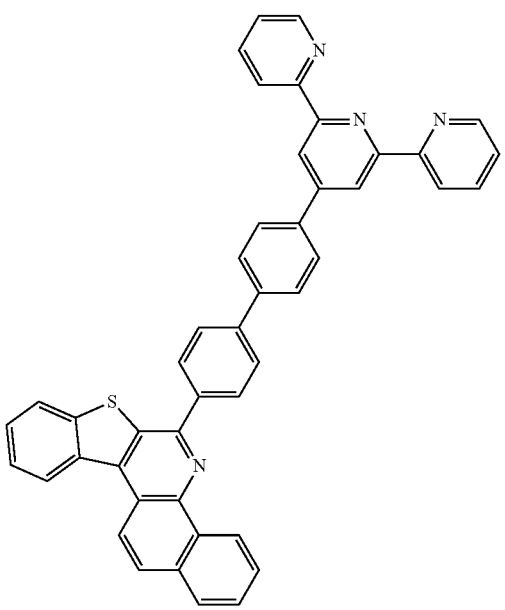
433
432
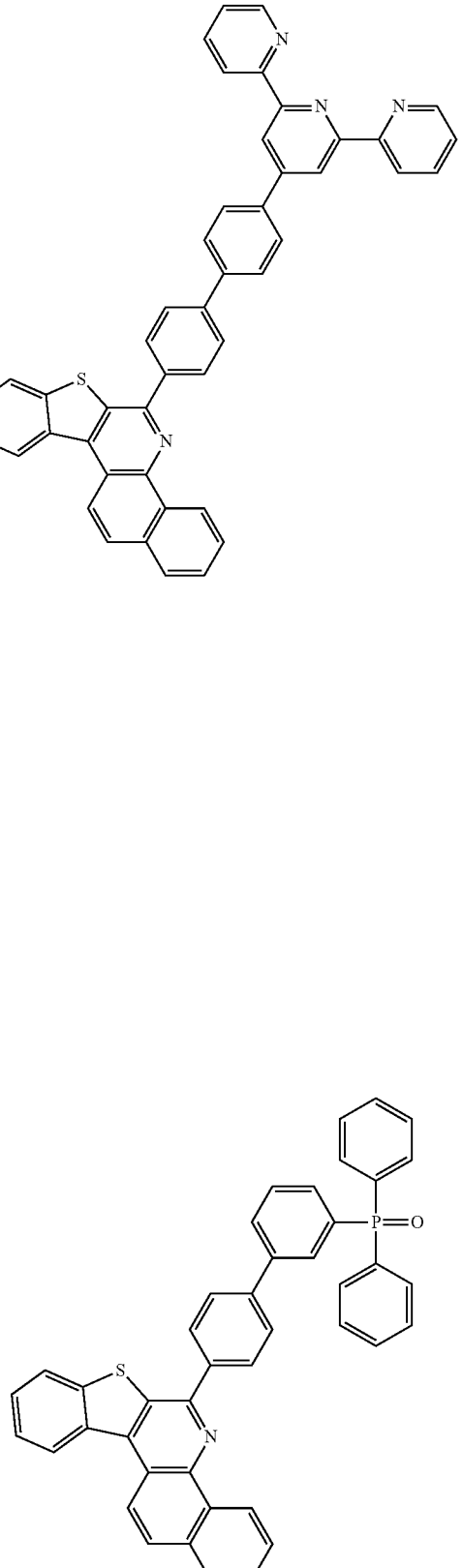
434

885
-continued
435
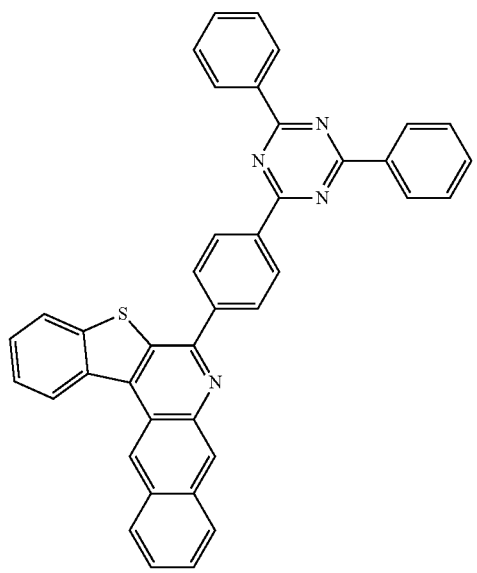
436
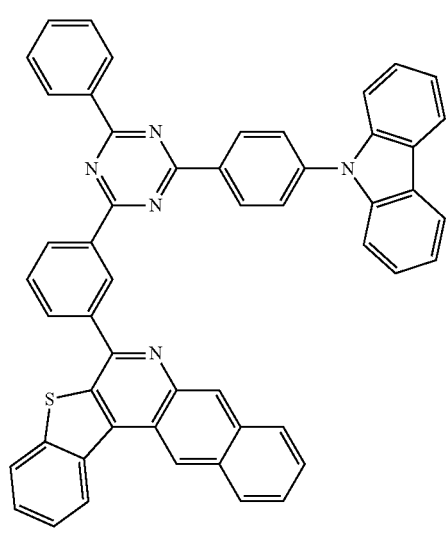
886
-continued
437
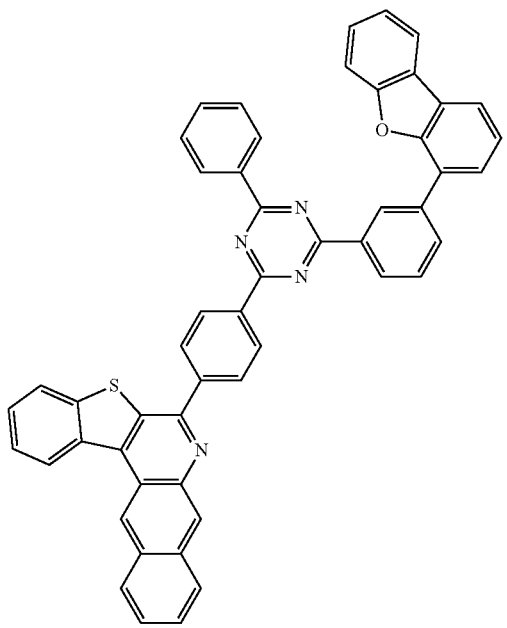
438
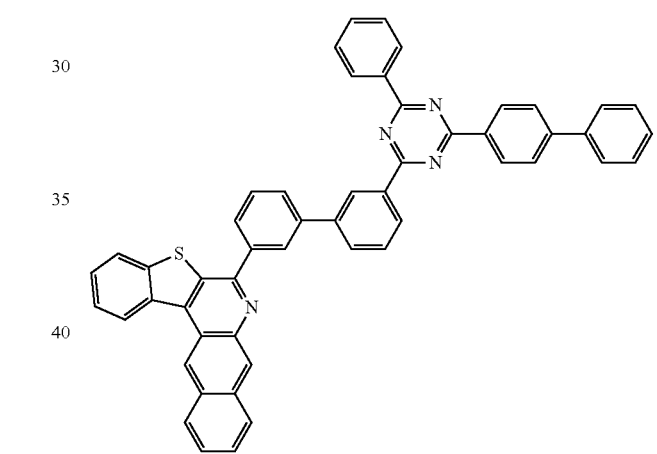
439
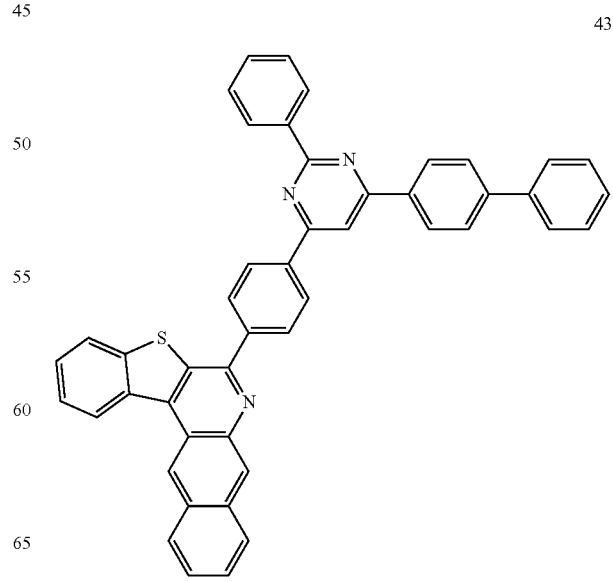

440
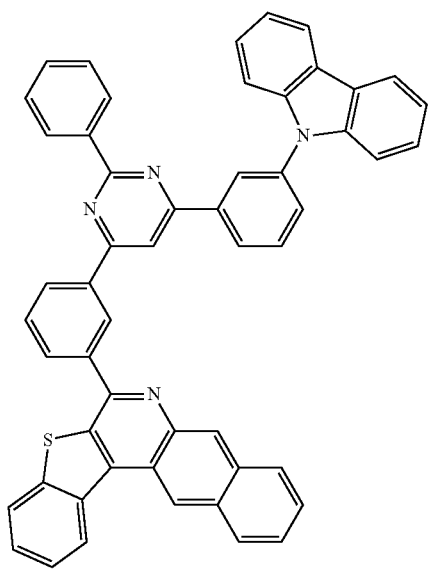
441
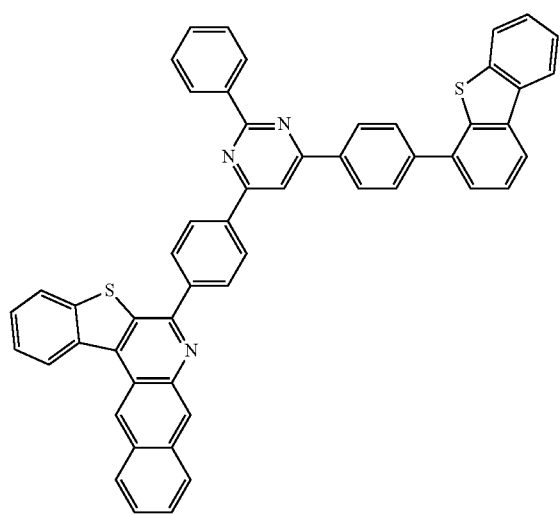
442
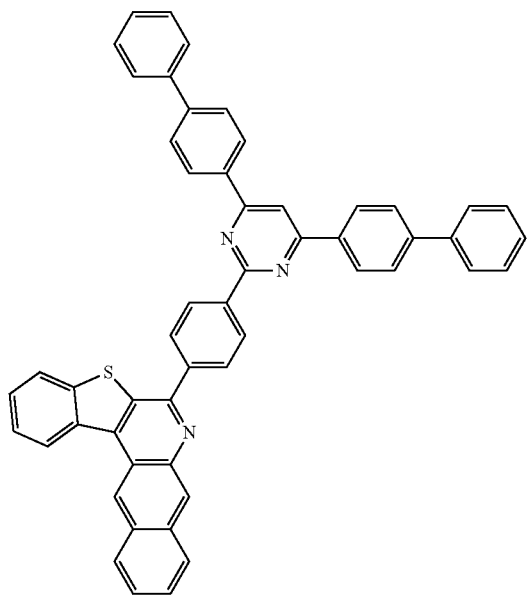
443
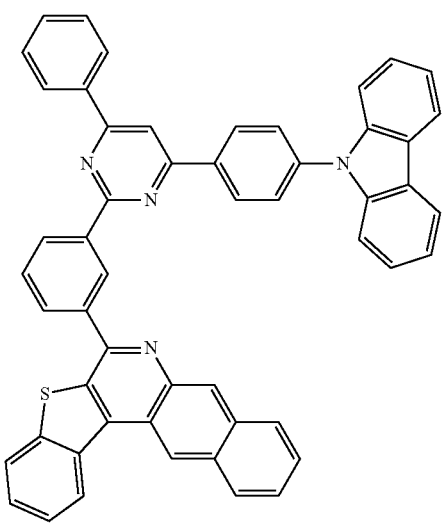

889
-continued
444
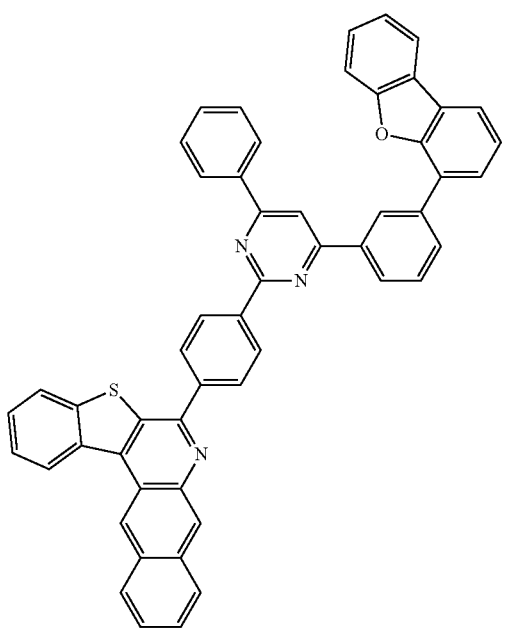
445
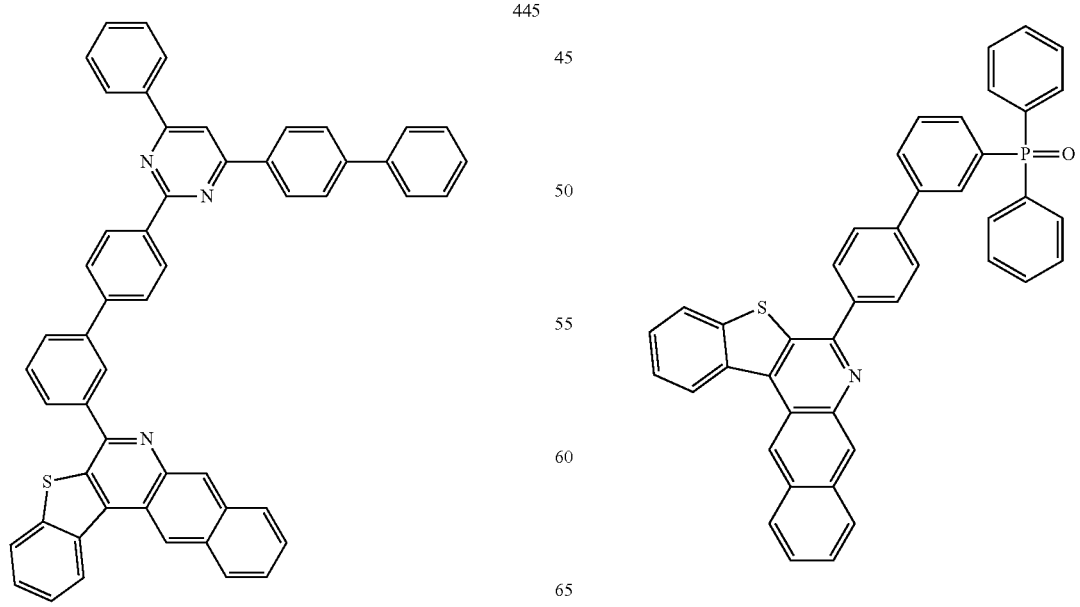
890
-continued
446
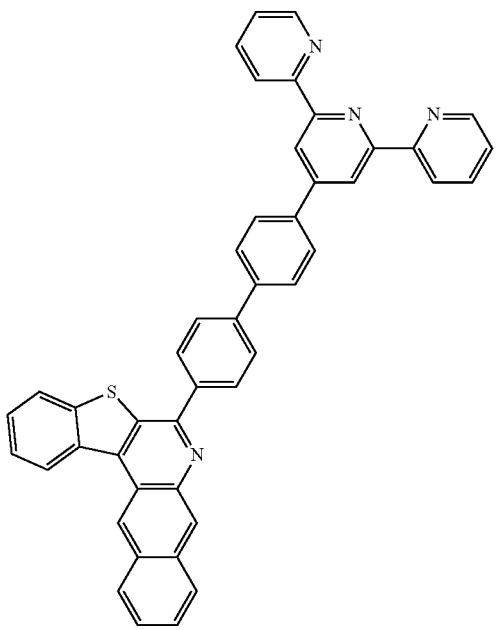
447

891
-continued
448
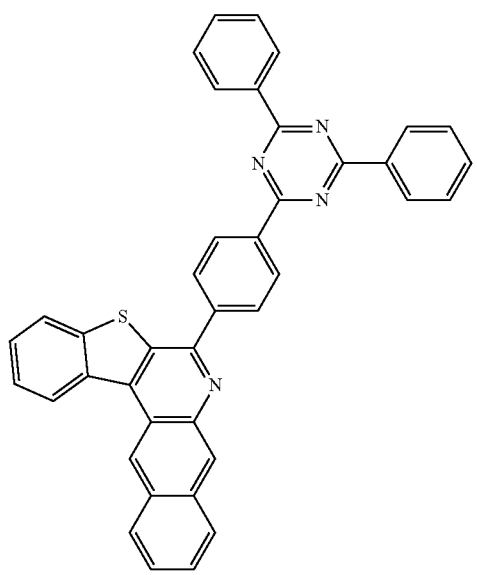
449
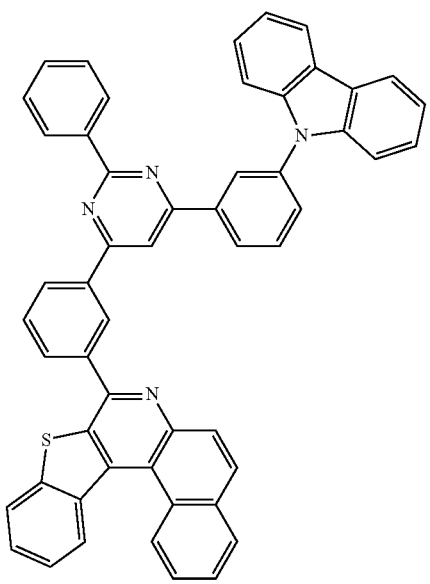
892
-continued
450
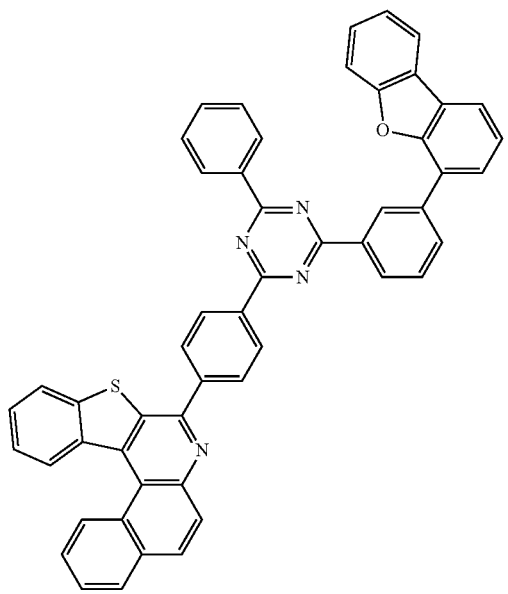
451
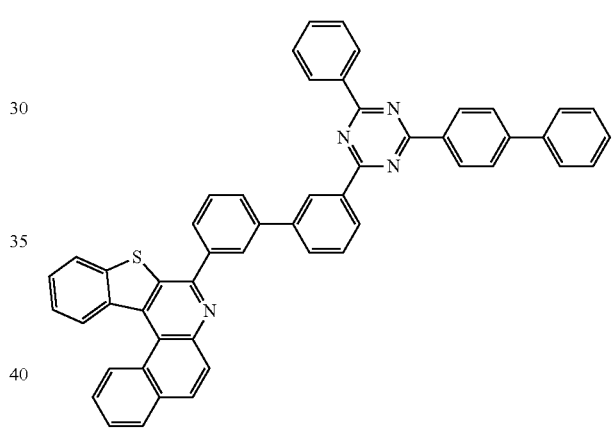
452

893
-continued
454
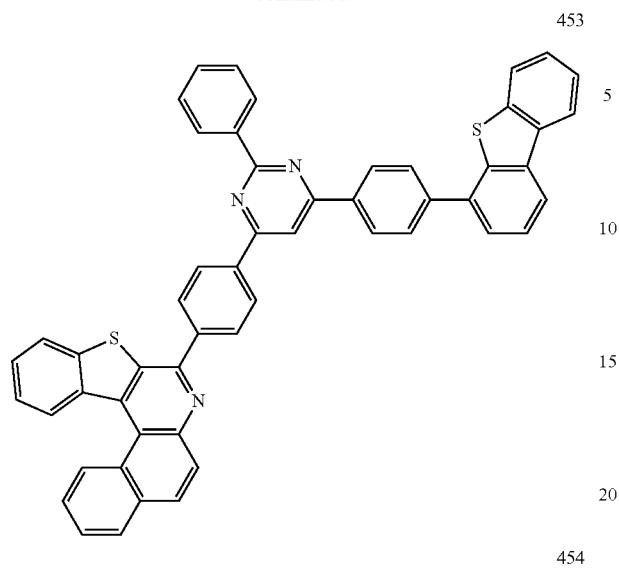
455
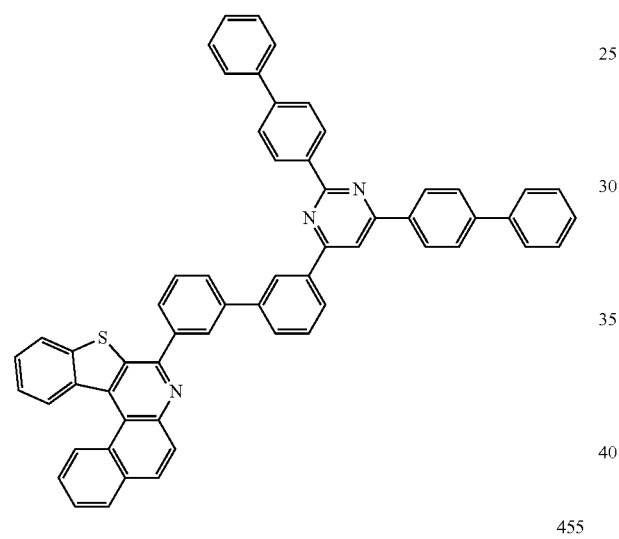
894
-continued
456
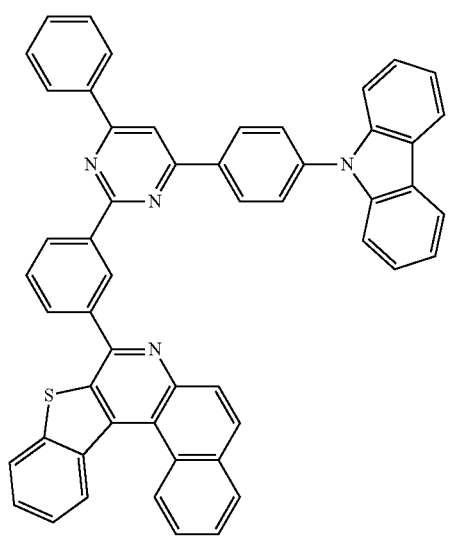
457
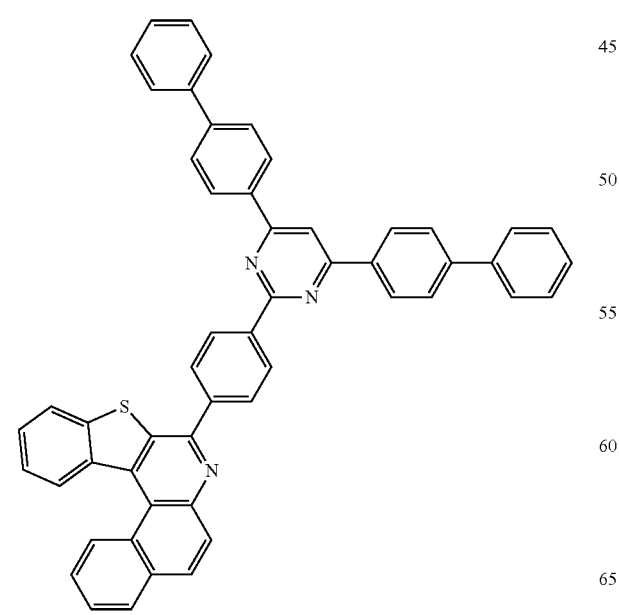

895
-continued
458
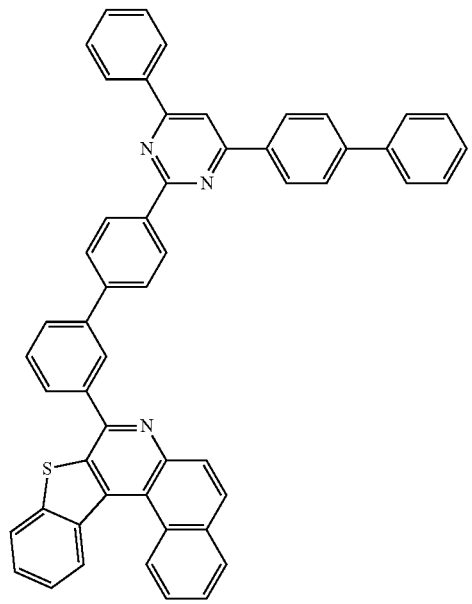
459
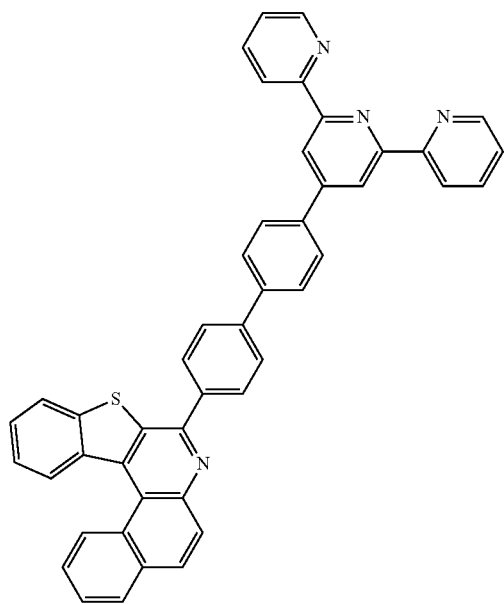
896
-continued
460
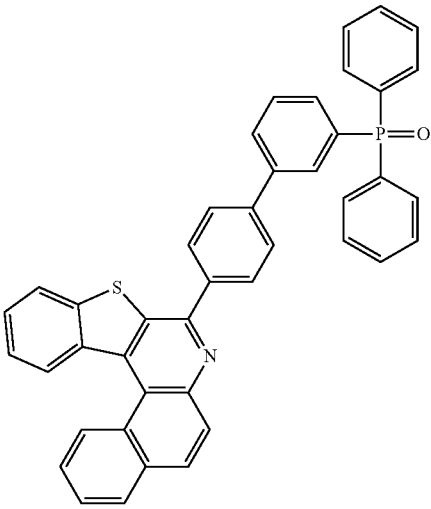
461
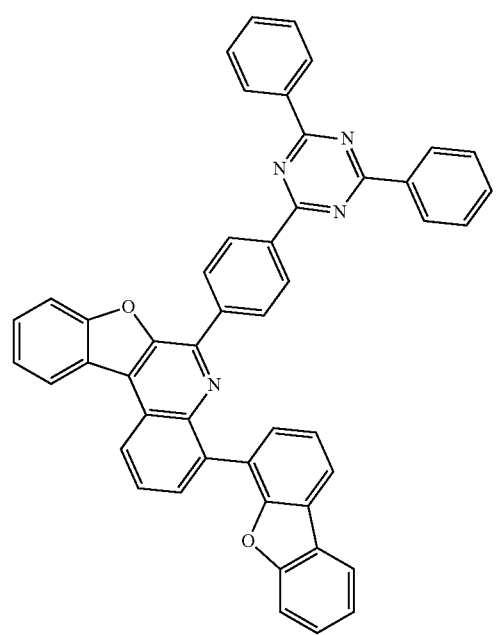
462

897
-continued
463
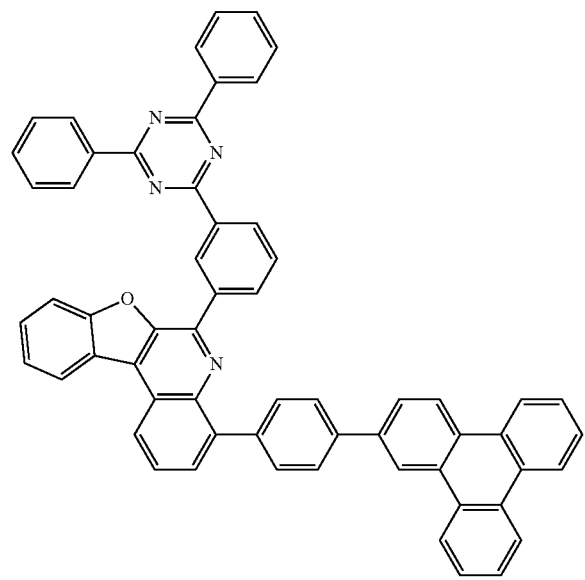
464
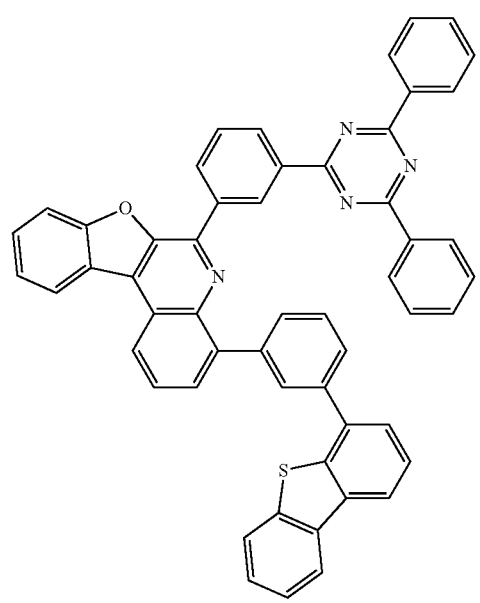
898
-continued
465
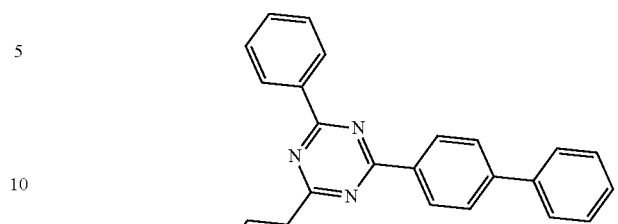
466
467
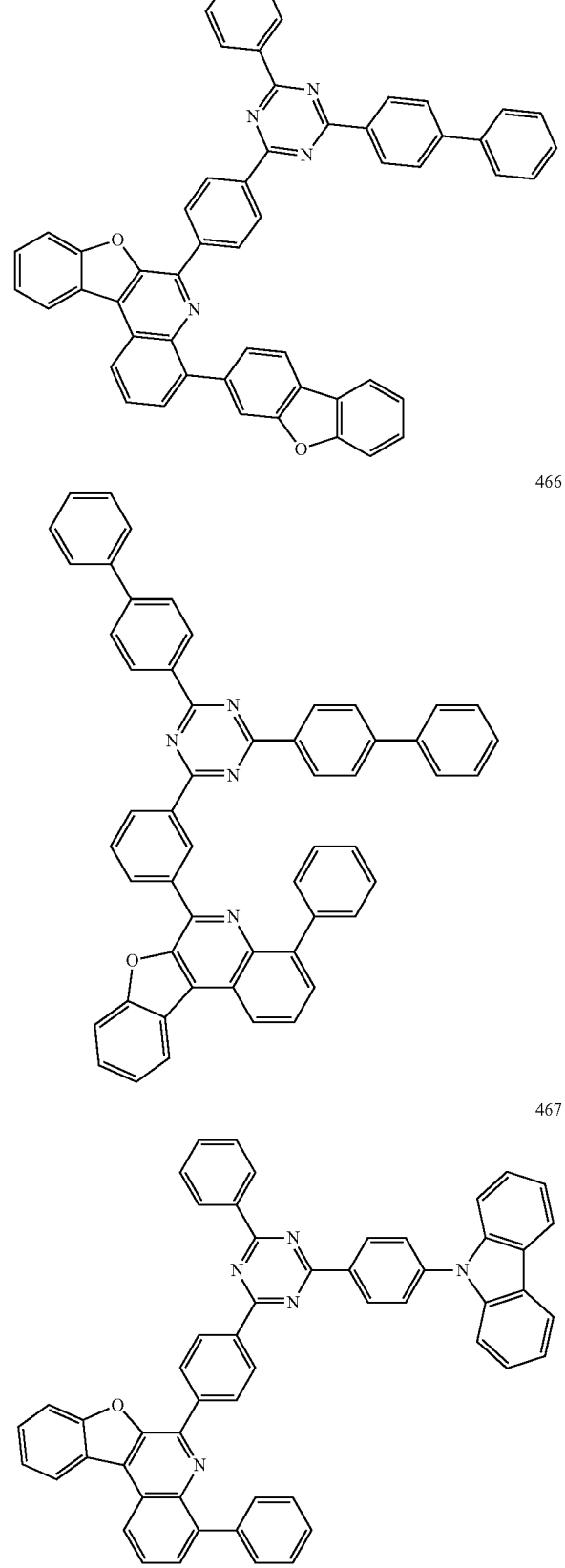

899
-continued
468
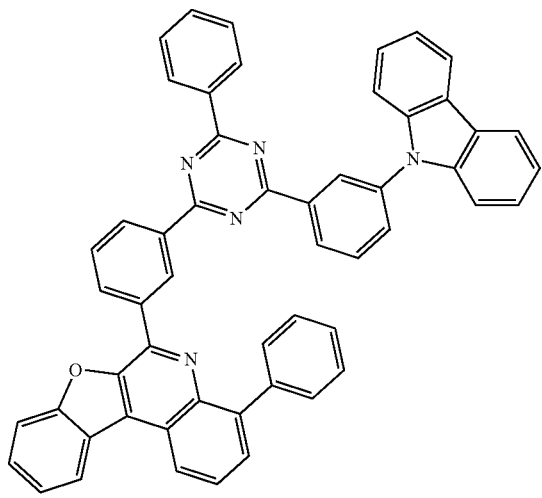
469
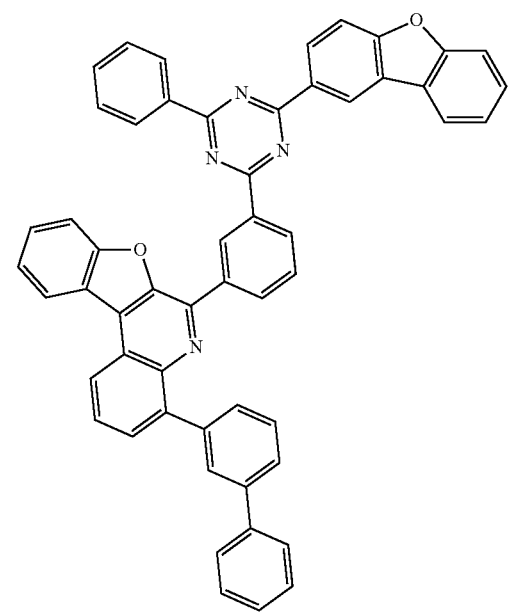
470
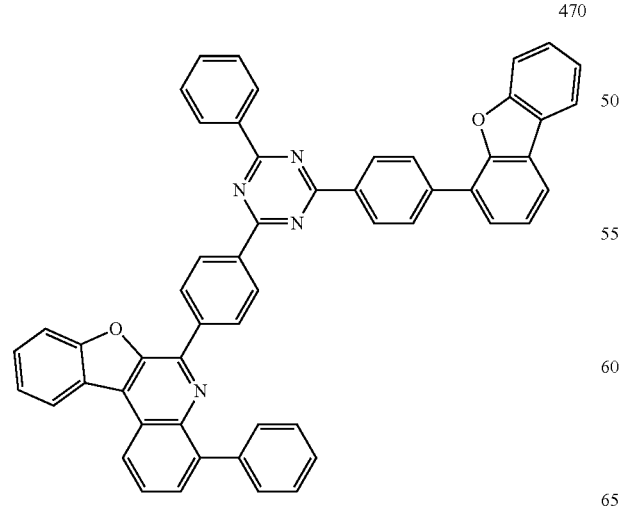
900
-continued
471
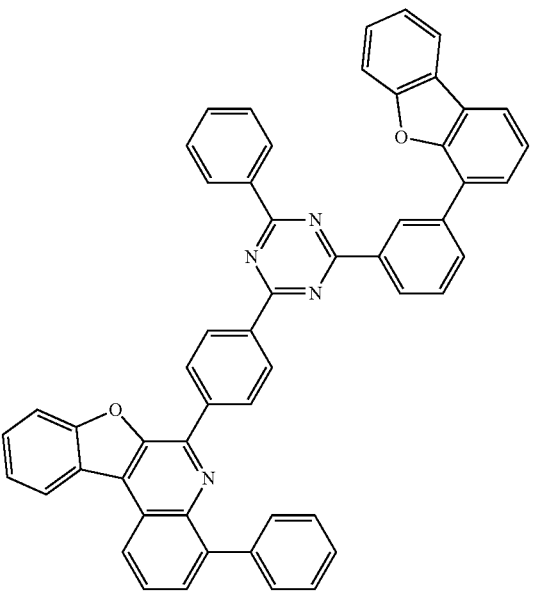
472
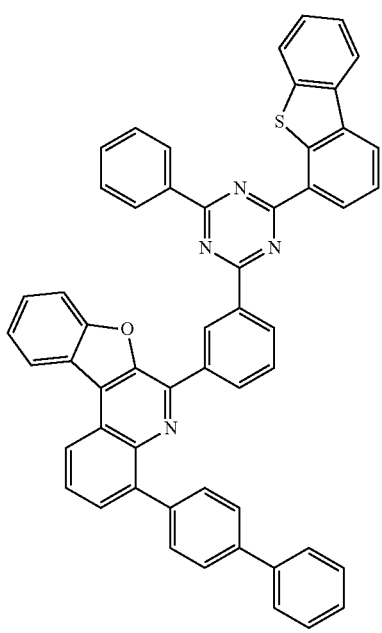

901
-continued
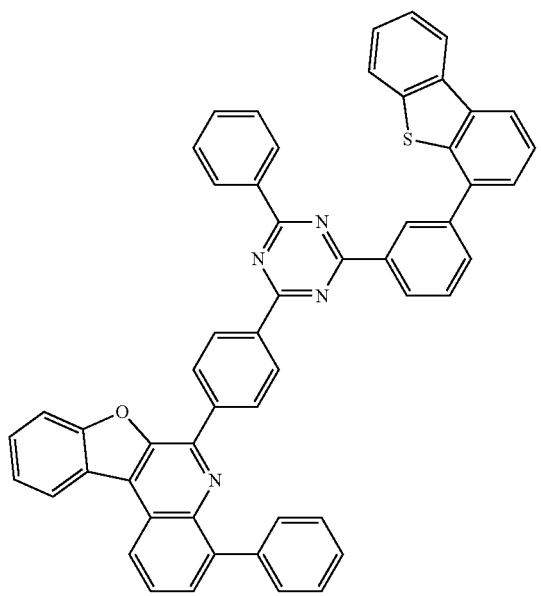
473
902
-continued
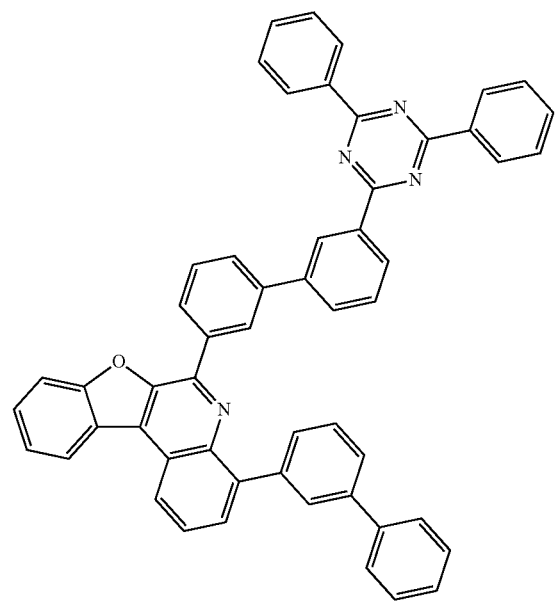
475
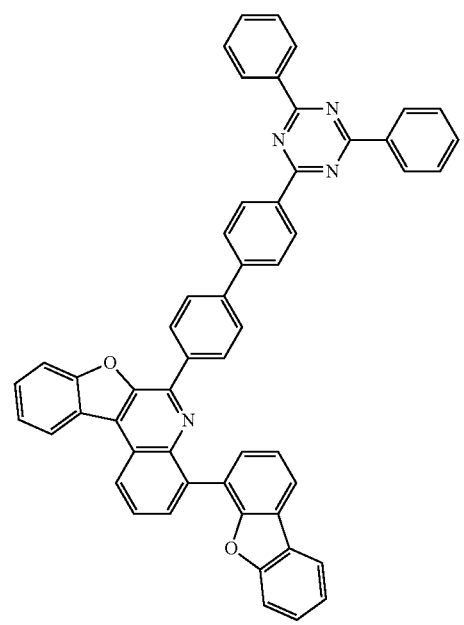
474
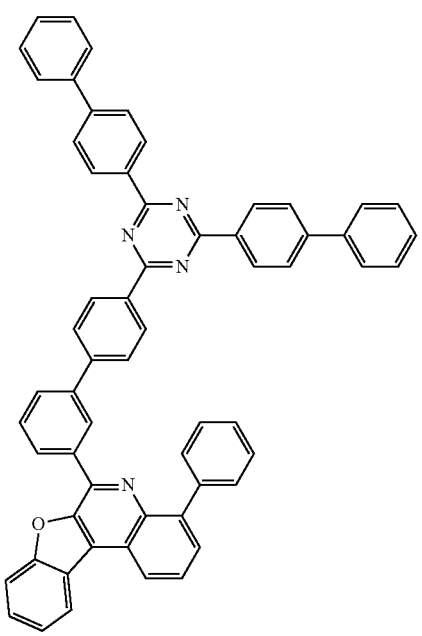
476

477
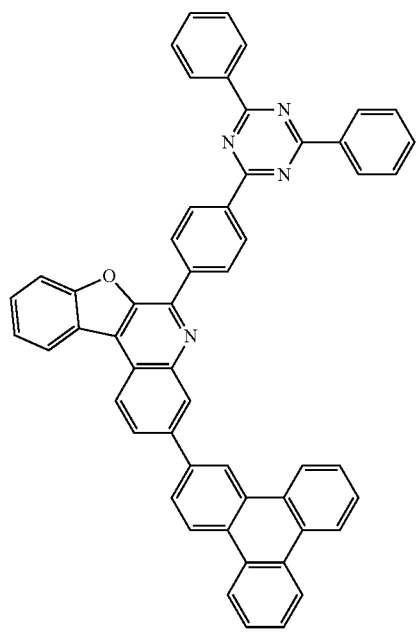
478
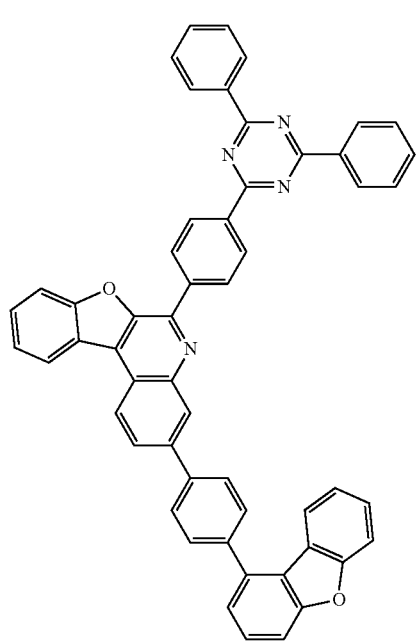
479
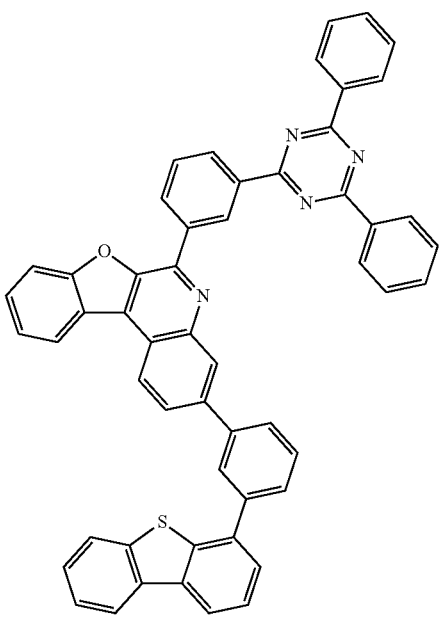
480
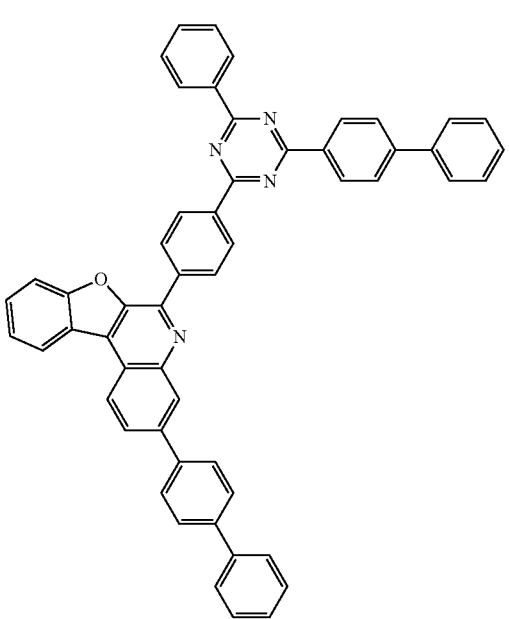

905
-continued
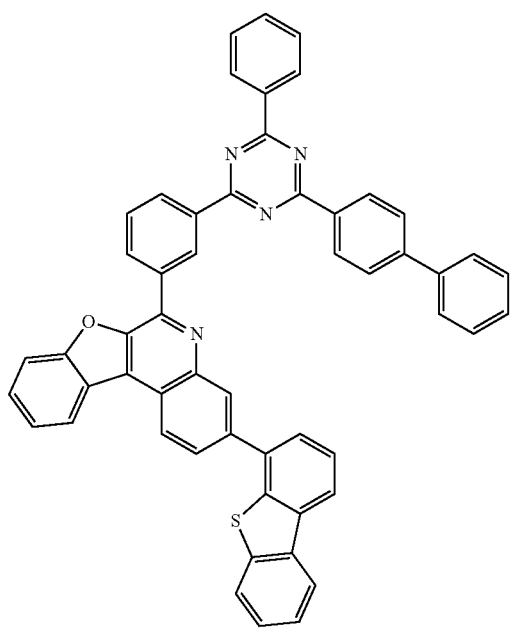
481
906
-continued
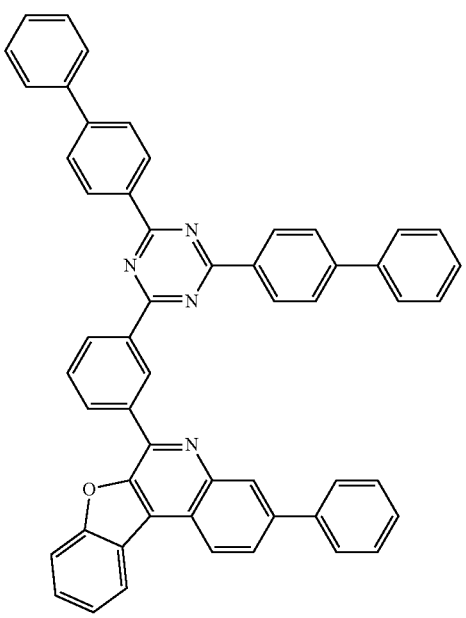
483
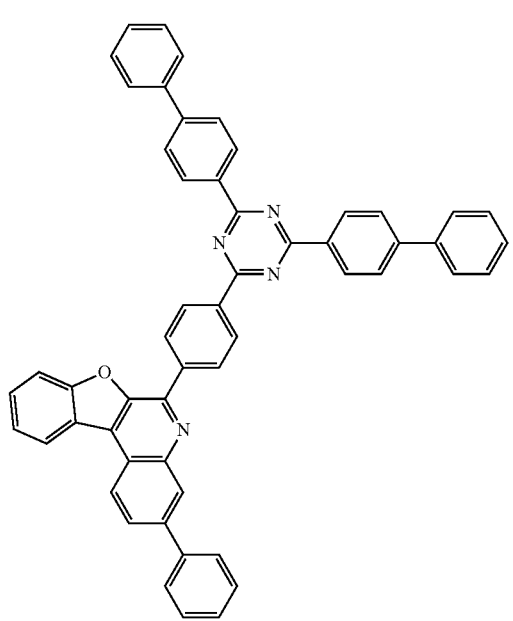
482
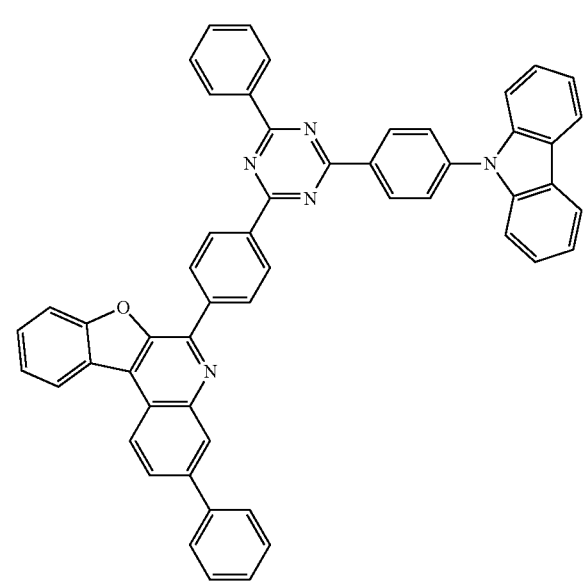
484

907
-continued
485
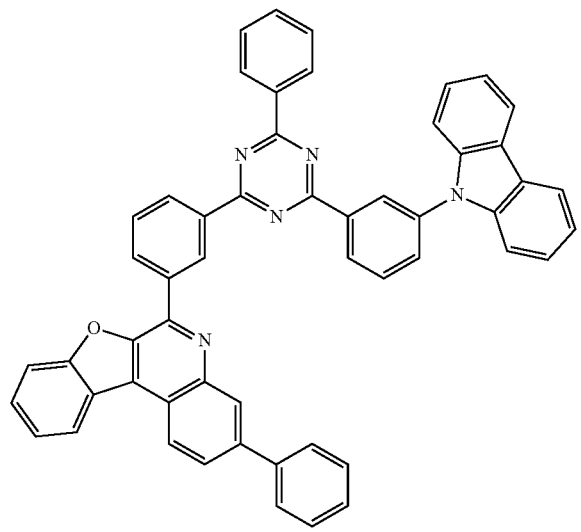
486
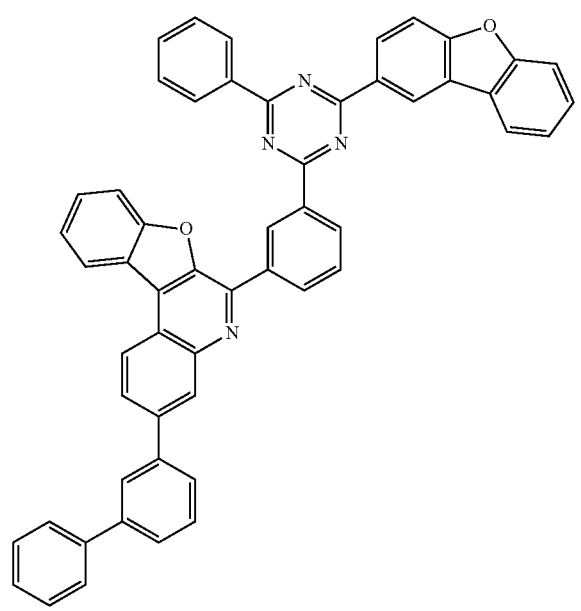
908
-continued
487
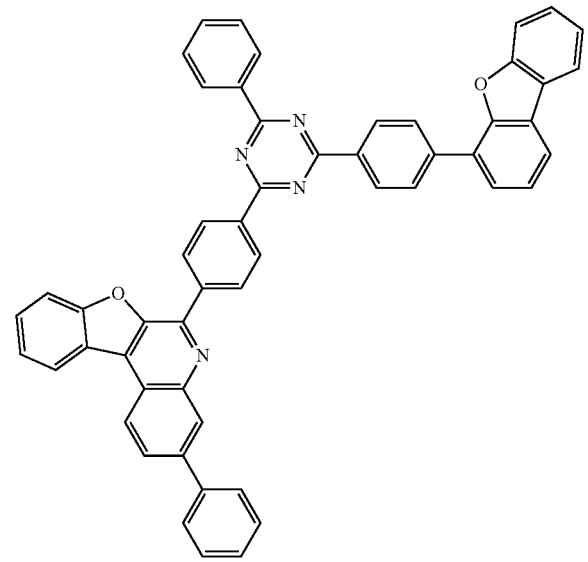
488
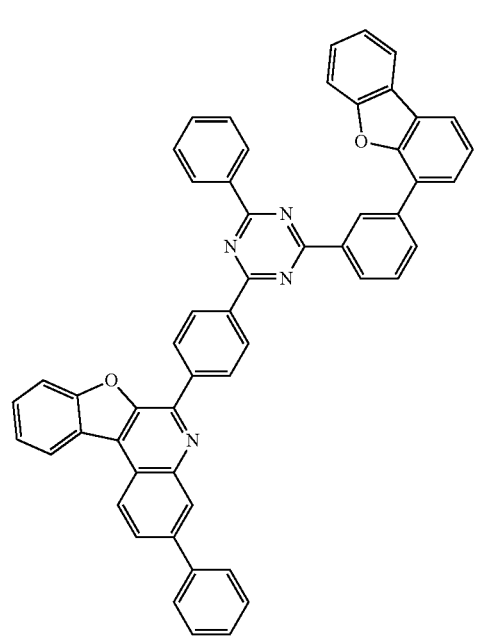

909
-continued
489
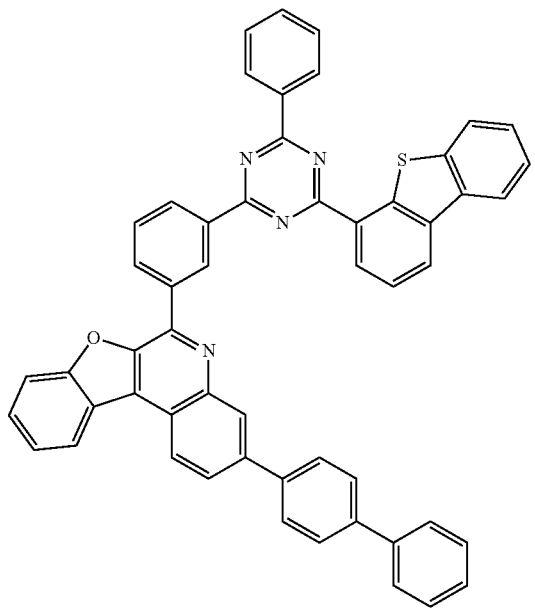
490
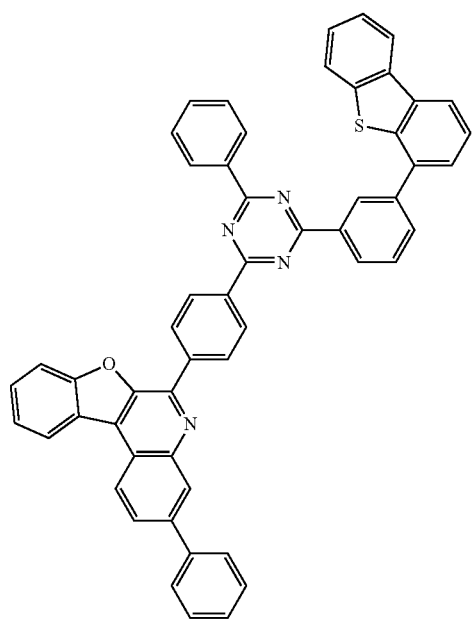
910
-continued
491
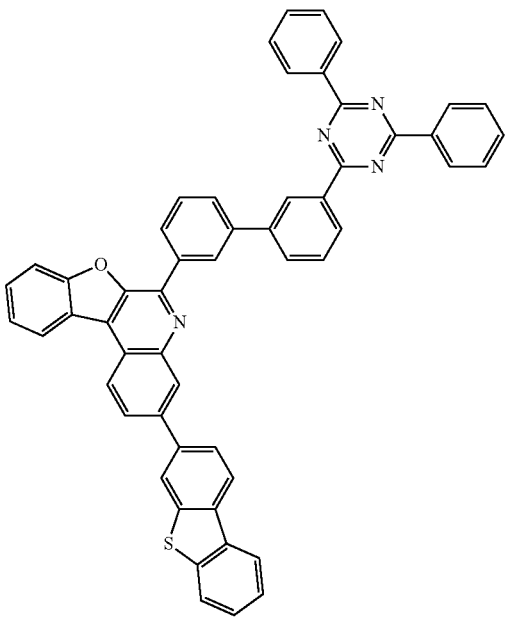
492

911
-continued
493
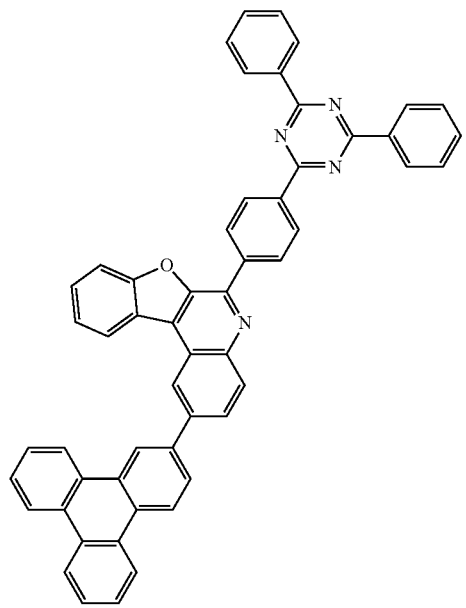
494
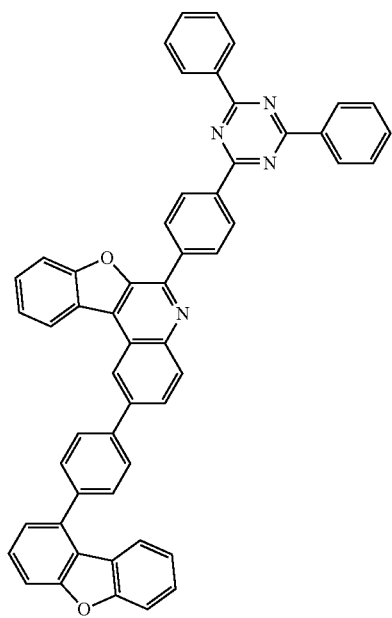
912
-continued
495
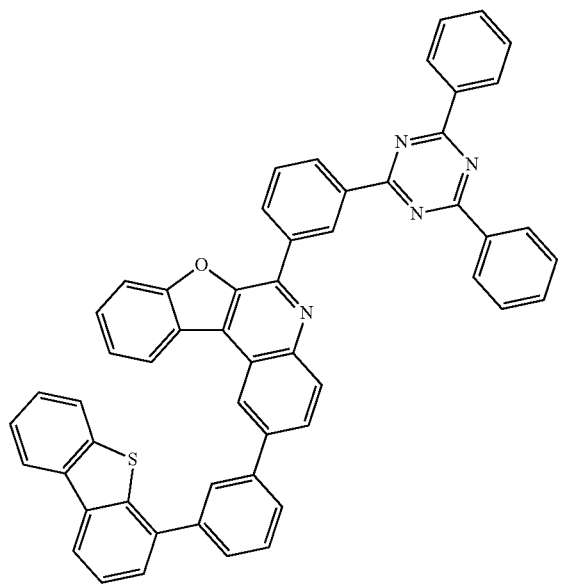
496
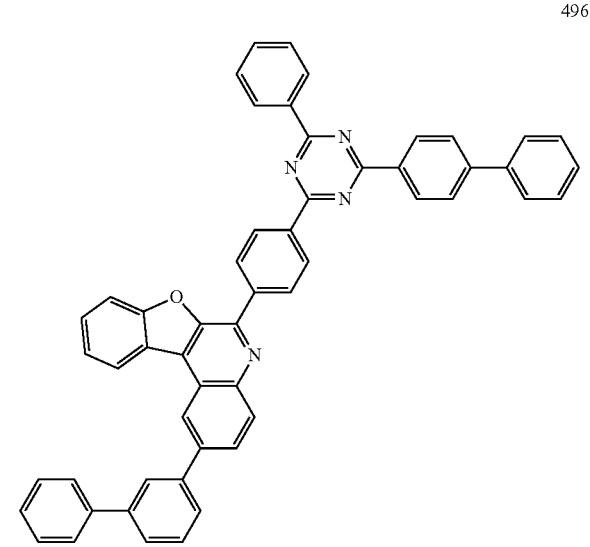

913
-continued
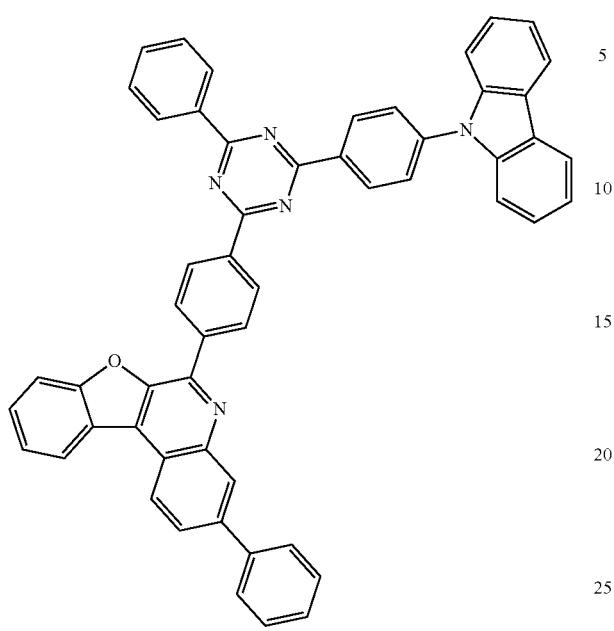
497
914
-continued
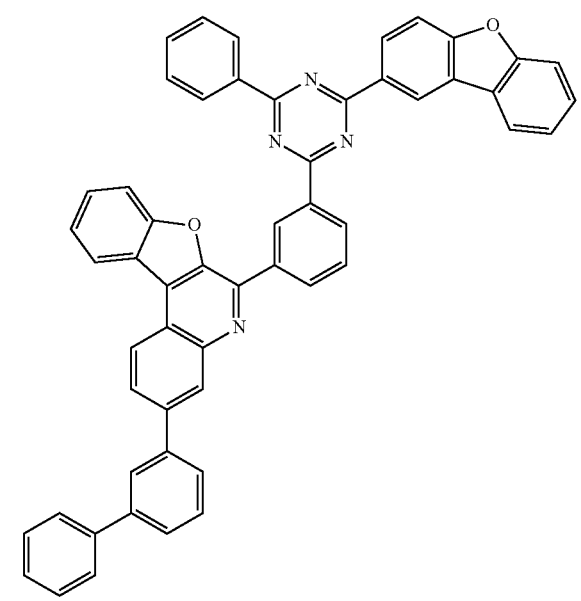
499
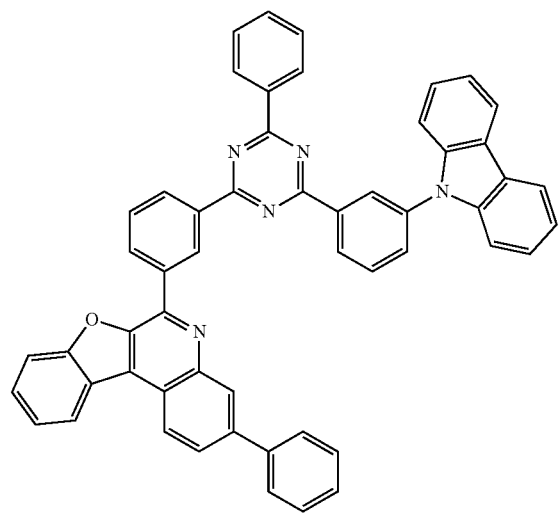
498
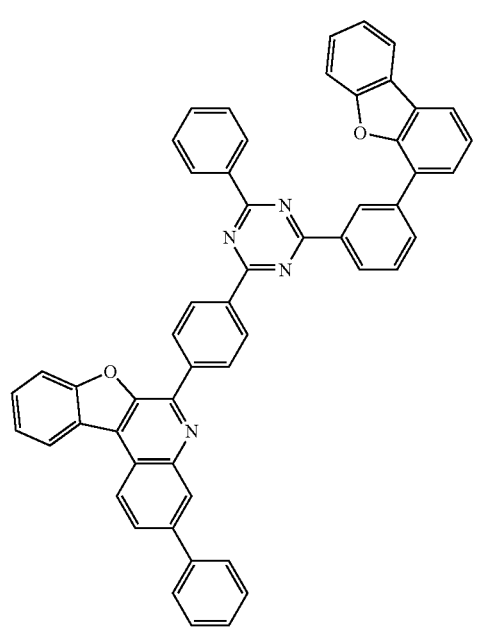
500

501
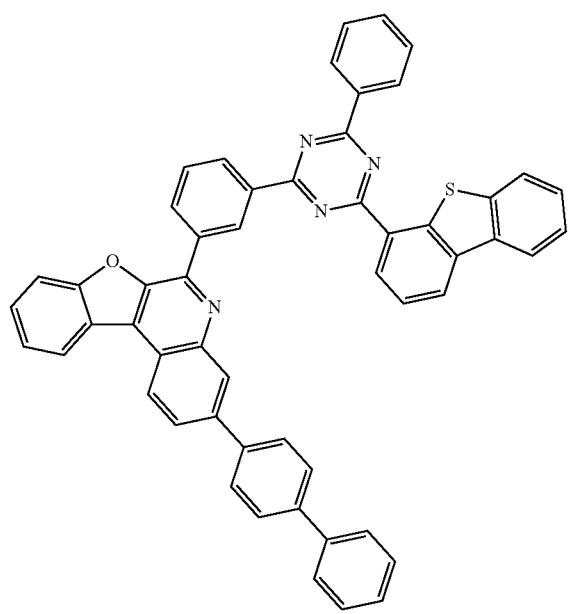
503
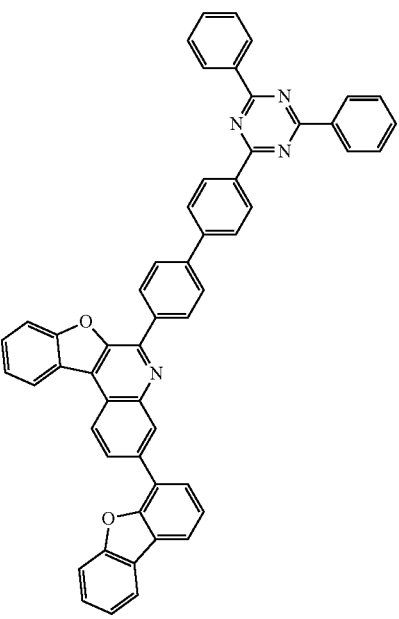
502
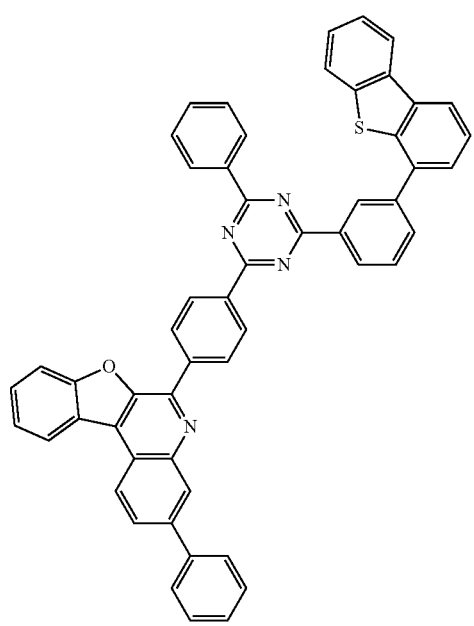
504
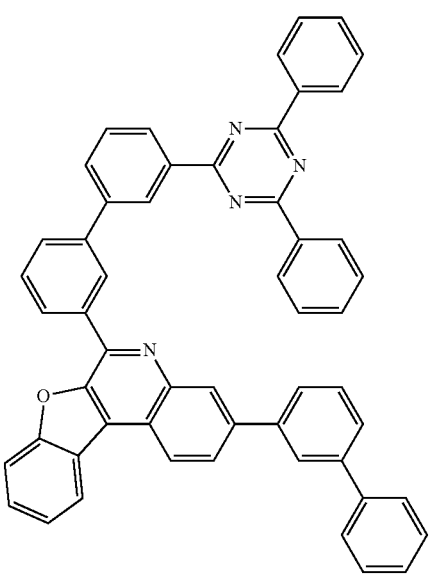

505
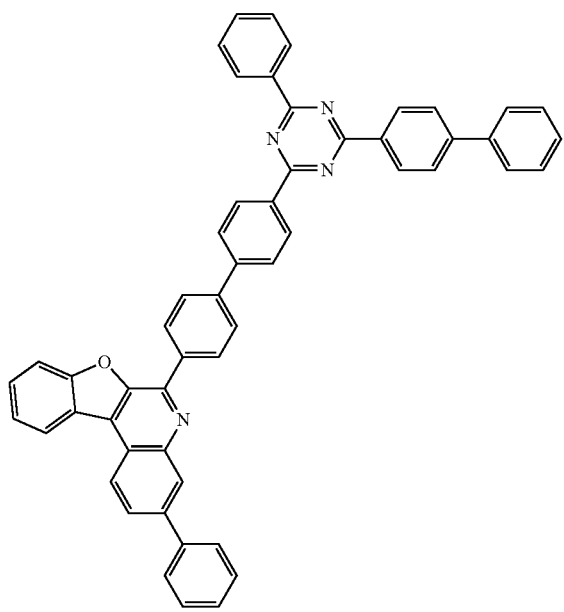
506
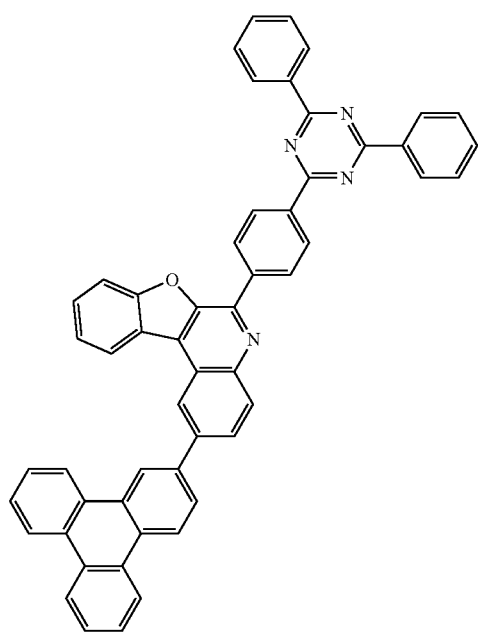
507
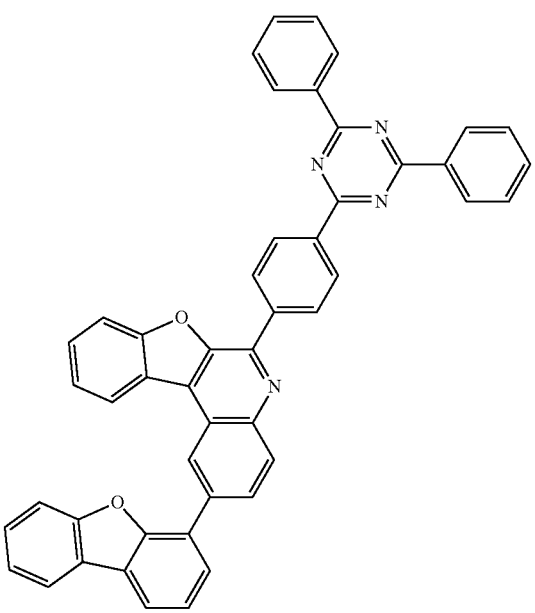
508
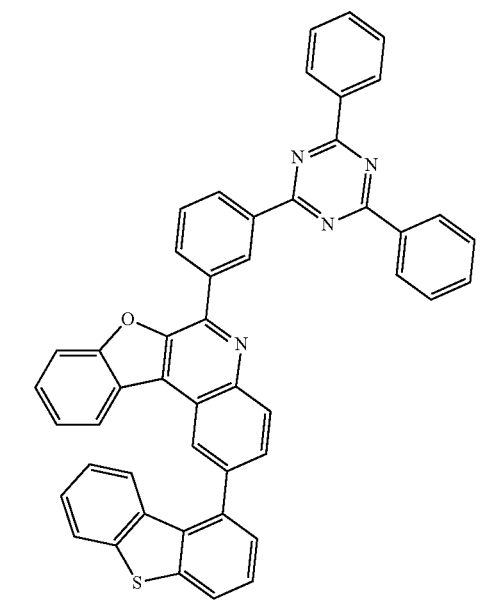

919
-continued
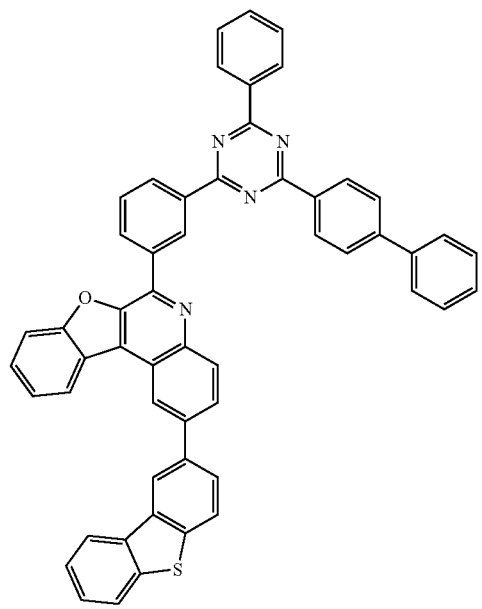
509
920
-continued
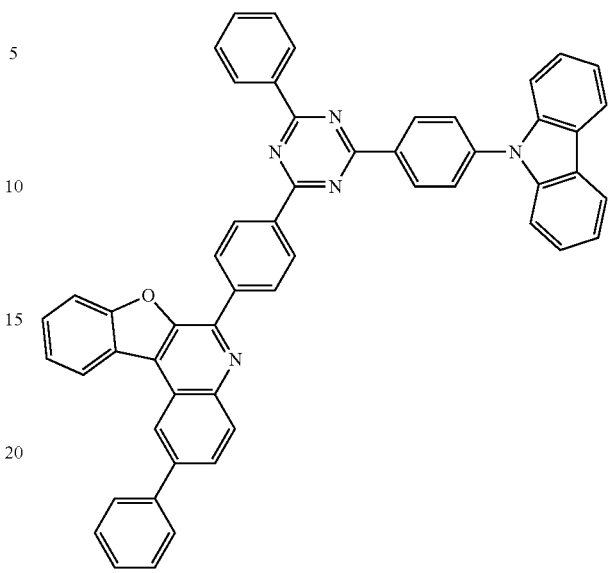
511
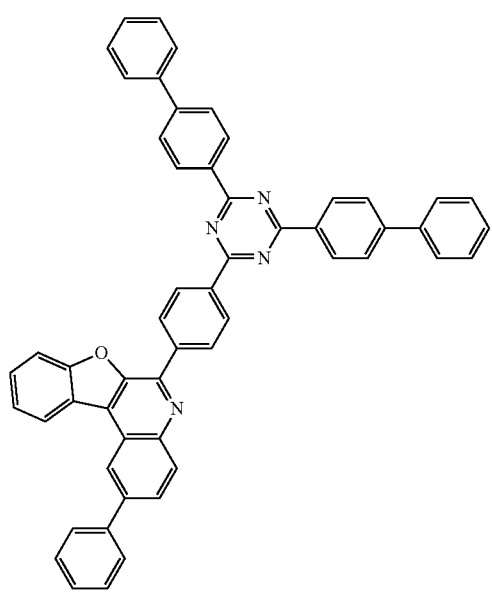
510
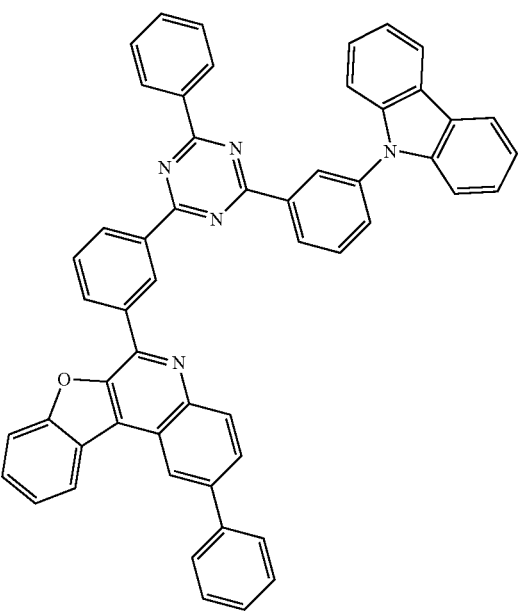
512

921
-continued
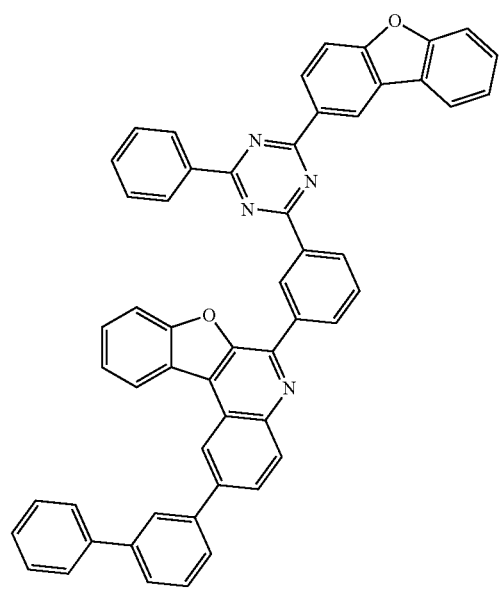
513
922
-continued
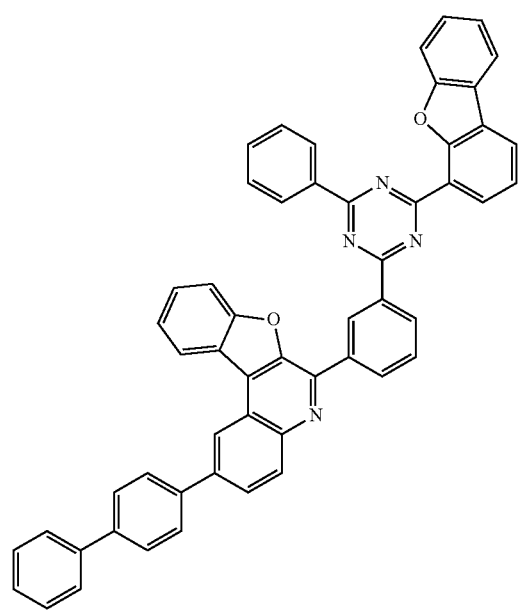
515
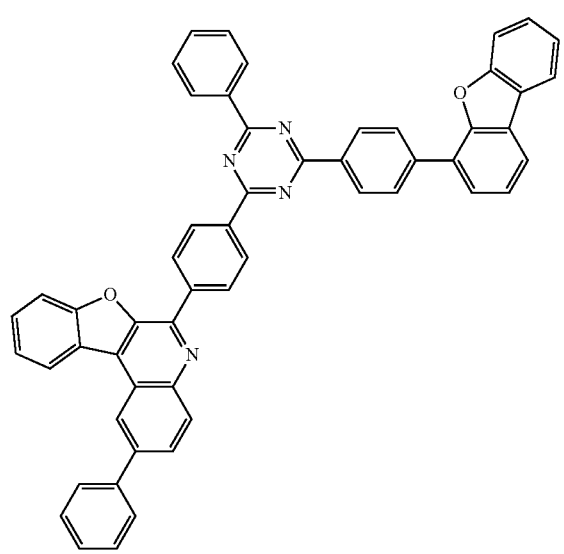
514
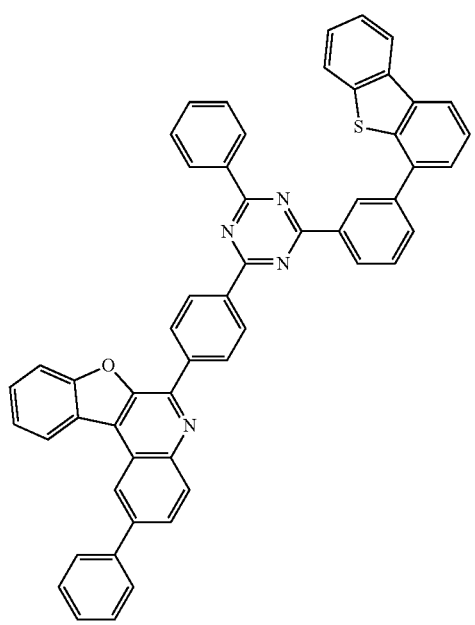
516

923
-continued
517
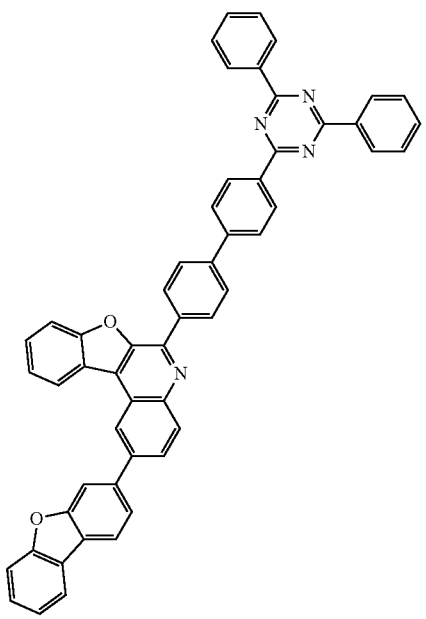
518
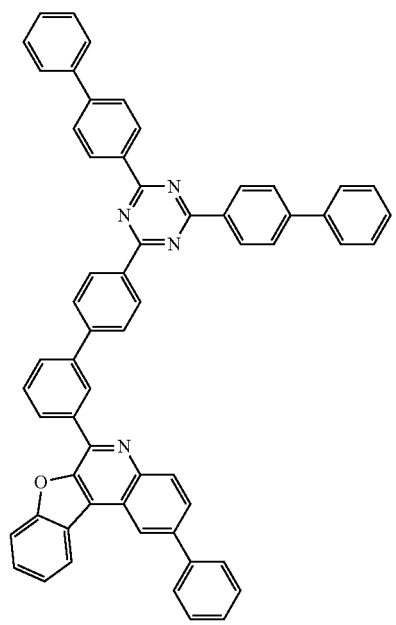
924
-continued
519
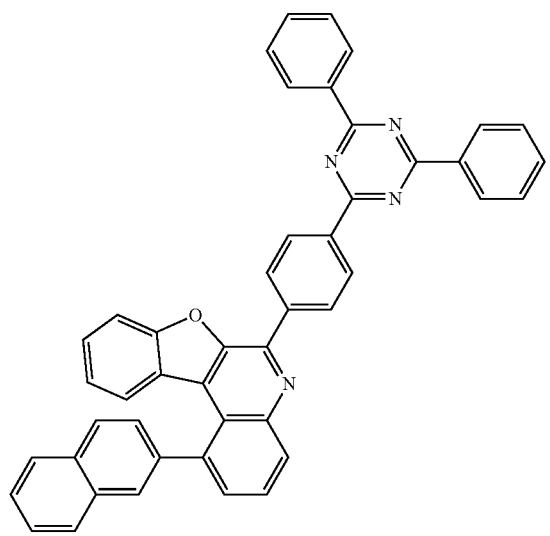
520

925
521
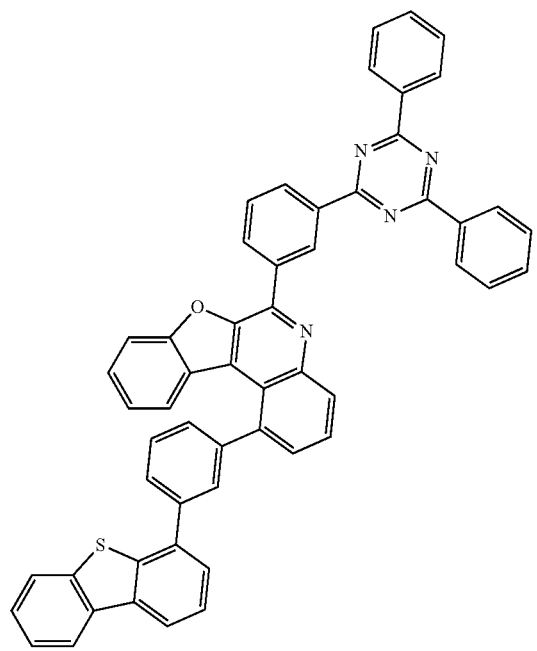
926
-continued
523
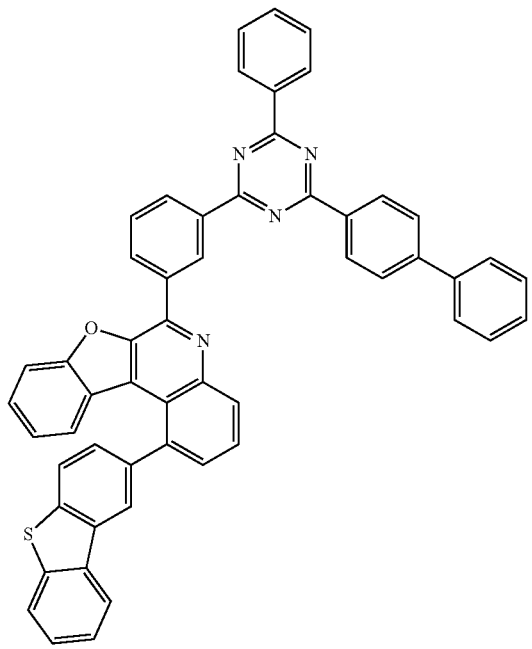
522
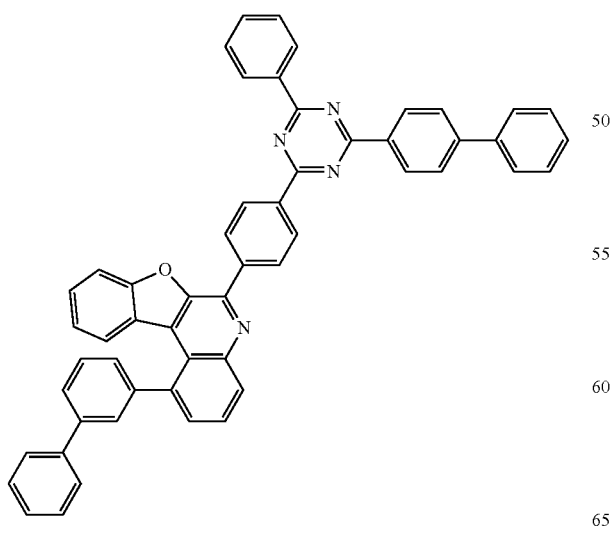
524
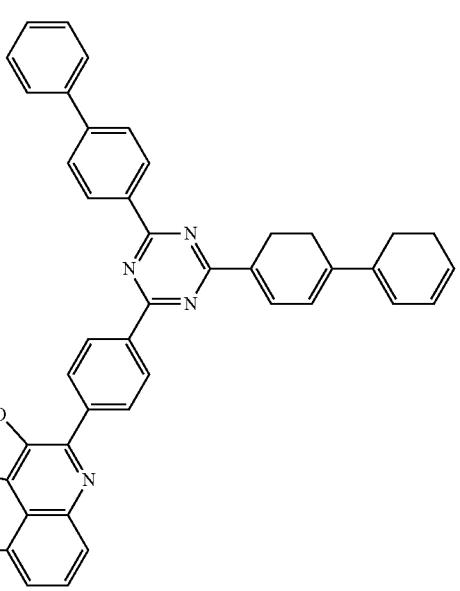

927
-continued
525
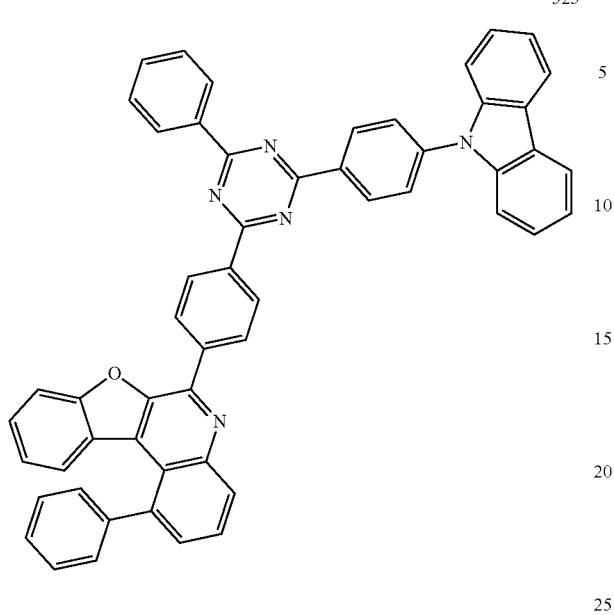
526
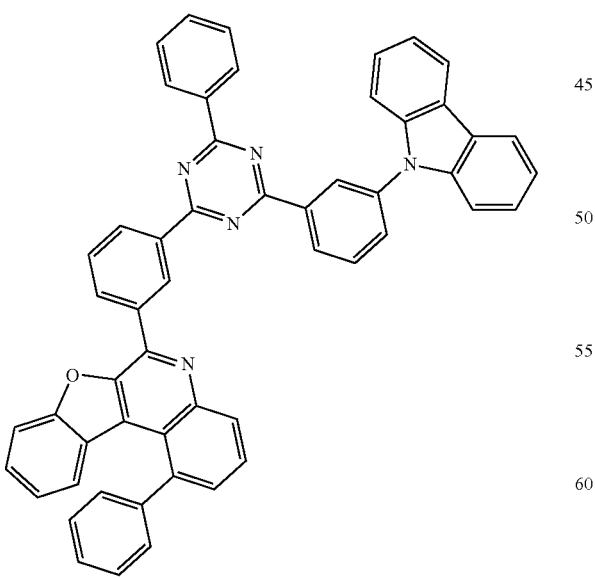
928
-continued
527
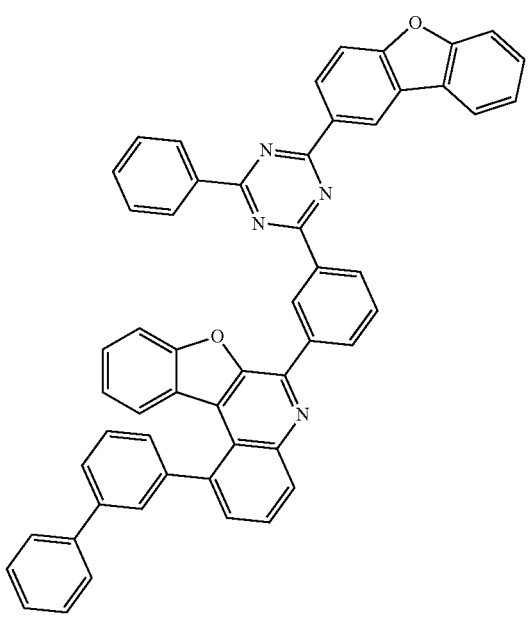
528
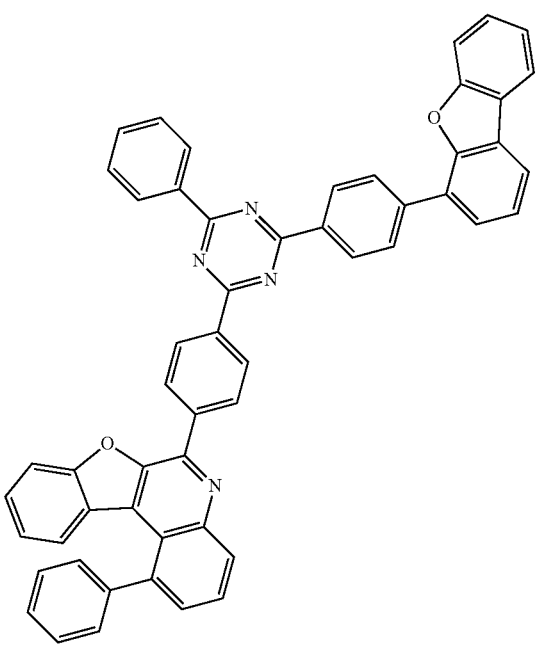

529
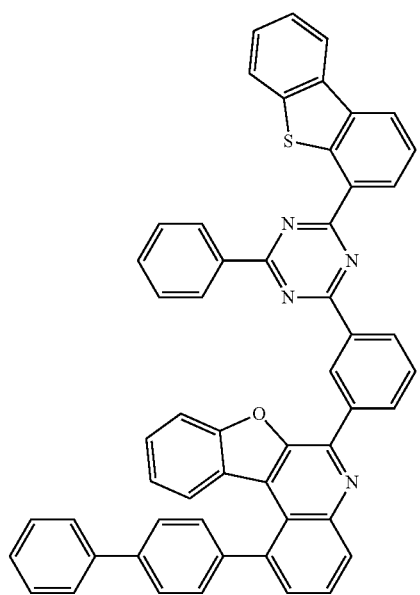
530
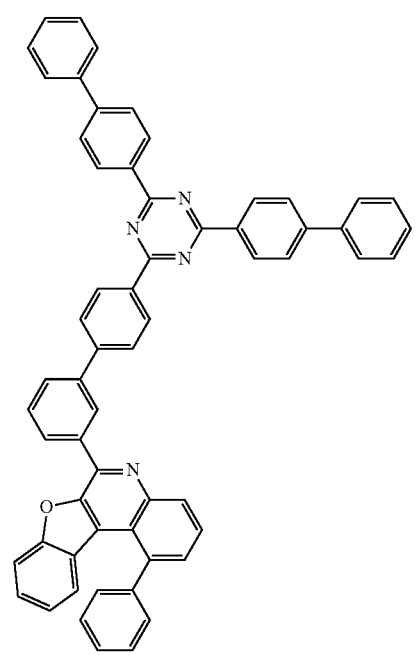
531
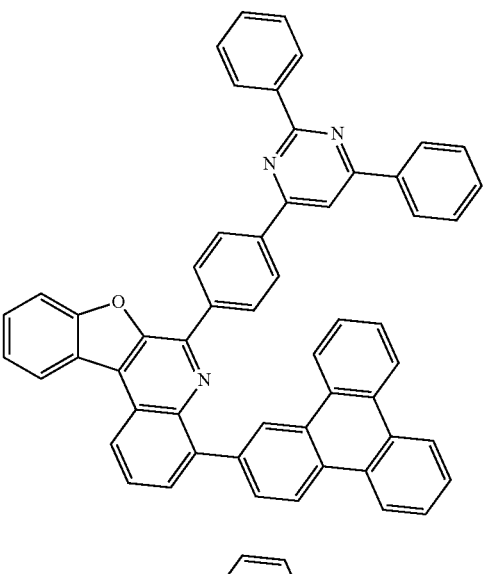
532
533
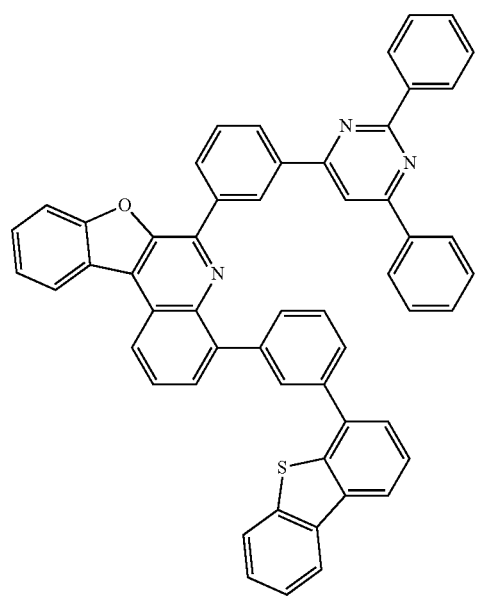

US 11,476,425 B2
931
-continued
534
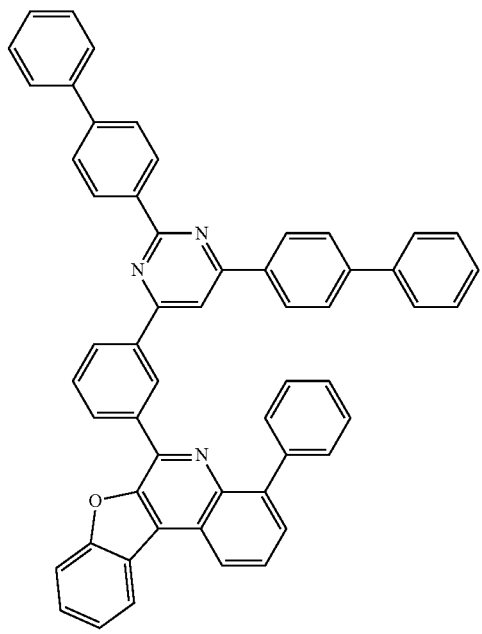
535
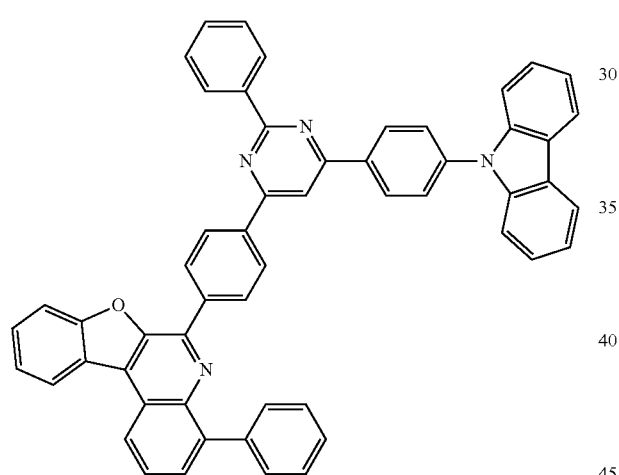
536
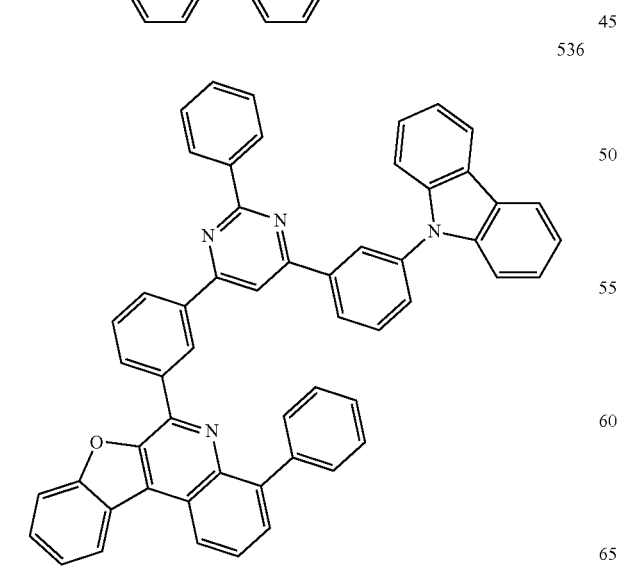
932
-continued
537
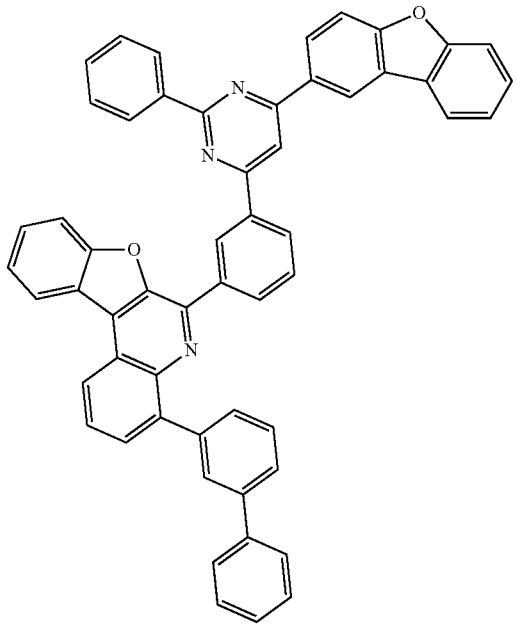
538
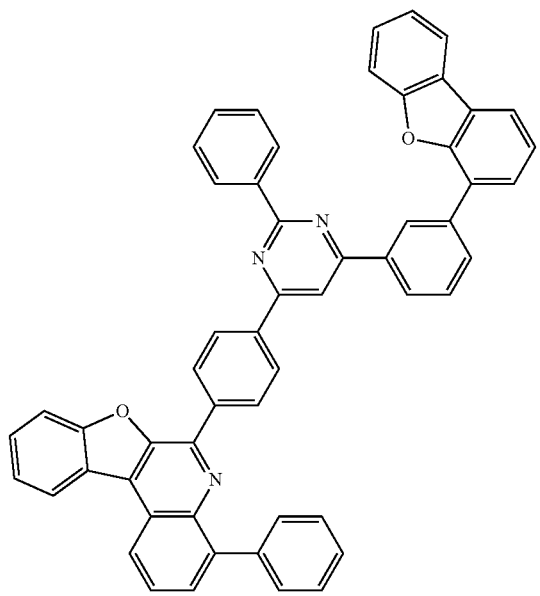

933
-continued
539
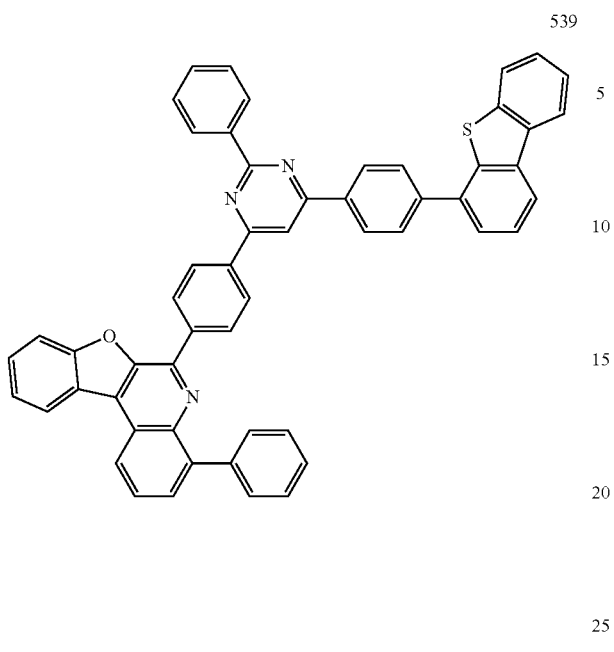
541
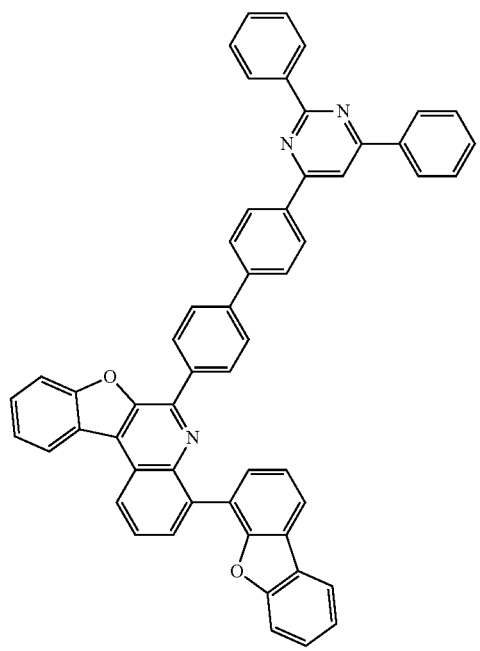
934
-continued
540
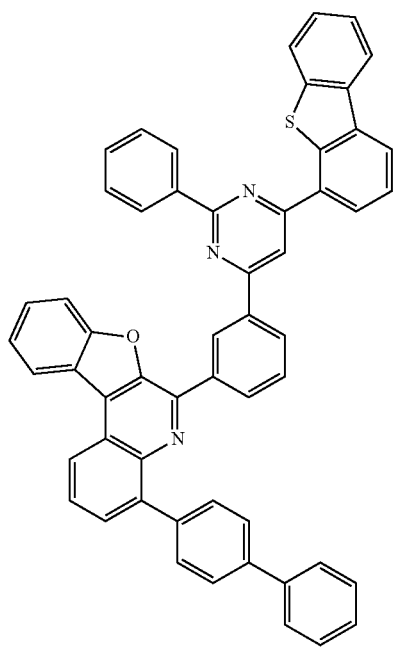
542
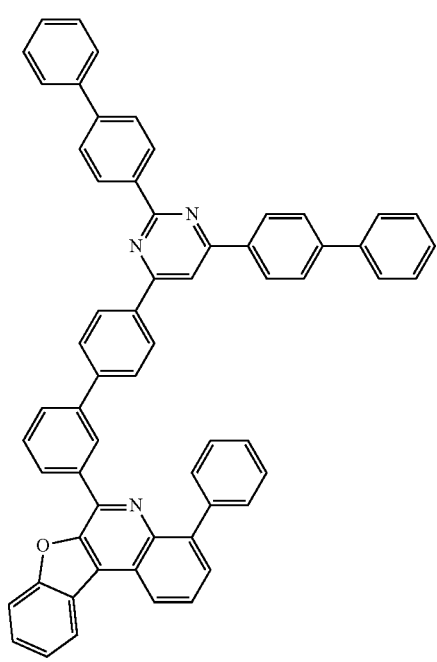

935
-continued
543
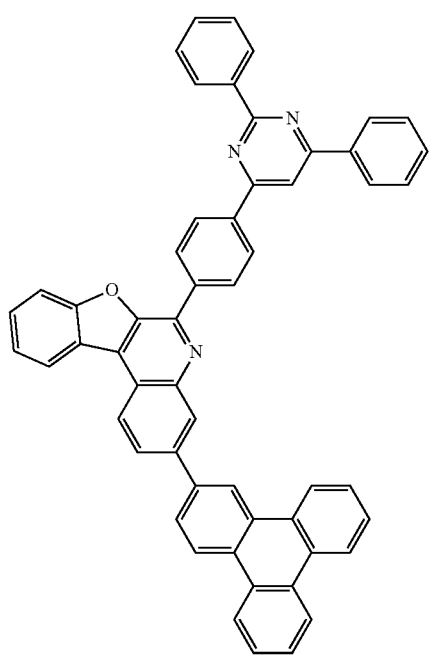
544
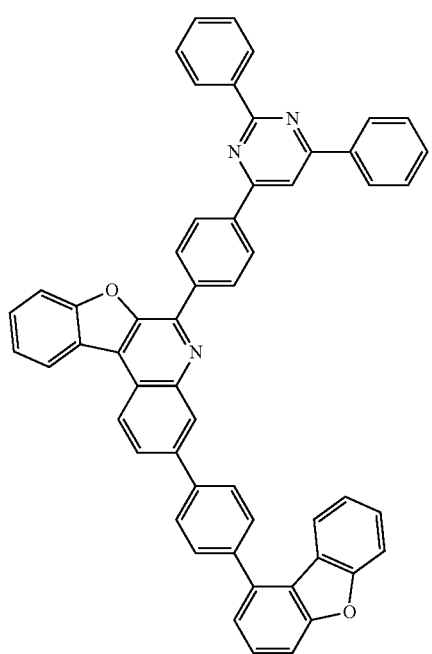
936
-continued
545
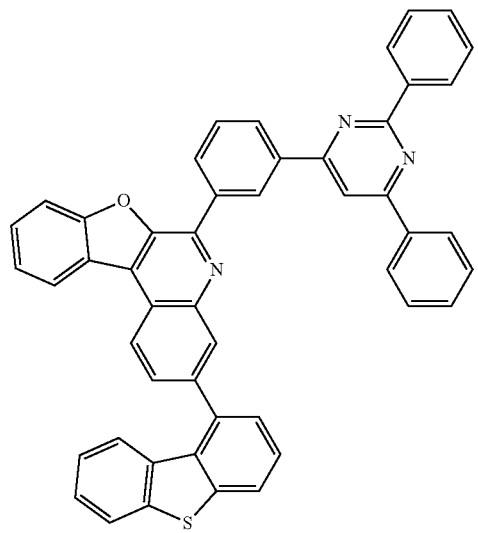
546
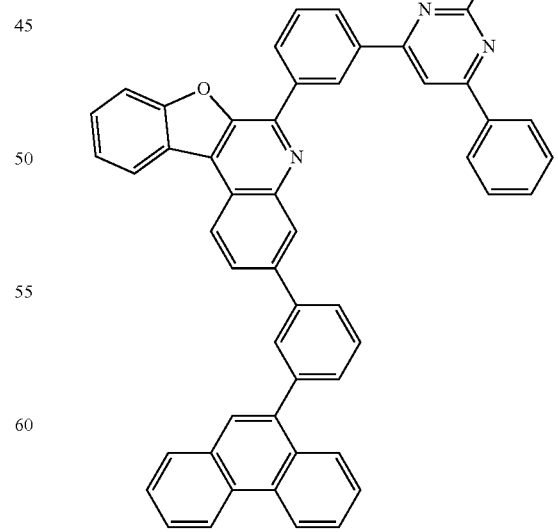

937
-continued
547
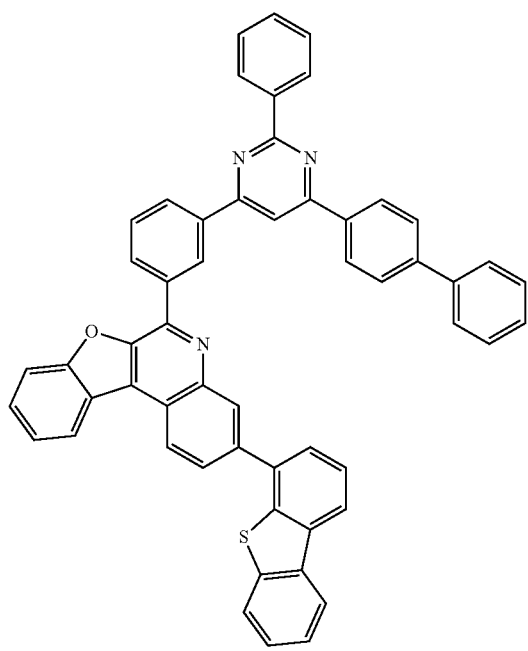
548
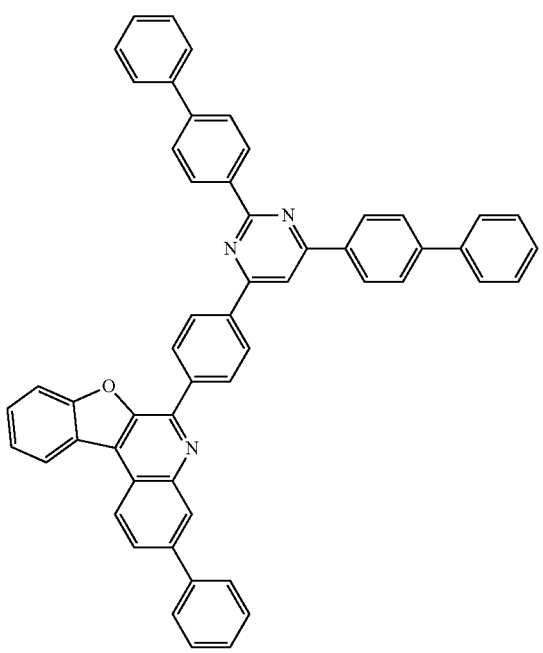
938
-continued
549
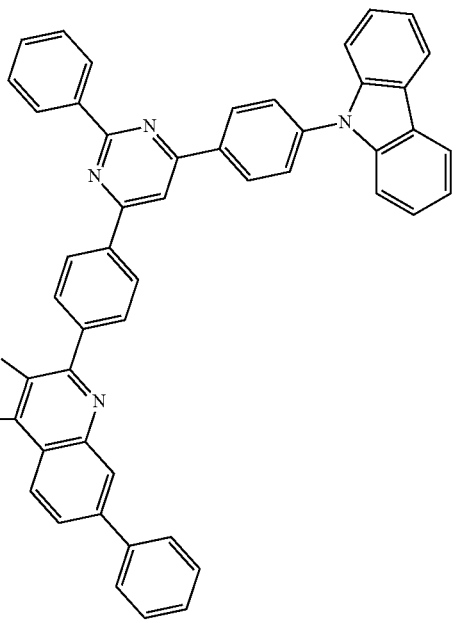
550

939
940
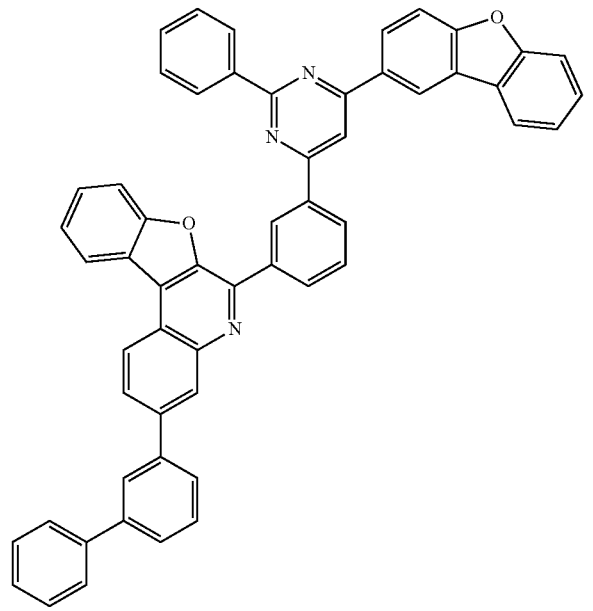
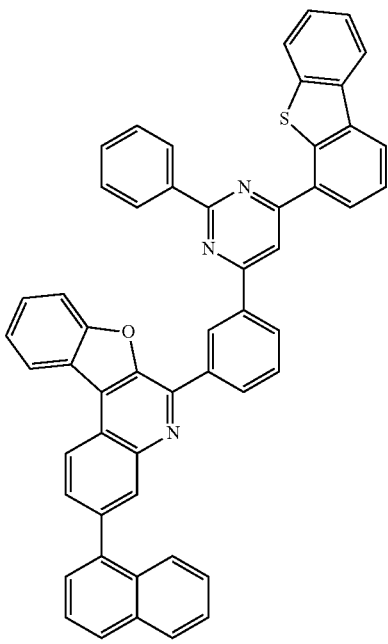
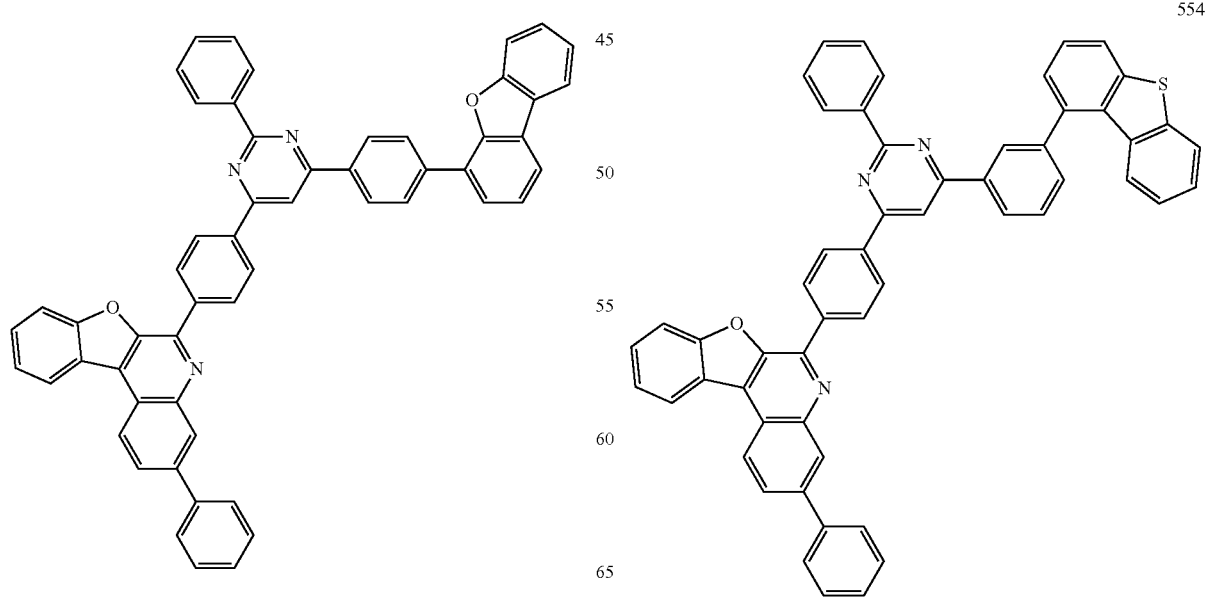

941
-continued
555
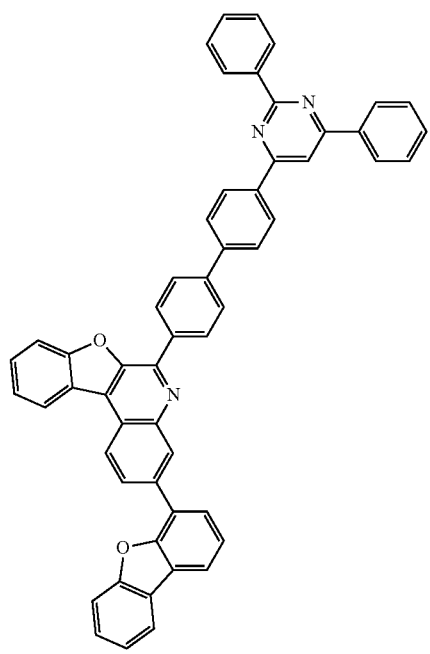
556
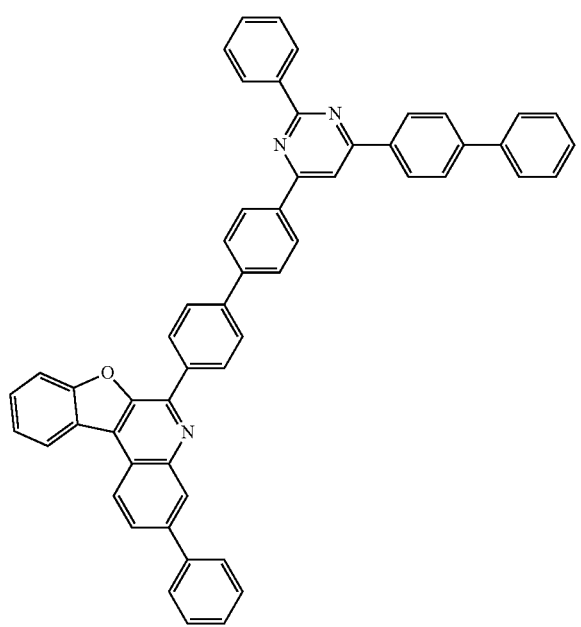
942
-continued
557
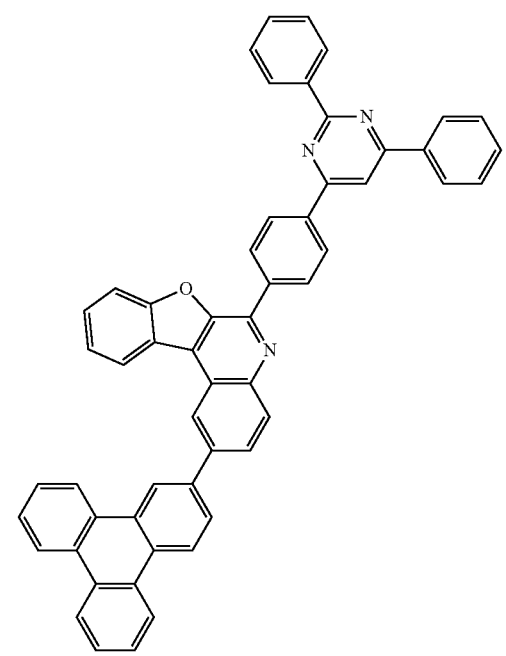
558
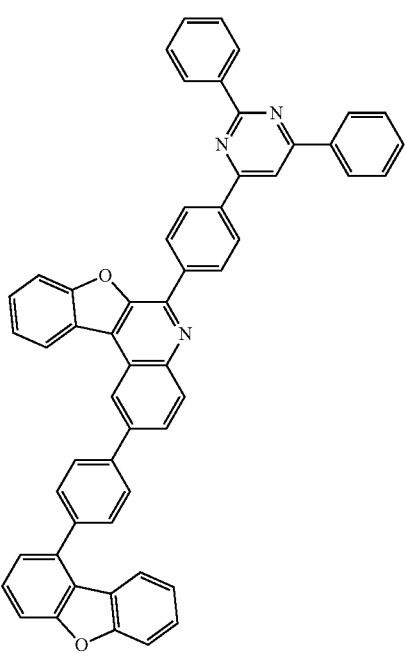

559
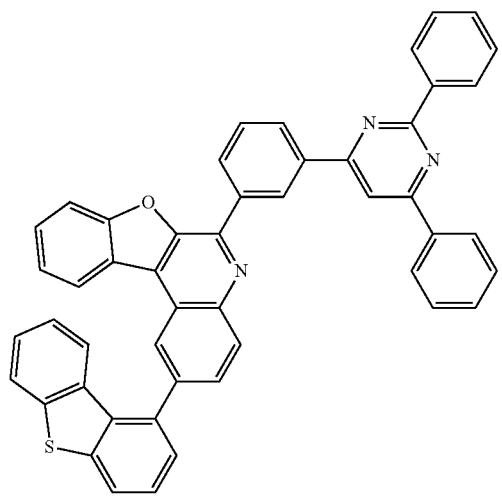
561
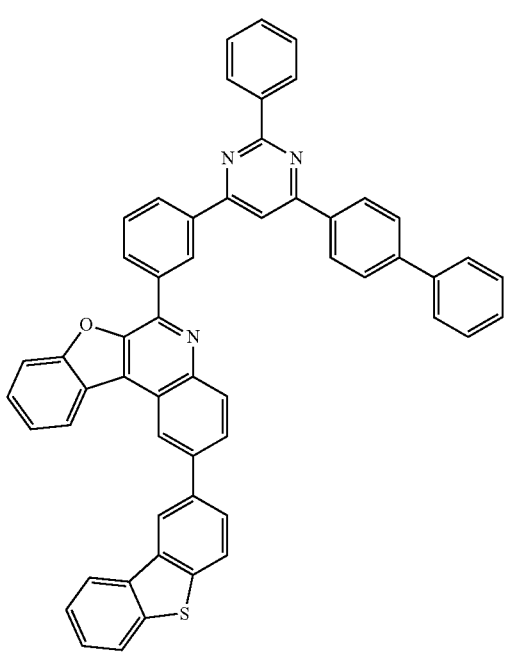
560
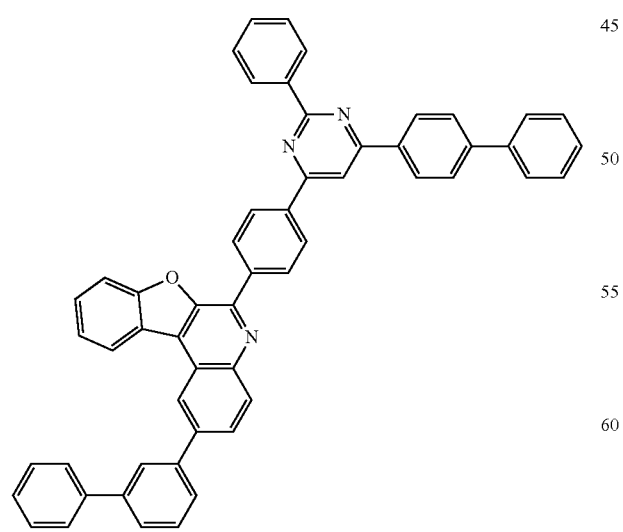
562
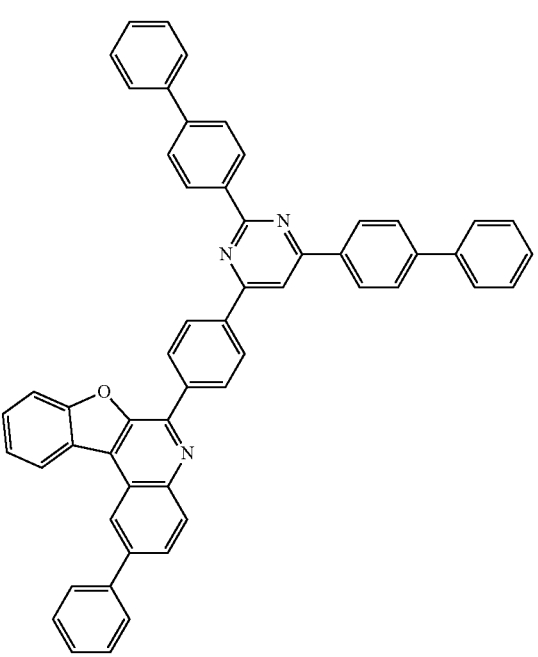

563
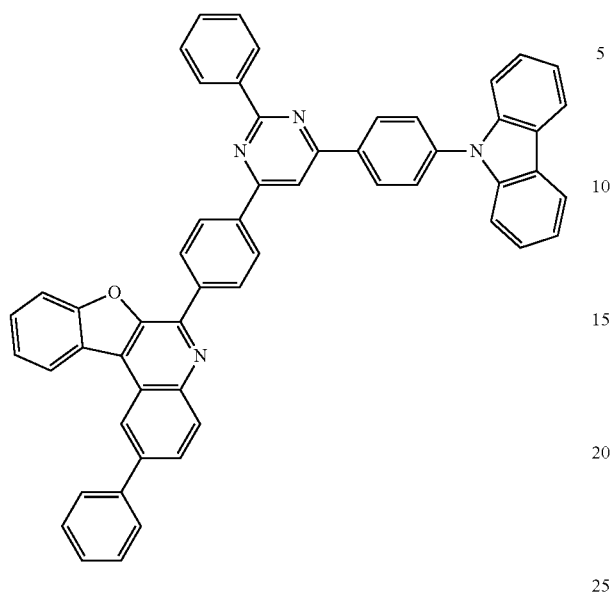
564
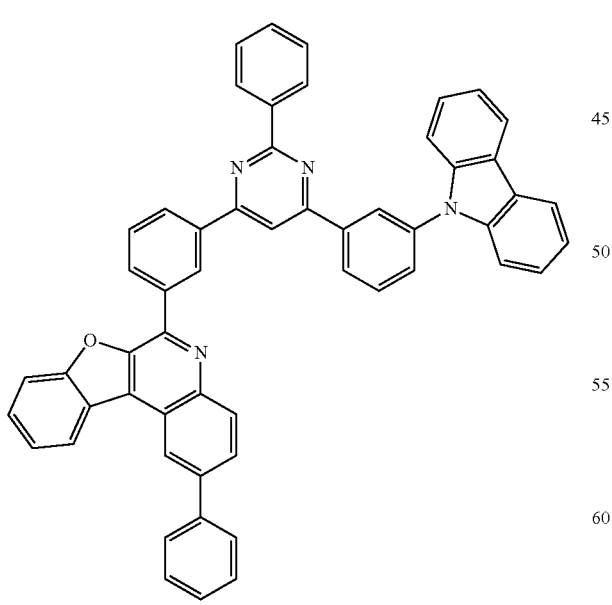
565
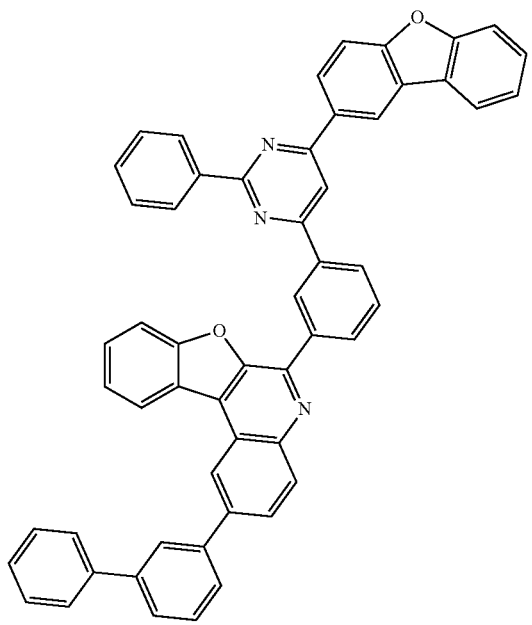
566
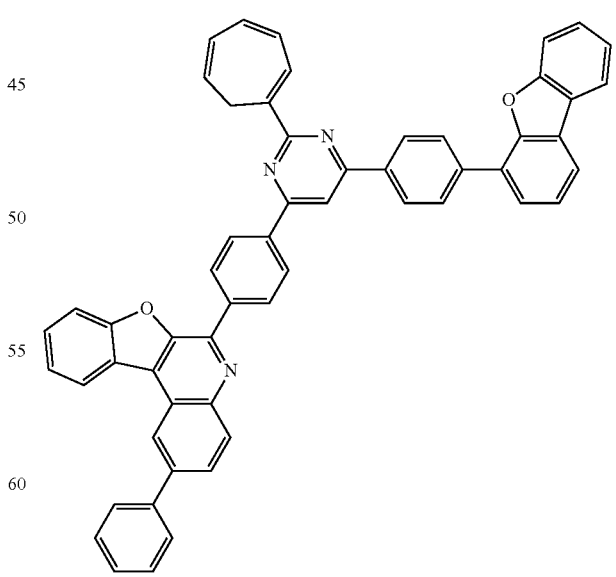

947
-continued
567
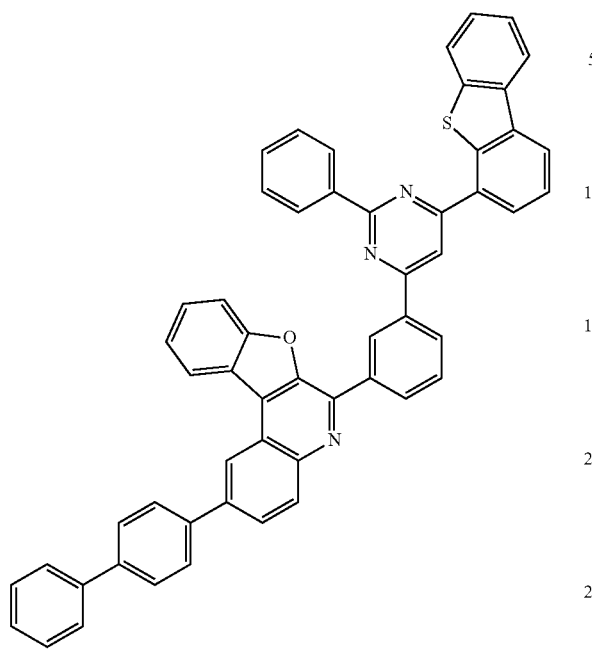
568
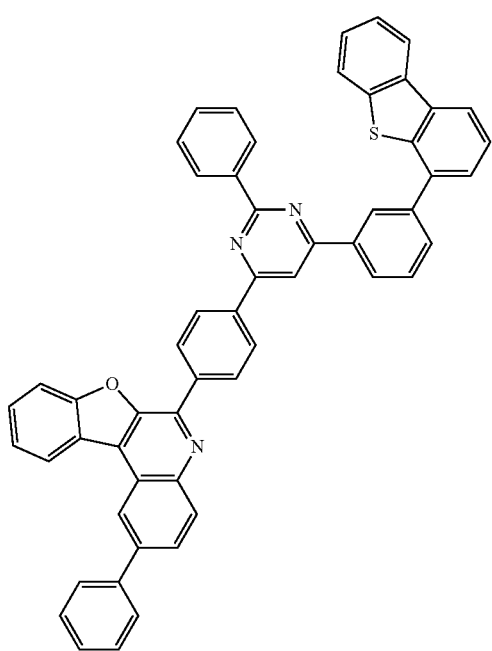
948
-continued
569
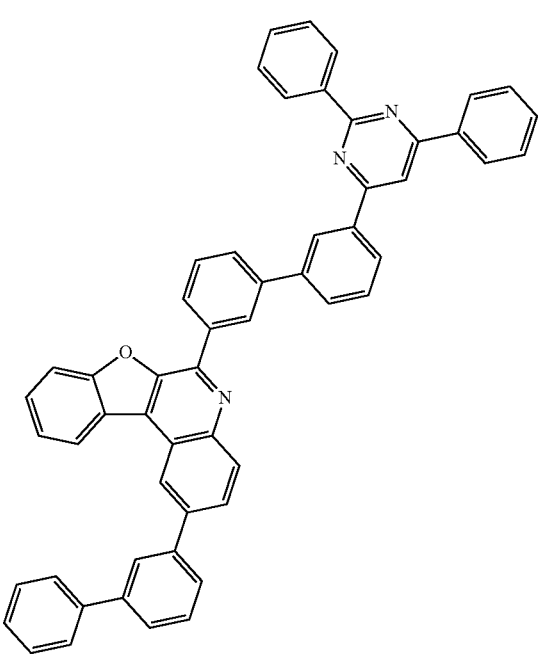
570
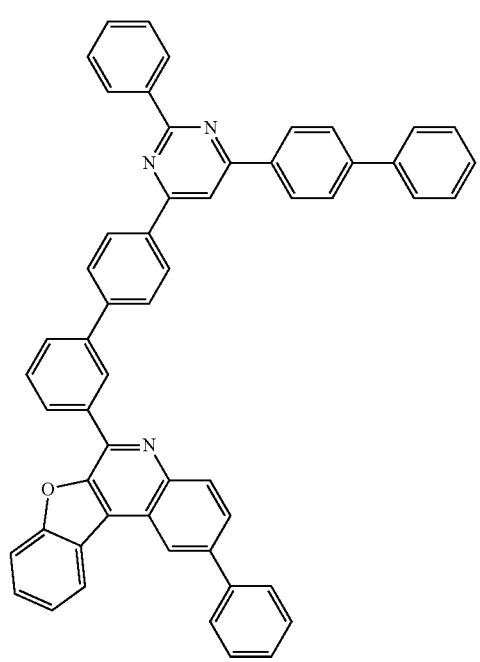

949
-continued
571
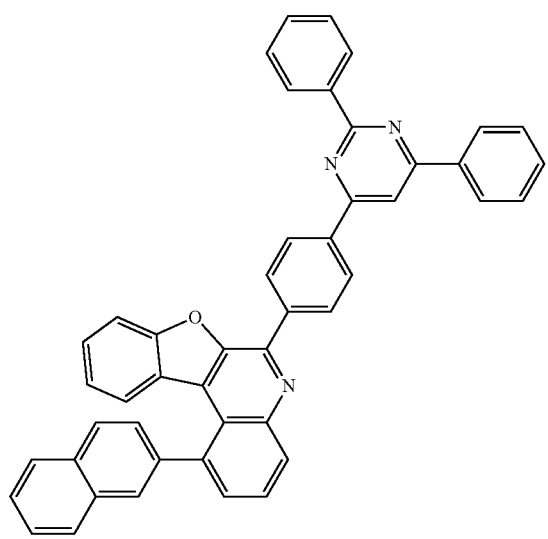
572
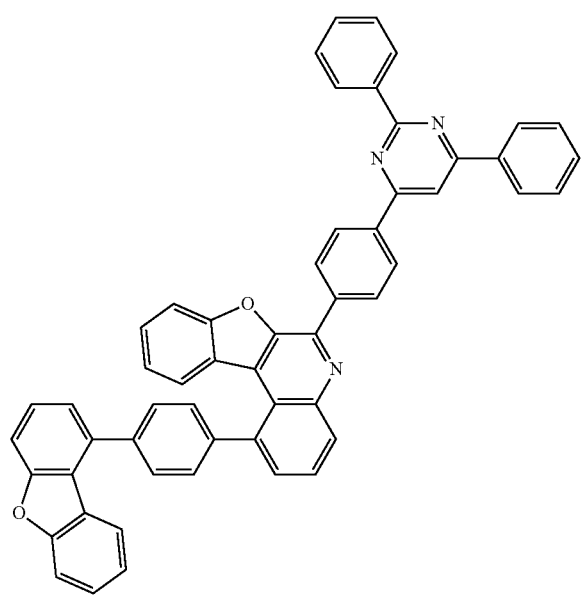
950
-continued
573
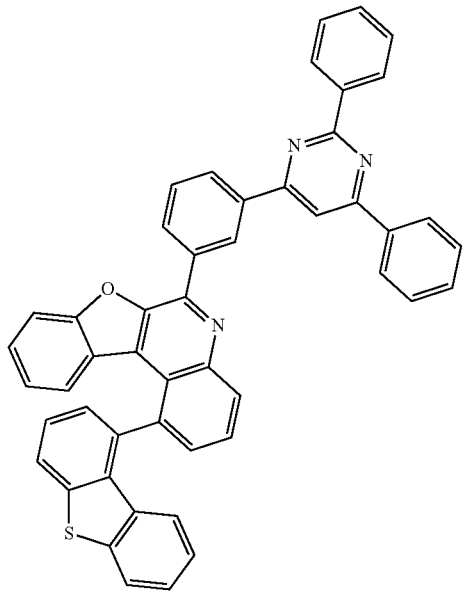
574
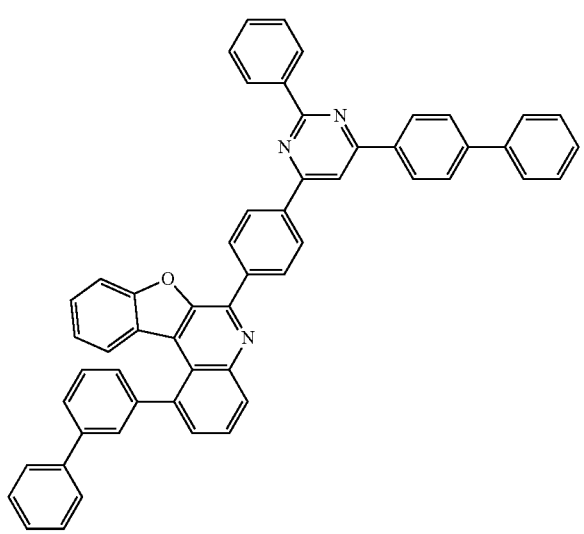

951
-continued
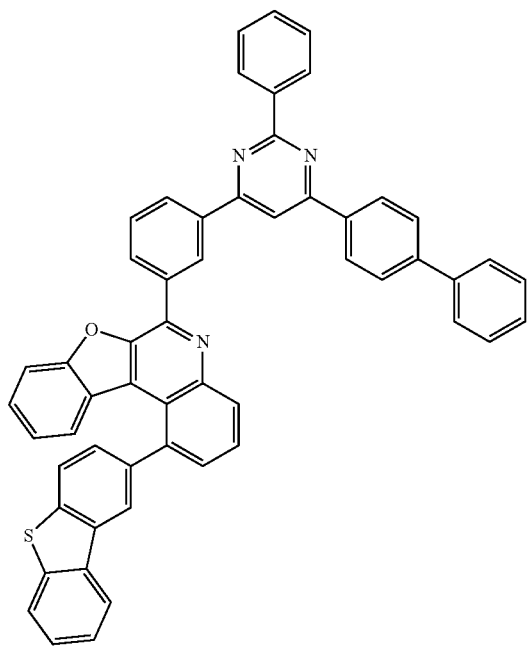
952
-continued
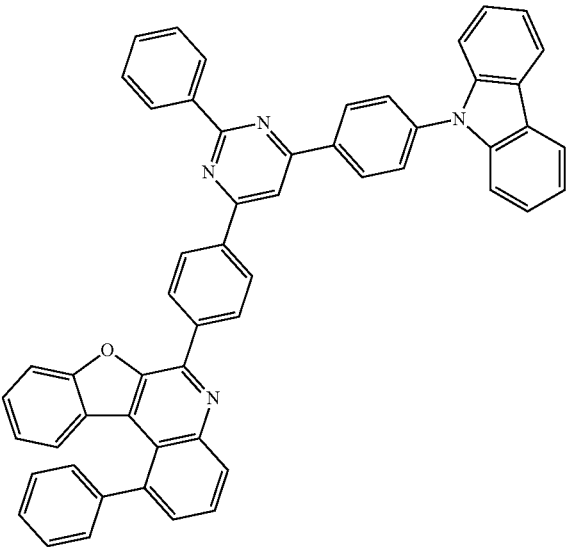
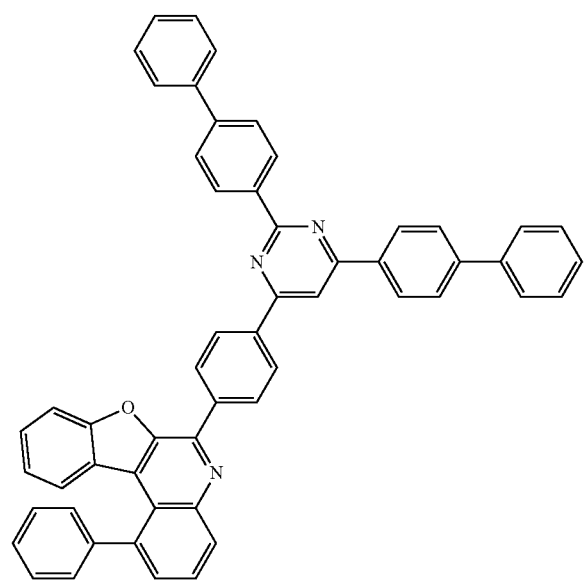
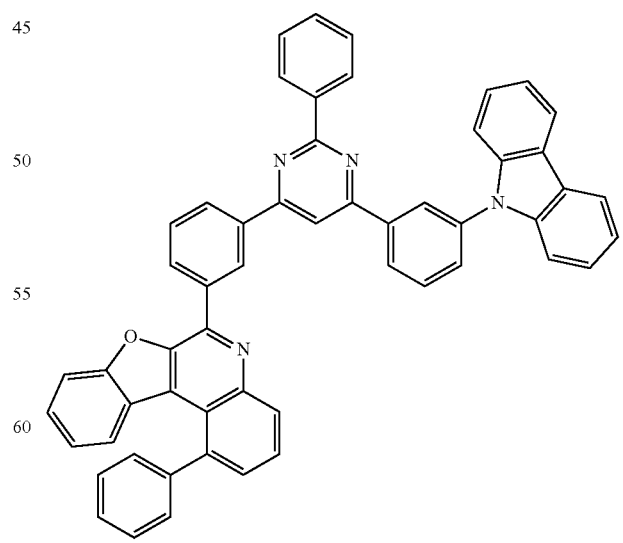

953
-continued
579
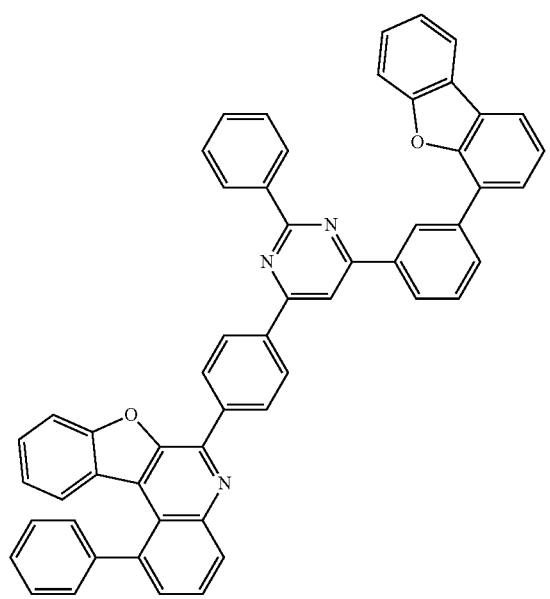
580
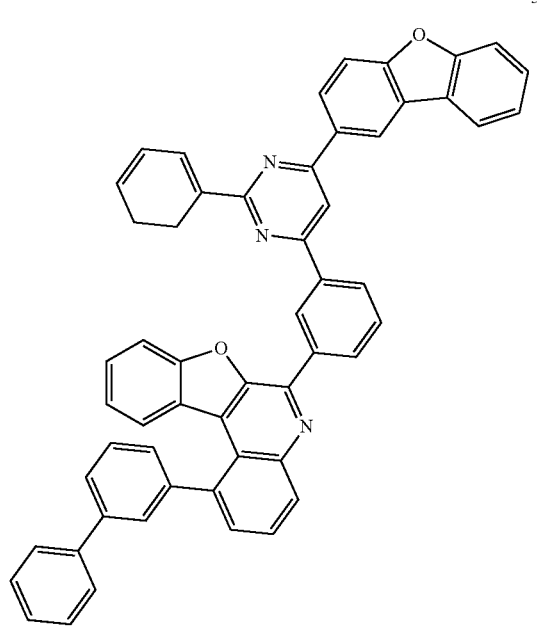
954
-continued
581
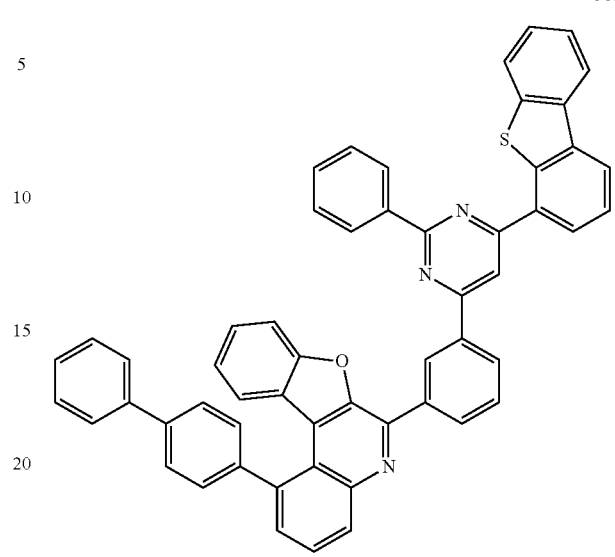
582
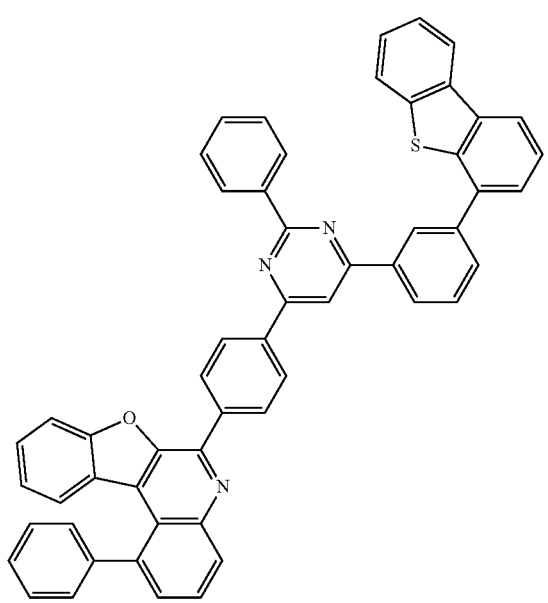

583
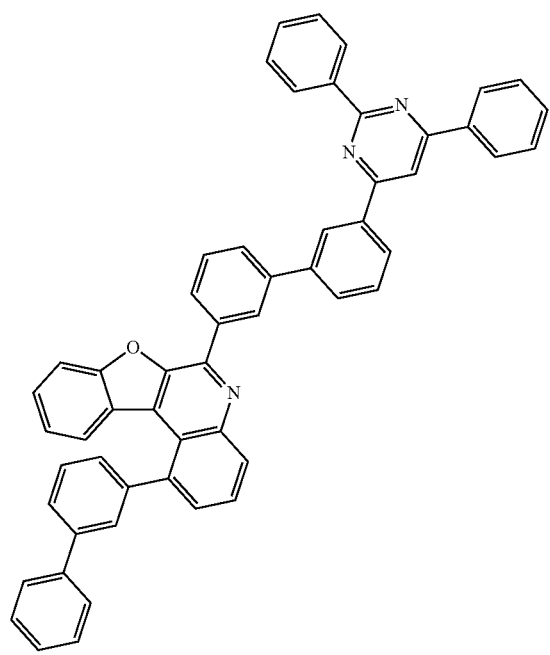
585
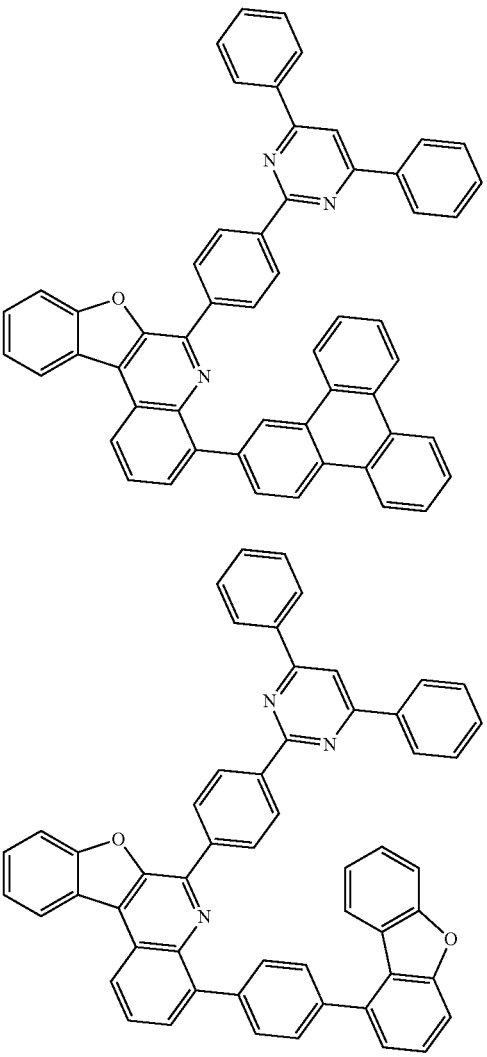
586
584
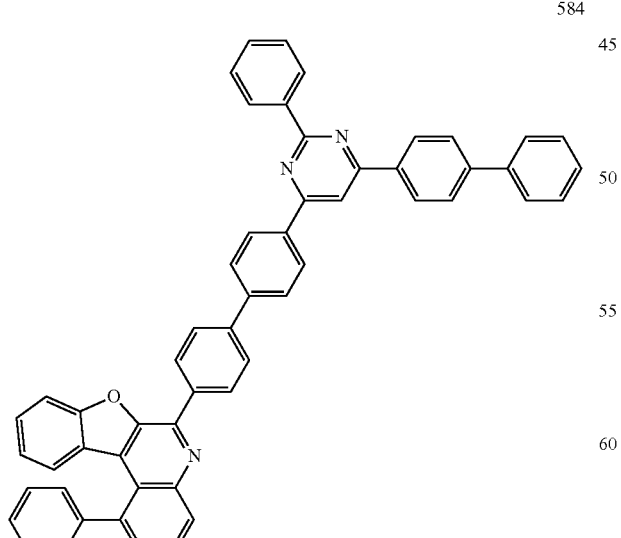
587
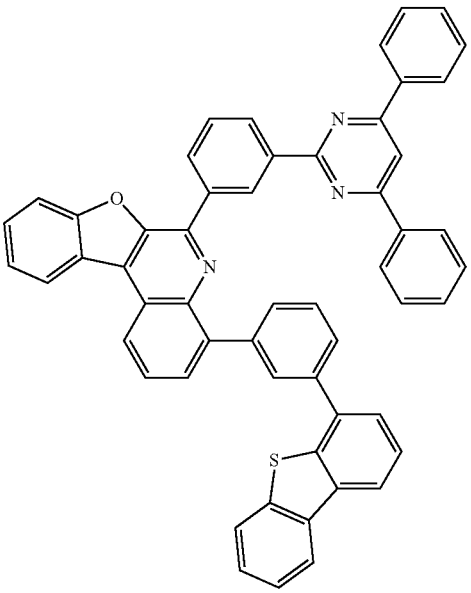

957
-continued
588
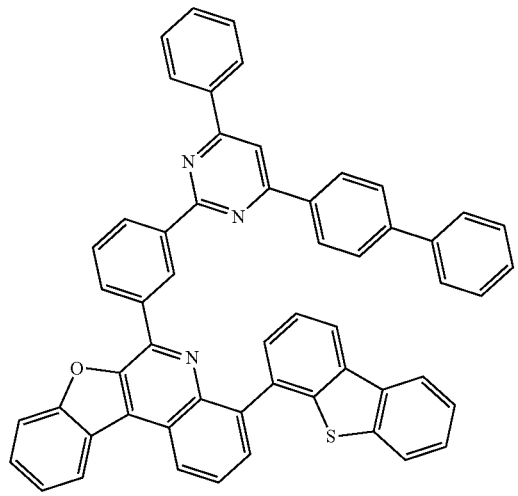
589
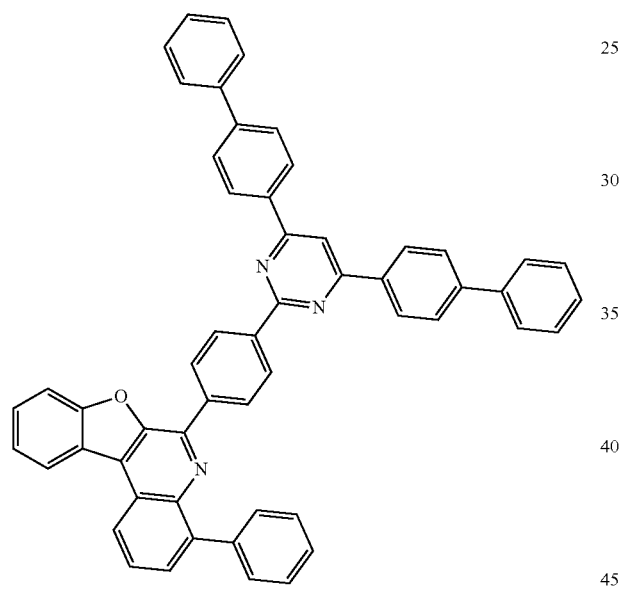
590
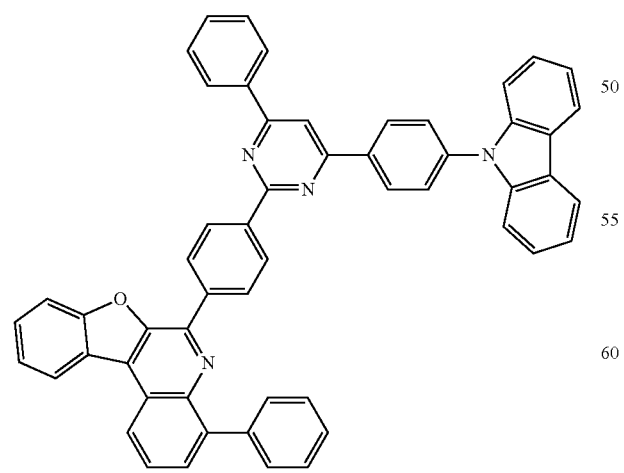
958
-continued
591
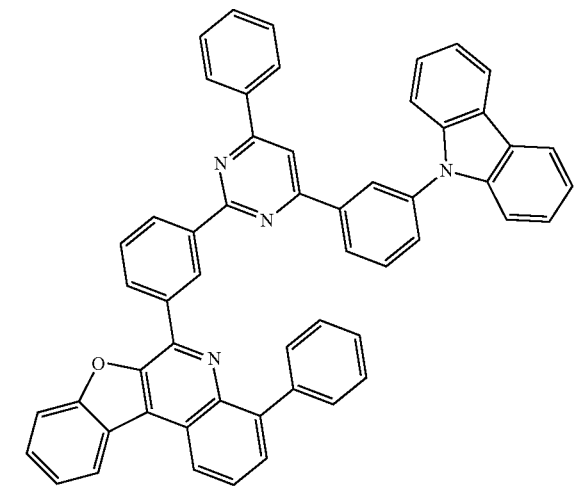
592
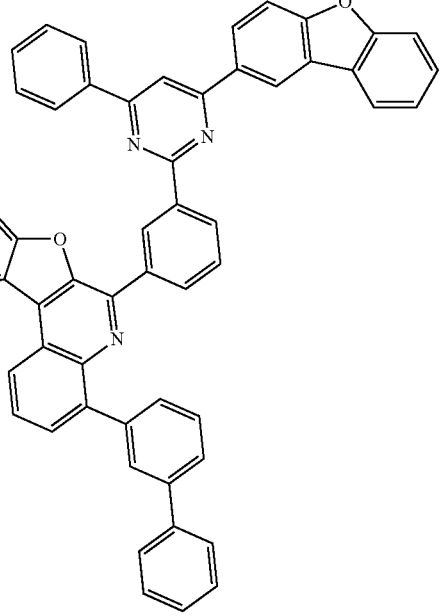

959
-continued
593
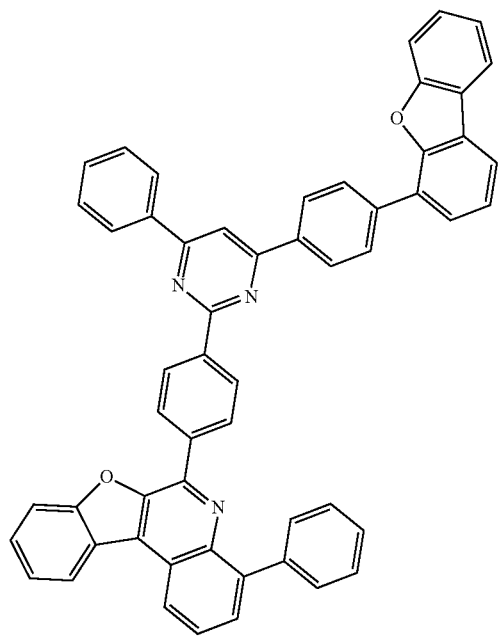
594
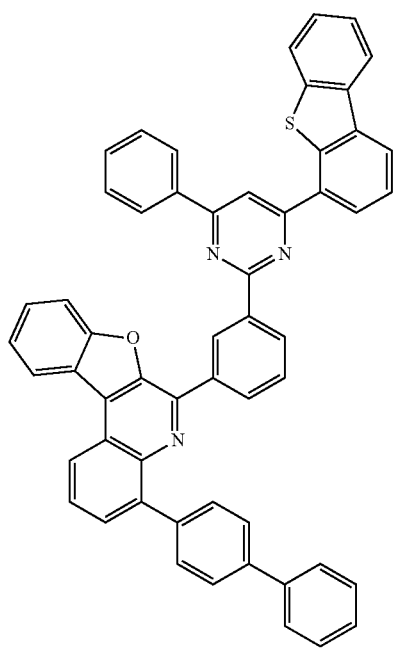
960
-continued
595
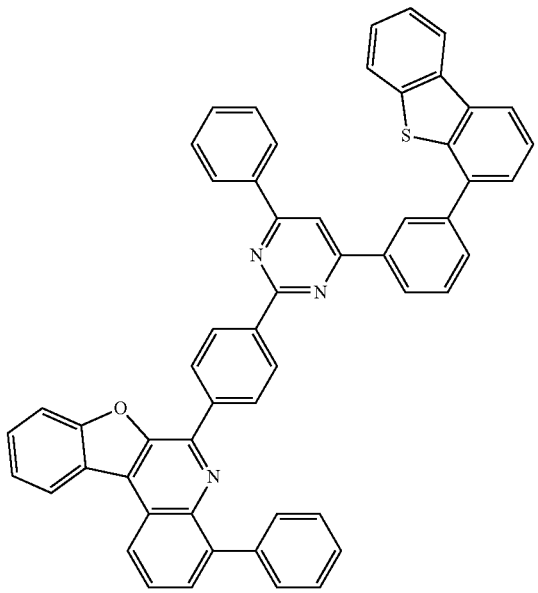
596
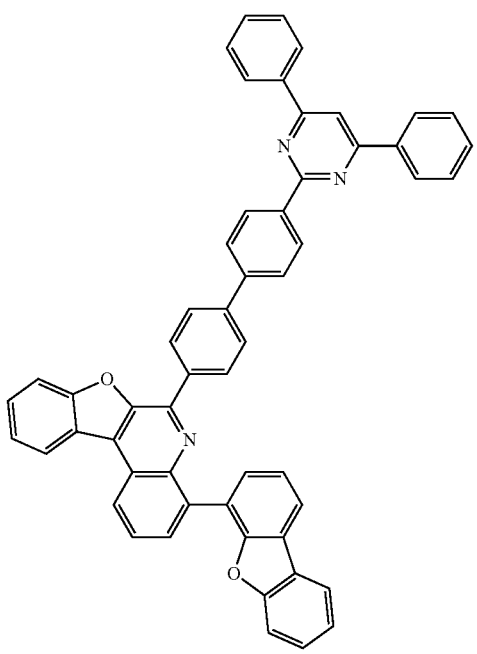

961
-continued
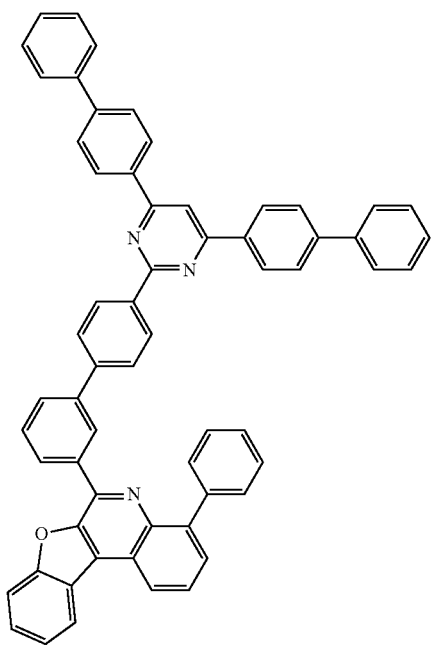
962
-continued
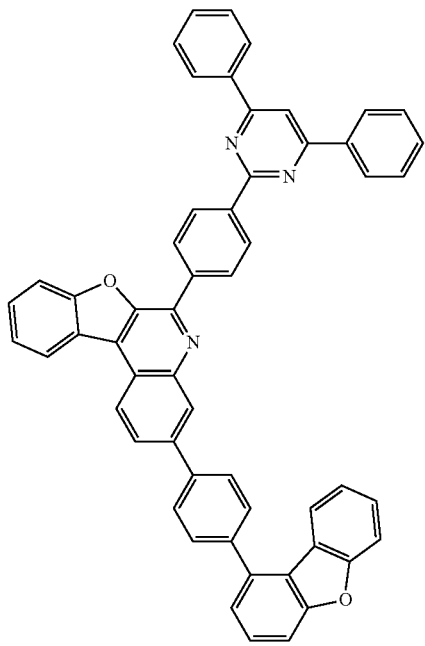
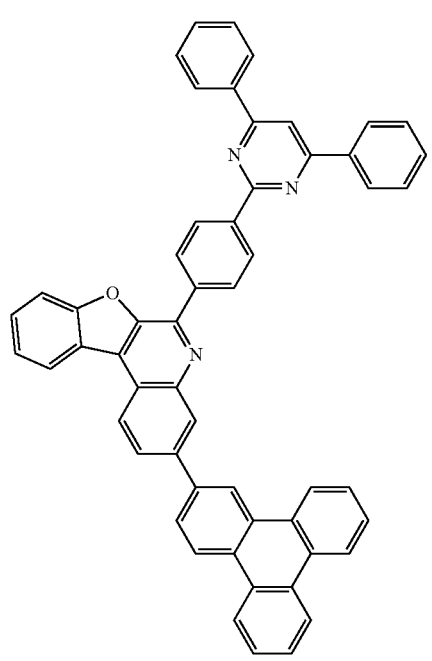
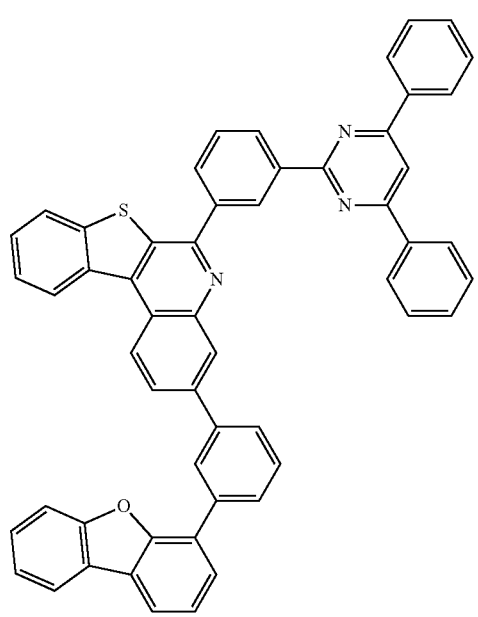

963
-continued
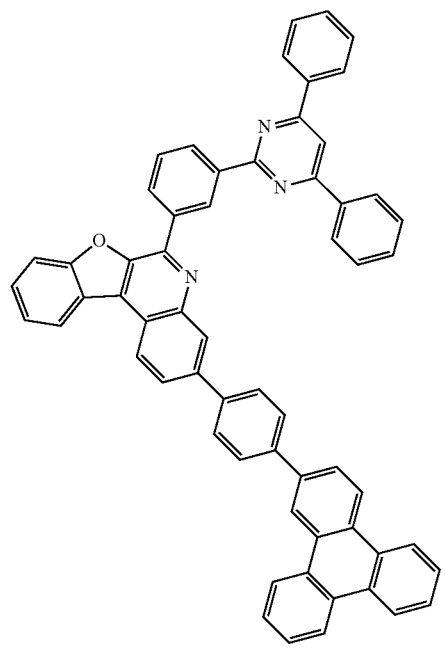
601
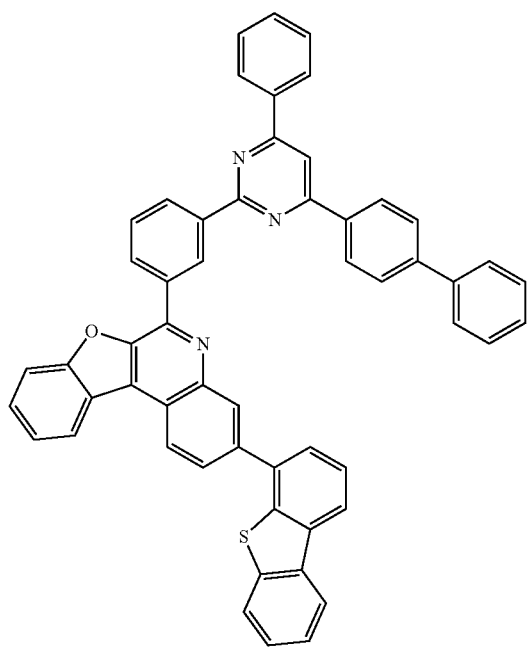
602
964
-continued
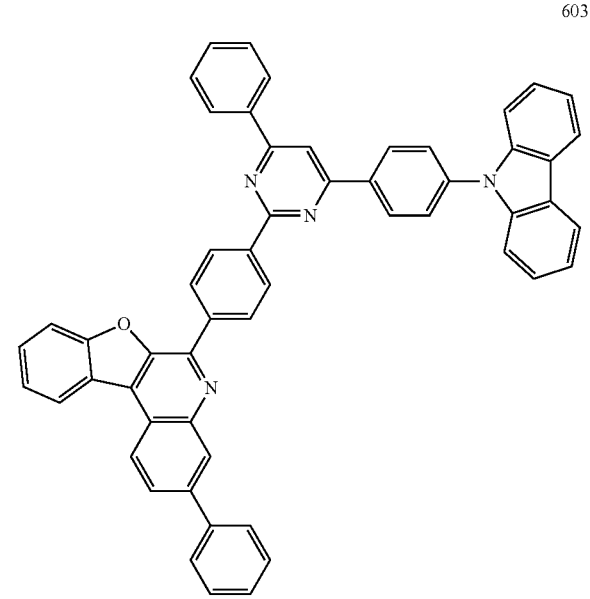
603
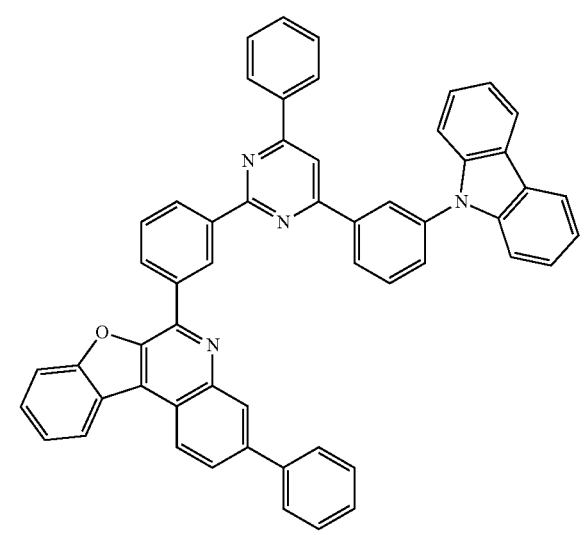
604

965
-continued
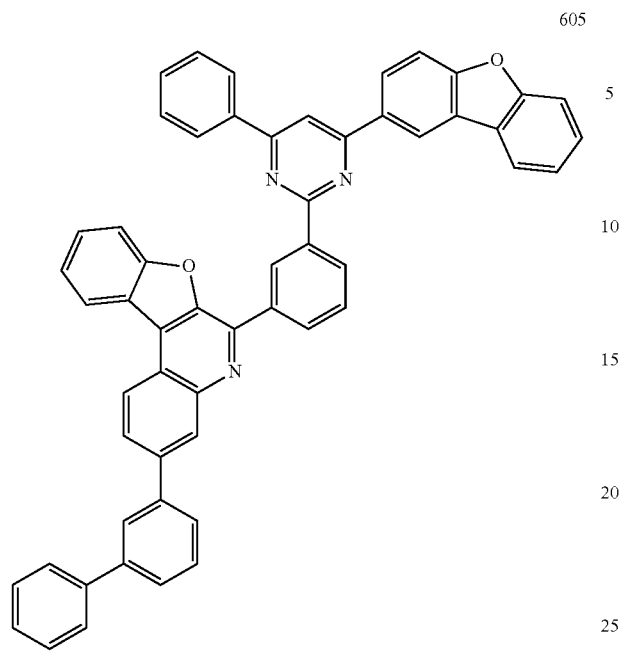
966
-continued
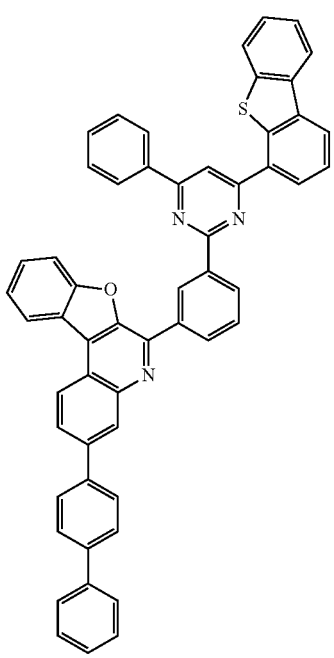
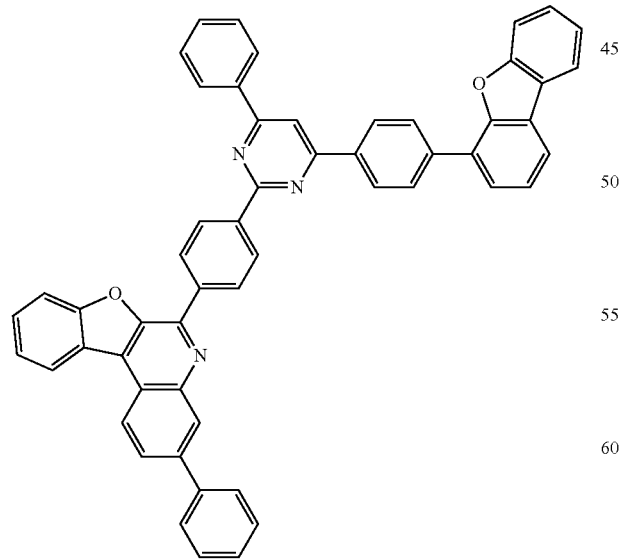
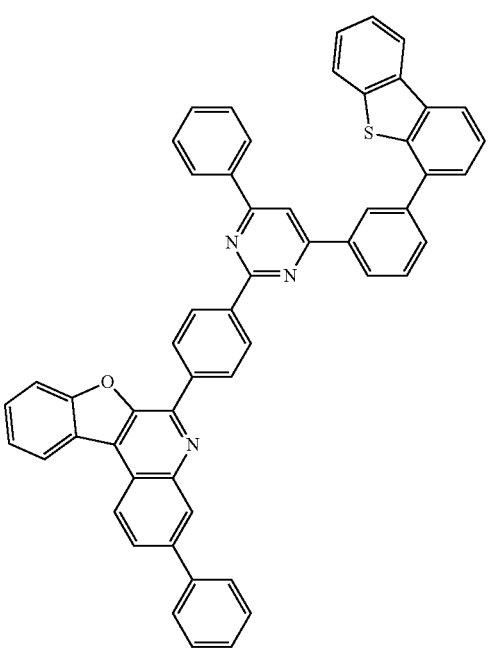

967
-continued
968
-continued
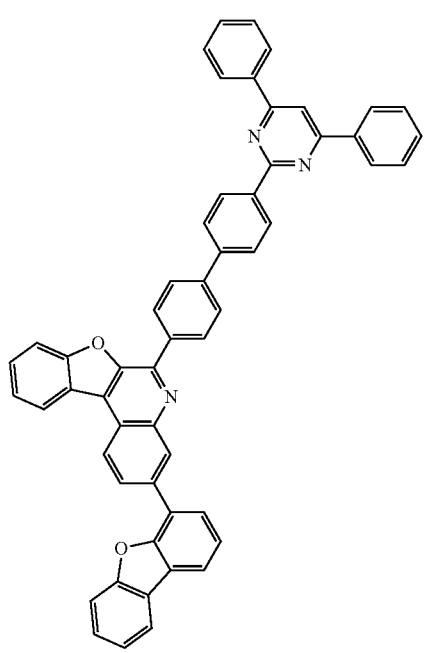
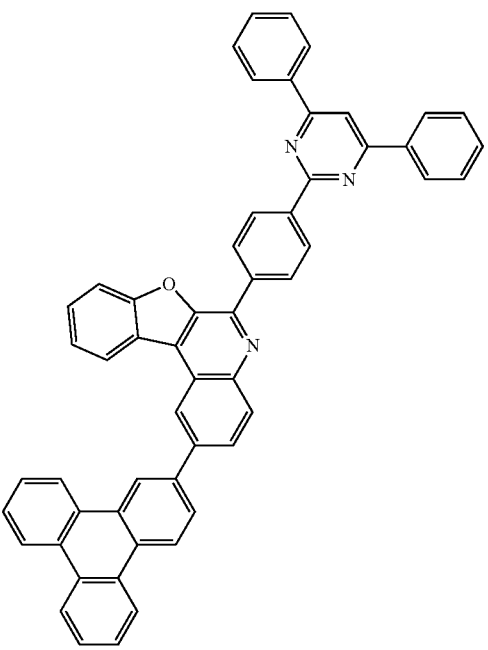
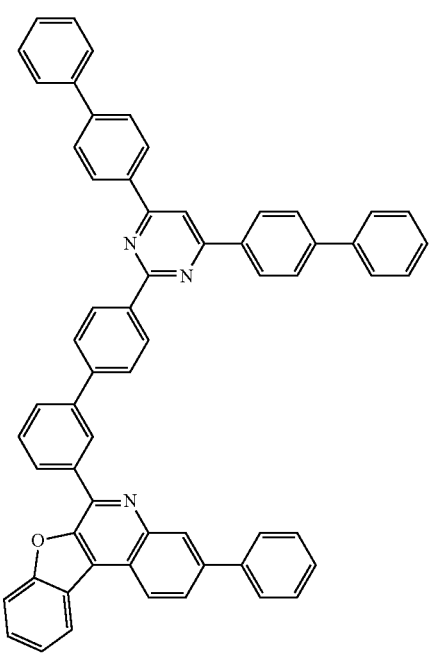
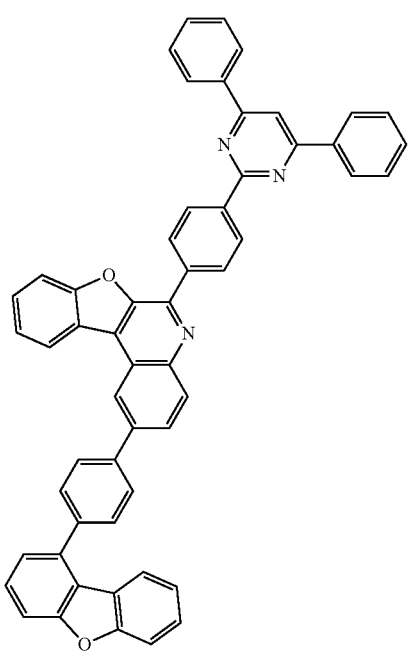

-continued
613
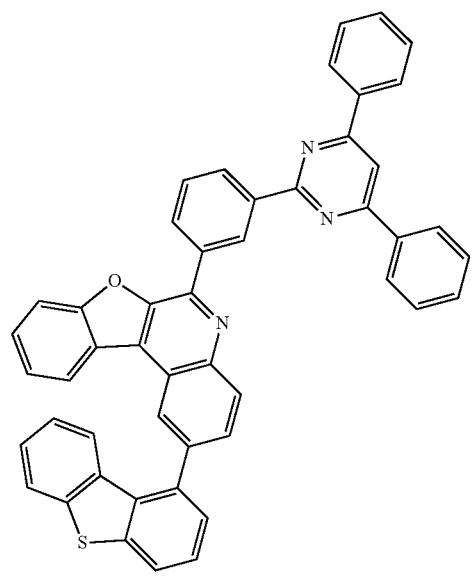
614
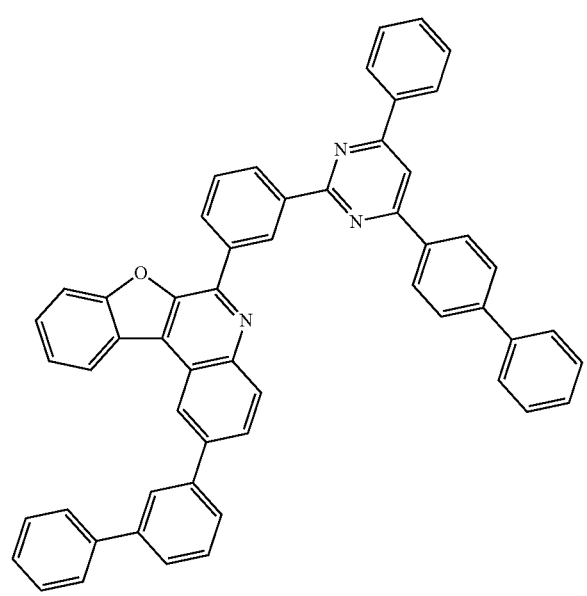
-continued
615
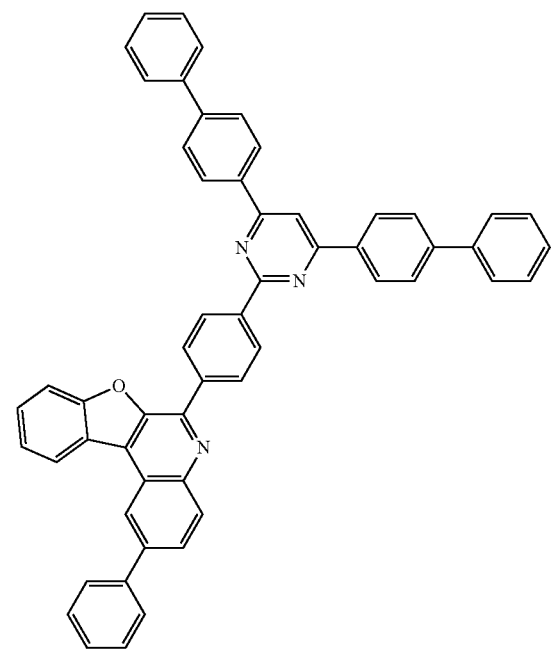
616
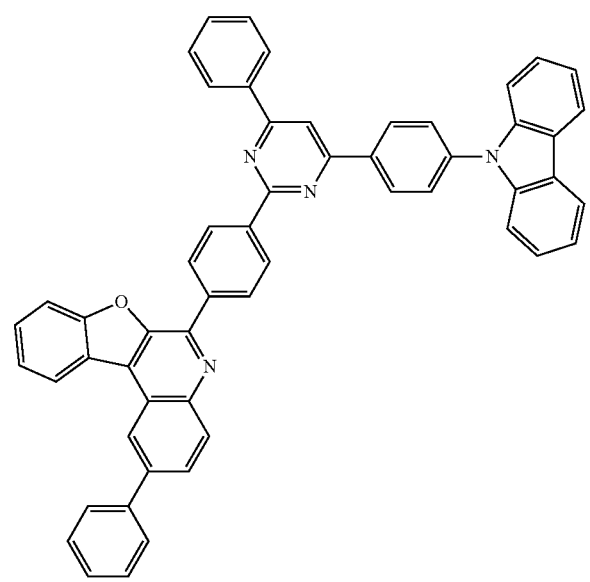

971
-continued
972
-continued
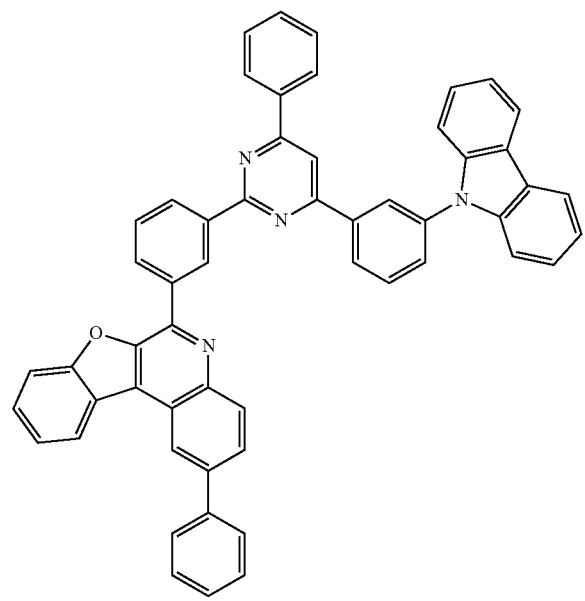
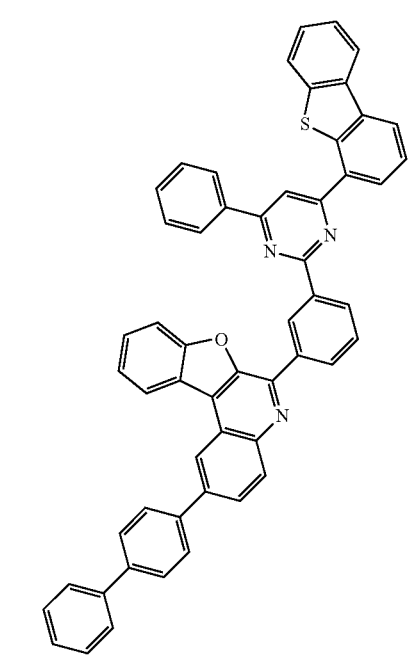

973
-continued
621
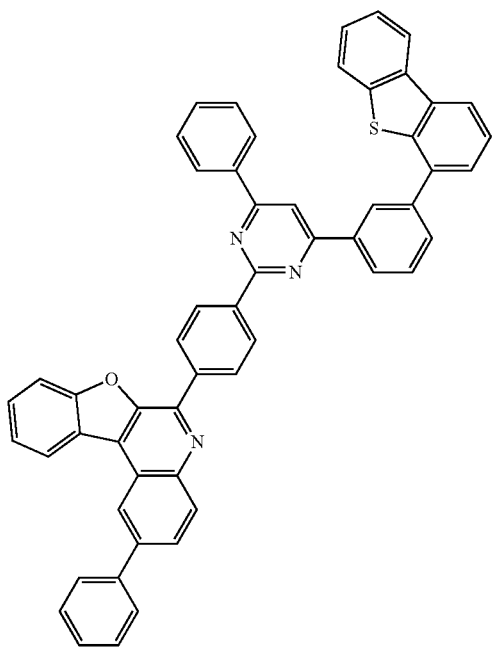
622
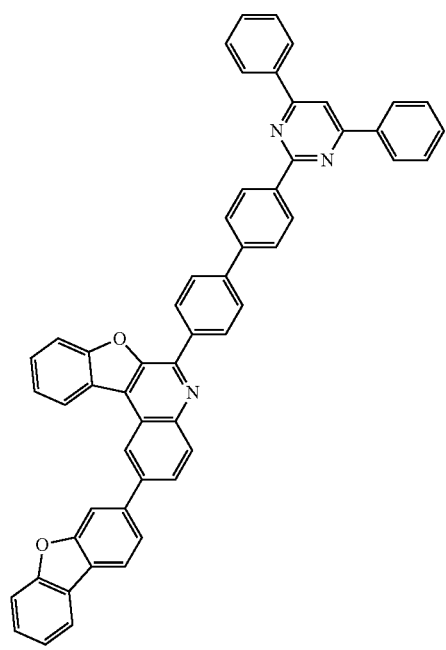
974
-continued
623
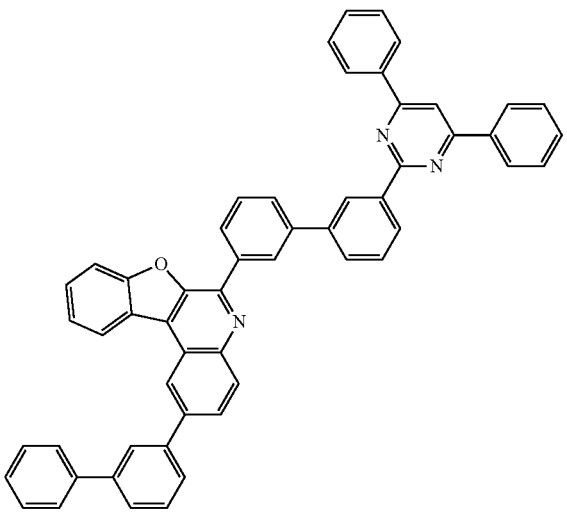
624

975
-continued
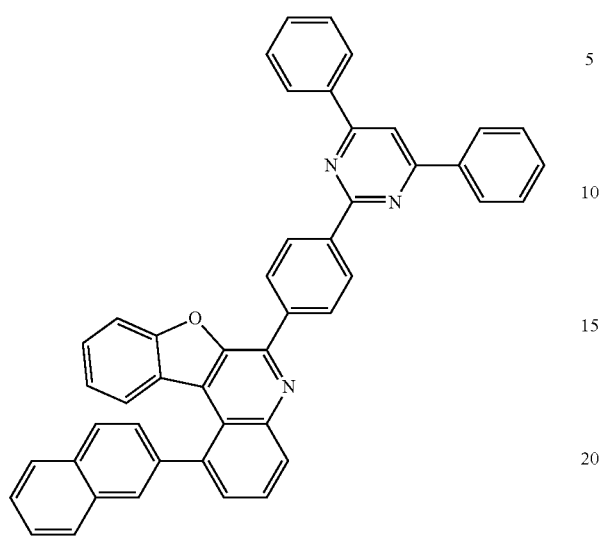
625
976
-continued
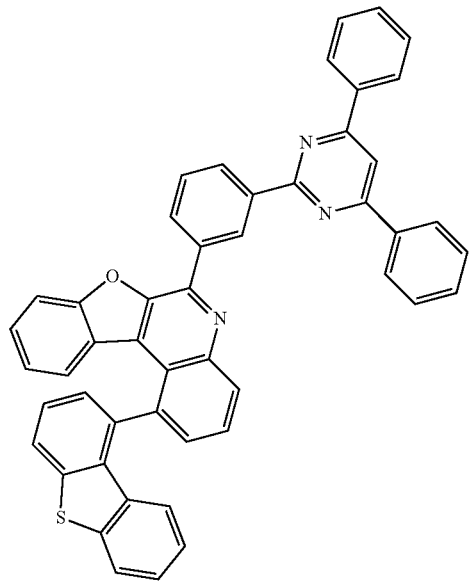
627
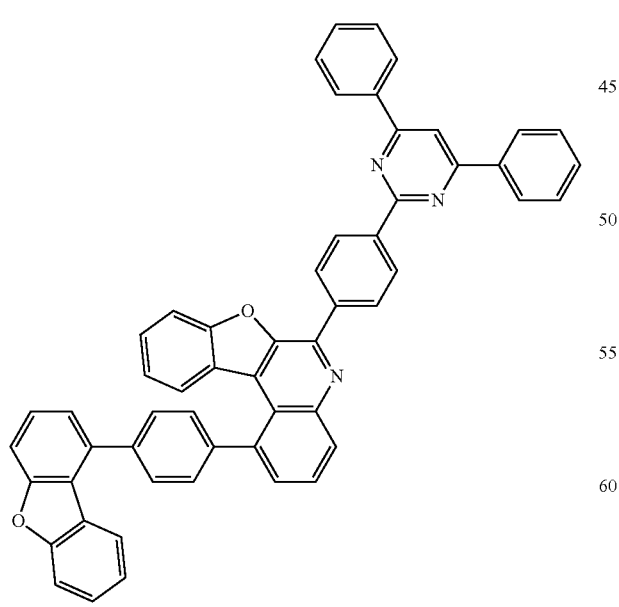
626
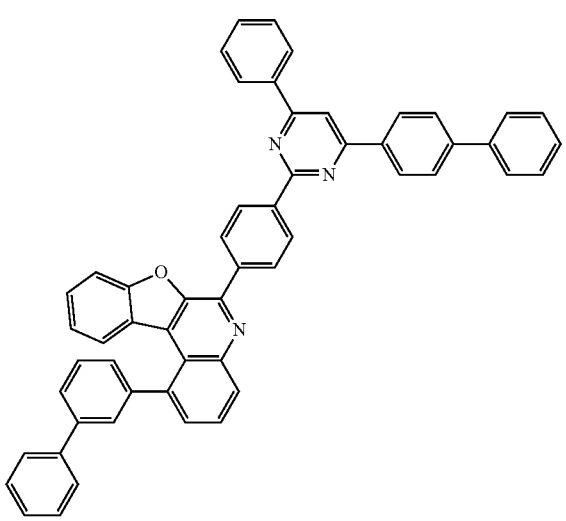
628

977
-continued
629
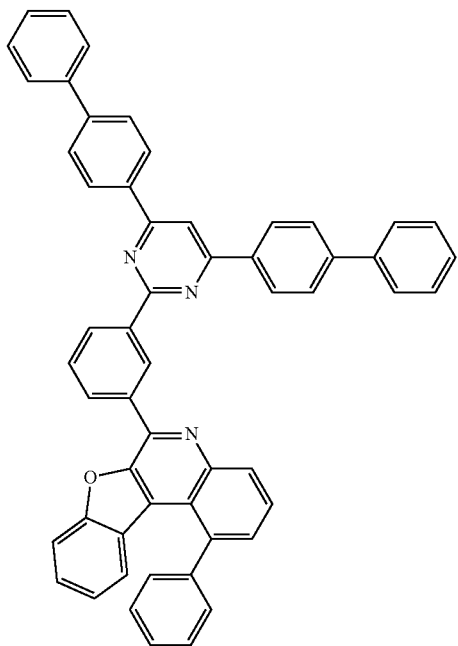
630
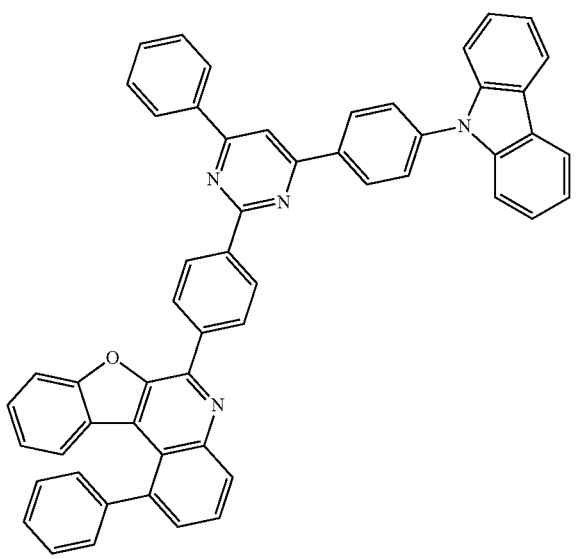
978
-continued
631
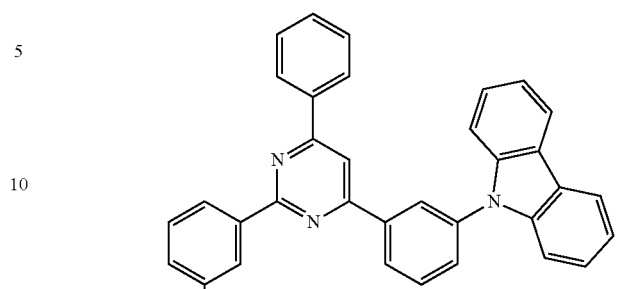
632
633
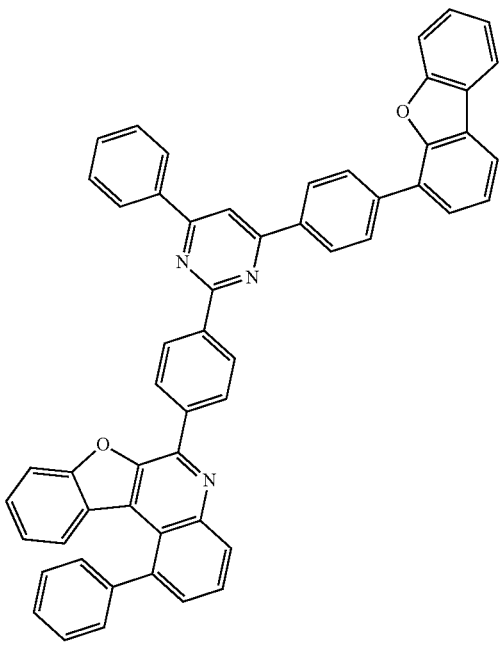

634
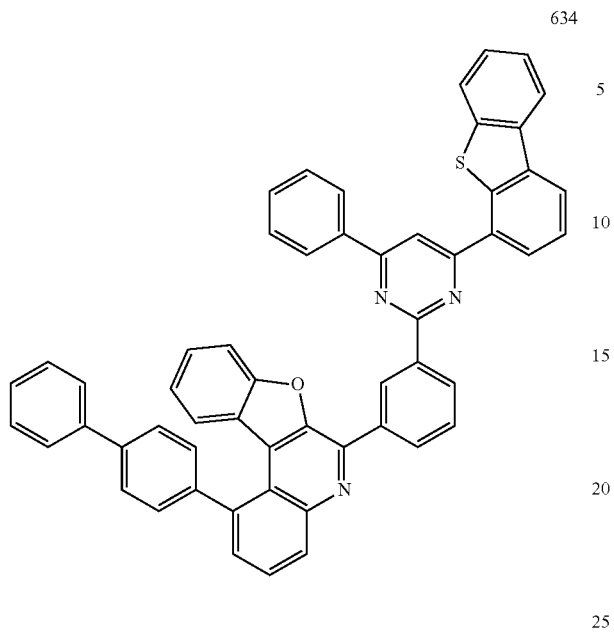
636
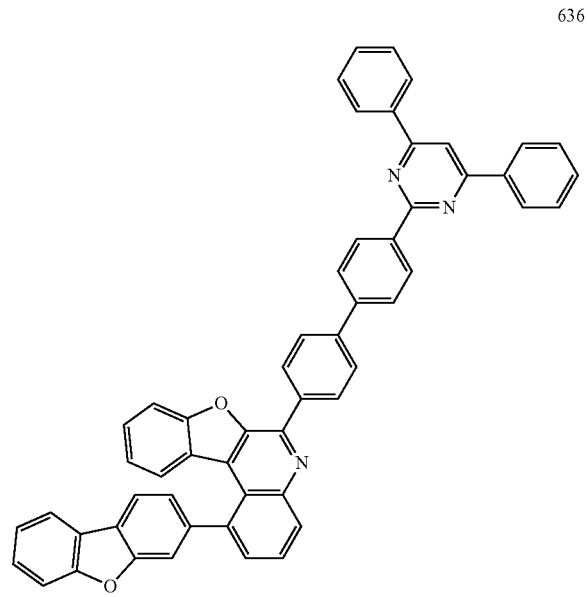
635
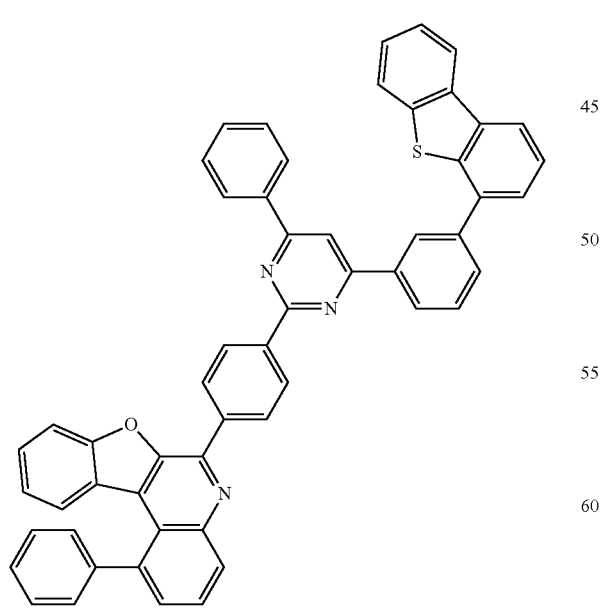
637
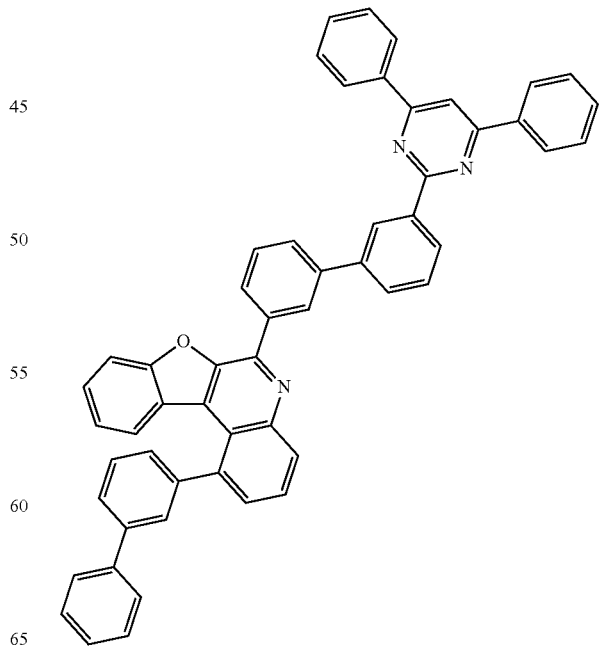

981
-continued
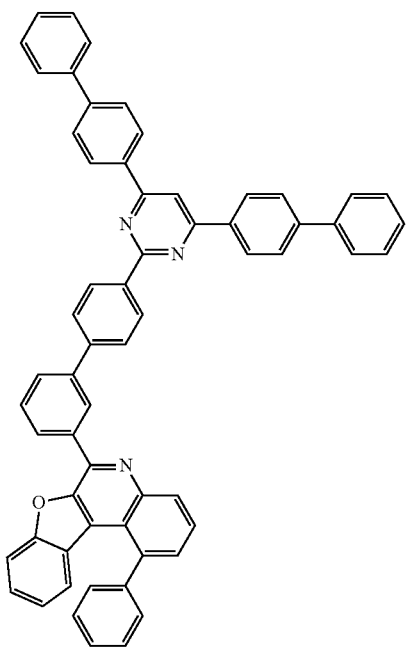
638
982
-continued
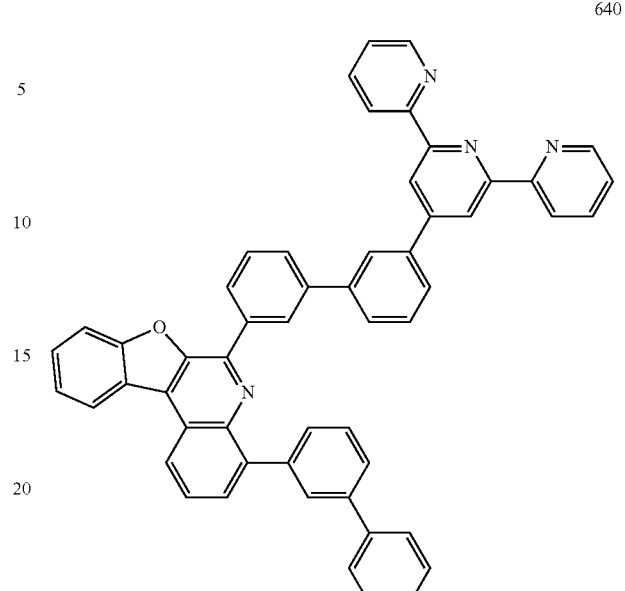
640
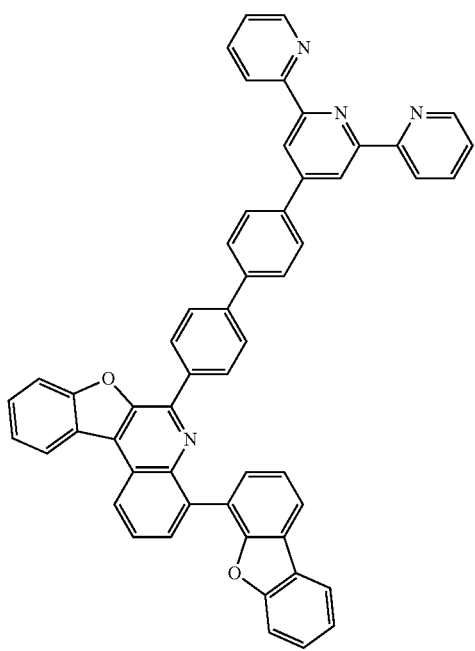
639
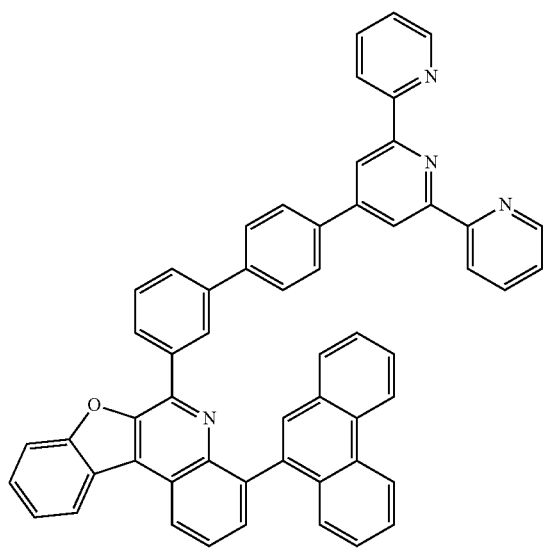
641

983
-continued
984
-continued
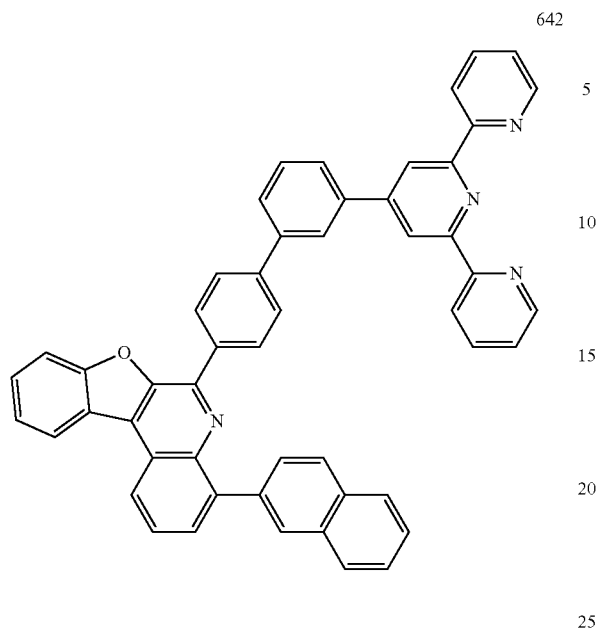
642
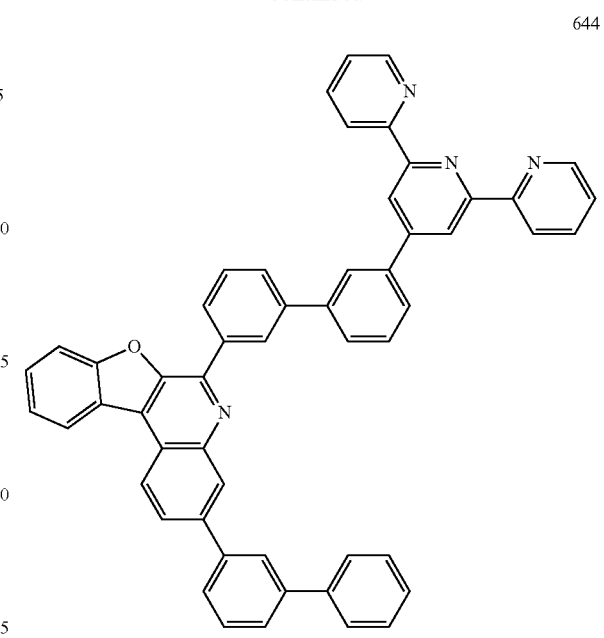
644

985
-continued
646
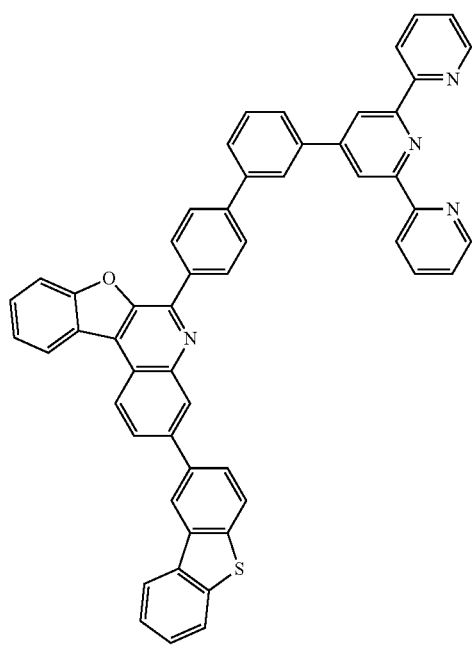
647
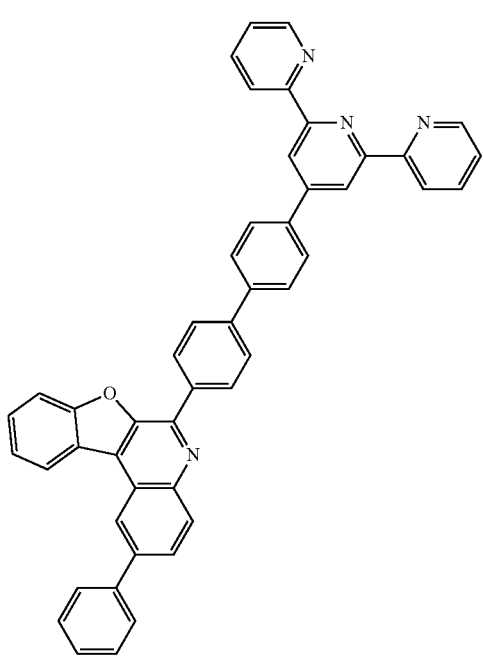
986
-continued
648
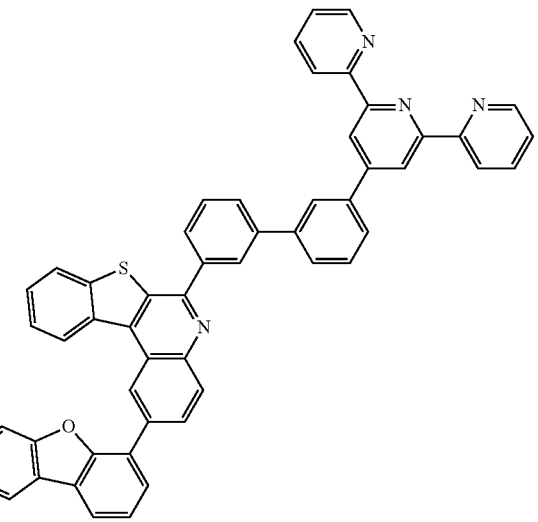
649
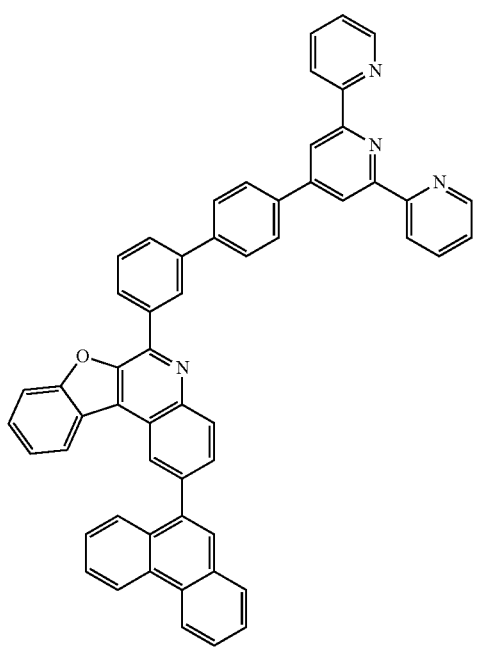

-continued
650
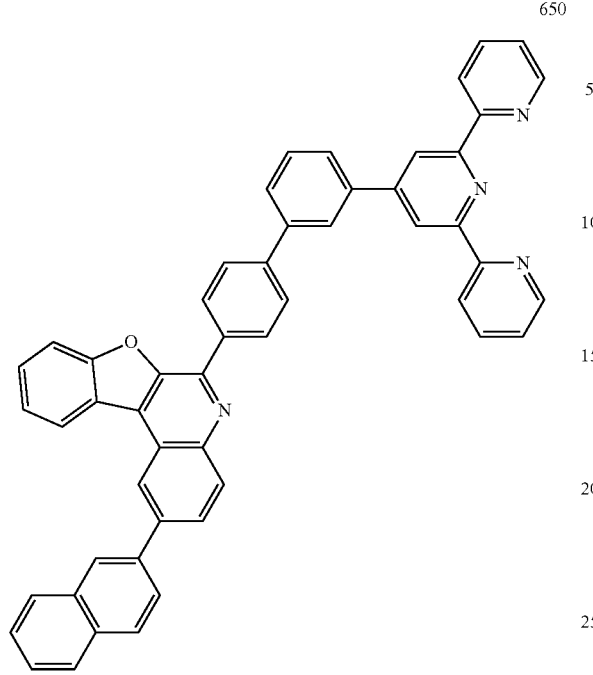
651
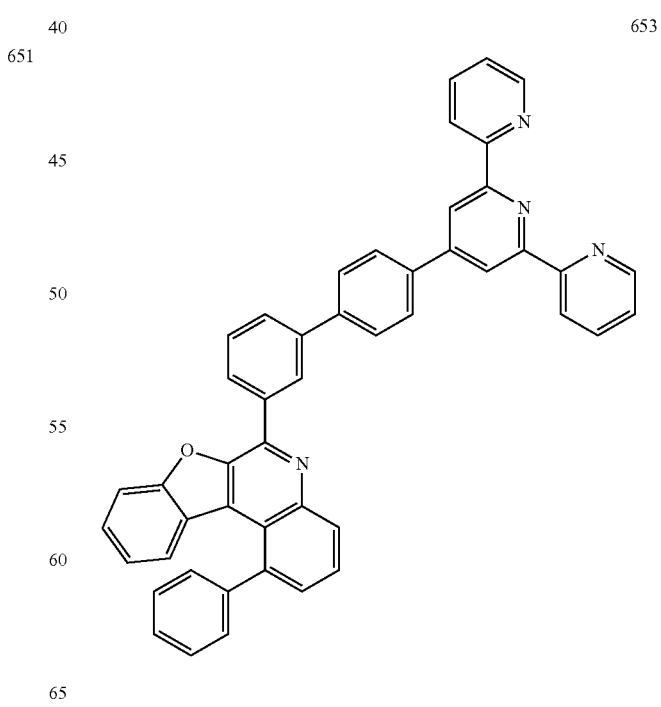
-continued
652
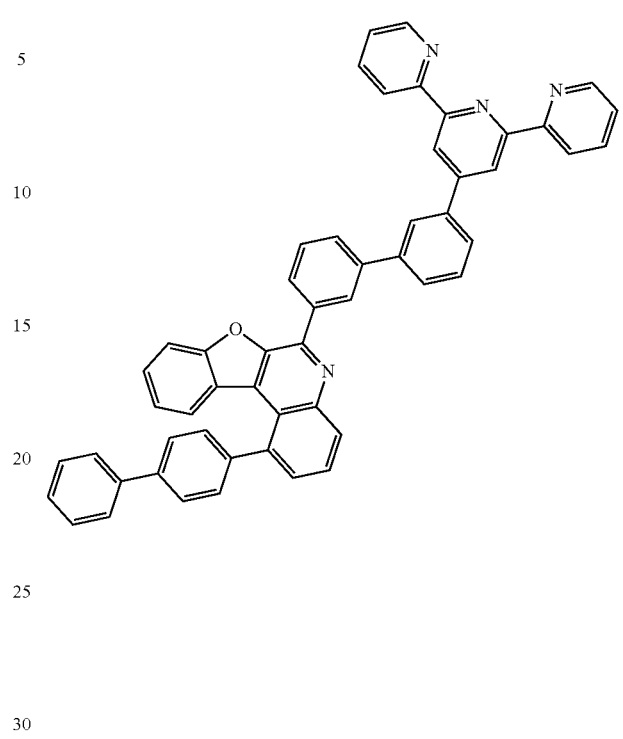
653

-continued
654
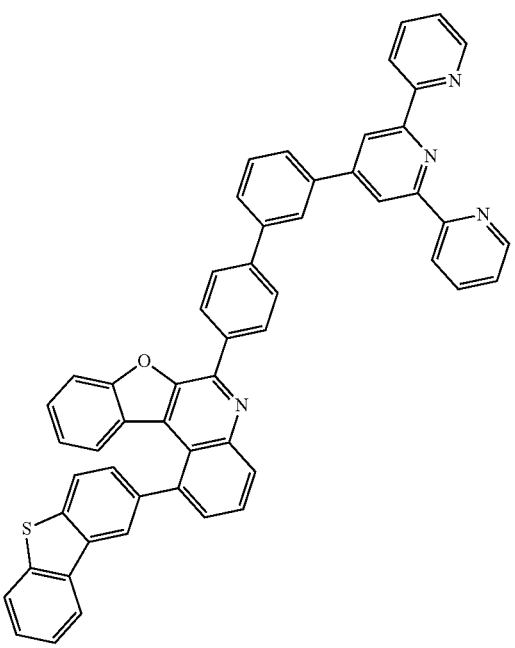
655
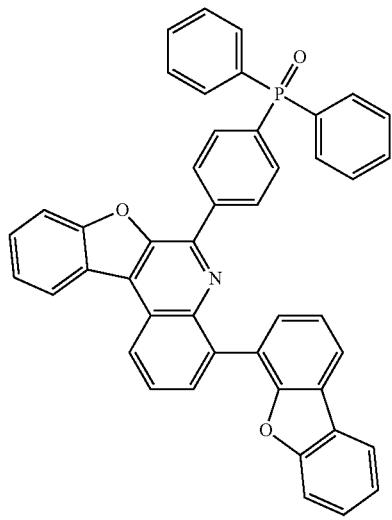
-continued
656
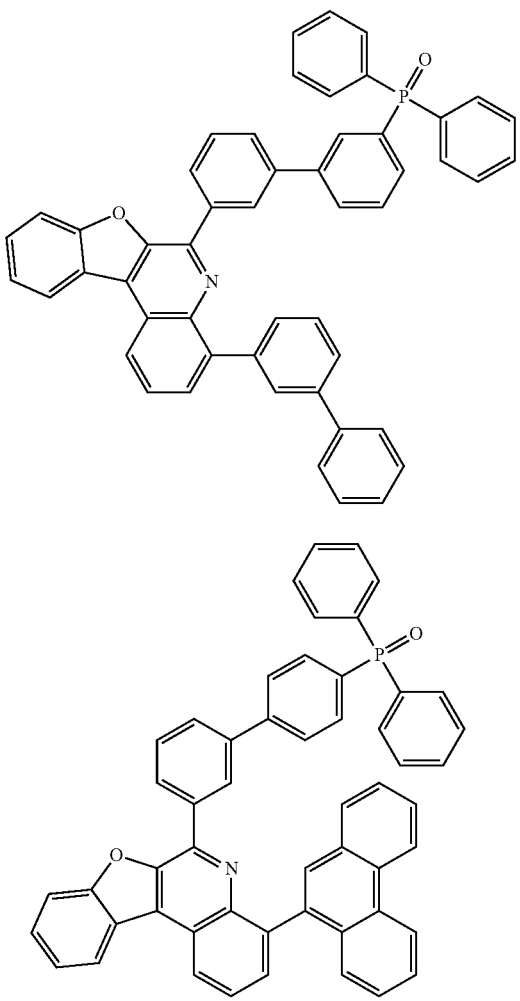
657
658
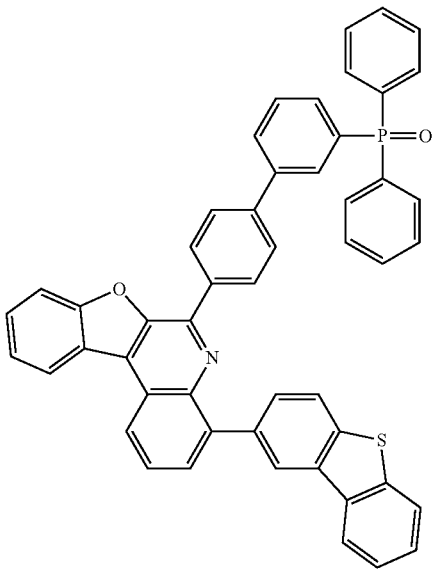

-continued
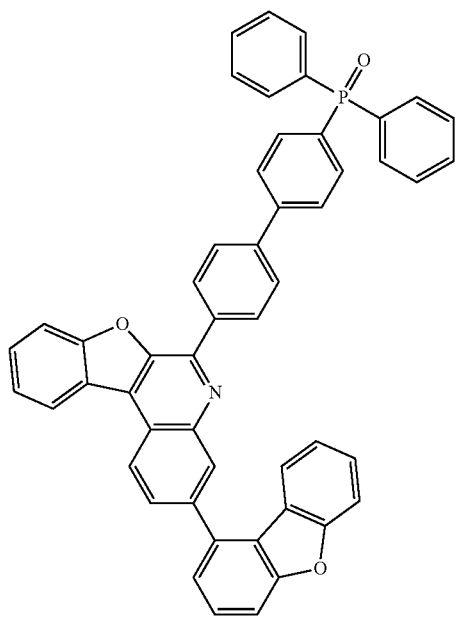
659
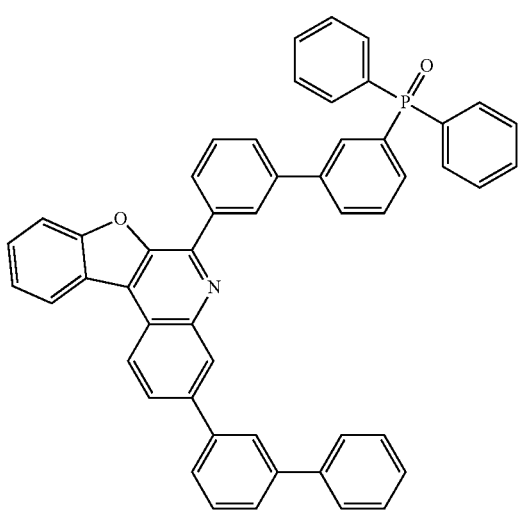
660
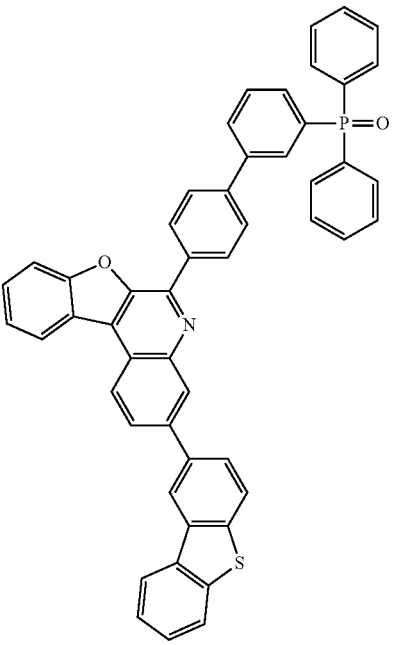
-continued
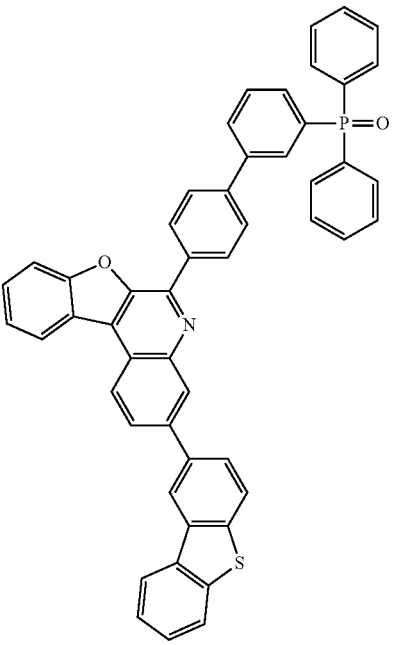
662
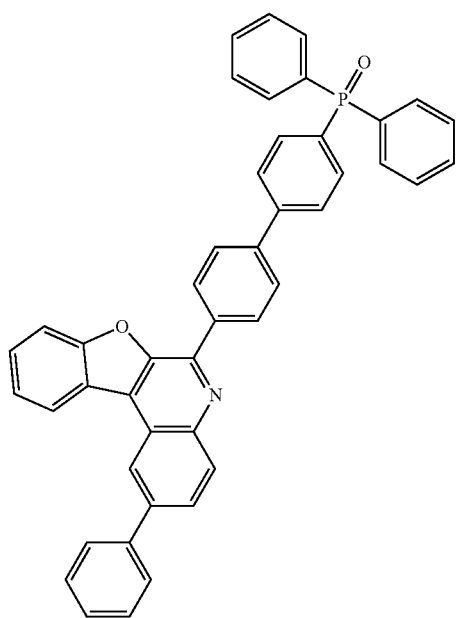
663

993
-continued
664
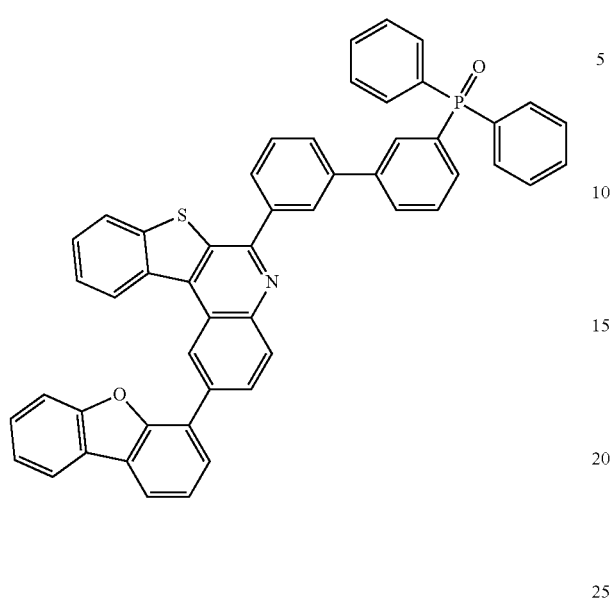
665
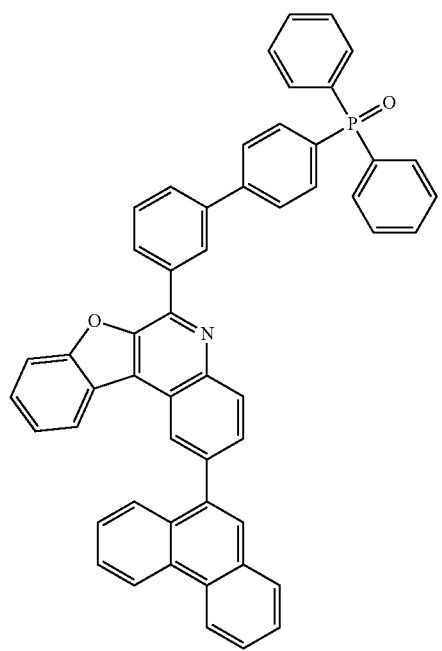
994
-continued
666
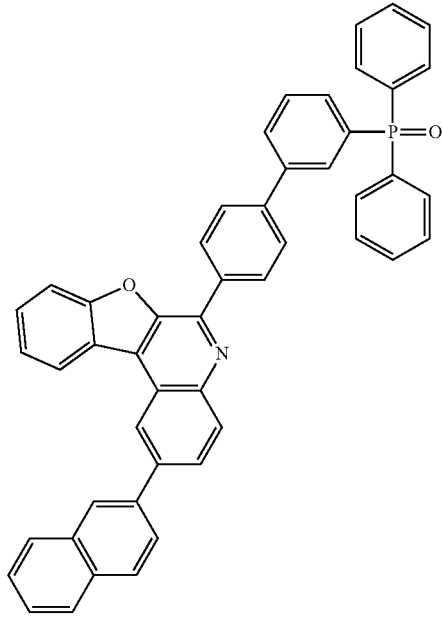
667
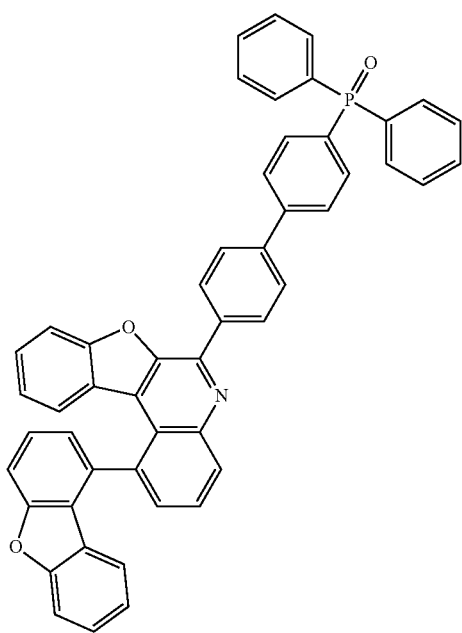

668
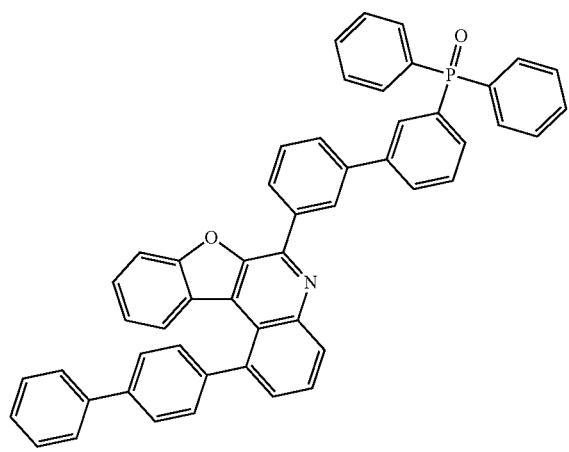
669
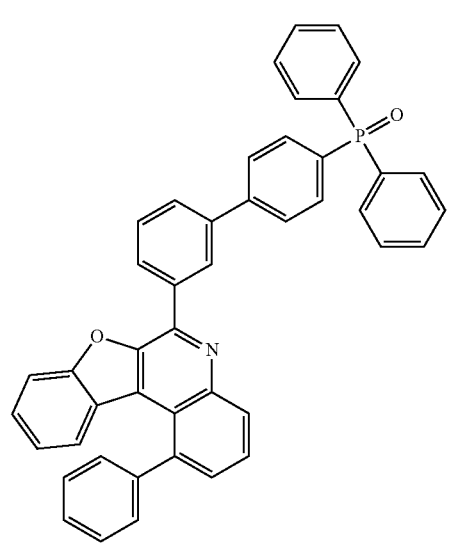
670
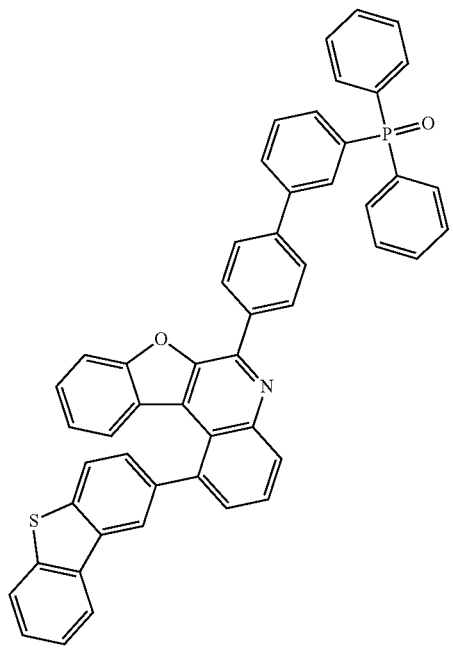
671
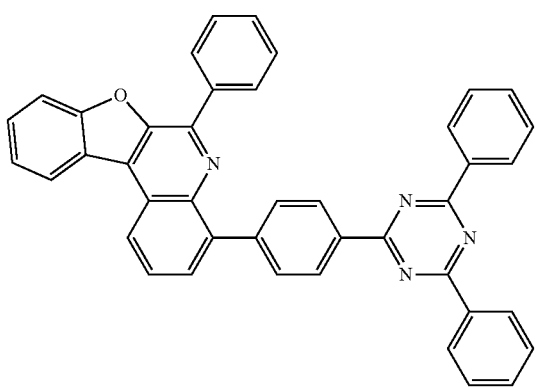
672
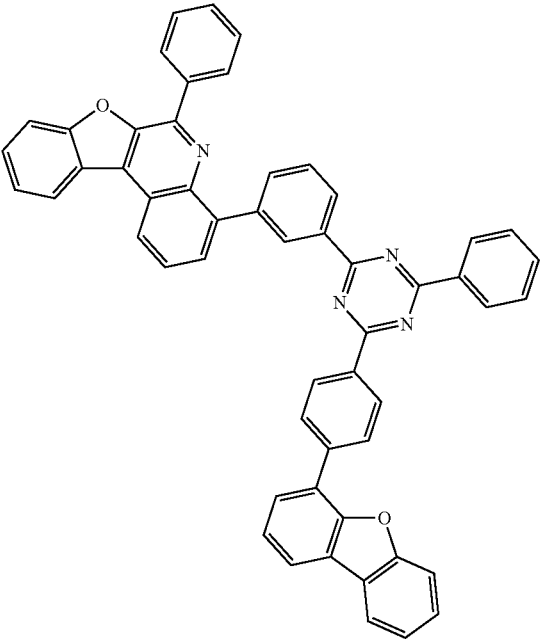
673

997 674
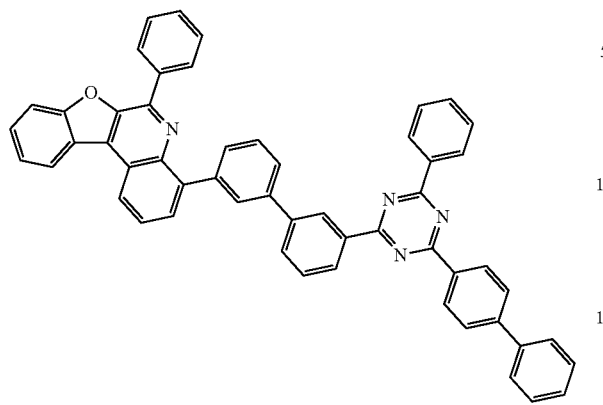
998 676
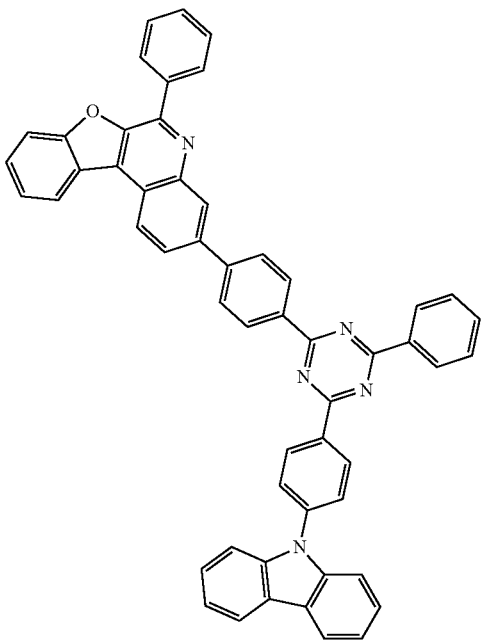
675
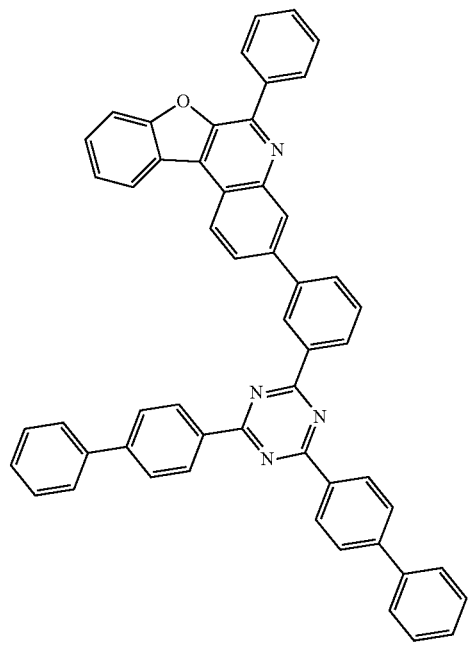
677
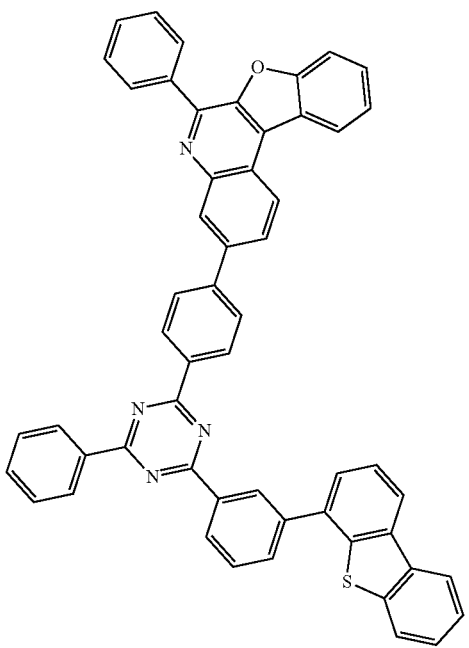

999
-continued
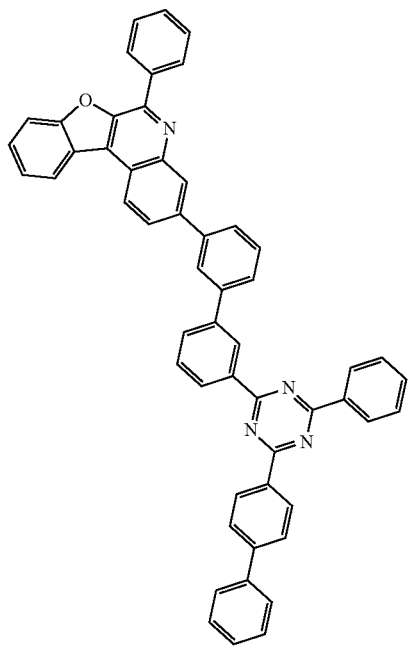
1000
-continued
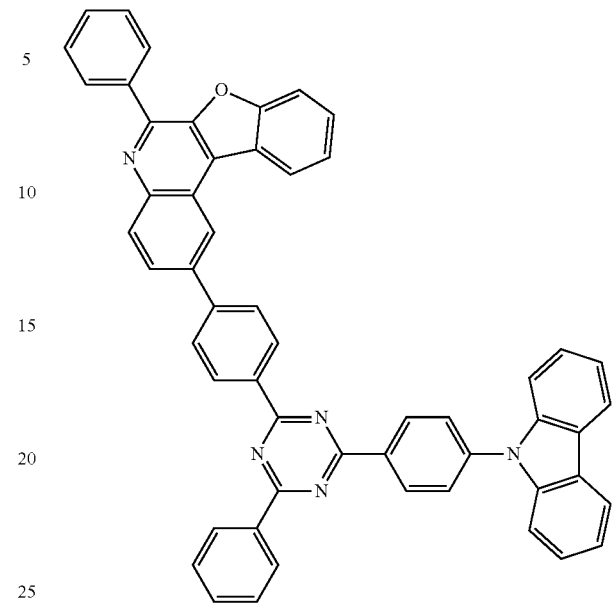
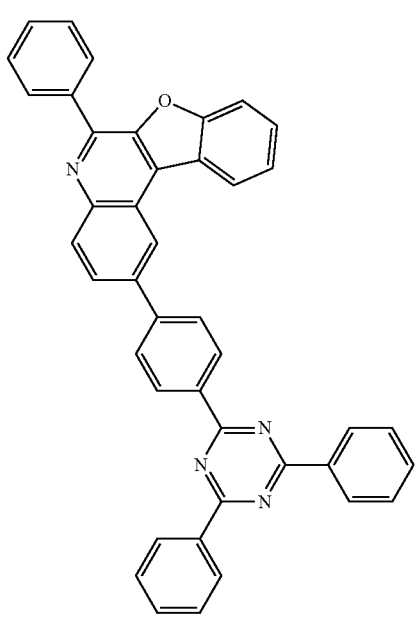
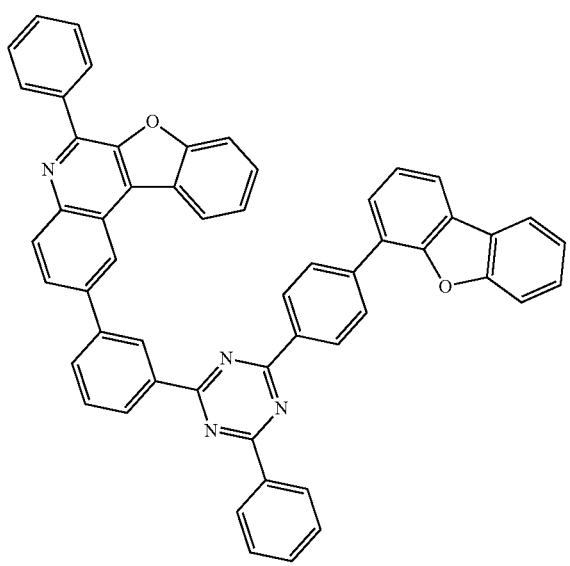

1001
-continued
682
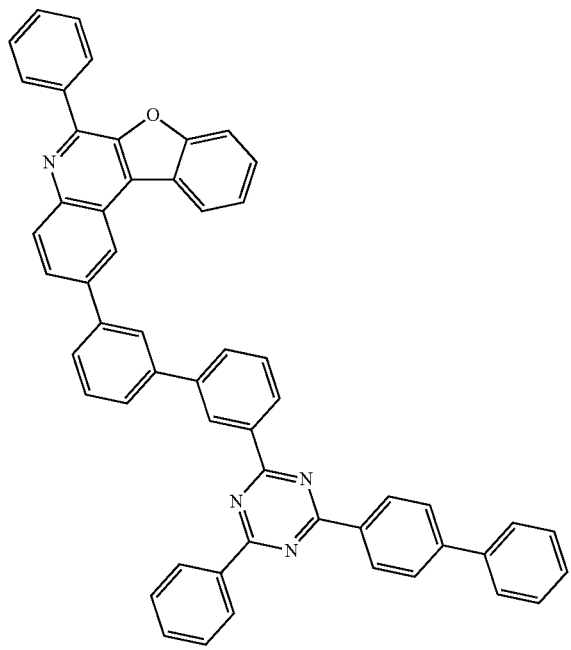
683
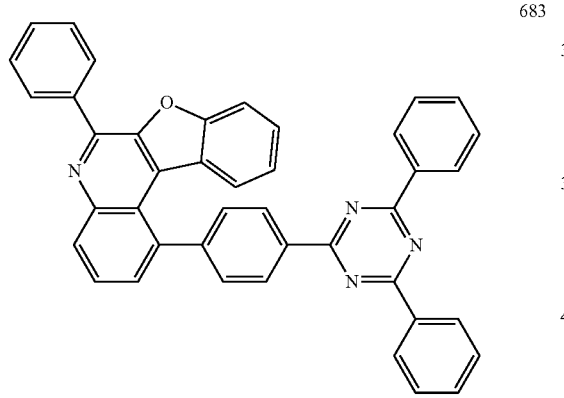
684
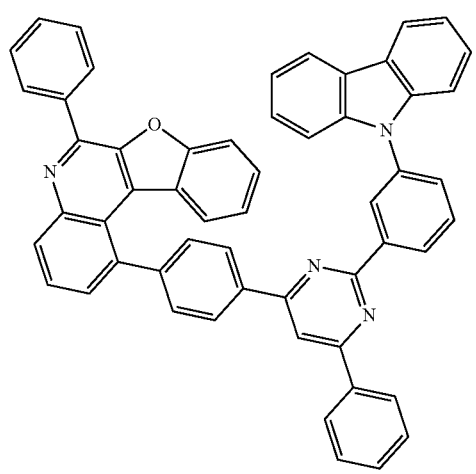
1002
-continued
685
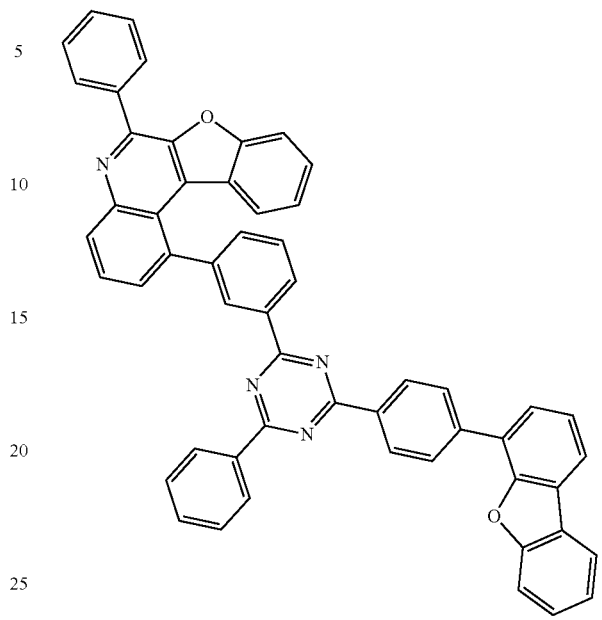
686
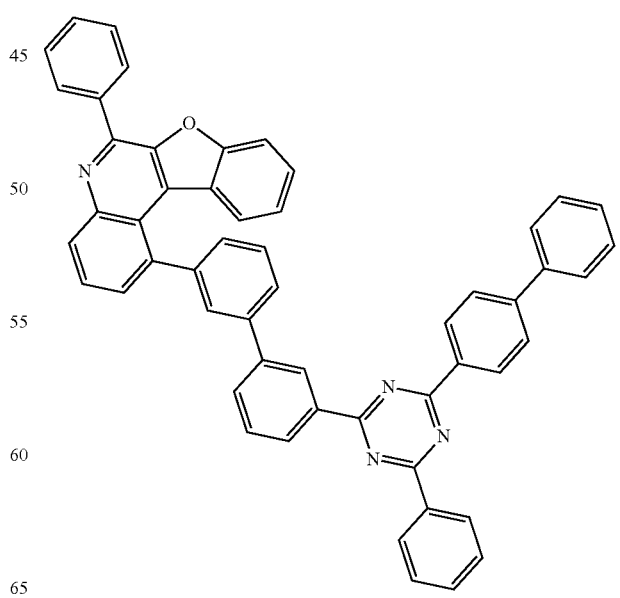

1003
-continued
687
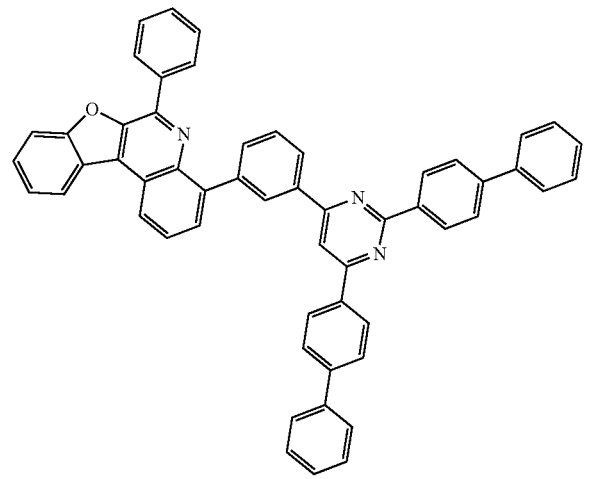
688
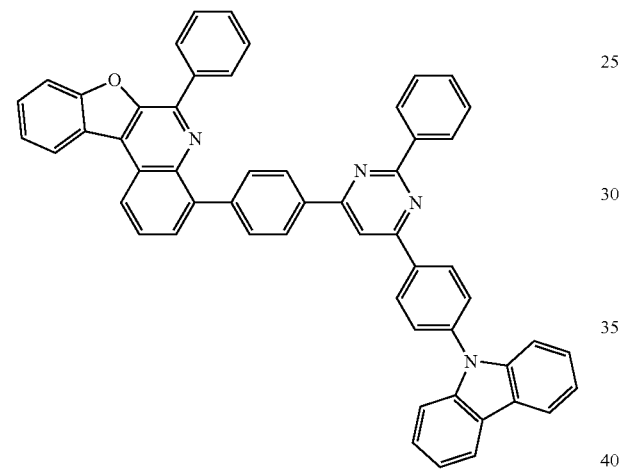
689
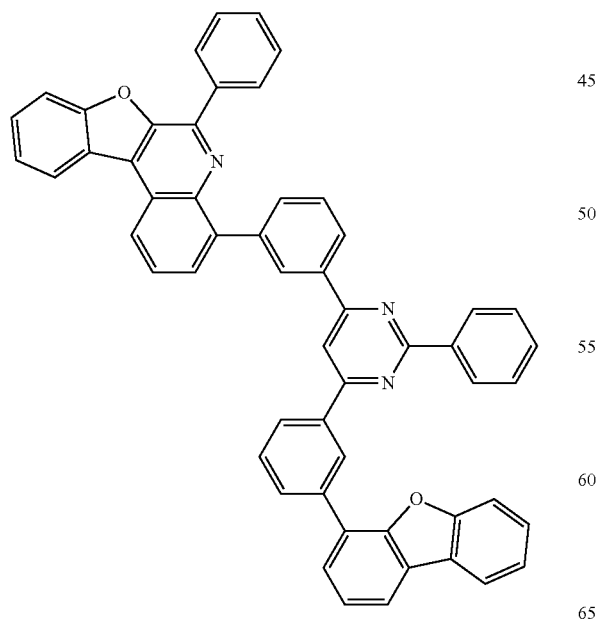
1004
-continued
690
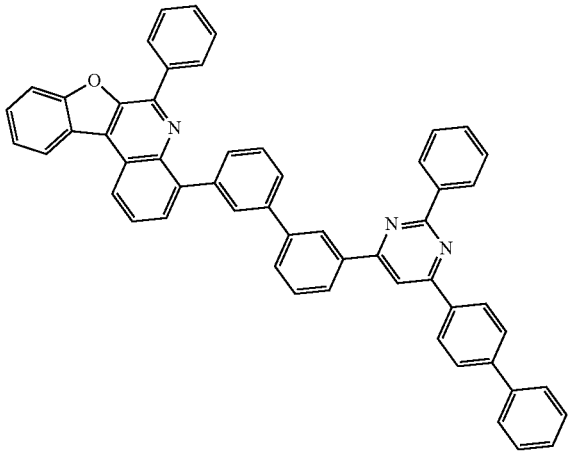
691
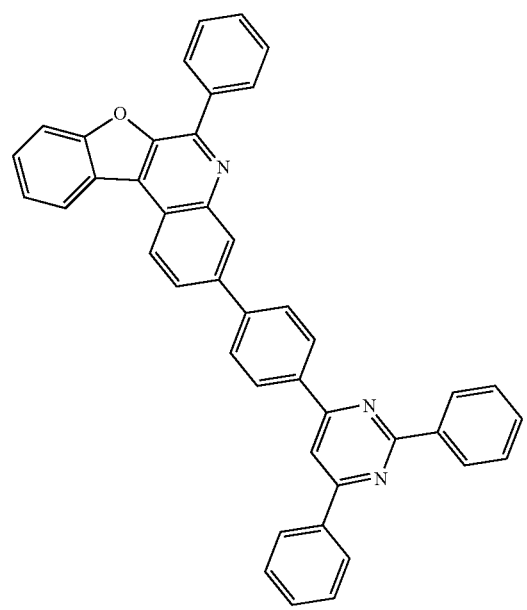

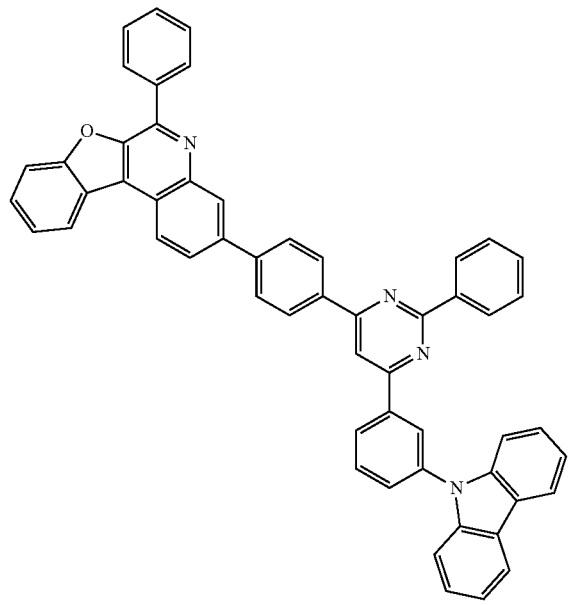
692
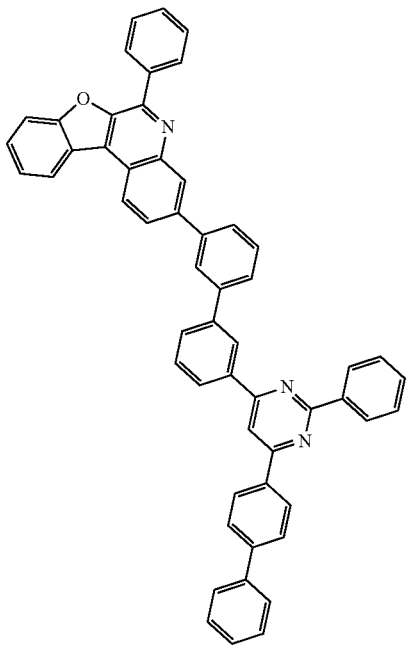
694
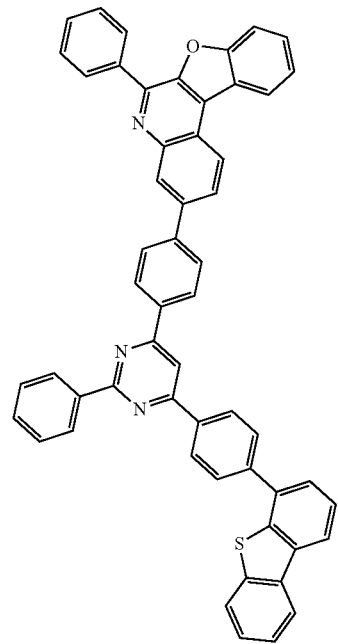
693
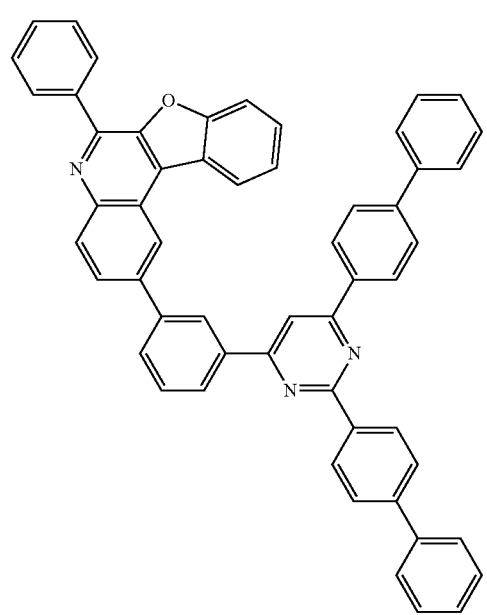
695

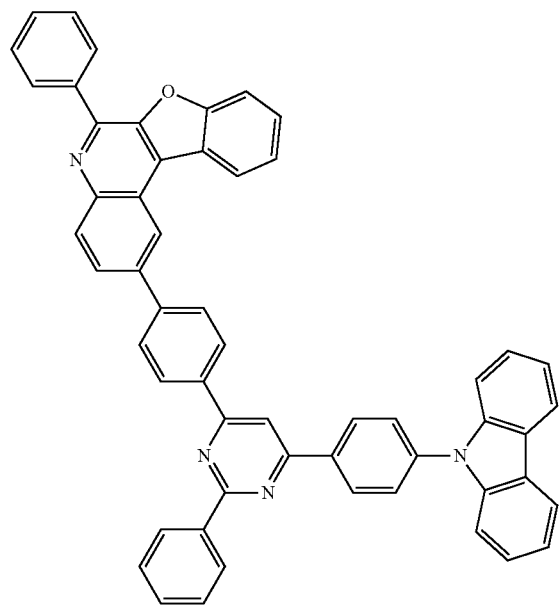
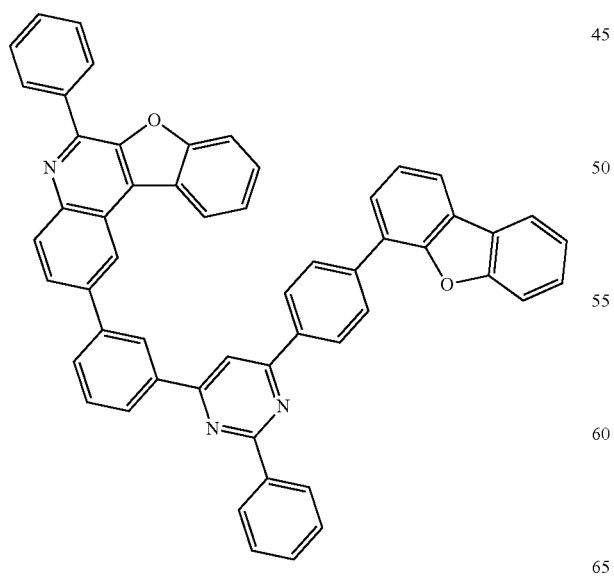
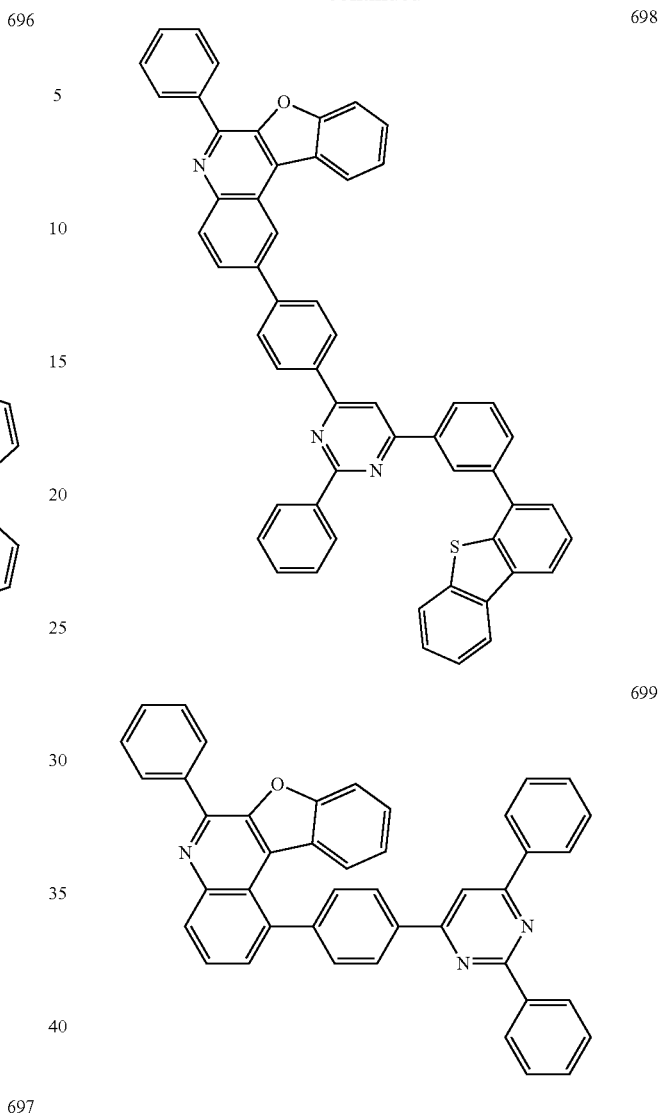

1009
-continued
1010
-continued
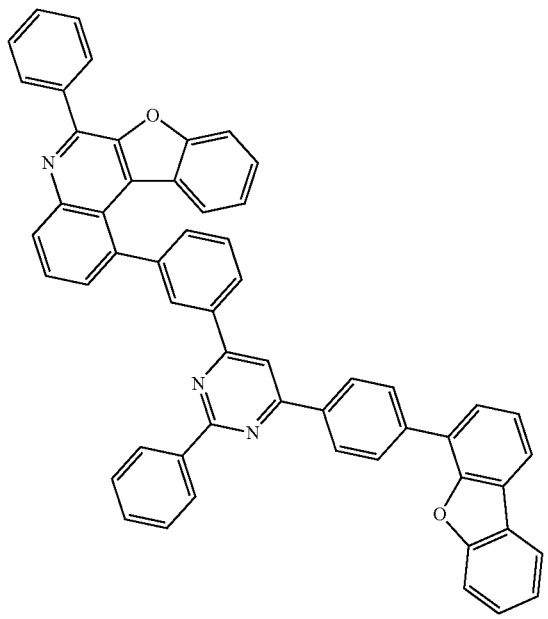
701
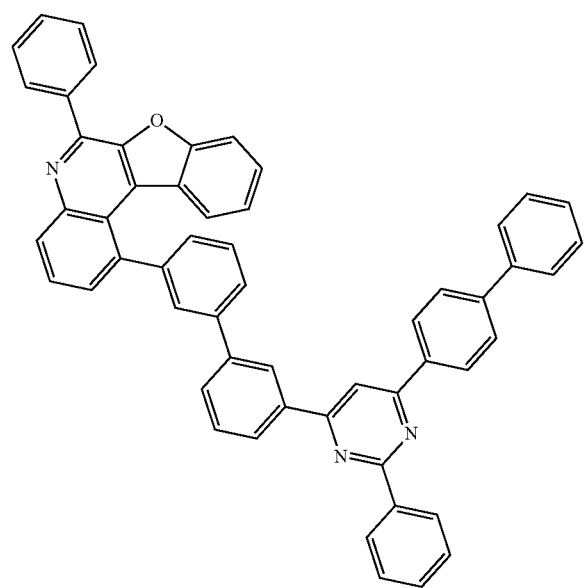
702
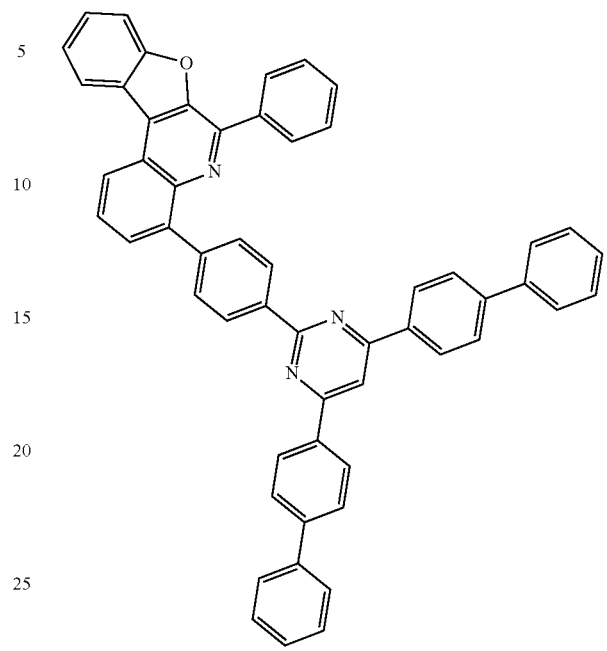
703
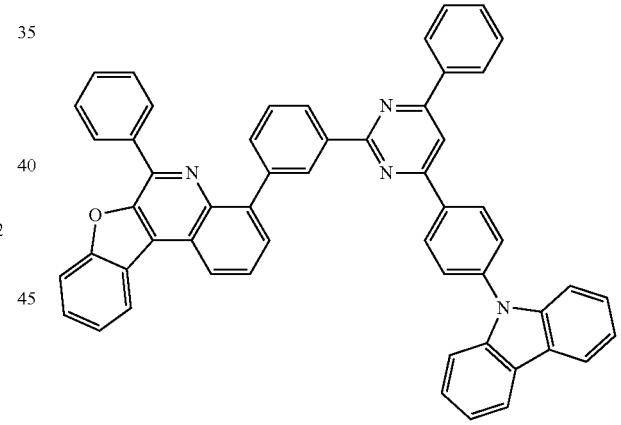
704
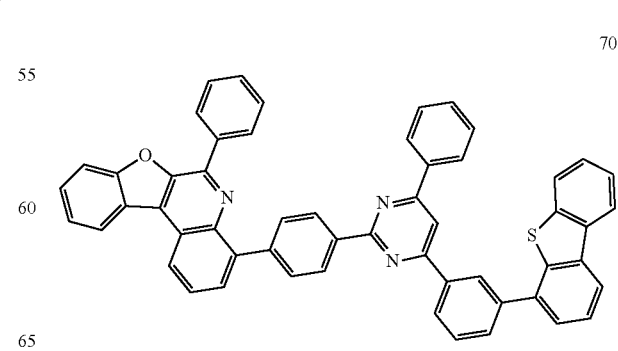
705

1011
-continued
1012
-continued
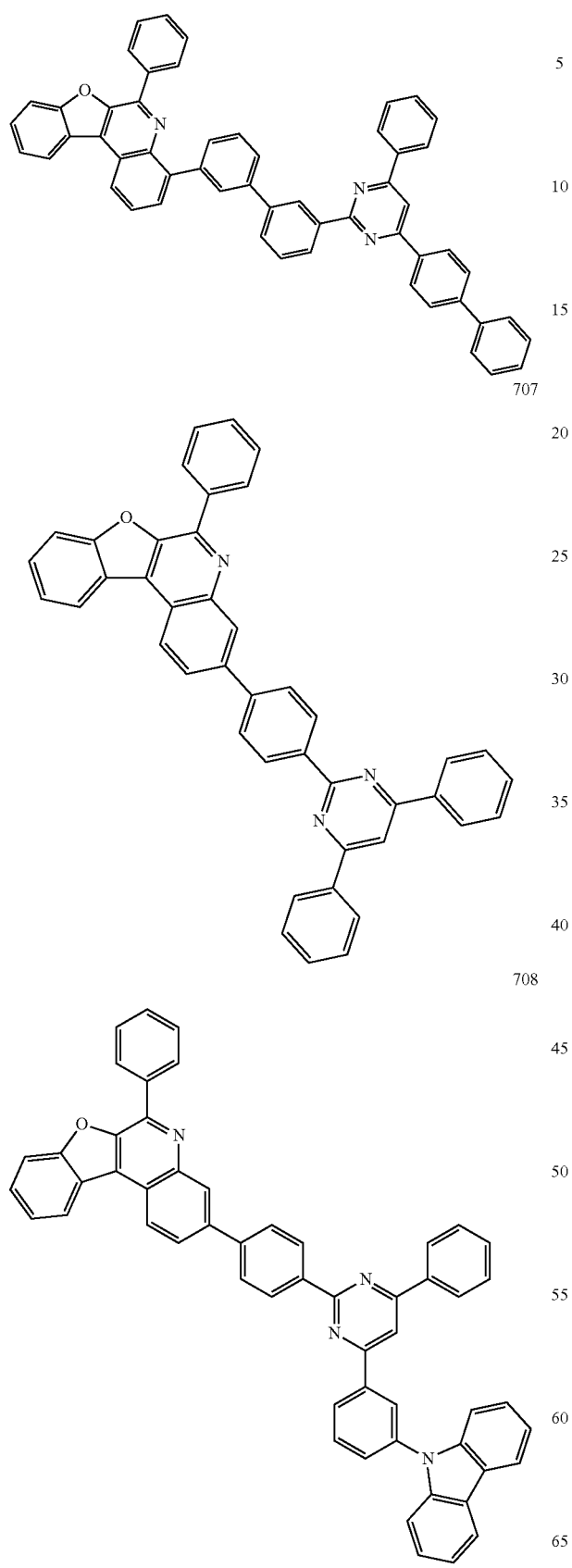
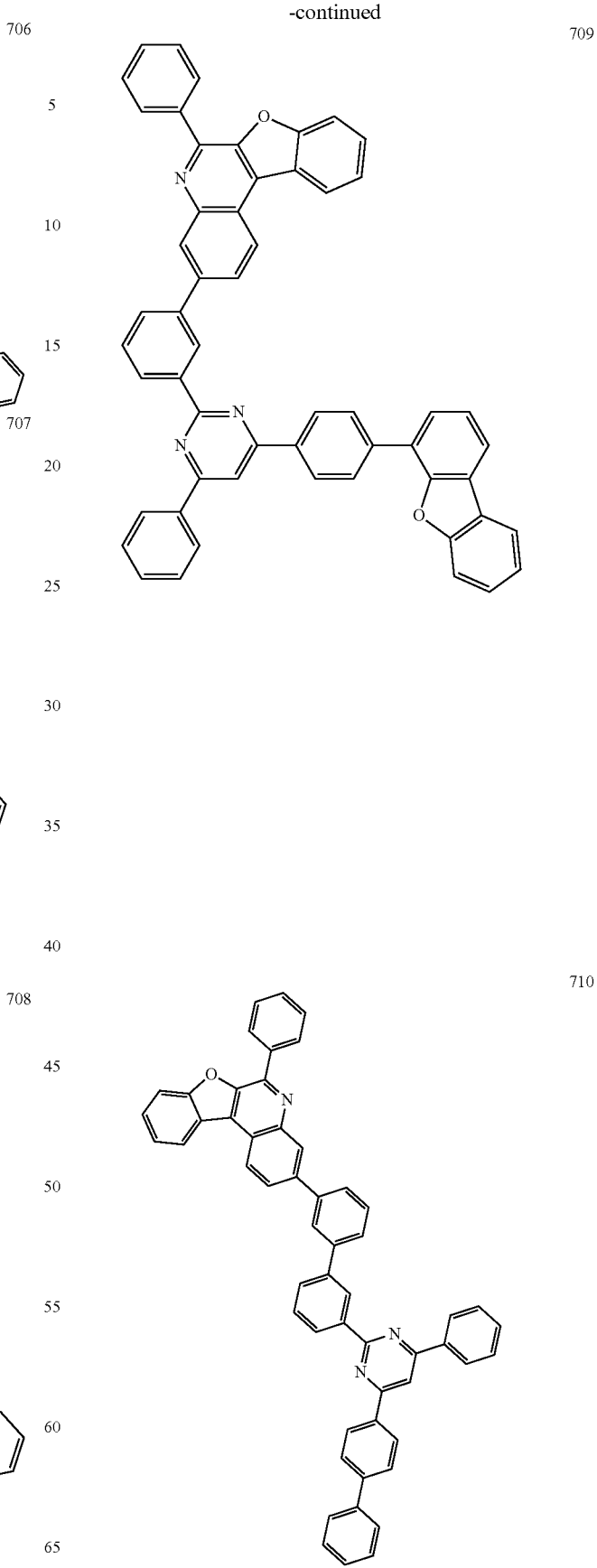

711
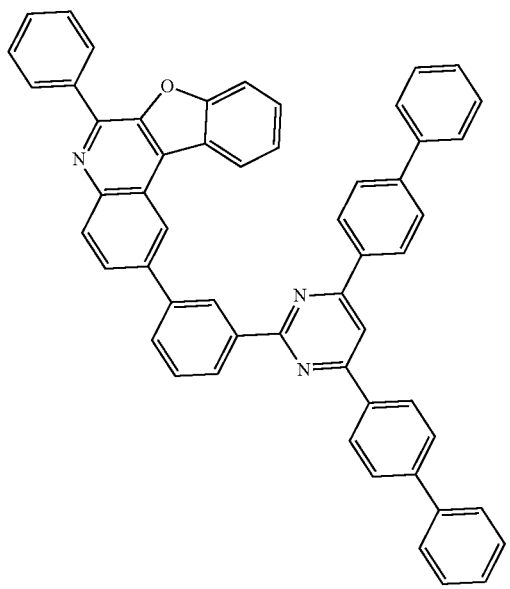
712
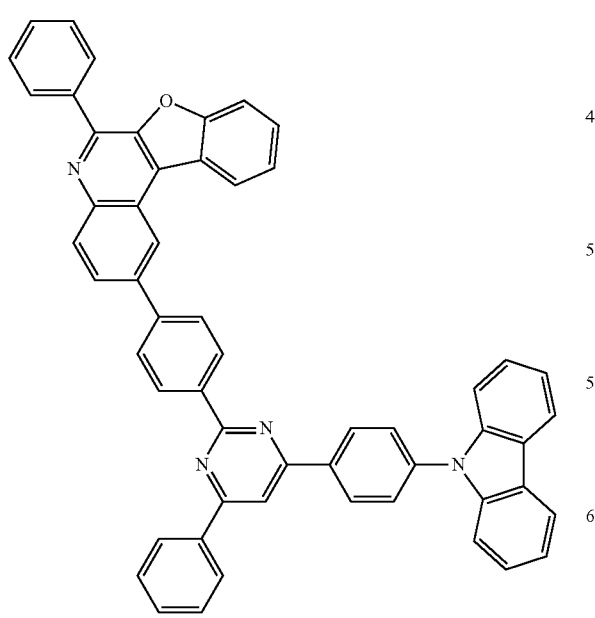
713
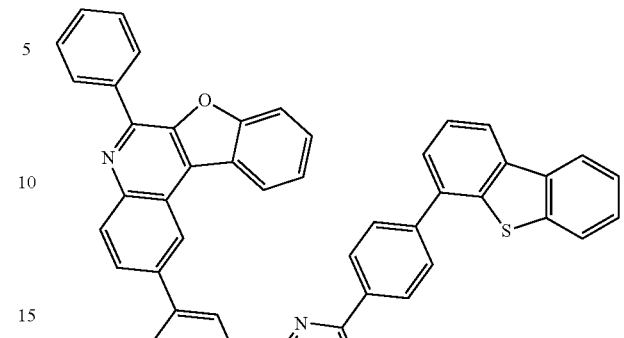
714
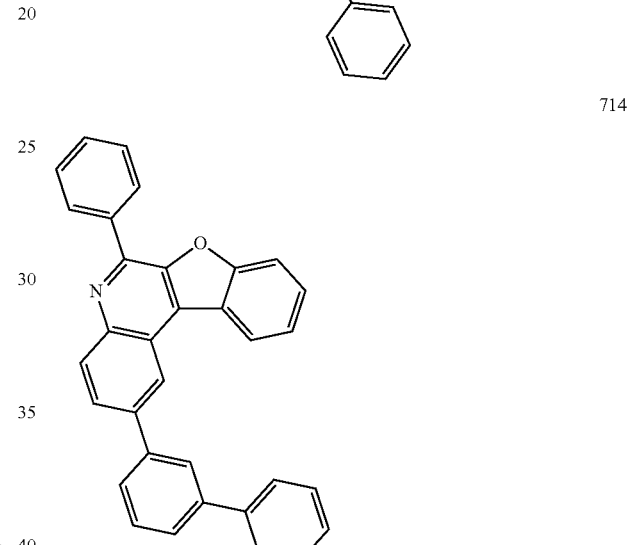
715
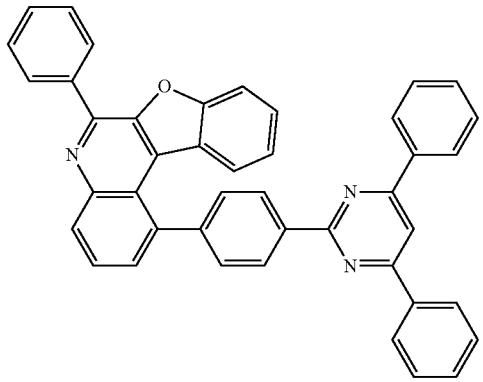

1015
-continued
716
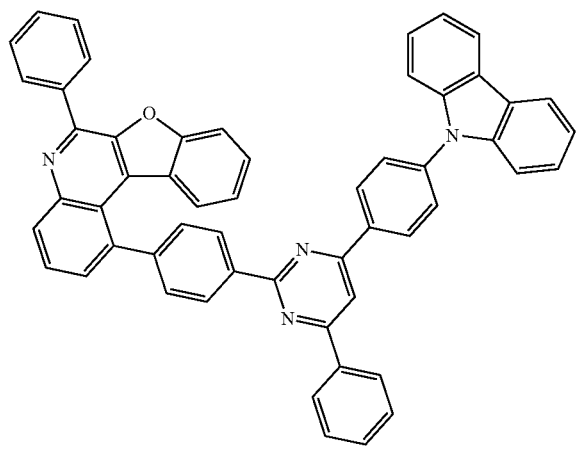
717
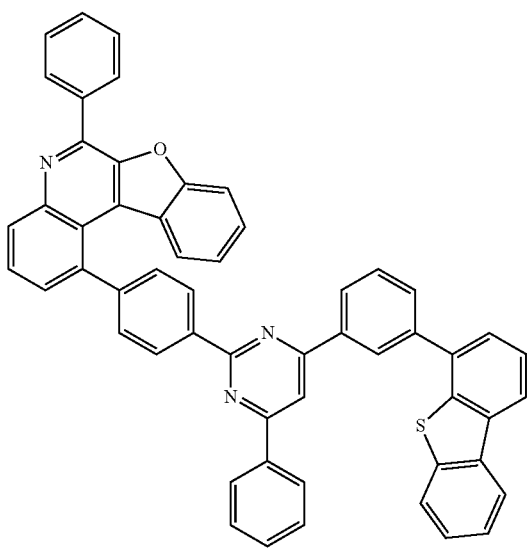
718
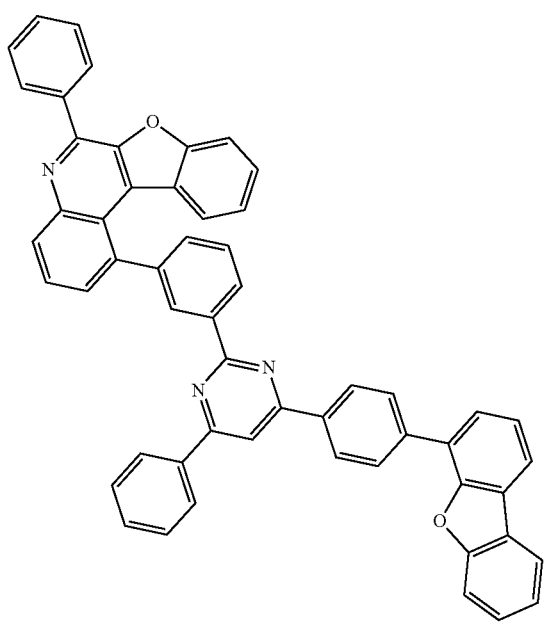
1016
-continued
719
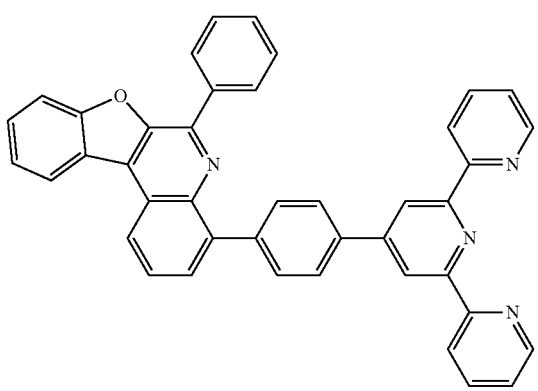
720
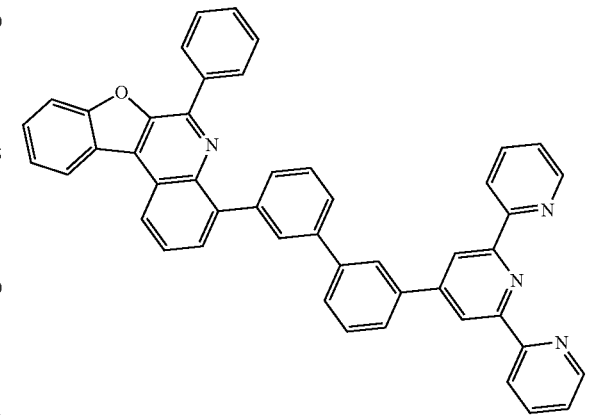
721

722
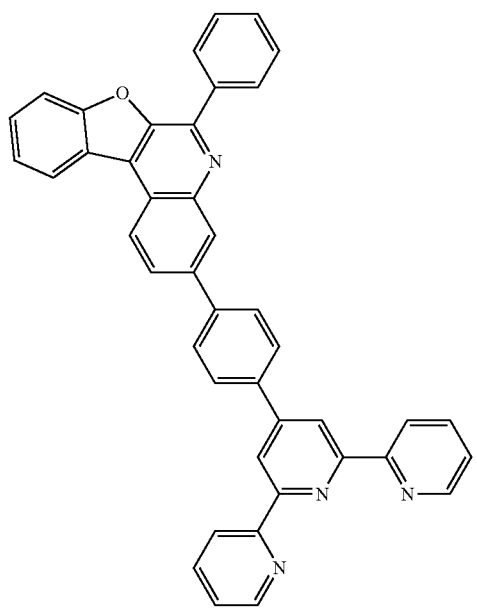
724
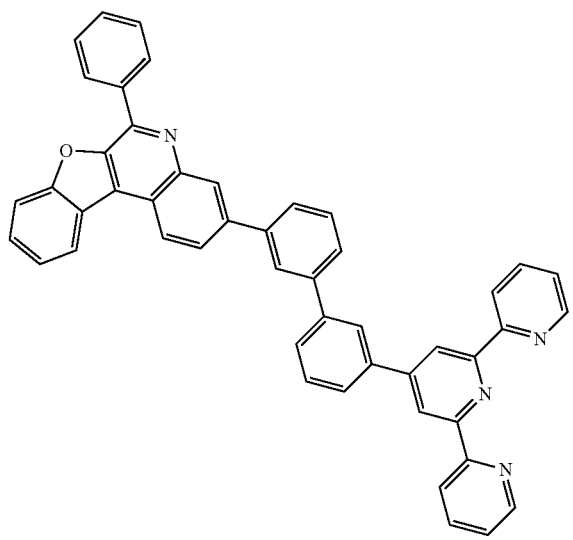
723
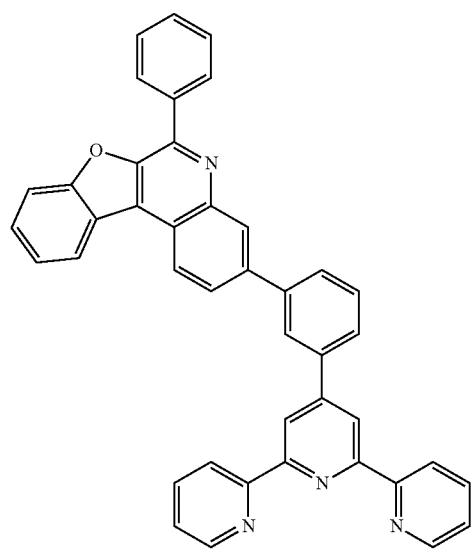
725
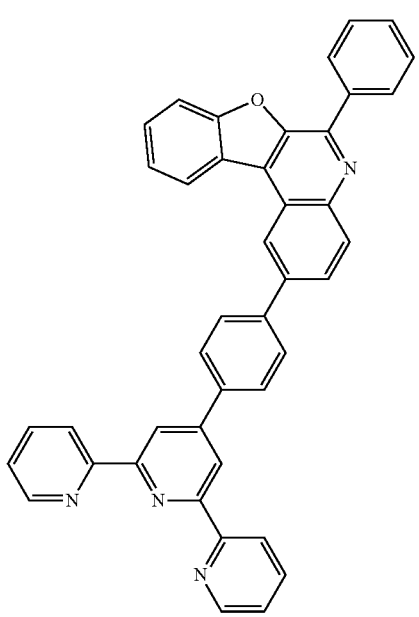 [SMILES: c1ccc(-c2nc3ccc(-c4ccc(-c5cc(-c6ccccn6)nc(-c6ccccn6)c5)cc4)cc3c3c2oc2ccccc23)cc1]

726 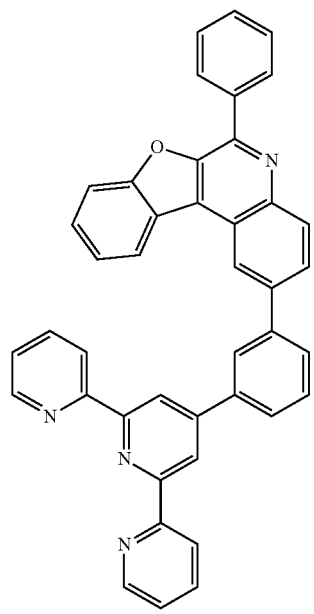
727 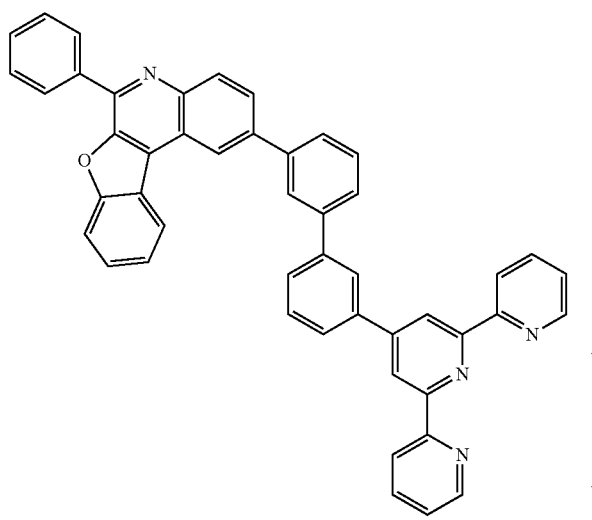
728 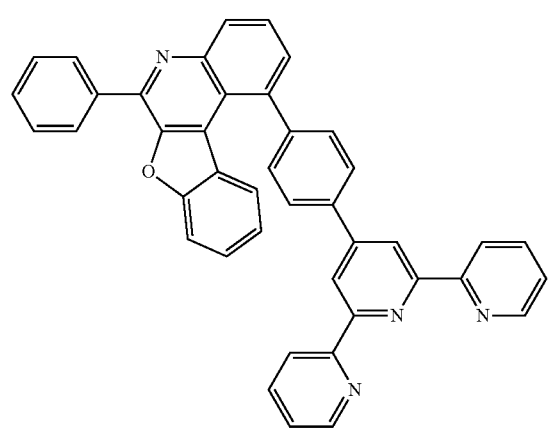
729 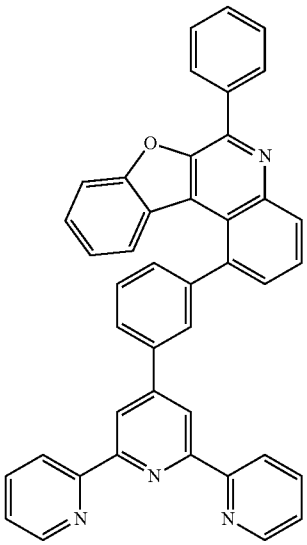
730 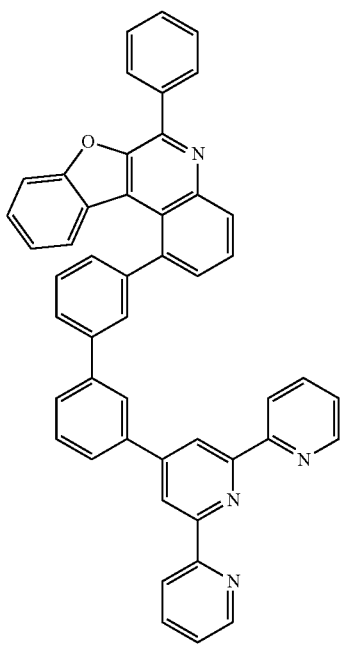
731 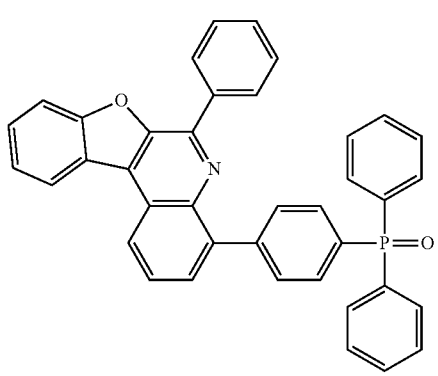

1021
-continued
732
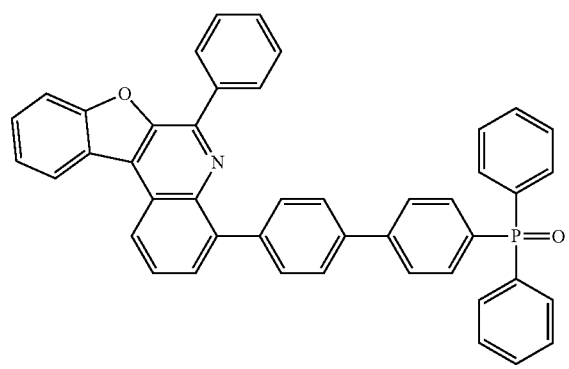
733
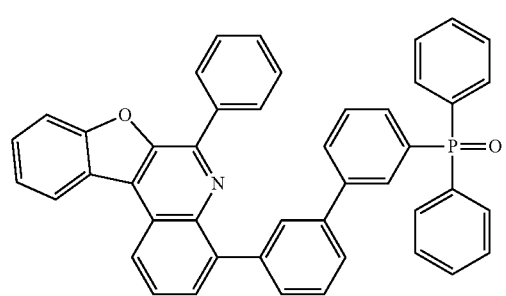
734
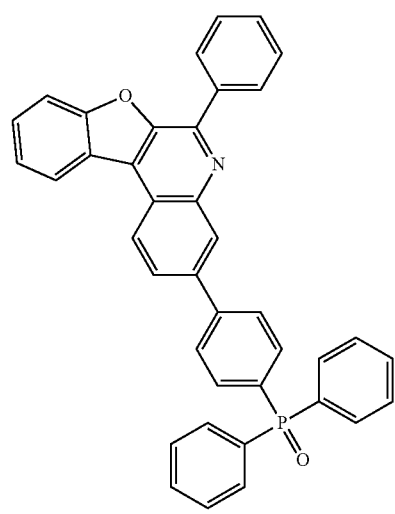
1022
-continued
735
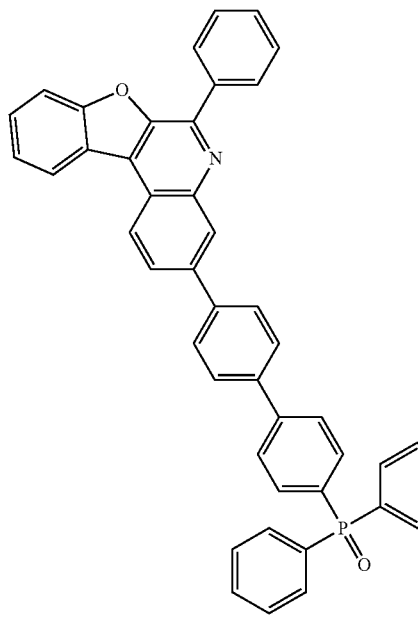
736
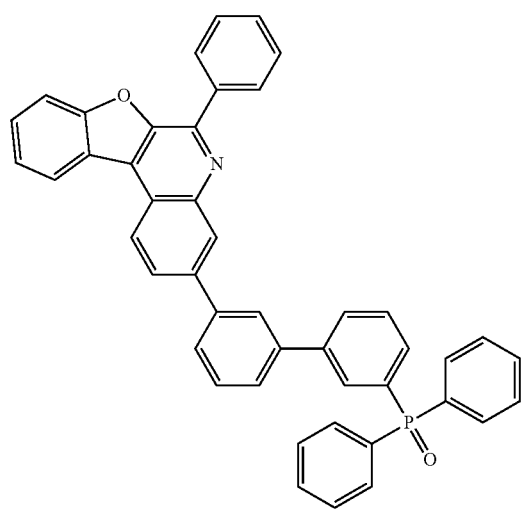
737
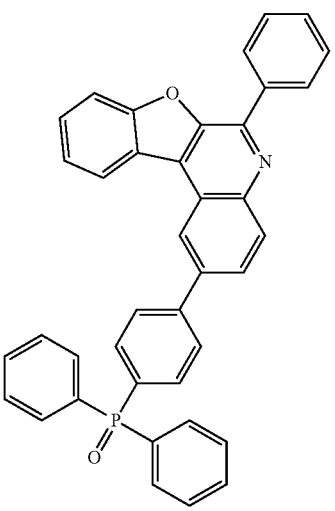

1023 -continued
738
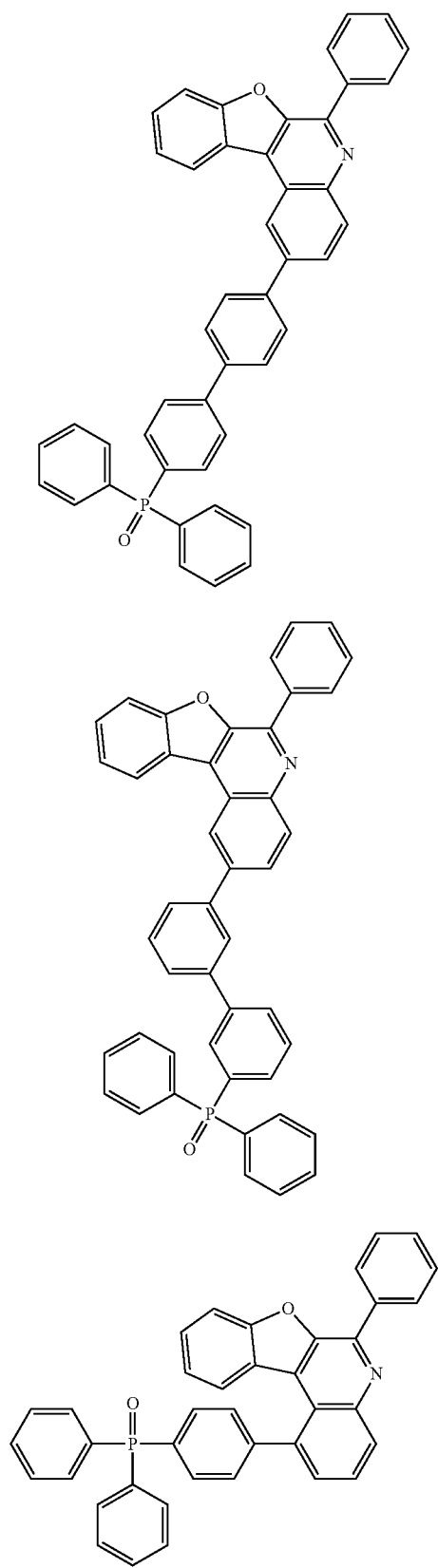
739
740
1024 -continued
741
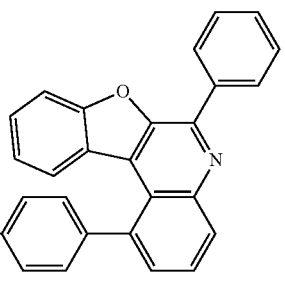
742
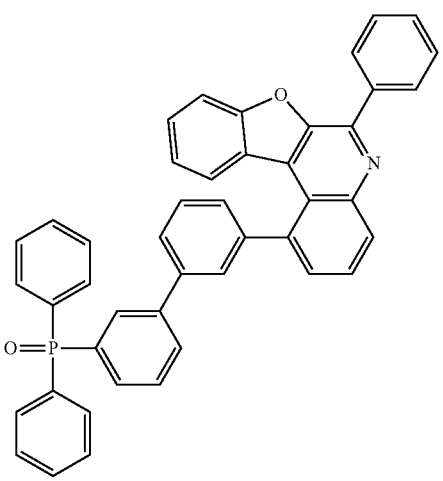
743
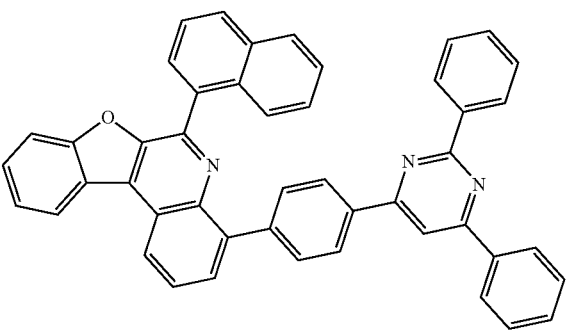
744
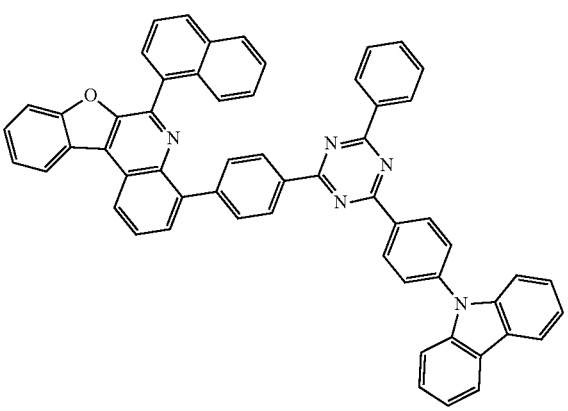

1025
-continued
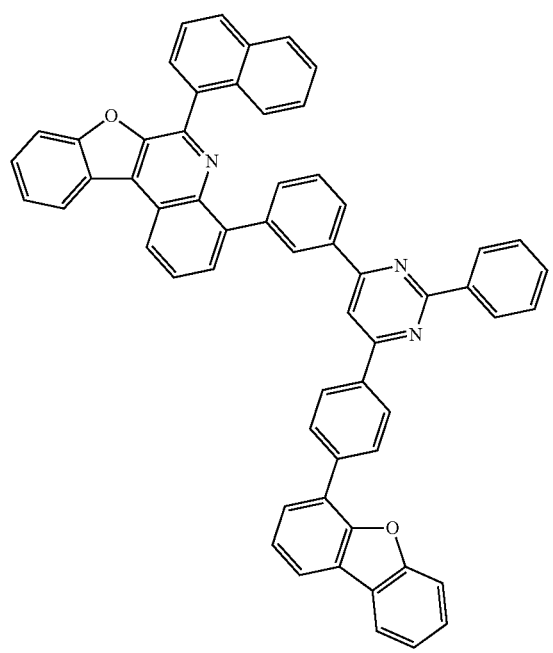
745
1026
-continued
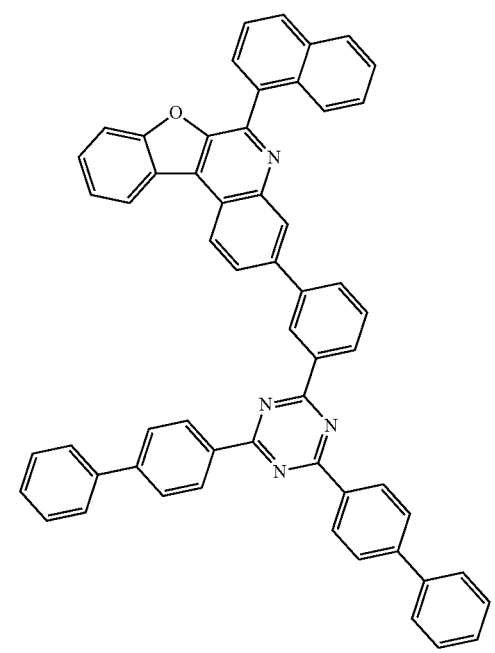
747
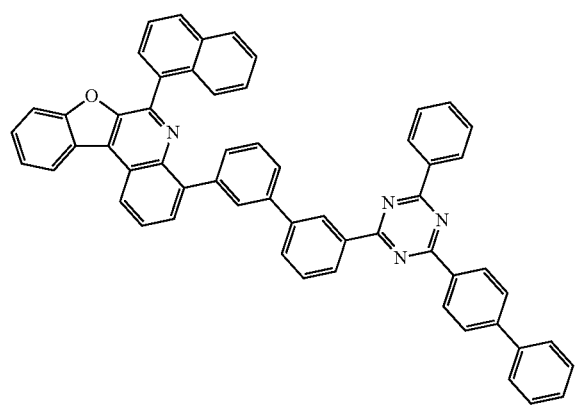
746
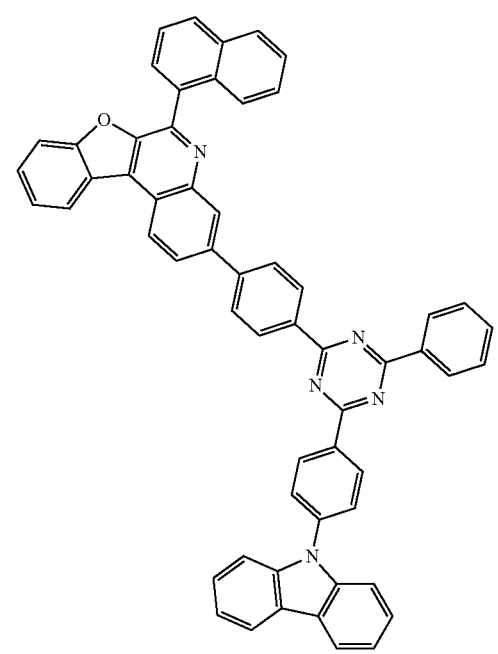
748

1027
-continued
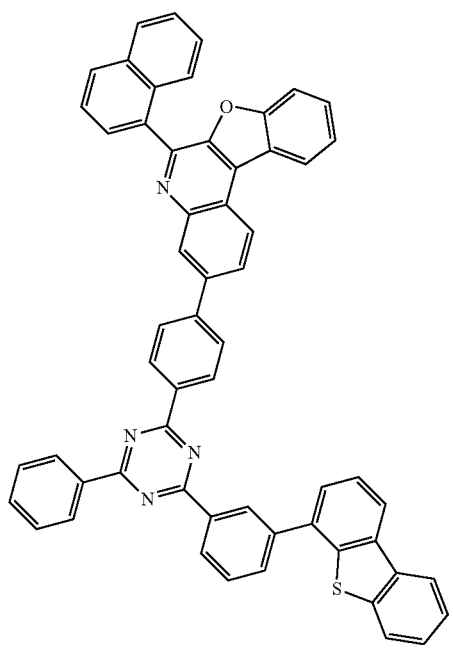
1028
-continued
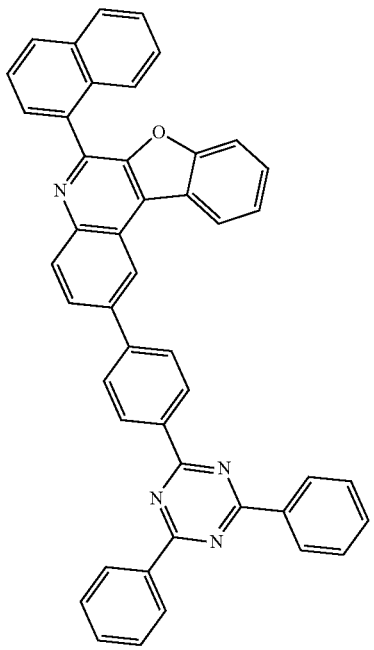
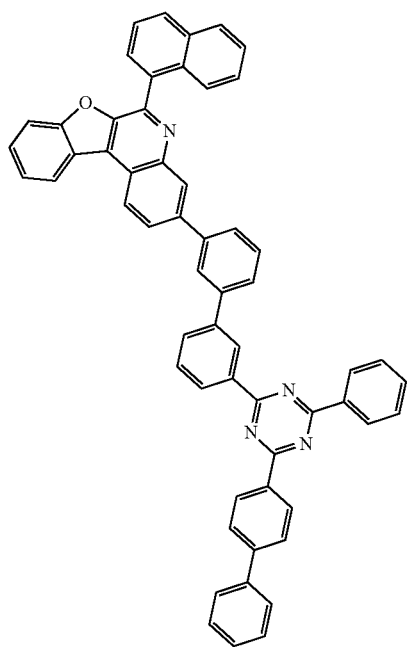
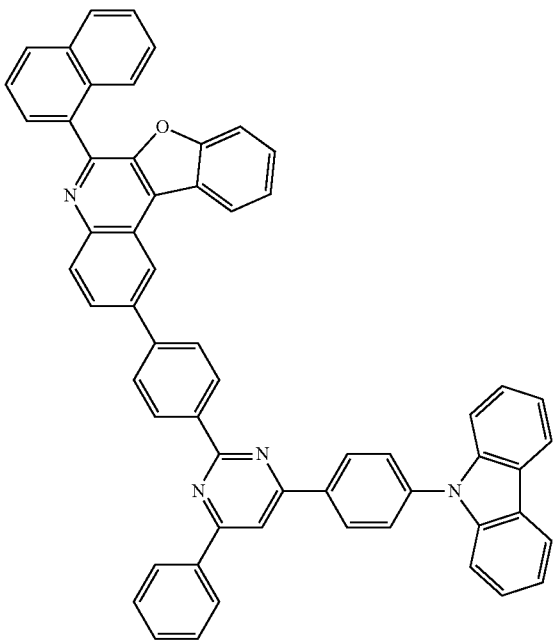

1029
-continued
753
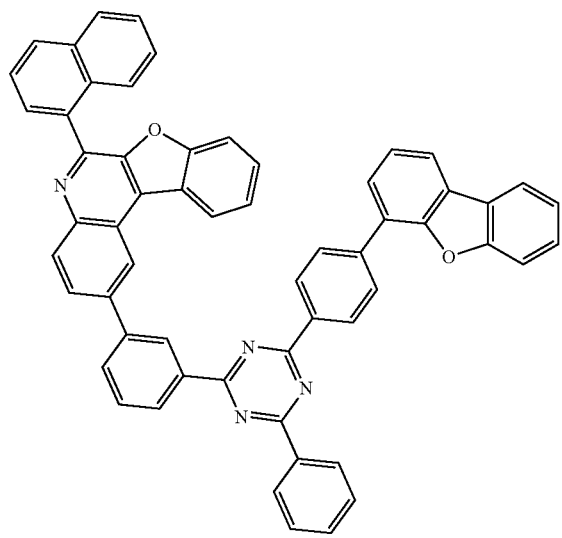
754
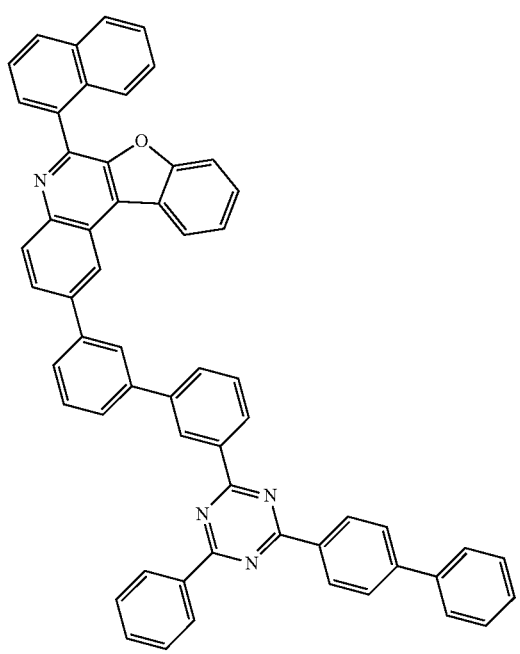
755
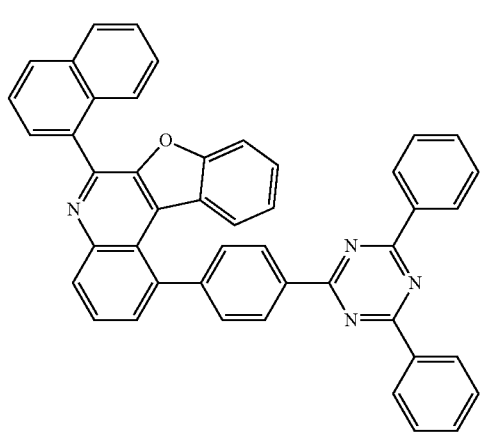
1030
-continued
756
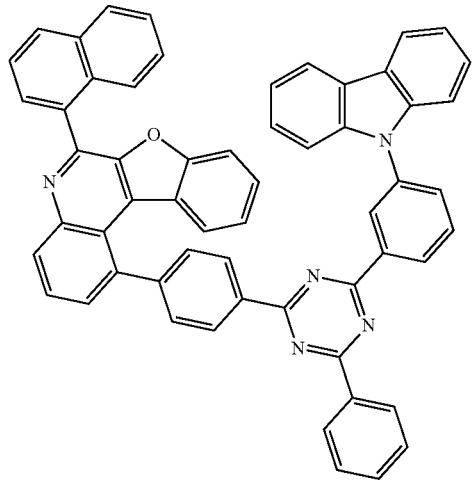
757
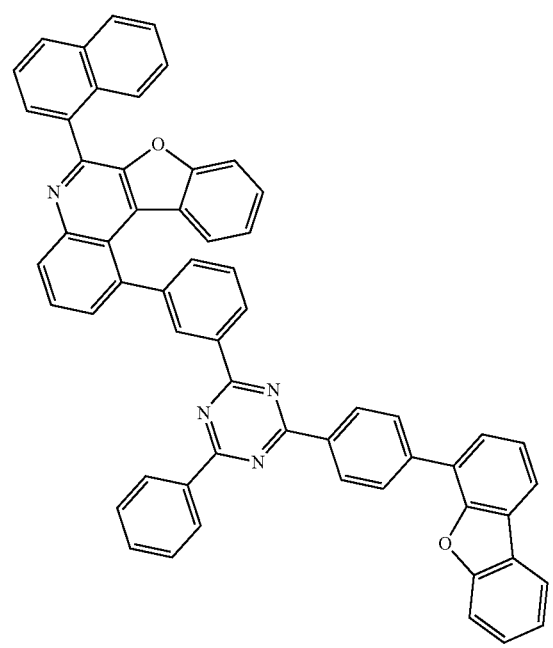

1031
-continued
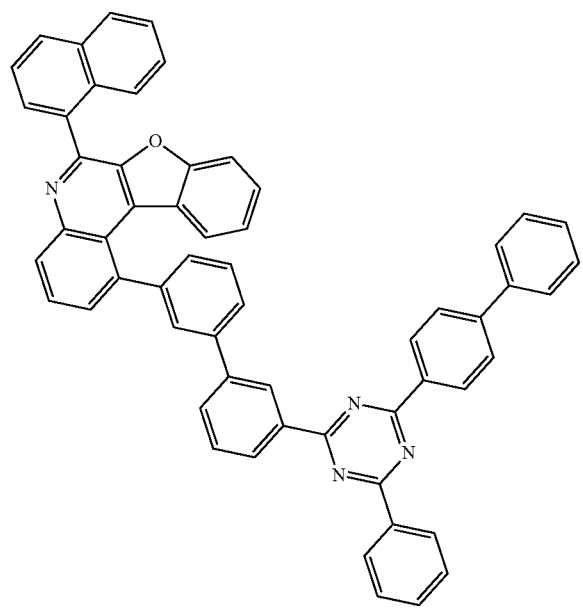
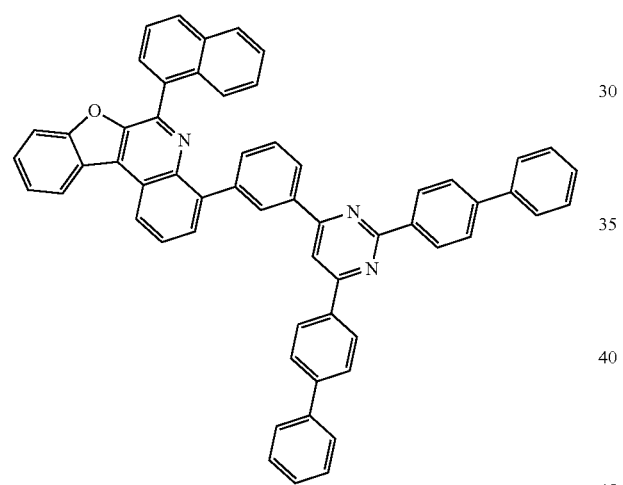
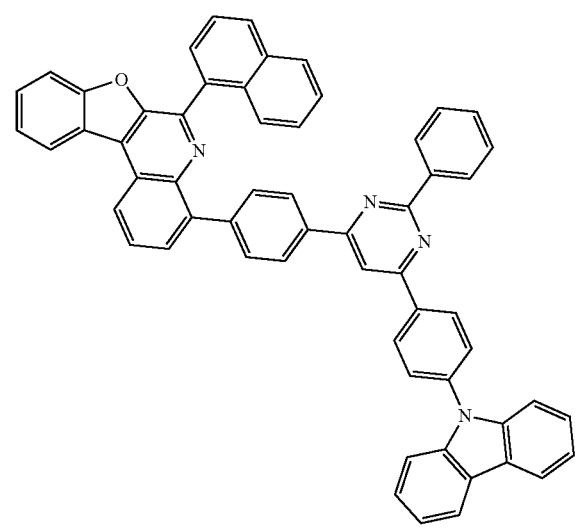
1032
-continued
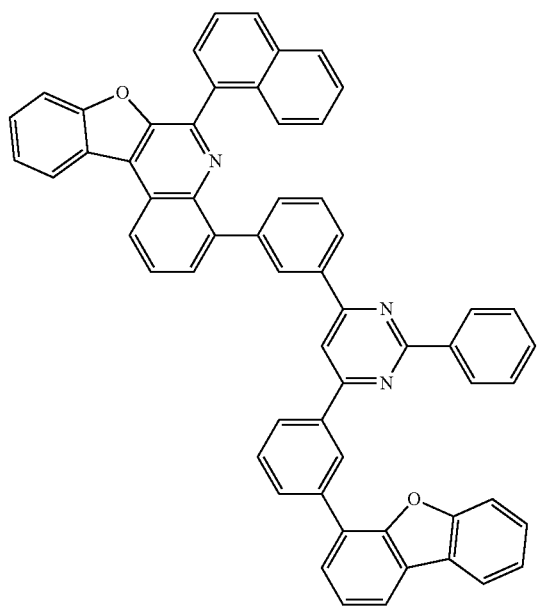
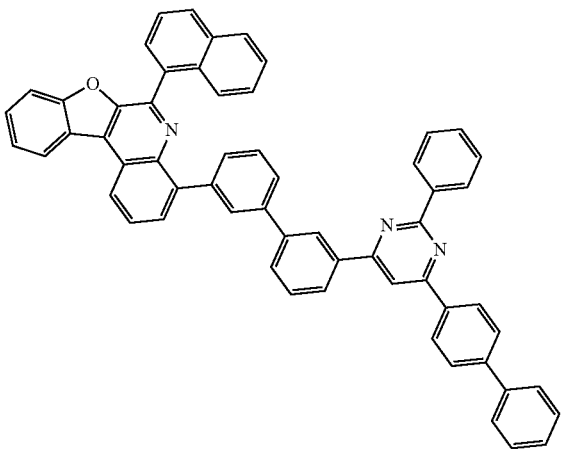

1033
-continued
763
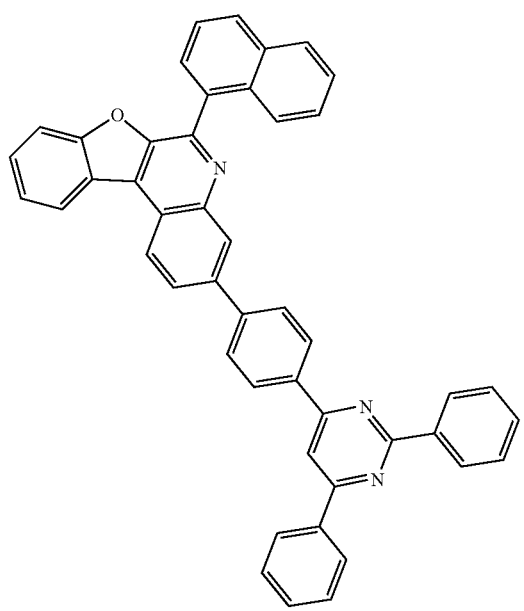
764
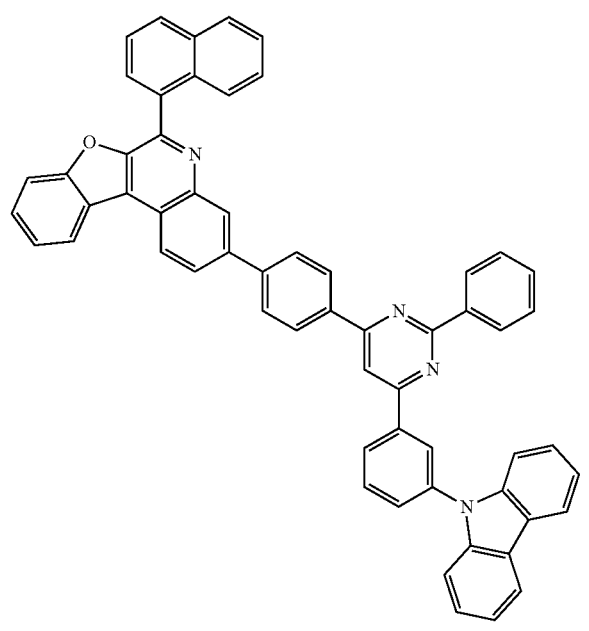
1034
-continued
765
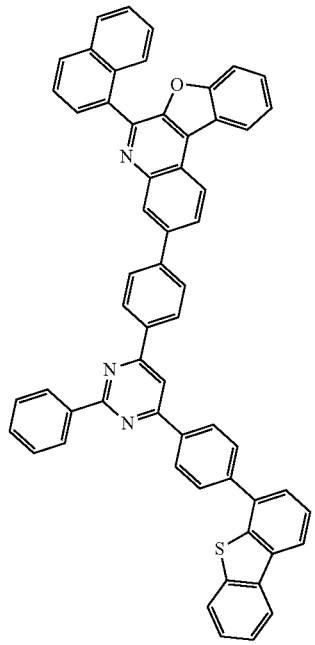
766
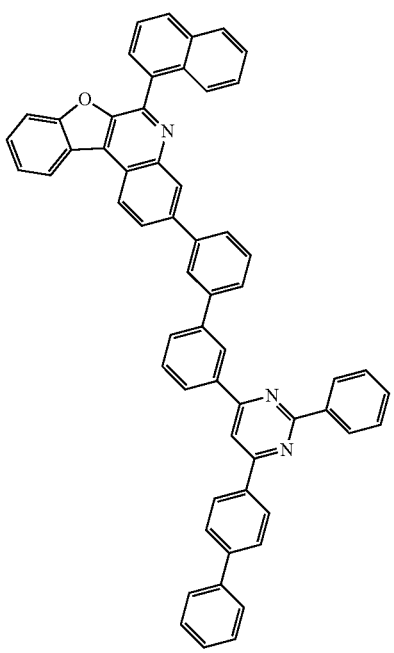

1035
-continued
1036
-continued
767
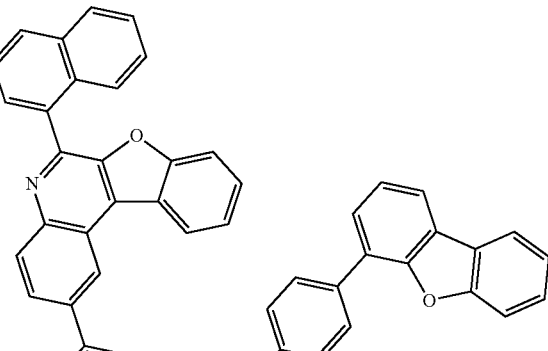
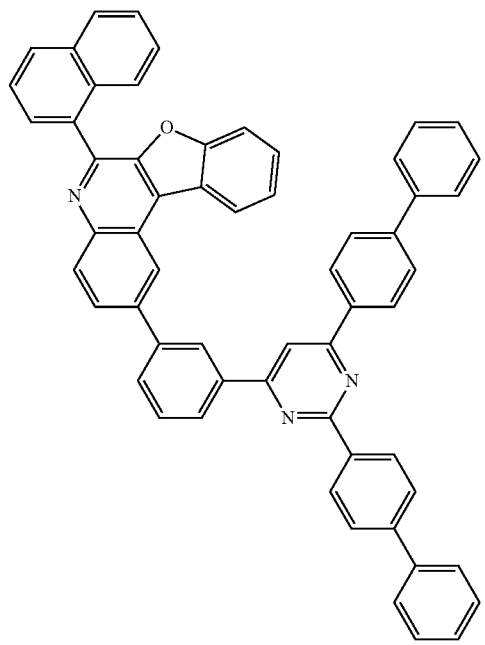
768
769
770
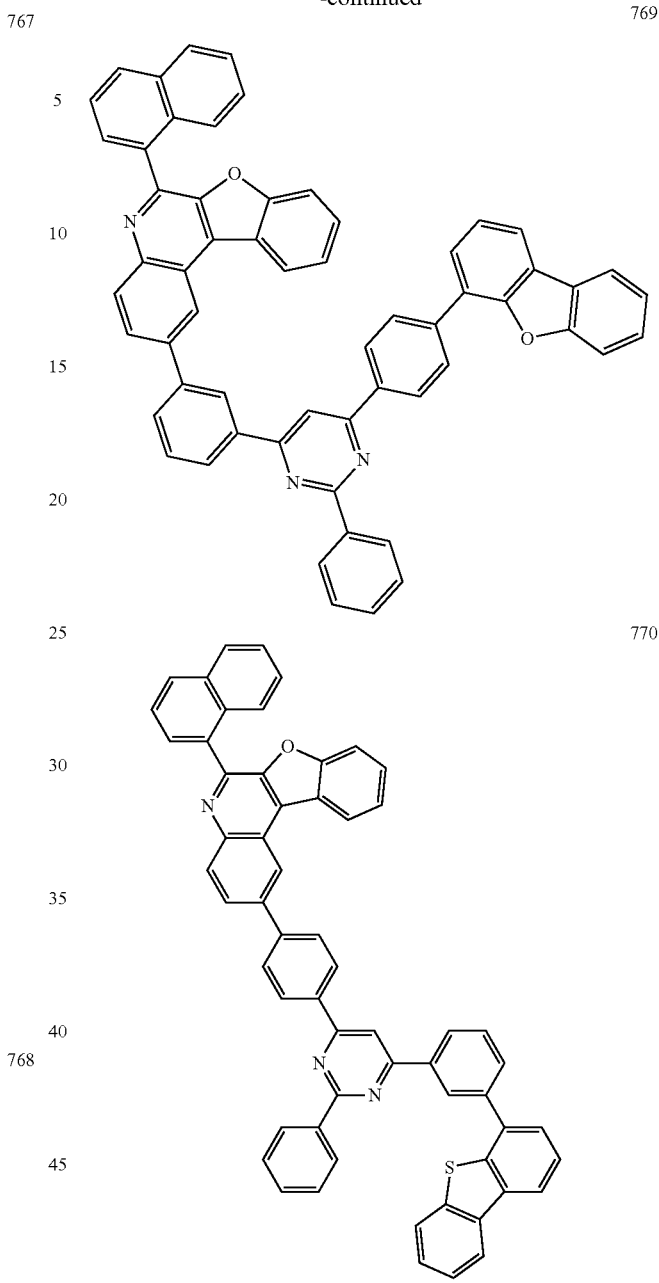
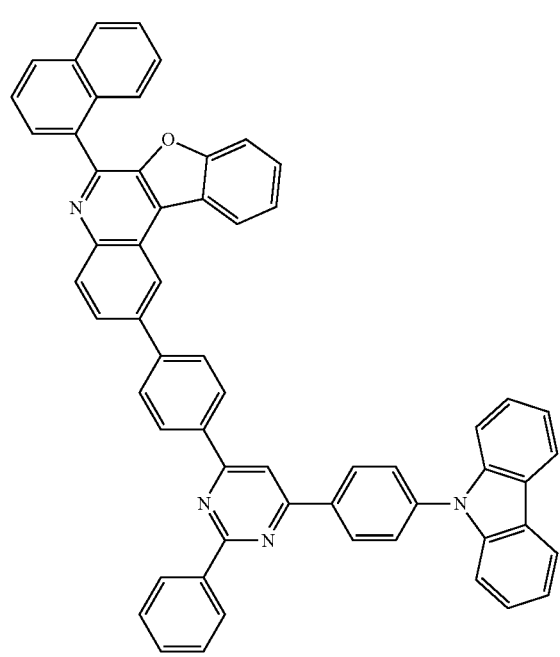
771
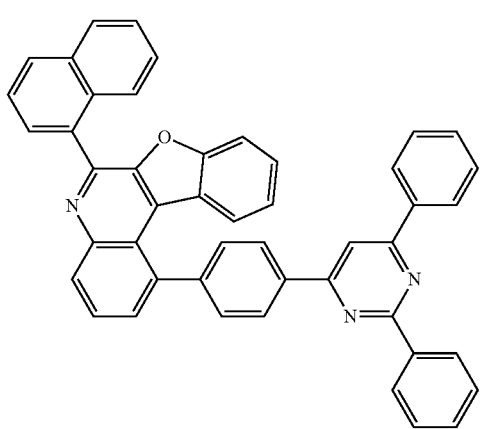

1037
-continued
772
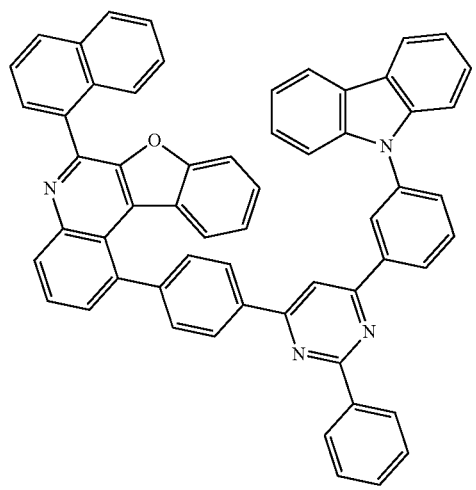
773
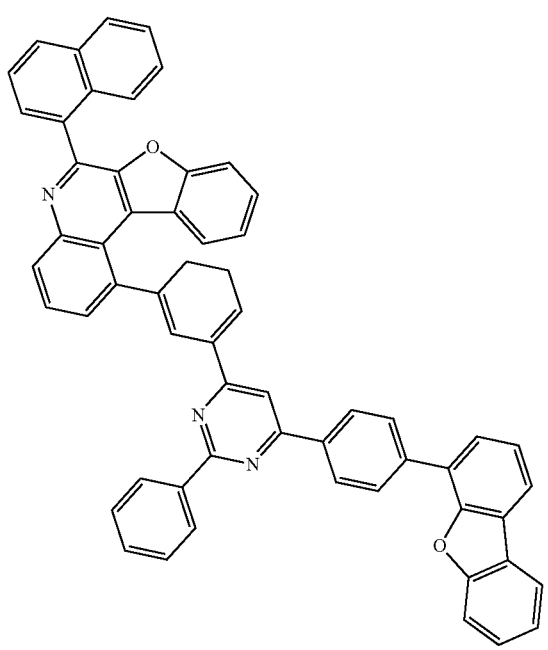
1038
-continued
774
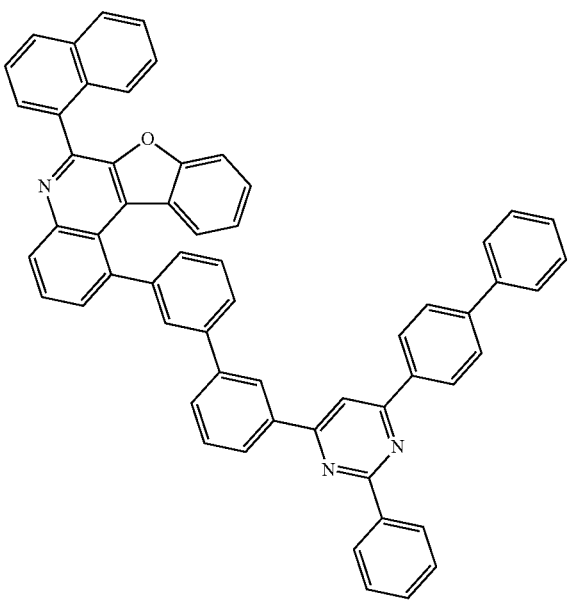
775
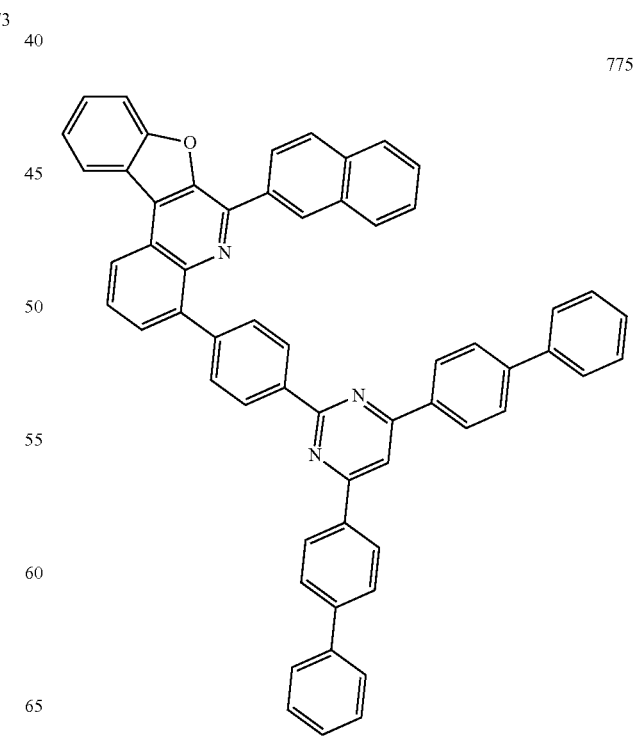

1039
-continued
776
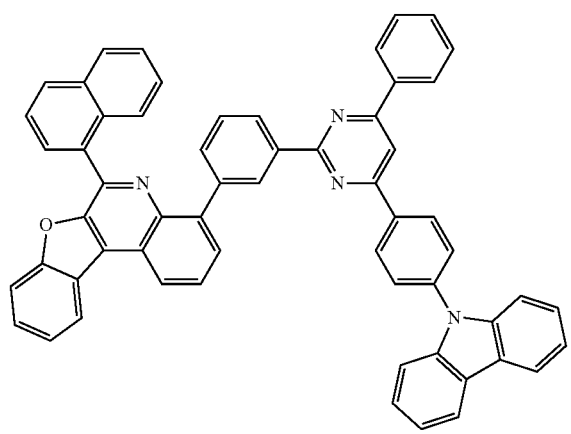
777
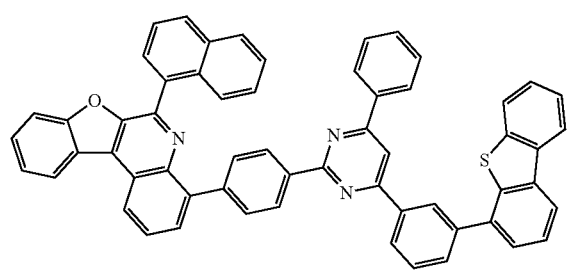
778
1040
-continued
779
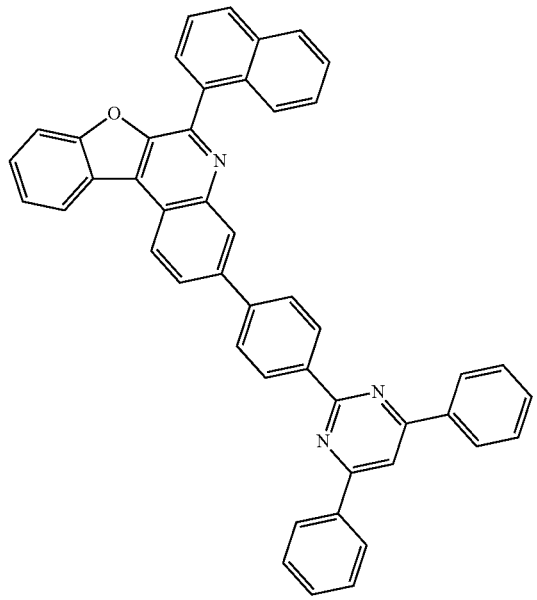
780
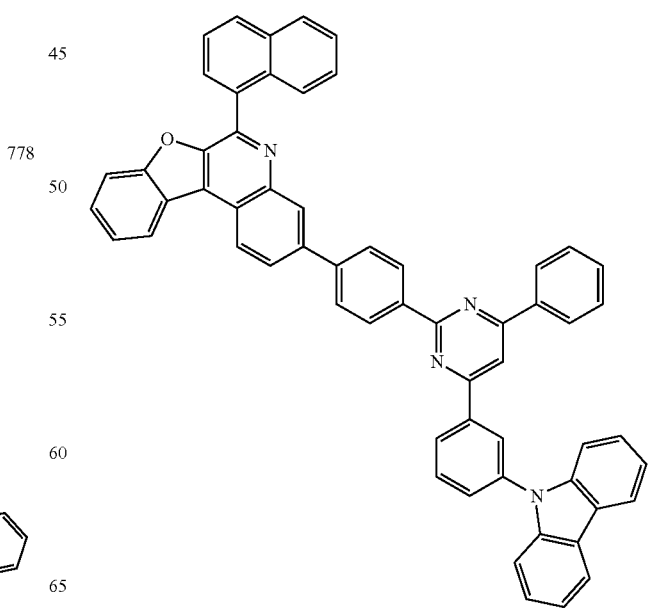

1041 -continued
781
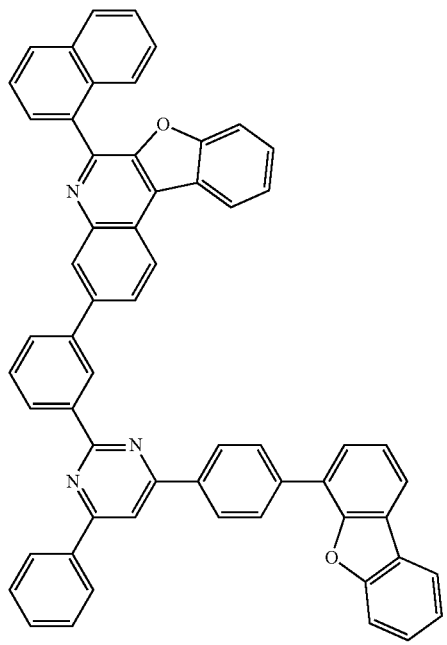
782
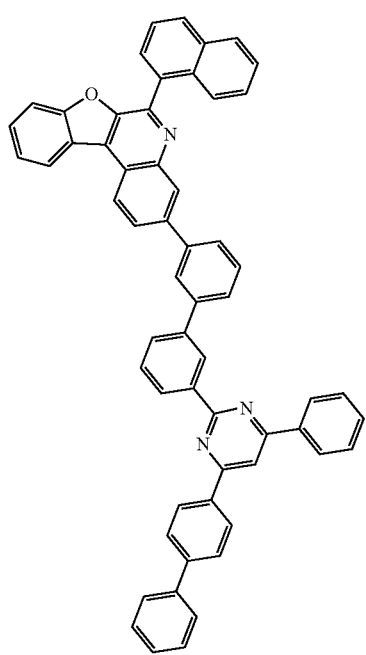
1042 -continued
783
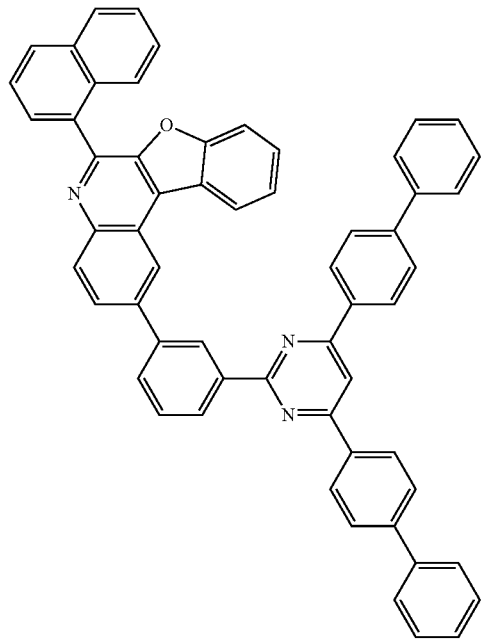
784

1043
-continued
1044
-continued
785
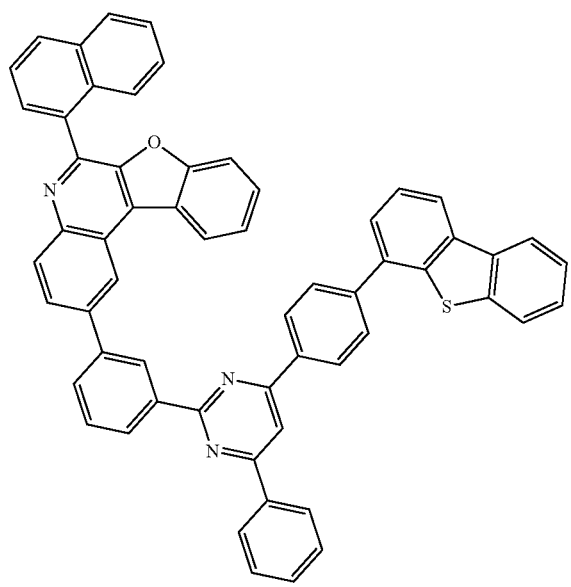
787
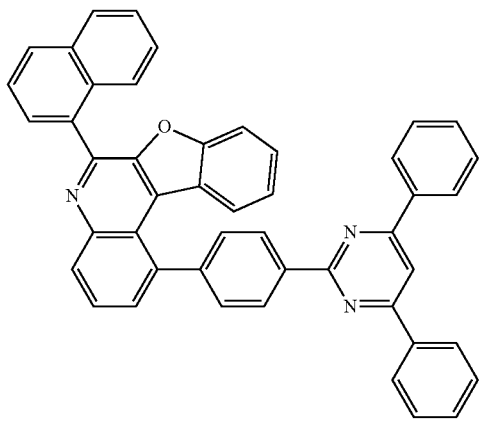
788
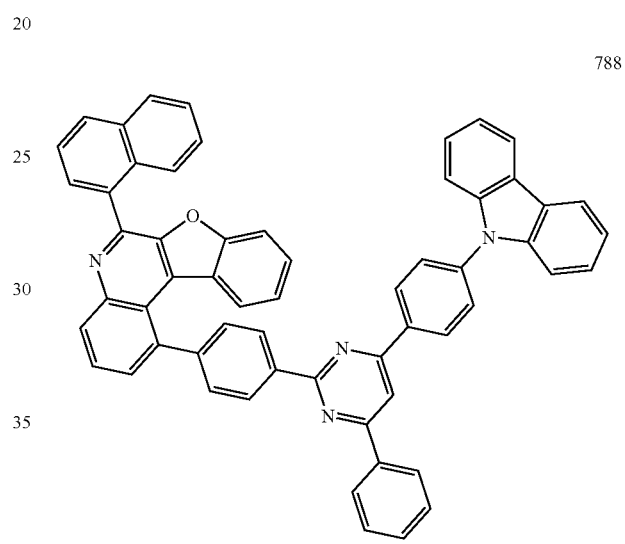
786
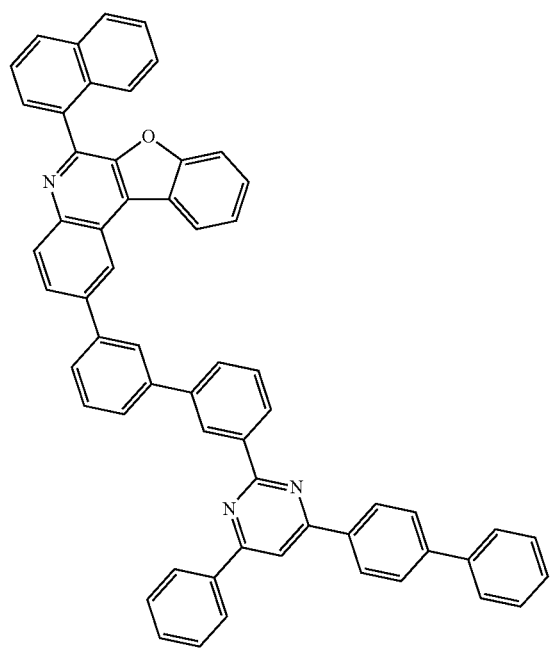
789
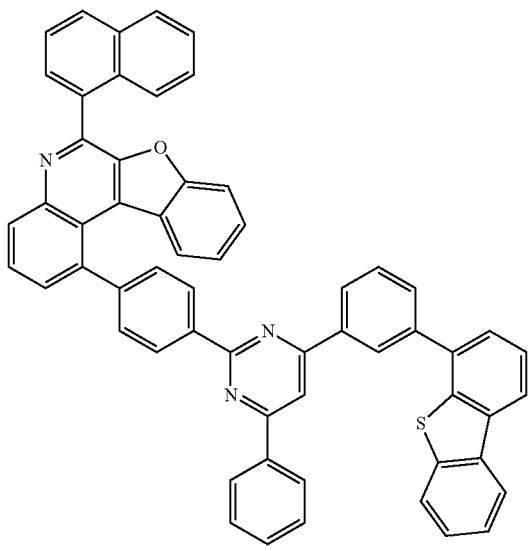

1045
-continued
790
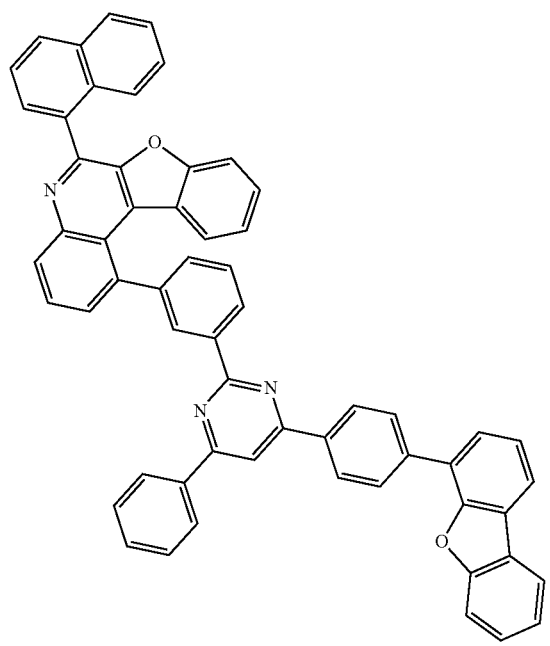
791
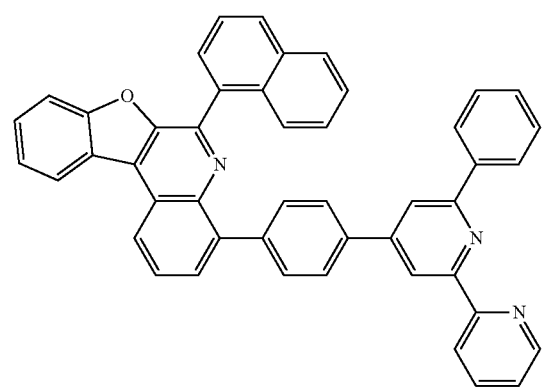
792
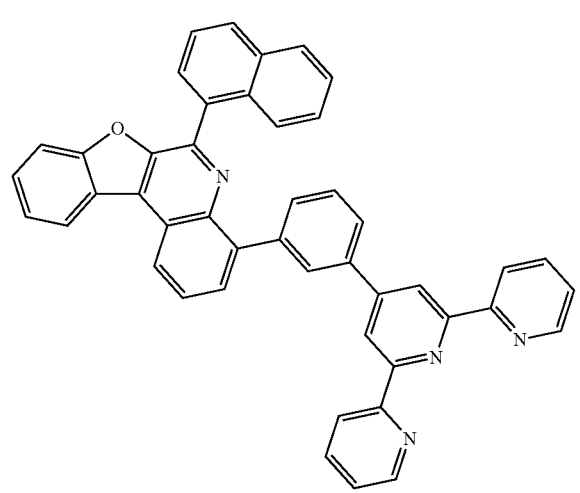
1046
-continued
793
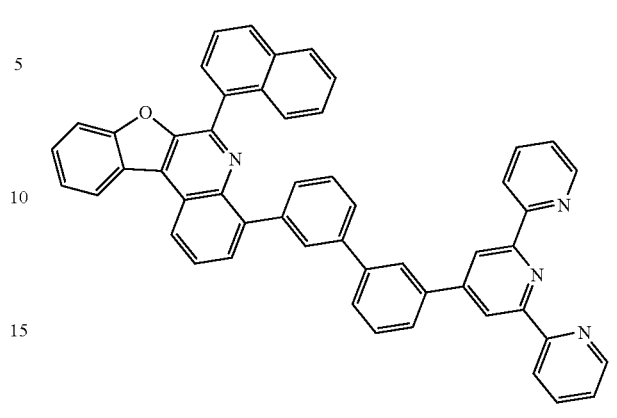
794
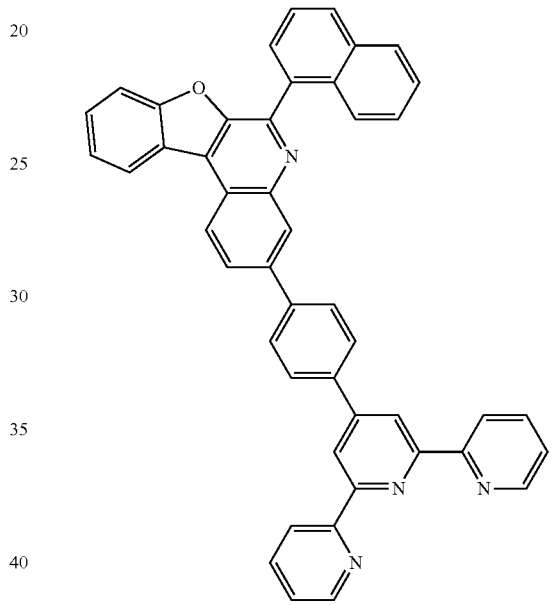
795
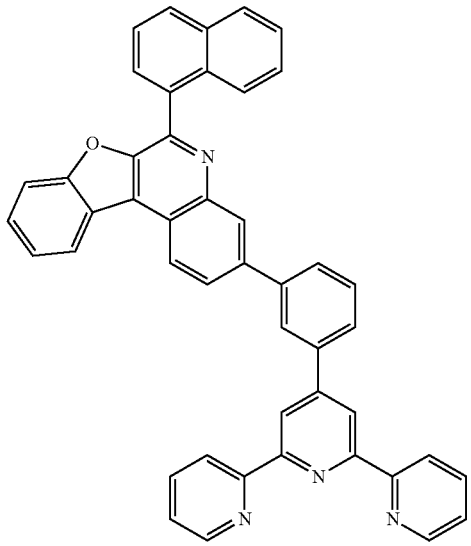

1047
-continued
1048
-continued
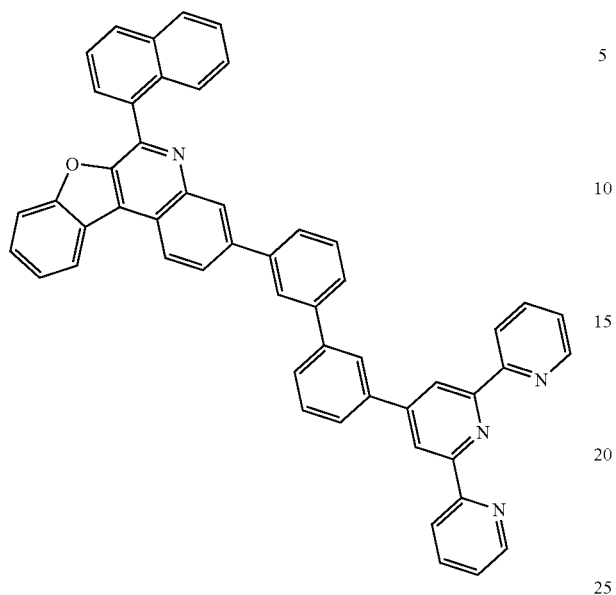
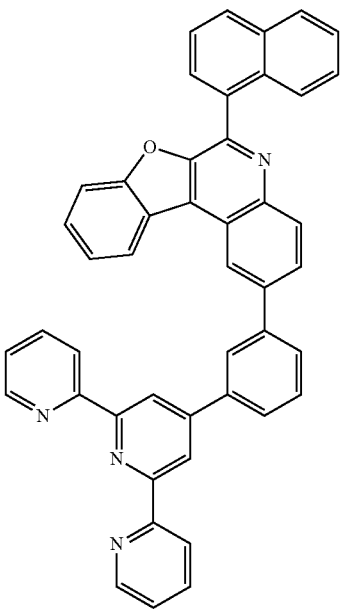
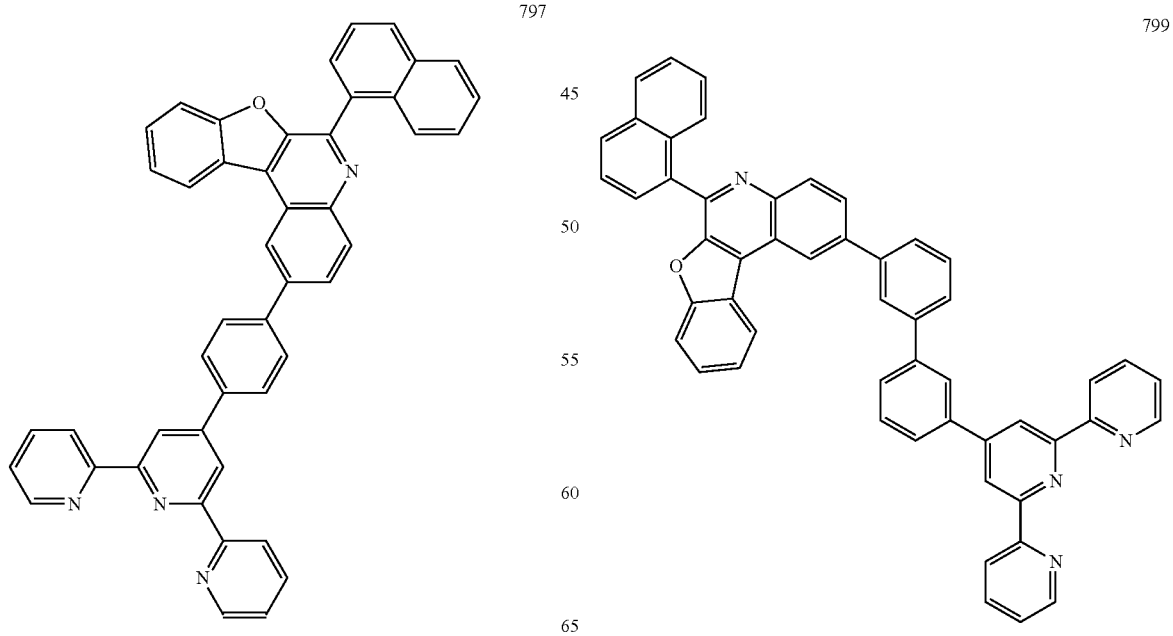

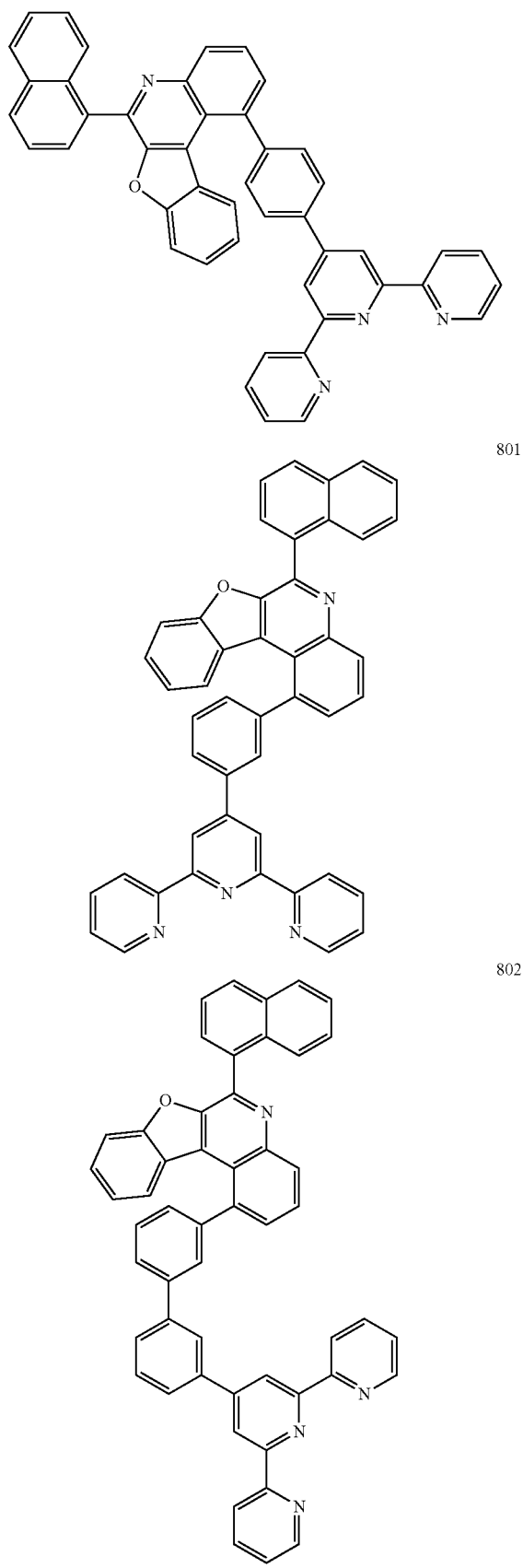
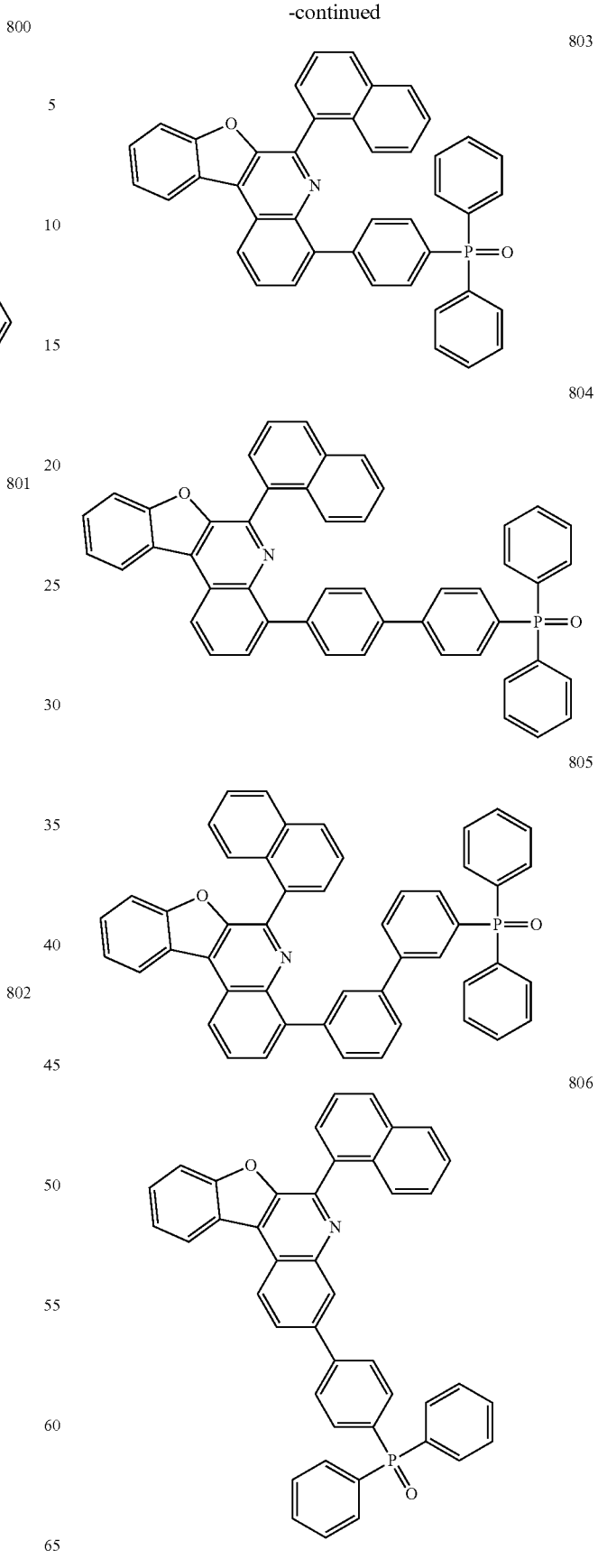

-continued
807
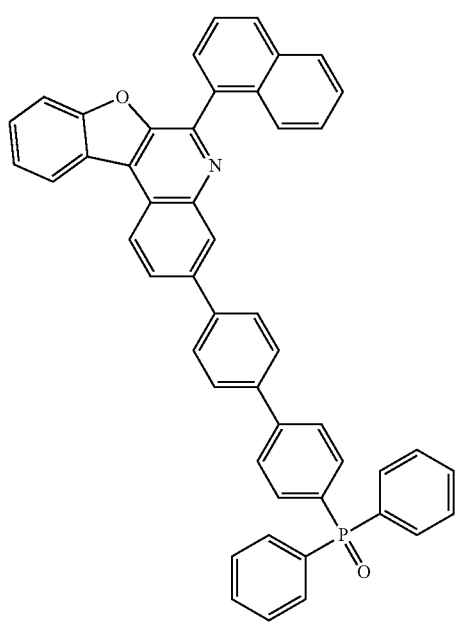
808
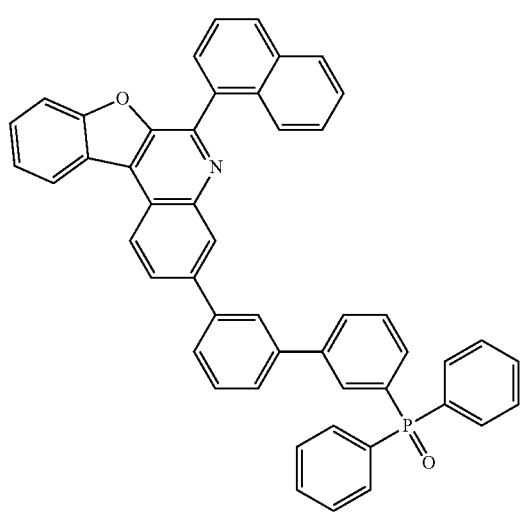
809
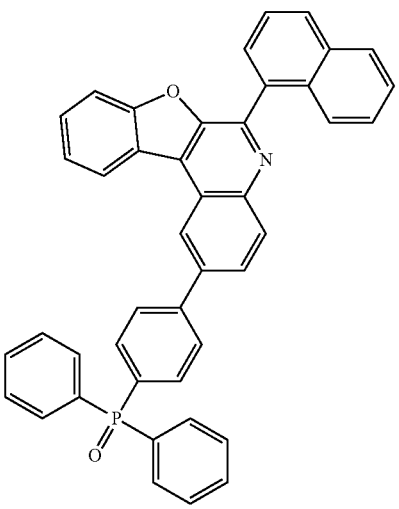
-continued
810
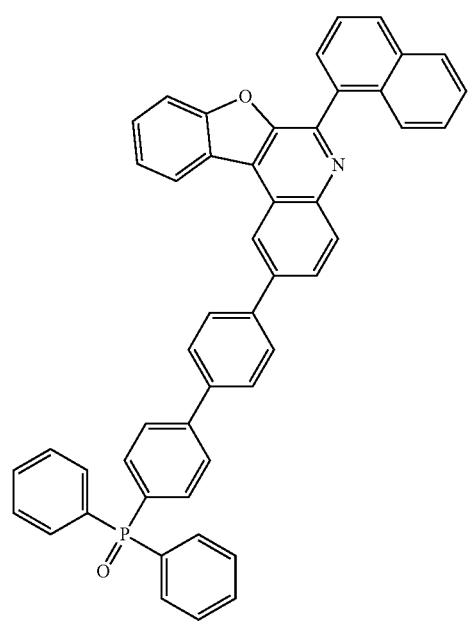
811
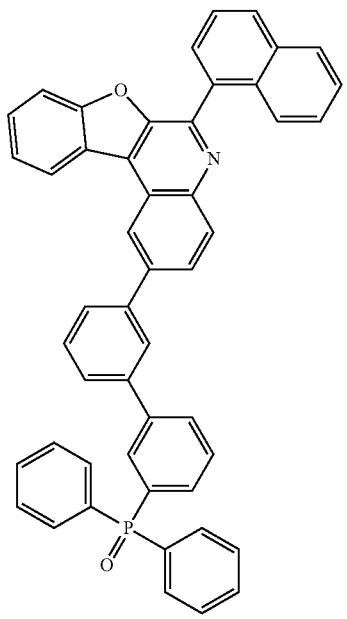
812
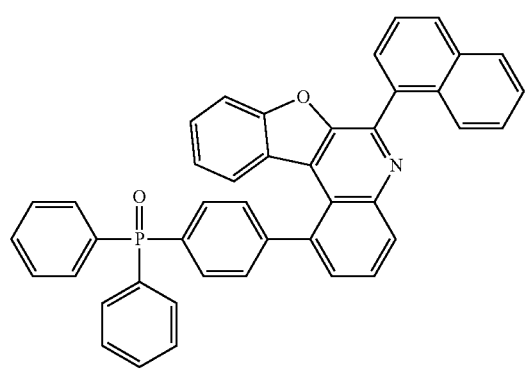

1053 -continued
813
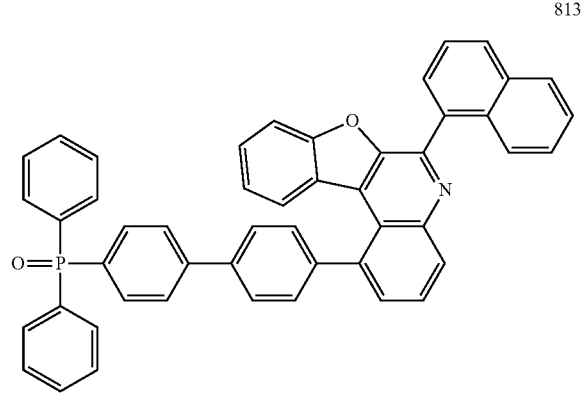
814
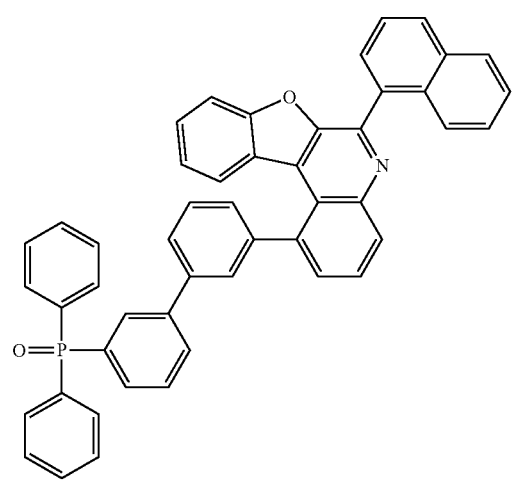
815
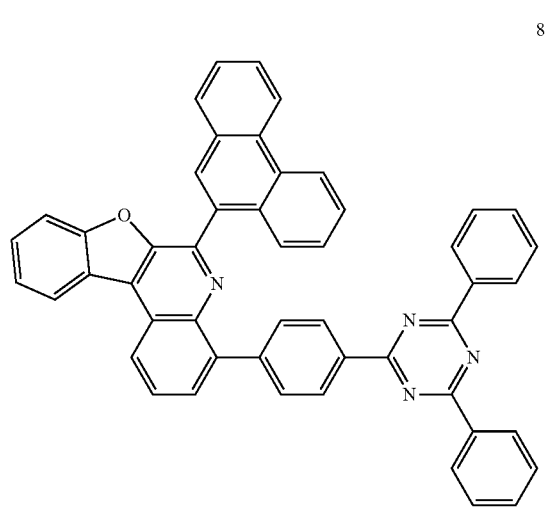
1054 -continued
816
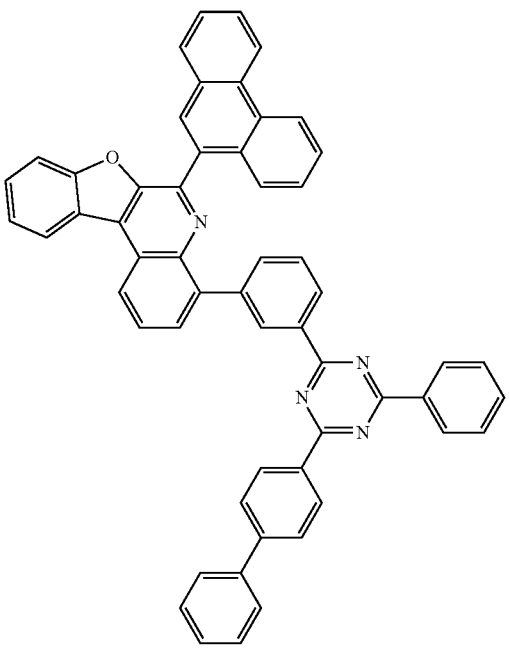
817
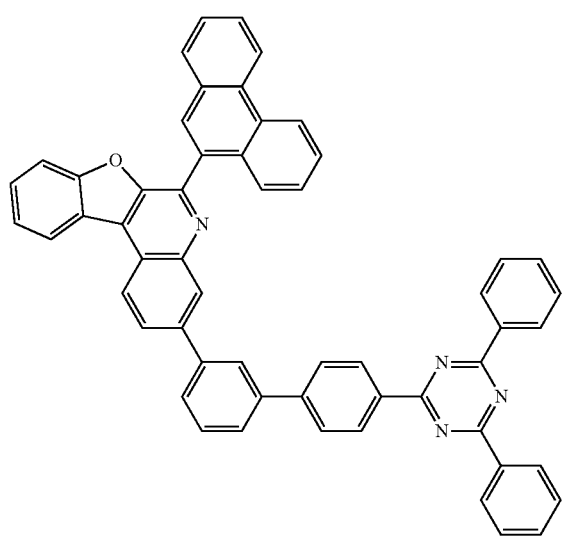

1055
-continued
818
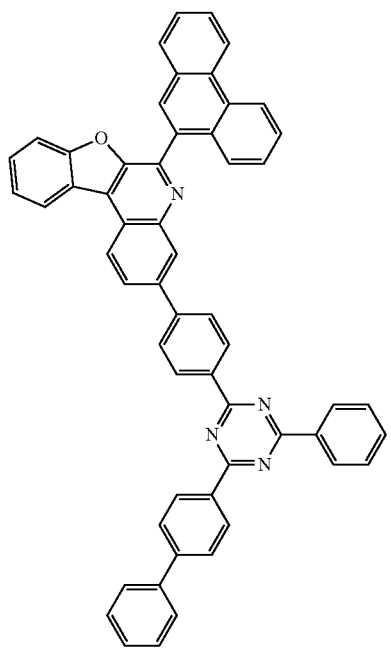
819
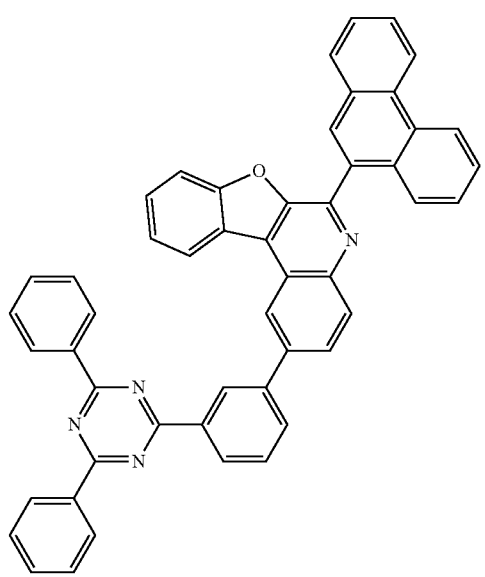 [SMILES: c1ccc(-c2cc(-c3cccc(-c4ccc5nc(-c6cc7ccccc7c7ccccc67)c6oc7ccccc7c6c5c4)c3)nc(-c3ccccc3)n2)cc1]
1056
-continued
820
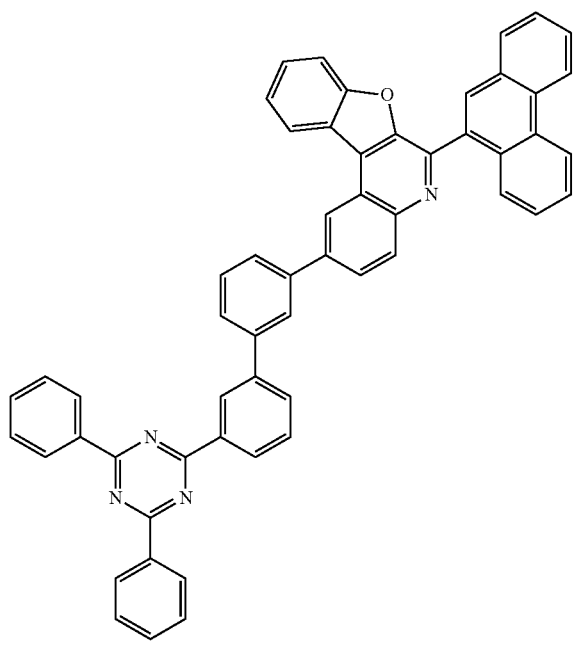
821
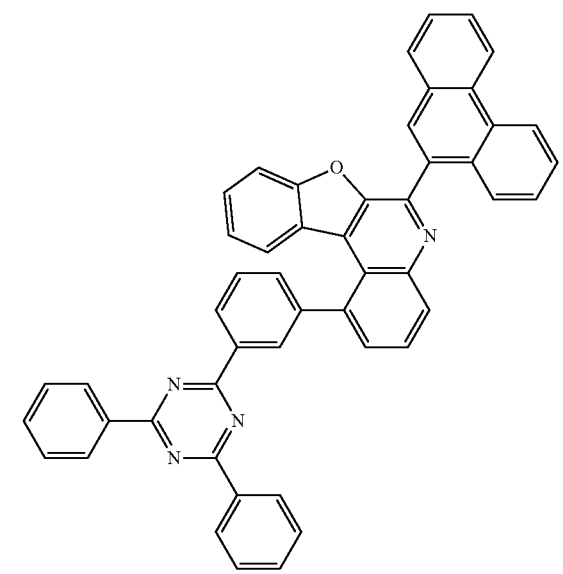

-continued
822
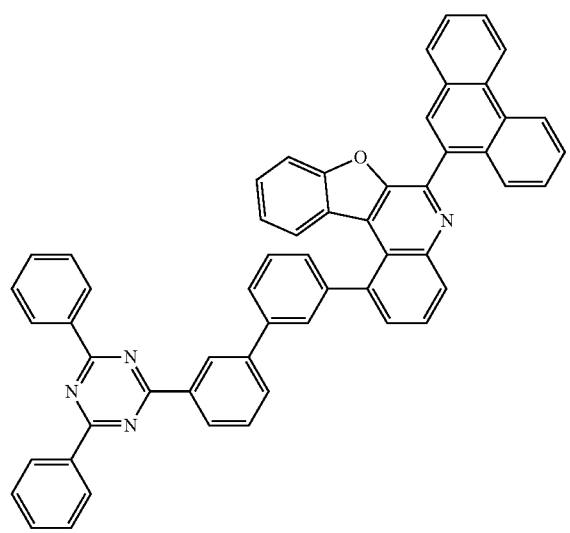
-continued
824
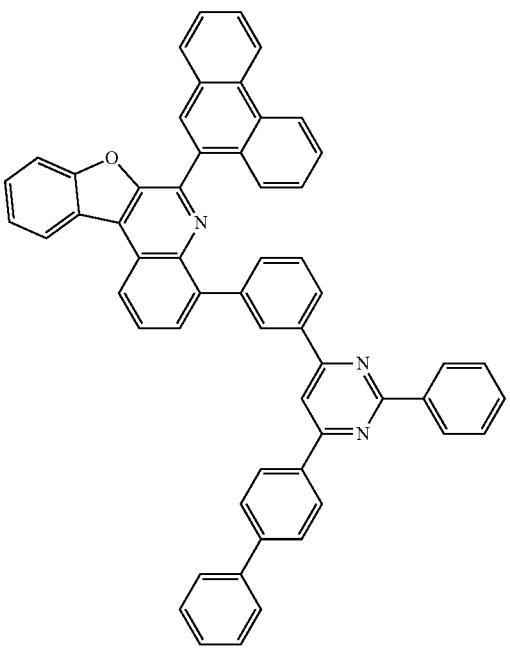
823
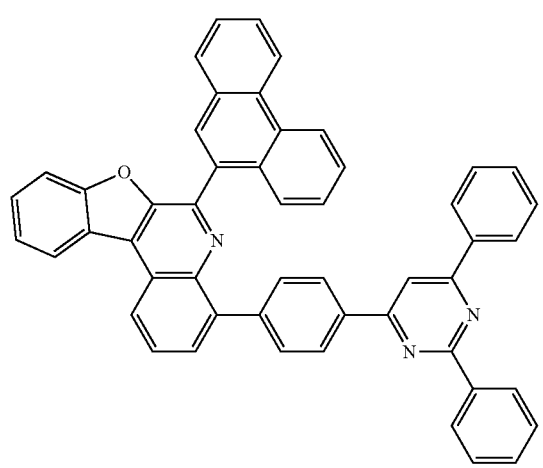
825
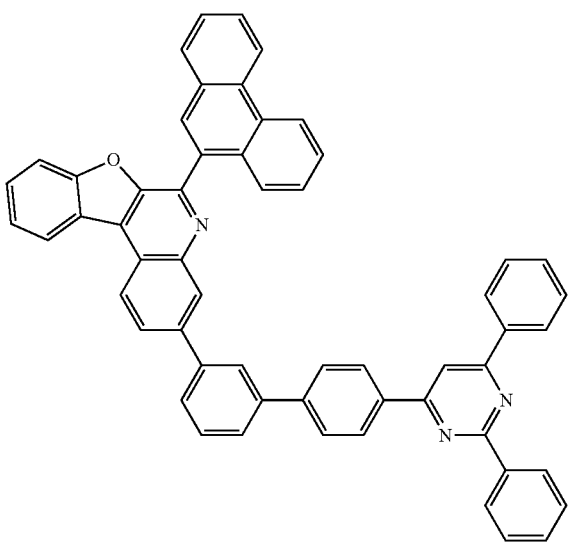

1059
-continued
1060
-continued
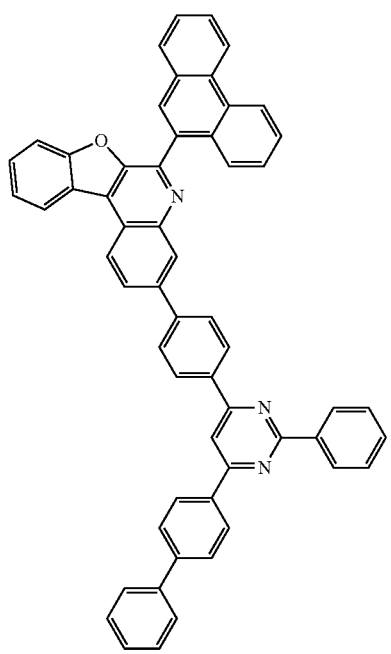
826
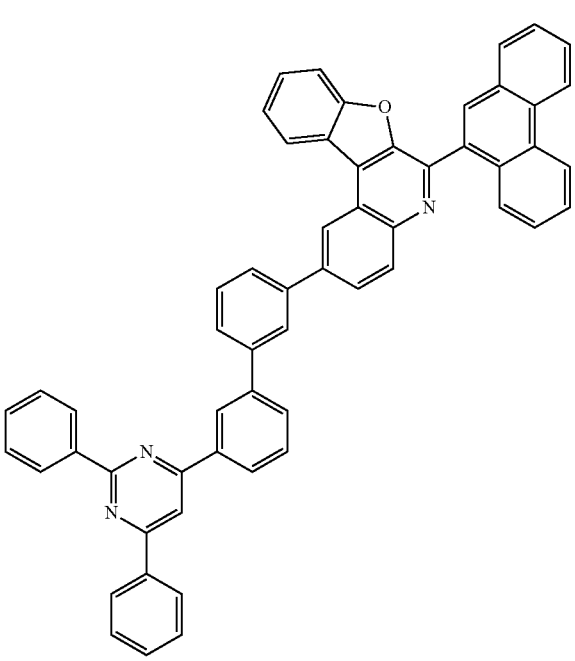
828
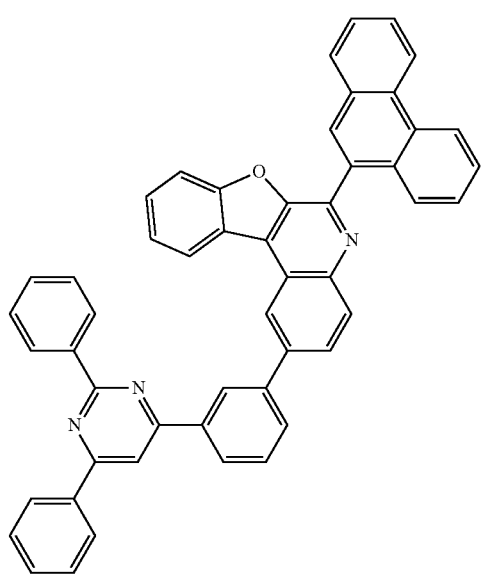
827
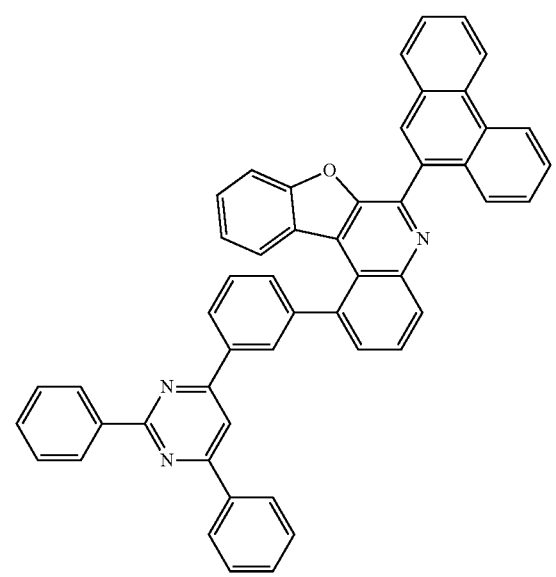
829

1061 -continued
830
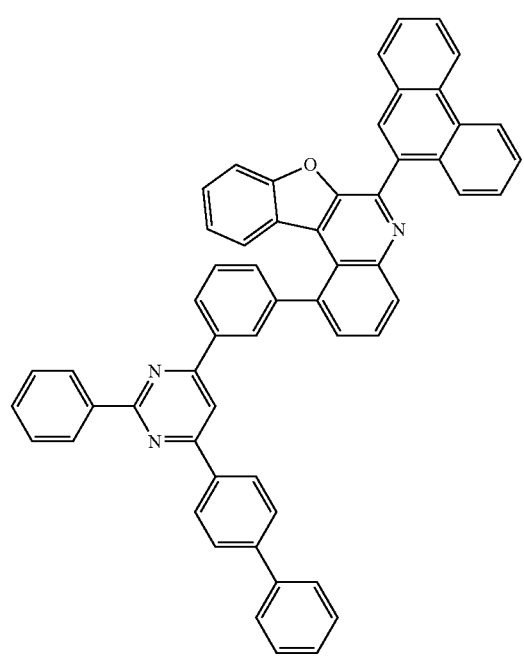
831
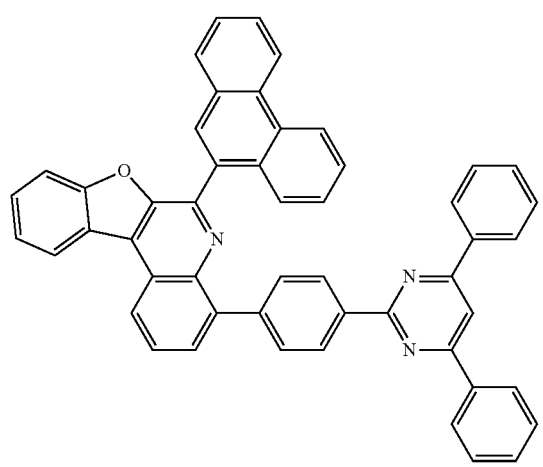
1062 -continued
832
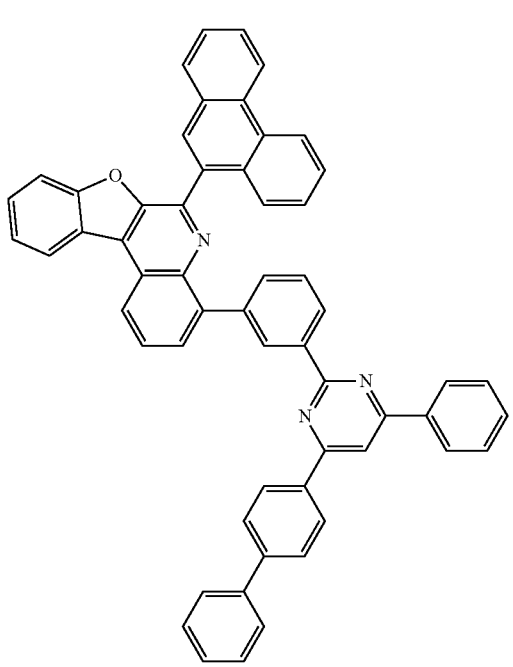
833
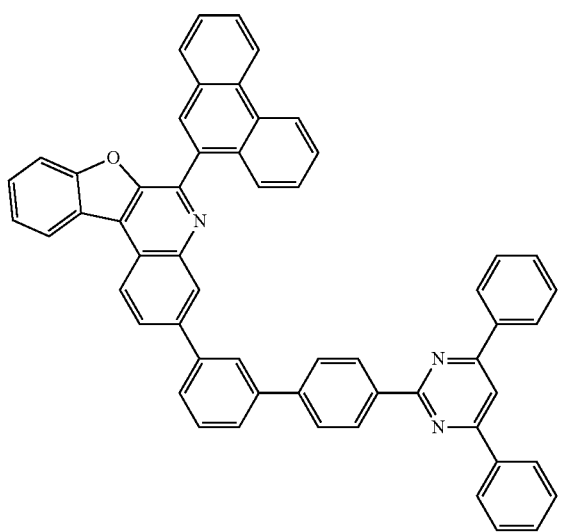

1063
-continued
834
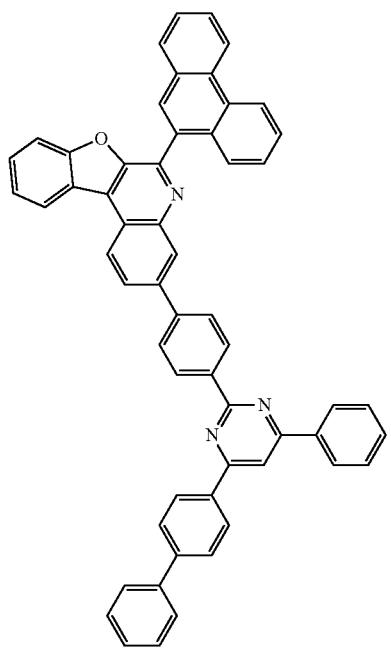
835
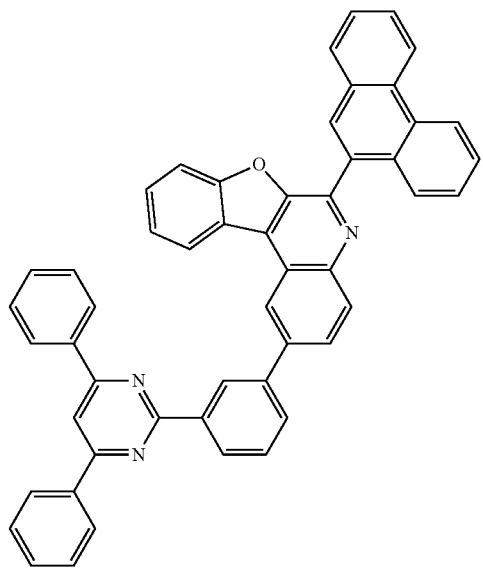
1064
-continued
836
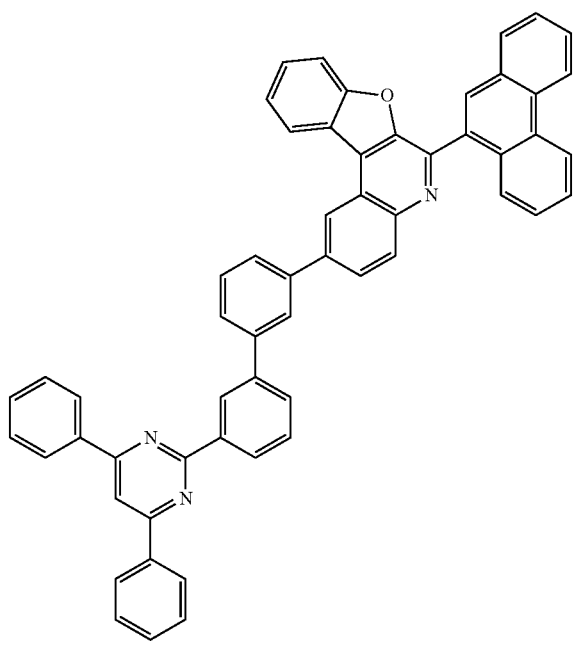
837
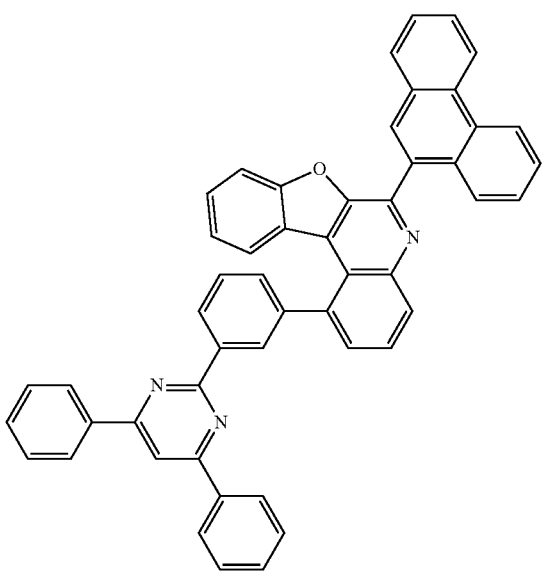

1065
-continued
838
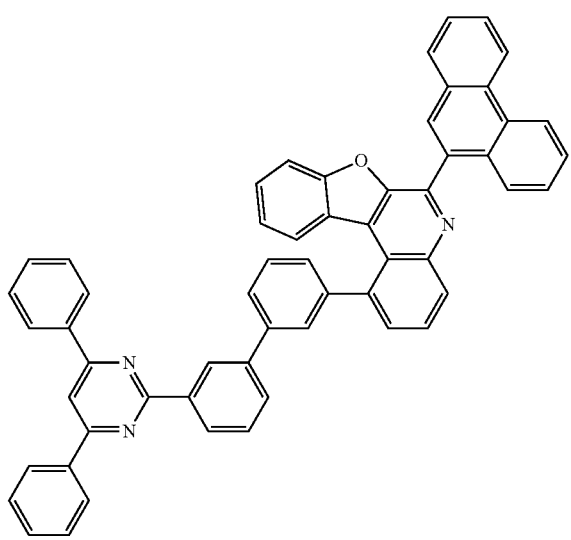
839
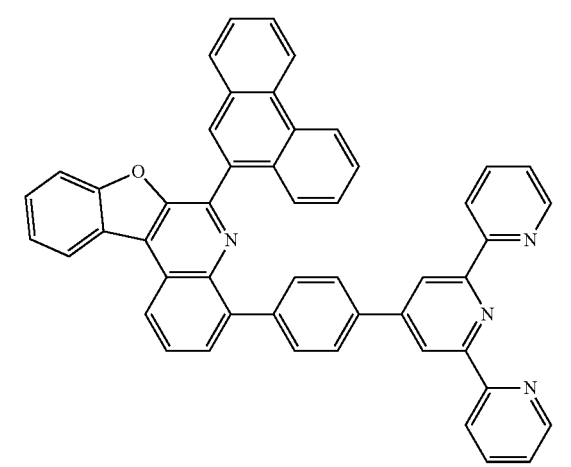
840
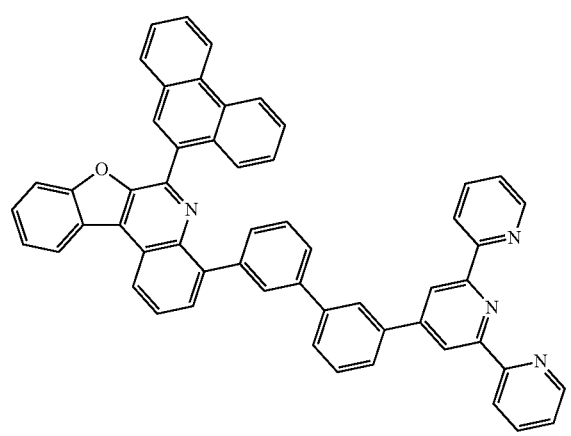
1066
-continued
841
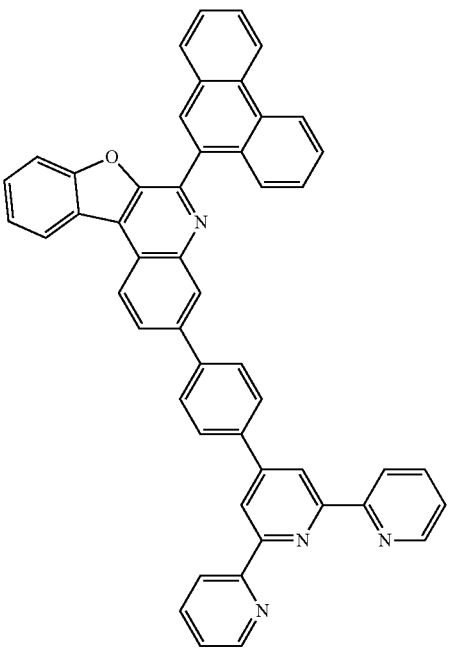
842
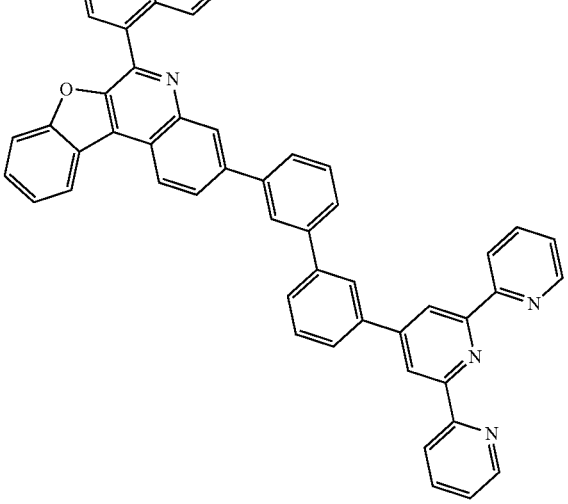

1067
-continued
843
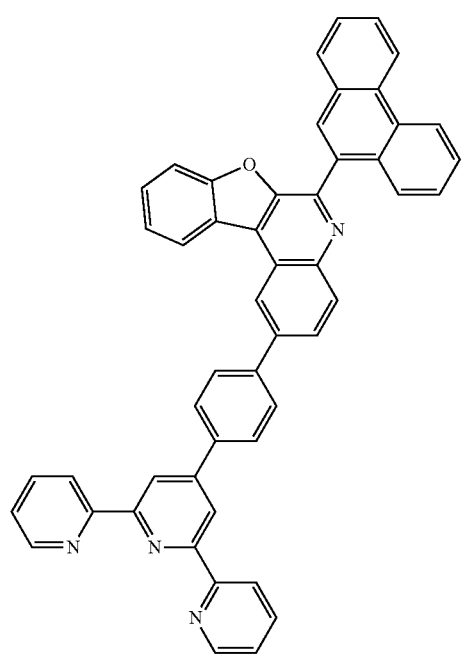
844
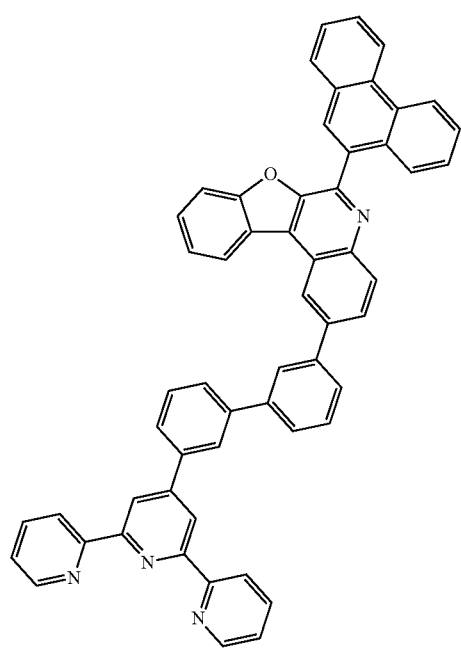
1068
-continued
845
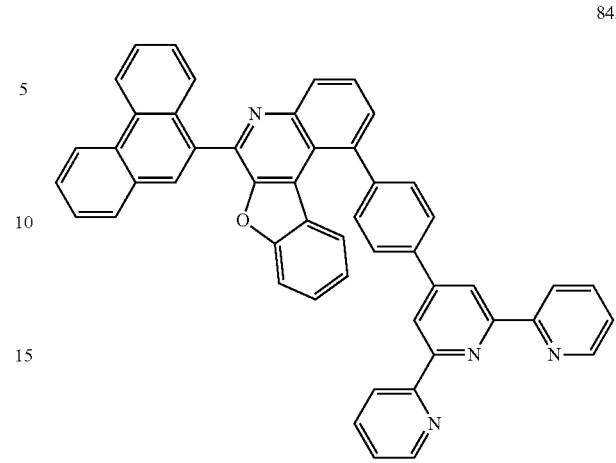
846
847
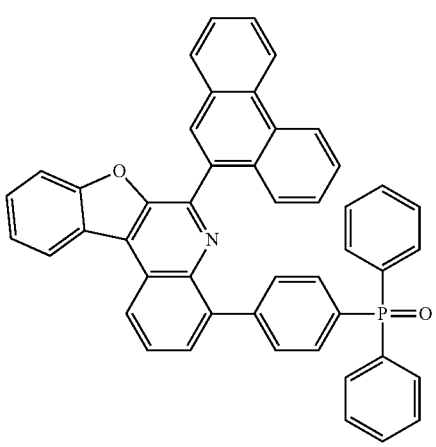

-continued
848
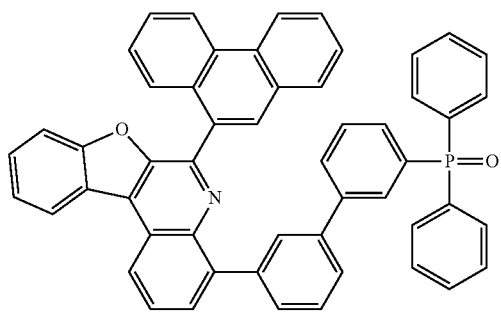
849
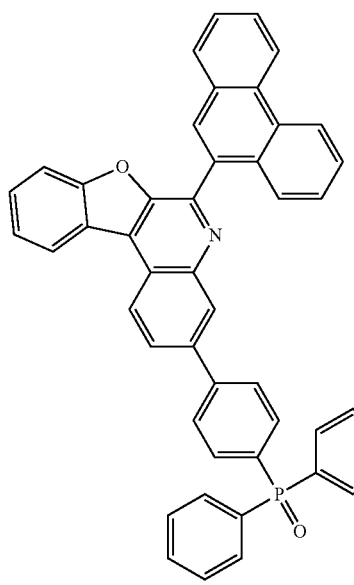
850
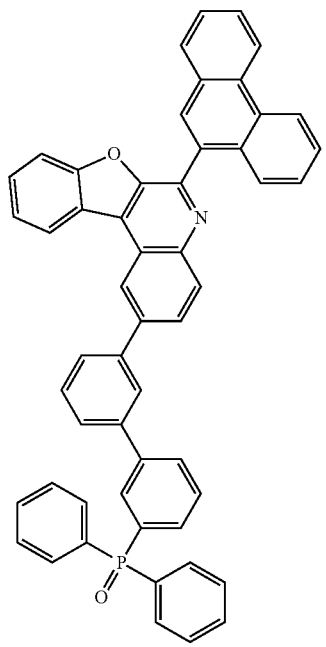
-continued
851
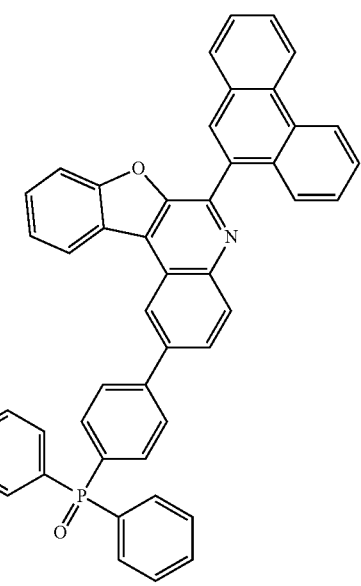
852
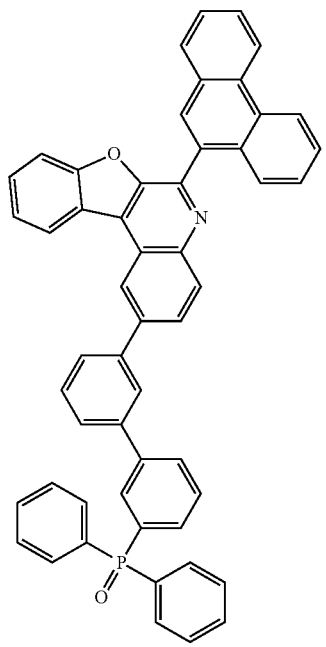
853
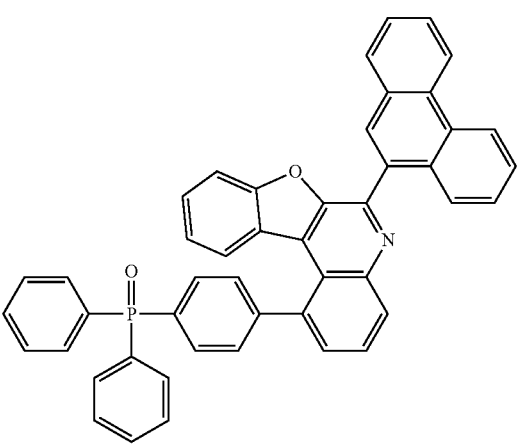 [SMILES: O=P(c1ccccc1)(c1ccccc1)c1ccc(-c2cccc3nc(-c4cc5ccccc5c5ccccc45)c4oc5ccccc5c4c23)cc1]

1071
-continued
854
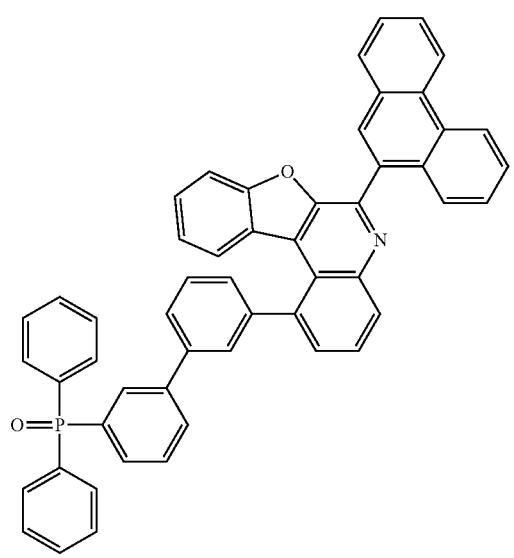
855
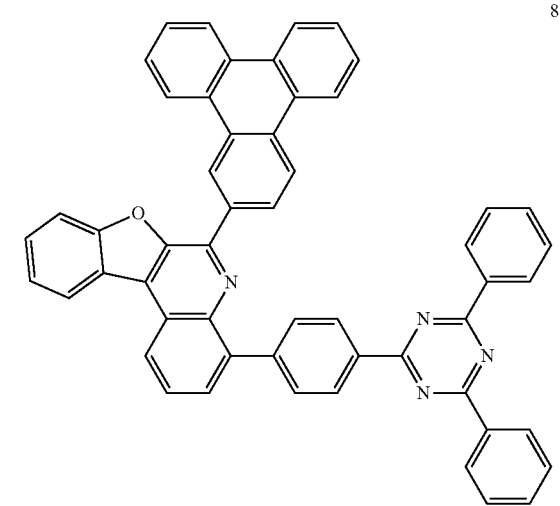
856
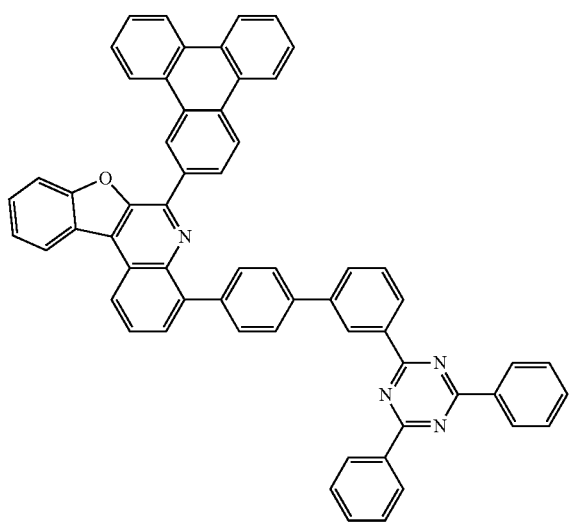
1072
-continued
857
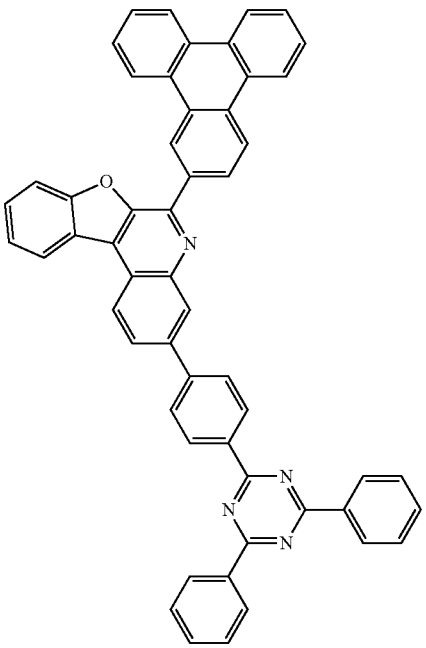
858
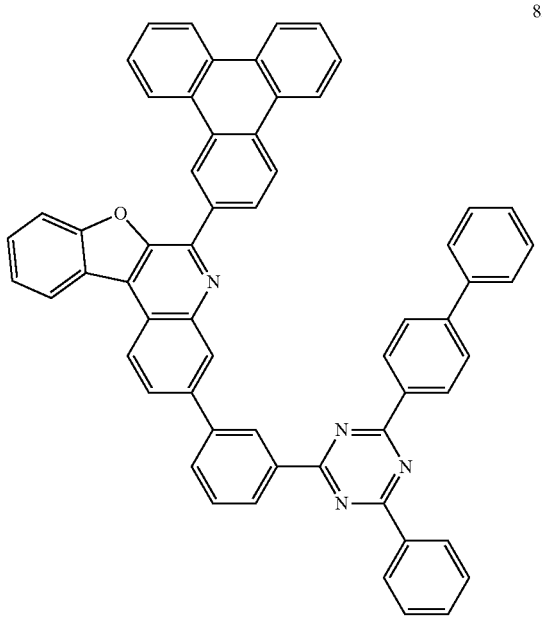

1073
-continued
859
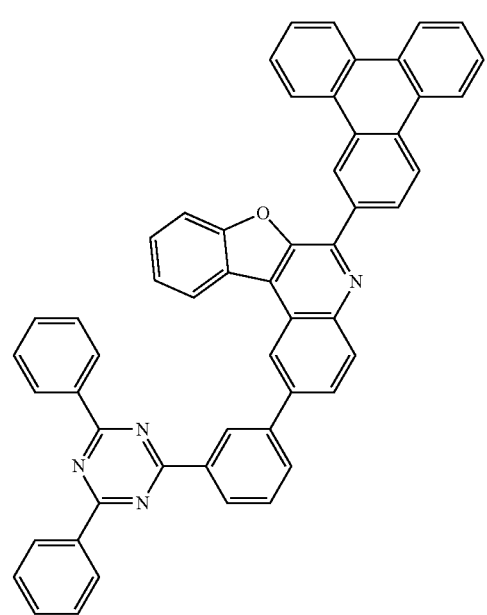
860
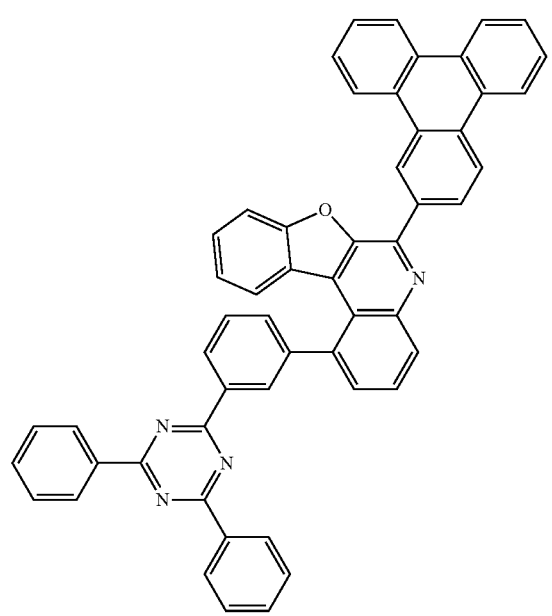 [SMILES: c1ccc(-c2cc(-c3cccc(-c4cccc5nc(-c6ccc7c8ccccc8c8ccccc8c7c6)c6oc7ccccc7c6c45)c3)nc(-c3ccccc3)n2)cc1]
1074
-continued
861
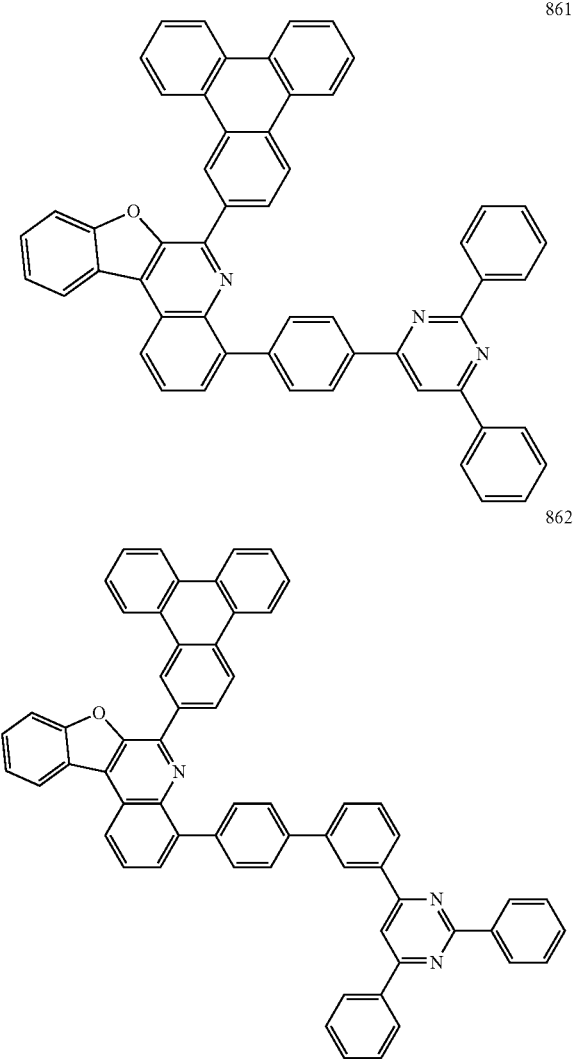
863
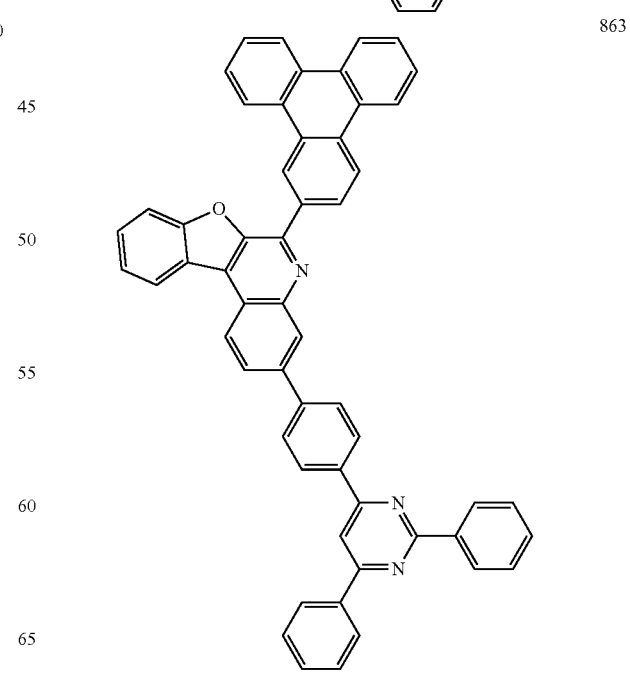

1075
-continued
864
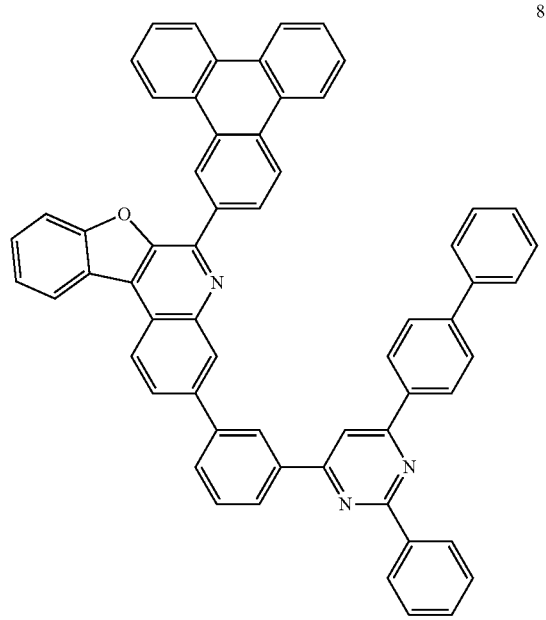
1076
-continued
866
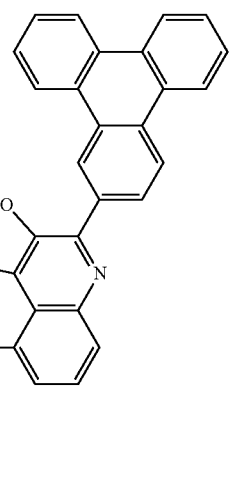
867
868
865
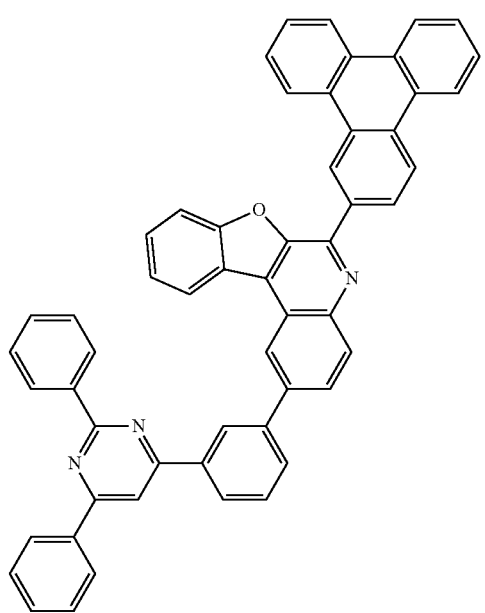
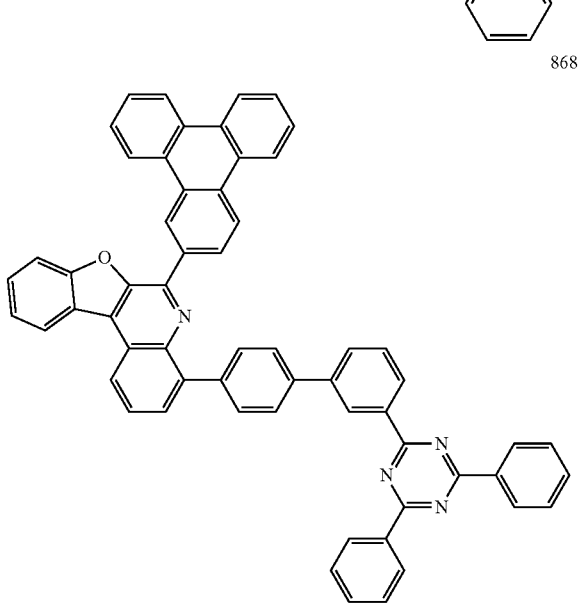

1077
-continued
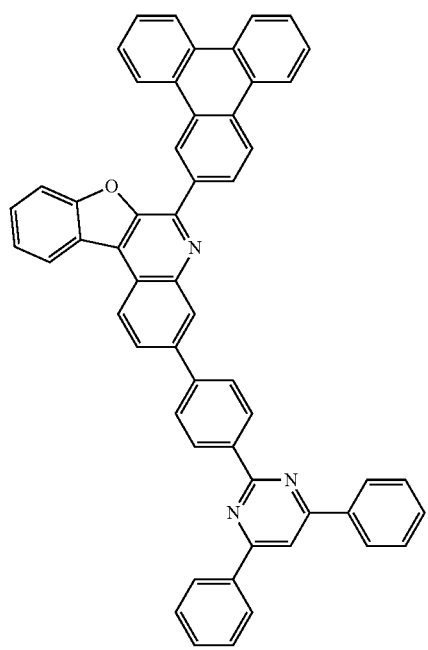
1078
-continued
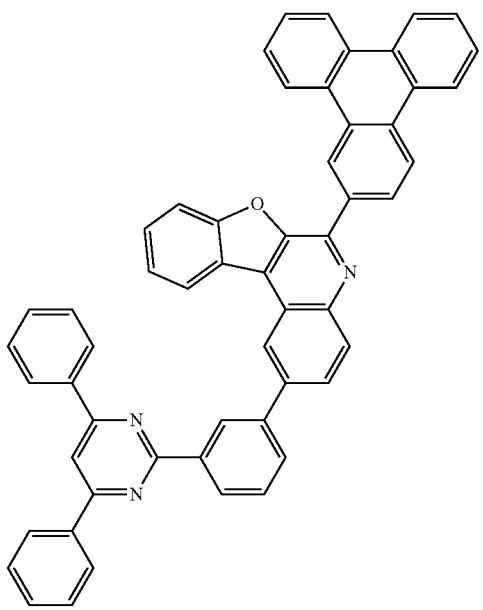
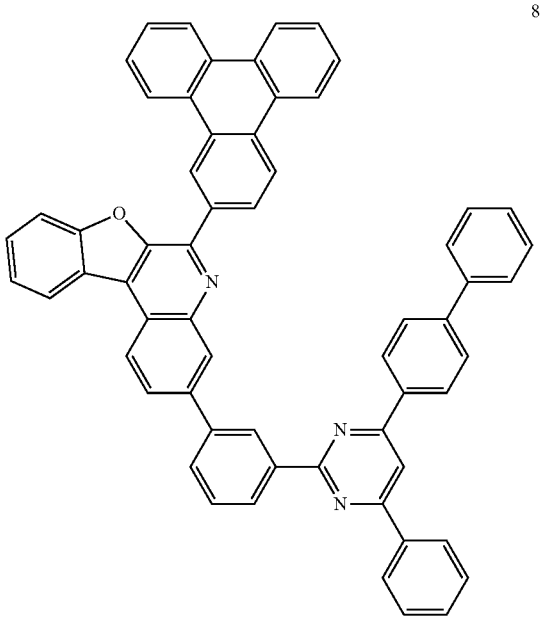
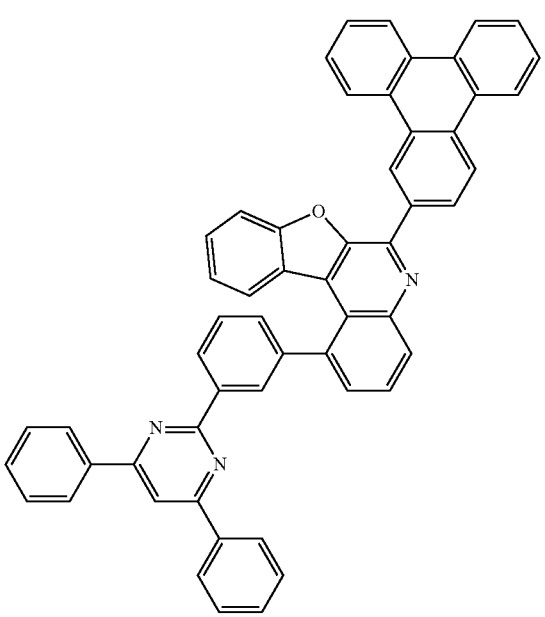

1079
-continued
873
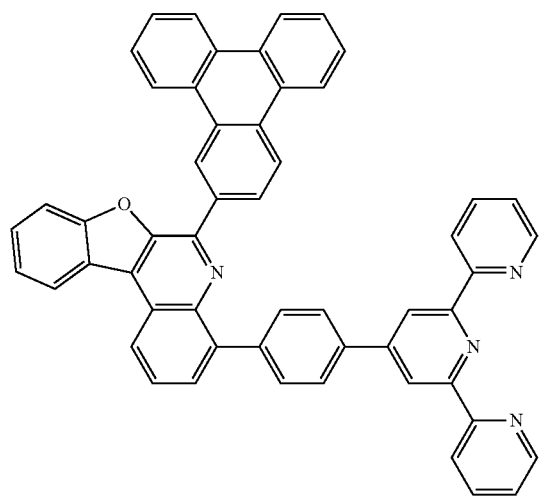
874
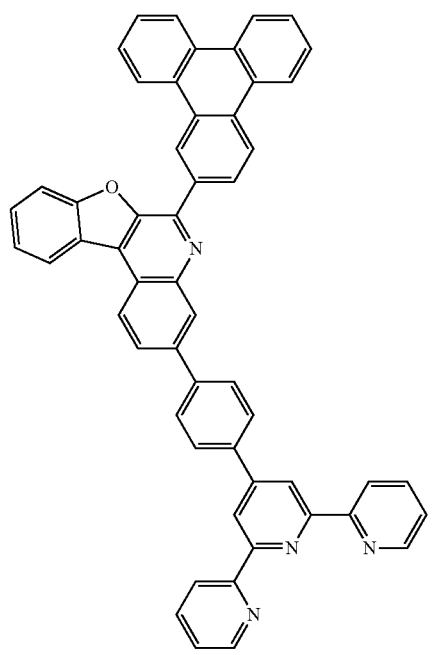
1080
-continued
875
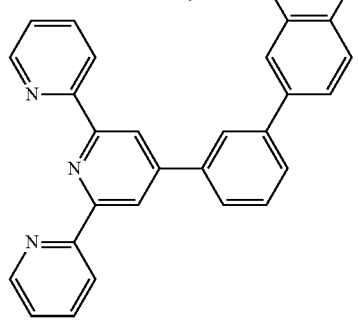
876
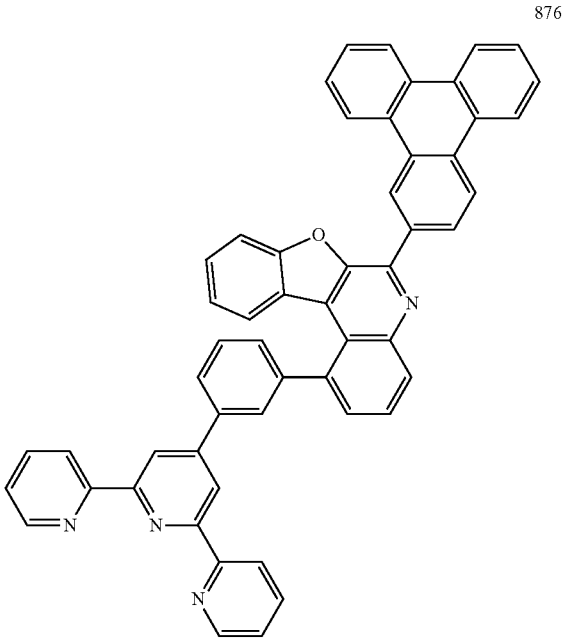

1081
-continued
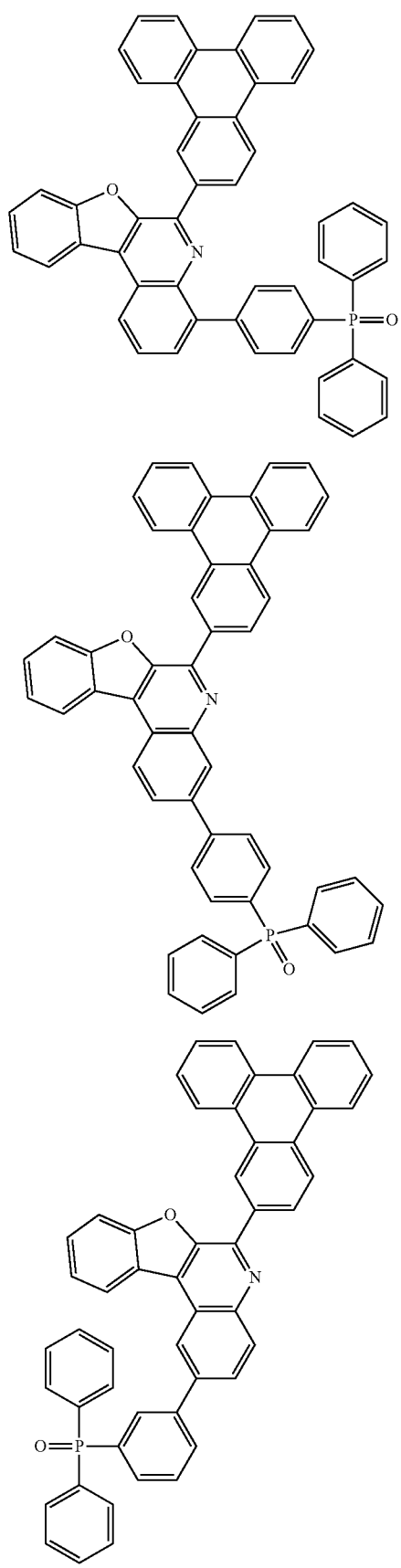
877
878
879
1082
-continued
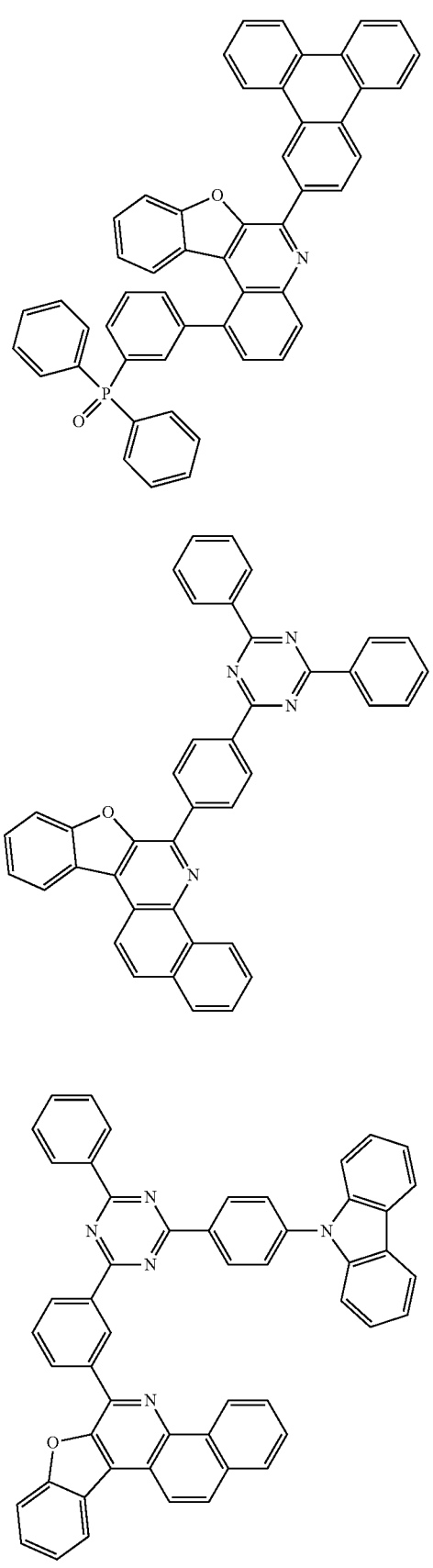
880
881
882

1083
883
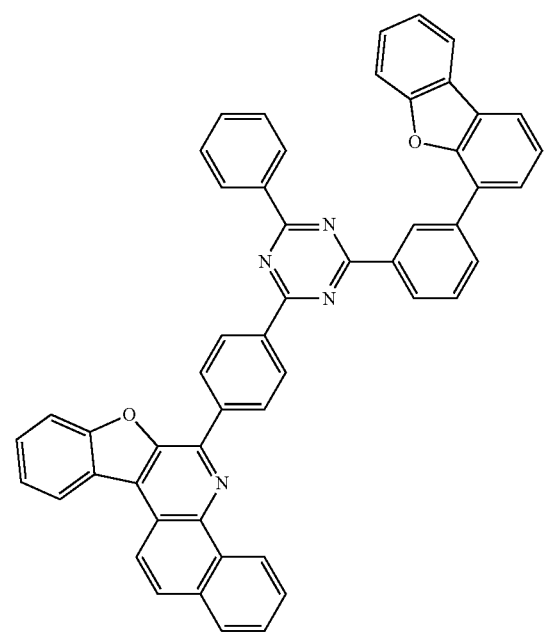
884
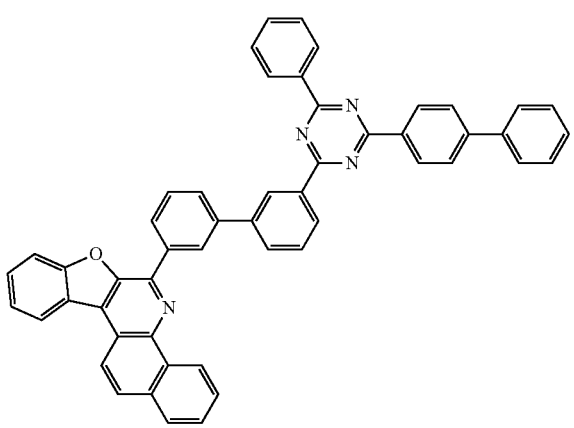
885
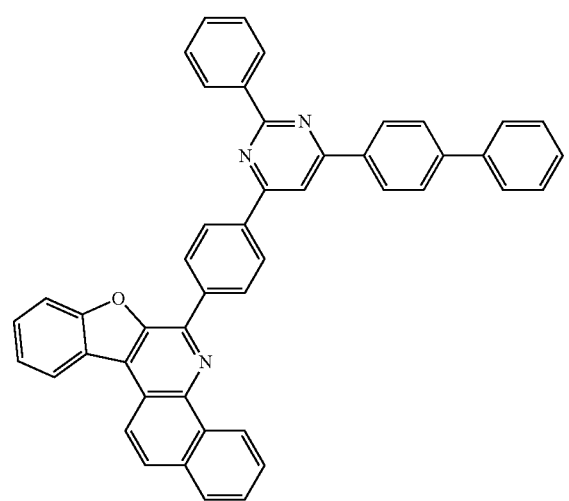
1084
886
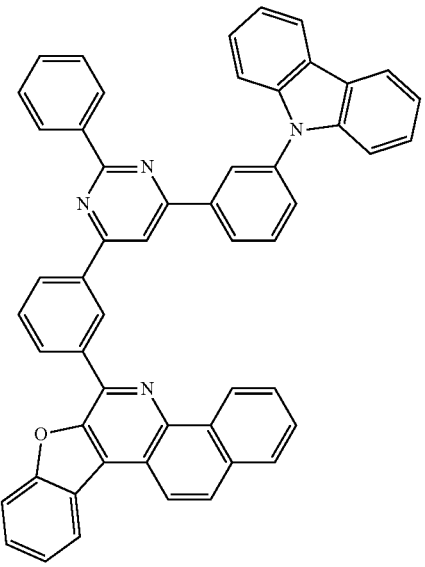
887
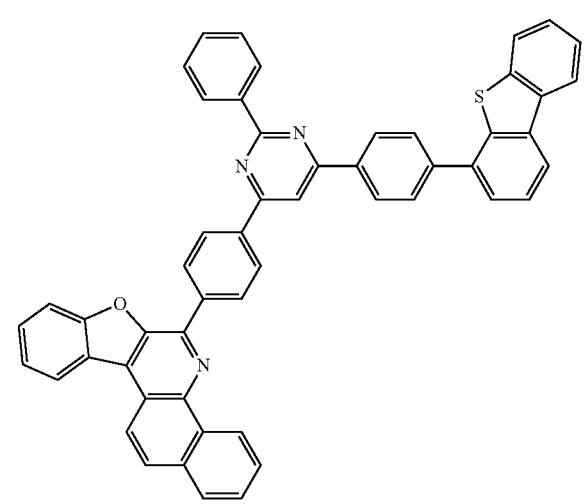
888
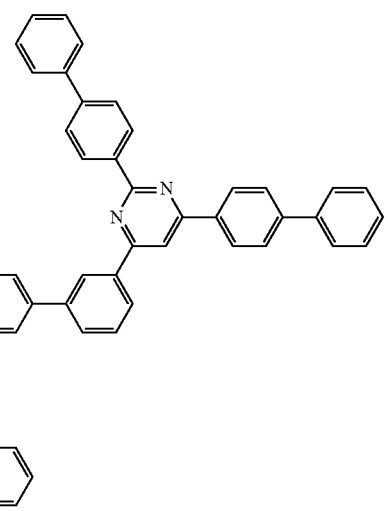

1085
-continued
889
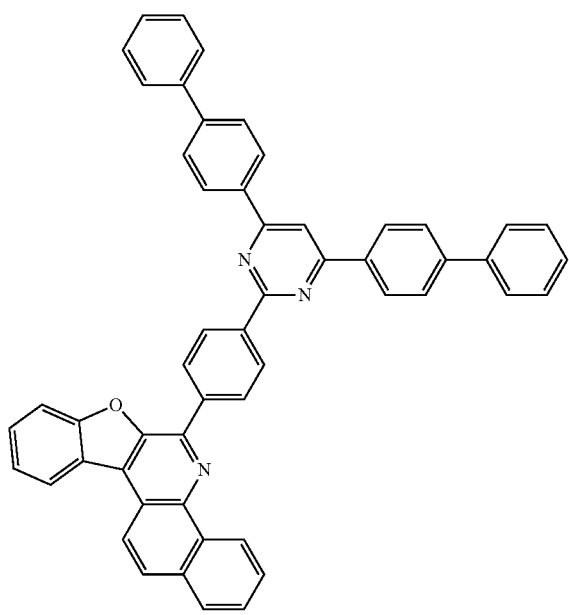
890
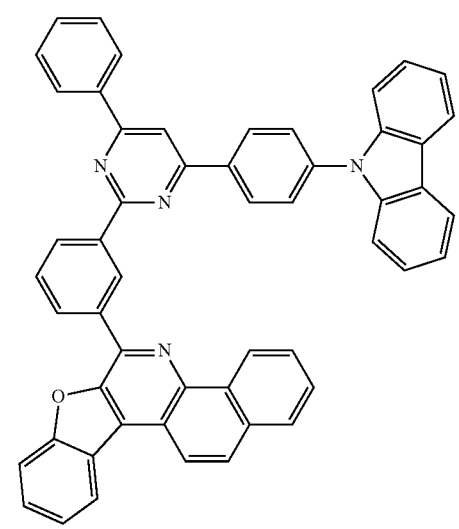
1086
-continued
891
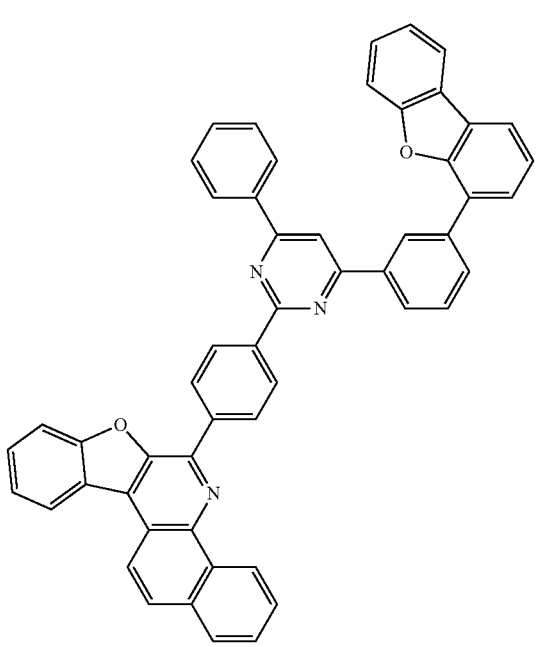
892
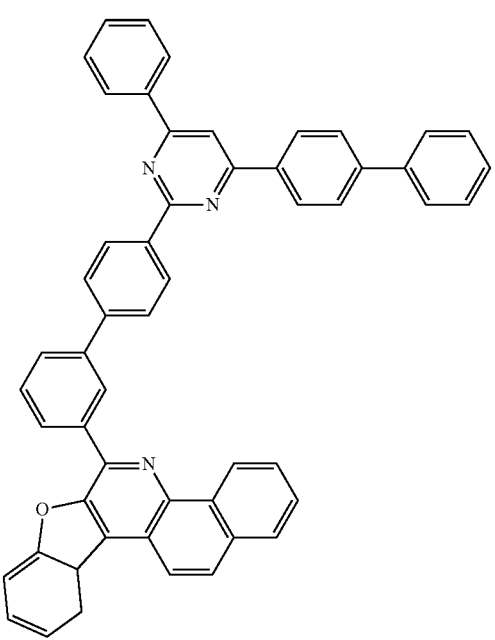

1087
-continued
893
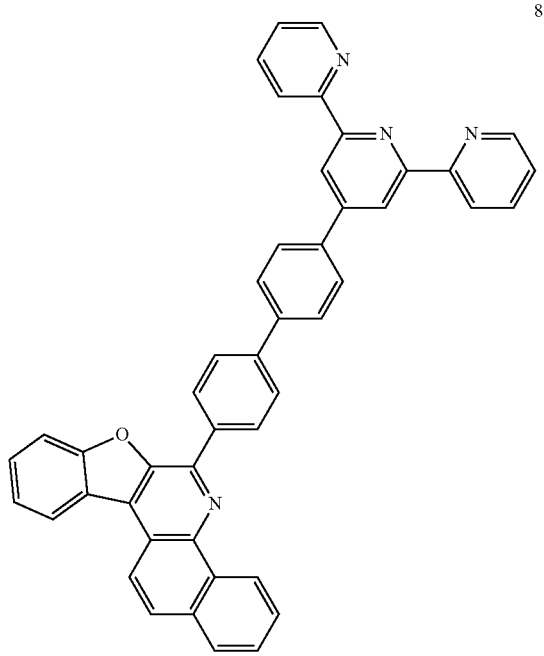
1088
-continued
895
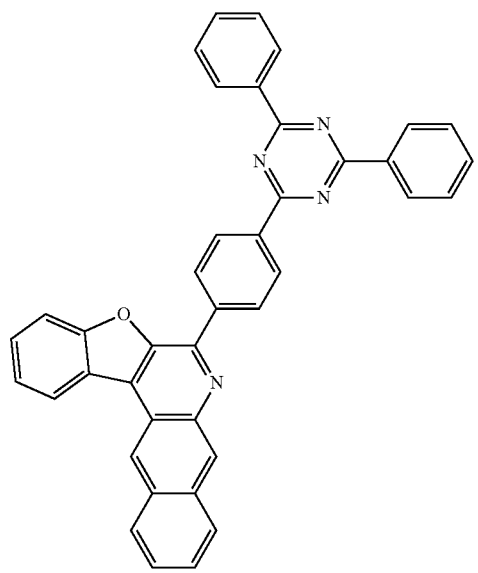 [SMILES: c1ccc(-c2nc(-c3ccccc3)nc(-c3ccc(-c4nc5cc6ccccc6cc5c5c4oc4ccccc45)cc3)n2)cc1]
894
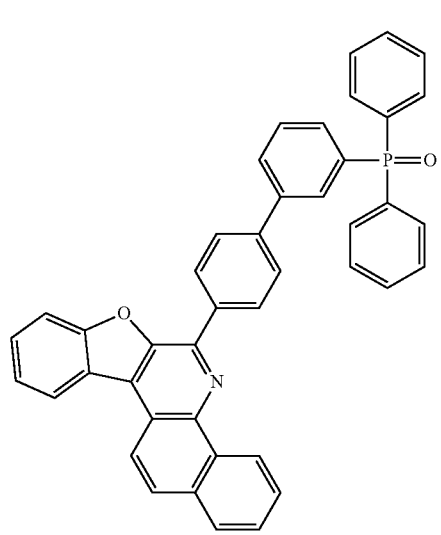
896
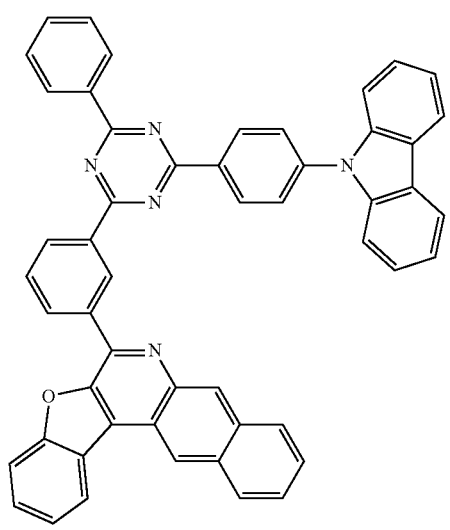

1089
-continued
897
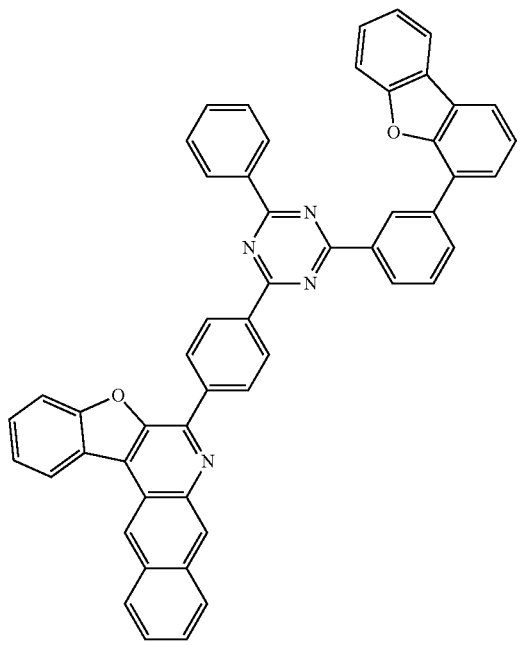
898
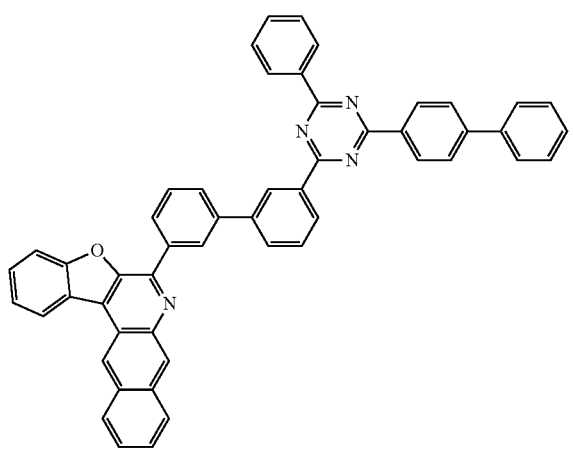
899
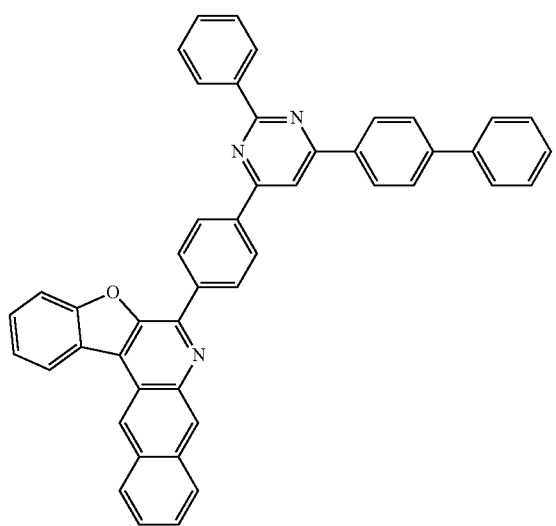
1090
-continued
900
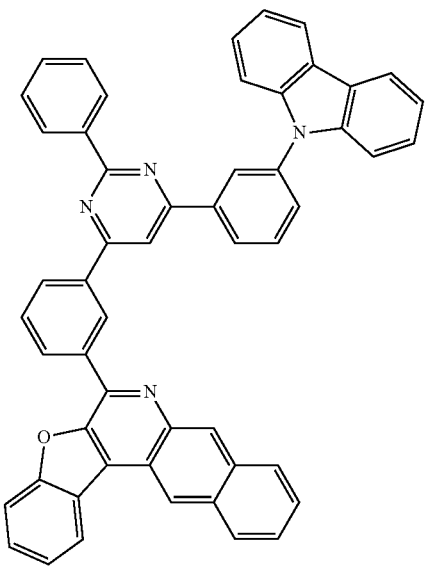
901
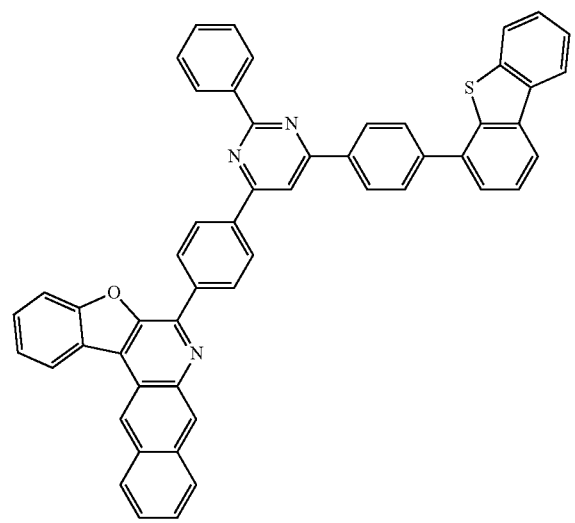 [SMILES: c1ccc(-c2nc(-c3ccc(-c4nc5cc6ccccc6cc5c5c4oc4ccccc45)cc3)cc(-c3ccc(-c4cccc5c4sc4ccccc45)cc3)n2)cc1]

1091
-continued
1092
-continued
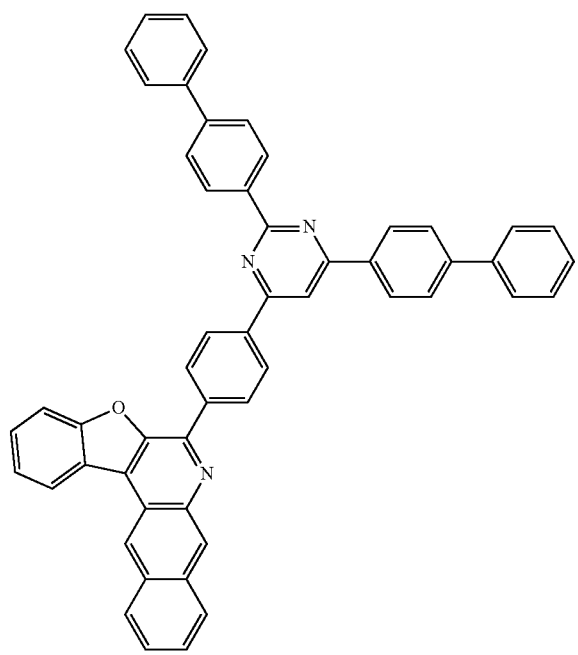
902
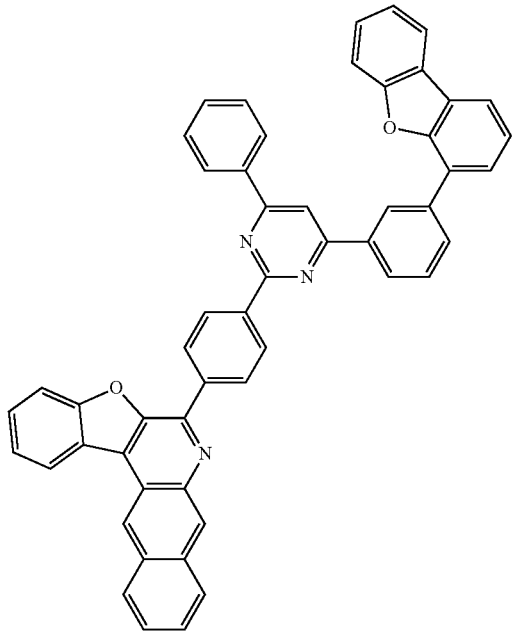 [SMILES: c1ccc(-c2cc(-c3cccc(-c4cccc5c4oc4ccccc45)c3)nc(-c3ccc(-c4nc5cc6ccccc6cc5c5c4oc4ccccc45)cc3)n2)cc1]
904
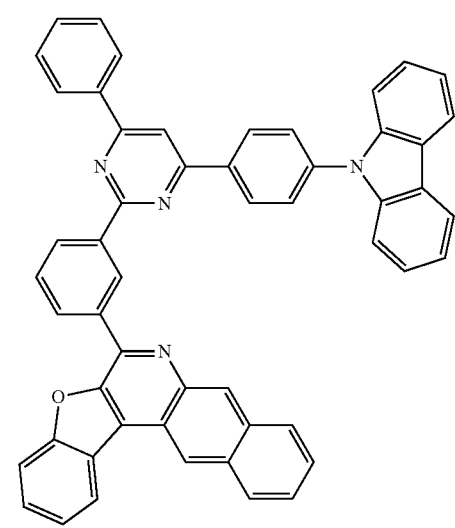
903
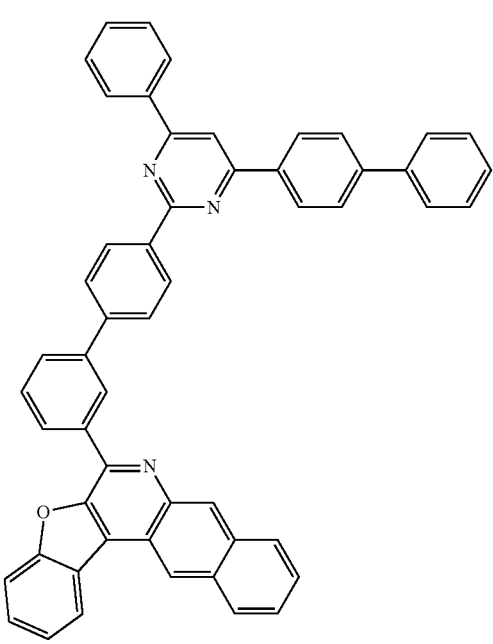
905

1093
-continued
1094
-continued
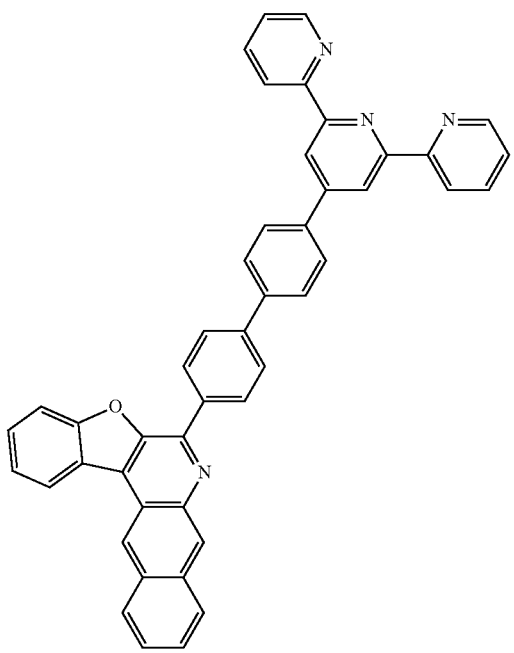
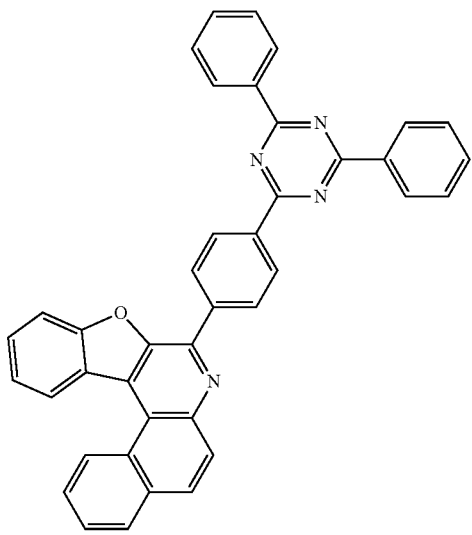

1095 -continued
910
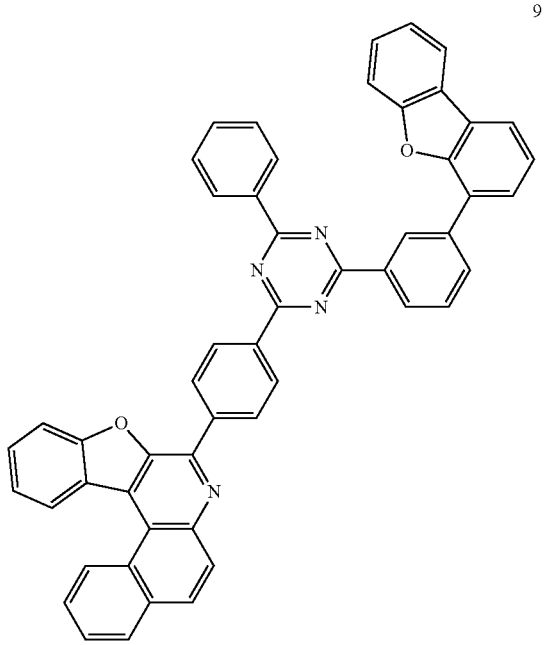
911
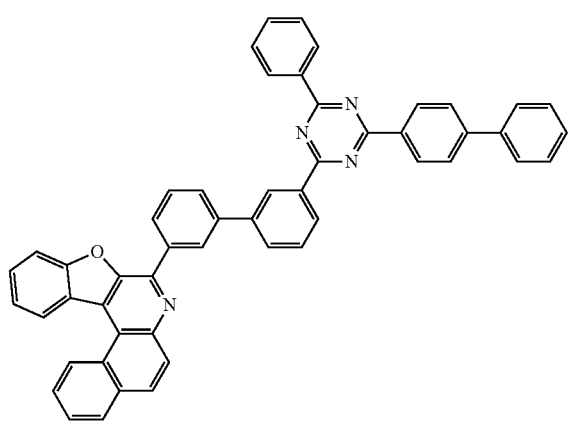
912
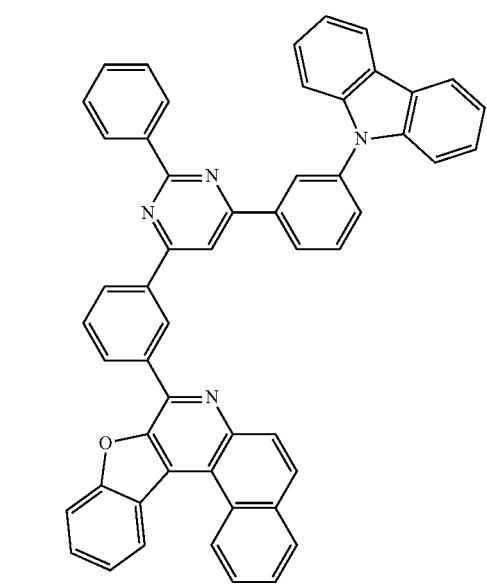
1096 -continued
913
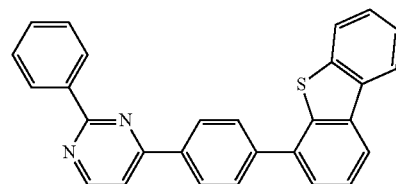
914
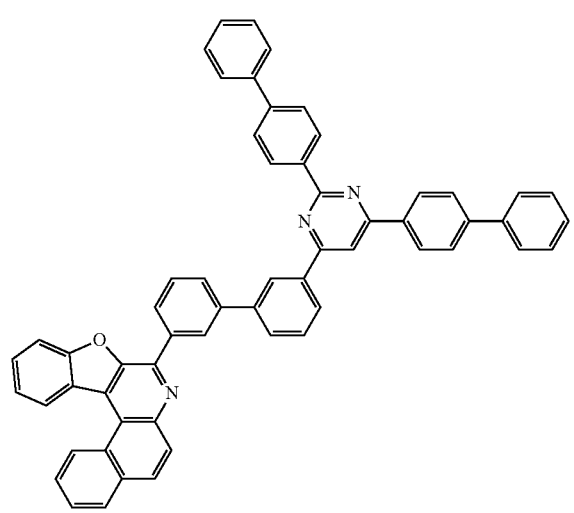
915
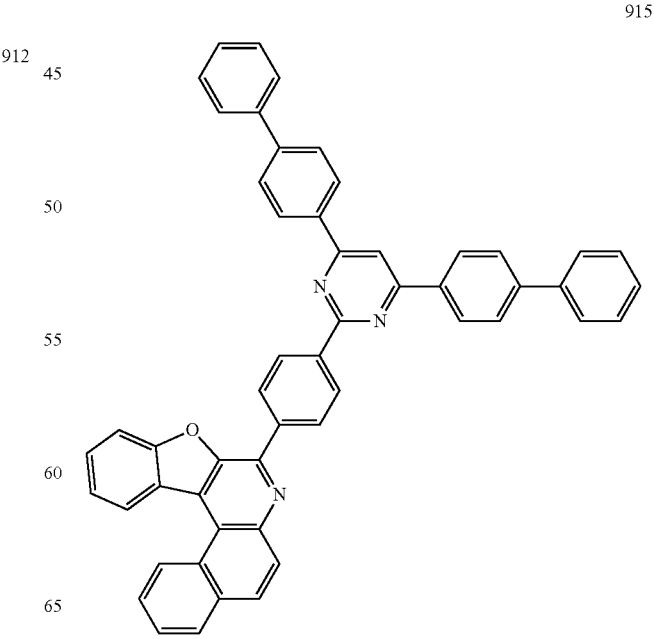

1097
-continued
1098
-continued
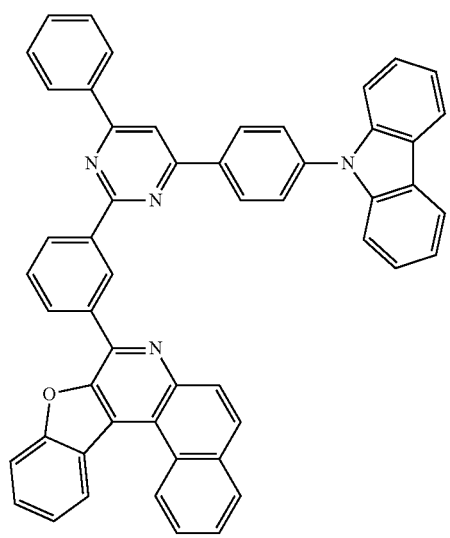
916
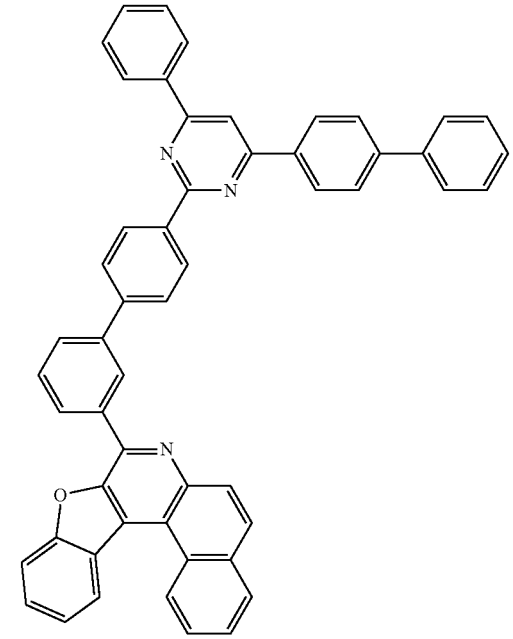
918
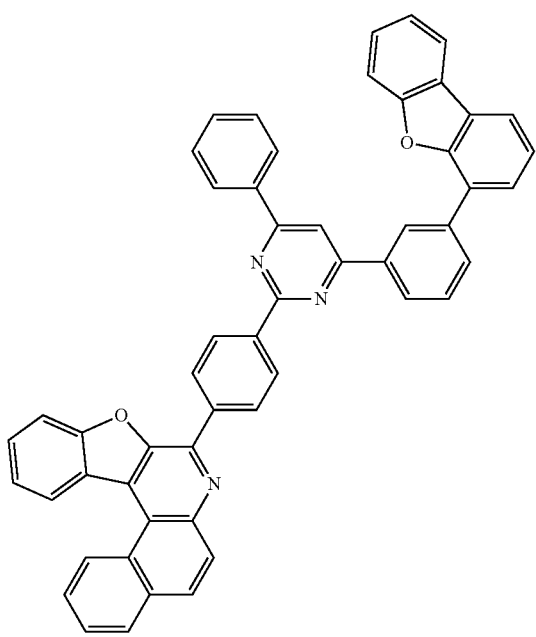
917
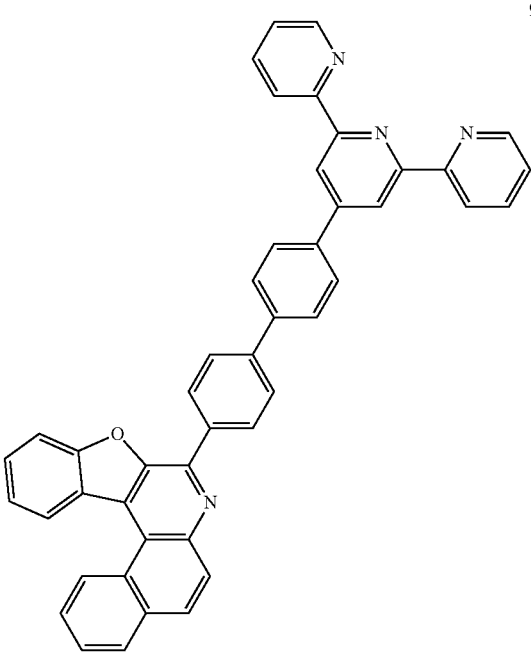
919

1099
-continued
920
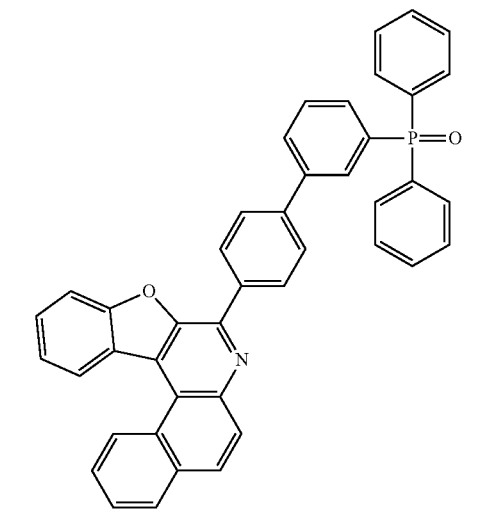
921
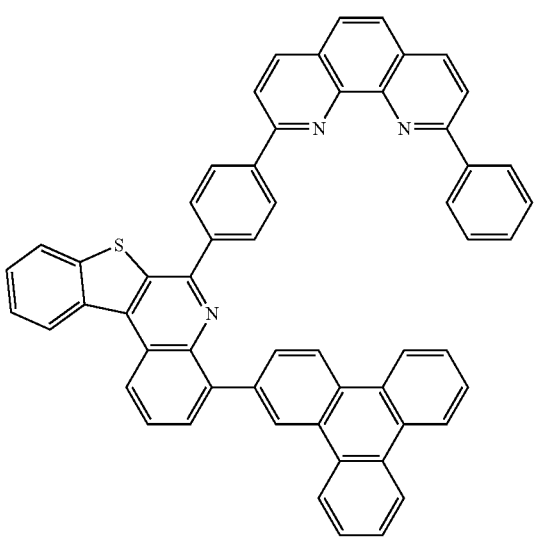
922
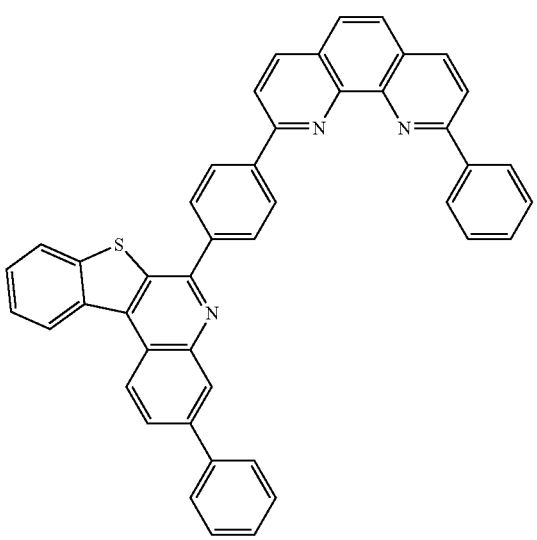
1100
-continued
923
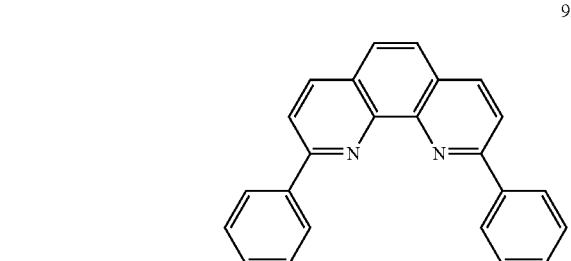
924
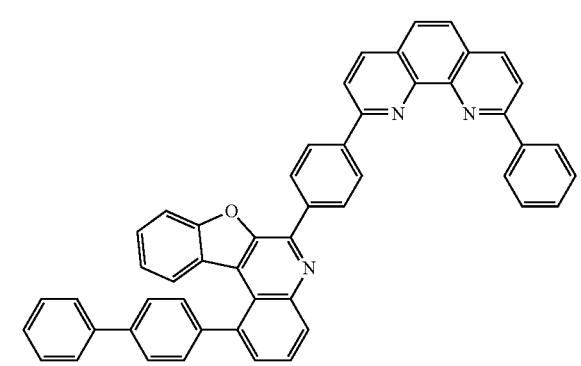
925
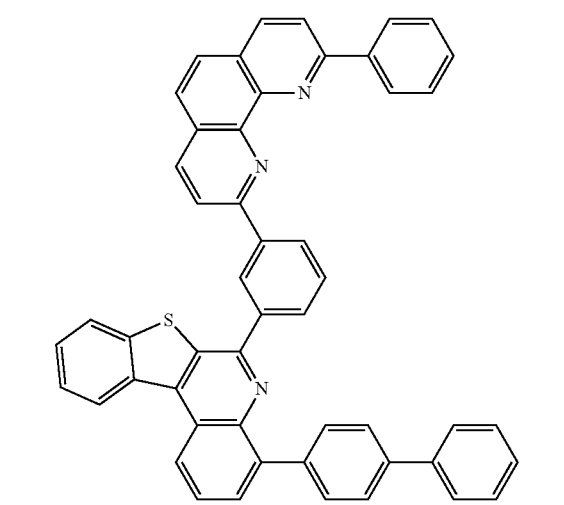

-continued
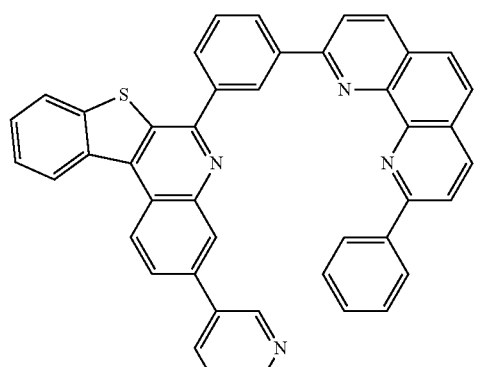
926
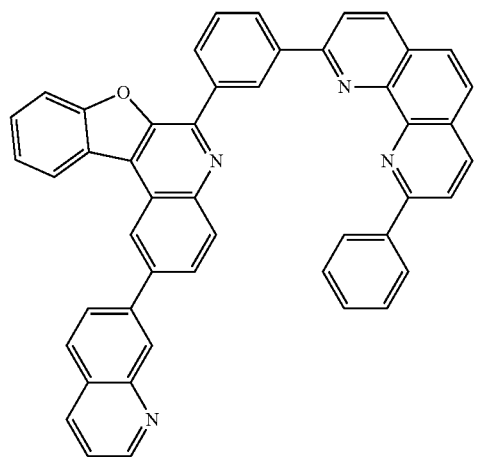
927
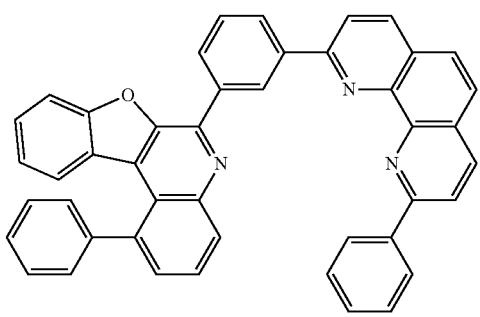
928
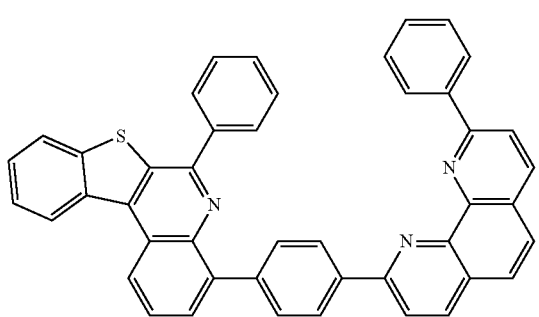
929
-continued
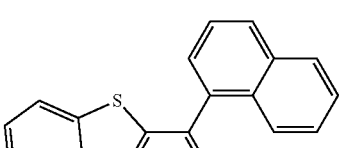
930
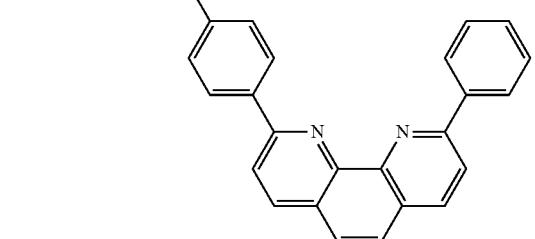
931

1103
-continued
932
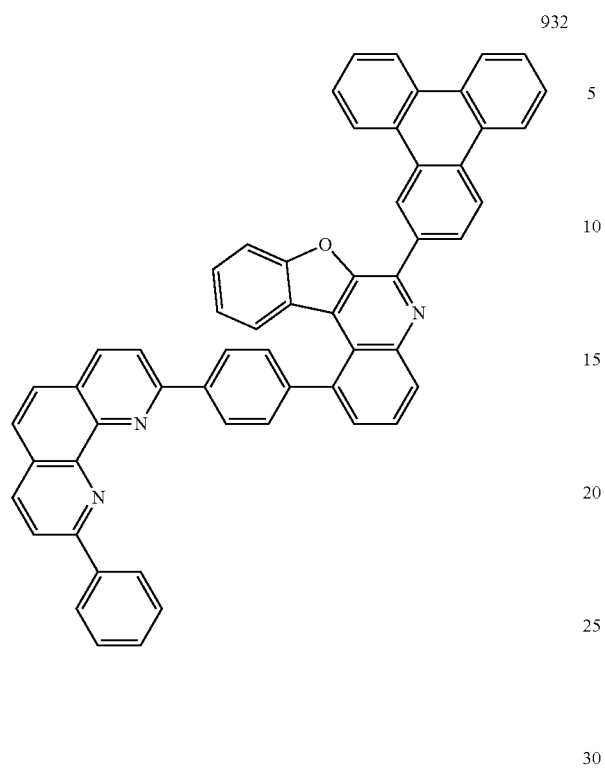
933
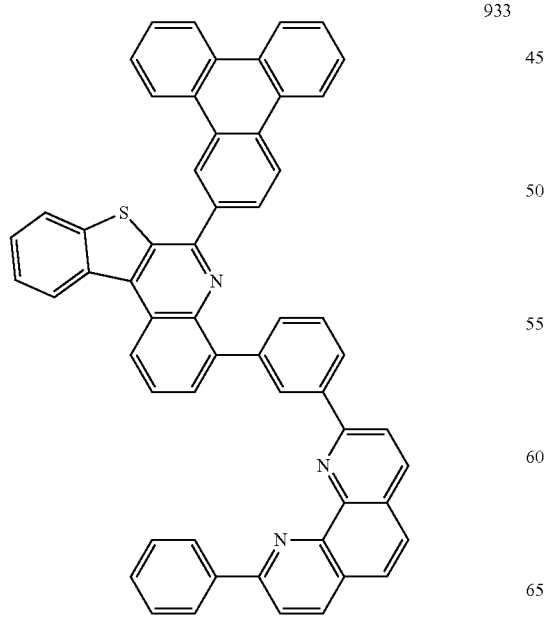
1104
-continued
934
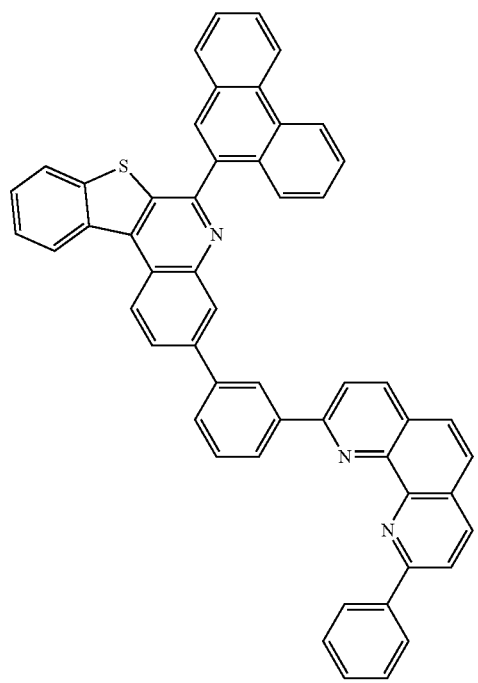
935
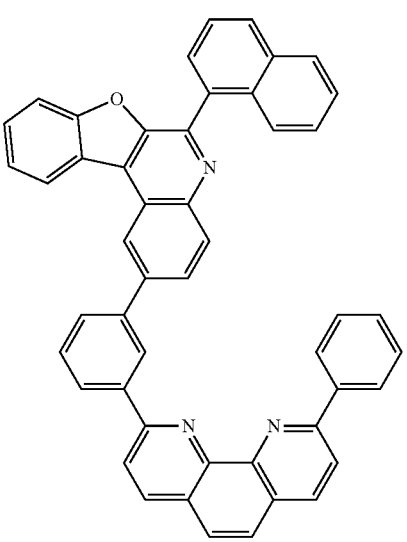

1105
-continued
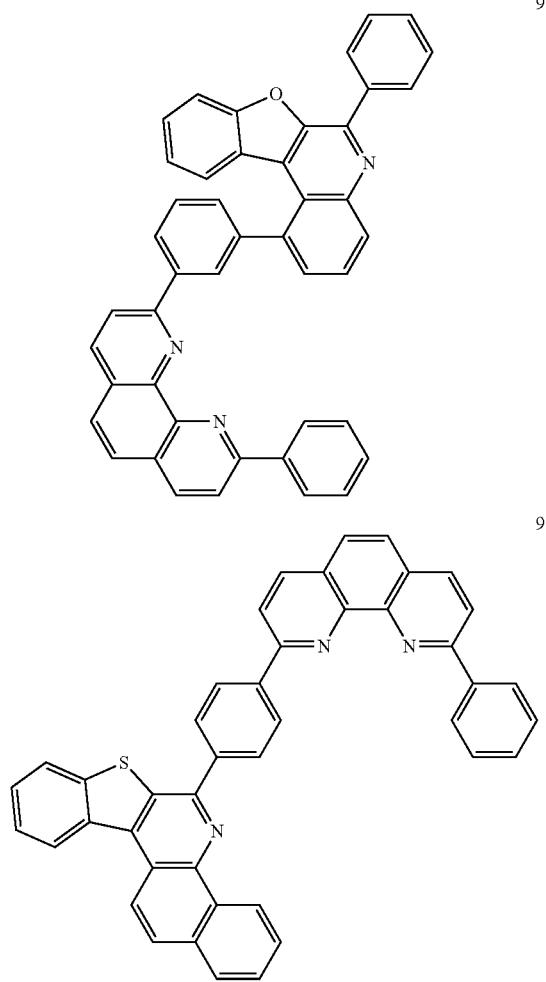
1106
-continued
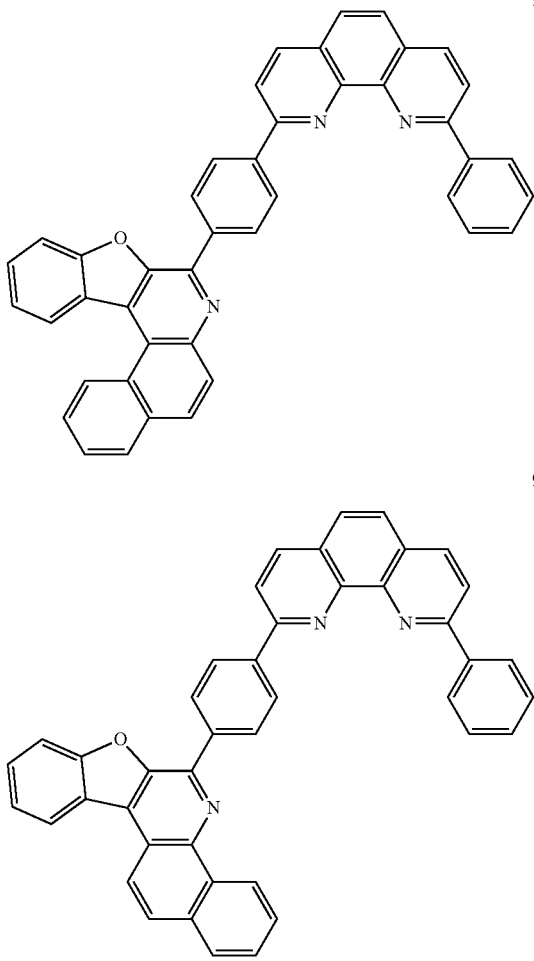

1107
-continued
942
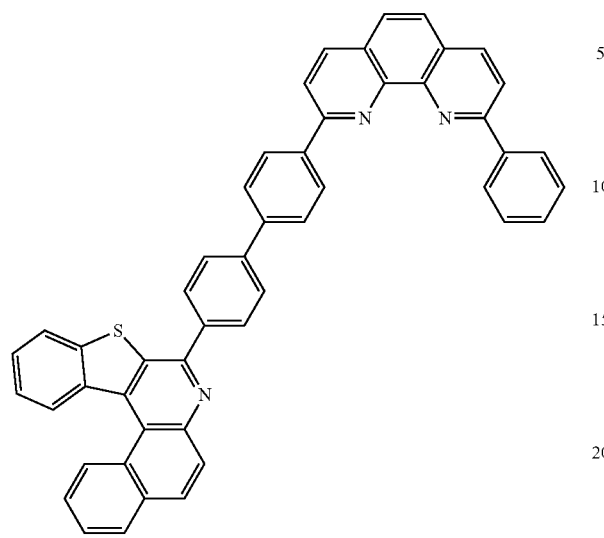
1108
-continued
944
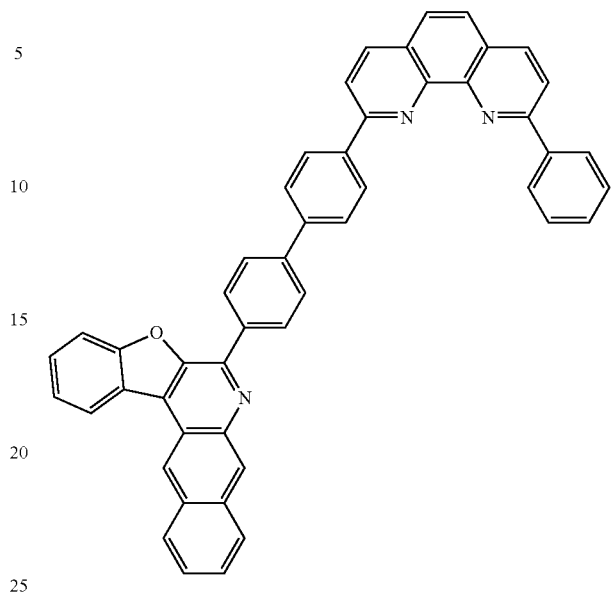
945
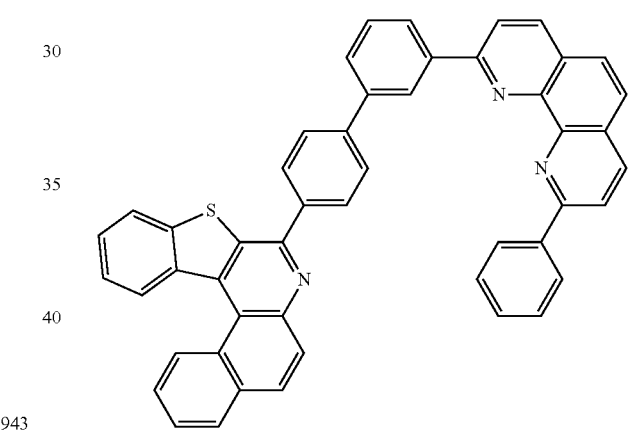
943
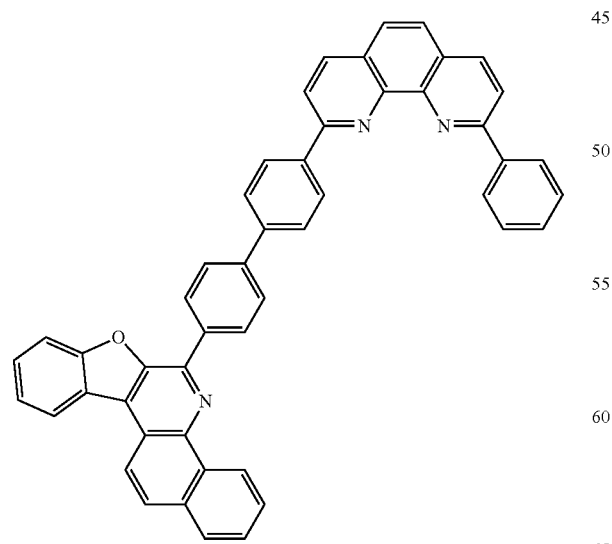
946
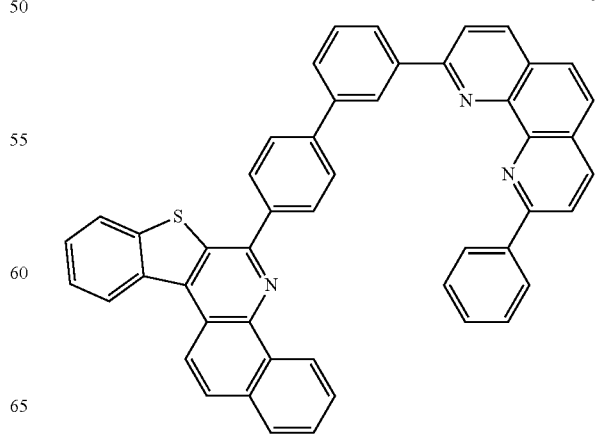

-continued

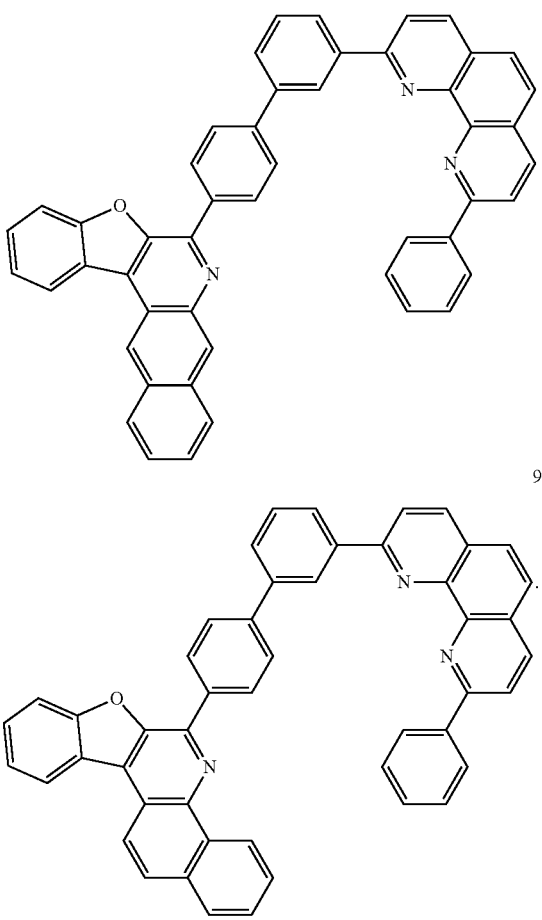

947

948

9. An organic light emitting device comprising:
a first electrode;
a second electrode provided opposite to the first electrode; and
one or more organic material layers provided between the first electrode and the second electrode,
wherein one or more layers of the organic material layers comprise the heterocyclic compound of claim 1.

10. The organic light emitting device of claim 9, wherein the organic material layer comprises a light emitting layer, and the light emitting layer comprises the heterocyclic compound.

11. The organic light emitting device of claim 9, wherein the organic material layer comprises a light emitting layer, the light emitting layer comprises a host material, and the host material comprises the heterocyclic compound.

12. The organic light emitting device of claim 9, wherein the organic material layer comprises an electron injection layer or an electron transfer layer, and the electron injection layer or the electron transfer layer comprises the heterocyclic compound.

13. The organic light emitting device of claim 9, wherein the organic material layer comprises an electron blocking layer or a hole blocking layer, and the electron blocking layer or the hole blocking layer comprises the heterocyclic compound.

14. The organic light emitting device of claim 9, further comprising one, two or more layers selected from the group consisting of a light emitting layer, a hole injection layer, a hole transfer layer, an electron injection layer, an electron transfer layer, an electron blocking layer and a hole blocking layer.

15. The organic light emitting device of claim 9, comprising:
a first electrode;
a first stack provided on the first electrode and comprising a first light emitting layer;
a charge generation layer provided on the first stack;
a second stack provided on the charge generation layer and comprising a second light emitting layer; and
a second electrode provided on the second stack.

16. The organic light emitting device of claim 15, wherein the charge generation layer comprises the heterocyclic compound.

\* \* \* \* \*